US011787803B2

(12) United States Patent
Schiller et al.

(10) Patent No.: US 11,787,803 B2
(45) Date of Patent: Oct. 17, 2023

(54) TETRAHYDRO-IMIDAZO QUINOLINE COMPOSITIONS AS CBP/P300 INHIBITORS

(71) Applicant: FORMA Therapeutics, Inc., Watertown, MA (US)

(72) Inventors: Shawn E. R. Schiller, Haverhill, MA (US); Torsten Herbertz, Stow, MA (US); Hongbin Li, Madison, CT (US); Bradford Graves, Nutley, NJ (US); Steven Mischke, Waltham, MA (US); Angela V. West, Franklin, MA (US); Jennifer R. Downing, Clinton, MA (US); Anna Ericsson, Shrewsbury, MA (US)

(73) Assignee: Forma Therapeutics, Inc., Watertown, MA (US)

(*) Notice: Subject to any disclaimer, the term of this patent is extended or adjusted under 35 U.S.C. 154(b) by 0 days.

(21) Appl. No.: 17/669,135

(22) Filed: Feb. 10, 2022

(65) Prior Publication Data

US 2022/0169647 A1 Jun. 2, 2022

Related U.S. Application Data

(63) Continuation of application No. 16/647,478, filed as application No. PCT/US2018/051235 on Sep. 14, 2018, now Pat. No. 11,292,791.

(60) Provisional application No. 62/692,593, filed on Jun. 29, 2018, provisional application No. 62/559,436, filed on Sep. 15, 2017.

(51) Int. Cl.

| | |
|---|---|
| *C07D 471/04* | (2006.01) |
| *C07D 519/00* | (2006.01) |
| *A61P 35/00* | (2006.01) |

(52) U.S. Cl.

CPC ............ *C07D 471/04* (2013.01); *A61P 35/00* (2018.01); *C07D 519/00* (2013.01)

(58) Field of Classification Search

CPC ...... C07D 471/04; C07D 519/00; A61P 35/00
See application file for complete search history.

(56) References Cited

U.S. PATENT DOCUMENTS

| | | | |
|---|---|---|---|
| 6,011,029 | A | 1/2000 | Ding et al. |
| 7,101,869 | B2 | 9/2006 | Blumenkopf et al. |
| 7,709,489 | B2 | 5/2010 | Aranyi et al. |
| 9,211,333 | B2 | 12/2015 | Zhang et al. |
| 9,975,896 | B2 | 5/2018 | Marineau et al. |
| 2004/0214825 | A1 | 10/2004 | McCall et al. |
| 2006/0106020 | A1 | 5/2006 | Rodgers et al. |
| 2006/0167047 | A1 | 7/2006 | Timmers et al. |
| 2007/0179165 | A1 | 8/2007 | Gyorkos et al. |
| 2007/0203236 | A1 | 8/2007 | Smith et al. |
| 2007/0254961 | A1 | 11/2007 | Tapas et al. |
| 2009/0326020 | A1 | 12/2009 | Yan et al. |
| 2010/0166781 | A1 | 7/2010 | Setiadi et al. |
| 2010/0179325 | A1 | 7/2010 | Suzuki et al. |
| 2010/0216853 | A1 | 8/2010 | Marmorstein et al. |
| 2010/0267672 | A1 | 10/2010 | Jung et al. |
| 2011/0257196 | A1 | 10/2011 | Yan et al. |
| 2012/0108581 | A1 | 5/2012 | Ashikawa et al. |
| 2012/0258953 | A1 | 10/2012 | Aay et al. |
| 2013/0158003 | A1 | 6/2013 | Campbell et al. |
| 2013/0324580 | A1 | 12/2013 | Zhang et al. |
| 2016/0158207 | A1 | 9/2016 | Adler et al. |
| 2016/0257692 | A1 | 9/2016 | Bair et al. |

FOREIGN PATENT DOCUMENTS

| | | | |
|---|---|---|---|
| EP | 2 412 710 | A1 | 1/2012 |
| WO | WO 1995/020589 | A1 | 8/1995 |
| WO | WO 2002/040614 | A1 | 5/2002 |
| WO | WO 2003/033517 | A1 | 4/2003 |
| WO | WO 2003/045929 | A1 | 6/2003 |
| WO | WO 2004/043392 | A2 | 5/2004 |
| WO | WO 2005/066162 | A1 | 7/2005 |
| WO | WO 2007/120339 | A1 | 10/2007 |
| WO | WO 2007/133653 | A2 | 11/2007 |
| WO | WO 2008/009348 | A1 | 1/2008 |
| WO | WO 2009/000413 | A1 | 12/2008 |
| WO | WO 2009/064251 | A1 | 5/2009 |
| WO | WO 2009/152072 | A1 | 12/2009 |
| WO | WO 2010/118208 | A1 | 10/2010 |
| WO | WO 2010/138490 | A1 | 12/2010 |
| WO | WO 2011/085039 | A2 | 7/2011 |
| WO | WO 2011/109059 | A1 | 9/2011 |

(Continued)

OTHER PUBLICATIONS

Gajer, J. M., "Histone acetyltransferase inhibitors block neuroblastoma cell growth in vivo." Oncogenesis 4.2 (2015) e137:1-10.*

"AR: Androgen Receptor", Depmap Portal, https://depmap.org/portal/gene/AR?tab=characterization (release 19Q2).

"Gene Set: Hallmark_Androgen Response", Gene Set Enrichment Analysis, http://software.broadinstitute.org/gsea/msigdb/cards/HALLMARK_ANDROGEN_RESPONSE.html.

Bowers, et al. Virtual Ligand Screening of the p300/CBP Histone Acetyltransferase: Identification of a Selective Small Molecule Inhibitor, Chemistry & Biology 17, pp. 471-482, May 28, 2010.

Chekler, Eugene L. et al. "Transcriptional Profiling of a Selective CREB Binding Protein Bromodomain Inhibitor Highlights Therapeutic Opportunities", *Chemistry and Biology*, 2015, 22(12), 1588-1596.

Crawford et al. "Discovery of a Potent and Selective Vivo Probe (GNE-272) for the Bromodomains fo CBP/EP300", J. Med. Chem., 2016, 56 pgs.

(Continued)

*Primary Examiner* — John M Mauro
(74) *Attorney, Agent, or Firm* — Wiggin and Dana LLP

(57) ABSTRACT

The present disclosure is directed to inhibitors of the CBP/p300 family of bromodomains. The compounds can be useful in the treatment of disease or disorders associated with the inhibition of the CBP/p300 family of bromodomains. For instance, the disclosure is concerned with compounds and compositions for inhibition of the CBP/p300 family of bromodomains, methods of treating, preventing, or ameliorating diseases or disorders associated with the inhibition of CBP/p300 family of bromodomains, and methods of synthesis of these compounds.

20 Claims, No Drawings

(56) References Cited

FOREIGN PATENT DOCUMENTS

| | | | |
|---|---|---|---|
| WO | WO 2011/150156 | A2 | 12/2011 |
| WO | WO 2012/019093 | A1 | 2/2012 |
| WO | WO 2012/080729 | A2 | 6/2012 |
| WO | WO 2012/082837 | A1 | 6/2012 |
| WO | WO 2012/116135 | A1 | 8/2012 |
| WO | WO 2013/004995 | A1 | 1/2013 |
| WO | WO 2013/006485 | A1 | 1/2013 |
| WO | WO 2013/148114 | A1 | 10/2013 |
| WO | WO 2014/045305 | A1 | 3/2014 |
| WO | WO 2014/133414 | A2 | 9/2014 |
| WO | WO 2014/182929 | A1 | 11/2014 |
| WO | WO 2015/002754 | A2 | 1/2015 |
| WO | WO 2015/004533 | A2 | 1/2015 |
| WO | WO 2015/013635 | A2 | 1/2015 |
| WO | WO 2015/022322 | A1 | 2/2015 |
| WO | WO 2015/073763 | A1 | 5/2015 |
| WO | WO 2015/074064 | A2 | 5/2015 |
| WO | WO 2015/074081 | A1 | 5/2015 |
| WO | WO 2016/044694 | A1 | 3/2016 |
| WO | WO 2016/086200 | A1 | 6/2016 |
| WO | WO 2016/110821 | A1 | 7/2016 |
| WO | WO 2016/128908 | A1 | 8/2016 |
| WO | WO 2016/170323 | A1 | 10/2016 |
| WO | WO 2016/170324 | A1 | 10/2016 |
| WO | WO 2017/197056 | A1 | 11/2017 |
| WO | WO 2017/197240 | A1 | 11/2017 |
| WO | WO 2017/205536 | A2 | 11/2017 |
| WO | WO 2018/073586 | A1 | 4/2018 |
| WO | WO 2018/073587 | A1 | 4/2018 |
| WO | WO 2019/055869 | A1 | 3/2019 |
| WO | WO 2019/055877 | A1 | 3/2019 |

OTHER PUBLICATIONS

Duncan, A. Hay et al. "Discovery and Optimization of Small Molecule Ligands for the CBP/p300 Bromodomains", *J. Am. Chem. Soc.*, 2014, 136(26), 9308-9319.

Extended European Search Report from corresponding application EP 19 18 3741 (dated Aug. 1, 2019).

Fan et al. "p300 Modulates the BRCA1 Inhibition of Estrogen Receptor Activity", *Cancer Research*, 2002, 62, 141-151.

Garcia-Carpizo et al. "CREBBP/EP300 bromodomain inhibition affects the proliferation of AR positive breast cancer cell lines", *Molecular Cancer Research*, 2019.

Goff, Corinne Le et al. "Synthesis of some novel fused tetracyclic quinolonecarboxylic acids via 7-methyl-6,7,8,9-tetrahydro-3H-imidazo[4,5-f]quinoline and 6-methyl-5,6,7,8-tetrahydro-1H-imidazo[4,5-g]quinoline", *Journal of Heterocyclic Chemistry*, 1994, 31(1), 153-160.

Hammtzsch, A, "CBP30, a selective CBP/p300 bromodomain inhibitor, suppresses human Th17 responses", Proceedings of the National Academy of Sciences 112.34 (2015): 10768-10773.

International Search Report from related Application No. PCT/US2020/022783 (dated Jun. 10, 2020).

International Search Report from related Application No. PCT/US2020/022818 (dated Jun. 15, 2020).

International Search Report from related Application No. PCT/US2020/022823 (dated Jun. 15, 2020).

International Search Report from related Application No. PCT/US2019/039936 (dated Sep. 23, 2019).

International Search Report from related application PCT/US2014/066198 (dated May 18, 2015).

International Search Report from related application PCT/US2017/034320 (dated Nov. 15, 2017).

International Search Report from related application PCT/US2018/051235 (dated Feb. 25, 2019).

International Search Report from related application PCT/US2018/051214 (dated Dec. 4, 2018).

Jiang et al., "Small molecule Nas-e targeting cAMP response element binding protein (CREB) and CREB-binding protein interaction inhibits breast cancer bone metastasis" Journal of Cellular and Molecular Medicine, Nov. 20, 2018, vol. 23, pp. 1224-1234.

Jin et al. "Therapeutic Targeting of the CBP/p300 Bromodomain Blocks the Growth of Castration-Resistant Prostate Cancer", *Cancer Research*, 2017, 77(20), 5564-5575.

Kumar et al. "Androgen Receptor Immunohistochemistry as a Companion Diagnostic Approach to Predict Clinical Response to Enzalutamide in Triple-Negative Breast Cancer", *JCO Precision Oncology*, 2017, DOI: 10.1200/PO.17.00075.

Lasko et al. "Discovery of a selective catalytic p300/CBP inhibitor that targets lineage-specific tumours", Nature, 2017, vol. 000, 17 pgs.

PubChem CID 136574372, deposited Jan. 24, 2019, pp. 1-8, p. 2.

PubChem CID: 138472436, create date, Aug. 20, 2019, p. 2 formula.

Robinson et al., "Androgen receptor driven transcription in molecular apocrine breast cancer is mediated by FoxA1", *The EMBO Journal*, 2011, 30, 3019-3027.

Safarpour, Damoun et al. "Androgen receptor (AR) expression in 400 breast carcinomas: is routine AR assessment justified?", *Am J Cancer Res*, 2014, 4(4), 353-368.

Scher et al. "Assessment of the Validity of Nuclear-Localized Androgen Receptor Splice Variant 7 in Circulating Tumor Cells as a Predictive Biomarker for Castration-sistant Prostate Cancer" *JAMA Oncology*, 2018, 4(9), 1179-1186.

Scher, Howard et al. "Association of AR-V7 on Circulating Tumor Cells as a Treatment-Specific Biomarker With Outcomes and Survival in Castration-Resistant Prostate Cancer", *JAMA Oncology*, 2016, 2(11), 1441-1449.

Snow et al., "Discovery of 2-Phenylamino-imidazo[4,5-h]isoquinolin-9-ones: a New Class of Inhibitors of Lck Kinase", Journal of Medicinal Chemistry, vol. 45, pp. 3394-3405.

Solankee et al. "Synthesis and evaluation of some novel S-triazine based chalcones and their derivatives",*Der Pharma Chemica*, 2011, 3(6), 317-324.

Traina et al. "Enzalutamide for the Treatment of Androgen Receptor-Expressing Triple-Negative Breast Cancer" *Journal of Clinical Oncology*, 2018, 36(9), 884-890.

Tucci, Marcello et al. "Enzalutamide-resistant castration-resistant prostate cancer challenges and solutions", *OncoTargets and Therapy*, 2018, 11, 7353-7368.

Wong et al. "Anti-tumor activity of targeted and cytotoxic agents in murine subcutaneous tumor models correlates with clinical response", *Clinical Cancer Research*, 2012.

European Search Report from corresponding application EP 20 77 3477 (dated Nov. 21, 2022).

Moustakim et al.,, "Discovery of a PCAF Bromodomain Chemical Probe", Angewandte chemie, Dec. 14, 2016 , pp. 845-849, vol. 129.

* cited by examiner

TETRAHYDRO-IMIDAZO QUINOLINE COMPOSITIONS AS CBP/P300 INHIBITORS

CROSS-REFERENCE TO RELATED APPLICATIONS

This application is a continuation of U.S. patent application Ser. No. 16/647,478, filed Mar. 13, 2020, which is a National Stage application of International Application No. PCT/US2018/051235, filed Sep. 14, 2018, which claims the benefit of priority of U.S. Provisional Application No. 62/559,436, filed Sep. 15, 2017 and U.S. Provisional Application No. 62/692,593, filed Jun. 29, 2018, all of which are incorporated herein by reference in their entireties.

FIELD OF DISCLOSURE

The present disclosure is directed to inhibitors of the CBP/p300 family of bromodomains useful in the treatment of disease or disorders associated with the inhibition of the CBP/p300 family of bromodomains. Specifically, the disclosure is concerned with compounds and compositions for inhibition of the CBP/p300 family of bromodomains, methods of treating, preventing, or ameliorating diseases or disorders associated with the inhibition of CBP/p300 family of bromodomains, and methods of synthesis of these compounds.

BACKGROUND OF DISCLOSURE p300 (also known as EP300 and KAT3B) is a large protein with multiple domains that bind to diverse proteins including many DNA-binding transcription factors. The cyclic AMP-responsive element-binding protein (CREB) binding protein (CBP, also known as KAT3A) is a cellular paralog of p300. p300 and CBP share extensive sequence identity and functional similarity. As such, they are often referred to as CBP/p300 in the scientific literature. CBP/p300 are lysine acetyltransferases that catalyze the attachment of an acetyl group to a lysine side chain of histones and other protein substrates. As large proteins, CBP/p300 were proposed to activate transcription in part by bridging DNA-binding transcription factors to RNA polymerase machinery or by helping assemble the transcriptional pre-initiation complex (PIC). Importantly, CBP/p300-catalyzed acetylation of histones and other proteins is pivotal to gene activation. Heightened p300 expression and activities have been observed in advanced human cancers such as prostate and liver (cancer and appear to be associated with poor prognosis of these cancer types. Compared to normal tissue counterparts, the expression levels of p300 are higher in human primary breast cancer specimens and in mouse mammary carcinomas induced by polyomavirus middle-T oncogene.

SUMMARY OF DISCLOSURE

Novel compounds useful for inhibiting CBP, including CBP Inhibitor Compounds and Selective CBP Inhibitor Compounds, are disclosed herein. A first aspect of the present disclosure relates to compounds of Formula (I):

(I)

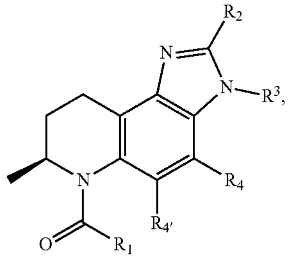

or a pharmaceutically acceptable salt, enantiomer, hydrate, solvate, isomer, or tautomer thereof, wherein:

$R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —$OR^5$, —$N(R^5)_2$, or —$NHR^5$;

$R^2$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl, wherein each alkyl, alkenyl, alkynyl, cycloalkyl, cycloalkenyl, heterocyclyl, heteroaryl, or aryl is optionally substituted with one or more $R^6$;

$R^3$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, spirocycloalkyl, spiroheterocyclyl, heterocyclyl, heteroaryl, or aryl, wherein each alkyl, alkenyl, alkynyl, cycloalkyl, cycloalkenyl, spirocycloalkyl, spiroheterocyclyl, heterocyclyl, heteroaryl, or aryl is optionally substituted with one or more $R^7$;

$R^4$ and $R^{4'}$ are each independently —H, halogen, —OH, —CN, or —$NH_2$;

each $R^5$ is independently —$C_1$-$C_6$alkyl, —$C_3$-$C_8$cycloalkyl, heterocyclyl, aryl, or heteroaryl;

$R^6$ and $R^7$ are each independently, at each occurrence, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —$C(O)R^{8'}$, —$C(O)OR^8$, —$C(O)NR^8R^9$, —$NR^8C(O)R^{9'}$, —$NR^8S(O)_2R^{9'}$, —$S(O)R^{8'}$, —$S(O)NR^8R^9$, or —$NR'S(O)R^{9'}$, wherein each alkyl, cycloalkyl, heterocyclyl, spirocycloalkyl, spiroheterocyclyl, heteroaryl, or aryl is optionally substituted with one or more $R^{10}$;

wherein any two $R^6$ or any two $R^7$, when on non-adjacent atoms, can combine to form a bridging cycloalkyl or heterocyclyl;

wherein any two $R^6$ or any two $R^7$, when on adjacent atoms, can combine to form a cycloalkyl, heterocyclyl, aryl or heteroaryl;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{8'}$ and $R^{9'}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^{9'}$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{10}$ and $R^{11}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$OC_3$-$C_6$cycloalkyl, —Oaryl, —Oheteroaryl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6alkyl)_2$, —$C(O)OC_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6alkyl)_2$, or —$N(C_1$-$C_6$alkyl)$S(O)(C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$;

wherein any two $R^{10}$ or any two $R^{11}$, when on non-adjacent atoms, can combine to form a bridging cycloalkyl or heterocyclyl;

wherein any two $R^{10}$ or any two $R^{11}$, when on adjacent atoms, can combine to form a cycloalkyl, heterocyclyl, aryl or heteroaryl;

$R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6alkyl)_2$, —$C(O)OC_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6alkyl)_2$, or —$N(C_1$-$C_6$alkyl)$S(O)(C_1$-$C_6$alkyl); and n is an integer from 1 to 4.

Another aspect of the present disclosure relates to a pharmaceutical composition comprising a compound of Formula (I), or a pharmaceutically acceptable salt, hydrate, solvate, prodrug, stereoisomer, or tautomer thereof and a pharmaceutically acceptable carrier. The pharmaceutically acceptable carrier can further include an excipient, diluent, or surfactant. The pharmaceutical composition can be effective for treating a disease or disorder associated with CBP/p300 modulation in a subject in need thereof. The pharmaceutical compositions can comprise the compounds of the present disclosure for use in treating diseases described herein. The compositions can contain at least one compound of the disclosure and a pharmaceutically acceptable carrier.

In another aspect, the present disclosure relates to a method of modulating one or more of CBP/p300-family bromodomains. The method can comprise administering to a patient in need thereof a therapeutically effective amount of a compound of Formula (I), or a pharmaceutically acceptable salt, hydrate, solvate, prodrug, stereoisomer, or tautomer thereof. Another aspect of the present disclosure relates to a method of inhibiting one or more of CBP/p300-family bromodomains. The method can comprise administering to a patient in need thereof a therapeutically effective amount of a compound of Formula (I), or a pharmaceutically acceptable salt, hydrate, solvate, prodrug, stereoisomer, or tautomer thereof. In another aspect, the present disclosure relates to a method of inhibiting one or more of CBP/p300-family bromodomains. The method can comprise administering to a patient in need thereof a therapeutically effective amount of a pharmaceutical composition described herein.

Another aspect of the present disclosure relates to a method of treating, preventing, inhibiting, or eliminating a disease or condition in a patient associated with the inhibition of one or more of CBP/p300-family bromodomains. The method can comprise administering to a patient in need thereof a therapeutically effective amount of a compound disclosed herein, such as a compound of Formula (I), or a pharmaceutically acceptable salt, hydrate, solvate, prodrug, stereoisomer, or tautomer thereof, wherein said disease or condition is selected from the group consisting of cancer The present disclosure further provides compounds and compositions with an improved efficacy and safety profile relative to known CBP/p300 domain inhibitors. The present disclosure also provides agents with novel mechanisms of action toward CBP/p300 proteins in the treatment of various types of diseases including cancers. The present disclosure can provide the medical community with a novel pharmacological strategy for the treatment of diseases and disorders associated with inhibition of CBP/p300 proteins, including the inhibition of CBP in the HTRF biochemical assay of Example 963 disclosed herein, with an $IC_{50}$ value of 0.001-1 micromolar.

DETAILED DESCRIPTION OF THE DISCLOSURE

The present disclosure relates to compounds and compositions that are capable of modulating the activity of the CBP/p300 family bromodomains. The disclosure features methods of treating, preventing or ameliorating a disease or disorder in which CBP/p300 bromodomains play a role by administering to a patient in need thereof a therapeutically effective amount of a compound of Formula (I), or a pharmaceutically acceptable salt, hydrate, solvate, prodrug, stereoisomer, or tautomer thereof. The methods of the present disclosure can be used in the treatment of a variety of CBP/p300 bromodomain dependent diseases and disorders by inhibiting the activity of a CBP/p300 bromodomains. Inhibition of CBP/p300 bromodomains provides a novel approach to the treatment, prevention, or amelioration of diseases including, but not limited to, cancer, inflammatory diseases, diabetes and obesity, and to develop male contraceptives.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

Unless otherwise indicated, "CBP Inhibitor Compound" as used herein refers to a compound having one or more of the following characteristics when tested according to the HTRF biochemical Assay Protocol of Example 963 below: (1) a CBP $IC_{50}$ value of less than 1 μM; and (2) a CBP $IC_{50}$ value of between 0.001 and 1 μM.

Unless otherwise indicated, a "Selective CBP Inhibitor Compound" as used herein refers to a CBP Inhibitor having a BRD4 $IC_{50}$ value greater than that of its CBP $IC_{50}$ value, preferably wherein its BRD4 $IC_{50}$ value greater than 1 μM (e.g., 1 micromolar to 10 micromolar, or greater), wherein the $IC_{50}$ values are as determined in the procedures set forth in Example 963.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups. In some embodiments, aryl groups have a total of 5 to 14 ring members, wherein at least one ring in the system is aromatic and wherein each ring in the system contains three to seven ring members. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)$(OH)_2$, —OC(O)$C_1$-$C_6$alkyl, —C(O)$C_1$-$C_6$alkyl, —OC(O)O$C_1$-$C_6$alkyl, —$NH_2$, —NH($C_1$-$C_6$alkyl), —N($C_1$-$C_6$alkyl)$_2$, —$S(O)_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl. In some embodiments, "heteroaryl" refers to groups having 5 to 10 ring atoms, preferably 5, 6, or 9 ring atoms; having 6, 10, or 14π electrons shared in a cyclic array; and/or having, in addition to carbon atoms, from one to five heteroatoms wherein the term "heteroatom" refers to nitrogen, oxygen, or sulfur, and includes any oxidized form of nitrogen or sulfur, and any quaternized form of a basic nitrogen.

"Alkyl" refers to a straight or branched chain saturated hydrocarbon containing 1-12 carbon atoms. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propanyl, n-butynyl, iso-butynyl, pentynyl, or hexynyl. An alkynyl group can be unsubstituted or substituted.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, phosphorous, nitrogen, or sulfur and wherein there is not delocalized $\pi$ electrons (aromaticity) shared among the ring carbon or heteroatoms. In some embodiments, "heterocyclyl" refers to a stable 5- to 7-membered monocyclic or 7-10-membered bicyclic heterocyclic moiety that is either saturated or partially unsaturated, and having, in addition to carbon atoms, one or more, preferably one to four, heteroatoms selected from N, S, P, or O. Heterocyclyl rings can be fully saturated or partially unsaturated. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, pyridonyl, and homotropanyl. A heteroycyclyl or heterocycloalkyl ring can also be fused or bridged, e.g., can be a bicyclic ring.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "spirocycle" is understood as a bicyclic ring system with both rings connected through a single atom. A spirocycle can be fully saturated or can be partially unsaturated.

The term "spirocycloalkyl" is understood to mean a fully carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycloalkyl can be fused to another ring carbocyclic, heterocyclic, aromatic, or heteroaromatic ring. A ($C_5$-$C_{12}$) spirocycloalkyl is a spirocycle containing between 5 and 12 carbon atoms.

The term "spiroheterocycloalkyl" or "spiroheterocyclyl" is understood to mean a spirocycle as defined above wherein at least one of the rings is a heterocycle (e.g., at least one of the rings is furanyl, morpholinyl, or piperadinyl). Spiroheterocycloalkyl groups can be for instance, without limitation, azapiroheptanes; azaspirooctanes; azaspirononanes; azaspirodecanes; oxaspiroheptanes; oxaspirooctanes; octaspirononanes; or oxaspirodecanes.

As used herein, the term "halo" or "halogen" means a fluoro, chloro, bromo, or iodo group.

The term "carbonyl" refers to a functional group composing a carbon atom double-bonded to an oxygen atom. It can be abbreviated herein as C(O), or as C═O.

The term "oxo" refers to an oxygen atom that is double-bonded to another atom. An "oxo" group can be connected to a carbon atom (e.g., to form a carbonyl, as defined above) or can be connected to a heteroatom such as sulfur (e.g., to form a sulfoxide or a sulfone) or phosphorous (e.g., to form a phosphorous ylide).

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the disclosure.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The term "stereoisomers" refers to the set of compounds which have the same number and type of atoms and share the same bond connectivity between those atoms, but differ in three dimensional structure. The term "stereoisomer" refers to any member of this set of compounds. For instance, a stereoisomer may be an enantiomer or a diastereomer.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "diastereomers" refers to the set of stereoisomers which cannot be made superimposable by rotation around single bonds. Diastereomerism occurs when two or more stereoisomers of a compound have different configurations at one or more (but not all) of the equivalent (related) stereocenters and are not mirror images of each other. Compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of Formula (I), and salts, solvates, esters and prodrugs thereof, may exist in their tautomeric form (for example, as an amide or imino ether). All such tautomeric forms are contemplated herein as part of the present disclosure.

The compounds of Formula (I), may contain asymmetric or chiral centers, and, therefore, exist in different stereoisomeric forms. It is intended that all stereoisomeric forms of the compounds of Formula (I) as well as mixtures thereof, including racemic mixtures, form part of the present disclosure. In addition, the present disclosure embraces all geometric and positional isomers. For example, if a compound of Formula (I), incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this disclosure. Enantiomers can also be separated by use of a chiral HPLC column.

It is also possible that the compounds of Formula (I), may exist in different tautomeric forms, and all such forms are embraced within the scope of the disclosure. Also, for example, all keto-enol and imine-enamine forms of the compounds are included in the disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the disclosure. Also, for example, all keto-enol and imine-enamine forms of the compounds are included in the disclosure.) Individual stereoisomers of the compounds of the disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The present disclosure also embraces isotopically-labelled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, fluorine and chlorine, such as $^2H$ (or D), $^3H$, $^{13}C$, $^{14}C$, $^{15}N$, $^{18}O$, $^{17}O$ $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples herein below, by substituting an appropriate isotopically labelled reagent for a non-isotopically labelled reagent.

The compounds of Formula (I) may form salts which are also within the scope of this disclosure. Reference to a compound of the Formula (I) herein is understood to include reference to salts thereof, unless otherwise indicated.

The present disclosure relates to compounds which are modulators of one or more bromodomains of the CBP/p300 family. In one embodiment, the compounds of the present disclosure are inhibitors of one or more bromodomains of the CBP/p300 family.

Compounds of the Disclosure

The present disclosure relates to compounds, or pharmaceutically acceptable salts or isomers thereof, capable of modulating CBP/p300 family bromodomains which are useful for the treatment of diseases and disorders associated with modulation of CBP/p300 family bromodomains. The disclosure further relates to compounds, or pharmaceutically acceptable salts or isomers thereof, which are useful for inhibiting CBP/p300 family bromodomains.

One aspect of the present disclosure describes compounds of Formula (I):

(I)

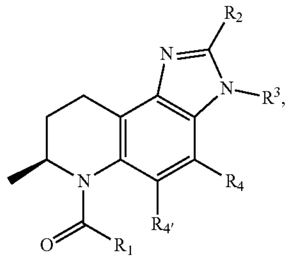

or a pharmaceutically acceptable salt, enantiomer, hydrate, solvate, isomer, or tautomer thereof, wherein:

$R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —$OR^5$, —$N(R^5)_2$, or —$NHR^5$;

$R^2$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl, wherein each alkyl, alkenyl, alkynyl, cycloalkyl, cycloalkenyl, heterocyclyl, heteroaryl, or aryl is optionally substituted with one or more $R^6$;

$R^3$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, spirocycloalkyl, spiroheterocyclyl, heterocyclyl, heteroaryl, or aryl, wherein each alkyl, alkenyl, alkynyl, cycloalkyl, cycloalkenyl, spirocycloalkyl, spiroheterocyclyl, heterocyclyl, heteroaryl, or aryl is optionally substituted with one or more $R^7$;

$R^4$ and $R^{4'}$ are each independently —H, halogen, —OH, —CN, or —$NH_2$;

each $R^5$ is independently —$C_1$-$C_6$alkyl, —$C_3$-$C_8$cycloalkyl, heterocyclyl, aryl, or heteroaryl;

$R^6$ and $R^7$ are each independently, at each occurrence, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —$C(O)R^{8'}$, —$C(O)OR^8$, —$C(O)NR^8R^9$, —$NR^8C(O)R^{9'}$, —NR'S$(O)_2R^{9'}$, —$S(O)R^{8'}$, —$S(O)NR^8R^9$, or —NR'S$(O)R^{9'}$, wherein each alkyl, cycloalkyl, heterocyclyl, spirocycloalkyl, spiroheterocyclyl, heteroaryl, or aryl is optionally substituted with one or more $R^{10}$;

wherein any two $R^6$ or any two $R^7$, when on non-adjacent atoms, can combine to form a bridging cycloalkyl or heterocyclyl;

wherein any two $R^6$ or any two $R^7$, when on adjacent atoms, can combine to form a cycloalkyl, heterocyclyl, aryl or heteroaryl;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{8'}$ and $R^{9'}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^{9'}$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{10}$ and $R^{11}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$OC_3$-$C_6$cycloalkyl, —Oaryl, —Oheteroaryl, —$NHC_1$-$C_6$alkyl, —N($C_1$-$C_6$alkyl)$_2$, —$S(O)_2$NH($C_1$-$C_6$alkyl), —$S(O)_2$N($C_1$-$C_6$alkyl)$_2$, —$S(O)_2C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)$OC_1$-$C_6$alkyl, —N($C_1$-$C_6$alkyl) $SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^2$;

wherein any two $R^{10}$ or any two $R^{11}$, when on non-adjacent atoms, can combine to form a bridging cycloalkyl or heterocyclyl;

wherein any two $R^{10}$ or any two $R^{11}$, when on adjacent atoms, can combine to form a cycloalkyl, heterocyclyl, aryl or heteroaryl;

$R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —N($C_1$-$C_6$alkyl)$_2$, —$S(O)_2$NH($C_1$-$C_6$alkyl), —$S(O)_2$N($C_1$-$C_6$alkyl)$_2$, —$S(O)_2C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)$OC_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl); and n is an integer from 1 to 4.

Another aspect of the present disclosure is the provision of pharmaceutical compositions comprising therapeutically effective amounts of at least one compound of Formula (I).

An aspect of the present disclosure concerns compounds which are, or can be, inhibitors of one or more bromodomains of the CBP/p300 family (e.g., compounds of Formula (I)).

An aspect of the present disclosure concerns the use of an inhibitor of CBP/p300 family bromodomains (e.g., a compound of Formula (I)) for the preparation of a medicament used in the treatment, prevention, inhibition or elimination of tumors (e.g., solid tumors).

An aspect of the present disclosure concerns the use of an inhibitor of CBP/p300 family bromodomains (e.g., a compound of Formula (I)) for the preparation of a medicament used in the treatment, prevention, inhibition or elimination of cancer. In some embodiments, the cancer is a hematological cancer such as leukemia (e.g., acute myeloid leukemia).

An aspect of the present disclosure concerns the use of an inhibitor of CBP/p300 family bromodomains (e.g., a compound of Formula (I)) for use in the treatment, prevention, inhibition or elimination of cancer.

In some embodiments, compounds of the disclosure are of Formula (I), or a pharmaceutically acceptable salt, enantiomer, hydrate, solvate, isomer, or tautomer thereof, wherein:

$R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, or —$OR^5$;

$R^2$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl, wherein each alkyl, alkenyl, alkynyl, cycloalkyl, cycloalkenyl, heterocyclyl, heteroaryl, or aryl is optionally substituted with one or more $R^6$, and wherein a —$C_1$-$C_6$alkyl group may have one or more methylene units replaced by —$NR^6$—, —O— or —S—;

$R^3$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, spirocycloalkyl, spiroheterocyclyl, heterocyclyl, heteroaryl, or aryl, wherein each alkyl, alkenyl, alkynyl, cycloalkyl, cycloalkenyl, spirocycloalkyl, spiroheterocyclyl, heterocyclyl, heteroaryl, or aryl is optionally substituted with one or more $R^7$;

$R^4$ and $R^{4'}$ are each independently —H, halogen, —OH, —CN, or —$NH_2$;

$R^8$ is —$C_1$-$C_6$alkyl, —$C_3$-$C_8$cycloalkyl, heterocyclyl, aryl, or heteroaryl;

$R^6$ and $R^7$ are each independently, at each occurrence, —H, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —C(O)$R^{8'}$, —C(O)$OR^8$, —C(O)$NR^8R^9$, —$NR^8$C(O)$R^{9'}$, —$NR^8$S(O)$_2R^{9'}$, —S(O)$R^{8'}$, —S(O)$NR^8R^9$, or —$NR^8$S(O)$R^{9'}$, wherein each alkyl, cycloalkyl, heterocyclyl, spirocycloalkyl, spiroheterocyclyl, heteroaryl, or aryl is optionally substituted with one or more $R^{10}$;

wherein any two $R^6$ or any two $R^7$, when on non-adjacent atoms, can combine to form a bridging cycloalkyl or heterocyclyl;

wherein any two $R^6$ or any two $R^7$, when on adjacent atoms, can combine to form a cycloalkyl, heterocyclyl, aryl or heteroaryl;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{8'}$ and $R^{9'}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^{9'}$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{10}$ and $R^{11}$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6alkyl)$, —$S(O)_2N(C_1$-$C_6alkyl)_2$, —$S(O)_2C_1$-$C_6alkyl$, —$C(O)C_1$-$C_6alkyl$, —$C(O)NH_2$, —$C(O)NH(C_1$-$C_6alkyl)$, —$C(O)N(C_1$-$C_6alkyl)_2$, —$C(O)OC_1$-$C_6alkyl$, —$N(C_1$-$C_6alkyl)SO_2C_1$-$C_6alkyl$, —$S(O)(C_1$-$C_6alkyl)$, —$S(O)N(C_1$-$C_6alkyl)_2$, or —$N(C_1$-$C_6alkyl)S(O)(C_1$-$C_6alkyl)$, wherein each alkyl, alkenyl, alkynyl, cycloalkyl, cycloalkenyl, heterocyclyl, heteroaryl, or aryl is optionally substituted with one or more —$R^2$;

wherein any two $R^{10}$ or any two $R^{11}$, when on non-adjacent atoms, can combine to form a bridging cycloalkyl or heterocyclyl;

wherein any two $R^{10}$ or any two $R^{11}$, when on adjacent atoms, can combine to form a cycloalkyl, heterocyclyl, aryl or heteroaryl;

$R^{12}$ is independently, at each occurrence, —H, —$C_1$-$C_6alkyl$, —$C_2$-$C_6alkenyl$, —$C_2$-$C_6alkynyl$, —$C_3$-$C_8cycloalkyl$, —$C_4$-$C_8cycloalkenyl$, heterocyclyl, heteroaryl, aryl, —OH, halogen, oxo, —$NO_2$, —CN, —$NH_2$, —$OC_1$-$C_6alkyl$, —$NHC_1$-$C_6alkyl$, —$N(C_1$-$C_6alkyl)_2$, —$S(O)_2NH(C_1$-$C_6alkyl)$, —$S(O)_2N(C_1$-$C_6alkyl)_2$, —$S(O)_2C_1$-$C_6alkyl$, —$C(O)C_1$-$C_6alkyl$, —$C(O)NH_2$, —$C(O)NH(C_1$-$C_6alkyl)$, —$C(O)N(C_1$-$C_6alkyl)_2$, —$C(O)OC_1$-$C_6alkyl$, —$N(C_1$-$C_6alkyl)SO_2C_1$-$C_6alkyl$, —$S(O)(C_1$-$C_6alkyl)$, —$S(O)N(C_1$-$C_6alkyl)_2$, or —$N(C_1$-$C_6alkyl)S(O)(C_1$-$C_6alkyl)$; and n is an integer from 1 to 4.

In some embodiments, compounds of the disclosure have the Formula (I-a):

(I-a)

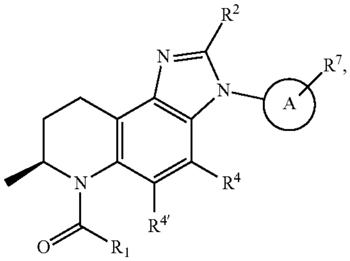

or a pharmaceutically acceptable salt thereof, wherein Ring A represents a —$C_3$-$C_8cycloalkyl$, —$C_4$-$C_8cycloalkenyl$, spirocycloalkyl, spiroheterocyclyl, heteroaryl, or aryl and wherein each of $R^1$, $R^2$, $R^4$, $R^{4'}$, and $R^7$ is as defined with respect to Formula (I) above and described in classes and subclasses herein, both singly and in combination.

In some embodiments, compounds of the disclosure have the Formula (I-b):

(I-b)

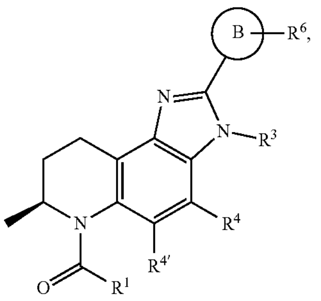

or a pharmaceutically acceptable salt thereof, wherein Ring B represents a —$C_3$-$C_8cycloalkyl$, —$C_4$-$C_8cycloalkenyl$, heterocyclyl, heteroaryl, or aryl and wherein each of $R^1$, $R^3$, $R^4$, $R^{4'}$, and $R^6$ is as defined with respect to Formula (I) above and described in classes and subclasses herein, both singly and in combination.

In some embodiments, compounds of the disclosure have the Formula (I-c):

(I-c)

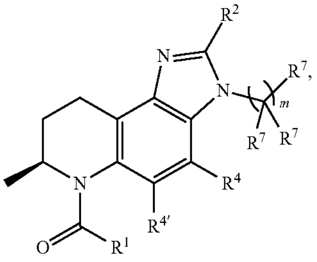

or a pharmaceutically acceptable salt thereof, wherein m is an integer from 1 to 4 and wherein each of $R^1$, $R^2$, $R^4$, $R^{4'}$, and $R^7$ is as defined with respect to Formula (I) above and described in classes and subclasses herein, both singly and in combination.

In some embodiments, compounds of the disclosure have the Formula (I-d):

(I-d)

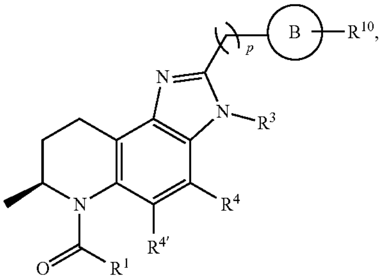

or a pharmaceutically acceptable salt thereof, wherein Ring B represents —$C_3$-$C_8cycloalkyl$, —$C_4$-$C_8cycloalkenyl$, heterocyclyl, aryl, spirocycloalkyl, spiroheterocyclyl, or heteroaryl, and wherein p is an integer from 1 to 2 and wherein each of $R^1$, $R^3$, $R^4$, $R^{4'}$, and $R^{10}$ is as defined with respect to Formula (I) above and described in classes and subclasses herein, both singly and in combination. In some embodiments, Ring B is —$C_3$-$C_8cycloalkyl$. In some embodiments, Ring B is —$C_4$-$C_8cycloalkenyl$. In some embodiments, Ring B is aryl. In some embodiments, Ring B is heterocyclyl. In some embodiments, Ring B is heteroaryl.

In some embodiments, compounds of the disclosure have the Formula (I-e):

(I-e)

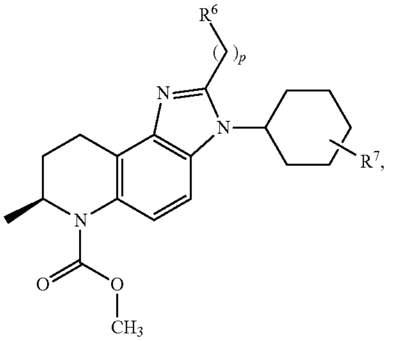

or a pharmaceutically acceptable salt thereof, wherein p is 1 or 2 and wherein each of $R^6$ and $R^7$ is as defined with respect to Formula (I) above and described in classes and subclasses herein, both singly and in combination.

In some embodiments (e.g., embodiments of Formula I-e), p is 1. In some embodiments (e.g., embodiments of Formula I-e), p is 2. In some embodiments (e.g., embodiments of Formula I-e), $R^7$ is —$S(O)_2NR^8R^9$, —$C(O)OR^8$, —$C(O)NR^8R^9$, or —$S(O)NR^8R^9$. In some embodiments (e.g., embodiments of Formula I-e), $R^7$ is —$S(O)_2NH_2$, —C(O)OH, —$C(O)NH_2$, or —$S(O)NH_2$. In some embodiments (e.g., embodiments of Formula I-e), $R^7$ is —C(O)OH. In some embodiments (e.g., embodiments of Formula I-e), $R^7$ is —$S(O)_2NH_2$. In some embodiments (e.g., embodiments of Formula I-e), $R^7$ is —$C(O)NH_2$. In some embodiments (e.g., embodiments of Formula I-e), $R^7$ is —S(O)$NH_2$. In some embodiments (e.g., embodiments of Formula I-e), $R^6$ is aryl or heteroaryl, wherein each aryl or heteroaryl is optionally substituted with one or more $R^{10}$.

In some embodiments, compounds of the disclosure have the Formula (I-f):

(I-f)

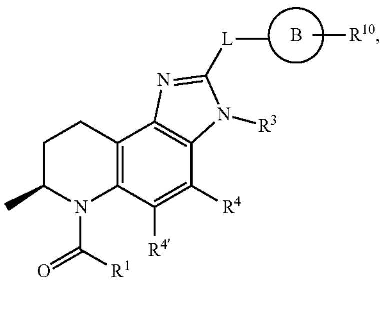

or pharmaceutically acceptable salt thereof, wherein Ring B is —$C_3$-$C_8$cycloalkyl, —$C_4$-$C_8$cycloalkenyl, heterocyclyl, aryl, spirocycloalkyl, spiroheterocyclyl, or heteroaryl; and L is a $C_1$-$C_6$ alkylene chain optionally substituted with one or more $R^6$ or L is a $C_1$-$C_6$ alkylene chain optionally substituted with one or more $R^6$, and wherein at least one methylene unit of L is replaced by —$NR^6$—, —O— or —S—; and wherein each of $R^1$, $R^3$, $R^4$, $R^{4'}$, $R^6$ and $R^{10}$ is as defined with respect to Formula (I) above and described in classes and subclasses herein, both singly and in combination. In some embodiments, Ring B is —$C_3$-$C_8$cycloalkyl. In some embodiments, Ring B is —$C_4$-$C_8$cycloalkenyl. In some embodiments, Ring B is aryl. In some embodiments, Ring B is heterocyclyl. In some embodiments Ring B is heteroaryl. In some embodiments, L is a $C_1$-$C_6$ alkylene chain optionally substituted with one or more $R^6$. In some embodiments, L is a $C_1$-$C_2$ alkylene chain optionally substituted with one or more $R^6$. In some embodiments, L is a $C_1$-$C_6$ alkylene chain optionally substituted with one or more $R^6$, and wherein at least one methylene unit is replaced by —$NR^6$—, —O— or —S—. In some embodiments, L is a $C_1$-$C_6$ alkylene chain optionally substituted with one or more $R^6$, and wherein at least one methylene unit of L is replaced by —$NR^6$. In some embodiments, L is a $C_1$-$C_6$ alkylene chain optionally substituted with one or more $R^6$, and wherein at least one methylene unit of L is replaced by —O—. In some embodiments, L is a $C_1$-$C_6$ alkylene chain optionally substituted with one or more $R^6$, and wherein at least one methylene unit of L is replaced by —S—. In some embodiments (e.g., embodiments of Formula I-f), L is a $C_1$-$C_2$ alkylene chain optionally substituted with $R^6$ wherein $R^6$ is —$CH_3$, —$S(O)_2NH_2$, —C(O)OH, —$C(O)NH_2$, or —$S(O)NH_2$. In some embodiments (e.g., embodiments of Formula I-f), L is a $C_1$-$C_2$ alkylene chain optionally substituted with $R^6$ wherein $R^6$ is —$CH_3$. In some embodiments (e.g., embodiments of Formula I-f), L is a $C_1$-$C_2$ alkylene chain optionally substituted with $R^6$ wherein $R^6$ is —$S(O)_2NH_2$. In some embodiments (e.g., embodiments of Formula I-f), L is a $C_1$-$C_2$ alkylene chain optionally substituted with $R^6$ wherein $R^6$ is —C(O)OH. In some embodiments (e.g., embodiments of Formula I-f), L is a $C_1$-$C_2$ alkylene chain optionally substituted with $R^6$ wherein $R^6$ is —$C(O)NH_2$. In some embodiments (e.g., embodiments of Formula I-f), L is a $C_1$-$C_2$ alkylene chain optionally substituted with $R^6$ wherein $R^6$ is —$S(O)NH_2$. In some embodiments (e.g., embodiments of Formula I-f), L is —$CH_2CH(C(O)OH)$—*, wherein "*" denotes the point of attachment to Ring B. In some embodiments, $R^1$ is —$C_1$-$C_6$alkyl, —$C_3$-$C_8$cycloalkyl, or —$OR^5$; L is —$C_1$-$C_6$alkyl, where L is optionally substituted with one or more $R^6$; Ring B is —$C_3$-$C_8$cycloalkyl, heterocyclyl, heteroaryl, or aryl; and $R^3$ is —H, —$C_1$-$C_6$alkyl, or —$C_3$-$C_8$cycloalkyl, wherein each alkyl or cycloalkyl, is optionally substituted with one or more $R^7$; $R^5$ is methyl; $R^7$ is —$C_1$-$C_6$alkyl, —$C_3$-$C_8$cycloalkyl, heterocyclyl, heteroaryl, aryl, —OH, halogen, —CN, —$OR^8$, —$NHR^8$, —$NR^8R^9$, —C(O)OH, —$C(O)NR^8R^9$, —$S(O)CH_3$, or —$S(O)NR^8R^9$; and $R^8$ or $R^9$ is —H or —$C_1$-$C_6$alkyl. In some embodiments $R^6$ is —C(O)OH. In some embodiments, $R^3$ is —$C_3$-$C_8$cycloalkyl, —$C_4$-$C_8$cycloalkenyl, heterocyclyl, aryl, or heteroaryl. In some embodiments, $R^3$ is cyclopentyl, cyclohexyl, 3-pyranyl, or 4-pyranyl. In some embodiments, $R^3$ is cyclopentyl, cyclohexyl or 3-pyranyl. In some embodiments, L is an $C_1$-$C_6$ alkylene chain optionally substituted with one or more $R^6$, and wherein at least one methylene unit is replaced by —$NR^6$—, —O— or —S—; and $R^3$ is —$C_3$-$C_8$cycloalkyl, —$C_4$-$C_8$cycloalkenyl, heterocyclyl, aryl, or heteroaryl, wherein each —$C_3$-$C_8$cycloalkyl, —$C_4$-$C_8$cycloalkenyl, heterocyclyl, aryl, or heteroaryl is optionally substituted with one or more $R^7$; and $R^6$ is independently, at each occurrence, —H, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —$C(O)R^{8'}$, —C(O)$NR^8R^9$, —$NR^8C(O)R^{9'}$, —$NR^8S(O)_2R^{9'}$, —$S(O)R^{8'}$, —$S(O)NR^8R^9$, or —$NR^8S(O)R^{9'}$, wherein each alkyl, cycloalkyl, heterocyclyl, spirocycloalkyl, spiroheterocyclyl, heteroaryl, or aryl is optionally substituted with one or more $R^{10}$, wherein $R^{10}$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, halogen, —$NO_2$, —CN, —$NH_2$, —$OC_1$-$C_6$alkyl, —$NHC_1$-$C_6$alkyl, —N($C_1$-

$C_6$alkyl)$_2$, —$S(O)_2NH(C_1$-$C_6$alkyl), —$S(O)_2N(C_1$-$C_6$alkyl)$_2$, —$S(O)_2C_1$-$C_6$alkyl, —$C(O)C_1$-$C_6$alkyl, —C(O)$NH_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$. In some embodiments, L is a $C_1$-$C_6$ alkylene chain, —$OCH_2$—, —$CH_2O$—, —$NR^6CH_2$—, or —$CH_2NR^6$—; and $R^6$ is H, —$C_1$-$C_6$alkyl, —$C_3$-$C_6$cycloalkyl or —C(O)$NR^8R^9$. In some embodiments, $R^3$ is cyclopentyl or cyclohexyl, wherein each cyclopentyl or cyclohexyl is optionally substituted with $R^7$. In some embodiments, $R^3$ is cyclopentyl or cyclohexyl, wherein each cyclopentyl or cyclohexyl is optionally substituted with $R^7$, wherein $R^7$ is —OH, halogen, oxo, —CN, —SH, —OH, —$NH_2$, —$S(O)_2NH_2$, —C(O)OH, or —C(O)$NH_2$.

In some embodiments, compounds of the disclosure have the Formula (I-g)

(I-g)

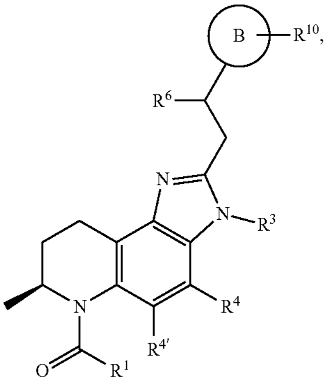

or a pharmaceutically acceptable salt thereof, wherein each of $R^1$, $R^3$, $R^4$, $R^{4'}$, $R^6$, Ring B and $R^{10}$ is as defined with respect to Formula (I) above and described in classes and subclasses herein, both singly and in combination.

In some embodiments, compounds of the disclosure have the Formula (I-h)

(I-h)

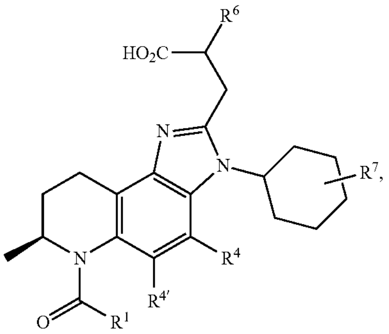

or a pharmaceutically acceptable salt thereof, wherein each of $R^1$, $R^4$, $R^{4'}$, $R^6$, and $R^7$ is as defined with respect to Formula (I) above and described in classes and subclasses herein, both singly and in combination.

In some embodiments, compounds of the disclosure have the Formula (I-h')

(I-h')

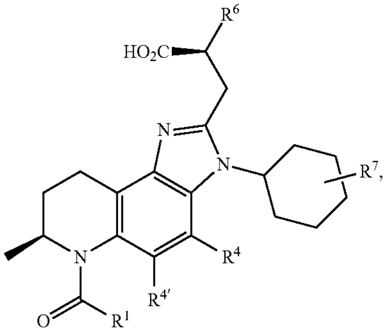

or a pharmaceutically acceptable salt thereof, wherein each of $R^1$, $R^4$, $R^{4'}$, $R^6$, and $R^7$ is as defined with respect to Formula (I) above and described in classes and subclasses herein, both singly and in combination.

In some embodiments, compounds of the disclosure have the Formula (I-h")

(I-h")

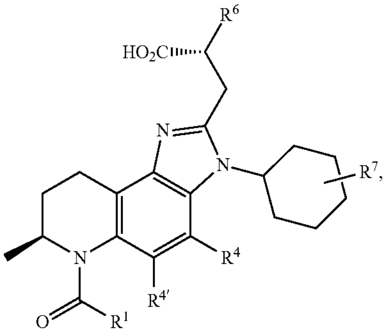

or a pharmaceutically acceptable salt thereof, wherein each of $R^1$, $R^4$, $R^{4'}$, $R^6$, and $R^7$ is as defined with respect to Formula (I) above and described in classes and subclasses herein, both singly and in combination.

In some embodiments, compounds of the disclosure have the Formula (I-i):

(I-i)

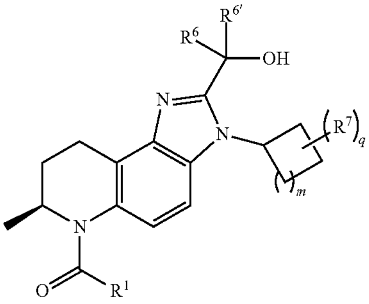

or a pharmaceutically acceptable salt thereof, wherein, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —$OR^5$, —$N(R^5)_2$, or —$NHR^5$;

$R^5$ is —$C_1$-$C_6$alkyl, —$C_3$-$C_8$cycloalkyl, heterocyclyl, aryl, or heteroaryl;

each $R^6$ is —OH, halogen, oxo, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —$NO_2$, —CN, —$NH_2$, —$(CH_2)_n$—$OR^8$, —C(O)$R^{8'}$, —C(O)$OR^8$, or —C(O)$NR^8R^9$, —NHC$_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —N($C_1$-$C_6$alkyl)$SO_2$$C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, cycloalkyl, heterocyclyl, spirocycloalkyl, spiroheterocyclyl, heteroaryl, or aryl is optionally substituted with one or more $R^{10}$;

$R^{6'}$ is H or —$C_1$-$C_6$alkyl;

$R^7$ is independently, at each occurrence, —H, halogen, —OH, —CN, —OC$_1$-$C_6$alkyl, —$NH_2$, —NHC$_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —S(O)$_2$OH, —C(O)$C_1$-$C_6$alkyl, —C(O)$NH_2$, —C(O)NH($C_1$-$C_6$alkyl), —C(O)N($C_1$-$C_6$alkyl)$_2$, —C(O)OH, —C(O)OC$_1$-$C_6$alkyl, —N($C_1$-$C_6$alkyl)$SO_2$$C_1$-$C_6$alkyl, —S(O)($C_1$-$C_6$alkyl), —S(O)N($C_1$-$C_6$alkyl)$_2$, —S(O)$_2$$NH_2$, —N($C_1$-$C_6$alkyl)S(O)($C_1$-$C_6$alkyl) or tetrazole;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$; or $R^8$ and $R^9$ may combine with the atom to which they are both attached to form a spiroheterocyclyl, heterocyclyl, or heteroaryl, wherein the formed spiroheterocyclyl, heterocyclyl, or heteroaryl is optionally substituted with one or more $R^{10}$;

$R^{8'}$ is each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$; or $R^{10}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —OC$_1$-$C_6$alkyl, —OC$_3$-$C_6$cycloalkyl, —Oaryl, —Oheteroaryl, —NHC$_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —C(O)$C_1$-$C_6$alkyl, —C(O)$NH_2$, —C(O)NH($C_1$-$C_6$alkyl), —NHC(O)$C_1$-$C_6$alkyl, —C(O)N($C_1$-$C_6$alkyl)$_2$, —C(O)OC$_1$-$C_6$alkyl, —N($C_1$-$C_6$alkyl)$SO_2$$C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$;

wherein any two $R^{10}$ when on non-adjacent atoms, can combine to form a bridging cycloalkyl or heterocyclyl;

wherein any two $R^{10}$ when on adjacent atoms, can combine to form a cycloalkyl, heterocyclyl, aryl or heteroaryl;

$R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —OC$_1$-$C_6$alkyl, —NHC$_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2$$C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)OC$_1$-$C_6$alkyl, —N($C_1$-$C_6$alkyl)$SO_2$$C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl); and m is an integer from 0 to 5;

n is an integer from 1 to 4; and q is an integer from 0 to 4.

In some embodiments, compounds of the disclosure have the Formula (I-j):

(I-j)

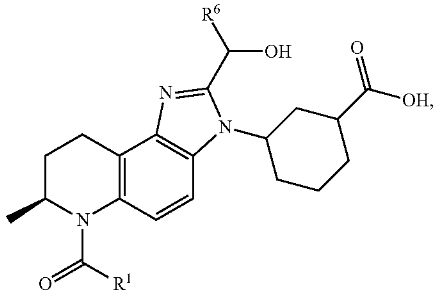

or a pharmaceutically acceptable salt thereof, wherein:

$R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —$OR^5$, —N($R^5$)$_2$, or —$NHR^5$;

$R^5$ is independently, at each occurrence, —$C_1$-$C_6$alkyl, —$C_3$-$C_8$cycloalkyl, heterocyclyl, aryl, or heteroaryl;

$R^6$ is —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, halogen, oxo, —$(CH_2)_n$—OR, —C(O)$R^{8'}$, —C(O)$OR^8$, or —C(O)$NR^8R^9$, wherein each alkyl, cycloalkyl, heterocyclyl, spirocycloalkyl, spiroheterocyclyl, heteroaryl, or aryl is optionally substituted with one or more $R^{10}$;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a spiroheterocyclyl, heterocyclyl, or heteroaryl, wherein the formed spiroheterocyclyl, heterocyclyl, or heteroaryl is optionally substituted with one or more $R^{10}$ or $R^{11}$;

$R^{8'}$ is each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$;

$R^{10}$ is each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —OC$_1$-$C_6$alkyl, —OC$_3$-$C_6$cycloalkyl, —Oaryl, —Oheteroaryl, —NHC$_1$-$C_6$alkyl, —N($C_1$-

$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)NH$_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)SO$_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$;

wherein any two $R^{10}$ when on non-adjacent atoms, can combine to form a bridging cycloalkyl or heterocyclyl;

wherein any two $R^{10}$ when on adjacent atoms, can combine to form a cycloalkyl, heterocyclyl, aryl or heteroaryl;

$R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —NO$_2$, —CN, —NH$_2$, —O$C_1$-$C_6$alkyl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)NH$_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)SO$_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl); and n is an integer from 1 to 4.

In some embodiments, for compounds of Formula (I-j) or a pharmaceutically acceptable salt thereof:

$R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —O$R^5$, —N($R^5$)$_2$, or —NH$R^5$;

$R^5$ is —$C_1$-$C_6$alkyl, —$C_3$-$C_8$cycloalkyl, heterocyclyl, aryl, or heteroaryl;

$R^6$ is —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, halogen, oxo, —(CH$_2$)$_n$—OR, —C(O)$R^{8'}$, —C(O)O$R^8$, or —C(O)N$R^8R^9$, wherein each alkyl, cycloalkyl, heterocyclyl, spirocycloalkyl, spiroheterocyclyl, heteroaryl, or aryl is optionally substituted with one or more $R^{10}$;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a spiroheterocyclyl, heterocyclyl, or heteroaryl, wherein the formed spiroheterocyclyl, heterocyclyl, or heteroaryl is optionally substituted with one or more $R^{10}$ or $R^{11}$;

$R^{8'}$ is each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^{10}$ is each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —NO$_2$, —CN, —NH$_2$, —O$C_1$-$C_6$alkyl, —O$C_3$-$C_6$cycloalkyl, —Oaryl, —Oheteroaryl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)NH$_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)SO$_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$.

wherein any two $R^{10}$ when on non-adjacent atoms, can combine to form a bridging cycloalkyl or heterocyclyl;

wherein any two $R^{10}$ when on adjacent atoms, can combine to form a cycloalkyl, heterocyclyl, aryl or heteroaryl;

$R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —NO$_2$, —CN, —NH$_2$, —O$C_1$-$C_6$alkyl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)NH$_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)SO$_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl); and n is an integer from 1 to 4.

In some embodiments, compounds of the disclosure have the Formula (I-k):

(I-k)

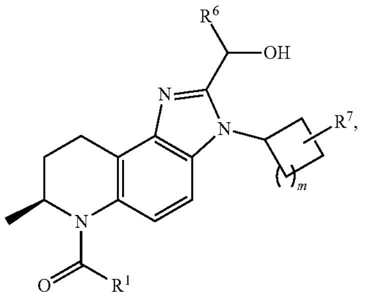

or a pharmaceutically acceptable salt thereof, wherein, $R^1$ is —O$R^5$;

$R^5$ is —$C_1$-$C_6$alkyl;

$R^6$ is —$C_3$-$C_8$cycloalkyl, —$C_4$-$C_8$cycloalkenyl, heterocyclyl, heteroaryl, aryl, wherein each cycloalkyl, cycloalkenyl, heterocyclyl, heteroaryl, or aryl is optionally substituted with one or more —$R^{10}$;

$R^7$ is —H, halogen, —OH, —CN, —O$C_1$-$C_6$alkyl, —NH$_2$, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —S(O)$_2$OH, —C(O)$C_1$-$C_6$alkyl, —C(O)NH$_2$, —C(O)NH($C_1$-$C_6$alkyl), —C(O)N($C_1$-$C_6$alkyl)$_2$, —C(O)OH, —C(O)O$C_1$-$C_6$alkyl, —N($C_1$-$C_6$alkyl)SO$_2C_1$-$C_6$alkyl, —S(O)($C_1$-$C_6$alkyl), —S(O)N($C_1$-$C_6$alkyl)$_2$, —S(O)$_2$NH$_2$, —N($C_1$-$C_6$alkyl)S(O)($C_1$-$C_6$alkyl) or tetrazole;

$R^{10}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —NO$_2$, —CN, —NH$_2$, —O$C_1$-$C_6$alkyl, —O$C_3$-$C_6$cycloalkyl, —Oaryl, —Oheteroaryl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)NH$_2$, —C(O)NH($C_1$-$C_6$alkyl), —NHC(O)$C_1$-$C_6$alkyl, —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$;

each $R^{12}$ is independently halogen;

m is an integer from 0 to 5.

In some embodiments, compounds of the disclosure have the Formula (I-l):

(I-l)

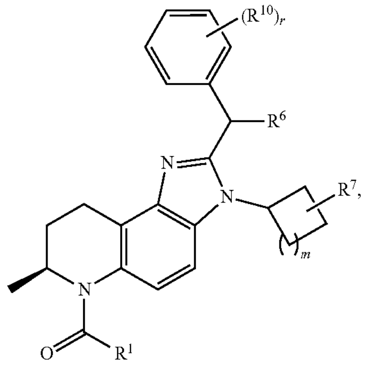

or a pharmaceutically acceptable salt thereof, wherein, $R^1$ is —O$R^5$;

$R^5$ is —$C_1$-$C_6$alkyl;

$R^6$ is —OH, halogen, oxo, —$NO_2$, —CN, —$NH_2$, —O$C_1$-$C_6$alkyl, —O$C_3$-$C_6$cycloalkyl, —Oaryl, —Oheteroaryl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{10}$;

$R^7$ is independently, at each occurrence, —H, halogen, —OH, —CN, —O$C_1$-$C_6$alkyl, —$NH_2$, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —S(O)$_2$OH, —C(O)$C_1$-$C_6$alkyl, —C(O)$NH_2$, —C(O)NH($C_1$-$C_6$alkyl), —C(O)N($C_1$-$C_6$alkyl)$_2$, —C(O)OH, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, —S(O)$_2NH_2$, —N($C_1$-$C_6$alkyl)S(O)($C_1$-$C_6$alkyl) or tetrazole;

$R^{10}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —O$C_1$-$C_6$alkyl, —O$C_3$-$C_6$cycloalkyl, —Oaryl, —Oheteroaryl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)$NH_2$, —C(O)NH($C_1$-$C_6$alkyl), —NHC(O)$C_1$-$C_6$alkyl, —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$;

each $R^{12}$ is independently halogen;

m is an integer from 0 to 5; and r is an integer from 0 to 5.

In some embodiments, compounds of the disclosure have the Formula (I-m)

(I-m)

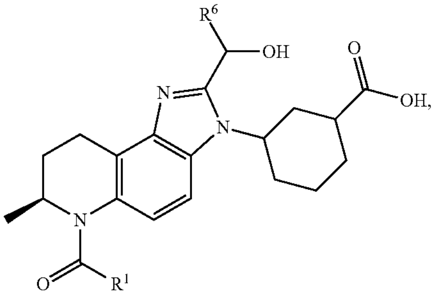

or a pharmaceutically acceptable salt, thereof, wherein:

$R^1$ is —O$R^5$;

$R^5$ is —$C_1$-$C_6$alkyl;

$R^6$ is phenyl optionally substituted with one or more $R^{10}$;

$R^{10}$ is each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —O$C_1$-$C_6$alkyl, —O$C_3$-$C_6$cycloalkyl, —Oaryl, —Oheteroaryl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$;

wherein any two $R^{10}$ when on non-adjacent atoms, can combine to form a bridging cycloalkyl or heterocyclyl;

wherein any two $R^{10}$ when on adjacent atoms, can combine to form a cycloalkyl, heterocyclyl, aryl or heteroaryl;

$R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —O$C_1$-$C_6$alkyl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl); and n is an integer from 1 to 4.

In some embodiments, compounds of the disclosure have the Formula (I-n)

(I-n)

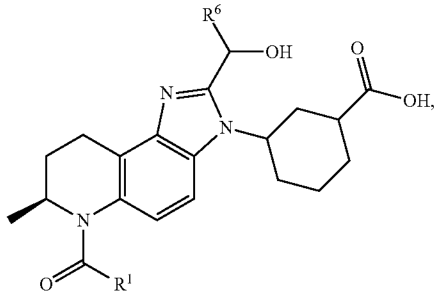

or a pharmaceutically acceptable salt thereof, wherein:

$R^1$ is —$OR^5$;

$R^5$ is —$C_1$-$C_3$alkyl;

$R^6$ is phenyl optionally substituted with one or more $R^{10}$;

$R^{10}$ is independently, at each occurrence halogen, —$OC_1$-$C_6$alkyl, —$OC_3$-$C_6$cycloalkyl, —Oaryl, or —Oheteroaryl, wherein each alkyl, cycloalkyl, aryl or heteroaryl is optionally substituted with one or more —$R^{12}$;

$R^{12}$ is independently halogen.

In some embodiments, for compounds of Formula (I-n), or a pharmaceutically acceptable salt thereof:

$R^1$ is —$OR^5$;

$R^5$ is —$C_1$-$C_3$alkyl;

$R^6$ is phenyl optionally substituted with one or more $R^{10}$;

$R^{10}$ is independently, at each occurrence halogen, —$OC_1$-$C_6$alkyl, —$OC_3$-$C_6$cycloalkyl, —Oaryl, or —Oheteroaryl, wherein each alkyl, cycloalkyl, aryl or heteroaryl is optionally substituted with one or more —$R^{12}$;

$R^{12}$ is halogen.

It will be appreciated that throughout the present disclosure, unless otherwise indicated, reference to a compound of Formula (I) is intended to also include formulae (I-a), (I-b), (I-c), (I-d), (I-e), (I-f), (I-g), (I-h), (I-h'), (I-h"), (I-i), (I-j), (I-k), (I-l), (I-m), and (I-n) and compound species of such formulae disclosed herein.

In some embodiments, $R^1$ is —$OCR^5$.

Compounds of the present disclosure can be compounds wherein $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —$OR^5$, —$N(R^5)_2$, or —$NHR^5$. Compounds of the present disclosure can be compounds wherein $R^1$ is —$OR^5$. Compounds of the present disclosure can be compounds wherein $R^1$ is —$OR^5$ and $R^5$ is methyl.

Compounds of the present disclosure can be compounds wherein $R^5$ is —$C_1$-$C_6$alkyl, —$C_3$-$C_8$cycloalkyl, heterocyclyl, aryl, or heteroaryl. Compounds of the present disclosure can be compounds wherein $R^5$ is —$C_1$-$C_6$alkyl. Compounds of the present disclosure can be compounds wherein $R^5$ is —$C_1$-$C_3$alkyl. Compounds of the present disclosure can be compounds wherein $R^5$ is methyl.

Compounds of the present disclosure can be compounds wherein $R^6$ is —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, halogen, oxo, —$(CH_2)_n$—$OR^8$, —$C(O)R^{8'}$, —$C(O)OR^8$, or —$C(O)NR^8R^9$, wherein each alkyl, cycloalkyl, heterocyclyl, spirocycloalkyl, spiroheterocyclyl, heteroaryl, or aryl is optionally substituted with one or more $R^{10}$. Compounds of the present disclosure can be compounds wherein $R^6$ is —$C_3$-$C_8$cycloalkyl, heterocyclyl, aryl, spirocycloalkyl, spiroheterocyclyl, or heteroaryl, wherein each cycloalkyl, heterocyclyl, spirocycloalkyl, spiroheterocyclyl, heteroaryl, or aryl is optionally substituted with one or more $R^{10}$. Compounds of the present disclosure can be compounds wherein $R^6$ is aryl optionally substituted with one or more $R^{10}$. Compounds of the present disclosure can be compounds wherein $R^6$ is phenyl optionally substituted with one or more $R^{10}$. Compounds of the present disclosure can be compounds wherein $R^6$ is phenyl substituted with one $R^{10}$. Compounds of the present disclosure can be compounds wherein $R^6$ is phenyl substituted with two $R^{10}$.

Compounds of the present disclosure can be compounds wherein $R^{10}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$OC_3$-$C_6$cycloalkyl, —Oaryl, —Oheteroaryl, —$NHC_1$-$C_6$alkyl, —$N(C_1$-$C_6alkyl)_2$, —$S(O)_2NH(C_1$-$C_6alkyl)$, —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6alkyl)$, —$C(O)N(C_1$-$C_6alkyl)_2$, —$C(O)OC_1$-$C_6$alkyl, —$N(C_1$-$C_6alkyl)SO_2C_1$-$C_6$alkyl, —$S(O)(C_1$-$C_6alkyl)$, —$S(O)N(C_1$-$C_6alkyl)_2$, or —$N(C_1$-$C_6alkyl)S(O)(C_1$-$C_6alkyl)$, wherein each alkyl, alkenyl, alkynyl, cycloalkyl, cycloalkenyl, heterocyclyl, heteroaryl, or aryl is optionally substituted with one or more —$R^{12}$. Compounds of the present disclosure can be compounds wherein $R^{10}$ is independently, at each occurrence, —$C_1$-$C_6$alkyl, —$C_3$-$C_8$cycloalkyl, heterocyclyl, heteroaryl, aryl, —OH, halogen, oxo, CN, —$OC_1$-$C_6$alkyl, —$OC_3$-$C_6$cycloalkyl, or —$NHC_1$-$C_6$alkyl, —$N(C_1$-$C_6alkyl)_2$ wherein each alkyl, cycloalkyl, heterocyclyl, heteroaryl, or aryl is optionally substituted with one or more —$R^{12}$. Compounds of the present disclosure can be compounds wherein $R^{10}$ is independently, at each occurrence, —$C_1$-$C_6$alkyl, —$OC_1$-$C_6$alkyl, —$OC_3$-$C_6$cycloalkyl, or halogen wherein each alkyl, or cycloalkyl, is optionally substituted with one or more —$R^{12}$ Compounds of the present disclosure can be compounds wherein $R^{10}$ is independently, at each occurrence, —$OC_1$-$C_6$alkyl, or halogen wherein each alkyl is optionally substituted with one or more —$R^{12}$.

Compounds of the present disclosure can be compounds wherein $R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6alkyl)$, —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6alkyl)$, —$C(O)N(C_1$-$C_6alkyl)_2$, —$C(O)OC_1$-$C_6$alkyl, —$N(C_1$-$C_6alkyl)SO_2C_1$-$C_6$alkyl, —$S(O)(C_1$-$C_6alkyl)$, —$S(O)N(C_1$-$C_6alkyl)_2$, or —$N(C_1$-$C_6alkyl)S(O)(C_1$-$C_6alkyl)$. Compounds of the present disclosure can be compounds wherein $R^{12}$ is independently, at each occurrence, halogen. Compounds of the present disclosure can be compounds wherein $R^{12}$ is fluoro. Compounds of the present disclosure can be compounds wherein $R^{12}$ is chloro.

Compounds of the present disclosure can be compounds wherein $R^1$ is —$OR^5$; $R^5$ is —$C_1$-$C_6$alkyl; $R^6$ is —$C_3$-$C_8$cycloalkyl, heterocyclyl, aryl, spirocycloalkyl, spiroheterocyclyl, or heteroaryl, wherein each cycloalkyl, heterocyclyl, spirocycloalkyl, spiroheterocyclyl, heteroaryl, or aryl is optionally substituted with one or more $R^{10}$; $R^{10}$ is independently, at each occurrence, —$C_1$-$C_6$alkyl, —$OC_1$-$C_6$alkyl, —$OC_3$-$C_6$cycloalkyl, or halogen wherein each alkyl, or cycloalkyl, is optionally substituted with one or more —$R^{12}$ and —$R^{12}$ is halogen.

Compounds of the present disclosure can be compounds wherein $R^1$ is —$OR^5$; $R^5$ is —$C_1$-$C_3$alkyl; $R^6$ is aryl optionally substituted with one or more $R^{10}$; $R^{10}$ is independently, at each occurrence, —$C_1$-$C_6$alkyl, —$OC_1$-$C_6$alkyl, —$OC_3$-$C_6$cycloalkyl, or halogen wherein each alkyl, or cycloalkyl, is optionally substituted with one or more —$R^{12}$ and —$R^{12}$ is halogen.

Compounds of the present disclosure can be compounds wherein $R^1$ is —$OR^5$; $R^5$ is —$C_1$-$C_3$alkyl; $R^6$ is aryl substituted with one $R^{10}$; $R^{10}$ is —$C_1$-$C_6$alkyl, —$OC_1$-$C_6$alkyl, —$OC_3$-$C_6$cycloalkyl, or halogen wherein each alkyl, or cycloalkyl, is optionally substituted with one or more —$R^{12}$ and —$R^{12}$ is halogen.

Compounds of the present disclosure can be compounds wherein $R^1$ is —$OR^5$; $R^5$ is —$C_1$-$C_3$alkyl; $R^6$ is aryl substituted with two $R^{10}$; $R^{10}$ is independently, at each occurrence, —$OC_1$-$C_6$alkyl or halogen wherein each alkyl is optionally substituted with one or more —$R^{12}$ and —$R^{12}$ is halogen.

Compounds of the present disclosure can be compounds wherein $R^1$ is —$OR^5$; $R^5$ is methyl; $R^6$ is phenyl substituted with two $R^{10}$; $R^{10}$ is independently, at each occurrence, —$OC_1$-$C_6$alkyl or halogen wherein each alkyl is optionally substituted with one or more —$R^{12}$ and —$R^{12}$ is halogen.

Compounds of the present disclosure can be compounds wherein $R^1$ is —$OR^5$; $R^5$ is methyl; and $R^6$ is phenyl.

Compounds of the present disclosure can be compounds wherein $R^6$ is aryl, optionally substituted with one or two $R^{10}$, wherein $R^{10}$ is independently, at each occurrence, halogen or —$OC_1$-$C_6$alkyl, wherein —$OC_1$-$C_6$alkyl is optionally substituted with halogen.

Compounds of the present disclosure can comprise aryl, wherein aryl can be ring systems having a total of five to fourteen ring members, wherein at least one ring in the system is aromatic and wherein each ring in the system contains 3 to 7 ring members. For example, aryl can include, but is not limited to, phenyl.

Compounds of the present disclosure can comprise heteroaryl, wherein heteroaryl is a group having 5 to 10 ring atoms, preferably 5, 6, or 9 ring atoms; having 6, 10, or 14π electrons shared in a cyclic array; and/or having, in addition to carbon atoms, from one to five heteroatoms wherein the term "heteroatom" refers to nitrogen, oxygen, or sulfur, and includes any oxidized form of nitrogen or sulfur, and any quaternized form of a basic nitrogen. For example, heteroaryl can include, but are is not limited to, pyridine, indole, benzapyrazole, benzoxale, furopyridine, or isoquinoline.

Compounds of the present disclosure can comprise heterocyclyl, wherein heterocyclyl is a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. For example, heterocyclyl can include, but are is not limited to, dihydrofuran, dihydrofuropyrine or dihydroisofuran.

In some embodiments, $R^1$ is —$OR^5$, —$N(R^5)_2$, —$NHR^5$, or —$C_1$-$C_6$alkyl. In some embodiments, $R^1$ is —$OR^5$ or —$C_1$-$C_6$alkyl. In some embodiments, $R^5$ of $R^1$ is —$C_1$-$C_6$alkyl. In some embodiments, $R^1$ is —$OCH_3$. In some embodiments, $R^1$ is —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl. In some embodiments, $R^1$ is —$C_1$-$C_6$alkyl. In some embodiments, $R^1$ is methyl, ethyl or propyl. In some embodiments, $R^1$ is methyl. In some embodiments, $R^1$ is —$C_2$-$C_6$alkenyl. In some embodiments, $R^1$ is aryl.

In some embodiments, $R^2$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl, wherein each alkyl, alkenyl, alkynyl, cycloalkyl, cycloalkenyl, heterocyclyl, heteroaryl, or aryl is optionally substituted with one or more $R^6$. In some embodiments, $R^2$ is —H. In some embodiments, $R^2$ is $C_1$-$C_6$alkyl optionally substituted with one or more $R^6$. In some embodiments, $R^2$ is aryl optionally substituted with one or more $R^6$. In some embodiments, $R^2$ is $C_3$-$C_8$cycloalkyl optionally substituted with one or more $R^6$. In some embodiments, $R^2$ is $C_1$-$C_2$alkyl substituted with aryl or heteroaryl, wherein each aryl or heteroaryl is optionally substituted with one or more $R^{10}$. In some embodiments $R^2$ is methyl optionally substituted with one or more $R^6$. In some embodiments $R^2$ is ethyl optionally substituted with one or more $R^6$. In some embodiments, $R^2$ is $C_1$-$C_2$alkyl substituted with aryl or heteroaryl, wherein each aryl or heteroaryl is optionally substituted with one or more $R^{10}$, and wherein $R^3$ is cyclohexyl optionally substituted with one or more —C(O)OH.

In some embodiments, $R^3$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, spirocycloalkyl, spiroheterocyclyl, heterocyclyl, heteroaryl, or aryl, wherein each alkyl, alkenyl, alkynyl, cycloalkyl, cycloalkenyl, spirocycloalkyl, spiroheterocyclyl, heterocyclyl, heteroaryl, or aryl is optionally substituted with one or more $R^7$. In some embodiments, $R^3$ or $R^{3'}$ is —H. In some embodiments, $R^3$ is —$C_1$-$C_6$alkyl. In some embodiments, $R^3$ is heterocyclyl optionally substituted with one or more $R^7$. In some embodiments, $R^3$ is heteroaryl optionally substituted with one or more $R^7$. In some embodiments, $R^3$ is spirocycloalkyl optionally substituted with one or more $R^7$. In some embodiments, $R^3$ is spiroheterocyclyl optionally substituted with one or more $R^7$. In some embodiments, $R^3$ is $C_3$-$C_8$cycloalkyl optionally substituted with one or more $R^7$. In some embodiments, $R^3$ is aryl optionally substituted with one or more $R^7$. In some embodiments, $R^3$ is cyclohexyl optionally substituted with one or more —$R^7$. In some embodiments, $R^3$ is cyclohexyl optionally substituted with one or more —C(O)OH.

In some embodiments, $R^3$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, spirocycloalkyl, spiroheterocyclyl, heterocyclyl, heteroaryl, or aryl, wherein each alkyl, alkenyl, alkynyl, cycloalkyl, cycloalkenyl, spirocycloalkyl, spiroheterocyclyl, heterocyclyl, heteroaryl, or aryl is optionally substituted with one or more $R^7$. In some embodiments, $R^3$ is —H. In some embodiments, $R^3$ is —$C_1$-$C_6$alkyl. In some embodiments, $R^3$ is heterocyclyl optionally substituted with one or more $R^7$. In some embodiments, $R^3$ is cyclopropyl, cyclobutyl, cyclopentyl or cyclohexyl optionally substituted with one or more $R^7$. In some embodiments, $R^3$ is cyclopropyl optionally substituted with one or more $R^7$. In some embodiments, $R^3$ is cyclobutyl optionally substituted with one or more $R^7$. In some embodiments, $R^3$ is cyclopentyl optionally substituted with one or more $R^7$. In some embodiments, $R^3$ is cyclohexyl optionally substituted with one or more $R^7$. In some embodiments, $R^3$ is heteroaryl optionally substituted with one or more $R^7$. In some embodiments, $R^3$ is spirocycloalkyl optionally substituted with one or more $R^7$. In some embodiments, $R^3$ is spiroheterocyclyl optionally substituted with one or more $R^7$. In some embodiments, $R^3$ is $C_3$-$C_8$cycloalkyl optionally substituted with one or more $R^7$. In some embodiments, $R^3$ is aryl optionally substituted with one or more $R^7$. In some embodiments, $R^3$ is cyclohexyl optionally substituted with one or more —$R^7$. In some embodiments, $R^3$ is cyclohexyl optionally substituted with one or more —C(O)OH.

In some embodiments, $R^4$ and $R^{4'}$ are independently hydrogen, halogen, —OH, —CN, or —$NH_2$. In some embodiments, $R^4$ and $R^{4'}$ are —H. In some embodiments, $R^4$ and $R^{4'}$ are halogen.

In some embodiments, $R^5$ is —$C_1$-$C_6$alkyl, —$C_3$-$C_8$cycloalkyl, heterocyclyl, aryl, or heteroaryl. In some embodiments, $R^5$ is —$C_1$-$C_6$alkyl. In some embodiments, $R^5$ is —$C_1$-$C_3$alkyl. In some embodiments, $R^5$ is methyl. In some embodiments, $R^5$ is ethyl.

In some embodiments, $R^6$ is —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —$C(O)R^{8'}$, —C(O)$OR^8$, —$C(O)NR^8R^9$, —$NR^8C(O)R^{9'}$, —$NR^8S(O)_2R^{9'}$, —$S(O)R^{8'}$, —$S(O)NR^8R^9$, or —$NR^8S(O)R^9$, wherein each alkyl, cycloalkyl, heterocyclyl, spirocycloalkyl, spiroheterocyclyl, heteroaryl, or aryl is optionally substituted with one or more $R^{10}$. In some embodiments, $R^6$ is —$C_1$-$C_6$alkyl, —$C_3$-$C_8$cycloalkyl, —$C_4$-$C_8$cycloalkenyl, heterocyclyl, or aryl. In some embodiments, $R^6$ is —$C_1$-$C_6$alkyl optionally substituted with one or more $R^{10}$. In some embodiments, $R^6$ is aryl optionally substituted with one or more $R^{10}$. In some embodiments, $R^6$ is heteroaryl optionally substituted with one or more $R^{10}$. In some embodiments, $R^6$ is —C(O)OH. In some embodiments, $R^6$ is halogen. In some embodiments, $R^6$ is —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, halogen, oxo, —$(CH_2)_n$—$OR^8$, —$C(O)R^{8'}$, —$C(O)OR^8$, or —$C(O)NR^8R^9$, wherein each alkyl, cycloalkyl, heterocyclyl, spirocycloalkyl, spiroheterocyclyl, heteroaryl, or aryl is optionally substituted with one or more $R^{10}$.

In some embodiments, $R^7$ is —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —$C(O)R^{8'}$, —C(O)$OR^8$, —$C(O)NR^8R^9$, —$NR^8C(O)R^{9'}$, —$NR^8S(O)_2R^{9'}$, —$S(O)R^{8'}$, —$S(O)NR^8R^9$, or —$NR^8S(O)R^{9'}$, wherein each alkyl, cycloalkyl, heterocyclyl, spirocycloalkyl, spiroheterocyclyl, heteroaryl, or aryl is optionally substituted with one or more $R^{10}$. In some embodiments, $R^7$ is —$C_1$-$C_6$alkyl, —$C_3$-$C_8$cycloalkyl, —$C_4$-$C_8$cycloalkenyl, heterocyclyl, or aryl. In some embodiments $R^7$ is —$C_1$-$C_6$alkyl optionally substituted with one or more $R^{10}$. In some embodiments, $R^7$ is aryl optionally substituted with one or more $R^{10}$. In some embodiments, $R^7$ is heteroaryl optionally substituted with one or more $R^{10}$. In some embodiments, $R^7$ is —C(O)OH. In some embodiments, $R^7$ is halogen.

In some embodiments, $R^8$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$. In some embodiments, $R^8$ is —H. In some embodiments, $R^8$ is —$C_1$-$C_6$alkyl, —$C_3$-$C_8$cycloalkyl, —$C_4$-$C_8$cycloalkenyl, heterocyclyl, or aryl, wherein $R^8$ is optionally substituted with $R^{10}$ or $R^{11}$. In some embodiments, $R^8$ is —$C_1$-$C_6$alkyl optionally substituted with one or more $R^{10}$ or $R^{11}$. In some embodiments, $R^8$ is aryl optionally substituted with one or more $R^{10}$ or $R^{11}$. In some embodiments, $R^8$ is heteroaryl optionally substituted with one or more $R^{10}$ or $R^{11}$.

In some embodiments, $R^{8'}$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$. In some embodiments, $R^{8'}$ is —$C_1$-$C_6$alkyl, —$C_3$-$C_8$cycloalkyl, —$C_4$-$C_8$cycloalkenyl, heterocyclyl, or aryl, wherein $R^{8'}$ is optionally substituted with $R^{10}$ or $R^{11}$. In some embodiments, $R^{8'}$ is —$C_1$-$C_6$alkyl optionally substituted with one or more $R^{10}$ or $R^{11}$. In some embodiments, $R^{8'}$ is aryl optionally substituted with one or more $R^{10}$ or $R^{11}$. In some embodiments, $R^{8'}$ is heteroaryl optionally substituted with one or more $R^{10}$ or $R^{11}$.

In some embodiments, $R^9$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$. In some embodiments, $R^9$ is —H. In some embodiments, $R^9$ is —$C_1$-$C_6$alkyl, —$C_3$-$C_8$cycloalkyl, —$C_4$-$C_8$cycloalkenyl, heterocyclyl, or aryl, wherein $R^9$ is optionally substituted with $R^{10}$ or $R^{11}$. In some embodiments, $R^9$ is —$C_1$-$C_6$alkyl optionally substituted with one or more $R^{10}$ or $R^{11}$. In some embodiments, $R^9$ is aryl optionally substituted with one or more $R^{10}$ or $R^{11}$. In some embodiments, $R^9$ is heteroaryl optionally substituted with one or more $R^{10}$ or $R^{11}$.

In some embodiments, $R^{9'}$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$. In some embodiments, $R^{9'}$ is —$C_1$-$C_6$alkyl, —$C_3$-$C_8$cycloalkyl, —$C_4$-$C_8$cycloalkenyl, heterocyclyl, or aryl, wherein $R^{9'}$ is optionally substituted with $R^{10}$ or $R^{11}$. In some embodiments, $R^{9'}$ is —$C_1$-$C_6$alkyl optionally substituted with one or more $R^{10}$ or $R^{11}$. In some embodiments, $R^{9'}$ is aryl optionally substituted with one or more $R^{10}$ or $R^{11}$. In some embodiments, $R^{9'}$ is heteroaryl optionally substituted with one or more $R^{10}$ or $R^{11}$.

In some embodiments, $R^{10}$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —$C(O)NH_2$, —C(O)NH($C_1$-$C_6$alkyl), —C(O)N($C_1$-$C_6alkyl)_2$, —C(O)OC-$C_6$alkyl, —N($C_1$-$C_6$alkyl)$SO_2C_1$-$C_6$alkyl, —S(O)($C_1$-$C_6$alkyl), —S(O)N($C_1$-$C_6alkyl)_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$. In some embodiments, $R^{10}$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, wherein $R^{10}$ is substituted with $R^{12}$. In some embodiments, $R^{10}$ is halogen. In some embodiments, $R^{10}$ is each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$OC_3$-$C_6$cycloalkyl, Oaryl, Oheteroaryl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —C(O)

$NH_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$; wherein any two $R^{10}$ when on non-adjacent atoms, can combine to form a bridging cycloalkyl or heterocyclyl; wherein any two $R^{10}$ when on adjacent atoms, can combine to form a cycloalkyl, heterocyclyl, aryl or heteroaryl. In some embodiments, $R^{10}$ is each independently, at each occurrence halogen or —O$C_1$-$C_6$alkyl, —O$C_3$-$C_6$cycloalkyl, Oaryl, Oheteroaryl, wherein each alkyl, cycloalkyl, aryl or heteroaryl is optionally substituted with one or more —$R^{12}$.

In some embodiments, $R^{11}$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —O$C_1$-$C_6$alkyl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$. In some embodiments, $R^{11}$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, wherein $R^{11}$ is substituted with $R^{12}$. In some embodiments, $R^{11}$ is halogen.

In some embodiments, $R^{12}$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —O$C_1$-$C_6$alkyl, —NH$C_1$-$C_6$alkyl, —N($C_1$-$C_6$alkyl)$_2$, —S(O)$_2$NH($C_1$-$C_6$alkyl), —S(O)$_2$N($C_1$-$C_6$alkyl)$_2$, —S(O)$_2C_1$-$C_6$alkyl, —C(O)$C_1$-$C_6$alkyl, —C(O)$NH_2$, —C(O)NH($C_1$-$C_6$alkyl), —C(O)N($C_1$-$C_6$alkyl)$_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6$alkyl)$_2$, or —N($C_1$-$C_6$alkyl)S(O)($C_1$-$C_6$alkyl). In some embodiments, $R^{12}$ is —H. In some embodiments, $R^{12}$ is halogen.

In some embodiments, n is 1. In some embodiments, n is 2. In some embodiments, n is 3. In some embodiments, n is 4.

In some embodiments $R^1$ is —$C_1$-$C_6$alkyl, —$C_3$-$C_8$cycloalkyl, or —O$R^5$; $R^2$ is —$C_1$-$C_6$alkyl, —$C_3$-$C_8$cycloalkyl, heterocyclyl, heteroaryl, or aryl, wherein each alkyl, cycloalkyl, heterocyclyl, heteroaryl, or aryl is optionally substituted with one or more $R^6$; $R^3$ is —H, —$C_1$-$C_6$alkyl, or —$C_3$-$C_8$cycloalkyl, wherein each alkyl, or cycloalkyl is optionally substituted with one or more $R^7$; $R^5$ is methyl; $R^7$ is-$C_1$-$C_6$alkyl, —$C_3$-$C_8$cycloalkyl, heterocyclyl, heteroaryl, aryl, —OH, halogen, —CN, —O$R^8$, —NH$R^8$, —N$R^8R^9$, —C(O)OH, —C(O)N$R^8R^9$, —S(O)$CH_3$, or —S(O)N$R^8R^9$; and $R^8$ or $R^9$ is —H, or —$C_1$-$C_6$alkyl.

In some embodiments $R^1$ is —$C_1$-$C_6$alkyl, —$C_3$-$C_8$cycloalkyl, or —O$R^5$; and $R^2$ is (—$CH_2$)$_{1-2}$cycloalkyl, (—$CH_2$)$_{1-2}$heterocyclyl, (—$CH_2$)$_{1-2}$heteroaryl, or (—$CH_2$)$_{1-2}$aryl wherein each alkyl, cycloalkyl, heterocyclyl, heteroaryl, or aryl is optionally substituted with one or more $R^6$; and $R^3$ is (—$CH_2$)$_{1-2}$cycloalkyl, (—$CH_2$)$_{1-2}$heterocyclyl, (—$CH_2$)$_{1-2}$heteroaryl, or (—$CH_2$)$_{1-2}$aryl wherein each alkyl, cycloalkyl, heterocyclyl, heteroaryl, or aryl is optionally substituted with one or more $R^7$; and $R^5$ is methyl; and $R^7$ is-$C_1$-$C_6$alkyl, —$C_3$-$C_8$cycloalkyl, heterocyclyl, heteroaryl, aryl, —OH, halogen, —CN, —O$R^8$, —NH$R^8$, —N$R^8R^9$, —C(O)OH, —C(O)N$R^8R^9$, —S(O)$CH_3$, or —S(O)N$R^8R^9$; and $R^8$ or $R^9$ is —H, or —$C_1$-$C_6$alkyl.

In some embodiments, $R^1$ is —O$R^5$ and $R^2$ is alkyl. In some embodiments, $R^1$ is —O$R^5$ and $R^2$ is cycloalkyl. In some embodiments, $R^1$ is —O$R^5$ and $R^2$ is aryl. In some embodiments, $R^1$ is —O$R^5$ and $R^2$ is heteroaryl. In some embodiments, $R^1$ is —O$R^5$ and $R^2$ is alkyl substituted with cycloalkyl. In some embodiments, $R^1$ is —O$R^5$ and $R^2$ is alkyl substituted with heterocycloalkyl. In some embodiments, $R^1$ is —O$R^5$ and $R^2$ is alkyl substituted with aryl. In some embodiments, $R^1$ is —O$R^5$ and $R^2$ is alkyl substituted with heteroaryl.

In some embodiments, $R^1$ is —O$R^5$, $R^2$ is alkyl, and $R^3$ is alkyl. In some embodiments, $R^1$ is —O$R^5$, $R^2$ is cycloalkyl, and $R^3$ is alkyl. In some embodiments, $R^1$ is —O$R^5$, $R^2$ is aryl, and $R^3$ is alkyl. In some embodiments, $R^1$ is —O$R^5$, $R^2$ is heteroaryl, and $R^3$ is alkyl. In some embodiments, $R^1$ is —O$R^5$, $R^2$ is alkyl substituted with cycloalkyl, and $R^3$ is alkyl. In some embodiments, $R^1$ is —O$R^5$, $R^2$ is alkyl substituted with heterocycloalkyl, and $R^3$ is alkyl. In some embodiments, $R^1$ is —O$R^5$, $R^2$ is alkyl substituted with aryl, and $R^3$ is alkyl. In some embodiments, $R^1$ is —O$R^5$, $R^2$ is alkyl substituted with heteroaryl, and $R^3$ is alkyl.

In some embodiments, $R^1$ is —O$R^5$, $R^2$ is alkyl, and $R^3$ is cycloalkyl. In some embodiments, $R^1$ is —O$R^5$, $R^2$ is cycloalkyl, and $R^3$ is cycloalkyl. In some embodiments, $R^1$ is —O$R^5$, $R^2$ is aryl, and $R^3$ is cycloalkyl. In some embodiments, $R^1$ is —O$R^5$, $R^2$ is heteroaryl, and $R^3$ is cycloalkyl. In some embodiments, $R^1$ is —O$R^5$, $R^2$ is alkyl substituted with cycloalkyl, and $R^3$ is cycloalkyl. In some embodiments, $R^1$ is —O$R^5$, $R^2$ is alkyl substituted with heterocycloalkyl, and $R^3$ is cycloalkyl. In some embodiments, $R^1$ is —O$R^5$, $R^2$ is alkyl substituted with aryl, and $R^3$ is cycloalkyl. In some embodiments, $R^1$ is —O$R^5$, $R^2$ is alkyl substituted with heteroaryl, and $R^3$ is cycloalkyl.

In some embodiments, $R^1$ is —O$R^5$, $R^2$ is alkyl, and $R^3$ is aryl. In some embodiments, $R^1$ is —O$R^5$, $R^2$ is cycloalkyl, and $R^3$ is aryl. In some embodiments, $R^1$ is —O$R^5$, $R^2$ is aryl, and $R^3$ is aryl. In some embodiments, $R^1$ is —O$R^5$, $R^2$ is heteroaryl, and $R^3$ is aryl. In some embodiments, $R^1$ is —O$R^5$, $R^2$ is alkyl substituted with cycloalkyl, and $R^3$ is aryl. In some embodiments, $R^1$ is —O$R^5$, $R^2$ is alkyl substituted with heterocycloalkyl, and $R^3$ is aryl. In some embodiments, $R^1$ is —O$R^5$, $R^2$ is alkyl substituted with aryl, and $R^3$ is aryl. In some embodiments, $R^1$ is —O$R^5$, $R^2$ is alkyl substituted with heteroaryl, and $R^3$ is aryl.

In some embodiments, $R^1$ is —O$R^5$, $R^2$ is alkyl, and $R^3$ is heteroaryl. In some embodiments, $R^1$ is —O$R^5$, $R^2$ is cycloalkyl, and $R^3$ is heteroaryl. In some embodiments, $R^1$ is —O$R^5$, $R^2$ is aryl, and $R^3$ is heteroaryl. In some embodiments, $R^1$ is —O$R^5$, $R^2$ is heteroaryl, and $R^3$ is heteroaryl. In some embodiments, $R^1$ is —O$R^5$, $R^2$ is alkyl substituted with cycloalkyl, and $R^3$ is heteroaryl. In some embodiments, $R^1$ is —O$R^5$, $R^2$ is alkyl substituted with heterocycloalkyl, and $R^3$ is heteroaryl. In some embodiments, $R^1$ is —O$R^5$, $R^2$ is alkyl substituted with aryl, and $R^3$ is heteroaryl. In some embodiments, $R^1$ is —O$R^5$, $R^2$ is alkyl substituted with heteroaryl, and $R^3$ is heteroaryl.

In some embodiments, $R^1$ is —O$R^5$, $R^2$ is alkyl, and $R^3$ is alkyl substituted with cycloalkyl. In some embodiments, $R^1$ is —O$R^5$, $R^2$ is cycloalkyl, and $R^3$ is alkyl substituted with cycloalkyl. In some embodiments, $R^1$ is —O$R^5$, $R^2$ is aryl, and $R^3$ is alkyl substituted with cycloalkyl. In some embodiments, $R^1$ is —O$R^5$, $R^2$ is heteroaryl, and $R^3$ is alkyl substituted with cycloalkyl. In some embodiments, $R^1$ is —$OR^5$, $R^2$ is alkyl substituted with cycloalkyl, and $R^3$ is alkyl substituted with cycloalkyl. In some embodiments, $R^1$ is —$OR^5$, $R^2$ is alkyl substituted with heterocycloalkyl, and $R^3$ is alkyl substituted with cycloalkyl. In some embodiments, $R^1$ is —$OR^5$, $R^2$ is alkyl substituted with aryl, and $R^3$ is alkyl substituted with cycloalkyl. In some embodiments, $R^1$ is —$OR^5$, $R^2$ is alkyl substituted with heteroaryl, and $R^3$ is alkyl substituted with cycloalkyl.

In some embodiments, $R^1$ is —$OR^5$, $R^2$ is alkyl, and $R^3$ is alkyl substituted with aryl. In some embodiments, $R^1$ is —$OR^5$, $R^2$ is cycloalkyl, and $R^3$ is alkyl substituted with aryl. In some embodiments, $R^1$ is —$OR^5$, $R^2$ is aryl, and $R^3$ is alkyl substituted with aryl. In some embodiments, $R^1$ is —$OR^5$, $R^2$ is heteroaryl, and $R^3$ is alkyl substituted with aryl. In some embodiments, $R^1$ is —$OR^5$, $R^2$ is alkyl substituted with cycloalkyl, and $R^3$ is alkyl substituted with aryl. In some embodiments, $R^1$ is —$OR^5$, $R^2$ is alkyl substituted with heterocycloalkyl, and $R^3$ is alkyl substituted with aryl. In some embodiments, $R^1$ is —$OR^5$, $R^2$ is alkyl substituted with aryl, and $R^3$ is alkyl substituted with aryl. In some embodiments, $R^1$ is —$OR^5$, $R^2$ is alkyl substituted with heteroaryl, and $R^3$ is alkyl substituted with aryl.

In some embodiments, $R^1$ is —$OR^5$, $R^2$ is alkyl, and $R^3$ is alkyl substituted with heteroaryl. In some embodiments, $R^1$ is —$OR^5$, $R^2$ is cycloalkyl, and $R^3$ is alkyl substituted with heteroaryl. In some embodiments, $R^1$ is —$OR^5$, $R^2$ is aryl, and $R^3$ is alkyl substituted with heteroaryl. In some embodiments, $R^1$ is —$OR^5$, $R^2$ is heteroaryl, and $R^3$ is alkyl substituted with heteroaryl. In some embodiments, $R^1$ is —$OR^5$, $R^2$ is alkyl substituted with cycloalkyl, and $R^3$ is alkyl substituted with heteroaryl. In some embodiments, $R^1$ is —$OR^5$, $R^2$ is alkyl substituted with heterocycloalkyl, and $R^3$ is alkyl substituted with heteroaryl. In some embodiments, $R^1$ is —$OR^5$, $R^2$ is alkyl substituted with aryl, and $R^3$ is alkyl substituted with heteroaryl. In some embodiments, $R^1$ is —$OR^5$, $R^2$ is alkyl substituted with heteroaryl, and $R^3$ is alkyl substituted with heteroaryl.

In some embodiments, $R^1$ is —$OR^5$, $R^2$ is alkyl, $R^3$ is alkyl, and $R^4$ and $R^{4'}$ are —H. In some embodiments, $R^1$ is —$OR^5$, $R^2$ is cycloalkyl, $R^3$ is alkyl, and $R^4$ and $R^{4'}$ are —H. In some embodiments, $R^1$ is —$OR^5$, $R^2$ is aryl, $R^3$ is alkyl, and $R^4$ and $R^{4'}$ are —H. In some embodiments, $R^1$ is —$OR^5$, $R^2$ is heteroaryl, $R^3$ is alkyl, and $R^4$ and $R^{4'}$ are —H. In some embodiments, $R^1$ is —$OR^5$, $R^2$ is alkyl substituted with cycloalkyl, $R^3$ is alkyl, and $R^4$ and $R^{4'}$ are —H. In some embodiments, $R^1$ is —$OR^5$, $R^2$ is alkyl substituted with heterocycloalkyl, $R^3$ is alkyl, and $R^4$ and $R^{4'}$ are —H. In some embodiments, $R^1$ is —$OR^5$, $R^2$ is alkyl substituted with aryl, $R^3$ is alkyl, and $R^4$ and $R^{4'}$ are —H. In some embodiments, $R^1$ is —$OR^5$, $R^2$ is alkyl substituted with heteroaryl, $R^3$ is alkyl, and $R^4$ and $R^{4'}$ are —H.

In some embodiments, $R^1$ is —$OR^5$, $R^2$ is alkyl, $R^3$ is cycloalkyl, and $R^4$ and $R^{4'}$ are —H. In some embodiments, $R^1$ is —$OR^5$, $R^2$ is cycloalkyl, $R^3$ is cycloalkyl, and $R^4$ and $R^{4'}$ are —H. In some embodiments, $R^1$ is —$OR^5$, $R^2$ is aryl, $R^3$ is cycloalkyl, and $R^4$ and $R^{4'}$ are —H. In some embodiments, $R^1$ is —$OR^5$, $R^2$ is heteroaryl, $R^3$ is cycloalkyl, and $R^4$ and $R^{4'}$ are —H. In some embodiments, $R^1$ is —$OR^5$, $R^2$ is alkyl substituted with cycloalkyl, $R^3$ is cycloalkyl, and $R^4$ and $R^{4'}$ are —H. In some embodiments, $R^1$ is —$OR^5$, $R^2$ is alkyl substituted with heterocycloalkyl, $R^3$ is cycloalkyl, and $R^4$ and $R^{4'}$ are —H. In some embodiments, $R^1$ is —$OR^5$, $R^2$ is alkyl substituted with aryl, $R^3$ is cycloalkyl, and $R^4$ and $R^{4'}$ are —H. In some embodiments, $R^1$ is —$OR^5$, $R^2$ is alkyl substituted with heteroaryl, $R^3$ is cycloalkyl, and $R^4$ and $R^{4'}$ are —H.

In some embodiments, $R^1$ is —$OR^5$, $R^2$ is alkyl, $R^3$ is aryl, and $R^4$ and $R^{4'}$ are —H. In some embodiments, $R^1$ is —$OR^5$, $R^2$ is cycloalkyl, $R^3$ is aryl, and $R^4$ and $R^{4'}$ are —H. In some embodiments, $R^1$ is —$OR^5$, $R^2$ is aryl, $R^3$ is aryl, and $R^4$ and $R^{4'}$ are —H. In some embodiments, $R^1$ is —$OR^5$, $R^2$ is heteroaryl, $R^3$ is aryl, and $R^4$ and $R^{4'}$ are —H. In some embodiments, $R^1$ is —$OR^5$, $R^2$ is alkyl substituted with cycloalkyl, $R^3$ is aryl, and $R^4$ and $R^{4'}$ are —H. In some embodiments, $R^1$ is —$OR^5$, $R^2$ is alkyl substituted with heterocycloalkyl, $R^3$ is aryl, and $R^4$ and $R^{4'}$ are —H. In some embodiments, $R^1$ is —$OR^5$, $R^2$ is alkyl substituted with aryl, $R^3$ is aryl, and $R^4$ and $R^{4'}$ are —H. In some embodiments, $R^1$ is —$OR^5$, $R^2$ is alkyl substituted with heteroaryl, $R^3$ is aryl, and $R^4$ and $R^{4'}$ are —H.

In some embodiments, $R^1$ is —$OR^5$, $R^2$ is alkyl, $R^3$ is heteroaryl, and $R^4$ and $R^{4'}$ are —H. In some embodiments, $R^1$ is —$OR^5$, $R^2$ is cycloalkyl, $R^3$ is heteroaryl, and $R^4$ and $R^{4'}$ are —H. In some embodiments, $R^1$ is —$OR^5$, $R^2$ is aryl, $R^3$ is heteroaryl, and $R^4$ and $R^{4'}$ are —H. In some embodiments, $R^1$ is —$OR^5$, $R^2$ is heteroaryl, $R^3$ is heteroaryl, and $R^4$ and $R^{4'}$ are —H. In some embodiments, $R^1$ is —$OR^5$, $R^2$ is alkyl substituted with cycloalkyl, $R^3$ is heteroaryl, and $R^4$ and $R^{4'}$ are —H. In some embodiments, $R^1$ is —$OR^5$, $R^2$ is alkyl substituted with heterocycloalkyl, $R^3$ is heteroaryl, and $R^4$ and $R^{4'}$ are —H. In some embodiments, $R^1$ is —$OR^5$, $R^2$ is alkyl substituted with aryl, $R^3$ is heteroaryl, and $R^4$ and $R^{4'}$ are —H. In some embodiments, $R^1$ is —$OR^5$, $R^2$ is alkyl substituted with heteroaryl, $R^3$ is heteroaryl, and $R^4$ and $R^{4'}$ are —H.

In some embodiments, $R^1$ is —$OR^5$, $R^2$ is alkyl, $R^3$ is alkyl substituted with cycloalkyl, and $R^4$ and $R^{4'}$ are —H. In some embodiments, $R^1$ is —$OR^5$, $R^2$ is cycloalkyl, $R^3$ is alkyl substituted with cycloalkyl, and $R^4$ and $R^{4'}$ are —H. In some embodiments, $R^1$ is —$OR^5$, $R^2$ is aryl, $R^3$ is alkyl substituted with cycloalkyl, and $R^4$ and $R^{4'}$ are —H. In some embodiments, $R^1$ is —$OR^5$, $R^2$ is heteroaryl, $R^3$ is alkyl substituted with cycloalkyl, and $R^4$ and $R^{4'}$ are —H. In some embodiments, $R^1$ is —$OR^5$, $R^2$ is alkyl substituted with cycloalkyl, $R^3$ is alkyl substituted with cycloalkyl, and $R^4$ and $R^{4'}$ are —H. In some embodiments, $R^1$ is —$OR^5$, $R^2$ is alkyl substituted with heterocycloalkyl, $R^3$ is alkyl substituted with cycloalkyl, and $R^4$ and $R^{4'}$ are —H. In some embodiments, $R^1$ is —$OR^5$, $R^2$ is alkyl substituted with aryl, $R^3$ is alkyl substituted with cycloalkyl, and $R^4$ and $R^{4'}$ are —H. In some embodiments, $R^1$ is —$OR^5$, $R^2$ is alkyl substituted with heteroaryl, $R^3$ is alkyl substituted with cycloalkyl, and $R^4$ and $R^{4'}$ are —H.

In some embodiments, $R^1$ is —$OR^5$, $R^2$ is alkyl, $R^3$ is alkyl substituted with aryl, and $R^4$ and $R^{4'}$ are —H. In some embodiments, $R^1$ is —$OR^5$, $R^2$ is cycloalkyl, $R^3$ is alkyl substituted with aryl, and $R^4$ and $R^{4'}$ are —H. In some embodiments, $R^1$ is —$OR^5$, $R^2$ is aryl, $R^3$ is alkyl substituted with aryl, and $R^4$ and $R^{4'}$ are —H. In some embodiments, $R^1$ is —$OR^5$, $R^2$ is heteroaryl, $R^3$ is alkyl substituted with aryl, and $R^4$ and $R^{4'}$ are —H. In some embodiments, $R^1$ is —$OR^5$, $R^2$ is alkyl substituted with cycloalkyl, $R^3$ is alkyl substituted with aryl, and $R^4$ and $R^{4'}$ are —H. In some embodiments, $R^1$ is —$OR^5$, $R^2$ is alkyl substituted with heterocycloalkyl, $R^3$ is alkyl substituted with aryl, and $R^4$ and $R^{4'}$ are —H. In some embodiments, $R^1$ is —$OR^5$, $R^2$ is alkyl substituted with aryl, $R^3$ is alkyl substituted with aryl, and $R^4$ and $R^{4'}$ are —H. In some embodiments, $R^1$ is —$OR^5$, $R^2$ is alkyl substituted with heteroaryl, $R^3$ is alkyl substituted with aryl, and $R^4$ and $R^{4'}$ are —H.

In some embodiments, $R^1$ is —$OR^5$, $R^2$ is alkyl, $R^3$ is alkyl substituted with heteroaryl, and $R^4$ and $R^{4'}$ are —H. In some embodiments, $R^1$ is —$OR^5$, $R^2$ is cycloalkyl, $R^3$ is alkyl substituted with heteroaryl, and $R^4$ and $R^{4'}$ are —H. In some embodiments, $R^1$ is —$OR^5$, $R^2$ is aryl, $R^3$ is alkyl substituted with heteroaryl, and $R^4$ and $R^{4'}$ are —H. In some embodiments, $R^1$ is —$OR^5$, $R^2$ is heteroaryl, $R^3$ is alkyl substituted with heteroaryl, and $R^4$ and $R^{4'}$ are —H. In some embodiments, $R^1$ is —$OR^5$, $R^2$ is alkyl substituted with cycloalkyl, $R^3$ is alkyl substituted with heteroaryl, and $R^4$ and $R^{4'}$ are —H. In some embodiments, $R^1$ is —$OR^5$, $R^2$ is alkyl substituted with heterocycloalkyl, $R^3$ is alkyl substituted with heteroaryl, and $R^4$ and $R^{4'}$ are —H. In some embodiments, $R^1$ is —$OR^5$, $R^2$ is alkyl substituted with aryl, $R^3$ is alkyl substituted with heteroaryl, and $R^4$ and $R^{4'}$ are —H. In some embodiments, $R^1$ is —$OR^5$, $R^2$ is alkyl substituted with heteroaryl, $R^3$ is alkyl substituted with heteroaryl, and $R^4$ and $R^{4'}$ are —H.

In some embodiments, $R^1$ is —$OR^5$, $R^2$ is alkyl, $R^3$ is alkyl, $R^4$ is —H and $R^{4'}$ is —OH. In some embodiments, $R^1$ is —$OR^5$, $R^2$ is cycloalkyl, $R^3$ is alkyl, $R^4$ is —H and $R^{4'}$ is —OH. In some embodiments, $R^1$ is —$OR^5$, $R^2$ is aryl, $R^3$ is alkyl, $R^4$ is —H and $R^{4'}$ is —OH. In some embodiments, $R^1$ is —$OR^5$, $R^2$ is heteroaryl, $R^3$ is alkyl, $R^4$ is —H and $R^{4'}$ is —OH. In some embodiments, $R^1$ is —$OR^5$, $R^2$ is alkyl substituted with cycloalkyl, $R^3$ is alkyl, $R^4$ is —H and $R^{4'}$ is —OH. In some embodiments, $R^1$ is —$OR^5$, $R^2$ is alkyl substituted with heterocycloalkyl, $R^3$ is alkyl, $R^4$ is —H and $R^{4'}$ is —OH. In some embodiments, $R^1$ is —$OR^5$, $R^2$ is alkyl substituted with aryl, $R^3$ is alkyl, $R^4$ is —H and $R^{4'}$ is —OH. In some embodiments, $R^1$ is —$OR^5$, $R^2$ is alkyl substituted with heteroaryl, $R^3$ is alkyl, $R^4$ is —H and $R^{4'}$ is —OH.

In some embodiments, $R^1$ is —$OR^5$, $R^2$ is alkyl, $R^3$ is cycloalkyl, $R^4$ is —H and $R^{4'}$ is —OH. In some embodiments, $R^1$ is —$OR^5$, $R^2$ is cycloalkyl, $R^3$ is cycloalkyl, $R^4$ is —H and $R^{4'}$ is —OH. In some embodiments, $R^1$ is —$OR^5$, $R^2$ is aryl, $R^3$ is cycloalkyl, $R^4$ is —H and $R^{4'}$ is —OH. In some embodiments, $R^1$ is —$OR^5$, $R^2$ is heteroaryl, $R^3$ is cycloalkyl, $R^4$ is —H and $R^{4'}$ is —OH. In some embodiments, $R^1$ is —$OR^5$, $R^2$ is alkyl substituted with cycloalkyl, $R^3$ is cycloalkyl, $R^4$ is —H and $R^{4'}$ is —OH. In some embodiments, $R^1$ is —$OR^5$, $R^2$ is alkyl substituted with heterocycloalkyl, $R^3$ is cycloalkyl, $R^4$ is —H and $R^{4'}$ is —OH. In some embodiments, $R^1$ is —$OR^5$, $R^2$ is alkyl substituted with aryl, $R^3$ is cycloalkyl, $R^4$ is —H and $R^{4'}$ is —OH. In some embodiments, $R^1$ is —$OR^5$, $R^2$ is alkyl substituted with heteroaryl, $R^3$ is cycloalkyl, $R^4$ is —H and $R^{4'}$ is —OH.

In some embodiments, $R^1$ is —$OR^5$, $R^2$ is alkyl, $R^3$ is aryl, $R^4$ is —H and $R^{4'}$ is —OH. In some embodiments, $R^1$ is —$OR^5$, $R^2$ is cycloalkyl, $R^3$ is aryl, $R^4$ is —H and $R^{4'}$ is —OH. In some embodiments, $R^1$ is —$OR^5$, $R^2$ is aryl, $R^3$ is aryl, $R^4$ is —H and $R^{4'}$ is —OH. In some embodiments, $R^1$ is —$OR^5$, $R^2$ is heteroaryl, $R^3$ is aryl, $R^4$ is —H and $R^{4'}$ is —OH. In some embodiments, $R^1$ is —$OR^5$, $R^2$ is alkyl substituted with cycloalkyl, $R^3$ is aryl, $R^4$ is —H and $R^{4'}$ is —OH. In some embodiments, $R^1$ is —$OR^5$, $R^2$ is alkyl substituted with heterocycloalkyl, $R^3$ is aryl, $R^4$ is —H and $R^{4'}$ is —OH. In some embodiments, $R^1$ is —$OR^5$, $R^2$ is alkyl substituted with aryl, $R^3$ is aryl, $R^4$ is —H and $R^{4'}$ is —OH. In some embodiments, $R^1$ is —$OR^5$, $R^2$ is alkyl substituted with heteroaryl, $R^3$ is aryl, $R^4$ is —H and $R^{4'}$ is —OH.

In some embodiments, $R^1$ is —$OR^5$, $R^2$ is alkyl, $R^3$ is heteroaryl, $R^4$ is —H and $R^{4'}$ is —OH. In some embodiments, $R^1$ is —$OR^5$, $R^2$ is cycloalkyl, $R^3$ is heteroaryl, $R^4$ is —H and $R^{4'}$ is —OH. In some embodiments, $R^1$ is —$OR^5$, $R^2$ is aryl, $R^3$ is heteroaryl, $R^4$ is —H and $R^{4'}$ is —OH. In some embodiments, $R^1$ is —$OR^5$, $R^2$ is heteroaryl, $R^3$ is heteroaryl, $R^4$ is —H and $R^{4'}$ is —OH. In some embodiments, $R^1$ is —$OR^5$, $R^2$ is alkyl substituted with cycloalkyl, $R^3$ is heteroaryl, $R^4$ is —H and $R^{4'}$ is —OH. In some embodiments, $R^1$ is —$OR^5$, $R^2$ is alkyl substituted with heterocycloalkyl, $R^3$ is heteroaryl, $R^4$ is —H and $R^{4'}$ is —OH. In some embodiments, $R^1$ is —$OR^5$, $R^2$ is alkyl substituted with aryl, $R^3$ is heteroaryl, $R^4$ is —H and $R^{4'}$ is —OH. In some embodiments, $R^1$ is —$OR^5$, $R^2$ is alkyl substituted with heteroaryl, $R^3$ is heteroaryl, $R^4$ is —H and $R^{4'}$ is —OH.

In some embodiments, $R^1$ is —$OR^5$, $R^2$ is alkyl, $R^3$ is alkyl substituted with cycloalkyl, $R^4$ is —H and $R^{4'}$ is —OH. In some embodiments, $R^1$ is —$OR^5$, $R^2$ is cycloalkyl, $R^3$ is alkyl substituted with cycloalkyl, $R^4$ is —H and $R^{4'}$ is —OH. In some embodiments, $R^1$ is —$OR^5$, $R^2$ is aryl, $R^3$ is alkyl substituted with cycloalkyl, $R^4$ is —H and $R^{4'}$ is —OH. In some embodiments, $R^1$ is —$OR^5$, $R^2$ is heteroaryl, $R^3$ is alkyl substituted with cycloalkyl, $R^4$ is —H and $R^{4'}$ is —OH. In some embodiments, $R^1$ is —$OR^5$, $R^2$ is alkyl substituted with cycloalkyl, $R^3$ is alkyl substituted with cycloalkyl, $R^4$ is —H and $R^{4'}$ is —OH. In some embodiments, $R^1$ is —$OR^5$, $R^2$ is alkyl substituted with heterocycloalkyl, $R^3$ is alkyl substituted with cycloalkyl, $R^4$ is —H and $R^{4'}$ is —OH. In some embodiments, $R^1$ is —$OR^5$, $R^2$ is alkyl substituted with aryl, $R^3$ is alkyl substituted with cycloalkyl, $R^4$ is —H and $R^{4'}$ is —OH. In some embodiments, $R^1$ is —$OR^5$, $R^2$ is alkyl substituted with heteroaryl, $R^3$ is alkyl substituted with cycloalkyl, $R^4$ is —H and $R^{4'}$ is —OH.

In some embodiments, $R^1$ is —$OR^5$, $R^2$ is alkyl, $R^3$ is alkyl substituted with aryl, $R^4$ is —H and $R^{4'}$ is —OH. In some embodiments, $R^1$ is —$OR^5$, $R^2$ is cycloalkyl, $R^3$ is alkyl substituted with aryl, $R^4$ is —H and $R^{4'}$ is —OH. In some embodiments, $R^1$ is —$OR^5$, $R^2$ is aryl, $R^3$ is alkyl substituted with aryl, $R^4$ is —H and $R^{4'}$ is —OH. In some embodiments, $R^1$ is —$OR^5$, $R^2$ is heteroaryl, $R^3$ is alkyl substituted with aryl, $R^4$ is —H and $R^{4'}$ is —OH. In some embodiments, $R^1$ is —$OR^5$, $R^2$ is alkyl substituted with cycloalkyl, $R^3$ is alkyl substituted with aryl, $R^4$ is —H and $R^{4'}$ is —OH. In some embodiments, $R^1$ is —$OR^5$, $R^2$ is alkyl substituted with heterocycloalkyl, $R^3$ is alkyl substituted with aryl, $R^4$ is —H and $R^{4'}$ is —OH. In some embodiments, $R^1$ is —$OR^5$, $R^2$ is alkyl substituted with aryl, $R^3$ is alkyl substituted with aryl, $R^4$ is —H and $R^{4'}$ is —OH. In some embodiments, $R^1$ is —$OR^5$, $R^2$ is alkyl substituted with heteroaryl, $R^3$ is alkyl substituted with aryl, $R^4$ is —H and $R^{4'}$ is —OH.

In some embodiments, $R^1$ is —$OR^5$, $R^2$ is alkyl, $R^3$ is alkyl substituted with heteroaryl, $R^4$ is —H and $R^{4'}$ is —OH. In some embodiments, $R^1$ is —$OR^5$, $R^2$ is cycloalkyl, $R^3$ is alkyl substituted with heteroaryl, $R^4$ is —H and $R^{4'}$ is —OH. In some embodiments, $R^1$ is —$OR^5$, $R^2$ is aryl, $R^3$ is alkyl substituted with heteroaryl, $R^4$ is —H and $R^{4'}$ is —OH. In some embodiments, $R^1$ is —$OR^5$, $R^2$ is heteroaryl, $R^3$ is alkyl substituted with heteroaryl, $R^4$ is —H and $R^{4'}$ is —OH. In some embodiments, $R^1$ is —$OR^5$, $R^2$ is alkyl substituted with cycloalkyl, $R^3$ is alkyl substituted with heteroaryl, $R^4$ is —H and $R^{4'}$ is —OH. In some embodiments, $R^1$ is —$OR^5$, $R^2$ is alkyl substituted with heterocycloalkyl, $R^3$ is alkyl substituted with heteroaryl, $R^4$ is —H and $R^{4'}$ is —OH. In some embodiments, $R^1$ is —$OR^5$, $R^2$ is alkyl substituted with aryl, $R^3$ is alkyl substituted with heteroaryl, $R^4$ is —H and $R^{4'}$ is —OH. In some embodiments, $R^1$ is —$OR^5$, $R^2$ is alkyl substituted with heteroaryl, $R^3$ is alkyl substituted with heteroaryl, $R^4$ is —H and $R^{4'}$ is —OH.

In some embodiments, $R^1$ is —$OR^5$, $R^2$ is alkyl, $R^3$ is alkyl, $R^4$ is —OH and $R^{4'}$ is —H. In some embodiments, $R^1$ is —$OR^5$, $R^2$ is cycloalkyl, $R^3$ is alkyl, $R^4$ is —OH and $R^{4'}$ is —H. In some embodiments, $R^1$ is —$OR^5$, $R^2$ is aryl, $R^3$ is alkyl, $R^4$ is —OH and $R^{4'}$ is —H. In some embodiments, $R^1$ is —$OR^5$, $R^2$ is heteroaryl, $R^3$ is alkyl, $R^4$ is —OH and $R^{4'}$ is —H. In some embodiments, $R^1$ is —$OR^5$, $R^2$ is alkyl substituted with cycloalkyl, $R^3$ is alkyl, $R^4$ is —OH and $R^{4'}$ is —H. In some embodiments, $R^1$ is —$OR^5$, $R^2$ is alkyl substituted with heterocycloalkyl, $R^3$ is alkyl, $R^4$ is —OH and $R^{4'}$ is —H. In some embodiments, $R^1$ is —$OR^5$, $R^2$ is alkyl substituted with aryl, $R^3$ is alkyl, $R^4$ is —OH and $R^{4'}$ is —H. In some embodiments, $R^1$ is —$OR^5$, $R^2$ is alkyl substituted with heteroaryl, $R^3$ is alkyl, $R^4$ is —OH and $R^{4'}$ is —H.

In some embodiments, $R^1$ is —$OR^5$, $R^2$ is alkyl, $R^3$ is cycloalkyl, $R^4$ is —OH and $R^{4'}$ is —H. In some embodiments, $R^1$ is —$OR^5$, $R^2$ is cycloalkyl, $R^3$ is cycloalkyl, $R^4$ is —OH and $R^{4'}$ is —H. In some embodiments, $R^1$ is —$OR^5$, $R^2$ is aryl, $R^3$ is cycloalkyl, $R^4$ is —OH and $R^{4'}$ is —H. In some embodiments, $R^1$ is —$OR^5$, $R^2$ is heteroaryl, $R^3$ is cycloalkyl, $R^4$ is —OH and $R^{4'}$ is —H. In some embodiments, $R^1$ is —$OR^5$, $R^2$ is alkyl substituted with cycloalkyl, $R^3$ is cycloalkyl, $R^4$ is —OH and $R^{4'}$ is —H. In some embodiments, $R^1$ is —$OR^5$, $R^2$ is alkyl substituted with heterocycloalkyl, $R^3$ is cycloalkyl, $R^4$ is —OH and $R^{4'}$ is —H. In some embodiments, $R^1$ is —$OR^5$, $R^2$ is alkyl substituted with aryl, $R^3$ is cycloalkyl, $R^4$ is —OH and $R^{4'}$ is —H. In some embodiments, $R^1$ is —$OR^5$, $R^2$ is alkyl substituted with heteroaryl, $R^3$ is cycloalkyl, $R^4$ is —OH and $R^{4'}$ is —H.

In some embodiments, $R^1$ is —$OR^5$, $R^2$ is alkyl, $R^3$ is aryl, $R^4$ is —OH and $R^{4'}$ is —H. In some embodiments, $R^1$ is —$OR^5$, $R^2$ is cycloalkyl, $R^3$ is aryl, $R^4$ is —OH and $R^{4'}$ is —H. In some embodiments, $R^1$ is —$OR^5$, $R^2$ is aryl, $R^3$ is aryl, $R^4$ is —OH and $R^{4'}$ is —H. In some embodiments, $R^1$ is —$OR^5$, $R^2$ is heteroaryl, $R^3$ is aryl, $R^4$ is —OH and $R^{4'}$ is —H. In some embodiments, $R^1$ is —$OR^5$, $R^2$ is alkyl substituted with cycloalkyl, $R^3$ is aryl, $R^4$ is —OH and $R^{4'}$ is —H. In some embodiments, $R^1$ is —$OR^5$, $R^2$ is alkyl substituted with heterocycloalkyl, $R^3$ is aryl, $R^4$ is —OH and $R^{4'}$ is —H. In some embodiments, $R^1$ is —$OR^5$, $R^2$ is alkyl substituted with aryl, $R^3$ is aryl, $R^4$ is —OH and $R^{4'}$ is —H. In some embodiments, $R^1$ is —$OR^5$, $R^2$ is alkyl substituted with heteroaryl, $R^3$ is aryl, $R^4$ is —OH and $R^{4'}$ is —H.

In some embodiments, $R^1$ is —$OR^5$, $R^2$ is alkyl, $R^3$ is heteroaryl, $R^4$ is —OH and $R^{4'}$ is —H. In some embodiments, $R^1$ is —$OR^5$, $R^2$ is cycloalkyl, $R^3$ is heteroaryl, $R^4$ is —OH and $R^{4'}$ is —H. In some embodiments, $R^1$ is —$OR^5$, $R^2$ is aryl, $R^3$ is heteroaryl, $R^4$ is —OH and $R^{4'}$ is —H. In some embodiments, $R^1$ is —$OR^5$, $R^2$ is heteroaryl, $R^3$ is heteroaryl, $R^4$ is —OH and $R^{4'}$ is —H. In some embodiments, $R^1$ is —$OR^5$, $R^2$ is alkyl substituted with cycloalkyl, $R^3$ is heteroaryl, $R^4$ is —OH and $R^{4'}$ is —H. In some embodiments, $R^1$ is —$OR^5$, $R^2$ is alkyl substituted with heterocycloalkyl, $R^3$ is heteroaryl, $R^4$ is —OH and $R^{4'}$ is —H. In some embodiments, $R^1$ is —$OR^5$, $R^2$ is alkyl substituted with aryl, $R^3$ is heteroaryl, $R^4$ is —OH and $R^{4'}$ is —H. In some embodiments, $R^1$ is —$OR^5$, $R^2$ is alkyl substituted with heteroaryl, $R^3$ is heteroaryl, $R^4$ is —OH and $R^{4'}$ is —H.

In some embodiments, $R^1$ is —$OR^5$, $R^2$ is alkyl, $R^3$ is alkyl substituted with cycloalkyl, $R^4$ is —OH and $R^{4'}$ is —H. In some embodiments, $R^1$ is —$OR^5$, $R^2$ is cycloalkyl, $R^3$ is alkyl substituted with cycloalkyl, $R^4$ is —OH and $R^{4'}$ is —H. In some embodiments, $R^1$ is —$OR^5$, $R^2$ is aryl, $R^3$ is alkyl substituted with cycloalkyl, $R^4$ is —OH and $R^{4'}$ is —H. In some embodiments, $R^1$ is —$OR^5$, $R^2$ is heteroaryl, $R^3$ is alkyl substituted with cycloalkyl, $R^4$ is —OH and $R^{4'}$ is —H. In some embodiments, $R^1$ is —$OR^5$, $R^2$ is alkyl substituted with cycloalkyl, $R^3$ is alkyl substituted with cycloalkyl, $R^4$ is —OH and $R^{4'}$ is —H. In some embodiments, $R^1$ is —$OR^5$, $R^2$ is alkyl substituted with heterocycloalkyl, $R^3$ is alkyl substituted with cycloalkyl, $R^4$ is —OH and $R^{4'}$ is —H. In some embodiments, $R^1$ is —$OR^5$, $R^2$ is alkyl substituted with aryl, $R^3$ is alkyl substituted with cycloalkyl, $R^4$ is —OH and $R^{4'}$ is —H. In some embodiments, $R^1$ is —$OR^5$, $R^2$ is alkyl substituted with heteroaryl, $R^3$ is alkyl substituted with cycloalkyl, $R^4$ is —OH and $R^{4'}$ is —H.

In some embodiments, $R^1$ is —$OR^5$, $R^2$ is alkyl, $R^3$ is alkyl substituted with aryl, $R^4$ is —OH and $R^{4'}$ is —H. In some embodiments, $R^1$ is —$OR^5$, $R^2$ is cycloalkyl, $R^3$ is alkyl substituted with aryl, $R^4$ is —OH and $R^{4'}$ is —H. In some embodiments, $R^1$ is —$OR^5$, $R^2$ is aryl, $R^3$ is alkyl substituted with aryl, $R^4$ is —OH and $R^{4'}$ is —H. In some embodiments, $R^1$ is —$OR^5$, $R^2$ is heteroaryl, $R^3$ is alkyl substituted with aryl, $R^4$ is —OH and $R^{4'}$ is —H. In some embodiments, $R^1$ is —$OR^5$, $R^2$ is alkyl substituted with cycloalkyl, $R^3$ is alkyl substituted with aryl, $R^4$ is —OH and $R^{4'}$ is —H. In some embodiments, $R^1$ is —$OR^5$, $R^2$ is alkyl substituted with heterocycloalkyl, $R^3$ is alkyl substituted with aryl, $R^4$ is —OH and $R^{4'}$ is —H. In some embodiments, $R^1$ is —$OR^5$, $R^2$ is alkyl substituted with aryl, $R^3$ is alkyl substituted with aryl, $R^4$ is —OH and $R^{4'}$ is —H. In some embodiments, $R^1$ is —$OR^5$, $R^2$ is alkyl substituted with heteroaryl, $R^3$ is alkyl substituted with aryl, $R^4$ is —OH and $R^{4'}$ is —H.

In some embodiments, $R^1$ is —$OR^5$, $R^2$ is alkyl, $R^3$ is alkyl substituted with heteroaryl, $R^4$ is —OH and $R^{4'}$ is —H. In some embodiments, $R^1$ is —$OR^5$, $R^2$ is cycloalkyl, $R^3$ is alkyl substituted with heteroaryl, $R^4$ is —OH and $R^{4'}$ is —H. In some embodiments, $R^1$ is —$OR^5$, $R^2$ is aryl, $R^3$ is alkyl substituted with heteroaryl, $R^4$ is —OH and $R^{4'}$ is —H. In some embodiments, $R^1$ is —$OR^5$, $R^2$ is heteroaryl, $R^3$ is alkyl substituted with heteroaryl, $R^4$ is —OH and $R^{4'}$ is —H. In some embodiments, $R^1$ is —$OR^5$, $R^2$ is alkyl substituted with cycloalkyl, $R^3$ is alkyl substituted with heteroaryl, $R^4$ is —OH and $R^{4'}$ is —H. In some embodiments, $R^1$ is —$OR^5$, $R^2$ is alkyl substituted with heterocycloalkyl, $R^3$ is alkyl substituted with heteroaryl, $R^4$ is —OH and $R^{4'}$ is —H. In some embodiments, $R^1$ is —$OR^5$, $R^2$ is alkyl substituted with aryl, $R^3$ is alkyl substituted with heteroaryl, $R^4$ is —OH and $R^{4'}$ is —H. In some embodiments, $R^1$ is —$OR^5$, $R^2$ is alkyl substituted with heteroaryl, $R^3$ is alkyl substituted with heteroaryl, $R^4$ is —OH and $R^{4'}$ is —H.

In some embodiments, $R^1$ is —$OR^5$, $R^2$ is alkyl, $R^3$ is alkyl, $R^4$ is —H and $R^{4'}$ is —$NH_2$. In some embodiments, $R^1$ is —$OR^5$, $R^2$ is cycloalkyl, $R^3$ is alkyl, $R^4$ is —H and $R^{4'}$ is —$NH_2$. In some embodiments, $R^1$ is —$OR^5$, $R^2$ is aryl, $R^3$ is alkyl, $R^4$ is —H and $R^{4'}$ is —$NH_2$. In some embodiments, $R^1$ is —$OR^5$, $R^2$ is heteroaryl, $R^3$ is alkyl, $R^4$ is —H and $R^{4'}$ is —$NH_2$. In some embodiments, $R^1$ is —$OR^5$, $R^2$ is alkyl substituted with cycloalkyl, $R^3$ is alkyl, $R^4$ is —H and $R^{4'}$ is —$NH_2$. In some embodiments, $R^1$ is —$OR^5$, $R^2$ is alkyl substituted with heterocycloalkyl, $R^3$ is alkyl, $R^4$ is —H and $R^{4'}$ is —$NH_2$. In some embodiments, $R^1$ is —$OR^5$, $R^2$ is alkyl substituted with aryl, $R^3$ is alkyl, $R^4$ is —H and $R^{4'}$ is —$NH_2$.

In some embodiments, $R^1$ is —$OR^5$, $R^2$ is alkyl substituted with heteroaryl, $R^3$ is alkyl, $R^4$ is —H and $R^{4'}$ is —$NH_2$. In some embodiments, $R^1$ is —$OR^5$, $R^2$ is alkyl, $R^3$ is cycloalkyl, $R^4$ is —H and $R^{4'}$ is —$NH_2$. In some embodiments, $R^1$ is —$OR^5$, $R^2$ is cycloalkyl, $R^3$ is cycloalkyl, $R^4$ is —H and $R^{4'}$ is —$NH_2$. In some embodiments, $R^1$ is —$OR^5$, $R^2$ is aryl, $R^3$ is cycloalkyl, $R^4$ is —H and $R^{4'}$ is —$NH_2$. In some embodiments, $R^1$ is —$OR^5$, $R^2$ is heteroaryl, $R^3$ is cycloalkyl, $R^4$ is —H and $R^{4'}$ is —$NH_2$. In some embodiments, $R^1$ is —$OR^5$, $R^2$ is alkyl substituted with cycloalkyl, $R^3$ is cycloalkyl, $R^4$ is —H and $R^{4'}$ is —$NH_2$. In some embodiments, $R^1$ is $—OR^5$, $R^2$ is alkyl substituted with heterocycloalkyl, $R^3$ is cycloalkyl, $R^4$ is —H and $R^{4'}$ is $—NH_2$. In some embodiments, $R^1$ is $—OR^5$, $R^2$ is alkyl substituted with aryl, $R^3$ is cycloalkyl, $R^4$ is —H and $R^{4'}$ is $—NH_2$. In some embodiments, $R^1$ is $—OR^5$, $R^2$ is alkyl substituted with heteroaryl, $R^3$ is cycloalkyl, $R^4$ is —H and $R^{4'}$ is $—NH_2$.

In some embodiments, $R^1$ is $—OR^5$, $R^2$ is alkyl, $R^3$ is aryl, $R^4$ is —H and $R^{4'}$ is $—NH_2$. In some embodiments, $R^1$ is $—OR^5$, $R^2$ is cycloalkyl, $R^3$ is aryl, $R^4$ is —H and $R^{4'}$ is $—NH_2$. In some embodiments, $R^1$ is $—OR^5$, $R^2$ is aryl, $R^3$ is aryl, $R^4$ is —H and $R^{4'}$ is $—NH_2$. In some embodiments, $R^1$ is $—OR^5$, $R^2$ is heteroaryl, $R^3$ is aryl, $R^4$ is —H and $R^{4'}$ is $—NH_2$. In some embodiments, $R^1$ is $—OR^5$, $R^2$ is alkyl substituted with cycloalkyl, $R^3$ is aryl, $R^4$ is —H and $R^{4'}$ is $—NH_2$. In some embodiments, $R^1$ is $—OR^5$, $R^2$ is alkyl substituted with heterocycloalkyl, $R^3$ is aryl, $R^4$ is —H and $R^{4'}$ is $—NH_2$. In some embodiments, $R^1$ is $—OR^5$, $R^2$ is alkyl substituted with aryl, $R^3$ is aryl, $R^4$ is —H and $R^{4'}$ is $—NH_2$. In some embodiments, $R^1$ is $—OR^5$, $R^2$ is alkyl substituted with heteroaryl, $R^3$ is aryl, $R^4$ is —H and $R^{4'}$ is $—NH_2$.

In some embodiments, $R^1$ is $—OR^5$, $R^2$ is alkyl, $R^3$ is heteroaryl, $R^4$ is —H and $R^{4'}$ is $—NH_2$. In some embodiments, $R^1$ is $—OR^5$, $R^2$ is cycloalkyl, $R^3$ is heteroaryl, $R^4$ is —H and $R^{4'}$ is $—NH_2$. In some embodiments, $R^1$ is $—OR^5$, $R^2$ is aryl, $R^3$ is heteroaryl, $R^4$ is —H and $R^{4'}$ is $—NH_2$. In some embodiments, $R^1$ is $—OR^5$, $R^2$ is heteroaryl, $R^3$ is heteroaryl, $R^4$ is —H and $R^{4'}$ is $—NH_2$. In some embodiments, $R^1$ is $—OR^5$, $R^2$ is alkyl substituted with cycloalkyl, $R^3$ is heteroaryl, $R^4$ is —H and $R^{4'}$ is $—NH_2$. In some embodiments, $R^1$ is $—OR^5$, $R^2$ is alkyl substituted with heterocycloalkyl, $R^3$ is heteroaryl, $R^4$ is —H and $R^{4'}$ is $—NH_2$. In some embodiments, $R^1$ is $—OR^5$, $R^2$ is alkyl substituted with aryl, $R^3$ is heteroaryl, $R^4$ is —H and $R^{4'}$ is $—NH_2$. In some embodiments, $R^1$ is $—OR^5$, $R^2$ is alkyl substituted with heteroaryl, $R^3$ is heteroaryl, $R^4$ is —H and $R^{4'}$ is $—NH_2$.

In some embodiments, $R^1$ is $—OR^5$, $R^2$ is alkyl, $R^3$ is alkyl substituted with cycloalkyl, $R^4$ is —H and $R^{4'}$ is $—NH_2$. In some embodiments, $R^1$ is $—OR^5$, $R^2$ is cycloalkyl, $R^3$ is alkyl substituted with cycloalkyl, $R^4$ is —H and $R^{4'}$ is $—NH_2$. In some embodiments, $R^1$ is $—OR^5$, $R^2$ is aryl, $R^3$ is alkyl substituted with cycloalkyl, $R^4$ is —H and $R^{4'}$ is $—NH_2$. In some embodiments, $R^1$ is $—OR^5$, $R^2$ is heteroaryl, $R^3$ is alkyl substituted with cycloalkyl, $R^4$ is —H and $R^{4'}$ is $—NH_2$. In some embodiments, $R^1$ is $—OR^5$, $R^2$ is alkyl substituted with cycloalkyl, $R^3$ is alkyl substituted with cycloalkyl, $R^4$ is —H and $R^{4'}$ is $—NH_2$. In some embodiments, $R^1$ is $—OR^5$, $R^2$ is alkyl substituted with heterocycloalkyl, $R^3$ is alkyl substituted with cycloalkyl, $R^4$ is —H and $R^{4'}$ is $—NH_2$. In some embodiments, $R^1$ is $—OR^5$, $R^2$ is alkyl substituted with aryl, $R^3$ is alkyl substituted with cycloalkyl, $R^4$ is —H and $R^{4'}$ is $—NH_2$. In some embodiments, $R^1$ is $—OR^5$, $R^2$ is alkyl substituted with heteroaryl, $R^3$ is alkyl substituted with cycloalkyl, $R^4$ is —H and $R^{4'}$ is $—NH_2$.

In some embodiments, $R^1$ is $—OR^5$, $R^2$ is alkyl, $R^3$ is alkyl substituted with aryl, $R^4$ is —H and $R^{4'}$ is $—NH_2$. In some embodiments, $R^1$ is $—OR^5$, $R^2$ is cycloalkyl, $R^3$ is alkyl substituted with aryl, $R^4$ is —H and $R^{4'}$ is $—NH_2$. In some embodiments, $R^1$ is $—OR^5$, $R^2$ is aryl, $R^3$ is alkyl substituted with aryl, $R^4$ is —H and $R^{4'}$ is $—NH_2$. In some embodiments, $R^1$ is $—OR^5$, $R^2$ is heteroaryl, $R^3$ is alkyl substituted with aryl, $R^4$ is —H and $R^{4'}$ is $—NH_2$. In some embodiments, $R^1$ is $—OR^5$, $R^2$ is alkyl substituted with cycloalkyl, $R^3$ is alkyl substituted with aryl, $R^4$ is —H and $R^{4'}$ is $—NH_2$. In some embodiments, $R^1$ is $—OR^5$, $R^2$ is alkyl substituted with heterocycloalkyl, $R^3$ is alkyl substituted with aryl, $R^4$ is —H and $R^{4'}$ is $—NH_2$. In some embodiments, $R^1$ is $—OR^5$, $R^2$ is alkyl substituted with aryl, $R^3$ is alkyl substituted with aryl, $R^4$ is —H and $R^{4'}$ is $—NH_2$. In some embodiments, $R^1$ is $—OR^5$, $R^2$ is alkyl substituted with heteroaryl, $R^3$ is alkyl substituted with aryl, $R^4$ is —H and $R^{4'}$ is $—NH_2$.

In some embodiments, $R^1$ is $—OR^5$, $R^2$ is alkyl, $R^3$ is alkyl substituted with heteroaryl, $R^4$ is —H and $R^{4'}$ is $—NH_2$. In some embodiments, $R^1$ is $—OR^5$, $R^2$ is cycloalkyl, $R^3$ is alkyl substituted with heteroaryl, $R^4$ is —H and $R^{4'}$ is $—NH_2$. In some embodiments, $R^1$ is $—OR^5$, $R^2$ is aryl, $R^3$ is alkyl substituted with heteroaryl, $R^4$ is —H and $R^{4'}$ is $—NH_2$. In some embodiments, $R^1$ is $—OR^5$, $R^2$ is heteroaryl, $R^3$ is alkyl substituted with heteroaryl, $R^4$ is —H and $R^{4'}$ is $—NH_2$. In some embodiments, $R^1$ is $—OR^5$, $R^2$ is alkyl substituted with cycloalkyl, $R^3$ is alkyl substituted with heteroaryl, $R^4$ is —H and $R^{4'}$ is $—NH_2$. In some embodiments, $R^1$ is $—OR^5$, $R^2$ is alkyl substituted with heterocycloalkyl, $R^3$ is alkyl substituted with heteroaryl, $R^4$ is —H and $R^{4'}$ is $—NH_2$. In some embodiments, $R^1$ is $—OR^5$, $R^2$ is alkyl substituted with aryl, $R^3$ is alkyl substituted with heteroaryl, $R^4$ is —H and $R^{4'}$ is $—NH_2$. In some embodiments, $R^1$ is $—OR^5$, $R^2$ is alkyl substituted with heteroaryl, $R^3$ is alkyl substituted with heteroaryl, $R^4$ is —H and $R^{4'}$ is $—NH_2$.

In some embodiments, $R^1$ is $—OR^5$, $R^2$ is alkyl, $R^3$ is alkyl, $R^4$ is $—NH_2$ and $R^{4'}$ is —H. In some embodiments, $R^1$ is $—OR^5$, $R^2$ is cycloalkyl, $R^3$ is alkyl, $R^4$ is $—NH_2$ and $R^{4'}$ is —H. In some embodiments, $R^1$ is $—OR^5$, $R^2$ is aryl, $R^3$ is alkyl, $R^4$ is $—NH_2$ and $R^{4'}$ is —H. In some embodiments, $R^1$ is $—OR^5$, $R^2$ is heteroaryl, $R^3$ is alkyl, $R^4$ is $—NH_2$ and $R^{4'}$ is —H. In some embodiments, $R^1$ is $—OR^5$, $R^2$ is alkyl substituted with cycloalkyl, $R^3$ is alkyl, $R^4$ is $—NH_2$ and $R^{4'}$ is —H. In some embodiments, $R^1$ is $—OR^5$, $R^2$ is alkyl substituted with heterocycloalkyl, $R^3$ is alkyl, $R^4$ is $—NH_2$ and $R^{4'}$ is —H. In some embodiments, $R^1$ is $—OR^5$, $R^2$ is alkyl substituted with aryl, $R^3$ is alkyl, $R^4$ is $—NH_2$ and $R^{4'}$ is —H. In some embodiments, $R^1$ is $—OR^5$, $R^2$ is alkyl substituted with heteroaryl, $R^3$ is alkyl, $R^4$ is $—NH_2$ and $R^{4'}$ is —H.

In some embodiments, $R^1$ is $—OR^5$, $R^2$ is alkyl, $R^3$ is cycloalkyl, $R^4$ is $—NH_2$ and $R^{4'}$ is —H. In some embodiments, $R^1$ is $—OR^5$, $R^2$ is cycloalkyl, $R^3$ is cycloalkyl, $R^4$ is $—NH_2$ and $R^{4'}$ is —H. In some embodiments, $R^1$ is $—OR^5$, $R^2$ is aryl, $R^3$ is cycloalkyl, $R^4$ is $—NH_2$ and $R^{4'}$ is —H. In some embodiments, $R^1$ is $—OR^5$, $R^2$ is heteroaryl, $R^3$ is cycloalkyl, $R^4$ is $—NH_2$ and $R^{4'}$ is —H. In some embodiments, $R^1$ is $—OR^5$, $R^2$ is alkyl substituted with cycloalkyl, $R^3$ is cycloalkyl, $R^4$ is $—NH_2$ and $R^{4'}$ is —H. In some embodiments, $R^1$ is $—OR^5$, $R^2$ is alkyl substituted with heterocycloalkyl, $R^3$ is cycloalkyl, $R^4$ is $—NH_2$ and $R^{4'}$ is —H. In some embodiments, $R^1$ is $—OR^5$, $R^2$ is alkyl substituted with aryl, $R^3$ is cycloalkyl, $R^4$ is $—NH_2$ and $R^{4'}$ is —H. In some embodiments, $R^1$ is $—OR^5$, $R^2$ is alkyl substituted with heteroaryl, $R^3$ is cycloalkyl, $R^4$ is $—NH_2$ and $R^{4'}$ is —H.

In some embodiments, $R^1$ is $—OR^5$, $R^2$ is alkyl, $R^3$ is aryl, $R^4$ is $—NH_2$ and $R^{4'}$ is —H. In some embodiments, $R^1$ is $—OR^5$, $R^2$ is cycloalkyl, $R^3$ is aryl, $R^4$ is $—NH_2$ and $R^{4'}$ is —H. In some embodiments, $R^1$ is $—OR^5$, $R^2$ is aryl, $R^3$ is aryl, $R^4$ is $—NH_2$ and $R^{4'}$ is —H. In some embodiments, $R^1$ is $—OR^5$, $R^2$ is heteroaryl, $R^3$ is aryl, $R^4$ is $—NH_2$ and $R^{4'}$ is —H. In some embodiments, $R^1$ is $—OR^5$, $R^2$ is alkyl substituted with cycloalkyl, $R^3$ is aryl, $R^4$ is $—NH_2$ and $R^{4'}$ is —H. In some embodiments, $R^1$ is $—OR^5$, $R^2$ is alkyl substituted with heterocycloalkyl, $R^3$ is aryl, $R^4$ is —$NH_2$ and $R^{4'}$ is —H. In some embodiments, $R^1$ is —$OR^5$, $R^2$ is alkyl substituted with aryl, $R^3$ is aryl, $R^4$ is —$NH_2$ and $R^{4'}$ is —H. In some embodiments, $R^1$ is —$OR^5$, $R^2$ is alkyl substituted with heteroaryl, $R^3$ is aryl, $R^4$ is —$NH_2$ and $R^{4'}$ is —H.

In some embodiments, $R^1$ is —$OR^5$, $R^2$ is alkyl, $R^3$ is heteroaryl, $R^4$ is —$NH_2$ and $R^{4'}$ is —H. In some embodiments, $R^1$ is —$OR^5$, $R^2$ is cycloalkyl, $R^3$ is heteroaryl, $R^4$ is —$NH_2$ and $R^{4'}$ is —H. In some embodiments, $R^1$ is —$OR^5$, $R^2$ is aryl, $R^3$ is heteroaryl, $R^4$ is —$NH_2$ and $R^{4'}$ is —H. In some embodiments, $R^1$ is —$OR^5$, $R^2$ is heteroaryl, $R^3$ is heteroaryl, $R^4$ is —$NH_2$ and $R^{4'}$ is —H. In some embodiments, $R^1$ is —$OR^5$, $R^2$ is alkyl substituted with cycloalkyl, $R^3$ is heteroaryl, $R^4$ is —$NH_2$ and $R^{4'}$ is —H. In some embodiments, $R^1$ is —$OR^5$, $R^2$ is alkyl substituted with heterocycloalkyl, $R^3$ is heteroaryl, $R^4$ is —$NH_2$ and $R^{4'}$ is —H. In some embodiments, $R^1$ is —$OR^5$, $R^2$ is alkyl substituted with aryl, $R^3$ is heteroaryl, $R^4$ is —$NH_2$ and $R^{4'}$ is —H. In some embodiments, $R^1$ is —$OR^5$, $R^2$ is alkyl substituted with heteroaryl, $R^3$ is heteroaryl, $R^4$ is —$NH_2$ and $R^{4'}$ is —H.

In some embodiments, $R^1$ is —$OR^5$, $R^2$ is alkyl, $R^3$ is alkyl substituted with cycloalkyl, $R^4$ is —$NH_2$ and $R^{4'}$ is —H. In some embodiments, $R^1$ is —$OR^5$, $R^2$ is cycloalkyl, $R^3$ is alkyl substituted with cycloalkyl, $R^4$ is —$NH_2$ and $R^{4'}$ is —H. In some embodiments, $R^1$ is —$OR^5$, $R^2$ is aryl, $R^3$ is alkyl substituted with cycloalkyl, $R^4$ is —$NH_2$ and $R^{4'}$ is —H. In some embodiments, $R^1$ is —$OR^5$, $R^2$ is heteroaryl, $R^3$ is alkyl substituted with cycloalkyl, $R^4$ is —$NH_2$ and $R^{4'}$ is —H. In some embodiments, $R^1$ is —$OR^5$, $R^2$ is alkyl substituted with cycloalkyl, $R^3$ is alkyl substituted with cycloalkyl, $R^4$ is —$NH_2$ and $R^{4'}$ is —H. In some embodiments, $R^1$ is —$OR^5$, $R^2$ is alkyl substituted with heterocycloalkyl, $R^3$ is alkyl substituted with cycloalkyl, $R^4$ is —$NH_2$ and $R^{4'}$ is —H. In some embodiments, $R^1$ is —$OR^5$, $R^2$ is alkyl substituted with aryl, $R^3$ is alkyl substituted with cycloalkyl, $R^4$ is —$NH_2$ and $R^{4'}$ is —H. In some embodiments, $R^1$ is —$OR^5$, $R^2$ is alkyl substituted with heteroaryl, $R^3$ is alkyl substituted with cycloalkyl, $R^4$ is —$NH_2$ and $R^{4'}$ is —H.

In some embodiments, $R^1$ is —$OR^5$, $R^2$ is alkyl, $R^3$ is alkyl substituted with aryl, $R^4$ is —$NH_2$ and $R^{4'}$ is —H. In some embodiments, $R^1$ is —$OR^5$, $R^2$ is cycloalkyl, $R^3$ is alkyl substituted with aryl, $R^4$ is —$NH_2$ and $R^{4'}$ is —H. In some embodiments, $R^1$ is —$OR^5$, $R^2$ is aryl, $R^3$ is alkyl substituted with aryl, $R^4$ is —$NH_2$ and $R^{4'}$ is —H. In some embodiments, $R^1$ is —$OR^5$, $R^2$ is heteroaryl, $R^3$ is alkyl substituted with aryl, $R^4$ is —$NH_2$ and $R^{4'}$ is —H. In some embodiments, $R^1$ is —$OR^5$, $R^2$ is alkyl substituted with cycloalkyl, $R^3$ is alkyl substituted with aryl, $R^4$ is —$NH_2$ and $R^{4'}$ is —H. In some embodiments, $R^1$ is —$OR^5$, $R^2$ is alkyl substituted with heterocycloalkyl, $R^3$ is alkyl substituted with aryl, $R^4$ is —$NH_2$ and $R^{4'}$ is —H. In some embodiments, $R^1$ is —$OR^5$, $R^2$ is alkyl substituted with aryl, $R^3$ is alkyl substituted with aryl, $R^4$ is —$NH_2$ and $R^{4'}$ is —H. In some embodiments, $R^1$ is —$OR^5$, $R^2$ is alkyl substituted with heteroaryl, $R^3$ is alkyl substituted with aryl, $R^4$ is —$NH_2$ and $R^{4'}$ is —H.

In some embodiments, $R^1$ is —$OR^5$, $R^2$ is alkyl, $R^3$ is alkyl substituted with heteroaryl, $R^4$ is —$NH_2$ and $R^{4'}$ is —H. In some embodiments, $R^1$ is —$OR^5$, $R^2$ is cycloalkyl, $R^3$ is alkyl substituted with heteroaryl, $R^4$ is —$NH_2$ and $R^{4'}$ is —H. In some embodiments, $R^1$ is —$OR^5$, $R^2$ is aryl, $R^3$ is alkyl substituted with heteroaryl, $R^4$ is —$NH_2$ and $R^{4'}$ is —H. In some embodiments, $R^1$ is —$OR^5$, $R^2$ is heteroaryl, $R^3$ is alkyl substituted with heteroaryl, $R^4$ is —$NH_2$ and $R^{4'}$ is —H. In some embodiments, $R^1$ is —$OR^5$, $R^2$ is alkyl substituted with cycloalkyl, $R^3$ is alkyl substituted with heteroaryl, $R^4$ is —$NH_2$ and $R^{4'}$ is —H. In some embodiments, $R^1$ is —$OR^5$, $R^2$ is alkyl substituted with heterocycloalkyl, $R^3$ is alkyl substituted with heteroaryl, $R^4$ is —$NH_2$ and $R^{4'}$ is —H. In some embodiments, $R^1$ is —$OR^5$, $R^2$ is alkyl substituted with aryl, $R^3$ is alkyl substituted with heteroaryl, $R^4$ is —$NH_2$ and $R^{4'}$ is —H. In some embodiments, $R^1$ is —$OR^5$, $R^2$ is alkyl substituted with heteroaryl, $R^3$ is alkyl substituted with heteroaryl, $R^4$ is —$NH_2$ and $R^{4'}$ is —H.

In some embodiments, $R^1$ is —$OR^5$, $R^2$ is alkyl, $R^3$ is alkyl, $R^4$ is —H and $R^{4'}$ is —CN. In some embodiments, $R^1$ is —$OR^5$, $R^2$ is cycloalkyl, $R^3$ is alkyl, $R^4$ is —H and $R^{4'}$ is —CN. In some embodiments, $R^1$ is —$OR^5$, $R^2$ is aryl, $R^3$ is alkyl, $R^4$ is —H and $R^{4'}$ is —CN. In some embodiments, $R^1$ is —$OR^5$, $R^2$ is heteroaryl, $R^3$ is alkyl, $R^4$ is —H and $R^{4'}$ is —CN. In some embodiments, $R^1$ is —$OR^5$, $R^2$ is alkyl substituted with cycloalkyl, $R^3$ is alkyl, $R^4$ is —H and $R^{4'}$ is —CN. In some embodiments, $R^1$ is —$OR^5$, $R^2$ is alkyl substituted with heterocycloalkyl, $R^3$ is alkyl, $R^4$ is —H and $R^{4'}$ is —CN. In some embodiments, $R^1$ is —$OR^5$, $R^2$ is alkyl substituted with aryl, $R^3$ is alkyl, $R^4$ is —H and $R^{4'}$ is —CN. In some embodiments, $R^1$ is —$OR^5$, $R^2$ is alkyl substituted with heteroaryl, $R^3$ is alkyl, $R^4$ is —H and $R^{4'}$ is —CN.

In some embodiments, $R^1$ is —$OR^5$, $R^2$ is alkyl, $R^3$ is cycloalkyl, $R^4$ is —H and $R^{4'}$ is —CN. In some embodiments, $R^1$ is —$OR^5$, $R^2$ is cycloalkyl, $R^3$ is cycloalkyl, $R^4$ is —H and $R^{4'}$ is —CN. In some embodiments, $R^1$ is —$OR^5$, $R^2$ is aryl, $R^3$ is cycloalkyl, $R^4$ is —H and $R^{4'}$ is —CN. In some embodiments, $R^1$ is —$OR^5$, $R^2$ is heteroaryl, $R^3$ is cycloalkyl, $R^4$ is —H and $R^{4'}$ is —CN. In some embodiments, $R^1$ is —$OR^5$, $R^2$ is alkyl substituted with cycloalkyl, $R^3$ is cycloalkyl, $R^4$ is —H and $R^{4'}$ is —CN. In some embodiments, $R^1$ is —$OR^5$, $R^2$ is alkyl substituted with heterocycloalkyl, $R^3$ is cycloalkyl, $R^4$ is —H and $R^{4'}$ is —CN. In some embodiments, $R^1$ is —$OR^5$, $R^2$ is alkyl substituted with aryl, $R^3$ is cycloalkyl, $R^4$ is —H and $R^{4'}$ is —CN. In some embodiments, $R^1$ is —$OR^5$, $R^2$ is alkyl substituted with heteroaryl, $R^3$ is cycloalkyl, $R^4$ is —H and $R^{4'}$ is —CN.

In some embodiments, $R^1$ is —$OR^5$, $R^2$ is alkyl, $R^3$ is aryl, $R^4$ is —H and $R^{4'}$ is —CN. In some embodiments, $R^1$ is —$OR^5$, $R^2$ is cycloalkyl, $R^3$ is aryl, $R^4$ is —H and $R^{4'}$ is —CN. In some embodiments, $R^1$ is —$OR^5$, $R^2$ is aryl, $R^3$ is aryl, $R^4$ is —H and $R^{4'}$ is —CN. In some embodiments, $R^1$ is —$OR^5$, $R^2$ is heteroaryl, $R^3$ is aryl, $R^4$ is —H and $R^{4'}$ is —CN. In some embodiments, $R^1$ is —$OR^5$, $R^2$ is alkyl substituted with cycloalkyl, $R^3$ is aryl, $R^4$ is —H and $R^{4'}$ is —CN. In some embodiments, $R^1$ is —$OR^5$, $R^2$ is alkyl substituted with heterocycloalkyl, $R^3$ is aryl, $R^4$ is —H and $R^{4'}$ is —CN. In some embodiments, $R^1$ is —$OR^5$, $R^2$ is alkyl substituted with aryl, $R^3$ is aryl, $R^4$ is —H and $R^{4'}$ is —CN. In some embodiments, $R^1$ is —$OR^5$, $R^2$ is alkyl substituted with heteroaryl, $R^3$ is aryl, $R^4$ is —H and $R^{4'}$ is —CN.

In some embodiments, $R^1$ is —$OR^5$, $R^2$ is alkyl, $R^3$ is heteroaryl, $R^4$ is —H and $R^{4'}$ is —CN. In some embodiments, $R^1$ is —$OR^5$, $R^2$ is cycloalkyl, $R^3$ is heteroaryl, $R^4$ is —H and $R^{4'}$ is —CN. In some embodiments, $R^1$ is —$OR^5$, $R^2$ is aryl, $R^3$ is heteroaryl, $R^4$ is —H and $R^{4'}$ is —CN. In some embodiments, $R^1$ is —$OR^5$, $R^2$ is heteroaryl, $R^3$ is heteroaryl, $R^4$ is —H and $R^{4'}$ is —CN. In some embodiments, $R^1$ is —$OR^5$, $R^2$ is alkyl substituted with cycloalkyl, $R^3$ is heteroaryl, $R^4$ is —H and $R^{4'}$ is —CN. In some embodiments, $R^1$ is —$OR^5$, $R^2$ is alkyl substituted with heterocycloalkyl, $R^3$ is heteroaryl, $R^4$ is —H and $R^{4'}$ is —CN. In some embodiments, $R^1$ is —$OR^5$, $R^2$ is alkyl substituted with aryl, $R^3$ is heteroaryl, $R^4$ is —H and $R^{4'}$ is —CN. In some embodiments, $R^1$ is —$OR^5$, $R^2$ is alkyl substituted with heteroaryl, $R^3$ is heteroaryl, $R^4$ is —H and $R^{4'}$ is —CN.

In some embodiments, $R^1$ is —$OR^5$, $R^2$ is alkyl, $R^3$ is alkyl substituted with cycloalkyl, $R^4$ is —H and $R^{4'}$ is —CN. In some embodiments, $R^1$ is —$OR^5$, $R^2$ is cycloalkyl, $R^3$ is alkyl substituted with cycloalkyl, $R^4$ is —H and $R^{4'}$ is —CN. In some embodiments, $R^1$ is —$OR^5$, $R^2$ is aryl, $R^3$ is alkyl substituted with cycloalkyl, $R^4$ is —H and $R^{4'}$ is —CN. In some embodiments, $R^1$ is —$OR^5$, $R^2$ is heteroaryl, $R^3$ is alkyl substituted with cycloalkyl, $R^4$ is —H and $R^{4'}$ is —CN. In some embodiments, $R^1$ is —$OR^5$, $R^2$ is alkyl substituted with cycloalkyl, $R^3$ is alkyl substituted with cycloalkyl, $R^4$ is —H and $R^{4'}$ is —CN. In some embodiments, $R^1$ is —$OR^5$, $R^2$ is alkyl substituted with heterocycloalkyl, $R^3$ is alkyl substituted with cycloalkyl, $R^4$ is —H and $R^{4'}$ is —CN. In some embodiments, $R^1$ is —$OR^5$, $R^2$ is alkyl substituted with aryl, $R^3$ is alkyl substituted with cycloalkyl, $R^4$ is —H and $R^{4'}$ is —CN. In some embodiments, $R^1$ is —$OR^5$, $R^2$ is alkyl substituted with heteroaryl, $R^3$ is alkyl substituted with cycloalkyl, $R^4$ is —H and $R^{4'}$ is —CN.

In some embodiments, $R^1$ is —$OR^5$, $R^2$ is alkyl, $R^3$ is alkyl substituted with aryl, $R^4$ is —H and $R^{4'}$ is —CN. In some embodiments, $R^1$ is —$OR^5$, $R^2$ is cycloalkyl, $R^3$ is alkyl substituted with aryl, $R^4$ is —H and $R^{4'}$ is —CN. In some embodiments, $R^1$ is —$OR^5$, $R^2$ is aryl, $R^3$ is alkyl substituted with aryl, $R^4$ is —H and $R^{4'}$ is —CN. In some embodiments, $R^1$ is —$OR^5$, $R^2$ is heteroaryl, $R^3$ is alkyl substituted with aryl, $R^4$ is —H and $R^{4'}$ is —CN. In some embodiments, $R^1$ is —$OR^5$, $R^2$ is alkyl substituted with cycloalkyl, $R^3$ is alkyl substituted with aryl, $R^4$ is —H and $R^{4'}$ is —CN. In some embodiments, $R^1$ is —$OR^5$, $R^2$ is alkyl substituted with heterocycloalkyl, $R^3$ is alkyl substituted with aryl, $R^4$ is —H and $R^{4'}$ is —CN. In some embodiments, $R^1$ is —$OR^5$, $R^2$ is alkyl substituted with aryl, $R^3$ is alkyl substituted with aryl, $R^4$ is —H and $R^{4'}$ is —CN. In some embodiments, $R^1$ is —$OR^5$, $R^2$ is alkyl substituted with heteroaryl, $R^3$ is alkyl substituted with aryl, $R^4$ is —H and $R^{4'}$ is —CN.

In some embodiments, $R^1$ is —$OR^5$, $R^2$ is alkyl, $R^3$ is alkyl substituted with heteroaryl, $R^4$ is —H and $R^{4'}$ is —CN. In some embodiments, $R^1$ is —$OR^5$, $R^2$ is cycloalkyl, $R^3$ is alkyl substituted with heteroaryl, $R^4$ is —H and $R^{4'}$ is —CN. In some embodiments, $R^1$ is —$OR^5$, $R^2$ is aryl, $R^3$ is alkyl substituted with heteroaryl, $R^4$ is —H and $R^{4'}$ is —CN. In some embodiments, $R^1$ is —$OR^5$, $R^2$ is heteroaryl, $R^3$ is alkyl substituted with heteroaryl, $R^4$ is —H and $R^{4'}$ is —CN. In some embodiments, $R^1$ is —$OR^5$, $R^2$ is alkyl substituted with cycloalkyl, $R^3$ is alkyl substituted with heteroaryl, $R^4$ is —H and $R^{4'}$ is —CN. In some embodiments, $R^1$ is —$OR^5$, $R^2$ is alkyl substituted with heterocycloalkyl, $R^3$ is alkyl substituted with heteroaryl, $R^4$ is —H and $R^{4'}$ is —CN. In some embodiments, $R^1$ is —$OR^5$, $R^2$ is alkyl substituted with aryl, $R^3$ is alkyl substituted with heteroaryl, $R^4$ is —H and $R^{4'}$ is —CN. In some embodiments, $R^1$ is —$OR^5$, $R^2$ is alkyl substituted with heteroaryl, $R^3$ is alkyl substituted with heteroaryl, $R^4$ is —H and $R^{4'}$ is —CN.

In some embodiments, $R^1$ is —$OR^5$, $R^2$ is alkyl, $R^3$ is alkyl, $R^4$ is —CN and $R^{4'}$ is —H. In some embodiments, $R^1$ is —$OR^5$, $R^2$ is cycloalkyl, $R^3$ is alkyl, $R^4$ is —CN and $R^{4'}$ is —H. In some embodiments, $R^1$ is —$OR^5$, $R^2$ is aryl, $R^3$ is alkyl, $R^4$ is —CN and $R^{4'}$ is —H. In some embodiments, $R^1$ is —$OR^5$, $R^2$ is heteroaryl, $R^3$ is alkyl, $R^4$ is —CN and $R^{4'}$ is —H. In some embodiments, $R^1$ is —$OR^5$, $R^2$ is alkyl substituted with cycloalkyl, $R^3$ is alkyl, $R^4$ is —CN and $R^{4'}$ is —H. In some embodiments, $R^1$ is —$OR^5$, $R^2$ is alkyl substituted with heterocycloalkyl, $R^3$ is alkyl, $R^4$ is —CN and $R^{4'}$ is —H. In some embodiments, $R^1$ is —$OR^5$, $R^2$ is alkyl substituted with aryl, $R^3$ is alkyl, $R^4$ is —CN and $R^{4'}$ is —H. In some embodiments, $R^1$ is —$OR^5$, $R^2$ is alkyl substituted with heteroaryl, $R^3$ is alkyl, $R^4$ is —CN and $R^{4'}$ is —H.

In some embodiments, $R^1$ is —$OR^5$, $R^2$ is alkyl, $R^3$ is cycloalkyl, $R^4$ is —CN and $R^{4'}$ is —H. In some embodiments, $R^1$ is —$OR^5$, $R^2$ is cycloalkyl, $R^3$ is cycloalkyl, $R^4$ is —CN and $R^{4'}$ is —H. In some embodiments, $R^1$ is —$OR^5$, $R^2$ is aryl, $R^3$ is cycloalkyl, $R^4$ is —CN and $R^{4'}$ is —H. In some embodiments, $R^1$ is —$OR^5$, $R^2$ is heteroaryl, $R^3$ is cycloalkyl, $R^4$ is —CN and $R^{4'}$ is —H. In some embodiments, $R^1$ is —$OR^5$, $R^2$ is alkyl substituted with cycloalkyl, $R^3$ is cycloalkyl, $R^4$ is —CN and $R^{4'}$ is —H. In some embodiments, $R^1$ is —$OR^5$, $R^2$ is alkyl substituted with heterocycloalkyl, $R^3$ is cycloalkyl, $R^4$ is —CN and $R^{4'}$ is —H. In some embodiments, $R^1$ is —$OR^5$, $R^2$ is alkyl substituted with aryl, $R^3$ is cycloalkyl, $R^4$ is —CN and $R^{4'}$ is —H. In some embodiments, $R^1$ is —$OR^5$, $R^2$ is alkyl substituted with heteroaryl, $R^3$ is cycloalkyl, $R^4$ is —CN and $R^{4'}$ is —H.

In some embodiments, $R^1$ is —$OR^5$, $R^2$ is alkyl, $R^3$ is aryl, $R^4$ is —CN and $R^{4'}$ is —H. In some embodiments, $R^1$ is —$OR^5$, $R^2$ is cycloalkyl, $R^3$ is aryl, $R^4$ is —CN and $R^{4'}$ is —H. In some embodiments, $R^1$ is —$OR^5$, $R^2$ is aryl, $R^3$ is aryl, $R^4$ is —CN and $R^{4'}$ is —H. In some embodiments, $R^1$ is —$OR^5$, $R^2$ is heteroaryl, $R^3$ is aryl, $R^4$ is —CN and $R^{4'}$ is —H. In some embodiments, $R^1$ is —$OR^5$, $R^2$ is alkyl substituted with cycloalkyl, $R^3$ is aryl, $R^4$ is —CN and $R^{4'}$ is —H. In some embodiments, $R^1$ is —$OR^5$, $R^2$ is alkyl substituted with heterocycloalkyl, $R^3$ is aryl, $R^4$ is —CN and $R^{4'}$ is —H. In some embodiments, $R^1$ is —$OR^5$, $R^2$ is alkyl substituted with aryl, $R^3$ is aryl, $R^4$ is —CN and $R^{4'}$ is —H. In some embodiments, $R^1$ is —$OR^5$, $R^2$ is alkyl substituted with heteroaryl, $R^3$ is aryl, $R^4$ is —CN and $R^{4'}$ is —H.

In some embodiments, $R^1$ is —$OR^5$, $R^2$ is alkyl, $R^3$ is heteroaryl, $R^4$ is —CN and $R^{4'}$ is —H. In some embodiments, $R^1$ is —$OR^5$, $R^2$ is cycloalkyl, $R^3$ is heteroaryl, $R^4$ is —CN and $R^{4'}$ is —H. In some embodiments, $R^1$ is —$OR^5$, $R^2$ is aryl, $R^3$ is heteroaryl, $R^4$ is —CN and $R^{4'}$ is —H. In some embodiments, $R^1$ is —$OR^5$, $R^2$ is heteroaryl, $R^3$ is heteroaryl, $R^4$ is —CN and $R^{4'}$ is —H. In some embodiments, $R^1$ is —$OR^5$, $R^2$ is alkyl substituted with cycloalkyl, $R^3$ is heteroaryl, $R^4$ is —CN and $R^{4'}$ is —H. In some embodiments, $R^1$ is —$OR^5$, $R^2$ is alkyl substituted with heterocycloalkyl, $R^3$ is heteroaryl, $R^4$ is —CN and $R^{4'}$ is —H. In some embodiments, $R^1$ is —$OR^5$, $R^2$ is alkyl substituted with aryl, $R^3$ is heteroaryl, $R^4$ is —CN and $R^{4'}$ is —H. In some embodiments, $R^1$ is —$OR^5$, $R^2$ is alkyl substituted with heteroaryl, $R^3$ is heteroaryl, $R^4$ is —CN and $R^{4'}$ is —H.

In some embodiments, $R^1$ is —$OR^5$, $R^2$ is alkyl, $R^3$ is alkyl substituted with cycloalkyl, $R^4$ is —CN and $R^{4'}$ is —H. In some embodiments, $R^1$ is —$OR^5$, $R^2$ is cycloalkyl, $R^3$ is alkyl substituted with cycloalkyl, $R^4$ is —CN and $R^{4'}$ is —H. In some embodiments, $R^1$ is —$OR^5$, $R^2$ is aryl, $R^3$ is alkyl substituted with cycloalkyl, $R^4$ is —CN and $R^{4'}$ is —H. In some embodiments, $R^1$ is —$OR^5$, $R^2$ is heteroaryl, $R^3$ is alkyl substituted with cycloalkyl, $R^4$ is —CN and $R^{4'}$ is —H. In some embodiments, $R^1$ is —$OR^5$, $R^2$ is alkyl substituted with cycloalkyl, $R^3$ is alkyl substituted with cycloalkyl, $R^4$ is —CN and $R^{4'}$ is —H. In some embodiments, $R^1$ is —$OR^5$, $R^2$ is alkyl substituted with heterocycloalkyl, $R^3$ is alkyl substituted with cycloalkyl, $R^4$ is —CN and $R^{4'}$ is —H. In some embodiments, $R^1$ is —$OR^5$, $R^2$ is alkyl substituted with aryl, $R^3$ is alkyl substituted with cycloalkyl, $R^4$ is —CN and $R^{4'}$ is —H. In some embodiments, $R^1$ is —$OR^5$, $R^2$ is alkyl substituted with heteroaryl, $R^3$ is alkyl substituted with cycloalkyl, $R^4$ is —CN and $R^{4'}$ is —H.

In some embodiments, $R^1$ is —$OR^5$, $R^2$ is alkyl, $R^3$ is alkyl substituted with aryl, $R^4$ is —CN and $R^{4'}$ is —H. In some embodiments, $R^1$ is —$OR^5$, $R^2$ is cycloalkyl, $R^3$ is alkyl substituted with aryl, $R^4$ is —CN and $R^{4'}$ is —H. In some embodiments, $R^1$ is —$OR^5$, $R^2$ is aryl, $R^3$ is alkyl substituted with aryl, $R^4$ is —CN and $R^{4'}$ is —H. In some embodiments, $R^1$ is —$OR^5$, $R^2$ is heteroaryl, $R^3$ is alkyl substituted with aryl, $R^4$ is —CN and $R^{4'}$ is —H. In some embodiments, $R^1$ is —$OR^5$, $R^2$ is alkyl substituted with cycloalkyl, $R^3$ is alkyl substituted with aryl, $R^4$ is —CN and $R^{4'}$ is —H. In some embodiments, $R^1$ is —$OR^5$, $R^2$ is alkyl substituted with heterocycloalkyl, $R^3$ is alkyl substituted with aryl, $R^4$ is —CN and $R^{4'}$ is —H. In some embodiments, $R^1$ is —$OR^5$, $R^2$ is alkyl substituted with aryl, $R^3$ is alkyl substituted with aryl, $R^4$ is —CN and $R^{4'}$ is —H. In some embodiments, $R^1$ is —$OR^5$, $R^2$ is alkyl substituted with heteroaryl, $R^3$ is alkyl substituted with aryl, $R^4$ is —CN and $R^{4'}$ is —H.

In some embodiments, $R^1$ is —$OR^5$, $R^2$ is alkyl, $R^3$ is alkyl substituted with heteroaryl, $R^4$ is —CN and $R^{4'}$ is —H. In some embodiments, $R^1$ is —$OR^5$, $R^2$ is cycloalkyl, $R^3$ is alkyl substituted with heteroaryl, $R^4$ is —CN and $R^{4'}$ is —H. In some embodiments, $R^1$ is —$OR^5$, $R^2$ is aryl, $R^3$ is alkyl substituted with heteroaryl, $R^4$ is —CN and $R^{4'}$ is —H. In some embodiments, $R^1$ is —$OR^5$, $R^2$ is heteroaryl, $R^3$ is alkyl substituted with heteroaryl, $R^4$ is —CN and $R^{4'}$ is —H. In some embodiments, $R^1$ is —$OR^5$, $R^2$ is alkyl substituted with cycloalkyl, $R^3$ is alkyl substituted with heteroaryl, $R^4$ is —CN and $R^{4'}$ is —H. In some embodiments, $R^1$ is —$OR^5$, $R^2$ is alkyl substituted with heterocycloalkyl, $R^3$ is alkyl substituted with heteroaryl, $R^4$ is —CN and $R^{4'}$ is —H. In some embodiments, $R^1$ is —$OR^5$, $R^2$ is alkyl substituted with aryl, $R^3$ is alkyl substituted with heteroaryl, $R^4$ is —CN and $R^{4'}$ is —H. In some embodiments, $R^1$ is —$OR^5$, $R^2$ is alkyl substituted with heteroaryl, $R^3$ is alkyl substituted with heteroaryl, $R^4$ is —CN and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is alkyl substituted with heterocycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl and $R^2$ is alkyl substituted with heteroaryl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, and $R^3$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, and $R^3$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, and $R^3$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, and $R^3$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, and $R^3$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, and $R^3$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, and $R^3$ is alkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, and $R^3$ is alkyl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, and $R^3$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, and $R^3$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, and $R^3$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, and $R^3$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, and $R^3$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, and $R^3$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, and $R^3$ is cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, and $R^3$ is cycloalkyl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, and $R^3$ is aryl. In some embodiments, $R^1$ is —$C_1$-$C_6$alkyl, —$C_2$-$C_6$alkenyl, —$C_2$-$C_6$alkynyl, —$C_3$-

$C_8$cycloalkyl, —$C_4$-$C_8$cycloalkenyl, heterocycloalkyl, heteroaryl, or aryl, $R^2$ is cycloalkyl, and $R^3$ is aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, and $R^3$ is aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, and $R^3$ is aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, and $R^3$ is aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, and $R^3$ is aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, and $R^3$ is aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, and $R^3$ is aryl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, and $R^3$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, and $R^3$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, and $R^3$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, and $R^3$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, and $R^3$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, and $R^3$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, and $R^3$ is heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, and $R^3$ is heteroaryl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, and $R^3$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, and $R^3$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, and $R^3$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, and $R^3$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, and $R^3$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, and $R^3$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, and $R^3$ is alkyl substituted with cycloalkyl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, and $R^3$ is alkyl substituted with cycloalkyl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, and $R^3$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, and $R^3$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, and $R^3$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, and $R^3$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, and $R^3$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, and $R^3$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, and $R^3$ is alkyl substituted with aryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, and $R^3$ is alkyl substituted with aryl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, and $R^3$ is alkyl substituted with heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, and $R^3$ is alkyl substituted with heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, and $R^3$ is alkyl substituted with heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, and $R^3$ is alkyl substituted with heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, and $R^3$ is alkyl substituted with heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, and $R^3$ is alkyl substituted with heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, and $R^3$ is alkyl substituted with heteroaryl. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, and $R^3$ is alkyl substituted with heteroaryl.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl, and $R^4$ and $R^{4'}$ are —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is cycloalkyl, and $R^4$ and $R^{4'}$ are —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is aryl, and $R^4$ and $R^{4'}$ are —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is heteroaryl, and $R^4$ and $R^{4'}$ are —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with cycloalkyl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with cycloalkyl, and $R^4$ and $R^{4'}$ are —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with aryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with aryl, and $R^4$ and $R^{4'}$ are —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with heteroaryl, and $R^4$ and $R^{4'}$ are —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with heteroaryl, and $R^4$ and $R^{4'}$ are —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl, $R^4$ is —H and $R^{4'}$ is —OH. In some embodiments, $R^1$ is —$C_1$-$C_6$alkyl, —$C_2$-

$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is cycloalkyl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is cycloalkyl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is aryl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is heteroaryl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is heteroaryl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with cycloalkyl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with cycloalkyl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with aryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with aryl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with heteroaryl, $R^4$ is —H and $R^{4'}$ is —OH. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with heteroaryl, $R^4$ is —H and $R^{4'}$ is —OH.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl, $R^4$ is —OH and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is cycloalkyl, $R^4$ is —OH and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is aryl, $R^4$ is —OH and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is heteroaryl, $R^4$ is —OH and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with cycloalkyl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with cycloalkyl, $R^4$ is —OH and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with aryl, $R^4$ is —OH and $R^{4'}$ is —H. In some embodiments, $R^1$ is —$C_1$-

$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with aryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with aryl, $R^4$ is —OH and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with heteroaryl, $R^4$ is —OH and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with heteroaryl, $R^4$ is —OH and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl, $R^4$ is —H and $R^{4'}$ is —$NH_2$.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is cycloalkyl, $R^4$ is —H and $R^{4'}$ is —$NH_2$.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is cycloalkyl, $R^4$ is —H and $R^{4'}$ is —$NH_2$.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is aryl, $R^4$ is —H and $R^{4'}$ is —$NH_2$.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is heteroaryl, $R^4$ is —H and $R^{4'}$ is —$NH_2$.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with cycloalkyl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with cycloalkyl, $R^4$ is —H and $R^{4'}$ is —$NH_2$.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with aryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with aryl, $R^4$ is —H and $R^{4'}$ is —$NH_2$.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with heteroaryl, $R^4$ is —H and $R^{4'}$ is —$NH_2$. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with heteroaryl, R$^4$ is —H and R$^{4'}$ is —$NH_2$. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heterocycloalkyl, R$^3$ is alkyl substituted with heteroaryl, R$^4$ is —H and R$^{4'}$ is —$NH_2$. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with aryl, R$^3$ is alkyl substituted with heteroaryl, R$^4$ is —H and R$^{4'}$ is —$NH_2$. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heteroaryl, R$^3$ is alkyl substituted with heteroaryl, R$^4$ is —H and R$^{4'}$ is —$NH_2$.

In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl, R$^3$ is alkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is cycloalkyl, R$^3$ is alkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is aryl, R$^3$ is alkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is heteroaryl, R$^3$ is alkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with cycloalkyl, R$^3$ is alkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heterocycloalkyl, R$^3$ is alkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with aryl, R$^3$ is alkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heteroaryl, R$^3$ is alkyl, R$^4$ is —$NH_2$ and R$^{4'}$ is —H.

In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl, R$^3$ is cycloalkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is cycloalkyl, R$^3$ is cycloalkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is aryl, R$^3$ is cycloalkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is heteroaryl, R$^3$ is cycloalkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with cycloalkyl, R$^3$ is cycloalkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heterocycloalkyl, R$^3$ is cycloalkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with aryl, R$^3$ is cycloalkyl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heteroaryl, R$^3$ is cycloalkyl, R$^4$ is —$NH_2$ and R$^{4'}$ is —H.

In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl, R$^3$ is aryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is cycloalkyl, R$^3$ is aryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is aryl, R$^3$ is aryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is heteroaryl, R$^3$ is aryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with cycloalkyl, R$^3$ is aryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heterocycloalkyl, R$^3$ is aryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with aryl, R$^3$ is aryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with heteroaryl, R$^3$ is aryl, R$^4$ is —$NH_2$ and R$^{4'}$ is —H.

In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl, R$^3$ is heteroaryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is cycloalkyl, R$^3$ is heteroaryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is aryl, R$^3$ is heteroaryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is heteroaryl, R$^3$ is heteroaryl, R$^4$ is —$NH_2$ and R$^{4'}$ is —H. In some embodiments, R$^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, R$^2$ is alkyl substituted with cycloalkyl, R$^3$ is heteroaryl, R$^4$ is —$NH_2$ and R$^{4'}$ is —H. In some embodiments, R$^1$ is —$C_1$-$C_6$alkyl, —$C_2$-$C_6$alkenyl, —$C_2$-

$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is heteroaryl, $R^4$ is —$NH_2$ and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with cycloalkyl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with cycloalkyl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with cycloalkyl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with cycloalkyl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with cycloalkyl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with cycloalkyl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with cycloalkyl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with cycloalkyl, $R^4$ is —$NH_2$ and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with aryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with aryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with aryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with aryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with aryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with aryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with aryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with aryl, $R^4$ is —$NH_2$ and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with heteroaryl, $R^4$ is —$NH_2$ and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with heteroaryl, $R^4$ is —$NH_2$ and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl, $R^4$ is —H and $R^{4'}$ is —CN.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is cycloalkyl, $R^4$ is —H and $R^{4'}$ is —CN.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is aryl, $R^4$ is —H and $R^{4'}$ is —CN.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is heteroaryl, $R^4$ is —H and $R^{4'}$ is —CN.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with cycloalkyl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with cycloalkyl, $R^4$ is —H and $R^{4'}$ is —CN.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with aryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with aryl, $R^4$ is —H and $R^{4'}$ is —CN.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with heteroaryl, $R^4$ is —H and $R^{4'}$ is —CN. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with heteroaryl, $R^4$ is —H and $R^{4'}$ is —CN.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl, $R^4$ is —CN and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is cycloalkyl, $R^4$ is —CN and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is cycloalkyl, $R^4$ is —CN and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is aryl, $R^4$ is —CN and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is heteroaryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is heteroaryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is heteroaryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is heteroaryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is heteroaryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is heteroaryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is heteroaryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is heteroaryl, $R^4$ is —CN and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with cycloalkyl, $R^3$ is alkyl substituted with cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heterocycloalkyl, $R^3$ is alkyl substituted with cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with aryl, $R^3$ is alkyl substituted with cycloalkyl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl substituted with heteroaryl, $R^3$ is alkyl substituted with cycloalkyl, $R^4$ is —CN and $R^{4'}$ is —H.

In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is alkyl, $R^3$ is alkyl substituted with aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is cycloalkyl, $R^3$ is alkyl substituted with aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is aryl, $R^3$ is alkyl substituted with aryl, $R^4$ is —CN and $R^{4'}$ is —H. In some embodiments, $R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocycloalkyl, heteroaryl, or aryl, $R^2$ is heteroaryl, $R^3$ is alkyl substituted with aryl, $R^4$ is —CN and $R^{4'}$ is —H. In some embodiments, $R^1$ is —$C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with cycloalkyl, $R^3$ is alkyl substituted with aryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with heterocycloalkyl, $R^3$ is alkyl substituted with aryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with aryl, $R^3$ is alkyl substituted with aryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with heteroaryl, $R^3$ is alkyl substituted with aryl, $R^4$ is —CN and $R^{4'}$ is —H.

In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl, $R^3$ is alkyl substituted with heteroaryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is cycloalkyl, $R^3$ is alkyl substituted with heteroaryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is aryl, $R^3$ is alkyl substituted with heteroaryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is heteroaryl, $R^3$ is alkyl substituted with heteroaryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with cycloalkyl, $R^3$ is alkyl substituted with heteroaryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with heterocycloalkyl, $R^3$ is alkyl substituted with heteroaryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with aryl, $R^3$ is alkyl substituted with heteroaryl, $R^4$ is —CN and $R^{4'}$ is —H. In some embodiments, $R^1$ is $—C_1$-$C_6$alkyl, $—C_2$-$C_6$alkenyl, $—C_2$-$C_6$alkynyl, $—C_3$-$C_8$cycloalkyl, $—C_4$-$C_8$cycloalkenyl, heterocycloalkyl, heteroaryl, or aryl, $R^2$ is alkyl substituted with heteroaryl, $R^3$ is alkyl substituted with heteroaryl, $R^4$ is —CN and $R^{4'}$ is —H.

Compounds of the present disclosure can be compounds wherein $R^6$ is aryl, optionally substituted with one or two $R^{10}$, wherein $R^{10}$ is independently, at each occurrence, halogen or $—OC_1$-$C_6$alkyl, wherein $—OC_1$-$C_6$alkyl is optionally substituted with halogen.

Compounds of the present disclosure can comprise aryl, wherein aryl can be ring systems having a total of five to fourteen ring members, wherein at least one ring in the system is aromatic and wherein each ring in the system contains 3 to 7 ring members. For example, aryl can include, but are is not limited to, phenyl.

Compounds of the present disclosure can comprise heteroaryl, wherein heteroaryl is a group having 5 to 10 ring atoms, preferably 5, 6, or 9 ring atoms; having 6, 10, or 14π electrons shared in a cyclic array; and/or having, in addition to carbon atoms, from one to five heteroatoms wherein the term "heteroatom" refers to nitrogen, oxygen, or sulfur, and includes any oxidized form of nitrogen or sulfur, and any quaternized form of a basic nitrogen. For example, heteroaryl can include, but are is not limited to, pyridine, indole, benzapyrazole, benzoxale, furopyridine, or isoquinoline.

Compounds of the present disclosure can comprise heterocycl, wherein heterocyclyl is a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. For example, heterocyclyl can include, but are is not limited to, dihydrofuran, dihydrofuropyrine or dihydroisofuran.

Method of Synthesizing the Compounds

The compounds of the present disclosure may be made by a variety of methods, including standard chemistry. Suitable synthetic routes are depicted in the examples given below.

The compounds of the present disclosure, i.e., compounds of Formula (I), or a pharmaceutically acceptable salt, enantiomer, hydrate, solvate, prodrug, isomer, or tautomer thereof, may be prepared by organic synthesis such as those as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, unless otherwise indicated, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-lnterscience, 1994).

The compounds described herein may be made from commercially available starting materials or synthesized using known organic, inorganic, and/or enzymatic processes.

Methods of Using the Disclosed Compounds

One aspect of the present disclosure relates to a compound of Formula (I) for use in medicine. Another aspect of the present disclosure relates to a method of modulating one or more of CBP/p300-family bromodomains, comprising administering to a patient in need thereof a therapeutically effective amount of a compound of Formula (I). Another aspect of the present disclosure relates to a method of inhibiting one or more of CBP/p300-family bromodomains, comprising administering to a patient in need thereof a therapeutically effective amount of a compound of Formula (I). In another aspect, the present disclosure relates to a method of inhibiting one or more of CBP/p300-family bromodomains, comprising administering to a patient in need thereof a therapeutically effective amount of a pharmaceutical composition comprising a compound of Formula (I).

In another aspect, the ratio of inhibition of CBP ($IC_{50}$ (μM gmean)) as compared to the inhibition of BRD4 ($IC_{50}$ (μM gmean)) is determined. In some embodiments, the inhibition of CBP ($IC_{50}$ (μM gmean)) is determined as outlined in Example 963. In some embodiments, the inhibition of BRD4 ($IC_{50}$ (μM gmean)) is determined as outlined in Example 963. It will be appreciated that a positive ratio of inhibition for CBP vs. BRD4 indicates that a compound selectively inhibits CBP over BRD4. In some embodiments, a compound is characterized in that the ratio of CBP $IC_{50}$ to BRD4 $IC_{50}$ is 10:1. In some embodiments, a compound is characterized in that the ratio of CBP $IC_{50}$ to BRD4 $IC_{50}$ is 20:1. In some embodiments, a compound is characterized in that the ratio of CBP $IC_{50}$ to BRD4 $IC_{50}$ is 50:1. In some embodiments, a compound is characterized in that the ratio of CBP $IC_{50}$ to BRD4 $IC_{50}$ is 100:1. In some embodiments, a compound is characterized in that the ratio of CBP $IC_{50}$ to BRD4 $IC_{50}$ is 250:1. In some embodiments, a compound is characterized in that the ratio of CBP $IC_{50}$ to BRD4 $IC_{50}$ is 500:1. In some embodiments, a compound is characterized in that the ratio of CBP $IC_{50}$ to BRD4 $IC_{50}$ is 750:1. In some embodiments, the ratio of CBP $IC_{50}$ to BRD4 $IC_{50}$ is 1,000:1. In some embodiments, a compound is characterized in that the ratio of CBP $IC_{50}$ to BRD4 $IC_{50}$ is 2,500:1. In some embodiments, a compound is characterized in that the ratio of CBP $IC_{50}$ to BRD4 $IC_{50}$ is 5,000:1. In some embodiments, a compound is characterized in that the ratio of CBP $IC_{50}$ to BRD4 $IC_{50}$ is 10,000:1. In some embodiments, a compound is characterized in that is has a BRD4 $IC_{50}$ of greater than 0.01 μM. In some embodiments, a compound is characterized in that is has a BRD4 $IC_{50}$ of greater than 0.1 μM. In some embodiments, a compound is characterized in that is has a BRD4 $IC_{50}$ of greater than 1 μM.

Another aspect of the present disclosure relates to a method of treating, preventing, inhibiting, or eliminating a disease or disorder in a patient associated with the inhibition of one or more of CBP/p300-family bromodomains, the method comprising administering a therapeutically effective amount of a compound of Formula (I). In one embodiment, the disease or disorder is selected from the group consisting of cancer. In some embodiments, the cancer is a solid tumor. In some embodiments, the cancer is cancer of the prostate including castration-resistant prostate cancer, and breast cancer.

The present disclosure also relates to the use of an inhibitor of CBP/p300 family bromodomains for the preparation of a medicament used in the treatment, prevention, inhibition or elimination of a disease or disorder mediated by CBP/p300 family bromodomains, wherein the medicament comprises a compound of Formula (I). In another aspect, the present disclosure relates to a method for the manufacture of a medicament for treating, preventing, inhibiting, or eliminating a disease or disorder mediated by CBP/p300 family bromodomains, wherein the medicament comprises a compound of Formula (I). Another aspect of the present disclosure relates to a pharmaceutical composition for use in a method for treating a disease or disorder mediated by CBP/p300 family bromodomains, wherein the pharmaceutical composition comprises a compound of Formula (I). In yet another aspect, the present disclosure relates to a compound for use in a method for treating a disease or disorder mediated by CBP/p300 family bromodomains, wherein the compound comprises a compound of Formula (I).

The present disclosure also relates to the use of an inhibitor of CBP/p300 family bromodomains for the preparation of a medicament used in the treatment, prevention, inhibition or elimination of tumors, wherein the medicament comprises a compound of Formula (I). The present disclosure further relates to the use of an inhibitor of CBP/p300 family bromodomains for the preparation of a medicament used in the treatment, prevention, inhibition or elimination of cancer, wherein the medicament comprises a compound of Formula (I).

Another embodiment of the present disclosure relates to a compound of Formula (I), or a pharmaceutically acceptable salt, enantiomer, hydrate, solvate, prodrug, isomer, or tautomer thereof, or a pharmaceutical composition comprising a compound of the present disclosure, or a pharmaceutically acceptable salt, enantiomer, hydrate, solvate, prodrug, isomer, or tautomer thereof, and a pharmaceutically acceptable carrier which provides, upon administration to a human, a decrease in tumor burden and/or metastases.

The disclosure is directed to compounds as described herein and pharmaceutically acceptable salts, enantiomers, hydrates, solvates, prodrugs, isomers, or tautomers thereof, and pharmaceutical compositions comprising one or more compounds as described herein, or pharmaceutically acceptable salts, enantiomers, hydrates, solvates, prodrugs, isomers, or tautomers thereof. The disclosure is directed to compounds as described herein and pharmaceutically acceptable salts thereof. The disclosure also includes pharmaceutical compositions comprising one or more compounds as described herein, or a pharmaceutically acceptable salt thereof, and a pharmaceutically acceptable excipient. In some embodiments, pharmaceutical compositions reported herein can be provided in a unit dosage form container (e.g., in a vial or bag or the like). In some embodiments, pharmaceutical compositions reported herein can be provided in an oral dosage form. In some embodiments, an oral dosage form of a compound of Formula (I) can be a capsule. In some embodiments, an oral dosage form of a compound of Formula (I) is a tablet. In some embodiments, an oral dosage form comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation.

The present disclosure also relates to a pharmaceutical composition comprising a compound of Formula (I) and a pharmaceutically acceptable carrier. The pharmaceutical acceptable carrier may further include an excipient, diluent, additive, or surfactant. The compounds or pharmaceutical compositions of the disclosure may be administered via any mode of administration for therapeutic agents. These modes include systemic or local administration such as oral administration. Depending on the intended mode of administration, the disclosed compounds or compositions can be in solid dosage form, such as, for example, tablets, or pills or the like, sometimes in unit dosages and consistent with conventional pharmaceutical practices. Likewise, they can also be administered using forms well known to those skilled in the pharmaceutical arts.

In one embodiment, the present disclosure relates to a method of preparing a pharmaceutical composition of the present disclosure by mixing at least one pharmaceutically acceptable compound of the present disclosure, and, optionally, one or more pharmaceutically acceptable carriers, additives, or excipients. Pharmaceutical compositions comprising a CBP Inhibitor can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume. The dosage forms of the present disclosure, may contain a mixture of one or more compounds of this disclosure, and may include additional materials known to those skilled in the art as pharmaceutical excipients. Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. In one embodiment, the stabilizing additives are gum acacia, gelatin and methyl cellulose.

Examples of pharmaceutical excipients and additives include, but are not limited to: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoromethane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octaacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate sodium formaldehyde sulfoxylate sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate ethylcellulose, gelatin, pharmaceutical glaze, hydroxypropyl cellulose, hydroxypropyl methylcellulose, hydroxypropyl methylcellulose phthalate methacrylic acid copolymer, methylcellulose, polyethylene glycol, polyvinyl acetate phthalate shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate glycerin, mono- and di-acetylated monoglycerides, polyethylene glycol, propylene glycol, triacetin, triethyl citrate); Polymers (e.g., cellulose acetate, alkyl celluloses, hydroxyalkylcelluloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol) may be used as excipients. This list is not meant to be exclusive, but instead merely representative of the classes of excipients and the particular excipients which may be used in dosage forms of the present disclosure.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

For preparing pharmaceutical compositions from the compounds described in this disclosure inert, pharmaceutically acceptable carriers can be either solid or liquid. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Since the compounds of this disclosure are intended for use in pharmaceutical compositions a skilled artisan will understand that they can be provided in substantially pure forms for example, at least 60% pure, more suitably at least 75% pure, preferably at least 85% pure and most preferably at least 98% pure (w/w).

The pharmaceutical preparation may be in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, from about 1 mg to about 500 mg, from about 1 mg to about 250 mg, or from about 1 mg to about 25 mg, according to the particular application.

The CBP Inhibitor Compounds provided herein are preferably administered in a therapeutically effective amount (e.g., an amount having a suitable favorable therapeutic index). The amount and frequency of administration of the compounds of the disclosure and/or the pharmaceutically acceptable salts thereof will be regulated according to the judgment of the attending clinician considering such factors as age, condition and size of the patient as well as severity of the medical condition being treated. The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses.

The compounds of Formula (I) can form salts (e.g., pharmaceutically acceptable salts) which are also within the scope of this disclosure. Reference to a compound of the Formula herein is understood to include reference to salts thereof, unless otherwise indicated.

All such acid salts and base salts are intended to be pharmaceutically acceptable salts within the scope of the disclosure and all acid and base salts are considered equivalent to the free forms of the corresponding compounds for purposes of the disclosure.

The following numbered embodiments, while non-limiting, are exemplary of certain aspects of the present disclosure:

1. A compound of Formula (I):

(I)

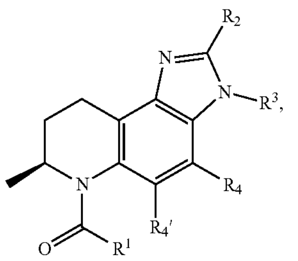

or a pharmaceutically acceptable salt thereof, wherein:

$R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, or —$OR^5$;

$R^2$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl, wherein each alkyl, alkenyl, alkynyl, cycloalkyl, cycloalkenyl, heterocyclyl, heteroaryl, or aryl is optionally substituted with one or more $R^6$, and wherein a —$C_1$-$C_6$alkyl group may have one or more methylene units replaced by —$NR^6$—, —O— or —S—;

$R^3$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, spirocycloalkyl, spiroheterocyclyl, heterocyclyl, heteroaryl, or aryl, wherein each alkyl, alkenyl, alkynyl, cycloalkyl, cycloalkenyl, spirocycloalkyl, spiroheterocyclyl, heterocyclyl, heteroaryl, or aryl is optionally substituted with one or more $R^7$; $R^4$ and $R^{4'}$ are each independently —H, halogen, —OH, —CN, or —$NH_2$;

$R^5$ is —$C_1$-$C_6$alkyl, —$C_3$-$C_8$cycloalkyl, heterocyclyl, aryl, or heteroaryl;

$R^6$ and $R^7$ are each independently, at each occurrence, —H, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —$C(O)R^{8'}$, —$C(O)OR^8$, —$C(O)NR^8R^9$, —$NR^8C(O)R^{9'}$, —$NR^8S(O)_2R^{9'}$, —$S(O)R^{8'}$, —$S(O)NR^8R^9$, or —$NR^8S(O)R^{9'}$, wherein each alkyl, cycloalkyl, heterocyclyl, spirocycloalkyl, spiroheterocyclyl, heteroaryl, or aryl is optionally substituted with one or more $R^{10}$;

wherein any two $R^6$ or any two $R^7$, when on non-adjacent atoms, can combine to form a bridging cycloalkyl or heterocyclyl;

wherein any two $R^6$ or any two $R^7$, when on adjacent atoms, can combine to form a cycloalkyl, heterocyclyl, aryl or heteroaryl;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{8'}$ and $R^{9'}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^{9'}$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{10}$ and $R^{11}$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6alkyl)_2$, —$C(O)OC_1$-$C_6$alkyl, —$N(C_1$-$C_6alkyl)SO_2C_1$-$C_6$alkyl, —$S(O)(C_1$-$C_6$alkyl), —$S(O)N(C_1$-$C_6alkyl)_2$, or —$N(C_1$-$C_6$alkyl)$S(O)(C_1$-$C_6$alkyl), wherein each alkyl, alkenyl, alkynyl, cycloalkyl, cycloalkenyl, heterocyclyl, heteroaryl, or aryl is optionally substituted with one or more —$R^2$;

wherein any two $R^{10}$ or any two $R^{11}$, when on non-adjacent atoms, can combine to form a bridging cycloalkyl or heterocyclyl;

wherein any two $R^{10}$ or any two $R^{11}$, when on adjacent atoms, can combine to form a cycloalkyl, heterocyclyl, aryl or heteroaryl;

$R^{12}$ is independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6alkyl)_2$, —$C(O)OC_1$-$C_6$alkyl, —$N(C_1$-$C_6alkyl)SO_2C_1$-$C_6$alkyl, —$S(O)(C_1$-$C_6$alkyl), —$S(O)N(C_1$-$C_6alkyl)_2$, or —$N(C_1$-$C_6$alkyl)$S(O)(C_1$-$C_6$alkyl); and n is an integer from 1 to 4.

2. The compound of embodiment 1, wherein $R^1$ is —$OR^5$ or —$C_1$-$C_6$alkyl.

3. The compound of embodiment 2, wherein $R^5$ is —$C_1$-$C_6$alkyl.

4. The compound of embodiment 2, wherein $R^1$ is —$OCH_3$.

5. The compound of embodiment 2, wherein $R^1$ is —$C_1$-$C_6$alkyl.

6. The compound any one of embodiments 1-5, wherein $R^3$ is —$C_1$-$C_6$alkyl.

7. The compound of any one of embodiments 1-5, wherein $R^3$ is heterocyclyl optionally substituted with one or more $R^7$.

8. The compound of any one of embodiments 1-5, wherein $R^3$ is heteroaryl optionally substituted with one or more $R^7$.

9. The compound of any one of embodiments 1-5, wherein $R^3$ is spirocycloalkyl optionally substituted with one or more $R^7$.

10. The compound of any one of embodiments 1-5, wherein $R^3$ is spiroheterocyclyl optionally substituted with one or more $R^7$.

11. The compound of any one of embodiments 1-5, wherein $R^3$ is $C_3$-$C_8$cycloalkyl optionally substituted with one or more $R^7$.

12. The compound of any one of embodiments 1-5, wherein $R^3$ is aryl optionally substituted with one or more $R^7$.

13. The compound of any one of embodiments 1-5, wherein $R^3$ is cyclopropyl, cyclobutyl, cyclopentyl or cyclohexyl optionally substituted with one or more —$R^7$.

14. The compound of any one of embodiments 1-5, wherein $R^3$ is cyclopentyl optionally substituted with one or more —$R^7$.

15. The compound of any one of embodiments 1-5, wherein $R^3$ is cyclohexyl optionally substituted with one or more —$R^7$.

16. The compound of any one of embodiments 1-5, wherein $R^3$ is cyclopropyl, cyclobutyl, cyclopentyl or cyclohexyl optionally substituted with one or more —$S(O)_2NH_2$, —C(O)OH, —$C(O)NH_2$, or —$S(O)NH_2$.

17. The compound of any one of embodiments 1-16, wherein $R^2$ is $C_1$-$C_6$alkyl optionally substituted with one or more $R^6$.

18. The compound of any one of embodiments 1-16, wherein $R^2$ is aryl optionally substituted with one or more $R^6$.

19. The compound of any one of embodiments 1-16, wherein $R^2$ is $C_3$-$C_8$cycloalkyl optionally substituted with one or more $R^6$.

20. The compound of any one of embodiments 1-16, wherein $R^2$ is $C_1$-$C_2$alkyl substituted with aryl or heteroaryl, wherein each aryl or heteroaryl is optionally substituted with one or more $R^{10}$.

21. The compound of embodiment 1, wherein $R^2$ is $C_1$-$C_2$alkyl substituted with aryl or heteroaryl, wherein each aryl or heteroaryl is optionally substituted with one or more $R^{10}$; and wherein $R^3$ is cyclohexyl optionally substituted with one or more —$S(O)_2NH_2$, —C(O)OH, —$C(O)NH_2$, or —$S(O)NH_2$.

22. The compound of any one of embodiments 1 or 6-21, wherein $R^1$ is —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, or aryl.

23. The compound of embodiment 1 having the Formula (I-a):

(I-a)

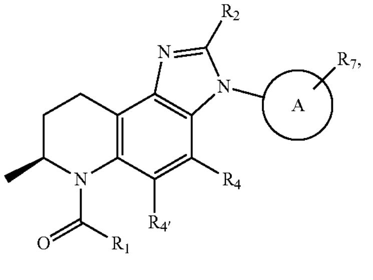

or a pharmaceutically acceptable salt thereof, wherein Ring A represents a —$C_3$-$C_8$cycloalkyl, —$C_4$-$C_8$cycloalkenyl, spirocycloalkyl, spiroheterocyclyl, heteroaryl, or aryl.

24. The compound of embodiment 1 having the Formula (I-b):

(I-b)

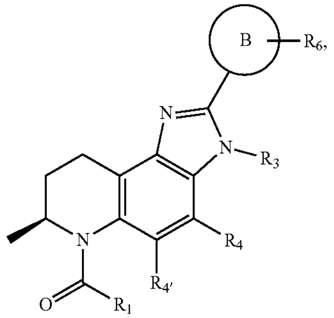

or a pharmaceutically acceptable salt thereof, wherein Ring B represents a —$C_3$-$C_8$cycloalkyl, —$C_4$-$C_8$cycloalkenyl, heteroaryl, or aryl.

25. The compound of embodiment 1 having the Formula (I-c):

(I-c)

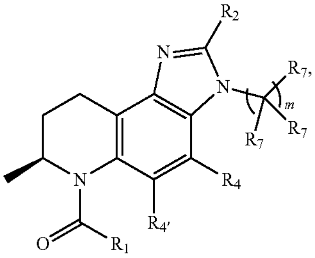

or a pharmaceutically acceptable salt thereof, wherein m is an integer from 1 to 4.

26. The compound of embodiment 1 having the Formula (I-d):

(I-d)

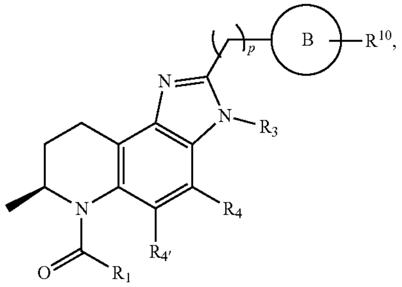

or a pharmaceutically acceptable salt thereof, wherein Ring B represents —$C_3$-$C_8$cycloalkyl, —$C_4$-$C_8$cycloalkenyl, heterocyclyl, aryl, spirocycloalkyl, spiroheterocyclyl, or heteroaryl, and wherein p is an integer from 1 to 2.

27. The compound of embodiment 26, wherein Ring B is —$C_3$-$C_8$cycloalkyl.

28. The compound of embodiment 26, wherein Ring B is —$C_4$-$C_8$cycloalkenyl.

29. The compound of embodiment 26, wherein Ring B is aryl.

30. The compound of embodiment 26, wherein Ring B is heterocyclyl.

31. The compound of embodiment 26, wherein Ring B is heteroaryl.

32. The compound of embodiment 1 having the Formula (I-f):

(I-f)

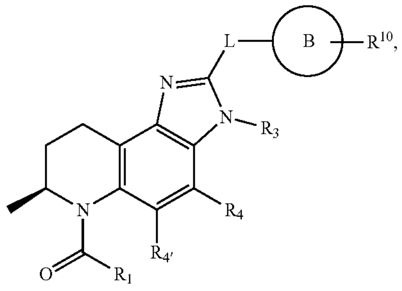

or a pharmaceutically acceptable salt thereof, wherein Ring B is-$C_3$-$C_8$cycloalkyl, —$C_4$-$C_8$cycloalkenyl, heterocyclyl, aryl, spirocycloalkyl, spiroheterocyclyl, or heteroaryl; and L is a $C_1$-$C_6$ alkylene chain optionally substituted with one or more $R^6$; or L is a $C_1$-$C_6$ alkylene chain optionally substituted with one or more $R^6$, and wherein at least one methylene unit of L is replaced by —$NR^6$—, —O— or —S—.

33. The compound of embodiment 32, wherein Ring B is —$C_3$-$C_8$cycloalkyl.

34. The compound of embodiment 32, wherein Ring B is —$C_4$-$C_8$cycloalkenyl.

35. The compound of embodiment 32, wherein Ring B is aryl.

36. The compound of embodiment 32, wherein Ring B is heterocyclyl.

37. The compound of embodiment 32, wherein Ring B is heteroaryl.

38. The compound of any of embodiments 33-37, wherein L is a $C_1$-$C_6$ alkylene chain optionally substituted with one or more $R^6$.

39. The compound of any one of embodiments 33-37, wherein L is $C_1$-$C_2$ alkylene.

40. The compound of any of embodiments 33-37, wherein L is a $C_1$-$C_6$ alkylene chain optionally substituted with one or more $R^6$, and wherein at least one methylene unit is replaced by —$NR^6$—, —O— or —S—.

41. The compound of embodiment 40, wherein L is a $C_1$-$C_6$ alkylene chain optionally substituted with one or more $R^6$, and wherein at least one methylene unit of L is replaced by —$NR^6$.

42. The compound of embodiment 40, wherein L is a $C_1$-$C_6$ alkylene chain optionally substituted with one or more $R^6$, and wherein at least one methylene unit of L is replaced by —O—.

43. The compound of embodiment 40, wherein L is a $C_1$-$C_6$ alkylene chain optionally substituted with one or more $R^6$, and wherein at least one methylene unit of L is replaced by —S—.

44. The compound of embodiment 38, wherein $R^6$ is —C(O)OH.

45. The compound of embodiment 44, wherein $R^3$ is —$C_3$-$C_8$cycloalkyl, —$C_4$-$C_8$cycloalkenyl, heterocyclyl, aryl, or heteroaryl.

46. The compound of embodiment 45, wherein $R^3$ is cyclopentyl, cyclohexyl, 3-pyranyl, or 4-pyranyl.

47. The compound of embodiment 46, wherein $R^3$ is cyclopentyl, cyclohexyl or 3-pyranyl.

48. The compound of embodiment 32, wherein L is an $C_1$-$C_6$ alkylene chain optionally substituted with one or more $R^6$, and wherein at least one methylene unit is replaced by —$NR^6$—, —O— or —S—; and $R^3$ is —$C_3$-$C_8$cycloalkyl, —$C_4$-$C_8$cycloalkenyl, heterocyclyl, aryl, or heteroaryl, wherein each —$C_3$-$C_8$cycloalkyl, —$C_4$-$C_8$cycloalkenyl, heterocyclyl, aryl, or heteroaryl is optionally substituted with one or more $R^7$; and $R^6$ is independently, at each occurrence, —H, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, —$NR^8R^9$, —$S(O)_2NR^8R^9$, —$S(O)_2R^{8'}$, —$C(O)R^{8'}$, —$C(O)NR^8R^9$, —$NR^8C(O)R^{9'}$, —$NR^8S(O)_2R^{9'}$, —$S(O)R^{8'}$, —$S(O)NR^8R^9$, or —$NR^8S(O)R^{9'}$, wherein each alkyl, cycloalkyl, heterocyclyl, spirocycloalkyl, spiroheterocyclyl, heteroaryl, or aryl is optionally substituted with one or more $R^{10}$;

wherein $R^{10}$ is —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, halogen, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —C(O)$C_1$-$C_6$alkyl, —$C(O)NH_2$, —C(O)NH($C_1$-$C_6$alkyl), —C(O)N($C_1$-$C_6alkyl)_2$, —C(O)O$C_1$-$C_6$alkyl, —N($C_1$-$C_6$alkyl)$SO_2C_1$-$C_6$alkyl, —S(O)($C_1$-$C_6$alkyl), —S(O)N($C_1$-$C_6alkyl)_2$, or —N($C_1$-$C_6$alkyl)S(O)($C_1$-$C_6$alkyl), wherein each alkyl, alkenyl, alkynyl, cycloalkyl, cycloalkenyl, heterocyclyl, heteroaryl, or aryl.

49. The compound of embodiment 48, wherein L is a $C_1$-$C_6$ alkylene chain, —$OCH_2$—, —$CH_2O$—, —$NR^6CH_2$—, or —$CH_2NR^6$—; and $R^6$ is H, —$C_1$-$C_6$alkyl, —$C_3$-$C_6$cycloalkyl or —$C(O)NR^8R^9$.

50. The compound of embodiment 48, wherein $R^3$ is cyclopentyl or cyclohexyl, wherein each cyclopentyl or cyclohexyl is optionally substituted with $R^7$.

51. The compound of embodiment 50, wherein $R^7$ is —OH, halogen, oxo, —CN, —SH, —OH, —$NH_2$, —$S(O)_2NH_2$, —C(O)OH, or —$C(O)NH_2$.

52. The compound of embodiment 1 having the Formula (I-g):

(I-g)

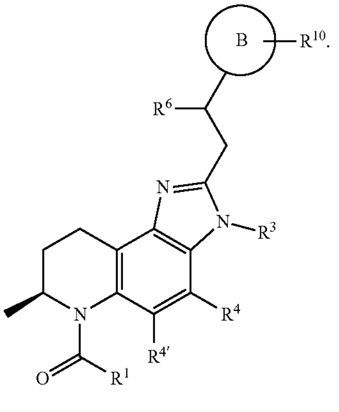

53. The compound of embodiment 1 having the Formula (I-h):

(I-h)

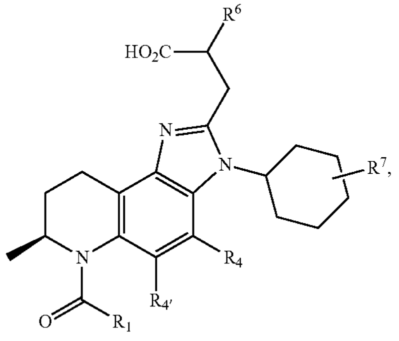

or a pharmaceutically acceptable salt thereof.

54. The compound of embodiment 1 having the Formula (I-h'):

(I-h')

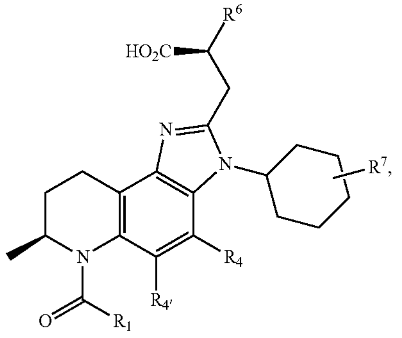

or a pharmaceutically acceptable salt thereof.

55. The compound of embodiment 1 having the Formula (I-h")

(I-h")

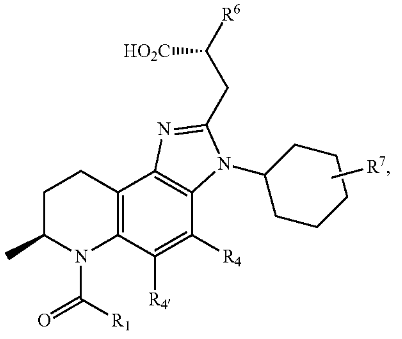

or a pharmaceutically acceptable salt thereof.

56. The compound of embodiment 1 having the Formula (I-e):

(I-e)

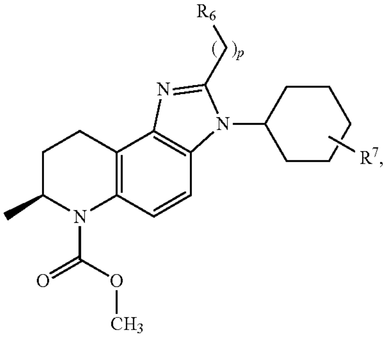

or a pharmaceutically acceptable salt thereof, wherein p is 1 or 2.

57. The compound of embodiment 56, wherein p is 1.

58. The compound of embodiment 56, wherein p is 2.

59. The compound of embodiment 56, wherein $R^7$ is —C(O)OH.

60. The compound of embodiment 56, wherein $R^6$ is aryl or heteroaryl, wherein each aryl or heteroaryl is optionally substituted with one or more $R^{10}$.

61. A compound of any one of embodiments 1-60 for use in the manufacture of a medicament for treating a disease associated with inhibiting one or more of CBP/p300-family bromodomains.

62. A compound of any one of embodiments 1-60 for use in the manufacture of a medicament for treating a disease or disorder in a patient in need thereof.

63. Use of a compound of any one of embodiments 1-60 in the treatment of a disease associated with inhibiting one or more of CBP/p300-family bromodomains.

64. Use of a compound of any one of embodiments 1-60 in the treatment of a disease or disorder in a patient in need thereof.

EXAMPLES

Definitions used in the following Schemes and elsewhere herein are:

ACN acetonitrile $Ac_2O$ acetic anhydride (±)BINAP (±)-2,2'-Bis(diphenylphosphino)-1,1'-binaphthalen Boc tert-butoxycarbonyl Brettphos Dicyclohexyl[3,6-dimethoxy-2',4',6'-tris(1-methylethyl)[1,1'-biphenyl]-2-yl]phosphine Brettphos Pd G3 or 3rd generation BrettPhos precatalyst: Methanesulfonato(2-dicyclohexylphosphino-3,6-dimethoxy-2',4',6'-tri-i-propyl-1,1'-biphenyl)(2'-amino-1,1'-biphenyl-2-yl)palladium(II)

n-BuOH butanol cm centimeter

DCE 1,2-dichloroethane

DCM dichloromethane or methylene chloride

D-CSA D-Camphorsulfonic acid

DEA diethylamine

DMC 2-Chloro-4,5-dihydro-1,3-dimethyl-1H-imidazolium chloride

DMP Dess-Martin periodinane, 1,1,1-Tris(acetyloxy)-1,1-dihydro-1,2-benziodoxol-3-(1H)-one DMTMM 4-(4,6-Dimethoxy-1,3,5-triazin-2-yl)-4-methylmorpholinium chloride DIEA N,N-diisopropylethylamine DMAP 4-(dimethylamino)pyridine
DMF N,N-dimethylformamide
DMSO dimethylsulfoxide
DPPA diphenylphosphoryl azide
dppf bis(diphenylphosphino)ferrocene
EDC 1-Ethyl-(3-dimethylaminopropyl)carbodiimide hydrochloride
ES electrospray ionization
$Et_3N$ triethylamine
EtOAc ethyl acetate
EtOH ethanol
FA formic acid
FCC flash column chromatography
h hours
HATU 2-(3H-[1,2,3]triazolo[4,5-b]pyridin-3-yl)-1,1,3,3-tetramethylisouronium hexafluorophosphate
HCl hydrogen chloride
HOAc acetic acid
HPLC high performance liquid chromatography
$[Ir(COD)Cl]_2$ chloro(1,5-cyclooctadiene)iridium(I) dimer
$(i\text{-}Pr)_2NEt$ N,N-diisopropylethylamine
L liter
LC/MS liquid chromatography/mass spectrometry
LCMS liquid chromatography/mass spectrometry
LDA lithium diisopropylamine
LRMS low resolution mass spectrometry
$K_2CO_3$ potassium carbonate
KHMDS Potassium hexamethyldisilazide
mCPBA 3-Chloroperoxybenzoic acid
MeOH methanol
mL milliliter
mmol millimole
mg milligram
MHz megahertz
MS mass spectrometry
m/z mass/charge ratio
NBS N-bromosuccinimide
nm nanometer
NMM 4-methylmorpholine
NMR nuclear magnetic resonance
$NH_4Cl$ ammonium chloride
$Pd_2(dba)_3$ tris(dibenzylideneacetone)dipalladium
$Ph_3P$ triphenylphosphine
PhCHO benzaldehyde
PhMe toluene
ppm parts per million
rt room temperature
RT retention time
(S)-(−)-MeO-BIPHEP (S)-(−)-2,2'-Bis(diphenylphosphino)-6,6'-dimethoxy-1,1'-biphenyl
SFC supercritical fluid chromatography
STAB sodium triacetoxyborohydride
TBS tert-Butyldimethylsilyl
TBDMS tert-Butyldimethylsilyl chloride
p-TSA para-toluenesulfonic anhydride
p-TsOH para-toluenesulfonic acid
TFA trifluoroacetic acid
TFAA trifluoroacetic anhydride
THE tetrahydrofuran
TMSCN trimethylsilyl cyanide
UV ultraviolet
XPhos 2-dicyclohexylphosphino-2',4',6'-triisopropylbiphenyl
$ZnI_2$ zinc iodide

Materials

Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen atmosphere and all reactions utilizing microwave irradiation were run on a Biotage Initiator EXP EU instrument.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C18 1.7 μm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 μm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

General Methods of Compound Preparation

Described herein are methods of synthesizing the compounds of the present disclosure. Compounds of the present disclosure can be synthesized according to the synthetic schemes provided below. Preparation of the starting material for Schemes 1 and 2 is described in "Preparation of Intermediates," see Intermediate 1. Preparation of the starting material for Schemes 3 and 4 can be found in Example 1, Part A of U.S. Pat. No. 4,404,207.

Unless otherwise specified, the substituents $R^2$ and $R^3$ and of the following reaction schemes are as defined in the description and claims.

Scheme 1 provides methods useful for synthesizing compounds of Formula I.

Scheme 1

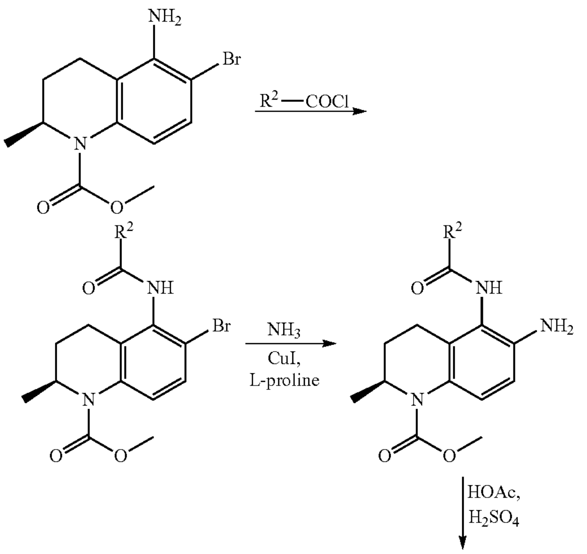

-continued
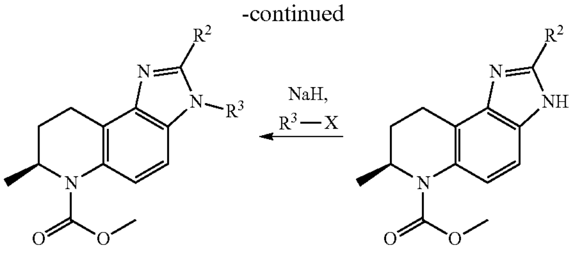
Scheme 2 provides methods useful for synthesizing compounds of Formula I.
Scheme 2
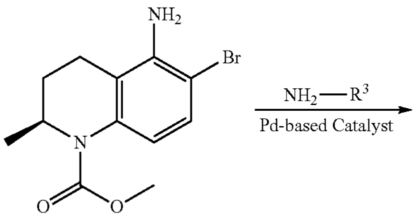
-continued
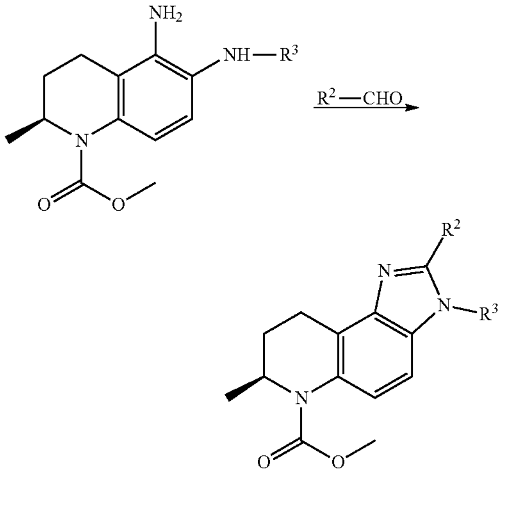
Alternatively, Scheme 3 provides methods useful for synthesizing certain compounds of Formula I.
Scheme 3
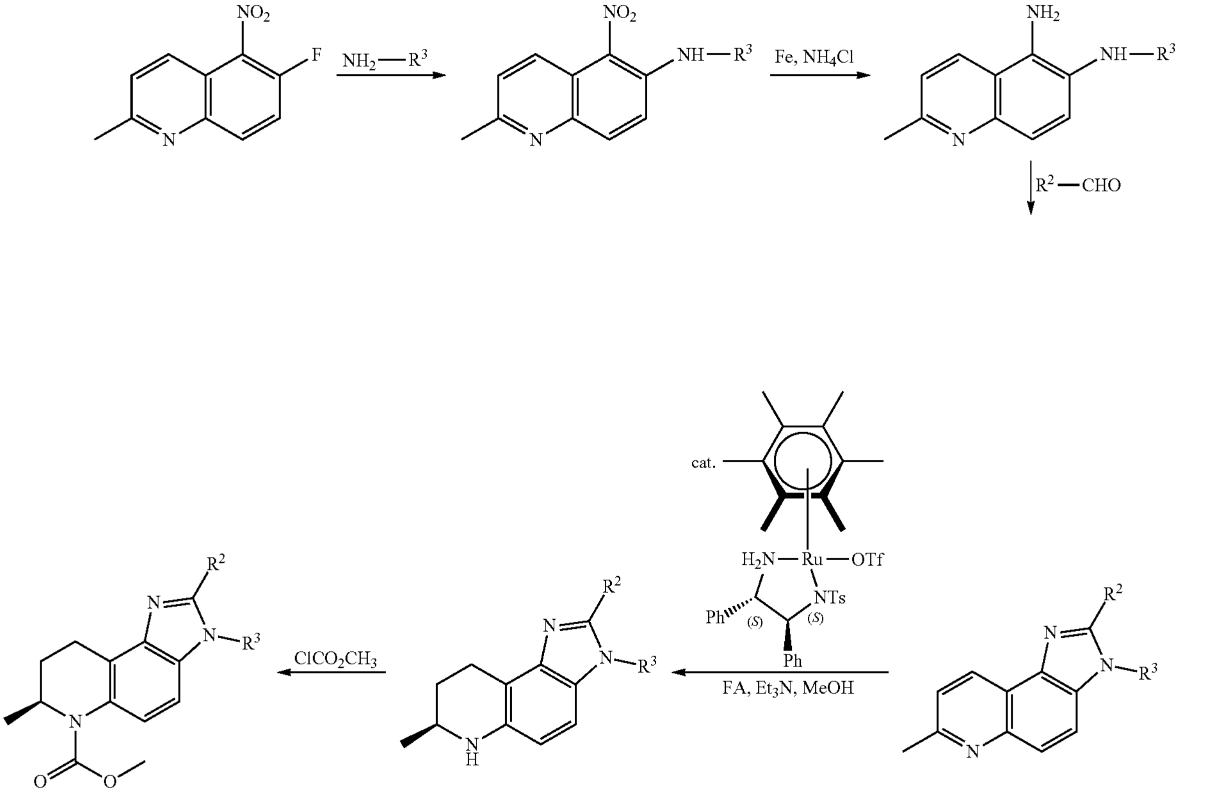

Alternatively, Scheme 4 provides methods useful for synthesizing certain compounds of Formula I.

Scheme 4

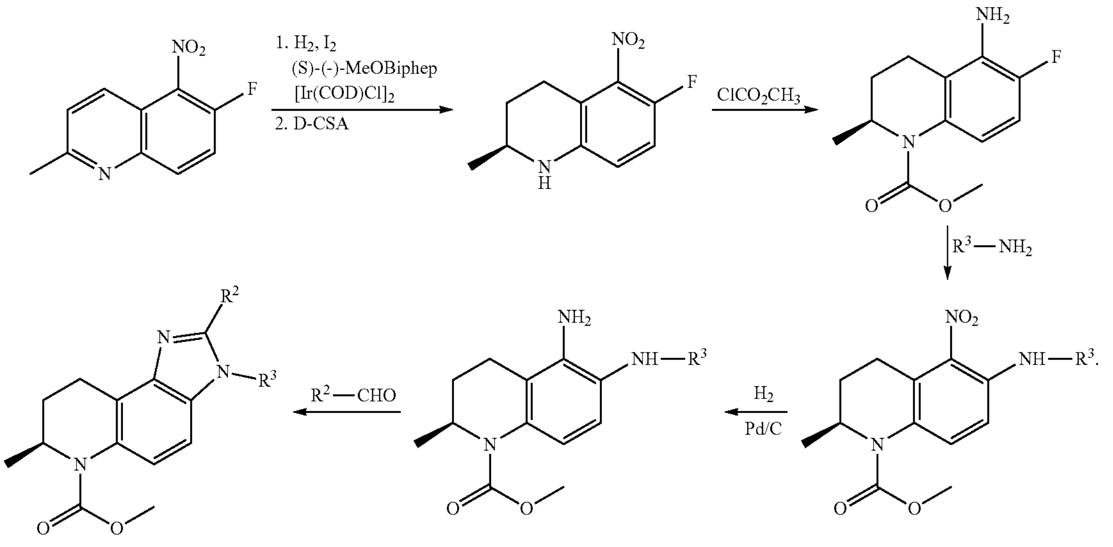

Unless otherwise specified, Ring B, $R^1$, $R^6$, $R^7$, $R^{10}$, m and q and of the following reaction schemes are as defined in the description and claims. The compounds described herein may be made from commercially available starting materials or synthesized using known organic, inorganic, and/or enzymatic processes. For example, 6-fluoro-2-methylquinoline can be nitrated under acidic conditions to afford 6-fluoro-2-methyl-5-nitroquinoline. Asymmetric iridium-catalyzed hydrogenation of the quinoline gives (S)-6-fluoro-2-methyl-5-nitro-1,2,3,4-tetrahydroquinoline. Carbamate formation and subsequent nucleophilic aromatic substitution yields a methyl 6-fluoro-2-methyl-5-nitroquinoline. Nitro reduction, acylation and acid-mediated cyclization yields the methyl (S)-7-methyl-3,7,8,9-tetrahydro-6H-imidazo[4,5-f]quinoline-6-carboxylate core of Formula I-i.

Scheme 5 provides methods useful for synthesizing certain compounds of Formula I-i.

Scheme 5

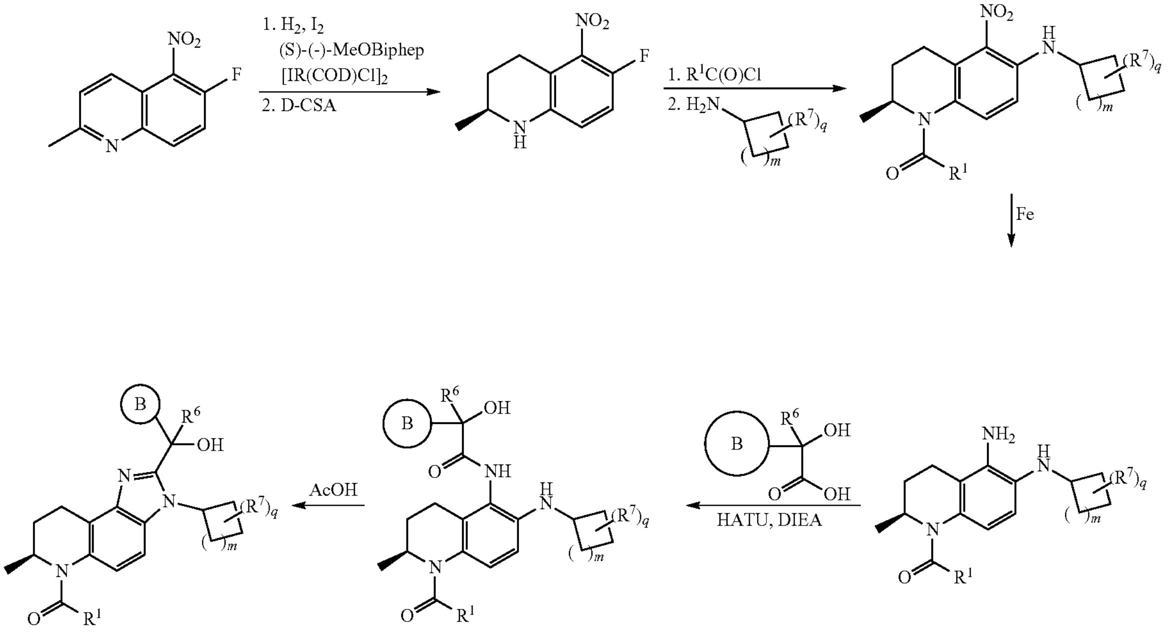

I-i

Preparation of Intermediates

Intermediate 1: methyl (S)-5-amino-6-bromo-2-methyl-3,4-dihydroquinoline-1(2H)-carboxylate

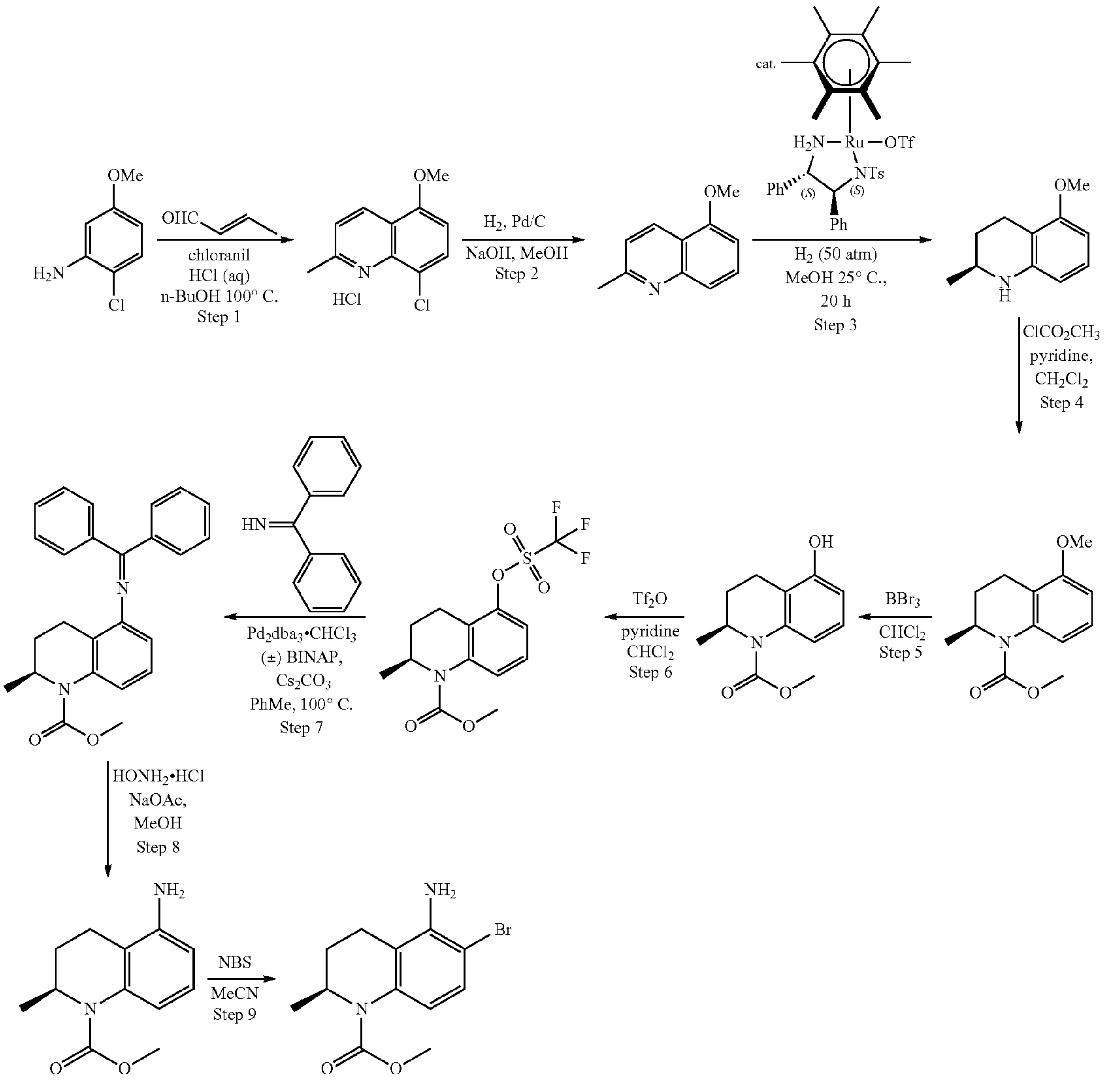

Intermediate 1

Step 1. 8-chloro-5-methoxy-2-methylquinoline hydrochloride

Into a 5 L 4-necked round-bottom flask purged and maintained with an inert atmosphere of nitrogen, 2-chloro-5-methoxyaniline (250 g, 1.59 mol) was dissolved in 1-butanol (1200 mL). Then hydrochloric acid (aq, 36.5%, 526.5 mL) and chloranil (456.5 g, 1.86 mol) were added. The resulting mixture was stirred for 1 h at 100° C. under nitrogen atmosphere. Then a solution of (E)-but-2-enal (169 mL, 2.06 mol) in 1-butanol (300 mL) was added dropwise. The resulting solution was stirred for 1 h at 100° C. under nitrogen atmosphere. The oil bath was cooled to 70° C. and tetrahydrofuran (1500 mL) was added. Then the resulting mixture was stirred for 1 h at 70° C. The reaction mixture was cooled to 0° C. and the solids were filtered. The solids were washed with tetrahydrofuran (3 L) at 0° C. This afforded the title compound (300 g, 77%) as a yellow solid. MS: (ES, m/z): 208, 210 $[M+H]^+$.

Step 2. 5-methoxy-2-methylquinoline

Into a 1000-mL 3-necked round-bottom flask, 8-chloro-5-methoxy-2-methylquinoline hydrochloride (50 g, 204.82 mmol) was dissolved in methanol (300 mL). Then sodium hydroxide (3M, 205 mL) and 10% palladium on carbon (25 g) were added. Hydrogen (g) was charged into the reaction mixture. The reaction mixture was stirred under a hydrogen atmosphere for 3 h at room temperature. The reaction was vented to nitrogen and the solids were filtered out over celite. The filtered solution was concentrated under vacuum. The residue was subjected to purification by FCC eluting with ethyl acetate/petroleum ether (1:5). This afforded the title compound (28.5 g, 80%) as a yellow oil. MS: (ES, m/z): 174 $[M+H]^+$.

Step 3. (2S)-5-methoxy-2-methyl-1,2,3,4-tetrahydroquinoline

Into a 30-mL pressure tank reactor (50 atm), 5-methoxy-2-methylquinoline (4.0 g, 23.09 mmol) was dissolved in methanol (10 mL). Then Ru(OTf)(η6-hexamethylbenzene)((S,S)-TsDPEN) ([N-[(1S,2S)-2-(amino-κN)-1,2-diphenylethyl]-4-methylbenzenesulfonamidato-κN][(1,2,3,4,5,6-η)-1,2,3,4,5,6-hexamethylbenzene](1,1,1-trifluoromethanesulfonato-κO)-ruthenium, prepared according to the procedure in *J. Am. Chem. Soc.* 2011, 133, 9878-9891 (150 mg, 0.23 mmol) was added. To the above hydrogen was introduced in. The resulting solution was stirred for 20 h at room temperature. The resulting mixture was concentrated under vacuum. The residue was subjected to purification by FCC eluting with ethyl acetate/petroleum ether (1:4). This afforded the title compound (3.0 g, 73%) as a yellow oil. MS: (ES, m/z): 178 $[M+H]^+$.

Step 4. methyl (S)-5-methoxy-2-methyl-3,4-dihydroquinoline-1(2H)-carboxylate

Into a 250-mL round-bottom flask, (2S)-5-methoxy-2-methyl-1,2,3,4-tetrahydroquinoline (18 g, 99.52 mmol) was dissolved in dichloromethane (100 mL). Then pyridine (23.6 g, 298.36 mmol) was added, followed by methyl carbonochloridate (9.4 g, 99.47 mmol). The resulting solution was stirred for 1 h at room temperature. The resulting solution was diluted with 100 mL of dichloromethane and washed with 3×200 mL of water. The organic layers were combined, dried over anhydrous sodium sulfate, filtered and concentrated under vacuum. The residue was subjected to purification by FCC eluting with ethyl acetate/petroleum ether (1:3). This afforded the title compound (21 g, 89%) as a yellow oil. MS: (ES, m/z): 236 $[M+H]^+$.

Step 5. methyl (S)-5-hydroxy-2-methyl-3,4-dihydroquinoline-1(2H)-carboxylate

Into a 500-mL 3-necked round-bottom flask, methyl (2S)-5-methoxy-2-methyl-1,2,3,4-tetrahydroquinoline-1-carboxylate (21 g, 89.36 mmol) was dissolved in dichloromethane (150 mL). Then boron tribromide (150 mL, 0.15 mol, 1 M in $CH_2Cl_2$) was added. The resulting solution was stirred for 1 h at room temperature. The reaction was then quenched by the addition of 300 mL of water. The resulting mixture was extracted with 3×300 mL of dichloromethane. The organic layers were combined, dried over anhydrous sodium sulfate, filtered and concentrated under vacuum. The residue was subjected to purification by FCC eluting with ethyl acetate/petroleum ether (1:2). This afforded the title compound (13.5 g, 68%) as a yellow solid. MS: (ES, m/z): 222 $[M+H]^+$.

Step 6. methyl (S)-2-methyl-5-(((trifluoromethyl)sulfonyl)oxy)-3,4-dihydroquinoline-1(2H)-carboxylate Into a 250-mL round-bottom flask, methyl (2S)-5-hydroxy-2-methyl-1,2,3,4-tetrahydroquinoline-1-carboxylate (5 g, 18.08 mmol) was dissolved in dichloromethane (50 mL). Then pyridine (14.3 g, 180.78 mmol) and trifluoromethanesulfonic anhydride (10.2 g, 36.15 mmol) were added. The resulting solution was stirred for 1 h at room temperature. The resulting mixture was washed with 3×100 mL of water. The organic layers were combined, dried over anhydrous sodium sulfate, filtered and concentrated under vacuum. The residue was subjected to purification by FCC eluting with ethyl acetate/petroleum ether (1:3). This afforded the title compound (5.5 g, 86%) as a yellow oil. MS: (ES, m/z): 354 $[M+H]^+$.

Step 7. methyl (S)-5-((diphenylmethylene)amino)-2-methyl-3,4-dihydroquinoline-1(2H)-carboxylate Into a 500-mL round-bottom flask purged and maintained with an inert atmosphere of nitrogen, methyl (2S)-2-methyl-5-[(trifluoromethane)sulfonyloxy]-1,2,3,4-tetrahydroquinoline-1-carboxylate (23.5 g, 65.18 mmol) was dissolved in toluene (100 mL). Then diphenylmethanimine (17.9 g, 97.78 mmol), tris(dibenzylideneacetone)dipalladium-chloroform adduct (1.19 g, 1.30 mmol), (+/−)-2,2'-Bis(diphenylphosphino)-1,1'-binaphthyl (2.43 g, 3.90 mmol) and cesium carbonate (42.4 g, 130.13 mmol) were added. The resulting solution was stirred overnight at 100° C. under nitrogen atmosphere. The reaction mixture was cooled and the solids were filtered out. The residue was subjected to purification by FCC eluting with ethyl acetate/petroleum ether (1:3). This afforded the title compound (33 g, 80%) as a yellow oil. MS: (ES, m/z): 385 $[M+H]^+$.

Step 8. methyl (S)-5-amino-2-methyl-3,4-dihydroquinoline-1(2H)-carboxylate

Into a 500-mL round-bottom flask, methyl (2S)-5-[(diphenylmethylidene)amino]-2-methyl-1,2,3,4-tetrahydroquinoline-1-carboxylate (33 g, 85.93 mmol) was dissolved in methanol (200 mL). Then sodium acetate (17 g, 207.23 mmol) and hydroxylamine hydrochloride (12.3 g, 177.00 mmol) were added. The resulting solution was stirred for 2 h at room temperature. The solids were filtered out. The resulting mixture was concentrated under vacuum. The residue was subjected to purification by FCC eluting with ethyl acetate/petroleum ether (1:2). This afforded the title compound (12.5 g, 66%) as a yellow solid. MS: (ES, m/z): 221 $[M+H]^+$.

Step 9. methyl (S)-5-amino-6-bromo-2-methyl-3,4-dihydroquinoline-1(2H)-carboxylate (Intermediate 1)

Into a 100-mL 3-necked round-bottom flask, methyl (2S)-5-amino-2-methyl-1,2,3,4-tetrahydroquinoline-1-carboxylate (1 g, 4.09 mmol) was dissolved in acetonitrile (20 mL). Then N-bromosuccinimide (730 mg, 4.10 mmol) was added. The resulting solution was stirred for 30 min at room temperature. The resulting mixture was concentrated under vacuum. The residue was subjected to purification by FCC eluting with ethyl acetate/petroleum ether (1:1). This afforded the title compound (1.1 g, 90%) as a yellow solid. MS: (ES, m/z): 299, 301 $[M+H]^+$.

H-NMR: (400 MHz, CD3OD, ppm): 7.19 (d, J=8.8 Hz, 1H), 6.84 (d, J=8.8 Hz, 1H), 4.73-4.69 (m, 1H), 3.74 (s, 3H), 2.64-2.57 (m, 1H), 2.55-2.44 (m, 1H), 2.12-2.05 (m, 1H), 1.82-1.79 (m, 1H), 1.17 (d, J=6.9 Hz, 3H).

Intermediate 2: 3-phenylbutanoyl chloride

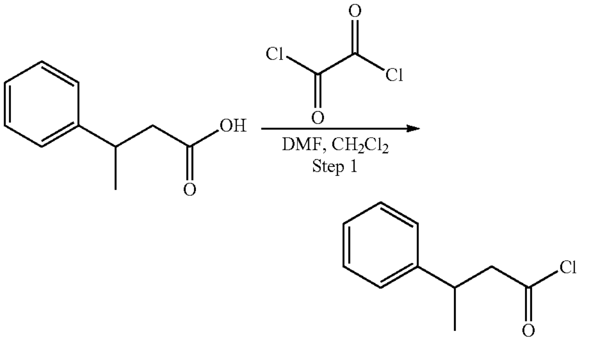

Into a 25-mL round-bottom flask, 3-phenylbutanoic acid (50 mg, 0.30 mmol) was dissolved in dichloromethane (5 mL). Then oxalyl chloride (2 mL) and one drop of N, N-dimethylformamide were added. The resulting solution was stirred for 3 h at room temperature. The resulting mixture was concentrated under vacuum. This afforded the title compound (51 mg, 90%) as yellow oil.

Intermediates 3 and 4: ethyl (trans)-4-amino-1-methylcyclohexane-1-carboxylate and ethyl (cis)-4-amino-1-methylcyclohexane-1-carboxylate

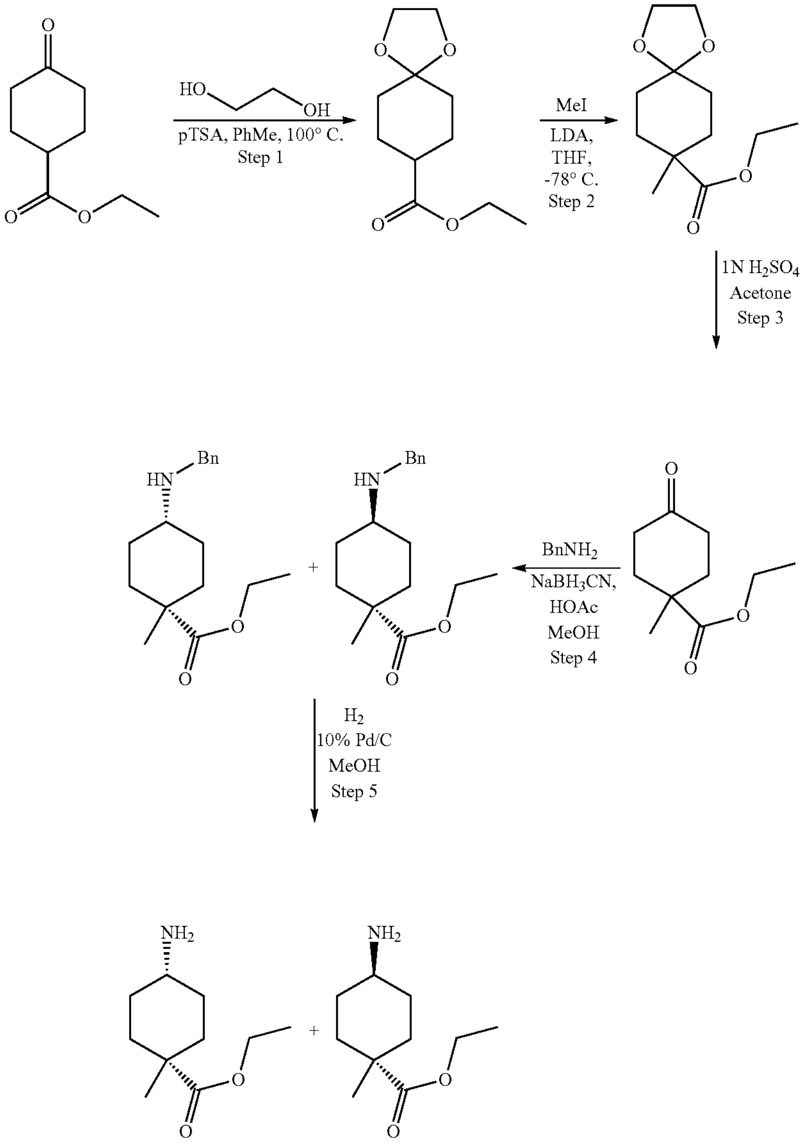

Step 1. Synthesis of ethyl 1,4-dioxaspiro[4.5]decane-8-carboxylate

Into a 250-mL round-bottom flask, ethyl 4-oxocyclohexane-1-carboxylate (10 g, 58.75 mmol) was dissolved in toluene (100 mL). Then ethane-1,2-diol (14.60 g, 235.23 mmol) was added, followed by p-toluenesulfonic acid (1.02 g, 5.92 mmol). The resulting solution was stirred for 14 h at 100° C. After cooled to room temperature, the resulting solution was diluted with 100 mL of water. The resulting solution was extracted with 3×100 mL of ethyl acetate. The organic layers were combined and washed with 3×100 mL of saturated sodium bicarbonate. The organic layer was dried over anhydrous sodium sulfate, filtered and concentrated under vacuum. The residue was subjected to purification by FCC eluting with ethyl acetate/petroleum ether (5:1). This afforded the title compound (3.0 g, 23%) as a yellow oil. MS: (ES, m/z): 215 [M+H]$^+$.

Step 2. Synthesis of ethyl 8-methyl-1,4-dioxaspiro[4.5]decane-8-carboxylate

Into a 250-mL 3-necked round-bottom flask, ethyl 1,4-dioxaspiro[4.5]decane-8-carboxylate (2.4 g, 11.20 mmol) was dissolved in tetrahydrofuran (100 mL). Then lithium diisopropylamide (2M in tetrahydrofuran, 8.4 mL, 16.77 mmol) was added dropwise. The mixture was stirred for 30 min at −78° C. To this was added iodomethane (2.38 g, 16.77 mmol). The resulting solution was stirred for 1 h at −78° C. The reaction was then quenched by the addition of 100 mL of ammonium chloride (aq, sat) and extracted with 3×100 ml of ethyl acetate. The organic layers were combined, dried over sodium sulfate, filtered and concentrated under vacuum. The residue was subjected to purification by FCC eluting with ethyl acetate/petroleum ether (1:2). This afforded the title compound (1.8 g, 69%) as a yellow oil. MS: (ES, m/z): 229 [M+H]$^+$.

Step 3. Synthesis of ethyl 1-methyl-4-oxocyclohexane-1-carboxylate

Into a 100-mL round-bottom flask, ethyl 8-methyl-1,4-dioxaspiro[4.5]decane-8-carboxylate (2.3 g, 10.08 mmol) was dissolved in acetone (20 mL). Then sulfuric acid (1M, 20 mL) was added. The resulting solution was stirred for 14 h at room temperature. The resulting solution was diluted with 50 ml of water and extracted with 3×50 ml of ethyl acetate. The organic layers were combined, dried over sodium sulfate, filtered and concentrated under vacuum. This afforded the title compound (1.8 g, crude) as a yellow oil. MS: (ES, m/z): 185 [M+H]$^+$.

Step 4. Synthesis of ethyl (trans)-4-(benzylamino)-1-methylcyclohexane-1-carboxylate and ethyl (cis)-4-(benzylamino)-1-methylcyclohexane-1-carboxylate Into a 100-mL round-bottom flask, ethyl 1-methyl-4-oxocyclohexane-1-carboxylate (1.7 g, 9.99 mmol) was dissolved in methanol (20 mL). Benzylamine (1.2 g, 11.20 mmol) and acetic acid (2.8 g, 46.63 mmol) were added, followed by sodium cyanoborohydride (2.9 g, 46.15 mmol). The resulting solution was stirred for 3 h at room temperature. The resulting solution was diluted with 30 mL of water and extracted with 3×30 mL of ethyl acetate. The organic layers were combined, dried over anhydrous sodium sulfate, filtered and concentrated under vacuum. The crude product was purified by Prep-SFC with the following conditions: Column, Chiralpak AD-H, 2×25 cm (5 um); mobile phase, $CO_2$ (80%), MeOH (2 mM $NH_3$-MeOH)(20%); Flow rate: 40 mL/min; Detector, UV 220 nm. This afforded the title compounds as follows: 280 mg (11%) of ethyl (trans)-4-(benzylamino)-1-methylcyclohexane-1-carboxylate (assumed stereochemistry, first eluting isomer, RT=3.75 min) as a yellow solid and 350 mg (13%) of ethyl (cis)-4-(benzylamino)-1-methylcyclohexane-1-carboxylate (assumed stereochemistry, second eluting isomer, RT=4.74 min) as a yellow solid. MS: (ES, m/z): 276 [M+H]$^+$.

Step 5. Synthesis of ethyl (trans)-4-amino-1-methylcyclohexane-1-carboxylate and ethyl (cis)-4-amino-1-methylcyclohexane-1-carboxylate Into a 50-mL round-bottom flask, ethyl trans-4-(benzylamino)-1-methylcyclohexane-1-carboxylate (280 mg, 1.02 mmol) or ethyl cis-4-(benzylamino)-1-methylcyclohexane-1-carboxylate (280 mg, 1.02 mmol) was dissolved in methanol (10 mL). Palladium carbon (280 mg, 10%) was added. Hydrogen (g) was introduced into the reaction mixture. The resulting solution was stirred for 5 h at room temperature under hydrogen atmosphere. The solids were filtered out and the resulting mixture was concentrated under vacuum. This afforded the independent title compounds (75 mg, crude) as yellow oils. MS: (ES, m/z): 186 [M+H]$^+$.

Intermediate 5: 2-(3-fluoro-4-methoxyphenyl)acetaldehyde

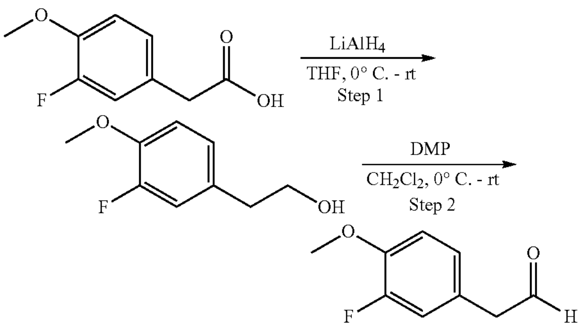

Step 1. Synthesis of 2-(3-fluoro-4-methoxyphenyl)ethan-1-ol 2-(3-fluoro-4-methoxyphenyl)acetic acid (400 mg, 2.17 mmol) was dissolved in THF (4 mL). The reaction solution was cooled to 0° C. Lithium aluminium hydride (90.8 mg, 2.39 mmol) was added portionwise. The flask was then wrapped with aluminum foil and the resulting solution was stirred for 1 h at room temperature. The reaction was then quenched by the addition of 2 mL of water/ice. The resulting mixture was concentrated under vacuum. The solution was extracted with 2×10 mL of ethyl acetate and the organic layers were combined and evaporated. This afforded 290 mg (78%) of 2-(3-fluoro-4-methoxyphenyl)ethan-1-ol as colorless oil.

Step 2. Synthesis of 2-(3-fluoro-4-methoxyphenyl)acetaldehyde

Into a 100-mL 3-necked round-bottom flask purged and maintained with an inert atmosphere of nitrogen, was placed 2-(3-fluoro-4-methoxyphenyl)ethan-1-ol (290 mg, 1.70 mmol) in dichloromethane (5 mL). The reaction was cooled to 0° C. and Dess-Martin Periodinane (940 mg, 2.22 mmol, 1.30 equiv) was added. The flask was wrapped with aluminum foil and the resulting solution was stirred for 2 h at room temperature. The resulting mixture was concentrated under vacuum. The residue was subjected to FCC eluting with ethyl acetate/petroleum ether (1:5). This afforded the title compound (150 mg, 52%) as a colorless oil. MS: (ES, m/z): 169 $[M+H]^+$.

Intermediate 6: 3-(2H-1,2,3-triazol-2-yl)propanal

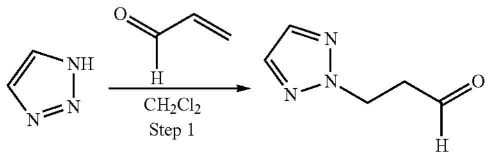

Step 1. Synthesis of 2-(3-fluoro-4-methoxyphenyl)acetaldehyde 1H-1,2,3-triazole (500 mg, 7.24 mmol) was dissolved in dichloromethane (15 mL) in a round bottom flask. Prop-2-enal (608 mg, 10.84 mmol) was added. The resulting solution was stirred for 1 h at room temperature. The resulting mixture was concentrated under vacuum. The residue was subjected to purification by FCC eluting with ethyl acetate/petroleum ether (1:2). This afforded the title compound (100 mg, 11%) as a yellow oil. MS: (ES, m/z): $126[M+H]^+$.

Intermediate 7: 3-(2-methyl-1,3-oxazol-5-yl)propanal

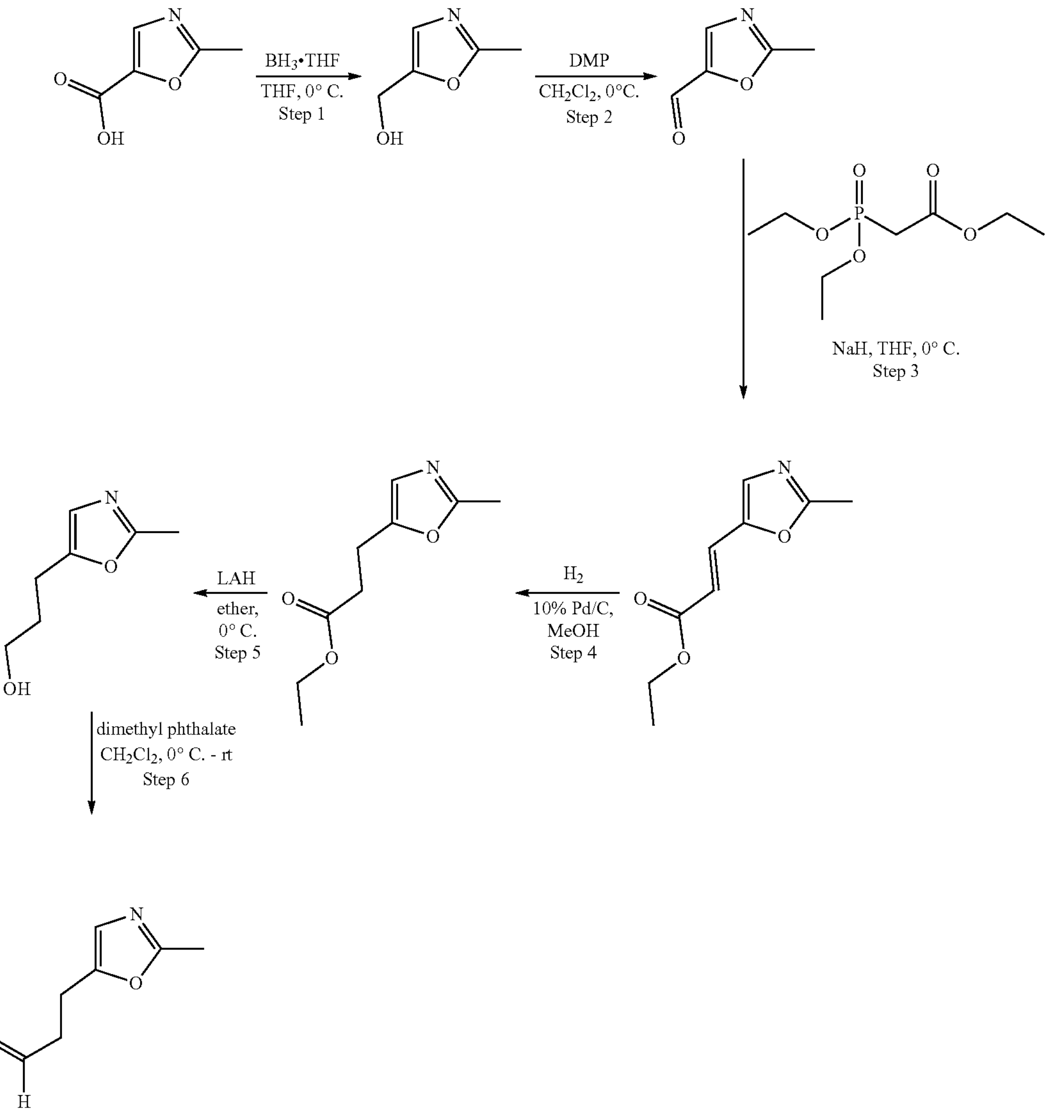

Step 1. Synthesis of (2-methyl-1,3-oxazol-5-yl)methanol

Into a 100-mL round-bottom flask purged and maintained with an inert atmosphere of nitrogen, 2-methyl-1,3-oxazole-5-carboxylic acid (1.0 g, 7.86 mmol) was dissolved in tetrahydrofuran (10 mL). Then borane-tetrahydrofuran complex (31.6 mL, 330.2 mmol) was added dropwise with stirring at 0° C. The resulting solution was stirred for 30 min at 0° C. The resulting solution was allowed to react, with stirring, for an additional 2 h at room temperature. The reaction was then quenched by the addition of 20 mL of water and extracted with 3×40 mL of ethyl acetate. The organic layers were combined, dried over anhydrous sodium sulfate, filtered and concentrated under vacuum. This afforded the title compound (1.43 g, crude) as an off-white solid. MS: (ES, m/z): 114 $[M+H]^+$.

Step 2. Synthesis of 2-methyl-1,3-oxazole-5-carbaldehyde

Into a 25-mL round-bottom flask, (2-methyl-1,3-oxazol-5-yl)methanol (1.43 g, 12.6 mmol) was dissolved in dichloromethane (10 mL). Then (1,1,1-triacetoxy)-1,1-dihydro-1,2-benziodoxol-3(1H)-one (6.97 g, 16.44 mmol) was added. The resulting solution was stirred for 30 min at 0° C. The resulting solution was allowed to react, with stirring, for an additional 2 h at room temperature. The reaction was then quenched by the addition of 20 mL of aqueous solution of sodium bicarbonate and 20 mL of aqueous solution of sodium bisulfite. The resulting solution was extracted with 3×30 mL of dichloromethane and the organic layers were combined, dried over anhydrous sodium sulfate, filtered and concentrated under vacuum. The residue was subjected to purification by FCC eluting with ethyl acetate/petroleum ether (1:1). This afforded the title compound (677.3 mg, 48.4%) as an off-white solid. MS: (ES, m/z): 112 $[M+H]^+$.

Step 3. Synthesis of ethyl (2E)-3-(2-methyl-1,3-oxazol-5-yl)prop-2-enoate

Into a 250-mL 3-necked round-bottom flask purged and maintained with an inert atmosphere of nitrogen, ethyl 2-(diethoxyphosphoryl)acetate (3.55 g, 15.9 mmol) was dissolved in tetrahydrofuran (20 mL). Then sodium hydride (3.29 g, 60% in oil, 137.3 mmol) in tetrahydrofuran (2 mL) was added dropwise with stirring at 0° C. The resulting mixture was stirred for 30 min at 0° C. To this was added a solution of 2-methyl-1,3-oxazole-5-carbaldehyde (677.3 mg, 6.10 mmol) in tetrahydrofuran (2 mL) dropwise with stirring at 0° C. The resulting solution was stirred for 1.5 h at 0° C. The reaction was then quenched by the addition of 40 mL of water and extracted with 3×80 mL of ethyl acetate. The organic layers were combined, dried over anhydrous sodium sulfate, filtered and concentrated under vacuum. The residue was subjected to purification by FCC eluting with ethyl acetate/petroleum ether (1:1). This afforded the title compound (145 mg, 13%) as a light yellow liquid. MS: (ES, m/z): 182 $[M+H]^+$.

Step 4. Synthesis of ethyl 3-(2-methyl-1,3-oxazol-5-yl)propanoate

Into a 25-mL round-bottom flask, ethyl (2E)-3-(2-methyl-1,3-oxazol-5-yl)prop-2-enoate (145 mg, 0.80 mmol) was dissolved in methanol (5 mL). Then 10% palladium carbon (145 mg) was added. To the above hydrogen (g) was introduced in. The resulting solution was stirred for 2 h at room temperature. The solids were filtered out. The resulting mixture was concentrated under vacuum. This afforded the title compound (150 mg, crude) as a colorless oil. MS: (ES, m/z): 184 $[M+H]^+$.

Step 5. Synthesis of 3-(2-methyl-1,3-oxazol-5-yl)propan-1-ol

Into a 25-mL 2-necked round-bottom flask purged and maintained with an inert atmosphere of nitrogen, ethyl 3-(2-methyl-1,3-oxazol-5-yl)propanoate (134.2 mg, 0.73 mmol) was dissolved in diethyl ether (5 mL). Then LAH (33.4 mg, 0.88 mmol) was added in portions at 0° C. The resulting solution was stirred for 1 h at 0° C. The reaction was then quenched by the addition of 5 mL of aqueous potassium sodium tartrate and extracted with 3×10 mL of ether. The organic layers were combined, dried over anhydrous sodium sulfate, filtered and concentrated under vacuum. This afforded the title compound (122 mg, crude) as a colorless oil. MS: (ES, m/z): 142 $[M+H]^+$.

Step 6. Synthesis of 3-(2-methyl-1,3-oxazol-5-yl)propanal

Into a 25-mL round-bottom flask, 3-(2-methyl-1,3-oxazol-5-yl)propan-1-ol (122 mg, 0.86 mmol) was dissolved in dichloromethane (5 mL). Then dimethyl phthalate (980 mg, 2.31 mmol) was added at 0° C. The resulting solution was stirred for 30 min at 0° C. The resulting solution was allowed to react, with stirring, for an additional 2 h at room temperature. The resulting mixture was concentrated under vacuum. The residue was subjected to purification by FCC eluting with ethyl acetate/petroleum ether (1:1). This afforded the title compound (98.8 mg, 82%) as a yellow solid. MS: (ES, m/z): 140 $[M+H]^+$.

Intermediate 8: 3-(1-methyl-1H-pyrazol-4-yl)propanal

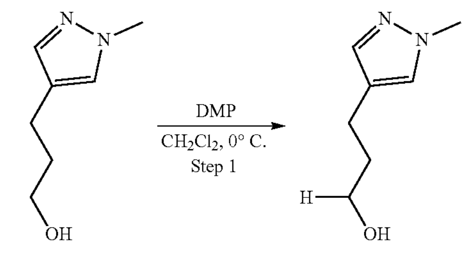

Into a 20-mL 2-necked round-bottom flask, was placed 3-(1-methyl-1H-pyrazol-4-yl)propan-1-ol (140 mg, 1.00 mmol) in dichloromethane (5 mL). Dess-Martin reagent (551 mg, 1.30 mmol) was added portionwise and the resulting solution was stirred for 1 h at room temperature. The resulting mixture was concentrated under vacuum. The residue was subjected to purification by FCC eluting with ethyl acetate/petroleum ether (1:1). This afforded the title compound as a yellow oil (110 mg, 80%). MS: (ES, m/z): 139 $[M+H]^+$.

The following intermediates in TABLE A were prepared using standard chemical manipulations and procedures similar to those used for the preparation of Intermediate 8.

TABLE A

| Intermediate Number | Structure and Compound Name | LRMS m/z [M + H]$^+$ |
|---|---|---|
| 9 | 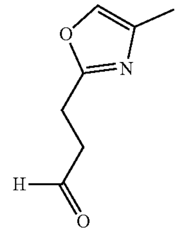 3-(4-methyloxazol-2-yl)propanal | 140 |
| 10 | 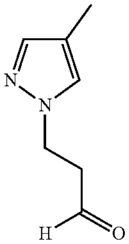 3-(4-methyl-1H-pyrazol-1-yl)propanal | 139 |
| 11 | 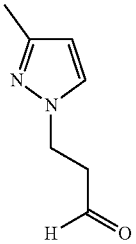 3-(3-methyl-1H-pyrazol-1-yl)propanal | 139 |
| 12 | 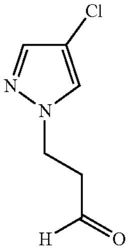 3-(4-chloro-1H-pyrazol-1-yl)propanal | 159 |
| 13 | 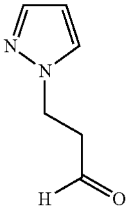 3-(1H-pyrazol-1-yl)propanal | 124 |

TABLE A-continued

| Intermediate Number | Structure and Compound Name | LRMS m/z [M + H]$^+$ |
|---|---|---|
| 14 | 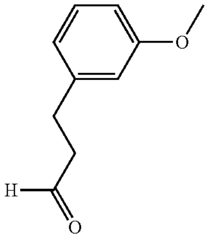 3-(3-methoxyphenyl)propanal | 164 |
| 15 | 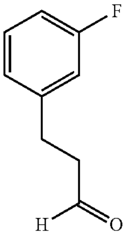 3-(3-fluorophenyl)propanal | 152 |
| 16 | 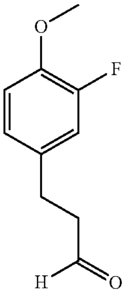 3-(3-fluoro-4-methoxyphenyl)propanal | 169 |
| 17 | 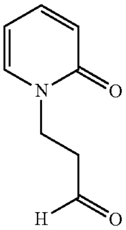 3-(2-oxopyridin-1(2H)-yl)propanal | 151 |
| 18 | 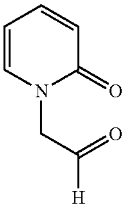 2-(2-oxopyridin-1(2H)-yl)acetaldehyde | 137 |

TABLE A-continued

| Intermediate Number | Structure and Compound Name | LRMS m/z $[M + H]^+$ |
|---|---|---|
| 19 | 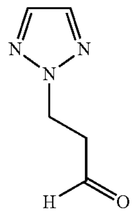 3-(2H-1,2,3-triazol-2-yl)propanal | 125 |

Intermediate 20: 3-(5-methyloxazol-2-yl)propanal

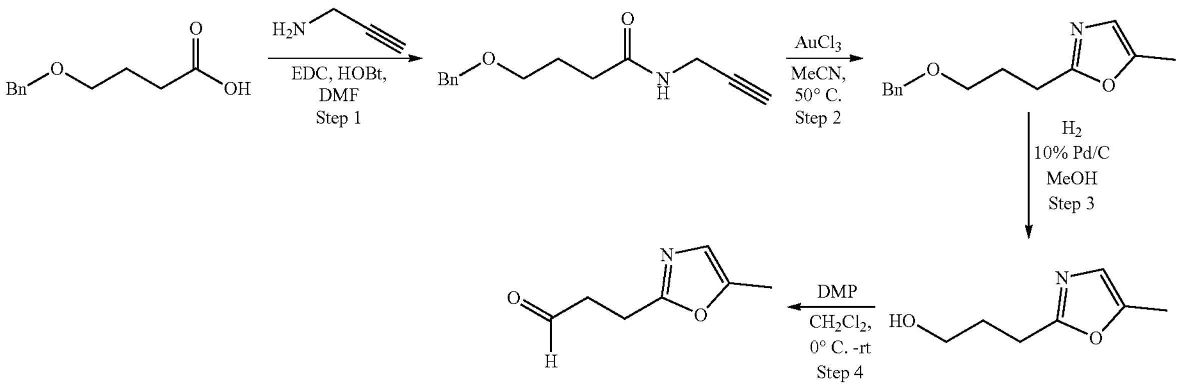

Step 1. Synthesis of 4-(benzyloxy)-N-(prop-2-yn-1-yl)butanamide

Into a 100-mL 3-necked round-bottom flask purged and maintained with an inert atmosphere of nitrogen, was placed 4-(benzyloxy)butanoic acid (515 mg, 2.65 mmol) in DMF (5 mL). Prop-2-yn-1-amine (146 mg, 2.65 mmol), 1H-1,2,3-benzotriazol-1-ol (358 mg, 2.65 mmol), and EDC (508 mg, 2.65 mmol) were added. The flask was wrapped with aluminum foil and the resulting solution was stirred for 12 h at room temperature. The reaction was then quenched by the addition of 5 mL of water/ice. The resulting solution was extracted with 3×10 mL of ethyl acetate and the organic layers combined. The resulting mixture was concentrated under vacuum affording the title compound (460 mg, 75%) as a colorless oil. MS: (ES, m/z): 232 $[M+H]^+$.

Step 2. Synthesis of 2-(3-(benzyloxy)propyl)-5-methyloxazole

Into a 100-mL round-bottom flask, was placed 4-(benzyloxy)-N-(prop-2-yn-1-yl)butanamide (460 mg, 1.99 mmol) in acetonitrile (10 mL). Goldtrichloride (30.05 mg, 0.1 mmol) was added and the resulting solution was stirred for 8 h at 50° C. The resulting mixture was concentrated under vacuum and the residue was subjected to purification by FCC eluting with ethyl acetate/petroleum ether (1:5). This afforded the title compound (280 mg, 61%) as a yellow oil. MS: (ES, m/z): 232 $[M+H]^+$.

Step 3. Synthesis of 3-(5-methyloxazol-2-yl)propan-1-ol

Into a 50-mL round-bottom flask, was placed 2-[3-(benzyloxy)propyl]-5-methyl-1,3-oxazole (280 mg, 1.21 mmol) and 10% palladium on carbon (28 g) in methanol (5 mL). A balloon filled with hydrogen (g) was charged in and the suspension was stirred for 12 h at room temperature. The reaction was vented to nitrogen and the solids were filtered out over celite. The resulting solution was concentrated under vacuum affording the title compound (150 mg, 88%) as a white solid. MS: (ES, m/z): 142 $[M+H]^+$.

Step 4. Synthesis of 3-(5-methyloxazol-2-yl)propanal

Into a 100-mL round-bottom flask, was placed 3-(5-methyl-1,3-oxazol-2-yl)propan-1-ol (150 mg, 1.06 mmol) in dichloromethane (5 mL). The reaction was cooled to 0° C. and Dess-Martin reagent (586.4 mg, 1.38 mmol) was added. The resulting mixture was stirred for 1.5 h at room temperature and then concentrated under vacuum. This afforded the title compound (100 mg, 68%) as a white solid. MS: (ES, m/z): 140 $[M+H]^+$.

Intermediate 21: 3-(3-methylisoxazol-5-yl)propanal

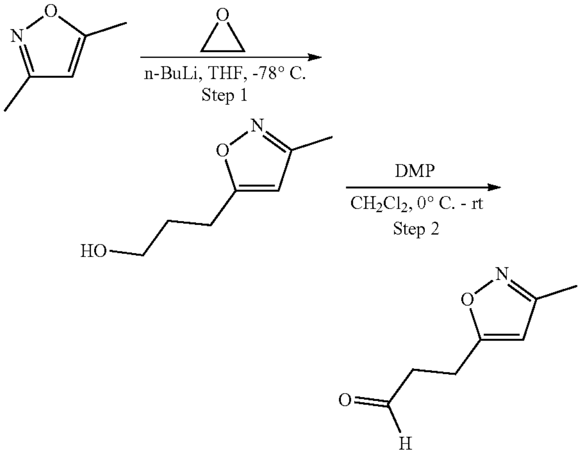

Step 1. Synthesis of 3-(3-methyl-1,2-oxazol-5-yl)propan-1-ol

Into a 100-mL round-bottom flask purged and maintained with an inert atmosphere of nitrogen, 3,5-dimethyl-1,2-oxazole (2 g, 20.59 mmol) was dissolved in tetrahydrofuran (20 mL). Then n-butyllithium (10 M in hexanes, 8.25 mL, 87.58 mmol) was added dropwise. The resulting mixture was stirred at −78° C. for 2 h. To this was added a solution of oxirane (2.72 g, 61.8 mmol) in tetrahydrofuran (5 mL). The resulting solution was stirred at −78° C. for 1 h. The resulting solution was diluted with 50 mL of ammonium chloride (aq.) and extracted with 3×50 mL of dichloromethane. The organic layers were combined, dried over anhydrous sodium sulfate, filtered and concentrated under vacuum. This afforded the title compound (1.47 g, crude) as an orange liquid. MS: (ES, m/z): 142 $[M+H]^+$.

Step 2. Synthesis of 3-(3-methyl-1,2-oxazol-5-yl)propanal

Into a 25-mL round-bottom flask, 3-(3-methyl-1,2-oxazol-5-yl)propan-1-ol (500 mg, 3.54 mmol) was dissolved in dichloromethane (5 mL). Then Dess-Martin periodinane (1.95 g, 4.61 mmol) was added. The resulting solution was stirred for 2 h at room temperature. The resulting solution was diluted with 50 mL of sodium bicarbonate and extracted with 3×50 mL of ethyl acetate. The organic layers were combined, dried over anhydrous sodium sulfate, filtered and concentrated under vacuum. The residue was subjected to purification by FCC eluting with ethyl acetate/petroleum ether (1:1). This afforded the title compound (247 mg, 50%) as a light yellow liquid. MS: (ES, m/z): 140 $[M+H]^+$.

Intermediate 22: 3-(5-methyl-1,3,4-oxadiazol-2-yl)propanal

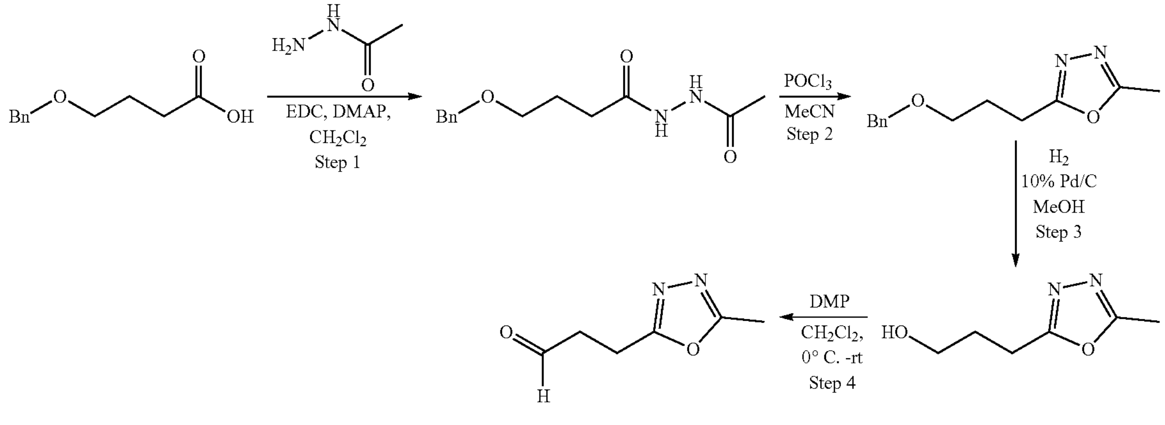

Step 1. Synthesis of N'-acetyl-4-(benzyloxy)butanehydrazide

Into a 250-mL 3-necked round-bottom flask purged and maintained with an inert atmosphere of nitrogen, was placed 4-(benzyloxy)butanoic acid (1.0 g, 5.15 mmol) in dichloromethane (10 mL). Acetohydrazide (724 mg, 9.77 mmol) was added followed by triethylamine (1.249 g, 12.34 mmol), 4-dimethylaminopyridine (1.25 g, 10.23 mmol) and EDC (1.98 g, 10.31 mmol). The resulting solution was stirred for 17 h at room temperature. The pH value of the solution was adjusted to 2 with hydrochloric acid (1N). The resulting solution was extracted with 2×20 mL of ethyl acetate and the organic layers combined. The resulting mixture was concentrated under vacuum affording the title compound (1 g, 78%) as a white solid. MS: (ES, m/z): 251 $[M+H]^+$.

Step 2. Synthesis of 2-(3-(benzyloxy)propyl)-5-methyl-1,3,4-oxadiazole

Into a 50-mL round-bottom flask, was placed N'-acetyl-4-(benzyloxy)butanehydrazide (300 mg, 1.20 mmol) in acetonitrile (5 mL). Phosphoryl trichloride (5 mL) was added and the resulting solution was stirred for 2 h at 60° C. The resulting mixture was concentrated under vacuum and the residue was subjected to purification by FCC eluting with ethyl acetate. This afforded the title compound (180 mg, 65%) as a yellow oil. MS: (ES, m/z): 233 $[M+H]^+$.

Step 3. Synthesis of 3-(5-methyl-1,3,4-oxadiazol-2-yl)propan-1-ol

Into a 50-mL round-bottom flask, was placed a suspension of 2-[3-(benzyloxy)propyl]-5-methyl-1,3,4-oxadiazole (180 mg, 0.77 mmol), and 10% palladium on carbon (18 mg) in methanol (5 mL). A balloon filled with hydrogen (g) was charged in and the reaction mixture was stirred for 24 h at room temperature. The reaction was vented to nitrogen and the solids were filtered out over celite. The filtered solution was concentrated in vacuo and the residue was subjected to purification by FCC eluting with ethyl acetate. This afforded the title compound (100 mg, 91%) as a white solid. MS: (ES, m/z): 143 $[M+H]^+$.

Step 4. Synthesis of 3-(5-methyl-1,3,4-oxadiazol-2-yl)propanal

Into a 100-mL 3-necked round-bottom flask, was placed 3-(5-methyl-1,3,4-oxadiazol-2-yl)propan-1-ol (100 mg, 0.70 mmol) in dichloromethane (5 mL). Dess-Martin periodinane reagent (388 mg, 0.91 mmol) was added and the resulting solution was stirred for 1 h at room temperature. The resulting mixture was concentrated under vacuum. The residue was dissolved in 5 mL of ethyl acetate. The solids were filtered out over celite and the filtered solution was concentrated in vacuo. The residue was subjected to purification by FCC eluting with ethyl acetate. This afforded the title compound (80 mg, 81%) as a yellow oil. MS: (ES, m/z): 141 $[M+H]^+$.

Intermediate 23: 3-(5-methyl-1,3,4-oxadiazol-2-yl)propanal

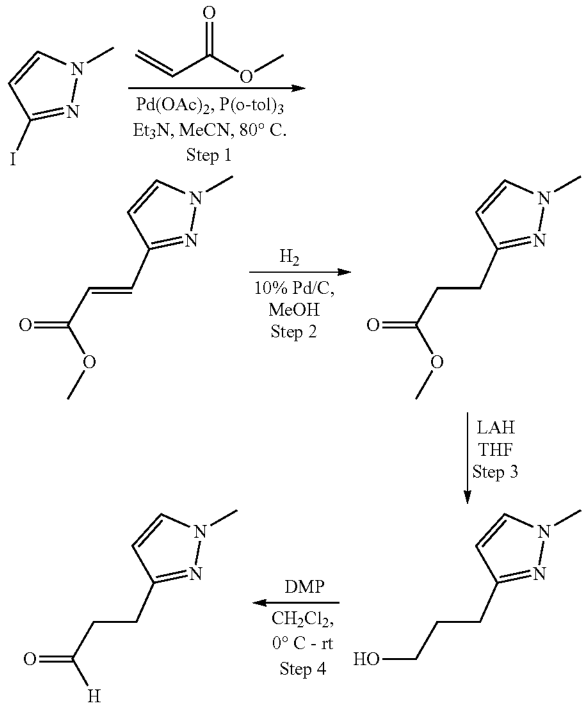

Step 1. Methyl (2E)-3-(1-methyl-1H-pyrazol-3-yl) prop-2-enoate

Into a 50-mL vial purged and maintained with an inert atmosphere of nitrogen, 3-iodo-1-methyl-1H-pyrazole (500 mg, 2.40 mmol) was dissolved in acetonitrile (10 mL). Then methyl prop-2-enoate (2.07 g, 24.03 mmol), palladium diacetate (108 mg, 0.48 mmol), tri-ortho-tolylphosphine (292 mg, 0.96 mmol) and triethylamine (1.216 g, 12.02 mmol) were added. The resulting solution was stirred for 2 h at 80° C. under nitrogen atmosphere. The reaction mixture was cooled and concentrated under vacuum. The residue was subjected to purification by FCC eluting with ethyl acetate/petroleum ether (1:1). This afforded the title compound (130 mg, 33%) as a yellow oil. MS: (ES, m/z): 167[M+H]$^+$.

Step 2. Methyl 3-(1-methyl-1H-pyrazol-3-yl)propanoate

Into a 50-mL round-bottom flask, methyl (2E)-3-(1-methyl-1H-pyrazol-3-yl)prop-2-enoate (130 mg, 0.78 mmol) was dissolved in methanol (10 mL). Then 10% palladium on carbon (80 mg, 0.75 mmol) was added. Hydrogen (g) was charged into the reaction mixture. The resulting solution was stirred for 1 h at room temperature under hydrogen atmosphere. The reaction was vented to nitrogen and the solids were filtered out and the resulting mixture was concentrated under vacuum. The residue was subjected to purification by FCC eluting with ethyl acetate/petroleum ether (1:1). This afforded the title compound (120 mg, 91%) as an off-white oil. MS: (ES, m/z): 169 [M+H]$^+$.

Step 3. 3-(1-Methyl-1H-pyrazol-3-yl)propan-1-ol

Into a 25-mL round-bottom flask, methyl 3-(1-methyl-1H-pyrazol-3-yl)propanoate (150 mg, 0.89 mmol) was dissolved in tetrahydrofuran (10 mL) Then lithium aluminium hydride (40 mg, 1.05 mmol) was added. The resulting solution was stirred for 1 h at room temperature. The reaction was then quenched by addition of water (20 mL). The resulting solution was extracted with 3×20 mL of ethyl acetate. The organic layers were combined, dried over sodium sulfate, filtered and concentrated under vacuum. The residue was subjected to purification by FCC eluting with ethyl acetate/petroleum ether (1:1). This afforded the title compound (120 mg, 96%) as an off-white oil. MS: (ES, m/z): 141 [M+H]$^+$.

Step 4. 3-(1-methyl-1H-pyrazol-3-yl)propanal

Into a 50-mL round-bottom flask, 3-(1-methyl-1H-pyrazol-3-yl)propan-1-ol (120 mg, 0.86 mmol) was dissolved in dichloromethane (10 mL). Then Dess-Martin periodinane (472 mg, 1.11 mmol) was added in portions. The resulting solution was stirred for 2 h at 0° C. in a water/ice bath. The reaction was then quenched by addition of water (20 mL). The resulting solution was extracted with 3×20 mL of dichloromethane. The organic layers were combined, dried over sodium sulfate, filtered and concentrated under vacuum. The residue was subjected to purification by FCC eluting with ethyl acetate/petroleum ether (1:1). This afforded the title compound (100 mg, 85%) as an off-white oil. MS: (ES, m/z): 139[M+H]$^+$.

Intermediate 24: 3-((tert-butyldimethylsilyl)oxy)-2-phenylpropanal

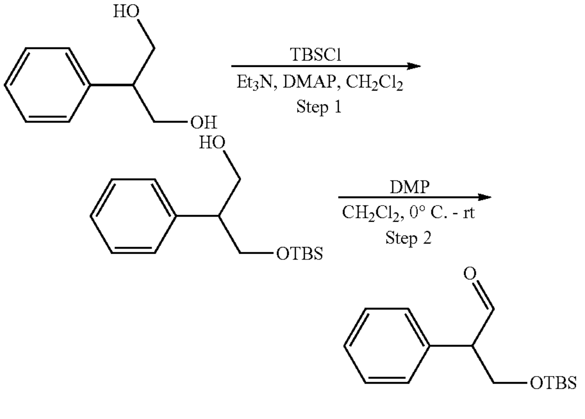

Step 1. Synthesis of 3-[(tert-butyldimethylsilyl) oxy]-2-phenylpropan-1-ol

Into a 100-mL round-bottom flask, 2-phenylpropane-1,3-diol (2.5 g, 16.43 mmol) was dissolved in dichloromethane (30 mL). Then tert-butyldimethylsilyl chloride (2.6 g, 17.25 mmol) and 4-dimethylaminopyridine (20 mg, 0.16 mmol) were added, followed by triethylamine (2.7 mL, 19.42 mmol). The mixture was stirred for 12 h at room temperature. The resulting mixture was concentrated under vacuum. The residue was subjected to purification by FCC eluting with ethyl acetate/petroleum ether (1:5). This afforded the title compound (2 g, 46%) as a yellow oil. MS: (ES, m/z): 267 [M+H]$^+$.

Step 2. Synthesis of 3-[(tert-butyldimethylsilyl) oxy]-2-phenylpropanal

Into a 50-mL round-bottom flask, 3-[(tert-butyldimethylsilyl)oxy]-2-phenylpropan-1-ol (1 g, 3.75 mmol) was dissolved in dichloromethane (20 mL) and cooled down to 0° C. Then Dess-Martin periodinane (2 g, 4.72 mmol) was added. The mixture was stirred for 8 h at room temperature. Then water was added. The mixture was extracted with 2×50 mL of dichloromethane. The organic layers were combined, dried over sodium sulfate, filtered and concentrated. The residue was subjected to purification by FCC eluting with ethyl acetate/petroleum ether (1:4). This afforded the title compound (800 mg, 81%) as a yellow oil. MS: (ES, m/z): 265 $[M+H]^+$.

Intermediate 25 and 26: methyl (cis)-4-amino-2,2-dimethylcyclohexane-1-carboxylate and methyl (trans)-4-amino-2,2-dimethylcyclohexane-1-carboxylate

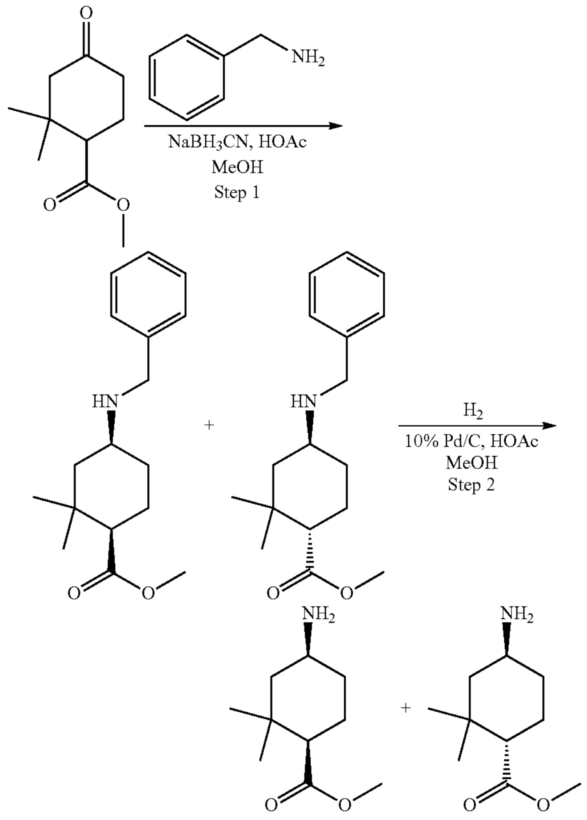

Step 1. Synthesis of cis-methyl 4-(benzylamino)-2,2-dimethylcyclohexanecarboxylic acid and trans-methyl 4-(benzylamino)-2,2-dimethylcyclohexanecarboxylic acid Into a 100-mL round-bottom flask, methyl 2,2-dimethyl-4-oxocyclohexane-1-carboxylate (1 g, 5.43 mmol) was dissolved in methanol (20 mL). Then phenylmethanamine (1.61 g, 10.86 mmol) was added. The resulting solution was stirred for 1 h at room temperature. Then sodium cyanoborohydride (1.37 g, 21.72 mmol) was added, followed by glacial acetic acid (980 mg, 16.33 mmol). The resulting solution was stirred for 8 h at room temperature. The solids were filtered out and the resulting mixture was concentrated under vacuum. The crude product was purified by Prep-HPLC with the following conditions: Column, XBridge C18 OBD Prep Column, 5 um, 19 mm×150 mm; mobile phase, A: Water (containing 10 mmol/L $NH_4HCO_3$) and B: ACN (20.0% to 40.0% ACN over 7 min); UV Detector: 254 nm. This result in 890 mg (60%) of the product as a yellow oil. The product was then purified by Chiral Prep-HPLC with the following conditions: Column: CHIRALPAK IF, 2*25 cm, 5 um; Mobile Phase, A: hexanes and B: EtOH (30% EtOH over 11.5 min); UV Detector: 254 nm; RT1:6.97 and RT2:7.25. This afforded the title compounds 380 mg of cis-methyl 4-(benzylamino)-2,2-dimethylcyclohexanecarboxylic acid as a yellow oil and 200 mg of trans-methyl 4-(benzylamino)-2,2-dimethylcyclohexanecarboxylic acid as a yellow oil. MS: (ES, m/z): 262 $[M+H]^+$.

Step 2. Synthesis of methyl (cis)-4-amino-2,2-dimethylcyclohexane-1-carboxylate and methyl (trans)-4-amino-2,2-dimethylcyclohexane-1-carboxylate Into a 100-mL round-bottom flask purged and maintained with an inert atmosphere of nitrogen, methyl 4-(benzyamino)-2,2-dimethylcyclohexane-1-carboxylate (380 mg, 1.38 mmol) was dissolved in methanol (14 mL). Then palladium on carbon (76 mg, 10%) was added, followed by acetic acid (0.7 mL). Hydrogen (g) was charged into the reaction mixture and the resulting solution was stirred under a hydrogen atmosphere for 8 h at room temperature. The reaction was vented to nitrogen and the solids were filtered out over celite. The filtered solution was concentrated under vacuum. This afforded the title compound (203 mg, crude) as a yellow oil, which could be used without further purification. MS: (ES, m/z): 186 $[M+H]^+$.

Intermediate 27: 2-methyl-3-phenylpropanal

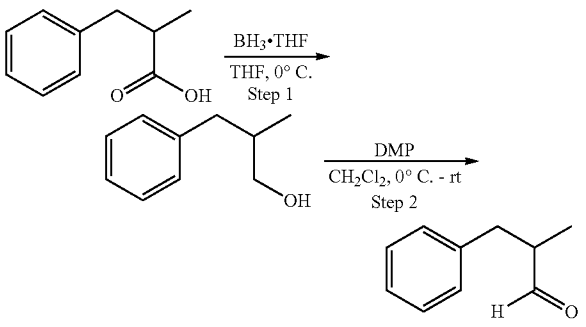

Step 1. Synthesis of 2-methyl-3-phenylpropan-1-ol

Into a 250-mL round-bottom flask, 2-methyl-3-phenylpropanoic acid (3.0 g, 18.3 mmol) was dissolved in tetrahydrofuran (30 mL). Then boron trifluoride tetrahydrofuran complex (27 mL, 282.1 mmol) was added dropwise with stirring at 0° C. The resulting solution was stirred for 2 h at room temperature. The reaction was then quenched by addition of 30 mL of water and extracted with 3×50 mL of ethyl acetate. The organic layers were combined, dried over anhydrous sodium sulfate, filtered and concentrated under vacuum. This afforded the title compound (2.0 g, 70%) as a yellow oil. MS: (ES, m/z): 151 $[M+H]^+$.

Step 2. Synthesis of 2-methyl-3-phenylpropanal

Into a 250-mL round-bottom flask, 2-methyl-3-phenylpropan-1-ol (2.0 g, 13.3 mmol) was dissolved in dichloromethane (50 mL). Then Dess-Martin periodinane reagent (11.3 g, 26.6 mmol) was added. The resulting solution was stirred for 5 h at room temperature. The reaction was then quenched by addition of 100 mL of saturated sodium bicarbonate solution and extracted with 3×50 mL of dichloromethane. The organic layers were combined, dried over anhydrous sodium sulfate, filtered and concentrated under vacuum. The residue was subjected to purification by FCC eluting with ethyl acetate/petroleum ether (1:4). This afforded the title compound (1.0 g, 49%) as a yellow oil. MS: (ES, m/z): 149 [M+H]$^+$.

Intermediate 28: 2-(3-isopropoxyphenyl)acetaldehyde

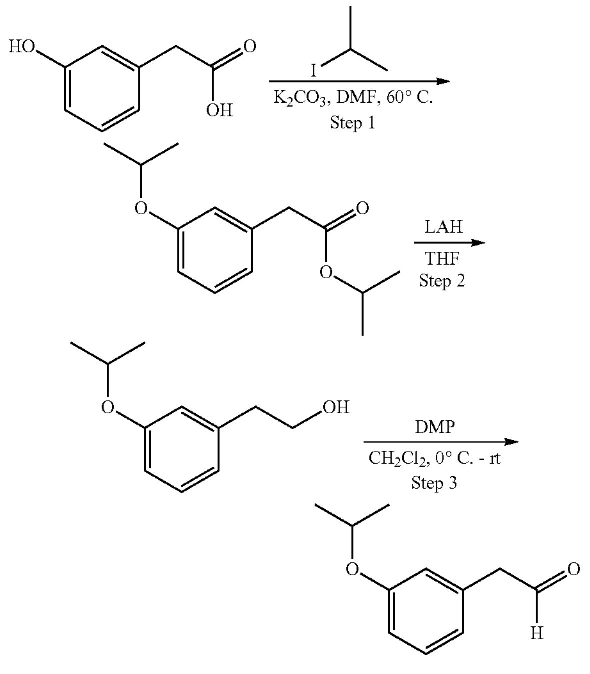

Step 1. Synthesis of propan-2-yl 2-[3-(propan-2-yloxy)phenyl]acetate

Into a 250-mL round-bottom flask, 2-(3-hydroxyphenyl) acetic acid (2 g, 13.15 mmol) was dissolved in N,N-dimethylformamide (50 mL). Then potassium carbonate (5.45 g, 39.43 mmol) was added, followed by 2-iodopropane (6.71 g, 39.47 mmol). The resulting solution was stirred for 5 h at 60° C. The reaction mixture was cooled to room temperature and diluted with 100 mL of water. The resulting solution was extracted with 3×100 mL of ethyl acetate. The organic layers were combined, dried over anhydrous sodium sulfate, filtered and concentrated under vacuum. This afforded the title compound (1.7 g, crude) as a yellow oil. MS: (ES, m/z): 237 [M+H]$^+$.

Step 2. Synthesis of 2-[3-(propan-2-yloxy)phenyl]ethan-1-ol

Into a 50-mL round-bottom flask, propan-2-yl 2-[3-(propan-2-yloxy)phenyl]acetate (1.5 g, 4.44 mmol) was dissolved in tetrahydrofuran (10 mL). Then lithium aluminum hydride (362 mg, 9.54 mmol) was added in portions. The resulting solution was stirred for 2 h at room temperature. The reaction was then quenched by the addition of 20 mL of potassium sodium tartrate (aq) and extracted with 3×30 mL of ethyl acetate. The organic layers were combined, dried over anhydrous sodium sulfate, filtered and concentrated under vacuum. The residue was subjected to purification by FCC eluting with ethyl acetate/petroleum ether (1:1). This afforded the title compound (0.9 g, 75%) as a yellow oil. MS: (ES, m/z): 181 [M+H]$^+$.

Step 3. Synthesis of 2-(3-isopropoxyphenyl)acetaldehyde

Into a 50-mL round-bottom flask, 2-[3-(propan-2-yloxy) phenyl]ethan-1-ol (150 mg, 0.83 mmol) was dissolved in chloroform (10 mL). Then Dess-Martin periodinane (530 mg, 1.25 mmol) was added. The resulting solution was stirred for 2 h at room temperature. The solids were filtered out and the filtrate was diluted with 30 mL of sodium bicarbonate(aq). The resulting solution was extracted with 3×30 mL of ethyl acetate. The organic layers were combined, dried over anhydrous sodium sulfate, filtered and concentrated under vacuum. The residue was subjected to purification by FCC eluting with ethyl acetate/petroleum ether (1:1). This afforded the title compound (75 mg, 48%) as a yellow oil. MS: (ES, m/z): 179 [M+H]$^+$.

Intermediate 29: 3-aminocyclohexane-1-carbonitrile hydrochloride

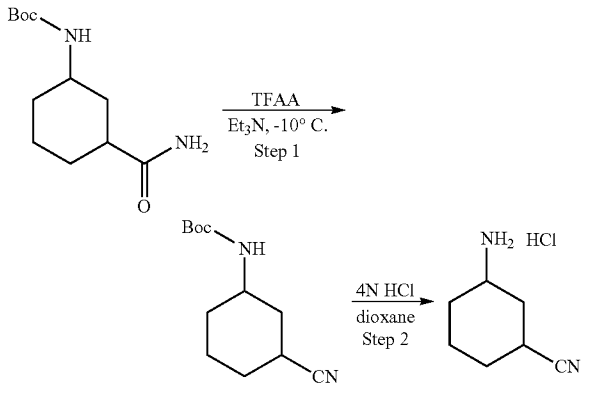

Step 1. Synthesis of tert-butyl N-(3-cyanocyclohexyl)carbamate

Into a 50-mL round-bottom flask, tert-butyl N-(3-carbamoylcyclohexyl)carbamate (2.0 g, 8.25 mmol) was dissolved in dichloromethane (20 mL). Then trifluoroacetic anhydride (3.8 g, 18.09 mmol) and triethylamine (1.8 g, 17.79 mmol) were added. The resulting solution was stirred for 3 h at −10° C. in an ice/salt bath. The resulting mixture was washed with 3×20 mL of water. The organic layer was concentrated under vacuum. The residue was subjected to purification by FCC eluting with ethyl acetate/petroleum ether (1:1). This afforded the title compound (1.27 g, 69%) as a white solid. MS: (ES, m/z): 225 [M+H]$^+$.

Step 2. Synthesis of 3-aminocyclohexane-1-carbonitrile hydrochloride

Into a 50-mL round-bottom flask, tert-butyl N-3-cyanocyclohexyl carbamate (500 mg, 2.01 mmol) was dissolved in 1, 4-dioxane. Then 4 N hydrochloric acid (2 mL) was added. The resulting solution was stirred for 4 h at room temperature. The resulting mixture was concentrated under vacuum. The residue was washed with 3×10 mL of petroleum ether. The solids were collected by filtration. This afforded the title compound (258 mg, 70%) as a white solid. MS: (ES, m/z): 125 $[M+H]^+$.

Intermediate 30: (3R,6S)-6-(((tert-butyldimethylsilyl)oxy)methyl)tetrahydro-2H-pyran-3-amine

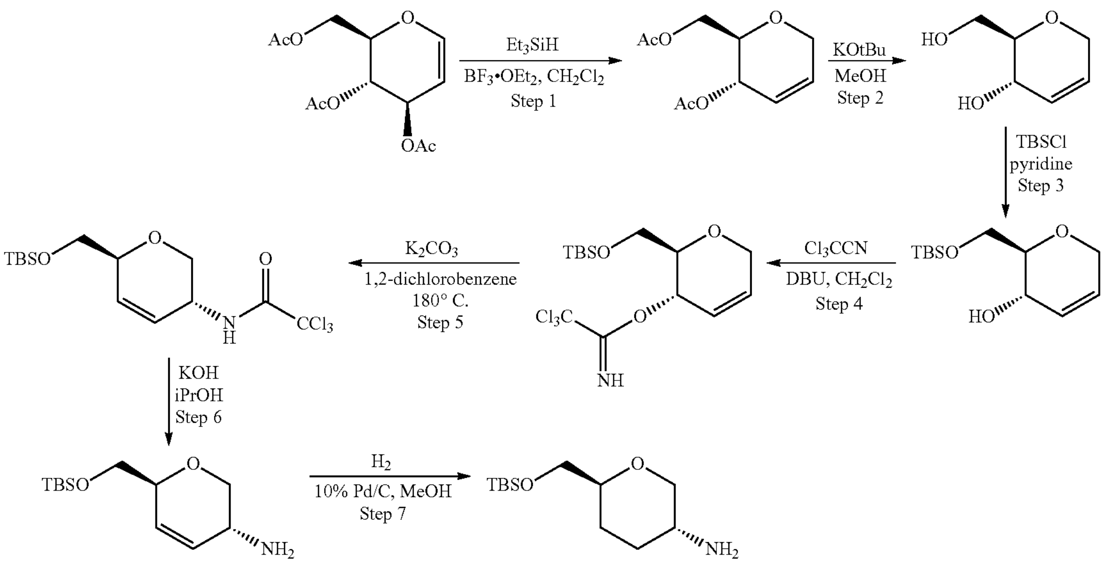

Step 1. Synthesis of [(2R,3S)-3-(acetyloxy)-3,6-dihydro-2H-pyran-2-yl]methyl acetate Into a 2-L 3-necked round-bottom flask, [(2R,3S,4R)-3,4-bis(acetyloxy)-3,4-dihydro-2H-pyran-2-yl]methyl acetate (100 g, 367.31 mmol) was dissolved in dichloromethane (500 mL). Then triethylsilane (43 g, 369.81 mmol) and $BF_3 \cdot Et_2O$ (68 g, 479.12 mmol) were added. The resulting solution was stirred for 2 h at room temperature. The reaction was then quenched by the addition of 100 mL of sodium bicarbonate. The mixture was washed with water (3×200 mL) and brine (200 mL). The organic layers were combined, dried over anhydrous sodium sulfate, filtered and concentrated. The residue was subjected to purification by FCC eluting with ethyl acetate/petroleum ether (1:3). This afforded the title compound (72 g, 92%) as a yellow oil. MS: (ES, m/z): 215 $[M+H]^+$.

Step 2. Synthesis of (2R,3S)-2-(hydroxymethyl)-3,6-dihydro-2H-pyran-3-ol

Into a 1-L round-bottom flask, [(2R,3S)-3-(acetyloxy)-3,6-dihydro-2H-pyran-2-yl]methyl acetate (36 g, 168.06 mmol) was dissolved in methanol (200 mL). Then t-BuOK (1.3 g, 11.59 mmol) was added. The resulting solution was stirred for 1 h at room temperature. Then the mixture was neutralized by Dowex (H+ Form). The solids were filtered out. The resulting mixture was concentrated under vacuum. The residue was subjected to purification by FCC eluting with dichloromethane/methanol (10:1). This afforded the title compound (19 g, 87%) as a yellow oil. MS: (ES, m/z): 131 $[M+H]^+$.

Step 3. Synthesis of (2R,3S)-2-[[(tert-butyldimethylsilyl)oxy]methyl]-3,6-dihydro-2H-pyran-3-ol Into a 1000-mL 3-necked round-bottom flask, (2R,3S)-2-(hydroxymethyl)-3,6-dihydro-2H-pyran-3-ol (19 g, 145.99 mmol) was dissolved in pyridine (200 mL). Then TBSCl (21.9 g, 145.30 mmol) was added. The resulting solution was stirred for 12 h at room temperature. The resulting mixture was concentrated under vacuum. The residue was subjected to purification by FCC eluting with ethyl acetate/petroleum ether (1:10). This afforded the title compound (28.4 g, 80%) as a light yellow oil. MS: (ES, m/z): 245 $[M+H]^+$.

Step 4. Synthesis of (2R,3S)-2-(((tert-butyldimethylsilyl)oxy)methyl)-3,6-dihydro-2H-pyran-3-yl 2,2,2-trichloroacetimidate Into a 1000-mL 3-necked round-bottom flask, (2R,3S)-2-[[(tert-butyldimethylsilyl)oxy]methyl]-3,6-dihydro-2H-pyran-3-ol (33 g, 135.02 mmol) was dissolved in dichloromethane (500 mL). Then DBU (26.7 g, 175.38 mmol) and Cl3CCN (25.2 g, 175.38 mmol) were added. The resulting solution was stirred for 2 h at room temperature. The resulting mixture was concentrated under vacuum. The residue was subjected to purification by FCC eluting with ethyl acetate/petroleum ether (1:10). This afforded the title compound (42 g, 80%) as a yellow oil. MS: (ES, m/z): 388, 390, 392 $[M+H]^+$.

Step 5. Synthesis of N-[(3R,6S)-6-[[(tert-butyldimethylsilyl)oxy]methyl]-3,6-dihydro-2H-pyran-3-yl]-2,2,2-trichloroacetamide Into a 1-L round-bottom flask, (2R,3S)-2-(((tert-butyldimethylsilyl)oxy)methyl)-3,6-dihydro-2H-pyran-3-yl 2,2,2-trichloroacetimidate (42 g, 108.03 mmol) was dissolved in 1,2-dichlorobenzene (300 mL). Then potassium carbonate (1.5 g, 10.85 mmol) was added. The resulting solution was stirred for 5 h at 180° C. The resulting mixture was cooled to room temperature and the solids were filtered out. The resulting mixture was concentrated under vacuum. The residue was subjected to purification by FCC eluting with ethyl acetate/petroleum ether (1:5). This afforded the title compound (36 g, 86%) as a white solid. MS: (ES, m/z): 388, 390, 392 $[M+H]^+$.

Step 6. Synthesis of (3R,6S)-6-[[(tert-butyldimethylsilyl)oxy]methyl]-3,6-dihydro-2H-pyran-3-amine Into a 100-mL round-bottom flask, N-[(3R,6S)-6-[[(tert-butyldimethylsilyl)oxy]methyl]-3,6-dihydro-2H-pyran-3-yl]-2,2,2-trichloroacetamide (2.0 g, 5.14 mmol) was dissolved in i-propanol (10 mL). Then potassium hydroxide (868 mg, 15.47 mmol) was added. The resulting solution was stirred for 12 h at room temperature. The solids were filtered out. The residue was subjected to purification by FCC eluting with dichloromethane/methanol (10:1). This afforded the title compound (1 g, 80%) as a yellow oil. MS: (ES, m/z): 244 $[M+H]^+$.

Step 7. Synthesis of (3R,6S)-6-(((tert-butyldimethylsilyl)oxy)methyl)tetrahydro-2H-pyran-3-amine Into a 100-mL round-bottom flask, (3R,6S)-6-[[(tert-butyldimethylsilyl)oxy]methyl]-3,6-dihydro-2H-pyran-3-amine (1 g, 4.11 mmol) was dissolved in methanol (10 mL). Then palladium on carbon (10%, 100 mg) was added. Hydrogen (g) was charged into the reaction mixture and the resulting mixture was stirred for 12 h at room temperature under hydrogen atmosphere. The reaction was vented to nitrogen and the solids were filtered out over celite. The filtered solution was concentrated under a vacuum and the residue was subjected to purification by FCC eluting with dichloromethane/methanol (10:1). This afforded the title compound (850 mg, 84%) as a yellow oil. MS: (ES, m/z): 246 $[M+H]^+$.

Intermediate 31: 1-thia-6-azaspiro[3.3]heptane 1,1-dioxide hydrochloride

Step 1. Synthesis of tert-butyl 3-(2-oxoethylidene)azetidine-1-carboxylate

Into a 250-mL round-bottom flask, tert-butyl 3-oxoazetidine-1-carboxylate (11 g, 63.61 mmol) was dissolved in dichloromethane (150 mL). Then 2-(triphenyl-lambda5-phosphanylidene)acetaldehyde (24 g, 78.08 mmol) was added. The resulting solution was stirred for 6 h at 40° C. The reaction mixture was cooled to room temperature. The resulting mixture was concentrated under vacuum. The residue was subjected to purification by FCC eluting with ethyl acetate/petroleum ether (1:5). This afforded the title compound (11 g, 79%) as a yellow oil. MS: (ES, m/z): 198 $[M+H]^+$.

Step 2. Synthesis of tert-butyl 3-(acetylthio)-3-(2-oxoethyl)azetidine-1-carboxylate Into a 250-mL round-bottom flask, tert-butyl 3-(2-oxoethylidene)azetidine-1-carboxylate (11 g, 55.77 mmol) was dissolved in tetrahydrofuran (100 mL). Then piperidine (0.39 mL, 3.90 mmol) and ethanethioic S-acid (6 mL, 83.65 mmol) were added. The resulting solution was stirred for 4 h at room temperature. The resulting mixture was concentrated under vacuum. The residue was subjected to purification by FCC eluting with ethyl acetate/petroleum ether (1:2). This afforded the title compound (11 g, 63%) of as a yellow oil. MS: (ES, m/z): 274 $[M+H]^+$.

Step 3. Synthesis of tert-butyl 3-(2-hydroxyethyl)-3-sulfonylazetidine-1-carboxylate Into a 500-mL 3-necked round-bottom flask, tert-butyl 3-(acetylsulfanyl)-3-(2-oxoethyl)azetidine-1-carboxylate (18 g, 65.85 mmol) was dissolved in ether (100 mL). Then $LiAlH_4$ (2.9 g, 76.41 mmol) was added. The resulting solution was stirred for 1 h at room temperature. The reaction was then quenched by the addition of 100 mL of sodium bicarbonate (sat.). The resulting solution was extracted with 3×100 mL of ethyl acetate. The organic layers were combined, dried over anhydrous sodium sulfate, fil-

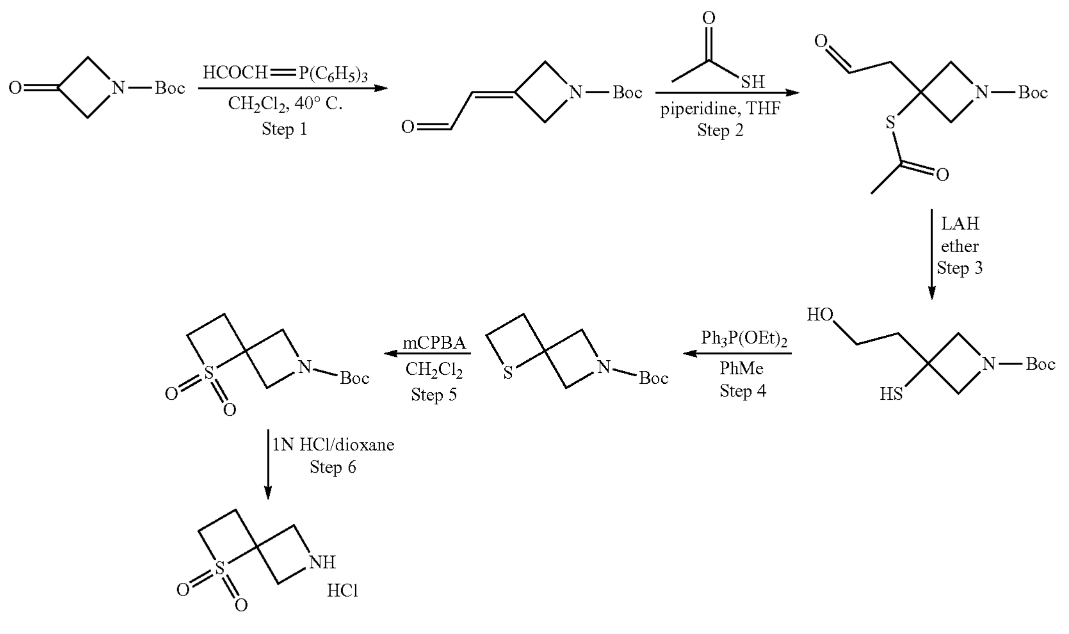

tered and concentrated. This afforded the title compound (9 g, 59%) as a brown oil. MS: (ES, m/z): 234 $[M+H]^+$.

Step 4. Synthesis of tert-butyl 1-thia-6-azaspiro[3.3] heptane-6-carboxylate Into a 100-mL 3-necked round-bottom flask, tert-butyl 3-(2-hydroxyethyl)-3-sulfanylazetidine-1-carboxylate (500 mg, 2.14 mmol) was dissolved in toluene (4 mL). Then diethyl triphenylphosphonite (1 g, 2.84 mmol) was added. The resulting solution was stirred for 12 h at room temperature. The resulting mixture was concentrated under vacuum. The residue was subjected to purification by FCC eluting with ethyl acetate/petroleum ether (1:5). This afforded the title compound (250 mg, 49%) as a light yellow oil. MS: (ES, m/z): 216 $[M+H]^+$.

Step 5. Synthesis of tert-butyl 1-thia-6-azaspiro[3.3] heptane-6-carboxylate 1,1-dioxide Into a 100-mL round-bottom flask, tert-butyl 1-thia-6-azaspiro[3.3]heptane-6-carboxylate (250 mg, 1.16 mmol) was dissolved in dichloromethane (10 mL). Then m-CPBA (400 mg, 2.32 mmol) was added. The resulting solution was stirred for 4 h at room temperature. The reaction was then quenched by the addition of 20 mL of sodium bicarbonate (sat.). The resulting solution was extracted with 3×100 mL of dichloromethane. Then the organic layers were combined, dried over anhydrous sodium sulfate, filtered and concentrated. The residue was subjected to purification by FCC eluting with ethyl acetate/petroleum ether (1:1). This afforded the title compound (200 mg, 70%) as a white solid. MS: (ES, m/z): 248 $[M+H]^+$.

Step 6. Synthesis of 1-thia-6-azaspiro[3.3]heptane 1,1-dioxide hydrochloride Into a 50-mL round-bottom flask, tert-butyl 1-thia-6-azaspiro[3.3]heptane-6-carboxylate 1,1-dioxide (50 mg, 0.20 mmol) was dissolved in HCl (1 M in dioxane) (2 mL). The resulting solution was stirred for 2 h at room temperature. The resulting mixture was concentrated under vacuum. This afforded the title compound (20 mg, crude) as a white solid. MS: (ES, m/z): 148 $[M+H]^+$.

Intermediate 32: methyl 4-oxo-2-phenylbutanoate

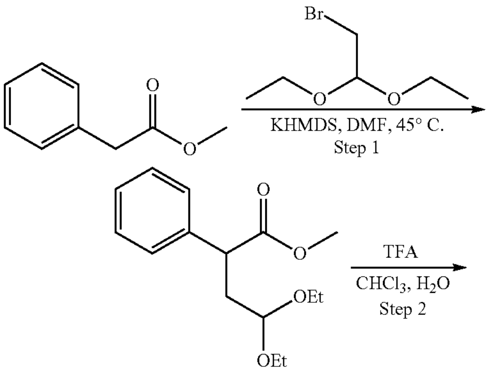

-continued

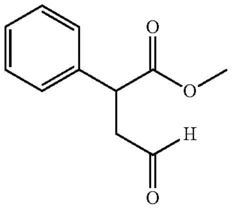

Step 1. Synthesis of methyl 4,4-diethoxy-2-phenylbutanoate

Into a 500-mL 3-necked round-bottom flask, methyl 2-phenylacetate (15 g, 99.88 mmol) was dissolved in N,N-dimethylformamide (150 mL). Then KHMDS (527.56 mmol in 120 mL DMF) and 2-bromo-1,1-diethoxyethane (23.7 g, 120.26 mmol) were added. The resulting solution was stirred for 30 min at 45° C. The resulting mixture was cooled to room temperature and quenched by the addition of 300 mL of $NH_4Cl$ (aq.). The resulting solution was extracted with 3×300 mL of ethyl acetate. The organic layers were combined, dried over anhydrous sodium sulfate, filtered and concentrated. The residue was subjected to purification by FCC eluting with ethyl acetate/petroleum ether (1:10). This afforded the title compound (19.25 g, 72%) as a yellow oil. MS: (ES, m/z): 267 $[M+H]^+$.

Step 2. Synthesis of methyl 4-oxo-2-phenylbutanoate

Into a 500-mL 3-necked round-bottom flask, methyl 4,4-diethoxy-2-phenylbutanoate (19.25 g, 72.28 mmol) was dissolved in chloroform (20 mL). Then water (10 mL) and trifluoroacetic acid (96 mL, 1.29 mol) were added. The resulting solution was stirred for 2 h at room temperature. The reaction was then quenched by the addition of 100 mL of potassium carbonate. The resulting solution was extracted with 3×100 mL of dichloromethane. The organic layers were combined, dried over anhydrous sodium sulfate, filtered and concentrated. This afforded the title compound (12.5 g, 90%) as a yellow oil. MS: (ES, m/z): 193 $[M+H]^+$.

The following intermediates in TABLE B were prepared using standard chemical manipulations and procedures similar to those used for the preparation of Intermediate 32.

TABLE B

| Intermediate Number | Structure and Compound Name | LRMS m/z $[M + H]^+$ |
|---|---|---|
| 33 | 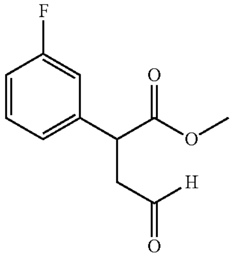 methyl 2-(3-fluorophenyl)-4-oxobutanoate | 211 |

TABLE B-continued

| Intermediate Number | Structure and Compound Name | LRMS m/z [M + H]+ |
|---|---|---|
| 34 | 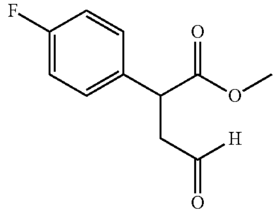 methyl 2-(4-fluorophenyl)-4-oxobutanoate | 211 |
| 35 | 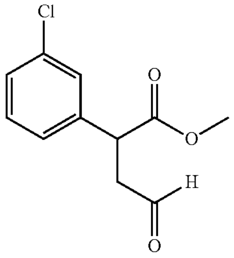 methyl 2-(3-chlorophenyl)-4-oxobutanoate | 226 |
| 36 | 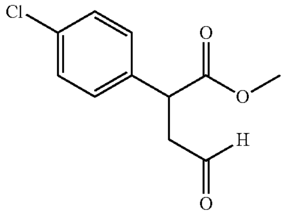 methyl 2-(4-chlorophenyl)-4-oxobutanoate | 226 |
| 37 | 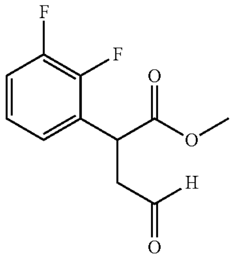 methyl 2-(2,3-difluorophen-yl-4-oxobutanoate | 228 |
| 38 | 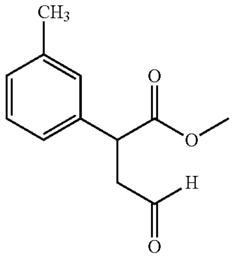 methyl 4-oxo-2-(m-tolyl)-butanoate | 207 |

TABLE B-continued

| Intermediate Number | Structure and Compound Name | LRMS m/z [M + H]+ |
|---|---|---|
| 39 | 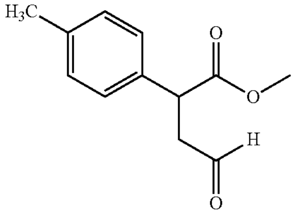 methyl 4-oxo-2-(p-tolyl)butanoate | 207 |
| 40 | 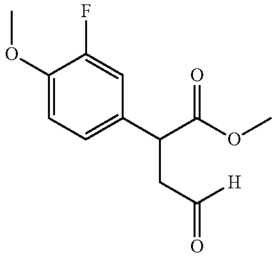 methyl 2-(3-fluoro-4-methoxy-phenyl)-4-oxobutanoate | 241 |
| 41 | 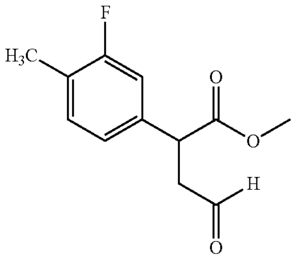 methyl 2-(3-fluoro-4-methylphenyl)-4-oxobutanoate | 225 |
| 42 | 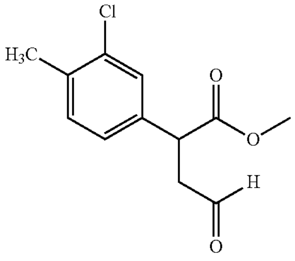 methyl 2-(3-chloro-4-methyl-phenyl)-4-oxobutanoate | 240 |

Intermediate 43: tert-butyl ((trans)-4-(methylsulfonyl)cyclohexyl)carbamate

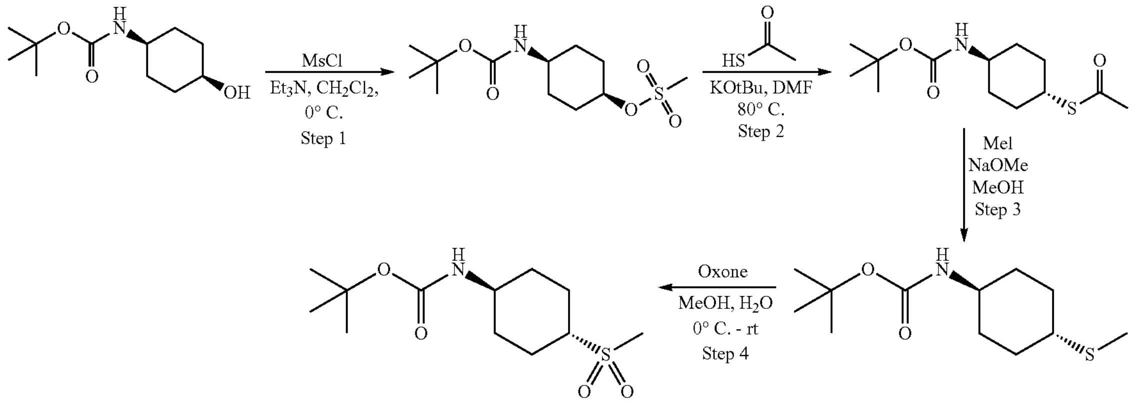

Step 1. Synthesis of cis-4-((tert-butoxycarbonyl)amino)cyclohexyl methanesulfonate A solution of cis-tert-butyl(4-hydroxycyclohexyl)carbamate (5.0 g, 23.22 mmol) and triethylamine (6.47 ml, 46.4 mmol) in dichloromethane (50 ml) was cooled to 0° C. Mesyl chloride (2.71 ml, 34.8 mmol) was slowly added. The reaction mixture was allowed to stir at 0° C. for 20 minutes. The reaction was then quenched with water (20 mL). The layers were allowed to separate and the organic layer was collected. The aqueous layer was washed with additional dichloromethane (2x5 mL). The organic layers were combined and washed with saturated ammonium chloride (10 mL), saturated sodium bicarbonate (10 mL) and brine (10 mL). The organic layer was then dried over sodium sulfate, filtered and concentrated to afford the title compound as a off-white solid. MS: (ES, m/z): 293 $[M+H]^+$.

Step 2. Synthesis of trans-4-((tert-butoxycarbonyl)amino)cyclohexyl) ethanethioate thioacetic acid (2.57 ml, 35.8 mmol) was added to a stirred suspension of potassium tert-butoxide (4.02 g, 35.8 mmol) in DMF (50 mL) at 0° C. The mixture was stirred for 5 mins and then a solution of cis-4-((tert-butoxycarbonyl)amino)cyclohexyl methanesulfonate (7.0 g, 23.86 mmol) in DMF (22.6 mL) was added. The mixture was heated to 80° C. for 4 hours and was then poured into a mixture of ethyl acetate (200 mL) and water (200 mL). The phases were separated and the aqueous phase was extracted with ethyl acetate (x2). The combined organic extracts were washed with 10% aqueous citric acid solution (200 mL), saturated sodium hydrogen carbonate solution (200 mL), and brine (200 mL), dried over sodium sulfate, filtered and concentrated under vacuum. The crude product was subjected to purification by FCC (Biotage SNAP 340 g; eluting with 10-30% EtOAc in hexanes) affording the title compound as a light orange solid. MS: (ES, m z): 273 $[M+H]^+$.

Step 3. Synthesis of tert-butyl-trans-4-(methylthio) cyclohexyl)carbamate

A stirred solution of trans-4-((tert-butoxycarbonyl)amino) cyclohexyl) ethanethioate (2.0 g, 7.32 mmol) in MeOH (48 ml) was treated with sodium methoxide (1.04 g, 19.25 mmol) followed by iodomethane (0.449 ml, 7.22 mmol). The mixture was stirred at ambient temperature for 3 hours then diluted with ethyl acetate (200 mL) and water (200 mL). The phases were separated and the aqueous phase was extracted with ethyl acetate (100 mLx2). The combined organic extracts were washed with 10% aqueous citric acid solution (200 mL), saturated sodium hydrogen carbonate solution (200 mL), and brine (200 mL), dried over sodium sulphate, filtered and concentrated under vacuum to give crude product. The crude product was subjected to purification by FCC (Biotage SNAP 100 g; eluting with 10-30% EtOAc in hexanes) affording the title compound as a white solid. MS: (ES, m/z): 246 $[M+H]^+$.

Step 4. Synthesis of tert-butyl ((trans)-4-(methylsulfonyl)cyclohexyl)carbamate

A solution of tert-butyl-trans-4-(methylthio)cyclohexyl) carbamate (1.0 g, 4.08 mmol) in MeOH (14 ml) was cooled to 0° C. and treated with a suspension of oxone (2.505 g, 4.08 mmol) in water (6 ml). The mixture was stirred at ambient temperature for 1 hour, then diluted with ethyl acetate (100 mL) and water (100 mL). The phases were separated and the aqueous phase was extracted with ethyl acetate (100 mLx2). The combined organic extracts were washed with 10% aqueous citric acid solution (100 mL), saturated sodium hydrogen carbonate solution (100 mL), and brine (100 mL), dried over sodium sulphate, filtered and concentrated under vacuum to afford the crude product. The crude product was subjected to purification by FCC (Biotage SNAP 100 g; eluting with 40-60% EtOAc in hexanes) affording the title compound as a white solid. MS: (ES, m/z): 278 $[M+H]^+$.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The synthetic schemes are presented for the synthesis of certain compounds herein disclosed. The process and results for the assays testing BET family bromodomain inhibition and effects on a cancer cell line proliferation are also described.

Examples 1 and 2: methyl (S)-3,7-dimethyl-2-((R)-2-phenylpropyl)-3,7,8,9-tetrahydro-6H-imidazo[4,5-f]quinoline-6-carboxylate and methyl (S)-3,7-dimethyl-2-((S)-2-phenylpropyl)-3,7,8,9-tetrahydro-6H-imidazo[4,5-f]quinoline-6-carboxylate

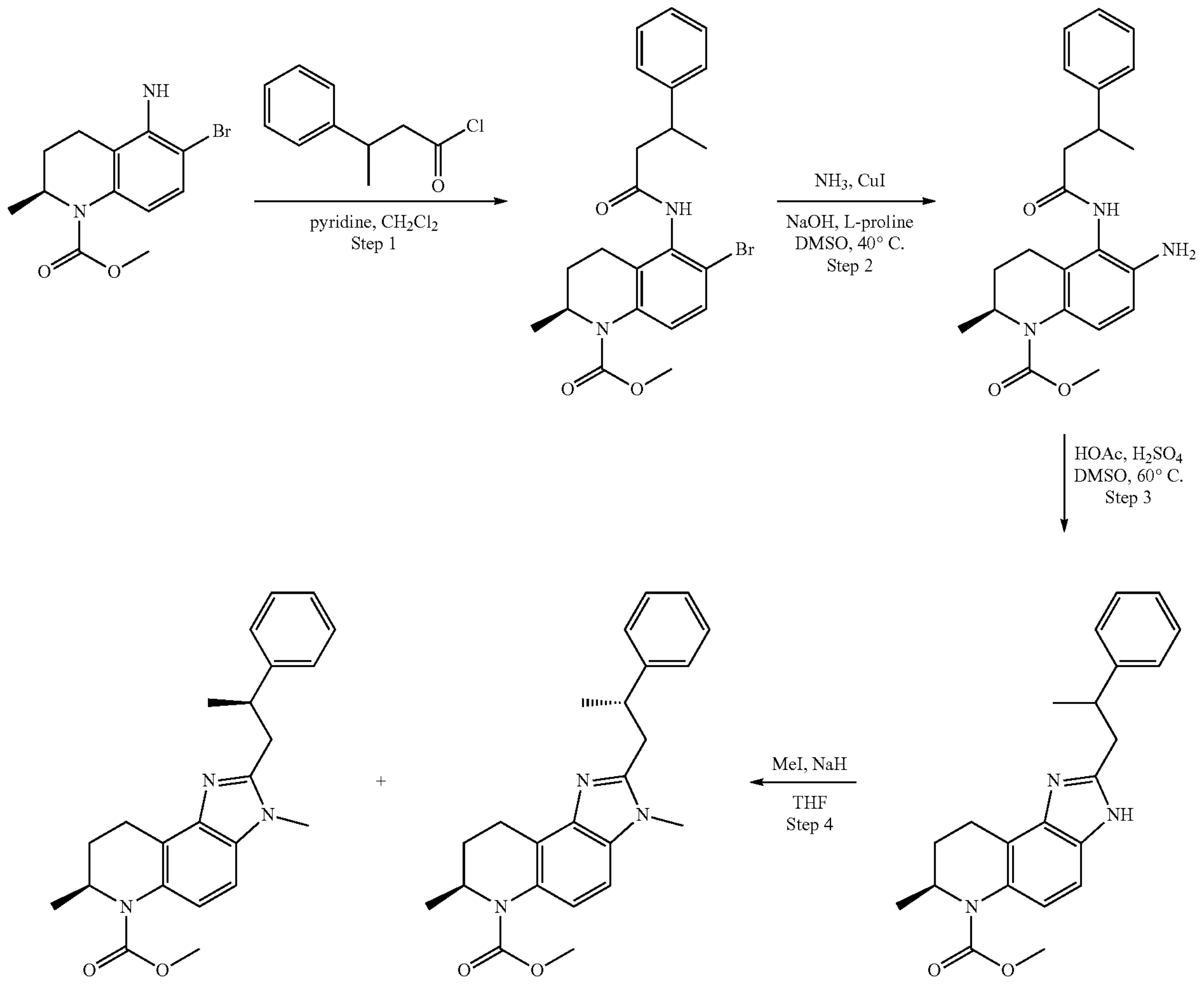

Step 1. methyl (2S)-6-bromo-2-methyl-5-(3-phenylbutanamido)-1,2,3,4-tetrahydroquinoline-1-carboxylate Into a 100-mL round-bottom flask, methyl (2S)-5-amino-6-bromo-2-methyl-1,2,3,4-tetrahydroquinoline-1-carboxylate (100 mg, 0.33 mmol, Intermediate 1) was dissolved in dichloromethane (8 mL). Then pyridine (132 mg, 1.67 mmol) was added, followed by the addition of a solution of 3-phenylbutanoyl chloride (73 mg, 0.40 mmol, Intermediate 2) in dichloromethane (2 mL) dropwise with stirring. The resulting solution was stirred overnight at room temperature. The resulting mixture was concentrated under vacuum. The residue was subjected to purification by FCC eluting with ethyl acetate/petroleum ether (1/10-1/1). This afforded the title compound (50 mg, 34%) as a white solid. MS: (ES, m/z): 445 [M+H]$^+$.

Step 2. Methyl (2S)-6-amino-2-methyl-5-(3-phenylbutanamido)-1,2,3,4-tetrahydroquinoline-1-carboxylate Into a 8-mL vial, was placed a solution of methyl (2S)-6-bromo-2-methyl-5-(3-phenylbutanamido)-1,2,3,4-tetrahydroquinoline-1-carboxylate (50 mg, 0.11 mmol) in dimethylsulfoxide (2 mL). Next, cuprous iodide (20 mg, 0.11 mmol), L-proline (30 mg, 0.26 mmol) and sodium hydroxide (25 mg, 0.63 mmol) were added. The mixture was stirred for 1 minute before addition of ammonium hydroxide (2 mL, 28%, 51.36 mmol). The resulting solution was stirred for 2 h at 50° C. The resulting solution was cooled to room temperature and diluted with 20 mL of water. The resulting solution was extracted with 3x20 mL of ethyl acetate. The organic layers were combined, dried over anhydrous sodium sulfate, filtered and concentrated under vacuum. This afforded the title compound (30 mg, 70%) as colorless oil. MS: (ES, m/z): 382 [M+H]$^+$.

Step 3. methyl (7S)-7-methyl-2-(2-phenylpropyl)-3H,6H,7H,8H,9H-imidazo[4,5-f]quinoline-6-carboxylate Into a 50-mL round-bottom flask, methyl (2S)-6-amino-2-methyl-5-(3-phenylbutanamido)-1,2,3,4-tetrahydroquinoline-1-carboxylate (30 mg, 0.08 mmol) was dissolved in dimethylsulfoxide (2 mL). Next, acetic acid (2 mL) and 3 drops of sulfuric acid were added. The resulting solution was stirred for 12 h at 60° C. The resulting solution was cooled to room temperature and diluted with 20 mL of water. The resulting solution was extracted with 3×20 mL of ethyl acetate. The organic layers were combined, dried over anhydrous sodium sulfate, filtered and concentrated under vacuum. This afforded the title compound (25 mg, 87%) as colorless oil. MS: (ES, m/z): 364 $[M+H]^+$.

Step 4. methyl (S)-3,7-dimethyl-2-((R)-2-phenyl-propyl)-3,7,8,9-tetrahydro-6H-imidazo[4,5-f]quinoline-6-carboxylate and methyl (S)-3,7-dimethyl-2-((S)-2-phenylpropyl)-3,7,8,9-tetrahydro-6H-imidazo[4,5-f]quinoline-6-carboxylate Into a 50-mL round-bottom flask, methyl (7S)-7-methyl-2-(2-phenylpropyl)-3H,6H,7H,8H,9H-imidazo[4,5-f]quinoline-6-carboxylate (45 mg, 0.12 mmol) was dissolved in tetrahydrofuran (5 mL). Then sodium hydride (12 mg, 0.25 mmol, 60%) was added, followed by the addition of iodomethane (35 mg, 0.25 mmol) dropwise with stirring. The resulting solution was stirred for 2 h at room temperature. The reaction was then quenched by the addition of 10 mL of water and concentrated. The crude product was purified by Flash-Prep-HPLC with the following conditions (IntelFlash-1): Column, C18 silica gel; mobile phase: A: MeCN and B: water (containing 0.05% TFA) from 5% increasing to 40% within 30 min; UV Detector: 254 nm. The crude product was purified by Chiral-Prep-HPLC with the following conditions: Column, CHIRAL ART Cellulose-SB, 250×20 mm I.D.; mobile phase, A: hexanes and B: ethanol (hold 15.0% ethanol in 15 min); UV Detector: 254 nm. This afforded the title compounds as follows: 2.5 mg (5%) of methyl (7S)-3,7-dimethyl-2-[(2R)-2-phenylpropyl]-3H,6H,7H,8H,9H-imidazo[4,5-f]quinoline-6-carboxylate (assumed stereochemistry, first eluting isomer) as a yellow oil and 3.5 mg (7%) of methyl (7S)-3,7-dimethyl-2-[(2S)-2-phenylpropyl]-3H,6H,7H,8H,9H-imidazo[4,5-f]quinoline-6-carboxylate (assumed stereochemistry, second eluting isomer) as a yellow oil First eluting isomer: $^1$H-NMR ($CDCl_3$, 400 MHz) δ (ppm): 7.48-7.40 (m, 1H), 7.27-7.13 (m, 5H), 7.01 (d, J=8.8 Hz, 1H), 4.81-4.77 (m, 1H), 3.78 (s, 3H), 3.40-3.35 (m, 1H), 3.30-3.22 (m, 5H), 3.06-3.00 (m, 2H), 2.31-2.22 (m. 1H), 1.76-1.68 (m, 1H), 1.44 (d, J=6.8 Hz, 3H), 1.17 (d, J=6.8 Hz, 3H). MS: (ES, m/z): 378 $[M+H]^+$.

Second eluting isomer: $^1$H-NMR ($CDCl_3$, 400 MHz) δ (ppm): 7.48-7.40 (m, 1H), 7.27-7.17 (m, 5H), 7.03 (d, J=8.8 Hz, 1H), 4.81-4.77 (m, 1H), 3.77 (s, 3H), 3.41-3.38 (m, 1H), 3.32-2.99 (m, 7H), 2.30-2.21 (m. 1H), 1.75-1.71 (m, 1H), 1.41 (d, J=6.8 Hz, 3H), 1.17 (d, J=6.4 Hz, 3H). MS: (ES, m/z): 378 $[M+H]^+$.

The following examples in TABLE 1 were prepared using standard chemical manipulations and procedures similar to those used for the preparation of Examples 1 and 2.

TABLE 1

| Example Number | Structure and Compound Name | LRMS m/z $[M + H]^+$ | $^1$HNMR |
|---|---|---|---|
| 3 and 4 | 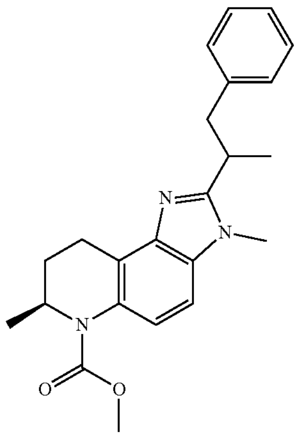 1st eluting isomer (3) 2nd eluting isomer (4) methyl (7S)-3,7-dimethyl-2-(1-phenylpropan-2-yl)-3,7,8,9-tetrahydro-6H-imidazo[4,5-f]quinoline-6-carboxylate | 1st eluting isomer = 378 2nd eluting isomer = 378 | 1st eluting isomer $^1$H-NMR ($CDCl_3$, 300 MHz) δ (ppm): 7.43-7.41 (m, 1H), 7.22-7.19 (m, 3H), 7.09-7.06 (m, 3H), 4.81-4.79 (m, 1H), 3.82 (s, 3H), 3.35-3.28 (m, 6H), 3.08-3.01 (m, 2H), 2.31-2.28 (m, 1H), 1.75-1.45 (m, 4H), 1.17 (d, J = 6.6 Hz, 3H) 2nd eluting isomer $^1$H-NMR ($CDCl_3$, 300 MHz) δ (ppm): 7.43-7.41 (m, 1H), 7.23-7.21 (m, 3H), 7.15-7.05 (m, 3H), 4.81-4.78 (m, 1H), 3.79 (s, 3H), 3.44-3.29 (m, 6H), 3.08-3.03 (m, 2H), 2.31-2.28 (m, 1H), 1.75-1.46 (m, 4H), 1.20 (d, J = 6.6 Hz, 3H) |

TABLE 1-continued

| Example Number | Structure and Compound Name | LRMS m/z $[M + H]^+$ | $^1$HNMR |
|---|---|---|---|
| 5 and 6 | 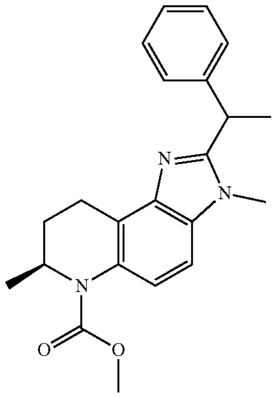 1st eluting isomer (5) 2nd eluting isomer (6) methyl (7S)-3,7-dimethyl-2-(1-phenylethyl)-3,7,8,9-tetrahydro-6H-imidazo[4,5-f]quinoline-6-carboxylate | 1st eluting isomer = 364 2nd eluting isomer = 364 | 1st eluting isomer $^1$H-NMR ($CDCl_3$, 400 MHz) δ (ppm): 7.58-7.52 (m, 1H), 7.34-7.30 (m, 3H), 7.25-7.23 (m, 2H), 7.10-7.05 (m, 1H), 4.82-4.76 (m, 1H), 4.56-4.51 (m, 1H), 3.78 (s, 3H), 3.48 (s, 3H), 3.39-3.31 (m, 1H), 3.09-3.35 (m, 1H), 2.31-2.22 (m, 1H), 1.91-1.89 (m, 3H), 1.77-1.72 (m, 1H), 1.25-1.16 (m, 3H) 2nd eluting isomer $^1$H-NMR ($CDCl_3$, 400 MHz) δ (ppm): 7.45-7.40 (m, 1H), 7.29-7.28 (m, 2H), 7.22-7.17 (m, 3H), 7.06 (d, J = 8.8 Hz, 1H), 4.80-4.75 (m, 1H), 4.40-4.37 (m, 1H), 3.77 (s, 3H), 3.43-4.31 (m, 4H), 3.05-2.98 (m, 1H), 2.34-2.26 (m, 1H), 1.87-1.85 (m, 3H), 1.72-1.67 (m, 1H), 1.25-1.16 (m, 3H) |

Example 7: methyl (S)-7-methyl-2-phenethyl-3,7,8,9-tetrahydro-6H-imidazo[4,5-f]quinoline-6-carboxylate

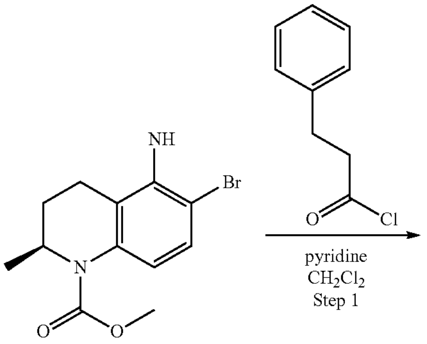

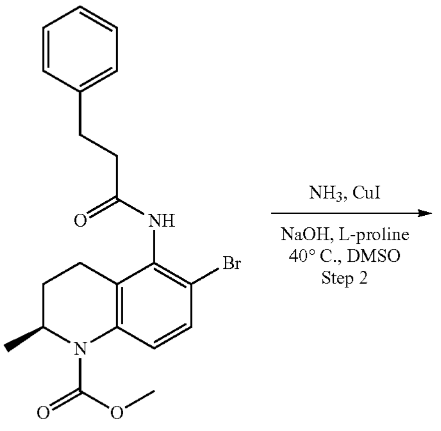

-continued

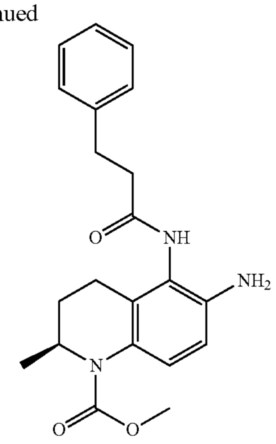

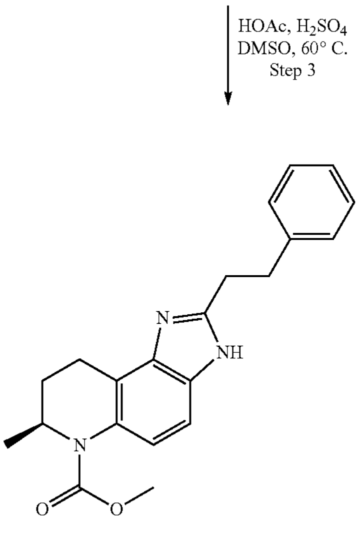

Step 1. Synthesis of methyl-(2S)-6-bromo-2-methyl-5-(3-phenylpropanamido)-1,2,3,4-tetrahydroquinoline-1-carboxylate Into a 50-mL round-bottom flask, methyl-(2S)-5,6-diamino-2-methyl-1,2,3,4-tetrahydroquinoline-1-carboxylate (100 mg, 0.43 mmol, Intermediate 1) was dissolved in dichloromethane (10 mL). Pyridine (1 mL) was added, followed by 3-phenylpropanoyl chloride (169 mg, 1.00 mmol). The resulting solution was stirred for 12 h at 40° C. The resulting mixture was concentrated under vacuum. The residue was subjected to purification by FCC eluting with ethyl acetate/petroleum ether (1:1). This afforded the title compound (100 mg, 55%) as a yellow solid. MS: (ES, m/z): 431,433 $[M+H]^+$.

Step 2. Synthesis of methyl-(2S)-6-amino-2-methyl-5-(3-phenylpropanamido)-1,2,3,4-tetrahydroquinoline-1-carboxylate Into a 8-mL sealed tube, methyl-(2S)-6-bromo-2-methyl-5-(3-phenylpropanamido)-1,2,3,4-tetrahydroquinoline-1-carboxylate (20 mg, 0.05 mmol) was dissolved in dimethyl sulfoxide (2 mL). Then ammonium hydroxide (1 mL, 28%, 25.68 mmol), copper iodide (4 mg, 0.02 mmol), L-proline (3 mg, 0.03 mmol) and sodium hydroxide (12 mg, 0.3 mmol) were added successively. The resulting solution was stirred for 12 h at 40° C. The resulting solution was diluted with 20 mL of water and extracted with 3×20 mL of ethyl acetate. The organic layers were combined, dried over anhydrous sodium sulfate, filtered and concentrated under vacuum. The resulting mixture was concentrated under vacuum. This afforded the title compound (10 mg, crude) as colorless oil. MS: (ES, m/z): 368 $[M+H]^+$.

Step 3. Synthesis of methyl-(7S)-7-methyl-2-(2-phenylethyl)-3H,6H,7H,8H,9H-imidazo[4,5-f]quinoline-6-carboxylate Into a 8-mL sealed tube, methyl-(2S)-6-amino-2-methyl-5-(3-phenylpropanamido)-1,2,3,4-tetrahydroquinoline-1-carboxylate (10 mg, 0.03 mmol) was dissolved in dimethyl sulfoxide (2 mL). Then acetic acid (1 mL) and sulfuric acid (0.1 mL) were added. The resulting solution was stirred for 12 h at 60° C. The resulting mixture was cooled to room temperature and diluted with water (10 mL). The resulting solution was extracted with 3×20 mL of ethyl acetate. The organic layers were combined, dried over anhydrous sodium sulfate, filtered and concentrated under vacuum. The crude product was purified with the following conditions: Column: XBridge Prep C18 OBD Column, 5 μm, 19×150 mm; Mobile Phase, A: water (containing 0.05% TFA) and B: ACN (5% B to 56% ACN over 7 min); UV Detector: 254 nm. This afforded the title compound (2.8 mg, 29%) as a brown oil.

$^1$H-NMR ($CDCl_3$, 400 MHz) δ (ppm): 7.70-7.68 (m, 1H), 7.38-7.31 (m, 1H), 7.29-7.20 (m, 1H), 6.99-6.95 (m, 4H), 4.80-4.78 (m, 1H), 3.79 (s, 3H), 3.23 (br, 2H), 2.99-2.68 (m, 4H), 2.12-2.04 (m, 1H), 1.82-1.72 (m, 1H), 1.08 (d, J=6.4 Hz, 3H). MS: (ES, m/z): 350 $[M+H]^+$.

The following examples in TABLE 2 were prepared using standard chemical manipulations and procedures similar to those used for the preparation of Example 7.

TABLE 2

| Example Number | Structure and Compound Name | LRMS m/z $[M + H]^+$ | $^1$HNMR |
|---|---|---|---|
| 8 | 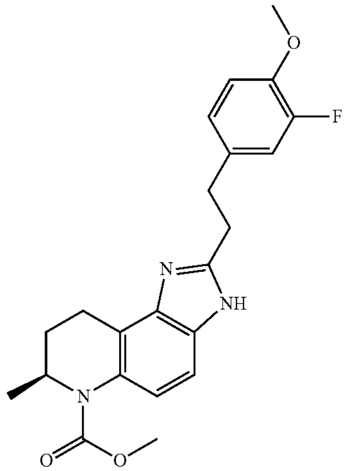 methyl (S)-2-(3-fluoro-4-methoxyphenethyl)-7-methyl-3,7,8,9-tetrahydro-6H-imidazo[4,5-f]quinoline-6-carboxylate | 398 | $^1$H-NMR ($CD_3OD$, 400 MHz) δ (ppm): 7.36 (d, J = 8.8 Hz, 1H), 7.30-7.29 (m, 1H), 6.99-6.91 (m, 3H), 4.79-4.73 (m, 1H), 3.83 (s, 3H), 3.78 (s, 3H), 3.17-3.06 (m, 5H), 2.87-2.83 (m, 1H), 2.28-2.21 (m, 1H), 1.78-1.70 (m, 1H), 1.15-1.13 (m, 3H) |

TABLE 2-continued

| Example Number | Structure and Compound Name | LRMS m/z [M + H]$^+$ | $^1$HNMR |
|---|---|---|---|
| 9 | 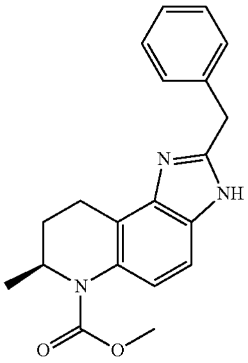 methyl (S)-2-benzyl-7-methyl-3,7,8,9-tetrahydro-6H-imidazo-[4,5-f]quinoline-6-carboxylate | 336 | $^1$H-NMR: ($CDCl_3$, 400 MHz) δ (ppm): 7.40-7.26 (m, 7H), 4.81-4.77 (m, 1H), 4.29 (s, 3.79 (s, 3H), 3.13-3.05 (m, 1H), 2.91-2.89 (m, 2.28-2.19 (m, 1H), 1.75-1.69 (m, 1H), 1.14 (d, J = 6.8 Hz, 3H) |
| 10 | 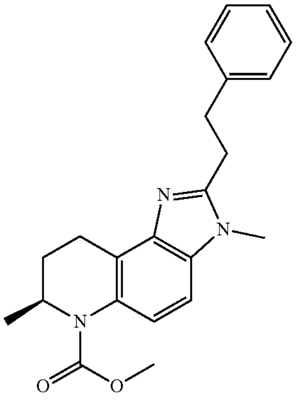 methyl (S)-3,7-dimethyl-2-phenethyl-3,7,8,9-tetrahydro-6H-imidazo[4,5-f]quinoline-6-carboxylate | 364 | $^1$H-NMR: ($CDCl_3$, 300 MHz) δ (ppm): 7.48 (d, J = 9.0 Hz, 1H), 7.33-7.19 (m, 5H), 7.08 (d, J = 9.0 Hz, 1H), 4.84-4.78 (m, 1H), 3.81 (s, 3H), 3.49 (s, 3H), 3.35-3.14 (m, 5H), 3.08-2.99 (m, 1H), 2.31-2.24 (m, 1H), 1.79-1.63 (m, 1H), 1.16-1.13 (m, 3H) |
| 11 | 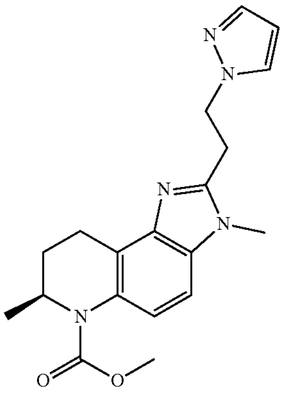 methyl (S)-2-(2-(1H-pyrazol-1-yl)-ethyl)-3,7-dimethyl-3,7,8,9-tetra-hydro-6H-imidazo[4,5-f]-quinoline-6-carboxylate | 354 | $^1$H-NMR: ($CDCl_3$, 400 MHz) δ (ppm): 7.84 (d, J = 9.2 Hz, 1H), 7.50 (s, 1H), 7.29-7.26 (m, 1H), 7.20-7.17 (m, 1H), 6.15 (s, 1H), 4.84-4.77 (m, 3H), 3.85-3.72 (m, 5H), 3.49 (s, 3H), 3.19-3.05 (m, 2H), 2.22-2.13 (m, 1H), 1.87-1.82 (m, 1H), 1.13 (d, J = 6.8 Hz, 3H) |

TABLE 2-continued
| Example Number | Structure and Compound Name | LRMS m/z $[M + H]^+$ | $^1$HNMR |
|---|---|---|---|
| 12 | 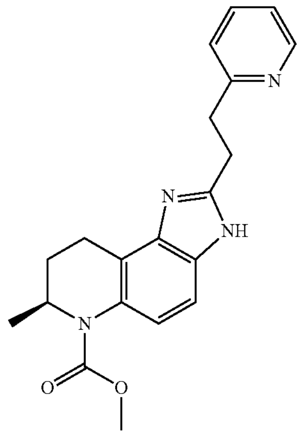 methyl (S)-7-methyl-2-(2-(pyridin-2-yl)ethyl)-3,7,8,9-tetrahydro-6H-imidazo[4,5-f]quinoline-6-carboxylate | 351 | $^1$H-NMR: ($CDCl_3$, 300 MHz) δ (ppm): 8.63-8.62 (m, 1H), 7.70-7.67 (m, 1H), 7.41-7.21 (m, 4H), 4.84-4.78 (m, 1H), 3.77 (s, 3H), 3.44-3.40 (m, 2H), 3.33-3.29 (m, 2H), 3.14-3.08 (m, 1H), 2.97-2.88 (m, 1H), 2.29-2.21 (m, 1H), 1.79-1.70 (m, 1H), 1.40 (d, J = 6.9 Hz, 3H) |
| 13 | 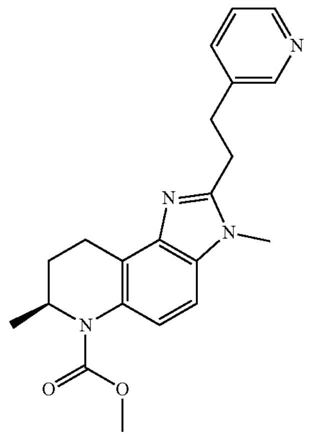 methyl (S)-3,7-dimethyl-2-(2-(pyridin-3-yl)ethyl)-3,7,8,9-tetrahydro-6H-imidazo[4,5-f]quinoline-6-carboxylate | 365 | $^1$H-NMR: ($CDCl_3$, 400 MHz) δ (ppm): 8.52-8.47 (m, 2H), 7.52-7.45 (m, 2H), 7.21-7.18 (m, 1H), 7.08-7.06 (m, 1H), 4.81-4.76 (m, 1H), 3.78 (s, 3H), 3.55 (s, 3H), 3.29-3.17 (m, 5H), 3.03-2.96 (m, 1H), 2.31-2.22 (m, 1H), 1.75-1.61 (m, 1H), 1.15-1.12 (m, 3H) |

TABLE 2-continued

| Example Number | Structure and Compound Name | LRMS m/z $[M + H]^+$ | $^1$HNMR |
|---|---|---|---|
| 14 | 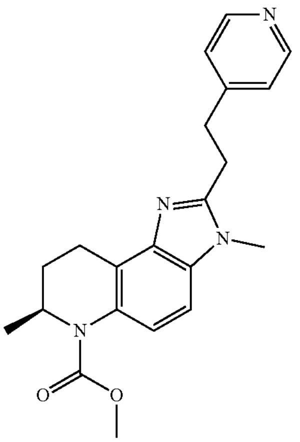 methyl (S)-3,7-dimethyl-2-(2-(pyridin-4-yl)ethyl)-3,7,8,9-tetrahydro-6H-imidazo[4,5-f]quinoline-6-carboxylate | 365 | $^1$H-NMR: ($CDCl_3$, 400 MHz) δ (ppm): 8.72 (s, 2H), 7.93 (d, J = 9.2 Hz, 1H), 7.804 (s, 2H), 7.30 (d, J = 9.2 Hz, 1H), 4.86-4.82 (m, 1H), 3.89 (s,3H), 3.82 (s, 3H), 3.78-3.68 (m, 2H), 3.47 (s, 2H), 3.18-3.06 (m, 2H), 2.24-2.17 (m, 1H), 1.88-1.85 (m, 1H), 1.14 (d, J = 6.4 Hz, 3H) |
| 15 | 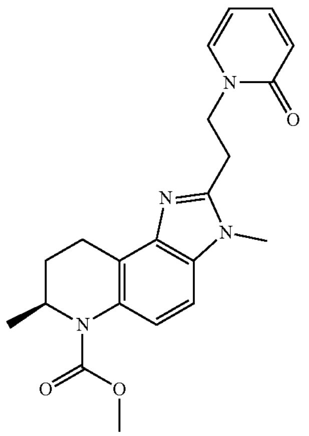 methyl (S)-3,7-dimethyl-2-(2-(2-oxopyridin-1(2H)-yl)ethyl)-3,7,8,9-tetrahydro-6H-imidazo[4,5-f]quinoline-6-carboxylate | 381 | $^1$H-NMR: ($CDCl_3$, 300 MHz) δ (ppm): 7.92 (d, J = 9.0 Hz, 1H), 7.71-7.69 (m, 1H), 7.48-7.42 (m, 1H), 7.32 (d, J = 9.0 Hz, 1H), 6.63 (d, J = 9.0 Hz, 1H), 6.33-6.31 (m, 1H), 4.89-4.84 (m, 1H), 4.53-4.48 (m, 2H), 4.08 (s, 3H), 3.84-3.78 (m, 5H), 3.19-3.12 (m, 2H), 2.25-2.18 (m, 1H), 1.91-1.85 (m, 1H), 1.19-1.15 (m, 3H) |

Example 16: (1R,3R)-3-((S)-2-benzyl-6-(methoxycarbonyl)-7-methyl-6,7,8,9-tetrahydro-3H-imidazo[4,5-f]quinolin-3-yl)cyclohexane-1-carboxylic acid -continued

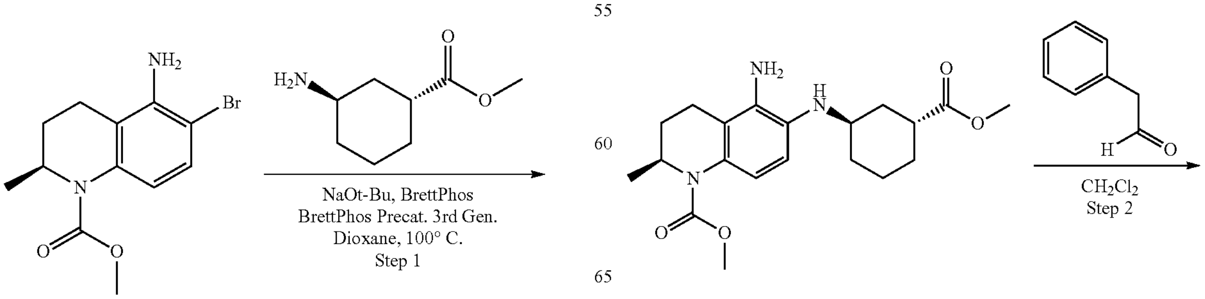

-continued

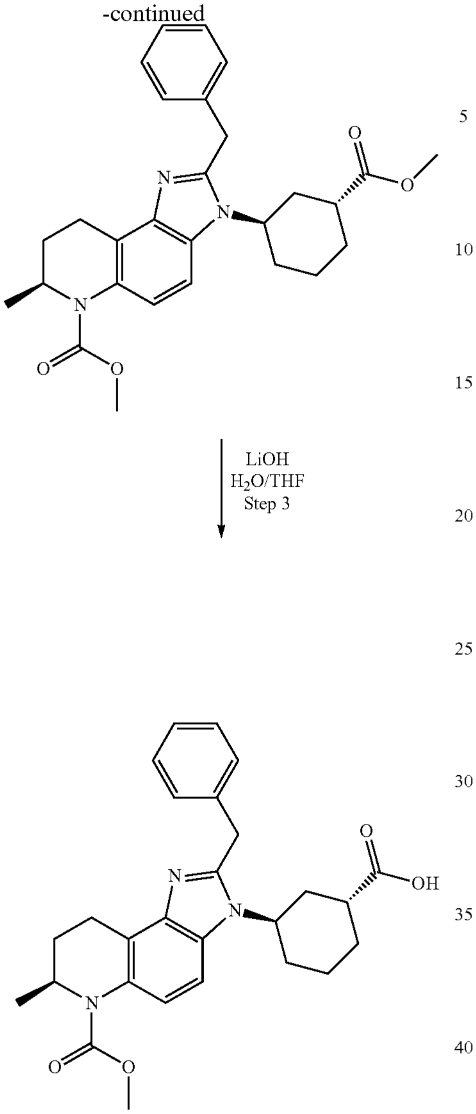

Step 1. methyl (S)-5-amino-6-(((1R,3R)-3-(methoxycarbonyl)cyclohexyl)amino)-2-methyl-3,4-dihydroquinoline-1(2H)-carboxylate Into a 10-mL round-bottom flask purged and maintained with an inert atmosphere of nitrogen, methyl (1R,3R)-3-aminocyclohexane-1-carboxylate hydrochloride (130 mg, 0.67 mmol) was dissolved in dioxane (4 mL). Then methyl (2S)-5-amino-6-bromo-2-methyl-1,2,3,4-tetrahydroquinoline-1-carboxylate (100 mg, 0.33 mmol, Intermediate 1), Brettphos (72 mg, 0.13 mmol), 3$^{rd}$ Generation Brettphos precatalyst (61 mg, 0.07 mmol) and sodium tert-butoxide (97 mg, 1.01 mmol) were added. The resulting solution was stirred for 1 h at 100° C. under nitrogen atmosphere. The reaction mixture was cooled and the solids were filtered out. The resulting mixture was concentrated under vacuum. The residue was subjected to purification by FCC eluting with ethyl acetate/petroleum ether (2:1). This afforded the title compound (41.3 mg, 33%) as a dark green solid. MS: (ES, m/z): 376 $[M+H]^+$.

Step 2. methyl (S)-2-benzyl-3-((1R,3R)-3-(methoxycarbonyl)cyclohexyl)-7-methyl-3,7,8,9-tetrahydro-6H-imidazo[4,5-f]quinoline-6-carboxylate Into a 25-mL round-bottom flask, methyl methyl (S)-5-amino-6-(((1R,3R)-3-(methoxycarbonyl)cyclohexyl) amino)-2-methyl-3,4-dihydroquinoline-1(2H)-carboxylate (165.4 mg, 0.44 mmol) was dissolved in dichloromethane (5 mL). Then 2-phenylacetaldehyde (158.8 mg, 1.32 mmol) was added. The resulting solution was stirred for 2 h at room temperature. The resulting mixture was concentrated under vacuum. The residue was subjected to purification by FCC eluting with ethyl acetate/petroleum ether (2:1). This afforded the title compound (122.9 mg, 59%) as a yellow solid. MS: (ES, m/z): 476 $[M+H]^+$.

Step 3. (1R,3R)-3-[(7S)-2-benzyl-6-(methoxycarbonyl)-7-methyl-3H,6H,7H,8H,9H-imidazo[4,5-f]quinolin-3-yl]cyclohexane-1-carboxylic acid Into a 25-mL round-bottom flask, methyl methyl (S)-2-benzyl-3-((1R,3R)-3-(methoxycarbonyl)cyclohexyl)-7-methyl-3,7,8,9-tetrahydro-6H-imidazo[4,5-f]quinoline-6-carboxylate (30 mg, 0.06 mmol) was dissolved in tetrahydrofuran (0.5 mL). Then water (0.5 mL) was added, followed by lithium hydroxide (7.0 mg, 0.29 mmol). The resulting solution was stirred for 3 h at 85° C. The pH value of the solution was adjusted to 5-6 with hydrochloric acid (1 mol/L). The resulting solution was extracted with ethyl acetate (3×20 mL). The organic layers were combined, dried over anhydrous sodium sulfate, filtered and concentrated under vacuum. The crude product was purified by Prep-HPLC with the following conditions: Column, XBridge C18 OBD Prep Column, 100 Å, 5 μm, 19 mm×250 mm; mobile phase, A: Water (containing 10 mmol/L $NH_4HCO_3$) and B: ACN (10.0% to 30.0% ACN over 10 min); UV Detector: 254 nm. This afforded the title compound (15.2 mg, 52%) as a white solid.

$^1H$ NMR ($CD_3OD$, 400 MHz) δ (ppm): 7.47 (d, J=9.0 Hz, 1H), 7.39 (d, J=8.9 Hz, 1H), 7.35-7.19 (m, 5H), 4.84-4.68 (m, 2H), 4.45-4.25 (m, 2H), 3.79 (s, 3H), 3.22-3.14 (m, 1H), 2.98-2.85 (m, 2H), 2.40-2.02 (m, 5H), 1.83-1.70 (m, 1H), 1.64-1.54 (m, 2H), 1.33-1.13 (m, 5H). MS: (ES, m z): 462 $[M+H]^+$.

The following examples in TABLE 3 were prepared using standard chemical manipulations and procedures similar to those used for the preparation of Example 16.

TABLE 3

| Example Number | Structure and Compound Name | LRMS m/z [M + H]+ | 1HNMR |
|---|---|---|---|
| 17 | 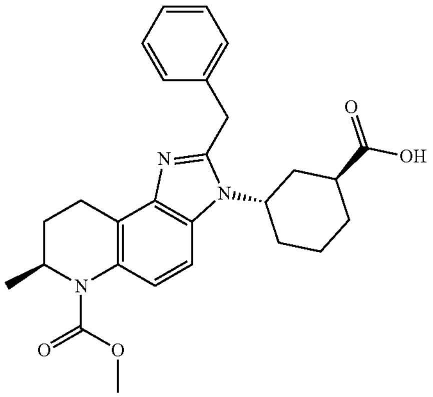 (1S,3S)-3-((S)-2-benzyl-6-(methoxycarbonyl)-7-methyl-6,7,8,9-tetrahydro-3H-imidazo[4,5-f]-quinolin-3-yl)cyclohexane-1-carboxylic acid | 462 | $^1$H-NMR ($CD_3OD$, 400 MHz) δ (ppm): 7.47 (d, J = 9.0 Hz, 1H), 7.39 (d, J = 8.9 Hz, 1H), 7.35-7.19 (m, 5H), 4.84-4.68 (m, 2H), 4.45-4.25 (m, 2H), 3.79 (s, 3H), 3.22-3.14 (m, 1H), 2.98-2.85 (m, 2H), 2.40-2.02 (m, 5H), 1.83-1.70 (m, 1H), 1.64-1.54 (m, 2H), 1.33-1.13 (m, 5H) |
| 18 | 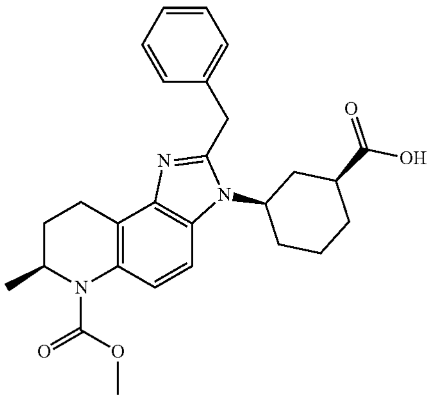 (1S,3R)-3-((S)-2-benzyl-6-(methoxycarbonyl)-7-methyl-6,7,8,9-tetrahydro-3H-imidazo[4,5-f]-quinolin-3-yl)cyclohexane-1-carboxylic acid | 462 | $^1$H-NMR ($CD_3OD$, 300 MHz) δ (ppm): 7.51-7.20 (m, 7H), 4.82-4.74 (m, 1H), 4.43 (s, 2H), 4.38-4.24 (m, 1H), 3.79 (s, 3H), 3.28-3.20 (m, 1H), 3.02-2.94 (m, 1H), 2.37-1.95 (m, 5H), 1.94-1.67 (m, 3H), 1.50-1.28 (m, 3H), 1.17 (d, J = 6.7 Hz, 3H) |
| 19 | 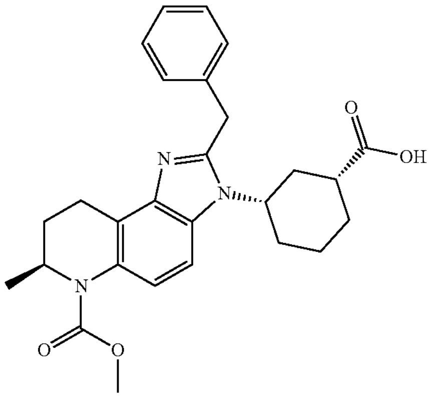 (1R,3S)-3-((S)-2-benzyl-6-(methoxycarbonyl)-7-methyl-6,7,8,9-tetrahydro-3H-imidazo[4,5-f]-quinolin-3-yl)cyclohexane-1-carboxylic acid | 462 | $^1$H-NMR ($CD_3OD$, 300 MHz) δ (ppm): 7.51-7.20 (m, 7H), 4.82-4.74 (m, 1H), 4.43 (s, 2H), 4.38-4.25 (m, 1H), 3.79 (s, 3H), 3.28-3.18 (m, 1H), 3.02-2.92 (m, 1H), 2.38-1.95 (m, 5H), 1.93-1.70 (m, 3H), 1.50-1.28 (m, 3H), 1.17 (d, J = 6.6 Hz, 3H) |

TABLE 3-continued

| Example Number | Structure and Compound Name | LRMS m/z $[M + H]^+$ | $^1$HNMR |
|---|---|---|---|
| 20 | 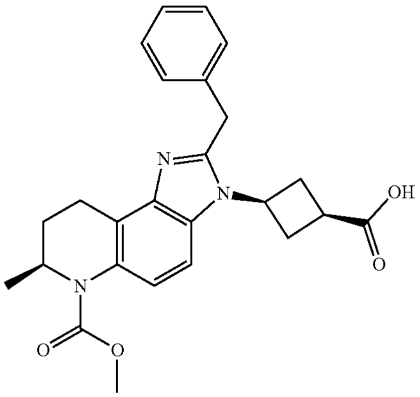 cis-3-((S)-2-benzyl-6-(methoxycarbonyl)-7-methyl-6,7,8,9-tetrahydro-3H-imidazo[4,5-f]-quinolin-3-yl)cyclohexane-1-carboxylic acid | 434 | $^1$H-NMR ($CD_3OD$, 300 MHz) δ (ppm): 7.51-7.20 (m, 7H), 4.82-4.74 (m, 1H), 4.43 (s, 2H), 4.38-4.25 (m, 1H), 3.79 (s, 3H), 3.28-3.18 (m, 1H), 3.02-2.92 (m, 1H), 2.38-1.95 (m, 5H), 1.93-1.70 (m, 3H), 1.50-1.28 (m, 3H), 1.17 (d, J = 6.6 Hz, 3H) |
| 21 | 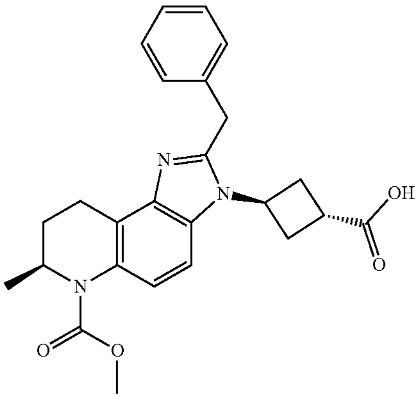 trans-3-((S)-2-benzyl-6-(methoxycarbonyl)-7-methyl-6,7,8,9-tetrahydro-3H-imidazo[4,5-f]-quinolin-3-yl)cyclohexane-1-carboxylic acid | 434 | $^1$H-NMR ($CD_3OD$, 400 MHz) δ (ppm): 7.89 (d, J = 9.0 Hz, 1H), 7.46 (d, J = 9.0 Hz, 1H), 7.39-7.12 (m, 5H), 4.98-4.94 (m, 1H), 4.82-4.73 (m, 1H), 4.42 (s, 2H), 3.80 (s, 3H), 3.31-2.79 (m, 5H), 2.52-2.19 (m, 3H), 1.86-1.69 (m, 1H), 1.17 (d, J = 6.6 Hz, 3H) |
| 22 | 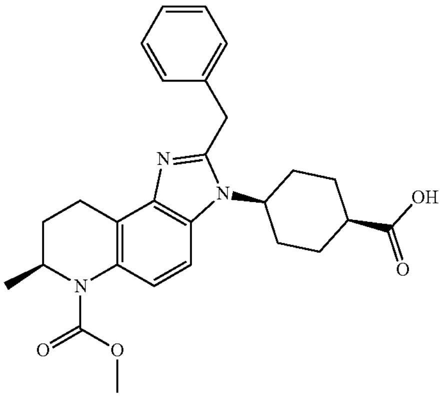 cis-4-((S)-2-benzyl-6-(methoxycarbonyl)-7-methyl-6,7,8,9-tetrahydro-3H-imidazo[4,5-f]quinolin-3-yl)cyclohexane-1-carboxylic acid | 462 | $^1$H-NMR ($CDCl_3$, 400 MHz) δ (ppm): 7.34-7.22 (m, 7H), 4.77-4.73 (m, 1H), 4.39 (s, 2H), 4.26-4.21 (m, 1H), 3.76 (s, 3H), 3.30-3.17 (m, 1H), 2.97-2.93 (m, 1H), 2.60 (s, 1H), 2.43-2.16 (m, 5H), 1.78-1.72 (s, 1H), 1.51-1.28 (m, 4H), 1.13 (d, J = 6.4 Hz, 3H) |

TABLE 3-continued

| Example Number | Structure and Compound Name | LRMS m/z $[M + H]^+$ | $^1$HNMR |
|---|---|---|---|
| 23 | 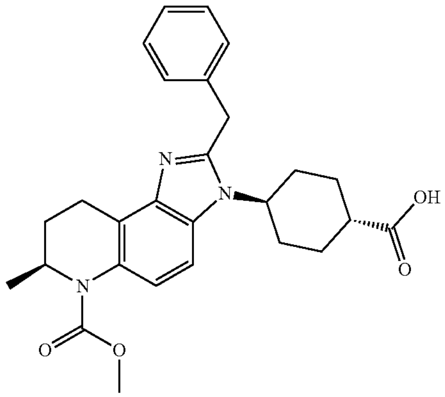 trans-4-((S)-2-benzyl-6-(methoxycarbonyl)-7-methyl-6,7,8,9-tetrahydro-3H-imidazo[4,5-f]quinolin-3-yl)cyclohexane-1-carboxylic acid | 462 | $^1$H-NMR ($CDCl_3$, 400 MHz) δ (ppm): 7.49-7.22 (m, 7H), 4.78-4.72 (m, 1H), 4.42 (s, 2H), 4.25-4.15 (m, 1H), 3.79 (s, 3H), 3.23-3.12 (m, 1H), 2.98-2.91 (m, 1H), 2.37-3.07 (m, 4H), 2.04-1.96 (m, 2H), 1.78-1.70 (m, 1H), 1.58-1.35 (m, 4H), 1.16 (d, J = 6.7 Hz, 3H) |
| 24 | 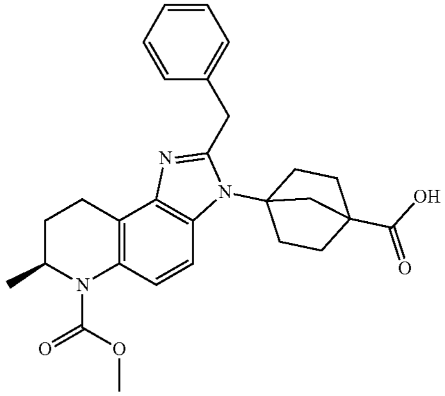 (S)-4-(2-benzyl-6-(methoxycarbonyl)-7-methyl-6,7,8,9-tetrahydro-3H-imidazo[4,5-f]quinolin-3-yl)bicyclo[2.2.1]heptane-1-carboxylic acid | 474 | $^1$H-NMR ($CD_3OD$, 300 MHz) δ (ppm): 7.62 (d, J = 9.2 Hz, 1H), 7.56-7.36 (m, 1H), 7.42-7.16 (m, 3H), 7.07-6.98 (m, 2H), 4.82-4.78 (m, 1H), 4.58 (s, 2H), 3.80 (s, 3H), 3.25-3.15 (m, 1H), 3.00-2.90 (m, 1H), 2.70-2.48 (m, 4H), 2.20-2.10 (m, 1H), 2.09-1.98 (m, 2H), 1.92-1.70 (m, 5H), 1.17 (d, J = 6.7 Hz, 3H) |
| 25 | 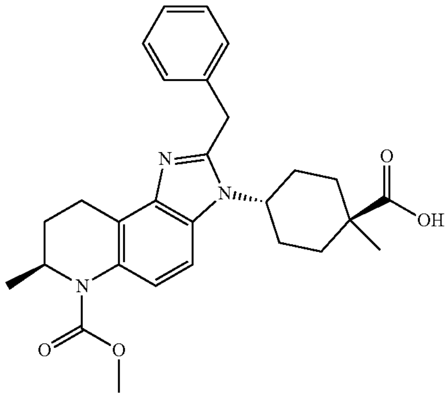 trans-4-((S)-2-benzyl-6-(methoxycarbonyl)-7-methyl-6,7,8,9-tetrahydro-3H-imidazo[4,5-f]quinolin-3-yl)-1-methylcyclohexane-1-carboxylic acid | 476 | $^1$H-NMR ($CD_3OD$, 300 MHz) δ (ppm): 7.32-7.27 (m, 3H), 7.24-7.19 (m, 4H), 4.74-4.71 (m, 1H), 4.36 (s, 2H), 4.30-4.15 (m, 1H), 3.73 (s, 3H), 3.23-3.08 (m, 1H), 3.01-2.84 (m, 1H), 2.36-2.08 (m, 5H), 1.81-1.64 (m, 1H), 1.39-1.28 (m, 2H), 1.16-1.05 (m, 8H) |

TABLE 3-continued

| Example Number | Structure and Compound Name | LRMS m/z $[M + H]^+$ | $^1$HNMR |
|---|---|---|---|
| 26 | 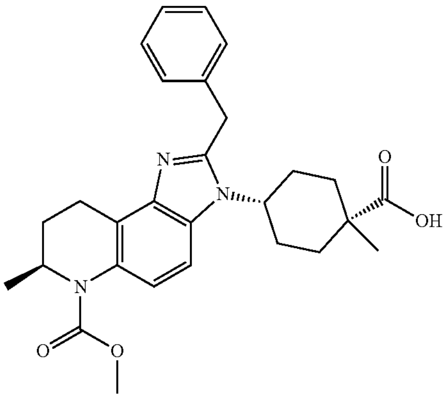 cis-4-((S)-2-benzyl-6-(methoxycarbonyl)-7-methyl-6,7,8,9-tetrahydro-3H-imidazo[4,5-f]quinolin-3-yl)-1-methylcyclohexane-1-carboxylic acid | 476 | $^1$H-NMR ($CD_3OD$, 300 MHz) δ (ppm): 7.37-7.30 (m, 2H), 7.28-7.17 (m, 5H), 4.77-4.71 (m, 1H), 4.37 (s, 2H), 4.20-4.16 (m, 1H), 3.74 (s, 3H), 3.19-3.14 (m, 1H), 2.99-2.91 (m, 1H), 2.31-2.18 (m, 3H), 1.76-1.62 (m, 5H), 1.41-1.20 (m, 5H), 1.12 (d, J = 6.9 Hz, 3H) |
| 27 | 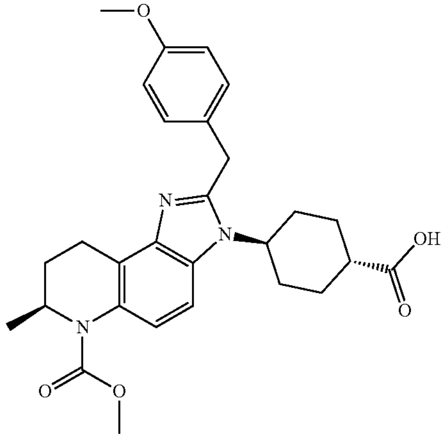 trans-4-((S)-2-(4-methoxybenzyl)-6-(methoxycarbonyl)-7-methyl-6,7,8,9-tetrahydro-3H-imidazo[4,5-f]quinolin-3-yl)cyclohexane-1-carboxylic acid | 492 | $^1$H-NMR ($CD_3OD$, 300 MHz) δ (ppm): 7.42-7.35 (m, 2H), 7.18 (d, J = 8.7 Hz, 2H), 6.89 (d, J = 8.7 Hz, 2H), 4.79-4.75 (m, 1H), 4.32-4.21 (m, 3H), 3.76-3.75 (m, 6H), 3.24-3.21 (m, 1H), 3.00-2.92 (m, 1H), 2.38-2.02 (m, 6H), 1.78-1.71 (m, 1H), 1.55-1.37 (m, 4H), 1.14 (d, J = 6.9 Hz, 3H) |
| 28 | 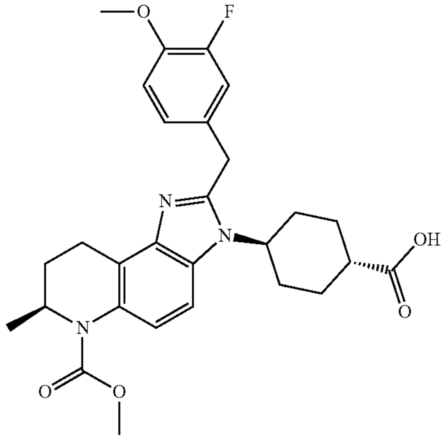 trans-4-((S)-2-(3-fluoro-4-methoxybenzyl)-6-(methoxycarbonyl)-7-methyl-6,7,8,9-tetrahydro-3H-imidazo[4,5-f]quinolin-3-yl)cyclohexane-1-carboxylic acid | 510 | $^1$H-NMR (DMSO-d6, 400 MHz) δ (ppm): 7.46 (s, 1H), 7.27 (d, J = 6.9 Hz, 1H), 7.14-7.11 (m, 2H), 7.08-7.02 (m, 1H), 4.67-4.62 (m, 1H), 4.28 (s, 3H), 3.78 (s, 3H), 3.66 (s, 3H), 3.10-3.02 (m, 1H), 2.87-2.81 (m, 1H), 2.36-2.33 (m, 1H), 2.15-2.08 (m, 3H), 1.95-1.91 (m, 2H), 1.67-1.62 (m, 1H), 1.49-1.37 (m, 4H), 1.07 (d, J = 6.8 Hz, 3H) |

TABLE 3-continued

| Example Number | Structure and Compound Name | LRMS m/z [M + H]$^+$ | $^1$HNMR |
| --- | --- | --- | --- |
| 29 | 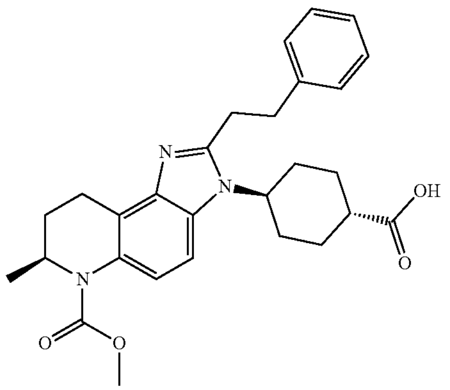 trans-4-((S)-6-(methoxycarbonyl)-7-methyl-2-phenethyl-6,7,8,9-tetrahydro-3H-imidazo[4,5-f]-quinolin-3-yl)cyclohexane-1-carboxylic acid | 476 | $^1$H-NMR ($CD_3OD$, 300 MHz) δ (ppm): 7.83-7.82 (m, 2H), 7.34-7.26 (m, 3H), 7.22-7.19 (m, 2H), 4.86-4.85 (m, 1H), 4.43-4.36 (m, 1H), 3.82 (s, 3H), 3.66-3.61 (m, 2H), 3.25-3.21 (m, 2H), 3.06-2.99 (m, 2H), 2.57-2.54 (m, 1H), 2.30-2.13 (m, 5H), 1.96-1.91 (m, 1H), 1.63-1.56 (m, 4H), 1.16 (d, J = 6.9 Hz, 3H) |
| 30 | 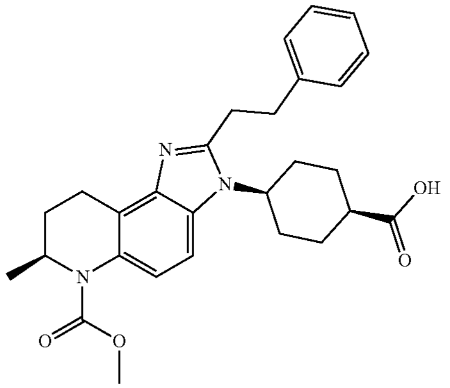 cis-4-((S)-2-benzyl-6-(methoxycarbonyl)-7-methyl-6,7,8,9-tetrahydro-3H-imidazo[4,5-f]quinolin-3-yl)-1-methylcyclohexane-1-carboxylic acid | 476 | $^1$H-NMR ($CD_3OD$, 300 MHz) δ (ppm): 7.32-7.27 (m, 3H), 7.24-7.19 (m, 4H), 4.74-4.71 (m, 1H), 4.36 (s, 2H), 4.30-4.15 (m, 1H), 3.73 (s, 3H), 3.23-3.08 (m, 1H), 3.01-2.84 (m, 1H), 2.36-2.08 (m, 5H), 1.81-1.64 (m, 1H), 1.39-1.28 (m, 2H), 1.16-1.05 (m, 8H) |
| 31 | 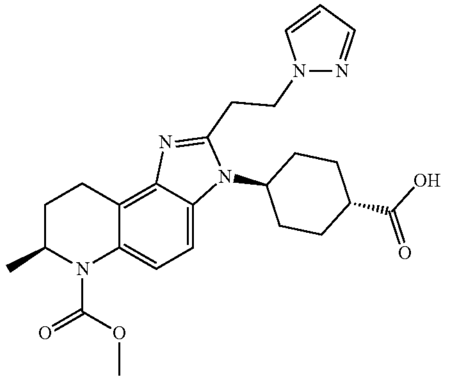 trans-4-((S)-2-(2-(1H-pyrazol-1-yl)ethyl)-6-(methoxycarbonyl)-7-methyl-6,7,8,9-tetrahydro-3H-imidazo-[4,5-f]quinolin-3-yl)cyclohexane-1-carboxylic acid | 466 | $^1$H-NMR ($CD_3OD$, 300 MHz) δ (ppm): 7.55-7.46 (m, 3H), 7.40-7.37 (d, J = 9 Hz, 1H), 6.24 (s, 1H), 4.80-4.71 (m, 1H), 4.69-4.64 (m, 2H), 4.24-4.15 (m, 1H), 3.78 (s, 3H), 3.55-3.51 (m, 2H), 3.19-3.13 (m, 1H), 2.99-2.89 (m, 1H), 2.51-2.44 (m, 1H), 2.29-2.13 (s, 5H), 1.80-1.60 (m, 5H), 1.15-1.13 (d, J = 6.6 Hz, 3H) |

TABLE 3-continued

| Example Number | Structure and Compound Name | LRMS m/z [M + H]+ | 1HNMR |
|---|---|---|---|
| 32 | 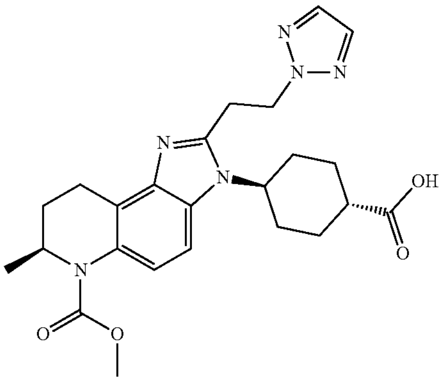 trans-4-((S)-2-(2-(2H-1,2,3-triazol-2-yl)ethyl)-6-(methoxycarbonyl)-7-methyl-6,7,8,9-tetrahydro-3H-imidazo[4,5-f]quinolin-3-yl)cyclohexane-1-carboxylic acid | 467 | 1H-NMR ($CDCl_3$, 400 MHz) δ (ppm): 7.83-7.81 (m, 1H), 7.63-7.62 (m, 2H), 7.43-7.37 (m, 1H), 5.11-5.08 (m, 2H), 4.84-4.82 (m, 1H), 4.18-3.99 (m, 3H), 3.81 (s, 3H), 3.15-3.13 (m, 2H), 2.48-2.43 (m, 1H), 2.21-2.18 (m, 5H), 1.90-1.86 (m, 1H), 1.71-1.59 (m, 4H), 1.16 (d, J = 5.1 Hz, 3H) |
| 33 | 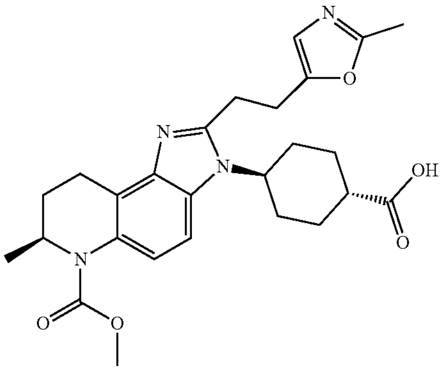 trans-4-((S)-6-(methoxycarbonyl)-7-methyl-2-(2-(2-methyloxazol-5-yl)ethyl)-6,7,8,9-tetrahydro-3H-imidazo[4,5-f]quinolin-3-yl)cyclohexane-1-carboxylic acid | 481 | 1H-NMR ($CD_3OD$, 400 MHz) δ (ppm): 7.51 (d, J = 9.0 Hz, 1H), 7.39 (d, J = 8.9 Hz, 1H), 6.72 (s, 1H), 4.77-4.72 (m, 1H), 4.32-4.23 (m, 1H), 3.78 (s, 3H), 3.33-3.30 (m, 2H), 3.23-3.09 (m, 3H), 2.92-2.84 (m, 1H), 2.51-2.16 (m, 9H), 1.88-1.82 (m, 2H), 1.72-1.62 (m, 3H), 1.14 (d, J = 6.6 Hz, 3H) |
| 34 | 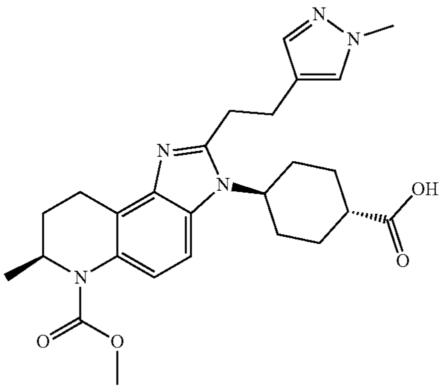 trans-4-((S)-6-(methoxycarbonyl)-7-methyl-2-(2-(1-methyl-1H-pyrazol-4-yl)ethyl)-6,7,8,9-tetrahydro-3H-imidazo[4,5-f]quinolin-3-yl)cyclohexane-1-carboxylic acid | 480 | 1H-NMR ($CD_3OD$, 300 MHz) δ (ppm): 7.50-7.47 (d, J = 9.0 Hz, 1H), 7.42-7.36 (m, 2H), 7.27 (s, 1H), 4.80-4.74 (m, 1H), 4.29-4.21 (m, 1H), 3.79 (s, 3H), 3.76 (s, 3H), 3.21-3.18 (m, 3H), 2.99-2.96 (m, 3H), 2.48-2.16 (m, 6H), 1.68-1.66 (m, 5H), 1.13-1.11 (d, J = 6.6 Hz, 3H) |

TABLE 3-continued

| Example Number | Structure and Compound Name | LRMS m/z $[M + H]^+$ | $^1$HNMR |
|---|---|---|---|
| 35 | 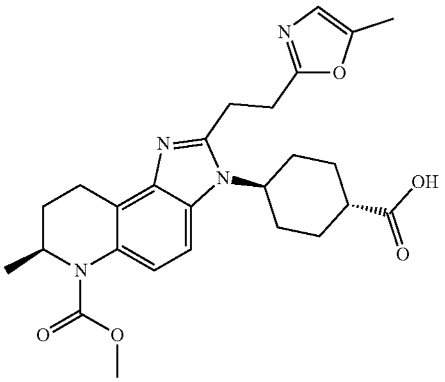 trans-4-((S)-6-(methoxycarbonyl)-7-methyl-2-(2-(5-methyloxazol-2-yl)ethyl)-6,7,8,9-tetrahydro-3H-imidazo[4,5-f]quinolin-3-yl)cyclohexane-1-carboxylic acid | 481 | $^1$H-NMR (DMSO-d6, 400 MHz) δ (ppm): 7.52-7.49 (d, J = 9.2 Hz, 1H), 7.27-7.25 (d, J = 9.2 Hz, 1H), 6.70 (s, 1H), 4.65-4.61 (m, 1H), 4.34 (s, 1H), 3.66 (s, 3H), 3.37-3.17 (m, 4H), 3.05-3.01 (m, 1H), 2.81-2.74 (m, 1H), 2.51-2.44 (m, 1H), 2.27-2.22 (m, 5H), 2.13-2.06 (m, 3H), 1.86-1.80 (m, 2H), 1.65-1.57 (m, 3H), 1.05-1.04 (d, J = 6.4 Hz, 3H) |
| 36 | 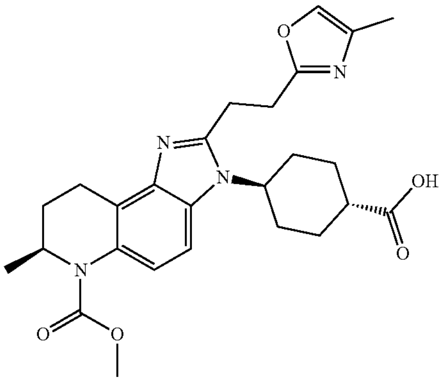 trans-4-((S)-6-(methoxycarbonyl)-7-methyl-2-(2-(4-methyloxazol-2-yl)ethyl)-6,7,8,9-tetrahydro-3H-imidazo[4,5-f]quinolin-3-yl)cyclohexane-1-carboxylic acid | 481 | $^1$H-NMR ($CD_3OD$, 300 MHz) δ (ppm): 7.47-7.33 (m, 2H), 6.05 (s, 1H), 4.77-4.65 (m, 1H), 4.26 (t, J = 12.5 Hz, 1H), 3.73 (s, 3H), 3.39-3.31 (m, 2H), 3.28-3.22 (m, 2H), 3.20-3.02 (m, 1H), 2.94-2.78 (m, 1H), 2.53-2.22 (m, 3H), 2.22-2.06 (m, 6H), 1.88-1.76 (m, 2H), 1.76-1.55 (m, 3H), 1.09 (d, J = 6.6 Hz, 3H) |
| 37 | 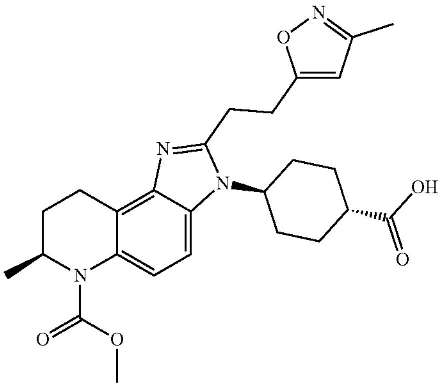 trans-4-((S)-6-(methoxycarbonyl)-7-methyl-2-(2-(3-methylisoxazol-5-yl)ethyl)-6,7,8,9-tetrahydro-3H-imidazo[4,5-f]quinolin-3-yl)cyclohexane-1-carboxylic acid | 481 | $^1$H-NMR ($CD_3OD$, 400 MHz) δ (ppm): 7.49-7.47 (m, 1H), 7.40 (d, J = 9.2 Hz, 1H), 6.10 (s, 1H), 4.78-4.70 (m, 1H), 4.36-1.25 (m, 1H), 3.79 (s, 3H), 3.43-3.34 (m, 2H), 3.25-3.21 (m, 2H), 3.23-3.10 (m, 1H), 2.91-2.83 (m, 1H), 2.50-2.40 (m, 1H), 2.39-2.15 (m, 8H), 1.88-1.58 (m, 5H), 1.14 (d, J = 6.8 Hz, 3H) |

TABLE 3-continued

| Example Number | Structure and Compound Name | LRMS m/z $[M + H]^+$ | $^1$HNMR |
|---|---|---|---|
| 38 | 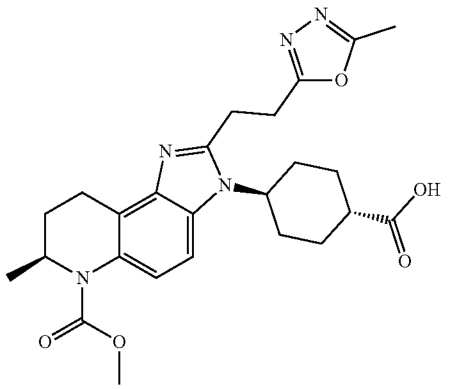 trans-4-((S)-6-(methoxycarbonyl)-7-methyl-2-(2-(5-methyl-1,3,4-oxadiazol-2-yl)ethyl)-6,7,8,9-tetrahydro-3H-imidazo[4,5-f]quinolin-3-yl)cyclohexane-1-carboxylic acid | 482 | $^1$H-NMR ($CD_3OD$, 300 MHz) δ (ppm): 7.51 (d, J = 9.0 Hz, 1H), 7.38 (d, J = 9.0 Hz, 1H), 4.76-4.70 (m, 1H), 4.41 (s, 1H), 3.76 (s, 3H), 3.50-3.36 (m, 4H), 3.11-3.06 (m, 1H), 2.90-2.83 (m, 1H), 2.49 (s, 3H), 2.43-2.18 (m, 6H), 2.00-1.97 (m, 2H), 1.78-1.66 (m, 3H), 1.12 (d, J = 6.9 Hz, 3H) |
| 39 | 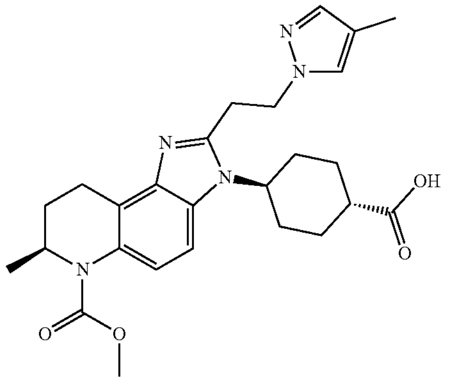 trans-4-((S)-6-(methoxycarbonyl)-7-methyl-2-(2-(3-methyl-1H-pyrazol-1-yl)ethyl)-6,7,8,9-tetrahydro-3H-imidazo[4,5-f]quinolin-3-yl)cyclohexane-1-carboxylic acid | 480 | $^1$H-NMR (DMSO-d6, 400 MHz) δ (ppm): 7.54 (s, 1H), 7.51 (d, J = 9.2 Hz, 1H), 7.27-7.24 (m, 2H), 4.66-4.62 (m, 1H), 4.53-4.49 (m, 2H), 4.19 (s, 1H), 3.66 (s, 3H), 3.43-3.40 (m, 2H), 3.09-3.01 (m, 1H), 2.84-2.80 (m, 1H), 2.50-2.44 (m, 1H), 2.22-2.11 (m, 3H), 2.10-1.98 (m, 5H), 1.75-1.57 (m, 5H), 1.06 (d, J = 6.8 Hz, 3H) |
| 40 | 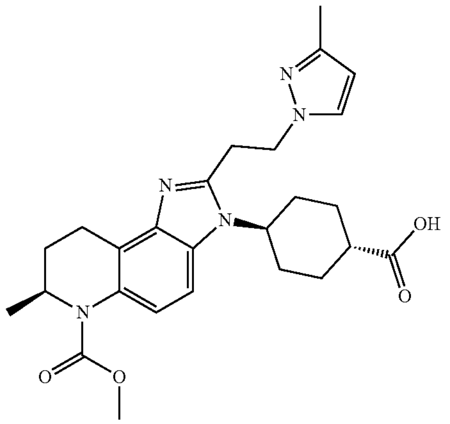 trans-4-((S)-6-(methoxycarbonyl)-7-methyl-2-(2-(3-methyl-1H-pyrazol-1-yl)ethyl)-6,7,8,9-tetrahydro-3H-imidazo[4,5-f]quinolin-3-yl)cyclohexane-1-carboxylic acid | 480 | $^1$H-NMR ($CD_3OD$, 400 MHz) δ (ppm): 7.47-7.35 (m, 3H), 5.97 (s, 1H), 4.77-4.73 (m, 1H), 4.61-4.53 (m, 2H), 4.10-4.09 (m, 1H), 3.76 (s, 3H), 3.48-3.45 (m, 2H), 3.20-3.12 (m, 1H), 2.96-2.89 (m, 1H), 2.42-2.39 (m, 1H), 2.26-2.10 (m, 5H), 2.01 (s, 3H), 1.75-1.59 (m, 5H), 1.12 (d, J = 6.8 Hz, 3H) |

TABLE 3-continued

| Example Number | Structure and Compound Name | LRMS m/z $[M + H]^+$ | $^1$HNMR |
|---|---|---|---|
| 41 | 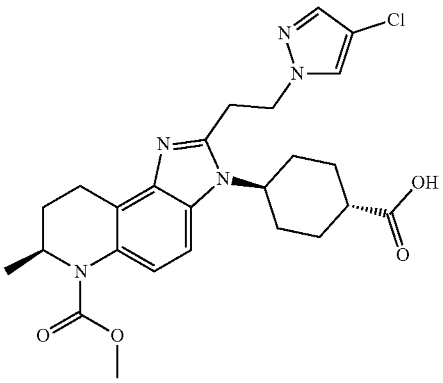 trans-4-((S)-2-(2-(4-chloro-1H-pyrazol-1-yl)ethyl)-6-(methoxycarbonyl)-7-methyl-6,7,8,9-tetrahydro-3H-imidazo[4,5-f]quinolin-3-yl)cyclohexane-1-carboxylic acid | 500 | $^1$H-NMR (DMSO-d6, 300 MHz) δ (ppm): 8.08 (s, 1H), 7.56-7.50 (m, 2H), 7.29-7.26 (d, J = 9.0 Hz, 1H), 4.66-4.57 (m, 3H), 4.28-4.20 (m, 1H), 3.67 (s, 3H), 3.18 (s, 1H), 3.05-3.02 (m, 2H), 2.86-2.78 (m, 1H), 2.46-2.41 (m, 1H), 2.22-2.01 (m, 5H), 1.75-1.57 (m, 5H), 1.07-1.05 (d, J = 6.6 Hz, 3H) |
| 42 | 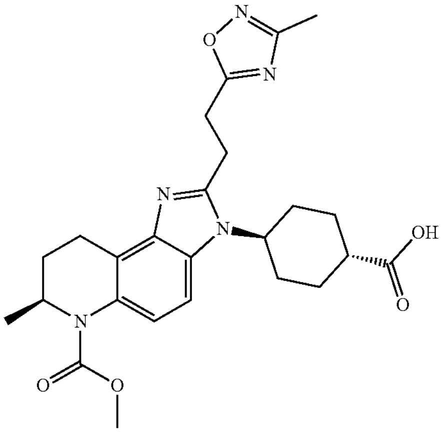 trans-4-((S)-6-(2-(methoxycarbonyl)-7-methyl-2-(2-(3-methyl-1,2,4-oxadiazol-5-yl)ethyl)-6,7,8,9-tetrahydro-3H-imidazo[4,5-f]quinolin-3-yl)cyclohexane-1-carboxylic acid | 482 | $^1$H-NMR ($CD_3OD$, 300 MHz) δ (ppm): 7.47 (d, J = 9.0 Hz, 1H), 7.34 (d, J = 8.9 Hz, 1H), 4.78-4.61 (m, 1H), 4.46-4.31 (m, 1H), 3.73 (s, 3H), 3.52-3.37 (m, 4H), 3.18-3.03 (m, 1H), 2.91-2.75 (m, 1H), 2.47-2.31 (m, 3H), 2.29 (s, 3H), 2.24-2.06 (m, 3H), 1.99-1.87 (m, 2H), 1.79-1.58 (m, 3H), 1.08 (d, J = 6.6 Hz, 3H) |
| 43 | 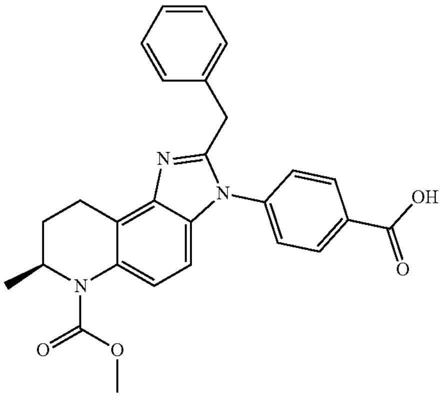 (S)-4-(2-benzyl-6-(methoxycarbonyl)-7-methyl-6,7,8,9-tetrahydro-3H-imidazo[4,5-f]quinolin-3-yl)benzoic acid | 456 | $^1$H-NMR ($CD_3OD$, 300 MHz) δ (ppm): 8.14-8.11 (m, 2H), 7.41-7.39 (m, 1H), 7.33-7.30 (m, 2H), 7.16-7.13 (m, 3H), 6.95-6.89 (m, 3H), 4.71-4.79 (m, 1H), 4.27 (s, 2H), 3.75 (s, 3H), 3.31-3.29 (m, 1H), 3.08-2.94 (m, 1H), 2.36-2.24 (m, 1H), 1.82-1.74 (m, 1H), 1.17 (d, J = 6.6 Hz, 3H) |

TABLE 3-continued

| Example Number | Structure and Compound Name | LRMS m/z [M + H]+ | 1HNMR |
|---|---|---|---|
| 44 | 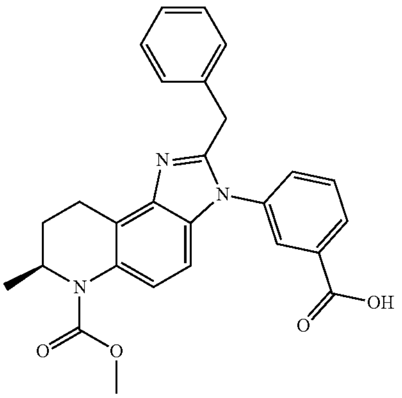 (S)-3-(2-benzyl-6-(methoxycarbonyl)-7-methyl-6,7,8,9-tetrahydro-3H-imidazo[4,5-f]quinolin-3-yl)benzoic acid | 456 | $^{1}$H-NMR ($CD_3OD$, 300 MHz) δ (ppm): 8.21-8.12 (m, 1H), 7.88-7.81 (m, 1H), 7.64-7.55 (t, J = 7.8 Hz, 1H), 7.48-7.37 (m, 2H), 7.23-7.07 (m, 3H), 6.99-6.85 (m, 3H), 4.85-4.76 (m, 1H), 4.28 (s, 2H), 3.78 (s, 3H), 3.31-3.22 (m, 1H), 3.07-2.95 (m, 1H), 2.36-2.24 (m, 1H), 1.82-1.74 (m, 1H), 1.17 (d, J = 6.6 Hz, 3H) |
| 45 | 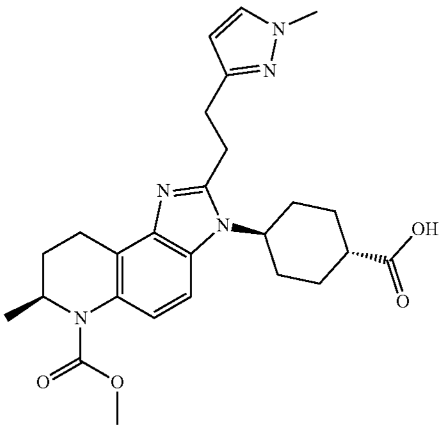 (trans)-4-((S)-6-(methoxycarbonyl)-7-methyl-2-(2-(1-methyl-1H-pyrazol-3-yl)ethyl)-6,7,8,9-tetrahydro-3H-imidazo[4,5-f]quinolin-3-yl)cyclohexane-1-carboxylic acid | 480 | $^{1}$H-NMR ($CD_3OD$, 300 MHz) δ (ppm): 7.51-7.48 (m, 2H), 7.43-7.37 (m, 1H), 6.10-6.09 (m, 1H), 4.77-4.75 (m, 1H), 4.35-4.30 (m, 1H), 3.84 (s, 3H), 3.78 (s, 3H), 3.17-3.07 (m, 5H), 2.95-2.89 (m, 1H), 2.50-2.17 (m, 6H), 1.79-1.70 (m, 5H), 1.16 (d, J = 6.9 Hz, 3H) |

Examples 46 and 47: methyl (7S)-2-[(1R)-2-hydroxy-1-phenylethyl]-7-methyl-3-(oxan-4-yl)-3H,6H,7H,8H,9H-imidazo[4,5-f]quinoline-6-carboxylate and methyl (7S)-2-[(1S)-2-hydroxy-1-phenylethyl]-7-methyl-3-(oxan-4-yl)-3H,6H,7H,8H,9H-imidazo[4,5-f]quinoline-6-carboxylate

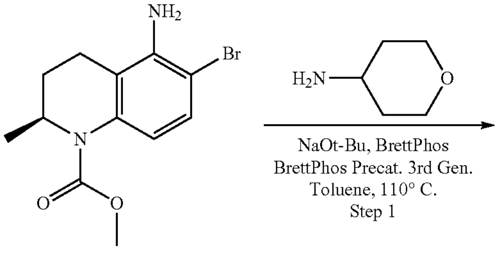

-continued

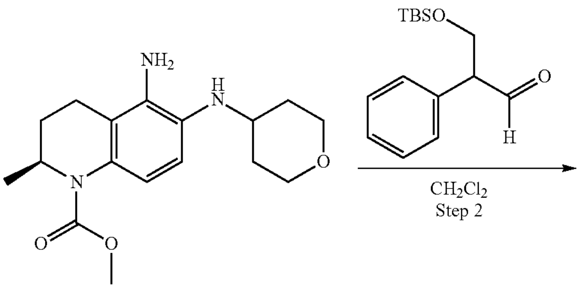

-continued

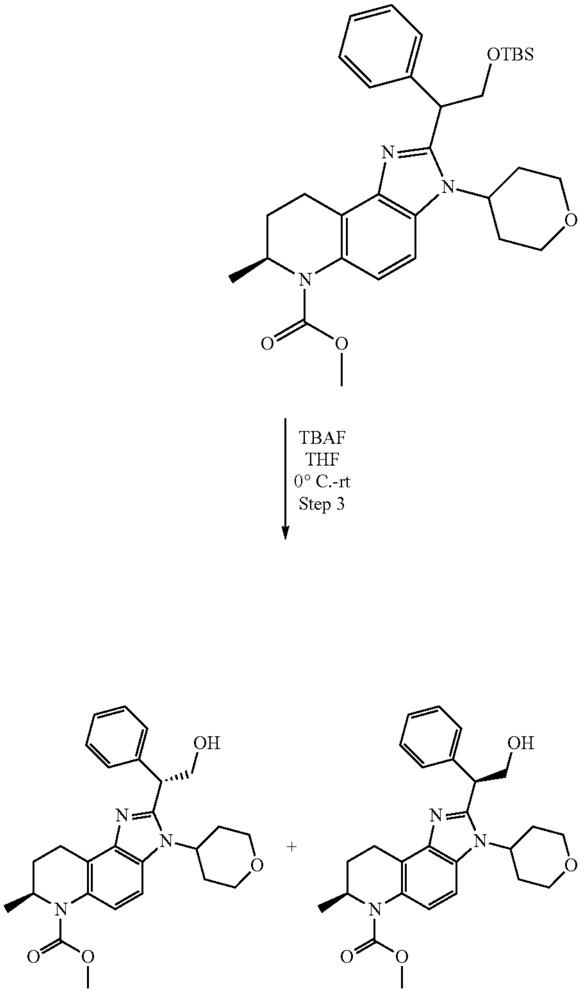

Step 1. Synthesis of methyl (2S)-5-amino-2-methyl-6-[(oxan-4-yl)amino]-1,2,3,4-tetrahydroquinoline-1-carboxylate Into a 50-mL round-bottom flask purged and maintained with an inert atmosphere of nitrogen, methyl (2S)-5-amino-6-bromo-2-methyl-1,2,3,4-tetrahydroquinoline-1-carboxylate (300 mg, 1.00 mmol, Intermediate 1) was dissolved in toluene (20 mL). Then oxan-4-amine (305 mg, 3.02 mmol), Brettphos (215 mg, 0.40 mmol), BrettPhos Pd G3 (182 mg, 0.20 mmol) and sodium tert-butoxide (289 mg, 3.01 mmol) were added. The resulting solution was stirred for 1 h at 110° C. in the nitrogen atmosphere. The reaction mixture was cooled and the resulting solids were filtered out. The filtrate was concentrated under vacuum. The residue was subjected to purification by FCC eluting with ethyl acetate/petroleum ether (1:1). This afforded the title compound (200 mg, 62%) as a yellow oil. MS: (ES, m/z): 320 $[M+H]^+$.

Step 2. Synthesis of methyl (7S)-2-[2-[(tert-butyldimethylsilyl)oxy]-1-phenylethyl]-7-methyl-3-(oxan-4-yl)-3H,6H,7H,8H,9H-imidazo[4,5-f]quinoline-6-carboxylate Into a 50-mL round-bottom flask, methyl (2S)-5-amino-2-methyl-6-[(oxan-4-yl)amino]-1,2,3,4-tetrahydroquinoline-1-carboxylate (150 mg, 0.47 mmol) was dissolved in dichloromethane (10 mL) Then 3-[(tert-butyldimethylsilyl)oxy]-2-phenylpropanal (300 mg, 1.13 mmol, Intermediate 24) was added. The mixture was stirred for 2 h at room temperature. The resulting mixture was concentrated under vacuum. The residue was subjected to purification by FCC eluting with ethyl acetate/petroleum ether (1:1). This afforded the title compound (150 mg, 57%) as a green oil. MS: (ES, m/z): 564 $[M+H]^+$.

Step 3. Synthesis of methyl (7S)-2-[(1R)-2-hydroxy-1-phenylethyl]-7-methyl-3-(oxan-4-yl)-3H,6H,7H,8H,9H-imidazo[4,5-f]quinoline-6-carboxylate and methyl (7S)-2-[(1S)-2-hydroxy-1-phenylethyl]-7-methyl-3-(oxan-4-yl)-3H,6H,7H,8H,9H-imidazo[4,5-f]quinoline-6-carboxylate Into a 25-mL round-bottom flask, methyl (7S)-2-[2-[(tert-butyldimethylsilyl)oxy]-1-phenylethyl]-7-methyl-3-(oxan-4-yl)-3H,6H,7H,8H,9H-imidazo[4,5-f]quinoline-6-carboxylate (150 mg, 0.27 mmol) was dissolved in tetrahydrofuran (5 mL). Then tetrabutylammonium fluoride (1 mL, 1M in THF) was added. The resulting solution was stirred for 30 min at 0° C. Then the resulting solution was allowed to react for 3 h at room temperature. The resulting solids were filtered out. The filtrate was concentrated under vacuum. The crude product was purified by Prep-HPLC with the following conditions: Column, XBridge C18 OBD Prep Column, 100 Å, 5 um, 19 mm×150 mm; mobile phase, A: Water (containing 10 mmol/L FA) and B: ACN (10.0% to 40.0% ACN over 7 min); UV Detector: 254 nm. This afforded the title compounds as follows: 2.9 mg (2%) of methyl (7S)-2-[(1R)-2-hydroxy-1-phenylethyl]-7-methyl-3-(oxan-4-yl)-3H,6H,7H,8H,9H-imidazo[4,5-f]quinoline-6-carboxylate (assumed stereochemistry, first eluting isomer, RT=5.2 min) as a white solid and 2.8 mg (2%) of methyl (7S)-2-[(1S)-2-hydroxy-1-phenylethyl]-7-methyl-3-(oxan-4-yl)-3H,6H,7H,8H,9H-imidazo[4,5-f]quinoline-6-carboxylate (assumed stereochemistry, second eluting isomer, RT=6.1 min) as a white solid.

First eluting isomer (46): $^1$H-NMR (300 MHz, Methanol-$d_4$) δ 7.49-7.21 (m, 7H), 4.82-4.70 (m, 1H), 4.68-4.58 (m, 1H), 4.58-4.42 (m, 2H), 4.23-4.14 (m, 1H), 4.14-4.04 (m, 1H), 3.90-3.81 (m, 1H), 3.79 (s, 3H), 3.60-3.48 (m, 1H), 3.31-3.25 (m, 1H), 3.22-3.07 (m, 1H), 3.07-2.97 (m, 1H), 2.64-2.46 (m, 1H), 2.40-2.16 (m, 2H), 1.88-1.65 (m, 2H), 1.17 (d, J=6.6 Hz, 3H), 0.82-0.70 (m, 1H). MS: (ES, m/z): 450 $[M+H]^+$.

Second eluting isomer (47): $^1$H-NMR (300 MHz, Methanol-$d_4$) δ 7.46-7.23 (m, 7H), 4.83-4.72 (m, 1H), 4.67-4.58 (m, 1H), 4.57-4.41 (m, 2H), 4.24-4.14 (m, 1H), 4.14-4.05 (m, 1H), 3.88-3.76 (m, 4H), 3.60-3.47 (m, 1H), 3.42-3.36 (m, 1H), 3.22-3.07 (m, 1H), 3.07-2.92 (m, 1H), 2.68-2.51 (m, 1H), 2.38-2.15 (m, 2H), 1.88-1.68 (m, 2H), 1.19 (d, J=6.6 Hz, 3H), 0.77-0.67 (m, 1H). MS: (ES, m/z): 450 $[M+H]^+$.

Examples 48 and 49: (1R,4S)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid and (1S,4R)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid

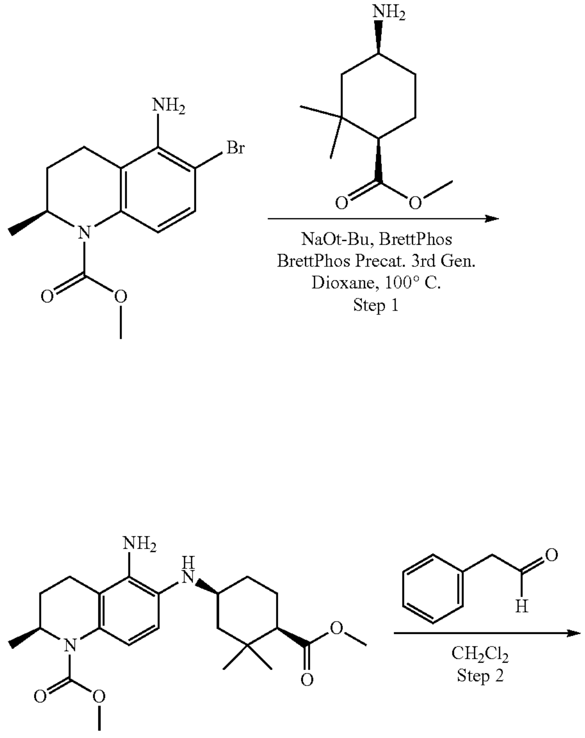

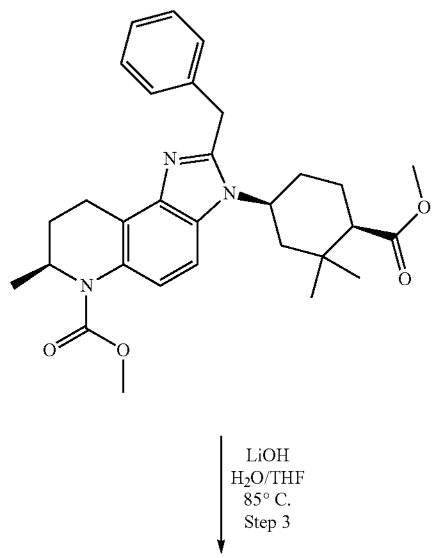

-continued

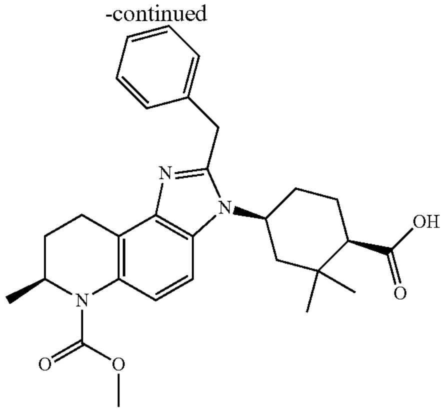

Step 1. Synthesis of methyl (S)-5-amino-6-(((1S,4R)-4-(methoxycarbonyl)-3,3-dimethylcyclohexyl)amino)-2-methyl-3,4-dihydroquinoline-1(2H)-carboxylate Into a 100-mL round-bottom flask purged and maintained with an inert atmosphere of nitrogen, methyl (2S)-5-amino-6-bromo-2-methyl-1,2,3,4-tetrahydroquinoline-1-carboxylate (272 mg, 0.91 mmol, Intermediate 1) was dissolved in toluene (20 mL). Then cis-methyl 4-amino-2,2-dimethylcyclohexane-1-carboxylate (203 mg, 1.09 mmol, Intermediate 25), BrettPhos Pd G3 (96 mg, 0.11 mmol), Brettphos (112 mg, 0.21 mmol) and sodium tert-butoxide (331 mg, 3.64 mmol) were added. The resulting solution was stirred for 1 h at 100° C. under a nitrogen atmosphere. The reaction mixture was cooled and the solids were filtered out. The filtrate was concentrated under vacuum. The residue was subjected to purification by FCC eluting with ethyl acetate/petroleum ether (1:1). This afforded the title compound (60 mg, 16%) as a yellow oil. MS: (ES, m/z): 404 $[M+H]^+$.

Step 2. Synthesis of methyl (S)-2-benzyl-3-((1S,4R)-4-(methoxycarbonyl)-3,3-dimethylcyclohexyl)-7-methyl-3,7,8,9-tetrahydro-6H-imidazo[4,5-f]quinoline-6-carboxylate Into a 25-mL round-bottom flask, (S)-methyl 5-amino-6-(cis-4-(methoxycarbonyl)-3,3-dimethylcyclohexylamino)-2-methyl-3,4-dihydroquinoline-1(2H)-carboxylate (26 mg, 0.06 mmol) was dissolved in dichloromethane (4 mL). Then 2-phenylacetaldehyde (60 mg, 0.50 mmol) was added. The resulting solution was stirred for 2 h at room temperature. The reaction mixture was concentrated under vacuum. The residue was subjected to purification by FCC eluting with ethyl acetate/petroleum ether (1:1). This afforded the title compound (21 mg, 65%) as a yellow oil. MS: (ES, m/z): 504 $[M+H]^+$.

Step 3. Synthesis of (1R,4S)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid and (1S,4R)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid Into a 10-mL round-bottom flask, (S)-methyl 3-(cis-4-(methoxycarbonyl)-3,3-dimethylcyclohexyl)-7-methyl-2-phenyl-8,9-dihydro-3H-imidazo[4,5-f]quinoline-6(7H)-carboxylate (21 mg, 0.042 mmol) was dissolved in tetrahydrofuran (3 mL). Water (1 mL) was added, followed by lithium hydroxide (10 mg, 0.42 mmol). The resulting solution was stirred for 8 h at 85° C. The reaction mixture was cooled and concentrated under vacuum. The crude product was purified by Prep-HPLC with the following conditions: Column, XBridge C18 OBD Prep Column, 100 Å, 5 um, 19 mm×250 mm; mobile phase, A: Water (containing 10 mmol/L FA) and B: ACN (10.0% to 40.0% ACN over 19 min); UV Detector: 254 nm. This afforded the title compounds as follows: 1.2 mg (5.8%) of (1R,4S)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid (assumed stereochemistry, first eluting isomer, RT=15.35 min) as a white solid and 4.8 mg (24%) of (1S,4R)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid (assumed stereochemistry, second eluting isomer, RT=17.15 min) as a white solid.

First eluting isomer: $^1$H-NMR (400 MHz, $CDCl_3$, ppm) δ 7.79 (d, J=9.2 Hz, 1H), 7.44-7.30 (m, 4H), 7.24-7.17 (m, 2H), 4.94-4.79 (m, 1H), 4.79-4.56 (m, 2H), 4.56-4.41 (m, 1H), 3.82 (s, 3H), 3.33-3.31 (m, 2H), 2.37-2.26 (m, 1H), 2.26-1.99 (m, 3H), 1.96-1.81 (m, 2H), 1.81-1.60 (m, 2H), 1.37-1.24 (m, 1H), 1.16 (d, J=6.4 Hz, 3H), 1.06 (s, 3H), 0.81 (s, 3H). MS: (ES, m/z): 490 [M+H]$^+$.

Second eluting isomer: $^1$H-NMR (400 MHz, $CDCl_3$, ppm) δ 7.81 (d, J=8.8 Hz, 1H), 7.40-7.29 (m, 4H), 7.25-7.19 (m, 2H), 4.91-4.75 (m, 1H), 4.68 (s, 2H), 4.57-4.39 (m, 1H), 3.82 (s, 3H), 3.30-3.00 (m, 2H), 2.36-2.25 (m, 1H), 2.25-2.13 (m, 1H), 2.13-1.98 (m, 2H), 1.94-1.78 (m, 2H), 1.78-1.52 (m, 2H), 1.45-1.33 (m, 1H), 1.15 (d, J=6.4 Hz, 3H), 1.08 (s, 3H), 0.84 (s, 3H). MS: (ES, m/z): 490 [M+H]$^+$.

Examples 50 and 51: (1R,4R)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid and (1S,4S)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid

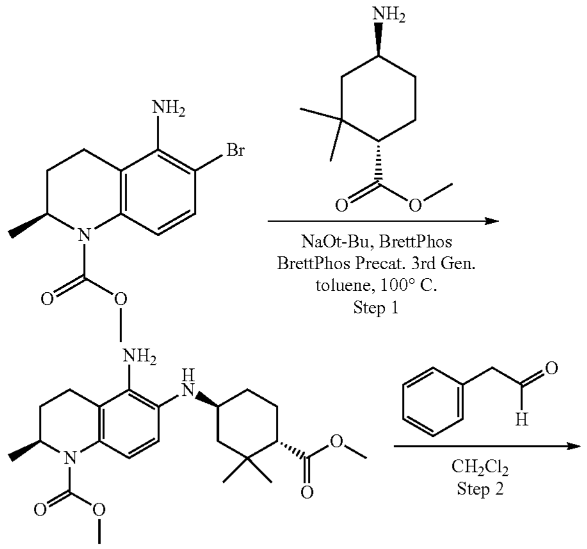

-continued

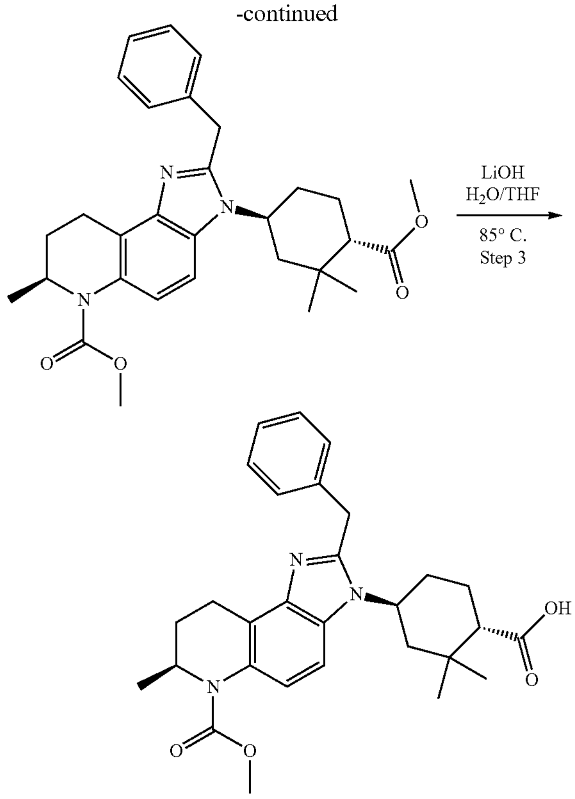

Step 1. Synthesis of methyl (2S)-5-amino-6-[[trans-4-(methoxycarbonyl)-3,3-dimethylcyclohexyl]amino]-2-methyl-1,2,3,4-tetrahydroquinoline-1-carboxylate Into a 10-mL round-bottom flask purged and maintained with an inert atmosphere of nitrogen, methyl (2S)-5-amino-6-bromo-2-methyl-1,2,3,4-tetrahydroquinoline-1-carboxylate (84 mg, 0.27 mmol, Intermediate 1) was dissolved in toluene (5 mL). Then trans-methyl 4-amino-2,2-dimethylcyclohexane-1-carboxylate (156 mg, 0.84 mmol, Intermediate 26), BrettPhos Pd G3 (51 mg, 0.06 mmol), Brettphos (67 mg, 0.13 mmol), tert-butoxide (105 mg, 1.10 mmol). The resulting solution was stirred for 1 h at 100° C. in the nitrogen atmosphere. The reaction mixture was cooled and the solids were filtered out. The filtrate was concentrated under vacuum. The residue was subjected to purification by FCC eluting with ethyl acetate/petroleum ether (1:1). This afforded the title compound (55 mg, 48%) as a green oil. MS: (ES, m/z): 404 [M+H]$^+$.

Step 2. Synthesis of (7S)-2-benzyl-3-[4-(methoxycarbonyl)-3,3-dimethylcyclohexyl]-7-methyl-3H,6H,7H,8H,9H-imidazo[4,5-f]quinoline-6-carboxylate Into a 10-mL round-bottom flask, methyl (2S)-5-amino-6-[[trans-4-(methoxycarbonyl)-3,3-dimethylcyclohexyl]amino]-2-methyl-1,2,3,4-tetrahydroquinoline-1-carboxylate (55 mg, 0.14 mmol) was dissolved in dichloromethane (5 mL). Then 2-phenylacetaldehyde (50 mg, 0.41 mmol) was added. The resulting solution was stirred for 2 h at room temperature. The reaction mixture was concentrated under vacuum. The residue was subjected to purification by FCC eluting with ethyl acetate/petroleum ether (1:1). This afforded the title compound (20 mg, 29%) as a yellow oil. MS: (ES, m/z): 504 $[M+H]^+$.

Step 3. Synthesis of (1R,4R)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid and (1S,4S)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid Into a 25-mL round-bottom flask, methyl (7S)-2-benzyl-3-[4-(methoxycarbonyl)-3,3-dimethylcyclohexyl]-7-methyl-3H,6H,7H,8H,9H-imidazo[4,5-f]quinoline-6-carboxylate (10 mg, 0.02 mmol) was dissolved in tetrahydrofuran (2 mL) then water (1 mL) was added, followed by lithium hydroxide (4.6 mg, 0.19 mmol). The resulting solution was stirred for 2 h at 85° C. The reaction mixture was cooled and concentrated under vacuum. The crude product was purified by Prep-HPLC with the following conditions: Column, XBridge C18 OBD Prep Column, 100 Å, 5 um, 19 mm×250 mm; mobile phase, A: Water (containing 10 mmol/L FA) and B: ACN (10.0% to 40.0% ACN over 19 min); UV Detector: 254 nm. This afforded the title compounds as follows: 2 mg (21%) of (1R,4R)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid (assumed stereochemistry, first eluting isomer, RT=14.7 min) as a white solid and 2 mg (21%) of (1S,4S)-4-[(7S)-2-benzyl-6-(methoxycarbonyl)-7-methyl-3H,6H,7H,8H,9H-imidazo[4,5-f]quinolin-3-yl]-2,2-dimethylcyclohexane-1-carboxylic acid (assumed stereochemistry, second eluting isomer, RT=15.6 min) as a white solid.

First eluting isomer: $^1H$ NMR (400 MHz, $CDCl_3$, ppm) δ 7.65 (d, J=9.2 Hz, 1H), 7.43-7.33 (m, 1H), 7.31-7.27 (m, 1H), 7.24-7.15 (m, 4H), 4.86-4.75 (m, 1H), 4.52 (d, J=16.4 Hz, 1H), 4.39-4.21 (m, 2H), 3.78 (s, 3H), 3.32-3.18 (m, 1H), 3.11-3.00 (m, 1H), 2.80-2.67 (m, 1H), 2.67-2.52 (m, 1H), 2.35-2.29 (m, 1H), 2.29-2.19 (m, 1H), 1.93-1.83 (m, 1H), 1.83-1.68 (m, 2H), 1.44-1.35 (m, 1H), 1.16 (d, J=6.8 Hz, 3H), 0.99-0.92 (m, 4H), 0.75 (s, 3H). MS: (ES, m/z): 490 $[M+H]^+$.

Second eluting isomer: $^1H$ NMR (400 MHz, $CDCl_3$, ppm) δ 7.64 (d, J=8.0 Hz, 1H), 7.43 (s, 1H), 7.32-7.27 (m, 1H), 7.24-7.15 (m, 4H), 4.85-4.73 (m, 1H), 4.51-4.32 (m, 2H), 4.31-4.22 (m, 1H), 3.79 (s, 3H), 3.33-3.20 (m, 1H), 3.15-3.00 (m, 1H), 2.78-2.65 (m, 1H), 2.55-2.38 (m, 1H), 2.33-2.17 (m, 2H), 1.83-1.60 (m, 3H), 1.16 (d, J=6.8 Hz, 4H), 1.01-0.95 (m, 4H), 0.80 (s, 3H). MS: (ES, m/z): 490 $[M+H]^+$.

Examples 52 and 53: trans-6-((S)-2-benzyl-6-(methoxycarbonyl)-7-methyl-6,7,8,9-tetrahydro-3H-imidazo[4,5-f]quinolin-3-yl)spiro[3.3]heptane-2-carboxylic acid and cis-6-((S)-2-benzyl-6-(methoxycarbonyl)-7-methyl-6,7,8,9-tetrahydro-3H-imidazo[4,5-f]quinolin-3-yl)spiro[3.3]heptane-2-carboxylic acid

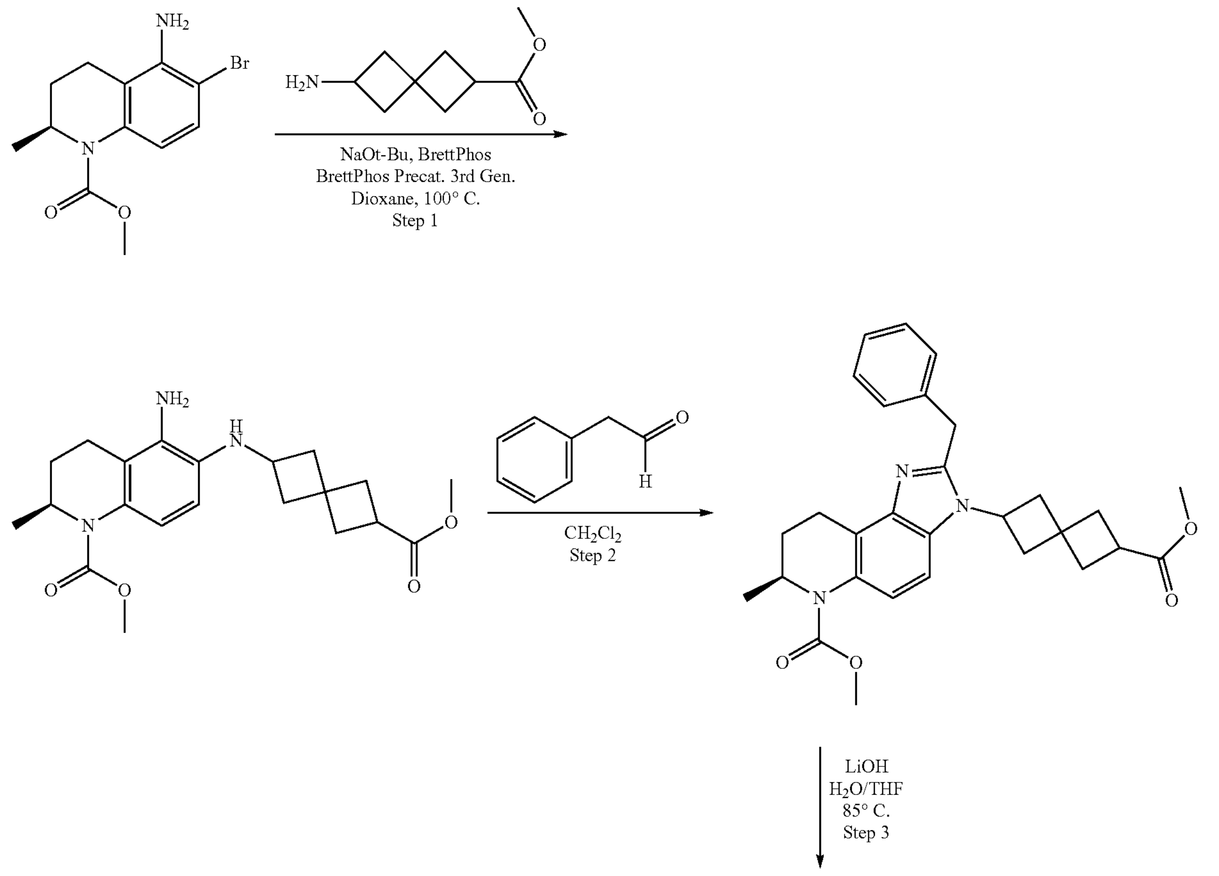

-continued

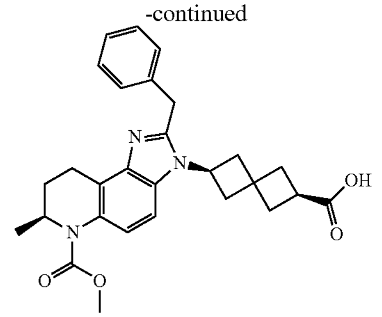

+

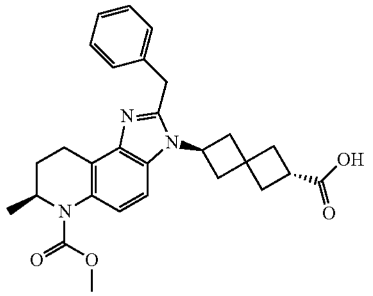

Step 1. methyl (2S)-5-amino-6-[[6-(methoxycarbonyl)spiro[3.3]heptan-2-yl]amino]-2-methyl-1,2,3,4-tetrahydroquinoline-1-carboxylate Into a 10-mL round-bottom flask purged and maintained with an inert atmosphere of nitrogen, methyl 6-aminospiro[3.3]heptane-2-carboxylate hydrochloride (138 mg, 0.67 mmol) was dissolved in dioxane (4 mL). Then methyl (2S)-5-amino-6-bromo-2-methyl-1,2,3,4-tetrahydroquinoline-1-carboxylate (100 mg, 0.33 mmol, Intermediate 1), Brettphos (72 mg, 0.13 mmol), $3^{rd}$ Generation BrettPhos precatalyst (61 mg, 0.07 mmol) and sodium tert-butoxide (97 mg, 1.01 mmol) were added. The resulting solution was stirred for 1 h at 100° C. under nitrogen atmosphere. The reaction mixture was cooled and the solids were filtered out. The resulting mixture was concentrated under vacuum. The residue was subjected to purification by FCC eluting with ethyl acetate/petroleum ether (3:1). This afforded the title compound (76.2 mg, 59%) as an orange oil. MS: (ES, m/z): 388 $[M+H]^+$.

Step 2. Synthesis of (7S)-2-benzyl-3-[6-(methoxycarbonyl)spiro[3.3]heptan-2-yl]-7-methyl-3H,6H,7H,8H,9H-imidazo[4,5-f]quinoline-6-carboxylate Into a 25-mL round-bottom flask, methyl (2S)-5-amino-6-[[6-(methoxycarbonyl)spiro[3.3]heptan-2-yl]amino]-2-methyl-1,2,3,4-tetrahydroquinoline-1-carboxylate (76.2 mg, 0.20 mmol) was dissolved in dichloromethane (5 mL). Then 2-phenylacetaldehyde (70.9 mg, 0.59 mmol) was added. The resulting solution was stirred for 2 h at room temperature. The resulting mixture was concentrated under vacuum. The residue was subjected to purification by FCC eluting with ethyl acetate/petroleum ether (2:1). This afforded the title compound (43.6 mg, 45%) as an orange solid. MS: (ES, m/z): 488 $[M+H]^+$.

Step 3. Synthesis of trans-6-((S)-2-benzyl-6-(methoxycarbonyl)-7-methyl-6,7,8,9-tetrahydro-3H-imidazo[4,5-f]quinolin-3-yl)spiro[3.3]heptane-2-carboxylic acid and cis-6-((S)-2-benzyl-6-(methoxycarbonyl)-7-methyl-6,7,8,9-tetrahydro-3H-imidazo[4,5-f]quinolin-3-yl)spiro[3.3]heptane-2-carboxylic acid Into a 10-mL round-bottom flask, methyl (7S)-2-benzyl-3-[6-(methoxycarbonyl)spiro[3.3]heptan-2-yl]-7-methyl-3H,6H,7H,8H,9H-imidazo[4,5-f]quinoline-6-carboxylate (43.6 mg, 0.09 mmol) was dissolved in tetrahydrofuran (1 mL). Then water (1 mL) was added, followed by lithium hydroxide (10.7 mg, 0.45 mmol). The resulting solution was stirred for 1 h at 85° C. The crude product was purified by Prep-HPLC with the following conditions: Column, XBridge C18 OBD Prep Column, 100 Å, 5 μm, 19 mm×250 mm; mobile phase, A: Water (0.1% FA) and B: ACN (10.0% to 25.0% ACN over 24 min); UV Detector: 254 nm. This offered the title compounds as follows: 5.4 mg (13%) of cis-6-((S)-2-benzyl-6-(methoxycarbonyl)-7-methyl-6,7,8,9-tetrahydro-3H-imidazo[4,5-f]quinolin-3-yl)spiro[3.3]heptane-2-carboxylic acid (assumed stereochemistry, first eluting isomer, RT=21.5 min) as a white solid and 4.5 mg (11%) of trans-6-((S)-2-benzyl-6-(methoxycarbonyl)-7-methyl-6,7,8,9-tetrahydro-3H-imidazo[4,5-f]quinolin-3-yl)spiro[3.3]heptane-2-carboxylic acid (assumed stereochemistry, second eluting isomer, RT=23.0 min) as a white solid.

First eluting isomer: $^1$H-NMR (300 MHz, $CD_3OD$, ppm): δ 7.42-7.37 (m, 2H), 7.38-7.22 (m, 3H), 7.19-7.12 (m, 2H), 4.86-4.72 (m, 2H), 4.39 (s, 2H), 3.80 (s, 3H), 3.21-3.10 (m, 1H), 3.10-2.75 (m, 4H), 2.45-2.20 (m, 7H), 1.83-1.70 (m, 1H), 1.16 (d, J=6.6 Hz, 3H). MS: (ES, m/z): 474 $[M+H]^+$.

Second eluting isomer: $^1$H-NMR (300 MHz, $CD_3OD$, ppm): δ 7.44-7.39 (m, 2H), 7.38-7.22 (m, 3H), 7.19-7.12 (m, 2H), 4.78-4.72 (m, 2H), 4.39 (s, 2H), 3.80 (s, 3H), 3.21-3.12 (m, 1H), 3.09-2.88 (m, 2H), 2.83-2.76 (m, 2H), 2.44-2.20 (m, 7H), 1.77-1.70 (m, 1H), 1.17 (d, J=6.7 Hz, 3H). MS: (ES, m/z): 474 $[M+H]^+$.

Examples 54 and 55: cis-3-((S)-2-benzyl-6-(methoxycarbonyl)-7-methyl-6,7,8,9-tetrahydro-3H-imidazo[4,5-f]quinolin-3-yl)cyclopentane-1-carboxylic acid and trans-3-((S)-2-benzyl-6-(methoxycarbonyl)-7-methyl-6,7,8,9-tetrahydro-3H-imidazo[4,5-f]quinolin-3-yl)cyclopentane-1-carboxylic acid

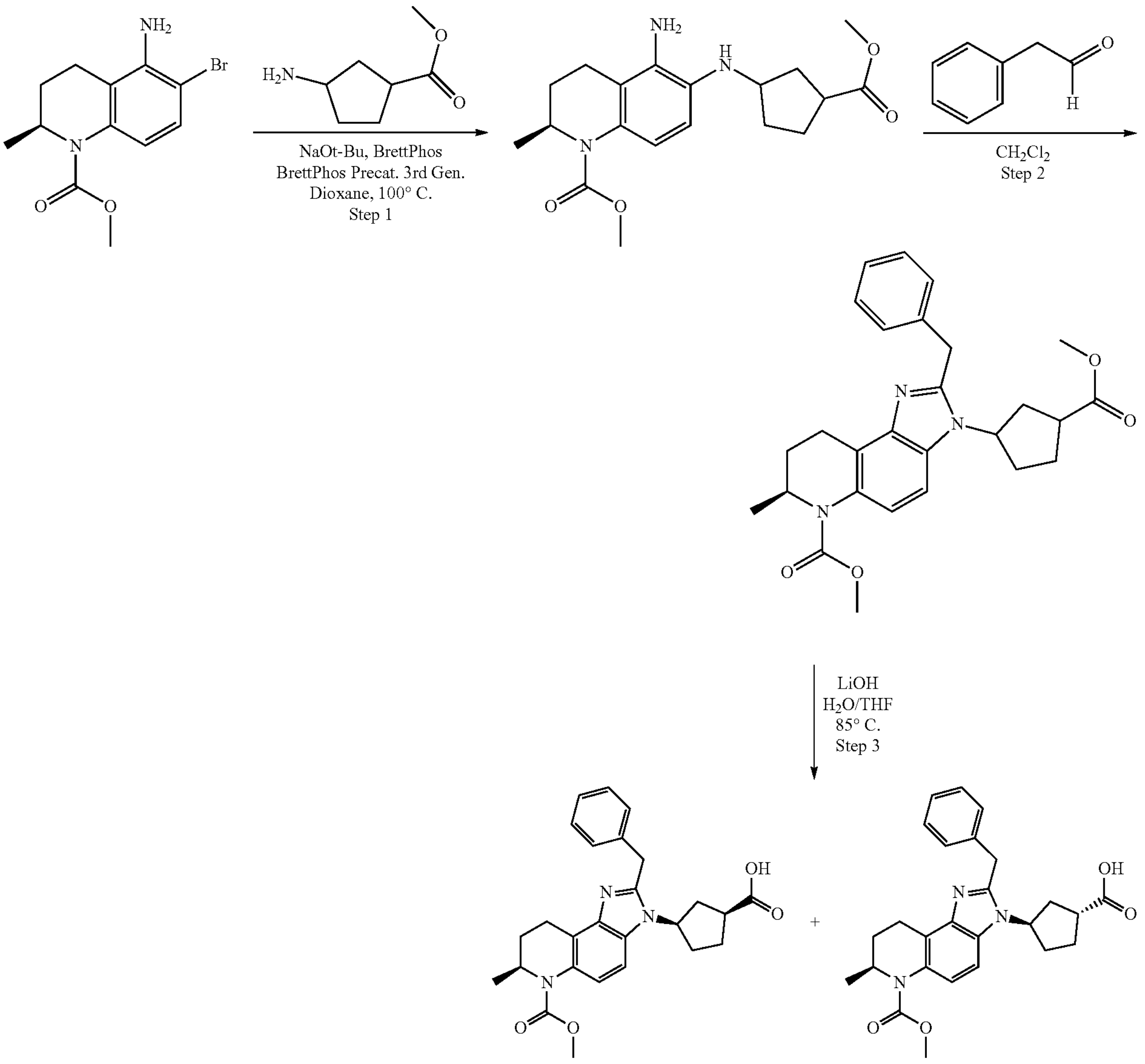

Step 1. Synthesis of methyl (2S)-5-amino-6-[[3-(methoxycarbonyl)cyclopentyl]amino]-2-methyl-1,2,3,4-tetrahydroquinoline-1-carboxylate Into a 8-mL round-bottom flask purged and maintained with an inert atmosphere of nitrogen, methyl (2S)-5-amino-6-bromo-2-methyl-1,2,3,4-tetrahydroquinoline-1-carboxylate (300 mg, 1.00 mmol, Intermediate 1) was dissolved in dioxane (5 mL). Then methyl 3-aminocyclopentane-1-carboxylate hydrochloride (540 mg, 3.01 mmol), 3$^{rd}$ Generation Brettphos precatalyst (273 mg, 0.30 mmol), BrettPhos (323 mg, 0.60 mmol) and sodium tert-butoxide (385 mg, 4.01 mmol) were added. The resulting solution was stirred for 3 h at 100° C. under nitrogen atmosphere. The reaction mixture was cooled to room temperature and concentrated under vacuum. The residue was subjected to purification by FCC eluting with ethyl acetate/petroleum ether (3:1). This afforded the title compound (130 mg, 36%) as a yellow oil. MS: (ES, m/z): 362 $[M+H]^+$.

Step 2. Synthesis of methyl (7S)-2-benzyl-3-[3-(methoxycarbonyl)cyclopentyl]-7-methyl-3H,6H,7H,8H,9H-imidazo[4,5-f]quinoline-6-carboxylate Into a 25-mL round-bottom flask, methyl (2S)-5-amino-6-[[3-(methoxycarbonyl)cyclopentyl]amino]-2-methyl-1,2, 3,4-tetrahydroquinoline-1-carboxylate (130 mg, 0.36 mmol) was dissolved in dichloromethane (5 mL). Then 2-phenylacetaldehyde (65 mg, 0.54 mmol) was added. The resulting solution was stirred overnight at room temperature. The resulting mixture was concentrated under vacuum. The residue was subjected to purification by FCC eluting with ethyl acetate/petroleum ether (2:1). This afforded the title compound (120 mg, 72%) as a yellow oil. MS: (ES, m/z): 462 $[M+H]^+$.

Step 3. Synthesis of cis-3-((S)-2-benzyl-6-(methoxycarbonyl)-7-methyl-6,7,8,9-tetrahydro-3H-imidazo[4,5-f]quinolin-3-yl)cyclopentane-1-carboxylic acid and trans-3-((S)-2-benzyl-6-(methoxycarbonyl)-7-methyl-6,7,8,9-tetrahydro-3H-imidazo[4,5-f]quinolin-3-yl)cyclopentane-1-carboxylic acid Into a 25-mL round-bottom flask, was placed methyl (7S)-2-benzyl-3-[3-(methoxycarbonyl)cyclopentyl]-7-methyl-3H,6H,7H,8H,9H-imidazo[4,5-f]quinoline-6-carboxylate (142 mg, 0.31 mmol) dissolved in tetrahydrofuran (2 mL). Then water (2 mL) was added, followed by lithium hydroxide (37 mg, 1.55 mmol). The resulting solution was stirred for 2 h at 85° C. The reaction mixture was cooled and the resulting mixture was concentrated under vacuum. The crude product was purified by Prep-HPLC with the following conditions: Column, XBridge C18 OBD Prep Column, 100 mm, 5 μm, 19 mm×250 mm; mobile phase, A: Water (10 mmol/L $NH_4HCO_3$) and B: ACN (15.0% to 35.0% ACN over 7 min); UV Detector: 254 nm. This offered the title compounds as follows: 23.6 mg (17%) of cis-3-((S)-2-benzyl-6-(methoxycarbonyl)-7-methyl-6,7,8,9-tetrahydro-3H-imidazo[4,5-f]quinolin-3-yl)cyclopentane-1-carboxylic acid (assumed stereochemistry, first eluting isomer, RT=5.8 min) as a white solid and 29.2 mg (21%) of trans-3-((S)-2-benzyl-6-(methoxycarbonyl)-7-methyl-6,7,8,9-tetrahydro-3H-imidazo[4,5-f]quinolin-3-yl)cyclopentane-1-carboxylic acid (assumed stereochemistry, second eluting isomer, RT=6.7 min) as a white solid.

First eluting isomer: $^1$H-NMR (300 MHz, $CD_3OD$, ppm): δ 7.56-7.17 (m, 7H), 4.89-4.73 (m, 2H), 4.44 (s, 2H), 3.79 (s, 3H), 3.30-3.18 (m, 1H), 3.01-2.90 (m, 1H), 2.89-2.78 (m, 1H), 2.52-2.07 (m, 4H), 2.02-1.70 (m, 4H), 1.17 (d, J=6.7 Hz, 3H). MS: (ES, m/z): 448 $[M+H]^+$.

Second eluting isomer: $^1$H-NMR (300 MHz, $CD_3OD$, ppm): δ 7.56-7.17 (m, 7H), 4.92-4.72 (m, 2H), 4.43 (s, 2H), 3.79 (s, 3H), 3.27-3.19 (m, 1H), 3.03-2.93 (m, 1H), 2.87-2.78 (m, 1H), 2.59-2.41 (m, 1H), 2.37-2.12 (m, 3H), 2.02-1.90 (m, 2H), 1.82-1.68 (m, 2H), 1.17 (d, J=6.7 Hz, 3H). MS: (ES, m/z): 448 $[M+H]^+$.

Examples 56 and 57: trans-4-[(7S)-6-(methoxycarbonyl)-7-methyl-2-[(1R)-1-phenylethyl]-3H,6H,7H,8H,9H-imidazo[4,5-f]quinolin-3-yl]cyclohexane-1-carboxylic acid and trans-4-[(7S)-6-(methoxycarbonyl)-7-methyl-2-[(1S)-1-phenylethyl]-3H,6H,7H,8H,9H-imidazo[4,5-f]quinolin-3-yl]cyclohexane-1-carboxylic acid

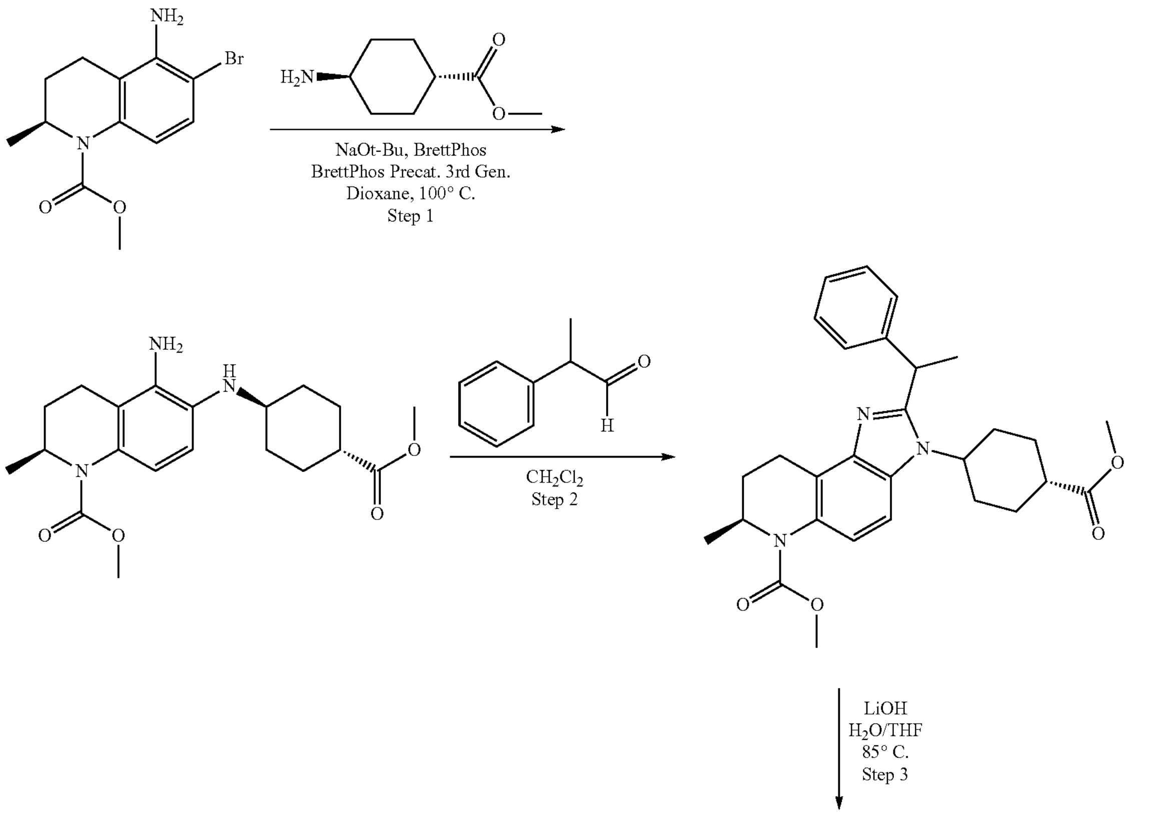

-continued

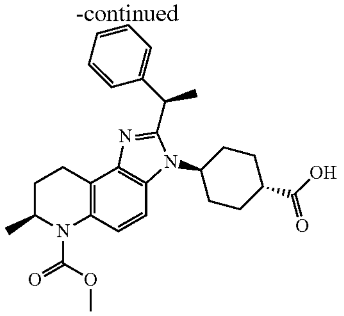

+

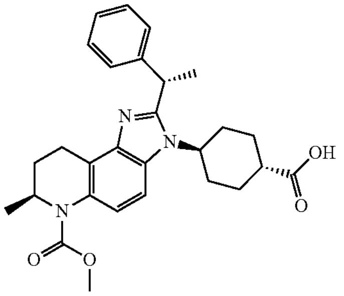

Step 1. Synthesis of methyl (2S)-5-amino-2-methyl-6-[[trans-4-(methoxycarbonyl)cyclohexyl]amino]-1,2,3,4-tetrahydroquinoline-1-carboxylate Into a 25-mL round-bottom flask purged and maintained with an inert atmosphere of nitrogen, trans-methyl-4-aminocyclohexane-1-carboxylate hydrochloride (259 mg, 1.34 mmol) were dissolved in dioxane (4 mL). Then methyl (2S)-5-amino-6-bromo-2-methyl-1,2,3,4-tetrahydroquinoline-1-carboxylate (200 mg, 0.67 mmol, Intermediate 1), Brettphos (144.2 mg, 0.27 mmol), 3$^{rd}$ Generation BrettPhos precatalyst (121.6 mg, 0.13 mmol) and sodium tert-butoxide (193.4 mg, 2.01 mmol) was added successively. The resulting solution was stirred for 1 h at 100° C. under nitrogen atmosphere. The reaction mixture was cooled and the resulting solids were filtered out. The filtrate was concentrated under vacuum. The residue was subjected to purification by FCC eluting with ethyl acetate/petroleum ether (2:1). This afforded the title compound (58.8 mg, 23%) as a green oil. MS: (ES, m/z): 376 $[M+H]^+$.

Step 2. Synthesis of methyl (7S)-7-methyl-2-(1-phenylethyl)-3-[trans-4-(methoxycarbonyl)cyclohexyl]-3H,6H,7H,8H,9H-imidazo[4,5-f]quinoline-6-carboxylate Into a 25-mL round-bottom flask, methyl (2S)-5-amino-2-methyl-6-[[trans-4-(methoxycarbonyl)cyclohexyl]amino]-1,2,3,4-tetrahydroquinoline-1-carboxylate (58.8 mg, 0.16 mmol) was dissolved in dichloromethane (5 mL). Then 2-phenylpropanal (126 mg, 0.94 mmol) was added. The resulting solution was stirred for 3 h at room temperature. The resulting mixture was concentrated under vacuum. The residue was subjected to purification by FCC eluting with ethyl acetate/petroleum ether (2:1). This afforded the title compound (28.1 mg, 37%) as a yellow solid. MS: (ES, m/z): 490 $[M+H]^+$.

Step 3. Synthesis of trans-4-[(7S)-6-(methoxycarbonyl)-7-methyl-2-[(1R)-1-phenylethyl]-3H,6H,7H,8H,9H-imidazo[4,5-f]quinolin-3-yl]cyclohexane-1-carboxylic acid and trans-4-[(7S)-6-(methoxycarbonyl)-7-methyl-2-[(1 S)-1-phenylethyl]-3H,6H,7H,8H,9H-imidazo[4,5-f]quinolin-3-yl]cyclohexane-1-carboxylic acid Into a 25-mL round-bottom flask, methyl (7S)-7-methyl-2-(1-phenylethyl)-3-[trans-4-(methoxycarbonyl)cyclohexyl]-3H,6H,7H,8H,9H-imidazo[4,5-f]quinoline-6-carboxylate (25 mg, 0.05 mmol) was dissolved in tetrahydrofuran (3 mL). Then water (3 mL) was added, followed by lithium hydroxide (6.1 mg, 0.25 mmol). The resulting solution was stirred for 2 h at 85° C. The resulting mixture was cooled to room temperature and concentrated under vacuum. The crude product was purified by Prep-HPLC with the following conditions: Column, XBridge Prep C18 OBD Column, 19×150 mm, 5 μm; mobile phase, A: Water (containing 10 mmol/$LNH_4HCO_3$) and B: ACN (18.0% to 38.0% ACN over 8 min); UV Detector: 254 nm. Then the product was purified by Chiral-Prep-HPLC with the following conditions: Column, CHIRAL ART Cellulose-SB, 2×25 cm, 5 μm; mobile phase, hexanes (1% TFA) and ethanol (hold 10.0% ethanol in 38 min); Detector, UV 254 nm. This afforded the title compounds as follows: 1.4 mg (6%) of trans-4-[(7S)-6-(methoxycarbonyl)-7-methyl-2-[(1S)-1-phenylethyl]-3H,6H,7H,8H,9H-imidazo[4,5-f]quinolin-3-yl]cyclohexane-1-carboxylic acid (assumed stereochemistry, first eluting isomer, RT=25.83 min) as a white solid and 2.9 mg (12%) of trans-4-[(7S)-6-(methoxycarbonyl)-7-methyl-2-[(1R)-1-phenylethyl]-3H,6H,7H,8H,9H-imidazo[4,5-f]quinolin-3-yl]cyclohexane-1-carboxylic acid (assumed stereochemistry, second eluting isomer, RT=32.76 min) as a white solid First eluting isomer: $^1$H-NMR ($CD_3OD$, 300 MHz) δ (ppm): 7.36-7.26 (m, 3H), 7.26-7.14 (m, 4H), 4.82-4.75 (m, 1H), 4.39-4.37 (m, 1H), 4.07-4.03 (m, 1H), 3.78 (s, 3H), 3.34-3.26 (m, 1H), 3.07-2.02 (m, 1H), 2.40-2.15 (m, 5H), 1.98-1.95 (m, 3H), 1.85 (d, J=6.9 Hz, 3H), 1.77-1.69 (m, 2H), 1.55-1.42 (m, 1H), 1.17 (d, J=6.6 Hz, 3H). MS: (ES, m/z): 476 $[M+H]^+$.

Second eluting isomer: $^1$H-NMR ($CD_3OD$, 300 MHz) δ (ppm): 7.37-7.29 (m, 1H), 7.28-7.26 (m, 2H), 7.24-7.17 (m, 4H), 4.81-4.75 (m, 1H), 4.44-4.41 (m, 1H), 4.06-4.02 (m, 1H), 3.78 (s, 3H), 3.56-3.27 (m, 1H), 3.06-2.99 (m, 1H), 2.40-2.06 (m, 5H), 1.99-1.96 (m, 2H), 1.84 (d, J=6.9 Hz, 3H), 1.79-1.70 (m, 3H), 1.49-1.42 (m, 1H), 1.20 (d, J=6.6 Hz, 3H). MS: (ES, m/z): 476 $[M+H]^+$.

Examples 58 and 59: methyl (S)-7-methyl-2-((R)-1-phenylethyl)-3-(piperidin-4-yl)-3,7,8,9-tetrahydro-6H-imidazo[4,5-f]quinoline-6-carboxylate and methyl (S)-7-methyl-2-((S)-1-phenylethyl)-3-(piperidin-4-yl)-3,7,8,9-tetrahydro-6H-imidazo[4,5-f]quinoline-6-carboxylate

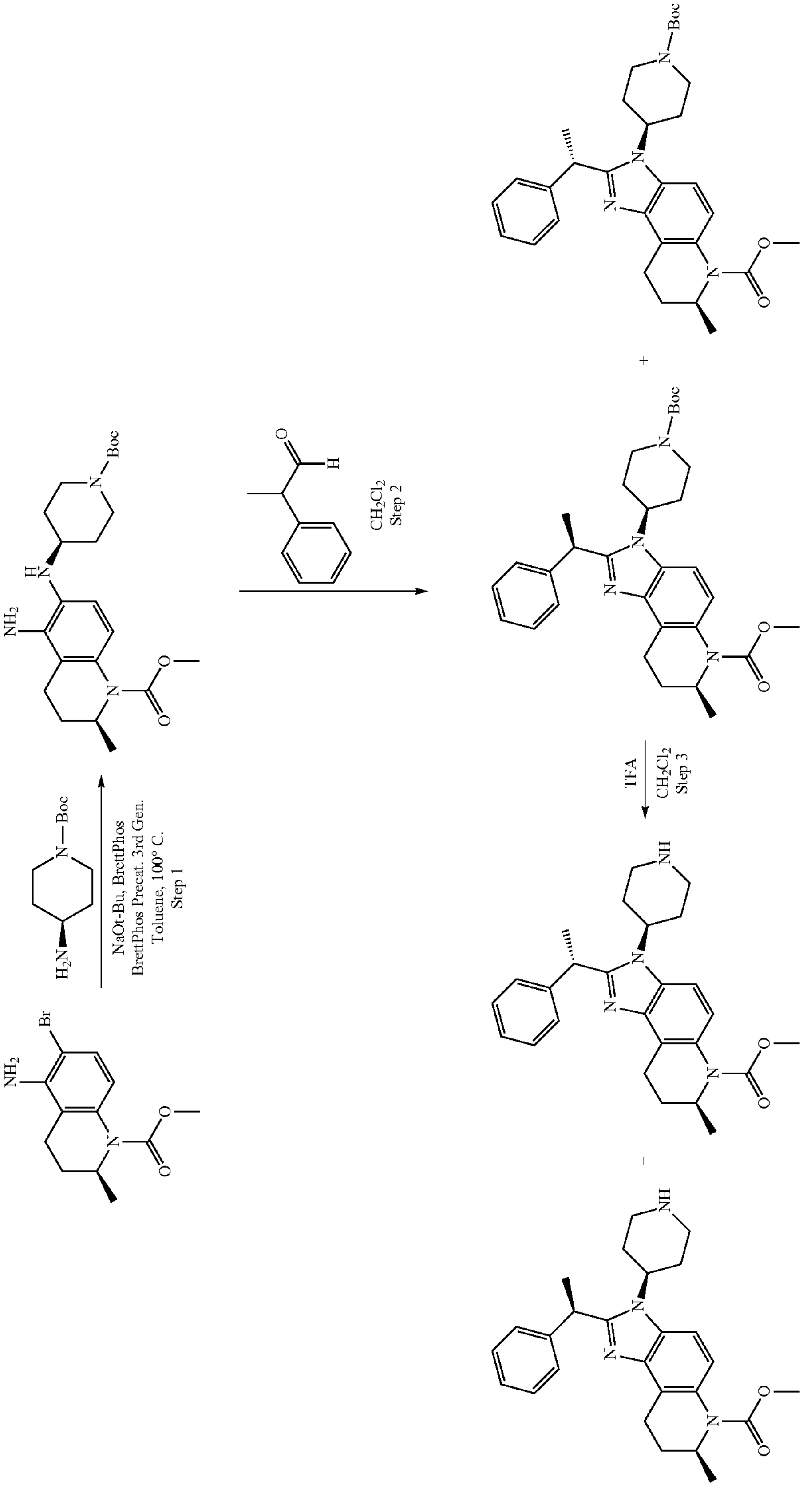
NaOt-Bu, BrettPhos
BrettPhos Precat. 3rd Gen.
Toluene, 100° C.
Step 1
$CH_2Cl_2$
Step 2
TFA
$CH_2Cl_2$
Step 3

Step 1. Synthesis of methyl (2S)-5-amino-6-([1-[(tert-butoxy)carbonyl]piperidin-4-yl]amino)-2-methyl-1,2,3,4-tetrahydroquinoline-1-carboxylate Into a 10-mL round-bottom flask purged and maintained with an inert atmosphere of nitrogen, tert-butyl 4-aminopiperidine-1-carboxylate (402.7 mg, 2.01 mmol) was dissolved in toluene (4 mL). Methyl (2S)-5-amino-6-bromo-2-methyl-1,2,3,4-tetrahydroquinoline-1-carboxylate (300 mg, 1.00 mmol, Intermediate 1), BrettPhos (216.2 mg, 0.40 mmol), 3rd Generation BrettPhos precatalyst (182.4 mg, 0.20 mmol) and sodium tert-butoxide (290 mg, 3.02 mmol) were added. The resulting solution was stirred for 1 h at 100° C. under nitrogen atmosphere. The reaction mixture was cooled and the solids were filtered out. The resulting mixture was concentrated under vacuum. The residue was subjected to purification by FCC eluting with ethyl acetate/petroleum ether (2:1). This afforded the title compound (197.1 mg, 47%) as a dark green solid. MS: (ES, m/z): 419 $[M+H]^+$.

Step 2. Synthesis of tert-butyl 4-[(7S)-6-(methoxycarbonyl)-7-methyl-2-[(1R)-1-phenylethyl]-3H,6H,7H,8H,9H-imidazo[4,5-f]quinolin-3-yl]piperidine-1-carboxylate and tert-butyl 4-[(7S)-6-(methoxycarbonyl)-7-methyl-2-[(1S)-1-phenylethyl]-3H,6H,7H,8H,9H-imidazo[4,5-f]quinolin-3-yl]piperidine-1-carboxylate Into a 25-mL round-bottom flask, methyl (2S)-5-amino-6-([1-[(tert-butoxy)carbonyl]piperidin-4-yl]amino)-2-methyl-1,2,3,4-tetrahydroquinoline-1-carboxylate (197.1 mg, 0.47 mmol) was dissolved in dichloromethane (5 mL). Then 2-phenylpropanal (379.2 mg, 2.83 mmol) was added. The resulting solution was stirred for 3 h at room temperature. The resulting mixture was concentrated under vacuum. The residue was subjected to purification by FCC eluting with ethyl acetate/petroleum ether (1:1). This afforded the title compounds as follows: 18.1 mg (7%) of tert-butyl 4-[(7S)-6-(methoxycarbonyl)-7-methyl-2-[(1R)-1-phenylethyl]-3H,6H,7H,8H,9H-imidazo[4,5-f]quinolin-3-yl]piperidine-1-carboxylate as a yellow solid and 15.6 mg (6%) of tert-butyl 4-[(7S)-6-(methoxycarbonyl)-7-methyl-2-[(1S)-1-phenylethyl]-3H,6H,7H,8H,9H-imidazo[4,5-f]quinolin-3-yl]piperidine-1-carboxylate as a yellow solid. MS: (ES, m/z): 533 $[M+H]^+$.

Step 3. Synthesis of methyl (S)-7-methyl-2-((R)-1-phenylethyl)-3-(piperidin-4-yl)-3,7,8,9-tetrahydro-6H-imidazo[4,5-f]quinoline-6-carboxylate and methyl (S)-7-methyl-2-((S)-1-phenylethyl)-3-(piperidin-4-yl)-3,7,8,9-tetrahydro-6H-imidazo[4,5-f]quinoline-6-carboxylate Into a 25-mL round-bottom flask, tert-butyl 4-[(7S)-6-(methoxycarbonyl)-7-methyl-2-[(1R)-1-phenylethyl]-3H,6H,7H,8H,9H-imidazo[4,5-f]quinolin-3-yl]piperidine-1-carboxylate (18.1 mg, 0.03 mmol) was dissolved dichloromethane (5 mL). Then trifluoroacetic acid (1 mL) was added dropwise with stirring. The resulting solution was stirred for 1.5 h at room temperature. The resulting mixture was concentrated under vacuum. The crude product was purified by Prep-HPLC with the following conditions: Column, XBridge C18 OBD Prep Column, 100 Å, 19 mm×250 mm; mobile phase, A: Water (10 mmol/L $NH_4HCO_3$) and B: ACN (25.0% to 50.0% ACN over 7 min); UV Detector: 254 nm. This afforded the title compound (7.7 mg, 52%) as a white solid. $^1$HNMR: (300 MHz, $CD_3OD$, ppm): δ 7.51 (d, J=9.0 Hz, 1H), 7.41-7.19 (m, 6H), 4.78-4.69 (m, 1H), 4.64-4.58 (m, 1H), 4.38-4.26 (m, 1H), 3.79 (s, 3H), 3.40-3.35 (m, 1H), 3.17-3.12 (m, 1H), 2.98-2.88 (m, 2H), 2.68-2.58 (m, 1H), 2.48-2.20 (m, 3H), 2.19-2.04 (m, 1H), 1.80 (d, J=7.3 Hz, 3H), 1.78-1.68 (m, 2H), 1.19 (d, J=6.6 Hz, 3H), 0.82-0.74 (m, 1H). MS: (ES, m/z): 433 $[M+H]^+$.

Into a 25-mL round-bottom flask, tert-butyl 4-[(7S)-6-(methoxycarbonyl)-7-methyl-2-[(1S)-1-phenylethyl]-3H,6H,7H,8H,9H-imidazo[4,5-f]quinolin-3-yl]piperidine-1-carboxylate (15.6 mg, 0.03 mmol) was dissolved dichloromethane (5 mL). Then trifluoroacetic acid (1 mL) was added dropwise with stirring. The resulting solution was stirred for 2 h at room temperature. The resulting mixture was concentrated under vacuum. The crude product was purified by Prep-HPLC with the following conditions: Column, XBridge C18 OBD Prep Column, 100 Å, 19 mm×250 mm; mobile phase, A: Water (10 mmol/L $NH_4HCO_3$) and B: ACN (25.0% to 50.0% ACN over 7 min); UV Detector: 254 nm. This afforded the title compounds (7.8 mg, 62%) as a white solid. $^1$HNMR: (300 MHz, $CD_3OD$, ppm): δ 7.51 (d, J=9.0 Hz, 1H), 7.41-7.19 (m, 6H), 4.78-4.72 (m, 1H), 4.64-4.58 (m, 1H), 4.38-4.26 (m, 1H), 3.79 (s, 3H), 3.40-3.35 (m, 1H), 3.17-3.12 (m, 1H), 2.98-2.88 (m, 2H), 2.68-2.58 (m, 1H), 2.48-2.20 (m, 3H), 2.19-2.04 (m, 1H), 1.80 (d, J=7.3 Hz, 3H), 1.78-1.68 (m, 2H), 1.19 (d, J=6.6 Hz, 3H), 0.82-0.74 (m, 1H). MS: (ES, m/z): 433 $[M+H]^+$.

Examples 60 and 61: cis-4-((S)-6-(methoxycarbonyl)-7-methyl-2-((R)-1-phenylpropan-2-yl)-6,7,8,9-tetrahydro-3H-imidazo[4,5-f]quinolin-3-yl)cyclohexane-1-carboxylic acid and trans-4-((S)-6-(methoxycarbonyl)-7-methyl-2-((S)-1-phenylpropan-2-yl)-6,7,8,9-tetrahydro-3H-imidazo[4,5-f]quinolin-3-yl)cyclohexane-1-carboxylic acid

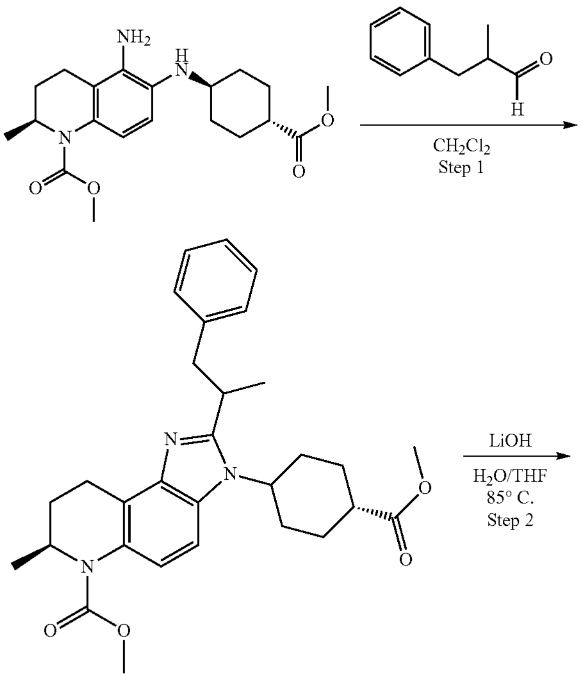

-continued

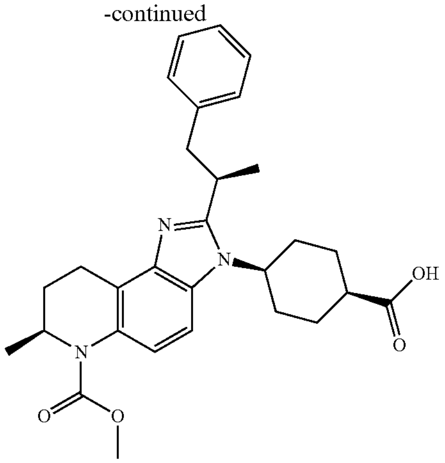

+

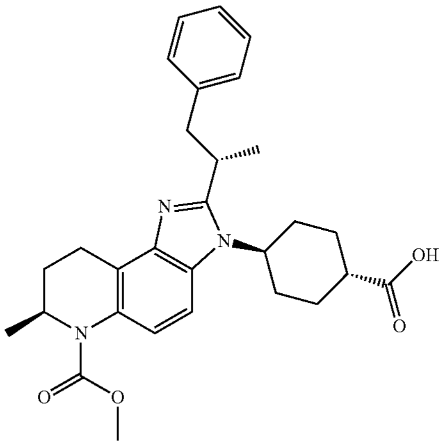

Step 1. Synthesis of methyl (7S)-7-methyl-2-(1-phenylpropan-2-yl)-3-[trans-4-(methoxycarbonyl)cyclohexyl]-3H,6H,7H,8H,9H-imidazo[4,5-f]quinoline-6-carboxylate Into a 25-mL round-bottom flask, methyl (2S)-5-amino-2-methyl-6-[[trans-4-(methoxycarbonyl)cyclohexyl]amino]-1,2,3,4-tetrahydroquinoline-1-carboxylate (150 mg, 0.40 mmol) was dissolved in dichloromethane (5 mL). Then 2-methyl-3-phenylpropanal (178 mg, 1.20 mmol, Intermediate 27) was added. The resulting solution was stirred for 3 h at room temperature. The resulting mixture was concentrated under vacuum. The residue was subjected to purification by FCC eluting with ethyl acetate/petroleum ether (1:2). This afforded the title compound (150 mg, 72%) as a yellow oil. MS: (ES, m/z): 504 $[M+H]^+$.

Step 2. Synthesis of cis-4-((S)-6-(methoxycarbonyl)-7-methyl-2-((R)-1-phenylpropan-2-yl)-6,7,8,9-tetrahydro-3H-imidazo[4,5-f]quinolin-3-yl)cyclohexane-1-carboxylic acid and trans-4-((S)-6-(methoxycarbonyl)-7-methyl-2-((S)-1-phenylpropan-2-yl)-6,7,8,9-tetrahydro-3H-imidazo[4,5-f]quinolin-3-yl)cyclohexane-1-carboxylic acid Into a 50-mL round-bottom flask, methyl (7S)-7-methyl-2-(1-phenylpropan-2-yl)-3-[trans-4-(methoxycarbonyl)cyclohexyl]-3H,6H,7H,8H,9H-imidazo[4,5-f]quinoline-6-carboxylate (150 mg, 0.30 mmol) was dissolved in tetrahydrofuran (5 mL). Water (5 mL) was added, followed by lithium hydroxide (36 mg, 1.50 mmol). The resulting solution was stirred for 1 h at 85° C. The resulting mixture was cooled and concentrated under vacuum. The crude product was purified by Prep-HPLC with the following conditions: Column, XBridge Shield RP18 OBD Column, 5 μm, 19×150 mm; mobile phase, A: Water (containing 10 mmol/L $NH_4HCO_3$) and B: ACN (10.0% to 67.0% ACN over 5 min); UV Detector: 254 nm. The crude product was purified by Chiral-Prep-HPLC with the following conditions: Column, CHIRALPAK IE, 2×25 cm, 5 μm; mobile phase, A: hexanes (0.1% FA) and B: ethanol (hold 35.0% ethanol in 10 min); UV Detector: 254 nm. This afforded the title compounds as follows: 42.1 mg (28%) of trans-4-[(7S)-6-(methoxycarbonyl)-7-methyl-2-[(2R)-1-phenylpropan-2-yl]-3H,6H,7H,8H,9H-imidazo[4,5-f]quinolin-3-yl]cyclohexane-1-carboxylic acid (assumed stereochemistry, first eluting isomer) as a white solid and 23.1 mg (15%) of trans-4-[(7S)-6-(methoxycarbonyl)-7-methyl-2-[(2S)-1-phenylpropan-2-yl]-3H,6H,7H,8H,9H-imidazo[4,5-f]quinolin-3-yl]cyclohexane-1-carboxylic acid (assumed stereochemistry, second eluting isomer) as a white solid.

First eluting isomer: $^1$H-NMR ($CD_3OD$, 300 MHz) δ (ppm): 7.37 (d, J=9.0 Hz, 1H), 7.29 (d, J=8.9 Hz, 1H), 7.22-6.98 (m, 5H), 4.80-4.67 (m, 1H), 4.08-3.97 (m, 1H), 3.77 (s, 3H), 3.68-3.54 (m, 1H), 3.24-2.87 (m, 4H), 2.43-1.88 (m, 6H), 1.79-1.50 (m, 6H), 1.39-1.07 (m, 4H), 0.59-0.56 (m, 1H). MS: (ES, m/z): 490 $[M+H]^+$.

Second eluting isomer: $^1$H-NMR ($CD_3OD$, 300 MHz) δ (ppm): 7.42-7.27 (m, 2H), 7.19-7.01 (m, 5H), 4.80-4.65 (m, 1H), 4.18-4.03 (m, 1H), 3.75 (s, 3H), 3.68-3.53 (m, 1H), 3.28-3.04 (m, 3H), 3.00-2.84 (m, 1H), 2.46-1.90 (m, 6H), 1.83-1.57 (m, 3H), 1.51 (d, J=6.8 Hz, 3H), 1.41-1.24 (m, 1H), 1.16 (d, J=6.6 Hz, 3H), 0.75-0.72 (m, 1H). MS: (ES, m/z): 490 $[M+H]^+$.

Examples 62 and 63: (1S,3R)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid and (1R,3S)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid

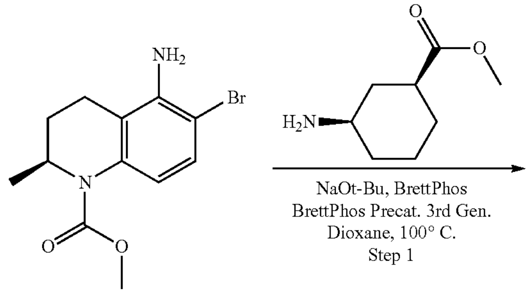

-continued

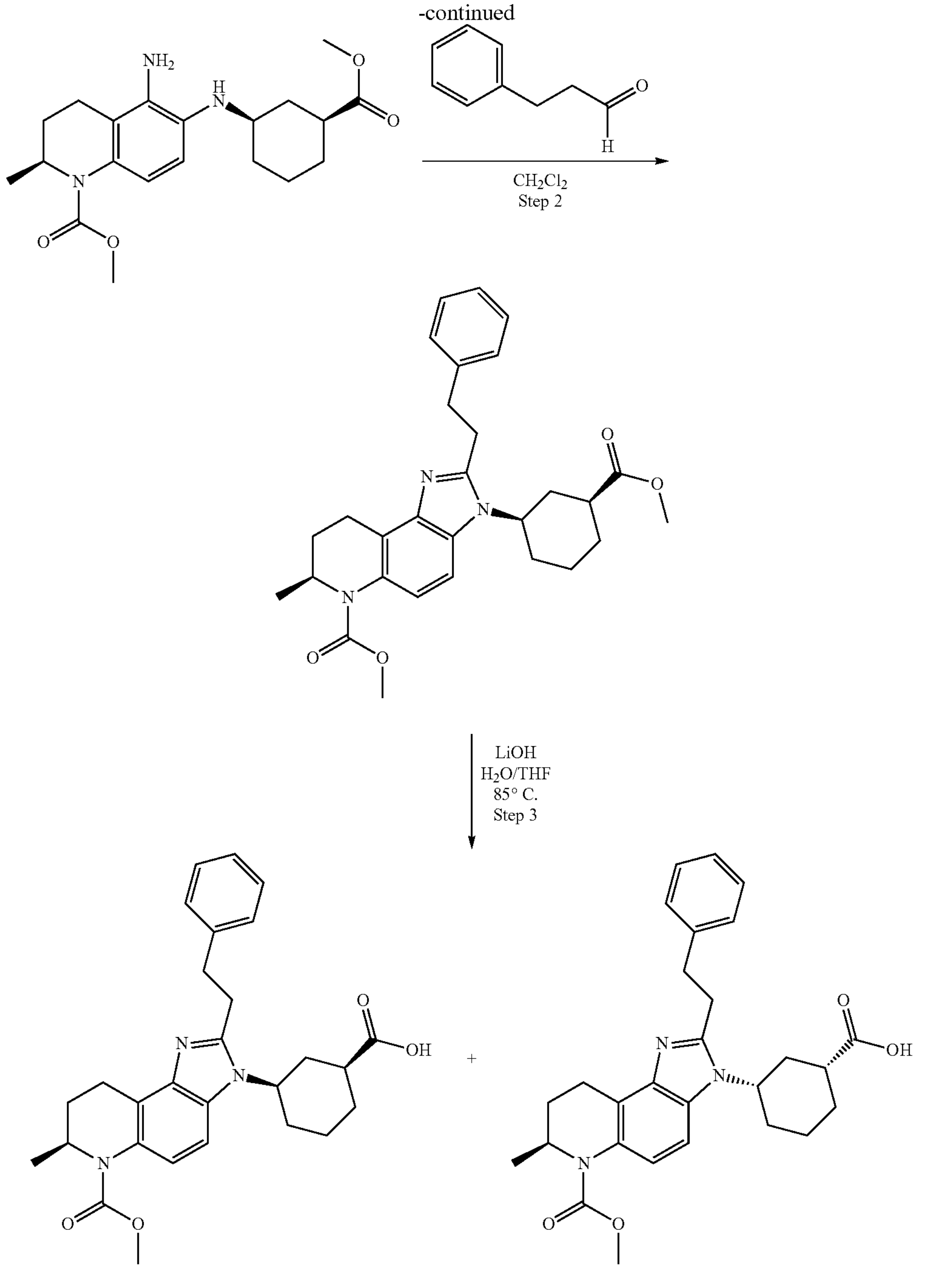

Step 1. Synthesis of methyl (2S)-5-amino-6-[[cis-3-(methoxycarbonyl)cyclohexyl]amino]-2-methyl-1,2,3,4-tetrahydroquinoline-1-carboxylate Into a 10-mL round-bottom flask purged and maintained with an inert atmosphere of nitrogen, methyl cis-3-amino-cyclohexane-1-carboxylate hydrochloride (260 mg, 1.34 mmol) was dissolved in dioxane (4 mL). Then methyl (2S)-5-amino-6-bromo-2-methyl-1,2,3,4-tetrahydroquinoline-1-carboxylate (200 mg, 0.66 mmol, Intermediate 1), Brettphos (144 mg, 0.26 mmol), Brettphos Pd G3 (122 mg, 0.14 mmol) and sodium tert-butoxide (194 mg, 2.02 mmol) were added. The resulting solution was stirred for 1 h at 100° C. under nitrogen atmosphere. The reaction mixture was cooled and the solids were filtered out. The resulting mixture was concentrated under vacuum. The residue was subjected to purification by FCC eluting with ethyl acetate/petroleum ether (2:1). This afforded the title compound (125.5 mg, 50%) as a green oil. MS: (ES, m/z): 376 [M+H]$^+$.

Step 2. Synthesis of methyl (7S)-3-[cis-3-(methoxycarbonyl)cyclohexyl]-7-methyl-2-(2-phenylethyl)-3H,6H,7H,8H,9H-imidazo[4,5-f]quinoline-6-carboxylate Into a 25-mL round-bottom flask, methyl (2S)-5-amino-6-[[cis-3-(methoxycarbonyl)cyclohexyl]amino]-2-methyl-1,2,3,4-tetrahydroquinoline-1-carboxylate (125.5 mg, 0.33 mmol) was dissolved in dichloromethane (5 mL). Then 3-phenylpropanal (134.5 mg, 1.00 mmol) was added. The resulting solution was stirred for 2 h at room temperature. The resulting mixture was concentrated under vacuum. The residue was subjected to purification by FCC eluting with ethyl acetate/petroleum ether (2:1). This afforded the title compound (105.1 mg, 64%) as a green solid. MS: (ES, m/z): 490 $[M+H]^+$.

Step 3. Synthesis of (1S,3R)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid and (1R,3S)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid Into a 25-mL round-bottom flask, methyl (7S)-3-[cis)-3-(methoxycarbonyl)cyclohexyl]-7-methyl-2-(2-phenylethyl)-3H,6H,7H,8H,9H-imidazo[4,5-f]quinoline-6-carboxylate (105.1 mg, 0.21 mmol) was dissolved in tetrahydrofuran (2 mL). Then water (2 mL) was added, followed by lithium hydroxide (25.8 mg, 1.08 mmol). The resulting solution was stirred for 2 h at 85° C. The resulting mixture was concentrated under vacuum. The crude product was purified by Prep-HPLC with the following conditions: Column, XBridge Shield RP18 OBD Column, 5 μm, 19×150 mm; mobile phase, A: water (10 mmol/L $NH_4HCO_3$) and B: ACN (20.0% to 45.0% ACN over 7 min); UV Detector: 254 nm. This afforded the title compounds as follow: 22.7 mg (22%) of Synthesis of (1S,3R)-3-((S)-6-(methoxycarbonyl)-

7-methyl-2-phenethyl-6,7,8,9-tetrahydro-3H-imidazo[4,5-f]quinolin-3-yl)cyclohexane-1-carboxylic acid (assumed stereochemistry, first eluting isomer, RT=4.8 min) as a white solid and 22.7 mg (22%) of (1R,3S)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid (assumed stereochemistry, second eluting isomer, RT=5.9 min) as a white solid.

First eluting isomer: $^1$H-NMR: (400 MHz, $CD_3OD$, ppm): δ 7.47-7.34 (m, 2H), 7.31-7.14 (m, 5H), 4.78-4.70 (m, 1H), 4.18-4.12 (m, 1H), 3.79 (s, 3H), 3.26-3.23 (m, 2H), 3.20-3.09 (m, 3H), 2.94-2.87 (m, 1H), 2.42-2.36 (m, 1H), 2.33-2.17 (m, 2H), 2.16-1.96 (m, 2H), 1.92-1.84 (m, 1H), 1.82-1.65 (m, 2H), 1.48-1.38 (m, 3H), 1.15 (d, J=6.8 Hz, 3H). MS: (ES, m/z): 476 $[M+H]^+$.

Second eluting isomer: $^1$H-NMR: (400 MHz, $CD_3OD$, ppm): δ 7.48-7.33 (m, 2H), 7.31-7.13 (m, 5H), 4.78-4.70 (m, 1H), 4.17-4.10 (m, 1H), 3.78 (s, 3H), 3.25-3.22 (m, 2H), 3.26-3.07 (m, 3H), 2.95-2.87 (m, 1H), 2.46-2.35 (m, 1H), 2.34-2.19 (m, 2H), 2.12-1.96 (m, 2H), 1.94-1.88 (m, 1H), 1.76-1.66 (m, 1H), 1.57-1.40 (m, 4H), 1.15 (d, J=6.8, 2.1 Hz, 3H).

Examples 64 and 65: (1R,3R)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid and (1S,3S)-3-((S)-6-(methoxycarbonyl)-7-methyl-2-phenethyl-6,7,8,9-tetrahydro-3H-imidazo[4,5-f]quinolin-3-yl) cyclohexane-1-carboxylic acid

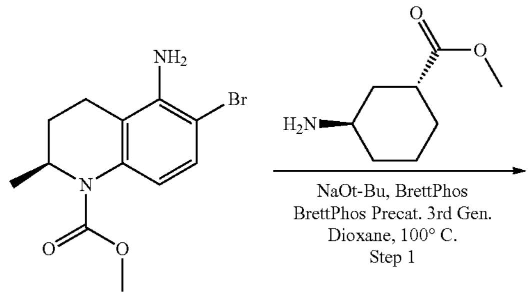

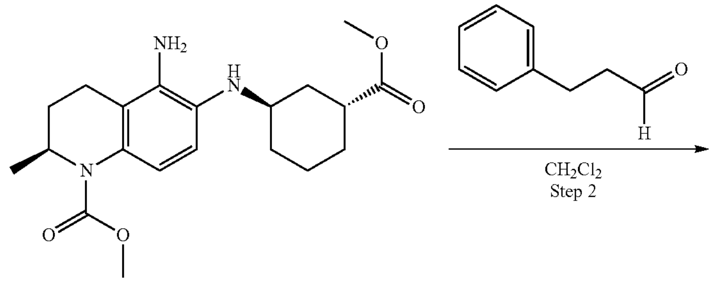

-continued

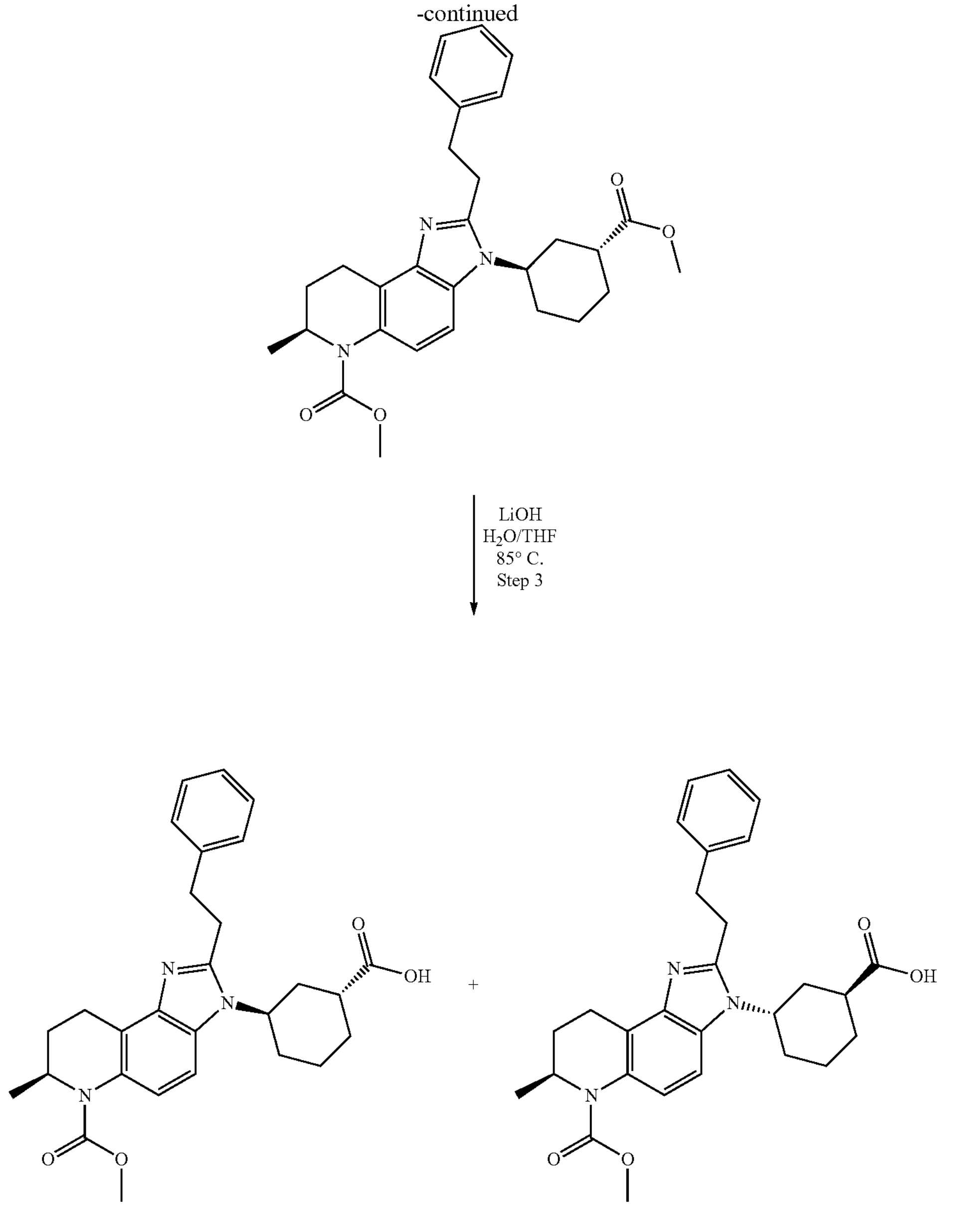

Step 1. Synthesis of methyl (2S)-5-amino-6-[[trans-3-(methoxycarbonyl)cyclohexyl]amino]-2-methyl-1,2,3,4-tetrahydroquinoline-1-carboxylate Into a 10-mL round-bottom flask purged and maintained with an inert atmosphere of nitrogen, trans-methyl-3-aminocyclohexane-1-carboxylate hydrochloride (260 mg, 1.34 mmol) was dissolved in dioxane (4 mL). Then methyl (2S)-5-amino-6-bromo-2-methyl-1,2,3,4-tetrahydroquinoline-1-carboxylate (200 mg, 0.66 mmol, Intermediate 1), Brettphos (144 mg, 0.26 mmol), $3^{rd}$ Generation BrettPhos precatalyst (122 mg, 0.14 mmol) and sodium tert-butoxide (194 mg, 2.02 mmol) were added. The resulting solution was stirred for 1 h at 100° C. under nitrogen atmosphere. The reaction mixture was cooled and the resulting solids were filtered out. The filtrate was concentrated under vacuum. The residue was subjected to purification by FCC eluting with ethyl acetate/petroleum ether (2:1). This afforded the title compound (80 mg, 45%) as green oil. MS: (ES, m/z): 376 $[M+H]^+$.

Step 2. Synthesis of methyl (7S)-3-[trans-3-(methoxycarbonyl)cyclohexyl]-7-methyl-2-(2-phenylethyl)-3H,6H,7H,8H,9H-imidazo[4,5-f]quinoline-6-carboxylate Into a 50-mL round-bottom flask, methyl (2S)-5-amino-6-[[trans-3-(methoxycarbonyl)cyclohexyl]amino]-2-methyl-1,2,3,4-tetrahydroquinoline-1-carboxylate (80 mg, 0.21 mmol) was dissolved in dichloromethane (5 mL). Then 3-phenylpropanal (57 mg, 0.42 mmol) was added. The resulting solution was stirred for 1 h at room temperature. The resulting mixture was concentrated under vacuum. The residue was subjected to purification by FCC eluting with ethyl acetate/petroleum ether (1:1). This afforded the title compound 75 mg (72%) as a yellow solid. MS: (ES, m/z): 490 $[M+H]^+$.

Step 3. Synthesis of (1R,3R)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid and (1S,3S)-3-((S)-6-(methoxycarbonyl)-7-methyl-2-phenethyl-6,7,8,9-tetrahydro-3H-imidazo[4,5-f]quinolin-3-yl)cyclohexane-1-carboxylic acid Into a 50-mL round-bottom flask, methyl (7S)-3-[trans-3-(methoxycarbonyl)cyclohexyl]-7-methyl-2-(2-phenylethyl)-3H,6H,7H,8H,9H-imidazo[4,5-f]quinoline-6-carboxylate (75 mg, 0.15 mmol) was dissolved in tetrahydrofuran (2 mL). Water (2 mL) was added, followed by lithium hydroxide (18.3 mg, 0.76 mmol). The resulting solution was stirred for 2 h at 85° C. The resulting mixture was concentrated under vacuum. The crude product was purified by Prep-HPLC with the following conditions: Column, XBridge C18 OBD Prep Column, 100 Å, 5 μm, 19 mm×250 mm; mobile phase, A: water (0.05% $NH_4OH$) and B: ACN (20.0% to 40.0% ACN over 12 min); UV Detector: 254 nm. This afforded the title compounds as follows: 2.6 mg (4%) of (1R,3R)-3-[(7S)-6-(methoxycarbonyl)-7-methyl-2-(2-phenylethyl)-3H,6H,7H,8H,9H-imidazo[4,5-f]quinolin-3-yl]cyclohexane-1-carboxylic acid (assumed stereochemistry, first eluting isomer, RT=8.9 min) as a white solid and 2.4 mg (3%) of (1S,3S)-3-[(7S)-6-(methoxycarbonyl)-7-methyl-2-(2-phenylethyl)-3H,6H,7H,8H,9H-imidazo[4,5-f]quinolin-3-yl]cyclohexane-1-carboxylic acid (assumed stereochemistry, second eluting isomer, RT=11.2 min) as a white solid.

First eluting isomer: 1H NMR (Methanol-d4, 400 MHz) δ (ppm): 7.47-7.45 (m, 1H), 7.36-7.33 (m, 1H), 7.25-7.24 (m, 4H), 7.19-7.16 (m, 1H), 4.76-4.72 (m, 1H), 4.64-4.59 (m, 2H), 3.76 (s, 3H), 3.26-3.11 (m, 3H), 3.02-2.88 (m, 3H), 2.33-2.20 (m, 5H), 1.76-1.70 (m, 3H), 1.48-1.48 (m, 2H), 1.13 (d, J=6.8 Hz, 3H). MS: (ES, m/z): 476 $[M+H]^+$.

Second eluting isomer: 1H NMR (Methanol-d4, 400 MHz) δ (ppm): 7.49-7.47 (m, 1H), 7.38-7.36 (m, 1H), 7.26-7.25 (m, 4H), 7.20-7.16 (m, 1H), 4.77-4.68 (m, 3H), 3.76 (s, 3H), 3.26-3.11 (m, 3H), 3.01-2.88 (m, 3H), 2.37-2.20 (m, 5H), 1.78-1.70 (m, 3H), 1.57-1.51 (m, 2H), 1.13 (d, J=6.8 Hz, 3H). MS: (ES, m/z): 476 $[M+H]^+$.

Example 66: methyl (S)-2-benzyl-3-((3R,6S)-6-(hydroxymethyl)tetrahydro-2H-pyran-3-yl)-7-methyl-3,7,8,9-tetrahydro-6H-imidazo[4,5-f]quinoline-6-carboxylate

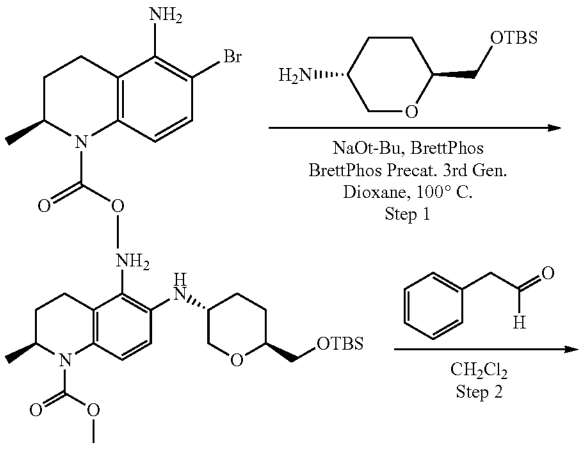

-continued

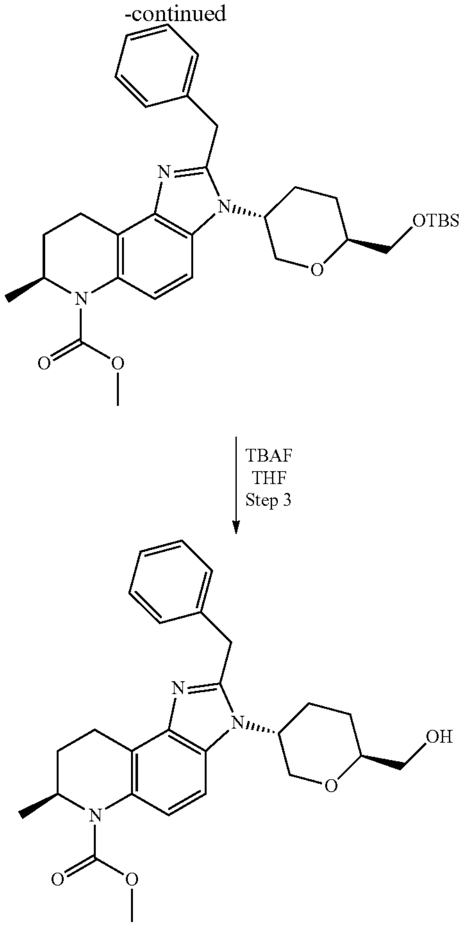

Step 1. Synthesis of methyl (2S)-5-amino-6-[[(3R,6S)-6-[[(tert-butyldimethylsilyl)oxy]methyl]oxan-3-yl]amino]-2-methyl-1,2,3,4-tetrahydroquinoline-1-carboxylate Into a 50-mL round-bottom flask, methyl (2S)-5-amino-6-bromo-2-methyl-1,2,3,4-tetrahydroquinoline-1-carboxylate (120 mg, 0.40 mmol, Intermediate 1) was dissolved in toluene (5 mL). Then (3R,6S)-6-[[(tert-butyldimethylsilyl)oxy]methyl]oxan-3-amine (292 mg, 1.19 mmol, Intermediate 30), Brettphos (86 mg, 0.16 mmol, 0.40 equiv), 3rd Generation Brettphos precatalyst (72 mg, 0.08 mmol) and sodium tert-butoxide (76 mg, 0.79 mmol) were added. The resulting solution was stirred for 2 h at 110° C. under nitrogen atmosphere. The reaction mixture was cooled and the resulting solids were filtered out. The filtrate was concentrated under vacuum. The residue was subjected to purification by FCC eluting with ethyl acetate/petroleum ether (1:1). This afforded the title compound (90 mg, 48%) as a brown oil. MS: (ES, m/z): 464 $[M+H]^+$.

Step 2. Synthesis of methyl (7S)-2-benzyl-3-[(3R,6S)-6-[[(tert-butyldimethylsilyl)oxy]methyl]oxan-3-yl]-7-methyl-3H,6H,7H,8H,9H-imidazo[4,5-f]quinoline-6-carboxylate Into a 50-mL round-bottom flask, methyl (2S)-5-amino-6-[[(3R,6S)-6-[[(tert-butyldimethylsilyl)oxy]methyl]oxan-3-yl]amino]-2-methyl-1,2,3,4-tetrahydroquinoline-1-carboxylate (90 mg, 0.19 mmol) was dissolved in dichloromethane (5 mL). Then 2-phenylacetaldehyde (23 mg, 0.19 mmol) was added. The resulting solution was stirred for 12 h at room temperature. The reaction mixture was concentrated under vacuum. The residue was subjected to purification by FCC eluting with ethyl acetate/petroleum ether (1:2). This afforded the title compound (70 mg, 64%) as a light yellow solid. MS: (ES, m/z): 564 $[M+H]^+$.

Step 3. Synthesis of (S)-methyl 2-benzyl-3-((3R,6S)-6-(hydroxymethyl)-tetrahydro-2H-pyran-3-yl)-7-methyl-8,9-dihydro-3H-imidazo[4,5-f]quinoline-6(7H)-carboxylate Into a 50-mL round-bottom flask, methyl (7S)-2-benzyl-3-[(3R,6S)-6-[[(tert-butyldimethylsilyl)oxy]methyl]oxan-3-yl]-7-methyl-3H,6H,7H,8H,9H-imidazo[4,5-f]quinoline-6-carboxylate (30 mg, 0.05 mmol) was dissolved in tetrahydrofuran (3 mL). Then tetrabutylammonium fluoride (1 M in THF, 0.08 mL, 0.08 mmol) was added. The resulting solution was stirred for 1 h at room temperature. The reaction mixture was concentrated under vacuum. The residue was subjected to purification by FCC eluting with ethyl acetate/petroleum ether (1:1). The crude product was purified by Prep-HPLC with the following conditions: Column, XBridge C18 OBD Prep Column, 100 Å, 5 μm, 19 mm×250 mm; mobile phase, A: Water (containing 0.05% TFA) and B: ACN (5.0% to 60.0% ACN over 30 min); UV Detector: 254 nm. This afforded the title compound (3.3 mg, 14%) as a yellow oil.

$^1$H-NMR: ($CDCl_3$, 300 MHz) δ (ppm): 7.85-7.81 (m, 1H), 7.41-7.29 (m, 6H), 4.86-4.77 (m, 2H), 4.61-4.51 (m, 3H), 4.10-4.03 (m, 1H), 3.84-3.81 (m, 4H), 3.69-3.56 (m, 3H), 3.18-3.15 (m, 2H), 2.38-2.33 (m, 1H), 2.20-2.14 (m, 1H), 1.91-1.85 (m, 1H), 1.79-1.75 (m, 1H), 1.63-1.59 (m, 1H), 1.46-1.42 (m, 1H), 1.15 (d, J=6.6 Hz, 3H). MS: (ES, m/z): 450 $[M+H]^+$.

The following examples in TABLE 4 were prepared using standard chemical manipulations and procedures similar to those used for the preparation of Example 66.

TABLE 4

| Example Number | Structure and Compound Name | LRMS m/z $[M + H]^+$ | $^1$HNMR |
|---|---|---|---|
| 67 | 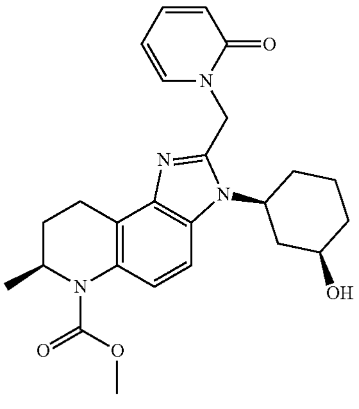 methyl (S)-3-((1S,3R)-3-hydroxycyclohexyl)-7-methyl-2-((2-oxopyridin-1(2H)-yl)methyl-3,7,8,9-tetrahydro-6H-imidazo-[4,5-f]quinoline-6-carboxylate | 451 | $^1$H-NMR (DMSO-d6, 400 MHz) δ (ppm): 7.66-7.64 (m, 1H), 7.55-7.49 (m, 2H), 7.45-7.43 (m, 1H), 6.62-6.60 (m, 1H), 6.42-6.38 (m, 1H), 5.58-5.48 (m, 2H), 4.75-4.66 (m, 2H), 3.76 (s, 3H), 3.70-3.66 (m, 1H), 3.17-3.13 (m, 1H), 2.94-2.90 (m, 1H), 2.23-2.10 (m, 3H), 2.0-1.88 (m, 3H), 1.75-1.67 (m, 2H), 1.42-1.39 (m, 1H), 1.36-1.28 (m, 1H), 1.13 (d, J = 6.8 Hz, 3H) |
| 68 | 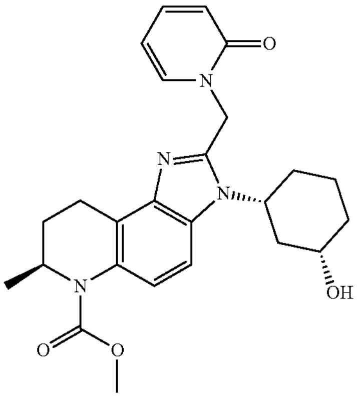 methyl (S)-3-((1R,3S)-3-hydroxycyclohexyl)-7-methyl-2-((2-oxopyridin-1(2H)-yl)methyl)-3,7,8,9-tetrahydro-6H-imidazo-[4,5-f]quinoline-6-carboxylate | 451 | $^1$H-NMR (DMSO-d6, 400 MHz) δ (ppm): 7.66-7.64 (m, 1H), 7.55-7.49 (m, 2H), 7.45-7.43 (m, 1H), 6.62-6.60 (m, 1H), 6.42-6.38 (m, 1H), 5.58-5.48 (m, 2H), 4.75-4.66 (m, 2H), 3.76 (s, 3H), 3.70-3.66 (m, 1H), 3.17-3.13 (m, 1H), 2.94-2.90 (m, 1H), 2.23-2.10 (m, 3H), 2.0-1.88 (m, 3H), 1.75-1.67 (m, 2H), 1.42-1.39 (m, 1H), 1.36-1.28 (m, 1H), 1.13 (d, J = 6.8 Hz, 3H) |

TABLE 4-continued

| Example Number | Structure and Compound Name | LRMS m/z [M + H]+ | $^1$HNMR |
|---|---|---|---|
| 69 | 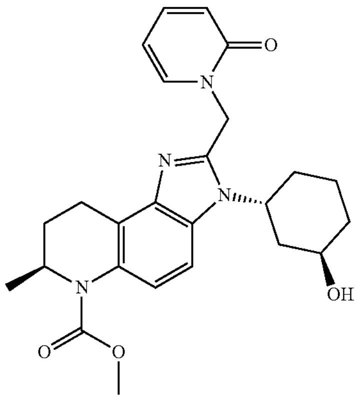 methyl (2)-3-((1R,3R)-3-hydroxycyclohexyl)-7-methyl-2-((2-oxopyridin-1(2H)-yl)methyl)-3,7,8,9-tetrahydro-6H-imidazo-[4,5-f]quinoline-6-carboxylate | 451 | $^1$H-NMR ($CD_3OD$, 400 MHz) δ (ppm): 7.69-7.67 (m, 1H), 7.56-7.49 (m, 2H), 7.42-7.40 (m, 1H), 6.59-6.57 (m, 1H), 6.42-6.39 (m, 1H), 5.68-5.64 (m, 1H), 5.35-5.32 (m, 1H), 4.98-4.85 (m, 1H), 4.73-4.71 (m, 1H), 4.28-4.26 (m, 1H), 3.75 (s, 3H), 3.13-3.11 (m, 1H), 2.89-2.85 (m, 1H), 2.52-2.50 (m, 1H), 2.25-2.18 (m, 2H), 1.98-1.82 (m, 2H), 1.71-1.69 (m, 2H), 1.68-1.64 (m, 3H), 1.11 (d, J = 6.4 Hz, 3H) |
| 70 | 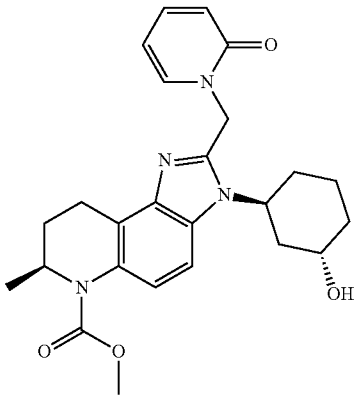 methyl (S)-3-((1S,3S)-3-hydroxycyclohexyl)-7-methyl-2-((2-oxopyridin-1(2H)-yl)methyl)-3,7,8,9-tetrahydro-6H-imidazo-[4,5-f]quinoline-6-carboxylate | 451 | $^1$H-NMR ($CD_3OD$, 400 MHz) δ (ppm): 7.66-7.64 (m, 1H), 7.55-7.49 (m, 2H), 7.45-7.43 (m, 1H), 6.62-6.60 (m, 1H), 6.42-6.38 (m, 1H), 5.58-5.47 (m, 2H), 4.75-4.66 (m, 2H), 3.76 (s, 3H), 3.70-3.68 (m, 1H), 3.17-3.13 (m, 1H), 2.95-2.91 (m, 1H), 2.22-2.11 (m, 3H), 2.09-2.00 (m, 2H), 1.87-1.75 (m, 1H), 1.73-7.64 (m, 2H), 1.52-1.37 (m, 2H), 1.12 (d, J = 6.8 Hz, 3H) |
| 71 | 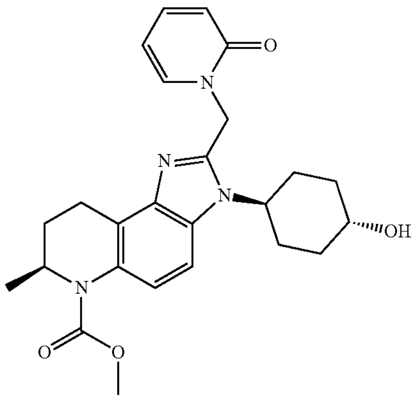 methyl (S)-3-((trans)-4-hydroxycyclohexyl)-7-methyl-2-((2-oxopyridin-1(2H)-yl)methyl)-3,7,8,9-tetrahydro-6H-imidazo[4,5-f]quinoline-6-carboxylate | 451 | $^1$H-NMR ($CDCl_3$, 300 MHz) δ (ppm): 7.47-7.44 (m, 2H), 7.34-7.27 (m, 2H), 6.64-6.61 (m, 1H), 6.16-6.11 (m, 1H), 5.67-5.62 (m, 1H), 5.45-5.40 (m, 1H), 4.81-4.79 (m, 1H), 4.68-4.65 (m, 1H), 3.77-3.72 (m, 4H), 3.21-3.12 (m, 1H), 3.05-3.01 (m, 1H), 2.25-2.17 (m, 3H), 2.11-2.05 (m, 2H), 1.76-1.72 (m, 2H), 1.60-1.49 (m, 3H), 1.17 (d, J = 6.9 Hz, 3H) |

Example 72: (2S,5R)-5-((S)-2-benzyl-6-(methoxycarbonyl)-7-methyl-6,7,8,9-tetrahydro-3H-imidazo[4,5-f]quinolin-3-yl)tetrahydro-2H-pyran-2-carboxylic acid

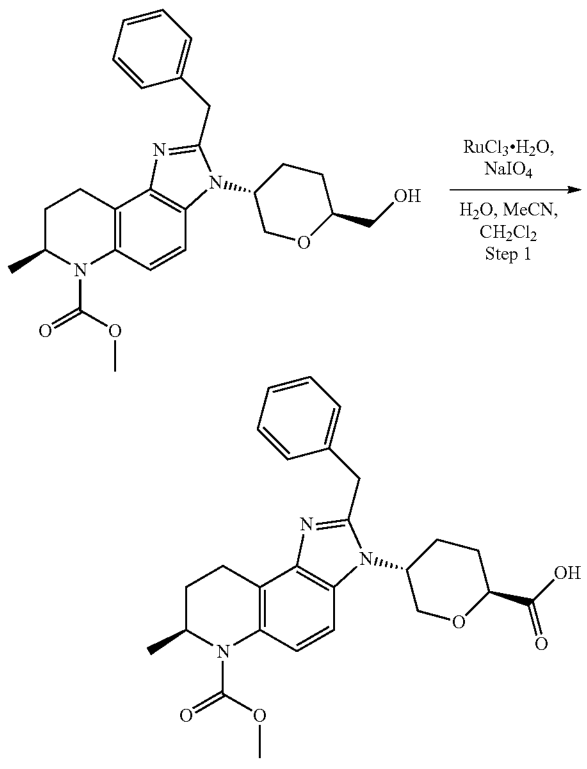

Step 1. Synthesis of (2S,5R)-5-((S)-2-benzyl-6-(methoxycarbonyl)-7-methyl-6,7,8,9-tetrahydro-3H-imidazo[4,5-f]quinolin-3-yl)tetrahydro-2H-pyran-2-carboxylic acid Into a 50-mL round-bottom flask, was placed methyl (7S)-2-benzyl-3-[(3R,6S)-6-(hydroxymethyl)oxan-3-yl]-7-methyl-3H,6H,7H,8H,9H-imidazo[4,5-f]quinoline-6-carboxylate (20 mg, 0.04 mmol, 1.00 equiv), water (1.5 mL), $CH_3CN$ (1 mL), dichloromethane (1 mL), $NaIO_4$ (47 mg, 0.22 mmol, 4.94 equiv), and $RuCl_3 \cdot H_2O$ (5 g, 22.18 mmol) was added at 0° C. The resulting solution was stirred for 12 h at room temperature. The solids were filtered out. The product was purified with the following conditions: Column: XBridge Shield RP18 OBD Column, 5 um, 19×150 mm; Mobile Phase A: Water (0.1% FA), Mobile Phase B: ACN; Flow rate: 20 mL/min; Gradient: 25% B to 55% B in 7 min; 254 nm; RT: 6.5 min. This resulted in 1.3 mg (6%) of (2S,5R)-5-[(7S)-2-benzyl-6-(methoxycarbonyl)-7-methyl-3H,6H,7H,8H,9H-imidazo[4,5-f]quinolin-3-yl]oxane-2-carboxylic acid as a yellow solid. $^1$H-NMR: (300 MHz, $CDCl_3$, ppm): 7.47-7.45 (m, 1H), 7.27-7.18 (m, 6H), 4.84-4.80 (m, 1H), 4.54-4.49 (m, 1H), 4.37-4.27 (m, 2H), 4.12-4.05 (m, 2H), 3.94-3.92 (m, 1H), 3.80 (s, 1H), 3.25-3.20 (m, 1H), 3.10-3.08 (m, 1H), 2.37-2.32 (m, 2H), 1.78-1.76 (m, 1H), 1.61-1.53 (m, 2H), 1.44-1.42 (m, 1H), 1.18-1.16 (m, 3H). MS: (ES, m/z): 464 $[M+H]^+$.

Example 73: methyl (S)-2-benzyl-3-((3R,6S)-6-carbamoyltetrahydro-2H-pyran-3-yl)-7-methyl-3,7,8,9-tetrahydro-6H-imidazo[4,5-f]quinoline-6-carboxylate

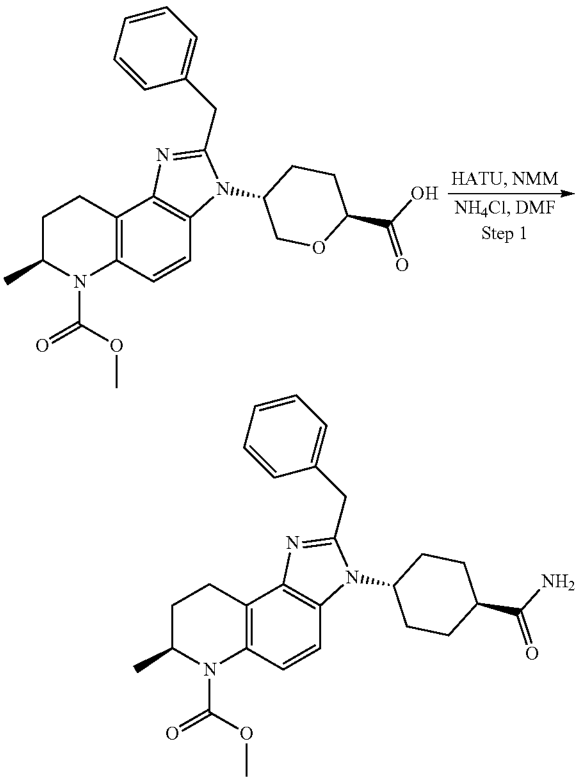

Step 1. Synthesis of methyl (S)-2-benzyl-3-((3R,6S)-6-carbamoyltetrahydro-2H-pyran-3-yl)-7-methyl-3,7,8,9-tetrahydro-6H-imidazo[4,5-f]quinoline-6-carboxylate Into a 50-mL round-bottom flask, was placed (2S,5R)-5-[(7S)-2-benzyl-6-(methoxycarbonyl)-7-methyl-3H,6H,7H,8H,9H-imidazo[4,5-f]quinolin-3-yl]oxane-2-carboxylic acid (20 mg, 0.04 mmol), N,N-dimethylformamide (2 mL), HATU (32 mg, 0.08 mmol), NMM (18 mg, 0.18 mmol), $NH_4Cl$ (4 mg, 0.07 mmol). The resulting solution was stirred for 1 h at room temperature. The product was purified with the following conditions: Column: XBridge Shield RP18 OBD Column, 5 um, 19*150 mm; Mobile Phase A: Water (10 mmol/L $NH_4HCO_3$), Mobile Phase B: ACN; Flow rate: 20 mL/min; Gradient: 25% B to 75% B in 7 min; 254 nm; RT: 6.5 min. This resulted in 1.5 mg (8%) of methyl (7S)-2-benzyl-3-[(3R,6S)-6-carbamoyloxan-3-yl]-7-methyl-3H,6H,7H,8H,9H-imidazo[4,5-f]quinoline-6-carboxylate as a white solid. $^1$H-NMR ($CD_3OD$, 300 MHz) δ (ppm): 7.55-7.53 (m, 1H), 7.46-7.45 (m, 1H), 7.35-7.30 (m, 2H), 7.24-7.22 (m, 3H), 4.79-4.74 (m, 1H), 4.47-4.43 (m, 3H), 4.17-4.11 (m, 1H), 4.06-4.02 (m, 1H), 3.76-3.70 (m, 4H), 3.23-3.15 (m, 1H), 2.98-2.95 (m, 1H), 2.54-2.46 (m, 1H), 2.28-2.15 (m, 2H), 1.78-1.61 (m, 2H), 1.48-1.42 (m, 1H), 1.13 (d, J=6.6 Hz, 3H). MS: (ES, m/z): 463 $[M+H]^+$.

Example 74: methyl (7S)-2-benzyl-7-methyl-3-[trans-4-carbamoylcyclohexyl]-3H,6H,7H,8H,9H-imidazo[4,5-f]quinoline-6-carboxylate

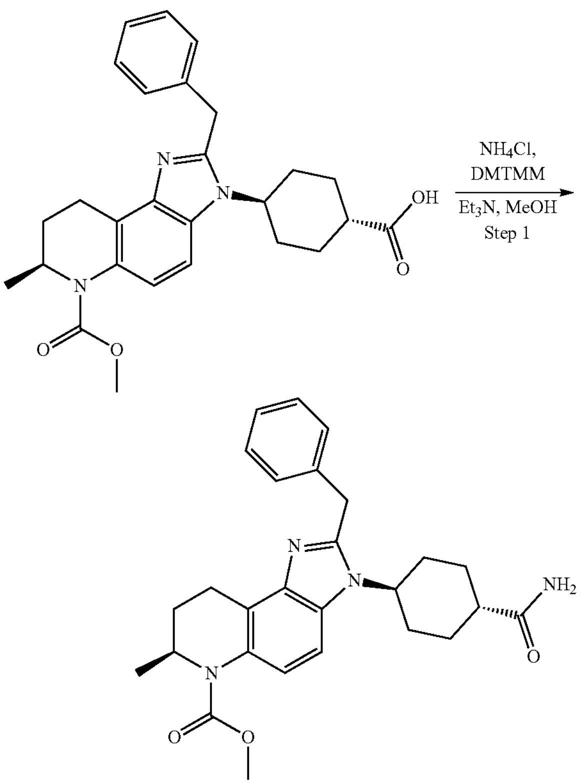

Step 1. Synthesis of methyl (7S)-2-benzyl-7-methyl-3-[trans-4-carbamoylcyclohexyl]-3H,6H,7H,8H,9H-imidazo[4,5-f]quinoline-6-carboxylate Into a 25-mL round-bottom flask, trans-4-[(7S)-2-benzyl-6-(methoxycarbonyl)-7-methyl-3H,6H,7H,8H,9H-imidazo[4,5-f]quinolin-3-yl]cyclohexane-1-carboxylic acid (30 mg, 0.07 mmol) was dissolved in methanol (3 mL). Then ammonium chloride (15.8 mg, 0.30 mmol), 4-(4,6-Dimethoxy-1,3,5-triazin-2-yl)-4-methyl morpholinium chloride (61.6 mg, 0.22 mmol) and triethylamine (15 mg, 0.15 mmol) were added. The resulting solution was stirred for overnight at room temperature. The crude product was purified by Prep-HPLC with the following conditions: Column, XBridge C18 OBD Prep Column, 100 Å, 5 μm, 19 mm×250 mm; mobile phase, A: water (10 mmol/L $NH_4HCO_3$) and B: ACN (22.0% to 38.0% ACN over 10 min); UV Detector: 254 nm. This offered the title compound (10.9 mg, 32%) as a white solid.

$^1$H-NMR ($CD_3OD$, 300 MHz) δ (ppm): 7.50-7.21 (m, 7H), 4.79-4.72 (m, 1H), 4.43 (s, 2H), 4.37-4.21 (m, 1H), 3.79 (s, 3H), 3.33-3.15 (m, 1H), 2.99-2.90 (m, 1H), 2.39-2.14 (m, 4H), 1.92-1.82 (m, 2H), 1.80-1.70 (m, 1H), 1.59-1.40 (m, 4H), 1.17 (d, J=6.7 Hz, 3H). MS: (ES, m/z): 461 $[M+H]^+$.

The following examples in TABLE 5 were prepared using standard chemical manipulations and procedures similar to those used for the preparation of Example 74.

TABLE 5

| Example Number | Structure and Compound Name | LRMS m/z $[M + H]^+$ | $^1$HNMR |
|---|---|---|---|
| 75 | 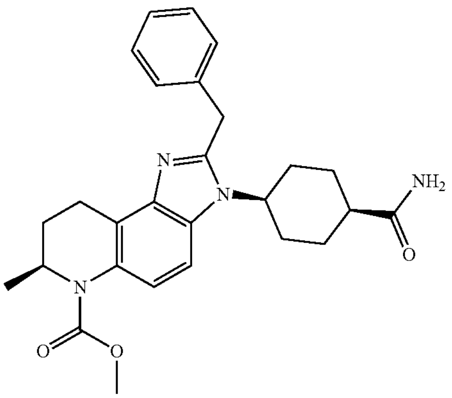 methyl (S)-2-benzyl-3-((cis)-4-carbamoylcyclohexyl)-7-methyl-3,7,8,9-tetrahydro-6H-imidazo[4,5-f]quinoline-6-carboxylate | 461 | $^1$H-NMR ($CD_3OD$, 300 MHz) δ (ppm): 7.52 (d, J = 9.0 Hz, 1H), 7.41-7.22 (m, 6H), 4.81-4.73 (m, 1H), 4.41 (s, 2H), 4.36-4.25 (m, 1H), 3.79 (s, 3H), 3.32-3.15 (m, 1H), 3.00-2.92 (m, 1H), 2.70-2.50 (m, 3H), 2.37-2.19 (m, 1H), 2.12-2.02 (m, 2H), 1.86-1.71 (m, 1H), 1.60-1.47 (m, 2H), 1.36-1.22 (m, 2H), 1.17 (d, J = 6.7 Hz, 3H) |

TABLE 5-continued

| Example Number | Structure and Compound Name | LRMS m/z [M + H]+ | $^1$HNMR |
|---|---|---|---|
| 76 | 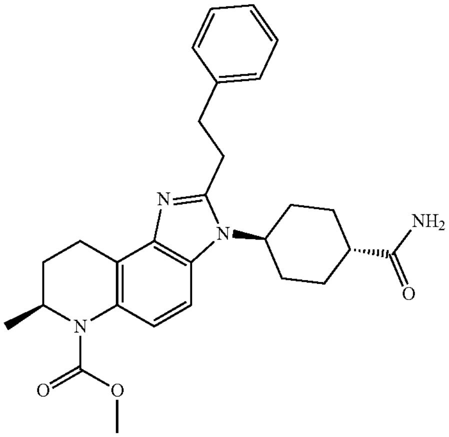 methyl (S)-3-((trans)-4-carbamoylcyclohexyl)-7-methyl-2-phenethyl-3,7,8,9-tetrahydro-6H-imidazo[4,5-f]quinoline-6-carboxylate | 475 | $^1$H-NMR ($CD_3OD$, 300 MHz) δ (ppm): 7.43-7.30 (m, 2H), 7.27-7.25 (m, 2H), 7.21-7.17 (m, 3H), 4.78-4.75 (m, 1H), 4.15-4.11 (m, 1H), 3.79 (s, 3H), 3.16-3.10 (m, 5H), 2.97-2.89 (m, 1H), 2.39-2.20 (m, 4H), 1.99-1.95 (m, 2H), 1.62-1.58 (m, 5H), 1.16 (d, J = 6.9 Hz, 3H) |
| 77 | 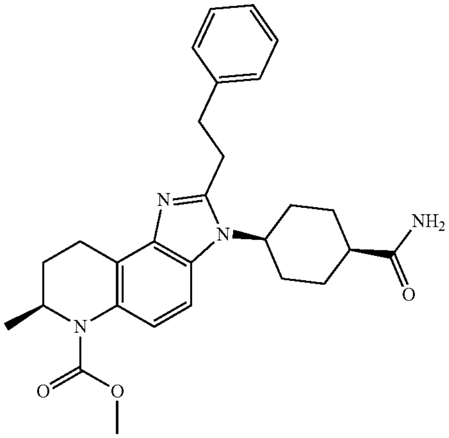 methyl (S)-3-((cis)-4-carbamoylcyclohexyl)-7-methyl-2-phenethyl-3,7,8,9-tetrahydro-6H-imidazo[4,5-f]-quinoline-6-carboxylate | 475 | $^1$H-NMR ($CD_3OD$, 300 MHz) δ (ppm): 7.52-7.49 (m, 1H), 7.33-7.25 (m, 3H), 7.20-7.17 (m, 3H), 4.79-4.73 (m, 1H), 4.22-4.15 (m, 1H), 3.78 (s, 3H), 3.34-3.09 (m, 5H), 2.92-2.88 (m, 1H), 2.64-2.60 (m, 3H), 2.26-2.11 (m, 3H), 1.77-1.70 (m, 3H), 1.41-1.29 (m, 2H), 1.16 (d, J = 6.9 Hz, 3H) |

Example 78: methyl (S)-3-(azetidin-3-yl)-2-benzyl-7-methyl-3,7,8,9-tetrahydro-6H-imidazo[4,5-f]quinoline-6-carboxylate

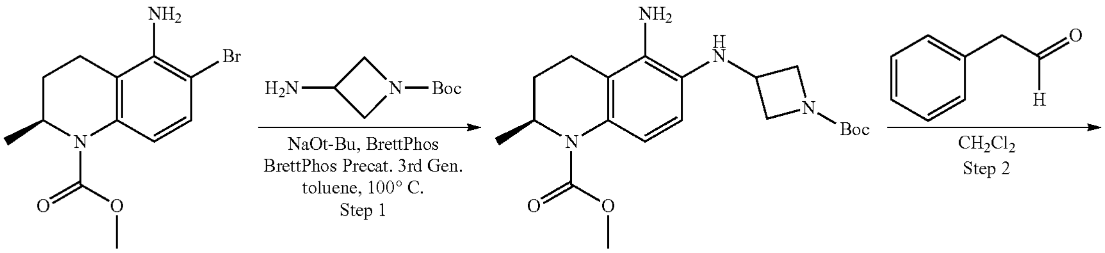

-continued

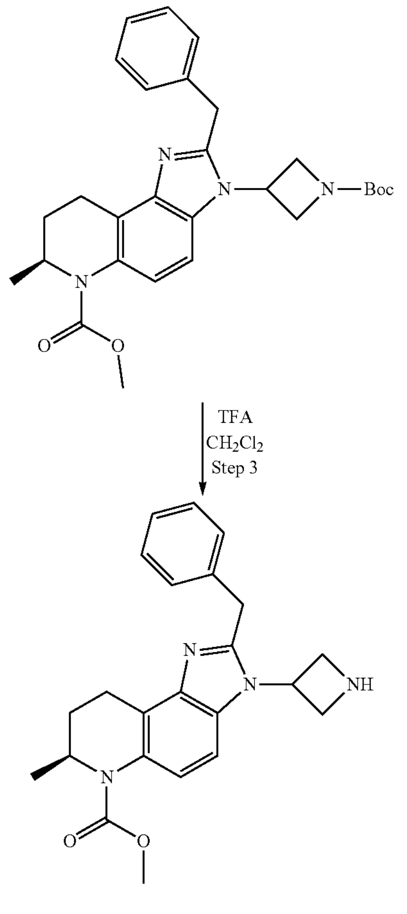

Step 1. Synthesis of methyl (2S)-5-amino-6-([1-[(tert-butoxy)carbonyl]azetidin-3-yl]amino)-2-methyl-1,2,3,4-tetrahydroquinoline-1-carboxylate Into a 10-mL round-bottom flask purged and maintained with an inert atmosphere of nitrogen, methyl (2S)-5-amino-6-bromo-2-methyl-1,2,3,4-tetrahydroquinoline-1-carboxylate (100 mg, 0.33 mmol, Intermediate 1) was dissolved in toluene (3 mL). Then tert-butyl 3-aminoazetidine-1-carboxylate (173.2 mg, 1.01 mmol), Brettphos (36 mg, 0.07 mmol), $3^{rd}$ Generation BrettPhos precatalyst (60.8 mg, 0.07 mmol) and sodium tert-butoxide (96.6 mg, 1.01 mmol) were added. The resulting solution was stirred for 1 h at 100° C. under nitrogen atmosphere. The reaction mixture was cooled to room temperature and the solids were filtered out. The filtrate was concentrated under vacuum. The residue was subjected to purification by FCC eluting with ethyl acetate/petroleum ether (2:1). This afforded the title compound (58 mg, 44%) as a brown solid. MS: (ES, m/z): 391 $[M+H]^+$.

Step 2. Synthesis of tert-butyl 3-[(7S)-2-benzyl-6-(methoxycarbonyl)-7-methyl-3H,6H,7H,8H,9H-imidazo[4,5-f]quinolin-3-yl]azetidine-1-carboxylate Into a 25-mL round-bottom flask, methyl (2S)-5-amino-6-([1-[(tert-butoxy)carbonyl]azetidin-3-yl]amino)-2-methyl-1,2,3,4-tetrahydroquinoline-1-carboxylate (58 mg, 0.15 mmol) was dissolved in dichloromethane (5 mL). Then 2-phenylacetaldehyde (107 mg, 0.89 mmol) was added. The resulting solution was stirred for 4 h at room temperature. The resulting mixture was concentrated under vacuum. The residue was subjected to purification by FCC eluting with ethyl acetate/petroleum ether (2:1). This afforded the title compound (43.3 mg, 59%) as a yellow oil. MS: (ES, m/z): 491 $[M+H]^+$.

Step 3. Synthesis of methyl (S)-3-(azetidin-3-yl)-2-benzyl-7-methyl-3,7,8,9-tetrahydro-6H-imidazo[4,5-f]quinoline-6-carboxylate Into a 25-mL round-bottom flask, tert-butyl 3-[(7S)-2-benzyl-6-(methoxycarbonyl)-7-methyl-3H,6H,7H,8H,9H-imidazo[4,5-f]quinolin-3-yl]azetidine-1-carboxylate (43.3 mg, 0.09 mmol) was dissolved in dichloromethane (5 mL). Then trifluoroacetic acid (1.5 mL) was added. The resulting solution was stirred for 3 h at room temperature. The resulting mixture was concentrated under vacuum. The crude product was purified by Prep-HPLC with the following conditions: Column, XBridge C18 OBD Prep Column, 100 Å, 5 um, 19 mm×250 mm; mobile phase, A: Waters (containing 10 mmol/L $NH_4HCO_3$) and B: ACN (25.0% to 45.0% ACN over 7 min); UV Detector: 254 nm. This afforded the title compounds (6 mg, 17%) of as a white solid. $^1$H-NMR ($CD_3OD$, 400 MHz) δ (ppm): 7.84 (d, J=9.0 Hz, 1H), 7.52 (d, J=8.9 Hz, 1H), 7.37-7.21 (m, 3H), 7.19-7.12 (m, 2H), 5.45-5.35 (m, 1H), 4.82-4.76 (m, 1H), 4.45-4.22 (m, 4H), 3.81 (s, 3H), 3.72-3.64 (m, 2H), 3.28-3.49 (m, 1H), 3.02-2.94 (m, 1H), 2.32-2.24 (m, 1H), 1.85-1.75 (m, 1H), 1.18 (d, J=6.7 Hz, 3H). MS: (ES, m/z): 391 $[M+H]^+$.

The following examples in TABLE 6 were prepared using standard chemical manipulations and procedures similar to those used for the preparation of Example 78.

TABLE 6
| Example Number | Structure and Compound Name | LRMS m/z [M + H]+ | $^1$HNMR |
|---|---|---|---|
| 79 | 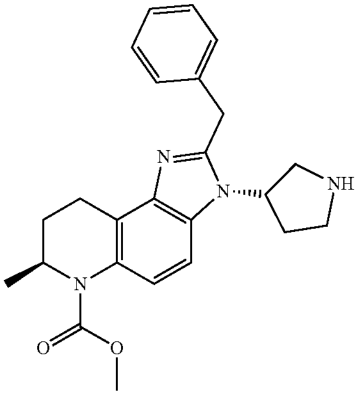 methyl (S)-2-benzyl-7-methyl-3-((S)-pyrrolidin-3-yl)-3,7,8,9-tetrahydro-6H-imidazo-[4,5-f]quinoline-6-carboxylate | 405 | $^1$H-NMR ($CD_3OD$, 400 MHz) δ (ppm): 7.49-7.18 (m, 7H), 5.04-4.99 (m, 1H), 4.79-4.74 (m, 1H), 4.46 (s, 2H), 3.79 (s, 3H), 3.32-3.12 (m, 3H), 3.07-2.91 (m, 3H), 2.35-2.12 (m, 2H), 1.92-1.86 (m, 1H), 1.78-1.71 (m, 1H), 1.17 (d, J = 6.7 Hz, 3H) |
| 80 | 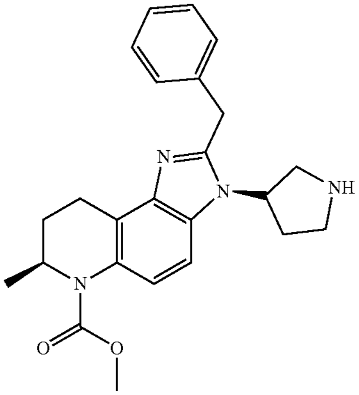 methyl (S)-2-benzyl-7-methyl-3-((S)-pyrrolidin-3-yl)-3,7,8,9-tetrahydro-6H-imidazo[4,5-f]-quinoline-6-carboxylate | 405 | $^1$H-NMR ($CD_3OD$, 300 MHz) δ (ppm): 7.49-7.17 (m, 7H), 5.05-4.95 (m, 1H), 4.80-4.74 (m, 1H), 4.46 (s, 2H), 3.80 (s, 3H), 3.33-3.16 (m, 2H), 3.14-2.83 (m, 4H), 2.38-2.13 (m, 2H), 2.04-1.86 (m, 1H), 1.86-1.69 (m, 1H), 1.17 (d, J = 6.7 Hz, 3H) |

TABLE 6-continued

| Example Number | Structure and Compound Name | LRMS m/z [M + H]+ | 1HNMR |
|---|---|---|---|
| 81 | 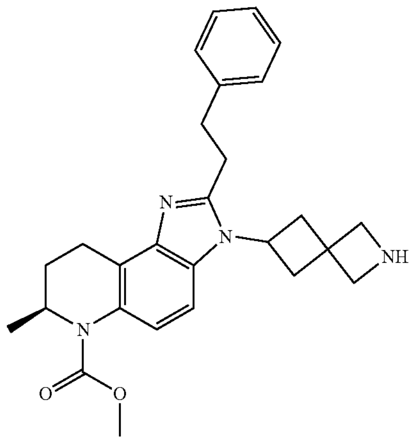 methyl (S)-7-methyl-2-phenethyl-3-(2-azaspiro[3.3]heptan-6-yl)-3,7,8,9-tetrahydro-6H-imidazo[4,5-f]quinoline-6-carboxylate | 445 | $^1$H-NMR ($CD_3OD$, 300 MHz) δ (ppm): 7.44-7.11 (m, 7H), 4.78-4.62 (m, 2H), 3.82-3.74 (m, 6H), 3.29-2.88 (m, 9H), 2.62-2.50 (m, 2H), 2.28-2.20 (m, 1H), 1.74-1.70 (m, 1H), 1.15 (d, J = 6.7 Hz, 3H) |
| 82 | 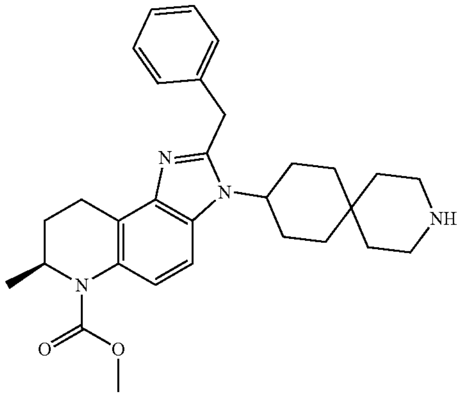 methyl (S)-2-benzyl-7-methyl-3-(3-azaspiro[5.5]-undecan-9-yl)-3,7,8,9-tetrahydro-6H-imidazo-[4,5-f]quinoline-6-carboxylate | 445 | $^1$H-NMR ($CDCl_3$, 300 MHz) δ (ppm): 7.39-7.36 (m, 1H), 7.35-7.30 (m, 1H), 7.30-7.18 (m, 5H), 4.81-4.77 (m, 1H), 4.41-4.27 (m, 2H), 4.03-3.99 (m, 1H), 3.78 (s, 3H), 3.27-3.21 (m, 1H), 3.09-3.02 (m, 1H), 2.89-2.83 (m, 4H), 2.28-2.19 (m, 3H), 1.82-1.68 (m, 5H), 1.37-1.35 (m, 3H), 1.18-1.16 (m, 4H), 1.04-0.96 (m, 2H) |
| 83 | 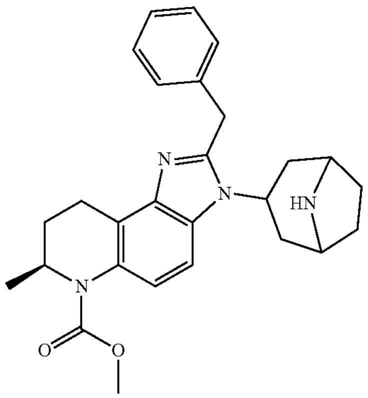 methyl (7S)-2-benzyl-3-(8-azabicyclo[3.2.1]-octan-3-yl)-7-methyl-3,7,8,9-tetrahydro-6H-imidazo[4,5-f]quinoline-6-carboxylate | 445 | $^1$H-NMR ($CDCl_3$, 400 MHz) δ (ppm): 7.38 (d, J = 8.8 Hz, 1H), 7.35-7.13 (m, 6H), 4.82-4.77 (m, 1H), 4.70-4.60 (m, 1H), 4.44-4.28 (m, 2H), 3.79 (s, 3H), 3.70-3.61 (m, 2H), 3.29-3.22 (m, 1H), 3.07-3.02 (m, 1H), 2.28-2.20 (m, 1H), 2.11-2.04 (m, 1H), 2.00-1.72 (m, 9H), 1.17 (d, J = 6.8 Hz, 3H) |

TABLE 6-continued

| Example Number | Structure and Compound Name | LRMS m/z [M + H]+ | 1HNMR |
|---|---|---|---|
| 84 | 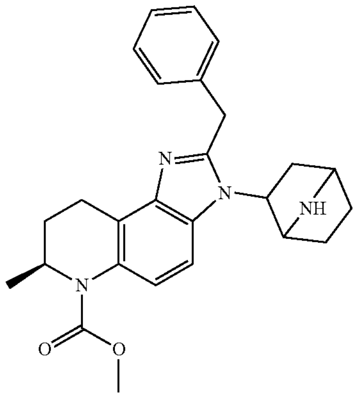 methyl (7S)-2-benzyl-3-(7-azabicyclo[2.2.1]-heptan-2-yl)-7-methyl-3,7,8,9-tetrahydro-6H-imidazo[4,5-f]quinoline-6-carboxylate | 431 | $^1$H-NMR ($CD_3OD$, 300 MHz) δ (ppm): 7.56-7.42 (m, 2H), 7.41-7.18 (m, 5H), 4.84-4.72 (m, 2H), 4.52-4.36 (m, 2H), 3.84-3.78 (m, 4H), 3.30-3.18 (m, 1H), 3.10-2.93 (m, 2H), 2.50-2.40 (m, 1H), 2.32-2.20 (m, 1H), 2.14-1.94 (m, 2H), 1.85-1.65 (m, 3H), 1.50-1.40 (m, 1H), 1.18-1.12 (m, 3H). |
| 85 | 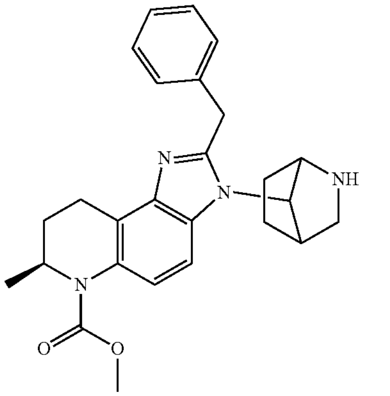 methyl (7S)-2-benzyl-3-(2-azabicyclo-[2.2.1]heptan-7-yl)-7-methyl-3,7,8,9-tetrahydro-6H-imidazo[4,5-f]quinoline-6-carboxylate | 431 | $^1$H-NMR ($CD_3OD$, 300 MHz) δ (ppm): 7.47 (d, J = 1.4 Hz, 2H), 7.40-7.20 (m, 3H), 7.20-7.10 (m, 2H), 4.82-4.76 (m, 1H), 4.52 (d, J = 2.3 Hz, 2H), 4.19-4.08 (m, 2H), 3.80 (s, 3H), 3.31-3.13 (m, 2H), 3.07-2.94 (m, 2H), 2.72-2.68 (m, 1H), 2.35-2.17 (m, 1H), 1.82-1.50 (m, 5H), 1.18-1.14 (m, 3H) |
| 86 | 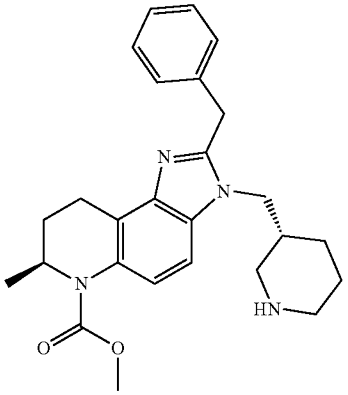 methyl (S)-2-benzyl-7-methyl-3-(((R)-piperidin-3-yl)methyl)-3,7,8,9-tetrahydro-6H-imidazo[4,5-f]quinoline-6-carboxylate | 433 | $^1$H-NMR ($CDCl_3$, 300 MHz) δ (ppm): 7.35 (d, J = 8.7 Hz, 1H), 7.31-7.19 (m, 5H), 7.11 (d, J = 8.7 Hz, 1H), 4.89-3.71 (m, 1H), 4.43-4.28 (m, 2H), 3.89-3.67 (m, 5H), 3.27-3.22 (m, 1H), 3.08-2.81 (m, 3H), 2.60-2.57 (m, 1H), 2.33-2.23 (m, 2H), 1.94-1.61 (m, 5H), 1.42-1.28 (m, 1H), 1.19-1.11 (m, 4H) |

TABLE 6-continued

| Example Number | Structure and Compound Name | LRMS m/z [M + H]+ | 1HNMR |
|---|---|---|---|
| 87 | 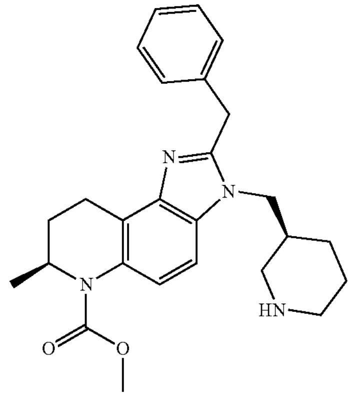 methyl (S)-2-benzyl-7-methyl-3-(((S)-piperidin-3-yl)methyl)-3,7,8,9-tetrahydro-6H-imidazo[4,5-f]quinoline-6-carboxylate | 433 | $^1$H-NMR ($CD_3OD$, 400 MHz) δ (ppm): 7.84 (d, J = 9.2 Hz, 1H), 7.62 (d, J = 9.2 Hz, 1H), 7.45-7.42 (m, 2H), 7.39-7.34 (m, 3H), 4.87-4.83 (m, 1H), 4.63-4.61 (m, 2H), 4.36 (d, J = 7.6 Hz, 2H), 3.82 (s, 3H), 3.33-3.32 (m, 1H), 3.25-3.22 (m, 2H), 3.14-2.98 (m, 1H), 2.89-2.77 (m, 2H), 2.32-2.25 (m, 2H), 1.94-1.85 (m, 2H), 1.74-1.71 (m, 1H), 1.61-1.57 (m, 1H), 1.37-1.33 (m, 1H), 1.18 (d, J = 6.8 Hz, 3H) |
| 88 | 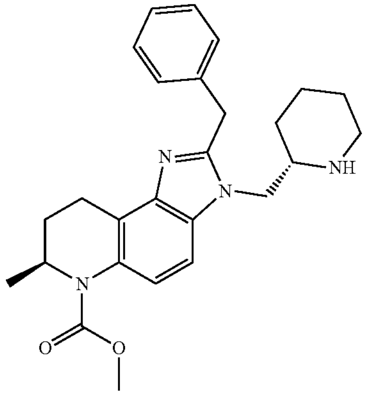 methyl (S)-2-benzyl-7-methyl-3-(((S)-piperidin-2-yl)methyl)-3,7,8,9-tetrahydro-6H-imidazo-[4,5-f]quinoline-6-carboxylate | 433 | $^1$H-NMR ($CDCl_3$, 300 MHz) δ (ppm): 7.46 (d, J = 8.8 Hz, 1H), 7.34-7.18 (m, 6H), 4.86-4.79 (m, 1H), 4.43 (q, J = 15.9 Hz, 2H), 3.91-3.88 (m, 2H), 3.81 (s, 3H), 3.33-3.30 (m, 1H), 3.11-2.93 (m, 2H), 2.76-2.73 (m, 1H), 2.46-2.21 (m, 2H), 1.82-1.73 (m, 2H), 1.59-1.41 (m, 3H), 1.21 (d, J = 6.6 Hz, 5H) |
| 89 | 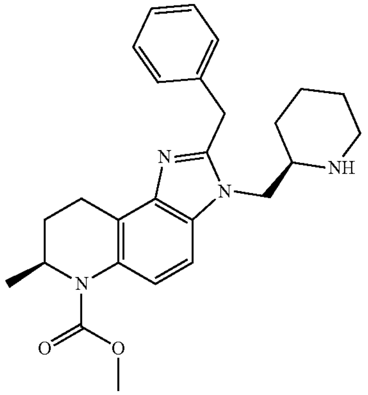 methyl (S)-2-benzyl-7-methyl-3-(((R)-piperidin-2-yl)methyl)-3,7,8,9-tetrahydro-6H-imidazo[4,5-f]quinoline-6-carboxylate | 433 | $^1$H-NMR ($CDCl_3$, 300 MHz) δ (ppm): 7.32 (d, J = 9.0 Hz, 1H), 7.30-7.16 (m, 6H), 4.83-4.77 (m, 1H), 4.39 (s, 2H), 3.81 (d, J = 6.6 Hz, 2H), 3.78 (s, 3H), 3.31-3.22 (m, 1H), 3.08-2.92 (m, 2H), 2.66-2.64 (m, 1H), 2.38-2.23 (m, 2H), 1.79-1.70 (m, 2H), 1.56-1.52 (m, 2H), 1.46-1.38 (m, 1H), 1.24-1.16 (m, 5H) |

TABLE 6-continued

| Example Number | Structure and Compound Name | LRMS m/z [M + H]+ | 1HNMR |
|---|---|---|---|
| 90 | 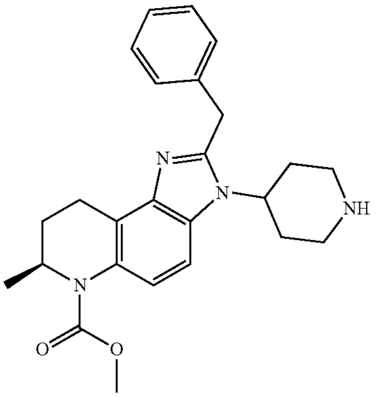 methyl (S)-2-benzyl-7-methyl-3-(piperidin-4-yl)-3,7,8,9-tetrahydro-6H-imidazo[4,5-f]-quinoline-6-carboxylate | 419 | $^1$H-NMR ($CD_3OD$, 300 MHz) δ (ppm): 7.54 (d, J = 9.0 Hz, 1H), 7.46-7.20 (m, 6H), 4.84-4.78 (m, 1H), 4.42-4.30 (m, 3H), 3.79 (s, 3H), 3.29-3.19 (m, 1H), 3.14-2.91 (m, 3H), 2.59-2.48 (m, 2H), 2.38-2.20 (m, 3H), 1.80-1.72 (m, 1H), 1.45-1.35 (m, 2H), 1.17 (d, J = 6.7 Hz, 3H) |
| 91 | 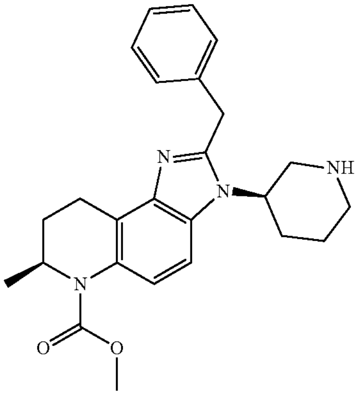 methyl (S)-2-benzyl-7-methyl-3-((R)-piperidin-3-yl)-3,7,8,9-tetrahydro-6H-imidazo[4,5-f]quinoline-6-carboxylate | 419 | $^1$H-NMR ($CDCl_3$, 400 MHz) δ (ppm): 7.39 (d, J = 8.8 Hz, 1H), 7.30-7.17 (m, 6H), 4.82-4.78 (m, 1H), 4.46-4.24 (m, 3H), 378 (s, 3H), 3.32-3.02 (m, 4H), 2.92-2.85 (m, 1H), 2.63-2.58 (m, 1H), 2.30-2.11 (m, 2H). 1.75-1.73 (m, 2H), 1.43-1.38 (m, 2H), 1.17 (d, J = 6.8 Hz, 3H) |
| 92 | 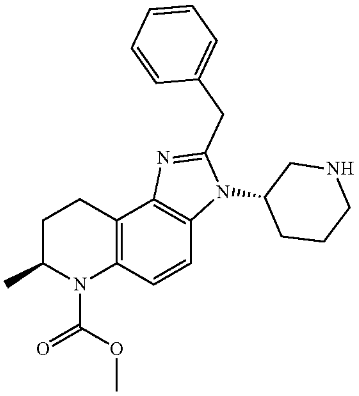 methyl (S)-2-benzyl-7-methyl-3-((S)-piperidin-3-yl)-3,7,8,9-tetrahydro-6H-imidazo[4,5-f]quinoline-6-carboxylate | 419 | $^1$H-NMR ($CD_3OD$, 300 MHz) δ (ppm): 7.55-7.20 (m, 7H), 4.82-4.78 (m, 1H), 4.52-4.31 (m, 3H), 3.79 (s, 3H), 3.36-3.34 (m, 1H), 3.28-3.15 (m, 1H), 3.01-2.92 (m, 2H), 2.87-2.80 (m, 1H), 2.68-2.58 (m, 1H), 2.30-2.12 (m, 2H), 1.81-1.71 (m, 2H), 1.48-1.40 (m, 2H), 1.17 (d, J = 6.6 Hz, 3H) |

TABLE 6-continued

| Example Number | Structure and Compound Name | LRMS m/z [M + H]$^+$ | $^1$HNMR |
|---|---|---|---|
| 93 | 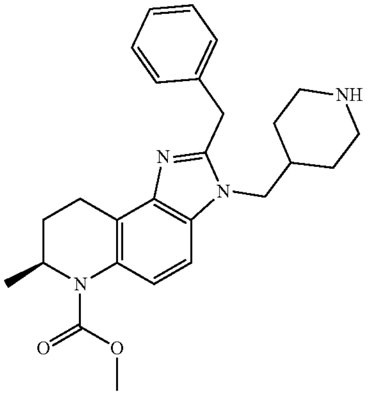 methyl (S)-2-benzyl-7-methyl-3-(piperidin-4-ylmethyl)-3,7,8,9-tetrahydro-6H-imidazo[4,5-f]quinoline-6-carboxylate | 433 | $^1$H-NMR ($CDCl_3$, 400 MHz) δ (ppm): 7.43 (d, J = 8.4 Hz, 1H), 7.31-7.19 (m, 5H), 7.06 (d, J = 8.8 Hz, 1H), 4.83-4.78 (m, 1H), 4.41-4.29 (m, 2H), 3.80 (d, J = 8 Hz, 5H), 3.31-3.01 (m, 4H), 2.47-2.23 (m, 3H), 1.77-1.72 (m, 6H), 1.60 (s, 3H) |
| 94 | 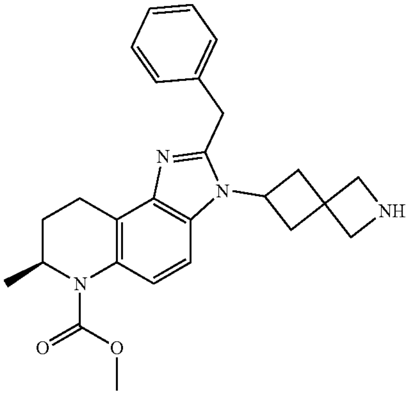 methyl (7S)-2-benzyl-3-(7-azabicyclo[2.2.1]-heptan-2-yl)-7-methyl-3,7,8,9-tetrahydro-6H-imidazo[4,5-f]quinoline-6-carboxylate | 431 | $^1$H-NMR ($CDCl_3$, 400 MHz) δ (ppm): 7.43 (d, J = 8.4 Hz, 1H), 7.31-7.19 (m, 4H), 7.06 (d, J = 8.8 Hz, 2H), 4.83-4.78 (m, 1H), 4.57-4.29 (m, 3H), 3.80-3.69 (m, 6H), 3.25-2.90 (m, 4H), 2.51-2.23 (m, 4H), 1.76-1.71 (m, 1H), 1.17 (d, J = 6.8 Hz, 3H) |
| 95 | 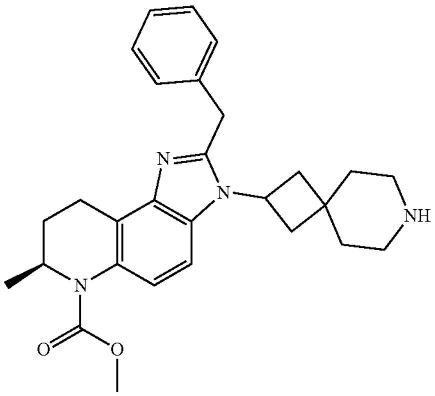 methyl (S)-2-benzyl-7-methyl-3-(7-azaspiro-[3.5]nonan-2-yl)-3,7.8,9-tetrahydro-6H-imidazo[4,5-f]quinoline-6-carboxylate | 459 | $^1$H-NMR ($CDCl_3$, 400 MHz) δ (ppm): 7.33 (d, J = 2 Hz, 2H), 7.32-7.24 (m, 3H), 7.14 (d, J = 8.8 Hz, 2H), 4.83-4.68 (m, 2H), 4.37 (d, J = 6 Hz, 2H), 3.82 (s, 3H), 3.30-3.03 (m, 2H), 2.81-2.53 (m, 6H), 2.30-2.01 (m, 3H), 1.82-1.53 (m, 6H), 1.20 (d, J = 8.8 Hz, 3H) |

TABLE 6-continued

| Example Number | Structure and Compound Name | LRMS m/z [M + H]$^+$ | $^1$HNMR |
|---|---|---|---|
| 96 | 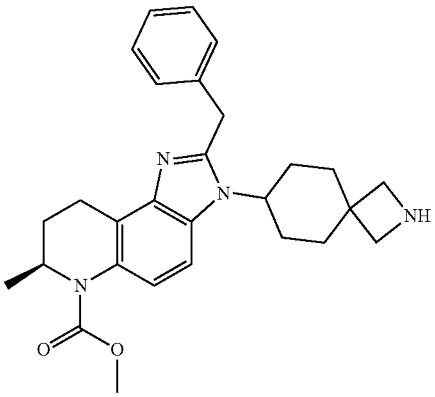 methyl (S)-2-benzyl-7-methyl-3-(2-azaspiro-[3.5]nonan-7-yl)-3,7,8,9-tetrahydro-6H-imidazo[4,5-f]quinoline-6-carboxylate | 459 | $^1$H-NMR ($CDCl_3$, 300 MHz) δ (ppm): 7.36 (d, J = 8.9 Hz, 1H), 7.30-7.28 (m, 1H), 7.27-7.26 (m, 1H), 7.25-7.17 (m, 3H), 7.06 (d, J = 8.9 Hz, 1H), 4.81-4.79 (m, 1H), 4.41-4.27 (m, 2H), 4.10-3.92 (m, 1H), 3.78 (s, 3H), 3.55 (s, 2H), 3.37 (s, 2H), 3.35-3.19 (m, 1H), 3.12-2.96 (m, 1H), 2.35-2.19 (m, 1H), 2.19-1.93 (m, 4H), 1.83-1.67 (m, 1H), 1.53-1.42 (m, 1H), 1.39-1.20 (m, 3H), 1.17 (d, J = 6.7 Hz, 3H) |
| 97 | 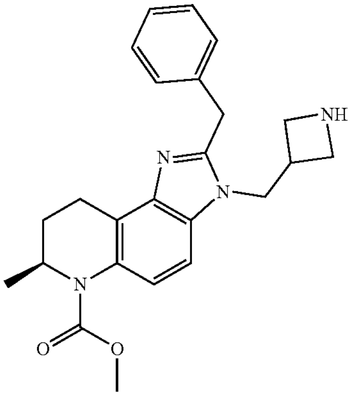 methyl (S)-3-(azetidin-3-ylmethyl)-2-benzyl-7-methyl-3,7,8,9-tetrahydro-6H-imidazo[4,5-f]quinoline-6-carboxylate | 405 | $^1$H-NMR ($CDCl_3$, 300 MHz) δ (ppm): 7.40 (d, J = 8.7 Hz, 1H), 7.31-7.11 (m, 6H), 4.82-4.76 (m, 1H), 4.36 (d, J = 6.0 Hz, 2H), 4.20 (d, J = 7.2 Hz, 2H), 3.77 (s, 3H), 3.61-3.53 (m, 2H), 3.34-3.21 (m, 3H), 3.07-2.92 (m, 2H), 2.28-2.20 (m, 1H), 1.78-1.70 (m, 1H), 1.17 (d, J = 6.9 Hz, 3H) |
| 98 | 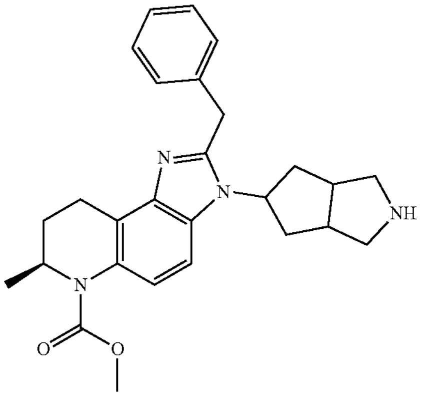 methyl (7S)-2-benzyl-7-methyl-3-(octahydro-cyclopenta[c]pyrrol-5-yl)-3,7,8,9-tetrahydro-6H-imidazo[4,5-f]quinoline-6-carboxylate | 445 | $^1$H-NMR ($CDCl_3$, 300 MHz) δ (ppm): 7.47-7.40 (m, 1H), 7.37-7.32 (m, 1H), 7.30-7.27 (m, 1H), 7.26-7.24 (m, 2H), 7.17-7.15 (m, 2H), 4.84-4.78 (m, 1H), 4.50-4.44 (m, 1H), 4.39-4.32 (m, 2H), 3.80 (s, 3H), 3.30-3.20 (m, 3H), 3.15-3.01 (m, 3H), 2.75-2.70 (m, 2H), 2.32-2.12 (m, 3H), 1.92-1.90 (m, 1H), 1.80-1.72 (m, 2H), 1.20 (d, J = 6.6 Hz, 3H) |

TABLE 6-continued

| Example Number | Structure and Compound Name | LRMS m/z [M + H]+ | 1HNMR |
|---|---|---|---|
| 99 | 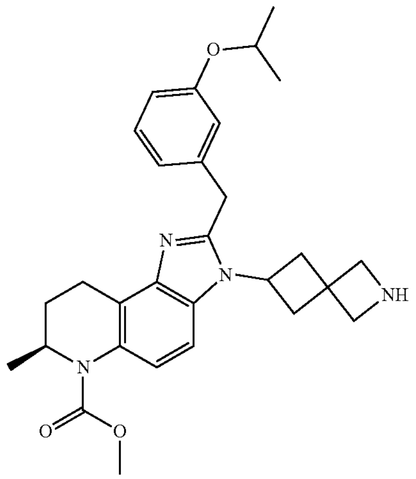 methyl (S)-2-(3-isopropoxybenzyl)-7-methyl-3-(2-azaspiro[3.3]heptan-6-yl)-3,7,8,9-tetrahydro-6H-imidazo[4,5-f]quinoline-6-carboxylate | 489 | $^1$H-NMR ($CDCl_3$, 300 MHz) δ (ppm): 7.43 (d, J = 8.8 Hz, 1H), 7.26-7.13 (m, 2H), 6.77-6.73 (m, 1H), 6.63-6.60 (m, 2H), 4.83-4.77 (m, 1H), 4.61-4.45 (m, 2H), 4.34-4.22 (m, 2H), 3.95 (d, J = 15.4 Hz, 4H), 3.79 (s, 3H), 3.30-3.19 (m, 1H), 3.07-2.97 (m, 3H), 2.59-2.49 (m, 2H), 2.31-2.20 (m, 1H), 1.79-1.69 (m, 1H), 1.29-1.24 (m, 6H), 1.17 (d, J = 6.6 Hz, 3H) |
| 100 | 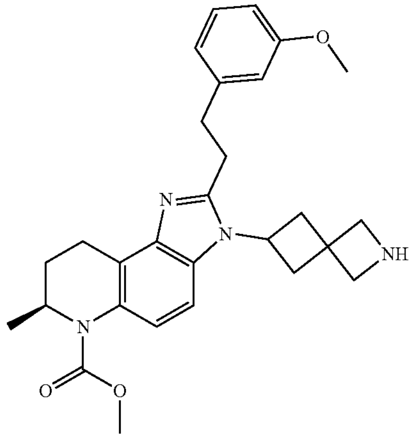 methyl (S)-2-(3-methoxyphenethyl)-7-methyl-3-(2-azaspiro[3.3]heptan-6-yl)-3,7,8,9-tetrahydro-6H-imidazo[4,5-f]quinoline-6-carboxylate | 475 | $^1$H-NMR ($CDCl_3$, 300 MHz) δ (ppm): 7.40-7.28 (m, 1H), 7.24-7.21 (m, 2H), 6.81-6.73 (m, 3H), 4.83-4.78 (m, 1H), 4.59-4.54 (m, 1H), 3.81-3.76 (m, 9H), 3.25-3.19 (m, 5H), 3.17-2.95 (m, 3H), 2.69-2.58 (m, 3H), 2.31-2.23 (m, 1H), 1.77-1.71 (m, 1H), 1.18 (d, J = 6.9 Hz, 3H) |

TABLE 6-continued

| Example Number | Structure and Compound Name | LRMS m/z [M + H]+ | $^1$HNMR |
|---|---|---|---|
| 101 | 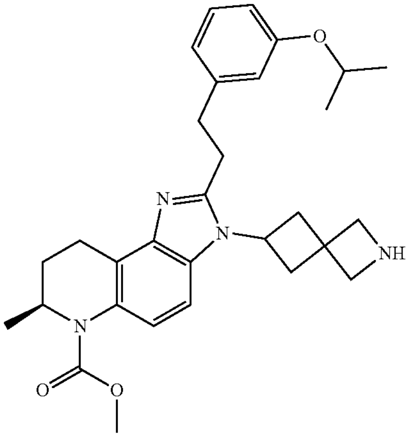 methyl (S)-2-(3-isopropoxyphenethyl)-7-methyl-3-(2-azaspiro[3.3]heptan-6-yl)-3,7,8,9-tetrahydro-6H-imidazo[4,5-f]quinoline-6-carboxylate | 503 | $^1$H-NMR ($CDCl_3$, 300 MHz) δ (ppm): 7.39 (d, J = 8.9 Hz, 1H), 7.26-7.16 (m, 2H), 6.77-6.69 (m, 3H), 4.80-4.78 (m, 1H), 4.57-4.43 (m, 2H), 3.85-3.83 (m, 3H), 3.79 (s, 3H), 3.23-2.95 (m, 9H), 2.66-2.60 (m, 2H), 2.26-2.24 (m, 1H), 1.75-1.71 (m, 1H), 1.30-1.25 (m, 6H), 1.16 (d, J = 6.7 Hz, 3H) |
| 102 | 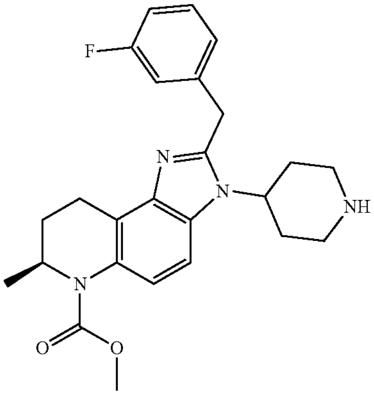 methyl (S)-2-(3-fluorobenzyl)-7-methyl-3-(piperidin-4-yl)-3,7,8,9-tetrahydro-6H-imidazo[4,5-f]quinoline-6-carboxylate | 437 | $^1$H-NMR ($CD_3OD$, 300 MHz) δ (ppm): 7.57 (d, J = 9.0 Hz, 1H), 7.48-7.29 (m, 2H), 7.14-6.95 (m, 3H), 4.85-4.73 (m, 1H), 4.49-4.29 (m, 3H), 3.80 (s, 3H), 3.33-2.91 (m, 4H), 2.62-2.54 (m, 2H), 2.47-2.19 (m, 3H), 1.87-1.70 (m, 1H), 1.50-1.42 (m, 2H), 1.17 (d, J = 6.6 Hz, 3H) |
| 103 | 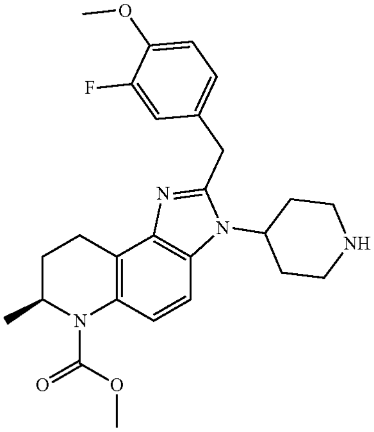 methyl (S)-2-(3-fluoro-4-methoxybenzyl)-7-methyl-3-(piperidin-4-yl)-3,7,8,9-tetrahydro-6H-imidazo[4,5-f]quinoline-6-carboxylate | 467 | $^1$H-NMR ($CDCl_3$, 300 MHz) δ (ppm): 7.52-7.41 (m, 2H), 6.94-6.85 (m, 3H), 4.83-4.77 (m, 1H), 4.35-4.23 (m, 3H), 3.85 (s, 3H), 3.79 (s, 3H), 3.39 (d, J = 10.6 Hz, 2H), 3.34-3.16 (m, 1H), 3.11-2.95 (m, 1H), 2.78-2.65 (m, 4H), 2.30-2.23 (m, 1H), 1.79-1.72 (m, 1H), 1.66-1.51 (m, 2H), 1.18 (d, J = 6.7 Hz, 3H) |

TABLE 6-continued

| Example Number | Structure and Compound Name | LRMS m/z $[M + H]^+$ | $^1$HNMR |
|---|---|---|---|
| 104 | 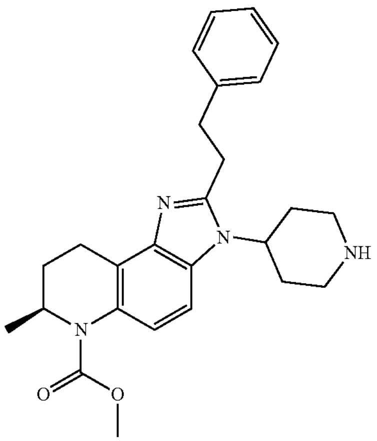 methyl (S)-7-methyl-2-phenethyl-3-(piperidin-4-yl)-3,7,8,9-tetrahydro-6H-imidazo[4,5-f]-quinoline-6-carboxylate | 433 | $^1$H-NMR ($CD_3OD$, 300 MHz) δ (ppm): 7.52 (d, J = 9.0 Hz, 1H), 7.41-7.13 (m, 6H), 4.86-4.69 (m, 1H), 4.30-4.18 (m, 1H), 3.79 (s, 3H), 3.33-3.07 (m, 7H), 2.98-2.88 (m, 1H), 2.76-2.57 (m, 2H), 2.44-2.18 (m, 3H), 1.83-1.67 (m, 1H), 1.51-1.29 (m, 2H), 1.16 (d, J = 6.7 Hz, 3H) |
| 105 | 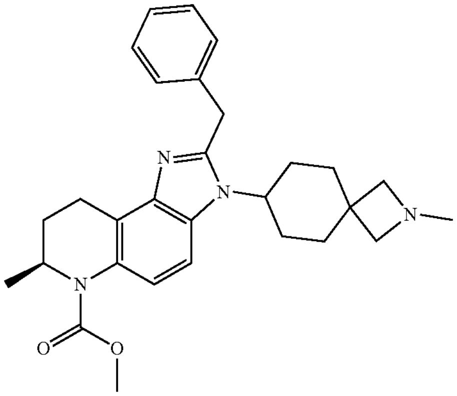 methyl (S)-2-benzyl-7-methyl-3-(2-methyl-2-azaspiro-[3.5]nonan-7-yl)-3,7,8,9-tetrahydro-6H-imidazo[4,5-f]quinoline-6-carboxylate | 473 | $^1$H-NMR ($CD_3OD$, 300 MHz) δ (ppm): 7.38-7.36 (m, 1H), 7.32-7.30 (m, 2H), 7.25-7.21 (m, 4H), 4.77-4.43 (m, 1H), 4.39-4.38 (m, 2H), 4.21-4.15 (m, 1H), 3.76 (s, 3H), 3.24-3.16 (m, 3H), 3.03-2.99 (m, 2H), 2.97-2.91 (m, 1H), 2.37 (s, 3H), 2.27-2.20 (m, 1H), 2.11-2.01 (m, 2H), 1.97-1.94 (m, 2H), 1.78-1.72 (m, 1H), 1.44-1.37 (m, 4H), 1.14 (d, J = 5.1 Hz, 3H) |
| 106 | 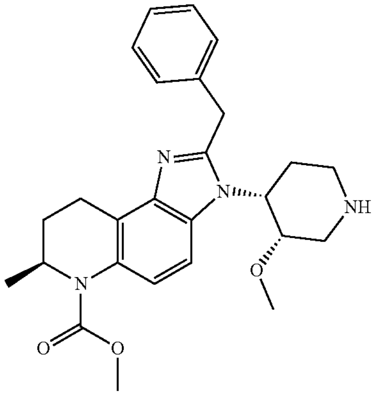 methyl (S)-2-benzyl-3-((3S,4R)-3-methoxy-piperidin-4-yl)-7-methyl-3,7,8,9-tetrahydro-6H-imidazo[4,5-f]quinoline-6-carboxylate | 449 | $^1$H-NMR ($CD_3OD$, 300 MHz) δ (ppm): 7.63 (d, J = 9.1 Hz, 1H), 7.39-7.17 (m, 6H), 4.80-4.68 (m, 1H), 4.42 (s, 3H), 3.75 (s, 3H), 3.27-3.13 (m, 1H), 3.12-2.99 (m, 2H), 2.98-2.83 (m, 4H), 2.82-2.68 (m, 1H), 2.65 (s, 1H), 2.60-2.34 (m, 2H), 2.32-2.14 (m, 1H), 1.82-1.65 (m, 1H), 1.36 (d, J = 12.4 Hz, 1H), 1.10 (d, J = 6.6 Hz, 3H) |

TABLE 6-continued

| Example Number | Structure and Compound Name | LRMS m/z [M + H]+ | 1HNMR |
|---|---|---|---|
| 107 | 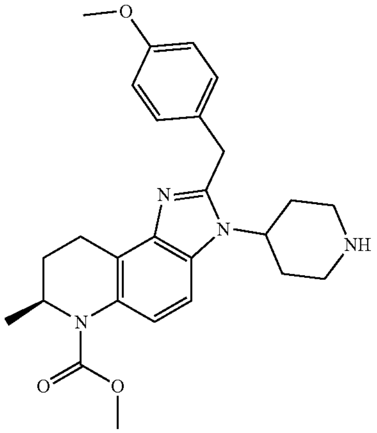 methyl (S)-2-(4-methoxybenzyl)-7-methyl-3-(piperidin-4-yl)-3,7,8,9-tetrahydro-6H-imidazo[4,5-f]quinoline-6-carboxylate | 449 | $^1$H-NMR ($CD_3OD$, 400 MHz) δ (ppm): 7.54-7.52 (d, J = 8.0 Hz, 1H), 7.41-7.39 (d, J = 8.8 Hz, 1H), 7.20-7.18 (d, J = 8.4 Hz, 2H), 6.91-6.89 (d, J = 8.8 Hz, 2H), 4.81-4.76 (m, 1H), 4.40-4.36 (m, 3H), 3.79-3.77 (m, 6H), 3.34-3.21 (m, 1H), 3.21-3.02 (m, 2H), 3.00-2.96 (m, 1H), 2.58-2.57 (m, 2H), 2.37-2.25 (m, 3H), 1.80-1.75 (m, 1H), 1.48-1.40 (m, 2H), 1.17-1.16 (d, J = 6.4 Hz, 3H) |
| 108 | 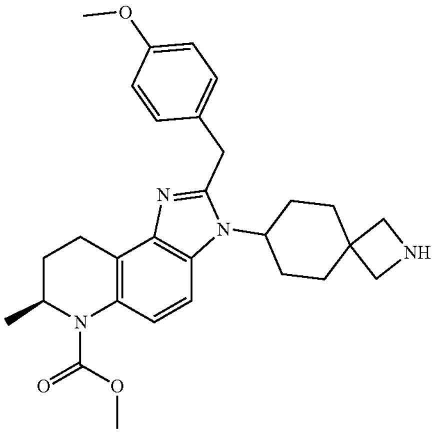 methyl (S)-2-(4-methoxybenzyl)-7-methyl-3-(2-azaspiro[3.5]nonan-7-yl)-3,7,8,9-tetrahydro-6H-imidazo[4,5-f]quinoline-6-carboxylate | 489 | $^1$H-NMR ($CD_3OD$, 300 MHz) δ (ppm): 7.41-7.38 (d, J = 9 Hz, 1H), 7.30-7.16 (m, 3H), 6.92-6.88 (m, 2H), 4.81-4.75 (m, 1H), 4.33 (s, 2H), 4.28-4.20 (m, 1H), 3.79-3.73 (m, 6H), 3.63 (s, 2H), 3.42 (s, 2H), 3.28-3.17 (m, 1H), 3.02-2.92 (m, 1H), 2.33-2.24 (m, 1H), 2.16-2.09 (m, 4H), 1.82-1.74 (m, 1H), 1.51-1.42 (m, 4H), 1.15-1.13 (d, J = 6.6 Hz, 3H) |
| 109 | 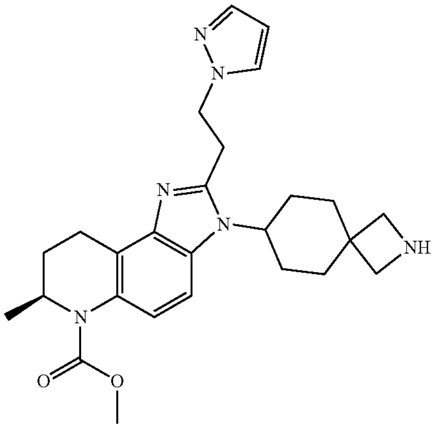 methyl (S)-2-(2-(1H-pyrazol-1-yl)ethyl)-7-methyl-3-(2-azaspiro[3.5]nonan-7-yl)-3,7,8,9-tetrahydro-6H-imidazo[4,5-f]quinoline-6-carboxylate | 463 | $^1$H-NMR ($CD_3OD$, 400 MHz) δ (ppm): 7.52-7.48 (m, 2H), 7.37-7.34 (m, 1H), 7.26-7.24 (m, 1H), 6.21-6.20 (m, 1H), 4.76-4.73 (m, 1H), 4.65-4.62 (m, 2H), 4.25-4.16 (m, 1H), 3.87-3.85 (m, 2H), 3.75 (s, 3H), 3.63-3.57 (m, 2H), 3.51-3.47 (m, 2H), 3.15-3.11 (m, 1H), 2.93-2.89 (m, 1H), 2.25-2.13 (m, 5H), 1.74-1.57 (m, 5H), 1.12 (d, J = 6.8 Hz, 3H) |

TABLE 6-continued

| Example Number | Structure and Compound Name | LRMS m/z [M + H]+ | ¹HNMR |
|---|---|---|---|
| 110 | 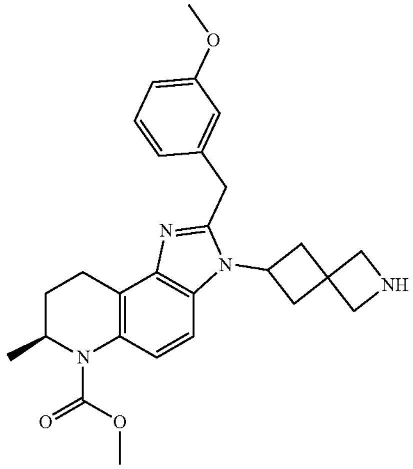<br>methyl (S)-2-(3-methoxybenzyl)-7-methyl-3-(2-azaspiro[3.3]heptan-6-yl)-3,7,8,9-tetrahydro-6H-imidazo[4,5-f]quinoline-6-carboxylate | 461 | ¹H-NMR ($CD_3OD$, 400 MHz) δ (ppm): 7.44-7.40 (m, 2H), 7.26-7.22 (m, 1H), 6.84-6.69 (m, 3H), 4.90-4.76 (m, 2H), 4.36 (s, 2H), 3.93-3.91 (m, 1H), 3.80-3.76 (m, 9H), 3.23-3.21 (m, 1H), 3.19-2.93 (m, 3H), 2.54-2.24 (m, 3H), 1.81-1.74 (m, 1H), 1.16 (d, J = 6.8 Hz, 3H) |

Examples 111 and 112: methyl (S)-2-benzyl-7-methyl-3-((S)-7-azaspiro[3.5]nonan-1-yl)-3,7,8,9-tetrahydro-6H-imidazo[4,5-f]quinoline-6-carboxylate and methyl (S)-2-benzyl-7-methyl-3-((R)-7-azaspiro[3.5]nonan-1-yl)-3,7,8,9-tetrahydro-6H-imidazo[4,5-f]quinoline-6-carboxylate

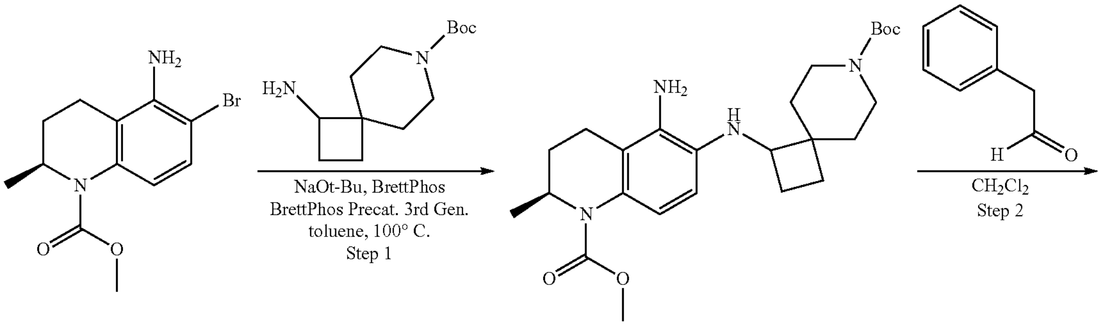

-continued

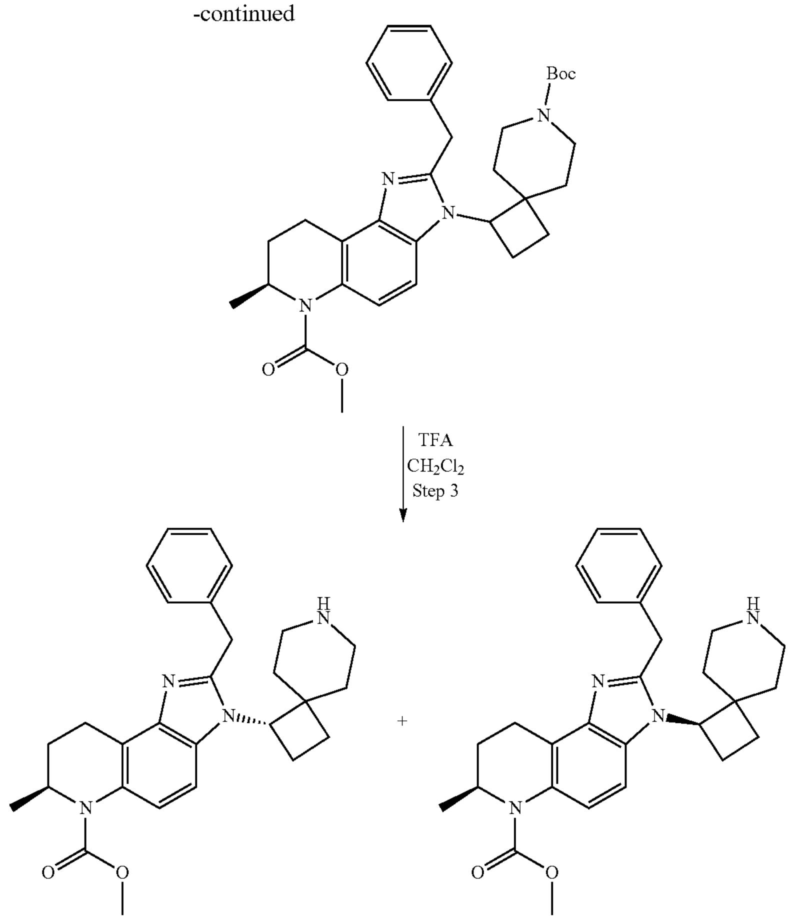

Step 1. Synthesis of methyl (2S)-5-amino-6-([7-[(tert-butoxy)carbonyl]-7-azaspiro[3.5]nonan-1-yl]amino)-2-methyl-1,2,3,4-tetrahydroquinoline-1-carboxylate Into a 10-mL round-bottom flask purged and maintained with an inert atmosphere of nitrogen, methyl (2S)-5-amino-6-bromo-2-methyl-1,2,3,4-tetrahydroquinoline-1-carboxylate (100 mg, 0.33 mmol, Intermediate 1) was dissolved in toluene (4 mL). Then tert-butyl 1-amino-7-azaspiro[3.5]nonane-7-carboxylate (242 mg, 1.01 mmol), Brettphos (36 mg, 0.07 mmol), 3rd Generation BrettPhos precatalyst (60.8 mg, 0.07 mmol) and sodium tert-butoxide (48.3 mg, 0.50 mmol) were added. The resulting solution was stirred for 1 h at 100° C. under nitrogen atmosphere. The reaction mixture was cooled to room temperature and the solids were filtered out. The filtrate was concentrated under vacuum. The residue was subjected to purification by FCC eluting with ethyl acetate/petroleum ether (2:1). This afforded the title compound (52.8 mg, 34%) as a brown solid. MS: (ES, m/z): 459 $[M+H]^+$.

Step 2. Synthesis of tert-butyl 1-[(7S)-2-benzyl-6-(methoxycarbonyl)-7-methyl-3H,6H,7H,8H,9H-imidazo[4,5-f]quinolin-3-yl]-7-azaspiro[3.5]nonane-7-carboxylate Into a 25-mL round-bottom flask, methyl (2S)-5-amino-6-([7-[(tert-butoxy)carbonyl]-7-azaspiro[3.5]nonan-1-yl]amino)-2-methyl-1,2,3,4-tetrahydroquinoline-1-carboxylate (52.8 mg, 0.12 mmol) was dissolved in dichloromethane (5 mL). Then 2-phenylacetaldehyde (83 mg, 0.69 mmol) was added. The resulting solution was stirred for 4 h at room temperature. The resulting mixture was concentrated under vacuum. The residue was subjected to purification by FCC eluting with ethyl acetate/petroleum ether (2:1). This afforded the title compound (25 mg, 39%) as a yellow oil. MS: (ES, m/z): 559 $[M+H]^+$.

Step 3. Synthesis of methyl (S)-2-benzyl-7-methyl-3-((S)-7-azaspiro[3.5]nonan-1-yl)-3,7,8,9-tetrahydro-6H-imidazo[4,5-f]quinoline-6-carboxylate and methyl (S)-2-benzyl-7-methyl-3-((R)-7-azaspiro[3.5]nonan-1-yl)-3,7,8,9-tetrahydro-6H-imidazo[4,5-f]quinoline-6-carboxylate Into a 25-mL round-bottom flask, tert-butyl 1-[(7S)-2-benzyl-6-(methoxycarbonyl)-7-methyl-3H,6H,7H,8H,9H-imidazo[4,5-f]quinolin-3-yl]-7-azaspiro[3.5]nonane-7-carboxylate (25 mg, 0.04 mmol) was dissolved in dichloromethane (5 mL). Then trifluoroacetic acid (1 mL) was added. The resulting solution was stirred for 2 h at room temperature. The resulting mixture was concentrated under vacuum. The crude product was purified by Prep-HPLC with the following conditions: Column, XBridge C18 OBD Prep Column, 100 Å, 5 um, 19 mm×250 mm; mobile phase, A: Water (containing 10 mmol/L $NH_4HCO_3$) and B: ACN (25.0% to 40.0% ACN over 8 min); UV Detector: 254 nm. This afforded the title compounds as follows: 2.4 mg (12%) of methyl (7S)-3-[(1R)-7-azaspiro[3.5]nonan-1-yl]-2-benzyl-7-methyl-3H,6H,7H,8H,9H-imidazo[4,5-f]quinoline-6-carboxylate (assumed stereochemistry, first eluting isomer, RT=5.8 min) as a white solid and 1.7 mg (8%) of methyl (7S)-3-[(1S)-7-azaspiro[3.5]nonan-1-yl]-2-benzyl-7-methyl-3H,6H,7H,8H,9H-imidazo[4,5-f]quinoline-6-carboxylate (assumed stereochemistry, second eluting isomer, RT=7.1 min) as a white solid.

First eluting isomer: $^1$H-NMR ($CD_3OD$, 400 MHz) δ (ppm): 7.69 (d, J=9.0 Hz, 1H), 7.48 (d, J=9.0 Hz, 1H), 7.39-7.23 (m, 3H), 7.21-7.14 (m, 2H), 4.82-4.78 (m, 1H), 4.68-4.62 (m, 1H), 4.50-4.32 (m, 2H), 3.80 (s, 3H), 3.28-3.06 (m, 2H), 3.02-2.96 (m, 1H), 2.88-2.81 (m, 1H), 2.77-2.55 (m, 3H), 2.40-2.15 (m, 3H), 1.89-1.66 (m, 4H), 1.48-1.40 (m, 1H), 1.18 (d, J=6.7 Hz, 3H), 1.09-1.02 (m, 1H). MS: (ES, m/z): 459 $[M+H]^+$.

Second eluting isomer: $^1$H-NMR ($CD_3OD$, 400 MHz) δ (ppm): 7.70 (d, J=9.0 Hz, 1H), 7.48 (d, J=9.0 Hz, 1H), 7.39-7.23 (m, 3H), 7.22-7.15 (m, 2H), 4.82-4.77 (m, 1H), 4.72-4.68 (m, 1H), 4.48-4.32 (m, 2H), 3.81 (s, 3H), 3.25-3.08 (m, 2H), 3.02-2.94 (m, 1H), 2.90-2.82 (m, 1H), 2.80-2.60 (m, 3H), 2.42-2.30 (m, 1H), 2.28-2.16 (m, 2H), 1.94-1.88 (m, 1H), 1.87-1.67 (m, 3H), 1.45-1.38 (m, 1H), 1.17 (d, J=6.7 Hz, 3H), 1.12-1.08 (m, 1H). MS: (ES, m/z): 459 $[M+H]^+$.

The following examples in TABLE 7 were prepared using standard chemical manipulations and procedures similar to those used for the preparation of Examples 111 and 112.

TABLE 7

| Example Number | Structure and Compound Name | LRMS m/z $[M + H]^+$ | $^1$HNMR |
|---|---|---|---|
| 113 and 114 | 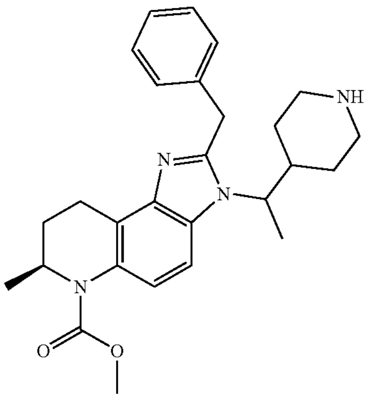<br>1st eluting isomer (113)<br>2nd eluting isomer (114)<br>methyl (7S)-2-benzyl-7-methyl-3-(1-(piperidin-4-yl)ethyl)-3,7,8,9-tetrahydro-6H-imidazo[4,5-f]quinoline-6-carboxylate | 1st eluting isomer = 447<br>2nd eluting isomer = 447 | 1st eluting isomer $^1$H-NMR ($CDCl_3$, 300 MHz) δ (ppm): 7.41-7.12 (m, 7H), 4.82-4.75 (m, 1H), 4.39-4.37 (m, 1H), 4.07-4.03 (m, 1H), 3.98-3.85 (m, 1H), 3.78 (s, 3H), 3.34-3.26 (m, 2H), 3.07-2.92 (m, 2H), 2.75-2.01 (m, 4H), 1.98-1.95 (m, 1H), 1.85-1.73 (m, 1H), 1.55-1.42 (m, 4H), 1.17 (d, J = 6.6 Hz, 3H), 1.12-0.88 (m, 2H)<br>2nd eluting isomer $^1$H-NMR ($CDCl_3$, 300 MHz) δ (ppm): 7.37 (d, J = 8.4 Hz, 1H), 7 28-7.26 (m, 1H), 7.24-7.17 (m, 5H), 4.81-4.75 (m, 1H), 4.44-4.41 (m, 1H), 4.21-4.12 (m, 1H), 4.01-3.88 (m, 1H), 3.78 (s, 3H), 3.56-3.27 (m, 2H), 3.06-2.99 (m, 2H), 2.72-2.06 (m, 5H), 1.99-1.96 (m, 2H), 1.48-1.29 (m, 3H), 120 (d, J = 6.6 Hz, 3H), 1.11-0.85 (m, 2H) |
| 115, 116, 117 and 118 | 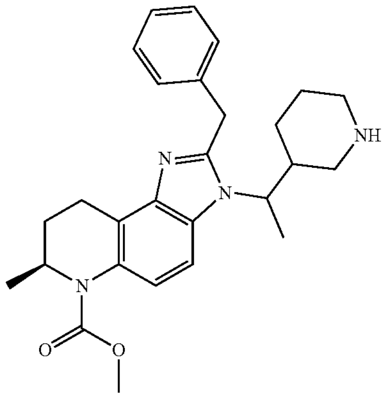<br>1st eluting isomer (115)<br>2nd eluting isomer (116)<br>3rd eluting isomer (117)<br>4th eluting isomer (118)<br>methyl (7S)-2-benzyl-7-methyl-3-(1-(piperidin-3-yl)ethyl)-3,7,8,9-tetrahydro-6H-imidazo[4,5-f]quinoline-6-carboxylate | 1st eluting isomer = 447<br>2nd eluting isomer = 447<br>3rd eluting isomer = 447<br>4th eluting isomer = 447 | 1st eluting isomer $^1$H-NMR ($CDCl_3$, 300 MHz) δ (ppm): 9.42 (s, 1H), 7.74 (d, J = 8.9 Hz, 1H), 7.57-7.51 (m, 1H), 7.52-7.23 (m, 5H), 4.94 (s, 1H), 4.93-4.74 (m, 2H), 4.45 (s, 1H), 3.81 (s, 3H), 3.35-2.90 (m, 4H), 2.66 (s, 3H), 2.02-1.53 (m, 3H), 1.44 (s, 2H), 1.21 (s, 3H), 1.14 (d, J = 6.6 Hz, 3H)<br>2nd eluting isomer $^1$H-NMR ($CD_3$, 300 MHz) δ (ppm): 7.38 (d, J = 8.8 Hz, 1H), 7.33-7.28 (m, 2H), 7.26-7.20 (m, 4H), 4.82-4.80 (m, 1H), 4.40-4.22 (m, 2H), 4.10-3.98 (m, 1H), 3.78 (s, 3H), 3.35-3.17 (m, 1H), 3.14-2.98 (m, 1H), 2.89 (d, J = 12.0 Hz, 1H), 2.48-2.37 (m, 2H), 2.34-2.16 (m, 2H), 2.00 (d, J = 13.1 Hz, 1H), 1.82-1.71 (m, 3H), 1.44 (s, 1H), 1.26 (d, J = 6.9 Hz, 3H), 1.19 (d, J = 6.7 Hz, 3H), 1.09-0.85 (m, 1H)<br>3rd eluting isomer $^1$H-NMR ($CDCl_3$, 300 MHz) δ (ppm): 7.42 (d, J = 8.9 Hz, 1H), 7.32-7.27 (m, 2H), 7.26-7.20 (m, 4H), 4.83-4.79 (m, 1H), 4.32 (s, 2H), 4.05-3.91 (m, 1H), 3.80 (s, 3H), 3.41-3.19 (m, 2H), 3.16-2.98 (m, 2H), 2.53-2.17 (m, 4H), 1.81-1.74 (m, 1H), 1.50- |

TABLE 7-continued

| Example Number | Structure and Compound Name | LRMS m/z [M + H]$^+$ | $^1$HNMR |
|---|---|---|---|
| | | | 1.38 (m, 2H), 1.29 (d, J = 6.9 Hz, 3H), 1.18 (d, J = 6.7 Hz, 3H), 1.15-1.04 (m, 1H), 0.38-0.25 (m, 1H) 4$^{th}$ eluting isomer $^1$H-NMR ($CDCl_3$, 300 MHz) δ (ppm): 7.42 (d, J = 8.9 Hz, 1H), 7.33-7.27 (m, 2H), 7.25-7.19 (m, 4H), 4.82-4.78 (m, 1H), 4.41-4.22 (m, 2H), 4.06-3.93 (m, 1H), 3.79 (s, 3H), 3.54 (d, J = 11.4 Hz, 1H), 3.39-3.17 (m, 2H), 3.14-2.98 (m, 1H), 2.81-2.53 (m, 2H), 2.44 (t, J = 11.9 Hz, 1H), 2.35-2.17 (m, 1H), 1.85-1.68 (m, 1H), 1.64 (s, 2H), 1.28-1.22 (m, 3H), 1.25-1.16 (m, 4H), 0.50 (s, 1H) |
| 119, 120, 121 and 122 | 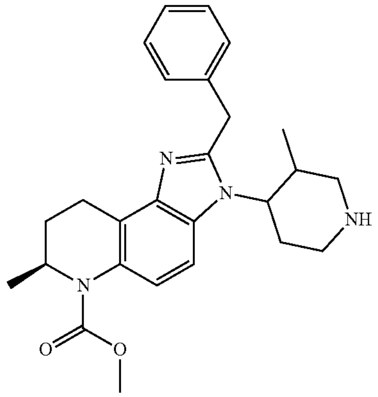 1$^{st}$ eluting isomer (119) 2$^{nd}$ eluting isomer (120) 3$^{rd}$ eluting isomer (121) 4$^{th}$ eluting isomer (122) methyl (7S)-2-benzyl-7-methyl-3-(3-methyl-piperidin-4-yl)-3,7,8,9-tetrahydro-6H-imidazo[4,5-f]quinoline-6-carboxylate | 1$^{st}$ eluting isomer = 433 2$^{nd}$ eluting isomer = 433 3$^{rd}$ eluting isomer = 433 4$^{th}$ eluting isomer = 433 | 1$^{st}$ eluting isomer $^1$H-NMR ($CDCl_3$, 400 MHz) δ (ppm): 7.46-7.34 (m, 2H), 7.33-7.27 (m, 2H), 7.26-7.17 (m, 3H), 4.85-4.76 (m, 1H), 4.52-4.38 (m, 1H), 4.36-1.21 (m, 1H), 3.85-3.65 (m, 4H), 3.34-3.18 (m, 2H), 3.18-3.01 (m, 2H), 2.64-2.53 (m, 1H), 2.51-2.40 (m, 1H), 2.36-2.16 (m, 3H), 1.82-1.71 (m, 1H), 1.30-1.22 (m, 1H), 1.15-1.20 (m, 3H), 1.06-0.80 (m, 1H), 0.45-0.34 (m, 3H) 2$^{nd}$ eluting isomer $^1$H-NMR ($CDCl_3$, 400 MHz) δ (ppm): 7.56-7.52 (m, 2H), 7.39-7.26 (m, 2H), 7.25-7.20 (m, 3H), 4.85-4.75 (m, 1H), 4.58-4.48 (m, 1H), 4.27-4.17 (m, 1H), 3.85-3.72 (m, 4H), 3.34-3.21 (m, 2H), 3.18-3.01 (m, 2H), 2.66-2.52 (m, 1H), 2.45-2.22 (m, 4H), 1.82-1.71 (m, 1H), 1.39-1.00 (m, 5H), 0.62-0.48 (m, 3H) 3$^{rd}$ eluting isomer $^1$H-NMR ($CDCl_3$, 400 MHz) δ (ppm): 7.46-7.26 (m, 4H), 7.25-7.16 (m, 3H), 4.86-4.75 (m, 1H), 4.47-4.25 (m, 3H), 3.78 (s, 3H), 3.41-3.20 (m, 2H), 3.12-3.01 (m, 1H), 2.93-2.73 (m, 3H), 2.60 (t, J = 12.0 Hz, 1H), 2.32-2.19 (m, 1H), 1.82-1.72 (m, 1H), 1.69-1.50 (m, 2H), 1.37-1.26 (m, 1H), 1.17 (d, J = 6.8 Hz, 3H), 1.11 (d, J = 7.2 Hz, 3H) 4$^{th}$ eluting isomer $^1$H-NMR ($CDCl_3$, 400 MHz) δ (ppm): 7.44-7.17 (m, 7H), 4.88-4.79 (m, 1H), 4.50-1.31 (m, 3H), 3.81 (s, 3H), 3.36-3.20 (m, 2H), 3.19-3.02 (m, 1H), 2.97-2.70 (m, 3H), 2.58-2.42 (m, 1H), 2.36-2.17 (m, 1H), 1.87-1.78 (m, 3H), 1.59-1.49 (m, 1H), 1.18 (d, J = 6.8 Hz, 3H), 1.11 (d, J = 7.2 Hz, 3H). |

TABLE 7-continued

| Example Number | Structure and Compound Name | LRMS m/z $[M + H]^+$ | $^1$HNMR |
|---|---|---|---|
| 123, 124, 125 and 126 | 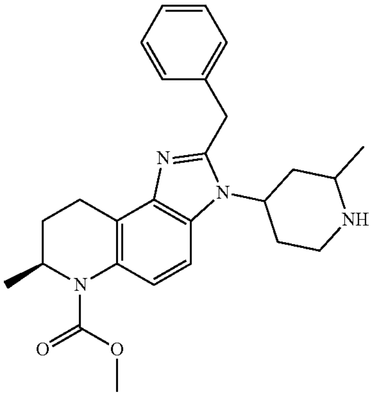<br>$1^{st}$ eluting isomer (123)<br>$2^{nd}$ eluting isomer (124)<br>$3^{rd}$ eluting isomer (125)<br>$4^{th}$ eluting isomer (126)<br>methyl (7S)-2-benzyl-7-methyl-3-(2-methyl-piperidin-4-yl)-3,7,8,9-tetrahydro-6H-imidazo[4,5-f]quinoline-6-carboxyla3e | $1^{st}$ eluting isomer = 433<br>$2^{nd}$ eluting isomer = 433<br>$3^{rd}$ eluting isomer = 433<br>$4^{th}$ eluting isomer = 433 | $1^{st}$ eluting isomer $^1$H-NMR ($CD_3OD$, 300 MHz) δ (ppm): 7.55 (d, J = 9.0 Hz, 1H), 7.46-7.20 (m, 6H), 4.82-4.72 (m, 1H), 4.65-4.42 (m, 3H), 3.80 (s, 3H), 3.30-3.18 (m, 1H), 3.02-2.82 (m, 3H), 2.58-2.48 (m, 1H), 2.40-2.20 (m, 2H), 1.82-1.74 (m, 1H), 1.62-1.52 (m, 1H), 1.32-1.13 (m, 5H), 1.00 (d, J = 7.1 Hz, 3H)<br>$2^{nd}$ eluting isomer $^1$H-NMR ($CD_3OD$, 300 MHz) δ (ppm): 7.55 (d, J = 9.0 Hz, 1H), 7.46-7.20 (m, 6H), 4.82-4.72 (m, 1H), 4.65-4.42 (m, 3H), 3.80 (s, 3H), 3.30-3.18 (m, 1H), 3.02-2.82 (m, 3H), 2.52-2.22 (m, 3H), 1.82-1.74 (m, 1H), 1.62-1.52 (m, 1H), 1.32-1.13 (m, 5H), 1.00 (d, J = 7.1 Hz, 3H)<br>$3^{rd}$ eluting isomer $^1$H-NMR ($CD_3OD$, 300 MHz) δ (ppm): 7.55 (d, J = 9.0 Hz, 1H), 7.46-7.20 (m, 6H), 4.82-4.72 (m, 1H), 4.65-4.42 (m, 3H), 3.80 (s, 3H), 3.30-3.18 (m, 1H), 3.02-2.92 (m, 2H), 2.64-2.52 (m, 2H), 2.32-2.12 (m, 2H), 2.00-1.72 (m, 2H), 1.45-1.30 (m, 2H), 1.26-1.13 (m, 3H), 1.08 (d, J = 6.3 Hz, 3H)<br>$4^{th}$ eluting isomer $^1$H-NMR ($CD_3OD$, 300 MHz) δ (ppm): 7.55 (d, J = 9.0 Hz, 1H), 7.46-7.20 (m, 6H), 4.82-4.72 (m, 1H), 4.65-4.42 (m, 3H), 3.80 (s, 3H), 3.30-3.18 (m, 1H), 3.02-2.92 (m, 2H), 2.64-2.52 (m, 2H), 2.32-2.12 (m, 2H), 2.00-1.72 (m, 2H), 1.45-1.30 (m, 2H), 1.26-1.13 (m, 3H), 1.08 (d, J = 6.3 Hz, 3H) |
| 127 and 128 | 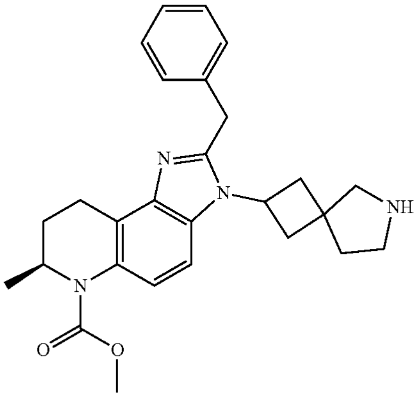<br>$1^{st}$ eluting isomer (127)<br>$2^{nd}$ eluting isomer (128)<br>methyl (S)-2-benzyl-7-methyl-3-(6-azaspiro-[3.4]octan-2-yl)-3,7,8,9-tetrahydro-6H-imidazo[4,5-f]quinoline-6-carboxylate | $1^{st}$ eluting isomer = 445<br>$2^{nd}$ eluting isomer = 445 | 1st eluting isomer $^1$H-NMR ($CD_3OD$, 400 MHz) δ (ppm): 7.58-7.45 (m, 2H), 7.38-7.15 (m, 5H), 5.03-4.89 (m, 1H), 4.84-4.74 (m, 1H), 4.43 (s, 2H), 3.80 (s, 3H), 3.29-3.12 (m, 5H), 3.02-2.92 (m, 3H), 2.39-2.21 (m, 3H), 2.17-2.12 (m, 2H), 1.79-1.72 (m, 1H), 1.17 (d, J = 6.6 Hz, 3H)<br>$2^{nd}$ eluting isomer $^1$H-NMR ($CD_3OD$, 400 MHz) δ (ppm): 7.55-7.44 (m, 2H), 7.38-7.15 (m, 5H), 5.02-4.92 (m, 1H), 4.82-4.78 (m, 1H), 4.43 (s, 2H), 3.80 (s, 3H), 3.30-3.15 (m, 5H), 3.04-2.88 (m, 3H), 2.34-2.17 (m, 3H), 2.08-2.02 (m, 2H), 1.79-1.72 (m, 1H), 1.17 (d, J = 6.6 Hz, 3H) |

TABLE 7-continued

| Example Number | Structure and Compound Name | LRMS m/z $[M + H]^+$ | $^1$HNMR |
|---|---|---|---|
| 129, 130, 131 and 132 | 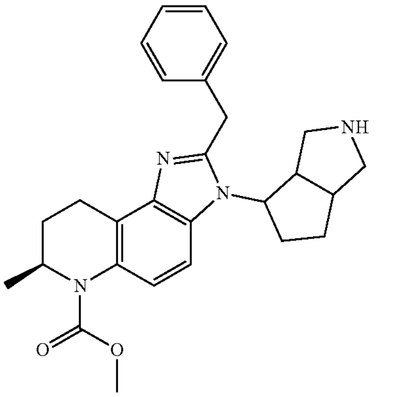<br>1st eluting isomer (129)<br>2nd eluting isomer (130)<br>3rd eluting isomer (131)<br>4th eluting isomer (132)<br>methyl (7S)-2-benzyl-7-methyl-3-(octa-hydrocyclopenta[c]pyrrol-4-yl)-3,7,8,9-tetrahydro-6H-imidazo[4,5-f]quinoline-6-carboxylate | 1st eluting isomer = 445<br>2nd eluting isomer = 445<br>3rd eluting isomer = 445<br>4th eluting isomer = 445 | 1st eluting isomer $^1$H-NMR ($CD_3OD$, 300 MHz) δ (ppm): 7.50-7.19 (m, 7H), 4.81-4.77 (m, 1H), 4.53-4.33 (m, 3H), 3.80 (s, 3H), 3.29-3.12 (m, 3H), 3.08-2.93 (m, 2H), 2.80-2.72 (m, 2H), 2.45-2.00 (m, 5H), 1.82-1.72 (m, 2H), 1.18 (d, J = 3.0 Hz, 1H)<br>2nd eluting isomer $^1$H-NMR ($CD_3OD$, 400 MHz) δ (ppm): 7.30-7.10 (m, 7H), 4.69-4.62 (m, 1H), 4.35-4.20 (m, 3H), 3.68 (s, 3H), 3.52-3.48 (m, 2H), 3.15-3.02 (m, 2H), 2.92-2.84 (m, 2H), 2.65-2.60 (m, 1H), 2.30-1.92 (m, 5H), 1.70-1.60 (m, 2H), 1.05 (d, J = 4.0 Hz, 3H)<br>3rd eluting isomer $^1$H-NMR ($CD_3OD$, 300 MHz) δ (ppm): 7.62 (d, J = 9.1 Hz, 1H), 7.50-7.17 (m, 6H), 4.86-4.75 (m, 1H), 4.48-4.46 (m, 2H), 3.80 (s, 3H), 3.28-2.78 (m, 5H), 2.69-2.52 (m, 3H), 2.50-2.38 (m, 2H), 2.30-2.22 (m, 1H), 2.00-1.90 (m, 1H), 1.85-1.69 (m, 3H), 1.19 (d, J = 6.6 Hz, 3H)<br>4th eluting isomer $^1$H-NMR ($CD_3OD$, 300 MHz) δ (ppm): 7.65-7.18 (m, 7H), 4.85-4.78 (m, 2H), 4.48-4.46 (m, 2H), 3.79 (s, 3H), 3.27-3.15 (m, 2H), 3.10-2.60 (m, 5H), 2.48-2.40 (m, 2H), 2.32-2.20 (m, 1H), 2.04-1.92 (m, 1H), 1.86-1.68 (m, 3H), 1.15 (d, J = 4.50 Hz, 3H) |

Examples 133 and 134: (2R)-3-[(7S)-6-(methoxycarbonyl)-3,7-dimethyl-3H,6H,7H,8H,9H-imidazo[4,5-f]quinolin-2-yl]-2-phenylpropanoic acid and (2S)-3-[(7S)-6-(methoxycarbonyl)-3,7-dimethyl-3H,6H,7H,8H,9H-imidazo[4,5-f]quinolin-2-yl]-2-phenylpropanoic acid

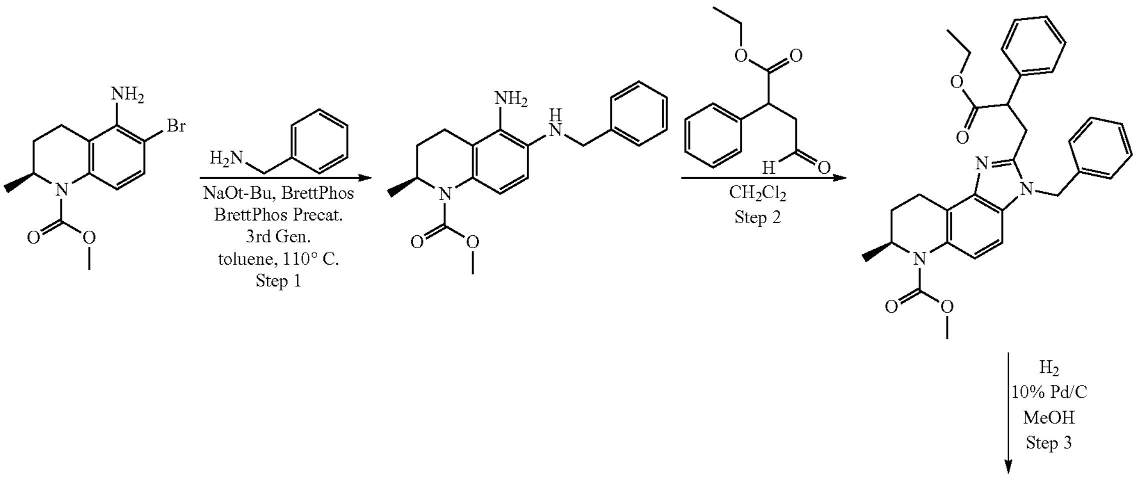

-continued

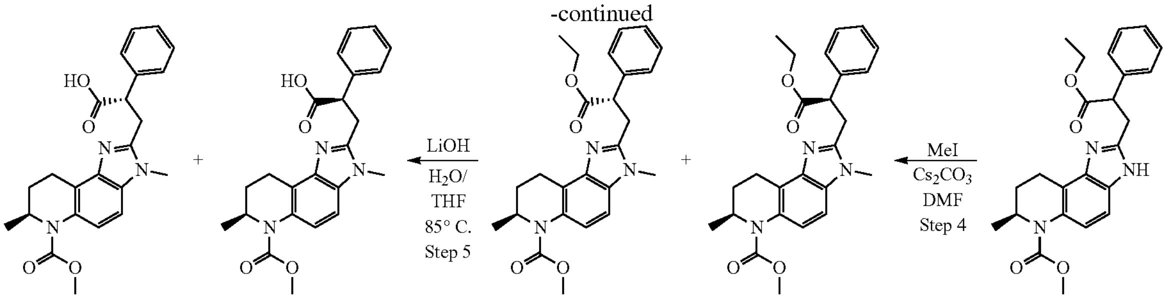

Step 1. Synthesis of methyl (S)-5-amino-6-(benzylamino)-2-methyl-3,4-dihydroquinoline-1(2H)-carboxylate Into a 50-mL round-bottom flask purged and maintained with an inert atmosphere of nitrogen, methyl (2S)-5-amino-6-bromo-2-methyl-1,2,3,4-tetrahydroquinoline-1-carboxylate (250 mg, 1.66 mmol, Intermediate 1) was dissolved in toluene (20 mL). Then benzyl amine (375 mg, 3.5 mmol), Brettphos (144 mg, 0.26 mmol), $3^{rd}$ Generation BrettPhos precatalyst (122 mg, 0.14 mmol) and sodium tert-butoxide (483 mg, 5.0 mmol) were added. The resulting solution was stirred for 1 h at 110° C. under nitrogen atmosphere. The reaction mixture was cooled to room temperature and the solids were filtered out. The filtrate was concentrated under vacuum. The residue was subjected to purification by FCC eluting with ethyl acetate/petroleum ether (2:1). This afforded the title compound (352 mg, 65%) as a yellow solid. MS: (ES, m/z): 325 $[M+H]^+$.

Step 2. Synthesis of methyl (7S)-3-benzyl-2-(3-ethoxy-3-oxo-2-phenylpropyl)-7-methyl-3H,6H,7H,8H,9H-imidazo[4,5-f]quinoline-6-carboxylate Into a 50-mL round-bottom flask purged and maintained with an inert atmosphere of nitrogen, methyl (2S)-5-amino-6-(benzylamino)-2-methyl-1,2,3,4-tetrahydronaphthalene-1-carboxylate (350 mg, 0.86 mmol) was dissolved in dichloromethane (10 mL). Then ethyl 4-oxo-2-phenylbutanoate (281 mg, 1.29 mmol, Intermediate 32) was added. The resulting solution was stirred for 2 h at room temperature. The resulting mixture was concentrated under vacuum. The residue was subjected to purification by FCC eluting with ethyl acetate/petroleum ether (1:2). This afforded the title compound (210 mg, 48%) as a yellow solid. MS: (ES, m/z): 512 $[M+H]^+$.

Step 3. Synthesis of methyl (7S)-2-(3-ethoxy-3-oxo-2-phenylpropyl)-7-methyl-3H,6H,7H,8H,9H-imidazo[4,5-f]quinoline-6-carboxylate Into a 50-mL round-bottom flask purged and maintained with an inert atmosphere of nitrogen, methyl (7S)-3-benzyl-2-(3-ethoxy-3-oxo-2-phenylpropyl)-7-methyl-3H,6H,7H,8H,9H-imidazo[4,5-f]quinoline-6-carboxylate (100 mg, 0.19 mmol) was dissolved in methanol (5 mL). Then palladium on carbon (10%, 50 mg) was added and hydrogen (g) was charged into the reaction mixture. The reaction mixture was stirred overnight at room temperature. The reaction was vented to nitrogen and the solids were filtered out over celite. The filtrate was concentrated under vacuum. This afforded the title compound (80 mg, 98%) as a yellow oil. MS: (ES, m/z): 422 $[M+H]^+$.

Step 4. Synthesis of methyl (7S)-2-[(2R)-3-ethoxy-3-oxo-2-phenylpropyl]-3,7-dimethyl-3H,6H,7H,8H,9H-imidazo[4,5-f]quinoline-6-carboxylate and methyl (7S)-2-[(2S)-3-ethoxy-3-oxo-2-phenylpropyl]-3,7-dimethyl-3H,6H,7H,8H,9H-imidazo[4,5-f]quinoline-6-carboxylate Into a 50-mL round-bottom flask purged and maintained with an inert atmosphere of nitrogen, methyl (7S)-2-(3-ethoxy-3-oxo-2-phenylpropyl)-7-methyl-3H,6H,7H,8H,9H-imidazo[4,5-f]quinoline-6-carboxylate (70 mg, 0.16 mmol) was dissolved in N,N-dimethylformamide (2 mL) and then cesium carbonate (107 mg, 0.32 mmol) were added. This was followed by the addition of methyl iodide (22.8 mg, 0.16 mmol) dropwise with stirring. The resulting solution was stirred for 1 h at rt (20° C.). The resulting solution was diluted with 20 mL of water and extracted with 3×20 mL of ethyl acetate. The organic layers were combined, dried over anhydrous sodium sulfate, filtered and concentrated under vacuum. The residue was subjected to purification by FCC eluting with ethyl acetate/petroleum ether (1:1). The crude product was purified by Chiral-Prep-HPLC with the following conditions (Prep-HPLC): Column, (R, R) WHELK-01 5/100 Kromasil, 25 cm×21.1 mm; mobile phase: A: Hex (0.1% DEA) and B: ethanol (hold 30.0% ethanol in 38 min); UV Detector: 254 nm. This afforded the title compounds as follows: 30 mg (43%) of methyl (7S)-2-[(2R)-3-ethoxy-3-oxo-2-phenylpropyl]-3,7-dimethyl-3H,6H,7H,8H,9H-imidazo[4,5-f]quinoline-6-carboxylate as a yellow oil (assumed stereochemistry, first eluting isomer) and 30 mg (43%) of (7S)-2-[(2S)-3-ethoxy-3-oxo-2-phenylpropyl]-3,7-dimethyl-3H,6H,7H,8H,9H-imidazo[4,5-f]quinoline-6-carboxylate (assumed stereochemistry, first eluting isomer) as a yellow oil. MS: (ES, m/z): 436 $[M+H]^+$.

Step 5A. Synthesis of (2R)-3-[(7S)-6-(methoxycarbonyl)-3,7-dimethyl-3H,6H,7H,8H,9H-imidazo[4,5-f]quinolin-2-yl]-2-phenylpropanoic acid Into a 50-mL round-bottom flask, methyl (7S)-2-[(2R)-3-ethoxy-3-oxo-2-phenylpropyl]-3,7-dimethyl-3H,6H,7H,8H,9H-imidazo[4,5-f]quinoline-6-carboxylate (30 mg, 0.07 mmol) was dissolved in tetrahydrofuran (2 mL). Then a solution of lithium hydroxide (8.2 mg, 0.34 mmol) in water (2 mL) was added. The resulting solution was stirred overnight at 85° C. in an oil bath. The reaction mixture was cooled to room temperature and the solids were filtered out. The crude product was purified by Prep-HPLC with the following conditions: Column, XBridge Prep C18 OBD Column, 5 μm, 19×150 mm; mobile phase: A: water (containing 0.05% TFA) and B: ACN (25.0% to ACN 45.0% over 7 min); UV Detector: 254 nm. This afforded the title compound (3.9 mg, 14%) as a white solid.

1H-NMR ($CDCl_3$, 400 MHz) δ (ppm): 7.85-7.90 (m, 1H), 7.33-7.22 (m, 4H), 7.20-7.16 (m, 2H), 4.84-4.80 (m, 1H), 4.67-4.63 (m, 1H), 3.88 (s, 3H), 3.68 (s, 3H), 3.56-3.49 (m, 1H), 3.21-3.16 (m, 2H), 3.03-2.94 (m, 1H), 2.17-2.11 (m, 1H), 1.84-1.79 (m, 1H), 1.12 (d, J=6.8 Hz, 3H). MS: (ES, m/z): 408 $[M+H]^+$.

Step 5B. Synthesis of (2S)-3-[(7S)-6-(methoxycarbonyl)-3,7-dimethyl-3H,6H,7H,8H,9H-imidazo[4,5-f]quinolin-2-yl]-2-phenylpropanoic acid Into a 50-mL round-bottom flask purged and maintained with an inert atmosphere of nitrogen, methyl (7S)-2-[(2S)-3-ethoxy-3-oxo-2-phenylpropyl]-3,7-dimethyl-3H,6H,7H,8H,9H-imidazo[4,5-f]quinoline-6-carboxylate (30 mg, 0.07 mmol) was dissolved in tetrahydrofuran (2 mL), and then a solution of lithium hydroxide (8.2 mg, 0.34 mmol) in water (2 mL) was added. The resulting solution was stirred overnight at 85° C. in an oil bath. The reaction mixture was cooled to rt (20° C.). The solids were filtered out. The crude product was purified by Prep-HPLC with the following conditions: Column, XBridge Prep C18 OBD Column, 5 um, 19×150 mm; mobile phase: A: Water (containing 0.05% TFA) and B: ACN (25.0% ACN up to 45.0% in 7 min); UV Detector: 254/220 nm. This afforded the title compound (3.8 mg, 14%) as a white solid. 1H-NMR ($CDCl_3$, 400 MHz) δ (ppm): 7.88-7.92 (m, 1H), 7.52-7.33 (m, 5H), 7.28-7.25 (m, 1H), 4.90-4.81 (m, 2H), 4.00-3.93 (m, 1H), 3.86-3.63 (m, 6H), 3.34-3.26 (m, 1H), 3.12-3.05 (m, 2H), 2.13-2.10 (m, 1H), 1.80-1.73 (m, 1H), 1.12-1.05 (m, 3H). MS: (ES, m/z): 408 $[M+H]^+$.

Examples 135 and 136: (S)-3-((S)-6-(methoxycarbonyl)-3,7-dimethyl-6,7,8,9-tetrahydro-3H-imidazo[4,5-f]quinolin-2-yl)-2-phenylpropanoic acid and (R)-3-((S)-6-(methoxycarbonyl)-3,7-dimethyl-6,7,8,9-tetrahydro-3H-imidazo[4,5-f]quinolin-2-yl)-2-phenylpropanoic acid

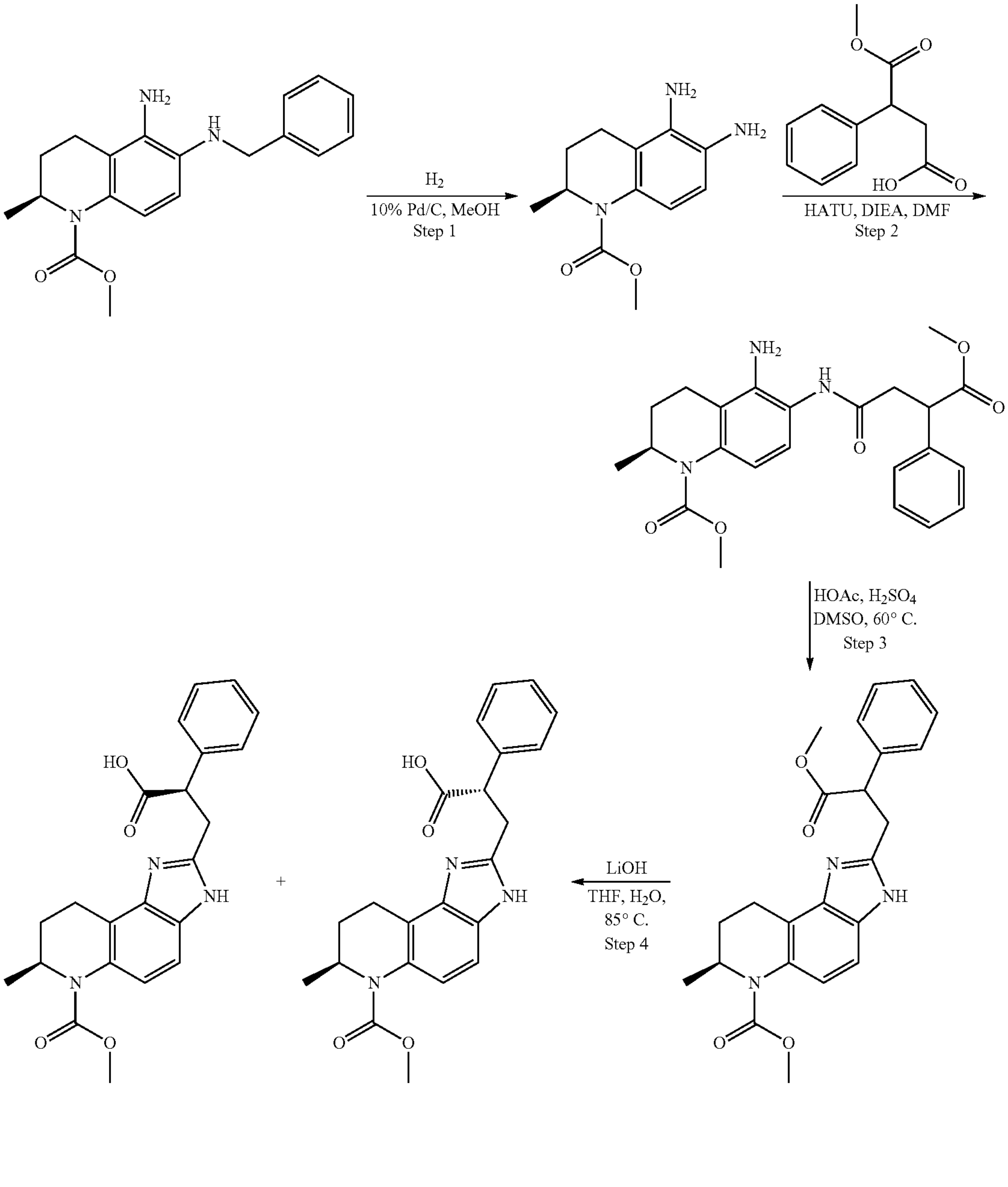

Step 1. Synthesis of methyl (S)-5,6-diamino-2-methyl-3,4-dihydroquinoline-1(2H)-carboxylate Into a 50-mL round-bottom flask, methyl (S)-5-amino-6-(benzylamino)-2-methyl-3,4-dihydroquinoline-1(2H)-carboxylate (160 mg, 0.49 mmol) was dissolved in methanol (25 mL). Then 10% palladium on carbon (20 mg) was added. Hydrogen (g) was charged into the reaction mixture and the reaction was stirred under a hydrogen atmosphere for 3 h at room temperature. The solids were filtered out over celite and the filtered solution was concentrated under vacuum affording the title compound (112 mg, 97%) as a yellow oil. MS: (ES, m/z): 236 $[M+H]^+$.

Step 2. Synthesis of methyl-(2S)-5-amino-6-(4-methoxy-4-oxo-3-phenylbutanamido)-2-methyl-1,2,3,4-tetrahydroquinoline-1-carboxylate Into a 50-mL round-bottom flask, methyl-(2S)-5,6-diamino-2-methyl-1,2,3,4-tetrahydroquinoline-1-carboxylate (110 mg, 0.47 mmol) was dissolved in N,N-dimethylformamide (3 mL). Then 4-methoxy-4-oxo-3-phenylbutanoic acid (97 mg, 0.47 mmol), diisopropylethylamine (182 mg, 1.41 mmol) and O-(7-azabenzotriazole-1-yl)-N,N,N',N'-tetramethyluronium hexafluorophosphate (268 mg, 0.70 mmol) were added, successively. The resulting solution was stirred for 1 h at room temperature. The resulting solution was diluted with 20 mL of water and extracted with 3×30 mL of ethyl acetate. The organic layers were combined, dried over anhydrous sodium sulfate, filtered and concentrated under vacuum. This afforded the title compound (40 mg, 20%) as a light yellow oil. MS: (ES, m/z): 426 $[M+H]^+$ Step 3. Synthesis of methyl-(7S)-2-(3-methoxy-3-oxo-2-phenylpropyl)-7-methyl-3H,6H,7H,8H,9H-imidazo[4,5-f]quinoline-6-carboxylate Into a 50-mL round-bottom flask, methyl-(2S)-5-amino-6-(4-methoxy-4-oxo-3-phenylbutanamido)-2-methyl-1,2,3,4-tetrahydroquinoline-1-carboxylate (40 mg, 0.09 mmol) was dissolved in dimethyl sulfoxide (2 mL). Then acetic acid (2 mL) and sulfuric acid (0.01 mL) were added. The resulting solution was stirred for 2 h at 60° C. The resulting solution was cooled to room temperature and diluted with 50 mL of water. The mixture was extracted with 3×50 mL of ethyl acetate. The organic layers were combined, dried over anhydrous sodium sulfate, filtered and concentrated under vacuum. This afforded the title compound (20 mg, 52%) as a light yellow oil. MS: (ES, m/z): 408 $[M+H]^+$ Step 4. Synthesis of (S)-3-((S)-6-(methoxycarbonyl)-3,7-dimethyl-6,7,8,9-tetrahydro-3H-imidazo[4,5-f]quinolin-2-yl)-2-phenylpropanoic acid and (R)-3-((S)-6-(methoxycarbonyl)-3,7-dimethyl-6,7,8,9-tetrahydro-3H-imidazo[4,5-f]quinolin-2-yl)-2-phenylpropanoic acid Into a 50-mL round-bottom flask, methyl-(7S)-2-(3-methoxy-3-oxo-2-phenylpropyl)-7-methyl-3H,6H,7H,8H,9H-imidazo[4,5-f]quinoline-6-carboxylate (20 mg, 0.05 mmol) was dissolved in tetrahydrofuran (2 mL). Then water (2 mL) was added, followed by lithium hydroxide (7 mg, 0.29 mmol). The resulting solution was stirred for 12 h at 85° C. The resulting mixture was cooled to room temperature and concentrated under vacuum. The pH value of the solution was adjusted to 3 with hydrogen chloride (1 mol/L). The resulting solution was extracted with 3×20 mL of ethyl acetate. The organic layers were combined, dried over anhydrous sodium sulfate, filtered and concentrated under vacuum. The crude product was purified by Prep-HPLC with the following conditions: Column, XBridge C18 OBD Prep Column, 100 Å, 5 m, 19 mm×250 mm; mobile phase, A: water (containing 0.05% TFA) and B: ACN (5.0% to 60% ACN over 30 min); UV Detector: 254 nm. Then the product was purified by Chiral-HPLC with the following conditions: Column: (R,R)-WHELK-O1-Kromasil, 5 cm×25 cm (5 m); Mobile Phase, A: Hexanes (containing 0.1% DEA) and B: EtOH (hold 40% EtOH in 38 min); UV Detector: 254 nm. This afforded the title compounds as follows: 3.3 mg (17%) of 3-[(7S)-6-(methoxycarbonyl)-7-methyl-3H,6H,7H,8H,9H-imidazo[4,5-f]quinolin-2-yl]-2R-phenylpropanoic acid (assumed stereochemistry, first eluting isomer, RT=21.72) as a white solid and 2.4 mg (12%) of 3-[(7S)-6-(methoxycarbonyl)-7-methyl-3H,6H,7H,8H,9H-imidazo[4,5-f]quinolin-2-yl]-2R-phenylpropanoic acid (assumed stereochemistry, second eluting isomer, RT=29.57) as white solid.

First eluting isomer: $^1$H-NMR: ($CD_3OD$, 300 MHz) δ (ppm): 7.40-7.18 (m, 7H), 4.80-4.75 (m, 1H), 4.15-4.10 (m, 1H), 3.77 (s, 3H), 3.61-3.58 (m, 1H), 2.85-2.75 (m, 1H), 2.25-2.20 (m, 2H), 1.75-1.70 (m, 2H), 1.14-1.12 (m, 3H). MS: (ES, m/z): 394 $[M+H]^+$ Second eluting isomer: $^1$H-NMR: ($CD_3OD$, 300 MHz) δ (ppm): 7.39-7.20 (m, 7H), 4.80-4.75 (m, 1H), 4.15-4.10 (m, 1H), 3.77 (s, 3H), 3.65-3.60 (m, 1H), 3.30-3.25 (m, 1H), 2.85-2.75 (m, 1H), 2.22-2.18 (m, 1H), 1.75-1.70 (m, 2H), 1.13-1.11 (d, J=6.0 Hz, 3H). MS: (ES, m/z): 394 $[M+H]^+$ Examples 137 and 138: (R)-3-((S)-3-(2-(dimethylamino)ethyl)-6-(methoxycarbonyl)-7-methyl-6,7,8,9-tetrahydro-3H-imidazo[4,5-f]quinolin-2-yl)-2-phenylpropanoic acid and (S)-3-((S)-3-(2-(dimethylamino)ethyl)-6-(methoxycarbonyl)-7-methyl-6,7,8,9-tetrahydro-3H-imidazo[4,5-f]quinolin-2-yl)-2-phenylpropanoic acid

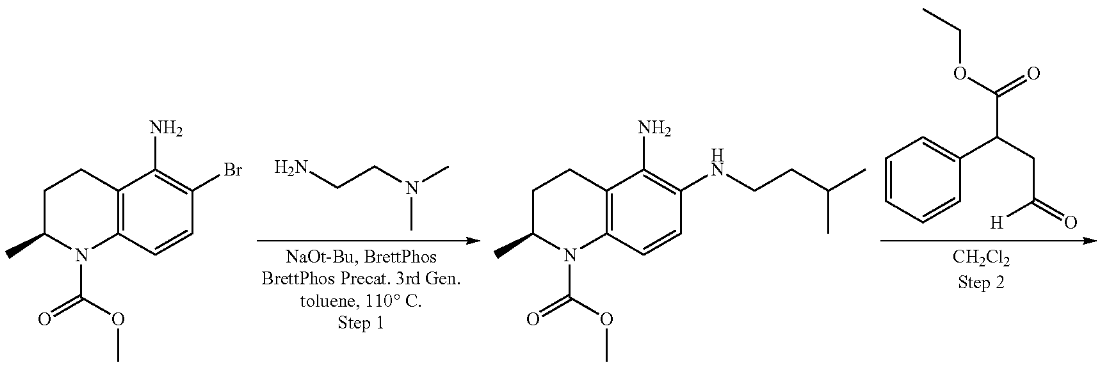

-continued

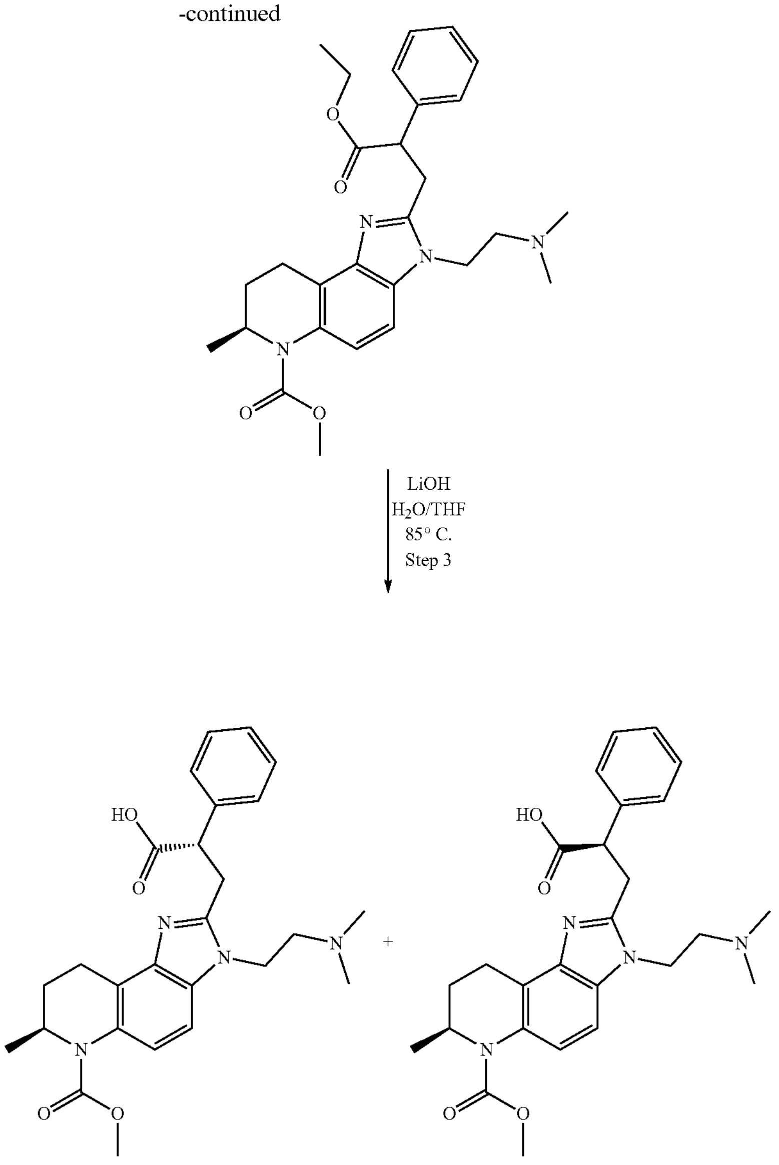

Step 1. Synthesis of methyl (2S)-5-amino-6-[[2-(dimethylamino) ethyl]amino]-2-methyl-1,2,3,4-tetrahydroquinoline-1-carboxylate Into a 8-mL sealed tube purged and maintained with an inert atmosphere of nitrogen, methyl (2S)-5-amino-6-bromo-2-methyl-1,2,3,4-tetrahydroquinoline-1-carboxylate (200 mg, 0.67 mmol, Intermediate 1) was dissolved in toluene (3 mL). Then (2-aminoethyl) dimethylamine (589.3 mg, 6.69 mmol), 3rd Generation BrettPhos precatalyst (121.2 mg, 0.13 mmol), sodium tert-butoxide (96.4 mg, 1.00 mmol) and Brettphos (143.5 mg, 0.27 mmol) were added. The resulting solution was stirred for 2 h at 110° C. under nitrogen atmosphere. The resulting mixture was cooled to room temperature and concentrated under vacuum. The crude product was purified by Flash-Prep-HPLC with the following conditions: Column, C18 silica gel; mobile phase, A: water (containing 0.5% TFA) and B: ACN (5.0% to 40.0% ACN over 30 min); UV Detector: 254 nm. This afforded the title compound (150 mg, 73%) as a yellow oil. MS: (ES, m/z): 307[M+H]$^+$.

Step 2. Synthesis of methyl (7S)-3-[2-(dimethylamino)ethyl]-2-(3-ethoxy-3-oxo-2-phenylpropyl)-7-methyl-3H,6H,7H,8H,9H-imidazo[4,5-f]quinoline-6-carboxylate Into a 8-mL sealed tube, methyl (2S)-5-amino-6-[[2-(dimethylamino)ethyl]amino]-2-methyl-1,2,3,4-tetrahydroquinoline-1-carboxylate (150 mg, 0.47 mmol) was dissolved in dichloromethane (2 mL). Then ethyl 4-oxo-2-phenylbutanoate (151.4 mg, 0.70 mmol, Intermediate 32) was added. The resulting solution was stirred for 2 h at room temperature. The resulting mixture was concentrated under vacuum. The crude product was purified by Flash-Prep-HPLC with the following conditions: Column, C18 silica gel; mobile phase, A: water (containing 0.5% TFA) and B: ACN (5.0% to 60.0% ACN over 30 min); UV Detector: 254 nm. This afforded the title compound (150 mg, 65%) as yellow oil. MS: (ES, m/z): 493[M+H]$^+$.

Step 3. Synthesis of (R)-3-((S)-3-(2-(dimethylamino)ethyl)-6-(methoxycarbonyl)-7-methyl-6,7,8,9-tetrahydro-3H-imidazo[4,5-f]quinolin-2-yl)-2-phenylpropanoic acid and (S)-3-((S)-3-(2-(dimethylamino)ethyl)-6-(methoxycarbonyl)-7-methyl-6,7,8,9-tetrahydro-3H-imidazo[4,5-f]quinolin-2-yl)-2-phenylpropanoic acid Into a 50-mL round-bottom flask, methyl (7S)-3-[2-(dimethylamino)ethyl]-2-(3-ethoxy-3-oxo-2-phenylpropyl)-7-methyl-3H,6H,7H,8H,9H-imidazo[4,5-f]quinoline-6-carboxylate (130 mg, 0.25 mmol) was dissolved in tetrahydrofuran (2 mL). Then water (2 mL) was added, followed by lithium hydroxide (31.6 mg, 1.27 mmol). The resulting solution was stirred overnight at 85° C. The reaction mixture was cooled to room temperature. The resulting mixture was concentrated under vacuum. The crude product was purified by Prep-HPLC with the following conditions: Column, XBridge Prep C18 OBD Column, 19×150 mm, 5 μm; mobile phase: A: water (containing 0.05% TFA) and B: ACN (8.0% to 48.0% ACN over 12 min); UV Detector: 254 nm. The crude product was purified by Chiral-Prep-HPLC with the following conditions: Column, (R, R)WHELK-01 5/100 Kromasil, 25 cm×21.1 mm; mobile phase: A: hexanes (containing 0.1% TFA) and B: ethanol (hold 30.0% ethanol in 38 min); UV Detector: 254 nm. This afforded the title compounds as follows: 15.1 mg (13%) of (2R)-3-[(7S)-3-[2-(dimethylamino)ethyl]-6-(methoxycarbonyl)-7-methyl-3H,6H,7H,8H,9H-imidazo[4,5-f]quinolin-2-yl]-2-phenylpropanoic acid (assumed stereochemistry, first eluting isomer, RT=18.6 min) as a white solid and 17.8 mg (15%) of (2S)-3-[(7S)-3-[2-(dimethylamino)ethyl]-6-(methoxycarbonyl)-7-methyl-3H,6H,7H,8H,9H-imidazo[4,5-f]quinolin-2-yl]-2-phenylpropanoic acid (assumed stereochemistry, second eluting isomer, RT=26.4 min) as a white solid.

First eluting isomer: $^1$H-NMR ($CDCl_3$, 300 MHz) δ (ppm): 7.86-7.84 (m, 1H), 7.63-7.59 (m, 1H), 7.28-7.19 (m, 5H), 4.91-4.65 (m, 4H), 3.84-3.78 (m, 4H), 3.65-3.36 (m, 3H), 3.02-2.89 (m, 8H), 2.10-2.03 (m, 1H), 1.77-1.70 (m, 1H), 1.12 (d, J=6.6 Hz, 3H). MS: (ES, m/z): 465[M+H]$^+$.

Second eluting isomer: $^1$H-NMR ($CDCl_3$, 300 MHz) δ (ppm): 7.86-7.83 (m, 1H), 7.52-7.48 (m, 1H), 7.28-7.19 (m, 5H), 4.83-4.68 (m, 4H), 3.95-3.82 (m, 4H), 3.50-3.45 (m, 2H), 3.14-3.08 (m, 1H), 2.98-2.96 (m, 2H), 2.85-2.75 (m, 6H), 2.14-2.12 (m, 1H), 1.78-1.73 (m, 1H), 1.09 (d, J=6.9 Hz, 3H). MS: (ES, m/z): 465[M+H]$^+$.

Examples 139 and 140: (S)-3-((S)-6-(methoxycarbonyl)-7-methyl-3-(tetrahydro-2H-pyran-4-yl)-6,7,8,9-tetrahydro-3H-imidazo[4,5-f]quinolin-2-yl)-2-phenylpropanoic acid and (R)-3-((S)-6-(methoxycarbonyl)-7-methyl-3-(tetrahydro-2H-pyran-4-yl)-6,7,8,9-tetrahydro-3H-imidazo[4,5-f]quinolin-2-yl)-2-phenylpropanoic acid

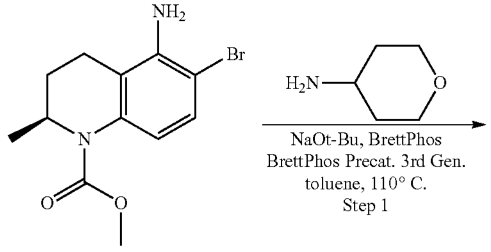

-continued

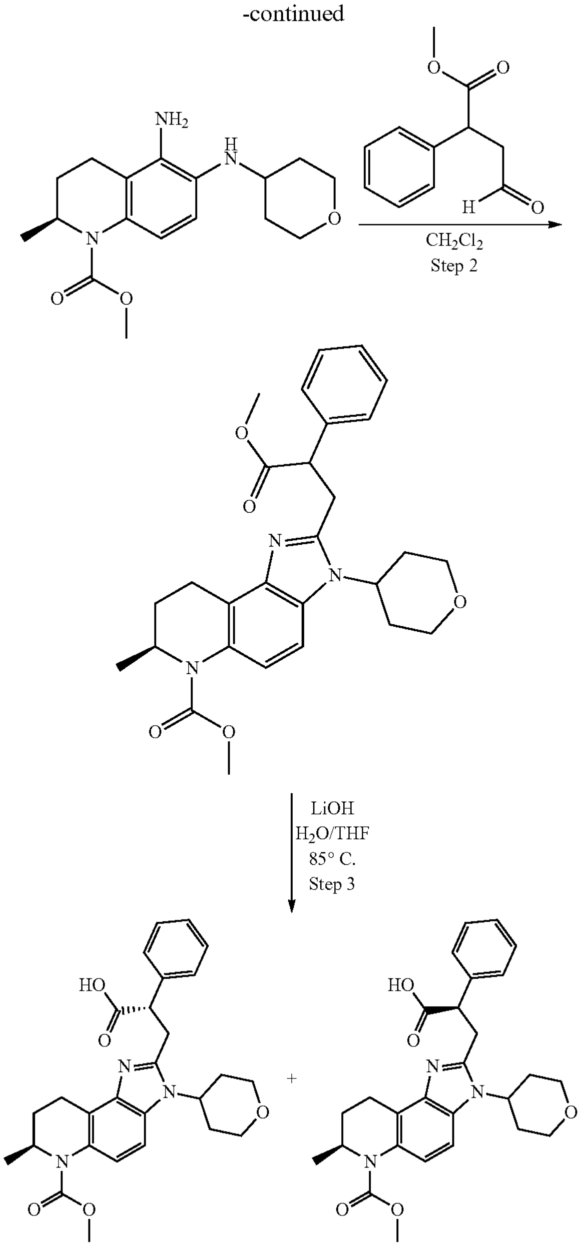

Step 1. Synthesis of methyl-(2S)-5-amino-2-methyl-6-[(oxan-4-yl)amino]-1,2,3,4-tetrahydroquinoline-1-carboxylate Into a 50-mL round-bottom flask purged and maintained with an inert atmosphere of nitrogen, methyl-(2S)-5-amino-6-bromo-2-methyl-1,2,3,4-tetrahydroquinoline-1-carboxylate (150 mg, 0.50 mmol, Intermediate 1) was dissolved in toluene (5 mL). Then oxan-4-amine (150 mg, 1.48 mmol), Brettphos (54 mg, 0.10 mmol), 3$^{rd}$ Generation BrettPhos precatalyst (45 mg, 0.05 mmol) and sodium tert-butoxide (100 mg, 1.04 mmol) were added successively. The resulting solution was stirred for 2 h at 110° C. in the nitrogen atmosphere. The reaction mixture was cooled and the resulting solids were filtered out. The filtrate was concentrated under vacuum. The residue was subjected to purification by FCC eluting with ethyl acetate/petroleum ether (2:1). This afforded the title compound (110 mg, 69%) as a green oil. MS: (ES, m/z): 420[M+H]$^+$ Step 2. Synthesis of methyl-(7S)-2-(3-methoxy-3-oxo-2-phenylpropyl)-7-methyl-3-(oxan-4-yl)-3H,6H,7H,8H,9H-imidazo[4,5-f]quinoline-6-carboxylate Into a 100-mL round-bottom flask, methyl-(2S)-5-amino-2-methyl-6-[(oxan-4-yl)amino]-1,2,3,4-tetrahydroquinoline-1-carboxylate (160 mg, 0.50 mmol) was dissolved in dichloromethane (10 mL). Then methyl-4-oxo-2-phenylbutanoate (192 mg, 1.00 mmol, Intermediate 32) was added. The resulting solution was stirred for 12 h at room temperature. The resulting mixture was concentrated under vacuum. The residue was subjected to purification by FCC with ethyl acetate/petroleum ether (2:1). This afforded the title compound (120 mg, 49%) as a yellow oil. MS: (ES, m/z): 492[M+H]$^+$ Step 3. Synthesis of (S)-3-((S)-6-(methoxycarbonyl)-7-methyl-3-(tetrahydro-2H-pyran-4-yl)-6,7,8,9-tetrahydro-3H-imidazo[4,5-f]quinolin-2-yl)-2-phenylpropanoic acid and (R)-3-((S)-6-(methoxycarbonyl)-7-methyl-3-(tetrahydro-2H-pyran-4-yl)-6,7,8,9-tetrahydro-3H-imidazo[4,5-f]quinolin-2-yl)-2-phenylpropanoic acid Into a 25-mL round-bottom flask, methyl-(7S)-2-(3-methoxy-3-oxo-2-phenylpropyl)-7-methyl-3-(oxan-4-yl)-3H,6H,7H,8H,9H-imidazo[4,5-f]quinoline-6-carboxylate (120 mg, 0.24 mmol) was dissolved in tetrahydrofuran (8 mL). Then lithium hydroxide (31 mg, 1.29 mmol) dissolved in water (2 mL) was added dropwise. The resulting solution was stirred for 12 h at 85° C. After cooled to room temperature, the resulting mixture was concentrated under vacuum. The product was purified with the following conditions: Column: XSelect CSH Prep C18 OBD Column, 19×250 mm, 5 um; Mobile Phases, A: Water (containing 0.05% TFA) and B: ACN (15% to 45% ACN over 7 min); UV Detector: 254/220 nm. The products was separated with the following conditions: Column: Phenomenex Lux 5u Cellulose-4£¬AXIA Packed, 2.12×25 cm, 5 um; Mobile Phases, A: Hexanes (containing 0.1% TFA) and B: EtOH (30% EtOH over 25 min); UV Detector: 254/220 nm; This afforded the title compounds as follows: 6.6 mg (6%) of 3-[(7S)-6-(methoxycarbonyl)-7-methyl-3-(oxan-4-yl)-3H,6H,7H,8H,9H-imidazo[4,5-f]quinolin-2-yl]-2R-phenylpropanoic acid (assumed stereochemistry, first eluting isomer, RT=14.37 min) as a light yellow solid and 8.7 mg (7%) of 3-[(7S)-6-(methoxycarbonyl)-7-methyl-3-(oxan-4-yl)-3H,6H,7H,8H,9H-imidazo[4,5-f]quinolin-2-yl]-2S-phenylpropanoic acid (assumed stereochemistry, first eluting isomer, RT=18.48 min) as a light yellow solid.

First eluting isomer: $^1$H-NMR: ($CD_3OD$, 400 MHz) δ (ppm): 7.82-7.74 (m, 2H), 7.41-7.32 (m, 5H), 4.85-4.82 (m, 2H), 4.28-4.22 (m, 1H), 4.14-4.10 (m, 1H), 4.03-3.98 (m, 2H), 3.79 (s, 3H), 3.74-3.64 (m, 2H), 3.49-3.48 (m, 1H), 3.06-3.04 (m, 1H), 2.96-2.95 (m, 1H), 2.61-2.55 (m, 1H), 2.45-2.35 (m, 1H), 2.21-2.15 (m, 1H), 1.98-1.90 (m, 2H), 1.16 (d, J=6.8 Hz, 4H). MS: (ES, m/z): 478[M+H]$^+$ Second eluting isomer: $^1$H-NMR: ($CD_3OD$, 400 MHz) δ (ppm): 7.78-7.73 (m, 2H), 7.39-7.31 (m, 5H), 4.87-4.80 (m, 2H), 4.28-4.24 (m, 1H), 4.12-4.09 (m, 1H), 4.03-3.97 (m, 2H), 3.79 (s, 3H), 3.74-3.64 (m, 2H), 3.48-3.47 (m, 1H), 3.03-2.98 (m, 2H), 2.55-2.35 (m, 2H), 2.21-2.19 (m, 1H), 1.98-1.85 (m, 2H), 1.14-1.11 (m, 4H). MS: (ES, m/z): 478[M+H]$^+$ The following examples in TABLE 8 were prepared using standard chemical manipulations and procedures similar to those used for the preparation of Examples 139 and 140.

TABLE 8

| Example Number | Structure and Compound Name | LRMS m/z [M + H]$^+$ | $^1$HNMR |
|---|---|---|---|
| 141 and 142 | 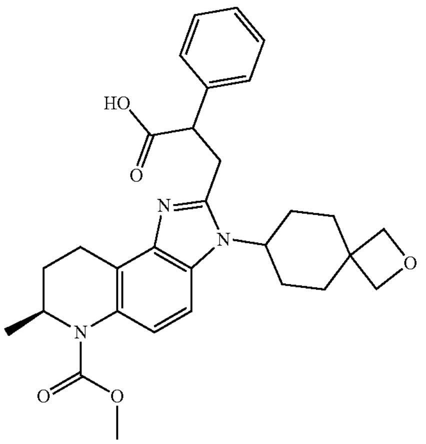<br>1$^{st}$ eluting isomer (141)<br>2$^{nd}$ eluting isomer (142)<br>3-((S)-6-(methoxycarbonyl)-7-methyl-3-(2-oxaspiro[3.5]nonan-7-yl)-6,7,8,9-tetrahydro-3H-imidazo[4,5-f]quinolin-2-yl)-2-phenylpropanoic acid | 1$^{st}$ eluting isomer = 518<br>2$^{nd}$ eluting isomer = 518 | 1$^{st}$ eluting isomer $^1$H-NMR ($CD_3OD$, 400 MHz) δ (ppm): 7.36-7.13 (m, 7H), 4.74-4.72 (m, 1H), 4.60 (s, 2H), 4.39 (s, 2H), 4.18-4.14 (m, 2H), 3.76 (s, 3H), 3.68-3.62 (m, 1H), 3.38-3.31 (m, 1H), 3.13-3.10 (m, 1H), 2.93-2.89 (m, 1H), 2.33-1.97 (m, 5H), 1.76-1.69 (m, 3H), 1.57-1.45 (m, 1H), 1.13-1.06 (m, 4H)<br>2$^{nd}$ eluting isomer $^1$H-NMR ($CD_3OD$, 400 MHz) δ (ppm): 7.39-7.12 (m, 7H), 4.74-4.71 (m, 1H), 4.60 (d, J = 3.3 Hz, 2H), 4.42-4.36 (m, 2H), 4.26-4.18 (m, 2H), 3.76 (s, 3H), 3.70-3.62 (m, 1H), 3.36 (d, J = 7.8 Hz, 1H), 3.18-3.11 (m, 1H), 2.91-2.85 (m, 1H), 2.28-2.12 (m, 3H), 2.31-1.92 (m, 5H), 1.74-1.53 (m, 1H), 1.10-1.01 (m, 4H) |

TABLE 8-continued

| Example Number | Structure and Compound Name | LRMS m/z [M + H]+ | 1HNMR |
|---|---|---|---|
| 143 and 144 | 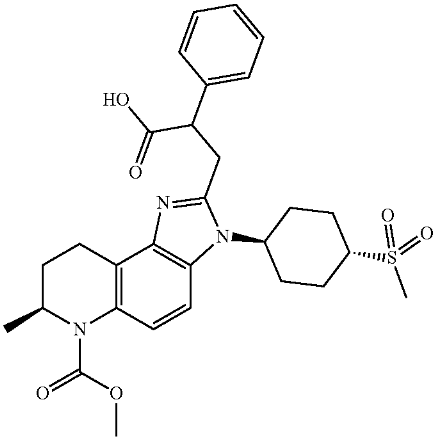<br>1st eluting isomer (143)<br>2nd eluting isomer (144)<br>3-((S)-6-(methoxycarbonyl)-7-methyl-3-((trans)-4-(methylsulfonyl)cyclohexyl)-6,7,8,9-tetrahydro-3H-imidazo[4,5-f]quinolin-2-yl)-2-phenylpropanoic acid | 1st eluting isomer = 554<br>2nd eluting isomer = 554 | 1st eluting isomer $^1$H-NMR (DMSO-d6, 300 MHz) δ (ppm): 7.44-7.19 (m, 7H), 4.66-4.61 (m, 1H), 4.37 (s, 1H), 4.12-4.07 (m, 1H), 3.67-3.45 (m, 6H), 3.21-3.14 (m, 1H), 3.08-2.95 (m, 4H), 2.85-2.76 (m, 1H), 2.25-2.18 (m, 2H), 2.16-2.09 (m, 2H), 2.08-1.96 (m, 1H), 1.76-1.47 (m, 3H), 1.36-1.25 (m, 1H), 1.17 (d, J = 6.6 Hz, 3H)<br>2nd eluting isomer $^1$H-NMR (DMSO-d6, 300 MHz) δ (ppm): 7.46-7.31 (m, 3H), 7.29-7.20 (m, 4H), 4.66-4.60 (m, 1H), 4.51-4.43 (m, 1H), 4.12-4.08 (m, 1H), 3.67-3.59 (m, 4H), 3.13-2.96 (m, 6H), 2.75-2.82 (m, 1H), 2.30-1.97 (m, 6H), 1.77-1.53 (m, 4H), 1.08-1.06 (d, J = 6.6 Hz, 3H) |
| 145 and 146 | 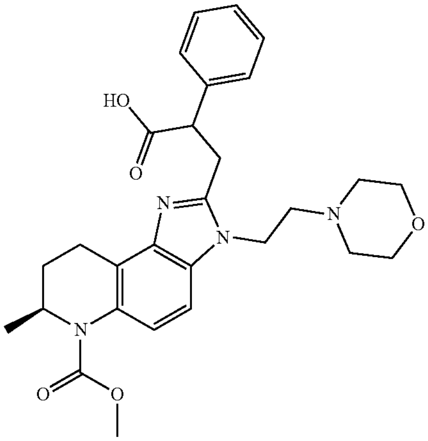<br>1st eluting isomer (145)<br>2nd eluting isomer (146)<br>3-((S)-6-(methoxycarbonyl)-7-methyl-3-(2-morpholinoethyl)-6,7,8,9-tetrahydro-3H-imidazo[4,5-f]quinolin-2-yl)-2-phenylpropanoic acid | 1st eluting isomer = 507<br>2nd eluting isomer = 507 | 1st eluting isomer $^1$H-NMR ($CDCl_3$, 400 MHz) δ (ppm): 7.58-7.52 (m, 1H), 7.35-7.30 (m, 5H), 7.14-7.10 (m, 1H), 4.77-4.74 (m, 1H), 4.61-4.58 (m, 1H), 4.29-4.23 (m, 1H), 4.11-4.02 (m, 1H), 3.82 (s, 3H), 3.80-3.79 (m, 1H), 3.76-3.61 (m, 4H), 3.39-3.35 (m, 1H), 3.11-3.05 (m, 1H), 2.96-2.90 (m, 1H), 2.63-2.49 (m, 6H), 2.15-2.09 (m, 1H), 1.71-1.63 (m, 1H), 1.12-1.08 (m, 3H)<br>2nd eluting isomer $^1$H-NMR ($CDCl_3$, 400 MHz) δ (ppm): 7.60-7.52 (m, 1H), 7.40-7.31 (m, 5H), 7.16-7.11 (m, 1H), 4.77-4.75 (m, 1H), 4.64-4.61 (m, 1H), 4.30-4.28 (m, 1H), 4.08-4.04 (m, 1H), 3.82 (s, 3H), 3.80-3.79 (m, 1H), 3.76-3.62 (m, 4H), 3.39-3.35 (m, 1H), 3.14-3.06 (m, 1H), 2.97-2.93 (m, 1H), 2.64-2.50 (m, 6H), 2.21-2.11 (m, 1H), 1.68-1.65 (m, 1H), 1.12-1.08 (m, 3H) |

TABLE 8-continued

| Example Number | Structure and Compound Name | LRMS m/z $[M + H]^+$ | $^1$HNMR |
| --- | --- | --- | --- |
| 147 and 148 | 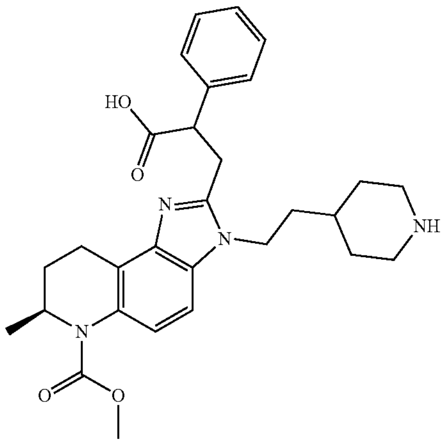<br>$1^{st}$ eluting isomer (147)<br>$2^{nd}$ eluting isomer (148)<br>3-((S)-6-(methoxycarbonyl)-7-methyl-3-(2-(piperidin-4-yl)ethyl)-6,7,8,9-tetrahydro-3H-imidazo[4,5-f]quinolin-2-yl)-2-phenylpropanoic acid | $1^{st}$ eluting isomer = 504<br>$2^{nd}$ eluting isomer = 504 | $1^{st}$ eluting isomer $^1$H-NMR ($CF_3CO_2D$, 300 MHz) δ (ppm): 7.86 (d, J = 9.0 Hz, 1H), 7.44-7.26 (m, 4H), 7.26-7.13 (m, 3H), 6.78 (s, 1H), 4.98-4.77 (m, 1H), 4.45-4.35 (m, 1H), 4.32-4.07 (m, 2H), 4.04-3.84 (m, 4H), 3.81-3.56 (m, 3H), 3.25-3.07 (m, 2H), 3.07-2.81 (m, 2H), 2.37-2.20 (m, 1H), 2.09-1.90 (m, 2H), 1.89-1.70 (m, 3H), 1.70-1.43 (m, 3H), 1.15 (d, J = 6.9 Hz, 3H)<br>$2^{nd}$ eluting isomer $^1$H-NMR ($CDCl_3$, 300 MHz) δ (ppm): 7.48-7.33 (m, 3H), 7.26-7.09 (m, 3H), 6.99 (d, J = 8.1 Hz, 1H), 4.72 (d, J = 8.1 Hz, 1H), 4.41 (s, 1H), 4.12-3.80 (m, 2H), 3.73 (s, 3H), 3.66-3.50 (m, 1H), 3.23-2.75 (m, 5H), 2.50-2.00 (m, 3H), 1.82-1.18 (m, 7H), 1.11 (d, J = 6.3 Hz, 4H) |
| 149 and 150 | 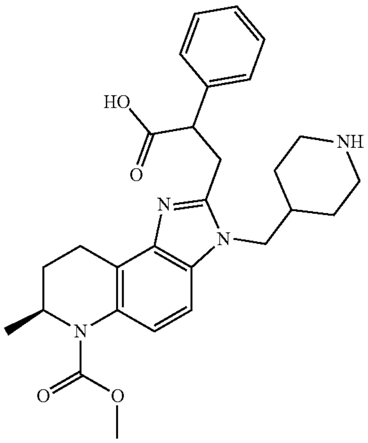<br>$1^{st}$ eluting isomer (149)<br>$2^{nd}$ eluting isomer (150)<br>3-((S)-6-(methoxycarbonyl)-7-methyl-3-(piperidin-4-ylmethyl)-6,7,8,9-tetrahydro-3H-imidazo[4,5-f]quinolin-2-yl)-2-phenyl)propanoic acid | $1^{st}$ eluting isomer = 491<br>$2^{nd}$ eluting isomer = 491 | $1^{st}$ eluting isomer $^1$H-NMR (DMSO-d6, 300 MHz) δ (ppm): 7.41 (d, J = 7.1 Hz, 2H), 7.32-7.12 (m, 5H), 4.63-4.59 (m, 1H), 4.14-4.07 (m, 2H), 3.88-3.82 (m, 1H), 3.67-3.55 (m, 4H), 3.09-2.89 (m, 4H), 2.83-2.72 (m, 1H), 2.45-2.40 (m, 1H), 2.17-2.09 (m, 1H), 2.04-1.70 (m, 1H), 1.62-1.44 (m, 3H), 1.32-1.20 (m, 3H), 1.05 (d, J = 6.6 Hz, 3H)<br>$2^{nd}$ eluting isomer $^1$H-NMR (DMSO-d6, 300 MHz) δ (ppm): 7.41 (d, J = 7.1 Hz, 2H), 7.34-7.13 (m, 5H), 4.67-4.59 (m, 1H), 4.18-4.08 (m, 2H), 3.93-3.87 (m, 1H), 3.68-3.50 (m, 4H), 3.11-2.92 (m, 4H), 2.81-2.72 (m, 1H), 2.40-2.00 (m, 3H), 1.61-1.41 (m, 3H), 1.40-1.10 (m, 3H), 1.05 (d, J = 6.6 Hz, 3H) |

TABLE 8-continued

| Example Number | Structure and Compound Name | LRMS m/z [M + H]$^+$ | $^1$HNMR |
|---|---|---|---|
| 151 and 152 | 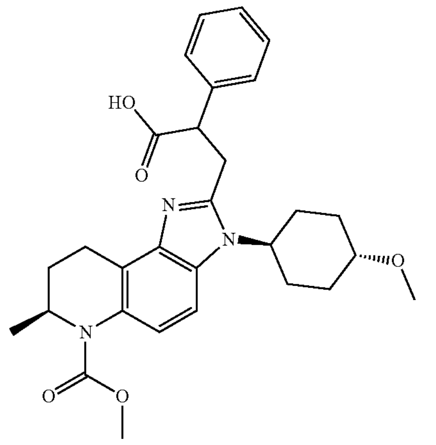<br>1st eluting isomer (151)<br>2nd eluting isomer (152)<br>3-((S)-6-(methoxycarbonyl)-3-((trans)-4-methoxy-cyclohexyl)-7-methyl-6,7,8,9-tetrahydro-3H-imidazo[4,5-f]quinolin-2-yl)-2-phenyl-propanoic acid | 1st eluting isomer = 506<br>2nd eluting isomer = 506 | 1st eluting isomer $^1$H-NMR ($CD_3OD$, 300 MHz) δ (ppm): 7.45-7.14 (m, 7H), 4.76-4.68 (m, 1H), 4.27-4.02 (m, 2H), 3.76 (s, 3H), 3.70-3.61 (m, 1H), 3.41-3.26 (m, 5H), 3.19-3.14 (m, 1H), 2.91-2.79 (m, 1H), 2.37-1.99 (m, 5H), 1.89-1.81 (m, 1H), 1.79-1.58 (m, 1H), 1.51-1.15 (m, 2H), 1.10 (d, J = 6.6 Hz, 3H), 1.01-0.90 (m, 1H)<br>2nd eluting isomer $^1$H-NMR ($CD_3OD$, 300 MHz) δ (ppm): 7.48-7.11 (m, 7H), 4.76-4.69 (m, 1H), 4.30-4.16 (m, 1H), 4.09-4.02 (m, 1H), 3.76 (s, 3H), 3.68-3.62 (m, 1H), 3.38-3.29 (m, 5H), 3.16 (m, 1H), 2.87 (m, 1H), 2.36-2.02 (m, 5H), 1.89-1.81 (m, 1H), 1.72-1.61 (m, 1H), 1.43-1.18 (m, 2H), 1.12 (d, J = 6.7 Hz, 3H), 1.11-1.03 (m, 1H) |
| 153 and 154 | 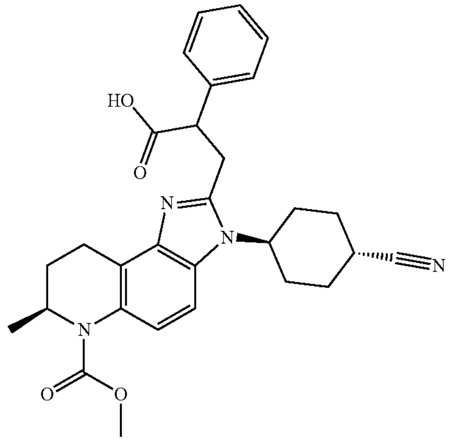<br>1st eluting isomer (153)<br>2nd eluting isomer (154)<br>3-((S)-3-((trans)-4-cyanocyclohexyl)-6-(methoxy-carbonyl)-7-methyl-6,7,8,9-tetrahydro-3H-imidazo[4,5-f]quinolin-2-yl)-2-phenyl-propanoic acid | 1st eluting isomer = 501<br>2nd eluting isomer = 501 | 1st eluting isomer $^1$H-NMR ($CD_3OD$, 400 MHz) δ (ppm): 7.39-7.35 (m, 3H), 7.35-7.25 (m, 3H), 7.25-7.21 (m, 1H), 4.88-4.73 (m, 1H), 4.26-4.21 (m, 1H), 4.07-4.04 (m, 1H), 3.78 (s, 3H), 3.70-3.65 (m, 1H), 3.51-3.39 (m, 2H), 3.33-3.14 (m, 1H), 2.95-2.91 (m, 1H), 2.91-2.77 (m, 1H), 2.28-2.22 (m, 3H), 2.22-2.11 (m, 2H), 1.98-1.90 (m, 1H), 1.74-1.71 (m, 1H), 1.63-1.60 (m, 1H), 1.12 (d, J = 6.7 Hz, 3H), 1.01 (s, 1H)<br>2nd eluting isomer $^1$H-NMR ($CD_3OD$, 400 MHz) δ (ppm): 7.43-7.22 (m, 7H), 4.91-4.73 (m, 1H), 4.30-4.06 (m, 1H), 4.04-4.02 (m, 1H), 3.78 (s, 3H), 3.72-3.66 (m, 1H), 3.38-3.33 (m, 1H), 3.18-3.16 (m, 1H), 2.97-2.81 (m, 2H), 2.31-2.15 (m, 5H), 2.13-1.87 (m, 2H), 1.87-1.62 (m, 2H), 1.15 (d, J = 6.6 Hz, 3H), 1.16-1.14 (m, 1H) |

TABLE 8-continued

| Example Number | Structure and Compound Name | LRMS m/z [M + H]$^+$ | $^1$HNMR |
|---|---|---|---|
| 155 and 156 | 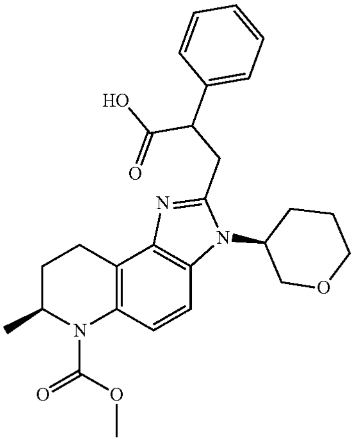<br>$1^{st}$ eluting isomer (155)<br>$2^{nd}$ eluting isomer (156)<br>3-((S)-6-(methoxycarbonyl)-7-methyl-3-((S)-tetrahydro-2H-pyran-3-yl)-6,7,8,9-tetrahydro-3H-imidazo[4,5-f]quinolin-2-yl)-2-phenylpropanoic acid | $1^{st}$ eluting isomer = 478<br>$2^{nd}$ eluting isomer = 478 | $1^{st}$ eluting isomer $^1$H-NMR ($CD_3OD$, 400 MHz) δ (ppm): 7.53-7.48 (m, 1H), 7.37-7.22 (m, 6H), 4.76-4.71 (m, 1H), 4.48-4.42 (m, 1H), 4.22-4.16 (m, 1H), 4.06-3.87 (m, 2H), 3.79 (s, 3H), 3.70-3.66 (m, 1H), 3.55-3.49 (m, 1H), 3.38-3.34 (m, 1H), 3.21-3.12 (m, 2H), 2.93-2.87 (m, 1H), 2.52-2.45 (m, 1H), 2.31-2.18 (m, 1H), 2.09-2.01 (m, 1H), 1.89-1.80 (m, 2H), 1.73-1.65 (m, 1H), 1.12 (d, J = 6.4 Hz, 3H)<br>$2^{nd}$ eluting isomer $^1$H-NMR ($CD_3OD$, 400 MHz) δ (ppm): 7.49 (d, J = 9.0 Hz, 1H), 7.47-7.34 (m, 3H), 7.33-7.31 (m, 2H), 7.24-7.20 (m, 1H), 4.78-4.75 (m, 1H), 4.43-4.32 (m, 1H), 4.21-4.16 (m, 1H), 4.06 (t, J = 10.8 Hz, 1H), 4.03-3.88 (m, 2H), 3.78 (s, 3H), 3.76-3.63 (m, 1H), 3.54-3.49 (m, 1H), 3.44-3.35 (m, 1H), 3.19-3.12 (m, 1H), 2.93-2.82 (m, 1H), 2.43-2.18 (m, 2H), 1.74-1.61 (m, 3H), 1.33-1.17 (m, 1H), 1.15 (d, J = 6.4 Hz, 3H) |
| 157 and 158 | 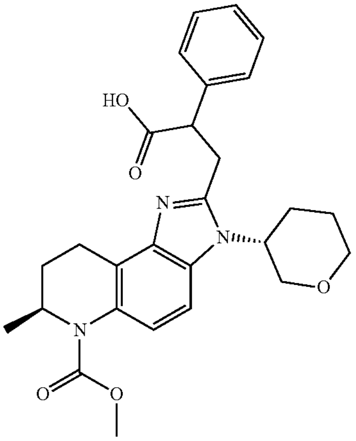<br>$1^{st}$ eluting isomer (157)<br>$2^{nd}$ eluting isomer (158)<br>3-((S)-6-(methoxycarbonyl)-7-methyl-3-(piperidin-4-ylmethyl)-6,7,8,9-tetrahydro-3H-imidazo[4,5-f]quinolin-2-yl)-2-phenylpropanoic acid | $1^{st}$ eluting isomer = 478<br>$2^{nd}$ eluting isomer = 478 | $1^{st}$ eluting isomer $^1$H-NMR ($CD_3OD$, 300 MHz) δ (ppm): 7.80-7.70 (m, 2H), 7.32-7.21 (m, 5H), 4.60-4.73 (m, 1H), 4.21 (t, J = 15.0 Hz, 1H), 3.97-3.83 (m, 3H), 3.70 (s, 3H), 3.64-3.48 (m, 2H), 3.35-3.25 (m, 1H), 3.02-2.81 (m, 2H), 2.58-2.38 (m, 1H), 2.20-2.05 (m, 2H), 1.98-1.75 (m, 3H), 1.21 (m, 1H), 1.05 (d, J = 6.9 Hz, 3H)<br>$2^{nd}$ eluting isomer $^1$H-NMR ($CD_3OD$, 300 MHz) δ (ppm): 7.80-7.70 (m, 2H), 7.32-7.21 (m, 5H), 4.62-4.50 (m, 1H), 4.20 (t, J = 15.0 Hz, 1H), 3.93 (d, J = 9.0 Hz, 2H), 3.92-3.83 (m, 2H), 3.71 (s, 3H), 3.69-3.48 (m, 2H), 2.98-2.86 (m, 2H), 2.38-2.08 (m, 2H), 1.88-1.60 (m, 3H), 1.32-1.20 (m, 2H), 1.04 (d, J = 3.3 Hz, 3H) |

TABLE 8-continued

| Example Number | Structure and Compound Name | LRMS m/z [M + H]+ | $^1$HNMR |
|---|---|---|---|
| 159, 160, 161 and 162 | 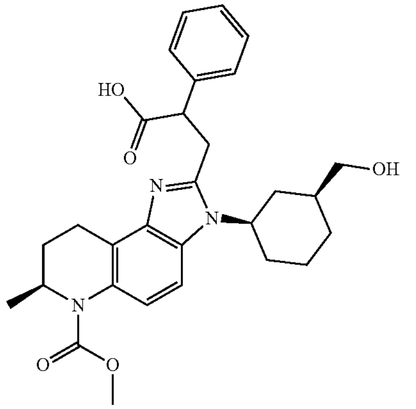 1$^{st}$ eluting isomer (159) 2$^{nd}$ eluting isomer (160) 3$^{rd}$ eluting isomer (161) 4$^{th}$ eluting isomer (162) 3-((S)-3-((cis)-3-(hydroxymethyl)cyclohexyl)-6-(methoxycarbonyl)-7-methyl-6,7,8,9-tetrahydro-3H-imidazo[4,5-f]quinolin-2-yl)-2-phenyl-propanoic acid | 1$^{st}$ eluting isomer = 506 2$^{nd}$ eluting isomer = 506 3$^{rd}$ eluting isomer = 506 4$^{th}$ eluting isomer = 506 | 1$^{st}$ eluting isomer $^1$H-NMR ($CD_3OD$, 400 MHz) δ (ppm): 7.45-7.26 (m, 7H), 4.76-4.74 (m, 1H), 4.30-4.22 (m, 2H), 3.76 (s, 3H), 3.71-3.66 (m, 1H), 3.43-3.30 (m, 3H), 3.15-3.12 (m, 1H), 2.92-2.87 (m, 1H), 2.22-2.17 (m, 2H), 1.98-1.72 (m, 5H), 1.57-1.54 (m, 2H), 1.13-1.09 (m, 5H) 2$^{nd}$ eluting isomer $^1$H-NMR ($CD_3OD$, 400 MHz) δ (ppm): 7.43-7.25 (m, 7H), 4.76-4.73 (m, 1H), 4.25-4.22 (m, 2H), 3.76 (s, 3H), 3.66-3.64 (m, 1H), 3.43-3.29 (m, 3H), 3.13-3.11 (m, 1H), 2.94-2.90 (m, 1H), 2.22-2.17 (m, 2H), 1.98-1.72 (m, 5H), 1.57-1.54 (m, 2H), 1.12-0.96 (m, 5H) 3$^{rd}$ eluting isomer $^1$H-NMR ($CD_3OD$, 400 MHz) δ (ppm): 7.45-7.24 (m, 7H), 4.76-4.74 (m, 1H), 4.30-4.22 (m, 2H), 3.76 (s, 3H), 3.71-3.66 (m, 1H), 3.43-3.30 (m, 3H), 3.15-3.12 (m, 1H), 2.92-2.87 (m, 1H), 2.22-2.21 (m, 1H), 2.04-1.72 (m, 7H), 1.41-1.38 (m, 1H), 1.12-1.07 (m, 5H) 4$^{th}$ eluting isomer $^1$H-NMR ($CD_3OD$, 400 MHz) δ (ppm): 7.46-7.25 (m, 7H), 4.76-4.74 (m, 1H), 4.30-4.22 (m, 2H), 3.76 (s, 3H), 3.71-3.66 (m, 1H), 3.43-3.30 (m, 3H), 3.15-3.12 (m, 1H), 2.92-2.87 (m, 1H), 2.22-2.21 (m, 1H), 2.04-1.72 (m, 7H), 1.41-1.38 (m, 1H), 1.20-1.09 (m, 5H) |
| 163, 164, 165 and 166 | 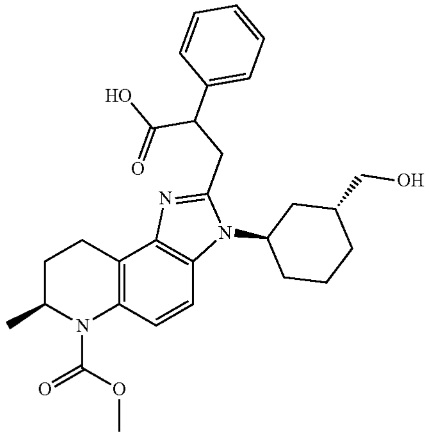 1$^{st}$ eluting isomer (163) 2$^{nd}$ eluting isomer (164) 3$^{rd}$ eluting isomer (165) 4$^{th}$ eluting isomer (166) 3-((S)-3-((trans)-3-(hydroxymethyl)cyclohexyl)-6-(methoxycarbonyl)-7-methyl-6,7,8,9-tetrahydro-3H-imidazo[4,5-f]quinolin-2-yl)-2-propanoic acid | 1$^{st}$ eluting isomer = 506 2$^{nd}$ eluting isomer = 506 3$^{rd}$ eluting isomer = 506 4$^{th}$ eluting isomer = 506 | 1$^{st}$ eluting isomer $^1$H-NMR ($CD_3OD$, 400 MHz) δ (ppm): 7.45-7.26 (m, 7H), 4.76-4.74 (m, 1H), 4.30-4.22 (m, 2H), 3.76 (s, 3H), 3.71-3.66 (m, 1H), 3.43-3.30 (m, 3H), 3.15-3.12 (m, 1H), 2.92-2.87 (m, 1H), 2.22-2.17 (m, 2H), 1.98-1.72 (m, 5H), 1.57-1.54 (m, 2H), 1.13-1.09 (m, 5H) 2$^{nd}$ eluting isomer $^1$H-NMR ($CD_3OD$, 400 MHz) δ (ppm): 7.43-7.25 (m, 7H), 4.76-4.73 (m, 1H), 4.25-4.22 (m, 2H), 3.76 (s, 3H), 3.66-3.64 (m, 1H), 3.43-3.29 (m, 3H), 3.13-3.11 (m, 1H), 2.94-2.90 (m, 1H), 2.22-2.17 (m, 2H), 1.98-1.72 (m, 5H), 1.57-1.54 (m, 2H), 1.12-0.96 (m, 5H) 3$^{rd}$ eluting isomer $^1$H-NMR ($CD_3OD$, 400 MHz) δ (ppm): 7.45-7.24 (m, 7H), 4.76-4.74 (m, 1H), 4.30-4.22 (m, 2H), 3.76 (s, 3H), 3.71-3.66 (m, 1H), 3.43-3.30 (m, 3H), 3.15-3.12 (m, 1H), 2.92-2.87 (m, 1H), 2.22-2.21 (m, 1H), 2.04-1.72 (m, 7H), 1.41-1.38 (m, 1H), 1.12-1.07 (m, 5H) 4$^{th}$ eluting isomer $^1$H-NMR ($CD_3OD$, 400 MHz) δ (ppm): 7.46-7.25 (m, 7H), 4.76-4.74 (m, 1H), 4.30-4.22 (m, 2H), 3.76 (s, 3H), 3.71-3.66 (m, 1H), 3.43-3.30 (m, 3H), 3.15-3.12 (m, 1H), 2.92-2.87 (m, 1H), 2.22-2.21 (m, 1H), 2.04-1.72 (m, 7H), 1.41-1.38 (m, 1H), 1.20-1.09 (m, 5H) |

TABLE 8-continued

| Example Number | Structure and Compound Name | LRMS m/z [M + H]+ | 1HNMR |
|---|---|---|---|
| 167 and 168 | 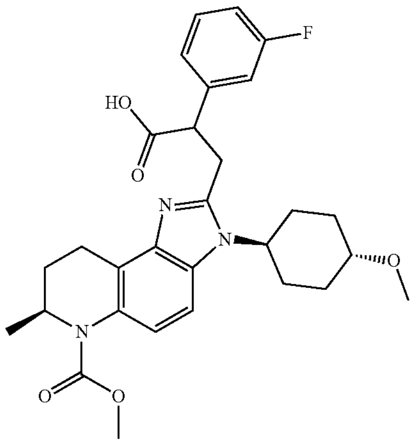<br>1st eluting isomer (167)<br>2nd eluting isomer (168)<br>2-(3-fluorophenyl)-3-((S)-6-(methoxycarbonyl)-3-((trans)-4-methoxycyclohexyl)-7-methyl-6,7,8,9-tetrahydro-3H-imidazo[4,5-f]quinolin-2-yl)propanoic acid | 1st eluting isomer = 524<br>2nd eluting isomer = 524 | 1st eluting isomer 1H-NMR ($CD_3OD$, 300 MHz) δ (ppm): 7.43-7.36 (m, 2H), 7.32-7.02 (m, 1H), 7.15-7.02 (m, 2H), 7.00-6.99 (m, 1H), 4.76-4.73 (m, 1H), 4.34-4.23 (m, 2H), 3.70-3.67 (m, 4H), 3.40-3.32 (m, 4H), 3.13-3.07 (m, 1H), 2.93-2.87 (m, 1H), 2.32-2.13 (m, 5H), 1.96 (d, J = 12.6 Hz, 1H), 1.76-1.69 (m, 1H), 1.56-1.19 (m, 3H), 1.12 (d, J = 6.6 Hz, 3H)<br>2nd eluting isomer 1H-NMR ($CD_3OD$, 300 MHz) δ (ppm): 7.41-7.34 (m, 2H), 7.34-7.24 (m, 1H), 7.24-7.16 (m, 1H), 7.16-7.14 (m, 1H), 7.00-6.96 (m, 1H), 4.77-4.72 (m, 1H), 4.34 (s, 1H), 4.14 (s, 1H), 3.77 (s, 3H), 3.77-3.65 (m, 1H), 3.41-3.31 (s, 5H), 3.16-3.13 (m, 1H), 2.91-2.85 (m, 1H), 2.40-2.13 (m, 5H), 1.98-1.94 (m, 1H), 1.76-1.69 (m, 1H), 1.50-1.46 (m, 1H), 1.34-1.26 (m, 2H), 1.13 (d, J = 6.7 Hz, 3H) |
| 169 and 170 | 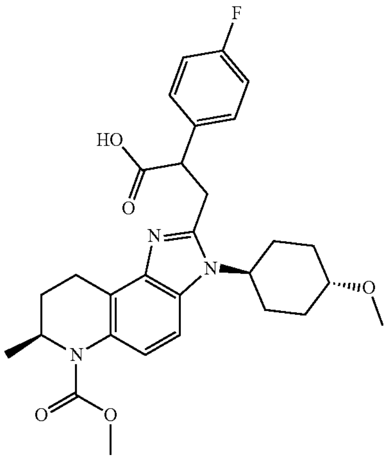<br>1st eluting isomer (169)<br>2nd eluting isomer (170)<br>2-(4-fluorophenyl)-3-((S)-6-(methoxycarbonyl)-3-((trans)-4-methoxycyclohexyl)-7-methyl-6,7,8,9-tetrahydro-3H-imidazo[4,5-f]quinolin-2-yl)propanoic acid | 1st eluting isomer = 524<br>2nd eluting isomer = 524 | 1st eluting isomer 1H-NMR (DMSO-d6, 400 MHz) δ (ppm): 7.40-7.07 (m, 6H), 4.64-4.59 (m, 1H), 4.28-4.14 (m, 2H), 3.65 (s, 3H), 3.58-3.52 (m, 1H), 3.34 (s, 4H), 3.16-3.11 (m, 1H), 3.04-2.96 (m, 1H), 2.81-2.67 (m, 1H), 2.14-2.01 (m, 5H), 1.86-1.83 (m, 1H), 1.62-1.57 (m, 1H), 1.36-1.23 (m, 3H), 1.04-1.03 (m, 3H)<br>2nd eluting isomer 1H-NMR (DMSO-d6, 400 MHz) δ (ppm): 7.46-7.10 (m, 6H), 4.64-4.59 (m, 1H), 4.36-4.17 (m, 2H), 3.65 (s, 3H), 3.65-3.57 (m, 1H), 3.34 (s, 4H), 3.16-3.11 (m, 1H), 3.04-2.96 (m, 1H), 2.81-2.67 (m, 1H), 2.14-2.01 (m, 5H), 1.86-1.83 (m, 1H), 1.62-1.23 (m, 4H), 1.05-1.04 (m, 3H) |

TABLE 8-continued

| Example Number | Structure and Compound Name | LRMS m/z [M + H]+ | 1HNMR |
|---|---|---|---|
| 171 and 172 | 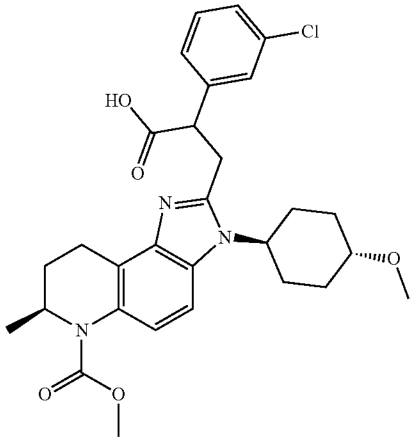<br>1st eluting isomer (171)<br>2nd eluting isomer (172)<br>2-(3-chlorophenyl)-3-((S)-6-(methoxycarbonyl)-3-((trans)-4-methoxycyclohexyl)-7-methyl-6,7,8,9-tetrahydro-3H-imidazo[4,5-f]quinolin-2-yl)-propanoic acid | 1st eluting isomer = 539<br>2nd eluting isomer = 539 | 1st eluting isomer 1H-NMR ($CDCl_3$, 300 MHz) δ (ppm): 7.47-7.42 (m, 1H), 7.39-7.32 (m, 1H), 7.22 (s, 3H), 4.74-4.72 (m, 1H), 4.35-4.10 (m, 2H), 3.76 (s, 3H), 3.70-3.60 (m, 1H), 3.35-3.31 (m, 5H), 3.30-2.93 (m, 2H), 2.26-2.18 (m, 5H), 2.16-1.90 (m, 1H), 1.80-1.12 (m, 4H), 1.10 (d, J = 6.6 Hz, 3H)<br>2nd eluting isomer 1H-NMR ($CDCl_3$, 300 MHz) δ (ppm): 7.48-7.22 (m, 6H), 4.74-4.72 (m, 1H), 4.40-4.11 (m, 2H), 3.76-3.65 (m, 4H), 3.40-3.32 (m, 5H), 3.31-2.80 (m, 2H), 2.28-2.15 (m, 5H), 1.89-1.30 (m, 5H), 1.28 (d, J = 67.2 Hz, 3H) |
| 173 and 174 | 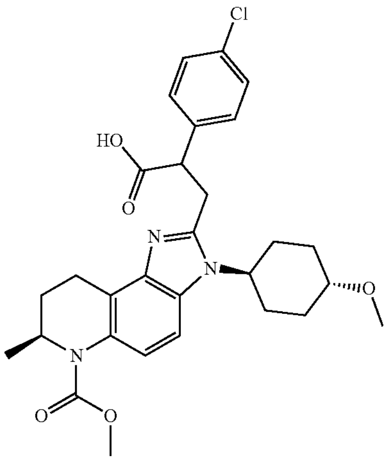<br>1st eluting isomer (173)<br>2nd eluting isomer (174)<br>2-(4-chlorophenyl)-3-((S)-6-(methoxycarbonyl)-3-((trans)-4-methoxycyclohexyl)-7-methyl-6,7,8,9-tetrahydro-3H-imidazo[4,5-f]quinolin-2-yl)propanoic acid | 1st eluting isomer = 539<br>2nd eluting isomer = 539 | 1st eluting isomer 1H-NMR ($CDCl_3$, 300 MHz) δ (ppm): 7.41-7.25 (m, 6H), 4.74-4.72 (m, 1H), 4.30-4.05 (m, 2H), 3.76 (s, 3H), 3.70-3.60 (m, 1H), 3.40-3.30 (m, 5H), 3.20-2.92 (m, 2H), 2.25-2.16 (m, 5H), 1.90-1.29 (m, 5H), 1.10 (d, J = 6.6 Hz, 3H)<br>2nd eluting isomer 1H-NMR ($CDCl_3$, 300 MHz) δ (ppm): 7.36-7.23 (m, 6H), 4.80-4.70 (m, 1H), 4.40-4.95 (m, 2H), 3.75 (s, 3H), 3.70-3.60 (m, 1H), 3.40-3.30 (m, 5H), 3.29-2.80 (m, 2H), 2.40-2.05 (m, 5H), 1.98-1.45 (m, 2H), 1.50-1.11 (m, 6H) |

TABLE 8-continued

| Example Number | Structure and Compound Name | LRMS m/z $[M + H]^+$ | $^1$HNMR |
|---|---|---|---|
| 175 and 176 | 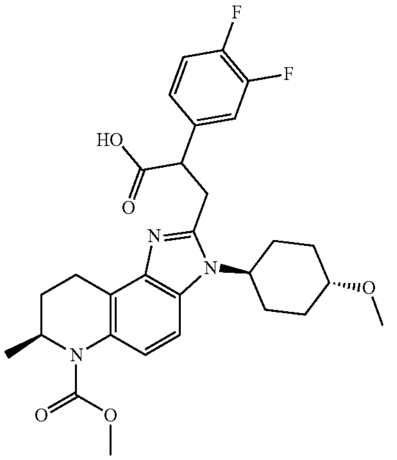 1st eluting isomer (175) 2nd eluting isomer (176) 2-(3,4-difluorophenyl)-3-((S)-6-(methoxy-carbonyl)-3-((trans)-4-methoxycyclohexyl)-7-methyl-6,7,8,9-tetrahydro-3H-imidazo[4,5-f]quinolin-2-yl)propanoic acid | 1st eluting isomer = 542 2nd eluting isomer = 542 | 1st eluting isomer $^1$H-NMR ($CD_3OD$, 400 MHz) δ (ppm): 7.47 (d, J = 9.0 Hz, 1H), 7.42-7.37 (m, 2H), 7.24-7.14 (m, 2H), 4.79-4.71 (m, 1H), 4.44-4.28 (m, 1H), 4.28-4.22 (m, 1H), 3.76-3.70 (m, 4H), 3.49-3.35 (m, 4H), 3.17-3.09 (m, 1H), 3.09-3.00 (m, 1H), 2.94-2.87 (m, 1H), 2.38-2.18 (m, 5H), 2.01-1.92 (m, 1H), 1.77-1.69 (m, 1H), 1.55-1.38 (m, 3H), 1.11 (d, J = 6.7 Hz, 3H) 2nd eluting isomer $^1$H-NMR ($CD_3OD$, 400 MHz) δ (ppm): 7.47 (d, J = 9.0 Hz, 1H), 7.42-7.37 (m, 2H), 7.24-7.14 (m, 2H), 4.79-4.71 (m, 1H), 4.44-4.28 (m, 1H), 4.28-4.22 (m, 1H), 3.76-3.70 (m, 4H), 3.49-3.35 (m, 5H), 3.17-3.09 (m, 1H), 2.94-2.87 (m, 1H), 2.38-2.18 (m, 5H), 2.01-1.96 (m, 1H), 1.77-1.69 (m, 1H), 1.55-1.38 (m, 3H), 1.11 (d, J = 6.7 Hz, 3H) |
| 177 and 178 | 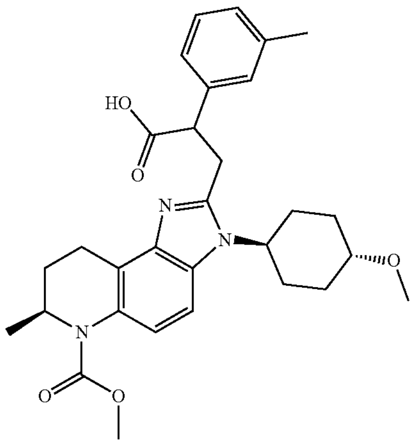 1st eluting isomer (177) 2nd eluting isomer (178) 3-((S)-6-(methoxycarbonyl)-3-((trans)-4-methoxy-cyclohexyl)-7-methyl-6,7,8,9-tetrahydro-3H-imidazo[4,5-f]quinolin-2-yl)-2-(m-tolyl)-propanoic acid | 1st eluting isomer = 520 2nd eluting isomer = 520 | 1st eluting isomer $^1$H-NMR ($CD_3OD$, 400 MHz) δ (ppm): 7.83-7.75 (m, 2H), 7.27-7.12 (m, 4H), 4.81-4.80 (m, 1H), 4.58-4.50 (m, 1H), 4.20-4.17 (m, 1H), 3.99-3.94 (m, 1H), 3.80 (s, 3H), 3.74-3.68 (m, 1H), 3.49-3.33 (m, 4H), 3.17-2.91 (m, 2H), 2.44-2.02 (m, 9H), 1.97-1.82 (m, 1H), 1.54-1.44 (m, 1H), 1.38-1.22 (m, 2H), 1.16 (d, J = 6.7 Hz, 3H) 2nd eluting isomer $^1$H-NMR ($CD_3OD$, 300 MHz) δ (ppm): 7.83-7.75 (m, 2H), 7.27-7.12 (m, 4H), 4.81-4.80 (m, 1H), 4.58-4.50 (m, 1H), 4.20-4.17 (m, 1H), 3.99-3.94 (m, 1H), 3.80 (s, 3H), 3.74-3.68 (m, 1H), 3.49-3.33 (m, 4H), 3.17-2.91 (m, 2H), 2.44-2.02 (m, 9H), 1.97-1.82 (m, 1H), 1.54-1.44 (m, 1H), 1.38-1.22 (m, 2H), 1.16 (d, J = 6.7 Hz, 3H) |

TABLE 8-continued

| Example Number | Structure and Compound Name | LRMS m/z [M + H]$^+$ | $^1$HNMR |
|---|---|---|---|
| 179 and 180 | 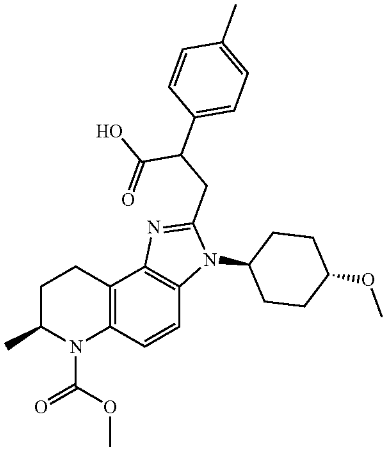<br>1$^{st}$ eluting isomer (179)<br>2$^{nd}$ eluting isomer (180)<br>3-((S)-6-(methoxycarbonyl)-3-((trans)-4-methoxycyclohexyl)-7-methyl-6,7,8,9-tetrahydro-3H-imidazo[4,5-f]quinolin-2-yl)-2-(p-tolyl)propanoic acid | 1$^{st}$ eluting isomer = 520<br>2$^{nd}$ eluting isomer = 520 | 1$^{st}$ eluting isomer $^1$H-NMR ($CD_3OD$, 300 MHz) δ (ppm): 7.36-7.27 (m, 2H), 7.26-7.18 (m, 2H), 7.07-7.02 (m, 2H), 4.82-4.68 (m, 1H), 4.11-4.03 (m, 1H), 4.02-3.92 (m, 1H), 3.77 (s, 3H), 3.68-3.52 (m, 1H), 3.43-3.34 (m, 4H), 3.21-3.04 (m, 1H), 2.99-2.80 (m, 1H), 2.33-1.99 (m, 8H), 1.97-1.82 (m, 1H), 1.79-1.62 (m, 1H), 1.49-1.04 (m, 6H), 0.98-0.81 (m, 1H)<br>2$^{nd}$ eluting isomer $^1$H-NMR ($CD_3OD$, 300 MHz) δ (ppm): 7.41-7.27 (m, 2H), 7.26-7.17 (m, 2H), 7.11-7.01 (m, 2H), 4.79-4.62 (m, 1H), 4.23-4.06 (m, 1H), 4.02-3.89 (m, 1H), 3.75 (s, 3H), 3.75-3.56 (m, 1H), 3.41-3.33 (m, 4H), 3.24-3.09 (m, 1H), 2.93-2.77 (m, 1H), 2.36-1.99 (m, 8H), 1.95-1.82 (m, 1H), 1.79-1.61 (m, 1H), 1.52-1.07 (m, 6H), 1.06-0.93 (m, 1H) |
| 181 and 182 | 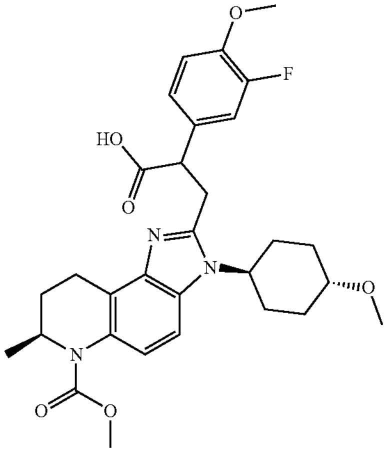<br>1$^{st}$ eluting isomer (181)<br>2$^{nd}$ eluting isomer (182)<br>2-(3-fluoro-4-methoxyphenyl)-3-((S)-6-(methoxycarbonyl)-3-((trans)-4-methoxycyclohexyl)-7-methyl-6,7,8,9-tetrahydro-3H-imidazo[4,5-f]quinolin-2-yl)propanoic acid | 1$^{st}$ eluting isomer = 554<br>2$^{nd}$ eluting isomer = 554 | 1$^{st}$ eluting isomer $^1$H-NMR ($CD_3OD$, 300 MHz) δ (ppm): 7.50-7.29 (m, 2H), 7.22 (d, 1H), 7.06-6.89 (m, 2H), 4.81-4.68 (m, 1H), 4.27-4.21 (m, 1H), 4.00 (t, J = 7.5 Hz, 1H), 3.81 (S, 3H), 3.78 (S, 3H), 3.70-3.56 (m, 1H), 3.48-3.34 (m, 5H), 3.23-3.06 (m, 1H), 2.99-2.83 (m, 1H), 2.34-2.09 (m, 5H), 1.93-1.85 (m, 1H), 1.79-1.62 (m, 1H), 1.52-1.22 (m, 2H), 1.20-1.07 (m, 4H)<br>2$^{nd}$ eluting isomer $^1$H-NMR ($CD_3OD$, 300 MHz) δ (ppm): 7.47-7.32 (m, 2H), 7.25 (d, J = 12.2 Hz, 1H), 7.10-6.91 (m, 2H), 4.81-4.68 (m, 1H), 4.32-4.26 (m, 1H), 4.05-3.96 (m, 1H), 3.80 (S, 3H), 3.78 (S, 3H), 3.72-3.58 (m, 1H), 3.48-3.34 (m, 5H), 3.25-3.08 (m, 1H), 2.95-2.79 (m, 1H), 2.38-2.10 (m, 5H), 1.93-1.85 (m, 1H), 1.78-1.65 (m, 1H), 1.54-1.20 (m, 3H), 1.14 (d, J = 6.6 Hz, 3H) |

TABLE 8-continued

| Example Number | Structure and Compound Name | LRMS m/z [M + H]+ | 1HNMR |
|---|---|---|---|
| 183 and 184 | 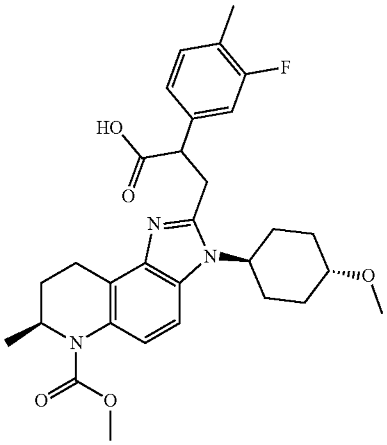<br>1st eluting isomer (183)<br>2nd eluting isomer (184)<br>2-(3-fluoro-4-methylphenyl)-3-((S)-6-(methoxycarbonyl)-3-((trans)-4-methoxycyclohexyl)-7-methyl-6,7,8,9-tetrahydro-3H-imidazo-[4,5-f]quinolin-2-yl)propanoic acid | 1st eluting isomer = 538<br>2nd eluting isomer = 538 | 1st eluting isomer 1H-NMR ($CD_3OD$, 300 MHz) δ (ppm): 7.45-7.28 (m, 2H), 7.14-7.08 (m, 2H), 7.00-6.97 (m, 1H), 4.73-4.71 (m, 1H), 4.24-4.10 (m, 1H), 4.07-4.04 (m, 1H), 3.77 (s, 3H), 3.64-3.61 (m, 1H), 3.40-3.32 (m, 5H), 3.23-3.07 (m, 1H), 2.96-2.88 (m, 1H), 2.34-2.07 (m, 8H), 1.93 (d, J = 12.5 Hz, 1H), 1.79-1.62 (m, 1H), 1.53-1.17 (m, 3H), 1.11 (d, J = 6.7 Hz, 3H)<br>2nd eluting isomer 1H-NMR ($CD_3OD$, 300 MHz) δ (ppm): 7.37-7.31 (m, 2H), 7.16-7.01 (m, 2H), 7.00-6.96 (m, 1H), 4.90 (s, 1H), 4.26-4.10 (m, 1H), 4.01-3.95 (m, 1H), 3.76 (s, 3H), 3.70-3.61 (m, 1H), 3.42-3.35 (m, 5H), 3.16-3.04 (m, 1H), 2.93-2.80 (m, 1H), 2.38-2.07 (m, 8H), 1.95-1.85 (m, 1H), 1.73-1.67 (m, 1H), 1.48-1.35 (m, 1H), 1.32-1.18 (m, 2H), 1.13 (d, J = 6.7 Hz, 3H) |
| 185 and 186 | 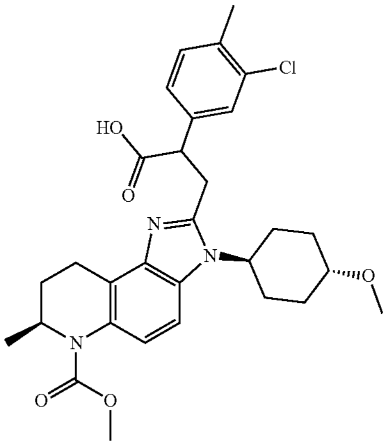<br>1st eluting isomer (185)<br>2nd eluting isomer (186)<br>2-(3-chloro-4-methylphenyl)-3-((S)-6-(methoxycarbonyl)-3-((trans)-4-methoxy-cyclohexyl)-7-methyl-6,7,8,9-tetrahydro-3H-imidazo[4,5-f]-quinolin-2-yl)-propanoic acid | 1st eluting isomer = 553<br>2nd eluting isomer = 553 | 1st eluting isomer 1H-NMR ($CD_3OD$, 400 MHz) δ (ppm): 7.83-7.75 (m, 2H), 7.27-7.12 (m, 4H), 4.81-4.80 (m, 1H), 4.58-4.50 (m, 1H), 4.20-4.17 (m, 1H), 3.99-3.94 (m, 1H), 3.80 (s, 3H), 3.74-3.68 (m, 1H), 3.49-3.33 (m, 4H), 3.17-2.91 (m, 2H), 2.44-2.02 (m, 9H), 1.97-1.82 (m, 1H), 1.54-1.44 (m, 1H), 1.38-1.22 (m, 2H), 1.16 (d, J = 6.7 Hz, 3H)<br>2nd eluting isomer 1H-NMR ($CD_3OD$, 300 MHz) δ (ppm): 7.83-7.75 (m, 2H), 7.27-7.12 (m, 4H), 4.81-4.80 (m, 1H), 4.58-4.50 (m, 1H), 4.20-4.17 (m, 1H), 3.99-3.94 (m, 1H), 3.80 (s, 3H), 3.74-3.68 (m, 1H), 3.49-3.33 (m, 4H), 3.17-2.91 (m, 2H), 2.44-2.02 (m, 9H), 1.97-1.82 (m, 1H), 1.54-1.44 (m, 1H), 1.38-1.22 (m, 2H), 1.16 (d, J = 6.7 Hz, 3H) |

TABLE 8-continued

| Example Number | Structure and Compound Name | LRMS m/z [M + H]+ | 1HNMR |
|---|---|---|---|
| 187 and 188 | 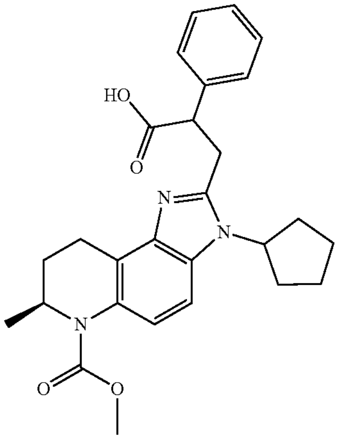 1st eluting isomer (179) 2nd eluting isomer (180) 3-((S)-3-cyclopentyl-6-(methoxycarbonyl)-7-methyl-6,7,8,9-tetrahydro-3H-imidazo-[4,5-f]quinolin-2-yl)-2-phenyl-propanoic acid | 1st eluting isomer = 461 2nd eluting isomer = 461 | 1st eluting isomer 1H-NMR ($CD_3OD$, 300 MHz) δ (ppm): 7.36-7.27 (m, 2H), 7.26-7.18 (m, 2H), 7.07-7.02 (m, 2H), 4.82-4.68 (m, 1H), 4.11-4.03 (m, 1H), 4.02-3.92 (m, 1H), 3.77 (s, 3H), 3.68-3.52 (m, 1H), 3.43-3.34 (m, 4H), 3.21-3.04 (m, 1H), 2.99-2.80 (m, 1H), 2.33-1.90 (m, 8H), 1.97-1.82 (m, 1H), 1.79-1.62 (m, 1H), 1.49-1.04 (m, 6H), 0.98-0.81 (m, 1H) 2nd eluting isomer 1H-NMR ($CD_3OD$, 300 MHz) δ (ppm): 7.41-7.27 (m, 2H), 7.26-7.17 (m, 2H), 7.11-7.01 (m, 2H), 4.79-4.62 (m, 1H), 4.23-4.06 (m, 1H), 4.02-3.89 (m, 1H), 3.75 (s, 3H), 3.75-3.56 (m, 1H), 3.41-3.33 (m, 4H), 3.24-3.09 (m, 1H), 2.93-2.77 (m, 1H), 2.36-1.99 (m, 8H), 1.95-1.82 (m, 1H), 1.79-1.61 (m, 1H), 1.52-1.07 (m, 6H), 1.06-0.93 (m, 1H) |
| 189 and 190 | 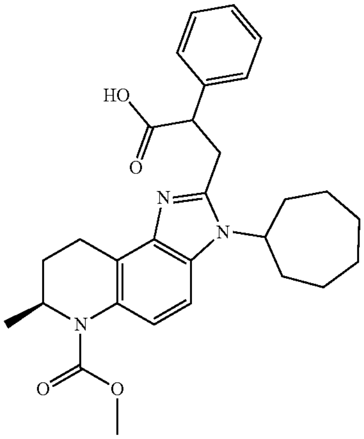 1st eluting isomer (189) 2nd eluting isomer (190) 3-((S)-3-cycloheptyl-6-(methoxycarbonyl)-7-methyl-6,7,8,9-tetrahydro-3H-imidazo[4,5-f]quinolin-2-yl)-2-phenylpropanoic acid | 1st eluting isomer = 489 2nd eluting isomer = 489 | 1st eluting isomer 1H-NMR ($CD_3OD$, 300 MHz) δ (ppm): 7.50-7.29 (m, 2H), 7.22 (d, 1H), 7.06-6.89 (m, 2H), 4.81-4.68 (m, 1H), 4.27-4.21 (m, 1H), 4.00 (t, J = 7.5 Hz, 1H), 3.81 (S, 3H), 3.78 (S, 3H), 3.70-3.56 (m, 1H), 3.48-3.34 (m, 5H), 3.23-3.06 (m, 1H), 2.99-2.83 (m, 1H), 2.34-2.09 (m, 5H), 1.93-1.85 (m, 1H), 1.79-1.62 (m, 1H), 1.52-1.22 (m, 2H), 1.20-1.07 (m, 4H) 2nd eluting isomer 1H-NMR ($CD_3OD$, 300 MHz) δ (ppm): 7.47-7.32 (m, 2H), 7.25 (d, J = 12.2 Hz, 1H), 7.10-6.91 (m, 2H), 4.81-4.68 (m, 1H), 4.32-4.26 (m, 1H), 4.05-3.96 (m, 1H), 3.80 (S, 3H), 3.78 (S, 3H), 3.72-3.58 (m, 1H), 3.48-3.34 (m, 5H), 3.25-3.08 (m, 1H), 2.95-2.79 (m, 1H), 2.38-2.10 (m, 5H), 1.93-1.85 (m, 1H), 1.78-1.65 (m, 1H), 1.54-1.20 (m, 3H), 1.14 (d, J = 6.6 Hz, 3H) |

TABLE 8-continued

| Example Number | Structure and Compound Name | LRMS m/z $[M + H]^+$ | $^1$HNMR |
|---|---|---|---|
| 191 and 192 | 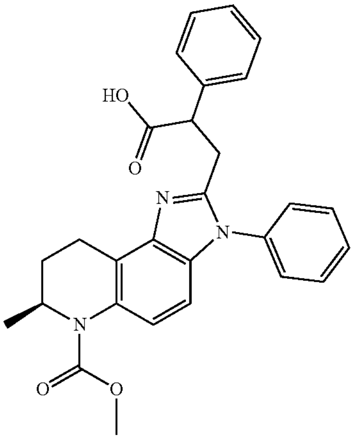 1st eluting isomer (191) 2nd eluting isomer (192) 3-((S)-6-(methoxycarbonyl)-7-methyl-3-phenyl-6,7,8,9-tetrahydro-3H-imidazo-[4,5-f]quinolin-2-yl)-2-phenyl-propanoic acid | 1st eluting isomer = 540 2nd eluting isomer = 540 | 1st eluting isomer $^1$H-NMR ($CD_3OD$, 300 MHz) δ (ppm): 7.58-7.49 (m, 3H), 7.39-6.90 (m, 7H), 6.78 (d, J = 9 Hz, 1H), 4.81-4.67 (m, 1H), 4.29-4.01 (m, 1H), 3.75 (s, 3H), 3.63-3.44 (m, 1H), 3.27-3.10 (m, 2H), 3.02-2.89 (m, 1H), 2.36-2.15 (m, 1H), 1.81-1.61 (m, 1H), 1.49-1.04 (m, 1H), 1.17-1.04 (d, J = 6.6 Hz, 3H) 2nd eluting isomer $^1$H-NMR ($CD_3OD$, 300 MHz) δ (ppm): 7.66-7.49 (m, 3H), 7.32 (d, J = 9 Hz, 1H), 7.26-6.99 (m, 7H), 6.80 (d, J = 9 Hz, 1H), 4.83-4.67 (m, 1H), 4.12-3.98 (m, 1H), 3.74 (s, 3H), 3.63-3.49 (m, 1H), 3.27-3.11 (m, 2H), 3.01-2.79 (m, 1H), 2.34-2.16 (m, 1H), 1.83-1.61 (m, 1H), 1.19 (d, J = 6.6 Hz, 3H) |
| 193 and 194 | 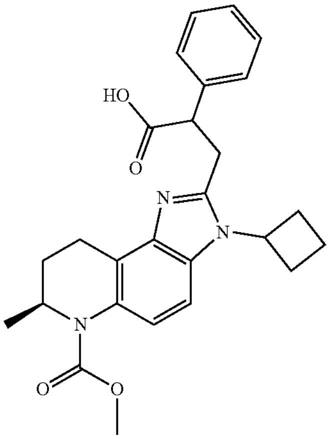 1st eluting isomer (193) 2nd eluting isomer (194) 3-((S)-3-cyclobutyl-6-(methoxycarbonyl)-7-methyl-6,7,8,9-tetrahydro-3H-imidazo-[4,5-f]quinolin-2-yl)-2-phenyl-propanoic acid | 1st eluting isomer = 447 2nd eluting isomer = 447 | 1st eluting isomer $^1$H-NMR ($CD_3OD$, 300 MHz) δ (ppm): 7.83-7.75 (m, 2H), 7.27-7.12 (m, 4H), 4.81-4.80 (m, 1H), 4.58-4.50 (m, 1H), 4.20-4.17 (m, 1H), 3.99-3.94 (m, 1H), 3.80 (s, 3H), 3.74-3.68 (m, 1H), 3.49-3.33 (m, 4H), 3.17-2.91 (m, 2H), 2.44-2.02 (m, 9H), 1.97-1.82 (m, 1H), 1.54-1.44 (m, 1H), 1.38-1.22 (m, 2H), 1.16 (d, J = 6.7 Hz, 3H) 2nd eluting isomer $^1$H-NMR ($CD_3OD$, 300 MHz) δ (ppm): 7.83-7.75 (m, 2H), 7.27-7.12 (m, 4H), 4.81-4.80 (m, 1H), 4.58-4.50 (m, 1H), 4.20-4.17 (m, 1H), 3.99-3.94 (m, 1H), 3.80 (s, 3H), 3.74-3.68 (m, 1H), 3.49-3.33 (m, 4H), 3.17-2.91 (m, 2H), 2.44-2.02 (m, 9H), 1.97-1.82 (m, 1H), 1.54-1.44 (m, 1H), 1.38-1.22 (m, 2H), 1.16 (d, J = 6.7 Hz, 3H) |

TABLE 8-continued

| Example Number | Structure and Compound Name | LRMS m/z [M + H]+ | 1HNMR |
|---|---|---|---|
| 195 and 196 | 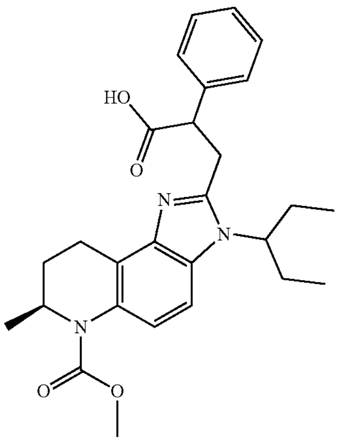 1st eluting isomer (195) 2nd eluting isomer (196) 3-((S)-6-(methoxycarbonyl)-7-methyl-3-(pentan-3-yl)-6,7,8,9-tetrahydro-3H-imidazo[4,5-f]quinolin-2-yl)-2-phenylpropanoic acid | 1st eluting isomer = 463 2nd eluting isomer = 463 | 1st eluting isomer 1H-NMR ($CD_3OD$, 300 MHz) δ (ppm): 7.36-7.27 (m, 2H), 7.26-7.18 (m, 2H), 7.07-7.02 (m, 2H), 4.82-4.68 (m, 1H), 4.11-4.03 (m, 1H), 4.02-3.92 (m, 1H), 3.77 (s, 3H), 3.68-3.52 (m, 1H), 3.43-3.34 (m, 4H), 3.21-3.04 (m, 1H), 2.99-2.80 (m, 1H), 2.33-1.99 (m, 8H), 1.97-1.82 (m, 1H), 1.79-1.62 (m, 1H), 1.49-1.04 (m, 6H), 0.98-0.81 (m, 1H) 2nd eluting isomer 1H-NMR ($CD_3OD$, 300 MHz) δ (ppm): 7.41-7.27 (m, 2H), 7.26-7.17 (m, 2H), 7.11-7.01 (m, 2H), 4.79-4.62 (m, 1H), 4.23-4.06 (m, 1H), 4.02-3.89 (m, 1H), 3.75 (s, 3H), 3.75-3.56 (m, 1H), 3.41-3.33 (m, 4H), 3.24-3.09 (m, 1H), 2.93-2.77 (m, 1H), 2.36-1.99 (m, 8H), 1.95-1.82 (m, 1H), 1.79-1.61 (m, 1H), 1.52-1.07 (m, 6H), 1.06-0.93 (m, 1H) |
| 197 and 198 | 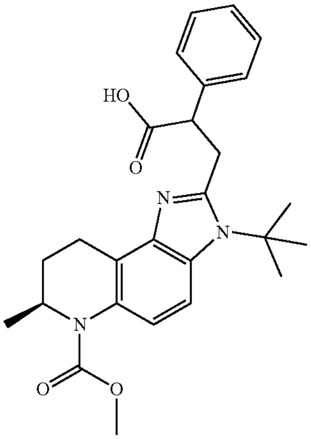 1st eluting isomer (197) 2nd eluting isomer (198) 3-((S)-3-(tert-butyl)-6-(methoxycarbonyl)-7-methyl-6,7,8,9-tetrahydro-3H-imidazo[4,5-f]quinolin-2-yl)-2-phenylpropanoic acid | 1st eluting isomer = 449 2nd eluting isomer = 449 | 1st eluting isomer 1H-NMR ($CD_3OD$, 300 MHz) δ (ppm): 7.50-7.29 (m, 2H), 7.22 (d, 1H), 7.06-6.89 (m, 2H), 4.81-4.68 (m, 1H), 4.27-4.21 (m, 1H), 4.00 (t, J = 7.5 Hz, 1H), 3.81 (S, 3H), 3.78 (S, 3H), 3.70-3.56 (m, 1H), 3.48-3.34 (m, 5H), 3.23-3.06 (m, 1H), 2.99-2.83 (m, 1H), 2.34-2.09 (m, 5H), 1.93-1.85 (m, 1H), 1.79-1.62 (m, 1H), 1.52-1.22 (m, 2H), 1.20-1.07 (m, 4H) 2nd eluting isomer 1H-NMR ($CD_3OD$, 300 MHz) δ (ppm): 7.47-7.32 (m, 2H), 7.25 (d, J = 12.2 Hz, 1H), 7.10-6.91 (m, 2H), 4.81-4.68 (m, 1H), 4.32-4.26 (m, 1H), 4.05-3.96 (m, 1H), 3.80 (S, 3H), 3.78 (S, 3H), 3.72-3.58 (m, 1H), 3.48-3.34 (m, 5H), 3.25-3.08 (m, 1H), 2.95-2.79 (m, 1H), 2.38-2.10 (m, 5H), 1.93-1.85 (m, 1H), 1.78-1.65 (m, 1H), 1.54-1.20 (m, 3H), 1.14 (d, J = 6.6 Hz, 3H) |

TABLE 8-continued

| Example Number | Structure and Compound Name | LRMS m/z [M + H]$^+$ | $^1$HNMR |
|---|---|---|---|
| 199 and 200 | 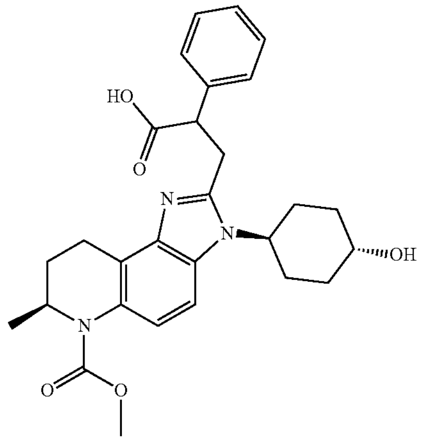 1$^{st}$ eluting isomer (199) 2$^{nd}$ eluting isomer (200) 3-((S)-3-((trans)-4-hydroxycyclohexyl)-6-(methoxycarbonyl)-7-methyl-6,7,8,9-tetrahydro-3H-imidazo[4,5-f]quinolin-2-yl)-2-phenylpropanoic acid | 1$^{st}$ eluting isomer = 492 2$^{nd}$ eluting isomer = 492 | 1$^{st}$ eluting isomer $^1$H-NMR ($CD_3OD$, 400 MHz) δ (ppm): 7.82-7.74 (m, 2H), 7.39-7.33 (m, 5H), 4.55-4.52 (m, 1H), 4.24-4.21 (m, 1H), 4.01-3.95 (m, 1H), 3.79-3.69 (m, 5H), 3.04-3.00 (m, 1H), 2.96-2.93 (m, 1H), 2.42-2.38 (m, 1H), 2.25-2.21 (m, 2H), 2.19-2.10 (m, 1H), 2.04-1.98 (m, 2H), 1.92-1.87 (m, 1H), 1.60-1.56 (m, 1H), 1.43-1.39 (m, 1H), 1.28-1.22 (m, 2H), 1.16 (d, J = 6.4 Hz, 3H) 2$^{nd}$ eluting isomer $^1$H-NMR ($CD_3OD$, 400 MHz) δ (ppm): 7.39-7.23 (m, 7H), 4.75-4.71 (m, 1H), 4.91-4.17 (m, 2H), 3.75 (s, 3H), 3.70-3.64 (m, 2H), 3.39-3.36 (m, 1H), 3.13-3.11 (m, 1H), 2.93-2.89 (m, 1H), 2.28-2.14 (m, 3H), 2.08-2.05 (m, 1H), 1.95-1.87 (m, 2H), 1.73-1.69 (m, 1H), 1.58-1.53 (m, 1H), 1.33-1.29 (m, 1H), 1.11 (d, J = 6.8 Hz, 3H), 1.00-0.95 (m, 1H) |
| 201 and 202 | 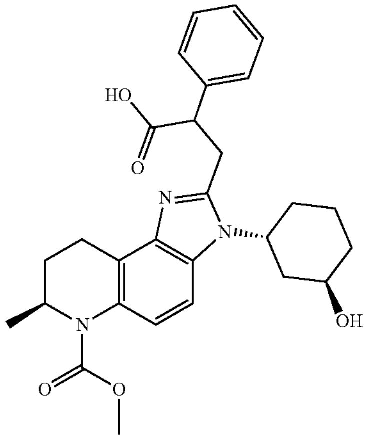 1$^{st}$ eluting isomer (201) 2$^{nd}$ eluting isomer (202) 3-((S)-3-((1R,3R)-3-hydroxycyclohexyl)-6-(methoxycarbonyl)-7-methyl-6,7,8,9-tetra-hydro-3H-imidazo[4,5-f]quinolin-2-yl)-2-phenylpropanoic acid | 1$^{st}$ eluting isomer = 492 2$^{nd}$ eluting isomer = 492 | 1$^{st}$ eluting isomer $^1$H-NMR ($CD_3OD$, 400 MHz) δ (ppm): 7.86-7.80 (m, 2H), 7.45-7.32 (m, 5H), 5.17-5.11 (m, 1H), 4.34-4.31 (m, 2H), 4.01-3.95 (m, 1H), 3.80 (s, 3H), 3.60-3.55 (m, 1H), 3.04-2.90 (m, 2H), 2.54-2.41 (m, 2H), 2.24-2.18 (m, 1H), 2.09-1.97 (m, 3H), 1.91-1.71 (m, 4H), 1.30-1.28 (m, 1H), 1.15 (d, J = 6.4 Hz, 3H) 2$^{nd}$ eluting isomer $^1$H-NMR ($CD_3OD$, 300 MHz) δ (ppm): 7.79-7.73 (m, 2H), 7.38-7.31 (m, 5H), 4.81-4.76 (m, 1H), 4.29-4.20 (m, 2H), 3.93-3.90 (m, 1H), 3.81-3.75 (m, 4H), 2.99-2.96 (m, 2H), 2.43-2.42 (m, 1H), 2.23-2.04 (m, 3H), 1.90-1.78 (m, 3H), 1.68-1.61 (m, 2H), 1.30-1.28 (m, 1H), 1.13-1.06 (m, 4H) |

TABLE 8-continued

| Example Number | Structure and Compound Name | LRMS m/z $[M + H]^+$ | $^1$HNMR |
|---|---|---|---|
| 203 and 204 | 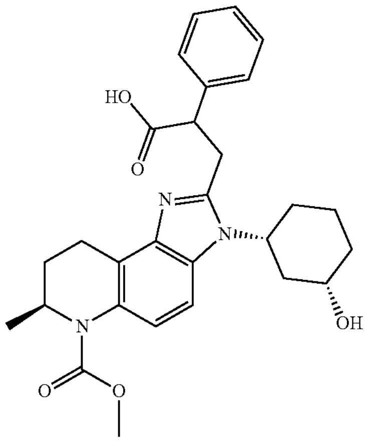<br>$1^{st}$ eluting isomer (203)<br>$2^{nd}$ eluting isomer (204)<br>3-((S)-3-((1R,3S)-3-hydroxycyclohexyl)-6-(methoxycarbonyl)-7-methyl-6,7,8,9-tetrahydro-3H-imidazo[4,5-f]quinolin-2-yl)-2-phenylpropanoic acid | $1^{st}$ eluting isomer = 492<br>$2^{nd}$ eluting isomer = 492 | $1^{st}$ eluting isomer $^1$H-NMR ($CD_3OD$, 300 MHz) δ (ppm): 7.42-7.30 (m, 4H), 7.28-7.24 (m, 3H), 4.76-4.71 (m, 1H), 4.32-4.30 (m, 1H), 4.16-4.15 (m, 1H), 3.75 (s, 3H), 3.71-3.65 (m, 1H), 3.57-3.56 (m, 1H), 3.35-3.33 (m, 1H), 3.16-3.12 (m, 1H), 2.90-2.86 (m, 1H), 2.24-2.19 (m, 1H), 2.11-1.99 (m, 3H), 1.97-1.85 (m, 2H), 1.74-1.69 (m, 1H), 1.52-1.49 (m, 2H), 1.33-1.30 (m, 1H), 1.13 (d, J = 6.4 Hz, 3H)<br>$2^{nd}$ eluting isomer $^1$H-NMR ($CD_3OD$, 300 MHz) δ (ppm): 7.43-7.24 (m, 7H), 4.76-4.72 (m, 1H), 4.28-4.25 (m, 2H), 3.76-3.67 (m, 5H), 3.39-3.33 (m, 1H), 3.14-3.12 (m, 1H), 2.94-2.90 (m, 1H), 2.23-1.95 (m, 5H), 1.78-1.71 (m, 2H), 1.35-1.28 (m, 2H), 1.12 (d, J = 6.4 Hz, 3H), 1.03-1.00 (m, 1H) |
| 205 and 206 | 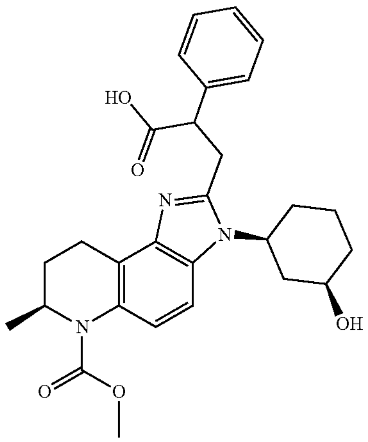<br>$1^{st}$ eluting isomer (205)<br>$2^{nd}$ eluting isomer (206)<br>3-((S)-3-((1S,3R)-3-hydroxycyclohexyl)-6-(methoxycarbonyl)-7-methyl-6,7,8,9-tetrahydro-3H-imidazo[4,5-f]quinolin-2-yl)-2-phenylpropanoic acid | $1^{st}$ eluting isomer = 492<br>$2^{nd}$ eluting isomer = 492 | $1^{st}$ eluting isomer $^1$H-NMR ($CD_3OD$, 300 MHz) δ (ppm): 7.41-7.24 (m, 7H), 4.75-4.71 (m, 1H), 4.25-4.16 (m, 2H), 3.75 (s, 3H), 3.69-3.65 (m, 1H), 3.54-3.52 (m, 1H), 3.35-3.33 (m, 1H), 3.13-3.09 (m, 1H), 2.93-2.89 (m, 1H), 2.23-2.22 (m, 1H), 2.06-1.97 (m, 3H), 1.91-1.85 (m, 2H), 1.73-1.68 (m, 1H), 1.51-1.29 (m, 3H), 1.11 (d, J = 6.4 Hz, 3H)<br>$2^{nd}$ eluting isomer $^1$H-NMR ($CD_3OD$, 300 MHz) δ (ppm): 7.41-7.24 (m, 7H), 4.75-4.71 (m, 1H), 4.25-4.16 (m, 2H), 3.75 (s, 3H), 3.69-3.65 (m, 1H), 3.54-3.52 (m, 1H), 3.35-3.33 (m, 1H), 3.13-3.09 (m, 1H), 2.93-2.89 (m, 1H), 2.23-2.22 (m, 1H), 2.06-1.97 (m, 3H), 1.91-1.85 (m, 2H), 1.73-1.68 (m, 1H), 1.51-1.29 (m, 3H), 1.11 (d, J = 6.4 Hz, 3H |

TABLE 8-continued

| Example Number | Structure and Compound Name | LRMS m/z [M + H]+ | $^1$HNMR |
|---|---|---|---|
| 207 and 208 | 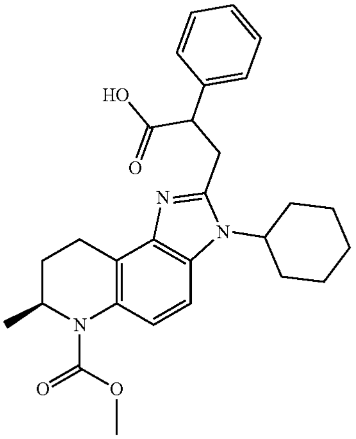<br>1st eluting isomer (207)<br>2nd eluting isomer (208)<br>3-((S)-3-cyclohexyl-6-(methoxycarbonyl)-7-methyl-6,7,8,9-tetrahydro-3H-imidazo-[4,5-f]quinolin-2-yl)-2-phenylpropanoic acid | 1st eluting isomer = 476<br>2nd eluting isomer = 476 | 1st eluting isomer $^1$H-NMR ($CD_3OD$, 400 MHz) δ (ppm): 7.85-7.75 (m, 2H), 7.37-7.32 (m, 5H), 4.86-4.82 (m, 1H), 4.50-4.40 (m, 1H), 4.24-4.20 (m, 1H), 3.99-3.93 (m, 1H), 3.80 (s, 3H), 3.74-3.70 (m, 1H), 2.99-2.97 (m, 2H), 2.26-2.20 (m, 2H), 2.14-2.12 (m, 1H), 2.02-1.83 (m, 4H), 1.78-1.76 (m, 1H), 1.52-1.42 (m, 1H), 1.45-1.30 (m, 2H), 1.20-1.12 (m, 4H)<br>2nd eluting isomer $^1$H-NMR ($CD_3OD$, 400 MHz) δ (ppm): .83-7.79 (m, 2H), 7.38-7.32 (m, 5H), 4.86-4.82 (m, 1H), 4.50-4.40 (m, 1H), 4.24-4.20 (m, 1H), 3.99-3.93 (m, 1H), 3.80 (s, 3H), 3.74-3.70 (m, 1H), 3.04-2.93 (m, 2H), 2.26-2.20 (m, 2H), 2.14-2.12 (m, 1H), 2.02-1.83 (m, 4H), 1.78-1.76 (m, 1H), 1.52-1.42 (m, 1H), 1.45-1.30 (m, 2H), 1.17-1.14 (m, 4H) |
| 209, 210, 211 and 212 | 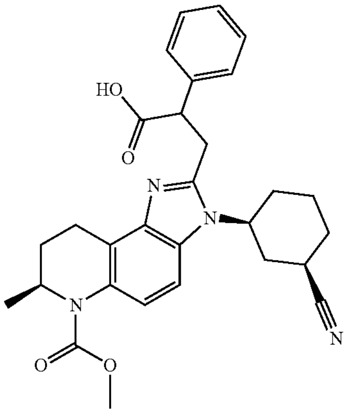<br>1st eluting isomer (209)<br>2nd eluting isomer (210)<br>3rd eluting isomer (211)<br>4th eluting isomer (212)<br>3-((S)-3-((cis)-3-cyanocyclohexyl)-6-(methoxycarbonyl)-7-methyl-6,7,8,9-tetrahydro-3H-imidazo[4,5-f]quinolin-2-yl)-2-phenylpropanoic acid | 1st eluting isomer = 501<br>2nd eluting isomer = 501<br>3rd eluting isomer = 501<br>4th eluting isomer = 501 | 1st eluting isomer $^1$H-NMR ($CD_3OD$, 400 MHz) δ (ppm): 7.88-7.71 (m, 2H), 7.49-7.27 (m, 5H), 4.63-4.42 (m, 1H), 4.36-4.18 (m, 1H), 4.02-3.91 (m, 1H), 3.83 (s, 3H), 3.80-3.62 (m, 1H), 3.11-2.96 (m, 2H), 2.82-2.69 (m, 1H), 2.40-2.21 (m, 3H), 2.21-2.09 (m, 1H), 2.09-1.98 (m, 2H), 1.98-1.86 (m, 1H), 1.86-1.61 (m, 2H), 1.38-1.27 (m, 1H), 1.22-1.11 (m, 4H)<br>2nd eluting isomer $^1$H-NMR ($CD_3OD$, 400 MHz) δ (ppm): 7.91-7.73 (m, 2H), 7.49-7.27 (m, 5H), 4.71-4.42 (m, 1H), 4.29-4.12 (m, 1H), 4.11-3.92 (m, 1H), 3.82-3.66 (m, 4H), 3.12-2.93 (m, 2H), 2.83-2.59 (m, 1H), 2.37-1.50 (m, 9H), 1.32-1.25 (m, 2H), 1.18 (d, J = 6.6 Hz, 3H)<br>3rd eluting isomer $^1$H-NMR ($CD_3OD$ ,400 MHz) δ (ppm): 7.51-7.40 (m, 1H), 7.40-7.31 (m, 3H), 7.28-7.19 (m, 2H), 7.19-7.06 (m, 1H), 4.81-4.68 (m, 1H), 4.41-4.23 (m, 1H), 4.11-3.99 (m, 1H), 3.77 (s, 3H), 3.70-3.59 (m, 1H), 3.29-3.20 (m, 1H), 3.20-3.06 (m, 1H), 3.02-2.84 (m, 2H), 2.42-2.31 (m, 1H), 2.31-2.15 (m, 2H), 2.15-2.02 (m, 2H), 1.93-1.82 (m, 1H), 1.74-1.62 (m, 2H), 1.51-1.39 (m, 1H), 1.19-1.04 (m, 4H)<br>4th eluting isomer $^1$H-NMR ($CD_3OD$, 400 MHz) δ (ppm): 7.50-7.18 (m, 7H), 4.79-4.61 (m, 1H), 4.49-4.31 (m, 1H), 4.19-4.03 (m, 1H), 3.78 (s, 3H), 3.72-3.57 (m, 1H), 3.27-3.09 (m, 2H), 3.02-2.80 (m, 2H), 2.55-2.33 (m, 1H), 2.33-2.04 (m, 4H), 1.96-1.79 (m, 1H), 1.79-1.53 (m, 2H), 1.53-1.31 (m, 1H), 1.25-1.01 (m, 4H) |

TABLE 8-continued

| Example Number | Structure and Compound Name | LRMS m/z $[M + H]^+$ | $^1$HNMR |
|---|---|---|---|
| 213, 214, 215 and 216 | 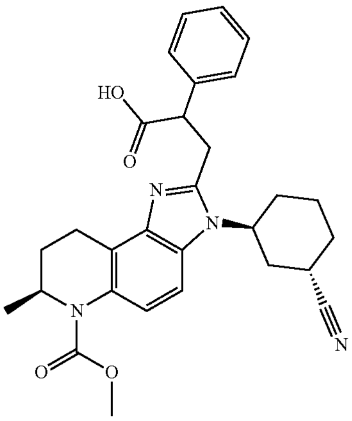<br>$1^{st}$ eluting isomer (213)<br>$2^{nd}$ eluting isomer (214)<br>$3^{rd}$ eluting isomer (215)<br>$4^{th}$ eluting isomer (216)<br>3-((S)-3-((trans)-3-cyanocyclohexyl)-6-(methoxycarbonyl)-7-methyl-6,7,8,9-tetra-hydro-3H-imidazo[4,5-f]quinolin-2-yl)-2-phenylpropanoic acid | $1^{st}$ eluting isomer = 501<br>$2^{nd}$ eluting isomer = 501<br>$3^{rd}$ eluting isomer = 501<br>$4^{th}$ eluting isomer = 501 | $1^{st}$ eluting isomer $^1$H-NMR ($CD_3OD$, 300 MHz) δ (ppm): 7.82-7.66 (m, 2H), 7.49-7.21 (m, 5H), 4.83-4.78 (m, 1H), 4.38-4.24 (m, 1H), 4.93-3.78 (m, 4H), 3.73-3.58 (m, 1H), 3.46-3.35 (m, 2H), 3.16-2.81 (m, 2H), 2.61-1.77 (m, 9H), 1.71-1.53 (m, 1H), 1.16 (d, J = 6.6 Hz, 3H)<br>$2^{nd}$ eluting isomer $^1$H-NMR ($CD_3OD$, 300 MHz) δ (ppm): 7.81-7.67 (m, 2H), 7.50-7.29 (m, 5H), 4.88-4.79 (m, 1H), 4.71-4.46 (m, 1H), 4.34-4.19 (m, 1H), 3.99-3.87 (m, 1H), 3.79 (s, 3H), 3.63-3.47 (m, 1H), 3.47-3.37 (m, 1H), 3.11-2.94 (m, 2H), 2.62-2.42 (m, 1H), 2.42-2.14 (m, 3H), 2.02-1.61 (m, 5H), 1.26-1.04 (m, 4H)<br>$3^{rd}$ eluting isomer $^1$H-NMR ($CD_3OD$, 300 MHz) δ (ppm): 7.51-7.21 (m, 7H), 4.81-4.61 (m, 1H), 4.39-4.22 (m, 1H), 4.13-4.01 (m, 1H), 3.76 (s, 3H), 3.71-3.55 (m, 1H), 3.44-3.33 (m, 1H), 3.24-3.07 (m, 1H), 3.02-2.81 (m, 2H), 2.52-2.13 (m, 3H), 2.09-1.91 (m, 2H), 1.83-1.71 (m, 3H), 1.62-1.43 (m, 1H), 1.14-1.11 (m, 4H)<br>$4^{th}$ eluting isomer $^1$H-NMR ($CD_3OD$, 300 MHz) δ (ppm): 7.43-7.25 (m, 7H), 4.79-4.68 (m, 1H), 4.46-4.32 (m, 1H), 4.26-4.07 (m, 1H), 3.82-3.61 (m, 4H), 3.43-3.32 (m, 1H), 3.23-3.06 (m, 1H), 2.96-2.83 (m, 2H), 2.54-2.38 (m, 1H), 2.33-2.04 (m, 4H), 1.99-1.83 (m, 1H), 1.83-1.54 (m, 2H), 1.44-1.31 (m, 1H), 1.24-0.98 (m, 4H) |

Example 217: methyl (S)-2-benzyl-3-(2-(1,1-dioxidothiomorpholino)ethyl)-7-methyl-3,7,8,9-tetrahydro-6H-imidazo[4,5-f]quinoline-6-carboxylate

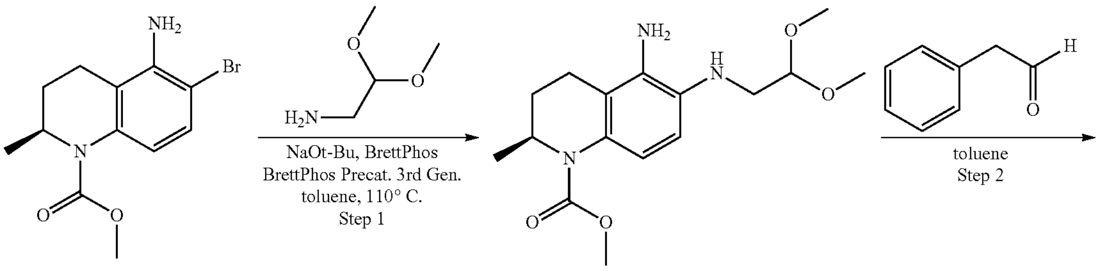

-continued

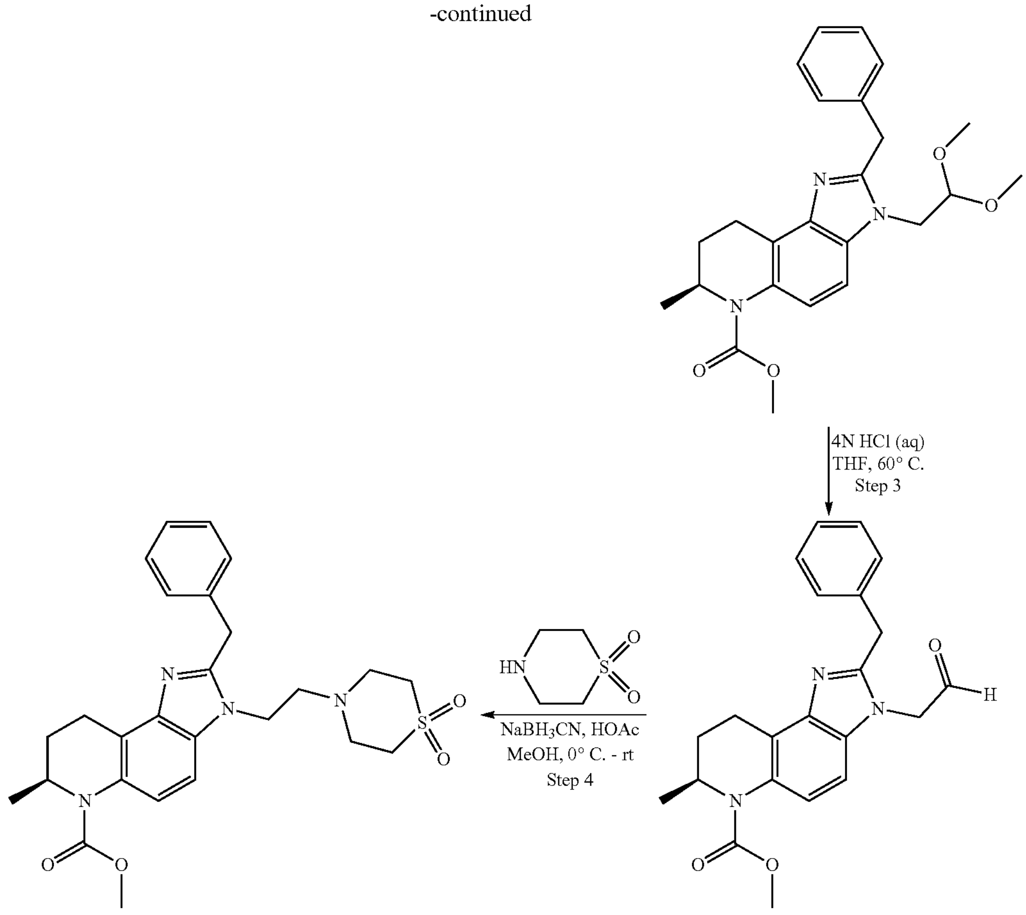

Step 1. Synthesis of methyl (2S)-5-amino-6-[(2,2-dimethoxyethyl)amino]-2-methyl-1,2,3,4-tetrahydro-quinoline-1-carboxylate Into a 50-mL round-bottom flask purged and maintained with an inert atmosphere of nitrogen, methyl (2S)-5-amino-6-bromo-2-methyl-1,2,3,4-tetrahydroquinoline-1-carboxylate (500 mg, 1.67 mmol, Intermediate 1) was dissolved in toluene (10 mL). Then 2,2-dimethoxyethan-1-amine (1.09 g, 10.37 mmol), sodium tert-butoxide (480 mg, 4.99 mmol), 3rd Generation BrettPhos precatalyst (150 mg, 0.17 mmol) and BrettPhos (180 mg, 0.34 mmol) were added successively. The resulting solution was stirred for 2 h at 110° C. under nitrogen atmosphere. The reaction mixture was cooled and the resulting solids were filtered out. The filtrate was concentrated under vacuum. The residue was subjected to purification by FCC eluting with ethyl acetate/petroleum ether (3:1). This afforded the title compound (530 mg, 98%) as a brown oil. MS: (ES, m/z): 324 $[M+H]^+$.

Step 2. Synthesis of methyl (7S)-2-benzyl-3-(2,2-dimethoxyethyl)-7-methyl-3H,6H,7H,8H,9H-imidazo[4,5-f]quinoline-6-carboxylate Into a 100-mL round-bottom flask purged and maintained with an inert atmosphere of nitrogen, methyl (2S)-5-amino-6-[(2,2-dimethoxyethyl)amino]-2-methyl-1,2,3,4-tetrahydroquinoline-1-carboxylate (530 mg, 1.64 mmol) was dissolved in toluene (15 mL). Then 2-phenylacetaldehyde (423 mg, 3.52 mmol) was added. The resulting solution was stirred for 14 h at room temperature. The resulting mixture was concentrated under vacuum. The residue was subjected to purification by FCC eluting with ethyl acetate/petroleum ether (1:1). This afforded the title compound (520 mg, 75%) as a yellow oil. MS: (ES, m/z): 424 $[M+H]^+$.

Step 3. Synthesis of methyl (7S)-2-benzyl-7-methyl-3-(2-oxoethyl)-3H,6H,7H,8H,9H-imidazo[4,5-f]quinoline-6-carboxylate Into a 100-mL round-bottom flask, methyl (7S)-2-benzyl-3-(2,2-dimethoxyethyl)-7-methyl-3H,6H,7H,8H,9H-imidazo[4,5-f]quinoline-6-carboxylate (520 mg, 1.23 mmol) was dissolved in tetrahydrofuran (4 mL). Then hydrochloric acid (4 M, 8 mL) was added. The resulting solution was stirred for 3 h at 60° C. The reaction mixture was cooled to room temperature. The resulting solution was diluted with 40 mL of water and extracted with 2×90 mL of ethyl acetate and the organic layers were combined, dried over anhydrous sodium sulfate, filtered and concentrated under vacuum. This afforded the title compound (450 mg, crude) as a yellow solid. MS: (ES, m/z): 396 $[M+H_2O]^+$.

Step 4. Synthesis of methyl (S)-2-benzyl-3-(2-(1,1-dioxidothiomorpholino)ethyl)-7-methyl-3,7,8,9-tetrahydro-6H-imidazo[4,5-f]quinoline-6-carboxylate Into a 50-mL round-bottom flask, methyl (7S)-2-benzyl-7-methyl-3-(2-oxoethyl)-3H,6H,7H,8H,9H-imidazo[4,5-f]quinoline-6-carboxylate (80 mg, 0.21 mmol) was dissolved in methanol (6 mL). Then thiomorpholine 1,1-dioxide (143 mg, 1.06 mmol) and acetic acid (127 mg, 2.11 mmol) were added. The mixture was stirred at room temperature for 30 min. To the mixture was added sodium cyanoborohydride (134 mg, 2.13 mmol) at 0° C. The resulting solution was stirred for 12 h at room temperature. Then water (20 mL) was added slowly. The resulting solution was extracted with 2×60 mL of ethyl acetate. The organic layers were combined, dried over anhydrous sodium sulfate, filtered and concentrated under vacuum. The crude product was purified by Prep-HPLC with the following conditions: Column, XBridge C18 OBD Prep Column, 100 Å, 5 μm, 19 mm×250 mm; mobile phase, A: water (containing 10 mmol/L $NH_4HCO_3$) and B: ACN (25.0% to 40.0% ACN over 10 min); UV Detector: 254 nm. This afforded the title compound (31 mg, 29%) as a white solid.

$^1$H-NMR (DMSO-$d_6$, 400 MHz) δ (ppm): 7.36-7.20 (m, 7H), 4.69-4.59 (m, 1H), 4.33 (s, 2H), 4.24-4.13 (m, 2H), 3.66 (s, 3H), 3.12-2.94 (m, 5H), 2.90-2.76 (m, 5H), 2.61-2.51 (m, 2H), 2.20-2.06 (m, 1H), 1.66-1.56 (m, 1H), 1.05 (d, J=6.8 Hz, 3H). MS: (ES, m/z): 497 $[M+H]^+$.

The following examples in TABLE 9 were prepared using standard chemical manipulations and procedures similar to those used for the preparation of Examples 217.

TABLE 9

| Example Number | Structure and Compound Name | LRMS m/z $[M + H]^+$ | $^1$HNMR |
|---|---|---|---|
| 218 | 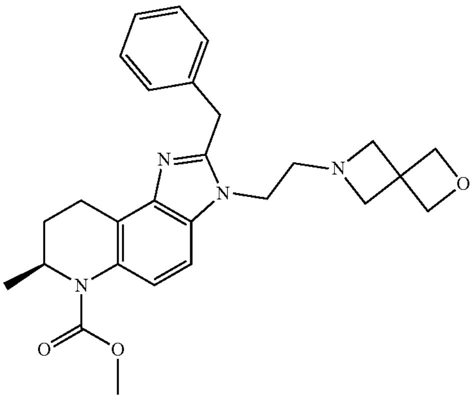 [SMILES: COC(=O)N1c2ccc3c(nc(Cc4ccccc4)n3CCN3CC4(COC4)C3)c2CC[C@@H]1C] methyl (S)-3-(2-(2-oxa-6-azaspiro[3.3]heptan-6-yl)ethyl)-2-benzyl-7-methyl-3,7,8,9-tetrahydro-6H-imidazo[4,5-f]quinoline-6-carboxylate | 461 | $^1$H-NMR (DMSO-d6, 400 MHz) δ (ppm): 7.35-7.19 (m, 7H), 4.69-4.59 (m, 1H), 4.52 (s, 4H), 4.28 (s, 2H), 4.04-3.94 (m, 2H), 3.66 (s, 3H), 3.16 (s, 4H), 3.10-2.99 (m, 1H), 2.80 (dt, J = 16.8, 6.0 Hz, 1H), 2.48-2.42 (m, 2H), 2.18-2.08 (m, 1H), 1.65-1.56 (m, 1H), 1.05 (d, J = 6.4 Hz, 3H) |
| 219 | 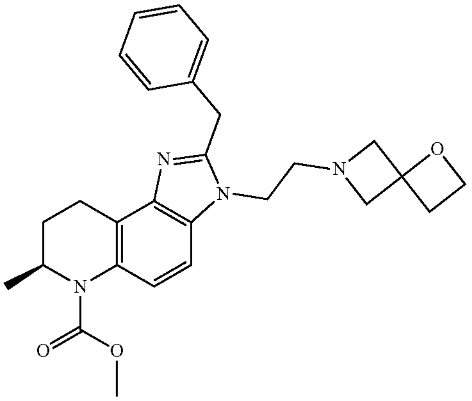 [SMILES: COC(=O)N1c2ccc3c(nc(Cc4ccccc4)n3CCN3CC4(CCO4)C3)c2CC[C@@H]1C] methyl (S)-3-(2-(1-oxa-6-azaspiro[3.3]heptan-6-yl)ethyl)-2-benzyl-7-methyl-3,7,8,9-tetrahydro-6H-imidazo[4,5-f]quinoline-6-carboxylate | 461 | $^1$H-NMR ($CDCl_3$, 300 MHz) δ (ppm): 7.43 (d, J = 8.8 Hz, 1H), 7.36-7.16 (m, 5H), 7.07 (d, J = 8.8 Hz, 1H), 4.88-4.71 (m, 1H), 4.47 (t, J = 7.5 Hz, 2H), 4.42-4.32 (m, 2H), 3.90 (t, J = 7.2 Hz, 2H), 3.78 (s, 3H), 3.50 (s, 2H), 3.36-3.19 (m, 1H), 3.11-2.94 (m, 3H), 2.80 (t, J = 7.5 Hz, 2H), 2.64-2.42 (m, 2H), 2.37-2.19 (m, 1H), 1.82-1.65 (m, 1H), 1.17 (d, J = 6.6 Hz, 3H) |

TABLE 9-continued

| Example Number | Structure and Compound Name | LRMS m/z [M + H]+ | 1HNMR |
|---|---|---|---|
| 220 | 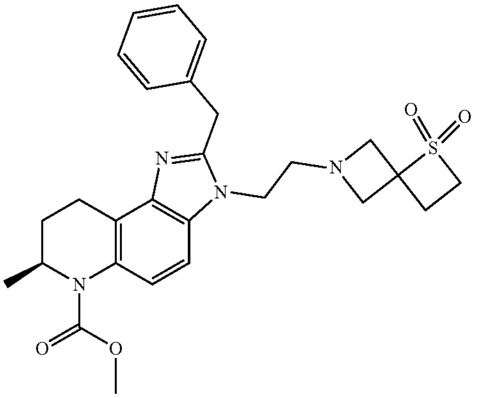 [SMILES: COC(=O)N1c2ccc3c(nc(Cc4ccccc4)n3CCN3CC4(CCS4(=O)=O)C3)c2CC[C@@H]1C] methyl (S)-2-benzyl-3-(2-(1,1-dioxido-1-thia-6-azaspiro[3.3]heptan-6-yl)ethyl)-7-methyl-3,7,8,9-tetrahydro-6H-imidazo[4,5-f]quinoline-6-carboxylate | 509 | 1H-NMR ($CD_3OD$, 400 MHz) δ (ppm): 7.90-7.85 (m, 1H), 7.68-7.65 (m, 1H), 7.45-7.30 (m, 5H), 4.88 (s, 3H), 4.69 (s, 2H), 4.47-4.43 (m, 2H), 4.00-3.98 (m, 4H), 3.80 (s, 3H), 3.12-2.93 (m, 4H), 2.27-2.20 (m, 3H), 1.89-1.86 (m, 1H), 1.16 (d, J = 6.4 Hz, 3H) |
| 221 | 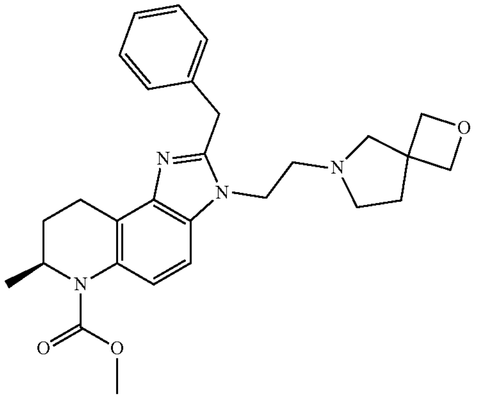 [SMILES: COC(=O)N1c2ccc3c(nc(Cc4ccccc4)n3CCN3CCC4(COC4)C3)c2CC[C@@H]1C] methyl (S)-3-(2-(2-oxa-6-azaspiro[3.4]octan-6-yl)ethyl)-2-benzyl-7-methyl-3,7,8,9-tetrahydro-6H-imidazo[4,5-f]quinoline-6-carboxylate | 475 | 1H-NMR ($CDCl_3$, 300 MHz) δ (ppm): 7.44 (d, J = 8.8 Hz, 1H), 7.32-7.27 (m, 2H), 7.26-7.21 (m, 3H), 7.09 (d, J = 8.8 Hz, 1H), 4.81-4.79 (m, 1H), 4.59 (t, J = 5.2 Hz, 4H), 4.55-4.29 (m, 2H), 4.03 (t, J = 7.5 Hz, 2H), 3.78 (s, 3H), 3.28-3.23 (m, 1H), 3.12-2.95 (m, 1H), 2.68 (s, 2H), 2.57-2.19 (m, 5H), 2.07 (t, J = 7.0 Hz, 2H), 1.77-1.71 (m, 1H), 1.17 (d, J = 6.6 Hz, 3H) |
| 222 | 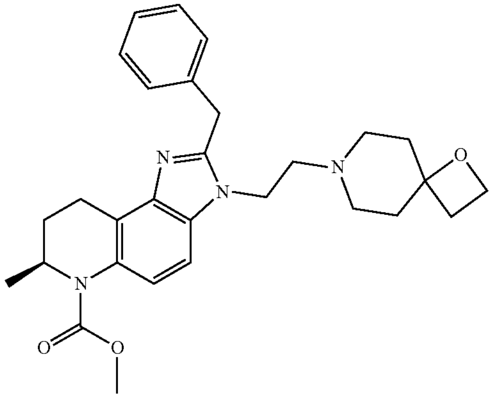 [SMILES: COC(=O)N1c2ccc3c(nc(Cc4ccccc4)n3CCN3CCC4(CCO4)CC3)c2CC[C@@H]1C] methyl (S)-3-(2-(1-oxa-7-azaspiro[3.5]nonan-7-yl)ethyl)-2-benzyl-7-methyl-3,7,8,9-tetrahydro-6H-imidazo[4,5-f]quinoline-6-carboxylate | 489 | 1H-NMR (DMSO-d6, 400 MHz) δ (ppm): 7.48 (d, J = 8.6 Hz, 1H), 7.35-7.28 (m, 2H), 7.28-7.20 (m, 4H), 4.69-4.59 (m, 1H), 4.38-4.28 (m, 4H), 4.20-4.07 (m, 2H), 3.66 (s, 3H), 3.12-2.99 (m, 1H), 2.84-2.75 (m, 1H), 2.46-2.35 (m 2H), 2.34-2.22 (m, 4H), 2.21-2.07 (m, 3H), 1.77-1.55 (m, 5H), 1.05 (d, J = 6.8 Hz, 3H) |

TABLE 9-continued

| Example Number | Structure and Compound Name | LRMS m/z [M + H]+ | 1HNMR |
|---|---|---|---|
| 223 | 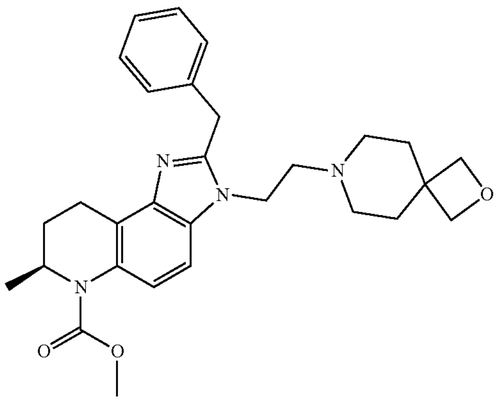 [SMILES: COC(=O)N1c2ccc3c(nc(Cc4ccccc4)n3CCN3CCC4(CC3)COC4)c2CC[C@@H]1C]<br>methyl (S)-3-(2-(2-oxa-7-azaspiro[3.5]nonan-7-yl)ethyl)-2-benzyl-7-methyl-3,7,8,9-tetrahydro-6H-imidazo[4,5-f]quinoline-6-carboxylate | 489 | $^1$H-NMR (DMSO-d6, 400 MHz) δ (ppm): 7.35-7.19 (m, 7H), 4.69-4.59 (m, 1H), 4.31 (s, 2H), 4.23 (s, 3H), 4.19-4.10 (m, 3H), 3.66 (s, 3H), 3.10-3.00 (m, 1H), 2.80-2.75 (m, 1H), 2.35-2.09 (m, 7H), 1.75-1.55 (m, 5H), 1.05 (d, J = 6.4 Hz, 3H) |
| 224 | 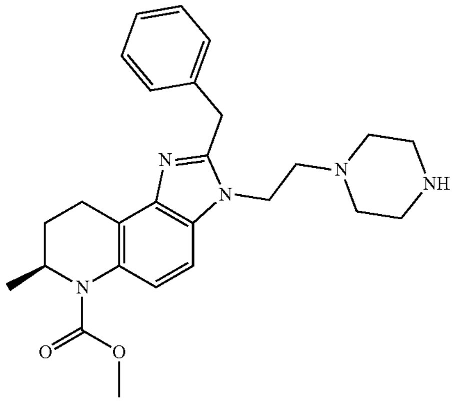 [SMILES: COC(=O)N1c2ccc3c(nc(Cc4ccccc4)n3CCN3CCNCC3)c2CC[C@@H]1C]<br>methyl (S)-2-benzyl-7-methyl-3-(2-(piperazin-1-yl)ethyl)-3,7,8,9-tetrahydro-6H-imidazo[4,5-f]quinoline-6-carboxylate | 448 | $^1$H-NMR ($CDCl_3$, 300 MHz) δ (ppm): 7.43 (d, J = 8.7 Hz, 1H), 7.32-7.26 (m, 2H), 7.26-7.19 (m, 3H), 7.09 (d, J = 8.8 Hz, 1H), 4.83-4.77 (m, 1H), 4.45-4.33 (m, 2H), 4.03 (t, J = 7.2 Hz, 2H), 3.78 (s, 3H), 3.31-3.23 (m, 1H), 3.07-2.98 (m, 1H), 2.88 (t, J = 4.9 Hz, 4H), 2.42-2.22 (m, 8H), 1.77-1.70 (m, 1H), 1.17 (d, J = 6.6 Hz, 3H) |
| 225 | 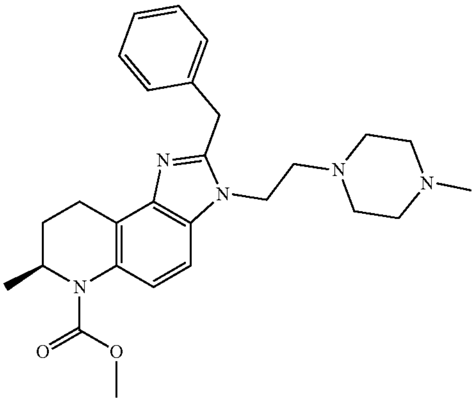<br>methyl (S)-2-benzyl-7-methyl-3-(2-(4-methylpiperazin-1-yl)ethyl)-3,7,8,9-tetrahydro-6H-imidazo[4,5-f]quinoline-6-carboxylate | 462 | $^1$H-NMR ($CDCl_3$, 300 MHz) δ (ppm): 7.43 (d, J = 8.8 Hz, 1H), 7.39-7.27 (m, 2H), 7.24-7.13 (m, 3H), 7.09 (d, J = 8.8 Hz, 1H), 4.83-4.79 (m, 1H), 4.51-4.29 (m, 2H), 4.02 (t, J = 7.2 Hz, 2H), 3.78 (s, 3H), 3.31-3.23 (m, 1H), 3.08-3.00 (m, 1H), 2.46-2.22 (m, 14H), 1.79-1.68 (m, 1H), 1.17 (d, J = 6.7 Hz, 3H) |

TABLE 9-continued

| Example Number | Structure and Compound Name | LRMS m/z $[M + H]^+$ | $^1$HNMR |
|---|---|---|---|
| 226 | 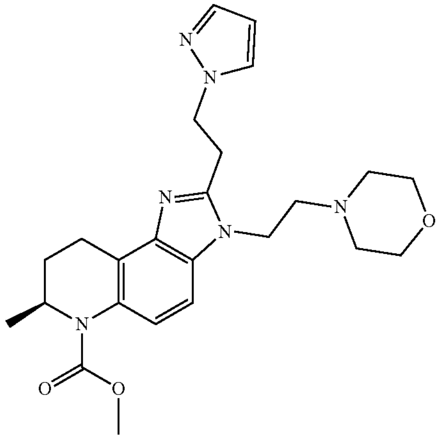 [SMILES: COC(=O)N1c2ccc3c(nc(CCn4cccn4)n3CCN3CCOCC3)c2CC[C@@H]1C]<br>methyl (S)-2-(2-(1H-pyrazol-1-yl)ethyl)-7-methyl-3-(2-morpholinoethyl)-3,7,8,9-tetrahydro-6H-imidazo[4,5-f]quinoline-6-carboxylate | 453 | $^1$H-NMR ($CDCl_3$, 300 MHz) δ (ppm): 7.55 (d, J = 9 Hz, 1H), 7.24 (s, 1H), 7.26-7.21 (m, 1H), 7.06 (d, J = 8.7 Hz, 1H), 6.19-6.00 (m, 1H), 4.82-4.77 (m, 1H), 4.76-4.65 (m, 2H), 4.01-3.88 (m, 2H), 3.88-3.73 (m, 3H), 3.73-3.61 (m, 4H), 3.50-3.41 (m, 2H), 3.32-3.13 (m, 1H), 3.11-2.89 (m, 1H), 2.57-2.49 (m, 2H), 2.49-2.39 (m, 4H), 2.35-2.19 (m, 1H), 1.79-1.64 (m, 1H), 1.16 (d, J = 6.6 Hz, 3H) |
| 227 | 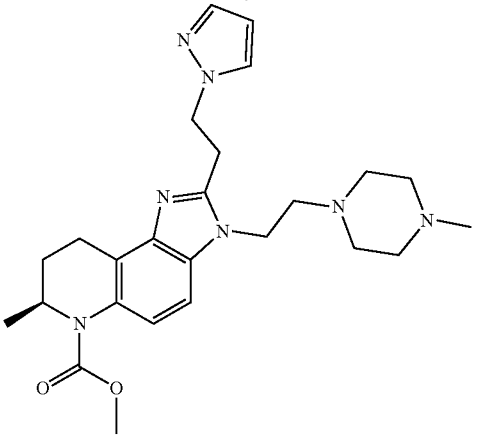<br>methyl (S)-2-(2-(1H-pyrazol-1-yl)ethyl)-7-methyl-3-(2-(4-methylpiperazin-1-yl)ethyl)-3,7,8,9-tetrahydro-6H-imidazo[4,5-f]quinoline-6-carboxylate | 466 | $^1$H-NMR ($CDCl_3$, 300 MHz) δ (ppm): 7.52 (d, J = 1.8 Hz, 1H), 7.43 (d, J = 8.9 Hz, 1H), 7.25-7.18 (m, 1H), 7.06 (d, J = 8.8 Hz, 1H), 6.13 (t, J = 2.1 Hz, 1H), 4.85-4.66 (m, 3H), 3.89 (t, J = 6.7 Hz, 2H), 3.78 (s, 3H), 3.51-3.36 (m, 2H), 3.32-3.15 (m, 1H), 3.08-2.91 (m, 1H), 2.66-2.13 (m, 14H), 1.81-1.64 (m, 1H), 1.16 (d, J = 6.6 Hz, 3H) |
| 228 | 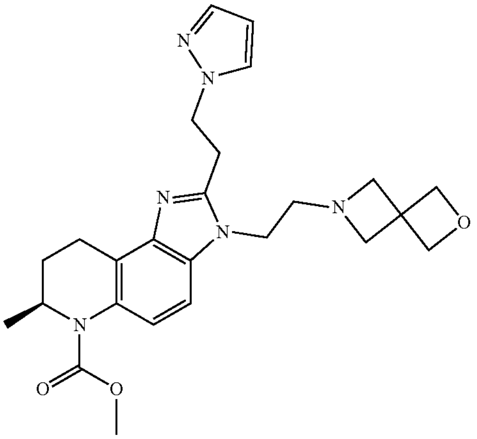 [SMILES: COC(=O)N1c2ccc3c(nc(CCn4cccn4)n3CCN3CC4(COC4)C3)c2CC[C@@H]1C]<br>methyl (S)-2-(2-(1H-pyrazol-1-yl)ethyl)-3-(2-(2-oxa-6-azaspiro[3.3]heptan-6-yl)ethyl)-7-methyl-3,7,8,9-tetrahydro-6H-imidazo[4,5-f]quinoline-6-caiboxylate | 465 | $^1$H-NMR ($CDCl_3$, 400 MHz) δ (ppm): 7.55 (s, 1H), 7.45 (d, J = 8.8 Hz, 1H), 7.29 (s, 1H), 7.06 (d, J = 8.8 Hz, 1H), 6.16 (s, 1H), 4.89-4.58 (m, 7H), 3.88-3.69 (m, 5H), 3.50-3.38 (m, 2H), 3.31-3.14 (m, 5H), 3.07-2.96 (m, 1H), 2.69-2.51 (m, 2H), 2.39-2.26 (m, 1H), 1.82-1.69 (m, 1H), 1.18 (d, J = 6.8 Hz, 3H) |

TABLE 9-continued

| Example Number | Structure and Compound Name | LRMS m/z [M + H]+ | 1HNMR |
|---|---|---|---|
| 229 | 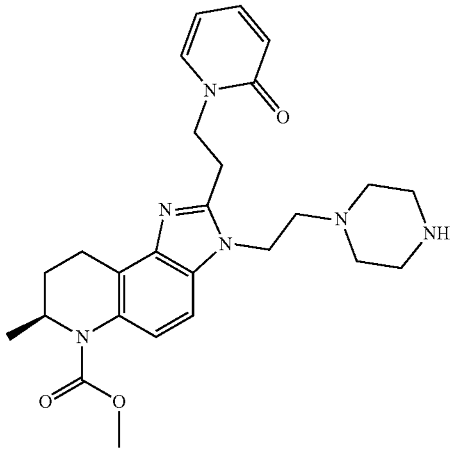 [SMILES: COC(=O)N1c2ccc3c(nc(CCn4ccccc4=O)n3CCN3CCNCC3)c2CC[C@@H]1C] methyl (S)-7-methyl-2-(2-(2-oxopyridin-1(2H)-yl)ethyl)-3-(2-(piperazin-1-yl)ethyl)-3,7,8,9-tetrahydro-6H-imidazo[4,5-f]quinoline-6-carboxylate | 479 | $^{1}$H-NMR ($CDCl_3$, 300 MHz) δ (ppm): 7.42-7.40 (m, 2H), 7.35-7.29 (m, 1H), 7.09 (d, J = 8.7 Hz, 1H), 6.56 (d, J = 9.0 Hz, 1H), 6.08-6.05 (m, 1H), 4.80-4.78 (m, 1H), 4.46-4.38 (m, 2H), 4.22-4.18 (m, 2H), 3.78 (s, 3H), 3.44-3.37 (m, 2H), 3.21-3.16 (m, 1H), 3.01-2.96 (m, 1H), 2.90-2.86 (m, 4H), 2.64-2.60 (m, 2H), 2.50-2.48 (m, 4H), 2.27-2.25 (m, 1H), 1.76-1.68 (m, 1H), 1.15 (d, J = 6.6 Hz, 3H) |
| 230 | 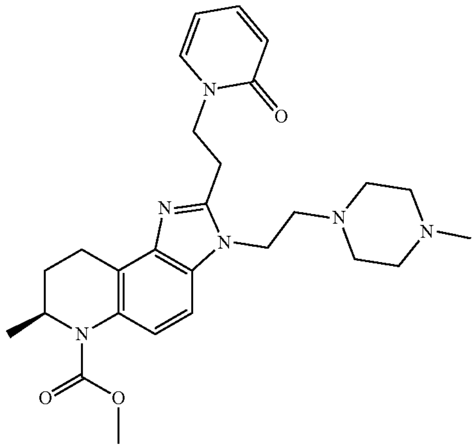 methyl (S)-7-methyl-3-(2-(4-methylpiperazin-1-yl)ethyl)-2-(2-(2-oxopyridin-1(2H)-yl)ethyl)-3,7,8,9-tetrahydro-6H-imidazo[4,5-f]quinoline-6-carboxylate | 493 | $^{1}$H-NMR ($CDCl_3$, 300 MHz) δ (ppm): 7.43-7.40 (m, 2H), 7.34-7.28 (m, 1H), 7.09 (d, J = 8.7 Hz, 1H), 6.58 (d, J = 9.0 Hz, 1H), 6.09-6.04 (m, 1H), 4.80-4.78 (m, 1H), 4.48-4.39 (m, 2H), 4.18-4.15 (m, 2H), 3.73 (s, 3H), 3.43-3.37 (m, 2H), 3.22-3.18 (m, 1H), 3.01-2.96 (m, 1H), 2.64-2.52 (m, 6H), 2.42-2.23 (m, 8H), 1.76-1.71 (m, 1H), 1.15 (d, J = 6.9 Hz, 3H) |

TABLE 9-continued

| Example Number | Structure and Compound Name | LRMS m/z $[M + H]^+$ | $^1$HNMR |
|---|---|---|---|
| 231 | 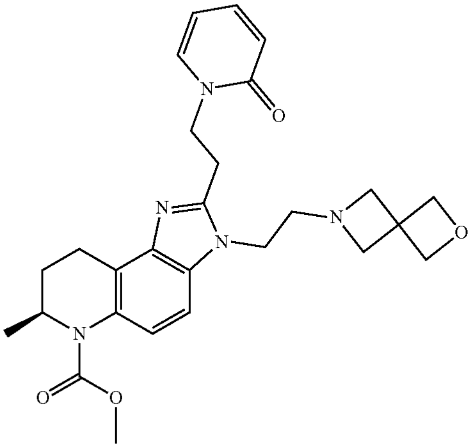 [SMILES: COC(=O)N1c2ccc3c(nc(CCn4ccccc4=O)n3CCN3CC4(COC4)C3)c2CC[C@@H]1C] methyl (S)-3-(2-(2-oxa-6-azaspiro[3.3]heptan-6-yl)ethyl)-7-methyl-2-(2-(2-oxopyridin-1(2H)-yl)ethyl)-3,7,8,9-tetrahydro-6H-imidazo[4,5-f]quinoline-6-carboxylate | 492 | $^1$H-NMR ($CDCl_3$, 300 MHz) δ (ppm): 7.42-7.40 (m, 2H), 7.35-7.29 (m, 1H), 7.08 (d, J = 9.0 Hz, 1H), 6.57 (d, J = 8.7 Hz, 1H), 6.08-6.05 (m, 1H), 4.80-4.78 (m, 1H), 4.66 (s, 4H), 4.46-4.38 (m, 2H), 4.07-4.02 (m, 2H), 3.78 (s, 3H), 3.41-3.34 (m, 2H), 3.29-3.18 (m, 5H), 3.01-2.96 (m, 1H), 2.69-2.65 (m, 2H), 2.30-2.20 (m, 1H), 1.77-1.71 (m, 1H), 1.15 (d, J = 6.6 Hz, 3H) |
| 232 | 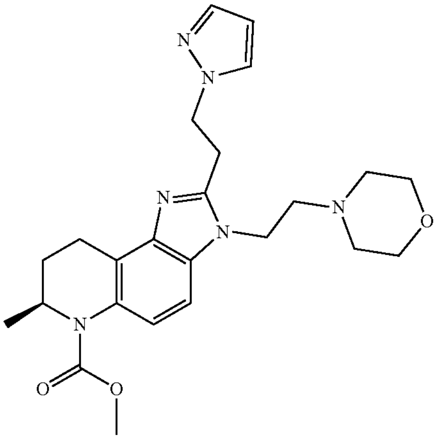 [SMILES: COC(=O)N1c2ccc3c(nc(CCn4cccn4)n3CCN3CCOCC3)c2CC[C@@H]1C] methyl (S)-2-(2-(1H-pyrazol-1-yl)ethyl)-7-methyl-3-(2-morpholinoethyl)-3,7,8,9-tetrahydro-6H-imidazo[4,5-f]quinoline-6-carboxylate | 439 | $^1$H-NMR ($CDCl_3$, 400 MHz) δ (ppm): 7.73-7.61 (m, 1H), 7.60-7.48 (m, 2H), 7.41-7.29 (m, 1H), 6.32-6.30 (m, 1H), 5.78 (s, 2H), 4.94-4.78 (m, 1H), 4.69-4.36 (m, 2H), 3.93-3.67 (m, 7H), 3.39-3.14 (m, 1H), 3.09-2.96 (m, 1H), 2.80-2.45 (m, 6H), 2.36-2.17 (m, 1H), 1.82-1.66 (m, 1H), 1.16 (d, J = 6.8 Hz, 3H) |

TABLE 9-continued

| Example Number | Structure and Compound Name | LRMS m/z [M + H]+ | 1HNMR |
|---|---|---|---|
| 233 | 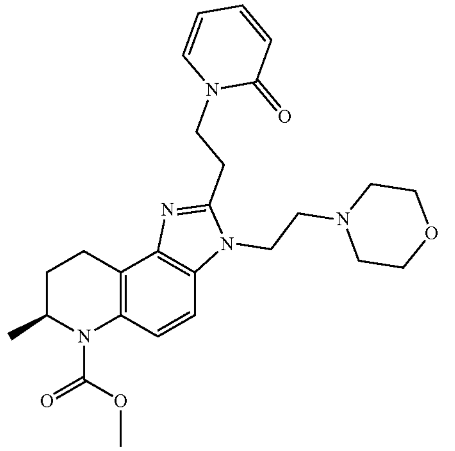 [SMILES: COC(=O)N1c2ccc3c(nc(CCn4ccccc4=O)n3CCN3CCOCC3)c2CC[C@@H]1C] methyl (S)-7-methyl-3-(2-morpholinoethyl)-2-(2-(2-oxopyridin-1(2H)-yl)ethyl)-3,7,8,9-tetrahydro-6H-imidazo[4,5-f]quinoline-6-carboxylate | 466 | 1H-NMR ($CDCl_3$, 400 MHz) δ (ppm): 7.71 (d, J = 6.8 Hz, 1H), 7.51 (d, J = 8.8 Hz, 1H), 7.34-7.28 (m, 1H), 7.19 (d, J = 8.4 Hz, 1H), 6.57 (d, J = 8.8 Hz, 1H), 6.18 (td, J = 6.8, 1.2 Hz, 1H), 5.55 (d, J = 14.8 Hz, 1H), 5.49 (d, J = 14.8 Hz, 1H), 4.83-4.74 (m, 1H), 4.58-4.36 (m, 2H), 3.77 (s, 3H), 3.71 (s, 4H), 3.27-3.16 (m, 1H), 3.01 (d, J = 17.2, 5.6 Hz, 1H), 2.70-2.40 (m, 6H), 2.30-2.19 (m, 1H), 1.77-1.68 (m, 1H), 1.14 (d, J = 6.8 Hz, 3H) |

Examples 234 and 235: methyl (7S)-2-benzyl-7-methyl-3-[2-[(4S)-1-oxa-6-azaspiro[3.4]octan-6-yl]ethyl]-3H,6H,7H,8H,9H-imidazo[4,5-f]quinoline-6-carboxylate and methyl (7S)-2-benzyl-7-methyl-3-[2-[(4R)-1-oxa-6-azaspiro[3.4]octan-6-yl]ethyl]-3H,6H,7H,8H,9H-imidazo[4,5-f]quinoline-6-carboxylate

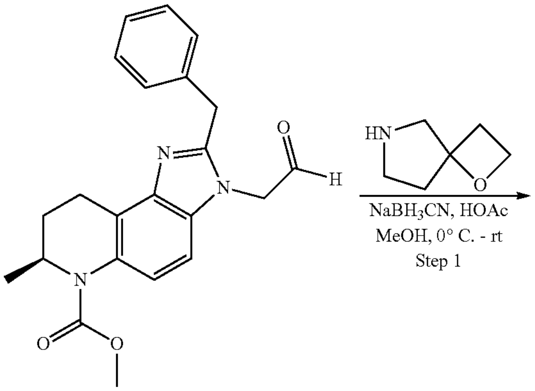

-continued

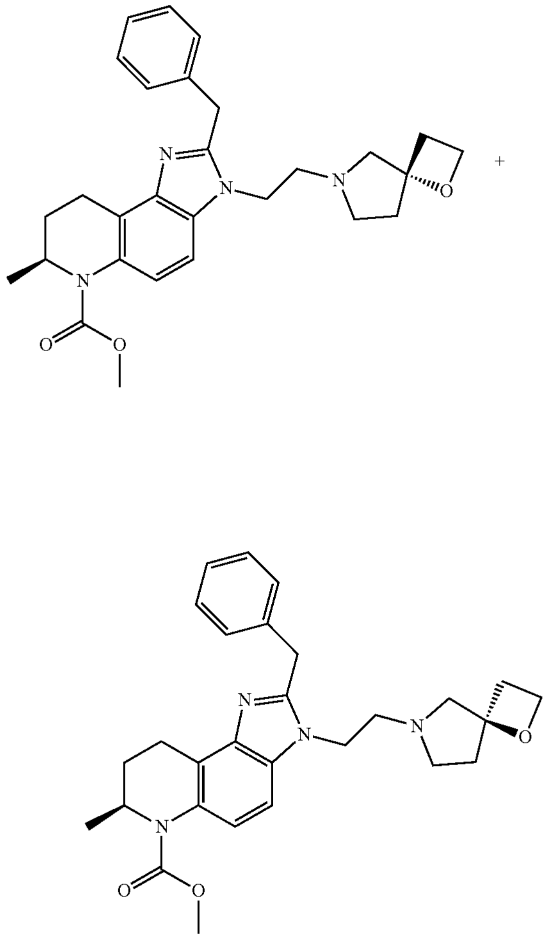

Step 1. Synthesis of methyl (7S)-2-benzyl-7-methyl-3-[2-[(4S)-1-oxa-6-azaspiro[3.4]octan-6-yl]ethyl]-3H,6H,7H,8H,9H-imidazo[4,5-f]quinoline-6-carboxylate and methyl (7S)-2-benzyl-7-methyl-3-[2-[(4R)-1-oxa-6-azaspiro[3.4]octan-6-yl]ethyl]-3H,6H,7H,8H,9H-imidazo[4,5-f]quinoline-6-carboxylate Into a 25-mL round-bottom flask, methyl (7S)-2-benzyl-7-methyl-3-(2-oxoethyl)-3H,6H,7H,8H,9H-imidazo[4,5-f]quinoline-6-carboxylate (100 mg, 0.26 mmol) was dissolved in methanol (5 mL). Then 1-oxa-6-azaspiro[3.4]octane (89.9 mg, 0.79 mmol) and acetic acid (79.6 mg, 1.33 mmol) were added. The mixture was stirred for 30 min at room temperature. To the mixture was added sodium cyanoborohydride (167.1 mg, 2.66 mmol) at 0° C. The resulting solution was stirred for 14 h at room temperature. The resulting solution was diluted with 10 mL of water and extracted with 3×10 mL of ethyl acetate. The organic layers were combined, dried over anhydrous sodium sulfate, filtered and concentrated under vacuum. The crude product was purified by Prep-HPLC with the following conditions: Column, XBridge Prep C18 OBD Column, 19×150 mm 5 μm; mobile phase, A: Water (containing 10 mmol/L $NH_4HCO_3$) and B: ACN (30.0% to 55.0% ACN over 7 min); UV Detector: 254 nm. The product was purified by Chiral-Prep-HPLC with the following conditions: Column, CHIRAL ART Cellulose-SB, 2×25 cm, 5 μm; mobile phase, Hexane and ethanol (hold 30.0% ethanol in 34 min); UV Detector: 220/254 nm. This afforded the title compounds as follows: 9.7 mg (8%) of methyl (7S)-2-benzyl-7-methyl-3-[2-[(4S)-1-oxa-6-azaspiro[3.4]octan-6-yl]ethyl]-3H,6H,7H,8H,9H-imidazo[4,5-f]quinoline-6-carboxylate (assumed stereochemistry, first eluting isomer, RT=21.50 min) as a white solid and 12.7 mg (10%) of methyl (7S)-2-benzyl-7-methyl-3-[2-[(4R)-1-oxa-6-azaspiro[3.4]octan-6-yl]ethyl]-3H,6H,7H,8H,9H-imidazo[4,5-f]quinoline-6-carboxylate (assumed stereochemistry, second eluting isomer, RT=22.71 min) as a white solid First eluting isomer: $^1$H-NMR ($CDCl_3$, 300 MHz) δ (ppm): 7.44 (d, J=8.7 Hz, 1H), 7.33-7.28 (m, 2H), 7.27-7.23 (m, 3H), 7.12 (d, J=8.8 Hz, 1H), 4.83-4.77 (m, 1H), 4.49-4.40 (m, 4H), 4.05 (s, 2H), 3.78 (s, 3H), 3.28-3.23 (m, 1H), 3.06-2.92 (m, 1H), 2.90 (d, J=10.6 Hz, 1H), 2.69-1.91 (m, 10H), 1.77-1.70 (m, 1H), 1.17 (d, J=6.7 Hz, 3H). MS: (ES, m/z): 475 $[M+H]^+$.

Second eluting isomer: $^1$H-NMR ($CDCl_3$, 300 MHz) δ (ppm): 7.50 (s, 1H), 7.35 (d, J=5.0 Hz, 4H), 7.34-7.26 (m, 2H), 4.83-4.78 (m, 1H), 4.51-4.42 (m, 6H), 3.79 (s, 4H), 3.38-3.20 (m, 1H), 3.12-3.00 (m, 1H), 2.75-2.62 (m, 6H), 2.50-1.66 (m, 5H), 1.17 (d, J=6.7 Hz, 3H). MS: (ES, m/z): 475 $[M+H]^+$.

Examples 236, 237 and 238: methyl (S)-2-benzyl-3-(2-((2S,6R)-2,6-dimethylmorpholino)ethyl)-7-methyl-3,7,8,9-tetrahydro-6H-imidazo[4,5-f]quinoline-6-carboxylate, methyl (S)-2-benzyl-3-(2-((2R,6R)-2,6-dimethylmorpholino)ethyl)-7-methyl-3,7,8,9-tetrahydro-6H-imidazo[4,5-f]quinoline-6-carboxylate, and methyl (S)-2-benzyl-3-(2-((2S,6S)-2,6-dimethylmorpholino)ethyl)-7-methyl-3,7,8,9-tetrahydro-6H-imidazo[4,5-f]quinoline-6-carboxylate

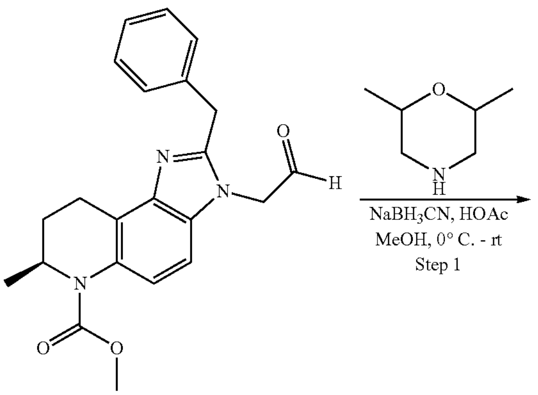

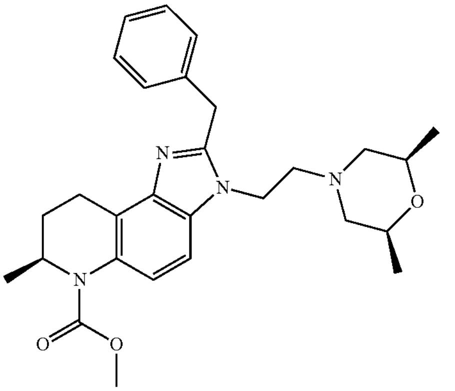

+

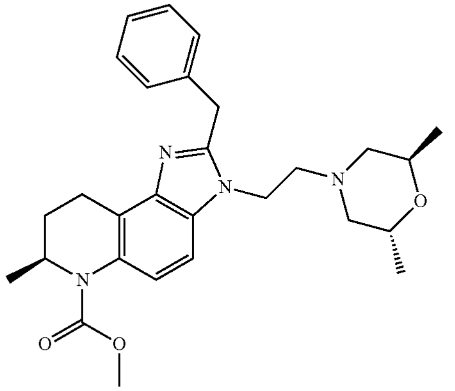

+

-continued

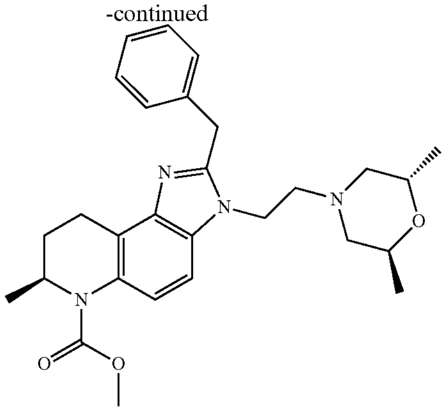

Step 1. Synthesis of methyl (7S)-2-benzyl-3-[2-[(2R,6S)-2,6-dimethylmorpholin-4-yl]ethyl]-7-methyl-3H,6H,7H,8H,9H-imidazo[4,5-f]quinoline-6-carboxylate and methyl (7S)-2-benzyl-3-[2-[(2R,6R)-2,6-dimethylmorpholin-4-yl]ethyl]-7-methyl-3H,6H,7H,8H,9H-imidazo[4,5-f]quinoline-6-carboxylate and methyl (7S)-2-benzyl-3-[2-[(2S,6S)-2,6-dimethylmorpholin-4-yl]ethyl]-7-methyl-3H,6H,7H,8H,9H-imidazo[4,5-f]quinoline-6-carboxylate Into a 25-mL round-bottom flask, methyl (7S)-2-benzyl-7-methyl-3-(2-oxoethyl)-3H,6H,7H,8H,9H-imidazo[4,5-f]quinoline-6-carboxylate (70 mg, 0.19 mmol) was dissolved in methanol (5 mL). Then 2,6-dimethylmorpholine (128 mg, 1.11 mmol) and acetic acid (67 mg, 1.12 mmol) were added. The mixture was stirred at room temperature for 30 min again. To the mixture was added sodium cyanoborohydride (70 mg, 1.11 mmol). The resulting solution was stirred for 12 h at room temperature. Water (10 ml) was added and the resulting solution was extracted with 2×60 mL of ethyl acetate. The organic layers were combined, dried over sodium sulfate, filtered and concentrated under vacuum. The crude product was purified by Prep-HPLC with the following conditions: Column, XBridge C18 OBD Prep Column, 100 Å, 5 μm, 19 mm×250 mm; mobile phase A: water (containing 10 mmol/L $NH_4HCO_3$) and B: ACN (30.0% to 45.0% ACN over 10 min); UV Detector: 254 nm. The crude product was purified by Prep-SFC with the following conditions: Column, CHIRALCEL OJ-H, 2×25 cm, 5 μm; mobile phase, $CO_2$ (90%), EtOH (2 mM $NH_3$/MeOH) (10%) and echo (0%); UV Detector: 220 nm. This afforded the title compounds as follows: 6.0 mg (7%) of methyl (7S)-2-benzyl-3-[2-[(2R,6S)-2,6-dimethylmorpholin-4-yl]ethyl]-7-methyl-3H,6H,7H,8H,9H-imidazo[4,5-f]quinoline-6-carboxylate (assumed stereochemistry, first eluting isomer) as a white solid and 3.4 mg (4%) of methyl (7S)-2-benzyl-3-[2-[(2R,6R)-2,6-dimethylmorpholin-4-yl]ethyl]-7-methyl-3H,6H,7H,8H,9H-imidazo[4,5-f]quinoline-6-carboxylate (assumed stereochemistry, second eluting isomer, RT=2.25 min) as a white solid and 3.9 mg (4%) of methyl (7S)-2-benzyl-3-[2-[(2S,6S)-2,6-dimethylmorpholin-4-yl]ethyl]-7-methyl-3H,6H,7H,8H,9H-imidazo[4,5-f]quinoline-6-carboxylate (assumed stereochemistry, third eluting isomer, RT=2.60 min) as a white solid.

First eluting isomer: $^1$H-NMR ($CDCl_3$, 400 MHz) δ (ppm): 7.45 (d, J=8.0 Hz, 1H), 7.32-7.27 (m, 2H), 7.26-7.16 (m, 3H), 7.10 (d, J=8.8 Hz, 1H), 4.80 (h, J=6.0 Hz, 1H), 4.47-4.33 (m, 2H), 4.03 (s, 2H), 3.78 (s, 3H), 3.63 (s, 2H), 3.34-3.23 (m, 1H), 3.04-2.98 (m, 1H), 2.54 (t, J=11.6 Hz, 2H), 2.43-2.34 (m, 1H), 2.34-2.21 (m, 2H), 1.80-1.62 (m, 3H), 1.17 (d, J=6.8 Hz, 3H), 1.15-1.11 (m, 6H). MS: (ES, m/z): 477 $[M+H]^+$.

Second eluting isomer: $^1$H-NMR ($CDCl_3$, 400 MHz) δ (ppm): 7.55-7.41 (m, 1H), 7.33-7.27 (m, 2H), 7.26-7.18 (m, 3H), 7.11 (d, J=8.4 Hz, 1H), 4.85-4.75 (m, 1H), 4.43 (s, 2H), 4.10-3.90 (m, 4H), 3.78 (s, 3H), 3.34-3.23 (m, 1H), 3.13-2.99 (m, 1H), 2.40-2.20 (m, 5H), 2.06-1.96 (m, 2H), 1.80-1.70 (m, 1H), 1.23-1.13 (m, 9H). MS: (ES, m/z): 477 $[M+H]^+$.

Third eluting isomer: $^1$H-NMR ($CDCl_3$, 400 MHz) δ (ppm): 7.55-7.41 (m, 1H), 7.33-7.27 (m, 2H), 7.26-7.17 (m, 3H), 7.11 (d, J=6.8 Hz, 1H), 4.87-4.74 (m, 1H), 4.43 (s, 2H), 4.11-3.91 (m, 4H), 3.78 (s, 3H), 3.35-3.23 (m, 1H), 3.13-2.98 (m, 1H), 2.46-2.17 (m, 5H), 2.04-1.94 (m, 2H), 1.82-1.69 (m, 1H), 1.22-1.12 (m, 9H). MS: (ES, m/z): 477 $[M+H]^+$.

Example 239: methyl (7S)-2-benzyl-3-[2-(2,2-dioxo-2lambda6-thia-6-azaspiro[3.3]heptan-6-yl)ethyl]-7-methyl-3H,6H,7H,8H,9H-imidazo[4,5-f]quinoline-6-carboxylate

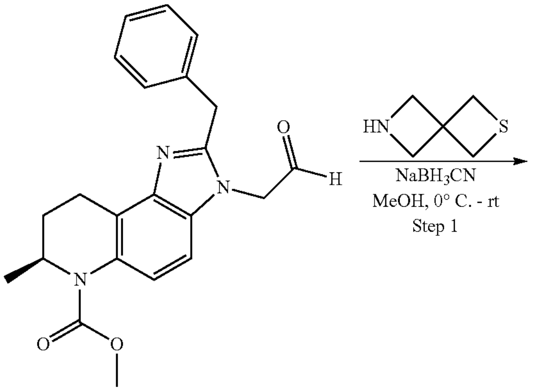

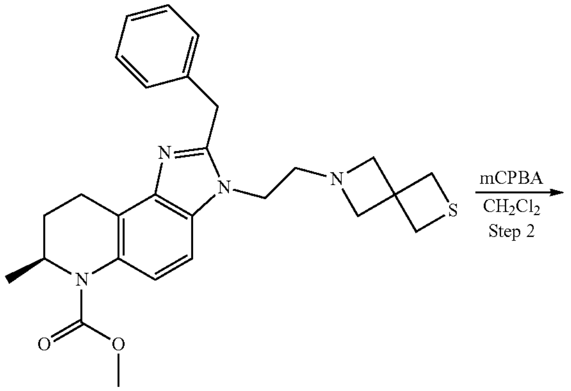

-continued

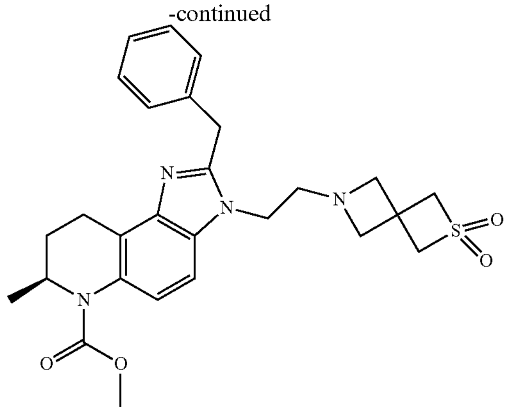

Step 1. Synthesis of methyl (7S)-2-benzyl-7-methyl-3-(2-[2-thia-6-azaspiro[3.3]heptan-6-yl]ethyl)-3H,6H,7H,8H,9H-imidazo[4,5-f]quinoline-6-carboxylate Into a 25-mL round-bottom flask, methyl (7S)-2-benzyl-7-methyl-3-(2-oxoethyl)-3H,6H,7H,8H,9H-imidazo[4,5-f]quinoline-6-carboxylate (50 mg, 0.13 mmol) was dissolved in methanol (5 mL). Then 2-thia-6-azaspiro[3.3]heptane oxalic acid salt (68 mg, 0.33 mmol) and sodium cyanoborohydride (13 mg, 0.21 mmol) were added. The resulting solution was stirred overnight at room temperature. The resulting mixture was concentrated under vacuum. The residue was subjected to purification by FCC eluting with dichloromethane/methanol (10:1). This afforded the title compound (40 mg, 63%) as a white solid. MS: (ES, m/z): 477 $[M+H]^+$.

Step 2. Synthesis of methyl (7S)-2-benzyl-3-[2-(2,2-dioxo-2lambda6-thia-6-azaspiro[3.3]heptan-6-yl)ethyl]-7-methyl-3H,6H,7H,8H,9H-imidazo[4,5-f]quinoline-6-carboxylate Into a 8-mL round-bottom flask, methyl (7S)-2-benzyl-7-methyl-3-(2-[2-thia-6-azaspiro[3.3]heptan-6-yl]ethyl)-3H,6H,7H,8H,9H-imidazo[4,5-f]quinoline-6-carboxylate (38 mg, 0.08 mmol) was dissolved in dichloromethane (4 mL). Then 3-chloroperoxybenzoic acid (55 mg, 0.32 mmol) was added. The resulting solution was stirred overnight at room temperature. The resulting mixture was concentrated under vacuum. The crude product was purified by Prep-HPLC with the following conditions: Column, XBridge C18 OBD Prep Column, 100 Å, 5 μm, 19 mm×250 mm; mobile phase, A: water (10 mmol/L $NH_4HCO_3$) and B: ACN (20.0% to 40.0% ACN over 8 min); UV Detector: 254 nm. This afforded the title compound (4.3 mg, 11%) as an off-white solid.

H-NMR: ($CDCl_3$, 400 MHz, ppm): 7.55 (d, J=8.6 Hz, 1H), 7.40-7.21 (m, 6H), 4.81-4.58 (m, 1H), 4.75-4.45 (m, 4H), 4.18-3.68 (m, 8H), 3.57-3.19 (m, 5H), 3.15-3.02 (m, 2H), 2.29-2.25 (m, 1H), 1.94-1.79 (m, 1H), 1.20 (d, J=6.8 Hz, 3H). MS: (ES, m/z): 509 $[M+H]^+$.

Example 240: methyl (S)-3-(2-(4-acetylpiperazin-1-yl)ethyl)-2-benzyl-7-methyl-3,7,8,9-tetrahydro-6H-imidazo[4,5-f]quinoline-6-carboxylate

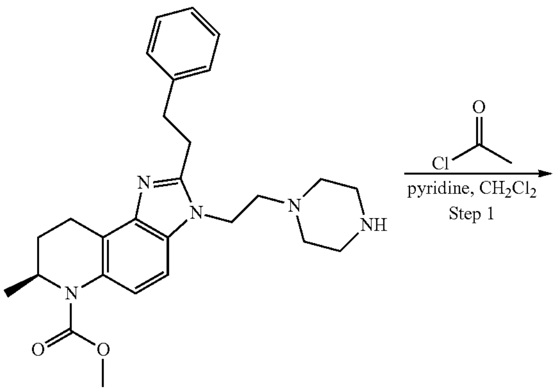

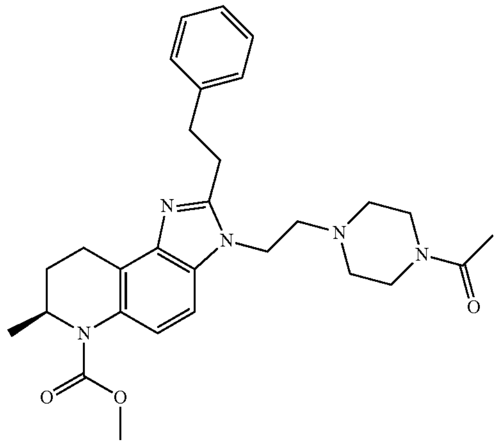

Into a 25-mL round-bottom flask, methyl (7S)-2-benzyl-7-methyl-3-[2-(piperazin-1-yl)ethyl]-3H,6H,7H,8H,9H-imidazo[4,5-f]quinoline-6-carboxylate (30 mg, 0.07 mmol) was dissolved in dichloromethane (2 mL). Then pyridine (16 mg, 0.20 mmol) was added, followed by of acetyl chloride (10.5 mg, 0.13 mmol). The resulting solution was stirred for 1 h at room temperature. The resulting mixture was concentrated under vacuum. The crude product was purified by Prep-HPLC with the following conditions: Column, XBridge C18 OBD Prep Column, 100 Å, 5 um, 19 mm×250 mm; mobile phase A: Water (containing 10 mmol/L $NH_4HCO_3$) and B: ACN (25.0% to 45.0% ACN over 8 min); UV Detector: 254 nm. This afforded the title compound (8.8 mg, 26%) as a white solid. $^1$H-NMR ($CDCl_3$, 300 MHz) δ (ppm): 7.48 (d, J=8.6 Hz, 1H), 7.33-7.28 (m, 2H), 7.24-7.20 (m, 3H), 7.09 (d, J=8.8 Hz, 1H), 4.83-4.77 (m, 1H), 4.43-4.41 (m, 2H), 4.05 (t, J=7.0 Hz, 2H), 3.79 (s, 3H), 3.58 (t, J=5.4 Hz, 2H), 3.40 (t, J=5.1 Hz, 2H), 3.39-3.23 (m, 1H), 3.21-3.03 (m, 1H), 2.44-2.22 (m, 7H), 2.07 (s, 3H), 1.78-1.72 (m, 1H), 1.17 (d, J=6.7 Hz, 3H). MS: (ES, m/z): 490 $[M+H]^+$.

Example 241: methyl (S)-2-benzyl-7-methyl-3-(2-(4-(methylsulfonyl)piperazin-1-yl)ethyl)-3,7,8,9-tetrahydro-6H-imidazo[4,5-f]quinoline-6-carboxylate

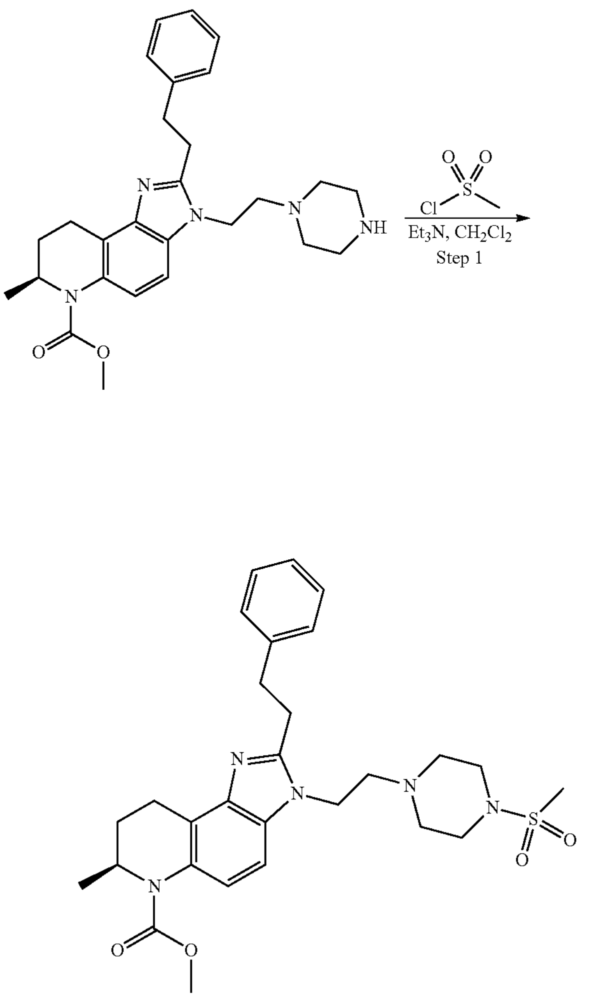

Into a 25-mL round-bottom flask, methyl (7S)-2-benzyl-7-methyl-3-[2-(piperazin-1-yl)ethyl]-3H,6H,7H,8H,9H-imidazo[4,5-f]quinoline-6-carboxylate (30 mg, 0.07 mmol) was added in dichloromethane (2 mL). Then triethylamine (20 mg, 0.20 mmol) was added, followed by methylsulfonyl chloride (15.3 mg, 0.1 mmol). The resulting solution was stirred for 1 h at room temperature. The resulting mixture was concentrated under vacuum. The crude product was purified by Prep-HPLC with the following conditions: Column, XBridge C18 OBD Prep Column, 100 Å, 5 um, 19 mm×250 mm; mobile phase, A: Water (containing 10 mmol/L $NH_4HCO_3$) and B: ACN (25.0% to 45.0% ACN over 8 min); UV Detector: 254 nm. This afforded the title compound (17.3 mg, 48%) as a white solid. $^1$H-NMR ($CDCl_3$, 300 MHz) δ (ppm): 7.50-7.47 (m, 1H), 7.33-7.28 (m, 3H), 7.25-7.20 (m, 2H), 7.08 (d, J=8.8 Hz, 1H), 4.83-4.77 (m, 1H), 4.41 (s, 2H), 4.04 (t, J=7.1 Hz, 2H), 3.79 (s, 3H), 3.32-3.23 (m, 1H), 3.23-3.16 (m, 4H), 3.16-3.03 (m, 1H), 2.77 (s, 3H), 2.47-2.36 (m, 6H), 2.36-2.22 (m, 1H), 1.79-1.72 (m, 1H), 1.17 (d, J=6.7 Hz, 3H). MS: (ES, m/z): 526 $[M+H]^+$.

Example 242: methyl-(7S)-3-[2-(dimethylamino)ethyl]-7-methyl-2-(2-phenylethyl)-3H,6H,7H,8H,9H-imidazo[4,5-f]quinoline-6-carboxylate

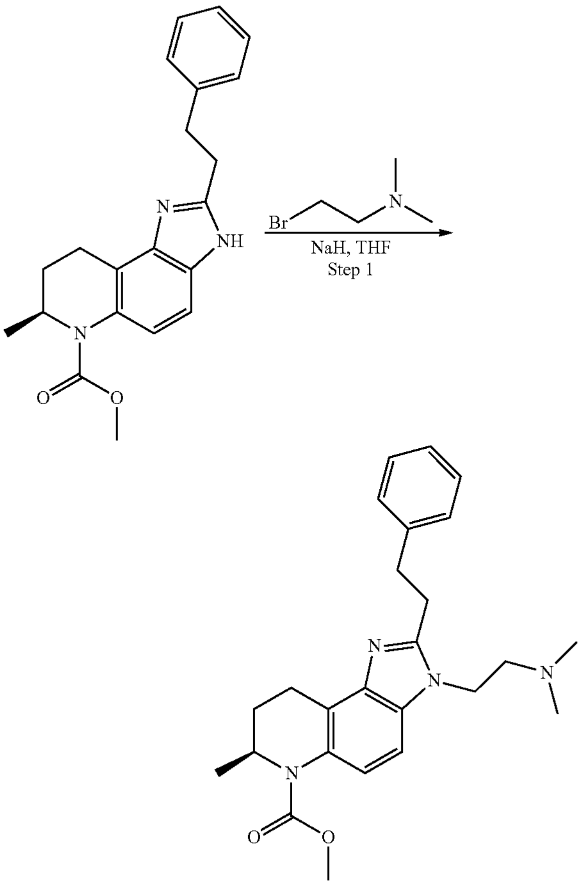

Into a 25-mL round-bottom flask, methyl-(7S)-7-methyl-2-(2-phenylethyl)-3H,6H,7H,8H,9H-imidazo[4,5-f]quinoline-6-carboxylate (30 mg, 0.09 mmol) was dissolved in tetrahydrofuran (3 mL). Then sodium hydride (60%, 10 mg, 0.25 mmol) was added. The mixture was stirred for 10 minutes at room temperature. Then (2-bromoethyl)dimethylamine (26 mg, 0.17 mmol) was added. The resulting solution was stirred for 3 h at room temperature. The resulting mixture was diluted with 10 mL of water and extracted with 3×10 mL of ethyl acetate. The organic layers were combined, dried over sodium sulfate, filtered and concentrated under vacuum. The residue was purified with the following conditions: Column: XBridge Prep C18 OBD Column 19*150 mm, 5 μm; Mobile Phase, A: water (containing 10 mmol/L $NH_4HCO_3$) and B: ACN (31% to 61% ACN over 8 min). UV Detector: 254 nm. This afforded the title compound (4.1 mg, 11%) as a brown oil.

$^1$H-NMR: ($CDCl_3$, 300 MHz) δ (ppm): 7.46 (d, J=9.0 Hz, 1H), 7.33-7.13 (m, 5H), 7.10 (d, J=8.7 Hz, 1H), 4.84-4.78 (m, 1H), 4.06-4.02 (m, 2H), 3.78 (s, 3H), 3.29-3.18 (m, 5H), 3.08-2.99 (m, 1H), 2.56-2.42 (m, 2H), 2.25-2.23 (m, 7H), 1.78-1.73 (m, 1H), 1.15-1.10 (m, 3H). MS: (ES, m/z): 421$[M+H]^+$ The following examples in TABLE 10 were prepared using standard chemical manipulations and procedures similar to those used for the preparation of Examples 242.

TABLE 10

| Example Number | Structure and Compound Name | LRMS m/z [M + H]+ | 1HNMR |
|---|---|---|---|
| 243 | 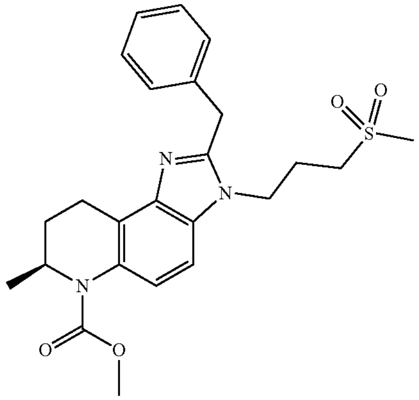 methyl (S)-2-benzyl-7-methyl-3-(3-(methylsulfonyl)propyl)-3,7,8,9-tetrahydro-6H-imidazo[4,5-f]quinoline-6-carboxylate | 456 | $^1$H-NMR ($CDCl_3$, 400 MHz) δ (ppm): 7.52-7.48 (m, 1H), 7.33-7.23 (m, 5H), 7.12 (d, J = 8.8 Hz, 1H), 4.83-4.78 (m, 1H), 4.42-4.38 (m, 2H), 4.19-4.17 (m, 2H), 3.78 (s, 3H), 3.33-3.25 (m, 1H), 3.09-3.05 (m, 1H), 2.72-2.67 (m, 5H), 2.29-2.23 (m, 1H), 2.06-1.96 (m, 2H), 1.78-1.77 (m, 1H), 1.18-1.15 (m, 3H) |
| 244 | 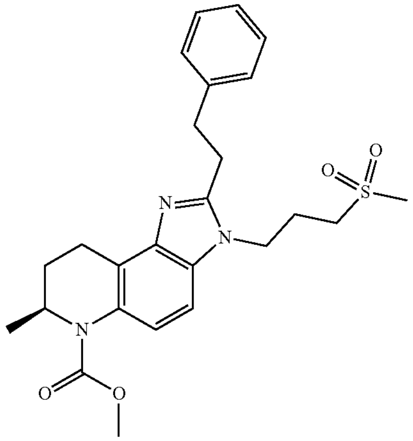 methyl (S)-7-methyl-3-(3-(methylsulfonyl)propyl)-2-phenethyl-3,7,8,9-tetrahydro-6H-imidazo[4,5-f]quinoline-6-carboxylate | 470 | $^1$H-NMR ($CDCl_3$, 400 MHz) δ (ppm): 7.47 (d, J = 8.8 Hz, 1H), 7.29-7.27 (m, 2H), 7.23-7.19 (m, 3H), 7.11 (d, J = 8.8 Hz, 1H), 4.81-4.77 (m, 1H), 4.13-4.09 (m, 2H), 3.79 (s, 3H), 3.29-3.15 (m, 5H), 3.16-3.00 (m, 1H), 2.92-2.87 (m, 5H), 2.29-2.19 (m, 3H), 1.75-1.70 (m, 1H), 1.17-1.13 (m, 3H) |
| 245 | 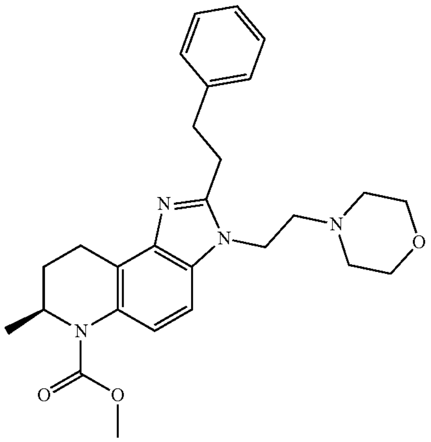 [SMILES: COC(=O)N1c2ccc3c(nc(CCc4ccccc4)n3CCN3CCOCC3)c2CC[C@@H]1C] methyl (S)-7-methyl-3-(2-morpholinoethyl)-2-phenethyl-3,7,8,9-tetrahydro-6H-imidazo[4,5-f]quinoline-6-carboxylate | 463 | $^1$H-NMR ($CDCl_3$, 300 MHz) δ (ppm): 7.50 (d, J = 8.7 Hz, 1H), 7.34-7.20 (m, 5H), 7.11 (d, J = 8.7 Hz, 1H), 4.84-4.78 (m, 1H), 4.03-3.99 (m, 2H), 3.81 (s, 3H), 3.70-3.67 (m, 4H), 3.33-3.21 (m, 5H), 3.08-3.03 (m, 1H), 2.58-2.50 (m, 2H), 2.46-2.43 (m, 4H), 2.29-2.25 (m, 1H), 1.79-1.73 (m, 1H), 1.18 (d, J = 6.6 Hz, 3H). |

TABLE 10-continued

| Example Number | Structure and Compound Name | LRMS m/z [M + H]+ | 1HNMR |
|---|---|---|---|
| 246 | 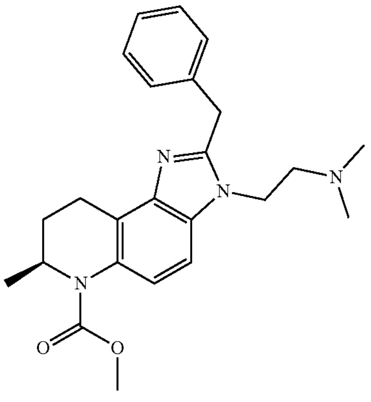 methyl (S)-2-benzyl-3-(2-(dimethylamino)ethyl)-7-methyl-3,7,8,9-tetrahydro-6H-imidazo[4,5-f]quinoline-6-carboxylate | 407 | $^1$H-NMR ($CDCl_3$, 300 MHz) δ (ppm): 7.46 (d, J = 8.7 Hz, 1H), 7.34-7.24 (m, 5H), 7.14 (d, J = 8.7 Hz, 1H), 4.85-4.79 (m, 1H), 4.47-4.33 (m, 2H), 4.13-4.08 (m, 2H), 3.80 (s, 3H), 3.35-3.24 (m, 1H), 3.15-3.01 (m, 2H), 2.43-2.20 (m, 8H), 1.75-1.68 (m, 1H), 1.19 (d, J = 6.8 Hz, 3H) |

Example 247: methyl (S)-2-cyclopropyl-7-methyl-3-(2-morpholinoethyl)-3,7,8,9-tetrahydro-6H-imidazo[4,5-f]quinoline-6-carboxylate

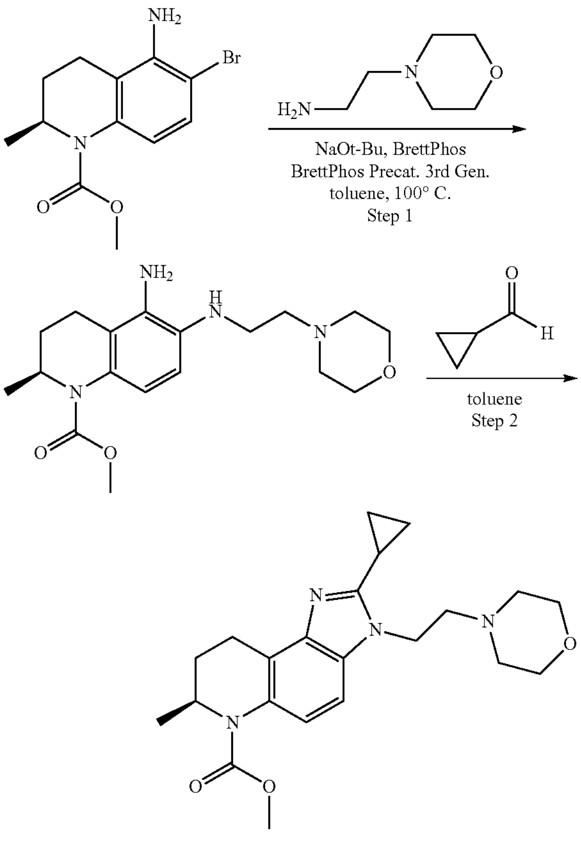

Step 1. Synthesis of methyl (2S)-5-amino-2-methyl-6-[[2-(morpholin-4-yl)ethyl]amino]-1,2,3,4-tetrahydroquinoline-1-carboxylate Into a 8-mL round-bottom flask purged and maintained with an inert atmosphere of nitrogen, methyl (2S)-5-amino-6-bromo-2-methyl-1,2,3,4-tetrahydroquinoline-1-carboxylate (100 mg, 0.33 mmol, Intermediate 1) and 2-(morpholin-4-yl)ethan-1-amine (435 mg, 3.34 mmol) were dissolved in toluene (5 mL) and then BrettPhos (60 mg, 0.11 mmol), sodium tert-butoxide (50 mg, 0.52 mmol) and 3$^{rd}$ Generation BrettPhos precatalyst (60 mg, 0.07 mmol) were added. The resulting solution was stirred for 3 h at 100° C. under nitrogen atmosphere. The reaction mixture was cooled and the resulting solids were filtered out. The resulting mixture was concentrated under vacuum. The residue was subjected to purification by FCC eluting with dichloromethane/methanol (10:1). This afforded the title compound (130 mg (crude)) as a yellow solid. MS: (ES, m/z): 349[M+H]$^+$.

Step 2. Synthesis of methyl (S)-2-cyclopropyl-7-methyl-3-(2-morpholinoethyl)-3,7,8,9-tetrahydro-6H-imidazo[4,5-f]quinoline-6-carboxylate Into a 8-mL round-bottom flask, methyl (2S)-5-amino-2-methyl-6-[[2-(morpholin-4-yl)ethyl]amino]-1,2,3,4-tetrahydroquinoline-1-carboxylate (40 mg, 0.11 mmol) was dissolved in toluene (2 mL). Then cyclopropanecarbaldehyde (12 mg, 0.17 mmol) was added. The resulting solution was stirred for 2 days at room temperature. The resulting mixture was concentrated under vacuum. The crude product was purified by Prep-HPLC with the following conditions: Column, XBridge C18 OBD Prep Column, 100 Å, 5 μm, 19 mm×250 mm; mobile phase: A: water (containing 0.05% $NH_4OH$) and B: ACN (25.0% ACN up to 50.0% in 8 min); UV Detector: 254 nm. This afforded the title compound (10.8 mg, 24%) as a yellow solid.

$^1$H-NMR ($CDCl_3$, 400 MHz) δ (ppm): 7.42 (d, J=8.8 Hz, 1H), 7.09 (d, J=8.8 Hz, 1H), 4.76-4.72 (m, 1H), 4.36-4.32 (m, 2H), 3.77-3.70 (m, 7H), 3.23-3.16 (m, 1H), 2.94-2.74

(m, 1H), 2.76 (t, J=7.1 Hz, 2H), 2.58-2.48 (m, 4H), 2.26-2.20 (m, 1H), 2.05-2.00 (m, 1H), 1.69-1.61 (m, 1H), 1.24 (s, 2H), 1.14-1.09 (m, 5H). MS: (ES, m/z): 399[M+H]$^+$.

The following examples in TABLE 11 were prepared using standard chemical manipulations and procedures similar to those used for the preparation of Example 247.

TABLE 11

| Example Number | Structure and Compound Name | LRMS m/z [M + H]$^+$ | $^1$HNMR |
|---|---|---|---|
| 248 | 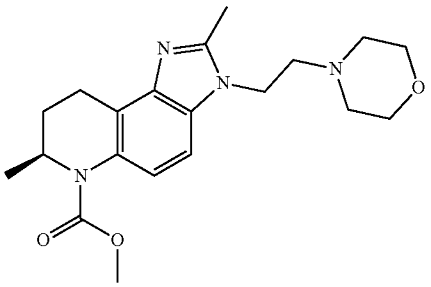 [SMILES: COC(=O)N1c2ccc3c(nc(C)n3CCN3CCOCC3)c2CC[C@@H]1C] methyl (S)-2,7-dimethyl-3-(2-morpliolinoethyl)-3,7,8,9-tetrahydro-6H-imidazo[4,5-f]quinoline-6-carboxylate | 373 | $^1$H-NMR ($CDCl_3$, 400 MHz) δ (ppm): 7.46 (s, 1H), 7.10 (d, J = 8.4 Hz, 1H), 4.81-4.78 (m, 1H), 4.19 (t, J = 6.8 Hz, 2H), 3.79 (s, 3H), 3.69 (t, J = 4.8 Hz, 4H), 3.27-3.18 (m, 1H), 3.01-2.97 (m, 1H), 2.69-2.66 (m, 5H), 2.54-2.45 (m, 4H), 2.29-2.22 (m, 1H), 1.74-1.69 (m, 1H), 1.14 (d, J = 6.7 Hz, 3H) |
| 249 | 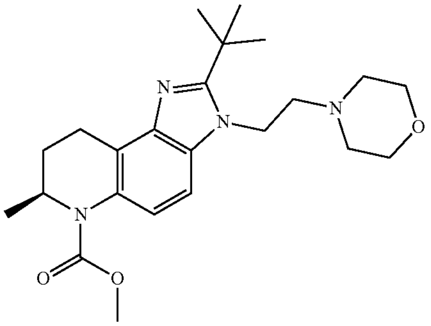 [SMILES: COC(=O)N1c2ccc3c(nc(C(C)(C)C)n3CCN3CCOCC3)c2CC[C@@H]1C] methyl (S)-2-(tert-butyl)-7-methyl-3-(2-morpliolinoethyl)-3,7,8,9-tetrahydro-6H-imidazo[4,5-f]quinoline-6-carboxylate | 415 | $^1$H-NMR ($CD_3OD$, 300 MHz) δ (ppm): 7.40 (d, J = 9 Hz, 1H), 7.29 (d, J = 9 Hz, 1H), 4.73 (q, J = 6.6 Hz, 1H), 4.60-4.55 (m, 2H), 3.79-3.74 (m, 7H), 3.34-3.29 (m, 1H), 2.90-2.78 (m, 3H), 2.65-2.62 (m, 4H), 2.30-2.27 (m, 1H), 1.69-1.62 (m, 10H), 1.14 (d, J = 6.6 Hz, 3H) |
| 250 | 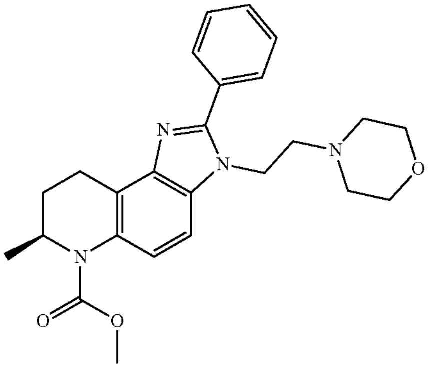 [SMILES: COC(=O)N1c2ccc3c(nc(-c4ccccc4)n3CCN3CCOCC3)c2CC[C@@H]1C] methyl (S)-7-methyl-3-(2-morpliolinoethyl)-2-phenyl-3,7,8,9-tetrahydro-6H-imidazo[4,5-f]quinoline-6-carboxylate | 435 | $^1$H-NMR ($CDCl_3$, 400 MHz) δ (ppm): 7.92 (d, J = 8.8 Hz, 1H), 7.77 (s, 2H), 7.66-7.54 (m, 3H), 7.50 (d, J = 8.8 Hz, 1H), 4.85-4.75 (m, 3H), 3.84 (s, 3H), 3.79 (d, J = 7.6 Hz, 4H), 3.18-3.14 (m, 3H), 3.08-2.96 (m, 1H), 2.96-2.74 (m, 4H), 2.17-2.16 (m, 1H), 1.85-1.82 (m, 1H), 1.15 (d, J = 6.8 Hz, 3H) |

TABLE 11-continued

| Example Number | Structure and Compound Name | LRMS m/z [M + H]+ | 1HNMR |
|---|---|---|---|
| 251 | 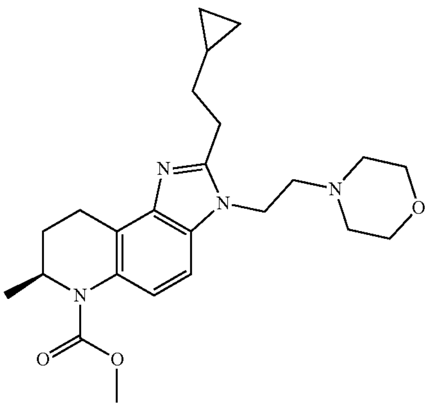 [SMILES: COC(=O)N1c2ccc3c(nc(CCC4CC4)n3CCN3CCOCC3)c2CC[C@@H]1C] methyl (S)-2-(2-cyclopropylethyl)-7-methyl-3-(2-morpholinoethyl)-3,7,8,9-tetrahydro-6H-imidazo[4,5-f]quinoline-6-carboxylate | 427 | $^1$H-NMR ($CDCl_3$, 300 MHz) δ (ppm): 7.51 (d, J = 8.7 Hz, 1H), 7.15 (d, J = 8.7 Hz, 1H), 4.82-4.76 (m, 1H), 4.28-4.23 (m, 2H), 3.80 (s, 3H), 3.75-3.72 (m, 4H), 3.24-2.19 (m, 1H), 3.10-2.98 (m, 3H), 2.76-2.71 (m, 2H), 2.56-2.53 (m, 4H), 2.29-2.21 (m, 1H) 1.83-1.70 (m, 3H), 1.15 (d, J = 6.6 Hz, 1H), 0.83-0.78 (m, 1H), 0.52-0.46 (m, 2H), 1.15-1.10 (m, 2H) |
| 252 | 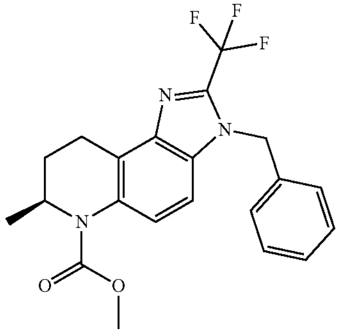 [SMILES: COC(=O)N1c2ccc3c(nc(C(F)(F)F)n3Cc3ccccc3)c2CC[C@@H]1C] methyl (S)-3-benzyl-7-methyl-2-(trifluoromethyl)-3,7,8,9-tetrahydro-6H-imidazo[4,5-f]quinoline-6-carboxylate | 404 | $^1$H-NMR ($CDCl_3$, 400 MHz) δ (ppm): 7.72 (d, J = 8.8 Hz, 1H), 7.48 (d, J = 8.8 Hz, 1H), 7.34-7.26 (m, 3H), 6.88 (d, J = 6.8 Hz, 1H), 5.77-5.65 (m, 2H), 4.66-4.61 (m, 1H), 3.76 (s, 3H), 2.94-2.87 (m, 1H), 2.64-2.57 (m, 1H), 2.09-2.01 (m, 1H), 1.36-1.27 (m, 1H), 1.03 (d, J = 6.4 Hz, 3H) |
| 253 | 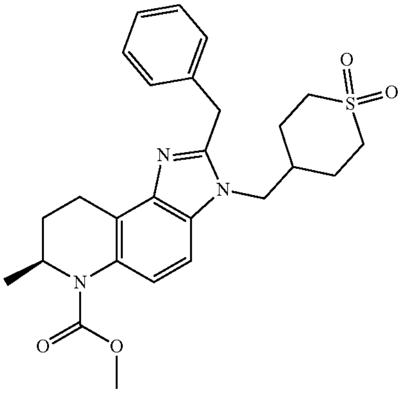 [SMILES: COC(=O)N1c2ccc3c(nc(Cc4ccccc4)n3CC3CCS(=O)(=O)CC3)c2CC[C@@H]1C] methyl (S)-2-benzyl-3-((1,1-dioxidotetrahydro-2H-thiopyran-4-yl)methyl)-7-methyl-3,7,8,9-tetrahydro-6H-imidazo[4,5-f]quinoline-6-carboxylate | 482 | $^1$H-NMR ($CD_3OD$, 400 MHz) δ (ppm): 7.46 (d, J = 8.9 Hz, 1H), 7.41-7.25 (m, 6H), 4.78-4.72 (m, 1H), 4.42 (s, 2H), 4.06 (d, J = 7.1 Hz, 2H), 3.79 (s, 3H), 3.23-3.16 (m, 1H), 3.03-2.77 (m, 5H), 2.27-2.21 (m, 1H), 1.93-1.69 (m, 6H), 1.16 (d, J = 6.6 Hz, 3H) |

TABLE 11-continued

| Example Number | Structure and Compound Name | LRMS m/z [M + H]+ | 1HNMR |
|---|---|---|---|
| 254 | 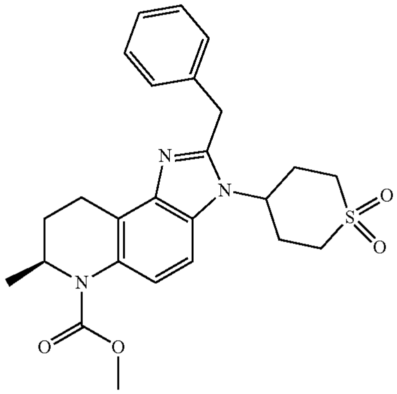 [SMILES: COC(=O)N1c2ccc3c(nc(Cc4ccccc4)n3C3CCS(=O)(=O)CC3)c2CC[C@@H]1C] methyl (S)-2-benzyl-3-(1,1-dioxidotetrahydro-2H-thiopyran-4-yl)-7-methyl-3,7,8,9-tetrahydro-6H-imidazo[4,5-f]quinoline-6-carboxylate | 468 | $^1$H-NMR ($CDCl_3$, 400 MHz) δ (ppm): 7.45 (d, J = 8.4 Hz, 1H), 7.31-7.19 (m, 4H), 7.21 (d, J = 8.8 Hz, 2H), 4.83-4.80 (m, 1H), 4.47-4.28 (m, 3H), 3.79 (s, 3H), 3.30-3.23 (m, 1H), 3.10-2.84 (m, 7H), 2.30-2.28 (m, 1H), 1.80-1.58 (m, 3H), 1.18 (d, J = 8.8 Hz, 3H) |
| 255 | 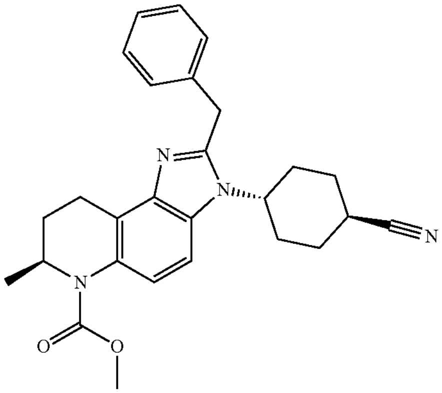 [SMILES: COC(=O)N1c2ccc3c(nc(Cc4ccccc4)n3[C@H]3CC[C@H](C#N)CC3)c2CC[C@@H]1C] methyl (S)-2-benzyl-3-((trans)-4-cyanocyclohexyl)-7-methyl-3,7,8,9-tetrahydro-6H-imidazo[4,5-f]quinoline-6-carboxylate | 443 | $^1$H-NMR ($CD_3OD$, 400 MHz) δ (ppm): 7.44-7.41 (d, J = 13.6 Hz, 1H), 7.39-7.28 (m, 6H), 4.79-4.77 (m, 1H), 4.43 (s, 2H), 4.30 (s, 1H), 3.79 (s, 3H), 3.23-3.19 (m, 1H), 3.00-2.96 (m, 1H), 2.79-2.78 (m, 1H), 2.30-2.21 (m, 5H), 1.80-1.75 (m, 1H), 1.61-1.47 (m, 4H), 1.17-1.15 (d, J = 6.4 Hz, 3H) |
| 256 | 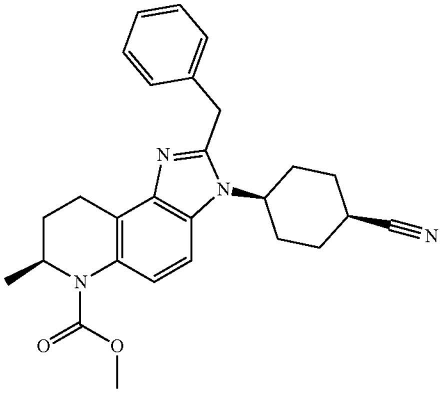 [SMILES: COC(=O)N1c2ccc3c(nc(Cc4ccccc4)n3[C@H]3CC[C@@H](C#N)CC3)c2CC[C@@H]1C] methyl (S)-2-benzyl-3-((cis)-4-cyanocyclohexyl)-7-methyl-3,7,8,9-tetrahydro-6H-imidazo[4,5-f]quinoline-6-carboxylate | 443 | $^1$H-NMR ($CDCl_3$, 400 MHz) δ (ppm): 7.49-7.46 (m, 2H), 7.36-7.32 (m, 2H), 7.28-7.26 (m, 3H), 4.80-4.78 (m, 1H), 4.43 (s, 2H), 4.33 (s, 1H), 3.80 (s, 3H), 3.34-3.32 (m, 1H), 3.30-3.34 (m, 1H), 3.12-2.97 (m, 1H), 2.48-2.41 (m, 2H), 2.40-2.29 (m, 1H), 2.05-2.01 (m, 2H), 1.81-1.76 (m, 1H), 1.69-1.63 (m, 2H), 1.55-1.52 (m, 2H), 1.18-1.17 (d, J = 6.4 Hz, 3H) |

TABLE 11-continued

| Example Number | Structure and Compound Name | LRMS m/z [M + H]+ | 1HNMR |
|---|---|---|---|
| 257 | 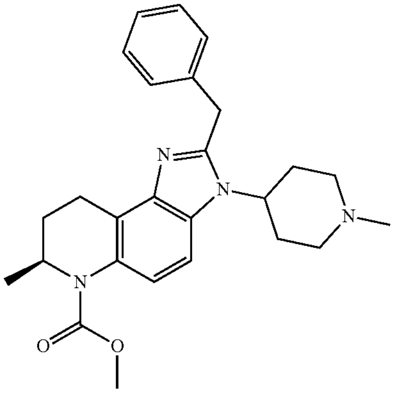 methyl (S)-2-benzyl-7-methyl-3-(1-methylpiperidin-4-yl)-3,7,8,9-tetrahydro-6H-imidazo[4,5-f]quinoline-6-carboxylate | 433 | 1H-NMR ($CDCl_3$, 300 MHz) δ (ppm): 7.41-7.33 (m, 2H), 7.30-7.29 (m, 2H), 7.25-7.21 (m, 3H), 4.84-4.79 (m, 1H), 4.45-4.31 (m, 2H), 4.07-4.01 (m, 1H), 3.80 (s, 3H), 3.35-3.24 (m, 1H), 3.11-3.01 (m, 1H), 2.91-2.87 (m, 2H), 2.47-2.43 (m, 2H), 2.34-2.25 (m, 4H), 1.93-1.71 (m, 3H), 1.47-1.44 (m, 1H), 1.34-1.30 (m, 1H), 1.21 (d, J = 6.9 Hz, 3H) |
| 258 | 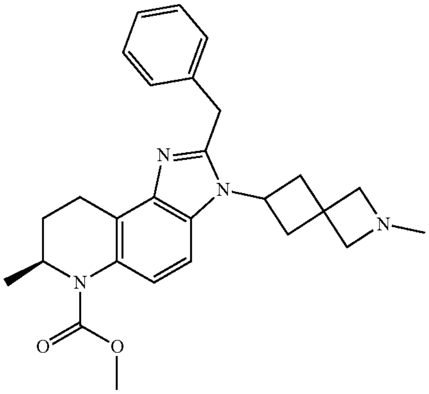 methyl (S)-2-benzyl-7-methyl-3-(2-methyl-2-azaspiro[3.3]heptan-6-yl)-3,7,8,9-tetrahydro-6H-imidazo[4,5-f]quinolino-6-carboxylate | 444 | 1H-NMR ($CDCl_3$, 300 MHz) δ (ppm): 7.41-7.32 (m, 1H), 7.27-7.22 (m, 4H), 7.12-7.09 (m, 2H), 4.85-4.79 (m, 1H), 4.61-4.55 (m, 1H), 4.41-4.29 (m, 2H), 3.81 (s, 3H), 3.46-3.22 (m, 5H), 3.09-2.93 (m, 3H), 2.49-2.22 (m, 6H), 1.79-1.73 (m, 1H), 1.21 (d, J = 6.6 Hz, 3H) |
| 259 | 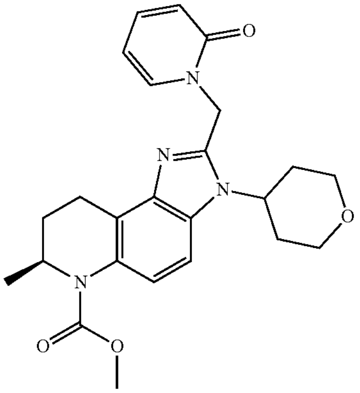 [SMILES: COC(=O)N1c2ccc3c(nc(Cn4ccccc4=O)n3C3CCOCC3)c2CC[C@@H]1C] methyl (S)-7-methyl-2-((2-oxopyridin-1(2H)-yl)methyl)-3-(tetrahydro-2H-pyran-4-yl)-3,7,8,9-tetrahydro-6H-imidazo[4,5-f]quinoline-6-carboxylate | 437 | 1H-NMR ($CD_3OD$, 400 MHz) δ (ppm): 7.75-7.73 (m, 1H), 7.57-7.53 (m, 2H), 7.48-7.46 (m, 1H), 6.63-6.61 (m, 1H), 6.45-6.41 (m, 1H), 5.63-5.51 (m, 2H), 5.01-4.95 (m, 1H), 4.77-4.75 (m, 1H), 4.14-4.08 (m, 2H), 3.78 (s, 3H), 3.64-3.58 (m, 2H), 3.18-3.16 (m, 1H), 2.96-2.92 (m, 1H), 2.59-2.52 (m, 2H), 2.26-2.23 (m, 1H), 1.76-1.68 (m, 3H), 1.14 (d, J = 6.4 Hz, 3H) |

TABLE 11-continued

| Example Number | Structure and Compound Name | LRMS m/z $[M + H]^+$ | $^1$HNMR |
|---|---|---|---|
| 260 | 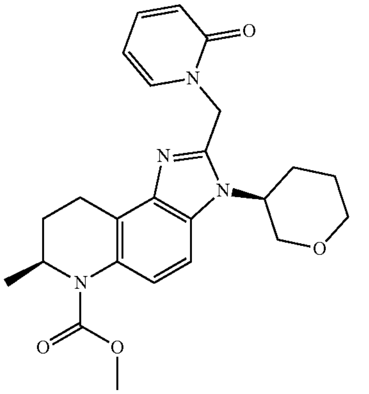 [SMILES: COC(=O)N1c2ccc3c(nc(Cn4ccccc4=O)n3[C@H]3CCCOC3)c2CC[C@@H]1C]<br>methyl (S)-7-methyl-2-((2-oxopyridin-1(2H)-yl)methyl)-3-((S)-tetrahydro-2H-pyran-3-yl)-3,7,8,9-tetrahydro-6H-imidazo[4,5-f]quinoline-6-carboxylate | 437 | $^1$H-NMR ($CD_3OD$, 300 MHz) δ (ppm): 7.75-7.72 (m, 1H), 7.62-7.59 (m, 2H), 7.47 (d, J = 9.0 Hz, 1H), 6.63 (d, J = 8.7 Hz, 1H), 6.44-6.43 (m, 1H), 5.68-5.62 (m, 1H), 5.47-5.42 (m, 1H), 4.75-4.70 (m, 2H), 4.20-4.10 (m, 1H), 4.01-3.95 (m, 1H), 4.90-3.85 (m, 1H), 3.78 (s, 3H), 3.65-3.55 (m, 1H), 3.21-3.12 (m, 1H), 2.98-2.87 (m, 1H), 2.55-2.45 (m, 1H), 2.25-2.18 (m, 1H), 1.95-1.85 (m, 3H), 1.80-1.70 (m, 1H), 1.13 (d, J = 6.6 Hz, 3H) |
| 261 | 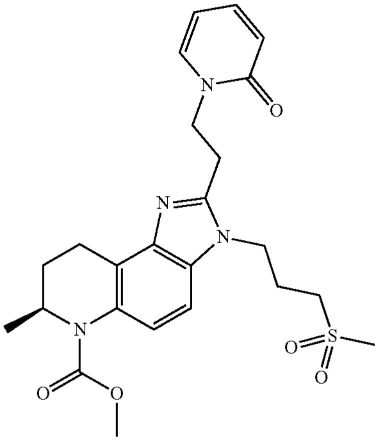<br>methyl (S)-7-methyl-3-(3-(methylsulfonyl)propyl)-2-(2-(2-oxopyridin-1(2H)-yl)ethyl)-3,7,8,9-tetrahydro-6H-imidazo[4,5-f]quinoline-6-carboxylate | 487 | $^1$H-NMR ($CDCl_3$, 300 MHz) δ (ppm): 7.51-7.46 (m, 2H), 7.41-7.35 (m, 1H), 7.22 (d, J = 9 Hz, 1H), 6.59 (d, J = 9 Hz, 1H), 6.19-6.14 (m, 1H), 4.84-4.80 (m, 1H), 4.45-4.38 (m, 4H), 3.81 (s, 3H), 3.46-3.39 (m, 2H), 3.24-2.21 (m, 1H), 3.18-3.03 (m, 3H), 2.98 (s, 3H), 2.41-2.25 (m, 3H), 1.79-1.73 (m, 1H), 1.19 (d, J = 6.6 Hz, 3H) |
| 262 | 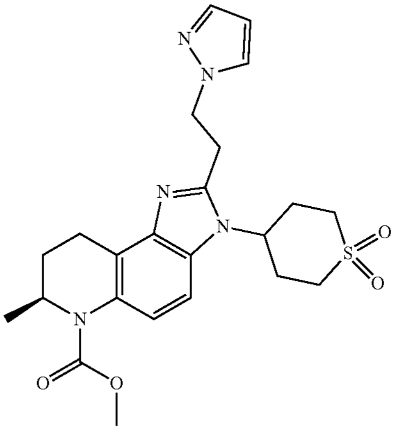 [SMILES: COC(=O)N1c2ccc3c(nc(CCn4cccn4)n3C3CCS(=O)(=O)CC3)c2CC[C@@H]1C]<br>methyl (S)-2-(2-(1H-pyrazol-1-yl)ethyl)-3-(1,1-dioxidotetrahydro-2H-thiopyran-4-yl)-7-methyl-3,7,8,9-tetrahydro-6H-imidazo[4,5-f]quinoline-6-carboxylate | 472 | $^1$H-NMR ($CD_3OD$, 300 MHz) δ (ppm): 7.56-7.54 (m, 2H), 7.44 (s, 2H), 6.25-6.23 (m, 1H), 4.80-4.64 (m, 4H), 3.79 (s, 3H), 3.63-3.39 (m, 4H), 3.28-3.10 (m, 3H), 3.08-2.86 (m, 3H), 2.35-2.17 (m, 1H), 2.02-1.94 (m, 2H), 1.80-1.70 (m, 1H), 1.15 (d, J = 6.7 Hz, 3H) |

TABLE 11-continued

| Example Number | Structure and Compound Name | LRMS m/z $[M + H]^+$ | $^1$HNMR |
|---|---|---|---|
| 263 | 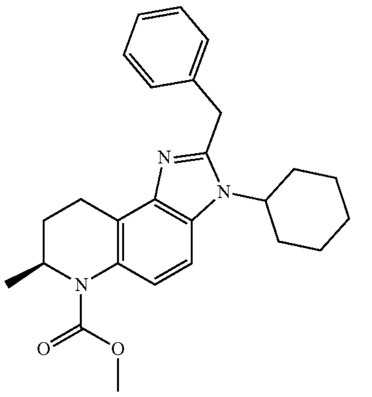 [SMILES: COC(=O)N1c2ccc3c(nc(Cc4ccccc4)n3C3CCCCC3)c2CC[C@@H]1C] methyl (S)-2-benzyl-3-cyclohexyl-7-methyl-3,7,8,9-tetrahydro-6H-imidazo[4,5-f]quinoline-6-carboxylate | 418 | $^1$H-NMR ($CD_3OD$ 300 MHz) δ (ppm): 7.45-7.22 (m, 7H), 4.78-4.73 (m, 1H), 4.38 (s, 2H), 4.21-4.17 (m, 1H), 3.76 (s, 3H), 3.23-3.16 (m, 1H), 2.99-2.93 (m, 1H), 2.28-2.22 (m, 1H), 2.14-2.06 (m, 2H), 1.79-1.66 (m, 4H), 1.50-1.44 (m, 2H), 1.28-1.22 (m, 3H), 1.12 (d, 3H, J = 6.8 Hz) |

Examples 264 and 265: methyl (S)-2-benzyl-3-((S)-1,1-dioxidotetrahydro-2H-thiopyran-3-yl)-7-methyl-3,7,8,9-tetrahydro-6H-imidazo[4,5-f]quinoline-6-carboxylate and methyl (S)-2-benzyl-3-((R)-1,1-dioxidotetrahydro-2H-thiopyran-3-yl)-7-methyl-3,7,8,9-tetrahydro-6H-imidazo[4,5-f]quinoline-6-carboxylate

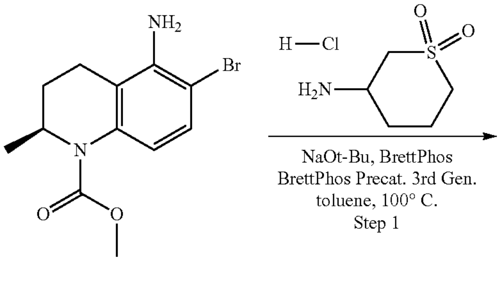

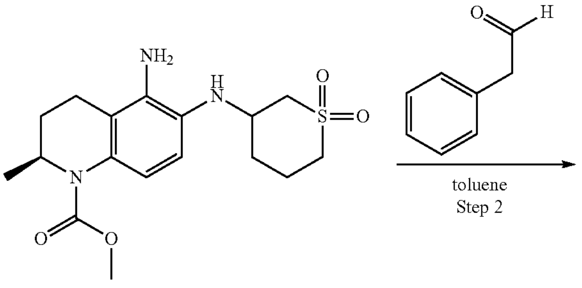

-continued

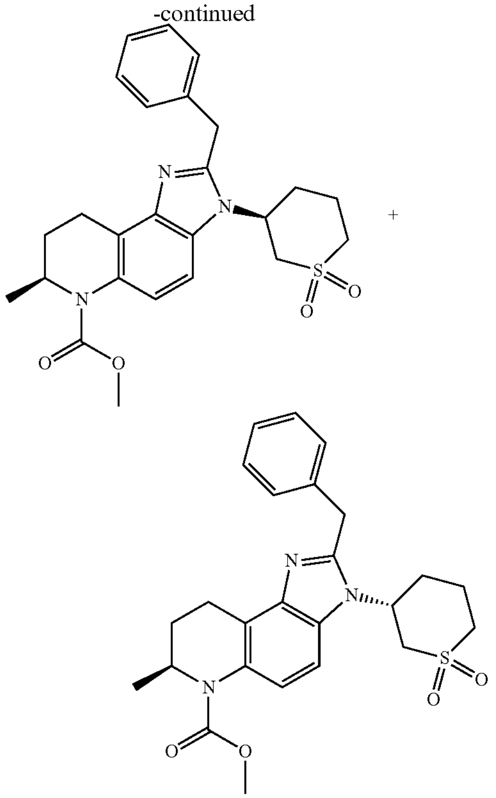

Step 1. Synthesis of methyl (2S)-5-amino-6-((1,1-dioxidotetrahydro-2H-thiopyran-3-yl)amino)-2-methyl-3,4-dihydroquinoline-1(2H)-carboxylate Into a 10-mL round-bottom flask purged and maintained with an inert atmosphere of nitrogen, methyl (2S)-5-amino-6-bromo-2-methyl-1,2,3,4-tetrahydroquinoline-1-carboxylate (100 mg, 0.33 mmol, Intermediate 1) was dissolved in toluene (3 mL). Then 3-aminotetrahydro-2H-thiopyran 1,1-dioxide hydrochloride (186 mg, 1.00 mmol), BrettPhos (36 mg, 0.07 mmol), 3rd Generation BrettPhos precatalyst (61 mg, 0.07 mmol) and sodium tert-butoxide (97 mg, 1.01 mmol) were added. The resulting solution was stirred for 2 h at 100° C. under nitrogen atmosphere. The reaction mixture was cooled to room temperature and the solids were filtered out. The filtrate was concentrated under vacuum. The residue was subjected to purification by FCC eluting with ethyl acetate/petroleum ether (2:1). This afforded the title compound (54.9 mg, 45%) as a yellow solid. MS: (ES, m/z): 368 $[M+H]^+$.

Step 2. Synthesis of methyl (S)-2-benzyl-3-((S)-1,1-dioxidotetrahydro-2H-thiopyran-3-yl)-7-methyl-3,7,8,9-tetrahydro-6H-imidazo[4,5-f]quinoline-6-carboxylate and methyl (S)-2-benzyl-3-((R)-1,1-dioxidotetrahydro-2H-thiopyran-3-yl)-7-methyl-3,7,8,9-tetrahydro-6H-imidazo[4,5-f]quinoline-6-carboxylate Into a 25-mL round-bottom flask, methyl (2S)-5-amino-6-((1,1-dioxidotetrahydro-2H-thiopyran-3-yl)amino)-2-methyl-3,4-dihydroquinoline-1(2H)-carboxylate (54.9 mg, 0.15 mmol) was dissolved in dichloromethane (5 mL). Then 2-phenylacetaldehyde (80.7 mg, 0.67 mmol) was added. The resulting solution was stirred for 4 h at room temperature. The resulting mixture was concentrated under vacuum. The crude product was purified by Prep-HPLC with the following conditions: Column, XBridge Shield RP18 OBD Column, 5 μm, 19×150 mm; mobile phase, A: water (containing 10 mmol/L $NH_4HCO_3$) and B: ACN (30.0% to 60.0% over 7 min); UV Detector: 254 nm. The crude product was purified by Chiral-Prep-HPLC with the following conditions (Prep-HPLC): Column, CHIRAL ART Cellulose-SB, 2×25 cm, 5 um; mobile phase, hexanes and ethanol (hold 40.0% ethanol in 30 min); UV Detector: 254 nm. This afforded the title compounds as follows: 8.9 mg (13%) of methyl (7S)-2-benzyl-3-[(3R)-1,1-dioxo-1lambda6-thian-3-yl]-7-methyl-3H,6H,7H,8H,9H-imidazo[4,5-f]quinoline-6-carboxylate (assumed stereochemistry, first eluting isomer, RT=20.61 min) as a white solid and 9.0 mg (13%) of methyl (7S)-2-benzyl-3-[(3S)-1,1-dioxo-1lambda6-thian-3-yl]-7-methyl-3H,6H,7H,8H,9H-imidazo[4,5-f]quinoline-6-carboxylate (assumed stereochemistry, second eluting isomer, RT=23.64 min) as a white solid.

First eluting isomer: $^1$H-NMR ($CD_3OD$, 400 MHz) δ (ppm): 7.56 (d, J=9.0 Hz, 1H), 7.46 (d, J=9.0 Hz, 1H), 7.41-7.24 (m, 5H), 4.91-4.72 (m, 2H), 4.50 (d, J=16.0 Hz, 1H), 4.39 (d, J=15.9 Hz, 1H), 3.91 (t, J=12.8 Hz, 1H), 3.79 (s, 3H), 3.28-3.16 (m, 2H), 3.11-2.94 (m, 3H), 2.43-2.21 (m, 2H), 2.07-2.01 (m, 1H), 1.78-1.68 (m, 2H), 1.47-1.42 (m, 1H), 1.16 (d, J=6.6 Hz, 3H). MS: (ES, m/z): 468 $[M+H]^+$. Second eluting isomer: $^1$H-NMR ($CD_3OD$, 400 MHz) δ (ppm): 7.56 (d, J=9.0 Hz, 1H), 7.46 (d, J=9.0 Hz, 1H), 7.41-7.24 (m, 5H), 4.92-4.73 (m, 2H), 4.51 (d, J=15.9 Hz, 1H), 4.40 (d, J=16.0 Hz, 1H), 3.95 (t, J=12.8 Hz, 1H), 3.79 (s, 3H), 3.32-3.17 (m, 2H), 3.10-2.93 (m, 3H), 2.40-2.21 (m, 2H), 2.06-1.98 (m, 1H), 1.85-1.67 (m, 2H), 1.43-1.38 (m, 1H), 1.17 (d, J=6.6 Hz, 3H). MS: (ES, m/z): 468 $[M+H]^+$.

The following examples in TABLE 12 were prepared using standard chemical manipulations and procedures similar to those used for the preparation of Examples 264 and 265.

TABLE 12

| Example Number | Structure and Compound Name | LRMS m/z $[M + H]^+$ | $^1$HNMR |
|---|---|---|---|
| 266 and 267 | 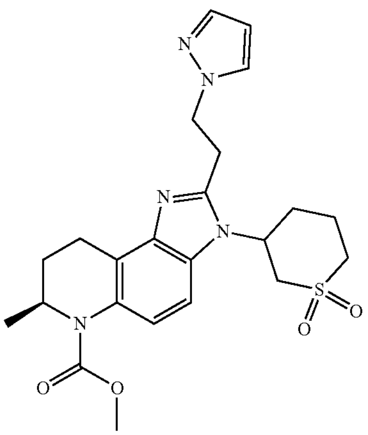<br>1st eluting isomer (177)<br>2nd eluting isomer (178)<br>methyl (7S)-2-(2-(1H-pyrazol-1-yl)ethyl)-3-(1,1-dioxidotetrahydro-2H-thiopyran-3-yl)-7-methyl-3,7,8,9-tetrahydro-6H-imidazo[4,5-f]quinoline-6-carboxylate | 1st eluting isomer = 472<br>2nd eluting isomer = 472 | 1st eluting isomer $^1$H-NMR ($CD_3OD$, 300 MHz) δ (ppm): 7.61-7.49 (m, 3H), 7.44 (d, J = 9.0 Hz, 1H), 6.22-6.20 (m, 1H), 4.85-4.63 (m, 4H), 3.96-3.88 (m, 1H), 3.79 (s, 3H), 3.54-3.48 (m, 2H), 3.38-3.36 (m, 1H), 3.22-3.04 (m, 3H), 2.96-2.88 (m, 1H), 2.50-2.32 (m, 1H), 2.34-1.97 (m, 3H), 1.83-1.60 (m, 2H), 1.14 (d, J = 6.6 Hz, 3H)<br>2nd eluting isomer $^1$H-NMR ($CD_3OD$, 400 MHz) δ (ppm): 7.61-7.49 (m, 3H), 7.44 (d, J = 9.0 Hz, 1H), 6.22-6.18 (m, 1H), 4.85-4.63 (m, 4H), 3.98-3.88 (m, 1H), 3.79 (s, 3H), 3.55-3.48 (m, 2H), 3.39-3.32 (m, 1H), 3.28-3.07 (m, 3H), 2.97-2.87 (m, 1H), 2.54-2.36 (m, 1H), 2.35-1.98 (m, 3H), 1.80-1.64 (m, 2H), 1.15 (d, J = 6.6 Hz, 3H) |

TABLE 12-continued

| Example Number | Structure and Compound Name | LRMS m/z $[M + H]^+$ | $^1$HNMR |
|---|---|---|---|
| 268 and 269 | 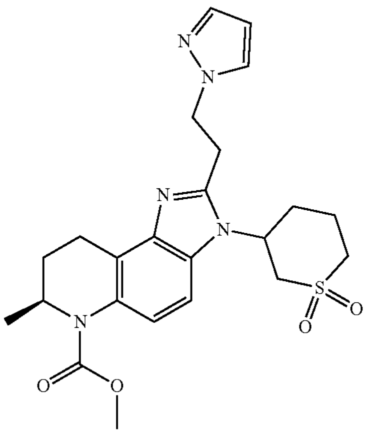 $1^{st}$ eluting isomer (179) $2^{nd}$ eluting isomer (180) methyl (7S)-2-(2-(2H-1,2,3-triazol-2-yl)ethyl)-3-(1,1-dioxidotetrahydro-2H-thiopyran-3-yl)-7-methyl-3,7,8,9-tetrahydro-6H-imidazo[4,5-f]quinoline-6-carboxylate | $1^{st}$ eluting isomer = 473 $2^{nd}$ eluting isomer = 473 | $1^{st}$ eluting isomer $^1$H-NMR ($CDCl_3$, 300 MHz) δ (ppm): 7.56-7.53 (m, 3H), 7.19 (d, J = 9 Hz, 1H), 5.11-5.07 (m, 2H), 4.92-4.75 (m, 2H), 3.80-3.79 (m, 4H), 3.76-3.66 (m, 2H), 3.24-3.13 (m, 3H), 3.10-2.99 (m, 2H), 2.40-2.15 (m, 4H), 2.02-1.98 (m, 1H), 1.80-1.71 (m, 1H), 1.15 (d, J = 6.6 Hz, 3H) $2^{nd}$ eluting isomer $^1$H-NMR ($CDCl_3$, 300 MHz) δ (ppm): 7.53-7.52 (m, 2H), 7.50-7.48 (m, 1H), 7.18 (d, J = 9 Hz, 1H), 5.11-5.04 (m, 2H), 4.88-4.76 (m, 2H), 3.82-3.73 (m, 4H), 3.67-3.62 (m, 2H), 3.22-3.09 (m, 3H), 3.05-2.96 (m, 2H), 2.28-2.15 (m, 4H), 2.08-2.04 (m, 1H), 1.77-1.70 (m, 1H), 1.15 (d, J = 6.9 Hz, 3H) |
| 270 | 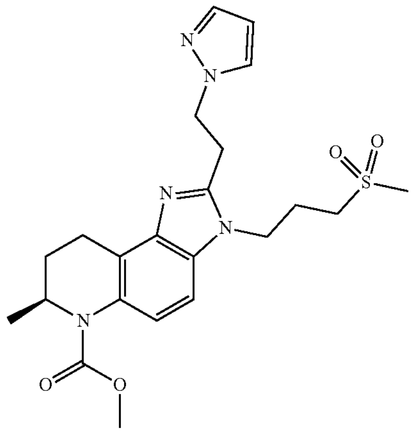 methyl (S)-2-(2-(1H-pyrazol-1-yl)ethyl)-7-methyl-3-(3-(methylsulfonyl)propyl)-3,7,8,9-tetrahydro-6H-imidazo[4,5-f]quinoline-6-carboxylate | 460 | $^1$H-NMR ($CDCl_3$, 300 MHz) δ (ppm): 7.50-7.49 (m, 2H), 7.28-7.26 (m, 1H), 7.15 (d, J = 9.0 Hz, 1H), 6.12-6.11 (m, 1H), 4.81-4.77 (m, 3H), 4.13-4.09 (m, 2H), 3.78 (s, 3H), 3.51-3.50 (m, 2H), 3.27-3.19 (m, 1H), 3.06-3.00 (m, 1H), 2.92-2.89 (m, 5H), 2.29-2.14 (m, 3H), 1.80-1.72 (m, 1H), 1.15 (d, J = 6.6 Hz, 3H) |

TABLE 12-continued

| Example Number | Structure and Compound Name | LRMS m/z [M + H]+ | 1HNMR |
|---|---|---|---|
| 271 | 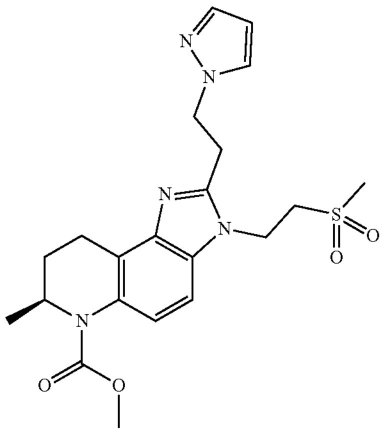 [SMILES: COC(=O)N1c2ccc3c(nc(CCn4cccn4)n3CCS(C)(=O)=O)c2CC[C@@H]1C] methyl (S)-2-(2-(1H-pyrazol-1-yl)ethyl)-7-methyl-3-(2-(methylsulfonyl)ethyl)-3,7,8,9-tetrahydro-6H-imidazo[4,5-f]quinoline-6-carboxylate | 446 | $^1$H-NMR ($CDCl_3$, 300 MHz) δ (ppm): 7.52-7.51 (m, 2H), 7.27-7.26 (m, 1H), 7.13 (d, J = 8.7 Hz, 1H), 6.14-6.12 (m, 1H), 4.82-4.76 (m, 3H), 4.40-4.35 (m, 2H), 3.79 (s, 3H), 3.54-3.48 (m, 2H), 3.28-3.17 (m, 3H), 3.04-2.97 (m, 1H), 2.74 (s, 3H), 2.30-2.19 (m, 1H), 1.79-1.70 (m, 1H), 1.15 (d, J = 6.6 Hz, 3H) |
| 272 | 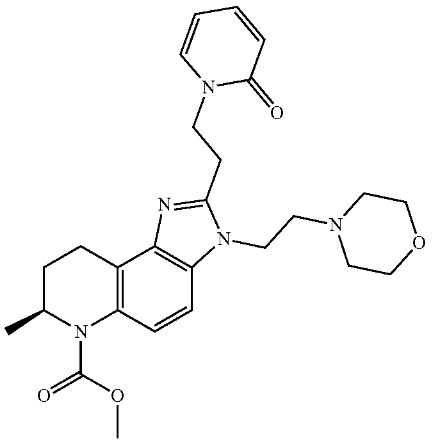 [SMILES: COC(=O)N1c2ccc3c(nc(CCn4ccccc4=O)n3CCN3CCOCC3)c2CC[C@@H]1C] methyl (S)-7-methyl-3-(2-morpholinoethyl)-2-(2-(2-oxopyridin-1(2H)-yl)ethyl)-3,7,8,9-tetrahydro-6H-imidazo[4,5-f]quinoline-6-carboxylate | 480 | $^1$H-NMR ($CDCl_3$, 300 MHz) δ (ppm): 7.48-7.41 (m, 2H), 7.36-7.30 (m, 1H), 7.12 (d, J = 9.0 Hz, 1H), 6.56 (d, J = 9.0 Hz, 1H), 6.11-6.07 (m, 1H), 4.83-4.77 (m, 1H), 4.48-4.36 (m, 2H), 4.23-4.18 (m, 2H), 3.78 (s, 3H), 3.65-3.63 (m, 4H), 3.44-3.42 (m, 2H), 3.22-3.17 (m, 1H), 3.05-2.97 (m, 1H), 2.65-2.61 (m, 2H), 2.48-2.45 (m, 4H), 2.27-2.22 (m, 1H), 1.77-1.70 (m, 1H), 1.15 (d, J = 6.6 Hz, 3H) |

TABLE 12-continued

| Example Number | Structure and Compound Name | LRMS m/z [M + H]+ | 1HNMR |
|---|---|---|---|
| 273 | 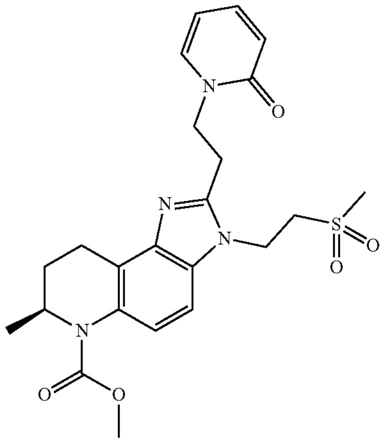 [SMILES: COC(=O)N1c2ccc3c(nc(CCn4ccccc4=O)n3CCS(C)(=O)=O)c2CC[C@@H]1C] methyl (S)-7-methyl-3-(2-(methylsulfonyl)ethyl)-2-(2-(2-oxopyridin-1(2H)-yl)ethyl)-3,7,8,9-tetrahydro-6H-imidazo[4,5-f]quinoline-6-carboxylate | 473 | $^1$H-NMR ($CDCl_3$, 300 MHz) δ (ppm): 7.52-7.43 (m, 1H), 7.41-7.35 (m, 2H), 7.23-7.20 (m, 1H), 6.60-6.57 (d, J = 9 Hz, 1H), 6.20-6.15 (m, 1H), 4.83-4.73 (m, 3H), 4.41-4.33 (m, 2H), 3.81 (s, 3H), 3.58-3.53 (m, 2H), 3.48-3.42 (m, 2H), 3.22-3.18 (m, 1H), 3.03-2.97 (m, 4H), 2.31-2.27 (m, 1H), 1.78-1.71 (m, 1H), 1.18 (d, J = 6.6 Hz, 3H) |
| 274 | 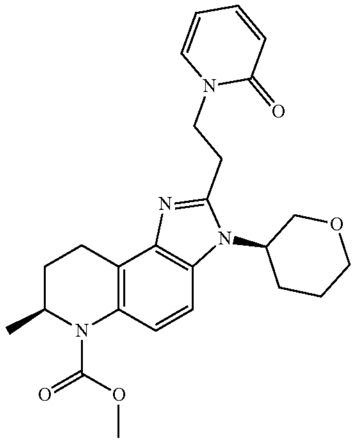 [SMILES: COC(=O)N1c2ccc3c(nc(CCn4ccccc4=O)n3[C@@H]3CCCOC3)c2CC[C@@H]1C] methyl (S)-7-methyl-2-(2-(2-oxopyridin-1(2H)-yl)ethyl)-3-((R)-tetrahydro-2H-pyran-3-yl)-3,7,8,9-tetrahydro-6H-imidazo[4,5-f]quinoline-6-carboxylate | 450 | $^1$H-NMR ($CDCl_3$, 300 MHz) δ (ppm): 7.52-7.51 (m, 2H), 7.27-7.26 (m, 1H), 7.13 (d, J = 8.7 Hz, 1H), 6.14-6.12 (m, 1H), 4.82-4.76 (m, 3H), 4.40-4.35 (m, 2H), 3.79 (s, 3H), 3.54-3.48 (m, 2H), 3.28-3.17 (m, 3H), 3.04-2.97 (m, 1H), 2.74 (s, 3H), 2.30-2.19 (m, 1H), 1.79-1.70 (m, 1H), 1.15 (d, J = 6.6 Hz, 3H) |

TABLE 12-continued

| Example Number | Structure and Compound Name | LRMS m/z $[M + H]^+$ | $^1$HNMR |
|---|---|---|---|
| 275 | 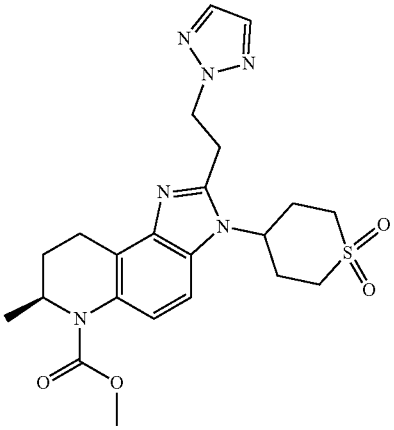 [SMILES: COC(=O)N1c2ccc3c(nc(CCn4nccn4)n3C3CCS(=O)(=O)CC3)c2CC[C@@H]1C] methyl (S)-2-(2-(2H-1,2,3-triazol-2-yl)ethyl)-3-(1,1-dioxidotetrahydro-2H-thiopyran-4-yl)-7-methyl-3,7,8,9-tetrahydro-6H-imidazo[4,5-f]quinoline-6-carboxylate | 473 | $^1$H-NMR ($CD_3OD$, 300 MHz) δ (ppm): 7.69 (s, 2H), 7.42-7.38 (m, 2H), 5.01-4.96 (m, 2H), 4.87-4.70 (m, 2H), 3.79 (s, 3H), 3.70-3.63 (m, 2H), 3.59-3.43 (m, 2H), 3.28-2.81 (m, 6H), 2.26-2.10 (m, 3H), 1.81-1.64 (m, 1H), 1.13 (d, J = 6.7 Hz, 3H) |

Examples 276: methyl (S)-3-((R)-1-(1H-tetrazol-5-yl)piperidin-3-yl)-2-benzyl-7-methyl-3,7,8,9-tetrahydro-6H-imidazo[4,5-f]quinoline-6-carboxylate

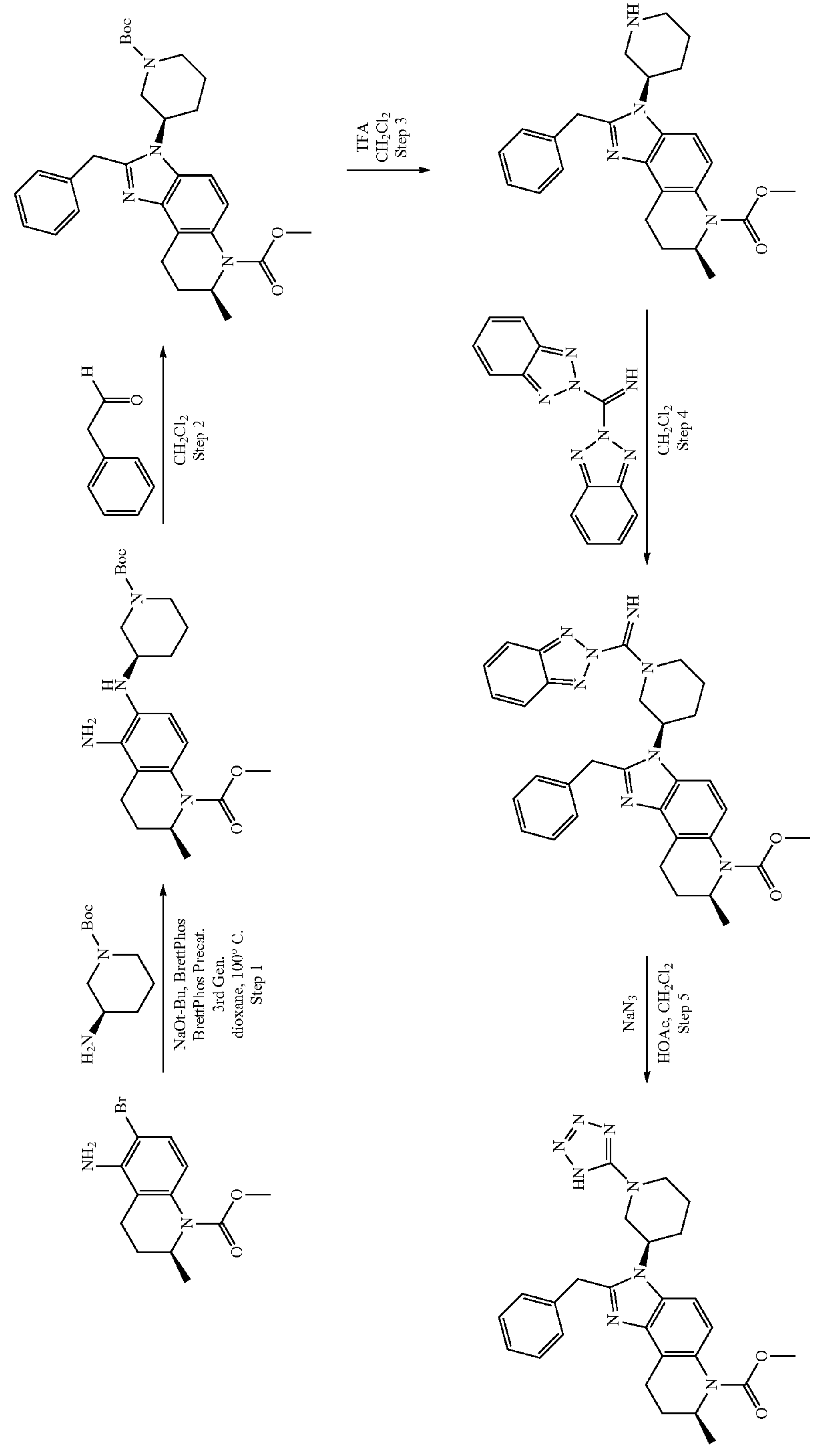
NaOt-Bu, BrettPhos
BrettPhos Precat.
3rd Gen.
dioxane, 100° C.
Step 1
$CH_2Cl_2$
Step 2
TFA
$CH_2Cl_2$
Step 3
$CH_2Cl_2$
Step 4
$NaN_3$
HOAc, $CH_2Cl_2$
Step 5

Step 1. Synthesis of methyl (2S)-5-amino-6-[[(3R)-1-[(tert-butoxy)carbonyl]piperidin-3-yl]amino]-2-methyl-1,2,3,4-tetrahydroquinoline-1-carboxylate Into a 50-mL round-bottom flask purged and maintained with an inert atmosphere of nitrogen, methyl (2S)-5-amino-6-bromo-2-methyl-1,2,3,4-tetrahydroquinoline-1-carboxylate (400 mg, 1.34 mmol, Intermediate 1) was dissolved in dioxane (10 mL). Then tert-butyl (3R)-3-aminopiperidine-1-carboxylate (800 mg, 3.99 mmol), BrettPhos (288 mg, 0.54 mmol), BrettPhos Pd $3^{rd}$ generation precatalyst (243 mg, 0.27 mmol) and sodium tert-butoxide (386 mg, 4.02 mmol) were added. The resulting solution was stirred for 2 h at 100° C. in the nitrogen atmosphere. The reaction mixture was cooled and the resulting solids were filtered out. The filtrate was concentrated under vacuum. The residue was subjected to purification by FCC eluting with ethyl acetate/petroleum ether (2:1). This afforded the title compound (300 mg, 54%) as a green solid. MS: (ES, m/z): 420 $[M+H]^+$.

Step 2. Synthesis of tert-butyl (3R)-3-[(7S)-2-benzyl-6-(methoxycarbonyl)-7-methyl-3H,6H,7H,8H,9H-imidazo[4,5-f]quinolin-3-yl]piperidine-1-carboxylate Into a 50-mL round-bottom flask, methyl (2S)-5-amino-6-[[(3R)-1-[(tert-butoxy)carbonyl]piperidin-3-yl]amino]-2-methyl-1,2,3,4-tetrahydroquinoline-1-carboxylate (300 mg, 0.72 mmol) was dissolved in dichloromethane (10 mL). Then 2-phenylacetaldehyde (258 mg, 2.15 mmol) was added. The resulting solution was stirred for 2 h at room temperature. The resulting mixture was concentrated under vacuum. The residue was subjected to purification by FCC eluting with ethyl acetate/petroleum ether (2:1). This afforded the title compound (200 mg, 54%) as a green solid. MS: (ES, m/z): 519 $[M+H]^+$.

Step 3. Synthesis of methyl (7S)-2-benzyl-7-methyl-3-[(3R)-piperidin-3-yl]-3H,6H,7H,8H,9H-imidazo[4,5-f]quinoline-6-carboxylate Into a 10-mL round-bottom flask, tert-butyl (3R)-3-[(7S)-2-benzyl-6-(methoxycarbonyl)-7-methyl-3H,6H,7H,8H,9H-imidazo[4,5-f]quinolin-3-yl]piperidine-1-carboxylate (200 mg, 0.39 mmol) was dissolved in dichloromethane (3 mL). Then trifluoroacetic acid (1 mL) was added. The flask was wrapped with aluminum foil and the resulting solution was stirred for 1 h at room temperature. The resulting mixture was concentrated under vacuum. After addition of water, the pH value of the mixture was adjusted to 8-9 with sodium bicarbonate. The resulting solution was extracted with 2×10 mL of dichloromethane. The organic layers were combined, dried over sodium sulfate, filtered and concentrated. The residue was subjected to purification by FCC eluting with ethyl acetate/petroleum ether (3:1). This afforded the title compound (140 mg, 87%) as a green solid. MS: (ES, m/z): 419 $[M+H]^+$.

Step 4. Synthesis of methyl (7S)-3-[(3R)-1-[(2H-1,2,3-benzotriazol-2-yl)carboximidoyl]piperidin-3-yl]-2-benzyl-7-methyl-3H,6H,7H,8H,9H-imidazo[4,5-f]quinoline-6-carboxylate Into a 25-mL round-bottom flask, methyl (7S)-2-benzyl-7-methyl-3-[(3R)-piperidin-3-yl]-3H,6H,7H,8H,9H-imidazo[4,5-f]quinoline-6-carboxylate (50 mg, 0.12 mmol) was dissolved in dichloromethane (5 mL). Then 2-[(2H-1,2,3-benzotriazol-2-yl)carboximidoyl]-2H-1,2,3-benzotriazole (31.45 mg, 0.12 mmol) was added. The resulting solution was stirred for 3 days at room temperature. The resulting mixture was concentrated under vacuum and this afforded the title compound (60 mg, crude) as green crude oil, which could be used into next step without further purification. MS: (ES, m/z): 563 $[M+H]^+$.

Step 5. Synthesis of methyl (7S)-2-benzyl-7-methyl-3-[(3R)-1-(1H-1,2,3,4-tetrazol-5-yl)piperidin-3-yl]-3H,6H,7H,8H,9H-imidazo[4,5-f]quinoline-6-carboxylate Into a 25-mL round-bottom flask, methyl (7S)-3-[(3R)-1-[(2H-1,2,3-benzotriazol-2-yl)carboximidoyl]piperidin-3-yl]-2-benzyl-7-methyl-3H,6H,7H,8H,9H-imidazo[4,5-f]quinoline-6-carboxylate (60 mg, 0.11 mmol) was dissolved in dichloromethane (5 mL). Then sodium azide (7.62 mg, 0.12 mmol) was added, followed by acetic acid (0.1 mL). The resulting solution was stirred for 1 day at room temperature. The resulting mixture was concentrated under vacuum. After addition of water, the pH value of the reaction mixture was adjusted to 9-10 with sodium bicarbonate. The resulting solution was extracted with 2×5 mL of dichloromethane. The organic layers were combined, dried over sodium sulfate, filtered and concentrated. The crude product was purified by Prep-HPLC with the following conditions: Column, XBridge C18 OBD Prep Column, 5 um, 19 mm×150 mm; mobile phase, A: Water (containing 10 mmol/L $NH_4HCO_3$) and B: ACN (30.0% to 50.0% ACN over 7 min); UV Detector: 254 nm. This afforded the title compound (9.3 mg, 18%) of as a white solid.

$^1$H-NMR: (300 MHz, $CD_3CD$, ppm): 7.57-7.54 (d, J=9 Hz, 1H), 7.46-7.43 (d, J=9 Hz, 1H), 7.18-7.30 (m, 5H), 4.86-4.80 (m, 1H), 4.47-4.45 (m, 3H), 3.82-3.76 (m, 6H), 3.30-3.11 (m, 2H), 3.05-2.96 (m, 1H), 2.43-2.23 (m, 2H), 1.85-1.73 (m, 2H), 1.61-1.46 (m, 2H), 1.18-1.16 (d, J=6.6 Hz, 3H). MS: (ES, m/z): 487 $[M+H]^+$.

The following examples in TABLE 13 were prepared using standard chemical manipulations and procedures similar to those used for the preparation of Examples 276.

TABLE 13

| Example Number | Structure and Compound Name | LRMS m/z [M + H]+ | 1HNMR |
|---|---|---|---|
| 277 | 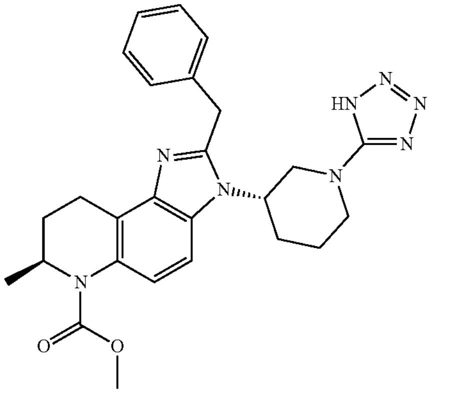 [SMILES: COC(=O)N1c2ccc3c(nc(Cc4ccccc4)n3[C@H]3CCCN(c4nnn[nH]4)C3)c2CC[C@@H]1C] methyl (S)-3-((S)-1-(1H-tetrazol-5-yl)piperidin-3-yl)-2-benzyl-7-methyl-3,7,8,9-tetrahydro-6H-imidazo[4,5-f]quinoline-6-carboxylate | 487 | $^1$H-NMR ($CD_3OD$, 300 MHz) δ (ppm): 7.57-7.54 (d, J = 9 Hz, 1H), 7.46-7.43 (d, J = 9 Hz, 1H), 7.18-7.30 (m, 5H), 4.83-4.77 (m, 1H), 4.52-4.40 (m, 3H), 3.92-3.79 (m, 6H), 3.29-3.15 (m, 2H), 3.04-2.95 (m, 1H), 2.35-2.23 (m, 2H), 1.85-1.76 (m, 2H), 1.57-1.48 (m, 2H), 1.19-1.17 (d, J = 6.9 Hz, 3H) |
| 278 | 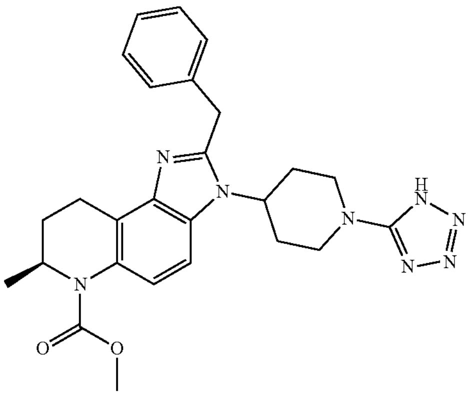 [SMILES: COC(=O)N1c2ccc3c(nc(Cc4ccccc4)n3C3CCN(c4nnn[nH]4)CC3)c2CC[C@@H]1C] methyl (S)-3-(1-(1H-tetrazol-5-yl)piperidin-4-yl)-2-benzyl-7-methyl-3,7,8,9-tetrahydro-6H-imidazo[4,5-f]quinoline-6-carboxylate | 487 | $^1$H-NMR ($CD_3OD$, 400 MHz) δ (ppm): 7.38-7.21 (m, 7H), 4.78-4.74 (m, 1H), 4.55-4.42 (m, 3H), 3.97-3.93 (m, 2H), 3.75 (s, 3H), 3.26-3.16 (m, 1H), 3.03-2.92 (m, 3H), 2.48-2.40 (m, 2H), 2.26-2.21 (m, 1H), 1.81-1.70 (m, 1H), 1.55-1.42 (m, 2H), 1.13 (d, J = 6.8 Hz, 3H). |

Examples 279 and 280: methyl (S)-3-((1R,3S)-3-(1H-tetrazol-5-yl)cyclohexyl)-2-benzyl-7-methyl-3,7,8,9-tetrahydro-6H-imidazo[4,5-f]quinoline-6-carboxylate and methyl (S)-3-((1S,3R)-3-(1H-tetrazol-5-yl)cyclohexyl)-2-benzyl-7-methyl-3,7,8,9-tetrahydro-6H-imidazo[4,5-f]quinoline-6-carboxylate

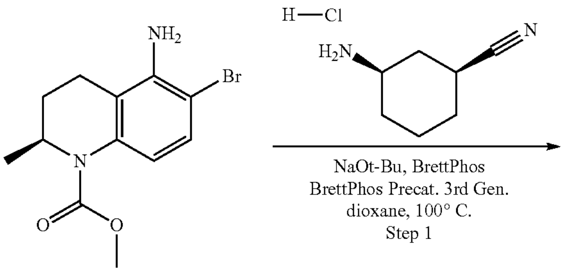

-continued

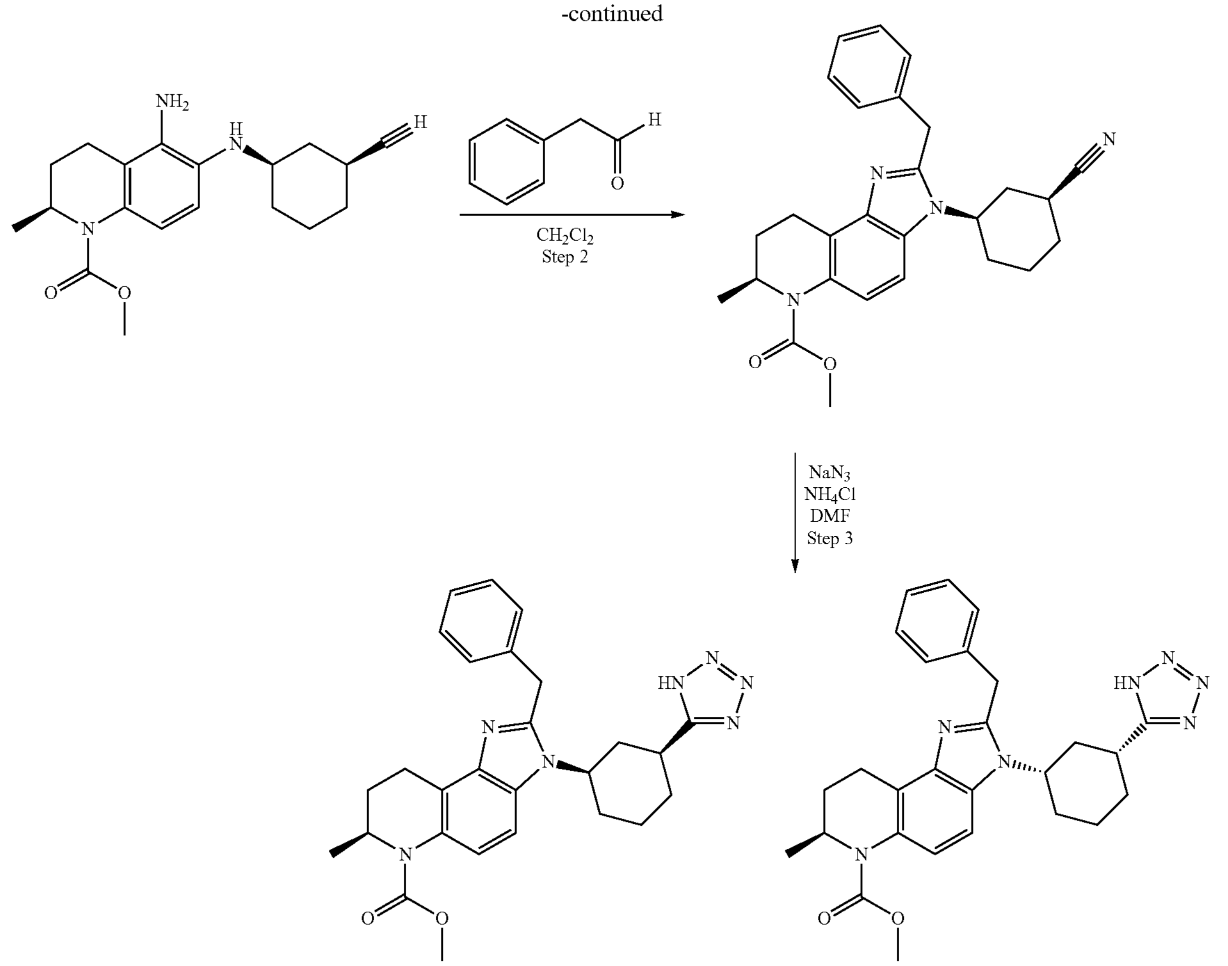

Step 1. Synthesis of methyl (S)-5-amino-6-(((cis)-3-cyanocyclohexyl)amino)-2-methyl-3,4-dihydroquinoline-1(2H)-carboxylate Into a 50-mL round-bottom flask purged and maintained with an inert atmosphere of nitrogen, was placed cis-3-aminocyclohexane-1-carbonitrile hydrochloride (714 mg, 4.00 mmol, Intermediate 29), NaOtBu (642 mg, 6.35 mmol), methyl (2S)-5-amino-6-bromo-2-methyl-1,2,3,4-tetrahydroquinoline-1-carboxylate (443 mg, 1.33 mmol, Intermediate 1), Brettphos (539 mg, 0.95 mmol), and BrettPhos Pd $3^{rd}$ generation precatalyst (269.5 mg, 0.28 mmol) in dioxane (10 mL). The resulting suspension was stirred for 2 h at 100° C. in an oil bath. The reaction mixture was cooled to room temperature. The solids were filtered out. The resulting mixture was concentrated under vacuum. The residue was subjected to FCC eluting with ethyl acetate/petroleum ether (1/1). This afforded the title compound (250 mg, 47%) as a green solid. MS: (ES, m/z): 343 $[M+H]^+$.

Step 2. Synthesis of methyl (S)-2-benzyl-3-((cis)-3-cyanocyclohexyl)-7-methyl-3,7,8,9-tetrahydro-6H-imidazo[4,5-f]quinoline-6-carboxylate Into a 50-mL round-bottom flask, was placed methyl (S)-5-amino-6-(((cis)-3-cyanocyclohexyl)amino)-2-methyl-3,4-dihydroquinoline-1(2H)-carboxylate (250 mg, 0.66 mmol), and 2-phenylacetaldehyde (263 mg, 2.08 mmol) in dichloromethane (5 mL). The resulting solution was stirred overnight at rt. The resulting mixture was concentrated under vacuum. The residue was subjected to FCC eluting with ethyl acetate/petroleum ether (2/1). This afforded the title compound (256 mg, 79%) as a light yellow solid. MS: (ES, m/z): 443 $[M+H]^+$.

Step 3. Synthesis of methyl (S)-3-((1R,3S)-3-(1H-tetrazol-5-yl)cyclohexyl)-2-benzyl-7-methyl-3,7,8,9-tetrahydro-6H-imidazo[4,5-f]quinoline-6-carboxylate and methyl (S)-3-((1S,3R)-3-(1H-tetrazol-5-yl)cyclohexyl)-2-benzyl-7-methyl-3,7,8,9-tetrahydro-6H-imidazo[4,5-f]quinoline-6-carboxylate Into a 20-mL sealed tube, was placed methyl (7S)-2-benzyl-3-(3-cyanocyclohexyl)-7-methyl-3H,6H,7H,8H,9H-imidazo[4,5-f]quinoline-6-carboxylate (256.0 mg, 0.52 mmol), sodium azide (213 mg, 3.12 mmol) and $NH_4Cl$ (175 mg, 3.12 mmol) in N,N-dimethylformamide (8 mL). The final reaction mixture was irradiated with microwave radiation for 3 h at 140° C. The reaction mixture was cooled to room temperature. The reaction was then quenched by the addition of 10 mL of saturated sodium bicarbonate. The resulting solution was extracted with 3×10 mL of ethyl acetate and the organic layers combined and dried over anhydrous sodium sulfate and concentrated under vacuum. The crude products were purified by Prep-HPLC with the following conditions: Column, XSelect CSH Prep C18 OBD Column, 19×250 mm, 5 um; mobile phase, Water (10 mmol/L $NH_4HCO_3$) and ACN (2.0% ACN up to 40.0% in 14 min); Detector, UV 254 nm.

This afforded the title compounds as follows: 22.6 mg (9%) of methyl (S)-3-((1R,3S)-3-(1H-tetrazol-5-yl)cyclohexyl)-2-benzyl-7-methyl-3,7,8,9-tetrahydro-6H-imidazo[4,5-f]quinoline-6-carboxylate (assumed stereochemistry, first eluting isomer) as a white solid, and 47.0 mg (18%) of methyl (S)-3-((1S,3R)-3-(1H-tetrazol-5-yl)cyclohexyl)-2-benzyl-7-methyl-3,7,8,9-tetrahydro-6H-imidazo[4,5-f]quinoline-6-carboxylate (assumed stereochemistry, second eluting isomer) as a white solid.

First eluting isomer: $^1$H-NMR ($CD_3OD$, 300 MHz) δ (ppm): 7.63-7.49 (m, 1H), 7.49-7.34 (m, 1H), 7.34-7.16 (m, 5H), 4.86-4.68 (m, 1H), 4.57-4.32 (m, 3H), 3.77 (s, 3H), 3.28-2.89 (m, 3H), 2.64-2.33 (m, 1H), 2.33-1.39 (m, 9H), 1.15 (d, J=6.6 Hz, 3H). MS: (ES, m/z): 486 [M+H]$^+$.

Second eluting isomer: $^1$H-NMR ($CD_3OD$, 300 MHz) δ (ppm): 7.63-7.49 (m, 1H), 7.48-7.36 (m, 1H), 7.36-7.16 (m, 5H), 4.83-4.70 (m, 1H), 4.57-4.38 (m, 3H), 3.76 (s, 3H), 3.20-2.89 (m, 3H), 2.63-2.47 (m, 1H), 2.32-1.99 (m, 3H), 1.99-1.82 (m, 2H), 1.82-1.40 (m, 4H), 1.16 (d, J=6.6 Hz, 3H). MS: (ES, m/z): 486 [M+H]$^+$.

Examples 281 and 282: methyl (S)-3-((1R,3R)-3-(1H-tetrazol-5-yl)cyclohexyl)-2-benzyl-7-methyl-3,7,8,9-tetrahydro-6H-imidazo[4,5-f]quinoline-6-carboxylate and methyl (S)-3-((1S,3S)-3-(1H-tetrazol-5-yl)cyclohexyl)-2-benzyl-7-methyl-3,7,8,9-tetrahydro-6H-imidazo[4,5-f]quinoline-6-carboxylate

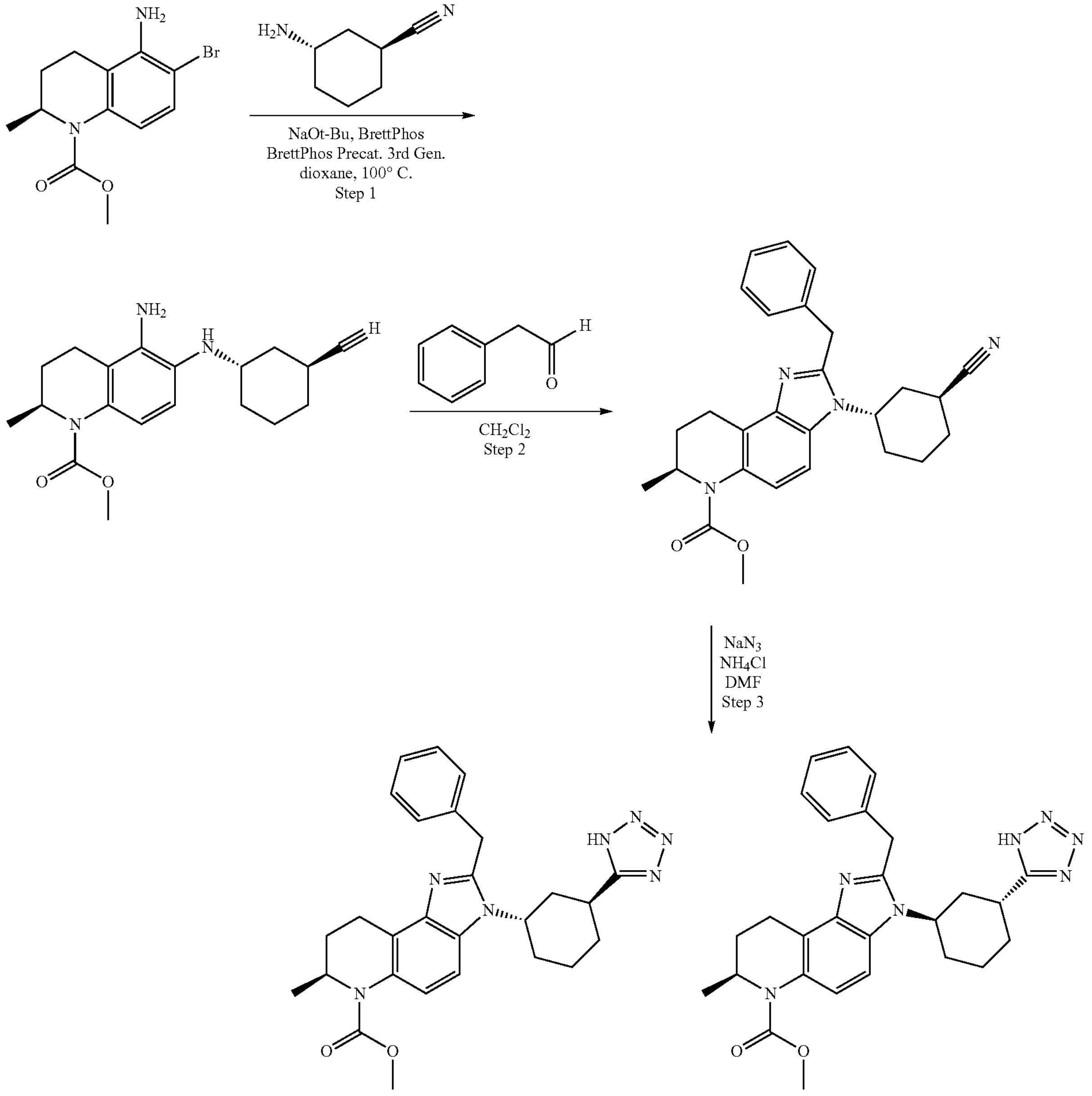

Step 1. Synthesis of methyl (S)-5-amino-6-(((trans)-3-cyanocyclohexyl)amino)-2-methyl-3,4-dihydroquinoline-1(2H)-carboxylate Into a 25-mL round-bottom flask purged and maintained with an inert atmosphere of nitrogen, was placed (trans)-3-aminocyclohexane-1-carbonitrile (134 mg, 1.03 mmol), NaOtBu (130 mg, 1.29 mmol), methyl (2S)-5-amino-6-bromo-2-methyl-1,2,3,4-tetrahydronaphthalene-1-carboxylate (100 mg, 0.30 mmol, Intermediate 1), Brettphos (72 mg, 0.13 mmol), and BrettPhos Pd G3 precatalyst (60 mg, 0.06 mmol) in dioxane (5 mL). The resulting solution was stirred for 1 h at 100° C. in an oil bath. The reaction mixture was cooled to room temperature. The solids were filtered out. The resulting mixture was concentrated under vacuum. The residue was subjected to purification by FCC eluting with ethyl acetate/petroleum ether (1:1). This afforded the title compound (60 mg, 47%) as a dark green solid. MS: (ES, m/z): 343 $[M+H]^+$.

Step 2. Synthesis of methyl (S)-2-benzyl-3-((trans)-3-cyanocyclohexyl)-7-methyl-3,7,8,9-tetrahydro-6H-imidazo[4,5-f]quinoline-6-carboxylate Into a 25-mL round-bottom flask, was placed methyl (2S)-5-amino-6-[[(trans)-3-cyanocyclohexyl]amino]-2-methyl-1,2,3,4-tetrahydroquinoline-1-carboxylate (60 mg, 0.15 mmol), and 2-phenylacetaldehyde (63 mg, 0.50 mmol) in dichloromethane (2 mL). The resulting solution was stirred for 1 h at rt. The resulting mixture was concentrated under vacuum. The residue was subjected to purification by FCC eluting with ethyl acetate/petroleum ether (0%-40%). This afforded the title compound (50 mg, 68%) as a yellow oil. MS: (ES, m/z): 443 $[M+H]^+$.

Step 3. Synthesis of methyl (S)-3-((1R,3R)-3-(1H-tetrazol-5-yl)cyclohexyl)-2-benzyl-7-methyl-3,7,8,9-tetrahydro-6H-imidazo[4,5-f]quinoline-6-carboxylate and methyl (S)-3-((1S,3S)-3-(1H-tetrazol-5-yl)cyclohexyl)-2-benzyl-7-methyl-3,7,8,9-tetrahydro-6H-imidazo[4,5-f]quinoline-6-carboxylate Into a 20-mL sealed tube, was placed methyl (S)-2-benzyl-3-((trans)-3-cyanocyclohexyl)-7-methyl-3,7,8,9-tetrahydro-6H-imidazo[4,5-f]quinoline-6-carboxylate (256.0 mg, 0.52 mmol), $NH_4Cl$ (175 mg, 3.12 mmol) and $NaN_3$ (213 mg, 3.12 mmol) in N,N-dimethylformamide (8 mL). The final reaction mixture was irradiated with microwave radiation for 3 h at 140° C. The reaction mixture was cooled to room temperature. The reaction was then quenched by the addition of 10 mL of saturated sodium bicarbonate. The resulting solution was extracted with 3×10 mL of ethyl acetate and the organic layers combined, dried over anhydrous sodium sulfate and concentrated under vacuum. The crude products were purified by Prep-HPLC with the following conditions: Column, XBridge C18 OBD Prep Column, 100 Å, 10 um, 19 mm×250 mm; mobile phase, Water (10 mmol/L $NH_4HCO_3$) and ACN (20.0% ACN up to 40.0% in 7 min); Detector, UV 254/220 nm.

This afforded the title compounds as follows: 9.8 mg (19%) of methyl (S)-3-((1R,3R)-3-(1H-tetrazol-5-yl)cyclohexyl)-2-benzyl-7-methyl-3,7,8,9-tetrahydro-6H-imidazo[4,5-f]quinoline-6-carboxylate (assumed stereochemistry, first eluting isomer) as a white solid, 2.1 mg (4%) of methyl (S)-3-((1S,3S)-3-(1H-tetrazol-5-yl)cyclohexyl)-2-benzyl-7-methyl-3,7,8,9-tetrahydro-6H-imidazo[4,5-f]quinoline-6-carboxylate (assumed stereochemistry, second eluting isomer) as a white solid.

First eluting isomer: $^1$H-NMR ($CD_3OD$, 300 MHz) δ (ppm): 7.57-7.44 (m, 1H), 7.42-7.31 (m, 1H), 7.19-7.04 (m, 3H), 7.01-7.6.82 (m, 2H), 4.81-4.72 (m, 1H), 4.62-4.43 (m, 1H), 4.41-4.19 (m, 2H), 3.77 (s, 3H), 3.59-2.46 (m, 1H), 3.27-3.13 (m, 1H), 3.04-2.88 (m, 1H), 2.71-2.42 (m, 2H), 2.42-2.03 (m, 3H), 1.97-1.63 (m, 2H), 1.62-1.44 (m, 1H), 1.32-1.22 (m, 1H), 1.15 (d, J=6.9 Hz, 3H), 1.04-0.91 (m, 1H). MS: (ES, m/z): 486 $[M+H]^+$.

Second eluting isomer: $^1$H-NMR ($CD_3OD$, 300 MHz) δ (ppm): 7.53-7.41 (m, 1H), 7.41-7.29 (m, 1H), 7.18-7.03 (m, 3H), 6.99-6.82 (m, 2H), 4.82-4.67 (m, 1H), 4.62-4.41 (m, 1H), 4.41-4.18 (m, 2H), 3.77 (s, 3H), 3.58-2.47 (m, 1H), 3.25-3.13 (m, 1H), 3.01-2.87 (m, 1H), 2.76-2.42 (m, 2H), 2.42-2.94 (m, 3H), 1.87-1.68 (m, 2H), 1.57-1.41 (m, 1H), 1.37-1.22 (m, 1H), 1.16 (d, J=6.9 Hz, 3H), 1.03-0.89 (m, 1H). MS: (ES, m/z): 486 $[M+H]^+$.

The following examples in TABLE 14 were prepared using standard chemical manipulations and procedures similar to those used for the preparation of Examples 281 and 282.

TABLE 14

| Example Number | Structure and Compound Name | LRMS m/z $[M + H]^+$ | $^1$HNMR |
|---|---|---|---|
| 283 | 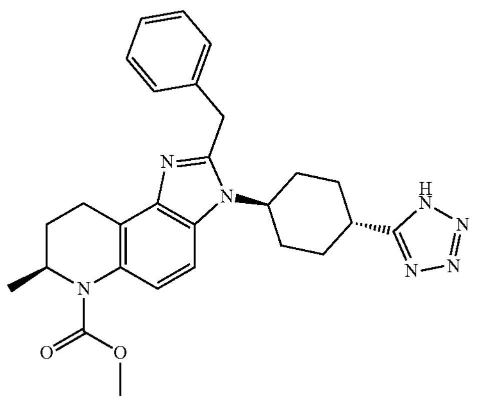 [SMILES: COC(=O)N1c2ccc3c(nc(Cc4ccccc4)n3[C@H]3CC[C@H](c4nnn[nH]4)CC3)c2CC[C@@H]1C] methyl (S)-3-((trans)-4-(1H-tetrazol-5-yl)cyclohexyl)-2-benzyl-7-methyl-3,7,8,9-tetrahydro-6H-imidazo[4,5-f]quinoline-6-carboxylate | 486 | $^1$H-NMR ($CDCl_3$, 300 MHz) δ (ppm): 7.60-7.56 (d, J = 9 Hz, 1H), 7.32-7.22 (m, 6H), 4.86-4.80 (m, 1H), 4.47-4.31 (m, 2H), 4.04-4.10 (m, 1H), 3.88 (s, 3H), 3.32-3.22 (m, 1H), 3.10-2.95 (m, 2H), 2.28-2.07 (m, 6H), 1.78-1.69 (m, 4H), 1.22-1.19 (d, J = 6.6 Hz, 3H) |

TABLE 14-continued

| Example Number | Structure and Compound Name | LRMS m/z $[M + H]^+$ | $^1$HNMR |
|---|---|---|---|
| 284 | 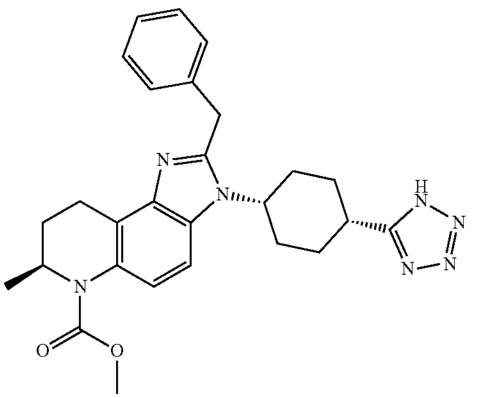 [SMILES: COC(=O)N1c2ccc3c(nc(Cc4ccccc4)n3[C@H]3CC[C@@H](c4nnn[nH]4)CC3)c2CC[C@@H]1C] methyl (S)-3-((cis)-4-(1H-tetrazol-5-yl)cyclohexyl)-2-benzyl-7-methyl-3,7,8,9-tetrahydro-6H-imidazo[4,5-f]quinoline-6-carboxylate | 486 | $^1$H-NMR ($CD_3OD$, 400 MHz) δ (ppm): 7.35-7.23 (m, 6H), 7.19-7.17 (d, J = 9.2 Hz, 1H), 4.77-4.72 (m, 1H), 4.41-4.38 (m, 3H), 3.75 (s, 3H), 3.31-3.30 (m, 1H), 3.21-3.15 (m, 1H), 2.97-2.91 (m, 1H), 2.45-2.41 (m, 2H), 2.26-2.21 (m, 3H), 1.88-1.71 (m, 3H), 1.40-1.28 (m, 2H), 1.13-1.12 (d, J = 9.2 Hz, 3H) |

Example 285: (S)-2-(2-benzyl-6-(methoxycarbonyl)-7-methyl-6,7,8,9-tetrahydro-3H-imidazo[4,5-f]quinolin-3-yl)acetic acid

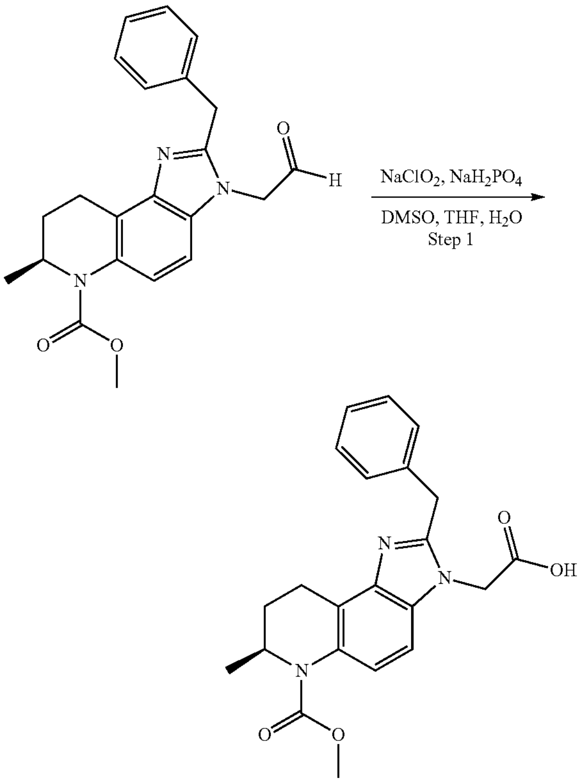

Into a 50-mL round-bottom flask, methyl (7S)-2-benzyl-7-methyl-3-(2-oxoethyl)-3H,6H,7H,8H,9H-imidazo[4,5-f]quinoline-6-carboxylate (60 mg, 0.16 mmol) was dissolved in tetrahydrofuran (2 mL). Then sodium dihydrogen orthophosphate (191 mg, 1.59 mmol), dimethyl sulfoxide (3 mL) and water (2 mL) were added, followed by a solution of sodium chlorite (143 mg, 1.26 mmol, 80%) in water (1 mL) dropwise. The resulting solution was stirred for 12 h at room temperature. The resulting solution was diluted with 20 mL of water and extracted with 2×30 mL of ethyl acetate. The organic layers were combined, dried over sodium sulfate, filtered and concentrated under vacuum. The crude product was purified with the following conditions: Column, XBridge Prep C18 OBD Column, 100 Å, 5 μm, 19 mm×250 mm; Mobile Phase, A: water (containing 0.1% FA) and B: ACN (20% to 37% ACN over 8 min); UV Detector: 254 nm. This afforded the title compound (5.7 mg, 9%) as a white solid. $^1$H-NMR (DMSO-d6, 400 MHz) δ(ppm): 13.14 (s, 1H), 7.33-7.24 (m, 5H), 7.24-7.16 (m, 2H), 4.98 (d, J=2.4 Hz, 2H), 4.66-4.62 (m, J=6.0 Hz, 1H), 4.24 (s, 2H), 3.66 (s, 3H), 3.11-3.01 (m, 1H), 2.84-2.77 (m, 1H), 2.20-2.09 (m, 1H), 1.66-1.56 (m, 1H), 1.06 (d, J=7.2 Hz, 3H). MS: (ES, m/z): 394 $[M+H]^+$.

Example 286: methyl (S)-3-(2-amino-2-oxoethyl)-2-benzyl-7-methyl-3,7,8,9-tetrahydro-6H-imidazo[4,5-f]quinoline-6-carboxylate

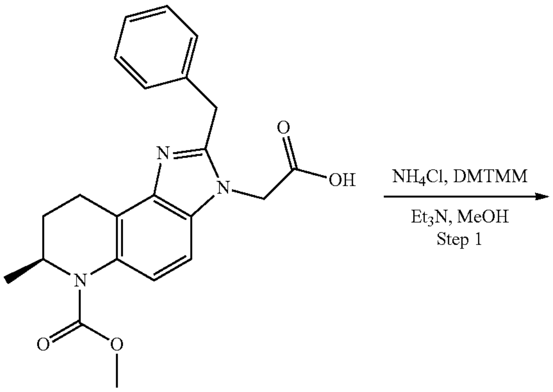

-continued

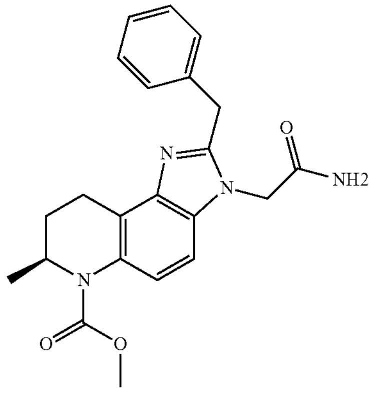

Into a 100-mL round-bottom flask, ammonium chloride (90 mg, 1.68 mmol) was dissolved in methanol (20 mL). Then triethylamine (72 mg, 0.71 mmol), 4-(4,6-Dimethoxy-1,3,5-triazin-2-yl)-4-methyl morpholinium chloride (351 mg, 1.27 mmol) and 2-[(7S)-2-benzyl-6-(methoxycarbonyl)-7-methyl-3H, 6H, 7H, 8H, 9H-imidazo[4, 5-f]quinolin-3-yl]acetic acid (130 mg, 0.33 mmol) were added. The resulting solution was stirred for 16 h at room temperature. The resulting solution was diluted with 100 mL of water and extracted with 3×50 mL of dichloromethane. The organic layers were combined, dried over anhydrous sodium sulfate, filtered and concentrated under vacuum. The crude product was purified by Prep-HPLC with the following conditions: Column, XBridge C18 OBD Prep Column, 100 Å, 5 μm, 19 mm×250 mm; mobile phase, A: water (10 mmol/L $NH_4HCO_3$) and B: ACN (30.0% to 60.0% ACN over 8 min); UV Detector: 254 nm. This afforded the title compound (8.6 mg, 7%) as a white solid. $^1H$ NMR (300 MHz, DMSO-$d_6$) δ 7.68 (s, 1H), 7.36-7.17 (m, 7H), 7.13 (d, J=9.0 Hz, 1H), 4.73 (s, 2H), 4.69-4.56 (m, 1H), 4.19 (s, 2H), 3.64 (s, 3H), 3.11-2.96 (m, 1H), 2.84-2.67 (m, 1H), 2.21-2.04 (m, 1H), 1.65-1.52 (m, 1H), 1.04 (d, J=6.6 Hz, 3H). MS: (ES, m/z): 393 $[M+H]^+$.

Example 287: methyl (S)-2-benzyl-3-(2-hydroxyethyl)-7-methyl-3,7,8,9-tetrahydro-6H-imidazo[4,5-f]quinoline-6-carboxylate

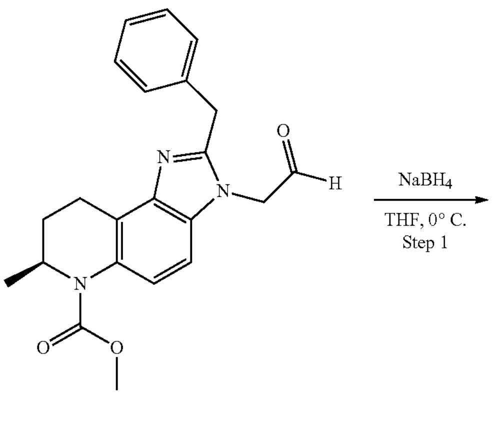

-continued

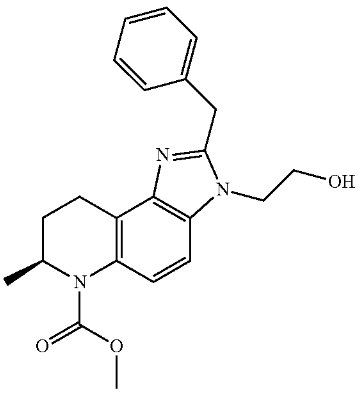

Into a 25-mL round-bottom flask purged and maintained with an inert atmosphere of nitrogen, methyl (7S)-2-benzyl-7-methyl-3-(2-oxoethyl)-3H,6H,7H,8H,9H-imidazo[4,5-f]quinoline-6-carboxylate (100 mg, 0.26 mmol) was dissolved in tetrahydrofuran (5 mL). Then sodium borohydride (11 mg, 0.30 mmol) was added. The resulting solution was stirred for 2 h at 0° C. in a water/ice bath. The resulting solution was diluted with 50 mL of water and extracted with 3×50 mL of ethyl acetate. The organic layers were combined, dried over anhydrous sodium sulfate, filtered and concentrated under vacuum. The crude product was purified by Prep-HPLC with the following conditions: Column, XBridge Prep C18 OBD Column, 19×150 mm 5 μm; mobile phase, A: Water (containing 10 mmol/L $NH_4HCO_3$) and B: ACN (5.0% to 55.0% ACN over 7 min); UV Detector: 254 nm. This afforded the title compound (3.1 mg, 3%) as a white solid. $^1H$ NMR (300 MHz, $CDCl_3$) δ(ppm): 7.45-7.42 (m, 1H), 7.34-7.22 (m, 3H), 7.22-7.15 (m, 2H), 7.13-7.11 (m, 1H), 4.82-4.76 (m, 1H), 4.42-4.31 (m, 2H), 4.12-4.08 (m, 2H), 3.78-3.72 (m, 5H), 3.29-3.18 (m, 1H), 3.03-2.93 (m, 1H), 2.39-2.32 (s, 1H), 2.30-2.20 (m, 1H), 1.77-1.75 (m, 1H), 1.15 (d, J=6.6 Hz, 3H). MS: (ES, m/z): 380 $[M+H]^+$.

Example 288: (S)-3-(2-benzyl-6-(methoxycarbonyl)-7-methyl-6,7,8,9-tetrahydro-3H-imidazo[4,5-f]quinolin-3-yl)propanoic acid

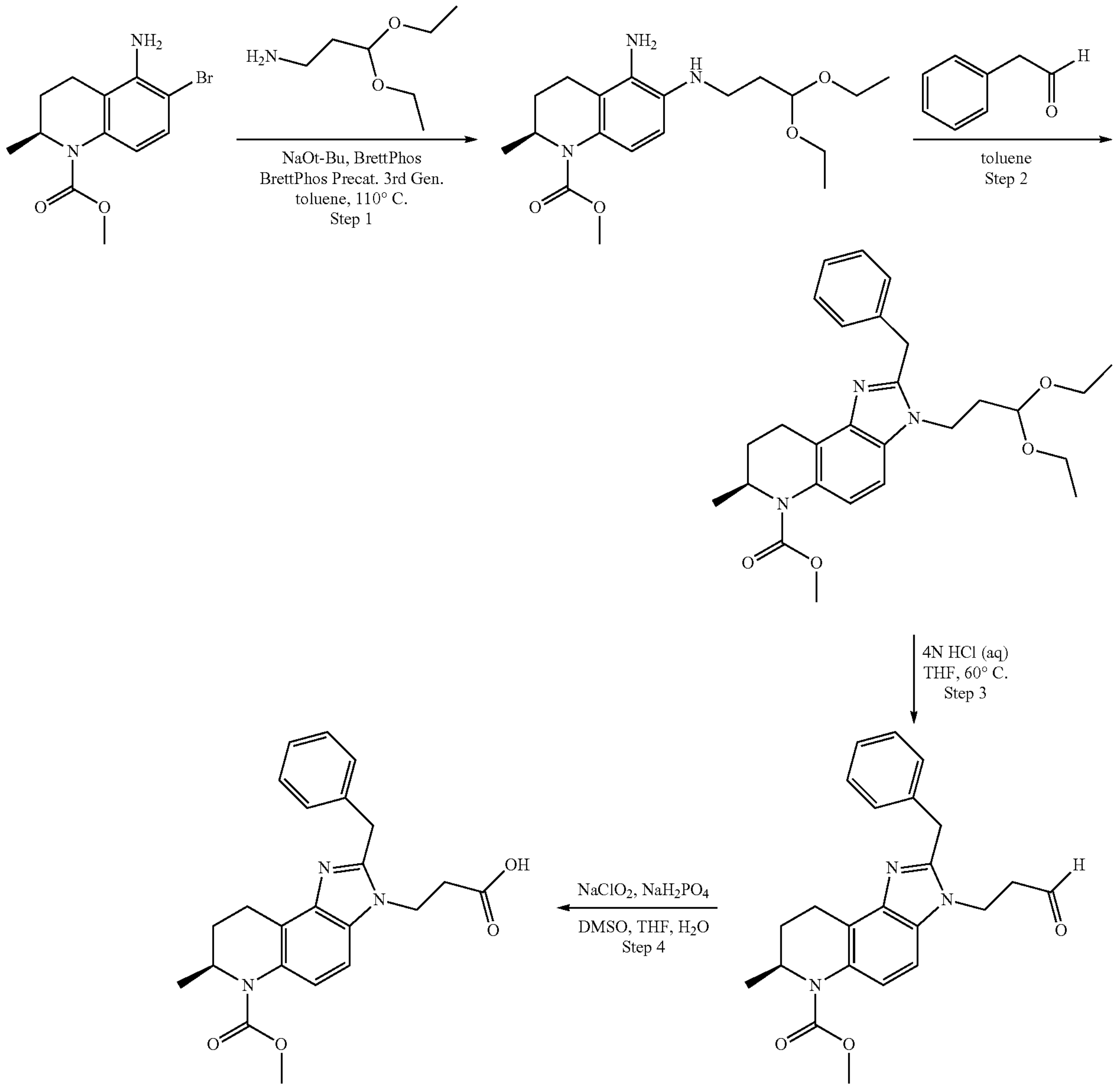

Step 1. Synthesis of methyl (2S)-5-amino-6-[(3,3-diethoxypropyl)amino]-2-methyl-1,2,3,4-tetrahydroquinoline-1-carboxylate Into a 25-mL round-bottom flask purged and maintained with an inert atmosphere of nitrogen, methyl (2S)-5-amino-6-bromo-2-methyl-1,2,3,4-tetrahydroquinoline-1-carboxylate (300 mg, 1.00 mmol, Intermediate 1) was dissolved in toluene (5 mL). Then 3,3-diethoxypropan-1-amine (885 mg, 6.01 mmol), 3rd Generation BrettPhos precatalyst (91 mg, 0.10 mmol), BrettPhos (108 mg, 0.20 mmol) and sodium tert-butoxide (289 mg, 3.01 mmol) were added successively. The resulting solution was stirred for 2 h at 110° C. under nitrogen atmosphere. The reaction mixture was cooled and the resulting solids were filtered out. The filtrate was concentrated under vacuum. The residue was subjected to purification by FCC eluting with ethyl acetate/petroleum ether (2:1). This afforded the title compound (240 mg, 62%) as a yellow oil. MS: (ES, m/z): 366 $[M+H]^+$.

Step 2. Synthesis of methyl (7S)-2-benzyl-3-(3,3-diethoxypropyl)-7-methyl-3H,6H,7H,8H,9H-imidazo[4,5-f]quinoline-6-carboxylate Into a 25-mL round-bottom flask, methyl (2S)-5-amino-6-[(3,3-diethoxypropyl)amino]-2-methyl-1,2,3,4-tetrahydroquinoline-1-carboxylate (240 mg, 0.66 mmol) was dissolved in toluene (3 mL). Then 2-phenylacetaldehyde (158 mg, 1.32 mmol) was added. The resulting solution was stirred for 14 h at room temperature. The resulting mixture was concentrated under vacuum. The residue was subjected to purification by FCC eluting with ethyl acetate/petroleum ether (1:1). This afforded the title compound (220 mg, 72%) as a yellow oil. MS: (ES, m/z): 466 $[M+H]^+$.

Step 3. Synthesis of methyl (7S)-2-benzyl-7-methyl-3-(3-oxopropyl)-3H,6H,7H,8H,9H-imidazo[4,5-f]quinoline-6-carboxylate Into a 25-mL round-bottom flask, methyl (7S)-2-benzyl-3-(3,3-diethoxypropyl)-7-methyl-3H,6H,7H,8H,9H-imidazo[4,5-f]quinoline-6-carboxylate (220 mg, 0.47 mmol) was dissolved in tetrahydrofuran (3 mL). Then hydrochloric acid (aq, 4 M, 6 mL) was added. The resulting solution was stirred for 3 h at 60° C. After cooled to room temperature, water was added. The resulting solution was extracted with 3×20 mL of ethyl acetate. The organic layers were combined, dried over anhydrous sodium sulfate, filtered and concentrated under vacuum. This afforded the title compound (140 mg, crude) as a yellow oil. MS: (ES, m/z): 392 $[M+H]^+$.

Step 4. Synthesis of (S)-3-(2-benzyl-6-(methoxycarbonyl)-7-methyl-6,7,8,9-tetrahydro-3H-imidazo[4,5-f]quinolin-3-yl)propanoic acid Into a 10-mL round-bottom flask, methyl (7S)-2-benzyl-7-methyl-3-(3-oxopropyl)-3H,6H,7H,8H,9H-imidazo[4,5-f]quinoline-6-carboxylate (50 mg, 0.13 mmol) was dissolved in tetrahydrofuran (1 mL). Then sodium chlorite (57.5 mg, 0.64 mmol), sodium dihydrogen orthophosphate (76 mg, 0.63 mmol), dimethyl sulfoxide (1 mL) and water (1 mL) were added successively. The resulting solution was stirred for 2 h at room temperature. The resulting solution was added 20 ml of water and extracted with 3×20 mL of ethyl acetate. The organic layers were combined, dried over anhydrous sodium sulfate, filtered and concentrated under vacuum. The crude product was purified by Prep-HPLC with the following conditions: Column, XBridge C18 OBD Prep Column, 100 Å, 5 μm, 19 mm×250 mm; mobile phase, A: Water (containing 10 mmol/L $NH_4HCO_3$) and B: ACN (20.0% to 40.0% ACN over 8 min); UV Detector: 254 nm. This afforded the title compound (5.4 mg, 10%) as a white solid. $^1$H-NMR ($CDCl_3$, 300 MHz) δ (ppm): 7.51 (d, J=8.1 Hz, 1H), 7.19-7.11 (m, 6H), 4.82-4.76 (m, 1H), 4.53-4.48 (m, 2H), 4.35-4.17 (s, 2H), 3.77 (s, 3H), 3.22-3.14 (m, 1H), 3.02-2.96 (m, 1H), 2.63-2.59 (m, 2H), 2.21-2.19 (m, 1H), 1.76-1.70 (m, 1H), 1.13 (d, J=6.3 Hz, 3H). MS: (ES, m/z): 408 $[M+H]^+$.

Example 289: methyl (7S)-2-benzyl-3-(2-carbamoylethyl)-7-methyl-3H,6H,7H,8H,9H-imidazo[4,5-f]quinoline-6-carboxylate -continued

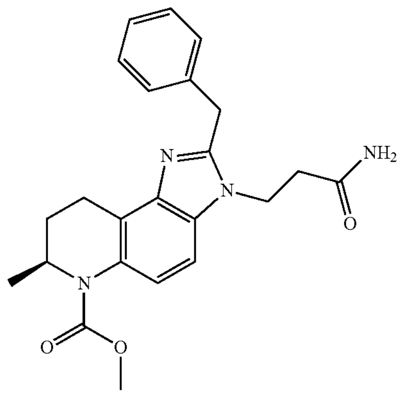

Into a 10-mL round-bottom flask, 3-[(7S)-2-benzyl-6-(methoxycarbonyl)-7-methyl-3H,6H,7H,8H,9H-imidazo[4,5-f]quinolin-3-yl]propanoic acid (50 mg, 0.12 mmol) was dissolved in methanol (2 mL). Then ammonium chloride (53.5 mg, 1.00 mmol), triethylamine (10 mg, 0.10 mmol) and 4-(4,6-dimethoxy-1,3,5-triazine-2-yl)-4-methyl morpholinium chloride (43.6 mg, 0.16 mmol) were added successively. The resulting solution was stirred for 12 h at room temperature. The solids were filtered out and the filtrate was concentrated under vacuum. The crude product was purified by Prep-HPLC with the following conditions (2 #-Analyse HPLC-SHIMADZU): Column, XBridge C18 OBD Prep Column, 100 Å, 5 um, 19 mm×250 mm; mobile phase, A: Water (containing 10 mmol/L $NH_4HCO_3$) and B: ACN (30.0% to 45.0% ACN over 8 min); UV Detector: 254 nm. This afforded the title compound (2.4 mg, 5%) as a white solid. $^1$H-NMR ($CDCl_3$, 300 MHz) δ (ppm): 7.46 (d, J=9.0 Hz, 1H), 7.33-7.29 (m, 4H), 7.24-7.22 (m, 1H), 7.12 (d, J=8.7 Hz, 1H), 5.19-5.12 (m, 2H), 4.82-4.77 (m, 1H), 4.50-4.29 (m, 4H), 3.78 (s, 3H), 3.31-3.22 (m, 1H), 3.09-2.99 (m, 1H), 2.32-2.17 (m, 3H), 1.79-1.71 (m, 1H), 1.16 (d, J=6.6 Hz, 3H). MS: (ES, m/z): 407 $[M+H]^+$.

Example 290: methyl (S)-2-(2-(1H-pyrazol-1-yl)ethyl)-7-methyl-3-(2-(((1-methyl-11H-pyrazol-3-yl)methyl)amino)ethyl)-3,7,8,9-tetrahydro-6H-imidazo[4,5-f]quinoline-6-carboxylate

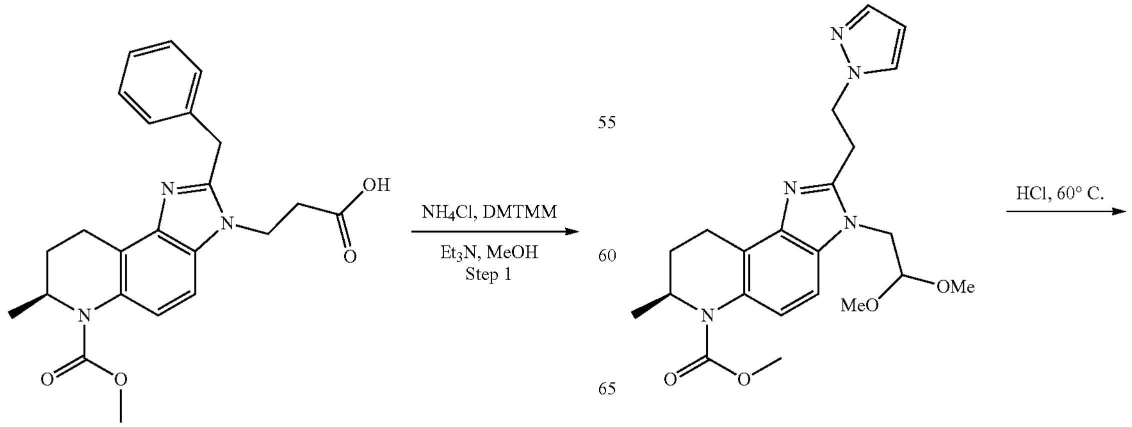

-continued

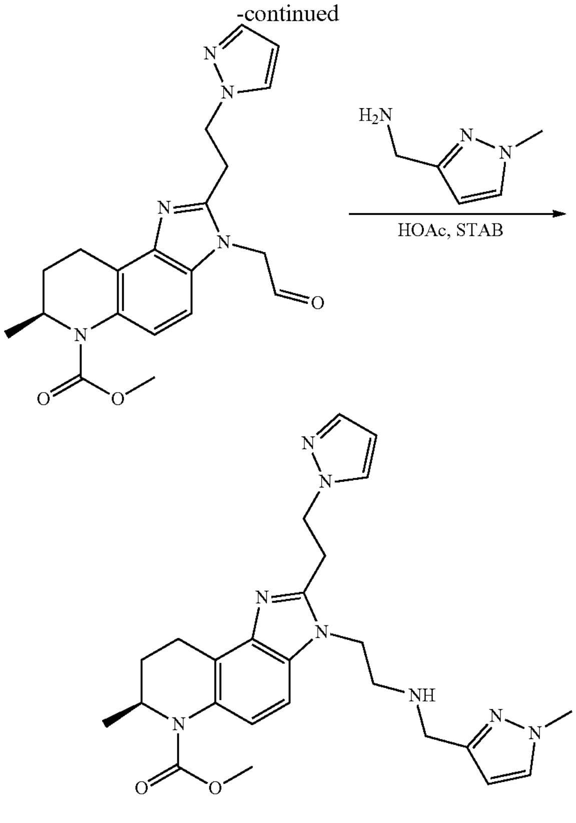

Step 1. Synthesis of methyl (S)-2-(2-(1H-pyrazol-1-yl)ethyl)-7-methyl-3-(2-oxoethyl)-3,7,8,9-tetrahydro-6H-imidazo[4,5-f]quinoline-6-carboxylate To a solution of methyl (S)-2-(2-(1H-pyrazol-1-yl)ethyl)-3-(2,2-dimethoxyethyl)-7-methyl-3,7,8,9-tetrahydro-6H-imidazo[4,5-f]quinoline-6-carboxylate (726 mg, 1.698 mmol) in THE (4.2 mL), was added HCl aqueous solution (4 M, 4.2 mL, 16.98 mmol). The mixture was heated at 60° C. for 4 h. After being cooled to rt, The mixture was basified with saturated sodium bicarbonate, and extracted with ethyl acetate. The combined organic layers were dried over sodium sulfate, filtered and concentrated. 680.2 mg of methyl (S)-2-(2-(1H-pyrazol-1-yl)ethyl)-7-methyl-3-(2-oxoethyl)-3,7,8,9-tetrahydro-6H-imidazo[4,5-f]quinoline-6-carboxylate was obtained (1.78 mmol, 105% yield). MS (ES, m/z): 400 ($M+H_2O+1$) and 414 (M+MeOH+1). The crude product was used for next step without further purification.

Step 2. Synthesis of methyl (S)-2-(2-(1H-pyrazol-1-yl)ethyl)-7-methyl-3-(2-(((1-methyl-11H-pyrazol-3-yl)methyl)amino)ethyl)-3,7,8,9-tetrahydro-6H-imidazo[4,5-f]quinoline-6-carboxylate To a solution of methyl (S)-2-(2-(1H-pyrazol-1-yl)ethyl)-7-methyl-3-(2-oxoethyl)-3,7,8,9-tetrahydro-6H-imidazo[4,5-f]quinoline-6-carboxylate (0.2 M in 1,4-dioxane with 10% HOAc, 100 μL, 0.02 mmol), was added (1-methyl-1H-pyrazol-3-yl)methanamine (1 M 1,4-dioxane, 200 μL, 0.2 mmol). The resulting mixture was put on a shaker at rt for 30 min before a solution of sodium triacetoxyborohydride (0.2 M in 1,2-DCE, 200 μL, 0.04 mmol) was added. The mixture was then put on a shaker at rt for 20 h. The mixture was diluted with ethyl acetate (0.8 mL) and 1N NaOH in brine (0.45 mL). the organic layer was separated. The aqueous layer was extracted with ethyl acetate (0.8 mL) one more time. The combined organic layers were dried down and the residue was purified by HPLC: Water Autopurification MS-directed HPLC prep fraction collection with the following conditions Column, Waters XBridge OBD C18, 5 um, 19x50 mm; flow rate 20 ml/min; mobile phase, water with 0.1% ammonium hydroxide (A) and methanol with 0.1% ammonium hydroxide (B) running the following gradient 0 to 2 mins (15% B), 2 to 6 mins (15-100% B); Detector ZQ Mass Detector in electrospray ionization mode. This provided 6.1 mg of methyl (S)-2-(2-(1H-pyrazol-1-yl)ethyl)-7-methyl-3-(2-(((1-methyl-1H-pyrazol-3-yl)methyl)amino)ethyl)-3,7,8,9-tetrahydro-6H-imidazo[4,5-f]quinoline-6-carboxylate (12.8 μmol, 64% yield) was obtained. MS (ESI, pos. ion) m/z: 477 (M+1).

The following examples in TABLE 15 were prepared using standard chemical manipulations and procedures similar to those used for the preparation of Example 290.

TABLE 15

| Example Number | Structure and Compound Name | LRMS m/z $[M + H]^+$ |
| --- | --- | --- |
| 291 | 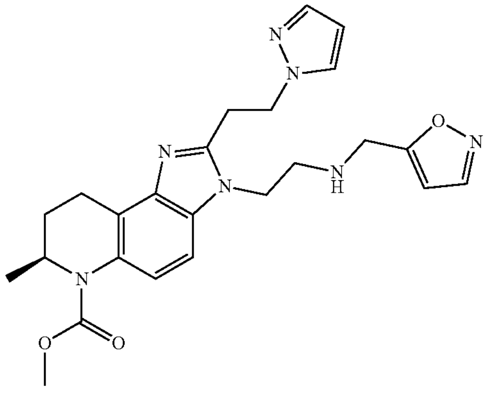 [SMILES: COC(=O)N1c2ccc3c(nc(CCn4cccn4)n3CCNCc3ccno3)c2CC[C@@H]1C] methyl (S)-2-(2-(1H-pyrazol-1-yl)ethyl)-3-(2-((isoxazol-5-ylmethyl)amino)ethyl)-7-methyl-3,7,8,9-tetrahydro-6H-imidazo[4,5-f]quinoline-6-carboxylate | 464 |

TABLE 15-continued

| Example Number | Structure and Compound Name | LRMS m/z [M + H]+ |
|---|---|---|
| 292 | 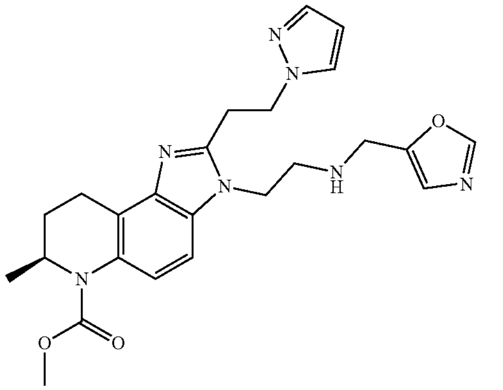 [SMILES: COC(=O)N1c2ccc3c(nc(CCn4cccn4)n3CCNCc3cnco3)c2CC[C@@H]1C] methyl (S)-2-(2-(1H-pyrazol-1-yl)ethyl)-7-methyl-3-(2-((oxazol-5-ylmethyl)amino)ethyl)-3,7,8,9-tetrahydro-6H-imidazo[4,5-f]quinoline-6-carboxylate | 464 |
| 293 | 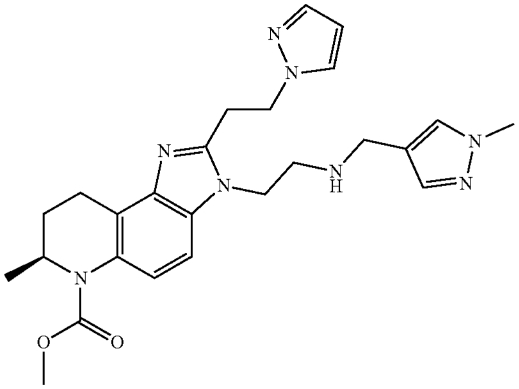 methyl (S)-2-(2-(1H-pyrazol-1-yl)ethyl)-7-methyl-3-(2-(((1-methyl-1H-pyrazol-4-yl)methyl)amino)ethyl)-3,7,8,9-tetrahydro-6H-imidazo[4,5-f]quinoline-6-carboxylate | 477 |
| 294 | 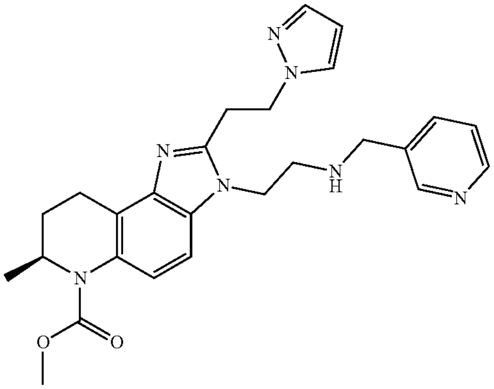 [SMILES: COC(=O)N1c2ccc3c(nc(CCn4cccn4)n3CCNCc3cccnc3)c2CC[C@@H]1C] methyl (S)-2-(2-(1H-pyrazol-1-yl)ethyl)-7-methyl-3-(2-((pyridin-3-ylmethyl)amino)ethyl)-3,7,8,9-tetrahydro-6H-imidazo[4,5-f]quinoline-6-carboxylate | 474 |

TABLE 15-continued

| Example Number | Structure and Compound Name | LRMS m/z [M + H]+ |
| --- | --- | --- |
| 295 | 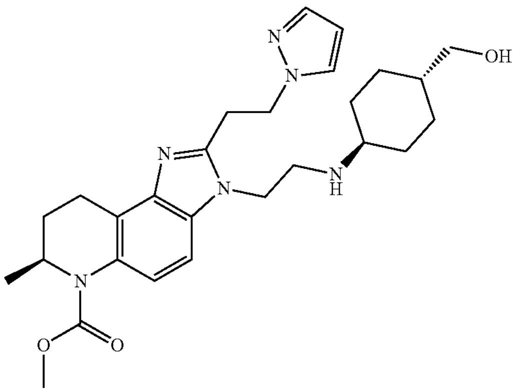 [SMILES: COC(=O)N1c2ccc3c(nc(CCn4cccn4)n3CCN[C@H]3CC[C@H](CO)CC3)c2CC[C@@H]1C] methyl (S)-2-(2-(1H-pyrazol-1-yl)ethyl)-3-(2-(((trans)-4-(hydroxymethyl)cyclohexyl)amino)ethyl)-7-methyl-3,7,8,9-tetrahydro-6H-imidazo[4,5-f]quinoline-6-carboxylate | 495 |
| 296 | 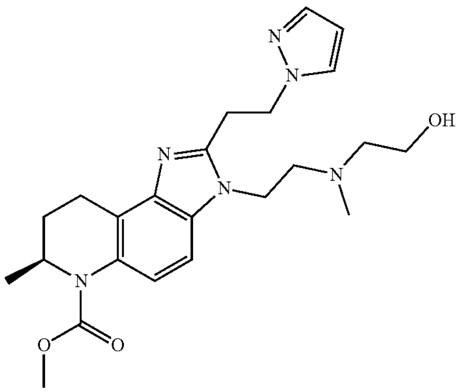 [SMILES: COC(=O)N1c2ccc3c(nc(CCn4cccn4)n3CCN(C)CCO)c2CC[C@@H]1C] methyl (S)-2-(2-(1H-pyrazol-1-yl)ethyl)-3-(2-((2-hydroxyethyl)(methyl)amino)ethyl)-7-methyl-3,7,8,9-tetrahydro-6H-imidazo[4,5-f]quinoline-6-carboxylate | 441 |
| 297 | 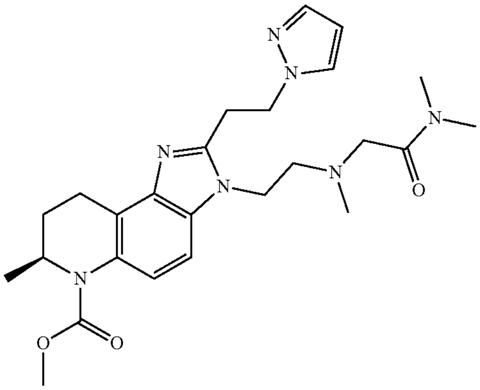 methyl (S)-2-(2-(1H-pyrazol-1-yl)ethyl)-3-(2-((2-(dimethylamino)-2-oxoethyl)(methyl)amino)ethyl)-7-methyl-3,7,8,9-tetrahydro-6H-imidazo[4,5-f]quinoline-6-carboxylate | 482 |

TABLE 15-continued

| Example Number | Structure and Compound Name | LRMS m/z [M + H]+ |
|---|---|---|
| 298 | 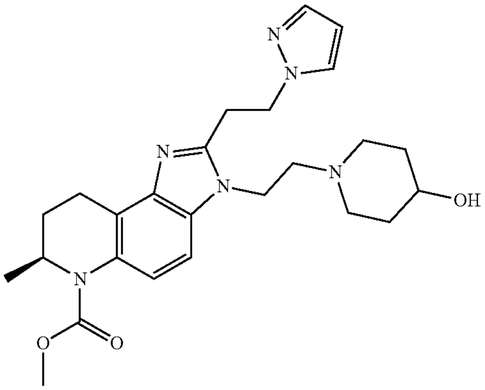 [SMILES: COC(=O)N1c2ccc3c(nc(CCn4cccn4)n3CCN3CCC(O)CC3)c2CC[C@@H]1C] methyl (S)-2-(2-(1H-pyrazol-1-yl)ethyl)-3-(2-(4-hydroxypiperidin-1-yl)ethyl)-7-methyl-3,7,8,9-tetrahydro-6H-imidazo[4,5-f]quinoline-6-carboxylate | 467 |
| 299 | 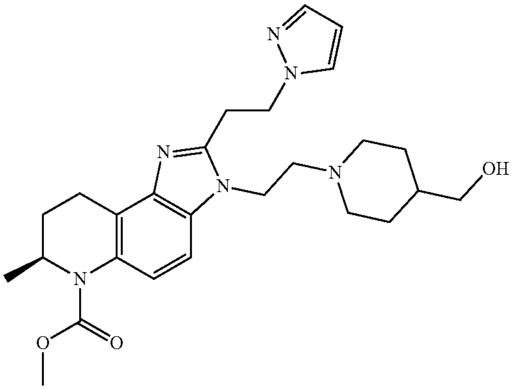 [SMILES: COC(=O)N1c2ccc3c(nc(CCn4cccn4)n3CCN3CCC(CO)CC3)c2CC[C@@H]1C] methyl (S)-2-(2-(1H-pyrazol-1-yl)ethyl)-3-(2-(4-(hydroxymethyl)piperidin-1-yl)ethyl)-7-methyl-3,7,8,9-tetrahydro-6H-imidazo[4,5-f]quinoline-6-carboxylate | 481 |
| 300 | 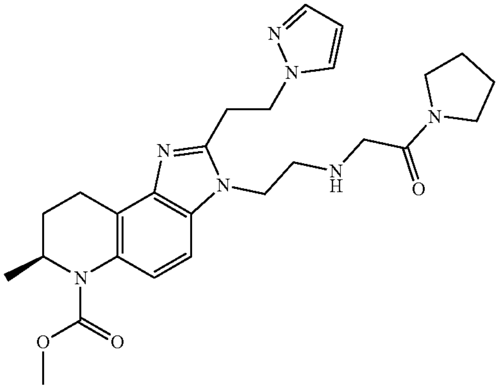 [SMILES: COC(=O)N1c2ccc3c(nc(CCn4cccn4)n3CCNCC(=O)N3CCCC3)c2CC[C@@H]1C] methyl (S)-2-(2-(1H-pyrazol-1-yl)ethyl)-7-methyl-3-(2-((2-oxo-2-(pyrrolidin-1-yl)ethyl)amino)ethyl)-3,7,8,9-tetrahydro-6H-imidazo[4,5-f]quinoline-6-carboxylate | 494 |

TABLE 15-continued

| Example Number | Structure and Compound Name | LRMS m/z [M + H]+ |
| --- | --- | --- |
| 301 | 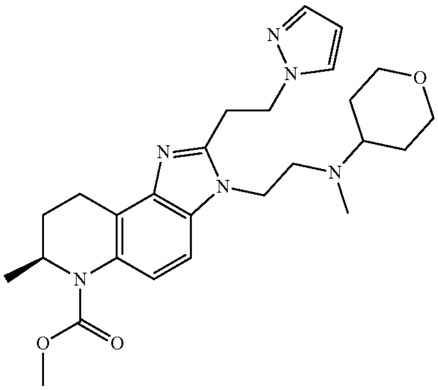 [SMILES: COC(=O)N1c2ccc3c(nc(CCn4cccn4)n3CCN(C)C3CCOCC3)c2CC[C@@H]1C] methyl (S)-2-(2-(1H-pyrazol-1-yl)ethyl)-7-methyl-3-(2-(methyl(tetrahydro-2H-pyran-4-yl)amino)ethyl)-3,7,8,9-tetrahydro-6H-imidazo[4,5-f]quinoline-6-carboxylate | 481 |
| 302 | 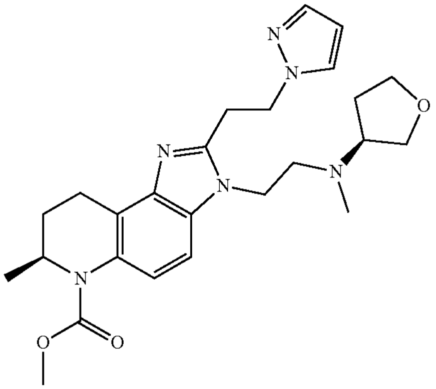 [SMILES: COC(=O)N1c2ccc3c(nc(CCn4cccn4)n3CCN(C)[C@H]3CCOC3)c2CC[C@@H]1C] methyl (S)-2-(2-(1H-pyrazol-1-yl)ethyl)-7-methyl-3-(2-(methyl((S)-tetrahydrofuran-3-yl)amino)ethyl)-3,7,8,9-tetrahydro-6H-imidazo[4,5-f]quinoline-6-carboxylate | 467 |
| 303 | 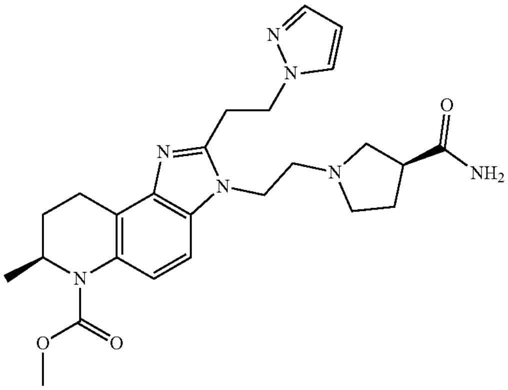 [SMILES: COC(=O)N1c2ccc3c(nc(CCn4cccn4)n3CCN3CC[C@H](C(N)=O)C3)c2CC[C@@H]1C] methyl (S)-2-(2-(1H-pyrazol-1-yl)ethyl)-3-(2-((S)-3-carbamoylprrolidin-1-yl)ethyl)-7-methyl-3,7,8,9-tetrahydro-6H-imidazo[4,5-f]quinoline-6-carboxylate | 480 |

TABLE 15-continued

| Example Number | Structure and Compound Name | LRMS m/z [M + H]+ |
| --- | --- | --- |
| 304 | 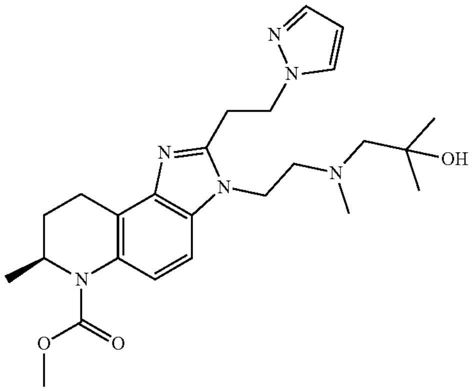 [SMILES: COC(=O)N1c2ccc3c(nc(CCn4cccn4)n3CCN(C)CC(C)(C)O)c2CC[C@@H]1C] methyl (S)-2-(2-(1H-pyrazol-1-yl)ethyl)-3-(2-((2-hydroxy-2-methylpropyl)(methyl)amino)ethyl)-7-methyl-3,7,8,9-tetrahydro-6H-imidazo[4,5-f]quinoline-6-carboxylate | 469 |
| 305 | 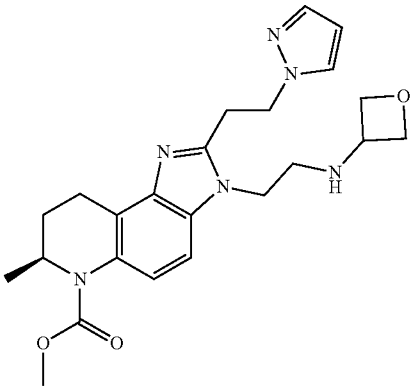 [SMILES: COC(=O)N1c2ccc3c(nc(CCn4cccn4)n3CCNC3COC3)c2CC[C@@H]1C] methyl (S)-2-(2-(1H-pyrazol-1-yl)ethyl)-7-methyl-3-(2-(oxetan-3-ylamino)ethyl)-3,7,8,9-tetrahydro-6H-imidazo[4,5-f]quinoline-6-carboxylate | 439 |
| 306 | 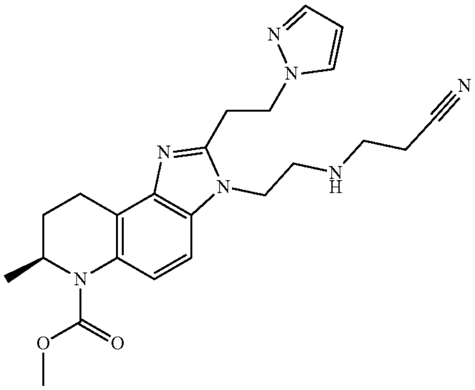 [SMILES: COC(=O)N1c2ccc3c(nc(CCn4cccn4)n3CCNCCC#N)c2CC[C@@H]1C] methyl (S)-2-(2-(1H-pyrazol-1-yl)ethyl)-3-(2-((2-cyanoethyl)amino)ethyl)-7-methyl-3,7,8,9-tetrahydro-6H-imidazo[4,5-f]quinoline-6-carboxylate | 436 |

TABLE 15-continued

| Example Number | Structure and Compound Name | LRMS m/z [M + H]+ |
|---|---|---|
| 307 | 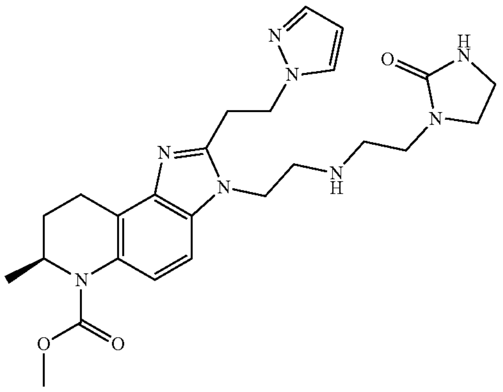 [SMILES: COC(=O)N1c2ccc3c(nc(CCn4cccn4)n3CCNCCN3CCNC3=O)c2CC[C@@H]1C]<br>methyl (S)-2-(2-(1H-pyrazol-1-yl)ethyl)-7-methyl-3-(2-((2-(2-oxoimidazolidin-1-yl)ethyl)amino)ethyl)-3,7,8,9-tetrahydro-6H-imidazo[4,5-f]quinoline-6-carboxylate | 495 |
| 308 | 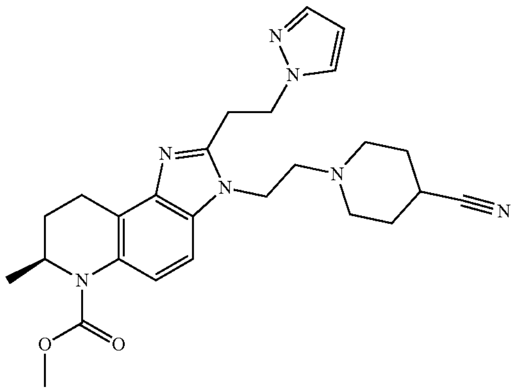 [SMILES: COC(=O)N1c2ccc3c(nc(CCn4cccn4)n3CCN3CCC(C#N)CC3)c2CC[C@@H]1C]<br>methyl (S)-2-(2-(1H-pyrazol-1-yl)ethyl)-3-(2-(4-cyanopiperidin-1-yl)ethyl)-7-methyl-3,7,8,9-tetrahydro-6H-imidazo[4,5-f]quinoline-6-carboxylate | 476 |
| 309 | 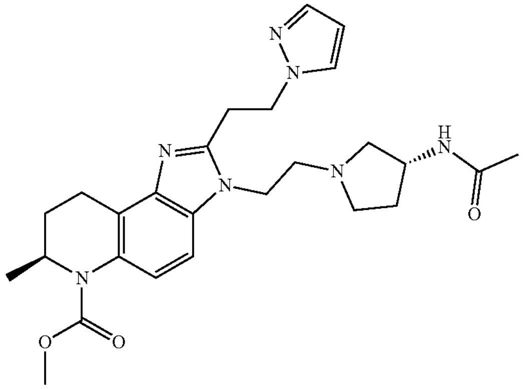 [SMILES: COC(=O)N1c2ccc3c(nc(CCn4cccn4)n3CCN3CC[C@@H](NC(C)=O)C3)c2CC[C@@H]1C]<br>methyl (S)-2-(2-(1H-pyrazol-1-yl)ethyl)-3-(2-((R)-3-acetamidopyrrolidin-1-yl)ethyl)-7-methyl-3,7,8,9-tetrahydro-6H-imidazo[4,5-f]quinoline-6-carboxylate | 494 |

TABLE 15-continued

| Example Number | Structure and Compound Name | LRMS m/z [M + H]+ |
|---|---|---|
| 310 | 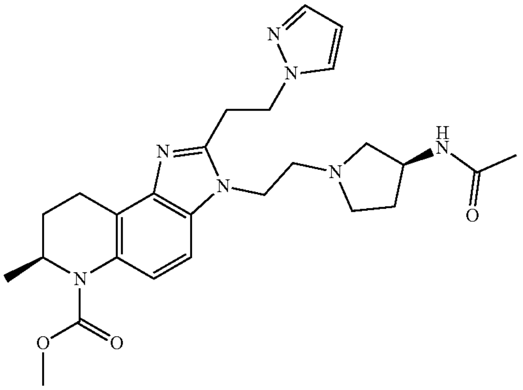 [SMILES: COC(=O)N1c2ccc3c(nc(CCn4cccn4)n3CCN3CC[C@H](NC(C)=O)C3)c2CC[C@@H]1C] methyl (S)-2-(2-(1H-pyrazol-1-yl)ethyl)-3-(2-((S)-3-acetamidopyrrolidin-1-yl)ethyl)-7-methyl-3,7,8,9-tetrahydro-6H-imidazo[4,5-f]quinoline-6-carboxylate | 494 |
| 311 | 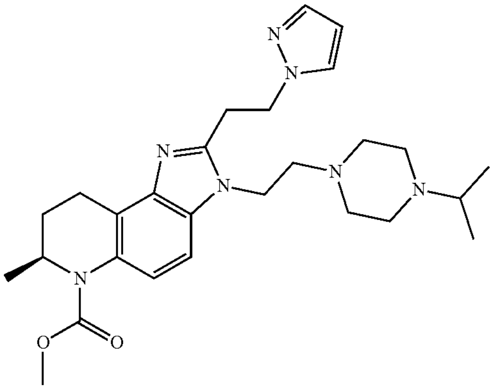 [SMILES: COC(=O)N1c2ccc3c(nc(CCn4cccn4)n3CCN3CCN(C(C)C)CC3)c2CC[C@@H]1C] methyl (S)-2-(2-(1H-pyrazol-1-yl)ethyl)-3-(2-(4-isopropylpiperazin-1-yl)ethyl)-7-methyl-3,7,8,9-tetrahydro-6H-imidazo[4,5-f]quinoline-6-carboxylate | 494 |
| 312 | 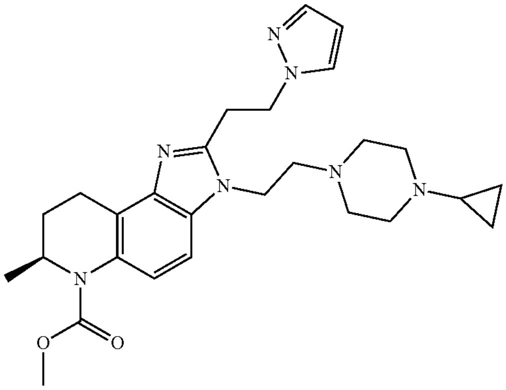 [SMILES: COC(=O)N1c2ccc3c(nc(CCn4cccn4)n3CCN3CCN(C4CC4)CC3)c2CC[C@@H]1C] methyl (S)-2-(2-(1H-pyrazol-1-yl)ethyl)-3-(2-(4-cyclopropylpiperazin-1-yl)ethyl)-7-methyl-3,7,8,9-tetrahydro-6H-imidazo[4,5-f]quinoline-6-carboxylate | 492 |

TABLE 15-continued

| Example Number | Structure and Compound Name | LRMS m/z [M + H]+ |
|---|---|---|
| 313 | 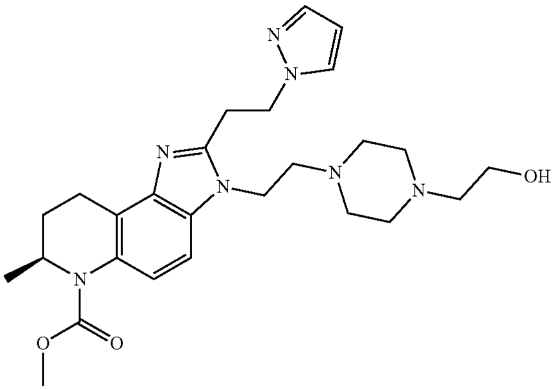 [SMILES: COC(=O)N1c2ccc3c(nc(CCn4cccn4)n3CCN3CCN(CCO)CC3)c2CC[C@@H]1C] methyl (S)-2-(2-(1H-pyrazol-1-yl)ethyl)-3-(2-(4-(2-hydroxyethyl)pipeiazin-1-yl)ethyl)-7-methyl-3,7,8,9-tetrahydro-6H-imidazo[4,5-f]quinoline-6-carboxylate | 496 |
| 314 | 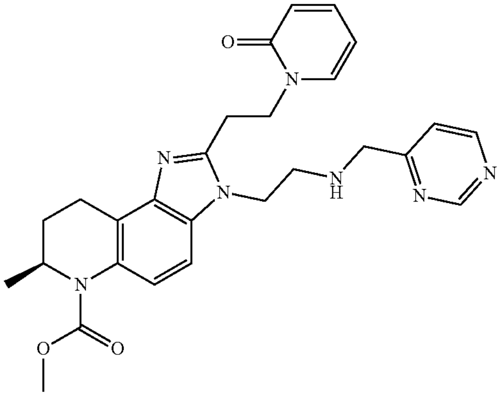 [SMILES: COC(=O)N1c2ccc3c(nc(CCn4ccccc4=O)n3CCNCc3ccncn3)c2CC[C@@H]1C] methyl (S)-7-methyl-2-(2-(2-oxopyridin-1(2H)-yl)ethyl)-3-(2-((pyrimidin-4-ylmethyl)amino)ethyl)-3,7,8,9-tetrahydro-6H-imidazo[4,5-f]quinoline-6-carboxylate | 502 |
| 315 | 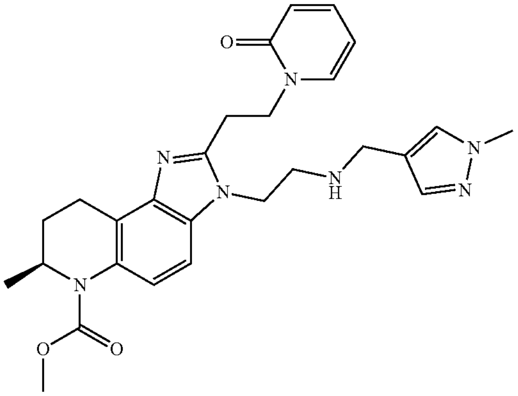 methyl (S)-7-methyl-3-(2-(((1-methyl-1H-pyrazol-4-yl)methyl)amino)ethyl)-2-(2-(2-oxopyridin-1(2H)-yl)ethyl)-3,7,8,9-tetrahydro-6H-imidazo[4,5-f]quinoline-6-carboxylate | 504 |

TABLE 15-continued

| Example Number | Structure and Compound Name | LRMS m/z [M + H]$^+$ |
|---|---|---|
| 316 | 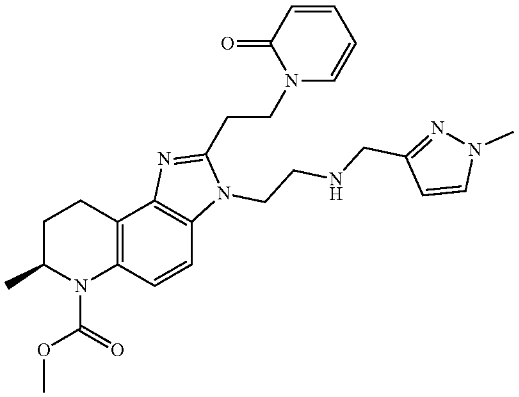 methyl (S)-7-methyl-3-(2-(((1-methyl-1H-pyrazol-3-yl)methyl)amino)ethyl)-2-(2-(2-oxopyridin-1(2H)-yl)ethyl)-3,7,8,9-tetrahydro-6H-imidazo[4,5-f]quinoline-6-carboxylate | 504 |
| 317 | 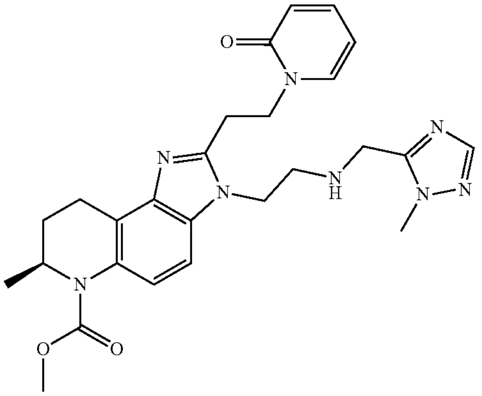 [SMILES: COC(=O)N1c2ccc3c(nc(CCn4ccccc4=O)n3CCNCc3ncnn3C)c2CC[C@@H]1C] methyl (S)-7-methyl-3-(2-(((1-methyl-1H-1,2,4-triazol-5-yl)methyl)amino)ethyl)-2-(2-(2-oxopyridin-1(2H)-yl)ethyl)-3,7,8,9-tetrahydro-6H-imidazo[4,5-f]quinoline-6-carboxylate | 505 |
| 318 | 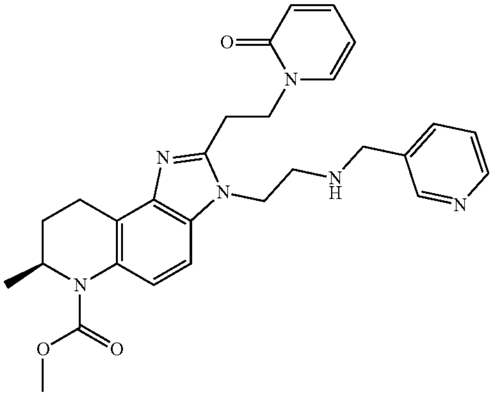 [SMILES: COC(=O)N1c2ccc3c(nc(CCn4ccccc4=O)n3CCNCc3cccnc3)c2CC[C@@H]1C] methyl (S)-7-methyl-2-(2-(2-oxopyridin-1(2H)-yl)ethyl)-3-(2-((pyridin-3-ylmethyl)amino)ethyl)-3,7,8,9-tetrahydro-6H-imidazo[4,5-f]quinoline-6-carboxylate | 501 |

TABLE 15-continued

| Example Number | Structure and Compound Name | LRMS m/z [M + H]+ |
|---|---|---|
| 319 | 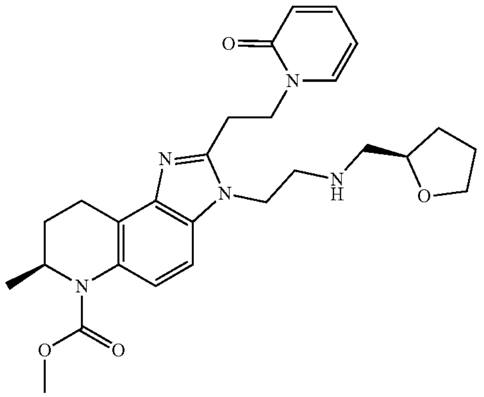 [SMILES: COC(=O)N1c2ccc3c(nc(CCn4ccccc4=O)n3CCNC[C@H]3CCCO3)c2CC[C@@H]1C] methyl (S)-7-methyl-2-(2-(2-oxopyridin-1(2H)-yl)ethyl)-3-(2-((((R)-tetrahydrofuran-2-yl)methyl)amino)ethyl)-3,7,8,9-tetrahydro-6H-imidazo[4,5-f]quinoline-6-carboxylate | 494 |
| 320 | 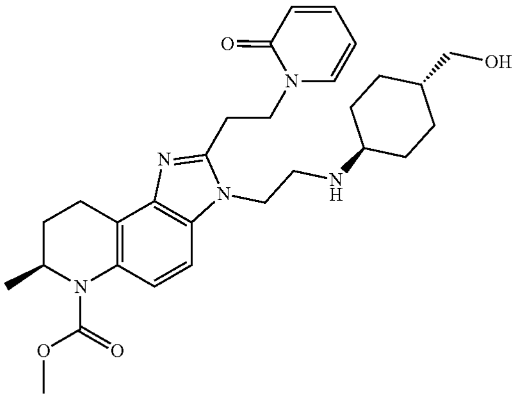 [SMILES: COC(=O)N1c2ccc3c(nc(CCn4ccccc4=O)n3CCN[C@H]3CC[C@H](CO)CC3)c2CC[C@@H]1C] methyl (S)-3-(2-(((trans)-4-(hydroxymethyl)cyclohexyl)amino)ethyl)-7-methyl-2-(2-(2-oxopyridin-1(2H)-yl)ethyl)-3,7,8,9-tetrahydro-6H-imidazo[4,5-f]quinoline-6-carboxylate | 436 |
| 321 | 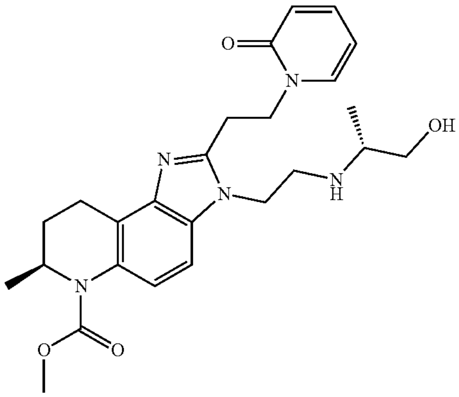 [SMILES: COC(=O)N1c2ccc3c(nc(CCn4ccccc4=O)n3CCN[C@H](C)CO)c2CC[C@@H]1C] methyl (S)-3-(2-(((R)-1-hydroxypropan-2-yl)amino)ethyl)-7-methyl-2-(2-(2-oxopyridin-1(2H)-yl)ethyl)-3,7,8,9-tetratydro-6H-imidazo[4,5-f]quinoline-6-carboxylate | 495 |

TABLE 15-continued

| Example Number | Structure and Compound Name | LRMS m/z [M + H]+ |
|---|---|---|
| 322 | 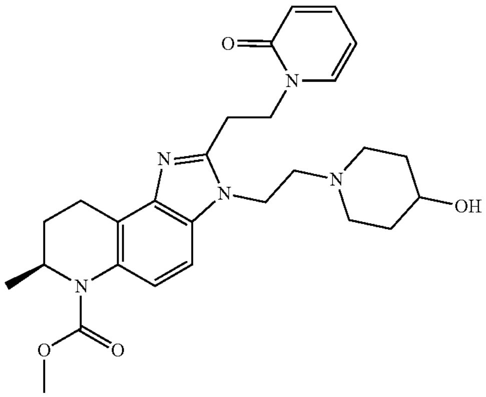 [SMILES: COC(=O)N1c2ccc3c(nc(CCn4ccccc4=O)n3CCN3CCC(O)CC3)c2CC[C@@H]1C] methyl (S)-3-(2-((2-(dimethylamino)-2-oxoethyl)(methyl)amino)ethyl)-7-methyl-2-(2-(2-oxopyridin-1(2H)-yl)ethyl)-3,7,8,9-tetrahydro-6H-imidazo[4,5-f]quinoline-6-carboxylate | 476 |
| 323 | 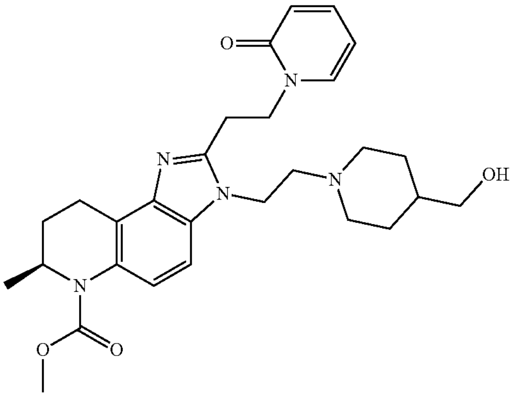 [SMILES: COC(=O)N1c2ccc3c(nc(CCn4ccccc4=O)n3CCN3CCC(CO)CC3)c2CC[C@@H]1C] methyl (S)-3-(2-(4-(hydroxymethyl)piperidin-1-yl)ethyl)-7-methyl-2-(2-(2-oxopyridin-1(2H)-yl)ethyl)-3,7,8,9-tetrahydro-6H-imidazo[4,5-f]quinoline-6-carboxylate | 494 |
| 324 | 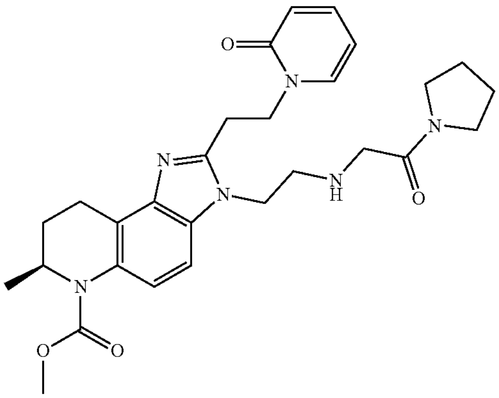 [SMILES: COC(=O)N1c2ccc3c(nc(CCn4ccccc4=O)n3CCNCC(=O)N3CCCC3)c2CC[C@@H]1C] methyl (S)-3-(2-((2-(dimethylamino)-2-oxoethyl)amino)ethyl)-7-methyl-2-(2-(2-oxopyridin-1(2H)-yl)ethyl)-3,7,8,9-tetrahydro-6H-imidazo[4,5-f]quinoline-6-carboxylate | 521 |

TABLE 15-continued

| Example Number | Structure and Compound Name | LRMS m/z [M + H]+ |
|---|---|---|
| 325 | 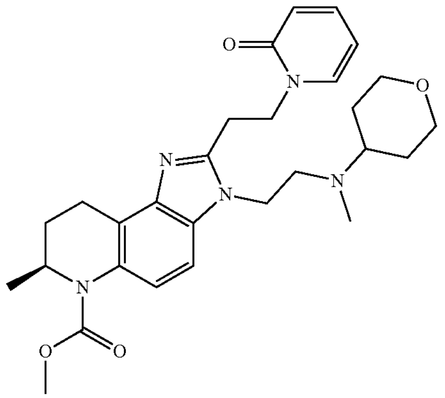 [SMILES: COC(=O)N1c2ccc3c(nc(CCn4ccccc4=O)n3CCN(C)C3CCOCC3)c2CC[C@@H]1C] methyl (S)-7-methyl-3-(2-(methyl(tetrahydro-2H-pyran-4-yl)amino)ethyl)-2-(2-(2-oxopyridin-1(2H)-yl)ethyl)-3,7,8,9-tetrahydro-6H-imidazo[4,5-f]quinoline-6-carboxylate | 508 |
| 326 | 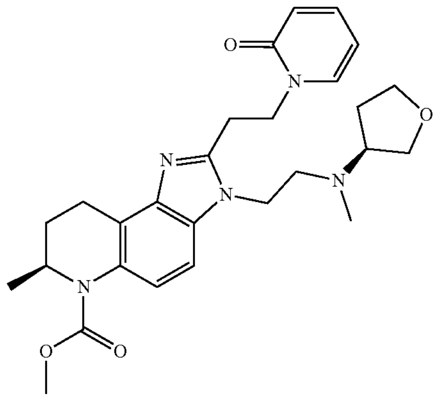 [SMILES: COC(=O)N1c2ccc3c(nc(CCn4ccccc4=O)n3CCN(C)[C@H]3CCOC3)c2CC[C@@H]1C] methyl (S)-2-(2-(1H-pyrazol-1-yl)ethyl)-3-(2-(4-cyclopropylpiperazin-1-yl)ethyl)-7-methyl-3,7,8,9-tetrahydro-6H-imidazo[4,5-f]quinoline-6-carboxylate | 494 |
| 327 | 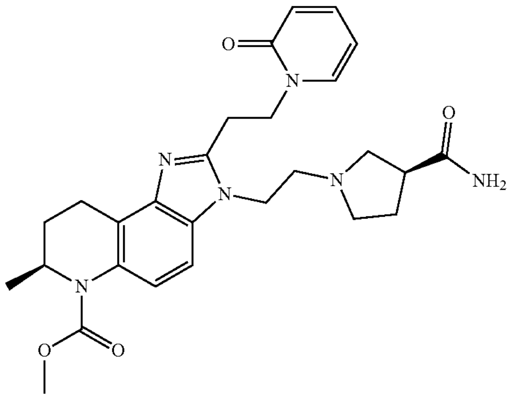 [SMILES: COC(=O)N1c2ccc3c(nc(CCn4ccccc4=O)n3CCN3CC[C@H](C(N)=O)C3)c2CC[C@@H]1C] methyl (S)-3-(2-((S)-3-carbamoylpyrrolidin-1-yl)ethyl)-7-methyl-2-(2-(2-oxopyridin-1(2H)-yl)ethyl)-3,7,8,9-tetrahydro-6H-imidazo[4,5-f]quinoline-6-carboxylate | 507 |

TABLE 15-continued

| Example Number | Structure and Compound Name | LRMS m/z [M + H]+ |
|---|---|---|
| 328 | 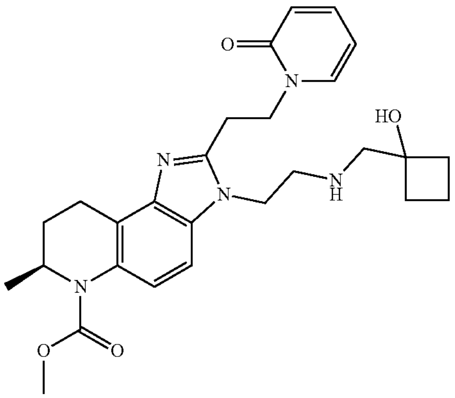 [SMILES: COC(=O)N1c2ccc3c(nc(CCn4ccccc4=O)n3CCNCC3(O)CCC3)c2CC[C@@H]1C] methyl (S)-3-(2-((S)-3-carbamoylpyrrolidin-1-yl)ethyl)-7-methyl-2-(2-(2-oxopyridin-1(2H)-yl)ethyl)-3,7,8,9-tetrahydro-6H-imidazo[4,5-f]quinoline-6-carboxylate | 494 |
| 329 | 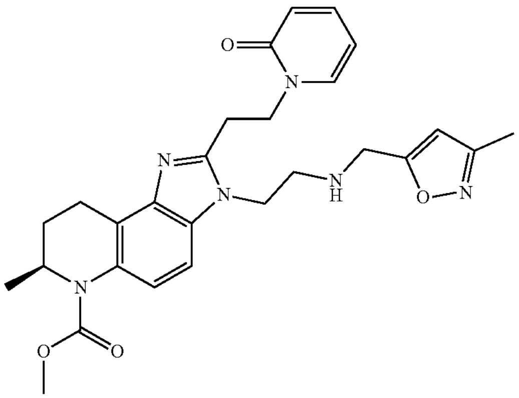 methyl (S)-7-methyl-3-(2-(((3-methylisoxazol-5-yl)methyl)amino)ethyl)-2-(2-(2-oxopyridin-1(2H)-yl)ethyl)-3,7,8,9-tetrahydro-6H-imidazo[4,5-f]quinoline-6-carboxylate | 505 |
| 330 | 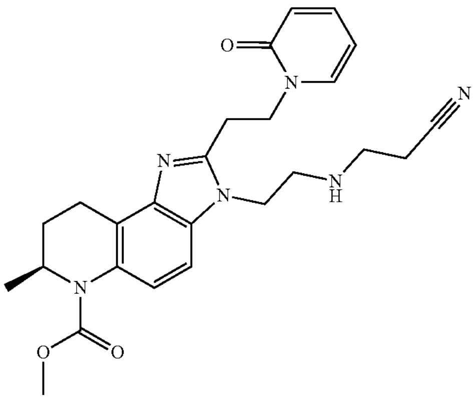 [SMILES: COC(=O)N1c2ccc3c(nc(CCn4ccccc4=O)n3CCNCCC#N)c2CC[C@@H]1C] methyl (S)-3-(2-((2-cyanoethyl)amino)ethyl)-7-methyl-2-(2-(2-oxopyridin-1(2H)-yl)ethyl)-3,7,8,9-tetrahydro-6H-imidazo[4,5-f]quinoline-6-carboxylate | 494 |

TABLE 15-continued

| Example Number | Structure and Compound Name | LRMS m/z [M + H]+ |
|---|---|---|
| 331 | 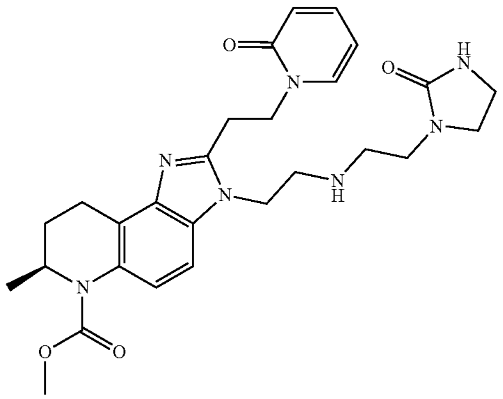 [SMILES: COC(=O)N1c2ccc3c(nc(CCn4ccccc4=O)n3CCNCCN3CCNC3=O)c2CC[C@@H]1C] methyl (S)-3-(2-((isoxazol-5-ylmethyl)amino)ethyl)-7-methyl-2-(2-(2-oxopyridin-1(2H)-yl)ethyl)-3,7,8,9-tetrahydro-6H-imidazo[4,5-f]quinoline-6-carboxylate | 494 |
| 332 | 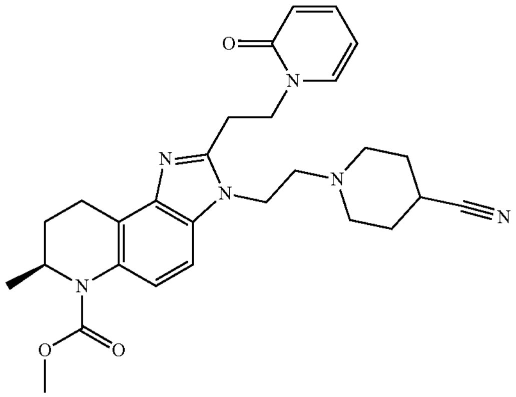 [SMILES: COC(=O)N1c2ccc3c(nc(CCn4ccccc4=O)n3CCN3CCC(C#N)CC3)c2CC[C@@H]1C] methyl (S)-3-(2-(4-cyanopiperidin-1-yl)ethyl)-7-methyl-2-(2-(2-oxopyridin-1(2H)-yl)ethyl)-3,7,8,9-tetrahydro-6H-imidazo[4,5-f]quinoline-6-carboxylate | 466 |
| 333 | 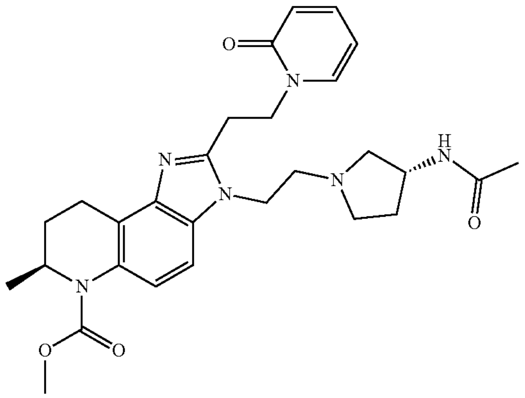 [SMILES: COC(=O)N1c2ccc3c(nc(CCn4ccccc4=O)n3CCN3CC[C@@H](NC(C)=O)C3)c2CC[C@@H]1C] methyl (S)-3-(2-((R)-3-acetamidopyrrolidin-1-yl)ethyl)-7-methyl-2-(2-(2-oxopyridin-1(2H)-yl)ethyl)-3,7,8,9-tetrahydro-6H-imidazo[4,5-f]quinoline-6-carboxylate | 521 |

TABLE 15-continued

| Example Number | Structure and Compound Name | LRMS m/z [M + H]+ |
| --- | --- | --- |
| 334 | 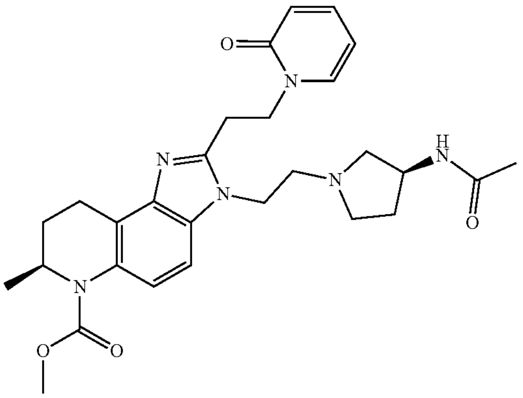 [SMILES: COC(=O)N1c2ccc3c(nc(CCn4ccccc4=O)n3CCN3CC[C@H](NC(C)=O)C3)c2CC[C@@H]1C] methyl (S)-3-(2-((S)-3-acetamidopyrrolidin-1-yl)ethyl)-7-methyl-2-(2-(2-oxopyridin-1(2H)-yl)ethyl)-3,7,8,9-tetrahydro-6H-imidazo[4,5-f]quinoline-6-carboxylate | 521 |

Example 335: methyl (S)-2-(2-(1H-pyrazol-1-yl)ethyl)-3-(2-((S)-3-acetamidopyrrolidin-1-yl)-2-oxoethyl)-7-methyl-3,7,8,9-tetrahydro-6H-imidazo[4,5-f]quinoline-6-carboxylate

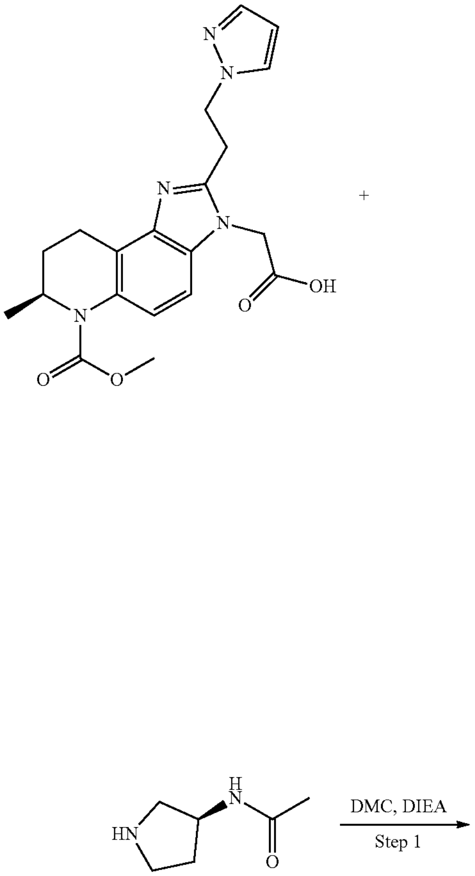

-continued

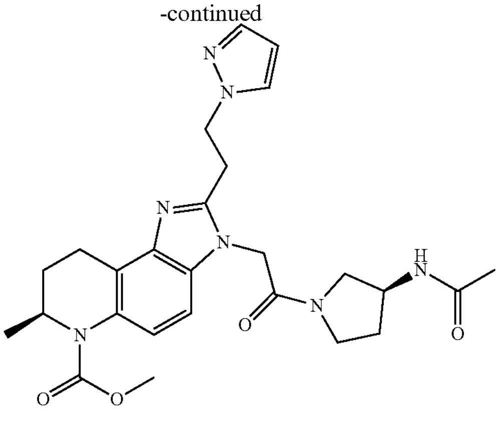

Step 1. Synthesis of methyl (S)-2-(2-(1H-pyrazol-1-yl)ethyl)-3-(2-((S)-3-acetamidopyrrolidin-1-yl)-2-oxoethyl)-7-methyl-3,7,8,9-tetrahydro-6H-imidazo[4,5-f]quinoline-6-carboxylate To a solution of (S)-2-(2-(2-(1H-pyrazol-1-yl)ethyl)-6-(methoxycarbonyl)-7-methyl-6,7,8,9-tetrahydro-3H-imidazo[4,5-f]quinolin-3-yl)acetic acid (0.2 M 1,4-dioxane with 10% DIEA, 100 μL, 0.02 mmol), was added a solution of (S)-N-(pyrrolidin-3-yl)acetamide (0.2 M in 1,4-dioxane, 120 μL, 0.024 mmol) and 2 a solution of DMC (0.2 M 1,2-DCE, 120 μL, 0.024 mmol). The resulting mixture was put on a shaker at rt for 20 h. The mixture was then diluted with ethyl acetate (0.8 mL) and brine (0.45 mL). The organic layer was separated and the aqueous layer was extracted with ethyl acetate. The combined organic layers were dried down and the residue was purified by HPLC: Water Autopurification MS-directed HPLC prep fraction collection with the following conditions Column, Waters XBridge OBD C18, 5 um, 19×50 mm; flow rate 20 ml/min; mobile phase, water with 0.1% ammonium hydroxide (A) and methanol with 0.1% ammonium hydroxide (B) running the following gradient: 0 to 2 mins (15% B), 2 to 6 mins (15-100% B); Detector ZQ Mass Detector in electrospray ionization mode. This provided 3.4 mg of methyl (S)-2-(2-(1H-pyrazol-1-yl) ethyl)-3-(2-((S)-3-acetamidopyrrolidin-1-yl)-2-oxoethyl)-7-methyl-3,7,8,9-tetrahydro-6H-imidazo[4,5-f]quinoline-6-carboxylate (6.70 μmol, 34% yield) was obtained. MS (ESI, pos. ion) m/z: 508 (M+1).

The following examples in TABLE 16 were prepared using standard chemical manipulations and procedures similar to those used for the preparation of Example 335.

TABLE 16

| Example Number | Structure and Compound Name | LRMS m/z $[M + H]^+$ |
|---|---|---|
| 336 | 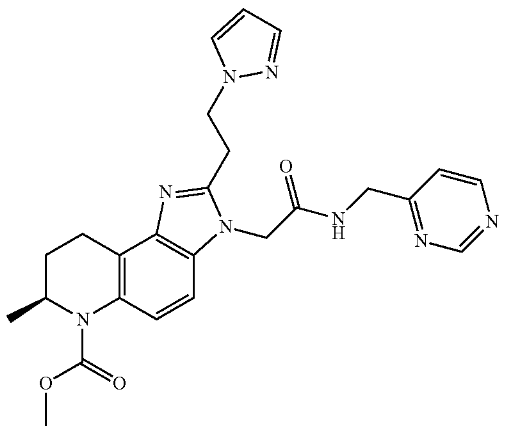 [SMILES: COC(=O)N1c2ccc3c(nc(CCn4cccn4)n3CC(=O)NCc3ccncn3)c2CC[C@@H]1C] methyl (S)-2-(2-(1H-pyrazol-1-yl)ethyl)-7-methyl-3-(2-oxo-2-((pyrimidin-4-ylmethyl)amino)ethyl)-3,7,8,9-tetrahydro-6H-imidazo[4,5-f]quinoline-6-carboxylate | 489 |
| 337 | 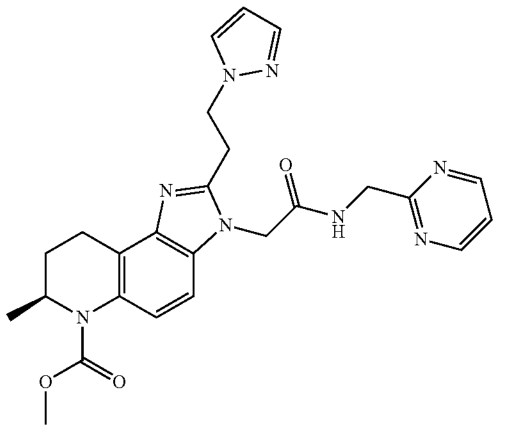 [SMILES: COC(=O)N1c2ccc3c(nc(CCn4cccn4)n3CC(=O)NCc3ncccn3)c2CC[C@@H]1C] methyl (S)-2-(2-(1H-pyrazol-1-yl)ethyl)-7-methyl-3-(2-oxo-2-((pyrimidin-2-ylmethyl)amino)ethyl)-3,7,8,9-tetrahydro-6H-imidazo[4,5-f]quinoline-6-carboxylate | 489 |

TABLE 16-continued

| Example Number | Structure and Compound Name | LRMS m/z $[M + H]^+$ |
|---|---|---|
| 338 | 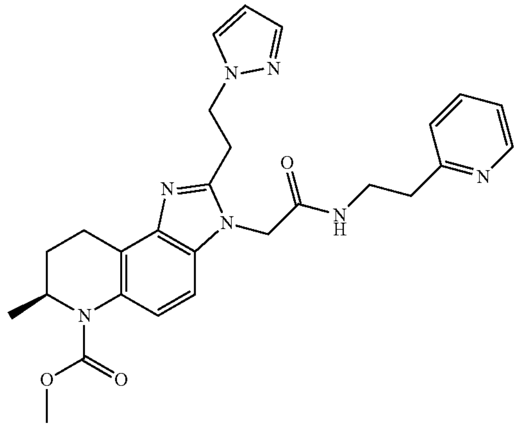 [SMILES: COC(=O)N1c2ccc3c(nc(CCn4cccn4)n3CC(=O)NCCc3ccccn3)c2CC[C@@H]1C]<br>methyl (S)-2-(2-(1H-pyrazol-1-yl)ethyl)-7-methyl-3-(2-oxo-2-((2-(pyridin-2-yl)ethyl)amino)ethyl)-3,7,8,9-tetrahydro-6H-imidazo[4,5-f]quinoline-6-carboxylate | 502 |
| 339 | 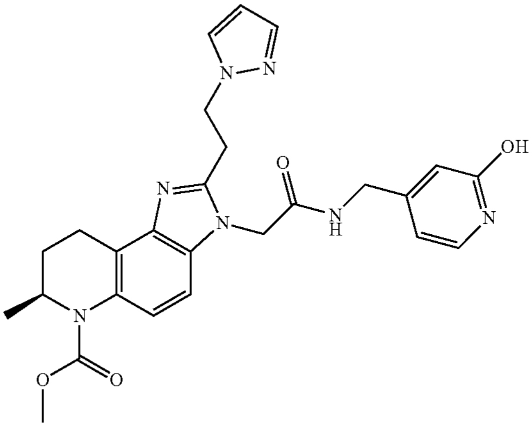 [SMILES: COC(=O)N1c2ccc3c(nc(CCn4cccn4)n3CC(=O)NCc3ccnc(O)c3)c2CC[C@@H]1C]<br>methyl (S)-2-(2-(1H-pyrazol-1-yl)ethyl)-3-(2-(((2-hydroxypyridin-4-yl)methyl)amino)-2-oxoethyl)-7-methyl-3,7,8,9-tetratydro-6H-imidazo[4,5-f]quinoline-6-carboxylate | 504 |
| 340 | 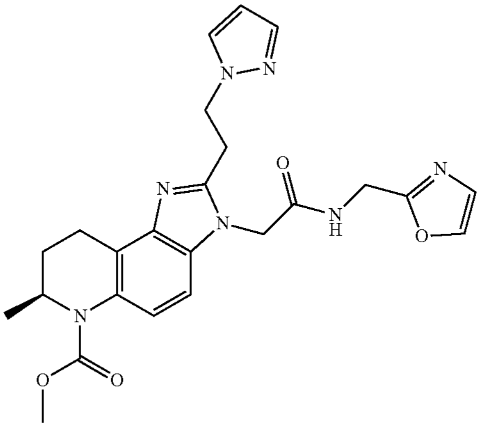 [SMILES: COC(=O)N1c2ccc3c(nc(CCn4cccn4)n3CC(=O)NCc3ncco3)c2CC[C@@H]1C]<br>methyl (S)-2-(2-(1H-pyrazol-1-yl)ethyl)-7-methyl-3-(2-((oxazol-2-ylmethyl)amino)-2-oxoethyl)-3,7,8,9-tetratydro-6H-imidazo[4,5-f]quinoline-6-carboxylate | 478 |

TABLE 16-continued

| Example Number | Structure and Compound Name | LRMS m/z [M + H]+ |
|---|---|---|
| 341 | 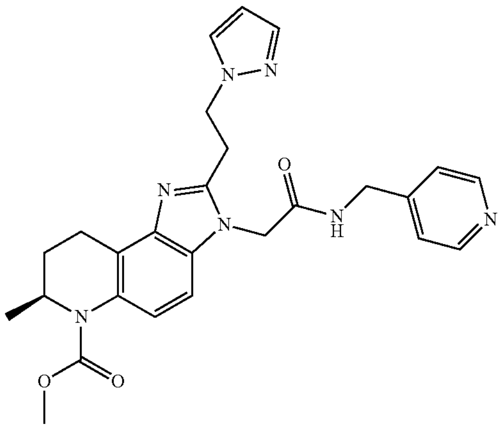 [SMILES: COC(=O)N1c2ccc3c(nc(CCn4cccn4)n3CC(=O)NCc3ccncc3)c2CC[C@@H]1C] methyl (S)-2-(2-(1H-pyrazol-1-yl)ethyl)-7-methyl-3-(2-oxo-2-((pyridin-4-ylmethyl)amino)ethyl)-3,7,8,9-tetrahydro-6H-imidazo[4,5-f]quinoline-6-carboxylate | 488 |
| 342 | 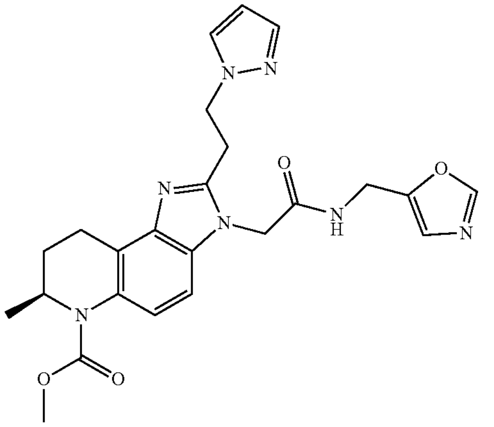 [SMILES: COC(=O)N1c2ccc3c(nc(CCn4cccn4)n3CC(=O)NCc3cnco3)c2CC[C@@H]1C] methyl (S)-2-(2-(1H-pyrazol-1-yl)ethyl)-7-methyl-3-(2-((oxazol-5-ylmethyl)amino)-2-oxoethyl)-3,7,8,9-tetrahydro-6H-imidazo[4,5-f]quinoline-6-carboxylate | 478 |
| 343 | 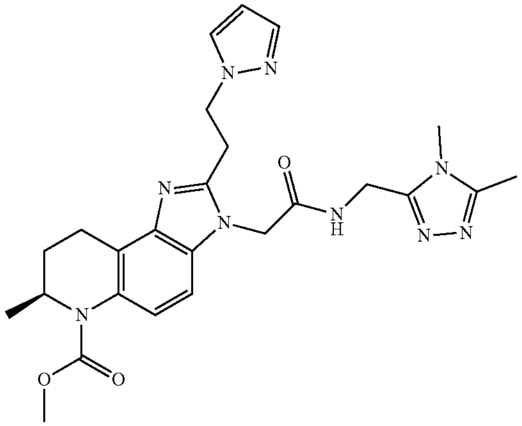 methyl (S)-2-(2-(1H-pyrazol-1-yl)ethyl)-3-(2-(((4,5-dimethyl-4H-1,2,4-triazol-3-yl)methyl)amino)-2-oxoethyl)-7-methyl-3,7,8,9-tetrahydro-6H-imidazo[4,5-f]quinoline-6-carboxylate | 506 |

TABLE 16-continued

| Example Number | Structure and Compound Name | LRMS m/z [M + H]+ |
|---|---|---|
| 344 | 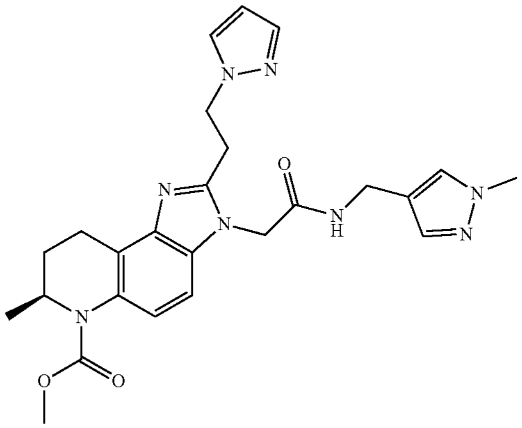 methyl (S)-2-(2-(1H-pyrazol-1-yl)ethyl)-7-methyl-3-(2-(((1-methyl-1H-pyrazol-4-yl)methyl)amino)-2-oxoethyl)-3,7,8,9-tetrahydro-6H-imidazo[4,5-f]quinoline-6-carboxylate | 491 |
| 345 | 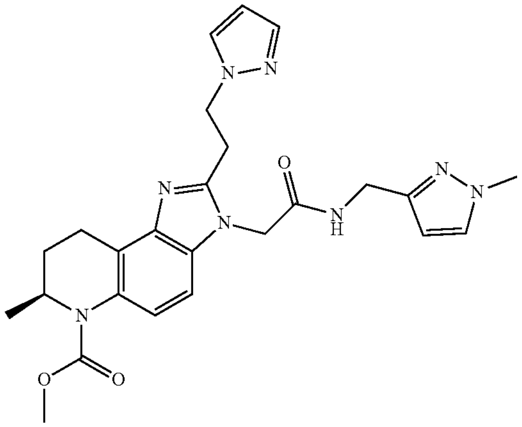 methyl (S)-2-(2-(1H-pyrazol-1-yl)ethyl)-7-methyl-3-(2-(((1-methyl-1H-pyrazol-3-yl)methyl)amino)-2-oxoethyl)-3,7,8,9-tetrahydro-6H-imidazo[4,5-f]quinoline-6-carboxylate | 491 |
| 346 | 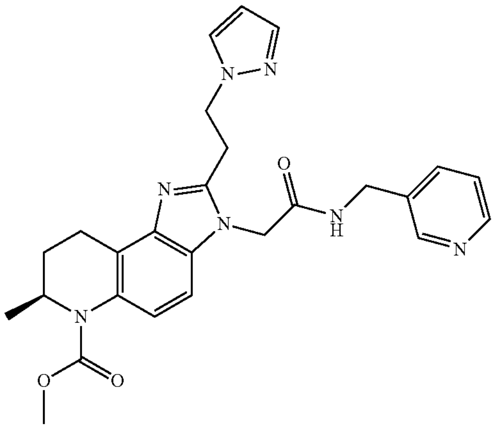 [SMILES: COC(=O)N1c2ccc3c(nc(CCn4cccn4)n3CC(=O)NCc3cccnc3)c2CC[C@@H]1C] methyl (S)-2-(2-(1H-pyrazol-1-yl)ethyl)-7-methyl-3-(2-oxo-2-((pyridin-3-ylmethyl)amino)ethyl)-3,7,8,9-tetrahydro-6H-imidazo[4,5-f]quinoline-6-carboxylate | 488 |

TABLE 16-continued

| Example Number | Structure and Compound Name | LRMS m/z [M + H]+ |
|---|---|---|
| 347 | 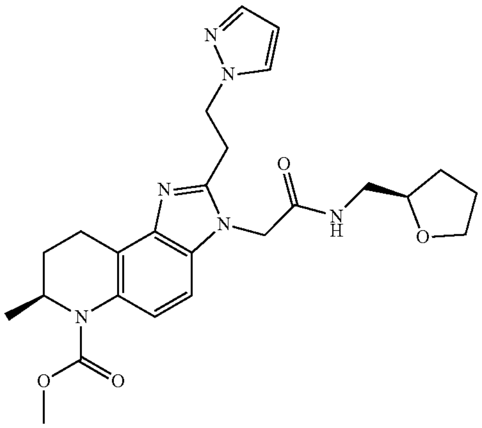 [SMILES: COC(=O)N1c2ccc3c(nc(CCn4cccn4)n3CC(=O)NC[C@H]3CCCO3)c2CC[C@@H]1C] methyl (S)-2-(2-(1H-pyrazol-1-yl)ethyl)-7-methyl-3-(2-oxo-2-((((R)-tetrahydrofuran-2-yl)methyl)amino)ethyl)-3,7,8,9-tetrahydro-6H-imidazo[4,5-f]quinoline-6-carboxylate | 481 |
| 348 | 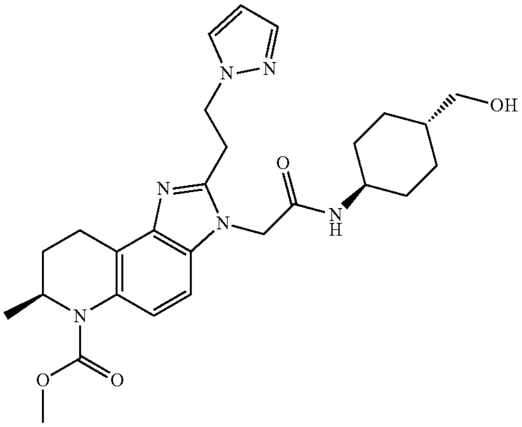 [SMILES: COC(=O)N1c2ccc3c(nc(CCn4cccn4)n3CC(=O)N[C@H]3CC[C@H](CO)CC3)c2CC[C@@H]1C] methyl (S)-2-(2-(1H-pyrazol-1-yl)ethyl)-3-(2-(((trans)-4-(hydroxymethyl)cyclohexyl)amino)-2-oxoethyl)-7-methyl-3,7,8,9-tetrahydro-6H-imidazo[4,5-f]quinoline-6-carboxylate | 509 |
| 349 | 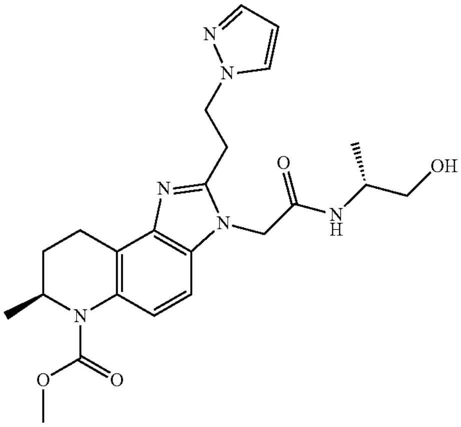 [SMILES: COC(=O)N1c2ccc3c(nc(CCn4cccn4)n3CC(=O)N[C@H](C)CO)c2CC[C@@H]1C] methyl (S)-2-(2-(1H-pyrazol-1-yl)ethyl)-3-(2-(((R)-1-hydroxypropan-2-yl)amino)-2-oxoethyl)-7-methyl-3,7,8,9-tetrahydro-6H-imidazo[4,5-f]quinoline-6-carboxylate | 455 |

TABLE 16-continued

| Example Number | Structure and Compound Name | LRMS m/z [M + H]+ |
|---|---|---|
| 350 | 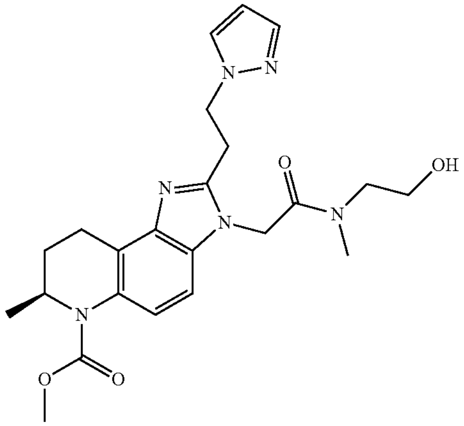 [SMILES: COC(=O)N1c2ccc3c(nc(CCn4cccn4)n3CC(=O)N(C)CCO)c2CC[C@@H]1C] methyl (S)-2-(2-(1H-pyrazol-1-yl)ethyl)-3-(2-((2-hydroxyethyl)(methyl)amino)-2-oxoethyl)-7-methyl-3,7,8,9-tetrahydro-6H-imidazo[4,5-f]quinoline-6-carboxylate | 455 |
| 351 | 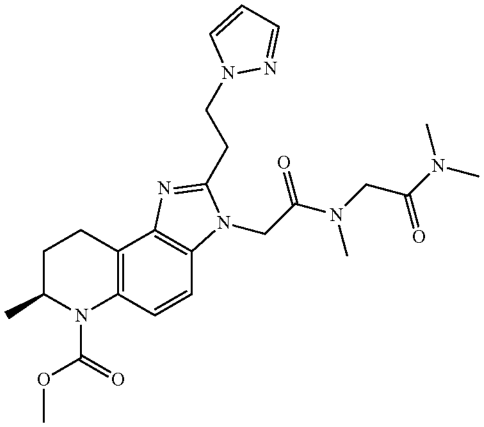 methyl (S)-2-(2-(1H-pyrazol-1-yl)ethyl)-3-(2-((2-(dimethylamino)-2-oxoethyl)(methyl)amino)-2-oxoethyl)-7-methyl-3,7,8,9-tetrahydro-6H-imidazo[4,5-f]quinoline-6-carboxylate | 496 |
| 352 | 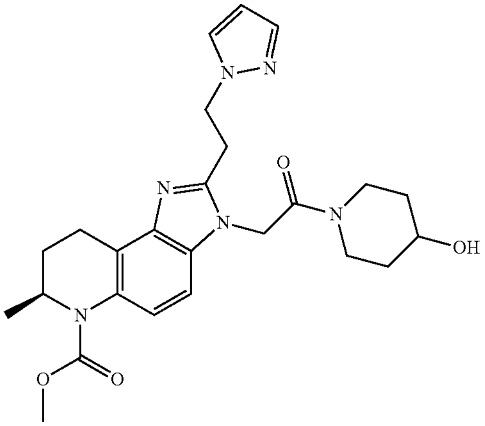 [SMILES: COC(=O)N1c2ccc3c(nc(CCn4cccn4)n3CC(=O)N3CCC(O)CC3)c2CC[C@@H]1C] methyl (S)-2-(2-(1H-pyrazol-1-yl)ethyl)-3-(2-(4-hydroxypiperidin-1-yl)-2-oxoethyl)-7-methyl-3,7,8,9-tetrahydro-6H-imidazo[4,5-f]quinoline-6-carboxylate | 481 |

TABLE 16-continued

| Example Number | Structure and Compound Name | LRMS m/z [M + H]+ |
|---|---|---|
| 353 | 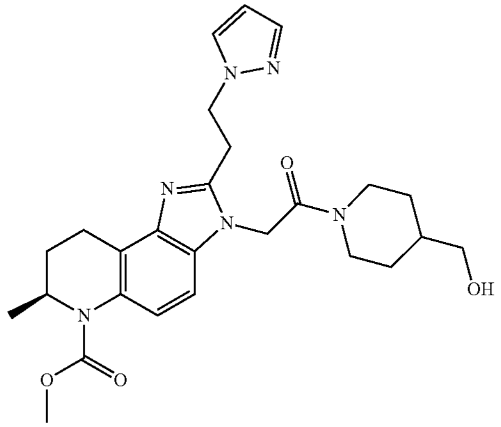 [SMILES: COC(=O)N1c2ccc3c(nc(CCn4cccn4)n3CC(=O)N3CCC(CO)CC3)c2CC[C@@H]1C] methyl (S)-2-(2-(1H-pyrazol-1-yl)ethyl)-3-(2-(4-(hydroxymethyl)piperidin-1-yl)-2-oxoetlyl)-7-methyl-3,7,8,9-tetrahydro-6H-imidazo[4,5-f]quinoline-6-carboxylate | 495 |
| 354 | 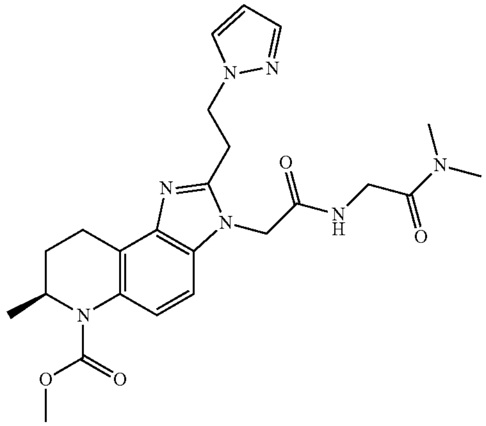 methyl (S)-2-(2-(1H-pyrazol-1-yl)ethyl)-3-(2-((2-(dimethylamino)-2-oxoethyl)amino)-2-oxoethyl)-7-methyl-3,7,8,9-tetrahydro-6H-imidazo[4,5-f]quinoline-6-carboxylate | 482 |
| 355 | 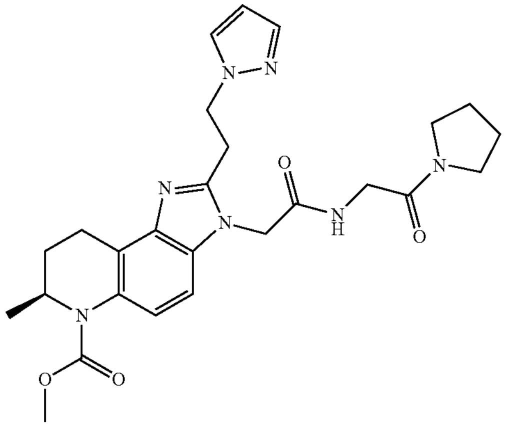 [SMILES: COC(=O)N1c2ccc3c(nc(CCn4cccn4)n3CC(=O)NCC(=O)N3CCCC3)c2CC[C@@H]1C] methyl (S)-2-(2-(1H-pyrazol-1-yl)ethyl)-7-methyl-3-(2-oxo-2-((2-oxo-2-(pyrrolidin-1-yl)ethyl)amino)ethyl)-3,7,8,9-tetrahydro-6H-imidazo[4,5-f]quinoline-6-carboxylate | 508 |

TABLE 16-continued

| Example Number | Structure and Compound Name | LRMS m/z [M + H]+ |
|---|---|---|
| 356 | 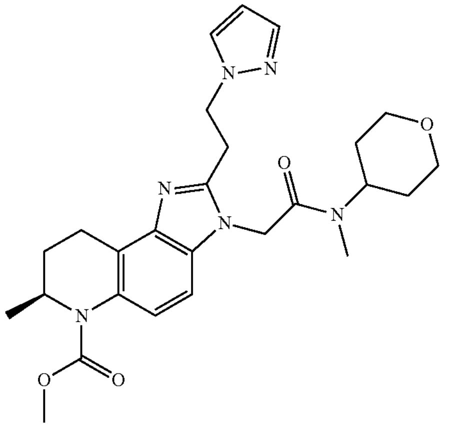 [SMILES: COC(=O)N1c2ccc3c(nc(CCn4cccn4)n3CC(=O)N(C)C3CCOCC3)c2CC[C@@H]1C] methyl (S)-2-(2-(1H-pyrazol-1-yl)ethyl)-7-methyl-3-(2-(methyl(tetrahydro-2H-pyran-4-yl)amino)-2-oxoethyl)-3,7,8,9-tetrahydro-6H-imidazo[4,5-f]quinoline-6-carboxylate | 495 |
| 357 | 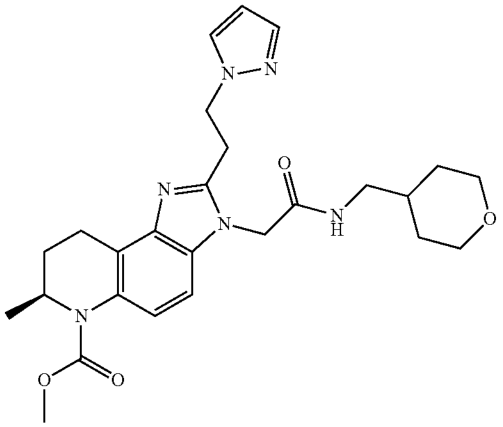 [SMILES: COC(=O)N1c2ccc3c(nc(CCn4cccn4)n3CC(=O)NCC3CCOCC3)c2CC[C@@H]1C] methyl (S)-2-(2-(1H-pyrazol-1-yl)ethyl)-7-methyl-3-(2-oxo-2-(((tetrahydro-2H-pyran-4-yl)methyl)amino)ethyl)-3,7,8,9-tetrahydro-6H-imidazo[4,5-f]quinoline-6-carboxylate | 495 |
| 358 | 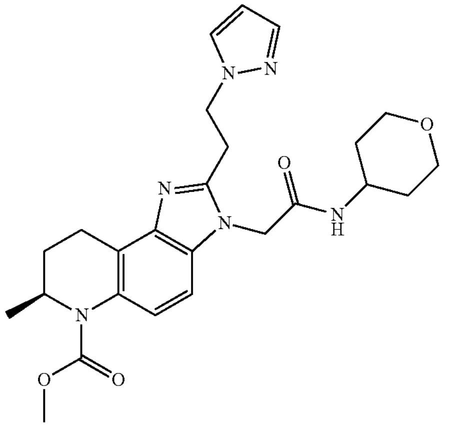 [SMILES: COC(=O)N1c2ccc3c(nc(CCn4cccn4)n3CC(=O)NC3CCOCC3)c2CC[C@@H]1C] methyl (S)-2-(2-(1H-pyrazol-1-yl)ethyl)-7-methyl-3-(2-oxo-2-((tetrahydro-2H-pyran-4-yl)amino)ethyl)-3,7,8,9-tetrahydro-6H-imidazo[4,5-f]quinoline-6-carboxylate | 481 |

TABLE 16-continued

| Example Number | Structure and Compound Name | LRMS m/z [M + H]+ |
|---|---|---|
| 359 | 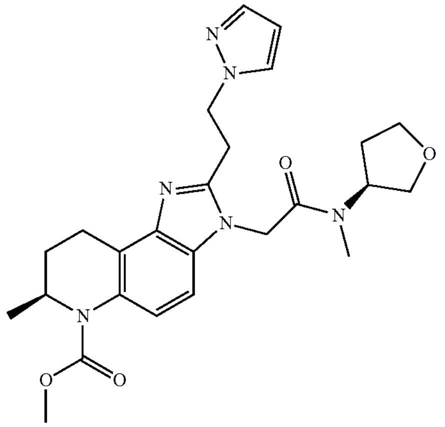 [SMILES: COC(=O)N1c2ccc3c(nc(CCn4cccn4)n3CC(=O)N(C)[C@H]3CCOC3)c2CC[C@@H]1C] methyl (S)-2-(2-(1H-pyrazol-1-yl)ethyl)-7-methyl-3-(2-(methyl((S)-tetrahydrofuran-3-yl)amino)-2-oxoethyl)-3,7,8,9-tetrahydro-6H-imidazo[4,5-f]quinoline-6-carboxylate | 481 |
| 360 | 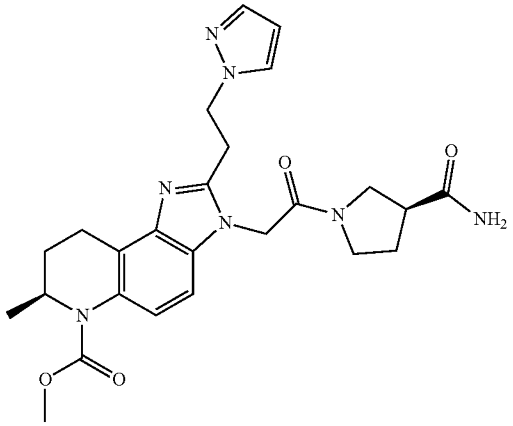 [SMILES: COC(=O)N1c2ccc3c(nc(CCn4cccn4)n3CC(=O)N3CC[C@H](C(N)=O)C3)c2CC[C@@H]1C] methyl (S)-2-(2-(1H-pyrazol-1-yl)ethyl)-3-(2-((S)-3-carbamoylpyrrolidin-1-yl)-2-oxoethyl)-7-methyl-3,7,8,9-tetrahydro-6H-imidazo[4,5-f]quinoline-6-carboxylate | 494 |
| 361 | 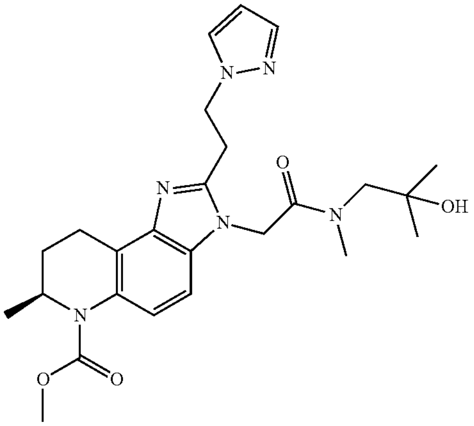 [SMILES: COC(=O)N1c2ccc3c(nc(CCn4cccn4)n3CC(=O)N(C)CC(C)(C)O)c2CC[C@@H]1C] methyl (S)-2-(2-(1H-pyrazol-1-yl)ethyl)-3-(2-((2-hydroxy-2-methylpropyl)(methyl)amino)-2-oxoethyl)-7-methyl-3,7,8,9-tetrahydro-6H-imidazo[4,5-f]quinoline-6-carboxylate | 483 |

TABLE 16-continued

| Example Number | Structure and Compound Name | LRMS m/z [M + H]+ |
|---|---|---|
| 362 | 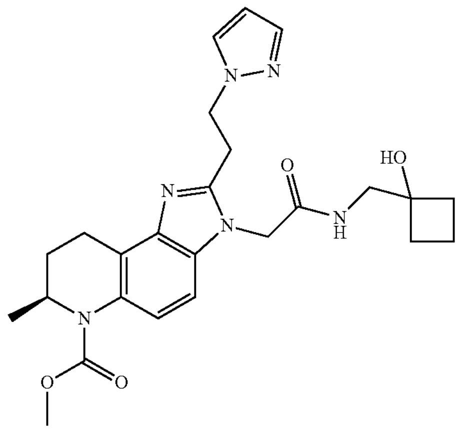 [SMILES: COC(=O)N1c2ccc3c(nc(CCn4cccn4)n3CC(=O)NCC3(O)CCC3)c2CC[C@@H]1C] methyl (S)-2-(2-(1H-pyrazol-1-yl)ethyl)-3-(2-(((1-hydroxycyclobutyl)methyl)amino)-2-oxoethyl)-7-methyl-3,7,8,9-tetrahydro-6H-imidazo[4,5-f]quinoline-6-carboxylate | 481 |
| 363 | 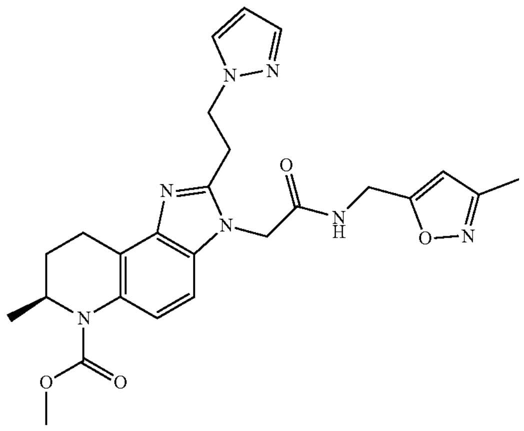 methyl (S)-2-(2-(1H-pyrazol-1-yl)ethyl)-7-methyl-3-(2-(((3-methylisoxazol-5-yl)methyl)amino)-2-oxoethyl)-3,7,8,9-tetrahydro-6H-imidazo[4,5-f]quinoline-6-carboxylate | 492 |
| 364 | 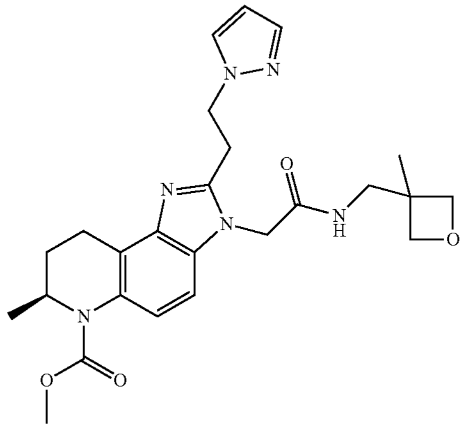 [SMILES: COC(=O)N1c2ccc3c(nc(CCn4cccn4)n3CC(=O)NCC3(C)COC3)c2CC[C@@H]1C] methyl (S)-2-(2-(1H-pyiazol-1-yl)ethyl)-7-methyl-3-(2-(((3-methyloxetan-3-yl)methyl)amino)-2-oxoethyl)-3,7,8,9-tetrahydro-6H-imidazo[4,5-f]quinoline-6-carboxylate | 481 |

TABLE 16-continued

| Example Number | Structure and Compound Name | LRMS m/z $[M + H]^+$ |
|---|---|---|
| 365 | 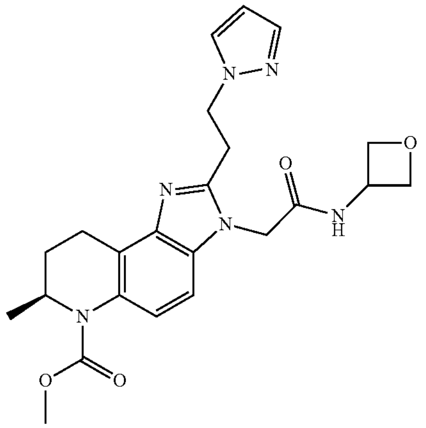 [SMILES: COC(=O)N1c2ccc3c(nc(CCn4cccn4)n3CC(=O)NC3COC3)c2CC[C@@H]1C] methyl (S)-2-(2-(1H-pyracol-1-yl)ethyl)-7-methyl-3-(2-(oxetan-3-ylamino)-2-oxoethyl)-3,7,8,9-tetrahydro-6H-imidazo[4,5-f]qninoline-6-carboxylate | 453 |
| 366 | 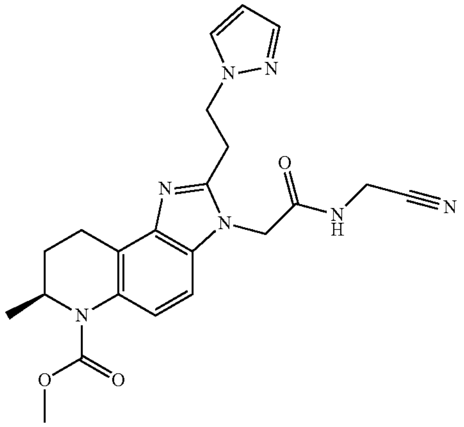 [SMILES: COC(=O)N1c2ccc3c(nc(CCn4cccn4)n3CC(=O)NCC#N)c2CC[C@@H]1C] methyl (S)-2-(2-(1H-pyrazol-1-yl)ethyl)-3-(2-((cyanomethyl)amino)-2-oxoethyl)-7-methyl-3,7,8,9-tetrahydno-6H-imidazo[4,5-f]quinoline-6-carboxylate | 436 |
| 367 | 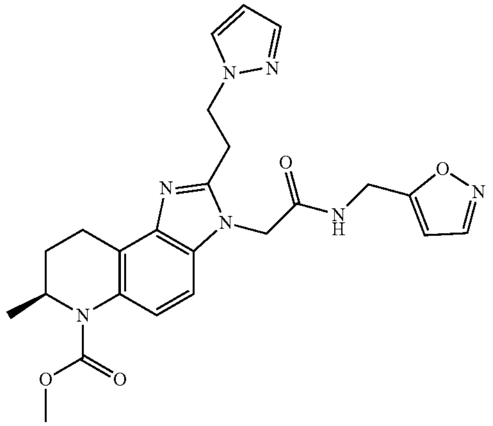 [SMILES: COC(=O)N1c2ccc3c(nc(CCn4cccn4)n3CC(=O)NCc3ccno3)c2CC[C@@H]1C] methyl (S)-2-(2-(1H-pyrazol-1-yl)ethyl)-3-(2-((isoxazol-5-ylmethyl)amino)-2-oxoethyl)-7-methyl-3,7,8,9-tetrahydro-6H-imidazo[4,5-f]quinoline-6-carboxylate | 478 |

TABLE 16-continued

| Example Number | Structure and Compound Name | LRMS m/z [M + H]+ |
|---|---|---|
| 368 | 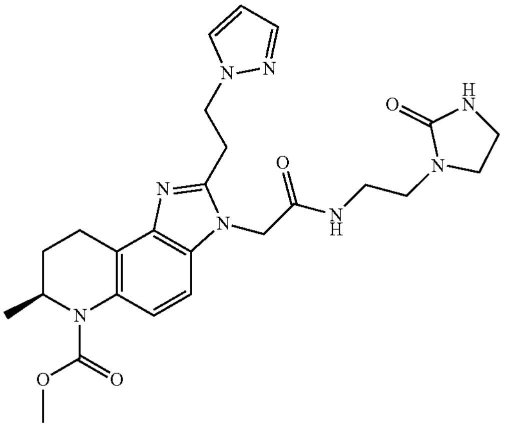 [SMILES: COC(=O)N1c2ccc3c(nc(CCn4cccn4)n3CC(=O)NCCN3CCNC3=O)c2CC[C@@H]1C] methyl (S)-2-(2-(1H-pyiazol-1-yl)ethyl)-7-methyl-3-(2-oxo-2-((2-(2-oxoimidazolidin-1-yl)ethyl)amino)ethyl)-3,7,8,9-tetrahydro-6H-imidazo[4,5-f]quinoline-6-carboxylate | 478 |
| 369 | 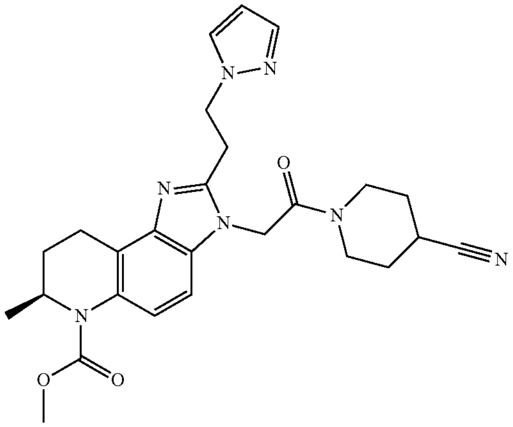 [SMILES: COC(=O)N1c2ccc3c(nc(CCn4cccn4)n3CC(=O)N3CCC(C#N)CC3)c2CC[C@@H]1C] methyl (S)-2-(2-(1H-pyrazol-1-yl)ethyl)-3-(2-(4-cyanopiperidin-1-yl)-2-oxoethyl)-7-methyl-3,7,8,9-tetrahydro-6H-imidazo[4,5-f]quinoline-6-carboxylate | 489 |
| 370 | 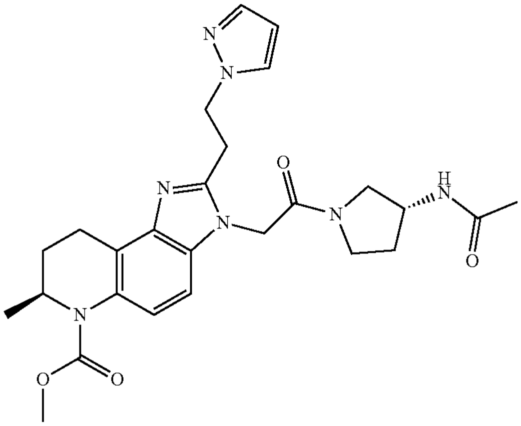 [SMILES: COC(=O)N1c2ccc3c(nc(CCn4cccn4)n3CC(=O)N3CC[C@@H](NC(C)=O)C3)c2CC[C@@H]1C] methyl (S)-2-(2-(1H-pyrazol-1-yl)ethyl)-3-(2-((R)-3-acetamidopyrrolidin-1-yl)-2-oxoethyl)-7-methyl-3,7,8,9-tetrahydro-6H-imidazo[4,5-f]quinoline-6-carboxylate | 508 |

TABLE 16-continued

| Example Number | Structure and Compound Name | LRMS m/z [M + H]+ |
| --- | --- | --- |
| 371 | 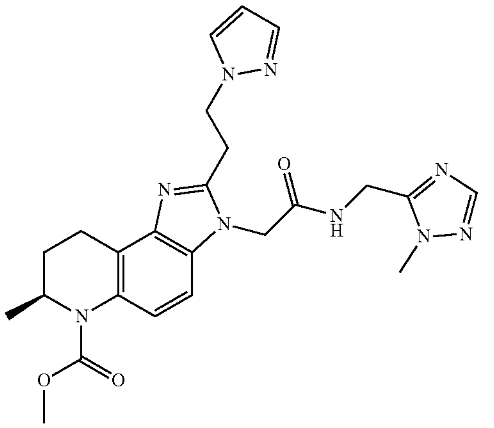 [SMILES: COC(=O)N1c2ccc3c(nc(CCn4cccn4)n3CC(=O)NCc3ncnn3C)c2CC[C@@H]1C] methyl (S)-2-(2-(1H-pyrazol-1-yl)ethyl)-7-methyl-3-(2-(((1-methyl-1H-1,2,4-triazol-5-yl)methyl)amino)-2-oxoethyl)-3,7,8,9-tetrahydro-6H-imidazo[4,5-f]quinoline-6-carboxylate | 492 |
| 372 | 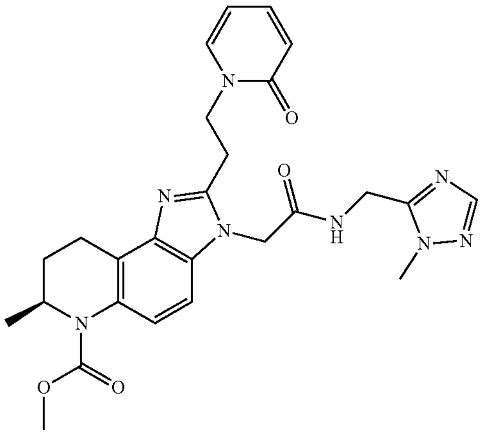 [SMILES: COC(=O)N1c2ccc3c(nc(CCn4ccccc4=O)n3CC(=O)NCc3ncnn3C)c2CC[C@@H]1C] methyl (S)-7-methyl-3-(2-(((1-methyl-1H-1,2,4-triazol-5-yl)methyl)amino)-2-oxoethyl)-2-(2-(2-oxopyridin-1(2H)-yl)ethyl)-3,7,8,9-tetrahydro-6H-imidazo[4,5-f]quinoline-6-carboxylate | 519 |
| 373 | 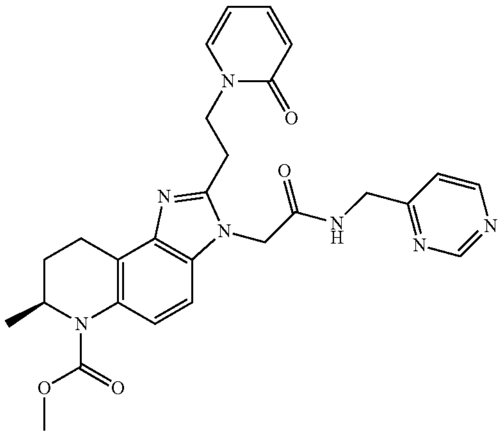 [SMILES: COC(=O)N1c2ccc3c(nc(CCn4ccccc4=O)n3CC(=O)NCc3ccncn3)c2CC[C@@H]1C] methyl (S)-7-methyl-3-(2-oxo-2-((pyrimidin-4-ylmethyl)amino)ethyl)-2-(2-(2-oxopyridin-1(2H)-yl)ethyl)-3,7,8,9-tetrahydro-6H-imidazo[4,5-f]quinoline-6-carboxylate | 516 |

TABLE 16-continued

| Example Number | Structure and Compound Name | LRMS m/z [M + H]$^+$ |
|---|---|---|
| 374 | 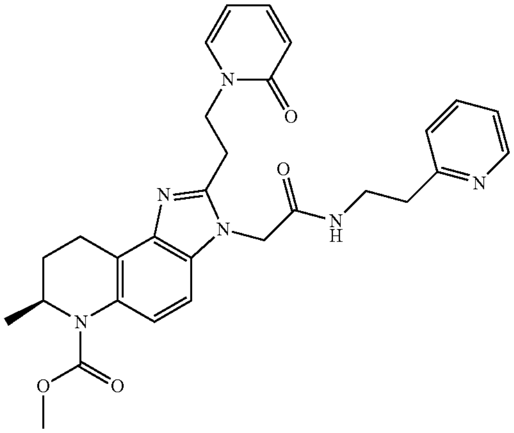 [SMILES: COC(=O)N1c2ccc3c(nc(CCn4ccccc4=O)n3CC(=O)NCCc3ccccn3)c2CC[C@@H]1C] methyl (S)-7-methyl-3-(2-oxo-2-((2-(pyridin-2-yl)ethyl)amino)ethyl)-2-(2-(2-oxopyridin-1(2H)-yl)ethyl)-3,7,8,9-tetrahydro-6H-imidazo[4,5-f]quinoline-6-carboxylate | 529 |
| 375 | 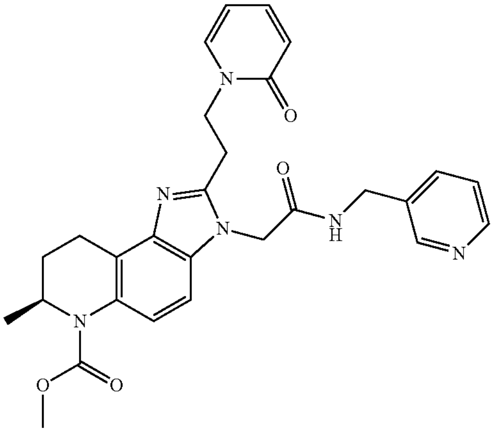 [SMILES: COC(=O)N1c2ccc3c(nc(CCn4ccccc4=O)n3CC(=O)NCc3cccnc3)c2CC[C@@H]1C] methyl (S)-7-methyl-3-(2-oxo-2-((pyridin-3-ylmethyl)amino)ethyl)-2-(2-(2-oxopyridin-1(2H)-yl)ethyl)-3,7,8,9-tetrahydro-6H-imidazo[4,5-f]quinoline-6-carboxylate | 515 |
| 376 | 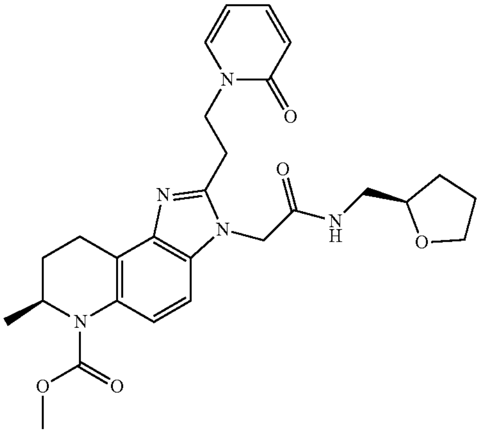 [SMILES: COC(=O)N1c2ccc3c(nc(CCn4ccccc4=O)n3CC(=O)NC[C@H]3CCCO3)c2CC[C@@H]1C] methyl (S)-7-methyl-3-(2-oxo-2-((((R)-tetrahydrofuran-2-yl)methyl)amino)ethyl)-2-(2-(2-oxopyridin-1(2H)-yl)ethyl)-3,7,8,9-tetrahydro-6H-imidazo[4,5-f]quinoline-6-carboxylate | 508 |

TABLE 16-continued

| Example Number | Structure and Compound Name | LRMS m/z [M + H]$^+$ |
| --- | --- | --- |
| 377 | 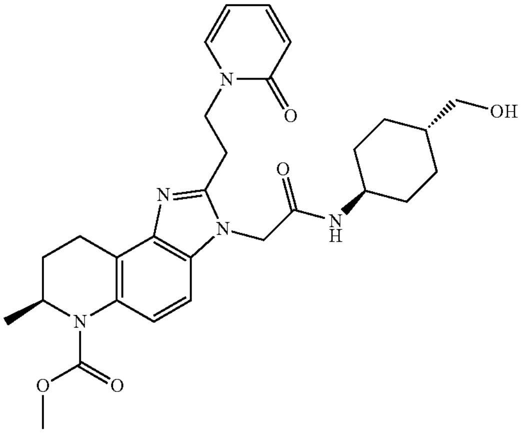 [SMILES: COC(=O)N1c2ccc3c(nc(CCn4ccccc4=O)n3CC(=O)N[C@H]3CC[C@H](CO)CC3)c2CC[C@@H]1C] methyl (S)-3-(2-(((trans)-4-(hydroxymethyl)cyclohexyl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 536 |
| 378 | 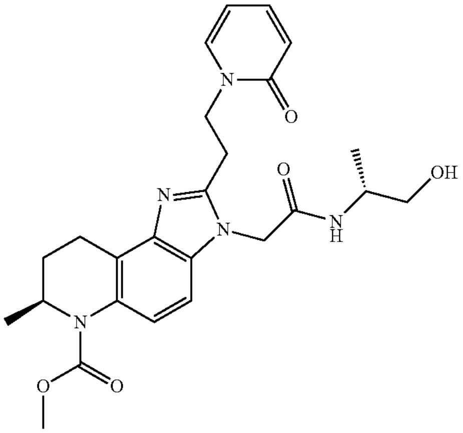 [SMILES: COC(=O)N1c2ccc3c(nc(CCn4ccccc4=O)n3CC(=O)N[C@H](C)CO)c2CC[C@@H]1C] mmethyl (S)-3-(2-(((R)-1-hydroxypropan-2-yl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 482 |
| 379 | 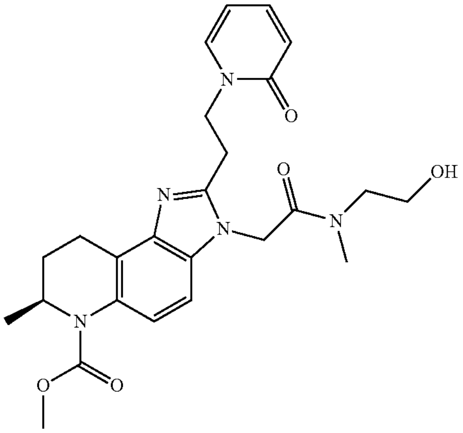 [SMILES: COC(=O)N1c2ccc3c(nc(CCn4ccccc4=O)n3CC(=O)N(C)CCO)c2CC[C@@H]1C] methyl (S)-3-(2-((2-hydroxyethyl)(methyl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 482 |

TABLE 16-continued

| Example Number | Structure and Compound Name | LRMS m/z [M + H]+ |
|---|---|---|
| 380 | 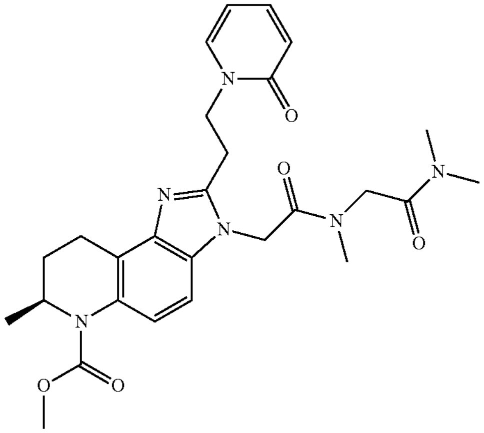 methyl (S)-3-(2-((2-(dimethylamino)-2-oxoethyl)(methyl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 523 |
| 381 | 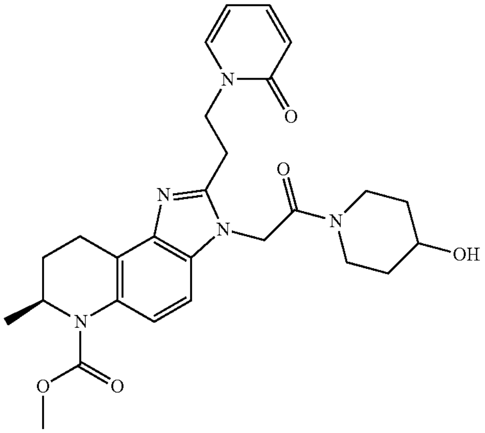 [SMILES: COC(=O)N1c2ccc3c(nc(CCn4ccccc4=O)n3CC(=O)N3CCC(O)CC3)c2CC[C@@H]1C] methyl (S)-3-(2-(4-hydroxypiperidin-1-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 508 |
| 382 | 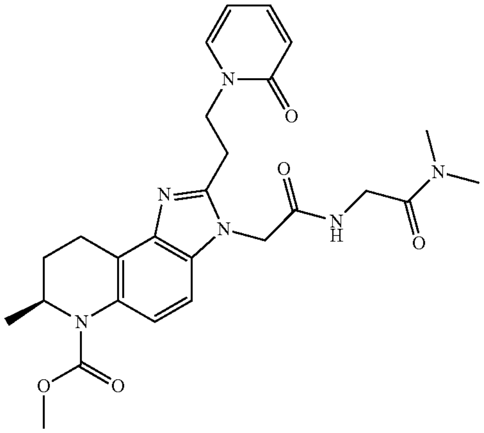 methyl (S)-3-(2-((2-(dimethylamino)-2-oxoethyl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 509 |

TABLE 16-continued

| Example Number | Structure and Compound Name | LRMS m/z [M + H]+ |
|---|---|---|
| 383 | 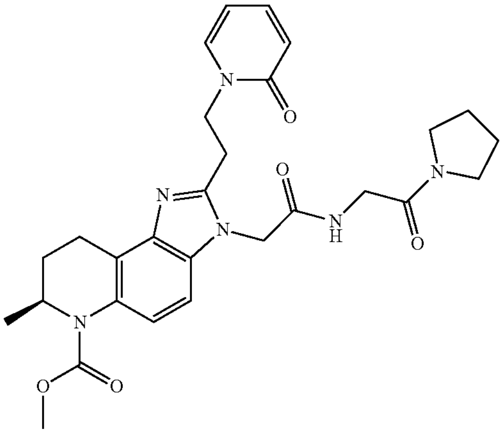 [SMILES: COC(=O)N1c2ccc3c(nc(CCn4ccccc4=O)n3CC(=O)NCC(=O)N3CCCC3)c2CC[C@@H]1C] methyl (S)-7-methyl-3-(2-oxo-2-((2-oxo-2-(pyrrolidin-1-yl)ethyl)amino)ethyl)-2-(2-(2-oxopyridin-1(2H)-yl)ethyl)-3,7,8,9-tetrahydro-6H-imidazo[4,5-f]quinoline-6-carboxylate | 535 |
| 384 | 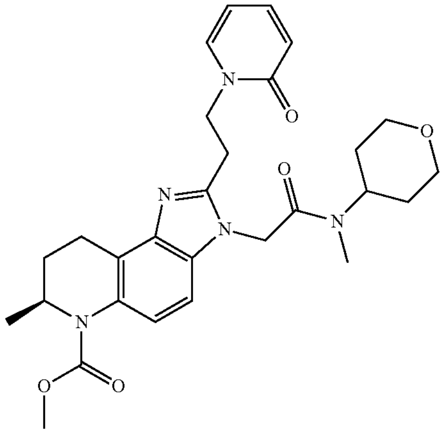 [SMILES: COC(=O)N1c2ccc3c(nc(CCn4ccccc4=O)n3CC(=O)N(C)C3CCOCC3)c2CC[C@@H]1C] methyl (S)-7-methyl-3-(2-(methyl(tetrahydro-2H-pyran-4-yl)amino)-2-oxoethyl)-2-(2-(2-oxopyridin-1(2H)-yl)ethyl)-3,7,8,9-tetrahydro-6H-imidazo[4,5-f]quinoline-6-carboxylate | 522 |
| 385 | 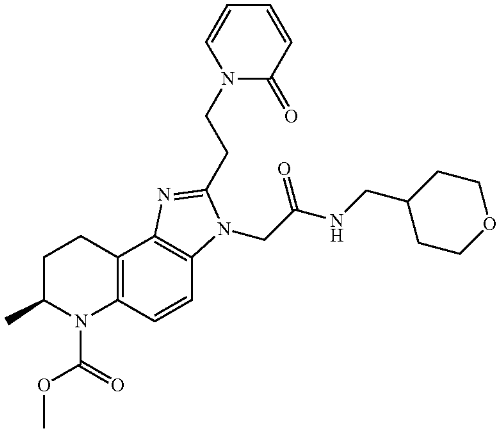 [SMILES: COC(=O)N1c2ccc3c(nc(CCn4ccccc4=O)n3CC(=O)NCC3CCOCC3)c2CC[C@@H]1C] methyl (S)-7-methyl-3-(2-oxo-2-(((tetrahydro-2H-pyran-4-yl)methyl)amino)ethyl)-2-(2-(2-oxopyridin-1(2H)-yl)ethyl)-3,7,8,9-tetrahydro-6H-imidazo[4,5-f]quinoline-6-carboxylate | 522 |

TABLE 16-continued

| Example Number | Structure and Compound Name | LRMS m/z [M + H]+ |
|---|---|---|
| 386 | 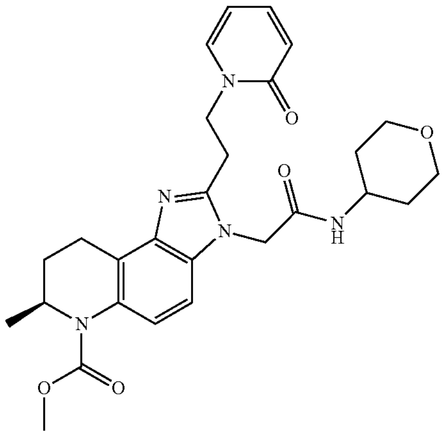 [SMILES: COC(=O)N1c2ccc3c(nc(CCn4ccccc4=O)n3CC(=O)NC3CCOCC3)c2CC[C@@H]1C] methyl (S)-7-methyl-3-(2-oxo-2-((tetrahydro-2H-pyran-4-yl)amino)ethyl)-2-(2-(2-oxopyridin-1(2H)-yl)ethyl)-3,7,8,9-tetrahydro-6H-imidazo[4,5-f]quinoline-6-carboxylate | 508 |
| 387 | 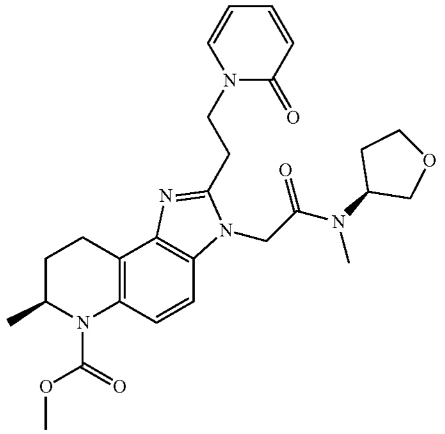 [SMILES: COC(=O)N1c2ccc3c(nc(CCn4ccccc4=O)n3CC(=O)N(C)[C@H]3CCOC3)c2CC[C@@H]1C] methyl (S)-7-methyl-3-(2-(methyl((S)-tetrahydrofuran-3-yl)amino)-2-oxoethyl)-2-(2-(2-oxopyridin-1(2H)-yl)ethyl)-3,7,8,9-tetrahydro-6H-imidazo[4,5-f]quinoline-6-carboxylate | 508 |
| 388 | 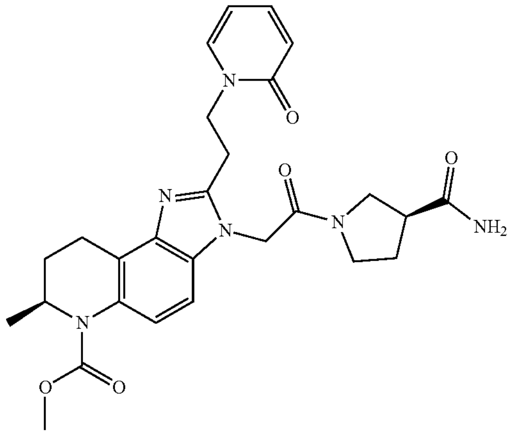 [SMILES: COC(=O)N1c2ccc3c(nc(CCn4ccccc4=O)n3CC(=O)N3CC[C@H](C(N)=O)C3)c2CC[C@@H]1C] methyl (S)-3-(2-((S)-3-carbamoylpyrrolidin-1-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 521 |

TABLE 16-continued

| Example Number | Structure and Compound Name | LRMS m/z [M + H]+ |
|---|---|---|
| 389 | 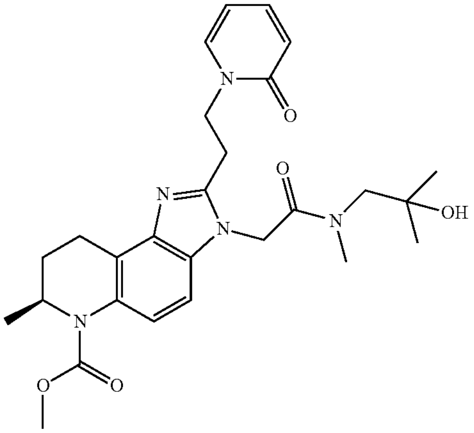 [SMILES: COC(=O)N1c2ccc3c(nc(CCn4ccccc4=O)n3CC(=O)N(C)CC(C)(C)O)c2CC[C@@H]1C] methyl (S)-3-(2-((2-hydroxy-2-methylpropyl)(methyl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 510 |
| 390 | 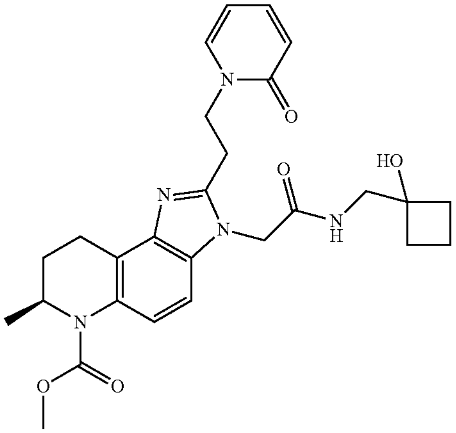 [SMILES: COC(=O)N1c2ccc3c(nc(CCn4ccccc4=O)n3CC(=O)NCC3(O)CCC3)c2CC[C@@H]1C] methyl (S)-3-(2-(((1-hydroxycyclobutyl)methyl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 508 |
| 391 | 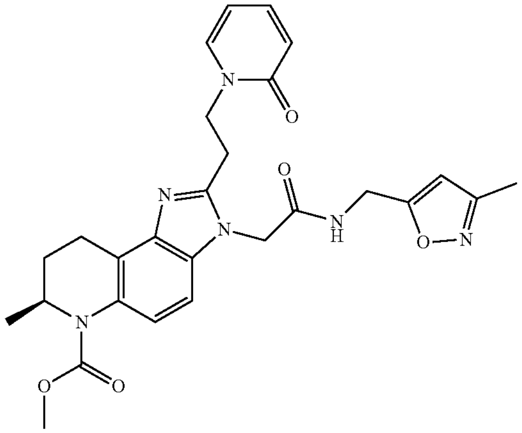 methyl (S)-7-methyl-3-(2-(((3-methylisoxazol-5-yl)methyl)amino)-2-oxoethyl)-2-(2-(2-oxopyridin-1(2H)-yl)ethyl)-3,7,8,9-tetrahydro-6H-imidazo[4,5-f]quinoline-6-carboxylate | 519 |

TABLE 16-continued

| Example Number | Structure and Compound Name | LRMS m/z [M + H]+ |
|---|---|---|
| 392 | 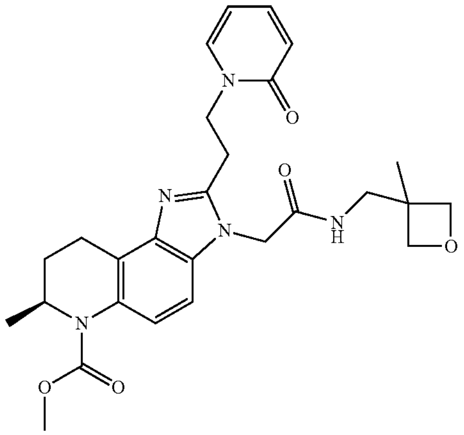 [SMILES: COC(=O)N1c2ccc3c(nc(CCn4ccccc4=O)n3CC(=O)NCC3(C)COC3)c2CC[C@@H]1C] mmethyl (S)-7-methyl-3-(2-(((3-methyloxetan-3-yl)methyl)amino)-2-oxoethyl)-2-(2-(2-oxopyridin-1(2H)-yl)ethyl)-3,7,8,9-tetrahydro-6H-imidazo[4,5-f]quinoline-6-carboxylate | 508 |
| 393 | 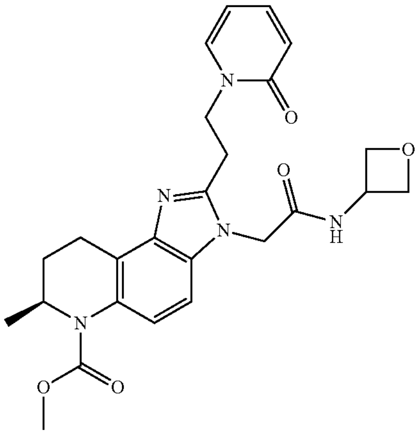 [SMILES: COC(=O)N1c2ccc3c(nc(CCn4ccccc4=O)n3CC(=O)NC3COC3)c2CC[C@@H]1C] methyl (S)-7-methyl-3-(2-(oxetan-3-ylamino)-2-oxoethyl)-2-(2-(2-oxopyridin-1(2H)-yl)ethyl)-3,7,8,9-tetrahydro-6H-imidazo[4,5-f]quinoline-6-carboxylate | 480 |
| 394 | 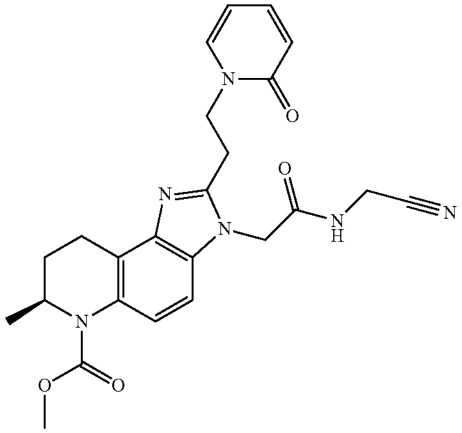 [SMILES: COC(=O)N1c2ccc3c(nc(CCn4ccccc4=O)n3CC(=O)NCC#N)c2CC[C@@H]1C] methyl (S)-3-(2-((cyanomethyl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 463 |

TABLE 16-continued

| Example Number | Structure and Compound Name | LRMS m/z [M + H]+ |
|---|---|---|
| 395 | 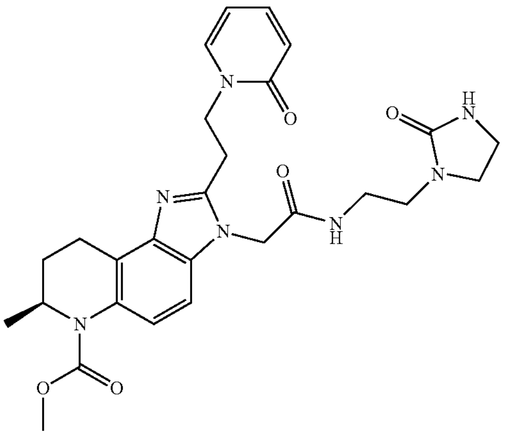 [SMILES: COC(=O)N1c2ccc3c(nc(CCn4ccccc4=O)n3CC(=O)NCCN3CCNC3=O)c2CC[C@@H]1C] methyl (S)-7-methyl-3-(2-oxo-2-((2-(2-oxoimidazolidin-1-yl)ethyl)amino)ethyl)-2-(2-(2-oxopyridin-1(2H)-yl)ethyl)-3,7,8,9-tetrahydro-6H-imidazo[4,5-f]quinoline-6-carboxylate | 536 |
| 396 | 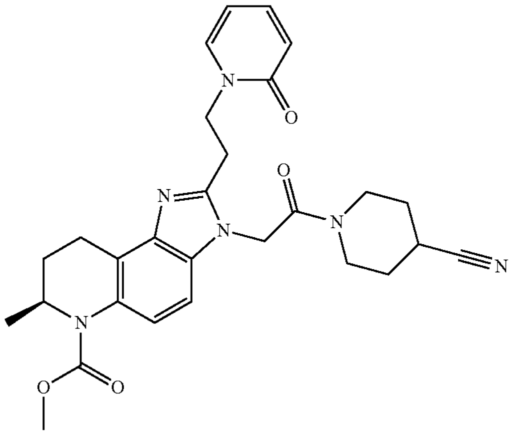 [SMILES: COC(=O)N1c2ccc3c(nc(CCn4ccccc4=O)n3CC(=O)N3CCC(C#N)CC3)c2CC[C@@H]1C] methyl (S)-3-(2-(4-cyanopiperidin-1-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 517 |
| 397 | 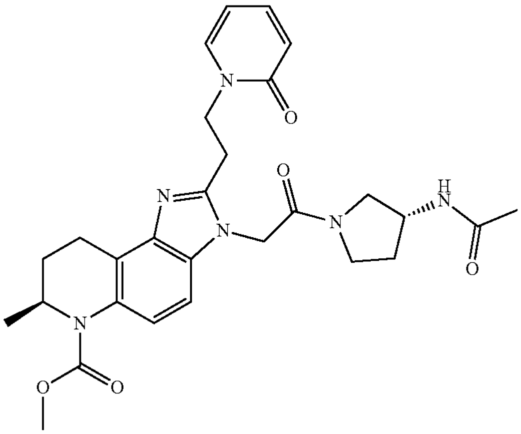 [SMILES: COC(=O)N1c2ccc3c(nc(CCn4ccccc4=O)n3CC(=O)N3CC[C@@H](NC(C)=O)C3)c2CC[C@@H]1C] methyl (S)-3-(2-((R)-3-acetamidopyrrolidin-1-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 535 |

TABLE 16-continued

| Example Number | Structure and Compound Name | LRMS m/z [M + H]+ |
| --- | --- | --- |
| 398 | 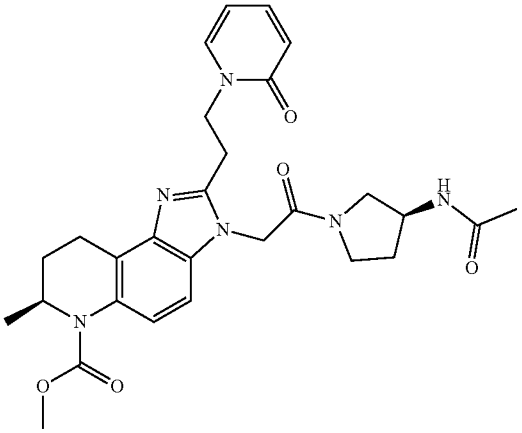 [SMILES: COC(=O)N1c2ccc3c(nc(CCn4ccccc4=O)n3CC(=O)N3CC[C@H](NC(C)=O)C3)c2CC[C@@H]1C] methyl (S)-3-(2-((S)-3-acetamidopyrrolidin-1-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 535 |
| 399 | 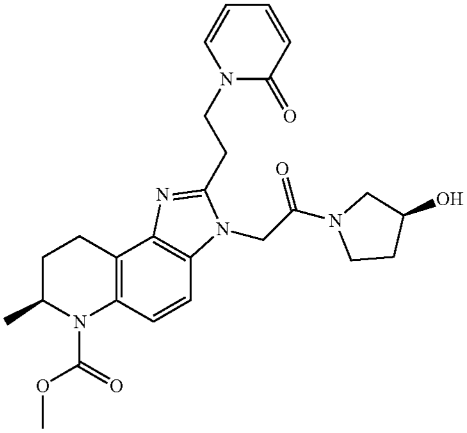 [SMILES: COC(=O)N1c2ccc3c(nc(CCn4ccccc4=O)n3CC(=O)N3CC[C@H](O)C3)c2CC[C@@H]1C] methyl (S)-3-(2-((S)-3-hydroxypyrrolidin-1-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 494 |
| 400 | 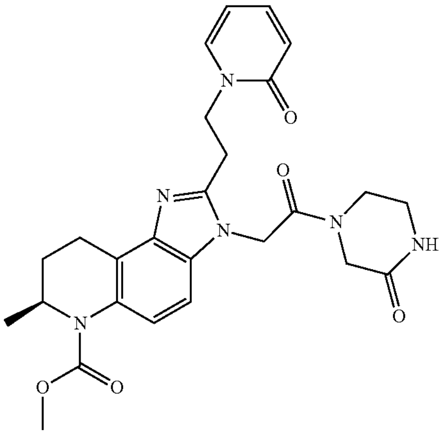 [SMILES: COC(=O)N1c2ccc3c(nc(CCn4ccccc4=O)n3CC(=O)N3CCNC(=O)C3)c2CC[C@@H]1C] methyl (S)-7-methyl-3-(2-oxo-2-(3-oxopiperazin-1-yl)ethyl)-2-(2-(2-oxopyridin-1(2H)-yl)ethyl)-3,7,8,9-tetrahydro-6H-imidazo[4,5-f]quinoline-6-carboxylate | 507 |

TABLE 16-continued

| Example Number | Structure and Compound Name | LRMS m/z [M + H]+ |
|---|---|---|
| 401 | 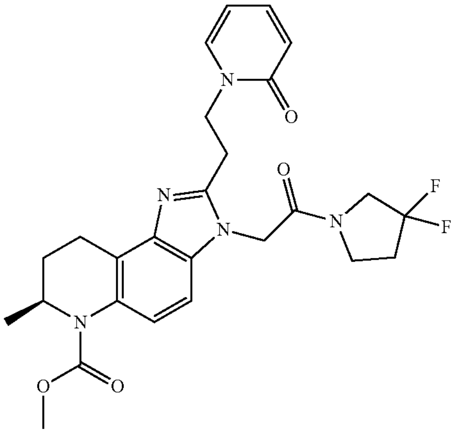 [SMILES: COC(=O)N1c2ccc3c(nc(CCn4ccccc4=O)n3CC(=O)N3CCC(F)(F)C3)c2CC[C@@H]1C] methyl (S)-3-(2-(3,3-difluoropyrrolidin-1-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 514 |
| 402 | 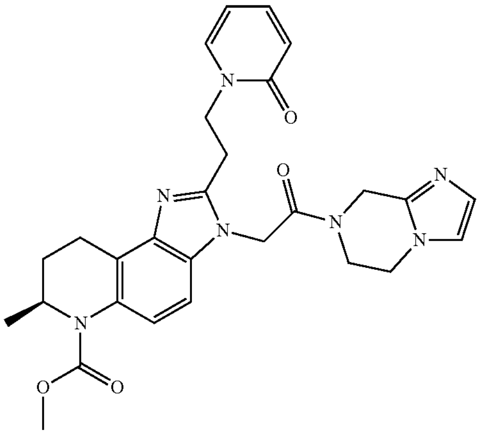 [SMILES: COC(=O)N1c2ccc3c(nc(CCn4ccccc4=O)n3CC(=O)N3CCn4ccnc4C3)c2CC[C@@H]1C] methyl (S)-3-(2-(5,6-dihydroimidazo[1,2-a]pyrazin-7(8H)-yl)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 530 |
| 403 | 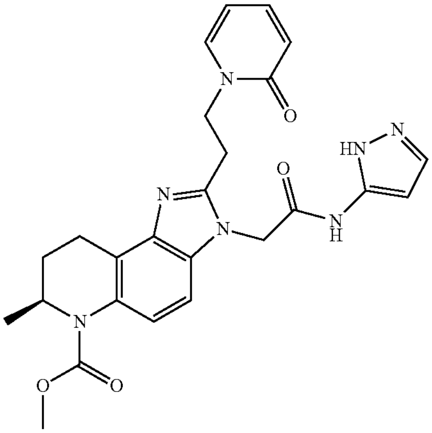 [SMILES: COC(=O)N1c2ccc3c(nc(CCn4ccccc4=O)n3CC(=O)Nc3ccn[nH]3)c2CC[C@@H]1C] methyl (S)-3-(2-((1H-pyrazol-5-yl)amino)-2-oxoethyl)-7-methyl-2-(2-(2-oxopyridin-1(2H)-yl)ethyl)-3,7,8,9-tetrahydro-6H-imidazo[4,5-f]quinoline-6-carboxylate | 490 |

Example 413 and 501: (1R,3R)-3-[(7S)-2-[(R)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid; and (1R,3R)-3-[(7S)-2-[(S)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid
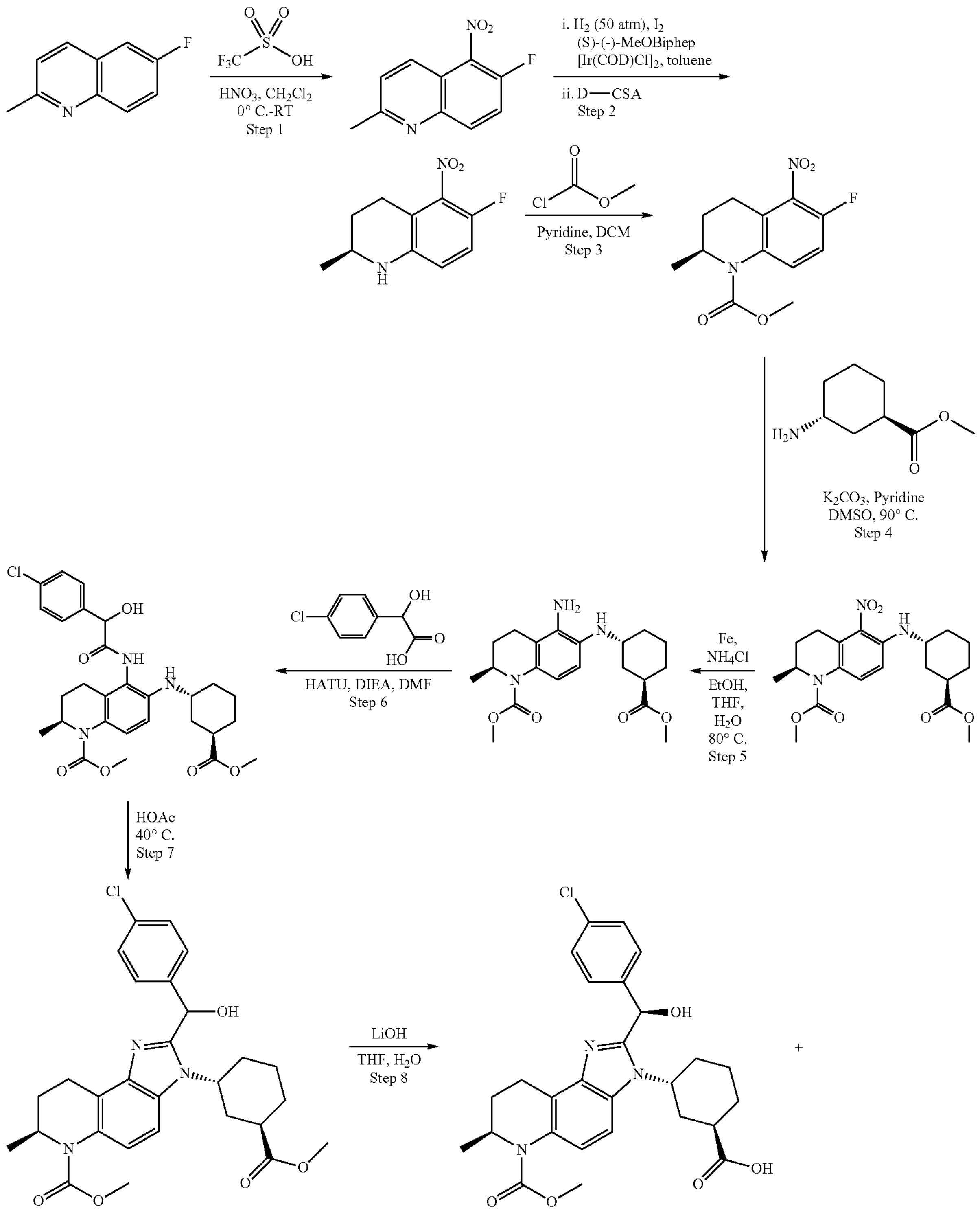

-continued

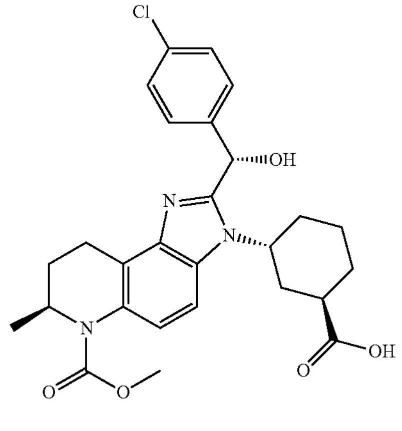 [SMILES: COC(=O)N1c2ccc3c(nc([C@@H](O)c4ccc(Cl)cc4)n3[C@@H]3CCC[C@@H](C(=O)O)C3)c2CC[C@@H]1C]

Step 1. 6-fluoro-2-methyl-5-nitroquinoline

A solution of trifluoromethanesulfonic acid (82.0 mL, 0.923 mol) in $HNO_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 hours at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 $[M+H]^+$ Step 2. (2S)-6-fluoro-2-methyl-5-nitro-1,2,3,4-tetrahydroquinoline A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of 12 (410 mg, 1.62 mmol), and 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers was dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 $[M+H]^+$ Step 3. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), and methyl carbonochloridate (18.7 mL, 0.242 mol) in dichloromethane (150 mL) was stirred for 3 h at room temperature (25° C.). The reaction was washed with 1N hydrogen chloride (aq., 2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 $[M+H]^+$ Step 4. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), and methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 $[M+H]^+$ Step 5. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), $NH_4Cl$ (24.3 g, 454.28 mmol), and Fe (powder, 64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]+

Step 6. methyl (2S)-5-[2-(4-chlorophenyl)-2-hydroxyacetamido]-6-[[(1R,3R)-3-(methoxycarbonyl) cyclohexyl]amino]-2-methyl-1,2,3,4-tetrahydroquinoline-1-carboxylate A solution of 2-(4-chlorophenyl)-2-hydroxyacetic acid (112 mg, 0.60 mmol), HATU (304 mg, 0.80 mmol), methyl (2S)-5-amino-6-[[(1R,3R)-3-(methoxycarbonyl)cyclohexyl]amino]-2-methyl-1,2,3,4-tetrahydroquinoline-1-carboxylate (150 mg, 0.40 mmol), and DIEA (155 mg, 1.20 mmol) in N,N-dimethylformamide (2 mL) was stirred for 15 h at room temperature (25° C.). The resulting solution was diluted with water (30 mL), and extracted with ethyl acetate (3×50 mL). The organic layers were combined and washed with brine (2×25 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-5-[2-(4-chlorophenyl)-2-hydroxyacetamido]-6-[[(1R,3R)-3-(methoxycarbonyl)cyclohexyl]amino]-2-methyl-1,2,3,4-tetrahydroquinoline-1-carboxylate as yellow oil (70.0 mg, 32%). LCMS (ES, m/z): 544 [M+H]+.

Step 7. methyl (7S)-2-[(4-chlorophenyl)(hydroxy) methyl]-3-[(1R,3R)-3-(methoxycarbonyl)cyclohexyl]-7-methyl-3H,6H,7H,8H,9H-imidazo[4,5-f] quinoline-6-carboxylate A solution of methyl (2S)-5-[2-(4-chlorophenyl)-2-hydroxyacetamido]-6-[[(1R,3R)-3-(methoxycarbonyl)cyclohexyl]amino]-2-methyl-1,2,3,4-tetrahydroquinoline-1-carboxylate (60.0 mg, 0.11 mmol) in AcOH (2 mL) was stirred for 15 h at 40° C. and then cooled to room temperature. The reaction mixture was diluted with water (10 mL). The pH value of the solution was adjusted to 8 with sodium bicarbonate (saturated aqueous solution). The resulting solution was extracted with ethyl acetate (3×15 mL). The organic layers were combined and dried over anhydrous sodium sulfate, filtered, and concentrated under vacuum. The resulting crude product was purified by silica gel chromatography (eluting with 1:1 ethyl acetate/petroleum ether) to afford methyl (7S)-2-[(4-chlorophenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate as yellow oil (46.0 mg, 79%). LCMS (ES, m/z): 526 [M+H]+.

Step 8. (1R,3R)-3-[(7S)-2-[(R)-(4-chlorophenyl) (hydroxy)methyl]-6-(methoxycarbonyl)-7-methyl-3H,6H,7H,8H,9H-imidazo[4,5-f]quinolin-3-yl]cyclohexane-1-carboxylic acid; and (1R,3R)-3-[(7S)-2-[(S)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid A solution of methyl (7S)-2-[(4-chlorophenyl)(hydroxy) methyl]-3-[(1R,3R)-3-(methoxycarbonyl)cyclohexyl]-7-methyl-3H,6H,7H,8H,9H-imidazo[4,5-f]quinoline-6-carboxylate (50.0 mg, 0.10 mmol), and LiOH (11.4 mg, 0.48 mmol) in tetrahydrofuran (1 mL) and water (1 mL) was stirred for 15 h at 25° C. The resulting mixture was concentrated under vacuum. The crude product was purified by Prep-HPLC (Column: XBridge Shield RP18 OBD Column, 5 um, 19×150 mm; Mobile Phase, A: water (containing 10 mmol/L $NH_4HCO_3$) and B: ACN (10% to 37% over 12 min); Detector: UV 254 nm). The product fractions were lyophilized to afford (1R,3R)-3-[(7S)-2-[(R)-(4-chlorophenyl)(hydroxy)methyl]-6-(methoxycarbonyl)-7-methyl-3H,6H,7H,8H,9H-imidazo[4,5-f]quinolin-3-yl]cyclohexane-1-carboxylic acid as a white solid (10.5 mg, 43%); and (1R,3R)-3-[(7S)-2-[(S)-(4-chlorophenyl)(hydroxy)methyl]-6-(methoxycarbonyl)-7-methyl-3H,6H,7H,8H,9H-imidazo [4,5-f]quinolin-3-yl]cyclohexane-1-carboxylic acid as a white solid (7.0 mg, 29%). The absolute stereochemisties are unknown and therefore are left undefined in Table 17. First eluting isomer (413): $^1$H-NMR ($CD_3OD$, 400 MHz) δ (ppm): 7.49 (d, J=9.0 Hz, 1H), 7.42-7.33 (m, 5H), 6.19 (s, 1H), 4.92-4.90 (m, 1H), 4.82-4.72 (m, 1H), 3.79 (s, 3H), 3.34-3.20 (m, 1H), 3.02-2.94 (m, 1H), 2.90-2.87 (m, 1H), 2.36-2.09 (m, 4H), 1.99-1.96 (m, 1H), 1.80-1.42 (m, 5H), 1.16 (d, J=6.6 Hz, 3H). LCMS (ES, m/z): 512 [M+H]+. Second eluting isomer (501): $^1$H-NMR ($CD_3OD$, 400 MHz) δ (ppm): 7.52-7.33 (m, 6H), 6.22 (s, 1H), 4.84-4.73 (m, 2H), 3.78 (s, 3H), 3.27-3.16 (m, 1H), 3.04-2.92 (m, 1H), 2.90-2.88 (m, 1H), 2.46-2.35 (m, 2H), 2.30-2.22 (m, 1H), 2.15-2.02 (m, 2H), 1.82-1.71 (m, 1H), 1.63-1.55 (m, 2H), 1.40-1.28 (m, 1H), 1.15 (d, J=6.6 Hz, 4H). LCMS (ES, m/z): 512 [M+H]+.

Examples 424 and 660: (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (424); (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (660)

Synthesis of intermediate 2-(5-fluoro-2-methoxyphenyl)-2-hydroxyacetic acid

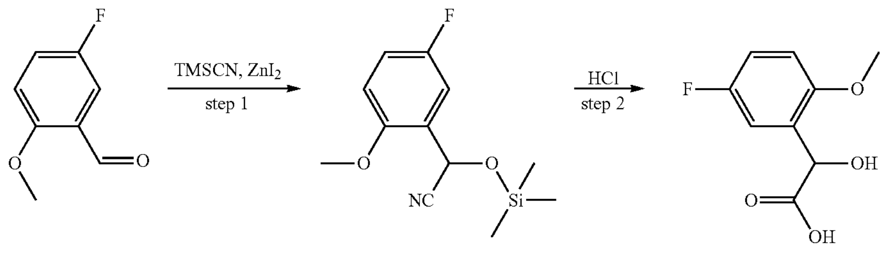

2-(5-fluoro-2-methoxyphenyl)-2-hdroxyacetic acid

-continued
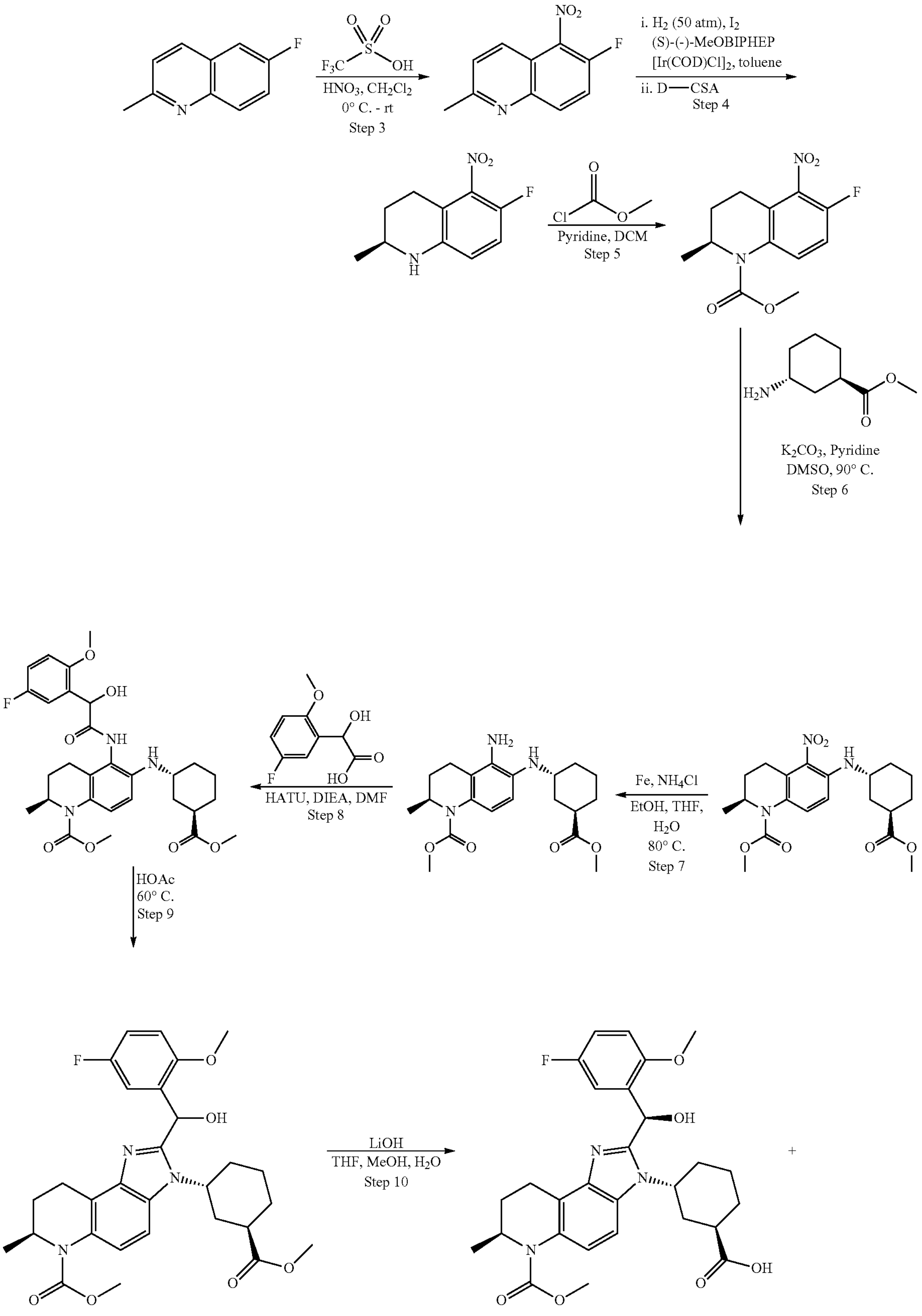
424

-continued

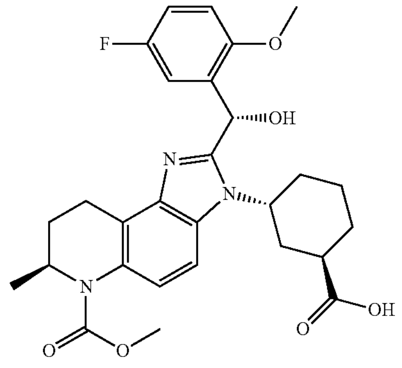

660

Step 1. 2-(5-fluoro-2-methoxyphenyl)-2-[(trimethylsilyl)oxy]acetonitrile

A solution of $ZnI_2$ (1.6 mg, 0.01 mmol), 5-fluoro-2-methoxybenzaldehyde (1.54 g, 9.99 mmol) in trimethylsilanecarbonitrile (1.5 mL, 11.25 mmol) was stirred for 1 h at room temperature. The resulting mixture was concentrated under vacuum. The resulting crude product was purified by silica gel chromatography (eluting with 1:1 ethyl acetate/petroleum ether) to afford 2-(5-fluoro-2-methoxyphenyl)-2-[(trimethylsilyl)oxy]acetonitrile as a white solid (2.0 g, 79%).

Step 2. 2-(5-fluoro-2-methoxyphenyl)-2-hydroxyacetic acid

A solution of 2-(5-fluoro-2-methoxyphenyl)-2-[(trimethylsilyl)oxy]acetonitrile (1.50 g, 5.92 mmol) in hydrogen chloride (10 mL, 12M). The resulting solution was stirred for 1 h at 25° C., and then stirred for 2 h at 70° C. The reaction mixture was cooled and concentrated under vacuum. The crude product was purified by reverse phase chromatography (Column: C18; Mobile phase, A: water (containing 0.05% TFA) and B: ACN (5% to 20% over 30 min); Detector, UV 254 nm) to afford 2-(5-fluoro-2-methoxyphenyl)-2-hydroxyacetic acid as a white solid (1.10 g, 93%).

Step 3. 6-fluoro-2-methyl-5-nitroquinoline

A solution of trifluoromethanesulfonic acid (82.0 mL, 0.923 mol) in $HNO_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 $[M+H]^+$ Step 4. (2S)-6-fluoro-2-methyl-5-nitro-1,2,3,4-tetrahydroquinoline A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of $I_2$ (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers was dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 $[M+H]^+$ Step 5. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1M hydrochorlic acid (2×70 mL). The combined organic layers was dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 $[M+H]^+$ Step 6. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers was dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 $[M+H]^+$ Step 7. methyl (2S)-5-amino-6-[[(1R,3R)-3-(methoxycarbonyl)cyclohexyl]amino]-2-methyl-1,2,3,4-tetrahydroquinoline-1-carboxylate A solution of methyl (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), $NH_4Cl$ (24.3 g, 454.28 mmol), Fe (64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers was dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 96%). LCMS (ES, m/z): 376 $[M+H]^+$ Step 8. methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate A solution of 2-(5-fluoro-2-methoxyphenyl)-2-hydroxyacetic acid (240 mg, 1.20 mmol), HATU (228 mg, 0.60 mmol), methyl (2S)-5-amino-6-[[(1R,3R)-3-(methoxycarbonyl)cyclohexyl]amino]-2-methyl-1,2,3,4-tetrahydroquinoline-1-carboxylate (150 mg, 0.40 mmol), and DIEA (0.19 mL, 1.20 mmol) in N,N-dimethylformamide (10 mL) was stirred for 1 h at 25° C. The resulting solution was diluted with $H_2O$ (10 mL). The resulting solution was extracted with ethyl acetate (3×15 mL) and the organic layers combined. The resulting mixture was washed with brine (2×20 mL). The mixture was dried over anhydrous sodium sulfate and concentrated under vacuum. The resulting crude product was purified by silica gel chromatography (eluting with 3:2 ethyl acetate/petroleum ether) to afford methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate as a yellow solid (180 mg, 81%). LCMS (ES, m z): 558 $[M+H]^+$ Step 9. methyl (7S)-2-[(5-fluoro-2-methoxyphenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate (180 mg, 0.32 mmol) in AcOH (8 mL) was stirred for overnight at 60° C. The reaction mixture was cooled and concentrated under vacuum. The resulting crude product was purified by silica gel chromatography (eluting with 1:1 ethyl acetate/petroleum ether) to afford methyl (7S)-2-[(5-fluoro-2-methoxyphenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate as a yellow solid (120 mg, 69%). LCMS (ES, m/z): 540 $[M+H]^+$ Step 10. (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid; (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid A solution of methyl (7S)-2-[(5-fluoro-2-methoxyphenyl)(hydroxy)methyl]-3-[(1R,3R)-3-(methoxycarbonyl)cyclohexyl]-7-methyl-3H,6H,7H,8H,9H-imidazo[4,5-f]quinoline-6-carboxylate (120 mg, 0.22 mmol), and LiOH (16 mg, 0.67 mmol) in tetrahydrofuran (2.0 mL), methanol (2.0 mL) and water (2.0 mL) was stirred overnight at 25° C. The resulting mixture was concentrated under vacuum. The crude product was purified by Prep-HPLC (Column, XBridge Prep C18 OBD Column, 19×150 mm, 5 um; Mobile phase, A: water (containing 10 mmol/L $NH_4HCO_3$) and B: ACN (15.0% to 29.0% over 14 min); Detector, UV 220/254 nm). The product was separated by Chiral-Prep-HPLC (Column, CHIRALPAK IE, 2×25 cm, 5 um; Mobile phase, A: Hex (containing 0.1% FA) and B: ethanol (hold 50.0% ethanol over 12 min); Detector, UV 220/254 nm). The product fractions were concentrated to afford (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid as a white solid (23.6 mg, 20%); and (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid as a white solid (23.8 mg, 2%). Enantiomeric excess was determined via HPLC: Column: CHIRALPAK IE-3, Column size: 0.46×5 cm; 3 μm; Mobile phase: Hex (0.1% FA): EtOH=50:50, Flow: 1.0 ml/min. For clarity, the absolute chemistry of each of compounds 424 and 660 was not included in table 17 however is shown in the scheme above.

First eluting isomer (424): $^1$H-NMR ($CD_3OD$, 400 MHz) δ (ppm): 7.56-7.47 (m, 1H), 7.47-7.31 (m, 1H), 7.21-7.09 (m, 1H), 7.09-6.89 (m, 2H), 6.53 (s, 1H), 4.81-4.61 (m, 2H), 3.85 (s, 3H), 3.78 (s, 3H), 3.31-3.18 (m, 1H), 3.06-2.82 (m, 2H), 2.57-2.41 (m, 1H), 2.41-2.31 (m, 1H), 2.31-2.09 (m, 3H), 1.83-1.58 (m, 3H), 1.49-1.21 (m, 2H), 1.16 (d, J=6.8 Hz, 3H). LCMS (ES, m/z): 526 $[M+H]^+$.

Second eluting isomer (660): $^1$H-NMR ($CD_3OD$, 400 MHz) δ (ppm): 7.69-7.44 (m, 2H), 7.44-7.29 (m, 1H), 7.12-6.99 (m, 1H), 6.98-6.82 (m, 1H), 6.37 (s, 1H), 5.03-4.91 (m, 1H), 4.81-4.69 (m, 1H), 3.78 (s, 3H), 3.61 (s, 3H), 3.22-3.04 (m, 1H), 3.02-2.87 (m, 2H), 2.54-2.41 (m, 1H), 2.41-2.27 (m, 1H), 2.27-2.08 (m, 3H), 1.82-1.58 (m, 3H), 1.58-1.41 (m, 2H), 1.14 (d, J=6.4 Hz, 3H). LCMS (ES, m/z): 526 $[M+H]^+$.

Examples 452 and 515: (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (515), (1R,3R)-3-[(7S)-2-[(R)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid (452)

Synthesis of intermediate 2-(2-(difluoromethoxy)-5-fluorophenyl)-2-hydroxyacetic acid

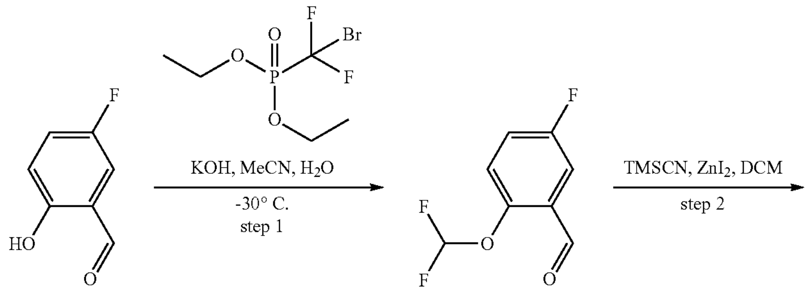

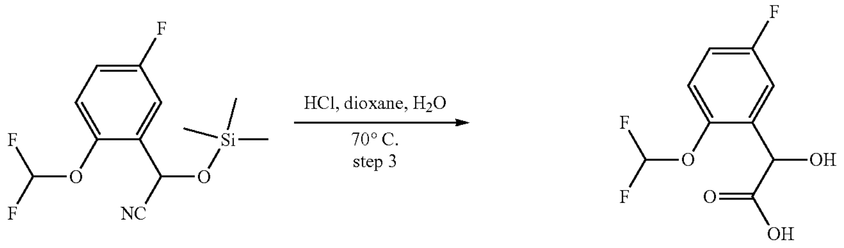

2-(2-(difluoromethoxy)-5-fluorophenyl)-2-hydroxyacetic acid

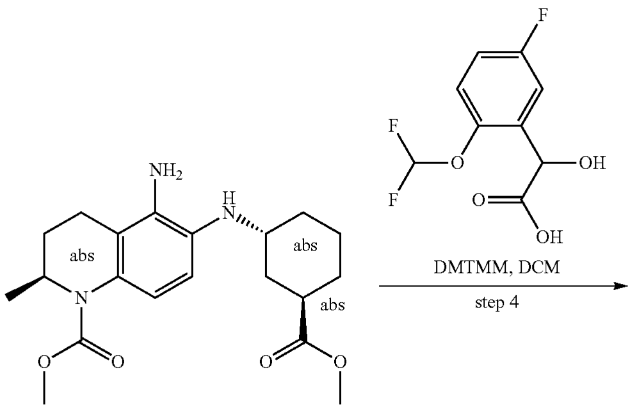

-continued

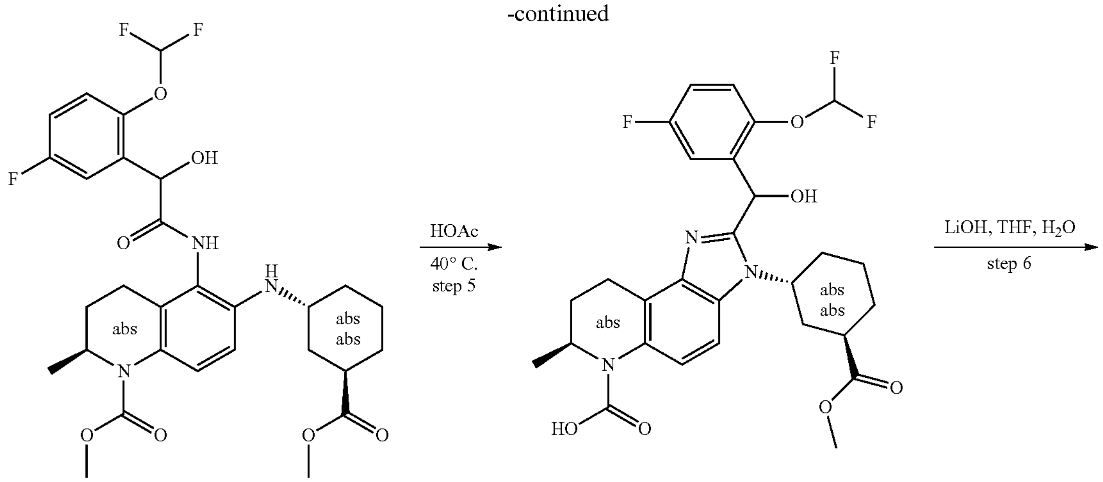

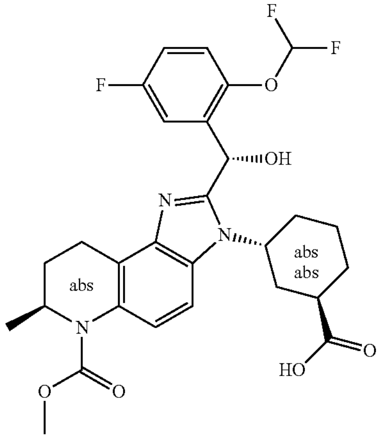

515

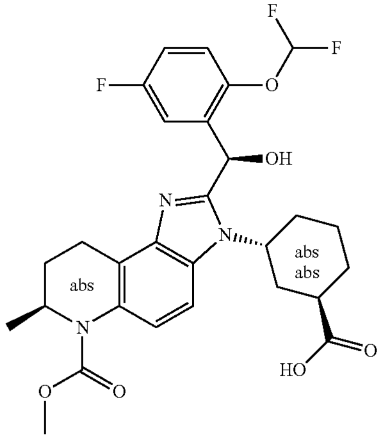

452

Step 1. 2-(difluoromethoxy)-5-fluorobenzaldehyde

A solution of 5-fluoro-2-hydroxybenzaldehyde (2.0 g, 14.3 mmol), diethyl (bromodifluoromethyl)phosphonate (5.69 g, 21.3 mmol), potassium hydroxide (16.0 g, 285 mmol) in MeCN (100 mL) and water (50 mL) was stirred for 1 h at −30° C. The reaction mixture was diluted with water (20 mL). The resulting solution was extracted with ethyl acetate (3×100 mL) and the organic layers combined and dried over anhydrous sodium sulfate. The solids were filtered out. The resulting mixture was concentrated under vacuum. The resulting crude product was purified by silica gel chromatography (eluting with 1:1 ethyl acetate/petroleum ether) to afford 2-(difluoromethoxy)-5-fluorobenzaldehyde as a yellow solid (1.46 g, 54%). LCMS (ES, m/z): 191 $[M+H]^+$ Step 2. 2-[2-(difluoromethoxy)-5-fluorophenyl]-2-[(trimethylsilyl)oxy]acetonitrile A solution of 2-(difluoromethoxy)-5-fluorobenzaldehyde (1.46 g, 7.68 mmol), TMSCN (760 mg, 7.66 mmol), $ZnI_2$ (50 mg, 0.16 mmol) in dichloromethane (3 mL) was stirred for 2 h at room temperature (25° C.). The resulting mixture was concentrated under vacuum. The resulting crude product was purified by silica gel chromatography (eluting with 1:1 ethyl acetate/petroleum ether) to afford 2-[2-(difluoromethoxy)-5-fluorophenyl]-2-[(trimethylsilyl)oxy]acetonitrile as a yellow solid (800 mg, 36%). LCMS (ES, m/z): 290 $[M+H]^+$ Step 3. 2-[2-(difluoromethoxy)-5-fluorophenyl]-2-hydroxyacetic acid A solution of 2-[2-(difluoromethoxy)-5-fluorophenyl]-2-[(trimethylsilyl)oxy]acetonitrile (800 mg, 2.77 mmol), 1,4-dioxane (2.0 mL), hydrogen chloride (1.0 mL, 12M) in water (2 mL) was stirred for 12 h at 70° C. and then cooled to room temperature. The resulting solution was concentrated under vacuum. The crude product was purified by reverse phase column chromatography (water (containing 0.05% TFA)/MeCN) to afford 2-[2-(difluoromethoxy)-5-fluorophenyl]-2-hydroxyacetic acid (400 mg, 61%). LCMS (ES, m/z): 237 $[M+H]^+$ Step 4. methyl (2S)-5-[2-[2-(difluoromethoxy)-5-fluorophenyl]-2-hydroxyacetamido]-6-[[(1R,3R)-3-(methoxycarbonyl)cyclohexyl]amino]-2-methyl-1,2,3,4-tetrahydroquinoline-1-carboxylate A solution of methyl (2S)-5-amino-6-[[(1R,3R)-3-(methoxycarbonyl)cyclohexyl]amino]-2-methyl-1,2,3,4-tetrahydroquinoline-1-carboxylate (prepared as in the scheme above for Example 424 and 660) (200 mg, 0.53 mmol), 2-[2-(difluoromethoxy)-5-fluorophenyl]-2-hydroxyacetic acid (220 mg, 0.93 mmol), DMTMM (350 mg, 1.26 mmol) in dichloromethane (5 mL) was stirred for 1 h room temperature (25° C.). The resulting solution was concentrated under vacuum. The resulting crude product was purified by silica gel chromatography (eluting with 1:1 ethyl acetate/petroleum ether) to afford methyl (2S)-5-[2-[2-(difluoromethoxy)-5-fluorophenyl]-2-hydroxyacetamido]-6-[[(1R,3R)-3-(methoxycarbonyl)cyclohexyl]amino]-2-methyl-1,2,3,4-tetrahydroquinoline-1-carboxylate as a yellow solid (70.0 mg, 22%). LCMS (ES, m/z): 594 $[M+H]^+$ Step 5. methyl (7S)-2-[[2-(difluoromethoxy)-5-fluorophenyl](hydroxy)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-[2-[2-(difluoromethoxy)-5-fluorophenyl]-2-hydroxyacetamido]-6-[[(1R,3R)-3-(methoxycarbonyl)cyclohexyl]amino]-2-methyl-1,2,3,4-tetrahydroquinoline-1-carboxylate (70.0 mg, 0.12 mmol) in glacial acetic acid (2.0 mL) was stirred for overnight at 40° C. and then cooled to room temperature. The resulting solution was concentrated under vacuum. The resulting crude product was purified by silica gel chromatography (eluting with 1:2 ethyl acetate/petroleum ether) to afford methyl (7S)-2-[[2-(difluoromethoxy)-5-fluorophenyl](hydroxy)methyl]-3-[(1R,3R)-3-(methoxycarbonyl)cyclohexyl]-7-methyl-3H,6H,7H,8H,9H-imidazo[4,5-f]quinoline-6-carboxylate as a yellow solid (50.0 mg, 74%). LCMS (ES, m/z): 576 $[M+H]^+$ Step 6. (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid; (1R,3R)-3-[(7S)-2-[(R)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid A solution of methyl (7S)-2-[[2-(difluoromethoxy)-5-fluorophenyl](hydroxy)methyl]-3-[(1R,3R)-3-(methoxycarbonyl)cyclohexyl]-7-methyl-3H,6H,7H,8H,9H-imidazo[4,5-f]quinoline-6-carboxylate (50.0 mg, 0.09 mmol), LiOH (10.0 mg, 0.42 mmol) in tetrahydrofuran (2.0 mL) and water (2.0 mL) was stirred for overnight at room temperature (25° C.). The resulting mixture was concentrated under vacuum. The crude product was purified by Prep-HPLC (Column, XBridge Shield RP18 OBD Column, 30×150 mm, 5 um; Mobile phase, A: water (containing 10 mmol/L $NH_4HCO_3$) and B: ACN (25.0% to 35.0% over 8 min); Detector, UV 254/220 nm). The product fractions were concentrated to afford (1R,3R)-3-[(7S)-2-[(S)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid as a white solid (4.50 mg, 9%), and (1R,3R)-3-[(7S)-2-[(R)-[2-(difluoromethoxy)-5-fluorophenyl](hydroxy)methyl]-6-(methoxycarbonyl)-7-methyl-3H,6H,7H,8H,9H-imidazo[4,5-f]quinolin-3-yl]cyclohexane-1-carboxylic acid as a white solid (4.30 mg, 9%). Enantiomeric excess was determined via HPLC: Column: CHIRALPAK IE-3, Column size: 0.46×5 cm; 3 μm; Co-Solvent: IPA (20 mM $NH_3$) Gradient (B %): 10% to 50% in 4.0 min, hold 2.0 min at 50%. For clarity, the absolute chemistry of each of compounds 452 and 515 was not included in table 17 however is shown in the scheme above. First eluting isomer (515): $^1$H-NMR ($CD_3OD$, 400 MHz) δ (ppm): 7.63-7.61 (m, 1H), 7.53 (d, J=8.8 Hz, 1H), 7.41 (d, J=9.2 Hz, 1H) 7.20-7.13 (m, 2H), 6.67-6.30 (m, 2H), 4.98-4.95 (m, 1H), 4.76-4.71 (m, 1H), 3.78 (s, 3H), 3.15-2.86 (m, 3H), 2.46-2.20 (m, 5H), 1.81-1.53 (m, 5H), 1.13 (d, J=6.8 Hz, 3H). LCMS (ES, m/z): 562 $[M+H]^+$.

Second eluting isomer (452): $^1$H-NMR ($CD_3OD$, 400 MHz) δ (ppm): 7.55-7.53 (m, 1H), 7.47-7.42 (m, 2H), 7.40-7.12 (m, 2H), 6.85-6.44 (m, 2H), 4.94-4.91 (m, 1H), 4.76-4.71 (m, 1H), 3.78 (s, 3H), 3.22-2.84 (m, 3H), 2.46-2.23 (m, 5H), 1.84-1.61 (m, 5H), 1.14 (d, J=6.4 Hz, 3H). LCMS (ES, m/z): 562 $[M+H]^+$; >99.99% ee.

Example 462: (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid

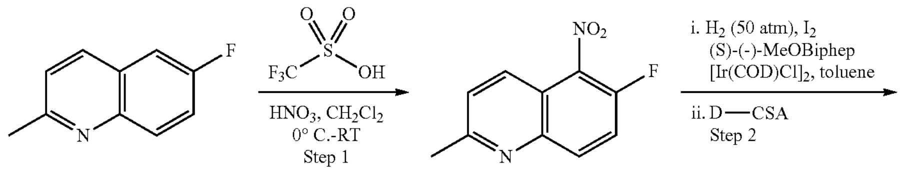

-continued

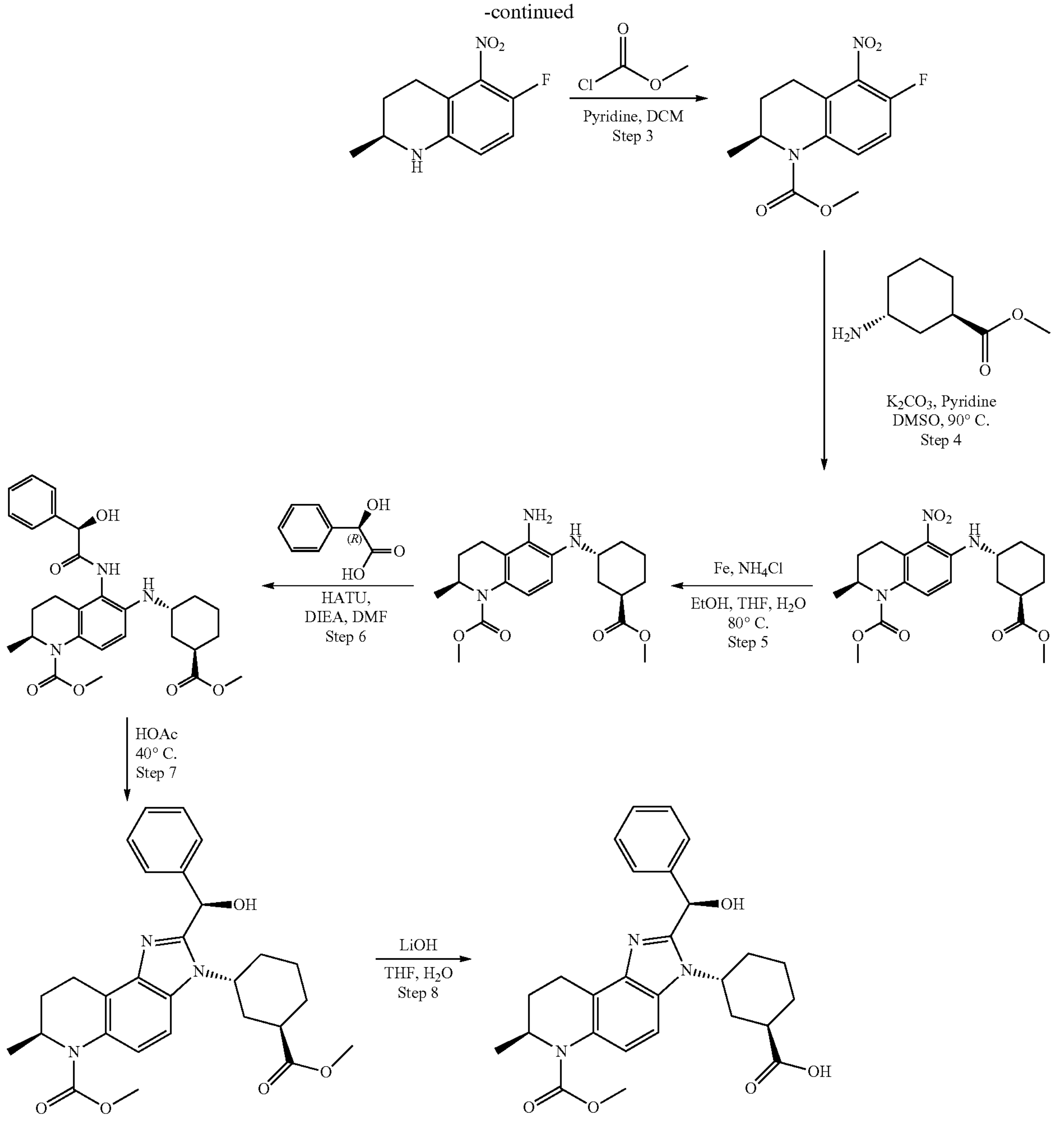

Step 1. 6-fluoro-2-methyl-5-nitroquinoline

A solution of trifluoromethanesulfonic acid (82.0 mL, 0.923 mol) in $HNO_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 $[M+H]^+$ Step 2. (2S)-6-fluoro-2-methyl-5-nitro-1,2,3,4-tetrahydroquinoline A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of $I_2$ (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers was dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 $[M+H]^+$ Step 3. methyl (2S)-6-fluoro-2-methyl-5-nitro-1,2,3,4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1M hydrogen chloride (2×70 mL). The combined organic layers was dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 $[M+H]^+$ Step 4. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2,3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers was dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl)cyclohexyl]amino]-2-methyl-5-nitro-1,2,3,4-tetrahydroquinoline-1-carboxylate as a red oil (32 g, 72%). LCMS (ES, m/z): 406 $[M+H]^+$ Step 5. methyl (2S)-5-amino-6-[[(1R,3R)-3-(methoxycarbonyl)cyclohexyl]amino]-2-methyl-1,2,3,4-tetrahydroquinoline-1-carboxylate A solution of (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), $NH_4Cl$ (24.3 g, 454.28 mmol), Fe (64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers was dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 $[M+H]^+$ Step 6. methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate A solution of (R)-2-hydroxy-2-phenylacetic acid (972 mg, 6.39 mmol), HATU (1.20 g, 3.16 mmol), methyl (2S)-5-amino-6-[[(1R,3R)-3-(methoxycarbonyl)cyclohexyl]amino]-2-methyl-1,2,3,4-tetrahydroquinoline-1-carboxylate (800 mg, 2.13 mmol), DIEA (1.08 mL, 6.20 mmol) in N,N-dimethylformamide (10 mL) was stirred for 5 h at room temperature (25° C.). The resulting solution was diluted with water (30 mL), and extracted with ethyl acetate (3×50 mL). The organic layers were combined and washed with brine (2×25 mL). The combined organic layers was dried over anhydrous sodium sulfate, filtered, and concentrated under vacuum. The resulting crude product was purified by silica gel chromatography (eluting with 1:1 ethyl acetate/petroleum ether) to afford methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate as a colorless oil (600 mg, 55%). LCMS (ES, m/z): 510 $[M+H]^+$ Step 7. methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate A solution of methyl (2S)-5-((R)-2-hydroxy-2-phenylacetamido)-6-[[(1R,3R)-3-(methoxycarbonyl)cyclohexyl]amino]-2-methyl-1,2,3,4-tetrahydroquinoline-1-carboxylate (600 mg, 1.18 mmol) in glacial acetic acid (5 mL, 98%) was stirred for overnight at 40° C. and then cooled to room temperature. The reaction mixture was diluted with water (10 mL). The pH value of the solution was adjusted to 8 with sodium bicarbonate (saturated aqueous solution). The resulting solution was extracted with ethyl acetate (3×15 mL). The organic layers were combined and dried over anhydrous sodium sulfate, filtered, and concentrated under vacuum. The resulting crude product was purified by silica gel chromatography (eluting with 1:1 ethyl acetate/petroleum ether) to afford methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate (400 mg, 69%) as a colorless oil. LCMS (ES, m/z): 492 $[M+H]^+$ Step 8. (1R,3R)-3-[(7S)-2-[(R)-hydroxy(phenyl)methyl]-6-(methoxycarbonyl)-7-methyl-3H,6H,7H,8H,9H-imidazo[4,5-f]quinolin-3-yl]cyclohexane-1-carboxylic acid A solution of methyl (7S)-2-[(R)-hydroxy(phenyl)methyl]-3-[(1R,3R)-3-(methoxycarbonyl)cyclohexyl]-7-methyl-3H,6H,7H,8H,9H-imidazo[4,5-f]quinoline-6-carboxylate (400 mg, 0.81 mmol), LiOH (100 mg, 4.17 mmol) in tetrahydrofuran (5 mL) and water (2 mL) was stirred for overnight at room temperature (25° C.). The resulting mixture was concentrated under vacuum. The crude product was purified by Prep-HPLC (Column: XBridge Shield RP18 OBD Column, 5 um, 19×150 mm; Mobile Phase, A: water (containing 10 mmol/L $NH_4HCO_3$) and B: ACN (3% to 30% over 21 min); Detector: UV 254 nm). The product fractions were lyophilized to afford (1R,3R)-3-[(7S)-2-[(R)-hydroxy (phenyl)methyl]-6-(methoxycarbonyl)-7-methyl-3H,6H, 7H,8H,9H-imidazo[4,5-f]quinolin-3-yl]cyclohexane-1-carboxylic acid as a white solid (83.7 mg, 22%). Enantiomeric excess was determined via HPLC: Column: CHIRALPAK IE-3, Column size: 0.46×5 cm; 3 μm; Mobile phase: Hex (0.1% FA): EtOH=85:15, Flow: 1.0 ml/min. For clarity, the absolute chemistry was not included in table 17 however is shown here instead. $^1$H-NMR ($CD_3OD$, 400 MHz) δ (ppm): 7.47-7.28 (m, 7H), 6.12 (s, 1H), 4.84-4.74 (m, 2H), 3.79 (s, 3H), 3.33-3.25 (m, 1H), 3.03-2.96 (m, 1H), 2.86-2.82 (m, 1H), 2.38-2.25 (m, 2H), 2.25-2.07 (m, 3H), 1.79-1.72 (m, 1H), 1.64-1.57 (m, 2H), 1.40-1.29 (m, 2H), 1.16 (d, J=6.8 Hz, 3H). LCMS (ES, m/z): 478 $[M+H]^+$; 99.13% ee.

The following examples in TABLE 17 were prepared using standard chemical manipulations and procedures similar to those used for the preparation of previous Examples.

TABLE 17

| Example Number | Structure and Compound Name | LRMS m/z [M + H] | $^1$H NMR |
|---|---|---|---|
| 404[1] | 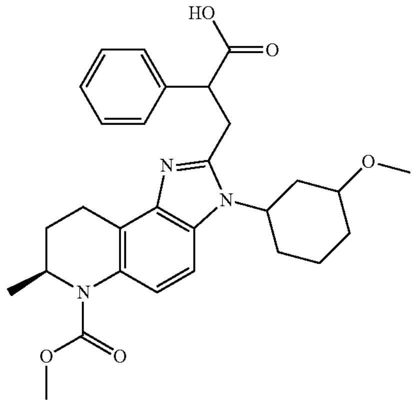 3-((7S)-6-(methoxycarbonyl)-3-(3-methoxycyclohexyl)-7-methyl-6,7,8,9-tetrahydro-3H-imidazo[4,5-f]quinolin-2-yl)-2-phenylpropanoic acid 2nd eluting isomer | 506 | $^1$HNMR ($CD_3OD$, 300 MHz) δ (ppm): 7.31-7.05 (m, 7H), 4.70-4.61 (m, 1H), 4.18-3.89 (m, 2H), 3.67 (s, 3H), 3.66-3.51 (m, 1H), 3.38-3.31 (m, 1H), 3.28 (s, 3H), 3.15-2.98 (m, 1H), 2.88-2.76 (m, 1H), 2.24-1.95 (m, 3H), 1.92-1.80 (m, 3H), 1.75-1.54 (m, 2H), 1.28-1.11 (m, 2H), 1.01 (d, J = 6.6 Hz, 3H), 0.86-0.81 (m, 1H). |
| 405[2] | 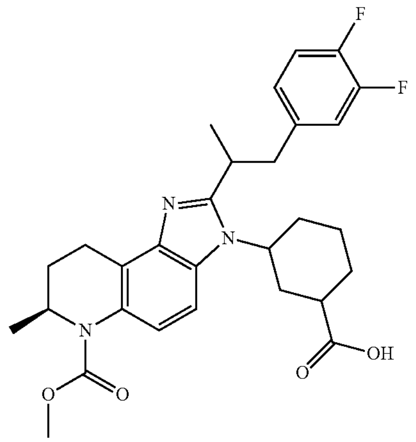 3-((7S)-2-(1-(3,4-difluorophenyl)propan-2-yl)-6-(methoxycarbonyl)-7-methyl-6,7,8,9-tetrahydro-3H-imidazo[4,5-f]quinolin-3-yl)cyclohexane-1-carboxylic acid 1st eluting isomer | 526 | $^1$HNMR ($CD_3OD$, 400 MHz) δ (ppm): 7.41 (d, J = 9.2 Hz, 1H), 7.29 (d, J = 8.8 Hz, 1H), 7.06-7.01 (m, 2H), 6.84-6.86 (m, 1H), 4.73-4.64 (m, 2H), 3.76 (s, 3H), 3.70-3.64 (m, 1H), 3.31-3.14 (m, 2H), 3.08-3.04 (m, 1H), 2.95-2.80 (m, 2H), 2.28-2.19 (m, 5H), 1.72-1.47 (m, 7H), 1.12 (d, J = 6.8 Hz, 3H), 1.09-0.92 (m, 1H). |

TABLE 17-continued

| Example Number | Structure and Compound Name | LRMS m/z [M + H] | $^1$H NMR |
|---|---|---|---|
| 406[2] | 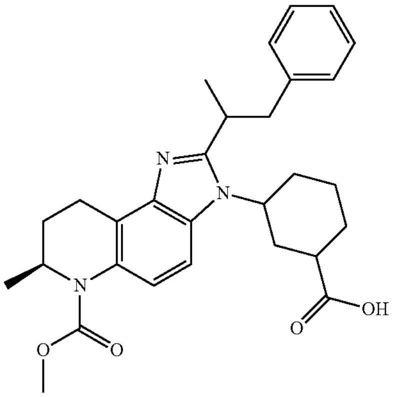 3-((7S)-6-(methoxycarbonyl)-7-methyl-2-(1-phenylpropan-2-yl)-6,7,8,9-tetrahydro-3H-imidazo[4,5-f]quinolin-3-yl)cyclohexane-1-carboxylic acid 1st eluting isomer | 490 | $^1$HNMR ($CD_3OD$, 400 MHz) δ (ppm): 7.37 (d, J = 9.2 Hz, 1H), 7.27 (d, J = 8.8 Hz, 1H), 7.17-7.10 (m, 3H), 7.03 (d, J = 6.8 Hz, 2H), 4.88-4.72 (m, 1H), 4.48-4.35 (m, 1H), 3.77 (s, 3H), 3.70-3.61 (m, 1H), 3.33-3.21 (m, 1H), 3.18-3.01 (m, 2H), 2.98-2.86 (m, 2H), 2.31-1.95 (m, 5H), 1.75-1.53 (m, 6H), 1.35-1.28 (m, 1H), 1.12 (d, J = 6.4 Hz, 3H), 0.90-0.81 (m, 1H). |
| 407[1] | 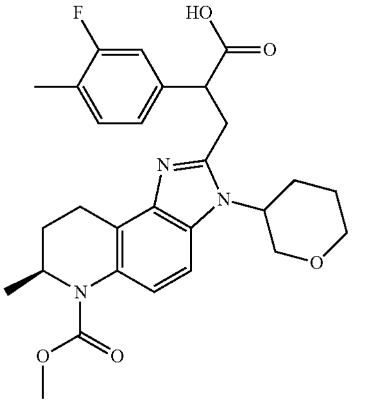 (7S)-2-(3-fluoro-4-methylphenyl)-3-(6-(methoxycarbonyl)-7-methyl-3-(tetrahydro-2H-pyran-3-yl)-6,7,8,9-tetrahydro-3H-imidazo[4,5-f]quinolin-2-yl)propanoic acid 2nd eluting isomer | 510 | $^1$HNMR ($CD_3OD$, 300 MHz) δ (ppm): 7.60 (d, J = 9.0 Hz, 1H), 7.49 (d, J = 9.0 Hz, 1H), 7.22 (t, J = 7.8 Hz, 1H), 7.13 (d, J = 7.2 Hz, 1H), 7.05 (d, J = 9.0 Hz, 1H), 4.88-4.77 (m, 1H), 4.65-4.60 (m, 1H), 4.33-4.28 (m, 1H), 3.96-3.80 (m, 3H), 3.77 (s, 3H), 3.75-3.72 (m, 1H), 3.58-3.34 (m, 2H), 3.24-3.09 (m, 2H), 2.51-2.20 (m, 5H), 1.83-1.74 (m, 3H), 1.44-1.35 (m, 1H), 1.14 (d, J = 6.6 Hz, 3H). |

TABLE 17-continued

| Example Number | Structure and Compound Name | LRMS m/z [M + H] | $^1$H NMR |
|---|---|---|---|
| 408[2] | 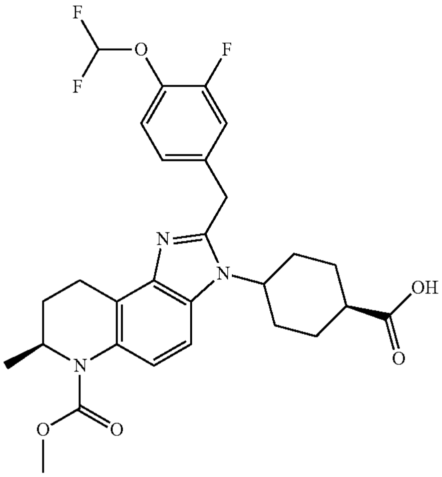 (1S,4R)-4-((S)-2-(4-(difluoromethoxy)-3-fluorobenzyl)-6-(methoxycarbonyl)-7-methyl-6,7,8,9-tetrahydro-3H-imidazo[4,5-f]quinolin-3-yl)cyclohexane-1-carboxylic acid | 546 | $^1$HNMR ($CD_3OD$, 400 MHz) δ (ppm): 7.47 (d, J = 8.8 Hz, 1H), 7.40 (d, J = 9.2 Hz, 1H), 7.26 (t, J = 8.0 Hz, 1H), 7.18 (d, J6.4 Hz, 1H), 7.08 (d, J = 8.4 Hz, 1H), 6.99-6.87 (t, 1H), 4.87-4.74 (m, 1H), 4.41 (s, 2H), 4.24-4.20 (m, 1H), 3.77 (s, 3H), 3.20-3.16 (m, 1H), 2.99-2.93 (m, 1H), 2.42-2.20 (m, 4H), 2.08-2.05 (m, 2H), 1.77-1.72 (m, 1H), 1.58-1.46 (m, 4H), 1.14 (d, J = 6.8 Hz, 3H). |
| 409[2] | 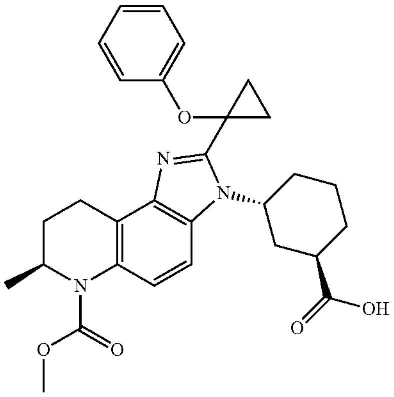 (1R,3R)-3-((S)-6-(methoxycarbonyl)-7-methyl-2-(1-phenoxycyclopropyl)-6,7,8,9-tetrahydro-3H-imidazo[4,5-f]quinolin-3-yl)cyclohexane-1-carboxylic acid | 504 | $^1$HNMR ($CD_3OD$, 400 MHz) δ (ppm): 7.49 (d, J = 9.2 Hz, 1H), 7.39 (d, J = 8.8 Hz, 1H), 7.24-7.19 (m, 4H), 6.90-6.82 (m, 1H), 5.48-5.40 (m, 1H), 4.74-4.69 (m, 1H), 3.77 (s, 3H), 3.28-2.92 (m, 3H), 2.58-2.29 (m, 5H), 1.84-1.59 (m, 6H), 1.43-1.30 (m, 3H), 1.13 (d, J = 6.4 Hz, 3H). |

TABLE 17-continued

| Example Number | Structure and Compound Name | LRMS m/z [M + H] | $^1$H NMR |
|---|---|---|---|
| 410[2] | 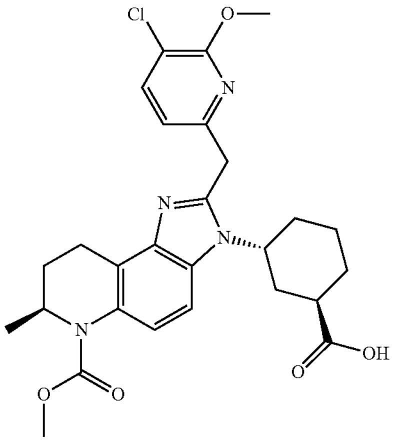 3-((7S)-2-((5-chloro-6-methoxypyridin-2-yl)methyl)-6-(methoxycarbonyl)-7-methyl-6,7,8,9-tetrahydro-3H-imidazo[4,5-f]quinolin-3-yl)cyclohexane-1-carboxylic acid | 527 | $^1$HNMR ($CD_3OD$, 400 MHz) δ (ppm): 7.68 (d, J = 8.0 Hz, 1H), 7.53 (d, J = 8.8 Hz, 1H), 7.42 (d, J = 9.2 Hz, 1H), 6.85 (d, J = 8.0 Hz, 1H), 4.91-4.76 (m, 3H), 4.52-4.45 (m, 1H), 3.92 (s, 3H), 3.79 (s, 3H), 3.24-3.16 (m, 1H), 2.98-2.92 (m, 2H), 2.41-2.19 (m, 5H), 1.78-1.61 (m, 3H), 1.48-1.29 (m, 2H), 1.15 (d, J = 6.8 Hz, 3H), |
| 411[2] | 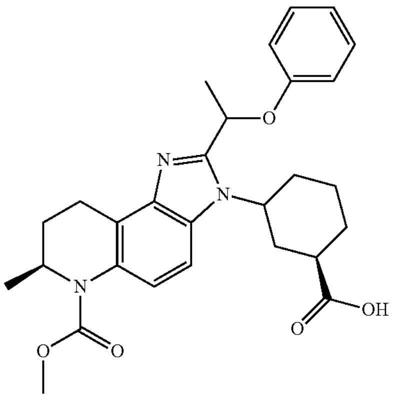 3-((7S)-6-(methoxycarbonyl)-7-methyl-2-(1-phenoxyethyl)-6,7,8,9-tetrahydro-3H-imidazo[4,5-f]quinolin-3-yl)cyclohexane-1-carboxylic acid 1st eluting isomer | 492 | $^1$HNMR ($CD_3OD$, 400 MHz) δ (ppm): 7.50 (d, J = 9.2 Hz, 1H), 7.41 (d, J = 9.2 Hz, 1H), 7.22-7.18 (m, 2H), 6.99-6.88 (m, 3H), 5.87-5.83 (m, 1H), 5.33-5.28 (m, 1H), 4.79-4.75 (m, 1H), 3.78 (s, 3H), 3.20-2.94 (m, 3H), 2.51-2.09 (m, 5H), 1.94 (d, J = 6.8 Hz, 3H), 1.76-1.58 (m, 4H), 1.37-1.29 (m, 1H), 1.14 (d, J = 6.4 Hz, 3H). |

TABLE 17-continued

| Example Number | Structure and Compound Name | LRMS m/z [M + H] | $^{1}$H NMR |
|---|---|---|---|
| 412[2] | 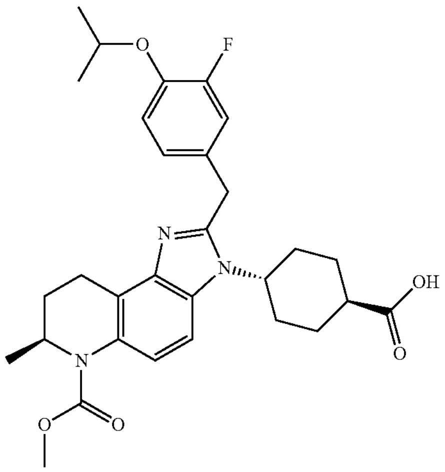 (1S,4R)-4-((S)-2-(3-fluoro-4-isopropoxybenzyl)-6-(methoxycarbonyl)-7-methyl-6,7,8,9-tetrahydro-3H-imidazo[4,5-f]quinolin-3-yl)cyclohexane-1-carboxylic acid | 538 | $^{1}$HNMR ($CD_3OD$, 400 MHz) δ (ppm): 7.44 (d, J = 8.8 Hz, 1H), 7.38 (d, J = 9.2 Hz, 1H), 7.07-6.89 (m, 3H), 4.78-4.74 (m, 1H), 4.56.4.53 (m, 1H), 4.32 (s, 2H), 4.25-4.21 (m, 1H), 3.77 (s, 3H), 3.31-3.16 (m, 1H), 2.99-2.93 (m, 1H), 2.41-2.17 (m, 4H), 2.07-2.03 (m, 2H), 1.77-1.73 (m, 1H), 1.55-1.43 (m, 4H), 1.28 (d, J = 6.0 Hz, 6H), 1.14 (d, J = 6.8 Hz, 3H). |
| 413 | 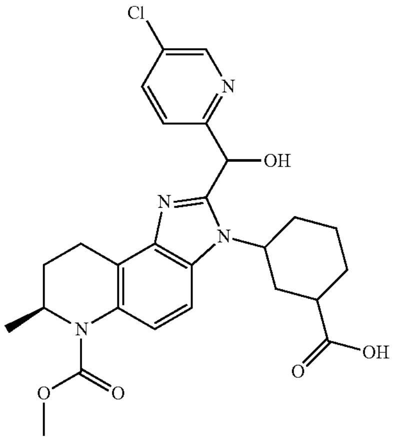 3-((7S)-2-((4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | 512 | $^{1}$HNMR ($CD_3OD$, 400 MHz) δ (ppm): 7.49 (d, J = 9.0 Hz, 1H), 7.42-7.33 (m, 5H), 6.19 (s, 1H), 4.92-4.90 (m, 1H), 4.82-4.72 (m, 1H), 3.79 (s, 3H), 3.34-3.20 (m, 1H), 3.02-2.94 (m, 1H), 2.90-2.87 (m, 1H), 2.36-2.09 (m, 4H), 1.99-1.96 (m, 1H), 1.80-1.42 (m, 5H), 1.16 (d, J = 6.6 Hz, 3H). |

[1]Prepared using standard chemical manipulations and procedures similar to those used for the preparation of Example 139.

[2]Prepared using standard chemical manipulations and procedures similar to those used for the preparation of Example 16.

The following examples in TABLE 18 were prepared using standard chemical manipulations and procedures similar to those used for the preparation of previous Examples.

TABLE 18

| Example Number | Structure and Compound Name | $^1$H NMR, LCMS |
|---|---|---|
| 414 | 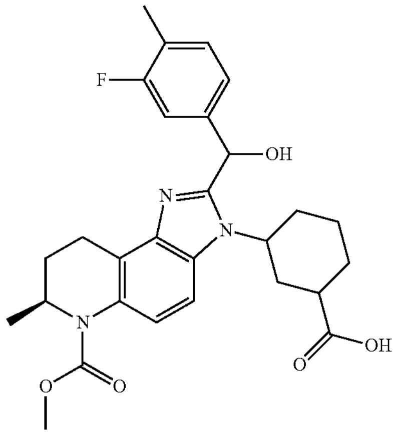 3-((7S)-2-((3-fluoro-4-methylphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H NMR ($CD_3OD$, 400 MHz) δ (ppm): 7.53-7.38 (m, 2H), 7.22-7.19 (m, 1H), 7.09-7.04 (m, 2H), 6.16 (s, 1H), 4.86-4.70 (m, 2H), 3.79 (s, 3H), 3.30-3.21 (m, 1H), 3.01-2.92 (m, 1H), 2.88-2.84 (m, 1H), 2.43-2.23 (m, 5H), 2.15-2.04 (m, 2H), 2.01-1.97 (m, 1H), 1.81-1.60 (m, 3H), 1.56-1.38 (m, 2H), 1.16 (d, J = 6.8 Hz, 3H). LCMS (ES, m/z): 510 $[M + H]^+$. |
| 415 | 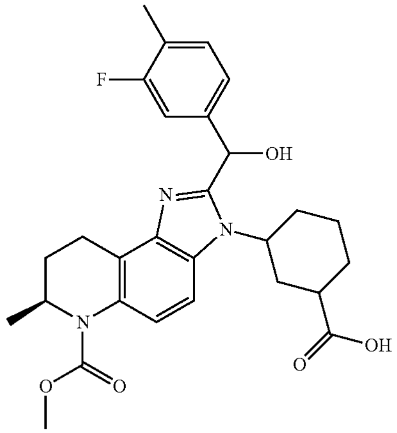 3-((7S)-2-((3-fluoro-4-methylphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H NMR ($CD_3OD$, 400 MHz) δ (ppm): 7.61-7.52 (m, 2H), 7.33-7.18 (m, 2H), 7.11-7.09 (m, 1H), 6.26 (s, 1H), 5.02-4.99 (m, 1H), 4.80-4.79 (m, 1H), 3.80 (s, 3H), 3.21-3.16 (m, 1H), 3.08-2.90 (m, 2H), 2.49-2.41 (m, 1H), 2.35-2.22 (m, 5H), 2.14-2.03 (m, 2H), 1.81-1.79 (m, 1H), 1.63-1.58 (m, 2H), 1.45-1.30 (m, 1H), 1.21-1.18 (m, 1H), 1.16 (d, J = 6.8 Hz, 3H). LCMS (ES, m/z): 510 $[M + H]^+$. |

TABLE 18-continued

| Example Number | Structure and Compound Name | $^1$H NMR, LCMS |
|---|---|---|
| 416 | 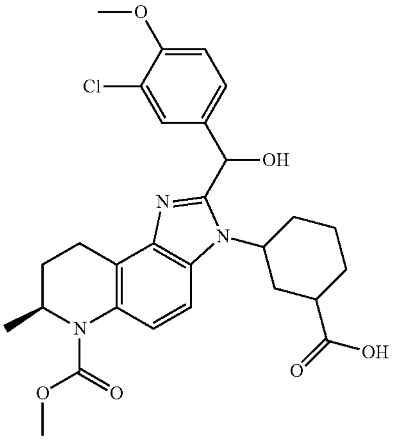 3-((7S)-2-((3-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.71-7.54 (m, 2H), 7.54-7.42 (m, 1H), 7.42-7.29 (m, 1H), 7.19-6.97 (m, 1H), 6.20 (s, 1H), 4.99-4.89 (m, 1H), 4.82-4.74 (m, 1H), 3.98 (s, 3H), 3.89 (s, 3H), 3.29-3.19 (m, 1H), 3.11-2.93 (m, 2H), 2.48-2.22 (m, 2H), 2.22-2.08 (m, 3H), 1.91-1.69 (m, 3H), 1.38-1.24 (m, 2H), 1.18 (d, J = 6.8 Hz, 3H). LCMS (ES, m/z): 542 $[M + H]^+$ |
| 417 | 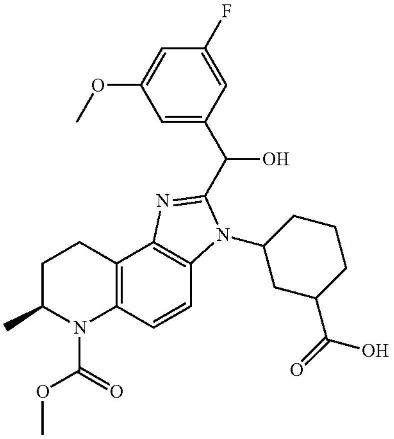 3-((7S)-2-((3-fluoro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.51-7.42 (m, 2H), 6.94 (s, 1H), 6.79-6.72 (m, 1H), 6.55-6.62 (m, 1H), 6.19 (s, 1H), 5.03-4.90 (m, 1H), 4.84-4.70 (m, 1H), 3.82 (s, 3H), 3.81 (s, 3H), 3.28-3.10 (m, 1H), 3.05-2.95 (m, 2H), 2.52-2.43 (m, 2H), 2.38-2.27 (m, 1H), 2.17-1.96 (m, 2H), 1.81-1.66 (m, 1H), 1.64-1.58 (m, 2H), 1.43-1.30 (m, 1H), 1.15 (d, J = 6.8 Hz, 3H), 1.02-0.98 (m, 1H). LCMS (ES, m/z): 526 $[M + H]^+$. |

TABLE 18-continued

| Example Number | Structure and Compound Name | $^1$H NMR, LCMS |
|---|---|---|
| 418 | 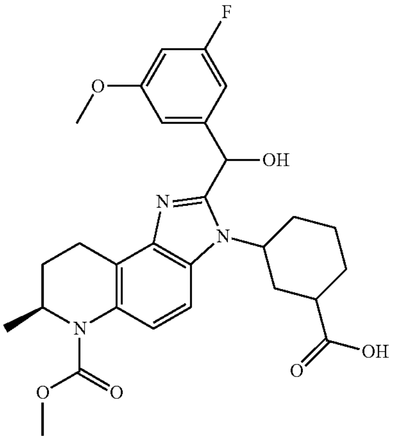 3-((7S)-2-((3-fluoro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.55-7.37 (m, 2H), 6.80 (s, 1H), 6.77-6.72 (m, 1H), 6.66-6.59 (m, 1H), 6.15 (s, 1H), 4.85-4.70 (m, 2H), 3.80 (s, 6H), 3.28-3.19 (m, 1H), 3.05-2.95 (m, 1H), 2.91-2.87 (m, 1H), 2.42-2.03 (m, 5H), 1.81-1.60 (m, 3H), 1.56-1.38 (m, 2H), 1.16 (d, J = 6.8 Hz, 3H). LCMS (ES, m/z): 526 $[M + H]^+$. |
| 419 | 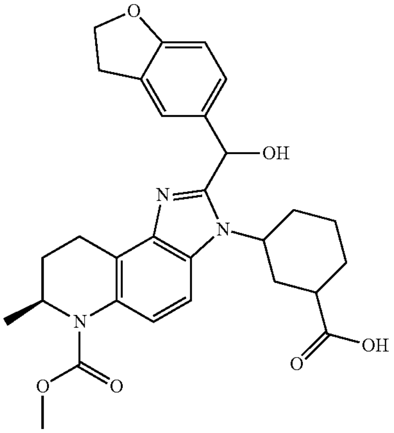 3-((7S)-2-((2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.48-7.38 (m, 2H), 7.25 (s, 1H), 7.15 (d, J = 8.4 Hz, 1H), 6.70 (d, J = 8.0 Hz, 1H), 6.11 (s, 1H), 4.81-4.74 (m, 2H), 4.53 (t, J = 8.8 Hz, 2H), 3.79 (s, 3H), 3.29-3.25 (m, 1H), 3.19-3.14 (m, 2H), 3.03-2.91 (m, 2H), 2.36-2.25 (m, 2H), 2.15-2.07 (m, 3H), 1.77-1.60 (m, 3H), 1.35-1.25 (m, 2H), 1.16 (d, J = 6.4 Hz, 3H). LCMS (ES, m/z): 520 $[M + H]^+$. |

TABLE 18-continued

| Example Number | Structure and Compound Name | $^{1}H$ NMR, LCMS |
|---|---|---|
| 420 | 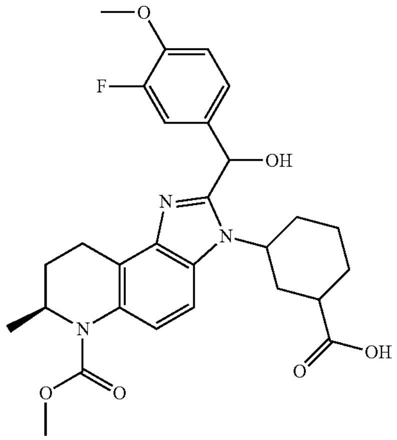<br>3-((7S)-2-((3-fluoro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^{1}H$-NMR ($CD_3OD$, 400 MHz) δ (ppm): 7.53-7.39 (m, 2H), 7.17-7.05 (m, 3H), 6.14 (s, 1H), 4.89-4.67 (m, 2H), 3.86 (s, 3H), 3.79 (s, 3H), 3.32-3.21 (m, 1H), 3.04-2.93 (m, 1H), 2.91-2.89 (s, 1H), 2.40-2.22 (m, 2H), 2.22-2.10 (m, 2H), 2.10-2.05 (m, 1H), 1.81-1.60 (m, 3H), 1.52-1.40 (m, 2H), 1.16 (d, J = 6.8 Hz, 3H). LCMS (ES, m/z): 526 $[M + H]^+$. |
| 421 | 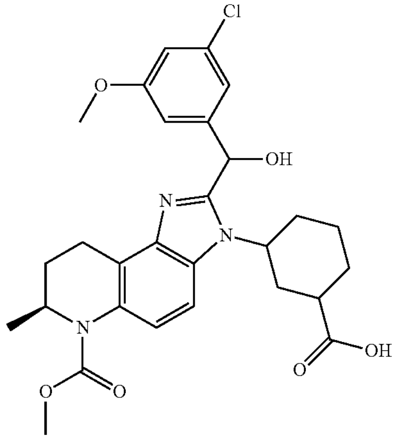<br>3-((7S)-2-((3-chloro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^{1}H$-NMR ($CD_3OD$, 400 MHz) δ (ppm): 7.52-7.42 (m, 2H), 7.00-6.89 (m, 3H), 6.13 (s, 1H), 4.85-4.73 (m, 2H), 3.81 (s, 3H), 3.79 (s, 3H), 3.33-3.22 (m, 1H), 3.04-2.90 (m, 2H), 2.42-2.22 (m, 2H), 2.16-2.07 (m, 3H), 1.78-1.54 (m, 3H), 1.48-1.32 (m, 2H), 1.17 (d, J = 6.8 Hz, 3H). LCMS (ES, m/z): 542 $[M + H]^+$. |

TABLE 18-continued

| Example Number | Structure and Compound Name | $^1$H NMR, LCMS |
|---|---|---|
| 422 | 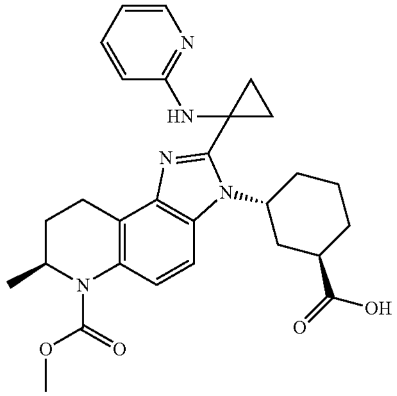 (1R,3R)-3-((S)-6-(methoxycarbonyl)-7-methyl-2-(1-(pyridin-2-ylamino)cyclopropyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.96-7.95 (m, 1H), 7.54-7.43 (m, 2H), 7.33 (d, J = 8.8 Hz, 1H), 7.20 (d, J = 8.4 Hz, 1H), 6.63-6.56 (m, 1H), 5.56-5.39 (m, 1H), 4.79-4.64 (m, 1H), 3.76 (s, 3H), 3.28-3.17 (m, 1H), 2.96-2.79 (m, 2H), 2.47-2.14 (m, 5H), 1.92-1.81 (m, 3H), 1.81-1.61 (m, 3H), 1.41-1.19 (m, 3H), 1.11 (d, J = 6.4 Hz, 3H). LCMS (ES, m/z): 504 $[M + H]^+$. |
| 423 | 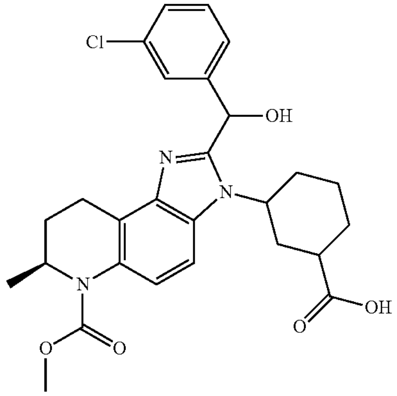 3-((7S)-2-((3-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.47-7.30 (m, 6H), 6.22 (s, 1H), 4.92-4.90 (m, 1H), 4.78-4.74 (m, 1H), 3.78 (m, 3H), 3.33-3.24 (m, 1H), 3.01-2.82 (m, 2H), 2.34-2.14 (m, 5H), 1.76-1.38 (m, 5H), 1.16 (d, J = 6.4 Hz, 3H). LCMS (ES, m/z): 512 $[M + H]^+$. |
| 424 | 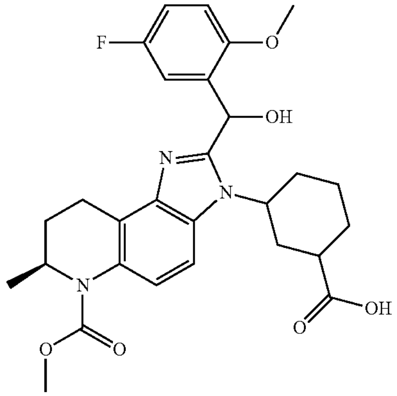 3-((7S)-2-((5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.56-7.47 (m, 1H), 7.47-7.31 (m, 1H), 7.21-7.09 (m, 1H), 7.09-6.89 (m, 2H), 6.53 (s, 1H), 4.81-4.61 (m, 2H), 3.85 (s, 3H), 3.78 (s, 3H), 3.31-3.18 (m, 1H), 3.06-2.82 (m, 2H), 2.57-2.41 (m, 1H), 2.41-2.31 (m, 1H), 2.31-2.09 (m, 3H), 1.83-1.58 (m, 3H), 1.49-1.21 (m, 2H), 1.15 (d, J = 6.8 Hz, 3H). LCMS (ES, m/z): 526 $[M + H]^+$ |

TABLE 18-continued

| Example Number | Structure and Compound Name | $^1$H NMR, LCMS |
|---|---|---|
| 425 | 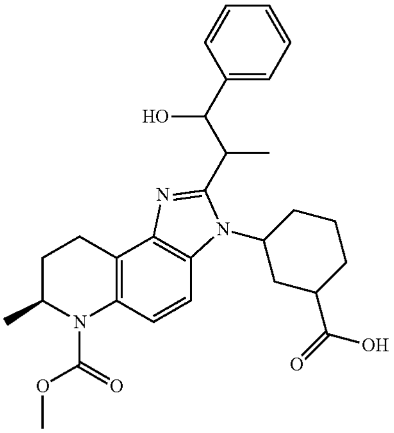 3-((7S)-2-(1-hydroxy-1-phenylpropan-2-yl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.42-7.28 (m, 2H), 7.22-7.10 (m, 5H), 5.08 (d, J = 9.2 Hz, 1H), 4.79-4.75 (m, 1H), 4.39-4.35 (m, 1H), 3.78 (s, 3H), 3.65-.3.53 (m, 1H), 3.26-3.20 (m, 1H), 3.05-2.96 (m, 2H), 2.42-2.20 (m, 1H), 2.20-1.92 (m, 4H), 1.79-1.70 (m, 1H), 1.70-1.50 (m, 5H), 1.40-1.35 (m, 1H), 1.14 (d, J = 6.8 Hz, 3H), 0.58-0.56 (m, 1H). LCMS (ES, m/z): 506 [M + H]$^+$ |
| 426 | 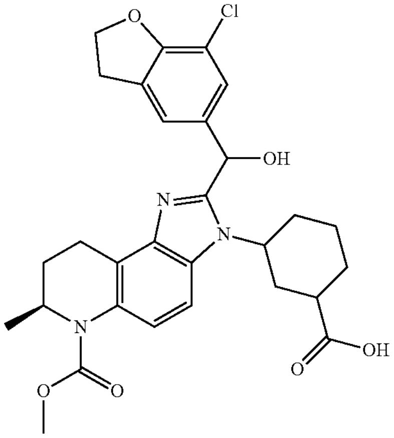 3-((7S)-2-((7-chloro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.52-7.51 (m, 2H), 7.23-7.13 (m, 2H), 6.10 (s, 1H), 4.85-4.70 (m, 2H), 4.63 (t, J = 8.4 Hz, 2H), 3.79 (s, 3H), 3.31-3.19 (m, 3H), 3.04-2.88 (m, 2H), 2.43-2.21 (m, 2H), 2.20-2.05 (m, 3H), 1.80-1.59 (m, 3H), 1.45-1.30 (m, 2H), 1.16 (d, J = 6.4 Hz, 3H). LCMS (ES, m/z): 554 [M + H]$^+$. |

TABLE 18-continued

| Example Number | Structure and Compound Name | $^1$H NMR, LCMS |
|---|---|---|
| 427 | 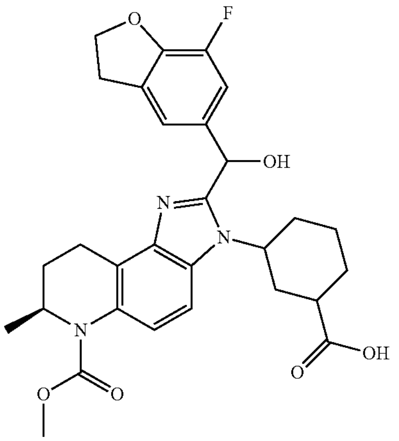 3-((7S)-2-((7-fluoro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.51-7.41 (m, 1H), 7.41-7.29 (m, 1H), 7.24-7.13 (m, 1H), 7.11-6.94 (m, 1H), 6.19 (s, 1H), 4.95-4.91 (m, 1H), 4.81-4.71 (m, 1H), 4.63 (t, J = 8.8 Hz, 2H), 3.78 (s, 3H), 3.32-3.18 (m, 3H), 3.08-2.91 (m, 1H), 2.82-2.67 (m, 1H), 2.39-2.18 (m, 4H), 2.16-1.98 (m, 1H), 1.82-1.68 (m, 1H), 1.68-1.50 (m, 2H), 1.50-1.38 (m, 1H), 1.16 (d, J = 6.8 Hz, 3H), 1.14-1.06 (m, 1H). LCMS (ES, m/z): 538 $[M + H]^+$ |
| 428 | 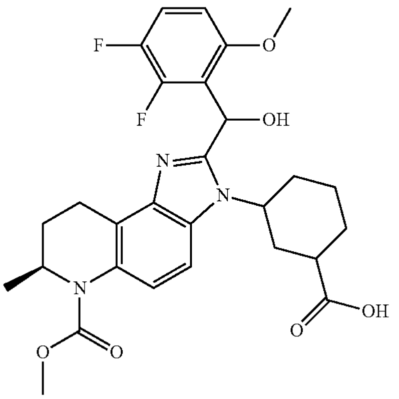 3-((7S)-2-((2,3-difluoro-6-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.58-7.44 (m, 1H), 7.44-7.34 (m, 1H), 7.31-7.19 (m, 1H), 6.96-6.78 (m, 1H), 6.57 (s, 1H), 4.81-4.66 (m, 1H), 4.52-4.29 (m, 1H), 3.87 (s, 3H), 3.79 (s, 3H), 3.33-3.21 (m, 1H), 3.08-2.84 (m, 2H), 2.59-2.41 (m, 1H), 2.39-2.22 (m, 2H), 2.22-2.12 (m, 1H), 2.12-1.96 (m, 1H), 1.82-1.68 (m, 1H), 1.69-1.52 (m, 2H), 1.24-1.07 (m, 4H), 1.24-0.99 (m, 1H). LCMS (ES, m/z): 544 $[M + H]^+$ |

TABLE 18-continued

| Example Number | Structure and Compound Name | $^1$H NMR, LCMS |
|---|---|---|
| 429 | 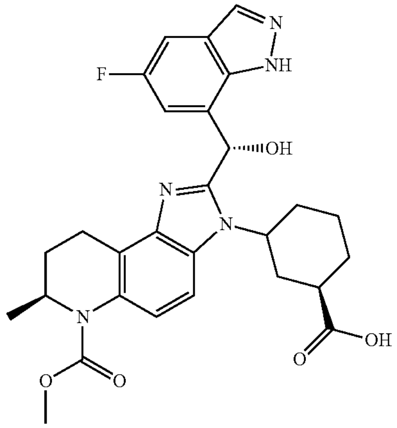 3-((7S)-2-((5-fluoro-1H-indazol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 8.06 (s, 1H), 7.56-7.50 (m, 1H), 7.48-7.39 (m, 2H), 7.16-7.08 (m, 1H), 6.59 (s, 1H), 5.06-4.95 (m, 1H), 4.82-4.73 (m, 1H), 3.79 (s, 3H), 3.31-3.22 (m, 1H), 3.05-2.92 (m, 2H), 2.47-2.10 (m, 5H), 1.82-1.64 (m, 3H), 1.5-1.28 (m, 2H), 1.17 (d, J = 6.8 Hz, 3H). LCMS (ES, m/z): 536 [M + H]$^+$. |
| 430 | 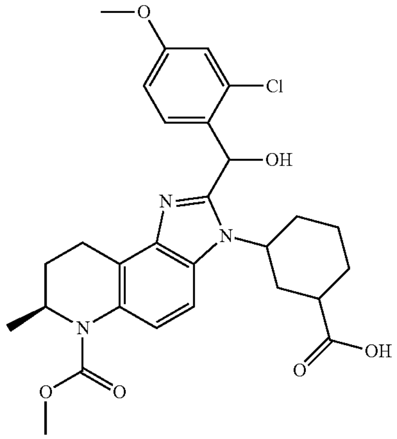 3-((7S)-2-((2-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.74 (d, J = 9.2 Hz, 1H), 7.52 (d, J = 8.8 Hz, 1H), 7.41 (d, J = 8.8 Hz, 1H), 6.99-6.97 (m, 2H), 6.40 (s, 1H), 4.85-4.81 (m, 1H), 4.74-4.71 (m, 1H), 3.82 (s, 3H), 3.78 (s, 3H), 3.20-3.13 (m, 1H), 2.95-2.90 (m, 1H), 2.89-2.85 (m, 1H), 2.47-2.45 (m, 1H), 2.30-2.17 (m, 4H), 1.75-1.64 (m, 4H), 1.54-1.45 (m, 1H), 1.14 (d, J = 6.8 Hz, 3H). LCMS (ES, m/z): 542 [M + H]$^+$. |

TABLE 18-continued

| Example Number | Structure and Compound Name | $^1$H NMR, LCMS |
|---|---|---|
| 431 | 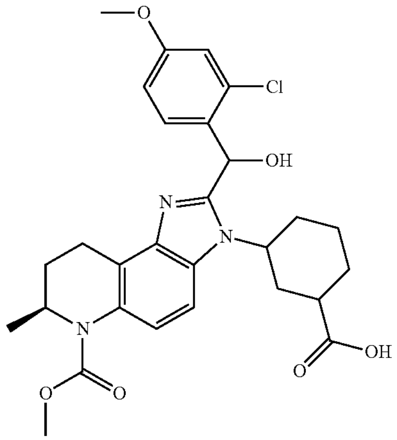 3-((7S)-2-((2-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.59 (d, J = 9.2 Hz, 1H), 7.41 (d, J = 9.2 Hz, 1H), 7.24 (d, J = 8.8 Hz, 1H), 7.02 (s, 1H), 6.84 (d, J = 8.8 Hz, 1H), 6.50 (s, 1H), 4.77-4.72 (m, 1H), 4.54-4.53 (m, 1H), 3.80 (s, 3H), 3.79 (s, 3H), 3.29-3.23 (m, 1H), 2.98-2.91 (m, 2H), 2.47-2.45 (m, 1H), 2.36-2.33 (m, 1H), 2.28-2.17 (m, 2H), 2.08-2.03 (m, 1H), 1.72-1.65 (m, 3H), 1.37-1.21 (m, 1H), 1.21-1.18 (m, 1H), 1.15 (d, J = 6.8 Hz, 3H). LCMS (ES, m/z): 542 [M + H]$^+$. |
| 432 | 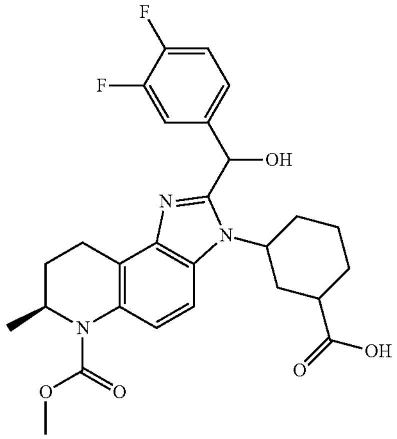 3-((7S)-2-((3,4-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H NMR ($CD_3OD$, 400 MHz) δ (ppm): 7.51 (d, J = 9.0 Hz, 1H), 7.44 (d, J = 9.0 Hz, 1H), 7.40-7.31 (m, 1H), 7.23-7.18 (m, 1H), 7.15-7.11 (m, 1H), 6.18 (s, 1H), 4.93-4.91 (m, 1H), 4.80-4.76 (m, 1H), 3.79 (s, 3H), 3.26-3.21 (m, 1H), 3.01-2.94 (m, 1H), 2.86-2.84 (m, 1H), 2.41-2.09 (m, 4H), 1.92-1.89 (m, 1H), 1.78-1.48 (m, 5H), 1.16 (d, J = 6.4 Hz, 3H). LCMS (ES, m/z): 514 [M + H]$^+$. |

TABLE 18-continued

| Example Number | Structure and Compound Name | $^1$H NMR, LCMS |
| --- | --- | --- |
| 433 | 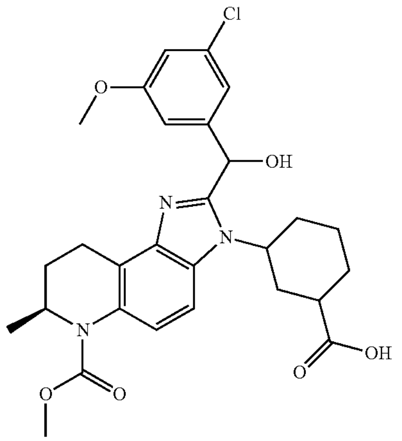 3-((7S)-2-((3-chloro-5-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.62-7.51 (m, 2H), 7.12-7.07 (m, 1H), 7.03-6.97 (m, 1H), 6.86-6.80 (m, 1H), 6.20 (s, 1H), 5.03-4.92 (m, 1H), 4.78 (m, 1H), 3.81 (s, 3H), 3.79 (s, 3H), 3.24-3.22 (m, 1H), 3.06-2.96 (m, 2H), 2.53-2.36 (m, 2H), 2.32-2.28 (m, 1H), 2.14-2.12 (m, 1H), 2.04-2.00 (m, 1H), 1.83-1.71 (m, 1H), 1.61-1.52 (m, 2H), 1.40-1.31 (m, 1H), 1.16 (d, J = 6.8 Hz, 3H), 1.05-0.97 (m, 1H). LCMS (ES, m/z): 542 [M + H]$^+$. |
| 434 | 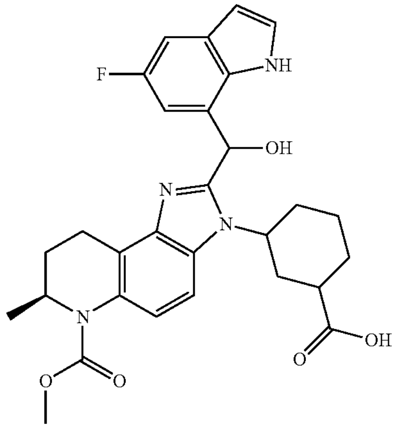 3-((7S)-2-((5-fluoro-1H-indol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.87-7.74 (m, 2H), 7.43-7.30 (m, 2H), 7.02-6.92 (m, 1H), 6.76 (s, 1H), 6.59-6.52 (m, 1H), 4.86-4.71 (m, 2H), 3.82 (s, 3H), 3.29-3.09 (m, 2H), 3.06-2.97 (m, 1H), 2.47-2.36 (m, 2H), 2.35-2.24 (m, 1H), 2.16-2.08 (m, 1H), 2.05-1.85 (m, 2H), 1.74-1.60 (m, 1H), 1.59-1.45 (m, 1H), 1.20 (d, J = 6.8 Hz, 3H), 0.93-0.77 (m, 1H), 0.75-0.61 (m, 1H). LCMS (ES, m/z): 535 [M + H]$^+$. |
| 435 | 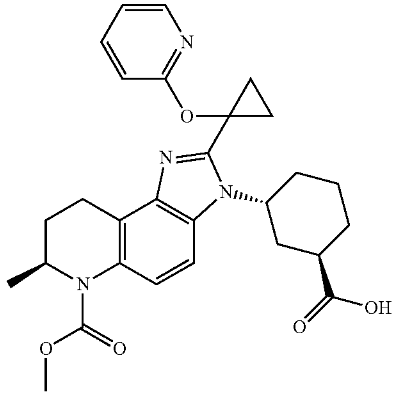 (1R,3R)-3-((S)-6-(methoxycarbonyl)-7-methyl-2-(1-(pyridin-2-yloxy)cyclopropyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.21-8.01 (m, 1H), 7.79-7.62 (m, 1H), 7.56-7.44 (m, 1H), 7.44-7.33 (m, 1H), 7.33-7.16 (m, 1H), 7.03-6.88 (m, 1H), 5.52-5.31 (m, 1H), 4.81-4.61 (m, 1H), 3.76 (s, 3H), 3.31-3.12 (m, 1H), 3.02-2.87 (m, 2H), 2.59-2.41 (m, 1H), 2.35-2.12 (m, 4H), 2.04-1.92 (m, 1H), 1.91-1.59 (m, 6H), 1.47-1.31 (m, 2H), 1.14 (d, J = 6.4 Hz, 3H). LCMS (ES, m/z): 505 [M + H]$^+$. |

TABLE 18-continued

| Example Number | Structure and Compound Name | $^1$H NMR, LCMS |
|---|---|---|
| 436 | 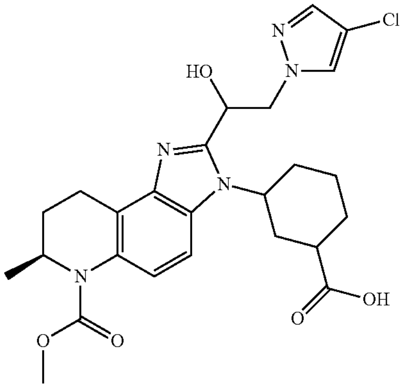 3-((7S)-2-(2-(4-chloro-1H-pyrazol-1-yl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.87 (s, 1H), 7.57 (d, J = 8.8 Hz, 1H), 7.52-7.38 (m, 2H), 5.51-5.44 (m, 1H), 5.36-5.25 (m, 1H), 5.03-4.92 (m, 1H), 4.82-4.71 (m, 1H), 4.60-4.52 (m, 1H), 3.79 (s, 3H), 3.24-3.11 (m, 1H), 3.09-2.86 (m, 2H), 2.49-2.19 (m, 4H), 1.96-1.85 (m, 2H), 1.80-1.60 (m, 3H), 1.36-1.29 (m, 1H), 1.14 (d, J = 6.8 Hz, 3H). LCMS (ES, m/z): 516 $[M + H]^+$. |
| 437 | 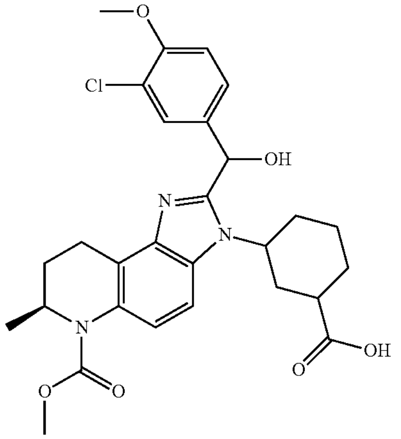 3-((7S)-2-((3-chloro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.64-7.39 (m, 3H), 7.39-7.21 (m, 1H), 7.16-6.89 (m, 1H), 6.17 (s, 1H), 5.03-4.91 (m, 1H), 4.82-4.68 (m, 1H), 3.87 (s, 3H), 3.78 (s, 3H), 3.29-3.12 (m, 1H), 3.02-2.89 (m, 2H), 2.51-2.21 (m, 3H), 2.19-1.93 (m, 2H), 1.84-1.71 (m, 1H), 1.69-1.54 (m, 2H), 1.51-1.36 (m, 1H), 1.16 (d, J = 6.4 Hz, 3H), 1.10-0.97 (m, 1H). LCMS (ES, m/z): 542 $[M + H]^+$ |

TABLE 18-continued

| Example Number | Structure and Compound Name | $^1$H NMR, LCMS |
|---|---|---|
| 438 | 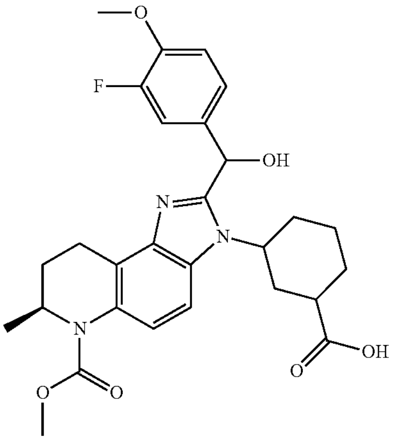 3-((7S)-2-((3-fluoro-4-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.52-7.40 (m, 2H), 7.32-7.24 (m, 1H), 7.16-7.10 (m, 1H), 7.08-7.00 (m, 1H), 6.17 (s, 1H), 4.98-4.90 (m, 1H), 4.82-4.71 (m, 1H), 3.86 (s, 3H), 3.79 (s, 3H), 3.30-3.17 (m, 1H), 3.04-2.94 (m, 2H), 2.50-2.29 (m, 2H), 2.27-2.18 (m, 1H), 2.13-1.95 (m, 2H), 1.80-1.68 (m, 1H), 1.61-1.54 (m, 2H), 1.44-1.27 (m, 1H), 1.15 (d, J = 6.8, 3H), 1.09-1.06 (m, 1H). LCMS (ES, m/z): 526 [M + H]$^+$. |
| 439 | 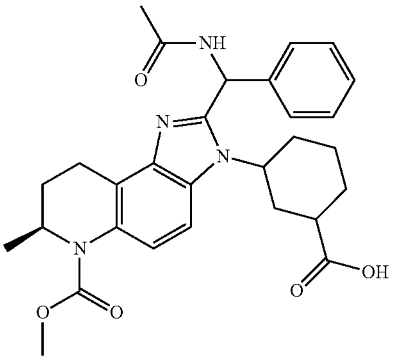 3-((7S)-2-(acetamido(phenyl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.52-7.50 (m, 1H), 7.43-7.40 (m, 1H), 7.40-7.37 (m, 2H), 7.32-7.30 (m, 3H), 6.89 (s, 1H), 4.81-4.78 (m, 1H), 4.52-4.48 (m, 1H), 3.79 (s, 3H), 3.30-3.18 (m, 1H), 3.10-2.94 (m, 1H), 2.40-2.20 (m, 2H), 2.18-2.09 (m, 6H), 1.82-1.76 (m, 1H), 1.72-1.67 (m, 2H), 1.43-1.35 (m, 1H), 1.32-1.29 (m, 1H), 1.16 (d, J = 6.7 Hz, 3H), 1.12-1.03 (m, 1H). LCMS (ES, m/z): 519 [M + H]$^+$. |
| 440 | 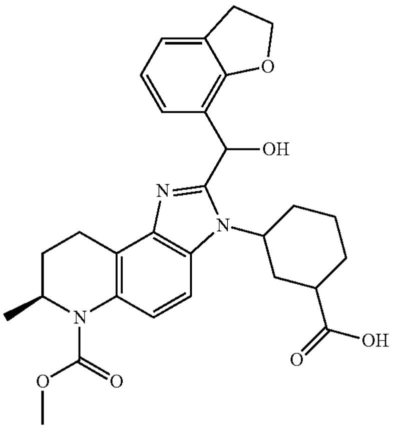 3-((7S)-2-((2,3-dihydrobenzofuran-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.83 (s, 2H), 7.30 (d, J = 6.8 Hz, 1H), 7.23 (d, J = 8.0 Hz, 1H), 6.93 (t, J = 7.6 Hz, 1H), 6.42 (s, 1H), 4.85-4.62 (m, 3H), 4.53-4.41 (m, 1H), 3.833 (s, 3H), 3.27-2.98 (m, 5H), 2.53-2.35 (m, 2H), 2.34-2.09 (m, 3H), 1.92-1.85 (m, 1H), 1.75-1.62 (m, 2H), 1.22-1.01 (m, 5H). LCMS (ES, m/z): 520 [M + H]$^+$ |

TABLE 18-continued

| Example Number | Structure and Compound Name | $^1$H NMR, LCMS |
|---|---|---|
| 441 | 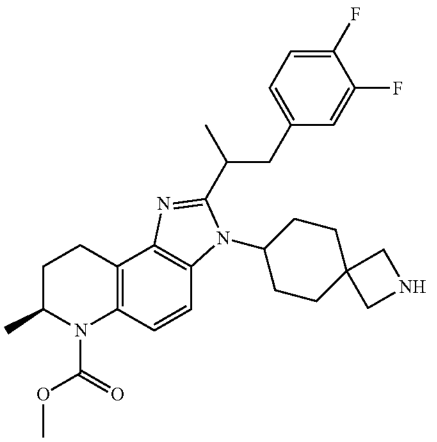 methyl (7S)-2-(1-(3,4-difluorophenyl)propan-2-yl)-7-methyl-3-(2-azaspiro[3.5]nonan-7-yl)-3,7,8,9-tetrahydro-6H-imidazo[4,5-f]quinoline-6-carboxylate 1$^{st}$ eluting isomer | $^1$H-NMR ($CD_3OD$, 400 MHz) δ (ppm): 7.30 (d, J = 8.8 Hz, 1H), 7.18 (d, J = 8.8 Hz, 1H), 7.10-6.96 (m, 2H), 6.83-6.73 (m, 1H), 4.82-4.68 (m, 1H), 4.21-4.05 (m, 1H), 3.82-3.69 (m, 5H), 3.62-3.49 (m, 3H), 3.30-3.12 (m, 2H), 3.11-3.02 (m, 1H), 2.99-2.87 (m, 1H), 2.35-2.01 (m, 5H), 1.76-1.64 (m, 3H), 1.57-1.45 (m, 4H), 1.12 (d, J = 6.8 Hz, 3H), 0.92-0.71 (m, 1H). LCMS (ES, m/z): 523 $[M + H]^+$. |
| 442 | 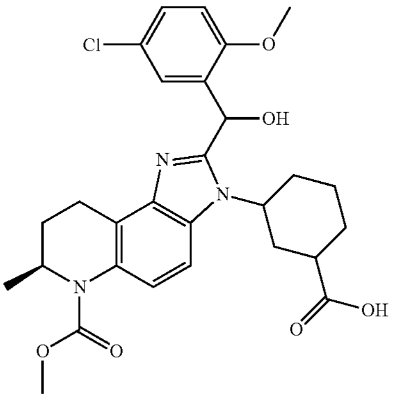 3-((7S)-2-((5-chloro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.59-7.47 (m, 1H), 7.47-7.32 (m, 2H), 7.12-6.99 (m, 1H), 7.09-6.93 (m, 1H), 6.51 (s, 1H), 4.82-4.57 (m, 2H), 3.87 (s, 3H), 3.78 (s, 3H), 3.32-3.18 (m, 1H), 3.05-2.79 (m, 2H), 2.57-2.41 (m, 1H), 2.41-2.31 (m, 1H), 2.31-2.05 (m, 3H), 1.82-1.67 (m, 3H), 1.52-1.22 (m, 2H), 1.16 (d, J = 6.8 Hz, 3H). LCMS (ES, m/z): 542 $[M + H]^+$ |
| 443 | 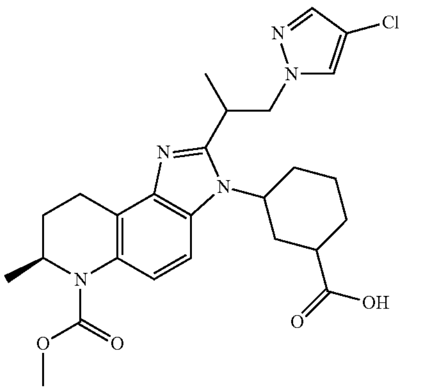 3-((7S)-2-(1-(4-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.81-7.75 (m, 3H), 7.34 (s, 1H), 4.87-4.72 (m, 2H), 4.71-4.62 (m, 2H), 4.30-4.15 (m, 1H), 3.79 (s, 3H), 3.18-2.96 (m, 3H), 2.45-2.20 (m, 5H), 1.95-1.70 (m, 3H), 1.65-1.60 (m, 1H), 1.62 (d, J = 6.8 Hz, 3H), 1.55-1.40 (m, 1H), 1.16 (d, J = 6.4 Hz, 3H). LCMS (ES, m/z): 514 $[M + H]^+$. |

TABLE 18-continued

| Example Number | Structure and Compound Name | $^1$H NMR, LCMS |
|---|---|---|
| 444 | 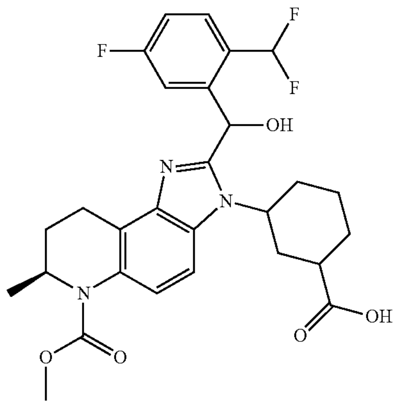 3-((7S)-2-((2-(difluoromethyl)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.86-7.83 (m, 3H), 7.51-7.34 (m, 2H), 7.29-7.23 (m, 1H), 6.64-6.62 (m, 1H), 4.89-4.76 (m, 3H), 3.83 (s, 3H), 3.27-3.02 (m, 3H), 2.48-2.14 (m, 5H), 1.90-1.85 (m, 1H), 1.76-1.69 (m, 2H), 1.27-1.15 (m, 5H). LCMS (ES, m/z): 546 [M + H]$^+$. |
| 445 | 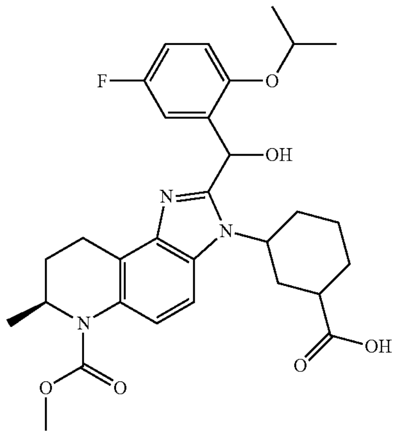 3-((7S)-2-((5-fluoro-2-isopropoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.58-7.52 (m, 1H), 7.45-7.40 (m, 1H), 7.31-7.29 (m, 1H), 7.08-6.90 (m, 2H), 6.38 (s, 1H), 4.86-4.75 (m, 2H), 4.62-4.50 (m, 1H), 3.79 (s, 3H), 3.30-3.17 (m, 1H), 2.95-2.86 (m, 2H), 2.48-2.44 (m, 1H), 2.32-2.24 (m, 4H), 1.80-1.50 (m, 5H), 1.18 (d, J = 6.0 Hz, 3H), 1.13 (d, J = 6.4 Hz, 3H), 1.03 (d, J = 6.0 Hz, 3H). LCMS (ES, m/z): 554 [M + H]$^+$. |

TABLE 18-continued

| Example Number | Structure and Compound Name | $^1$H NMR, LCMS |
|---|---|---|
| 446 | 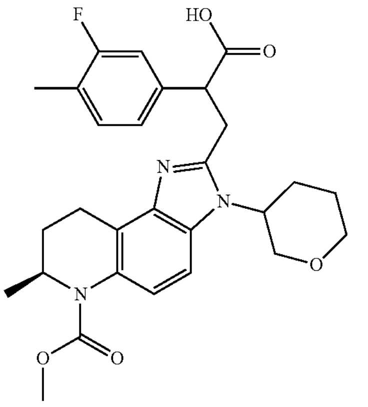 2-(3-fluoro-4-methylphenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1$H-NMR ($CD_3OD$, 400 MHz) δ (ppm): 7.56-7.54 (m, 1H), 7.44-7.41 (m, 1H), 7.20-7.04 (m, 3H), 4.80-4.70 (m, 1H), 4.65-4.50 (m, 1H), 4.35-4.25 (m, 1H), 4.05-3.95 (m, 2H), 3.80-3.50 (m, 5H), 3.40-3.10 (m, 3H), 2.98-2.85 (m, 1H), 2.55-2.15 (m, 6H), 1.95-1.65 (m, 3H), 1.12 (d, J = 6.8 Hz, 3H). LCMS (ES, m/z): 510 $[M + H]^+$ |
| 447 | 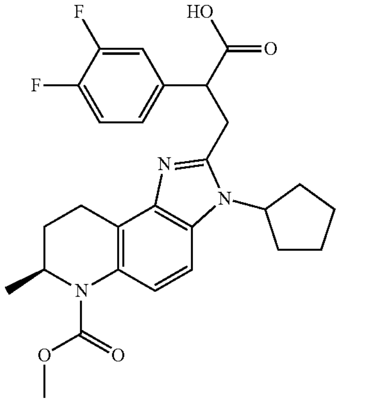 3-((7S)-3-cyclopentyl-6-(methoxycarbonyl)-7-methyl-6,7,8,9-tetrahydro-3H-imidazo[4,5-f]quinolin-2-yl)-2-(3,4-difluorophenyl)propanoic acid 2nd eluting isomer | $^1$H-NMR ($CD_3OD$, 400 MHz) δ (ppm): 7.78 (d, J = 9.2 Hz, 1H), 7.59 (d, J = 9.2 Hz, 1H), 7.49-7.32 (m, 1H), 7.30-7.16 (m, 2H), 5.30-5.14 (m, 1H), 4.84-4.74 (m, 1H), 4.34-4.25 (m, 1H), 4.02-3.90 (m, 1H), 3.82 (s, 3H), 3.62-3.49 (m, 1H), 3.13-2.92 (m, 2H), 2.41-2.32 (m, 1H), 2.28-2.02 (m, 5H), 2.02-1.95 (m, 1H), 1.95-1.82 (m, 3H), 1.16 (d, J = 6.8 Hz, 3H). LCMS (ES, m/z): 498 $[M + H]^+$. |
| 448 | 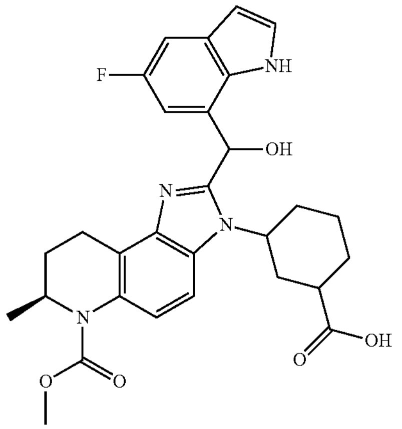 3-((7S)-2-((5-fluoro-1H-indol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.87-7.76 (m, 2H), 7.42 (s, 1H), 7.32-7.22 (m, 1H), 6.85-6.74 (m, 2H), 6.54-6.51 (m, 1H), 5.27-5.16 (m, 1H), 4.85-4.76 (m, 1H), 3.82 (s, 3H), 3.20-3.03 (m, 2H), 3.02-2.93 (m, 1H), 2.54-2.33 (m, 2H), 2.32-2.20 (m, 1H), 2.14-1.86 (m, 3H), 1.70-1.56 (m, 1H), 1.55-1.44 (m 1H), 1.19 (d, J = 6.8 Hz, 3H), 1.05-0.81 (m, 2H). LCMS (ES, m/z): 535 $[M + H]^+$. |

TABLE 18-continued

| Example Number | Structure and Compound Name | $^1$H NMR, LCMS |
| --- | --- | --- |
| 449 | 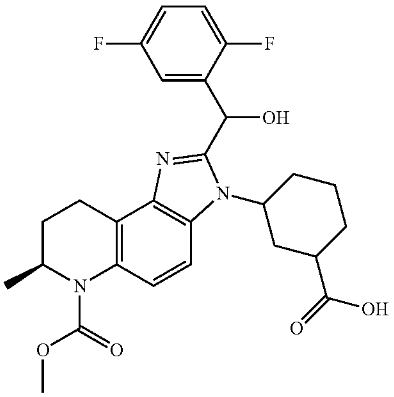 3-((7S)-2-((2,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.55-7.50 (m, 1H), 7.43-7.41 (m, 1H), 7.36-7.32 (m, 1H), 7.14-7.08 (m, 2H), 6.42 (s, 1H), 4.87-4.72 (m, 2H), 3.78 (s, 3H), 3..33-3.20 (m, 1H), 2.96-2.88 (m, 2H), 2.47-2.2.42 (m, 1H), 2.32-2.12 (m, 4H), 1.80-1.67 (m, 3H), 1.59-1.48 (m, 2H), 1.15 (d, J = 6.4 Hz, 3H). LCMS (ES, m/z): 514 $[M + H]^+$ |
| 450 | 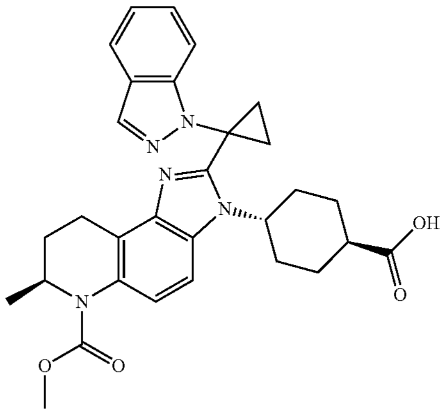 (1S,4R)-4-((S)-2-(1-(1H-indazol-1-yl)cyclopropyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 8.22 (s, 1H), 7.99-7.90 (m, 1H), 7.82-7.73 (m, 1H), 7.71-7.62 (m, 1H), 7.51-7.37 (m, 2H), 7.23-7.12 (m, 1H), 5.40-5.25 (m, 1H), 4.73-4.62 (m, 1H), 3.67 (s, 3H), 3.18-3.02 (m, 1H), 3.02-2.86 (m, 1H), 2.58-2.50 (m, 1H), 2.24-1.88 (m, 9H), 1.80-1.68 (m, 1H), 1.66-1.44 (m, 3H), 1.38-1.29 (m, 1H), 1.05 (d, J = 6.6, 3H). LCMS (ES, m/z): 528 $[M + H]^+$. |
| 451 | 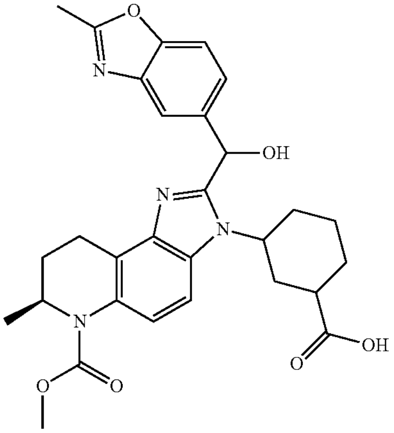 3-((7S)-2-(hydroxy(2-methylbenzo[d]oxazol-5-yl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.68 (s, 1H), 7.50 (d, J = 8.4 Hz, 1H), 7.49-7.40 (m, 3H), 6.32 (s, 1H), 4.89-4.74 (m, 2H), 3.79 (s, 3H), 3.29-3.25 (m, 1H), 3.04-2.98 (m, 1H), 2.85-2.83 (m, 1H), 2.64 (s, 3H), 2.35-2.31 (m, 2H), 2.29-2.26 (m, 2H), 2.13-1.97 (m, 1H), 1.78-1.74 (m, 1H), 1.67-1.61 (m, 2H), 1.44-1.20 (m, 2H), 1.17 (d, J = 6.4 Hz, 3H). LCMS (ES, m/z): 533 $[M + H]^+$. |

TABLE 18-continued

| Example Number | Structure and Compound Name | $^1$H NMR, LCMS |
|---|---|---|
| 452 | 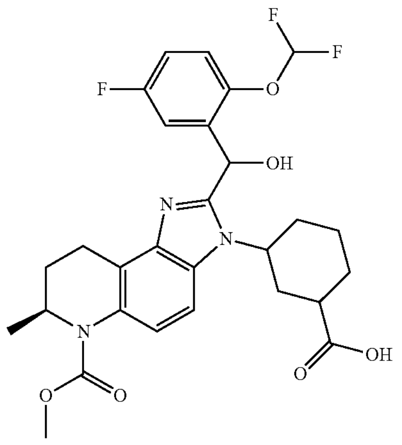 3-((7S)-2-((2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.54 (d, J = 8.8 Hz, 1H), 7.47-7.42 (m, 2H), 7.40-7.12 (m, 2H), 6.85-6.45 (m, 1H), 6.44 (s, 1H), 4.94-4.91 (m, 1H), 4.76-4.71 (m, 1H), 3.78 (s, 3H), 3.22-2.84 (m, 3H), 2.46-2.23 (m, 5H), 1.84-1.61 (m, 5H), 1.14 (d, J = 6.4 Hz, 3H). LCMS (ES, m/z): 562 [M + H]$^+$. |
| 453 | 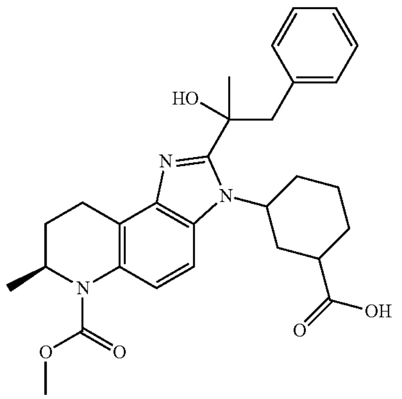 3-((7S)-2-(2-hydroxy-1-phenylpropan-2-yl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.55 (d, J = 8.8 Hz, 1H), 7.38 (d, J = 8.8 Hz, 1H), 7.28-7.15 (m, 5H), 5.73-5.54 (m, 1H), 4.78-7.64 (m, 1H), 3.80 (s, 3H), 3.51-3.33 (m, 2H), 3.28-3.17 (m, 2H), 3.02-2.83 (m, 2H), 2.64-2.52 (m, 1H), 2.45-2.21 (m, 4H), 1.91-1.80 (m, 2H), 1.75-1.62 (m, 5H), 1.15 (d, J = 6.4 Hz, 3H). LCMS (ES, m/z): 506 [M + H]$^+$. |
| 454 | 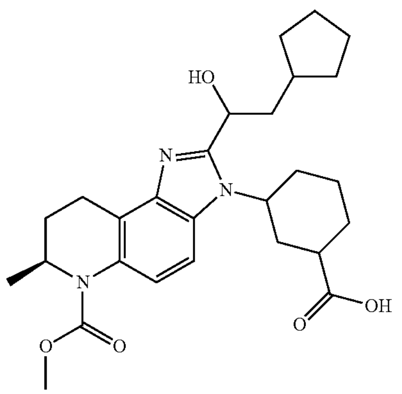 3-((7S)-2-(2-cyclopentyl-1-hydroxyethyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.55 (d, J = 9.2 Hz, 1H), 7.41 (d, J = 8.8 Hz, 1H), 5.27-5.12 (m, 2H), 4.80-4.76 (m, 1H), 3.79 (s, 3H), 3.23-3.16 (m, 1H), 3.08-2.88 (m, 2H), 2.58-2.53 (m, 1H), 2.39-2.19 (m, 5H), 1.98-1.88 (m, 4H), 1.75-1.66 (m, 6H), 1.53-1.48 (m, 2H), 1.33-1.18 (m, 3H), 1.14 (d, J = 6.8 Hz, 3H). LCMS (ES, m/z): 484 [M + H]$^+$. |

TABLE 18-continued

| Example Number | Structure and Compound Name | $^1$H NMR, LCMS |
|---|---|---|
| 455 | 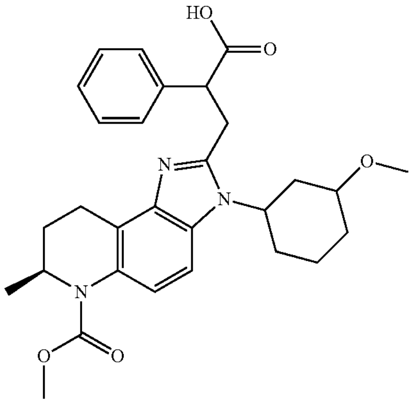 3-((7S)-6-(methoxycarbonyl)-3-(3-methoxycyclohexyl)-7-methyl-6,7,8,9-tetrahydro-3H-imidazo[4,5-f]quinolin-2-yl)-2-phenylpropanoic acid 4th eluting isomer | $^1$H-NMR ($CD_3OD$, 400 MHz) δ (ppm): 7.46-7.38 (m, 2H), 7.30-7.25 (m, 5H), 4.75-4.74 (m, 1H), 4.50-4.46 (m, 1H), 4.26-4.25 (m, 1H), 3.76-3.74 (m, 4H), 3.69-3.63 (m, 1H), 3.41-3.35 (m, 4H), 3.11-3.09 (m, 1H), 2.94-2.90 (m, 1H), 2.27-2.09 (m, 3H), 2.00-1.96 (m, 1H), 1.75-1.72 (m, 1H), 1.61-1.48 (m, 3H), 1.29-1.25 (m, 1H), 1.11 (d, J = 6.8 Hz, 3H), 1.07-1.05 (m, 1H). LCMS (ES, m/z): 506 [M + H]+. |
| 456 | 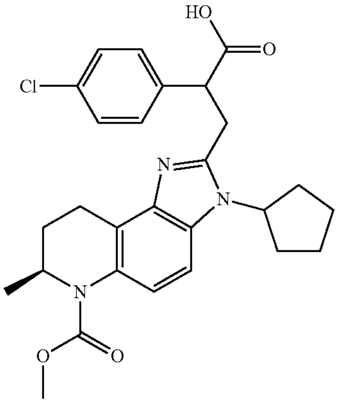 2-(4-chlorophenyl)-3-((7S)-3-cyclopentyl-6-(methoxycarbonyl)-7-methyl-6,7,8,9-tetrahydro-3H-imidazo[4,5-f]quinolin-2-yl)propanoic acid 2nd eluting isomer | $^1$H-NMR ($CD_3OD$, 400 MHz) δ (ppm): 7.58-7.52 (m, 1H), 7.48-7.39 (m, 5H), 5.05-4.91 (m, 1H), 4.85-4.72 (m, 1H), 4.35-4.20 (m, 1H), 3.85-3.73 (m, 4H), 3.44-3.35 (m, 1H), 3.15-3.02 (m, 1H), 2.98-2.85 (m, 1H), 2.31-1.95 (m, 6H), 1.90-1.68 (m, 4H), 1.12 (d, J = 6.8 Hz, 3H). LCMS (ES, m/z): 496 $[M + H]^+$. |
| 457 | 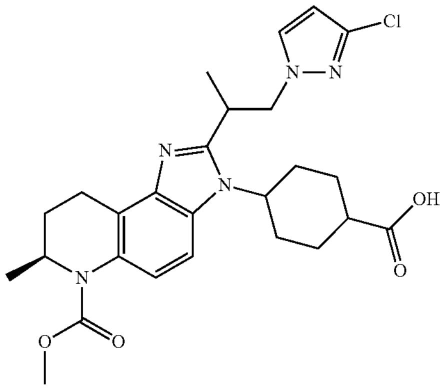 4-((7S)-2-(1-(3-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 300 MHz) δ (ppm): 7.53-7.38 (m, 1H), 7.38-7.23 (m, 2H), 6.03 (s, 1H), 4.83-4.68 (m, 1H), 4.68-4.51 (m, 1H), 4.51-4.36 (m, 1H), 4.36-4.17 (m, 1H), 4.03-3.88 (m, 1H), 3.76 (s, 3H), 3.27-3.09 (m, 1H), 3.01-2.82 (m, 1H), 2.59-2.07 (m, 6H), 1.99-1.59 (m, 4H), 1.59-1.39 (m, 4H), 1.14-1.12 (d, J = 6.6 Hz, 3H). LCMS: (ES, m/z): 514 $[M + H]^+$. |

TABLE 18-continued

| Example Number | Structure and Compound Name | $^1$H NMR, LCMS |
|---|---|---|
| 458 | 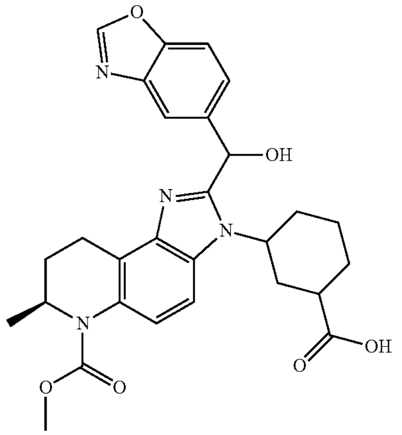<br>3-((7S)-2-(benzo[d]oxazol-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 8.49 (s, 1H), 7.85-7.77 (m, 1H), 7.67 (d, J = 8.4 Hz, 1H), 7.59-7.51 (m, 1H), 7.50-7.45 (m, 1H), 7.44-7.37 (m, 1H), 6.35 (s, 1H), 4.88-4.83 (m, 1H), 4.81-4.73 (m, 1H), 3.79 (s, 3H), 3.30-3.24 (m, 1H), 3.07-2.93 (m, 1H), 2.86-2.77 (m, 1H), 2.41-2.23 (m, 2H), 2.21-2.05 (m, 2H), 2.03-1.90 (m, 1H), 1.83-1.71 (m, 1H), 1.70-1.53 (m, 2H), 1.52-1.29 (m, 2H), 1.17 (d, J = 6.8 Hz, 3H). LCMS (ES, m/z): 519 $[M + H]^+$. |
| 459 | 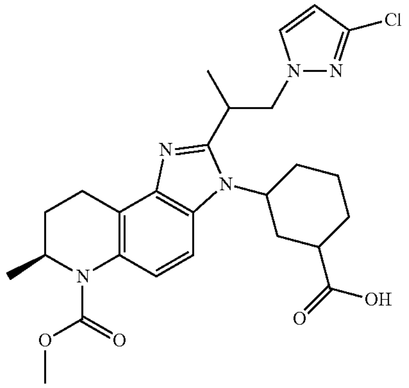<br>3-((7S)-2-(1-(3-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 300 MHz) δ (ppm): 7.93-7.66 (m, 2H), 7.66-7.46 (m, 1H), 6.17 (s, 1H), 4.83-4.72 (m, 1H), 4.72-4.53 (m, 2H), 4.33-4.09 (m, 1H), 3.80 (s, 3H), 3.18-2.88 (m, 3H), 2.59-2.13 (m, 5H), 1.99-1.66 (m, 4H), 1.63 (d, J = 7.2 Hz, 3H), 1.59-1.40 (m, 1H), 1.34-1.23 (m, 1H), 1.15 (d, J = 6.6 Hz, 3H). LCMS (ES, m/z): 514 $[M + H]^+$. |

TABLE 18-continued

| Example Number | Structure and Compound Name | $^1$H NMR, LCMS |
|---|---|---|
| 460 | 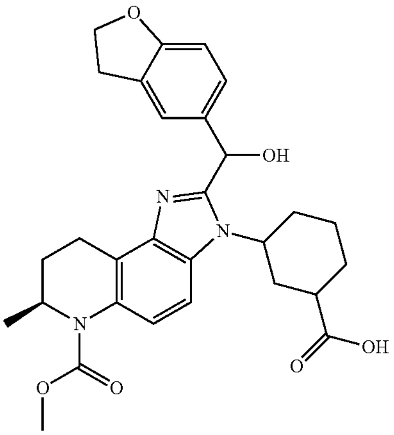 3-((7S)-2-((2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.4-7.33 (m, 2H), 7.34 (s, 1H), 7.15 (d, J = 8.0 Hz, 1H), 6.68 (d, J = 8.0 Hz, 1H), 6.18 (s, 1H), 4.94-4.88 (m, 1H), 4.79-4.75 (m, 1H), 4.53 (t, J = 8.4 Hz, 2H), 3.78 (s, 3H), 3.25-3.15 (m, 3H), 3.01-2.92 (m, 2H), 2.43-2.30 (m, 3H), 2.28-1.98 (m, 2H), 1.78-1.73 (m, 1H), 1.64-1.58 (m, 2H), 1.40-1.31 (m, 1H), 1.15 (d, J = 6.8 Hz, 3H), 1.07-1.04 (m, 1H). LCMS (ES, m/z): 520 $[M + H]^+$. |
| 461 | 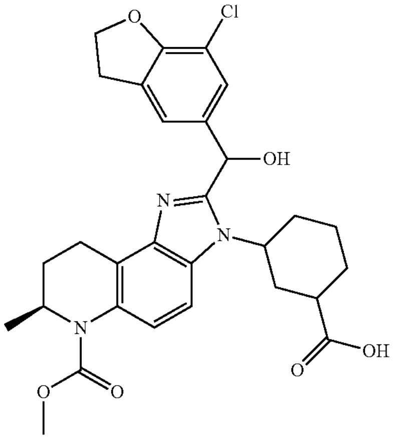 3-((7S)-2-((7-chloro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.57-7.42 (m, 2H), 7.29 (s, 1H), 7.22 (s, 1H), 6.18 (s, 1H), 5.08-4.93 (m, 1H), 4.83-4.71 (m, 1H), 4.63 (t, J = 8.4 Hz, 2H), 3.79 (s, 3H), 3.30-3.12 (m, 3H), 3.04-2.90 (m, 2H), 2.51-2.38 (m, 1H), 2.39-2.20 (m, 2H), 2.16-1.98 (m, 2H), 1.82-1.71 (m, 1H), 1.70-1.62 (m, 2H), 1.54-1.39 (m, 1H), 1.16 (d, J = 6.4 Hz, 3H), 1.14-1.09 (m, 1H). LCMS (ES, m/z): 554 $[M + H]^+$. |

TABLE 18-continued

| Example Number | Structure and Compound Name | $^1$H NMR, LCMS |
|---|---|---|
| 462 | 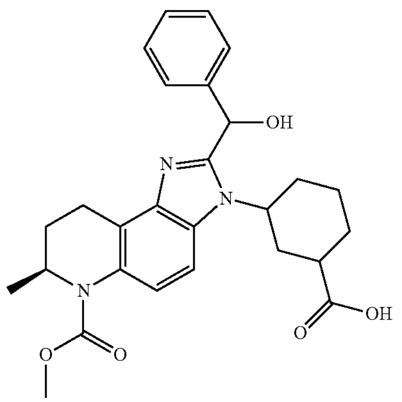 3-((7S)-2-(hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.51-7.25 (m, 7H), 6.20 (s, 1H), 4.98-4.72 (m, 2H), 3.79 (s, 3H), 3.33-3.25 (m, 1H), 3.06-2.81 (m, 2H), 2.41-2.20 (m, 2H), 2.18-2.05 (m, 3H), 1.81-1.72 (m, 1H), 1.70-1.53 (m, 2H), 1.48-1.25 (m, 2H), 1.16 (d, J = 6.4 Hz, 3H). LCMS (ES, m/z): 478 [M + H]$^+$. |
| 463 | 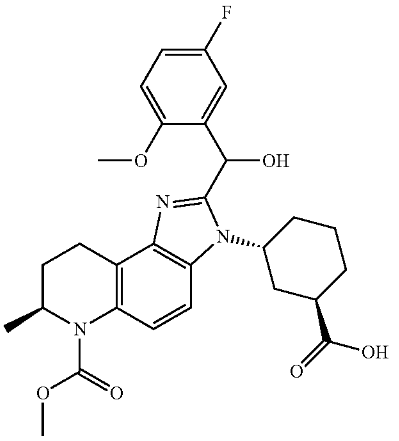 (1R,3R)-3-((S)-2-(5-fluoro-2-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.68-7.66 (m, 2H), 7.10-6.96 (m, 3H), 4.85-4.75 (m, 2H), 4.54-4.38 (m, 2H), 3.82 (s, 3H), 3.80 (s, 3H), 3.16-3.12 (m, 1H), 3.06-2.94 (m, 2H), 2.44-2.39 (m, 1H), 2.34-2.11 (m, 4H), 1.84-1.65 (m, 3H), 1.33-1.25 (m, 2H), 1.17 (d, J = 6.8 Hz, 3H). LCMS (ES, m/z): 510 [M + H]$^+$ |
| 464 | 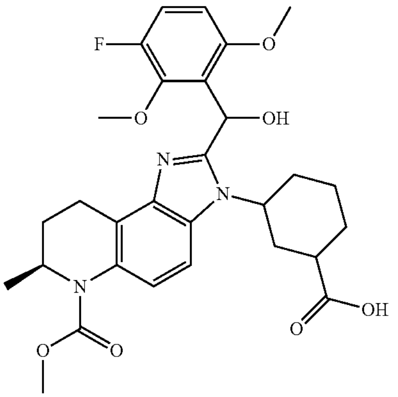 3-((7S)-2-((3-fluoro-2,6-dimethoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.49-7.41 (m, 2H), 7.17-7.12 (m, 1H), 6.77-6.74 (m, 1H), 6.55 (s, 1H), 4.86-4.76 (m, 1H), 4.38-4.34 (m, 1H), 3.84 (s, 3H), 3.79 (s, 3H), 3.53 (s, 3H), 3.33-325 (m, 1H), 3.05-2.98 (m, 1H), 2.94-2.92 (m, 1H), 2.50-2.48 (m, 1H), 2.31-2.18 (m, 3H), 2.02-1.93 (m, 1H), 1.79-1.75 (m, 1H), 1.61-1.58 (m, 2H), 1.18-1.16 (m, 4H), 0.99-0.96 (m, 1H). LCMS (ES, m/z): 556 [M + H]$^+$ |

TABLE 18-continued

| Example Number | Structure and Compound Name | $^1$H NMR, LCMS |
|---|---|---|
| 465 | 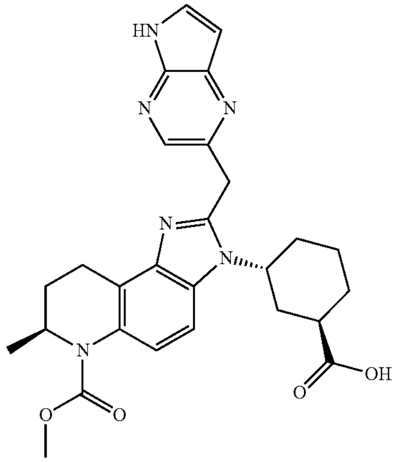 (1R,3R)-3-((S)-2-((5H-pyrrolo[2,3-b]pyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.46 (s, 1H), 8.89 (s, 2) 8.86 (s, 1H), 7.78 (d, J = 3.6 Hz, 1H), 5.13-5.02 (m, 1H), 4.97 (d, J = 6.8 Hz, 2H), 4.87-4.81 (m, 1H), 3.84 (s, 3H), 3.33-2.99 (m, 3H), 2.45-2.15 (m, 5H), 1.88-1.70 (m, 4H), 1.43-1.28 (m, 1H), 1.19 (d, J = 6.8 Hz, 3H). LCMS (ES, m/z): 503 $[M + H]^+$. |
| 466 | 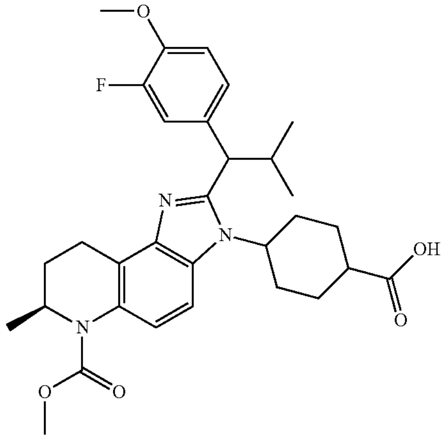 4-((7S)-2-(1-(3-fluoro-4-methoxyphenyl)-2-methylpropyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 300 MHz) δ (ppm): 7.53-7.41 (m, 2H), 7.18-7.06 (m, 3H), 4.85-4.70 (m, 1H), 4.60-4.50 (m, 1H), 4.12-4.00 (m, 1H), 3.85 (s, 3H), 3.78 (s, 3H), 3.12-2.75 (m, 2H), 2.55-1.65 (m, 9H), 1.60-1.45 (m, 1H), 1.40-1.25 (m, 1H), 1.18 (d, J = 6.9 Hz, 3H), 1.18-1.10 (m, 4H), 0.93 (d, J = 6.6 Hz, 3H). LCMS (ES, m/z): 552 $[M + H]^+$ |

TABLE 18-continued

| Example Number | Structure and Compound Name | $^1$H NMR, LCMS |
|---|---|---|
| 467 | 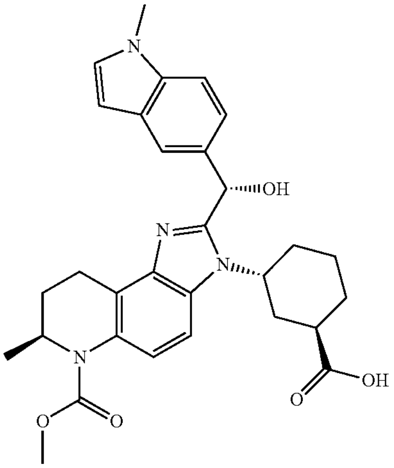 3-((7S)-2-(hydroxy(1-methyl-1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.61 (s, 1H), 7.45-7.38 (m, 3H), 7.38-7.32 (m, 1H), 7.17-7.15 (m, 1H), 6.42 (s, 1H), 6.41 (s, 1H), 4.91-4.75 (m, 2H), 3.79 (s, 3H), 3.78 (s, 3H), 3.31-3.22 (m, 1H), 3.11-3.00 (m, 1H), 2.91-2.85 (m, 1H), 2.45-2.31 (m, 2H), 2.28-2.21 (m, 1H), 2.12-2.00 (m, 1H), 1.99-1.80 (m, 1H), 1.79-1.70 (m, 1H), 1.62-1.40 (m, 2H), 1.17 (d, J = 6.4 Hz, 3H), 1.12-1.09 (m, 1H), 0.92-0.89 (m, 1H). LCMS (ES, m/z): 531 $[M + H]^+$. |
| 468 | 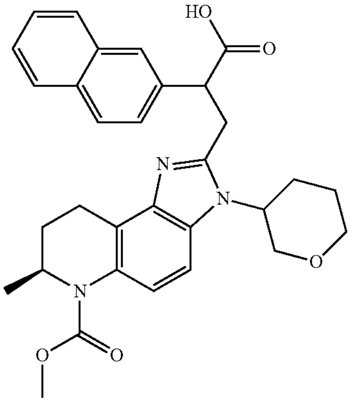 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(naphthalen-2-yl)propanoic acid 1st eluting isomer | $^1$H-NMR ($CD_3OD$, 400 MHz) δ (ppm): 7.85-7.76 (m, 4H), 7.56-7.53 (m, 1H), 7.49-7.43 (m, 3H), 7.37-7.34 (m, 1H), 4.87-4.72 (m, 1H), 4.60-4.56 (m, 1H), 4.50-4.45 (m, 1H), 3.94-3.70 (m, 6H), 3.51-3.50 (m, 1H), 3.45-3.38 (m, 1H), 3.22-3.11 (m, 2H), 2.94 (m, 1H), 2.60-2.05 (m, 3H), 2.00-1.71 (m, 3H), 1.12 (d, J = 6.8 Hz, 3H). LCMS (ES, m/z): 528 $[M + H]^+$ |

TABLE 18-continued

| Example Number | Structure and Compound Name | $^1$H NMR, LCMS |
|---|---|---|
| 469 | 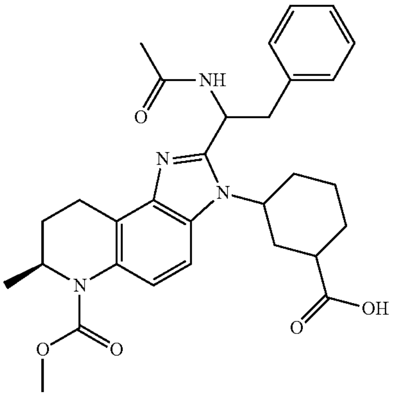<br>3-((7S)-2-(1-acetamido-2-phenylethyl)-6-(methoxycarbonyl)-7-methyl-6,7,8,9-tetrahydro-3H-imidazo[4,5-f]quinolin-3-yl)cyclohexane-1-carboxylic acid<br>2nd eluting isomer | $^1$H-NMR ($CD_3OD$, 400 MHz) δ (ppm): 7.50-7.48 (m, 1H), 7.41-7.37 (m, 1H), 7.307-7.01 (m, 5H), 5.65-5.50 (m, 1H), 5.05-4.96 (m, 1H), 4.80-4.69 (m, 1H), 3.79 (s, 3H), 3.50-3.35 (m, 1H), 3.30-3.15 (m, 2H), 2.99-2.82 (m, 2H), 2.35-2.22 (m, 4H), 1.94-1.80 (m, 6H), 1.79-1.60 (m, 3H), 1.16 (d, J = 6.8 Hz, 3H). LCMS (ES, m/z): 533 $[M + H]^+$. |
| 470 | 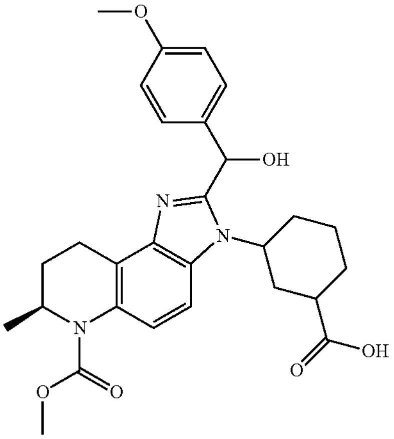<br>3-((7S)-2-(hydroxy(4-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid<br>1st eluting isomer | $^1$H-NMR (DMSO, 400 MHz) δ (ppm): 7.49-7.45 (m, 1H), 7.32-7.27 (m, 3H), 6.89-6.86 (m, 2H), 6.50-6.20 (m, 1H), 6.03 (s, 1H), 4.86-4.79 (m, 1H), 4.67-4.62 (m, 1H), 3.72 (s, 3H), 3.67 (s, 3H), 3.08-3.01 (m, 1H), 2.88-2.82 (m, 2H), 2.34-2.29 (m, 1H), 2.18-2.10 (m, 2H), 1.95-1.88 (m, 2H), 1.66-1.61 (m, 1H), 1.58-1.48 (m, 2H), 1.26-1.22 (m, 1H), 1.06 (d, J = 6.8 Hz, 3H), 1.94-0.90 (m, 1H). LCMS (ES, m/z): 508 $[M + H]^+$. |
| 471 | 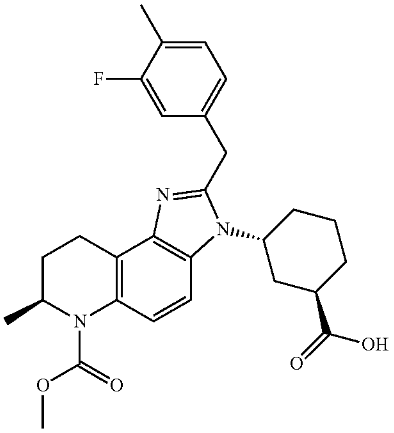<br>(1R,3R)-3-((S)-2-(3-fluoro-4-methylbenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.46 (d, J = 8.8 Hz, 1H), 7.39 (d, J = 8.8 Hz, 1H), 7.19-7.10 (m, 1H), 6.97-6.87 (m, 2H), 4.81-4.62 (m, 2H), 4.42-4.23 (m, 2H), 3.76 (s, 3H), 3.25-3.10 (m, 1H), 3.02-2.88 (m, 2H), 2.37-2.06 (m, 8H), 1.81-1.59 (m, 3H), 1.34-1.20 (m, 2H), 1.13 (d, J = 6.4 Hz, 3H). LCMS (ES, m/z): 494 $[M + H]^+$. |

TABLE 18-continued

| Example Number | Structure and Compound Name | $^1H$ NMR, LCMS |
|---|---|---|
| 472 | 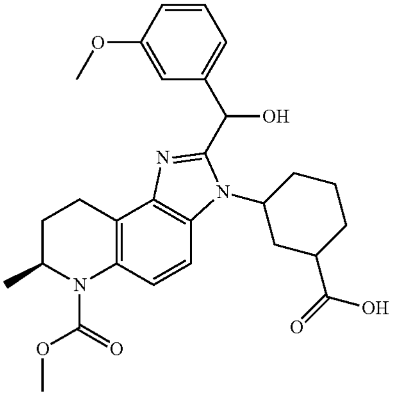 3-((7S)-2-(hydroxy(3-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1H$-NMR ($CD_3OD$, 400 MHz) δ (ppm): 7.50-7.40 (m, 2H), 7.27-7.08 (m, 2H), 6.94-6.84 (m, 2H), 6.23 (s, 1H), 4.91-4.88 (m, 1H), 3.79 (s, 6H), 3.34-2.96 (m, 2H), 2.78-2.68 (m, 1H), 2.36-2.05 (m, 5H), 1.78-1.55 (m, 3H), 1.31-1.15 (m, 6H). LCMS (ES, m/z): 508 $[M + H]^+$. |
| 473 | 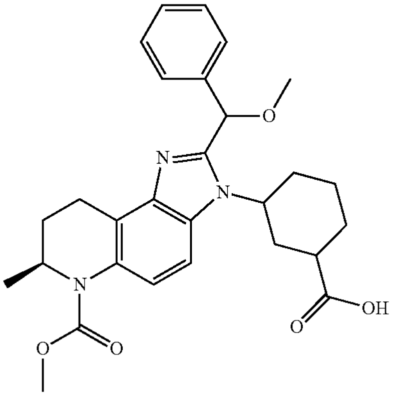 3-((7S)-2-(methoxy(phenyl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 7.53-7.24 (m, 7H), 5.80 (s, 1H), 4.80-4.72 (m, 2H), 3.79 (s, 3H), 3.52 (s, 3H), 3.32-3.25 (m, 1H), 3.05-2.86 (m, 2H), 2.38-2.19 (m, 2H), 2.18-2.02 (m, 3H), 1.78-1.55 (m, 3H), 1.52-1.30 (m, 2H), 1.17 (d, J = 6.8 Hz, 3H). LCMS (ES, m/z): 492 $[M + H]^+$. |

TABLE 18-continued

| Example Number | Structure and Compound Name | $^1H$ NMR, LCMS |
|---|---|---|
| 474 | 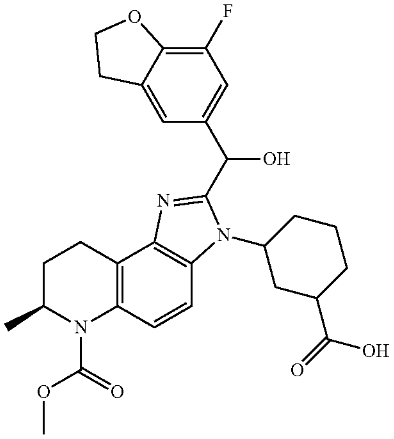 3-((7S)-2-((7-fluoro-2,3-dihydrobenzofuran-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1H$-NMR ($CD_3OD$, 400 MHz) δ (ppm): 7.58-7.46 (m, 1H), 7.46-7.37 (m, 1H), 7.17-7.01 (m, 2H), 6.15 (s, 1H), 5.03-4.92 (m, 1H), 4.83-4.71 (m, 1H), 4.63 (t, J = 8.4 Hz, 2H), 3.78 (s, 3H), 3.31-3.18 (m, 3H), 3.02-2.83 (m, 2H), 2.52-2.31 (m, 2H), 2.31-2.21 (m, 1H), 2.16-2.08 (m, 1H), 2.08-1.98 (m, 1H), 1.84-1.69 (m, 1H), 1.69-1.51 (m, 2H), 1.47-1.33 (m, 1H), 1.15 (d, J = 6.8 Hz, 3H), 1.12-1.04 (m, 1H). LCMS (ES, m/z): 538 $[M + H]^+$ |
| 475 | 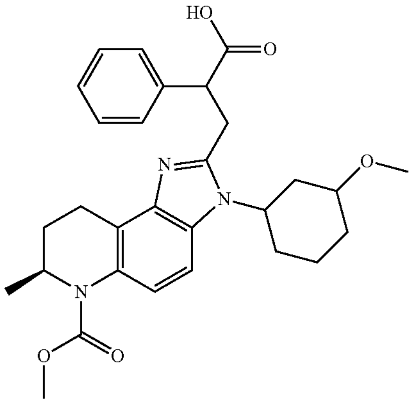 3-((7S)-6-(methoxycarbonyl)-3-(3-methoxycyclohexyl)-7-methyl-6,7,8,9-tetrahydro-3H-imidazo[4,5-f]quinolin-2-yl)-2-phenylpropanoic acid 6th eluting isomer | $^1H$-NMR ($CD_3OD$, 400 MHz) δ (ppm): 7.49-7.47 (m, 1H), 7.40-7.37 (m, 3H), 7.34-7.25 (m, 3H), 4.77-4.71 (m, 2H), 4.32-4.30 (m, 1H), 3.76-3.66 (m, 5H), 3.39 (s, 3H), 3.27-3.22 (m, 1H), 3.13-3.10 (m, 1H), 2.92-2.87 (m, 1H), 2.38-2.21 (m, 3H), 2.08-2.04 (m, 1H), 1.96-1.86 (m, 3H), 1.74-1.69 (m, 2H), 1.55-1.50 (m, 1H), 1.12 (d, J = 6.8 Hz, 3H). LCMS (ES, m/z): 506 [M + H]+. |

TABLE 18-continued

| Example Number | Structure and Compound Name | $^1H$ NMR, LCMS |
|---|---|---|
| 476 | 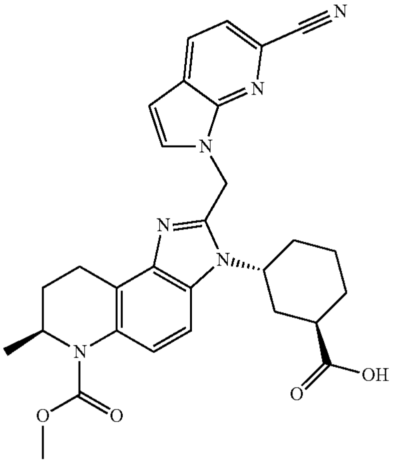 (1R,3R)-3-((S)-2-((6-cyano-1H-pyrrolo[2,3-b]pyridin-1-yl)methyl)-6-(methoxycarbonyl)-7-methyl-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 8.15-8.12 (m, 1H), 7.75-7.71 (m, 1H), 7.58-7.55 (m, 2H), 7.47-7.44 (m, 1H), 6.71-6.69 (m, 1H), 6.10-6.06 (m, 1H), 5.70-5.66 (m, 1H), 5.15-5.06 (m, 1H), 4.78-4.74 (m, 1H), 3.78 (s, 3H), 3.22-3.14 (m, 1H), 2.98-2.90 (m, 2H), 2.43-2.37 (m, 1H), 2.32-2.20 (m, 4H), 1.74-1.68 (m, 3H), 1.54-1.46 (m, 2H), 1.14 (d, J = 6.8 Hz, 3H). LCMS (ES, m/z): 527 $[M + H]^+$. |
| 477 | 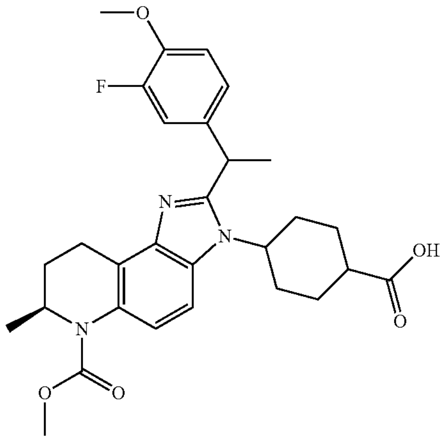 4-((7S)-2-(1-(3-fluoro-4-methoxyphenyl)ethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 7.50-7.30 (m, 2H), 7.12-6.93 (m, 3H), 4.80-4.70 (m, 1H), 4.64-4.53 (m, 1H), 4.32-4.20 (m, 1H), 3.85 (s, 3H), 3.78 (s, 3H), 3.04-2.89 (m, 1H), 2.49-2.23 (m, 3H), 2.23-2.05 (m, 2H), 1.97 (s, 1H), 1.92-1.65 (m, 5H), 1.64-1.52 (m, 1H), 1.38-1.23 (m, 2H), 1.16 (d, J = 6.8 Hz, 1H), 1.12-1.08 (m, 1H). LCMS (ES, m/z): 524 $[M + H]^+$. |

TABLE 18-continued

| Example Number | Structure and Compound Name | $^1H$ NMR, LCMS |
|---|---|---|
| 478 | 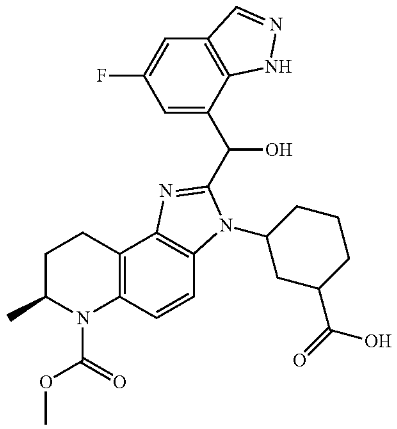 3-((7S)-2-((5-fluoro-1H-indazol-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 8.09 (s, 1H), 7.52-7.50 (m, 1H), 7.49-7.40 (m, 2H), 7.24-7.20 (m, 1H), 6.63 (s, 1H), 5.20-5.08 (m, 1H), 5.85-5.75 (m, 1H), 3.80 (s, 3H), 3.28-3.15 (m, 1H), 3.04-2.91 (m, 2H), 2.48-2.41 (m, 2H), 2.34-2.25 (m, 1H), 2.15-1.95 (m, 2H), 1.80-1.45 (m, 3H), 1.14 (d, J = 6.4 Hz, 3H), 1.10-1.00 (m, 1H), 0.98-0.88 (m, 1H). LCMS (ES, m/z): 536 $[M + H]^+$. |
| 479 | 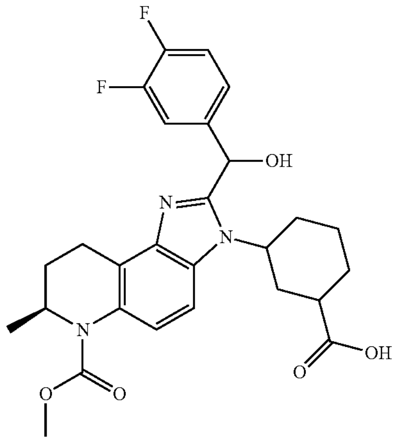 3-((7S)-2-((3,4-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$ NMR ($CD_3OD$, 400 MHz) δ (ppm): 7.54-7.38 (m, 3H), 7.22-7.14 (m, 2H), 6.20 (s, 1H), 4.96-4.93 (m, 1H), 4.79-4.74 (m, 1H), 3.78 (s, 3H), 3.24-3.18 (m, 1H), 3.01-2.94 (m, 2H), 2.50-2.21 (m, 3H), 2.17-1.97 (m, 2H), 1.78-1.72 (m, 1H), 1.63-1.55 (m, 2H), 1.49-1.31 (m, 1H), 1.14 (d, J = 6.8 Hz, 3H), 1.09-1.04 (m, 1H). LCMS (ES, m/z): 514 $[M + H]^+$. |

TABLE 18-continued

| Example Number | Structure and Compound Name | $^1$H NMR, LCMS |
|---|---|---|
| 480 | 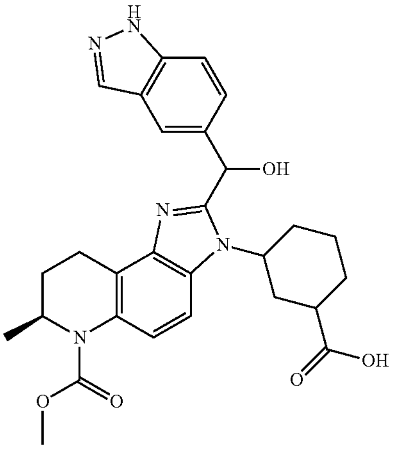 3-((7S)-2-(hydroxy(1H-indazol-5-yl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.87 (s, 1H), 7.53 (s, 1H), 7.51-7.37 (m, 4H), 6.33 (s, 1H), 4.94-4.89 (m, 1H), 4.79-4.74 (m, 1H), 3.78 (s, 3H), 3.32-3.27 (m, 1H), 3.04-2.98 (m, 1H), 2.97-2.84 (m, 1H), 2.33-2.25 (m, 2H), 2.15-1.95 (m, 3H), 1.78-1.72 (m, 1H), 1.62-1.54 (m, 2H), 1.31-1.24 (m, 1H), 1.16 (d, J = 6.4 Hz, 3H), 1.15-1.13 (m, 1H). LCMS (ES, m/z): 518 $[M + H]^+$. |
| 481 | 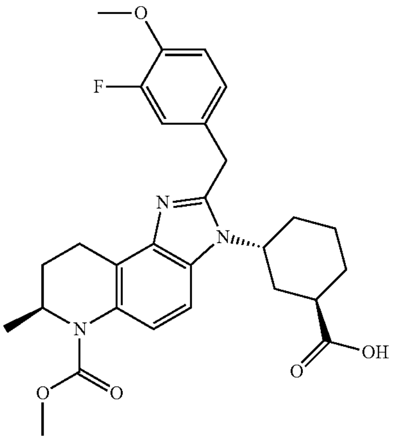 (1R,3R)-3-((S)-2-(3-fluoro-4-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.48-7.38 (m, 2H), 7.04-7.01 (m, 3H), 4.86-4.67 (m, 2H), 4.40-4.15 (m, 2H), 3.85 (s, 3H), 3.76 (s, 3H), 3.30-3.10 (m, 1H), 2.99-2.89 (m, 2H), 2.48-2.05 (m, 5H), 1.85-1.65 (m, 3H), 1.40-1.20 (m, 2H), 1.13 (d, J = 6.4 Hz, 3H) LCMS (ES, m/z): 510 $[M + H]^+$. |

TABLE 18-continued

| Example Number | Structure and Compound Name | $^1$H NMR, LCMS |
|---|---|---|
| 482 | 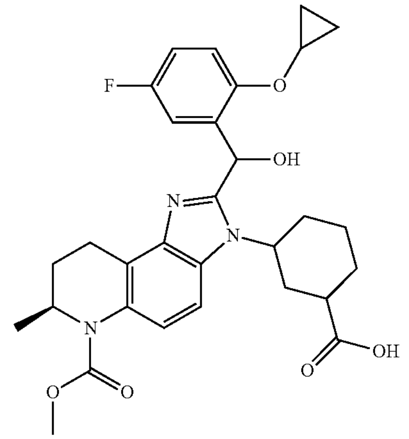 3-((7S)-2-((2-cyclopropoxy-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.70-7.65 (m, 2H), 7.39-7.29 (m, 2H), 7.17-7.11 (m, 1H), 6.36 (s, 1H), 4.87-4.79 (m, 2H), 3.82 (s, 3H), 3.73-3.71 (m, 1H), 3.33-2.99 (m, 3H), 2.46-2.18 (m, 5H), 1.83-1.68 (m, 3H), 1.46-1.22 (m, 2H), 1.17 (d, J = 6.8 Hz, 3H), 0.70-0.63 (m, 2H), 0.43-0.36 (m, 2H). LCMS (ES, m/z): 552 $[M + H]^+$. |
| 483 | 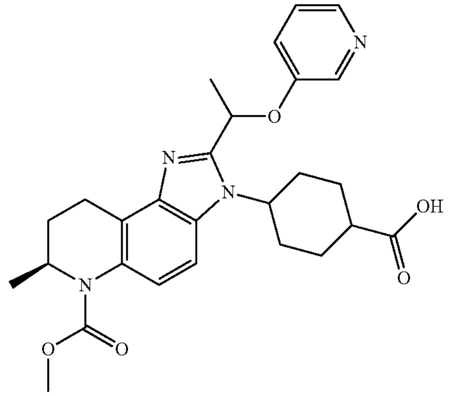 4-((7S)-6-(methoxycarbonyl)-7-methyl-2-(1-(pyridin-3-yloxy)ethyl)-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 8.35 (S, 1H), 8.16 (d, J = 4.8 Hz, 1H), 7.54-7.52 (m, 2H), 7.46-7.43 (m, 1H), 7.37-7.34 (m, 1H), 6.02-5.96 (m, 1H), 4.84-4.64 (m, 2H), 3.79 (s, 3H), 3.25-3.11 (m, 1H), 2.96-2.81 (m, 1H), 2.60-2.10 (m, 6H), 2.09-2.01 (m, 1H), 1.91 (d, J = 6.8 Hz, 3H), 1.79-1.53 (m, 4H), 1.13 (d, J = 6.4 Hz, 3H). LCMS (ES, m/z): 493 $[M + H]^+$. |
| 484 | 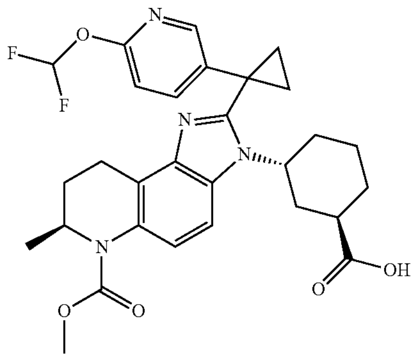 (1R,3R)-3-((S)-2-(1-(6-(difluoromethoxy)pyridin-3-yl)cyclopropyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.05 (s, 1H), 7.77-7.63 (m, 1H), 7.55-7.27 (m, 3H), 6.92 (d, J = 8.4 Hz, 1H), 5.12-4.95 (m, 1H), 4.81-4.68 (m, 1H), 3.79 (s, 3H), 3.29-3.15 (m, 1H), 3.04-2.86 (m, 2H), 2.49-2.34 (m, 1H), 2.33-2.25 (m, 1H), 2.24-2.13 (m, 3H), 1.97-1.80 (m, 2H), 1.78-1.61 (m, 3H), 1.59-1.50 (m, 1H), 1.46-1.28 (m, 3H), 1.15 (d, J = 6.4 Hz, 3H). LCMS (ES, m/z): 555 $[M + H]^+$. |

TABLE 18-continued

| Example Number | Structure and Compound Name | $^1$H NMR, LCMS |
|---|---|---|
| 485 | 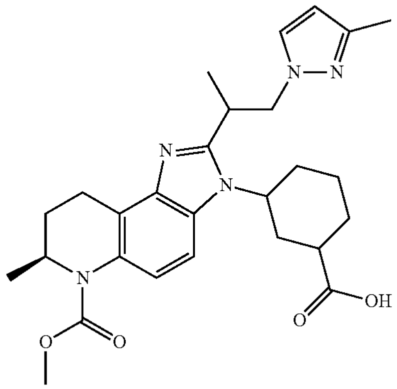 3-((7S)-6-(methoxycarbonyl)-7-methyl-2-(1-(3-methyl-1H-pyrazol-1-yl)propan-2-yl)-6,7,8,9-tetrahydro-3H-imidazo[4,5-f]quinolin-3-yl)cyclohexane-1-carboxylic acid 1st eluting isomer | $^1$H-NMR ($CD_3OD$, 300 MHz) δ (ppm): 7.44 (d, J = 9.0 Hz, 1H), 7.33 (d, J = 9.0 Hz, 1H), 7.16 (s, 1H), 5.93-5.62 (m, 1H), 4.78-4.66 (m, 1H), 4.62-4.34 (m, 3H), 3.97-3.84 (m, 1H), 3.76 (s, 3H), 3.28-3.14 (m, 1H), 3.02-2.73 (m, 2H), 2.37-2.05 (m, 8H), 1.89-1.59 (m, 3H), 1.59-1.39 (m, 5H), 1.13 (d, J = 6.6 Hz, 3H). LCMS (ES, m/z): 494 $[M + H]^+$ |
| 486 | 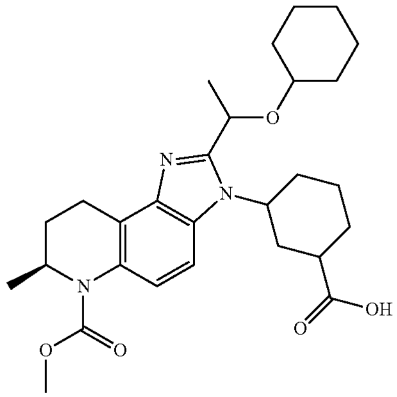 3-((7S)-2-(1-(cyclohexyloxy)ethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H NMR ($CD_3OD$, 400 MHz) δ (ppm): 7.57-7.56 (m, 1H), 7.43-7.41 (m, 1H), 5.32-5.30 (m, 1H), 5.15-5.13 (m, 1H), 4.78-4.76 (m, 1H), 3.78 (s, 3H), 3.32-3.31 (m, 1H), 3.20-3.11 (m, 1H), 2.96-2.90 (m, 2H), 2.51-2.48 (m, 1H), 2.48-2.36 (m, 2H), 2.36-2.27 (m, 2H), 2.08-2.04 (m, 1H), 1.93-1.86 (m, 2H), 1.72-1.61 (m, 9H), 1.56-1.51 (m, 1H), 1.38-1.25 (m, 5H), 1.14 (d, J = 6.4 Hz, 3H). LCMS (ES, m/z): 498 $[M + H]^+$. |
| 487 | 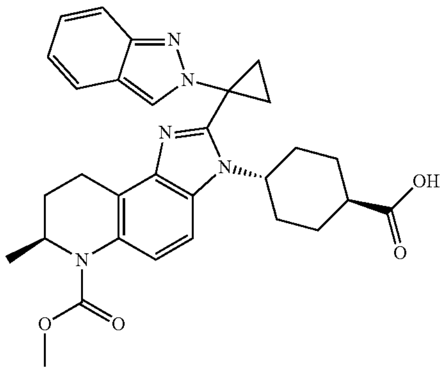 (1S,4r)-4-((S)-2-(1-(2H-indazol-2-yl)cyclopropyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 8.67 (s, 1H), 7.76-7.63 (m, 2H), 7.62-7.54 (m, 1H), 7.54-7.46 (m, 1H), 7.32-7.21 (m, 7.00 (m, 1H), 5.09-4.96 (m, 1H), 4.74-4.60 (m, 1H), 3.69 (s, 3H), 3.18-3.01 (m, 1H), 2.99-2.84 (m, 1H), 2.47 (s, 1H), 2.22-2.07 (m, 5H), 2.03-1.92 (m, 4H), 1.80-1.64 (m, 1H), 1.59-1.36 (m, 4H), 1.05 (d, J = 6.3, 3H). LCMS (ES, m/z): 528 $[M + H]^+$. |

TABLE 18-continued

| Example Number | Structure and Compound Name | $^1H$ NMR, LCMS |
|---|---|---|
| 488 | 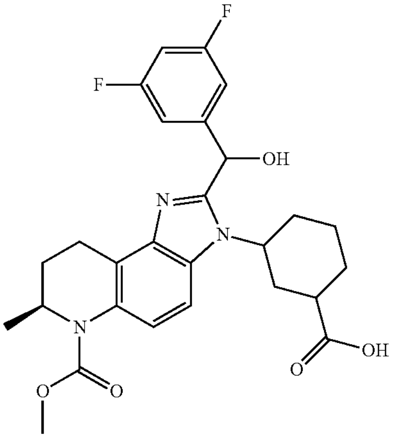 3-((7S)-2-((3,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 7.63-7.47 (m, 2H), 7.12 (d, J = 6.8 Hz, 3H), 6.90-6.87 (m, 1H), 6.26 (s, 1H), 5.04-4.93 (m, 1H), 4.81-4.78 (m, 1H), 3.79 (s, 3H), 3.24-3.15 (m, 1H), 3.02-2.98 (m, 2H), 2.52-2.06 (m, 5H), 1.81-1.59 (m, 3H), 1.52-1.42 (m, 1H), 1.22-1.17 (m, 1H), 1.15 (d, J = 6.4 Hz, 3H). LCMS (ES, m/z): 514 $[M + H]^+$. |
| 489 | 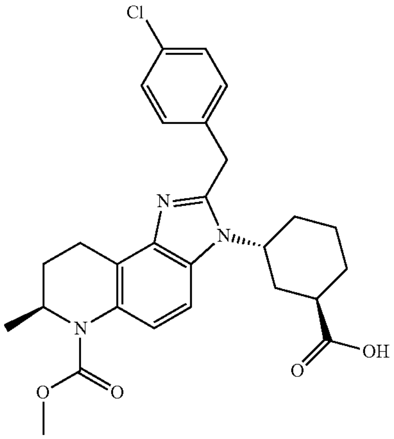 (1R,3R)-3-((S)-2-(4-chlorobenzyl)-6-(methoxycarbonyl)-7-methyl-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 7.46 (d, J = 8.8 Hz, 1H), 7.38 (d, J = 9.2 Hz, 1H), 7.30 (d, J = 8.4 Hz, 2H), 7.23 (d, J = 8.4 Hz, 2H), 4.81-4.62 (m, 2H), 4.45-4.22 (m, 2H), 3.79 (s, 3H), 3.28-3.12 (m, 1H), 3.00-2.86 (m, 2H), 2.35-2.10 (m, 5H), 1.81-1.61 (m, 3H), 1.33-1.20 (m, 2H), 1.16 (d, J = 6.8 Hz, 3H). LCMS (ES, m/z): 496 $[M + H]^+$. |
| 490 | 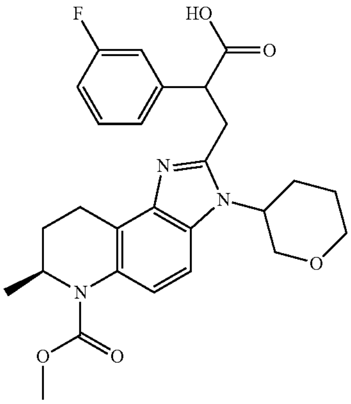 2-(3-fluorophenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1H$-NMR ($CD_3OD$, 300 MHz) δ (ppm): 7.48-7.24 (m, 3H), 7.19-6.95 (m, 3H), 4.74-4.55 (m, 2H), 4.20-3.95 (m, 3H), 3.76-3.55 (m, 5H), 3.40-3.00 (m, 2H), 2.92-2.85 (m, 1H), 2.55-2.05 (m, 3H), 1.87-1.68 (m, 4H), 1.10 (d, J = 6.9 Hz, 3H). LCMS (ES, m/z): 496 $[M + H]^+$ |

TABLE 18-continued

| Example Number | Structure and Compound Name | $^1$H NMR, LCMS |
|---|---|---|
| 491 | 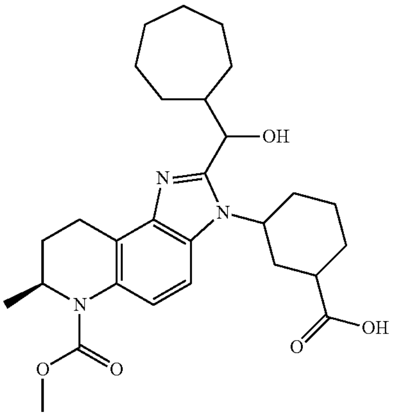 3-((7S)-2-(cycloheptyl(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.65-7.49 (m, 1H), 7.48-7.23 (m, 1H), 5.33-5.12 (m, 1H), 4.82-4.58 (m, 2H), 3.78 (s, 3H), 3.28-3.12 (m, 1H), 3.04-2.86 (m, 2H), 2.59-2.41 (m, 2H), 2.41-2.19 (m, 5H), 2.02-1.82 (m, 2H), 1.82-1.53 (m, 9H), 1.53-1.41 (m, 3H), 1.25-1.11 (m, 5H). LCMS (ES, m/z): 498 [M + H]$^+$. |
| 492 | 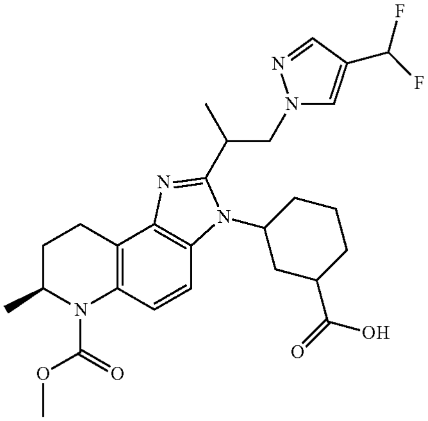 3-((7S)-2-(1-(4-(difluoromethyl)-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 300 MHz) δ (ppm): 7.75 (s, 1H), 7.62 (s, 1H), 7.44-7.33 (m, 2H), 6.85-6.48 (m, 1H), 4.79-4.46 (m, 4H), 4.12-3.86 (m, 1H), 3.76 (s, 3H), 3.28-3.12 (m, 1H), 3.02-2.84 (m, 2H), 2.44-2.11 (m, 5H), 1.88-1.62 (m, 3H), 1.59-1.40 (m, 5H), 1.13-1.11 (d, J = 6.6 Hz, 3H). LCMS (ES, m/z): 530 [M + H]$^+$. |

TABLE 18-continued

| Example Number | Structure and Compound Name | $^1$H NMR, LCMS |
|---|---|---|
| 493 | 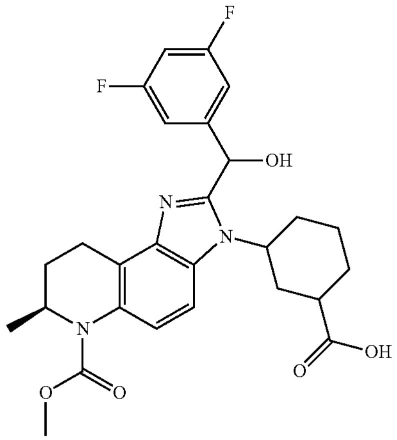 3-((7S)-2-((3,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.67-7.45 (m, 2H), 7.02 (d, J = 6.4 Hz, 3H), 6.94-6.91 (m, 1H), 6.23 (s, 1H), 4.93-4.92 (m, 1H), 4.81-4.79 (m, 1H), 3.80 (s, 3H), 3.28-3.18 (m, 1H), 3.01-2.88 (m, 2H), 2.42-2.12 (m, 4H), 2.03-1.99 (m, 1H), 1.83-1.63 (m, 4H), 1.52-1.42 (m, 1H), 1.17 (d, J = 6.8 Hz, 3H). LCMS (ES, m/z): 514 [M + H]$^+$. |
| 494 | 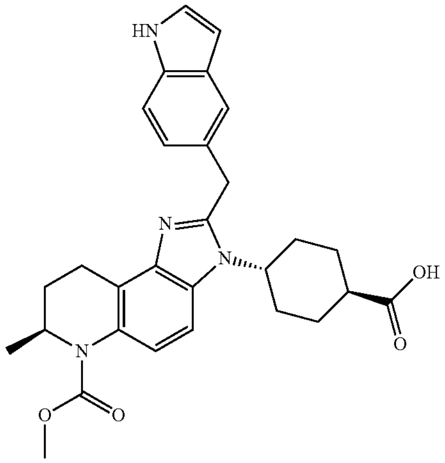 (1S,4r)-4-((S)-2-((1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.46-7.24 (m, 4H), 7.20 (d, J = 3.2 Hz, 1H), 6.99 (d, J = 8.0 Hz, 1H), 6.37 (s, 1H), 4.77-4.67 (m, 1H), 4.44 (s, 2H), 4.40-4.25 (m, 1H), 3.76 (s, 3H), 3.27-3.15 (m, 1H), 3.02-2.88 (m, 1H), 2.42-2.21 (m, 2H), 2.21-2.01 (m, 2H), 2.01-1.85 (m, 2H), 1.81-1.68 (m, 1H), 1.48-1.29 (m, 4H), 1.15 (d, J = 6.8 Hz, 3H). LCMS (ES, m/z): 501 [M + H]$^+$ |

TABLE 18-continued

| Example Number | Structure and Compound Name | $^1$H NMR, LCMS |
|---|---|---|
| 495 | 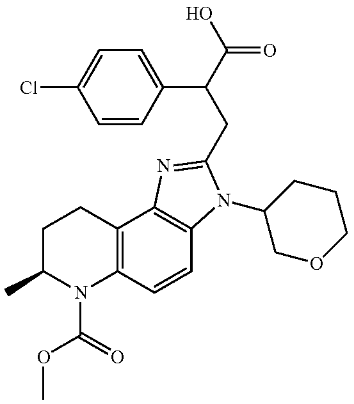 2-(4-chlorophenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1$H-NMR ($CD_3OD$, 400 MHz) δ (ppm): 7.52 (d, J = 8.8 Hz, 1H), 7.43-7.27 (m, 5H), 4.80-4.67 (m, 1H), 4.60-4.49 (m, 1H), 4.35-4.26 (m, 1H), 4.09-3.91 (m, 2H), 3.76 (s, 3H), 3.74-3.65 (m, 1H), 3.61-3.50 (m, 1H), 3.42-3.35 (m, 1H), 3.29-3.23 (m, 1H), 3.20-3.07 (m, 1H), 2.95-2.83 (m, 1H), 2.56-2.41 (m, 1H), 2.29-2.16 (m, 1H), 2.16-2.04 (m, 1H), 1.98-1.80 (m, 2H), 1.78-1.65 (m, 1H), 1.11 (d, J = 6.4 Hz, 3H). LCMS (ES, m/z): 512 $[M + H]^+$. |
| 496 | 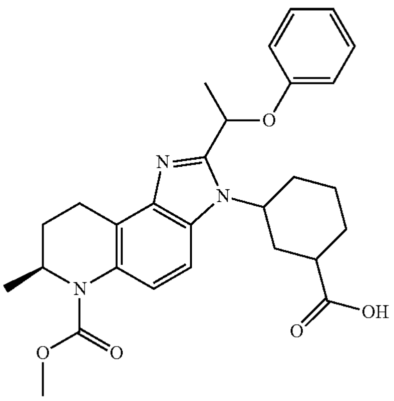 3-((7S)-6-(methoxycarbonyl)-7-methyl-2-(1-phenoxyethyl)-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.46-7.41 (m, 2H), 7.30-7.26 (m, 2H), 7.06-7.02 (m, 2H), 6.95-6.91 (m, 1H), 5.89-5.86 (m, 1H), 5.02-4.93 (m, 1H), 4.80-4.76 (m, 1H), 3.79 (s, 3H), 3.29-3.23 (m, 1H), 2.94-2.90 (m, 2H), 2.50-2.48 (m, 1H), 2.37-2.18 (m, 4H), 1.90-1.69 (m, 7H), 1.50 (m, 1H), 1.15 (d, J = 6.8 Hz, 3H). LCMS (ES, m/z): 492 $[M + H]^+$. |
| 497 | 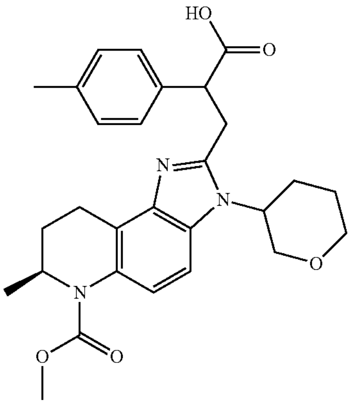 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(p-tolyl)propanoic acid 2nd eluting isomer | $^1$H-NMR ($CD_3OD$, 300 MHz) δ (ppm): 7.52 (d, J = 9.0 Hz, 1H), 7.41 (d, J = 9.3 Hz, 1H), 7.23 (d, J = 8.4 Hz, 2H), 7.16 (d, J = 8.1 Hz, 2H), 4.86-4.74 (m, 1H), 4.28-4.23 (m, 2H), 4.06-3.93 (m, 3H), 3.79 (s, 3H), 3.72-3.65 (m, 1H), 3.68-3.62 (m, 1H), 3.60-3.50 (m, 1H), 3.45-3.32 (m, 1H), 2.99-2.92 (m, 1H), 2.32-2.21 (m, 5H), 1.78-1.72 (m, 3H), 1.23-1.12 (m, 4H). LCMS (ES, m/z): 492 $[M + H]^+$. |

TABLE 18-continued

| Example Number | Structure and Compound Name | $^1$H NMR, LCMS |
|---|---|---|
| 498 | 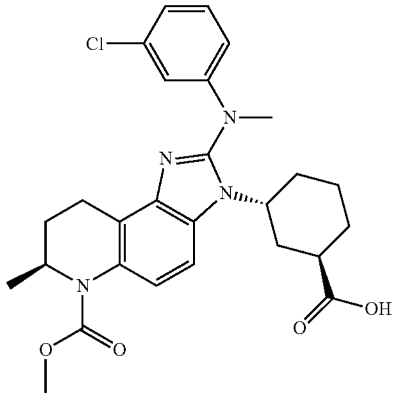 (1R,3R)-3-((S)-2-((3-chlorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 $[M + H]^+$ |
| 499 | 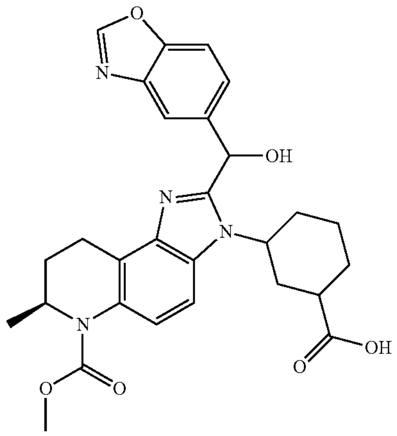 3-((7S)-2-(benzo[d]oxazol-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 8.49 (s, 1H), 7.99 (s, 1H), 7.65 (d, J = 8.8 Hz, 1H), 7.54-7.45 (m, 2H), 7.44-7.37 (m, 1H), 6.38 (s, 1H), 5.05-4.93 (m, 1H), 4.83-4.71 (m, 1H), 3.79 (s, 3H), 3.30-3.14 (m, 1H), 3.07-2.95 (m, 1H), 2.94-2.86 (m, 1H), 2.49-2.33 (m, 2H), 2.32-2.22 (m, 1H), 2.15-2.03 (m, 1H), 2.02-1.90 (m, 1H), 1.83-1.68 (m, 1H), 1.65-1.44 (m, 2H), 1.31-1.20 (m, 1H), 1.16 (d, J = 6.8 Hz, 3H), 0.97-0.86 (m, 1H). LCMS (ES, m/z): 519 $[M + H]^+$. |
| 500 | 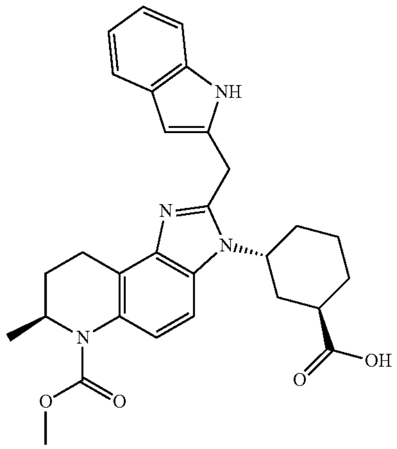 (1R,3R)-3-((S)-2-((1H-indol-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.47 (d, J = 9.0 Hz, 1H), 7.45-7.30 (m, 2H), 7.27 (d, J = 8.3 Hz, 1H), 7.10-6.86 (m, 2H), 6.20 (s, 1H), 5.00-4.88 (m, 1H), 4.81-4.65 (m, 1H), 4.57-4.47 (m, 2H), 3.76 (s, 3H), 3.24-3.09 (m, 1H), 3.02-2.84 (m, 2H), 2.37-2.06 (m, 5H), 1.83-1.53 (m, 3H), 1.52-1.40 (m, 1H), 1.40-1.22 (m, 1H), 1.13 (d, J = 6.6 Hz, 3H). LCMS (ES, m/z): 501 $[M + H]^+$ |

TABLE 18-continued

| Example Number | Structure and Compound Name | $^1$H NMR, LCMS |
|---|---|---|
| 501 | 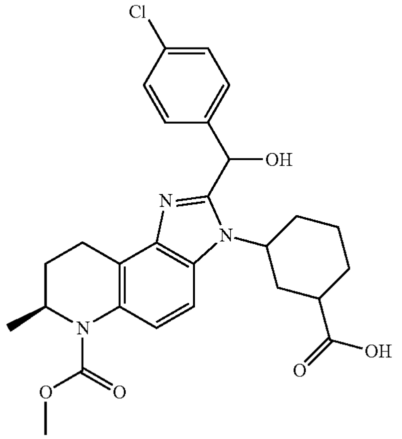<br>3-((7S)-2-((4-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid<br>2nd eluting isomer | $^1$H-NMR ($CD_3OD$, 400 MHz) δ (ppm): 7.52-7.33 (m, 6H), 6.22 (s, 1H), 4.84-4.73 (m, 2H), 3.78 (s, 3H), 3.27-3.16 (m, 1H), 3.04-2.92 (m, 1H), 2.90-2.88 (m, 1H), 2.46-2.35 (m, 2H), 2.30-2.22 (m, 1H), 2.15-2.02 (m, 2H), 1.82-1.71 (m, 1H), 1.63-1.55 (m, 2H), 1.40-1.28 (m, 1H), 1.15 (d, J = 6.8 Hz, 3H), 1.14-1.01 (m, 1H). LCMS (ES, m/z): 512 $[M + H]^+$. |
| 502 | 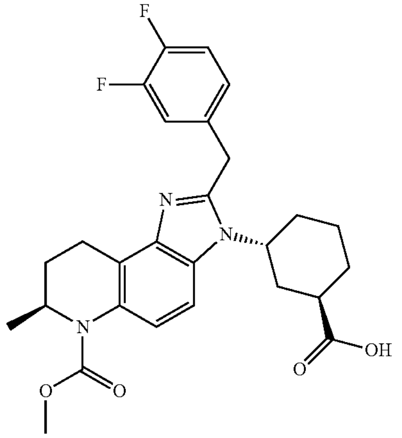<br>(1R,3R)-3-((S)-2-(3,4-difluorobenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.48 (d, J = 8.8 Hz, 1H), 7.40 (d, J = 9.2 Hz, 1H), 7.23-7.18 (m, 2H), 7.05-7.02 (m, 1H), 4.78-4.65 (m, 2H), 4.40-4.22 (m, 2H), 3.79 (s, 3H), 3.26-3.15 (m, 1H), 3.03-2.96 (m, 2H), 2.38-2.12 (m, 5H), 1.79-1.62 (m, 3H), 1.41-1.23 (m, 2H), 1.16 (d, J = 6.4 Hz, 3H). LCMS (ES, m/z): 498 $[M + H]^+$. |
| 503 | 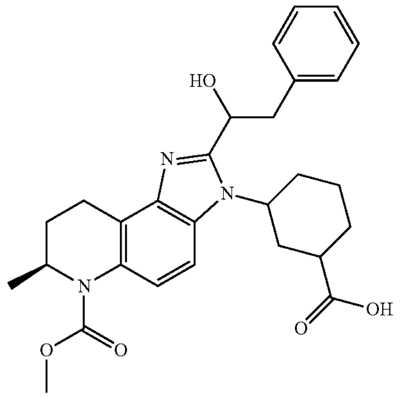<br>3-((7S)-2-(1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid<br>2nd eluting isomer | $^1$H-NMR ($CD_3OD$, 400 MHz) δ (ppm): 7.50 (d, J = 9.2 Hz, 1H), 7.39 (d, J = 8.8 Hz, 1H), 7.28-7.15 (m, 5H), 5.40-5-31 (m, 1H), 5.06-4.98 (m, 1H), 4.80-4.76 (m, 1H), 3.82 (s, 3H), 3.56-3.40 (m, 1H), 3.29-3.24 (m, 1H), 3.22-3.12 (m, 1H), 3.04-2.84 (m, 2H), 2.46-2.32 (m, 2H), 2.32-2.15 (m, 3H), 1.80-1.65 (m, 3H), 1.53-1.38 (m, 2H), 1.13 (d, J = 6.4 Hz, 3H). LCMS (ES, m/z): 492 $[M + H]^+$ |

TABLE 18-continued

| Example Number | Structure and Compound Name | $^1$H NMR, LCMS |
|---|---|---|
| 504 | 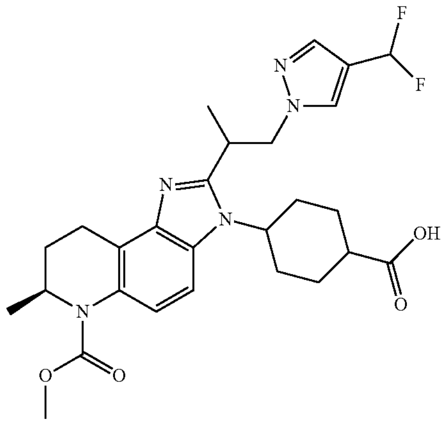 4-((7S)-2-(1-(4-(difluoromethyl)-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 300 MHz) δ (ppm): 7.82-7.53 (m, 2H), 7.51-7.36 (m, 1H), 7.36-7.22 (m, 1H), 6.93-6.39 (m, 1H), 4.79-4.59 (m, 2H), 4.59-4.43 (m, 1H), 4.40-4.09 (m, 1H), 4.05-3.85 (m, 1H), 3.76 (s, 3H), 3.26-3.10 (m, 1H), 3.10-2.83 (m, 1H), 2.61-2.41 (m, 1H), 2.35-2.08 (m, 4H), 1.96-1.79 (m, 1H), 1.79-1.53 (m, 3H), 1.49-1.36 (m, 4H), 1.32-1.22 (m, 1H), 1.13 (d, J = 6.6 Hz, 3H). LCMS (ES, m/z): 530 $[M + H]^+$ |
| 505 | 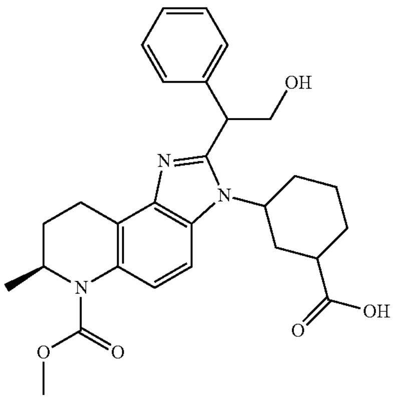 3-((7S)-2-(2-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.86-7.68 (m, 2H), 7.50-7.26 (m, 5H), 5.07-4.94 (m, 2H), 4.88-4.80 (m, 1H), 4.56-4.47 (m, 1H), 4.29-4.20 (m, 1H), 3.83 (s, 3H), 3.29-3.02 (m, 3H), 2.46-2.37 (m, 2H), 2.34-2.14 (m, 3H), 1.96-1.84 (m, 1H), 1.83-1.66 (m, 2H), 1.23-1.07 (m, 5H). LCMS (ES, m/z): 492 $[M + H]^+$. |

TABLE 18-continued

| Example Number | Structure and Compound Name | $^1$H NMR, LCMS |
|---|---|---|
| 506 | 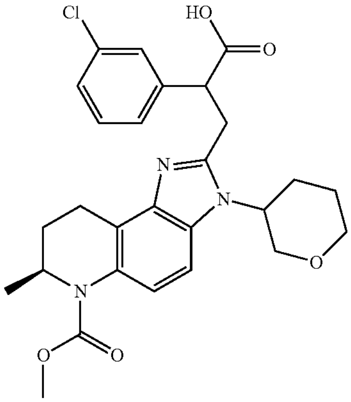 2-(3-chlorophenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1$H-NMR ($CD_3OD$, 300 MHz) δ (ppm): 7.52-7.38 (m, 3H), 7.32-7.28 (m, 3H), 4.77-4.59 (m, 2H), 4.23-3.98 (m, 6H), 3.78-3.45 (m, 2H), 3.35-2.89 (m, 4H), 2.52-2.48 (m, 1H), 2.25-2.16 (m, 2H), 1.90-1.43 (m, 3H), 1.14 (d, J = 6.6 Hz, 3H). LCMS (ES, m/z): 512 [M + H]$^+$ |
| 507 | 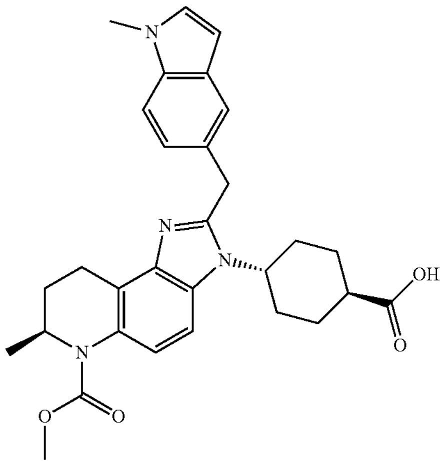 (1S,4R)-4-((S)-6-(methoxycarbonyl)-7-methyl-2-((1-methyl-1H-indol-5-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.49-7.38 (m, 3H), 7.37-7.30 (m, 1H), 7.14 (d, J = 3.2 Hz, 1H), 7.11-7.03 (m, 1H), 6.38 (d, J = 3.2 Hz, 1H), 4.83-4.69 (m, 1H), 4.47 (s, 2H), 4.41-4.27 (m, 1H), 3.78 (s, 6H), 3.31-3.18 (m, 1H), 3.08-2.92 (m, 1H), 2.41-2.23 (m, 2H), 2.20-2.04 (m, 2H), 2.02-1.88 (m, 2H), 1.84-1.69 (m, 1H), 1.50-1.32 (m, 4H), 1.17 (d, J = 6.8 Hz, 3H). LCMS (ES, m/z): 515 [M + H]+. |
| 508 | 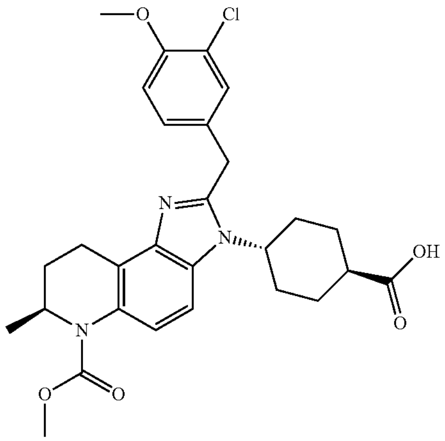 (1S,4R)-4-((S)-2-(3-chloro-4-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.43-7.37 (m, 3H), 7.27-7.17 (m, 2H), 4.86-4.77 (m, 1H), 4.35-4.25 (m, 3H), 3.84 (s, 3H), 3.76 (s, 3H), 3.25-2.85 (m, 2H), 2.69 (s, 1H), 2.45-2.03 (m, 6H), 1.78-1.71 (m, 1H), 1.54-1.45 (m, 3H), 1.14 (d, J = 6.6 Hz, 3H). LCMS (ES, m/z): 526 [M + H]$^+$ |

TABLE 18-continued

| Example Number | Structure and Compound Name | $^1$H NMR, LCMS |
|---|---|---|
| 509 | 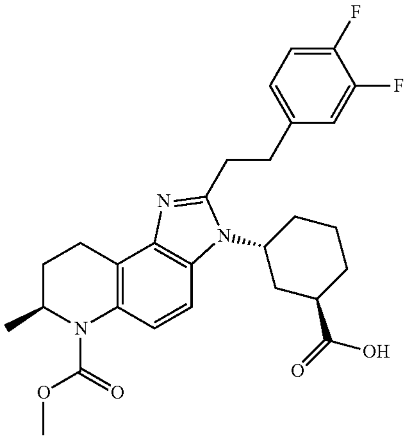 (1R,3R)-3-((S)-2-(3,4-difluorophenethyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.56-7.48 (m, 1H), 7.44-7.37 (m, 1H), 7.33-7.23 (m, 1H), 7.23-7.08 (m, 2H), 4.82-4.71 (m, 2H), 3.79 (s, 3H), 3.32-3.10 (m, 4H), 3.09-2.85 (m, 3H), 2.41-2.17 (m, 5H), 1.91-1.82 (m, 1H), 1.81-1.67 (m, 3H), 1.63-1.48 (m, 1H), 1.15 (d, J = 6.8 Hz, 3H). LCMS (ES, m/z): 512 [M + H]$^+$. |
| 510 | 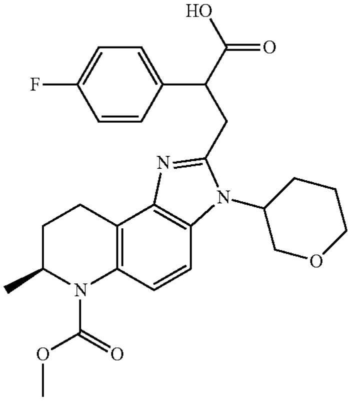 (4-fluorophenyl)-3-((7S)-6-(methoxycarbonyl)-7-methyl-3-((S)-tetrahydro-2H-pyran-3-yl)-6,7,8,9-tetrahydro-3H-imidazo[4,5-f]quinolin-2-yl)propanoic acid 1st eluting isomer | $^1$H-NMR ($CD_3OD$, 400 MHz) δ (ppm): 7.50 (d, J = 8.8 Hz, 1H), 7.43-7.32 (m, 3H), 7.07-6.96 (m, 2H), 4.80-4.66 (m, 1H), 4.59-4.46 (m, 1H), 4.29-4.16 (m, 1H), 4.04-3.91 (m, 2H), 3.76 (s, 3H), 3.72-3.61 (m, 1H), 3.61-3.47 (m, 1H), 3.31-3.22 (m, 2H), 3.20-3.07 (m, 1H), 2.95-2.83 (m, 1H), 2.54-2.37 (m, 1H), 2.27-2.17 (m, 1H), 2.15-2.02 (m, 1H), 2.00-1.78 (m, 2H), 1.78-1.63 (m, 1H), 1.10 (d, J = 6.7, 2.0 Hz, 3H). LCMS (ES, m/z): 496 [M + H]$^+$. |
| 511 | 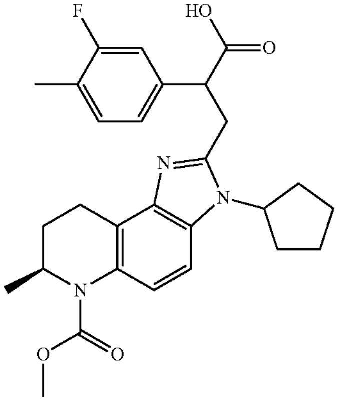 3-((7S)-3-cyclopentyl-6-(methoxycarbonyl)-7-methyl-6,7,8,9-tetrahydro-3H-imidazo[4,5-f]quinolin-2-yl)-2-(3-fluoro-4-methylphenyl)propanoic acid 2nd eluting isomer | $^1$H-NMR ($CD_3OD$, 400 MHz) δ (ppm): 7.44 (d, J = 8.8 Hz, 1H), 7.33 (d, J = 8.8 Hz, 1H), 7.18-6.98 (m, 3H), 5.05-4.90 (m, 1H), 4.85-4.72 (m, 1H), 4.28-4.21 (m, 1H), 3.77 (s, 3H), 3.73-3.65 (m, 1H), 3.42-3.33 (m, 1H), 3.18-3.10 (m, 1H), 2.92-2.85 (m, 1H), 2.31-2.12 (m, 6H), 2.11-1.92 (m, 3H), 1.90-1.67 (m, 4H), 1.12 (d, J = 6.8 Hz, 3H). LCMS (ES, m/z): 491 [M + H]$^+$. |

TABLE 18-continued

| Example Number | Structure and Compound Name | $^1$H NMR, LCMS |
|---|---|---|
| 512 | 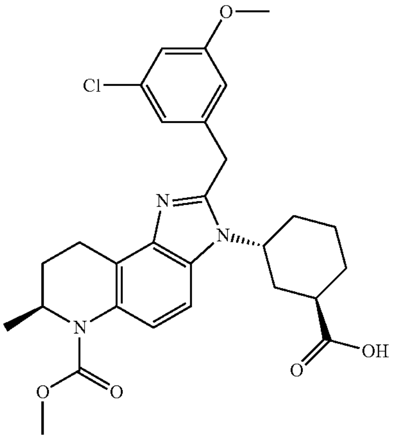 (1R,3R)-3-((S)-2-(3-chloro-5-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR (d6-DMSO, 400 MHz) δ (ppm): 7.90-7.84 (m, 1H), 7.69-7.62 (m, 1H), 7.00 (s, 2H), 6.93 (s, 1H), 4.91-4.81 (m, 1H), 4.78-4.68 (m, 1H), 4.68-4.60 (m, 1H), 4.39-4.31 (m, 1H), 3.77 (s, 3H), 3.71 (s, 3H), 3.05-2.93 (m, 3H), 2.36-2.24 (m, 1H), 2.24-2.05 (m, 3H), 2.04-1.96 (m, 1H), 1.86-1.65 (m, 3H), 1.40-1.33 (m, 1H), 1.27-1.13 (m, 1H), 1.09 (d, J = 6.4 Hz, 3H). LCMS (ES, m/z): 526 $[M + H]^+$. |
| 513 | 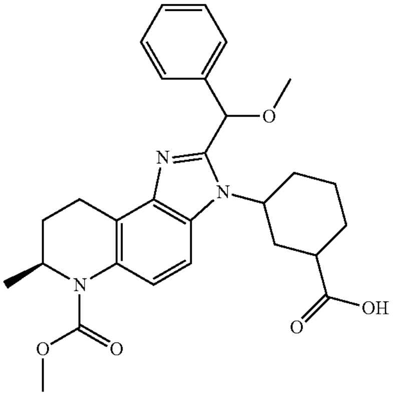 3-((7S)-2-(methoxy(phenyl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.52-7.30 (m, 7H), 5.84 (s, 1H), 4.80-4.72 (m, 2H), 3.79 (s, 3H), 3.55 (s, 3H), 3.32-3.21 (m, 1H), 3.08-2.90 (m, 2H), 2.64-2.35 (m, 3H), 2.13-2.05 (m, 1H), 1.98-1.73 (m, 2H), 1.61-1.45 (m, 2H), 1.35-1.21 (m, 1H), 1.17 (d, J = 6.8 Hz, 3H), 0.85-0.77 (m, 1H),. LCMS (ES, m/z): 492 $[M + H]^+$. |
| 514 | 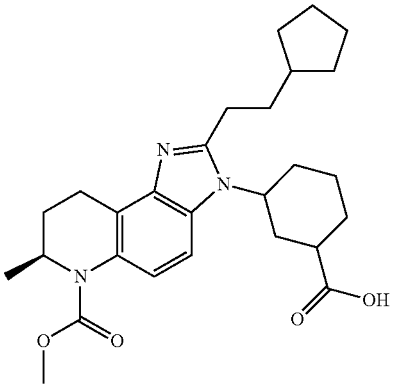 3-((7S)-2-(2-cyclopentylethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.55 (d, J = 8.8 Hz, 1H), 7.38 (d, J = 9.2 Hz, 1H), 4.83-4.65 (m, 2H), 3.79 (s, 3H), 3.23-3.09 (m, 1H), 3.09-2.95 (m, 3H), 2.95-2.79 (m, 1H), 2.51-2.33 (m, 2H), 2.33-2.15 (m, 3H), 1.99-1.82 (m, 6H), 1.82-1.49 (m, 8H), 1.29-1.25 (m, 2H), 1.13 (d, J = 6.8 Hz, 3H). LCMS (ES, m/z): 468 $[M + H]^+$. |

TABLE 18-continued

| Example Number | Structure and Compound Name | $^1$H NMR, LCMS |
|---|---|---|
| 515 | 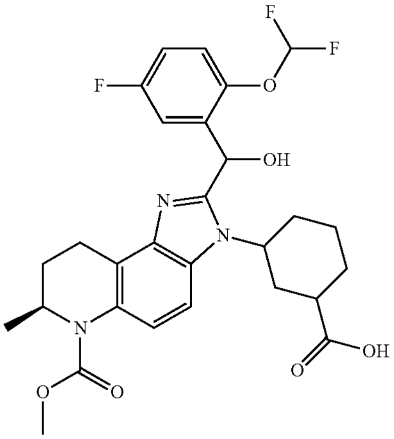<br>3-((7S)-2-((2-(difluoromethoxy)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid<br>1st eluting isomer | $^1$H-NMR ($CD_3OD$, 400 MHz) δ (ppm): 7.62 (d, J = 9.2 Hz, 1H), 7.53 (d, J = 8.8 Hz, 1H), 7.41 (d, J = 9.2 Hz, 1) 7.20-7.13 (m, 2H), 6.67-6.30 (m, 2H), 4.98-4.95 (m, 1H), 4.76-4.71 (m, 1H), 3.78 (s, 3H), 3.15-2.86 (m, 3H), 2.46-2.20 (m, 5H), 1.81-1.53 (m, 5H), 1.13 (d, J = 6.8 Hz, 3H). LCMS (ES, m/z): 562 [M + H]$^+$. |
| 516 | 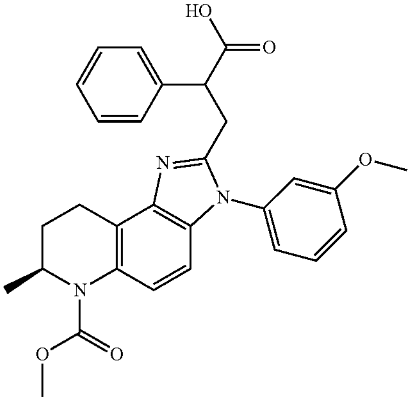<br>3-((7S)-6-(methoxycarbonyl)-3-(3-methoxyphenyl)-7-methyl-6,7,8,9-tetrahydro-3H-imidazo[4,5-f]quinolin-2-yl)-2-phenylpropanoic acid<br>1st eluting isomer | $^1$H-NMR ($CD_3OD$, 400 MHz) δ (ppm): 7.47 (t, J = 8.0 Hz, 1H), 7.35 (d, J = 8.8 Hz, 1H), 7.28-7.16 (m, 3H), 7.16-7.03 (m, 3H), 6.91-6.59 (m, 3H), 4.81-4.68 (m, 1H), 4.35-4.24 (m, 1H), 3.84 (s, 3H), 3.75 (s, 3H), 3.59-3.48 (m, 1H), 3.29-3.13 (m, 2H), 3.07-2.91 (m, 1H), 2.33-2.21 (m, 1H), 1.79-1.66 (m, 1H), 1.13 (d, J = 6.4 Hz, 3H). LCMS (ES, m/z): 500 [M + H]$^+$. |

TABLE 18-continued

| Example Number | Structure and Compound Name | $^1$H NMR, LCMS |
|---|---|---|
| 517 | 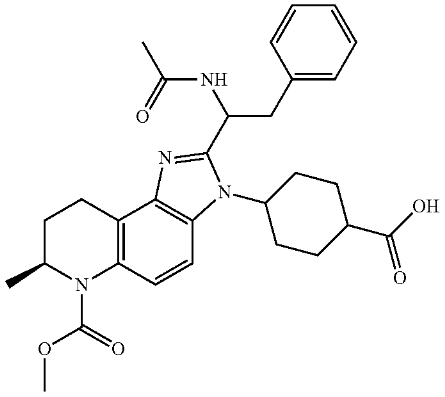<br>4-((7S)-2-(1-acetamido-2-phenylethyl)-6-(methoxycarbonyl)-7-methyl-6,7,8,9-tetrahydro-3H-imidazo[4,5-f]quinolin-3-yl)cyclohexane-1-carboxylic acid<br>1st eluting isomer | $^1$H NMR ($CD_3OD$, 400 MHz) δ (ppm): 7.81-7.75 (m, 2H), 7.27-7.26 (m, 3H), 7.19-7.15 (m, 2H), 5.72-5.66 (m, 1H), 4.84-4.83 (m, 1H), 4.42-4.37 (m, 1H), 3.82 (s, 3H), 3.62-3.60 (m, 1H), 3.33-3.27 (m, 1H), 3.12-3.09 (m, 2H), 2.52-2.49 (m, 1H), 2.26-2.02 (m, 4H), 2.00 (s, 3H), 1.95-1.88 (m, 3H), 1.69-1.65 (m, 1H), 1.45-1.37 (m, 1H), 1.16 (d, J = 6.4 Hz, 3H), 0.38-0.36 (m, 1H). LCMS (ES, m/z): 533 [M + H]$^+$. |
| 518 | 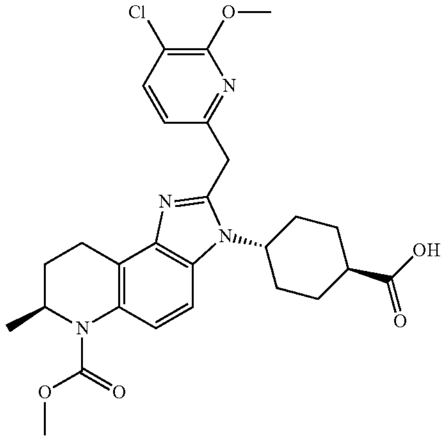<br>(1S,4R)-4-((S)-2-((5-chloro-6-methoxypyridin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.72 (d, J = 8.0 Hz, 1H), 7.63 (d, J = 9.2 Hz, 1H), 7.41-7.39 (d, J = 9.2 Hz, 1H), 6.90 (d, J = 7.6 Hz, 1H), 4.72-4.74 (m, 1H), 4.50-4.39 (m, 3H), 3.95 (s, 3H), 3.79 (s, 3H), 3.26-3.15 (m, 1H), 3.03-2.96 (m, 1H), 2.49-2.40 (m, 1H), 2.38-2.25 (m, 3H), 2.15-2.07 (m, 2H), 1.80-1.36 (m, 3H), 1.61-1.45 (m, 2H), 1.16 (d, J = 6.8 Hz, 3H). LCMS (ES, m/z): 527, 529 [M + H]$^+$. |
| 519 | 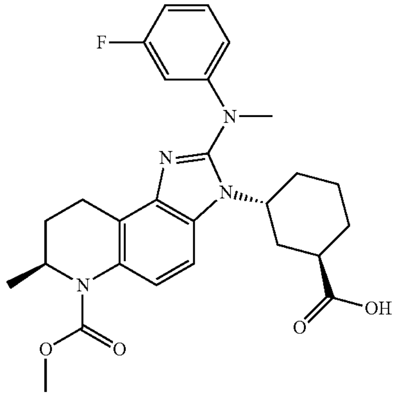<br>(1R,3R)-3-((S)-2-((3-fluorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 496 [M + H]$^+$. |

TABLE 18-continued

| Example Number | Structure and Compound Name | $^1$H NMR, LCMS |
|---|---|---|
| 520 | 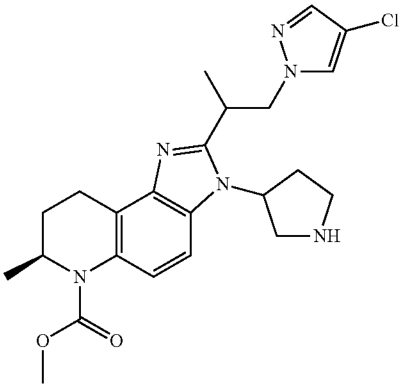<br>methyl 2-((7S)-1-(4-chloro-1H-pyrazol-1-yl)propan-2-yl)-7-methyl-3-(pyrrolidin-3-yl)-3,7,8,9-tetrahydro-6H-imidazo[4,5-f]quinoline-6-carboxylate<br>4$^{th}$ eluting isomer | $^1$H-NMR ($CD_3OD$, 300 MHz) δ (ppm): 7.53 (s, 1H), 7.46 (s, 1H), 7.42-7.34 (m, 2H), 5.18-5.00 (m, 1H), 4.83-4.70 (m, 1H), 4.70-4.57 (m, 1H), 4.57-4.43 (m, 1H), 4.03-3.86 (m, 1H), 3.79 (s, 3H), 3.43-3.35 (m, 2H), 3.26-3.11 (m, 3H), 3.04-2.88 (m, 1H), 2.37-2.18 (m, 2H), 2.18-2.01 (m, 1H), 1.82-1.64 (m, 1H), 1.44 (d, J = 6.9 Hz, 3H), 1.15 (d, J = 6.6 Hz, 3H). LCMS (ES, m/z): 457 [M + H]$^+$. |
| 521 | 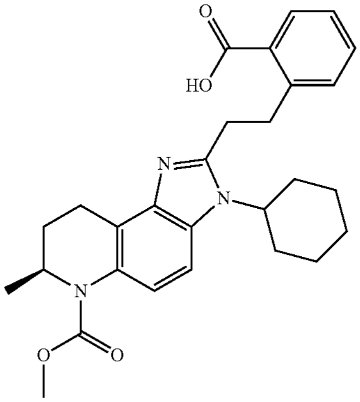<br>(S)-2-(2-(3-cyclohexyl-6-(methoxycarbonyl)-7-methyl-6,7,8,9-tetrahydro-3H-imidazo[4,5-f]quinolin-2-yl)ethyl)benzoic acid | $^1$H-NMR ($CD_3OD$, 400 MHz) δ (ppm): 7.87-7.81 (m, 1H), 7.55-7.48 (m, 1H), 7.47-7.40 (m, 1H), 7.40-7.32 (m, 1H), 7.32-7.21 (m, 2H), 4.82-4.73 (m, 1H), 4.57-4.46 (m, 1H), 3.79 (s, 3H), 3.49-3.38 (m, 4H), 3.23-3.10 (m, 1H), 3.00-2.88 (m, 1H), 2.32-2.14 (m, 3H), 1.96-1.88 (m, 2H), 1.84-1.71 (m, 3H), 1.70-1.55 (m, 3H), 1.46-1.36 (m, 1H), 1.14 (d, J = 6.8 Hz, 3H). LCMS (ES, m/z): 476 [M + H]$^+$. |
| 522 | 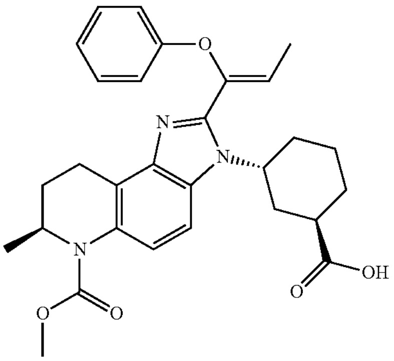<br>(1R,3R)-3-((S)-6-(methoxycarbonyl)-7-methyl-2-((Z)-1-phenoxyprop-1-en-1-yl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.48 (d, J = 9.2 Hz, 1H), 7.40 (d, J = 8.8 Hz, 1H), 7.25-7.21 (m, 2H), 7.15-7.12 (m, 2H), 6.97-6.93 (m, 1H), 6.07-6.05 (m, 1H), 5.15-5.02 (m, 1H), 4.77-4.74 (m, 1H), 3.77 (s, 3H), 3.18-3.15 (m, 1H), 3.03-2.92 (m, 1H), 2.47-2.36 (m, 1H), 2.26-2.20 (m, 4H), 1.93 (d, J = 6.8 Hz, 3H), 1.85-1.81 (m, 1H), 1.76-1.60 (m, 5H), 1.12 (d, J = 6.8 Hz, 3H). LCMS (ES, m/z): 504 [M + H]$^+$. |

TABLE 18-continued

| Example Number | Structure and Compound Name | $^1$H NMR, LCMS |
|---|---|---|
| 523 | 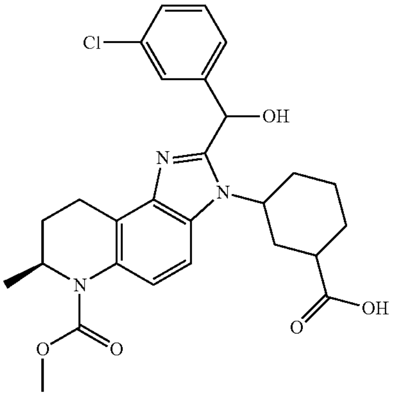 3-((7S)-2-((3-chlorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.51-7.30 (m, 6H), 6.24 (s, 1H), 4.93-4.74 (m, 2H), 3.78 (s, 3H), 3.33-3.17 (m, 1H), 3.01-2.94 (m, 1H), 2.82 (m, 1H), 2.37-2.35 (m, 2H), 2.29-2.24 (m, 2H), 2.08-2.05 (m, 1H), 1.77-1.72 (m, 1H), 1.60-1.54 (m, 2H), 1.34-1.30 (m, 1H), 1.15 (d, J = 6.8 Hz, 3H), 1.14-1.05 (m, 1H). LCMS (ES, m/z): 512 $[M + H]^+$. |
| 524 | 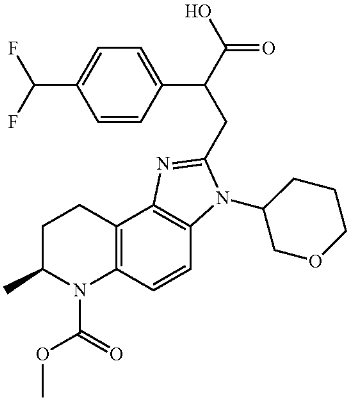 2-(4-(difluoromethyl)phenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1$H-NMR ($CD_3OD$, 400 MHz) δ (ppm): 7.59-7.45 (m, 5H), 7.39 (d, J = 8.8 Hz, 1H), 6.92-6.56 (m, 1H), 4.82-4.68 (m, 1H), 4.48-4.29 (m, 2H), 4.10-3.89 (m, 3H), 3.83-3.68 (m, 4H), 3.62-3.47 (m, 1H), 3.45-3.34 (m, 1H), 3.21-3.06 (m, 1H), 3.00-2.86 (m, 1H), 2.45-2.31 (m, 1H), 2.30-2.15 (m, 1H), 1.83-1.62 (m, 3H), 1.28-1.17 (m, 1H), 1.13 (d, J = 6.4 Hz, 3H). LCMS (ES, m/z): 528 $[M + H]^+$. |
| 525 | 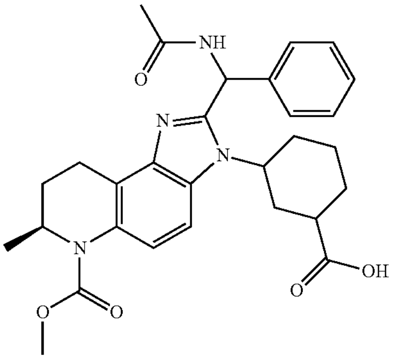 3-((7S)-2-(acetamido(phenyl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.48-7.46 (m, 1H), 7.42-7.39 (m, 6H), 6.56 (s, 1H), 4.81-4.79 (m, 1H), 4.75-4.60 (m, 1H), 3.79 (s, 3H), 3.31-3.29 (m, 1H), 3.03-2.93 (m, 2H), 2.40-2.31 (m, 3H), 2.15-2.01 (m, 5H), 1.82-1.74 (m, 1H), 1.65-1.60 (m, 2H), 1.18-1.08 (m, 4H), 1.02-0.91 (m, 1H). LCMS (ES, m/z): 519 $[M + H]^+$. |

TABLE 18-continued

| Example Number | Structure and Compound Name | $^1$H NMR, LCMS |
|---|---|---|
| 526 | 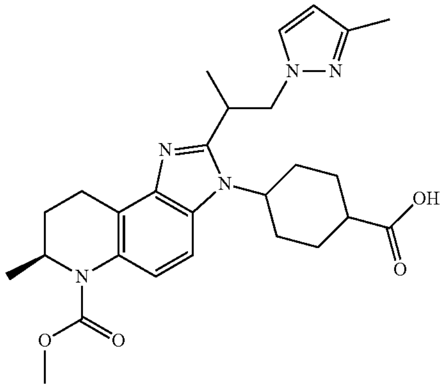 4-((7S)-6-(methoxycarbonyl)-7-methyl-2-(1-(3-methyl-1H-pyrazol-1-yl)propan-2-yl)-6,7,8,9-tetrahydro-3H-imidazo[4,5-f]quinolin-3-yl)cyclohexane-1-carboxylic acid 1st eluting isomer | $^1$H-NMR ($CD_3OD$, 300 MHz) δ (ppm): 7.51-7.37 (m, 2H), 7.17 (d, J = 2.1 Hz, 1H), 5.88 (s, 1H), 4.81-4.68 (m, 1H), 4.57-4.34 (m, 2H), 4.34-4.18 (m, 1H), 4.05-3.88 (m, 1H), 3.76 (s, 3H), 3.24-3.11 (m, 1H), 3.01-2.85 (m, 1H), 2.62-2.38 (m, 1H), 2.38-2.08 (m, 8H), 1.95-1.79 (m, 1H), 1.79-1.55 (m, 3H), 1.55-1.40 (m, 3H), 1.35-1.27 (m, 1H), 1.12 (d, J = 6.6 Hz, 3H). LCMS (ES, m/z): 494 $[M + H]^+$ |
| 527 | 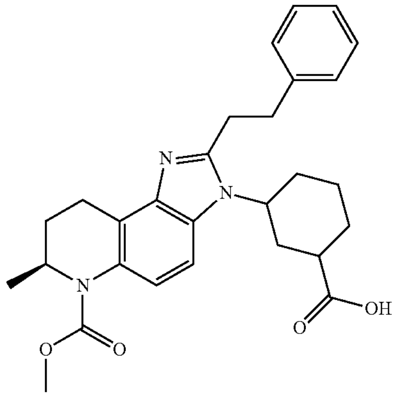 3-((7S)-6-(methoxycarbonyl)-7-methyl-2-phenethyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.47 (d, J = 9.2 Hz, 1H), 7.36 (d, J = 9.2 Hz, 1H), 7.25-7.23 (m, 4H), 7.21-7.13 (m, 1H), 4.81-4.57 (m, 2H), 3.77 (s, 3H), 3.33-3.12 (m, 4H), 3.06-2.81 (m, 3H), 2.41-2.14 (m, 5H), 1.83-1.65 (m, 3H), 1.52-1.39 (m, 2H), 1.12 (d, J = 6.8 Hz, 3H). LCMS (ES, m/z): 476 $[M + H]^+$. |
| 528 | 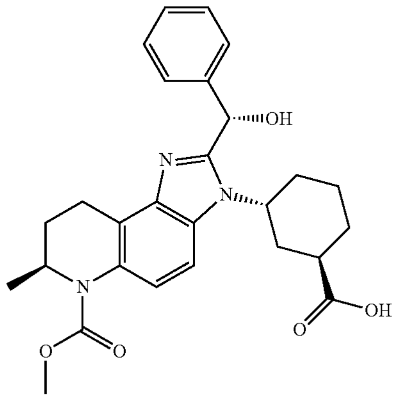 (1R,3R)-3-((S)-2-((S)-hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.57-7.40 (m, 4H), 7.30-7.28 (m, 3H), 6.12 (s, 1H), 4.95-4.90 (m, 1H), 4.84-4.79 (m, 1H), 3.79 (s, 3H), 3.33-3.25 (m, 1H), 3.03-2.82 (m, 2H), 2.49-2.30 (m, 2H), 2.29-2.21 (m, 1H), 2.12-2.07 (m, 1H), 1.99-1.90 (m, 1H), 1.85-1.79 (m, 1H), 1.64-1.49 (m, 2H), 1.40-1.29 (m, 1H), 1.16 (d, J = 6.4 Hz, 3H), 0.95-0.89 (m, 1H). LCMS (ES, m/z): 478 $[M + H]^+$. |

TABLE 18-continued

| Example Number | Structure and Compound Name | $^1$H NMR, LCMS |
|---|---|---|
| 529 | 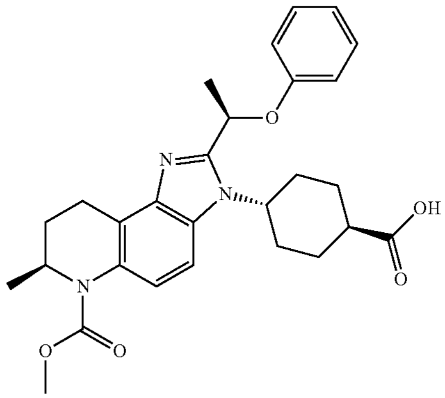 (1R,4R)-4-((S)-6-(methoxycarbonyl)-7-methyl-2-((R)-1-phenoxyethyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.55-7.40 (m, 2H), 7.30-7.26 (m, 2H), 7.05 (d, J = 7.5 Hz, 2H), 7.00-6.95 (m, 1H), 5.91-5.88 (m, 1H), 4.85-4.77 (m, 2H), 3.78 (s, 3H), 3.27-3.14 (m, 1H), 2.97-2.90 (m, 1H), 2.55-2.30 (m, 2H), 2.30-2.17 (m, 3H), 2.17-2.08 (m, 1H), 2.04-1.91 (m, 1H), 1.87-1.80 (m, 3H), 1.76-170 (m, 1H), 1.62-1.40 (m, 3H), 1.13 (d, J = 6.9 Hz, 1H). LCMS (ES, m/z): 492 $[M + H]^+$. |
| 530 | 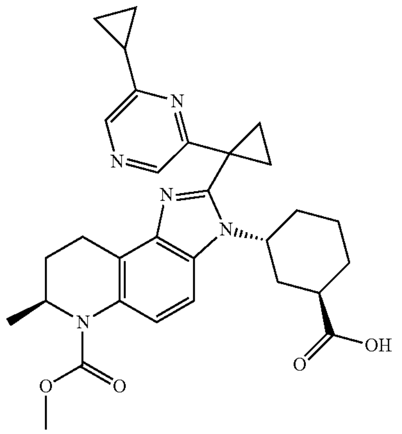 (1R,3R)-3-((S)-2-(1-(6-cyclopropylpyrazin-2-yl)cyclopropyl)-6-(methoxycarbonyl)-7-methyl-6,7,8,9-tetrahydro-3H-imidazo[4,5-f]quinolin-3-yl)cyclohexane-1-carboxylic acid | 8.30 (s, 1H), 7.69 (s, 1H), 7.57 (d, J = 9.2 Hz, 1H), 7.47 (d, J = 9.2 Hz, 1H), 4.84-4.74 (m, 2H), 3.79 (s, 3H), 3.23-3.15 (m, 1H), 3.03-2.86 (m, 2H), 2.56-2.42 (m, 1H), 2.52-2.05 (m, 6H), 1.79-1.63 (m, 7H), 1.35-1.24 (m, 1H), 1.16 (d, J = 6.4 Hz, 3H), 1.07-1.05 (m, 4H). LCMS (ES, m/z): 530 $[M + H]^+$. |
| 531 | 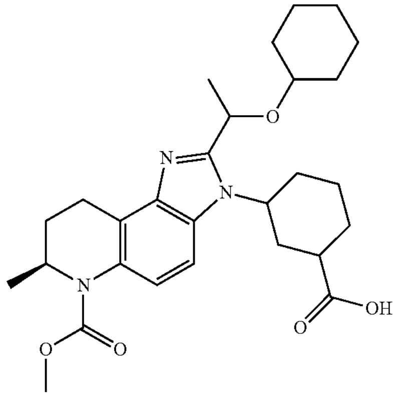 3-((7S)-2-(1-(cyclohexyloxy)ethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H NMR ($CD_3OD$, 400 MHz) δ (ppm): 7.57-7.55 (m, 1H), 7.44-7.42 (m, 1H), 5.14-5.04 (m, 2H), 4.79-4.75 (m, 1H), 3.78 (s, 3H), 3.44-3.40 (m, 1H), 3.24-3.20 (m, 1H), 2.95-2.88 (m, 2H), 2.54-2.48 (m, 1H), 2.38-2.25 (m, 4H), 1.95-1.87 (m, 4H), 1.87-1.73 (m, 5H), 1.69-1.67 (m, 3H), 1.55-1.51 (m, 1H), 1.41-1.19 (m, 5H), 1.15 (d, J = 6.4 Hz, 3H). LCMS (ES, m/z): 498 $[M + H]^+$. |

TABLE 18-continued

| Example Number | Structure and Compound Name | $^1$H NMR, LCMS |
|---|---|---|
| 532 | 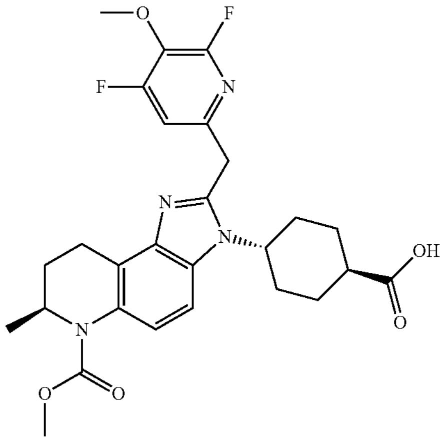 (1S,4R)-4-((S)-2-(3,5-difluoro-4-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.50-7.35 (m, 2H), 7.05-6.71 (m, 2H), 4.78-4.74 (m, 1H), 4.37 (s, 2H), 4.27-4.19 (m, 1H), 3.94 (s, 3H), 3.79 (s, 3H), 3.22-3.16 (m, 1H), 2.98-2.90 (m, 1H), 2.59-2.46 (m, 1H), 2.36-2.19 (m, 3H), 2.12-1.92 (m, 2H), 1.85-1.69 (m, 1H), 1.55-1.44 (m, 4H), 1.16 (d, J = 6.9 Hz, 3H). LCMS (ES, m/z): 528 $[M + H]^+$. |
| 533 | 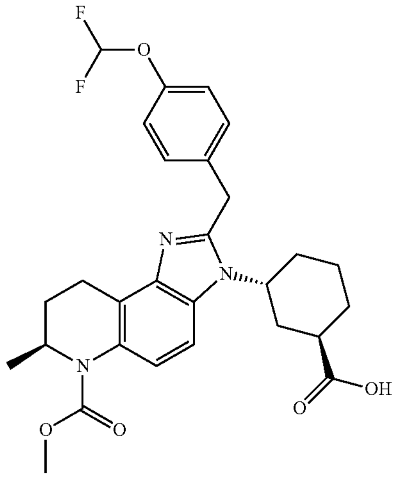 (1R,3R)-3-((S)-2-(4-(difluoromethoxy)benzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR (d6-DMSO, 400 MHz) δ (ppm): 12.60 (br, 1H), 7.91-7.84 (m, 1H), 7.69-7.62 (m, 1H), 7.43-7.38 (m, 2H), 7.32-7.05 (m, 3H), 4.85-4.65 (m, 3H), 4.43-4.36 (m, 1H), 3.71 (s, 3H), 3.07-2.91 (m, 3H), 2.35-2.25 (m, 1H), 2.22-2.08 (m, 3H), 2.04-1.96 (m, 1H), 1.82-1.66 (m, 3H), 1.49-1.41 (m, 1H), 1.29-1.21 (m, 1H), 1.09 (d, J = 6.4 Hz, 3H). LCMS (ES, m/z): 528 $[M + H]^+$. |
| 534 | 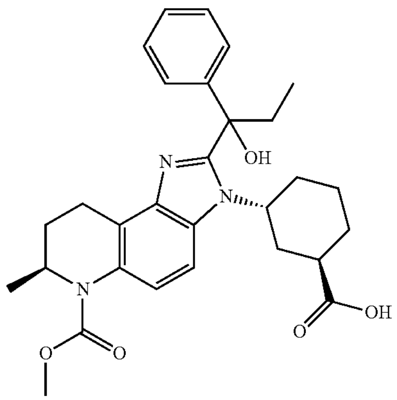 (1R,3R)-3-((7S)-2-(1-hydroxy-1-phenylpropyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.84-7.80 (m, 2H), 7.58-7.56 (m, 2H), 7.48-7.43 (m, 3H), 4.86-4.82 (m, 1H), 4.69-4.65 (m, 1H), 3.82 (s, 3H), 3.26-3.08 (m, 3H), 3.03-2.98 (m, 1H), 2.65-2.45 (m, 2H), 2.52-1.82 (m, 5H), 1.69-1.62 (m, 1H), 1.52-1.48 (m, 1H), 1.20 (d, J = 6.4 Hz, 3H), 1.01 (t, J = 7.2 Hz, 3H), 0.88-0.79 (m, 2H). LCMS (ES, m/z): 506 $[M + H]^+$. |

TABLE 18-continued

| Example Number | Structure and Compound Name | $^1$H NMR, LCMS |
|---|---|---|
| 535 | 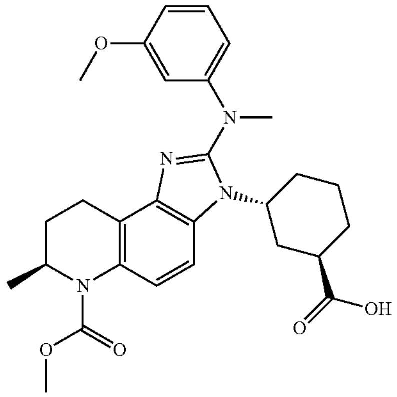 (1R,3R)-3-((S)-6-(methoxycarbonyl)-2-((3-methoxyphenyl)(methyl)amino)-7-methyl-6,7,8,9-tetrahydro-3H-imidazo[4,5-f]quinolin-3-yl)cyclohexane-1-carboxylic acid | LCMS (ES, m/z): 507 $[M + H]^+$. |
| 536 | 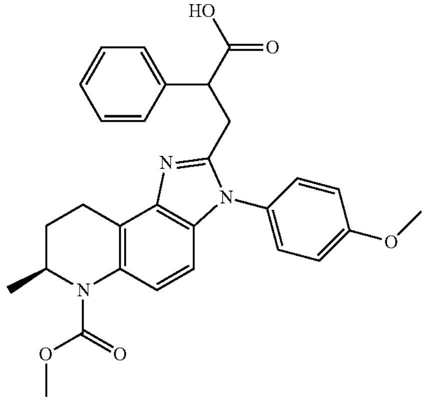 3-((7S)-6-(methoxycarbonyl)-3-(4-methoxyphenyl)-7-methyl-6,7,8,9-tetrahydro-3H-imidazo[4,5-f]quinolin-2-yl)-2-phenylpropanoic acid 2nd eluting isomer | $^1$H-NMR ($CD_3OD$, 300 MHz) δ (ppm): 7.30 (d, J = 8.7 Hz, 1H), 7.21-7.06 (m, 9H), 6.77 (d, J = 8.7 Hz, 1H), 4.86-4.71 (m, 1H), 4.30-4.20 (m, 1H), 3.89 (s, 3H), 3.75 (s, 3H), 3.55-3.42 (m, 1H), 3.32-2.82 (m, 3H), 2.32-2.21 (m, 1H), 1.75-1.58 (m, 1H), 1.12 (d, J = 6.6 Hz, 3H). LCMS (ES, m/z): 500 $[M + H]^+$. |
| 537 | 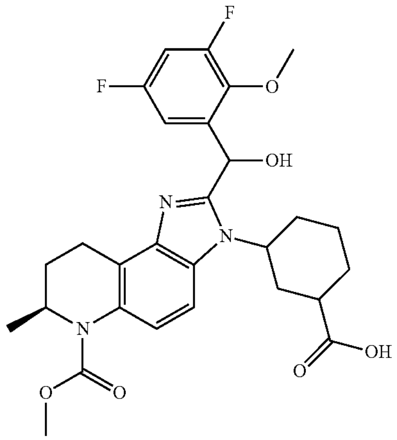 3-((7S)-2-((3,5-difluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H NMR ($CD_3OD$, 400 MHz) δ (ppm): 7.63 (d, J = 8.8 Hz, 1H), 7.55 (d, J = 9.2 Hz, 1H), 7.21-7.19 (m, 1H), 7.08-7.04 (m, 1H), 6.46 (s, 1H), 4.94-4.92 (m, 1H), 4.80-4.78 (m, 1H), 3.79 (s, 3H), 3.78 (s, 3H), 3.27-3.21 (m, 1H), 3.05-2.89 (m, 2H), 2.51-2.41 (m, 1H), 2.38-2.15 (m, 4H), 1.80-1.69 (m, 3H), 1.52-1.43 (m, 2H), 1.15 (d, J = 6.4 Hz, 3H). LCMS (ES, m/z): 544 $[M + H]^+$. |

TABLE 18-continued

| Example Number | Structure and Compound Name | $^1$H NMR, LCMS |
|---|---|---|
| 538 | 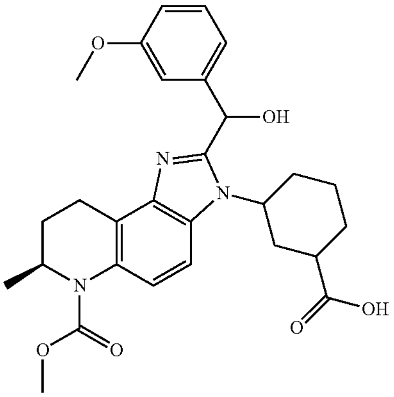 3-((7S)-2-(hydroxy(3-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.47-7.24 (m, 3H), 7.04-6.86 (m, 3H), 6.21 (s, 1H), 4.87-4.73 (m, 1H), 3.77 (s, 6H), 3.33-3.32 (m, 1H), 3.00-2.77 (m, 2H), 2.29-2.05 (m, 5H), 1.75-1.31 (m, 5H), 1.79-1.45 (m, 4H). LCMS (ES, m/z): 508 $[M + H]^+$. |
| 539 | 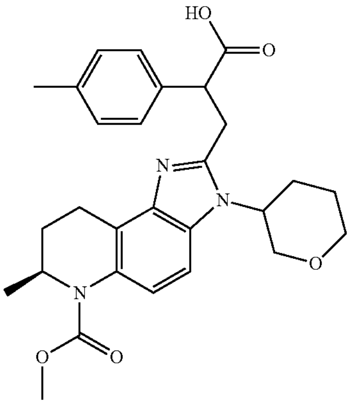 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2(p-tolyl)propanoic acid 1st eluting isomer | $^1$H-NMR ($CD_3OD$, 300 MHz) δ (ppm): 7.47 (d, J = 9.0 Hz, 1H), 7.34 (d, J = 9.0 Hz, 1H), 7.20 (d, J = 8.1 Hz, 2H), 7.08 (d, J = 7.8 Hz, 2H), 4.84-4.70 (m, 1H), 4.44-4.42 (m, 1H), 4.17-4.12 (m, 1H), 3.95-3.88 (m, 2H), 3.76 (s, 3H), 3.67-3.52 (m, 2H), 3.34-3.08 (m, 3H), 2.93-2.87 (m, 1H), 2.44-2.08 (m, 6H), 1.95-1.65 (m, 3H), 1.10 (d, J = 6.6 Hz, 3H). LCMS (ES, m/z): 492 $[M + H]^+$ |
| 540 | 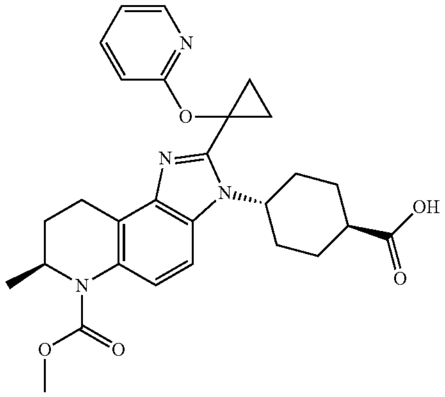 (1S,4R)-4-((S)-6-(methoxycarbonyl)-7-methyl-2(1-(pyridin-2-yloxy)cyclopropyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.11-8.09 (m, 1H), 7.84 (s, 2H), 7.81-7.73 (m, 1H), 7.09-7.02 (m, 1H), 7.02-6.95 (m, 1H), 5.28-5.13 (m, 1H), 3.83 (m, 3H), 3.40-3.30 (m, 1H), 3.25-3.10 (m, 1H), 3.10-2.99 (m, 1H), 2.70-2.56 (m, 1H), 2.54-2.36 (m, 2H), 2.36-2.20 (m, 3H), 2.09-1.83 (m, 5H), 1.83-1.67 (m, 4H), 1.22-1.10 (d, J = 6.4 Hz, 3H). LCMS (ES, m/z): 505 $[M + H]^+$. |

TABLE 18-continued

| Example Number | Structure and Compound Name | $^1$H NMR, LCMS |
|---|---|---|
| 541 | 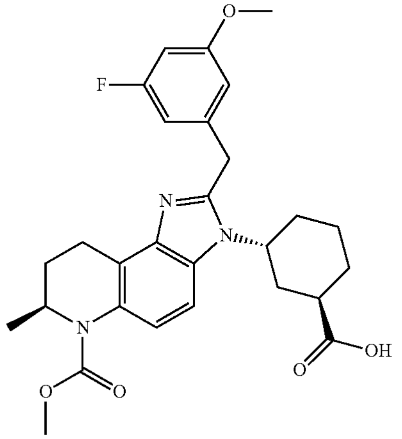 (1R,3R)-3-((S)-2-(3-fluoro-5-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.49 (d, J = 8.8 Hz, 1H), 7.40 (d, J = 8.8 Hz, 1H), 6.70-6.68 (m, 1H), 6.67-6.51 (m, 2H), 4.82-4.72 (m, 1H), 4.50-4.31 (m, 2H), 3.76 (s, 3H), 3.74 (s, 3H), 3.28-3.12 (m, 1H), 3.04-2.92 (m, 1H), 2.78-2.76 (m, 1H), 2.40-2.21 (m, 4H), 2.21-2.02 (m, 1H), 1.83-1.69 (m, 1H), 1.69-1.50 (m, 2H), 1.48-1.20 (m, 3H), 1.15 (d, J = 6.4 Hz, 3H). LCMS (ES, m/z): 510 [M + H]$^+$. |
| 542 | 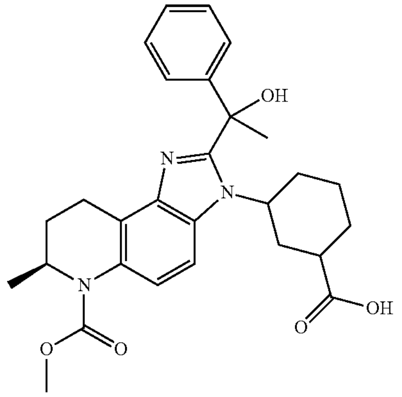 3-((7S)-2-(1-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.48-7.45 (m, 1H), 7.44-7.29 (m, 5H), 7.28-7.21 (m, 1H), 4.81-4.66 (m, 2H), 3.78 (s, 3H), 3.41-3.33 (m, 1H), 3.05-2.92 (m, 1H), 2.78-2.71 (m, 1H), 2.43-2.22 (m, 2H), 2.11 (s, 3H), 2.10-1.95 (m, 2H), 1.79-1.71 (m, 2H), 1.65-1.30 (m, 4H), 1.17 (d, J = 6.4 Hz, 3H). LCMS (ES, m/z): 492 [M + H]$^+$. |
| 543 | 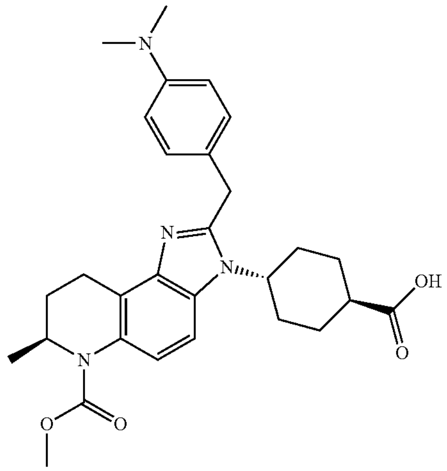 (1S,4R)-4-((S)-2-(4-(dimethylamino)benzyl)-6-(methoxycarbonyl)-7-methyl-6,7,8,9-tetrahydro-3H-imidazo[4,5-f]quinolin-3-yl)cyclohexane-1-carboxylic acid | $^1$H NMR ($CD_3OD$, 300 MHz) δ (ppm): 7.88-7.81 (m, 2H), 7.22 (d, J = 8.7 Hz, 2H), 6.89 (d, J = 8.7 Hz, 2H), 4.89-4.87 (m, 1H), 4.62-4.54 (m, 3H), 3.82 (s, 3H), 3.09-3.00 (m, 2H), 2.98 (s, 6H), 2.54-2.50 (m, 1H), 2.35-2.21 (m, 3H), 2.17-2.13 (m, 2H), 1.98-1.92 (m, 1H), 1.64-1.52 (m, 4H), 1.19 (d, J = 6.6 Hz, 3H). LCMS (ES, m/z): 505 [M + H]$^+$. |

TABLE 18-continued

| Example Number | Structure and Compound Name | $^1$H NMR, LCMS |
|---|---|---|
| 544 | 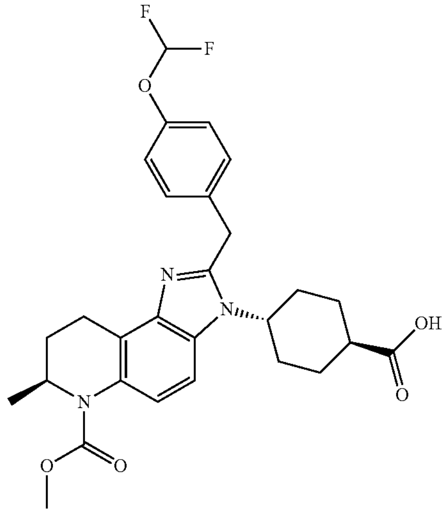 (1S,4R)-4-((S)-2-(4-(difluoromethoxy)benzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.53-7.36 (m, 2H), 7.31 (d, J = 8.4 Hz, 2H), 7.12 (d, J = 8.4 Hz, 2H), 7.03-6.51 (m, 1H), 4.81-4.67 (m, 1H), 4.41 (s, 2H), 4.31-4.15 (m, 1H), 3.78 (s, 3H), 3.27-3.10 (m, 1H), 3.03-2.87 (m, 1H), 2.47-2.32 (m, 1H), 2.32-2.15 (m, 3H), 2.15-1.97 (m, 2H), 1.84-1.66 (m, 1H), 1.64-1.37 (m, 4H), 1.16 (d, J = 6.4 Hz, 3H). LCMS (ES, m/z): 528 [M + H]$^+$ |
| 545 | 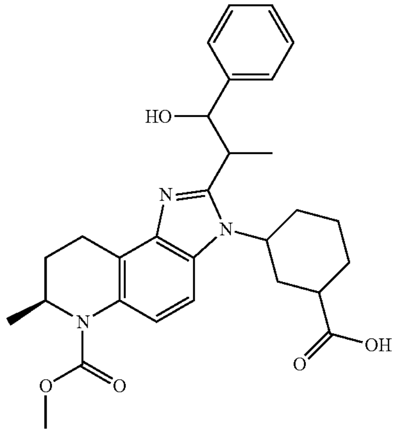 3-((7S)-2-(1-hydroxy-1-phenylpropan-2-yl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.62-7.42 (m, 4H), 7.34-7.01 (m, 3H), 5.22 (d, J = 7.2 Hz, 1H), 4.88-4.70 (m, 2H), 3.78 (s, 3H), 3.70-3.51 (m, 1H), 3.23-3.15 (m, 1H), 3.01-2.94 (m, 2H), 2.45-2.15 (m, 4H), 1.92-1.51 (m, 6H), 1.47 (d, J = 6.8 Hz, 3H), 1.14 (d, J = 6.8 Hz, 3H). LCMS (ES, m/z): 506 [M + H]$^+$ |

TABLE 18-continued

| Example Number | Structure and Compound Name | $^1$H NMR, LCMS |
|---|---|---|
| 546 | 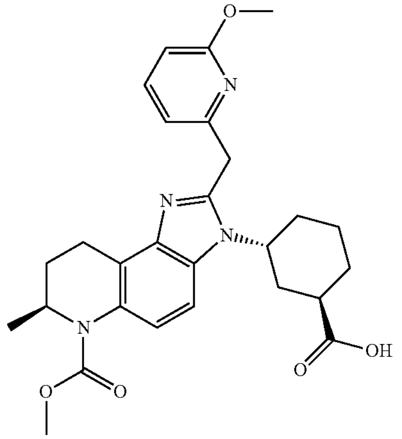 (1R,3R)-3-((S)-6-(methoxycarbonyl)-2-((6-methoxypyridin-2-yl)methyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.56-7.47 (m, 3H), 6.81 (d, J = 7.5 Hz, 1H), 6.61 (d, J = 8.4 Hz, 1H), 4.78-4.72 (m, 3H), 4.44 (s, 1H), 3.81 (3, 3H), 3.76 (s, 3H), 3.25-3.15 (m, 1H), 2.99-2.85 (m, 2H), 2.45-2.15 (m, 5H), 1.80-1.55 (m, 3H), 1.35-1.25 (m, 2H), 1.13 (d, J = 6.6 Hz, 3H). LCMS (ES, m/z): 493 $[M + H]^+$. |
| 547 | 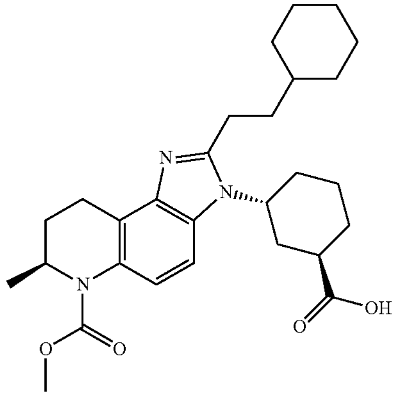 (1R,3R)-3-((S)-2-(2-cyclohexylethyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.52 (d, J = 9.2 Hz, 1H), 7.38 (d, J = 9.2 Hz, 1H), 4.78-4.74 (m, 2H), 3.79 (s, 3H), 3.16-3.14 (m, 1H), 3.03-2.92 (m, 4H), 2.45-2.42 (m, 2H), 2.29-2.24 (m, 2H), 1.94-1.89 (m, 4H), 1.77-1.59 (m, 8H), 1.40-1.25 (m, 5H), 1.14 (d, J = 6.4 Hz, 3H), 1.08-1.02 (m, 2H). LCMS (ES, m/z): 482 $[M + H]^+$. |
| 548 | 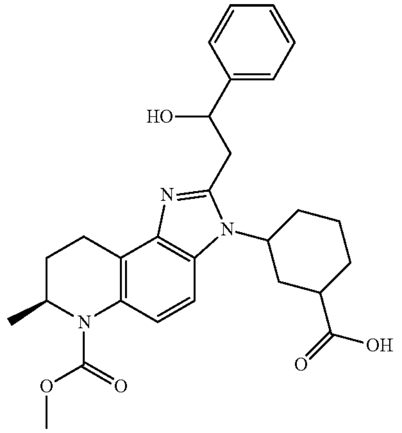 3-((7S)-2-(2-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.62-7.50 (m, 2H), 7.42-7.24 (m, 5H), 5.21-5.13 (m, 1H), 4.83-4.70 (m, 2H), 3.80 (s, 3H), 3.51 (d, J = 7.2 Hz, 2H), 3.17-3.05 (m, 1H), 3.02-2.89 (m, 2H), 2.31-2.14 (m, 5H), 1.86-1.67 (m, 3H), 1.51-1.40 (m, 1H), 1.32-1.24 (m, 1H), 1.14 (d, J = 6.4 Hz, 3H). LCMS (ES, m/z): 492 $[M + H]^+$. |

TABLE 18-continued

| Example Number | Structure and Compound Name | $^1$H NMR, LCMS |
|---|---|---|
| 549 | 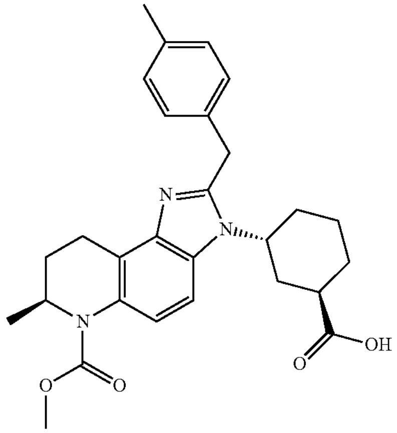<br>(1R,3R)-3-((S)-6-(methoxycarbonyl)-7-methyl-2-(4-methylbenzyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.45-7.35 (m, 2H), 7.12-7.08 (m, 4H), 4.86-4.60 (m, 2H), 4.39-4.23 (m, 2H), 3.76 (s, 3H), 3.30-3.10 (m, 1H), 2.99-2.86 (m, 2H), 2.40-2.00 (m, 8H), 1.80-1.52 (m, 3H), 1.35-1.12 (m, 5H) LCMS (ES, m/z): 476 $[M + H]^+$. |
| 550 | 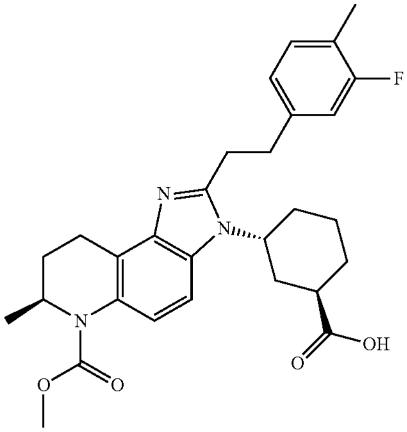<br>(1R,3R)-3-((S)-2-(3-fluoro-4-methylphenethyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.48 (d, J = 8.8 Hz, 1H), 7.37 (d, J = 8.8 Hz, 1H), 7.05-7.13 (m, 1H), 7.00-6.90 (m, 2H), 4.62-4.77 (m, 2H), 3.77 (s, 3H), 3.27-3.09 (m, 4H), 3.04-2.84 (m, 3H), 2.38-2.17 (m, 8H), 1.83-1.62 (m, 3H), 1.61-1.43 (m, 2H), 1.12 (d, J = 6.8 Hz, 3H). LCMS (ES, m/z): 508 $[M + H]^+$. |
| 551 | 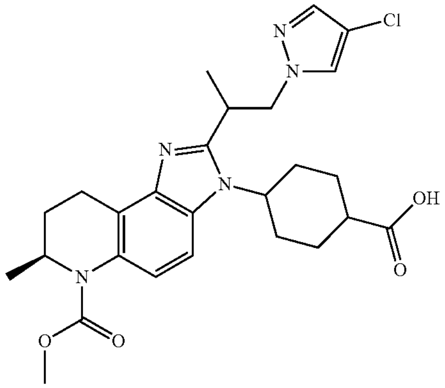<br>4-((7S)-2-(1-(4-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.94-7.79 (m, 3H), 7.40 (s, 1H), 4.75-4.61 (m, 2H), 4.61-4.43 (m, 1H), 4.43-4.28 (m, 1H), 3.83 (s, 3H), 3.19-3.01 (m, 2H), 2.69-2.54 (m, 1H), 2.46-2.17 (m, 5H), 2.12-1.99 (m, 1H), 1.99-1.86 (m, 1H), 1.86-1.71 (m, 1H), 1.71-1.51 (m, 5H), 1.38-1.24 (m, 1H), 1.18 (d, J = 6.8 Hz, 3H). LCMS (ES, m/z): 514 $[M + H]^+$. |

TABLE 18-continued

| Example Number | Structure and Compound Name | $^1$H NMR, LCMS |
|---|---|---|
| 552 | 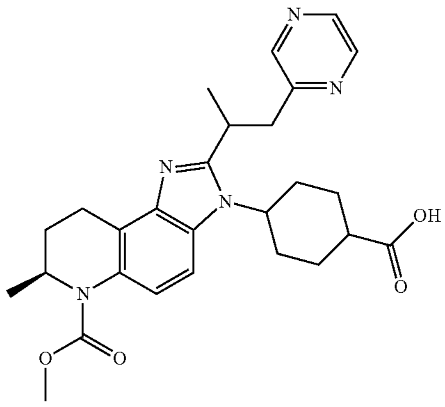 4-((7S)-6-(methoxycarbonyl)-7-methyl-2-(1-(pyrazin-2-yl)propan-2-yl)-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 8.54 (s, 1H), 8.45 (s, 1H), 8.38 (d, J = 2.4 Hz, 1H), 7.45 (d, J = 8.8 Hz, 1H), 7.35 (d, J = 9.2 Hz, 1H), 4.84-4.74 (m, 1H), 4.50-4.35 (m, 1H), 4.01-3.85 (m, 1H), 3.79 (s, 3H), 3.60-3.45 (m, 1H), 3.25-3.11 (m, 2H), 2.96-2.81 (m, 1H), 2.60-2.49 (m, 1H), 2.46-2.11 (m, 5H), 2.01-1.85 (m, 1H), 1.79-1.61 (m, 3H), 1.61-1.51 (m, 1H), 1.50 (d, J = 6.8 Hz, 3H), 1.13 (d, J = 6.8 Hz, 3H). LCMS (ES, m/z): 492 $[M + H]^+$. |
| 553 | 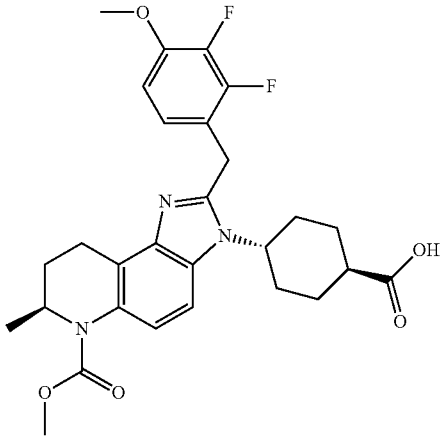 (1S,4R)-4-((S)-2-(2,3-difluoro-4-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.48 (d, J = 8.8 Hz, 1H), 7.40 (d, J = 9.2 Hz, 1H), 6.92-6.76 (m, 2H), 4.78-4.67 (m, 1H), 4.37 (s, 2H), 4.29-4.15 (m, 1H), 3.86 (s, 3H), 3.76 (s, 3H), 3.21-3.10 (m, 1H), 2.98-2.80 (m, 1H), 2.53-2.38 (m, 1H), 2.38-2.19 (m, 3H), 2.19-2.04 (m, 2H), 1.78-1.59 (m, 3H), 1.59-1.38 (m, 2H), 1.13 (d, J = 6.4 Hz, 3H). LCMS (ES, m/z): 528 $[M + H]^+$ |
| 554 | 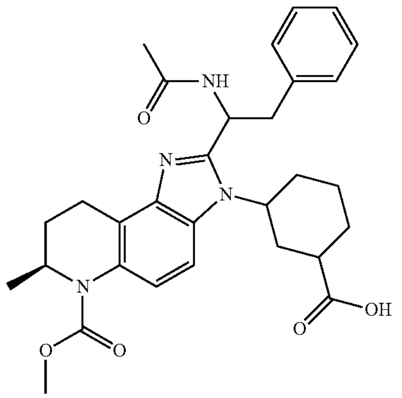 3-((7S)-2-(1-acetamido-2-phenylethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.47-7.01 (m, 7H), 5.65-5.50 (m, 1H), 4.84-4.74 (m, 1H), 4.51-4.35 (m, 1H), 3.79 (s, 3H), 3.50-3.15 (m, 3H), 3.03-2.82 (m, 2H), 2.41-2.22 (m, 2H), 2.20-1.95 (m, 6H), 1.81-1.70 (m, 1H), 1.69-1.55 (m, 2H), 1.35-1.20 (m, 1H), 1.16 (d, J = 6.8 Hz, 3H), 0.70-0.60 (m, 1H). LCMS (ES, m/z): 533 $[M + H]^+$. |

TABLE 18-continued

| Example Number | Structure and Compound Name | $^1$H NMR, LCMS |
|---|---|---|
| 555 | 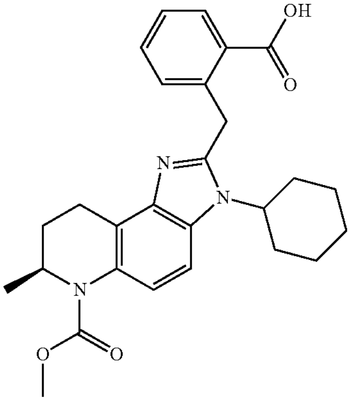 (S)-2-((3-cyclohexyl-6-(methoxycarbonyl)-7-methyl-6,7,8,9-tetrahydro-3H-imidazo[4,5-f]quinolin-2-yl)methyl)benzoic acid | $^1$H-NMR ($CD_3OD$, 400 MHz) δ (ppm): 8.02 (d, J = 7.6 Hz, 1H), 7.54-7.36 (m, 4H), 7.12 (d, J = 7.6 Hz, 1H) 4.88-4.76 (m, 3H), 4.39-4.33 (m, 1H), 3.78 (s, 3H), 3.21-2.84 (m, 2H), 2.28-2.13 (m, 3H), 1.83-1.56 (m, 6H), 1.39-1.21 (m, 3H), 1.16 (d, J = 6.8 Hz, 3H). LCMS (ES, m/z): 462 $[M + H]^+$ |
| 556 | 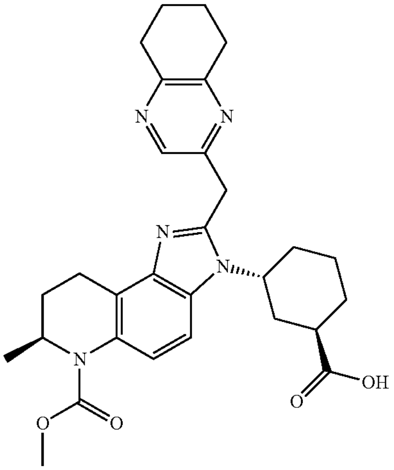 (1R,3R)-3-((S)-6-(methoxycarbonyl)-7-methyl-2-((5,6,7,8-tetrahydroquinoxalin-2-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.34 (s, 1H), 7.53-7.50 (m, 1H), 7.31-7.28 (m, 1H), 4.78-4.58 (m, 2H), 4.50-4.32 (m, 2H), 3.69 (s, 3H), 3.05-2.96 (m, 1H), 2.87-2.75 (m, 6H), 2.31-2.10 (m, 3H), 2.09-2.03 (m, 2H), 1.75-1.58 (m, 4H), 1.749-1.70 (m, 4H), 1.45-1.30 (m, 1H), 1.11 (d, J = 6.8 Hz, 3H). LCMS (ES, m/z): 518 $[M + H]^+$. |
| 557 | 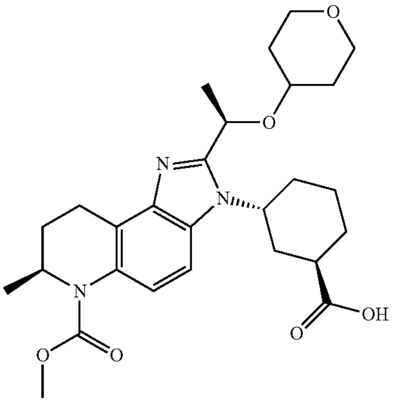 3-((7S)-6-(methoxycarbonyl)-7-methyl-2-(1-((tetrahydro-2H-pyran-4-yl)oxy)ethyl)-6,7,8,9-tetrahydro-3H-imidazo[4,5-f]quinolin-3-yl)cyclohexane-1-carboxylic acid 2nd eluting isomer | $^1$H NMR (400 MHz, $CD_3OD$) δ (ppm): 7.57 (d, J = 8.8 Hz, 1H), 7.43 (d, J = 9.2 Hz, 1H), 5.28-5.16 (m, 2H), 4.77-4.76 (m, 1H), 3.94-3.92 (m, 1H), 3.87-3.84 (m, 1H), 3.79 (s, 3H), 3.60-3.58 (m, 1H), 3.46-3.37 (m, 2H), 3.16-3.14 (m, 1H), 3.02-3.00 (m, 1H), 2.95-2.90 (m, 1H), 2.55-2.53 (m, 1H), 2.39-2.36 (m, 2H), 2.30-2.24 (m, 2H), 2.09-2.06 (m, 1H), 1.92-1.90 (m, 2H), 1.78-1.52 (m, 9H), 1.14 (d, J = 6.4 Hz, 3H). LCMS (ES, m/z): 500 $[M + H]^+$ |

TABLE 18-continued

| Example Number | Structure and Compound Name | $^{1}H$ NMR, LCMS |
|---|---|---|
| 558 | 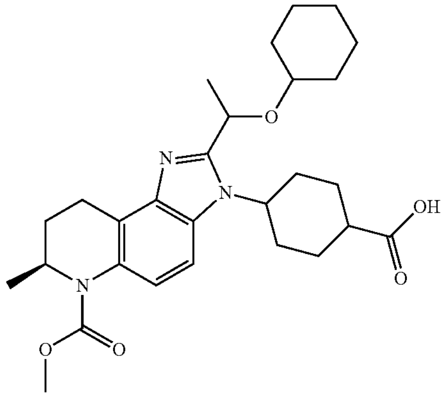<br>4-((7S)-2-(1-(cyclohexyloxy)ethyl)-6-(methoxycarbonyl)-7-methyl-6,7,8,9-tetrahydro-3H-imidazo[4,5-f]quinolin-3-yl)cyclohexane-1-carboxylic acid<br>1st eluting isomer | $^{1}H$-NMR ($CD_3OD$, 400 MHz) δ (ppm): 7.58-7.56 (m, 1H), 7.43-7.41 (m, 1H), 5.19-5.16 (m, 1H), 5.05-5.00 (m, 1H), 4.78-4.76 (m, 1H), 3.79 (s, 3H), 3.42-3.38 (m, 1H), 3.21-3.05 (m, 1H), 2.93-2.89 (m, 1H), 2.64-2.54 (m, 1H), 2.53-2.37 (m, 2H), 2.29-2.25 (m, 3H), 2.15-2.90 (m, 3H), 1.75-1.60 (m, 5H), 1.65 (d, J = 8.0 Hz, 3H), 1.57-1.51 (m, 1H), 1.42-1.35 (m, 2H), 1.36-1.21 (m, 4H), 1.14 (d, J = 6.4 Hz, 3H). LCMS (ES, m/z): 498 $[M + H]^+$. |
| 559 | 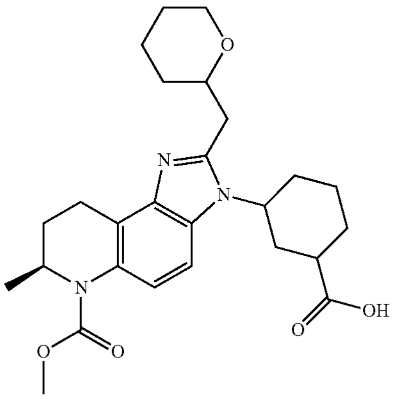<br>3-((7S)-6-(methoxycarbonyl)-7-methyl-2-((tetrahydro-2H-pyran-2-yl)methyl)-6,7,8,9-tetrahydro-3H-imidazo[4,5-f]quinolin-3-yl)cyclohexane-1-carboxylic acid<br>1st eluting isomer | $^{1}H$-NMR ($CD_3OD$, 400 MHz) δ (ppm): 7.58 (d, J = 9.2 Hz, 1H), 7.40 (d, J = 9.2 Hz, 1H), 4.89-4.81 (m, 1H), 4.85-4.81 (m, 1H), 3.96-3.89 (m, 1H), 3.88-3.80 (m, 1H), 3.79 (s, 3H), 3.48 (m, 1H), 3.17 (m, 3H), 3.01-2.92 (m, 2H), 2.52-2.32 (m, 2H), 2.32-2.18 (m, 3H), 1.99-1.87 (m, 3H), 1.79-1.69 (m, 2H), 1.69-1.62 (m, 2H), 1.59-1.45 (m, 3H), 1.40-1.29 (m, 1H), 1.15 (d, J = 6.8 Hz, 3H). LCMS (ES, m/z): 470 $[M + H]^+$. |
| 560 | 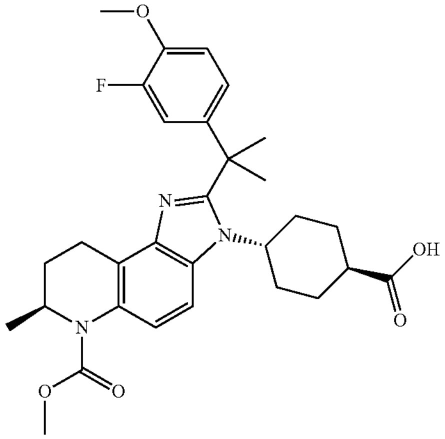<br>(1S,4R)-4-((S)-2-(2-(3-fluoro-4-methoxyphenyl)propan-2-yl)-6-(methoxycarbonyl)-7-methyl-6,7,8,9-tetrahydro-3H-imidazo[4,5-f]quinolin-3-yl)cyclohexane-1-carboxylic acid | $^{1}H$-NMR ($CD_3OD$, 400 MHz) δ (ppm): 7.47-7.29 (m, 2H), 7.19-7.06 (m, 1H), 7.07-6.94 (m, 2H), 4.81-4.67 (m, 1H), 4.03-3.92 (m, 1H), 3.88 (s, 3H), 3.78 (s, 3H), 3.33-3.25 (m, 1H), 3.01-2.89 (m, 1H), 2.41-2.26 (m, 2H), 2.26-2.12 (m, 2H), 2.06-1.92 (m, 2H), 1.84 (s, 6H), 1.76-1.62 (m, 1H), 1.51-1.41 (m, 2H), 1.26-1.03 (m, 5H). LCMS (ES, m/z): 538 $[M + H]^+$. |

TABLE 18-continued

| Example Number | Structure and Compound Name | $^1H$ NMR, LCMS |
|---|---|---|
| 561 | 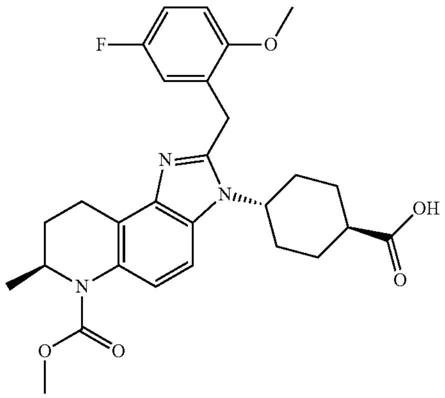 (1S,4R)-4-((S)-2-(5-fluoro-2-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.49-7.40 (m, 2H), 7.10-6.95 (m, 2H), 6.80-6.70 (m, 1H), 4.80-4.70 (m, 1H), 4.35 (s, 2H), 4.30-4.15 (m, 1H), 3.95 (s, 3H), 3.75 (s, 3H), 3.25-2.85 (m, 2H), 2.45-2.05 (m, 6H), 1.80-1.30 (m, 5H), 1.14 (d, J = 6.8 Hz, 3H). LCMS (ES, m/z): 510 $[M + H]^+$. |
| 562 | 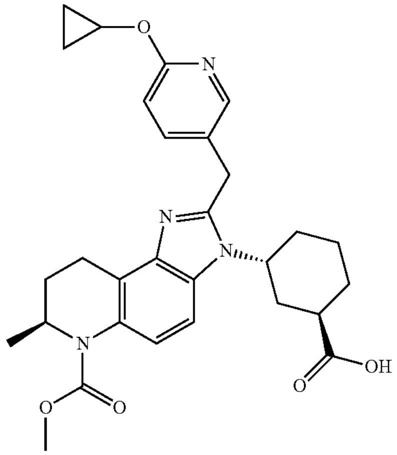 (1R,3R)-3-((S)-2-((6-cyclopropoxypyridin-3-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.26 (s, 1H), 7.88 (s, 2H), 7.80-7.72 (m, 1H), 7.01-6.95 (m, 1H), 5.14-5.03 (m, 1H), 4.90-4.83 (m, 1H), 4.72-4.55 (m, 2H), 4.20-4.11 (m, 1H), 3.83 (s, 3H), 3.17-2.99 (m, 3H), 2.50-2.39 (m, 1H), 2.37-2.17 (m, 4H), 1.99-1.88 (m, 1H), 1.88-1.75 (m, 2H), 1.68-1.60 (m, 1H), 1.50-1.35 (m, 1H), 1.18 (d, J = 6.8 Hz, 3H), 0.87-0.79 (m, 2H), 0.79-0.67 (m, 2H). LCMS (ES, m/z): 519 $[M + H]^+$. |
| 563 | 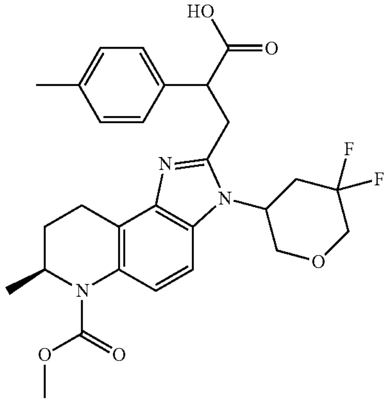 3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-(p-tolyl)propanoic acid 2nd eluting isomer | $^1$H-NMR ($CD_3OD$, 400 MHz) δ (ppm): 7.55-7.34 (m, 2H), 7.25-7.07 (m, 4H), 4.83-4.62 (m, 2H), 4.32-4.21 (m, 1H), 4.18-4.07 (m, 1H), 4.06-3.90 (m, 2H), 3.88-3.70 (m, 4H), 3.70-3.54 (m, 1H), 3.26-3.10 (m, 2H), 3.02-2.89 (m, 1H), 2.81-2.61 (m, 1H), 2.36-2.18 (m, 4H), 1.80-1.71 (m, 1H), 1.67-1.55 (m, 1H), 1.13 (d, J = 6.4 Hz, 3H). LCMS (ES, m/z): 528 $[M + H]^+$. |

TABLE 18-continued

| Example Number | Structure and Compound Name | $^1$H NMR, LCMS |
|---|---|---|
| 564 | 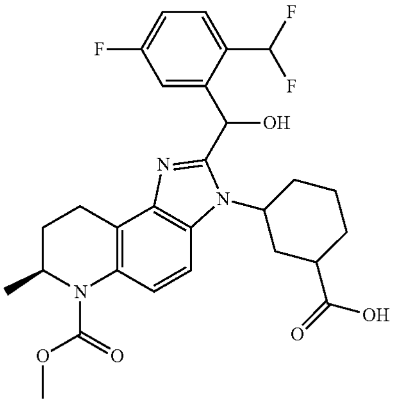 3-((7S)-2-((2-(difluoromethyl)-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.89-7.83 (m, 2H), 7.77-7.72 (m, 1H), 7.53-7.50 (m, 1H), 7.34-7.31 (m, 1H), 7.21-6.93 (m, 1H), 6.74-6.72 (m, 1H), 4.95-4.93 (m, 1H), 4.85-4.81 (m, 2H), 3.83 (s, 3H), 3.19-3.12 (m, 1H), 3.02-2.95 (m, 2H), 2.50-2.48 (m, 1H), 2.30-2.16 (m, 4H), 1.89-1.73 (m, 4H), 1.50-1.42 (m, 1H), 1.16 (d, J = 6.4 Hz, 3H). LCMS (ES, m/z): 546 $[M + H]^+$. |
| 565 | 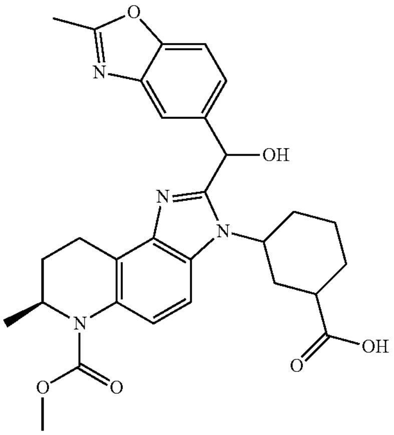 3-((7S)-2-(hydroxy(2-methylbenzo[d]oxazol-5-yl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.82 (s, 1H), 7.52 (d, J = 8.4 Hz, 1H), 7.48-7.40 (m, 3H), 6.35 (s, 1H), 4.96-4.89 (m, 1H), 4.79-4.75 (m, 1H), 3.78 (s, 3H), 3.30-3.24 (m, 1H), 3.22-3.01 (m, 1H), 3.00-2.91 (m, 1H), 2.64 (s, 3H), 2.43-2.42 (m, 2H), 2.40-2.25 (m, 1H), 2.09-2.00 (m, 1H), 1.99-1.96 (m, 1H), 1.78-1.73 (m, 1H), 1.56-1.47 (m, 2H), 1.32-1.26 (m, 1H), 1.15 (d, J = 6.4 Hz, 3H), 0.95-0.92 (m, 1H). LCMS (ES, m/z): 533 $[M + H]^+$. |

TABLE 18-continued

| Example Number | Structure and Compound Name | $^1$H NMR, LCMS |
|---|---|---|
| 566 | 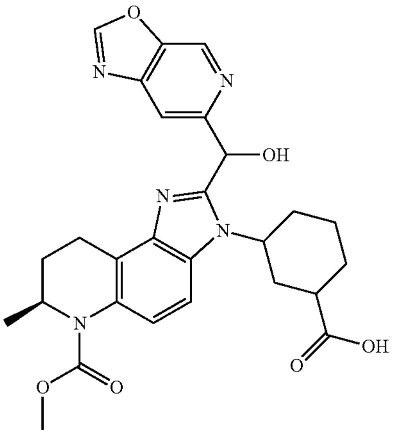 3-((7S)-2-(furo[2,3-clpyridin-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 8.72 (s, 1H), 8.02-7.95 (m, 2H), 7.55-7.45 (m, 1H), 7.45-7.38 (m, 1H), 6.99 (s, 1H), 6.38 (s, 1H), 5.06-4.96 (m, 1H), 4.81-4.72 (m, 1H), 3.78 (s, 3H), 3.30-3.18 (m, 1H), 2.99-2.87 (m, 1H), 2.84-2.80 (m, 1H), 2.43-2.31 (m, 1H), 2.29-2.20 (m, 2H), 2.18-2.11 (m, 1H), 2.08-2.00 (m, 1H), 1.83-1.67 (m, 3H), 1.67-1.50 (m, 2H), 1.15 (d, J = 6.8 Hz, 3H). LCMS (ES, m/z): 519 [M + H]$^+$. |
| 567 | 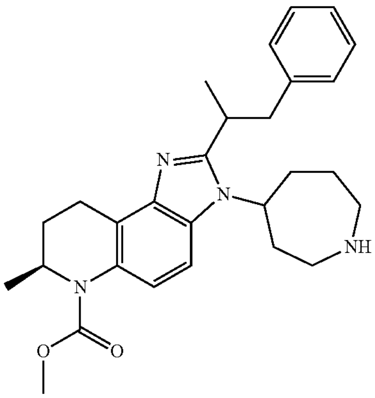 methyl 3-((7S)-azepan-4-yl)-7-methyl-2-(1-phenylpropan-2-yl)-3,7,8,9-tetrahydro-6H-imidazo[4,5-f]quinoline-6-carboxylate 2nd eluting isomer | $^1$H-NMR ($CD_3OD$, 400 MHz) δ (ppm): 7.38-7.21 (m, 2H), 7.18-7.04 (m, 3H), 7.04-6.96 (m, 2H), 4.78-4.65 (m, 1H), 4.38-4.33 (m, 1H), 3.77 (s, 3H), 3.63-3.51 (m, 1H), 3.29-3.19 (m, 1H), 3.19-2.89 (m, 6H), 2.90-2.74 (m, 1H), 2.35-2.16 (m, 3H), 1.98-1.92 (m, 1H), 1.77-1.56 (m, 2H), 1.54 (d, J = 6.8 Hz, 3H), 1.41-1.34 (m, 1H), 1.12 (d, J = 6.8 Hz, 3H), 0.77-0.69 (m, 1H). LCMS (ES, m/z): 461 [M + H]$^+$. |
| 568 | 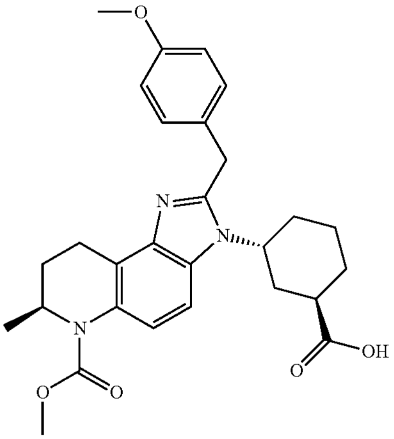 (1R,3R)-3-((S)-2-(4-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.43 (d, J = 9.2 Hz, 1H), 7.36 (d, J = 8.8 Hz, 1H), 7.16 (d, J = 8.8 Hz, 2H), 6.84 (d, J = 9.2 Hz, 2H), 4.81-4.63 (m, 2H), 4.40-4.19 (m, 2H), 3.82-3.70 (m, 6H), 3.26-3.12 (m, 1H), 3.02-2.85 (m, 2H), 2.37-1.98 (m, 5H), 1.80-1.69 (m, 1H), 1.68-1.55 (m, 2H), 1.37-1.09 (m, 5H). LCMS (ES, m/z): 492 [M + H]$^+$. |

TABLE 18-continued

| Example Number | Structure and Compound Name | $^1$H NMR, LCMS |
|---|---|---|
| 569 | 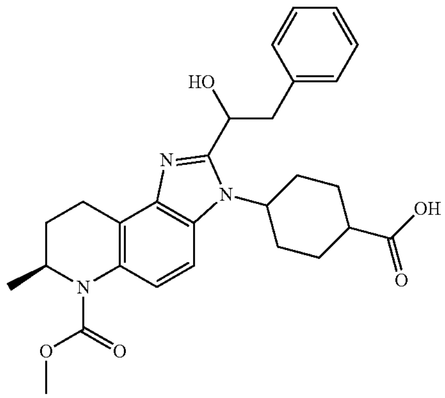 4-((7S)-2-(1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H NMR ($CD_3OD$, 400 MHz) δ (ppm): 7.47 (d, J = 9.2 Hz, 1H), 7.38 (d, J = 8.8 Hz, 1H), 7.26-7.17 (m, 5H), 5.29 (t, J = 7.2 Hz, 1H), 4.78-4.76 (m, 1H), 4.60-4.55 (m, 1H), 3.78 (s, 3H), 3.34-3.32 (m, 2H), 3.20-3.17 (m, 1H), 2.96-2.92 (m, 1H), 2.51-2.46 (m, 1H), 2.30-2.19 (m, 4H), 2.16-2.05 (m, 1H), 1.97-1.95 (m, 1H), 1.72-1.32 (m, 4H), 1.13 (d, J = 6.8 Hz, 3H). LCMS (ES, m/z): 492 $[M + H]^+$. |
| 570 | 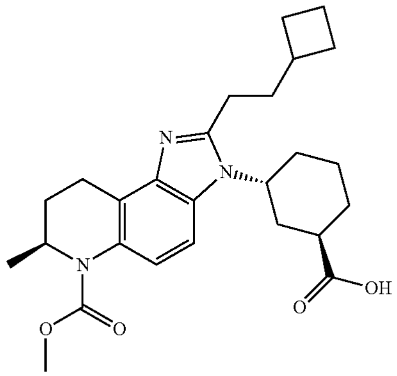 (1R,3R)-3-((S)-2-(2-cyclobutylethyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.52 (d, J = 9.2 Hz, 1H), 7.39 (d, J = 9.2 Hz, 1H), 4.81-4.68 (m, 2H), 3.78 (s, 3H), 3.20-3.16 (m, 1H), 3.09-2.98 (m, 1H), 2.90-2.84 (m, 3H), 2.42-2.34 (m, 3H), 2.32-2.18 (m, 3H), 2.14-2.05 (m, 2H), 1.93-1.82 (m, 6H), 1.82-1.58 (m, 5H), 1.17-1.10 (d, J = 6.8 Hz, 3H). LCMS (ES, m/z): 454 $[M + H]^+$. |
| 571 | 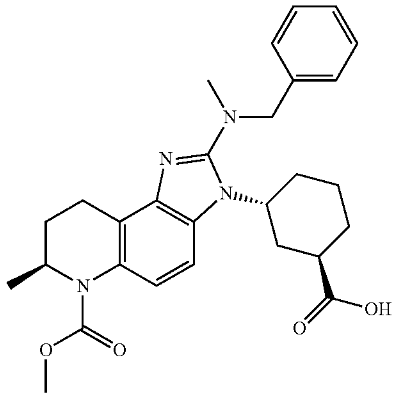 (1R,3R)-3-((S)-2-(benzyl(methyl)amino)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.55-7.21 (m, 7H), 4.81-4.63 (m, 1H), 4.59-4.41 (m, 1H), 4.41-4.21 (m, 1H), 4.22-4.04 (m, 1H), 3.78 (s, 2H), 3.22-3.09 (m, 1H), 3.04-2.92 (m, 1H), 2.92-2.74 (m, 3H), 2.59-2.41 (m, 1H), 2.40-2.00 (m, 4H), 1.91-1.51 (m, 5H), 1.42-1.32 (m, 2H), 1.15 (d, J = 6.0 Hz, 3H). LCMS (ES, m/z): 491 $[M + H]^+$ |

TABLE 18-continued

| Example Number | Structure and Compound Name | $^1H$ NMR, LCMS |
|---|---|---|
| 572 | 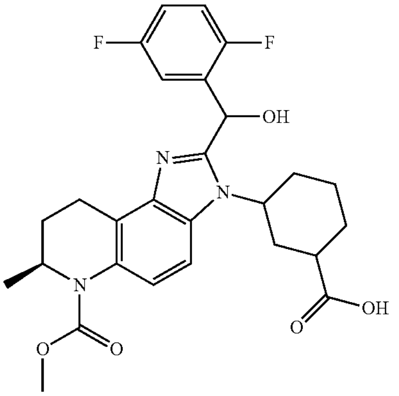 3-((7S)-2-((2,5-difluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 7.68-7.64 (m, 1H), 7.53-7.50 (m, 1H), 7.43-7.40 (m, 1H), 7.08-7.05 (m, 2H), 6.39 (s, 1H), 5.01-4.95 (m, 1H), 4.87-4.72 (m, 1H), 3.81 (s, 3H), 3.31-3.13 (m, 1H), 2.97-2.96 (m, 1H), 2.94-2.86 (m, 1H), 2.50-2.46 (m, 1H), 2.44-2.32 (m, 1H), 2.28-2.17 (m, 3H), 1.74-1.60 (m, 3H), 1.53-1.15 (m, 2H), 1.14 (d, J = 6.4 Hz, 3H). LCMS (ES, m/z): 514 $[M + H]^+$ |
| 573 | 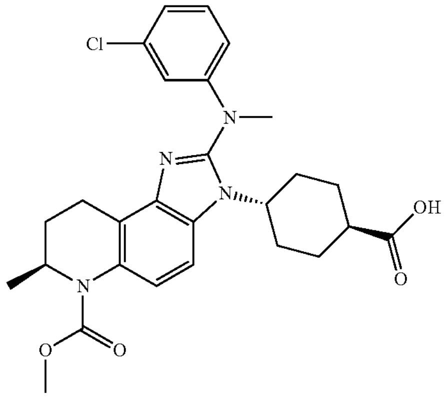 (1S,4R)-4-((S)-2-((3-chlorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 $[M + H]^+$ |
| 574 | 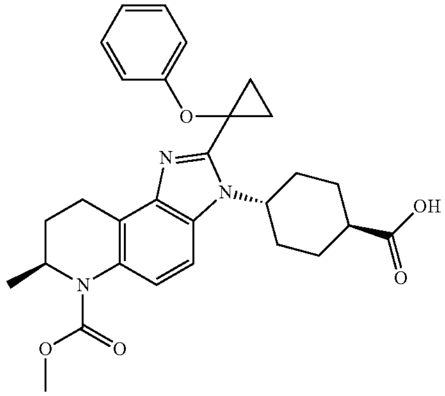 (1S,4R)-4-((S)-6-(methoxycarbonyl)-7-methyl-2-(1-phenoxycyclopropyl)-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 7.48 (d, J = 8.8 Hz, 1H), 7.41 (d, J = 8.8 Hz, 1H), 7.27-7.14 (m, 4H), 6.92-6.90 (m, 1H), 5.15-5.04 (m, 1H), 4.73-4.50 (m, 1H), 3.77 (s, 3H), 3.23-3.15 (m, 1H), 2.94-2.85 (m, 1H), 2.60-2.49 (m, 1H), 2.41-2.18 (m, 5H), 1.89-1.70 (m, 2H), 1.86-1.65 (m, 5H), 1.54-1.46 (m, 2H), 1.13 (d, J = 6.8 Hz, 3H) LCMS (ES, m/z): 504 $[M + H]^+$. |

TABLE 18-continued

| Example Number | Structure and Compound Name | $^1$H NMR, LCMS |
|---|---|---|
| 575 | 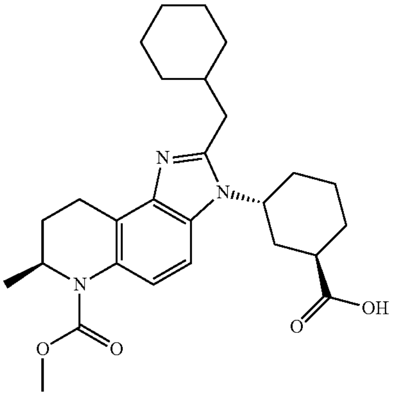 (1R,3R)-3-((S)-2-(cyclohexylmethyl)-6-(methoxycarbonyl)-7-methyl-6,7,8,9-tetrahydro-3H-imidazo[4,5-f]quinolin-3-yl)cyclohexane-1-carboxylic acid | $^1$H NMR ($CD_3OD$, 400 MHz) δ (ppm): 7.53 (d, J = 8.8 Hz, 1H), 7.39 (d, J = 8.8 Hz, 1H), 4.76-4.73 (m, 2H), 3.72 (s, 3H), 3.22-3.17 (m, 1H), 3.21-3.13 (m, 1H), 2.94-2.86 (m, 3H), 2.47-2.40 (m, 2H), 2.27-2.25 (m, 3H), 1.94-1.89 (m, 3H), 1.76-1.62 (m, 8H), 1.48-1.29 (m, 4H), 1.17-1.02 (m, 4H). LCMS (ES, m/z): 468 [M + H]$^+$. |
| 576 | 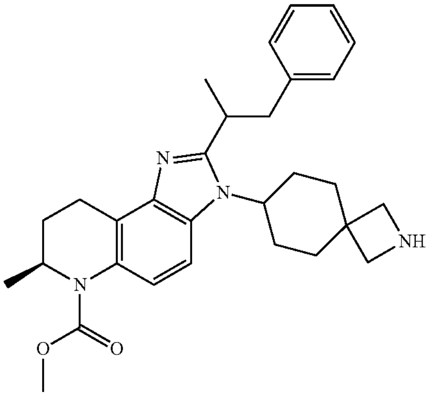 methyl (7S)-7-methyl-2-(1-phenylpropan-2-yl)-3-(2-azaspiro[3.5]nonan-7-yl)-3,7,8,9-tetrahydro-6H-imidazo[4,5-f]quinoline-6-carboxylate. 1$^{st}$ eluting isomer | $^1$H-NMR ($CD_3OD$, 300 MHz) δ (ppm): 7.26 (d, J = 9.0 Hz, 1H), 7.15-7.10 (m, 4H), 7.03-7.01 (m, 2H), 4.85-4.71 (m, 1H), 3.76-3.62 (m, 7H), 3.43 (s, 2H), 3.32-3.08 (m, 4H), 2.35-1.66 (m, 8H), 1.58 (d, J = 6.6 Hz, 3H), 1.45-1.30 (m, 1H), 1.12 (d, J = 6.6 Hz, 3H), 0.60-0.40 (m, 1H). LCMS (ES, m/z): 487 [M + H]+. |
| 577 | 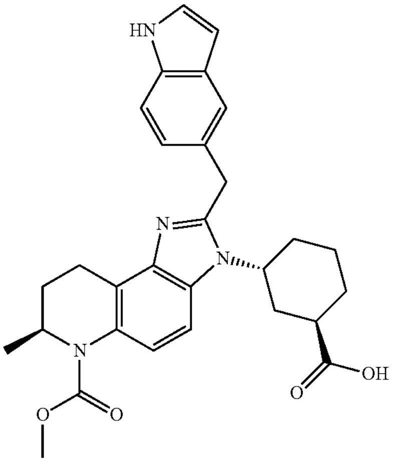 (1R,3R)-3-((S)-2-((1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.51-7.41 (m, 3H), 7.41-7.29 (m, 1H), 7.24-7.13 (m, 1H), 7.11-6.94 (m, 1H), 6.19 (s, 1H), 4.81-4.71 (m, 2H), 4.71-4.57 (m, 2H), 3.78 (s, 3H), 3.32-3.18 (m, 1H), 3.08-2.91 (m, 1H), 2.82-2.67 (m, 1H), 2.39-2.18 (m, 3H), 2.16-1.98 (m, 1H), 1.82-1.68 (m, 1H), 1.68-1.60 (m, 1H), 1.50-1.38 (m, 2H), 1.21-1.02 (m, 4H), 0.97-0.94 (m, 1H). LCMS (ES, m/z): 501 [M + H]$^+$ |

TABLE 18-continued

| Example Number | Structure and Compound Name | $^1$H NMR, LCMS |
|---|---|---|
| 578 | 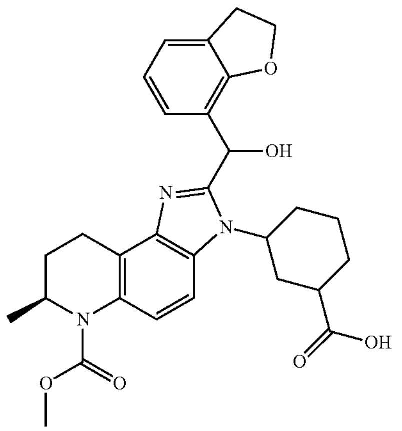 3-((7S)-2-((2,3-dihydrobenzofuran-7-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.52-7.45 (m, 2H), 7.41-7.36 (m, 1H), 7.17 (d, J = 7.2 Hz, 1H), 6.90 (t, J = 7.6 Hz, 1H), 6.28 (s, 1H), 4.85-4.70 (m, 2H), 4.53-4.38 (m, 2H), 3.78 (s, 3H), 3.33-3.12 (m, 3H), 2.98-2.85 (m, 2H), 2.48-2.37 (m, 1H), 2.31-2.21 (m, 2H), 2.15-1.92 (m, 2H), 1.78-1.53 (m, 3H), 1.49-1.28 (m, 2H), 1.15 (d, J = 6.4 Hz, 3H). LCMS (ES, m/z): 520 [M + H]$^+$ |
| 579 | 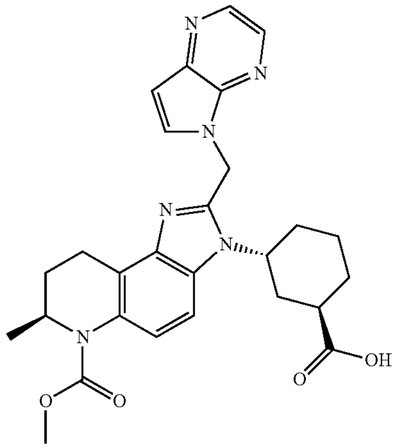 (1R,3R)-3-((S)-2-((5H-pyrrolo[2,3-b]pyrazin-5-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.43 (s, 1H), 8.42 (s, 1H), 7.80 (d, J = 2.8 Hz, 1H), 7.52-7.46 (m, 2H), 6.72-6.10 (m, 2H), 5.62 (d, J = 9.2 Hz, 1H), 4.99-4.91 (m, 1H), 4.76-4.59 (m, 1H), 3.78 (s, 3H), 3.20 (m, 1H), 2.97 (m, 2H), 2.43-2.31 (m, 2H), 2.30-2.02 (m, 3H), 1.82-1.75 (m, 1H), 1.72-1.60 (m, 2H), 1.21-1.02 (m, 5H). LCMS (ES, m/z): 503 [M + H]$^+$ |

TABLE 18-continued

| Example Number | Structure and Compound Name | $^1$H NMR, LCMS |
|---|---|---|
| 580 | 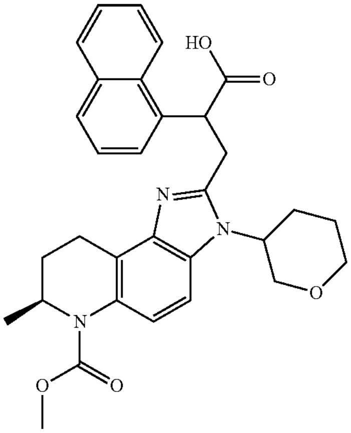 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(naphthalen-1-yl)propanoic acid 1$^{st}$ eluting isomer | $^1$H-NMR ($CD_3OD$, 300 MHz) δ (ppm): 8.32-8.23 (m, 1H), 7.93-7.85 (m, 2H), 7.58 (d, J = 6.6 Hz, 1H), 7.46-7.40 (m, 4H), 7.35-7.22 (m, 1H), 5.12-5.08 (m, 1H), 4.77-4.74 (m, 1H), 4.45-4.37 (m, 1H), 3.97-3.77 (m, 3H), 3.78 (s, 3H), 3.52-3.48 (m, 2H), 3.20-3.18 (m, 1H), 3.04-2.88 (m, 2H), 2.45-2.25 (m, 2H), 2.12-1.98 (m, 1H), 1.79 (m, 3H), 1.14 (d, J = 6.6 Hz, 3H). LCMS (ES, m/z): 528 [M + H]$^+$ |
| 581 | 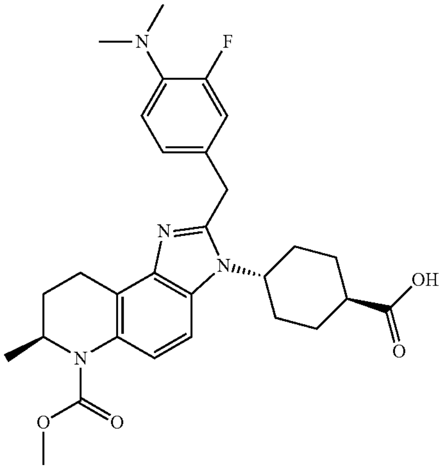 (1S,4R)-4-((S)-2-(4-(dimethylamino)-3-fluorobenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.89-7.86 (m, 2H), 7.85-7.07 (m, 3H), 4.75-4.50 (m, 4H), 3.80 (s, 3H), 3.25-3.30 (m, 2H), 2.85 (s, 6H), 2.60-2.10 (m, 6H), 2.00-1.45 (m, 5H), 1.19 (d, J = 6.6 Hz, 3H). LCMS (ES, m/z): 523 [M + H]$^+$ |

TABLE 18-continued

| Example Number | Structure and Compound Name | $^1$H NMR, LCMS |
|---|---|---|
| 582 | 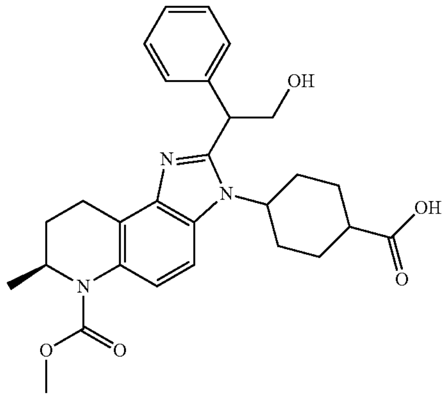 4-((7S)-2-(2-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.43-7.41 (m, 1H), 7.36-7.33 (m, 3H), 7.31-7.24 (m, 3H), 4.87-4.73 (m, 1H), 4.58-4.53 (m, 1H), 4.45-4.40 (m, 1H), 4.22-4.14 (m, 2H), 3.76 (s, 3H), 3.30-3.26 (m, 1H), 2.99-2.95 (m, 1H), 2.39-2.29 (m, 3H), 2.28-2.13 (m, 1H), 2.12-1.85 (m, 3H), 1.78-1.68 (m, 1H), 1.67-1.55 (m, 1H), 1.16-1.13 (m, 4H), 1.00-0.91 (m, 1H). LCMS (ES, m/z): 492 [M + H]$^+$. |
| 583 | 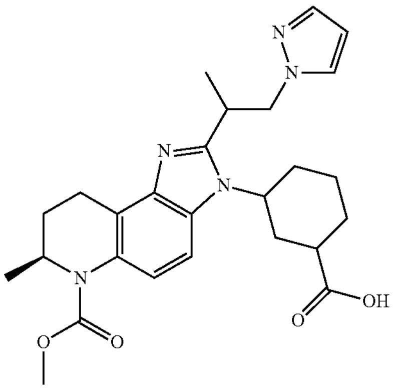 3-((7S)-2-(1-(1H-pyrazol-1-yl)propan-2-yl)-6-(methoxycarbonyl)-7-methyl-6,7,8,9-tetrahydro-3H-imidazo[4,5-flquinolin-3-yl)cyclohexane-1-carboxylic acid 1$^{st}$ eluting isomer | $^1$H-NMR ($CD_3OD$, 400 MHz) δ (ppm): 7.84-7.80 (m, 2H), 7.66 (d, J = 2.0 Hz, 1H), 7.41 (d, J = 1.6 Hz, 1H), 6.25 (m, 1H), 4.86-4.67 (m, 3H), 4.26 (m, 1H), 3.80 (s, 3H), 3.17-2.99 (m, 3H), 2.31-2.22 (m, 5H), 1.89-1.85 (m, 3H), 1.68-1.54 (m, 4H), 1.48 (m, 1H), 1.36-1.25 (m, 1H), 1.15 (d, J = 6.8 Hz, 3H). LCMS (ES, m/z): 480 [M + H]$^+$. |
| 584 | 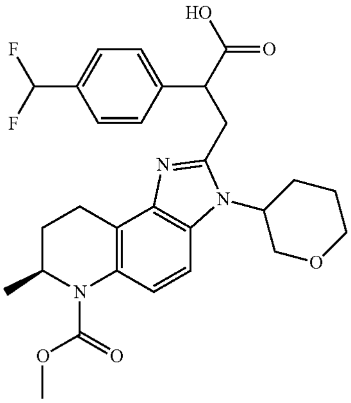 2-(4-(difluoromethyl)phenyl)-3((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1$^{st}$ eluting isomer | $^1$H-NMR ($CD_3OD$, 400 MHz) δ (ppm): 7.52-7.48 (m, 5H), 7.39 (d, J = 8.8 Hz, 1H), 6.93-6.60 (m, 1H), 4.82-4.66 (m, 1H), 4.58-4.56 (m, 1H), 4.38-4.35 (m, 1H), 4.06-3.92 (m, 2H), 3.78-3.74 (m, 4H), 3.63-3.49 (m, 1H), 3.43-3.34 (m, 2H), 3.16-3.08 (m, 1H), 2.92-2.88 (m, 1H), 2.49-2.42 (m, 1H), 2.28-2.05 (m, 2H), 2.03-1.81 (m, 2H), 1.81-1.65 (m, 1H), 1.13 (d, J = 6.8 Hz, 3H). LCMS (ES, m/z): 528 [M + H]$^+$. |

TABLE 18-continued

| Example Number | Structure and Compound Name | $^1$H NMR, LCMS |
|---|---|---|
| 585 | 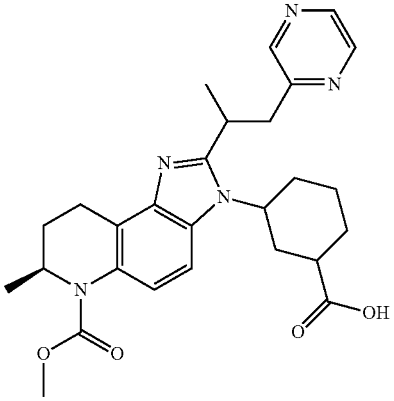 3-((7S)-6-(methoxycarbonyl)-7-methyl-2-(1-(pyrazin-2-yl)propan-2-yl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 8.51-8.35 (m, 3H), 7.45 (d, J = 8.8 Hz, 1H), 7.34 (d, J = 8.8 Hz, 1H), 4.77-4.72 (m, 2H), 3.96-3.93 (m, 1H), 3.77 (s, 3H), 3.60-3.54 (m, 1H), 3.33-3.20 (m, 2H), 2.99-2.88 (m, 2H), 2.45-2.22 (m, 5H), 1.84-1.54 (m, 8H), 1.14 (d, J = 6.4 Hz, 3H). LCMS (ES, m/z): 492 $[M + H]^+$. |
| 586 | 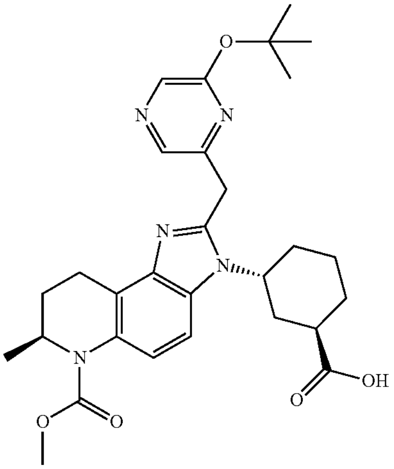 (1R,3R)-3-((S)-2-((6-(tert-butoxy)pyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.32 (s, 1H), 8.02 (s, 1H), 7.88 (s, 2H), 4.98-4.89 (m, 2H), 4.78-4.71 (m, 2H), 3.84 (s, 3H), 3.05-2.95 (m, 3H), 2.50-2.12 (m, 5H), 2.09-1.71 (m, 4H), 1.51-1.40 (m, 1H), 1.27 (s, 9H), 1.17 (d, J = 6.8 Hz, 3H). LCMS (ES, m/z): 536 $[M + H]^+$ |

TABLE 18-continued

| Example Number | Structure and Compound Name | $^1$H NMR, LCMS |
|---|---|---|
| 587 | 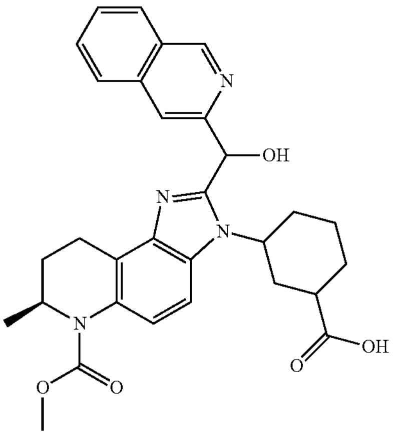 3-((7S)-2-(hydroxy(isoquinolin-3-yl)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 9.16 (s, 1H), 8.08-8.97 (m, 3H), 7.79-7.40 (m, 4H), 6.47 (s, 1H), 5.12 (s, 1H), 4.77-4.73 (m, 1H), 3.78 (s, 3H), 3.34-3.20 (m, 1H), 2.93-2.82 (m, 2H), 2.38-2.15 (m, 5H), 1.76-1.54 (m, 5H), 1.15 (d, J = 6.8 Hz, 3H). LCMS (ES, m/z): 529 $[M + H]^+$. |
| 588 | 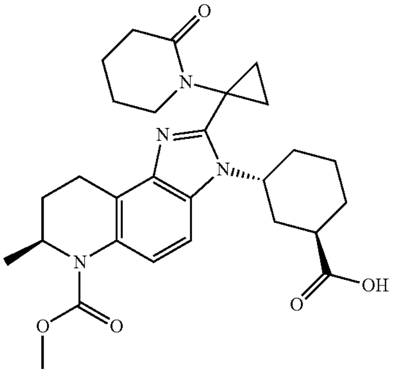 (1R,3R)-3-((S)-6-(methoxycarbonyl)-7-methyl-2-(1-(2-oxopiperidin-1-yl)cyclopropyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.54-7.51 (m, 1H), 7.32-7.29 (m, 1H), 5.66-5.61 (m, 1H), 4.66-4.62 (m, 1H), 3.66 (s, 3H), 3.56-3.52 (m, 1H), 3.45-3.41 (m, 1H), 3.07-3.00 (m, 1H), 2.99-2.77 (m, 2H), 2.39-2.34 (m, 1H), 2.24-2.20 (m, 1H), 2.20-2.11 (m, 5H), 1.68-1.51 (m, 11H), 1.35-1.15 (m, 2H), 1.09 (d, J = 6.4 Hz, 3H). LCMS (ES, m/z): 509 $[M + H]^+$ |
| 589 | 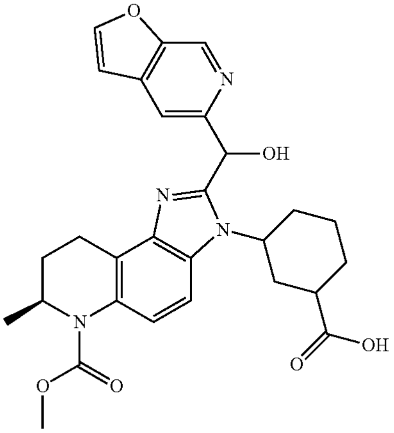 3-((7S)-2-(furo[2,3-c]pyridin-5-yl(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 8.73 (s, 1H), 8.11 (s, 1H), 8.07-8.02 (m, 1H), 7.51-7.45-7.38 (m, 2H), 7.03 (s, 1H), 6.36 (s, 1H), 4.80-4.72 (m, 2H), 3.78 (s, 3H), 3.27-3.14 (m, 1H), 3.01-2.89 (m, 2H), 2.45-2.38 (m, 2H), 2.28-2.20 (m, 1H), 2.12-1.98 (m, 2H), 1.76-1.73 (m, 1H), 1.63-1.47 (m, 2H), 1.25-1.09 (m, 4H), 1.08-1.01 (m, 1H). LCMS (ES, m/z): 519 $[M + H]^+$. |

TABLE 18-continued

| Example Number | Structure and Compound Name | $^1$H NMR, LCMS |
|---|---|---|
| 590 | 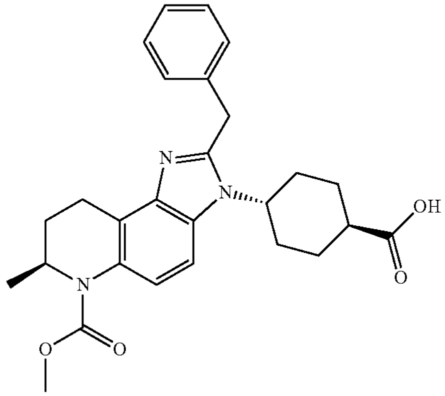 (1S,4R)-4-((S)-2-benzyl-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.45-7.35 (m, 2H), 7.34-7.19 (m, 5H), 4.82-4.71 (m, 1H), 4.39 (s, 2H), 4.28-4.14 (m, 1H), 3.76 (s, 3H), 3.28-3.15 (m, 1H), 3.02-2.89 (m, 1H), 2.41-2.10 (m, 4H), 2.06-1.92 (m, 2H), 1.79-1.69 (m, 1H), 1.45-1.36 (m, 4H), 1.14 (d, J = 6.8 Hz, 3H). LCMS (ES, m/z): 462 $[M + H]^+$ |
| 591 | 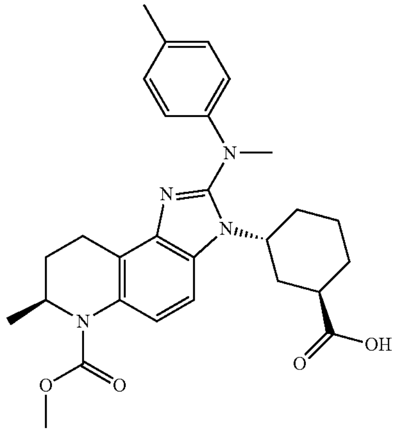 (1R,3R)-3-((S)-6-(methoxycarbonyl)-7-methyl-2-(methyl(p-tolyl)amino)-6,7,8,9-tetrahydro-3H-imidazo[4,5-f]quinolin-3-yl)cyclohexane-1-carboxylic acid | LCMS (ES, m/z): 491 $[M + H]^+$ |
| 592 | 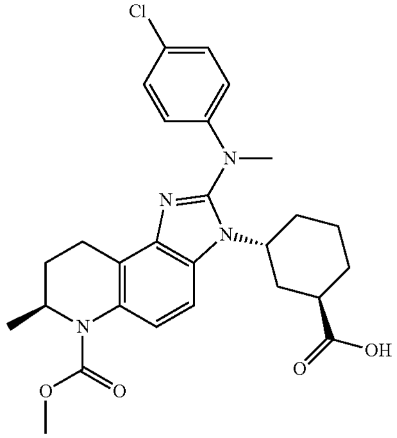 (1R,3R)-3-((S)-2-((4-chlorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 $[M + H]^+$ |

TABLE 18-continued

| Example Number | Structure and Compound Name | $^1$H NMR, LCMS |
| --- | --- | --- |
| 593 | 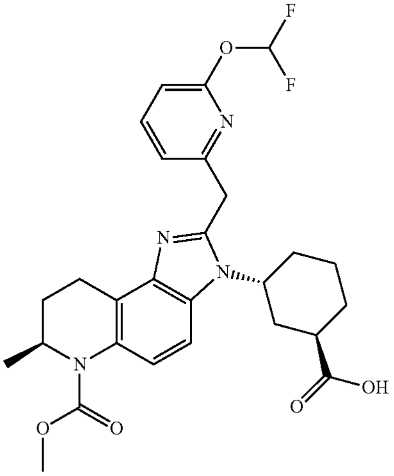 (1R,3R)-3-((S)-2-((6-(difluoromethoxy)pyridin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H NMR ($CD_3OD$, 400 MHz) δ (ppm): 7.98-7.94 (m, 1H), 7.88-7.86 (s, 2H), 7.43-7.41 (m, 1H), 7.40-7.15 (m, 1H), 6.98-6.97 (m, 1H), 5.05-5.01 (m, 1H), 4.84-4.72 (m, 3H), 3.83 (s, 3H), 3.19-2.98 (m, 3H), 2.50-2.30 (m, 2H), 2.30-2.10 (m, 3H), 2.00-1.70 (m, 4H), 1.42-1.30 (m, 1H), 1.18 (d, J = 6.8 Hz, 3H). LCMS (ES, m/z): 529 $[M + H]^+$ |
| 594 | 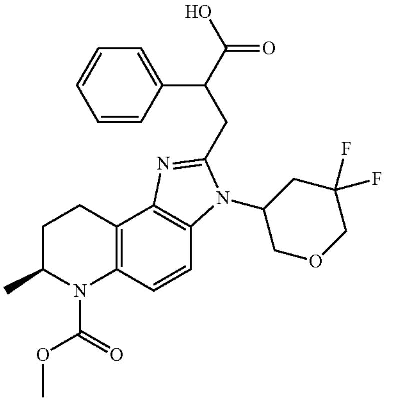 3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-phenylpropanoic acid 2nd eluting isomer | $^1$H-NMR ($CD_3OD$, 400 MHz) δ (ppm): 7.58-7.41 (m, 2H), 7.37-7.31 (m, 5H), 4.81-4.66 (m, 2H), 4.41-4.27 (m, 1H), 4.22-4.11 (m, 1H), 4.10-4.02 (m, 1H), 4.01-3.93 (m, 1H), 3.91-3.76 (m, 4H), 3.71-3.59 (m, 1H), 3.42-3.34 (m, 1H), 3.23-3.14 (m, 1H), 3.04-2.89 (m, 1H), 2.87-2.63 (m, 1H), 2.34-2.17 (m, 1H), 1.86-1.66 (m, 2H), 1.14 (d, J = 6.0 Hz, 3H). LCMS (ES, m/z): 514 $[M + H]^+$. |

TABLE 18-continued

| Example Number | Structure and Compound Name | $^1$H NMR, LCMS |
|---|---|---|
| 595 | 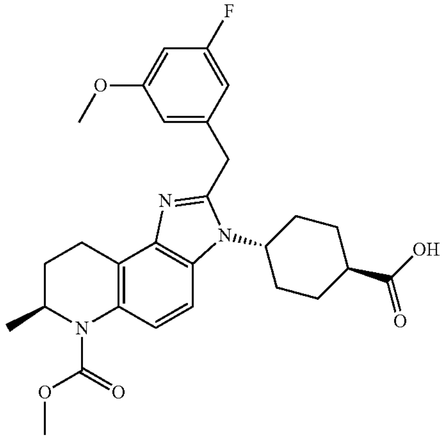 (1S,4R)-4-((S)-2-(3-fluoro-5-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.86 (s, 2H), 6.84-6.68 (m, 3H), 4.89-4.82 (m, 1H), 4.67 (s, 2H), 4.63-4.49 (m, 1H), 3.83 (s, 6H), 3.21-2.98 (m, 2H), 2.65-2.50 (m, 1H), 2.40-2.12 (m, 5H), 2.00-1.88 (m, 1H), 1.84-1.68 (m, 2H), 1.62-1.47 (m, 2H), 1.19 (d, J = 6.9 Hz, 3H). LCMS (ES, m/z): 510 $[M + H]^+$. |
| 596 | 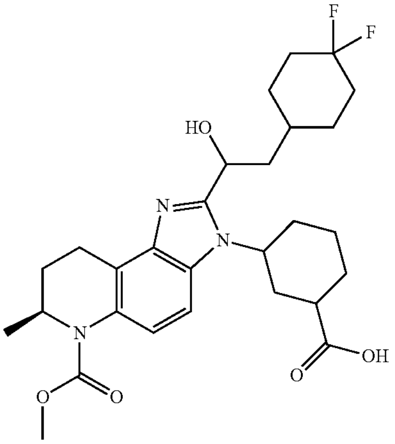 3-((7S)-2-(2-(4,4-difluorocyclohexyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.71-7.51 (m, 1H), 7.50-7.27 (m, 1H), 5.37-5.12 (m, 2H), 4.82-4.71 (m, 1H), 3.78 (s, 3H), 3.24-3.09 (m, 1H), 3.03-2.88 (m, 2H), 2.59-2.41 (m, 1H), 2.41-2.13 (m, 5H), 2.11-1.91 (m, 5H), 1.91-1.61 (m, 8H), 1.42-1.32 (m, 2H), 1.15 (d, J = 6.4 Hz, 3H). LCMS (ES, m/z): 534 $[M + H]^+$. |

TABLE 18-continued

| Example Number | Structure and Compound Name | $^1$H NMR, LCMS |
|---|---|---|
| 597 | 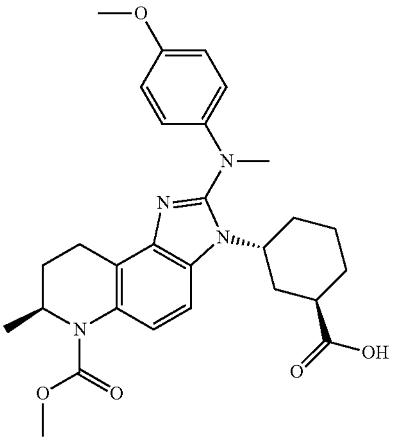 (1R,3R)-3-((S)-6-(methoxycarbonyl)-2-((4-methoxyphenyl)(methyl)amino)-7-methyl-6,7,8,9-tetrahydro-3H-imidazo[4,5-f]quinolin-3-yl)cyclohexane-1-carboxylic acid | LCMS (ES, m/z): 508 $[M + H]^+$ |
| 598 | 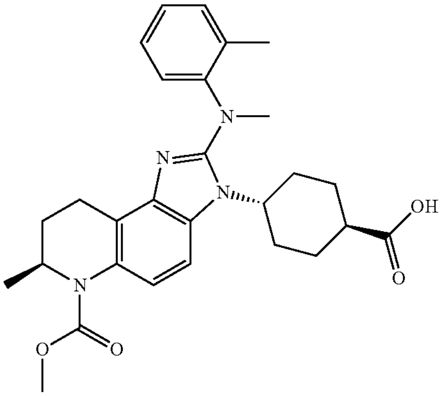 (1S,4R)-4-((S)-6-(methoxycarbonyl)-7-methyl-2-(methyl(o-tolyl)amino)-6,7,8,9-tetrahydro-3H-imidazo[4,5-f]quinolin-3-yl)cyclohexane-1-carboxylic acid | LCMS (ES, m/z): 491 $[M + H]^+$ |
| 599 | 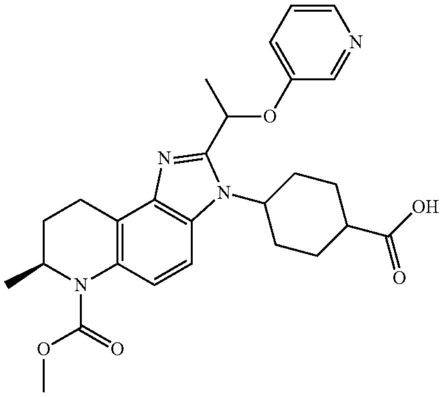 4-((7S)-6-(methoxycarbonyl)-7-methyl-2-(1-(pyridin-3-yloxy)ethyl)-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 8.35 (s, 1H), 8.16 (d, J = 4.4 Hz, 1H), 7.54-7.52 (m, 2H), 7.46-7.43 (m, 1H), 7.37-7.34 (m, 1H), 6.02-5.96 (m, 1H), 4.84-4.64 (m, 2H), 3.79 (s, 3H), 3.25-3.11 (m, 1H), 3.08-2.86 (m, 1H), 2.60-2.10 (m, 6H), 2.09-2.01 (m, 1H), 1.87 (d, J = 6.4 Hz, 3H), 1.79-1.53 (m, 4H), 1.13 (d, J = 6.8 Hz, 3H). LCMS (ES, m/z): 493 $[M + H]^+$. |

TABLE 18-continued

| Example Number | Structure and Compound Name | $^1$H NMR, LCMS |
|---|---|---|
| 600 | 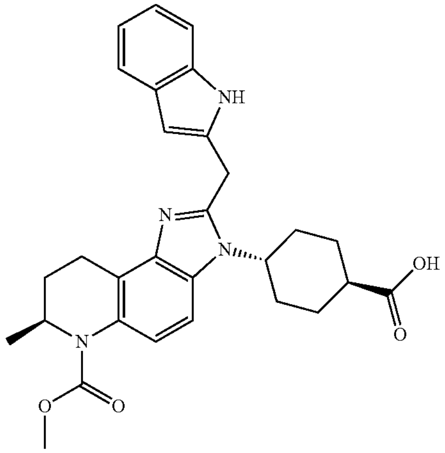 (1S,4R)-4-((S)-2-((1H-indol-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.44-7.26 (m, 4H), 7.06-6.93 (m, 2H), 6.22 (s, 1H), 4.86-4.74 (m, 1H), 4.53 (s, 2H), 4.52-4.39 (m, 1H), 3.75 (s, 3H), 3.30-2.90 (m, 2H), 2.55-1.95 (m, 6H), 1.75-1.45 (m, 5H), 1.14 (d, J = 6.6 Hz, 3H). LCMS (ES, m/z): 501 [M + H]$^+$. |
| 601 | 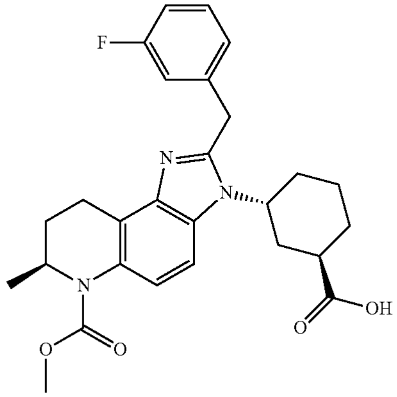 (1R,3R)-3-((S)-2-(3-fluorobenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.55-7.26 (m, 3H), 7.09-6.96 (m, 3H), 4.81-4.65 (m, 2H), 4.49-4.32 (m, 2H), 3.79 (s, 3H), 3.28-3.17 (m, 1H), 3.03-2.96 (m, 2H), 2.45-2.10 (m, 5H), 1.81-1.68 (m, 3H), 1.33-1.20 (m, 2H), 1.16 (d, J = 6.6 Hz, 3H). LCMS (ES, m/z): 480 [M + H]$^+$. |
| 602 | 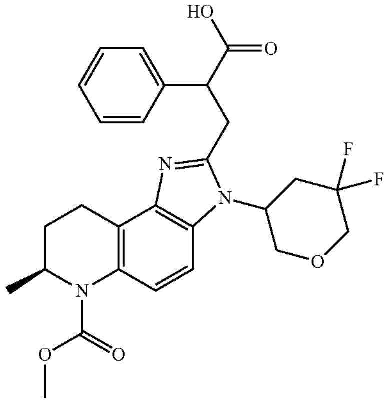 3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-phenylpropanoic acid 1$^{st}$ eluting isomer | $^1$H-NMR ($CD_3OD$, 400 MHz) δ (ppm): 7.58-7.53 (m, 1H), 7.52-7.41 (m, 1H), 7.38-7.23 (m, 5H), 4.83-4.69 (m, 2H), 4.41-4.30 (m, 1H), 4.13-3.92 (m, 2H), 3.91-3.76 (m, 4H), 3.75-3.62 (m, 1H), 3.25-3.10 (m, 3H), 3.02-2.76 (m, 2H), 2.74-2.57 (m, 1H), 2.31-2.16 (m, 1H), 1.78-1.68 (m, 1H), 1.14 (d, J = 5.6 Hz, 3H). LCMS (ES, m/z): 514 [M + H]$^+$. |

TABLE 18-continued

| Example Number | Structure and Compound Name | $^1$H NMR, LCMS |
|---|---|---|
| 603 | 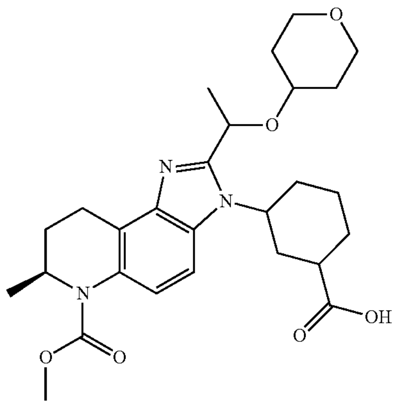 3-((7S)-6-(methoxycarbonyl)-7-methyl-2-(1-((tetrahydro-2H-pyran-4-yl)oxy)ethyl)-6,7,8,9-tetrahydro-3H-imidazo[4,5-f]quinolin-3-yl)cyclohexane-1-carboxylic acid 1st eluting isomer | $^1$H NMR (400 MHz, $CD_3OD$) δ (ppm): 7.57 (d, J = 8.8 Hz, 1H), 7.45 (d, J = 8.8 Hz, 1H), 5.17-5.08 (m, 2H), 4.77-4.74 (m, 1H), 3.95-3.89 (m, 2H), 3.79 (s, 3H), 3.71-3.68 (m, 1H), 3.48-3.39 (m, 2H), 3.20-3.18 (m, 1H), 3.02-3.00 (m, 1H), 2.94-2.90 (m, 1H), 2.57-2.55 (m, 1H), 2.40-2.24 (m, 4H), 1.97-1.90 (m, 4H), 1.76-1.62 (m, 8H), 1.15 (d, J = 6.8 Hz, 3H). LCMS (ES, m/z): 500 [M + H]$^+$ |
| 604 | 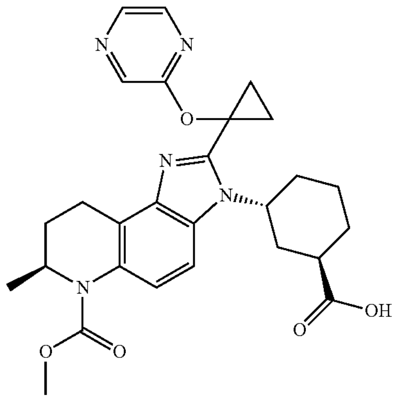 (1R,3R)-3-((S)-6-(methoxycarbonyl)-7-methyl-2-(1-(pyrazin-2-yloxy)cyclopropyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.53-8.46 (m, 1H), 8.18-8.09 (m, 2H), 7.50 (d, J = 9.2 Hz, 1H), 7.40 (d, J = 9.2 Hz, 1H), 5.46-5.36 (m, 1H), 4.79-4.70 (m, 1H), 3.77 (s, 3H), 3.28-3.18 (m, 1H), 3.00 (s, 1H), 2.96-2.87 (m, 1H), 2.53-2.41 (m, 1H), 2.32-2.19 (m, 4H), 1.87 (s, 1H), 1.80-1.60 (m, 7H), 1.58-1.47 (m, 1H), 1.13 (d, J = 6.4 Hz, 3H). LCMS (ES, m/z): 506 [M + H]$^+$. |
| 605 | 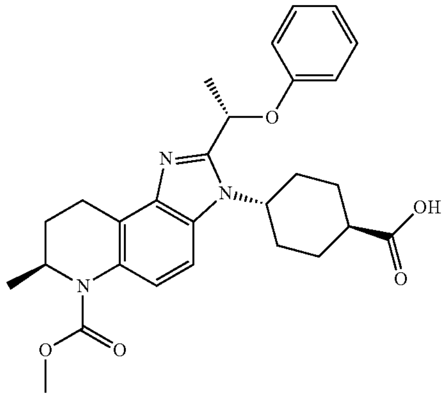 (1S,4R)-4-((S)-6-(methoxycarbonyl)-7-methyl-2-((S)-1-phenoxyethyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.51-7.38 (m, 2H), 7.30-7.21 (m, 2H), 7.02 (d, J = 7.5 Hz, 2H), 6.95-6.80 (m, 1H), 5.88-5.70 (m, 1H), 4.85-4.70 (m, 2H), 3.78 (s, 3H), 3.23-3.10 (m, 1H), 3.00-2.85 (m, 1H), 2.55-2.30 (m, 2H), 2.30-2.15 (m, 3H), 2.19-2.03 (m, 1H), 2.03-1.97 (d, J = 12.9 Hz, 1H), 1.84 (d, J = 6.9 Hz, 3H), 1.80-1.76 (m, 1H), 1.70-1.50 (m, 3H), 1.13 (d, J = 6.3 Hz, 3H). LCMS (ES, m/z): 492 [M + H]$^+$. |

TABLE 18-continued

| Example Number | Structure and Compound Name | $^1$H NMR, LCMS |
|---|---|---|
| 606 | 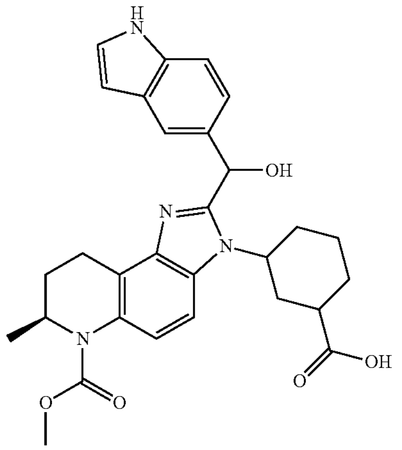 3-((7S)-2-(hydroxy(1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.74 (s, 1H), 7.66-7.53 (m, 2H), 7.42 (d, J = 8.4 Hz, 1H), 7.29 (d, J = 3.2 Hz, 1H), 7.13 (d, J = 8.8 Hz, 1H), 6.51-6.45 (m, 2H), 4.83-4.67 (m, 2H), 3.80 (s, 3H), 3.31-3.22 (m, 1H), 3.11-3.00 (m, 1H), 2.36-1.78 (m, 7H), 1.62-1.54 (m, 1H), 1.39-1.25 (m, 3H), 1.19 (d, J = 6.8 Hz, 3H). LCMS (ES, m/z): 517 [M + H]$^+$. |
| 607 | 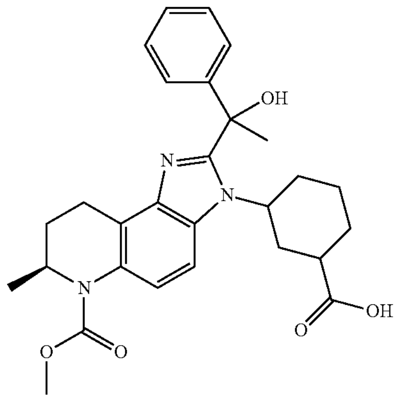 3-((7S)-2-(1-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.49-7.20 (m, 7H), 4.85-4.71 (m, 2H), 3.78 (s, 3H), 3.43-3.33 (m, 1H), 3.04-2.92 (m, 1H), 2.91-2.80 (m, 1H), 2.41-2.25 (m, 3H), 2.10-1.99 (m, 4H), 1.97-1.82 (m, 1H), 1.75-1.62 (m, 1H), 1.55-1.35 (m, 2H), 1.16 (d, J = 6.4 Hz, 3H), 1.11-0.95 (m, 1H), 0.78-0.62 (m, 1H). LCMS (ES, m/z): 492 [M + H]$^+$. |

TABLE 18-continued

| Example Number | Structure and Compound Name | $^1$H NMR, LCMS |
|---|---|---|
| 608 | 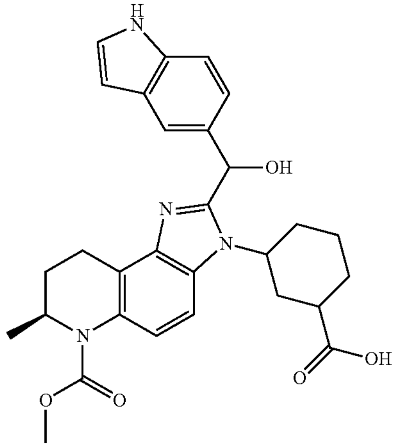 3-((7S)-2-(hydroxy(1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.86-7.69 (m, 3H), 7.48 (d, J = 8.4 Hz, 1H), 7.32 (d, J = 3.2 Hz, 1H), 7.17 (d, J = 7.6 Hz, 1H), 6.52-6.49 (m, 2H), 4.88-4.86 (m, 1H), 4.76-4.59 (m, 1H), 3.82 (s, 3H), 3.31-3.24 (m, 1H), 3.15-3.01 (m, 1H), 2.35-2.21 (m, 1H), 2.23-2.06 (m, 2H), 2.06-1.85 (m, 4H), 1.73-1.69 (m, 1H), 1.48-1.40 (m, 2H), 1.27-1.22 (m, 1H), 1.21 (d, J = 6.8 Hz, 3H). LCMS (ES, m/z): 517 [M + H]$^+$. |
| 609 | 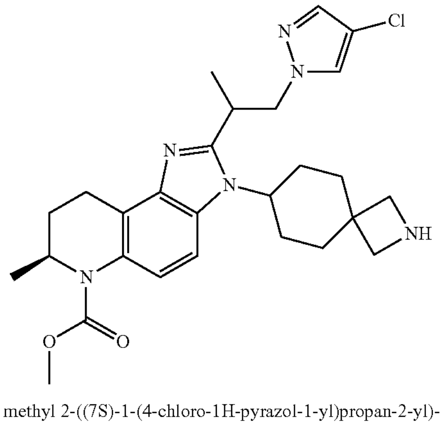 methyl 2-((7S)-1-(4-chloro-1H-pyrazol-1-yl)propan-2-yl)-7-methyl-3-(2-azaspiro[3.5]nonan-7-yl)-3,7,8,9-tetrahydro-6H-imidazo[4,5-f]quinoline-6-carboxylate 2$^{nd}$ eluting isomer | $^1$H-NMR (DMSO, 400 MHz) δ (ppm): 7.95 (s, 1H), 7.55 (s, 1H), 7.31-7.15 (m, 2H), 4.62-455 (m, 1H), 4.54-4.35 (m, 2H), 4.30-4.15 (m, 1H), 3.85-3.70 (m, 2H), 3.65 (s, 3H), 3.45-3.35 (m, 2H), 3.35-3.25 (m, 2H), 3.12-3.01 (m, 1H), 2.85-2.75 (m, 1H), 2.20-2.01 (m, 4H), 2.00-1.91 (m, 1H), 1.75-1.50 (m, 4H), 1.48-1.32 (m, 1H), 1.18 (d, J = 6.8 Hz, 3H), 1.06 (d, J = 6.8 Hz, 3H). LCMS (ES, m/z): 511 [M + H]$^+$. |

TABLE 18-continued

| Example Number | Structure and Compound Name | $^1$H NMR, LCMS |
| --- | --- | --- |
| 610 | 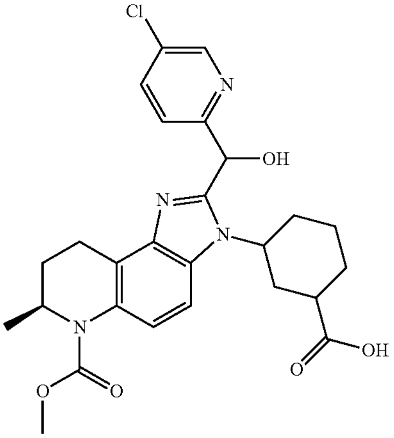 3-((7S)-2-((5-chloropyridin-2-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 8.45 (s, 1H), 8.00-7.97 (m, 1H), 7.89-7.87 (m, 1H), 7.82-7.45 (m, 2H), 6.46 (s, 1H), 5.11-5.05 (m, 1H), 4.87-4.83 (m, 1H), 3.82 (s, 3H), 3.18-3.12 (m, 1H), 3.03-2.94 (m, 2H), 2.45-2.11 (m, 5H), 1.94-1.73 (m, 4H), 1.52-1.48 (m, 1H), 1.18 (d, J = 6.8 Hz, 3H). LCMS (ES, m/z): 513 [M + H]$^+$. |
| 611 | 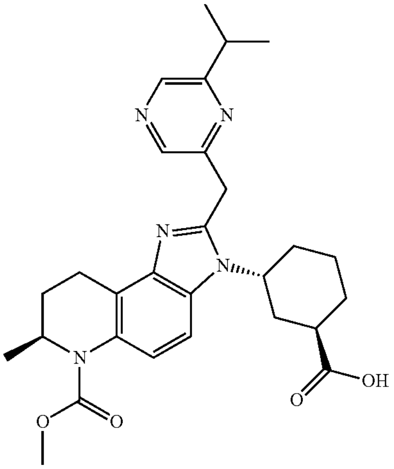 (1R,3R)-3-((S)-2-((6-isopropylpyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.68 (s, 1H), 8.51 (s, 1H), 7.97-7.86 (m, 2H), 5.5.11-4.85 (m, 4H), 3.84 (s, 3H), 3.13-2.97 (m, 4H), 2.50-2.35 (m, 2H), 2.33-2.17 (m, 3H), 1.97-1.76 (m, 4H), 1.52-1.38 (m, 1H), 1.22-1.13 (m, 9H). LCMS (ES, m/z): 506 [M + H]$^+$. |

TABLE 18-continued

| Example Number | Structure and Compound Name | $^1$H NMR, LCMS |
|---|---|---|
| 612 | 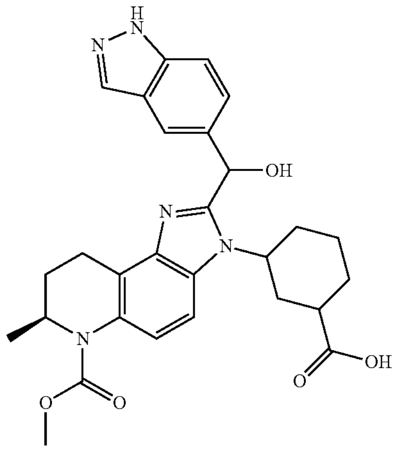 3-((7S)-2-(hydroxy(1H-indazol-5-yl)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 8.05 (s, 1H), 8.01 (s, 1H), 7.51-7.46 (m, 2H), 7.42-7.38 (m, 2H), 6.37 (s, 1H), 5.00-4.98 (m, 1H), 4.80-4.75 (m, 1H), 3.78 (s, 3H), 3.27-3.20 (m, 1H), 3.02-2.98 (m, 1H), 2.89-2.84 (m, 1H), 2.38-2.36 (m, 2H), 2.31-2.25 (m, 1H), 2.11-1.97 (m, 2H), 1.79-1.76 (m, 1H), 1.56-1.41 (m, 2H), 1.20-1.16 (m, 1H), 1.15 (d, J = 6.8 Hz, 3H), 0.99-0.96 (m, 1H). LCMS (ES, m/z): 518 [M + H]$^+$. |
| 613 | 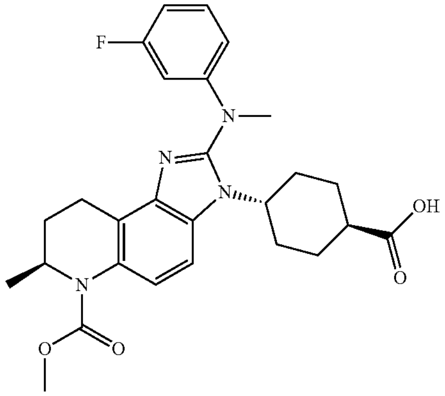 (1S,4R)-4-((S)-2-((3-fluorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 495 [M + H]$^+$ |
| 614 | 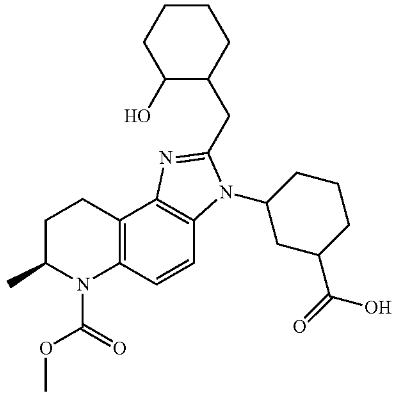 3-((7S)-2-((2-hydroxycyclohexyl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H NMR (400 MHz, $CD_3OD$) δ (ppm): 7.55 (d, J = 8.8 Hz, 1H), 7.41 (d, J = 8.8 Hz, 1H), 4.83-4.76 (m, 2H), 3.79 (s, 3H), 3.53-3.48 (m, 1H), 3.23-3.17 (m, 1H), 3.15-3.14 (m, 1H), 2.99-2.89 (m, 1H), 2.79-2.73 (m, 1H), 2.46-2.41 (m, 2H), 2.39-2.24 (m, 3H), 2.01-1.99 (m, 1H), 1.93-1.91 (m, 2H), 1.77-1.59 (m, 7H), 1.34-1.30 (m, 2H), 1.21-1.14 (m, 6H). LCMS (ES, m/z): 484 [M + H]$^+$ |

TABLE 18-continued

| Example Number | Structure and Compound Name | $^1H$ NMR, LCMS |
|---|---|---|
| 615 | 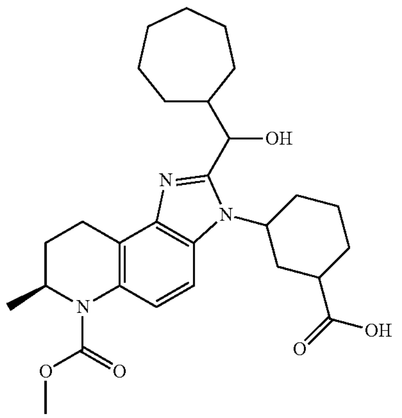 3-((7S)-2-(cycloheptyl(hydroxy)methyl)-6-(methoxycarbonyl)-7-methyl-6,7,8,9-tetrahydro-3H-imidazo[4,5-f]quinolin-3-yl)cyclohexane-1-carboxylic acid $2^{nd}$ eluting isomer | $^1H$-NMR ($CD_3OD$, 400 MHz) δ (ppm): 7.65-7.48 (m, 1H), 7.48-7.22 (m, 1H), 5.13-4.94 (m, 1H), 4.82-4.67 (m, 2H), 3.78 (s, 3H), 3.29-3.12 (m, 1H), 3.08-2.82 (m, 2H), 2.61-2.19 (m, 6H), 2.19-2.01 (m, 1H), 2.01-1.82 (m, 2H), 1.82-1.46 (m, 12H), 1.42-1.32 (m, 2H), 1.15 (d, J = 6.4 Hz, 3H). LCMS (ES, m/z): 498 $[M + H]^+$. |
| 616 | 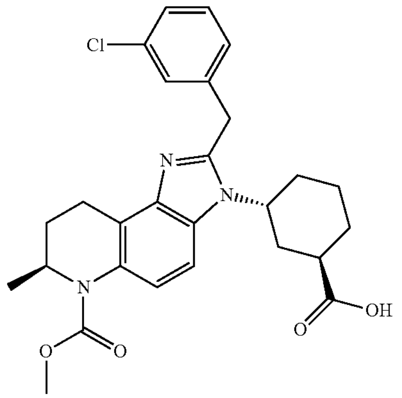 (1R,3R)-3-((S)-2-(3-chlorobenzyl)-6-(methoxycarbonyl)-7-methyl-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 7.48-7.45 (m, 1H), 7.40-7.38 (m, 1H), 7.30-7.23 (m, 3H), 7.18-7.17 (m, 1H), 4.77-4.68 (m, 2H), 4.44-4.40 (m, 1H), 4.33-4.29 (m, 1H), 3.76 (s, 3H), 3.19-3.15 (m, 1H), 2.98-2.94 (m, 2H), 2.33-2.13 (m, 5H), 1.76-1.64 (m, 3H), 1.24-1.23 (m, 2H), 1.13 (d, J = 6.8 Hz, 3H). LCMS (ES, m/z): 496 $[M + H]^+$. |
| 617 | 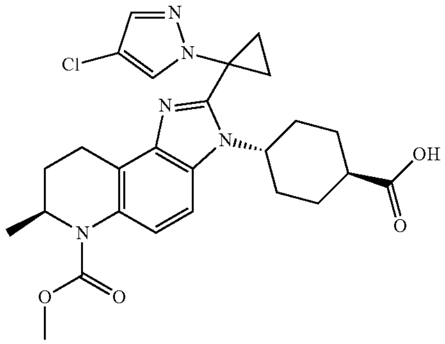 (1S,4R)-4-((S)-2-(1-(4-chloro-1H-pyrazol-1-yl)cyclopropyl)-6-(methoxycarbonyl)-7-methyl-6,7,8,9-tetrahydro-3H-imidazo[4,5-f]quinolin-3-yl)cyclohexane-1-carboxylic acid | $^1H$-NMR ($CD_3OD$, 300 MHz) δ (ppm): 7.93 (s, 1H), 7.56-7.33 (m, 3H), 5.22-5.03 (m, 1H), 4.81-4.65 (m, 1H), 3.76 (s, 3H), 3.26-3.07 (m, 1H), 3.02-2.87 (m, 1H), 2.56-2.37 (m, 1H), 2.37-2.07 (m, 5H), 1.96-1.86 (m, 2H), 1.78-1.52 (m, 7H), 1.11 (d, J = 6.9 Hz, 3H). LCMS (ES, m/z): 512 $[M + H]^+$ |

TABLE 18-continued

| Example Number | Structure and Compound Name | $^1$H NMR, LCMS |
|---|---|---|
| 618 | 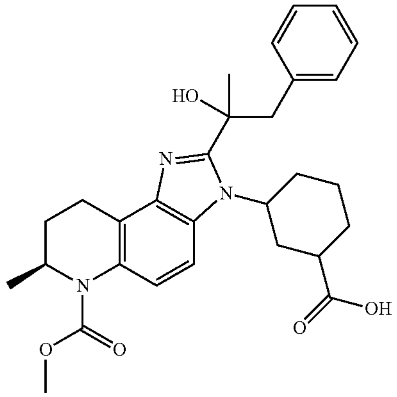 3-((7S)-2-(2-hydroxy-1-phenylpropan-2-yl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.60 (d, J = 8.8 Hz, 1H), 7.40 (d, J = 9.2 Hz, 1H), 7.24-7.15 (m, 3H), 7.22-7.16 (m, 2H), 5.85-5.77 (m, 1H), 4.78-7.65 (m, 1H), 3.79 (s, 3H), 3.45-3.33 (m, 2H), 3.22-3.01 (m, 2H), 2.88-2.64 (m, 2H), 2.57-2.49 (m, 1H), 2.45-2.20 (m, 3H), 2.11-2.01 (m, 1H), 1.82-1.78 (m, 3H), 1.75 (s, 3H), 1.74-1.65 (m, 1H), 1.15 (d, J = 6.8 Hz, 3H). LCMS (ES, m/z): 506 [M + H]+. |
| 619 | 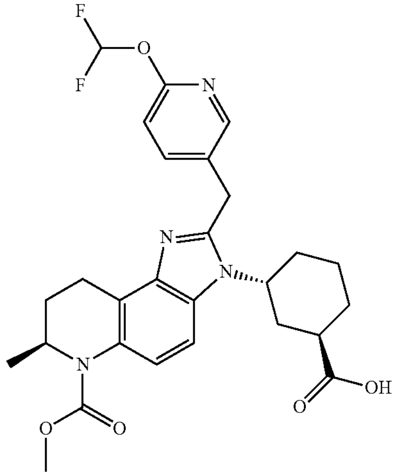 (1R,3R)-3-((S)-2-((6-(difluoromethoxy)pyridin-3-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.18 (s, 1H), 7.79-7.65 (m, 1H), 7.57-7.30 (m, 3H), 6.93 (d, J = 8.0 Hz, 1H), 4.84-4.66 (m, 2H), 4.44-4.36 (m, 2H), 3.79 (s, 3H), 3.28-3.12 (m, 1H), 3.05-2.91 (m, 2H), 2.43-2.10 (m, 5H), 1.84-1.65 (m, 3H), 1.56-1.30 (m, 2H), 1.15 (d, J = 6.4 Hz, 1H). LCMS (ES, m/z): 529 [M + H]$^+$. |

TABLE 18-continued

| Example Number | Structure and Compound Name | $^1H$ NMR, LCMS |
|---|---|---|
| 620 | 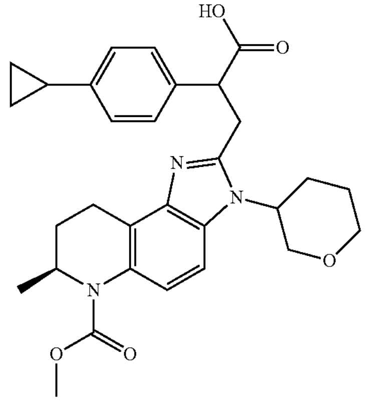 2-(4-cyclopropylphenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1H$-NMR ($CD_3OD$, 400 MHz) δ (ppm): 7.49 (d, J = 9.2 Hz, 1H), 7.38 (d, J = 9.2 Hz, 1H), 7.17 (d, J = 8.0 Hz, 2) 7.00 (d, J = 8.0 Hz, 2H), 4.74-4.73 (m, 1H), 4.42-4.35 (m, 1H), 4.42-4.23 (m, 1H), 3.94-3.87 (m, 2H), 3.76 (s, 3H), 3.73-3.50 (m, 2H), 3.35-3.30 (m, 1H), 3.29-3.03 (m, 2H), 2.93-2.88 (m, 1H), 2.52-2.31 (m, 1H), 2.30-2.19 (m, 1H), 2.14-2.01 (m, 1H), 1.98-1.80 (m, 3H), 1.80-1.70 (m, 1H), 1.11 (d, J = 6.8 Hz, 3H), 0.92-0.89 (m, 2H), 0.65-0.61 (m, 2H). LCMS (ES, m/z): 518 $[M + H]^+$. |
| 621 | 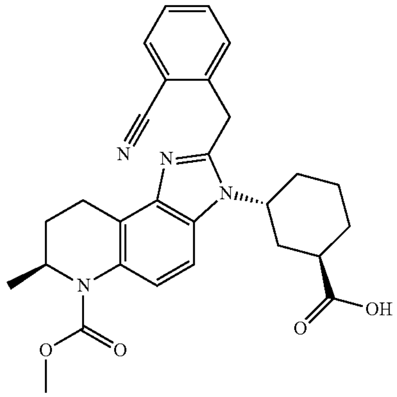 (1R,3R)-3-((S)-2-(2-cyanobenzyl)-6-(methoxycarbonyl)-7-methyl-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 7.79 (d, J = 7.6 Hz, 1H), 7.64-7.43 (m, 4H), 7.15-7.13 (m, 1H), 4.83-4.61 (m, 4H), 3.79 (s, 3H), 3.28-2.92 (m, 3H), 2.41-2.17 (m, 5H), 1.79-1.66 (m, 4H), 1.47-1.37 (m, 1H), 1.16 (d, J = 6.0 Hz, 3H). LCMS (ES, m/z): 487 $[M + H]^+$. |
| 622 | 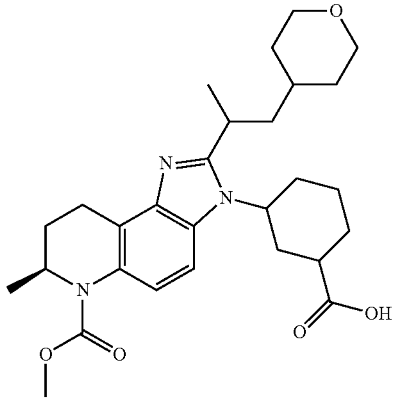 3-((7S)-6-(methoxycarbonyl)-7-methyl-2-(1-(tetrahydro-2H-pyran-4-yl)propan-2-yl)-6,7,8,9-tetrahydro-3H-imidazo[4,5-f]quinolin-3-yl)cyclohexane-1-carboxylic acid 2nd eluting isomer | $^1H$-NMR ($CD_3OD$, 400 MHz) δ (ppm): 7.65-7.58 (m, 1H), 7.48-7.42 (m, 1H), 4.81-4.70 (m, 1H), 3.96-3.86 (m, 2H), 3.79 (s, 3H), 3.55-3.43 (m, 1H), 3.43-3.35 (m, 2H), 3.28-3.13 (m, 1H), 3.13-2.99 (m, 2H), 2.99-2.84 (m, 1H), 2.56-2.38 (m, 2H), 2.33-2.16 (m, 3H), 2.02-1.86 (m, 3H), 1.86-1.53 (m, 7H), 1.48 (d, J = 6.8 Hz, 3H), 1.40-1.20 (m, 2H), 1.15 (d, J = 6.4 Hz, 3H). LCMS (ES, m/z): 498 $[M + H]^+$. |

TABLE 18-continued

| Example Number | Structure and Compound Name | $^1$H NMR, LCMS |
|---|---|---|
| 623 | 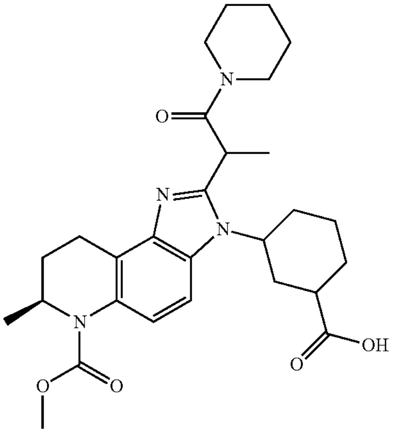 3-((7S)-6-(methoxycarbonyl)-7-methyl-2-(1-oxo-1-(piperidin-1-yl)propan-2-yl)-6,7,8,9-tetrahydro-3H-imidazo[4,5-f]quinolin-3-yl)cyclohexane-1-carboxylic acid 1st eluting isomer | $^1$H NMR (400 MHz, $CD_3OD$) δ (ppm): 7.51 (d, J = 8.8 Hz, 1H), 7.39 (d, J = 9.2 Hz, 1H), 4.77-4.72 (m, 1H), 4.59-4.52 (m, 2H), 3.78 (s, 3H), 3.63-3.56 (m, 4H), 3.25-3.23 (m, 1H), 3.02-2.99 (m, 1H), 2.94-2.90 (m, 1H), 2.50-2.48 (m, 1H), 2.33-2.24 (m, 4H), 1.92-1.85 (m, 2H), 1.77-1.74 (m, 7H), 1.72-1.55 (m, 5H), 1.14 (d, J = 6.4 Hz, 3H). LCMS (ES, m/z): 511 $[M + H]^+$ |
| 624 | 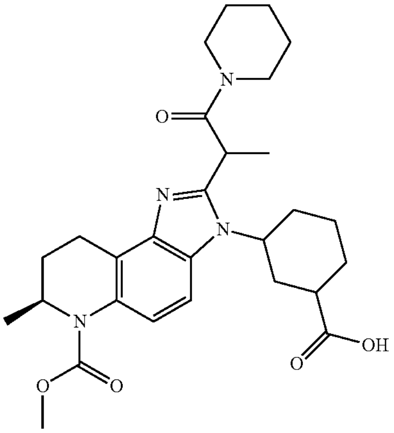 3-((7S)-6-(methoxycarbonyl)-7-methyl-2-(1-oxo-1-(piperidin-1-yl)propan-2-yl)-6,7,8,9-tetrahydro-3H-imidazo[4,5-f]quinolin-3-yl)cyclohexane-1-carboxylic acid 2nd eluting isomer | $^1$H NMR (400 MHz, $CD_3OD$) δ (ppm): 7.52 (d, J = 8.8 Hz, 1H), 7.39 (d, J = 9.2 Hz, 1H), 4.83-4.72 (m, 2H), 4.56-4.52 (m, 1H), 3.79 (s, 3H), 3.68-3.60 (m, 1H), 3.56-3.45 (m, 3H), 3.23-3.17 (m, 1H), 3.01-2.98 (m, 1H), 2.95-2.89 (m, 1H), 2.50-2.48 (m, 1H), 2.36-2.24 (m, 4H), 1.89-1.86 (m, 2H), 1.77-1.44 (m, 11H), 1.28-1.23 (m, 1H), 1.14 (d, J = 6.8 Hz, 3H). LCMS (ES, m/z): 511 $[M + H]^+$ |

TABLE 18-continued

| Example Number | Structure and Compound Name | $^1H$ NMR, LCMS |
|---|---|---|
| 625 | 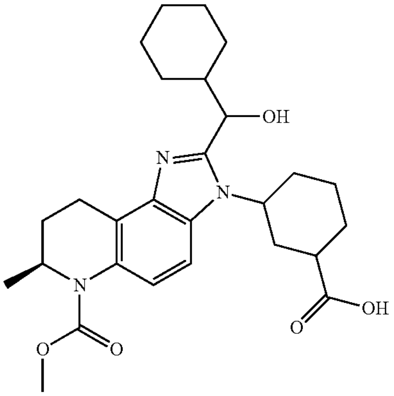 3-((7S)-2-(cyclohexyl(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1H$-NMR ($CD_3OD$, 400 MHz) δ (ppm): 7.60-7.53 (m, 1H), 7.45-7.39 (m, 1H), 5.07-4.97 (m, 1H), 4.80-4.69 (m, 2H), 3.79 (s, 3H), 3.27-3.15 (m, 1H), 3.01-2.86 (m, 2H), 2.53-2.13 (m, 6H), 2.08-2.00 (m, 1H), 1.96-1.80 (m, 3H), 1.80-1.73 (m, 5H), 1.35-1.22 (m, 4H), 1.21-1.12 (m, 5H). LCMS (ES, m/z): 484 $[M + H]^+$. |
| 626 | 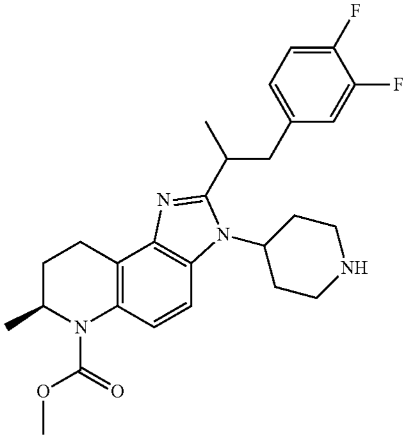 methyl (7S)-2-(1-(3,4-difluorophenyl)propan-2-yl)-7-methyl-3-(piperidin-4-yl)-3,7,8,9-tetrahydro-6H-imidazo[4,5-f]quinoline-6-carboxylate 1st eluting isomer | $^1H$-NMR ($CD_3OD$, 400 MHz) δ (ppm): 7.49 (d, J = 9.2 Hz, 1H), 7.35 (d, J = 8.8 Hz, 1H), 7.15-7.00 (m, 2H), 6.90-6.81 (m, 1H), 4.79-4.65 (m, 1H), 4.49-4.31 (m, 1H), 3.79 (s, 3H), 3.69-3.57 (m, 1H), 3.33-3.05 (m, 5H), 3.00-2.88 (m, 1H), 2.88-2.75 (m, 1H), 2.76-2.65 (m, 1H), 2.48-2.23 (m, 3H), 1.81-1.65 (m, 2H), 1.51 (d, J = 6.8 Hz, 3H), 1.15 (d, J = 6.4 Hz, 3H), 1.10-0.96 (m, 1H). LCMS (ES, m/z): 483 $[M + H]^+$. |
| 627 | 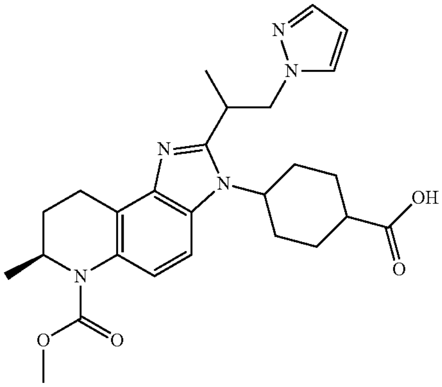 4-((7S)-2-(1-(1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 7.84-7.74 (m, 2H), 7.64 (d, J = 2.0 Hz, 1H), 7.41 (s, 1H), 6.28-6.26 (m, 1H), 4.78-4.63 (m, 2H), 4.61-4.41 (m, 1H), 4.41-4.26 (m, 1H), 3.81 (s, 3H), 3.20-2.99 (m, 2H), 2.63-2.46 (m, 1H), 2.42-2.11 (m, 5H), 2.08-1.94 (m, 1H), 1.94-1.82 (m, 1H), 1.82-1.68 (m, 1H), 1.68-1.42 (m, 5H), 1.32-1.21 (m, 1H), 1.16 (d, J = 6.8 Hz, 3H). LCMS: (ES, m/z): 480 $[M + H]^+$. |

TABLE 18-continued

| Example Number | Structure and Compound Name | $^1$H NMR, LCMS |
|---|---|---|
| 628 | 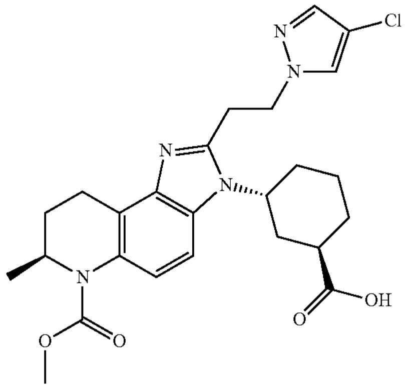 (1R,3R)-3-((S)-2-(2-(4-chloro-1H-pyrazol-1-yl)ethyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.95-7.81 (m, 3H), 7.39 (s, 1H), 4.87-4.67 (m, 3H), 3.86-3.71 (m, 5H), 3.12-2.91 (m, 3H), 2.53-2.36 (m, 3H), 2.36-2.15 (m, 2H), 2.01-1.79 (m, 4H), 1.69-1.51 (m, 1H), 1.17 (d, J = 6.9 Hz, 3H). LCMS (ES, m/z): 500 [M + H]$^+$. |
| 629 | 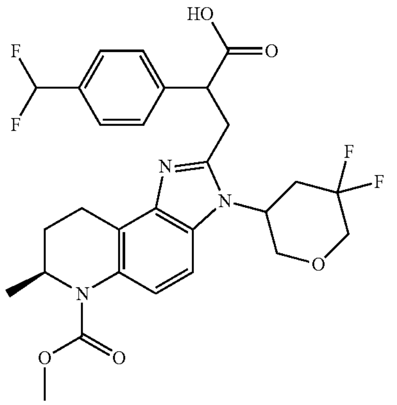 2-(4-(difluoromethyl)phenyl)-3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)propanoic acid 3$^{rd}$ eluting isomer | $^1$H-NMR ($CD_3OD$, 400 MHz) δ (ppm): 7.56-7.45 (m, 5H), 7.40 (d, J = 9.2 Hz, 1H), 6.91-6.53 (m, 1H), 4.86-4.68 (m, 2H), 4.40-4.27 (m, 1H), 4.19-4.04 (m, 2H), 4.03-3.92 (m, 1H), 3.91-3.80 (m, 1H), 3.79 (s, 3H), 3.73-3.61 (m, 1H), 3.31-3.27 (m, 1H), 3.23-3.11 (m, 1H), 2.99-2.89 (m, 1H), 2.87-2.71 (m, 1H), 2.32-2.18 (m, 1H), 1.90-1.78 (m, 1H), 1.77-1.66 (m, 1H), 1.13 (d, J = 6.8 Hz, 3H). LCMS (ES, m/z): 564 [M + H]$^+$. |
| 630 | 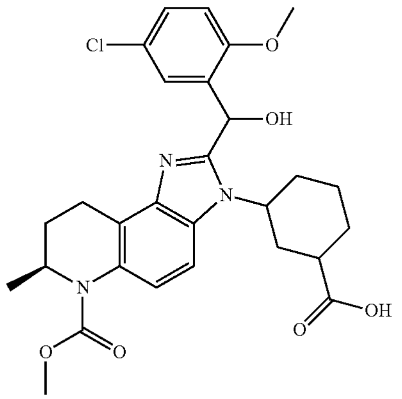 3-((7S)-2-((5-chloro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.86-7.73 (m, 1H), 7.58-7.48 (m, 1H), 7.48-7.34 (m, 1H), 7.34-7.23 (m, 1H), 6.99-6.84 (m, 1H), 6.37 (s, 1H), 5.08-4.92 (m, 1H), 4.81-4.61 (m, 1H), 3.78 (s, 3H), 3.64 (s, 3H), 3.27-3.04 (m, 1H), 3.01-2.93 (m, 1H), 2.93-2.82 (m, 1H), 2.59-2.39 (m, 1H), 2.39-2.28 (m, 1H), 2.28-2.07 (m, 3H), 1.85-1.60 (m, 3H), 1.59-1.38 (m, 2H), 1.14 (d, J = 6.8 Hz, 3H). LCMS (ES, m/z): 542 [M + H]$^+$ |

TABLE 18-continued

| Example Number | Structure and Compound Name | $^1$H NMR, LCMS |
|---|---|---|
| 631 | 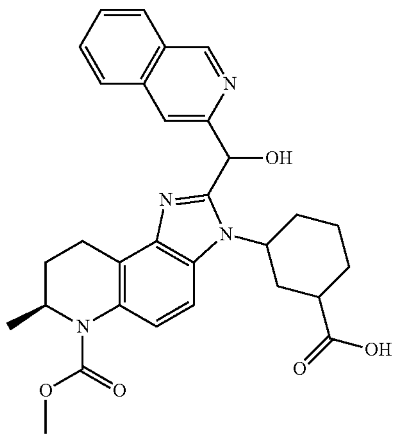 3-((7S)-2-(hydroxy(isoquinolin-3-yl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 9.17 (s, 1H), 8.26-8.02 (m, 3H), 7.82-7.50 (m, 4H), 6.51 (s, 1H), 5.08-4.75 (m, 2H), 3.78 (s, 3H), 3.33-3.15 (m, 1H), 2.99-2.77 (m, 2H), 2.45-2.02 (m, 5H), 1.75-1.48 (m, 3H), 1.15 (d, J = 6.4 Hz, 3H), 1.12-1.07 (m, 2H). LCMS (ES, m/z): 529 $[M + H]^+$. |
| 632 | 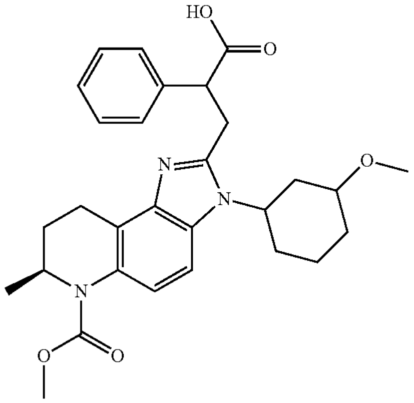 3-((7S)-6-(methoxycarbonyl)-3-(3-methoxycyclohexyl)-7-methyl-6,7,8,9-tetrahydro-3H-imidazo[4,5-f]quinolin-2-yl)-2-phenylpropanoic acid 3rd eluting isomer | $^1$H-NMR ($CD_3OD$, 400 MHz) δ (ppm): 7.51-7.47 (m, 1H), 7.42-7.38 (m, 3H), 7.34-7.25 (m, 3H), 4.79-4.71 (m, 2H), 4.32-4.30 (m, 1H), 3.76 (s, 3H), 3.75-3.67 (m, 2H), 3.40 (s, 3H), 3.27-3.22 (m, 1H), 3.14-3.12 (m, 1H), 2.90-2.86 (m, 1H), 2.37-2.21 (m, 3H), 2.09-2.05 (m, 1H), 1.96-1.86 (m, 3H), 1.75-1.69 (m, 2H), 1.54-1.50 (m, 1H), 1.12 (d, J = 6.8 Hz, 3H). LCMS (ES, m/z): 506 [M + H]+. |
| 633 | 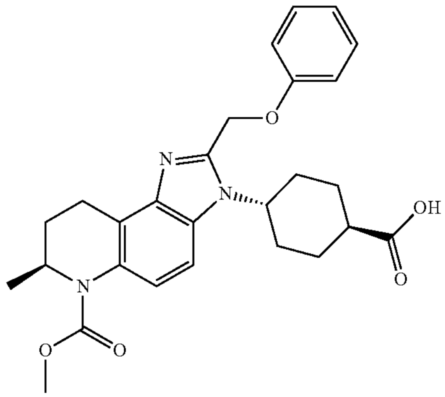 (1S,4R)-4-((S)-6-(methoxycarbonyl)-7-methyl-2-(phenoxymethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.59-7.45 (m, 2H), 7.39-7.29 (m, 2H), 7.10 (m, 2H), 7.02 (m, 1H), 5.42 (s, 2H), 4.78 (m, 1H), 4.51 (m, 1H), 3.79 (s, 3H), 3.19 (m, 1H), 2.97 (m, 1H), 2.55-2.44 (m, 1H), 2.43-2.20 (m, 5H), 2.03 (m, 2H), 1.77 (m, 1H), 1.62 (m, 2H), 1.15 (d, J = 6.4 Hz, 3H). LCMS (ES, m/z): 478 $[M + H]^+$. |

TABLE 18-continued

| Example Number | Structure and Compound Name | $^1$H NMR, LCMS |
|---|---|---|
| 634 | 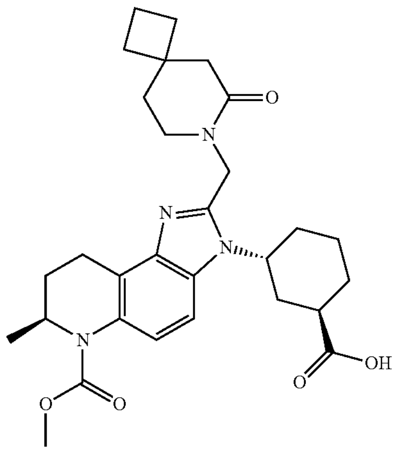 (1R,3R)-3-((S)-6-(methoxycarbonyl)-7-methyl-2-((6-oxo-7-azaspiro[3.5]nonan-7-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.55 (d, J = 9.2 Hz, 1H), 7.44 (d, J = 8.8 Hz, 1H), 5.22-5.03 (m, 1H), 4.82-4.64 (m, 3H), 3.79 (s, 3H), 3.31-3.26 (m, 2H), 3.25-3.11 (m, 1H), 3.01-2.87 (m, 2H), 2.73-2.59 (m, 1H), 2.55-2.40 (m, 2H), 2.32-2.19 (m, 4H), 2.02-1.89 (m, 6H), 1.88-1.78 (m, 4H), 1.77-1.56 (m, 3H), 1.15 (d, J = 6.8 Hz, 3H). LCMS (ES, m/z): 523 [M + H]$^+$. |
| 635 | 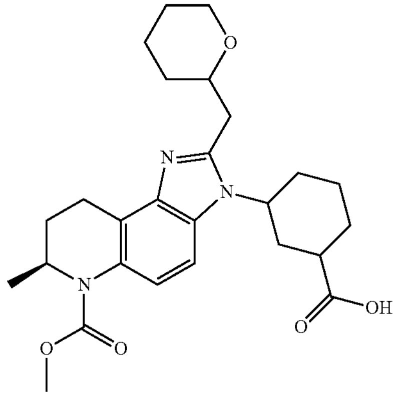 3-((7S)-6-(methoxycarbonyl)-7-methyl-2-((tetrahydro-2H-pyran-2-yl)methyl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.92-7.81 (m, 2H), 5.13-5.02 (m, 1H), 4.89-4.81 (m, 1H), 3.96-3.88 (m, 2H), 3.83 (s, 3H), 3.52-3.35 (m, 2H), 3.32-3.25 (m, 1H), 3.15-2.90 (m, 3H), 2.52-2.45 (m, 2H), 2.38-2.26 (m, 3H), 2.24-2.06 (m, 1H), 2.00-1.80 (m, 5H), 1.72-1.45 (m, 5H), 1.18 (d, J = 6.8 Hz, 3H). LCMS (ES, m/z): 470 [M + H]$^+$. |

TABLE 18-continued

| Example Number | Structure and Compound Name | $^1$H NMR, LCMS |
|---|---|---|
| 636 | 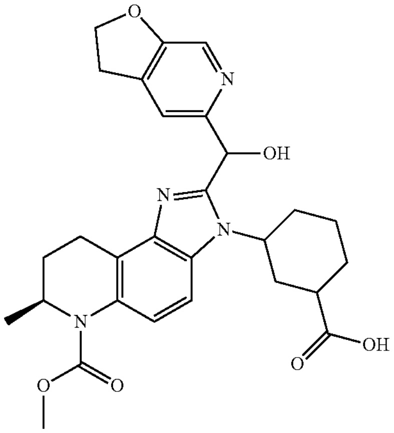 3-((7S)-2-((2,3-dihydrofuro[2,3-c]pyridin-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.89 (s, 1H), 7.62-7.62 (m, 1H), 7.62-7.52 (m, 1H), 7.47-7.45 (m, 1H), 6.22 (s, 1H), 4.92-4.90 (m, 1H), 4.82-4.72 (m, 1H), 4.70-4.45 (m, 2H), 3.79 (s, 3H), 3.43-3.34 (m, 1H), 3.34-3.17 (m, 2H), 3.02-2.92 (m, 2H), 2.51-2.32 (m, 1H), 2.30-2.09 (m, 3H), 2.01-1.97 (m, 1H), 1.82-1.78 (m, 3H), 1.72-1.40 (m, 2H), 1.16 (d, J = 6.8 Hz, 3H). LCMS (ES, m/z): 521 [M + H]$^+$. |
| 637 | 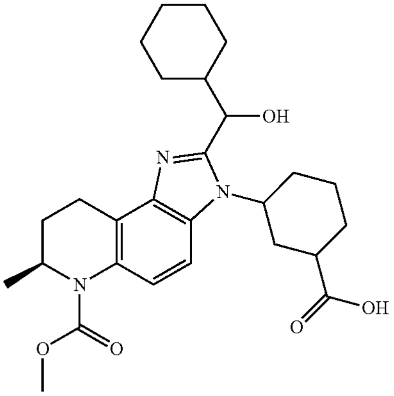 3-((7S)-2-(cyclohexyl(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.58-7.51 (m, 1H), 7.44-7.37 (m, 1H), 5.23-5.16 (m, 1H), 4.80-4.72 (m, 1H), 4.72-4.65 (m, 1H), 3.79 (s, 3H), 3.24-3.12 (m, 1H), 3.00-2.85 (m, 2H), 2.53 (td, J = 13.2, 5.5 Hz, 1H), 2.37-2.20 (m, 6H), 2.01-1.93 (m, 1H), 1.90-1.63 (m, 7H), 1.52-1.41 (m, 1H), 1.36-1.18 (m, 2H), 1.17-0.97 (m, 6H). LCMS (ES, m/z): 484 [M + H]$^+$. |

TABLE 18-continued

| Example Number | Structure and Compound Name | $^1H$ NMR, LCMS |
|---|---|---|
| 638 | 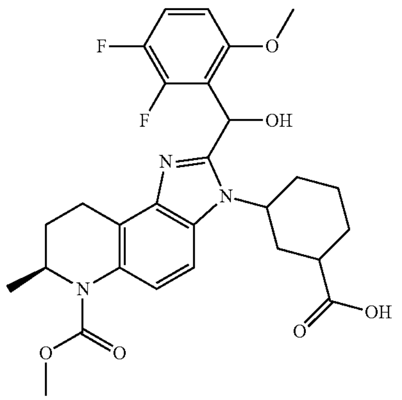<br>3-((7S)-2-((2,3-difluoro-6-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid<br>2nd eluting isomer | $^1H$-NMR ($CD_3OD$, 400 MHz) δ (ppm): 7.62-7.51 (m, 1H), 7.49-7.34 (m, 1H), 7.31-7.11 (m, 1H), 6.91-6.78 (m, 1H), 6.58 (s, 1H), 4.89-4.81 (m, 1H), 4.78-4.66 (m, 1H), 3.83 (s, 3H), 3.78 (s, 3H), 3.27-3.12 (m, 1H), 3.01-2.89 (m, 1H), 2.89-2.76 (m, 1H), 2.54-2.41 (m, 1H), 2.41-2.27 (m, 1H), 2.27-2.12 (m, 3H), 2.12-2.02 (m, 1H), 1.95-1.83 (m, 1H), 1.78-1.61 (m, 3H), 1.14 (d, J = 6.4 Hz, 3H), LCMS (ES, m/z): 544 [M + H]$^+$. |
| 639 | 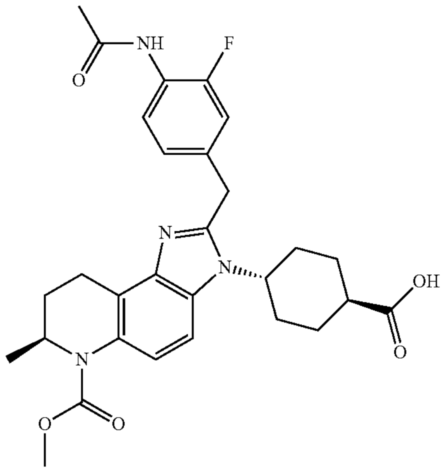<br>(1S,4R)-4-((S)-2-(4-acetamido-3-fluorobenzyl)-6-(methoxycarbonyl)-7-methyl-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 7.88-7.84 (m, 1H), 7.47-7.38 (m, 2H), 7.08-7.04 (m, 2H), 4.80-4.50 (m, 2H), 4.40 (s, 2H), 4.35-4.15 (m, 1H), 3.75 (s, 3H), 3.25-3.10 (m, 1H), 3.00-2.90 (m, 1H), 2.50-2.00 (m, 7H), 1.75-1.40 (m, 6H), 1.14 (d, J = 6.8 Hz, 3H). LCMS (ES, m/z): 537 [M + H]$^+$. |
| 640 | 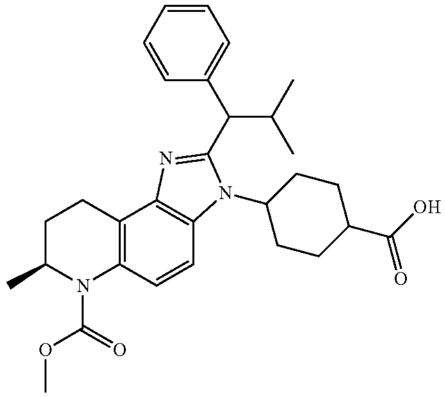<br>4-((7S)-6-(methoxycarbonyl)-7-methyl-2-(2-methyl-1-phenylpropyl)-6,7,8,9-tetrahydro-3H-imidazo[4,5-f]quinolin-3-yl)cyclohexane-1-carboxylic acid<br>1st eluting isomer | $^1H$ NMR ($CD_3OD$, 300 MHz) δ (ppm): 7.40-7.19 (m, 7H), 4.84-4.68 (m, 1H), 4.50-4.42 (m, 1H), 3.97 (d, J = 10.4 Hz, 1H), 3.74 (s, 3H), 3.31-3.25 (m, 1H), 3.05-2.88 (m, 2H), 2.41-2.25 (m, 3H), 2.25-1.91 (m, 6H), 1.72-1.64 (m, 1H), 1.14 (t, J = 6.3 Hz, 6H), 0.92-0.88 (m, 4H). LCMS (ES, m/z): 504 [M + H]$^+$. |

TABLE 18-continued

| Example Number | Structure and Compound Name | $^1$H NMR, LCMS |
|---|---|---|
| 641 | 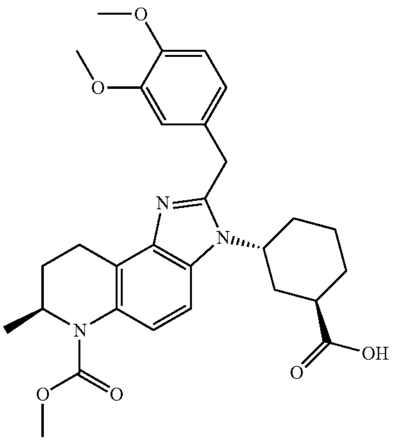<br>(1R,3R)-3-((S)-2-(3,4-dimethoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.43 (d, J = 9.2 Hz, 1H), 7.33 (d, J = 8.8 Hz, 1H), 6.96 (s, 1H), 6.94-6.76 (m, 2H), 4.97-4.88 (m, 1H), 4.80-4.68 (m, 1H), 4.37-4.25 (m, 2H), 3.83-3.71 (m, 9H), 3.26-3.14 (m, 1H), 3.00-2.88 (m, 1H), 2.76-2.74 (m, 1H), 2.34-2.13 (m, 4H), 2.10-1.93 (m, 1H), 1.78-1.67 (m, 1H), 1.61-1.45 (m, 2H), 1.42-1.25 (m, 1H), 1.18-1.03 (m, 4H). LCMS (ES, m/z): 522 [M + H]$^+$. |
| 642 | 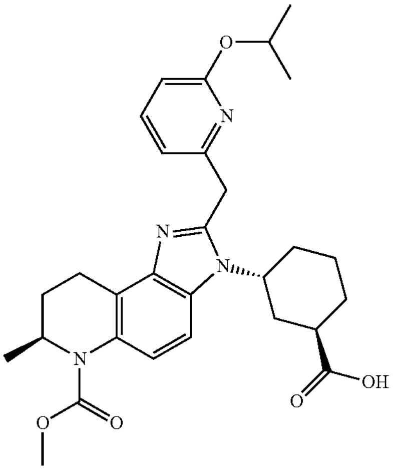<br>(1R,3R)-3-((S)-2-((6-isopropoxypyridin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.58-7.39 (m, 3H), 6.82 (d, J = 7.2 Hz, 1H), 6.54 (d, J = 8.4 Hz, 1H), 5.20-5.17 (m, 1H), 4.81-4.77 (m, 2H), 4.45-4.42 (m, 2H), 3.79 (s, 3H), 3.24-3.16 (m, 1H), 2.97-2.92 (m, 2H), 2.36-2.19 (m, 5H), 1.78-1.71 (m, 3H), 1.42 (m, 2H), 1.22 (d, J = 6.0 Hz, 3H), 1.16 (t, J = 6.4 Hz, 6H). LCMS (ES, m/z): 521 [M + H]$^+$ |

TABLE 18-continued

| Example Number | Structure and Compound Name | $^1$H NMR, LCMS |
|---|---|---|
| 643 | 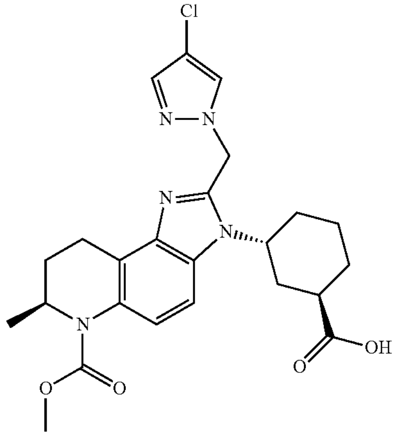 (1R,3R)-3-((S)-2-((4-chloro-1H-pyrazol-1-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.88 (s, 1H), 7.58-7.40 (m, 3H), 5.90-5.75 (m, 1H), 5.60-5.48 (m, 1H), 4.80-4.65 (m, 2H), 3.80 (s, 3H), 3.25-2.75 (m, 3H), 2.40-2.10 (m, 5H), 1.75-1.45 (m, 5H), 1.12 (d, J = 6.6 Hz, 3H) LCMS (ES, m/z): 486 $[M + H]^+$. |
| 644 | 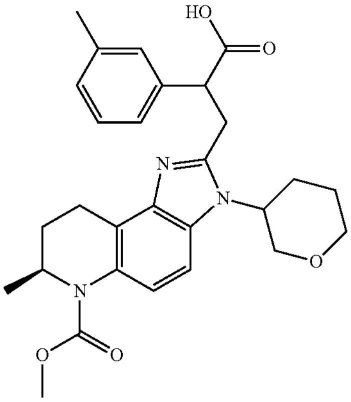 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(m-tolyl)propanoic acid 1st eluting isomer | $^1$H-NMR ($CD_3OD$, 400 MHz) δ (ppm): 7.48 (d, J = 9.2 Hz, 1H), 7.36 (d, J = 8.8 Hz, 1H), 7.23-7.11 (m, 2H), 7.12-7.03 (m, 2H), 4.80-4.67 (m, 1H), 4.52-4.38 (m, 1H), 4.26-4.15 (m, 1H), 3.98-3.87 (m, 2H), 3.76 (s, 3H), 3.71-3.59 (m, 1H), 3.59-3.44 (m, 1H), 3.35-3.33 (m, 1H), 3.21-3.05 (m, 2H), 2.98-2.85 (m, 1H), 2.52-2.34 (m, 1H), 2.30 (s, 3H), 2.28-2.16 (m, 1H), 2.07-2.01 (m, 1H), 1.97-1.79 (m, 2H), 1.78-1.66 (m, 1H), 1.11 (d, J = 6.8 Hz, 3H). LCMS (ES, m/z): 492 $[M + H]^+$. |
| 645 | 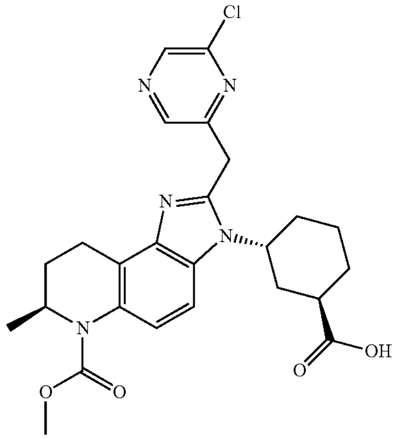 (1R,3R)-3-((S)-2-((6-chloropyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 8.62 (s, 1H), 8.53 (s, 1H), 7.53 (d, J = 9.3 Hz, 1H), 7.40 (d, J = 9.0 Hz, 1H), 4.87 (s, 1H), 4.75-4.73 (m, 1H), 3.76 (s, 3H), 3.31-3.29 (m, 1H), 2.92-2.86 (m, 2H), 2.33-2.20 (m, 6H), 1.75-1.69 (m, 6H), 1.13 (d, J = 6.6 Hz, 3H). LCMS (ES, m/z): 498 $[M + H]^+$. |

TABLE 18-continued

| Example Number | Structure and Compound Name | $^1$H NMR, LCMS |
|---|---|---|
| 646 | 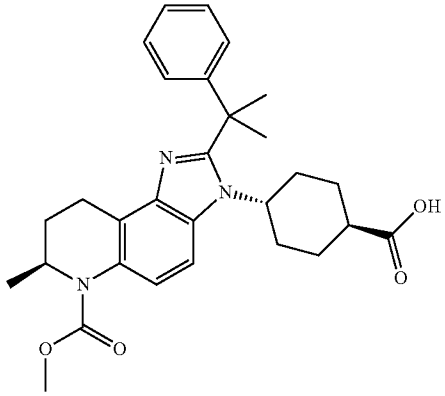 (1S,4R)-4-((S)-6-(methoxycarbonyl)-7-methyl-2-(2-phenylpropan-2-yl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.50-7.20 (m, 7H), 4.80-4.60 (m, 1H), 4.02-3.80 (m, 1H), 3.79 (s, 3H), 3.40-3.30 (m, 1H), 3.01-2.80 (m, 1H), 2.40-2.25 (m, 2H), 2.22-2.12 (m, 2H), 2.00-1.90 (m, 2H), 1.85 (s, 6H), 1.78-1.60 (m, 1H), 1.45-1.35 (m, 2H), 1.15 (d, J = 6.8 Hz, 3H), 1.12-0.97 (m, 2H). LCMS (ES, m/z): 490 $[M + H]^+$. |
| 647 | 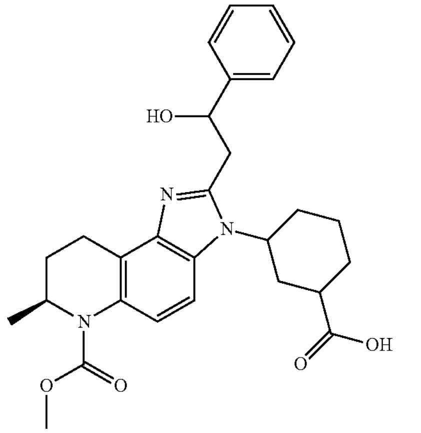 3-((7S)-2-(2-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.58-7.50 (m, 3H), 7.43-7.32 (m, 3H), 7.32-7.24 (m, 1H), 5.25-5.18 (m, 1H), 5.05-4.94 (m, 1H), 4.82-4.71 (m, 1H), 3.79 (s, 3H), 3.50-3.40 (m, 1H), 3.30-3.23 (m, 1H), 3.23-3.14 (m, 1H), 2.99-2.88 (m, 2H), 2.41-2.32 (m, 2H), 2.31-2.18 (m, 3H), 1.97-1.84 (m, 2H), 1.81-1.70 (m, 2H), 1.69-1.56 (m, 1H), 1.15 (d, J = 6.4 Hz, 3H). LCMS (ES, m/z): 492 $[M + H]^+$. |
| 648 | 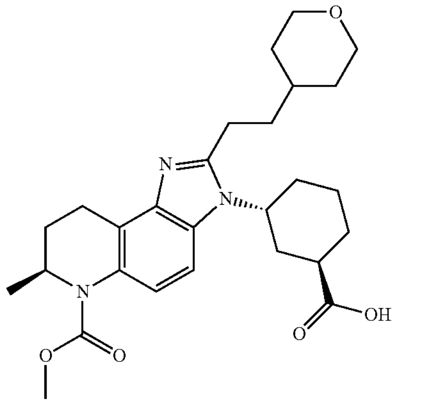 (1R,3R)-3-((S)-6-(methoxycarbonyl)-7-methyl-2-(2-(tetrahydro-2H-pyran-4-yl)ethyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.52 (d, J = 9.0 Hz, 1H), 7.38 (d, J = 9.0 Hz, 1H), 4.86-4.73 (m, 2H), 3.98-3.95 (m, 2H), 3.78 (m, 3H), 3.49-3.40 (m, 2H), 3.34-3.11 (m, 1H), 3.07-2.87 (m, 4H), 2.45-2.24 (m, 5H), 1.94-1.63 (m, 10H), 1.43-1.38 (m, 2H), 1.14 (d, J = 6.6 Hz, 3H). LCMS (ES, m/z): 484 $[M + H]^+$. |

TABLE 18-continued

| Example Number | Structure and Compound Name | $^1$H NMR, LCMS |
|---|---|---|
| 649 | 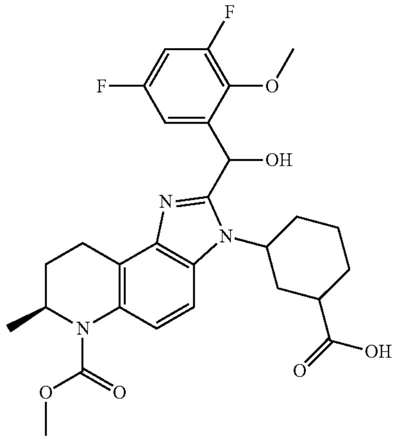 3-((7S)-2-((3,5-difluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H NMR ($CD_3OD$, 400 MHz) δ (ppm): 7.90 (s, 2H), 7.42-7.38 (m, 1H), 7.15-7.10 (m, 1H), 6.51 (s, 1H), 5.09-5.02 (m, 1H), 4.88-4.86 (m, 1H), 3.83 (s, 3H), 3.72 (s, 3H), 3.24-2.94 (m, 3H), 2.53-2.49 (m, 1H), 2.31-2.12 (m, 4H), 1.92-1.89 (m, 1H), 1.81-1.71 (m, 2H), 1.56-1.37 (m, 2H), 1.19 (d, J = 6.8 Hz, 3H). LCMS (ES, m/z): 544 [M + H]$^+$. |
| 650 | 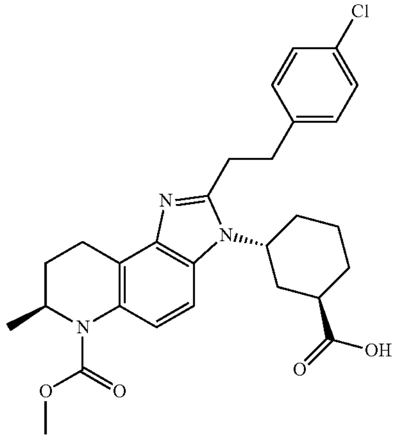 (1R,3R)-3-((S)-2-(4-chlorophenethyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CDCl_3$, 300 MHz) δ (ppm): 7.83-7.80 (m, 1H), 7.40-7.38 (m, 1H), 7.26-7.17 (m, 3H), 4.83-4.15 (m, 4H), 3.83 (s, 4H), 3.58-3.50 (m, 1H), 3.16 (s, 4H), 2.96 (s, 1H), 2.33-1.91 (m, 7H), 1.36-1.26 (m, 2H), 1.14 (d, J = 6.3 Hz, 3H). LCMS (ES, m/z): 510 [M + H]$^+$. |

TABLE 18-continued

| Example Number | Structure and Compound Name | $^1$H NMR, LCMS |
|---|---|---|
| 651 | 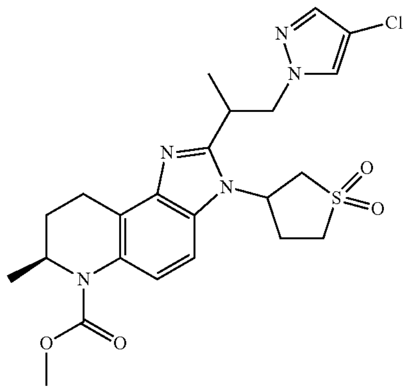 methyl (7S)-2-(1-(4-chloro-1H-pyrazol-1-yl)propan-2-yl)-3-(1,1-dioxidotetrahydrothiophen-3-yl)-7-methyl-3,7,8,9-tetrahydro-6H-imidazo[4,5-f]quinoline-6-carboxylate 3rd eluting isomer | $^1$H-NMR ($CD_3OD$, 300 MHz) δ (ppm): 7.58-7.42 (m, 4H), 5.60-5.40 (m, 1H), 4.90-4.44 (m, 3H), 4.02-3.91 (m, 1H), 3.77 (s, 3H), 3.65-3.15 (m, 5H), 2.98-2.80 (m, 2H), 2.62-2.52 (m, 1H), 2.32-2.18 (m, 1H), 1.75-1.68 (m, 1H), 1.43 (d, J = 6.9 Hz, 3H), 1.13 (d, J = 6.6 Hz, 3H). LCMS (ES, m/z): 506 [M + H]$^+$. |
| 652 | 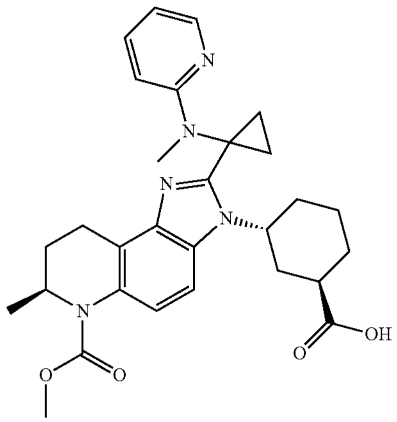 (1R,3R)-3-((S)-6-(methoxycarbonyl)-7-methyl-2-(1-(methyl(pyridin-2-yl)amino)cyclopropyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.32-8.30 (m, 1H), 8.20-8.09 (m, 2H), 7.57 (d, J = 9.2 Hz, 1H), 7.46 (d, J = 9.2 Hz, 1H), 7.09 (t, J = 7.2 Hz, 1H), 5.46-5.30 (m, 1H), 4.81-4.70 (m, 1H), 3.95 (s, 3H), 3.78 (s, 3H), 3.27-3.09 (m, 2H), 3.02-2.89 (m, 1H), 2.56-2.19 (m, 4H), 2.13-1.42 (m, 10H), 1.10 (d, J = 6.8 Hz, 3H). LCMS (ES, m/z): 518 [M + H]$^+$. |
| 653 | 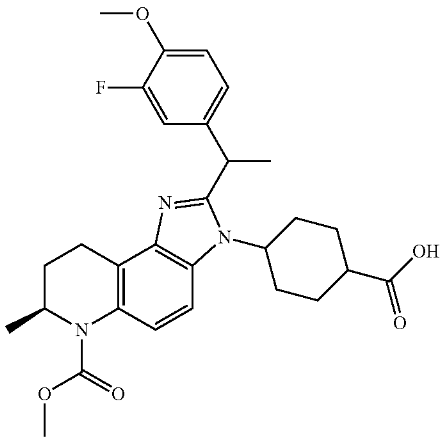 4-((7S)-2-(1-(3-fluoro-4-methoxyphenyl)ethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.48-7.26 (m, 2H), 7.12-6.89 (m, 3H), 4.80-4.70 (m, 1H), 4.65-4.52 (d, J = 7.6 Hz, 1H), 4.32-4.21 (m, 1H), 3.85 (s, 3H), 3.79 (s, 3H), 3.12-2.91 (m, 1H), 2.49-2.19 (m, 3H), 2.20-2.00 (m, 2H), 2.00-1.89 (m, 1H), 1.88-1.62 (m, 5H), 1.61-1.47 (m, 1H), 1.45-1.27 (m, 2H), 1.17 (d, J = 6.4 Hz, 3H), 1.11-0.96 (m, 1H). LCMS (ES, m/z): 524 [M + H]$^+$. |

TABLE 18-continued

| Example Number | Structure and Compound Name | $^1$H NMR, LCMS |
|---|---|---|
| 654 | 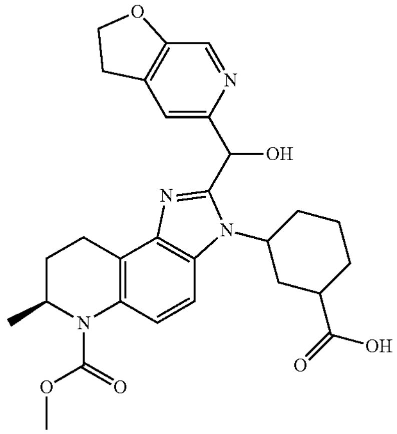 3-((7S)-2-((2,3-dihydrofuro[2,3-c]pyridin-5-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 8.05-7.93 (s, 1H), 7.64 (d, J = 4.0 Hz, 1H), 7.52-7.49 (m, 1H), 7.42-7.31 (m, 1H), 6.17 (s, 1H), 4.82-4.71 (m, 2H), 4.70-4.45 (m, 2H), 3.78 (s, 3H), 3.21 (m, 1H), 3.29-3.27 (m, 1H), 3.20-3.15 (m, 1H), 3.05-2.94 (m, 2H), 2.50-2.31 (m, 2H), 2.26-2.20 (m, 1H), 2.16-2.03 (m, 2H), 1.74-1.70 (m, 1H), 1.70-1.61 (m, 2H), 1.33 (m, 1H), 1.21-1.11 (m, 4H). LCMS (ES, m/z): 521 [M + H]$^+$. |
| 655 | 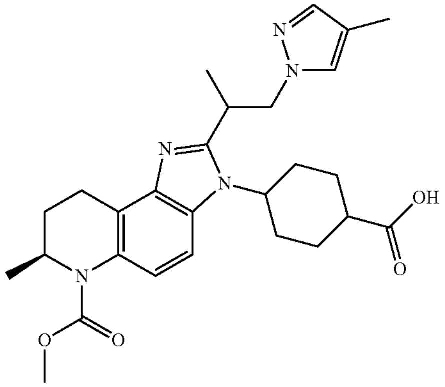 4-((7S)-6-(methoxycarbonyl)-7-methyl-2-(1-(4-methyl-1H-pyrazol-1-yl)propan-2-yl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 300 MHz) δ (ppm): 7.51-7.39 (m, 1H), 7.39-7.24 (m, 2H), 7.19-7.01 (m, 1H), 4.81-4.63 (m, 1H), 4.63-4.48 (m, 1H), 4.43-4.38 (m, 1H), 4.24-4.18 (m, 1H), 4.01-3.81 (m, 1H), 3.76 (s, 3H), 3.29-3.11 (m, 1H), 3.02-2.82 (m, 1H), 2.62-2.39 (m, 1H), 2.39-2.01 (m, 5H), 2.00-1.80 (m, 4H), 1.80-1.51 (m, 3H), 1.43 (d, J = 6.9 Hz, 3H), 1.15 (d, J = 6.9 Hz, 3H). LCMS: (ES, m/z): 494 [M + H]$^+$. |

TABLE 18-continued

| Example Number | Structure and Compound Name | $^1$H NMR, LCMS |
|---|---|---|
| 656 | 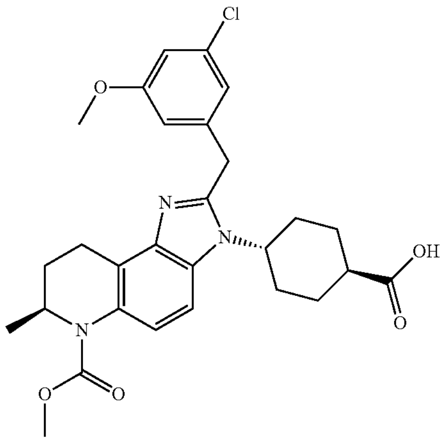 (1S,4R)-4-((S)-2-(3-chloro-5-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.87 (d, J = 9.3 Hz, 1H), 7.62 (d, J = 9.3 Hz, 1H), 7.11 (s, 1H), 7.05-6.97 (m, 2H), 4.78-4.51 (m, 4H), 3.77 (s, 3H), 3.71 (s, 3H), 3.14-2.87 (m, 2H), 2.61-2.53 (m, 1H), 2.29-2.07 (m, 3H), 2.04-1.95 (m, 2H), 1.86-1.74 (m, 1H), 1.65-1.41 (m, 4H), 1.09 (d, J = 6.6 Hz, 3H). LCMS (ES, m/z): 526 $[M + H]^+$. |
| 657 | 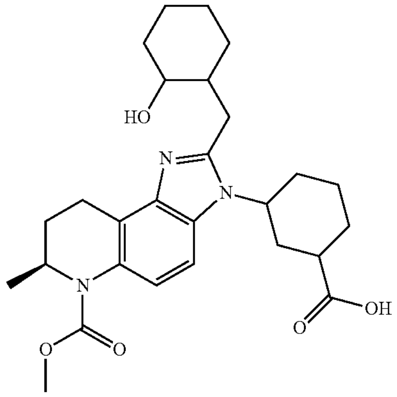 3-((7S)-2-((2-hydroxycyclohexyl)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H NMR (400 MHz, $CD_3OD$) δ (ppm): 7.55 (d, J = 8.8 Hz, 1H), 7.42 (d, J = 8.8 Hz, 1H), 4.81-4.76 (m, 2H), 3.79 (s, 3H), 3.58-3.53 (m, 1H), 3.33-3.23 (m, 2H), 3.17-3.14 (m, 1H), 2.94-2.89 (m, 1H), 2.74-2.68 (m, 1H), 2.49-2.30 (m, 2H), 2.28-2.24 (m, 3H), 2.02-1.92 (m, 1H), 1.79-1.76 (m, 3H), 1.75-1.73 (m, 3H), 1.64-1.62 (m, 3H), 1.41-1.21 (m, 3H), 1.16-1.12 (m, 4H). LCMS (ES, m/z): 484 $[M + H]^+$ |
| 658 | 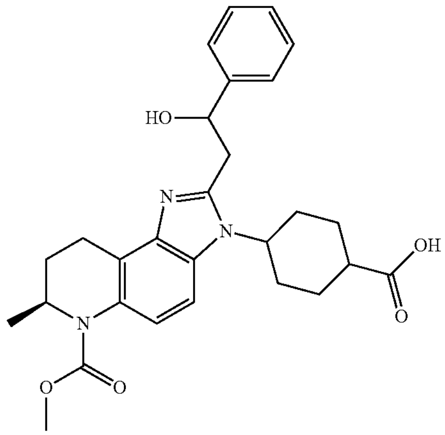 4-((7S)-2-(2-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.53-7.45 (m, 1H), 7.45-7.31 (m, 5H), 7.31-7.23 (m, 1H), 5.20-5.09 (m, 1H), 4.81-4.72 (m, 1H), 4.36-4.22 (m, 1H), 3.79 (s, 3H), 3.51-3.39 (m, 1H), 3.38-3.36 (m, 1H), 3.24-3.13 (m, 1H), 2.99-2.90 (m, 1H), 2.51-2.47 (m, 1H), 2.38-2.11 (m, 4H), 2.11-2.02 (m, 1H), 2.02-1.90 (m, 1H), 1.83-1.70 (m, 1H), 1.70-1.61 (m, 1H), 1.61-1.45 (m, 1H), 1.29-1.22 (m, 1H), 1.14 (d, J = 6.8 Hz, 3H). LCMS (ES, m/z): 492 $[M + H]^+$. |

TABLE 18-continued

| Example Number | Structure and Compound Name | $^1$H NMR, LCMS |
| --- | --- | --- |
| 659 | 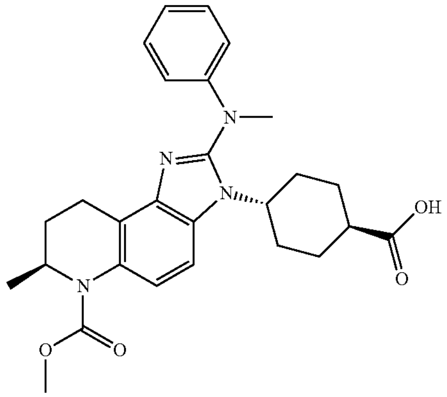 (1S,4R)-4-((S)-6-(methoxycarbonyl)-7-methyl-2-(methyl(phenyl)amino)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.48-7.39 (m, 2H), 7.36-7.30 (m, 2H), 6.95-7.02 (m, 1H), 6.87 (d, J = 7.8 Hz, 2H), 4.78-4.73 (m, 1H), 4.17-4.07 (m, 1H), 3.80 (s, 3H), 3.47 (s, 3H), 3.20-3.12 (m, 1H), 2.94-2.87 (m, 1H), 2.42-2.26 (m, 4H), 2.23-2.06 (m, 2H), 1.81-1.70 (m, 3H), 1.38-1.31 (m, 2H), 1.17 (d, J = 6.6 Hz, 3H). LCMS (ES, m/z): 477 $[M + H]^+$. |
| 660 | 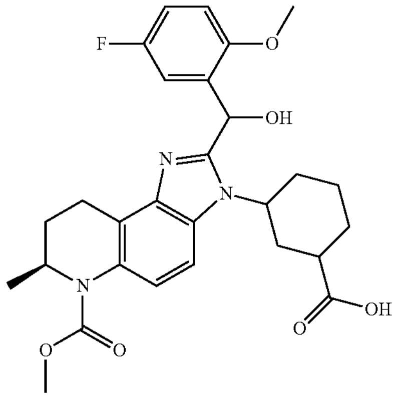 3-((7S)-2-((5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.69-7.44 (m, 2H), 7.44-7.29 (m, 1H), 7.12-6.99 (m, 1H), 6.98-6.82 (m, 1H), 6.37 (s, 1H), 5.03-4.91 (m, 1H), 4.81-4.69 (m, 1H), 3.78 (s, 3H), 3.61 (s, 3H), 3.22-3.04 (m, 1H), 3.02-2.87 (m, 2H), 2.54-2.41 (m, 1H), 2.41-2.27 (m, 1H), 2.27-2.08 (m, 3H), 1.82-1.58 (m, 3H), 1.58-1.41 (m, 2H), 1.14 (d, J = 6.4 Hz, 3H). LCMS (ES, m/z): 526 $[M + H]^+$ |
| 661 | 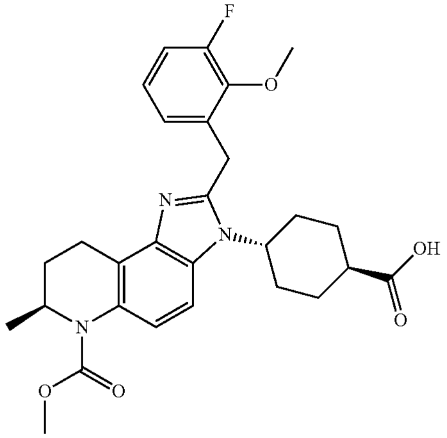 (1S,4R)-4-((S)-2-(3-fluoro-2-methoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.85 (s, 2H), 7.28-7.16 (m, 3H), 4.90-4.89 (m, 1H), 4.68 (s, 2H), 4.56-4.54 (m, 1H), 3.87 (d, J = 2.7 Hz, 3H), 3.83 (s, 3H), 3.12-3.04 (m, 2H), 2.56-2.51 (m, 1H), 2.39-2.29 (m, 3H), 2.26-2.15 (m, 2H), 1.96-1.91 (m, 1H), 1.90-1.73 (m, 2H), 1.69-1.50 (m, 2H), 1.18 (d, J = 6.9 Hz, 3H). LCMS (ES, m/z): 510 $[M + H]^+$. |

TABLE 18-continued

| Example Number | Structure and Compound Name | $^1$H NMR, LCMS |
|---|---|---|
| 662 | 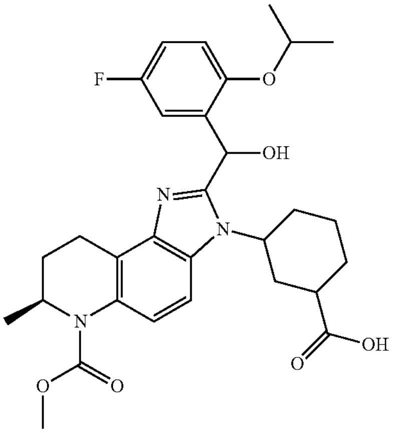 3-((7S)-2-((5-fluoro-2-isopropoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H NMR ($CD_3OD$, 400 MHz) δ (ppm): δ 7.61 (m, 1H), 7.52-7.42 (m, 2H), 7.05-6.98 (m, 1H), 6.90-6.85 (m, 1H), 6.32 (s, 1H), 4.96-4.85 (m, 1H), 4.81-4.76 (m, 1H), 4.49-4.43 (m, 1H), 3.79 (s, 3H), 3.20-3.16 (m, 1H), 2.98-2.85 (m, 2H), 2.51-2.35 (m, 2H), 2.29-2.07 (m, 3H), 1.78-1.60 (m, 3H), 1.50-1.39 (m, 2H), 1.18 (d, J = 6.8 Hz, 3H), 1.12 (d, J = 6.0 Hz, 3H), 0.65 (d, J = 6.0 Hz, 3H). LCMS (ES, m/z): 554 [M + H]$^+$. |
| 663 | 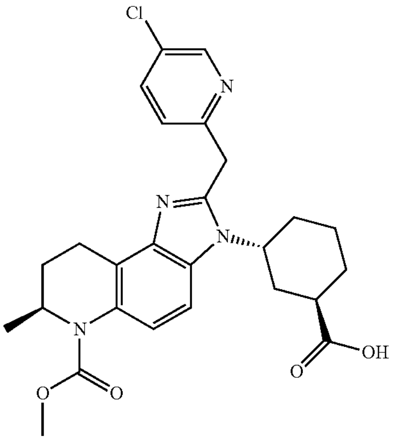 (1R,3R)-3-((S)-2-((5-chloropyridin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.44 (s, 1H), 7.79 (d, J = 2.4 Hz, 1H), 7.54 (d, J = 2.4 Hz, 1H), 7.42 (d, J = 8.8 Hz, 1H), 7.35 (d, J = 8.8 Hz, 1H), 4.90-4.85 (m, 1H), 4.80-4.75 (m, 2H), 4.57-4.54 (m, 1H), 3.79 (s, 3H), 3.23-3.15 (m, 1H), 2.98-2.92 (m, 2H), 2.41-2.28 (m, 5H), 1.65-1.80 (m, 4H), 1.46-1.43 (m, 1H), 1.16 (d, J = 6.8 Hz, 3H). LCMS (ES, m/z): 497 [M + H]$^+$. |

TABLE 18-continued

| Example Number | Structure and Compound Name | $^1$H NMR, LCMS |
|---|---|---|
| 664 | 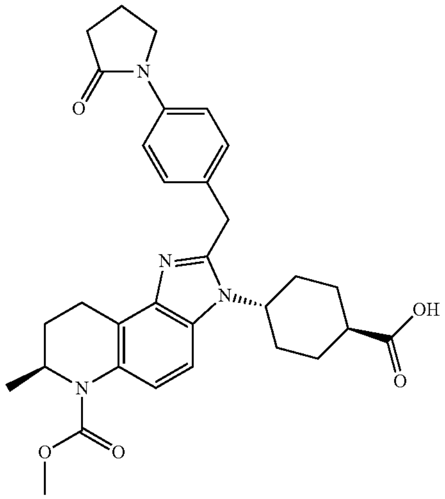 (1S,4R)-4-((S)-6-(methoxycarbonyl)-7-methyl-2-(4-(2-oxopyrrolidin-1-yl)benzyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.93-7.85 (m, 1H), 7.74-7.60 (m, 3H), 7.46-7.36 (m, 2H), 4.80-4.50 (m, 4H), 3.85-3.69 (m, 6H), 3.15-2.89 (m, 4H), 2.18-1.94 (m, 7H), 1.82 (s, 1H), 1.56-1.42 (m, 4H), 1.16-1.06 (m, 3H). LCMS (ES, m/z): 545 $[M + H]^+$. |
| 665 | 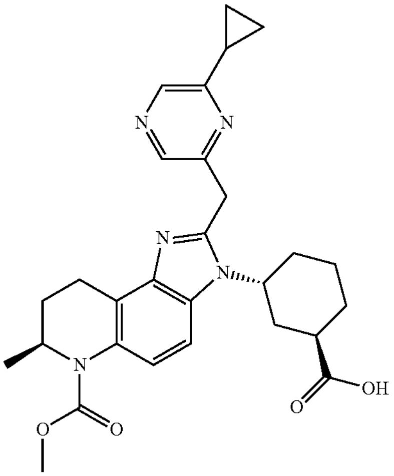 (1R,3R)-3-((S)-2-((6-cyclopropylpyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.56 (s, 1H), 8.50 (s, 1H), 7.94-7.83 (m, 2H), 4.99 (s, 2H), 4.87-4.76 (m, 2H), 3.84 (s, 3H), 3.14-2.99 (m, 3H), 2.48-2.34 (m, 2H), 2.31-2.18 (m, 3H), 2.17-2.08 (m, 1H), 1.95-1.75 (m, 4H), 1.52-1.40 (m, 1H), 1.7 (d, J = 6.8 Hz, 3H), 1.03-0.95 (m, 2H), 0.78-1.72 (m, 2H). LCMS (ES, m/z): 504 $[M + H]^+$. |

TABLE 18-continued

| Example Number | Structure and Compound Name | $^1$H NMR, LCMS |
|---|---|---|
| 666 | 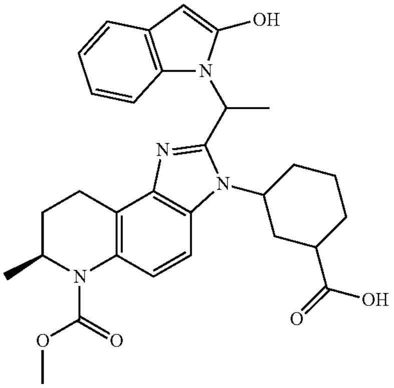 3-((7S)-2-(1-(2-hydroxy-1H-indol-1-yl)ethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 300 MHz) δ (ppm): 7.52-7.31 (m, 2H), 7.28-6.01 (m, 4H), 4.83-4.69 (m, 1H), 4.67-3.90 (m, 1H), 3.85-3.61 (m, 4H), 3.33-3.20 (m, 1H), 3.10-2.81 (m, 2H), 2.55-2.10 (m, 5H), 1.98-1.55 (m, 6H), 1.41-1.25 (m, 4H), 1.14 (d, J = 6.6 Hz, 3H). LCMS (ES, m/z): 531 $[M + H]^+$. |
| 667 | 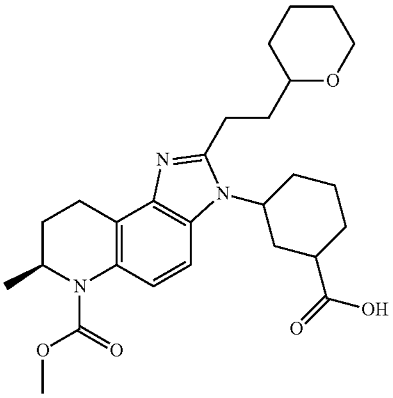 3-((7S)-6-(methoxycarbonyl)-7-methyl-2-(2-(tetrahydro-2H-pyran-2-yl)ethyl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.51 (d, J = 9.2 Hz, 1H), 7.38 (d, J = 8.8 Hz, 1H), 4.81-4.68 (m, 2H), 4.02-3.91 (m, 1H), 3.78 (s, 3H), 3.55-3.38 (m, 2H), 3.26-3.10 (m, 2H), 3.07-2.93 (m, 2H), 2.52-2.34 (m, 2H), 2.33-2.15 (m, 3H), 2.12-1.89 (m, 3H), 1.88-1.79 (m, 2H), 1.78-1.63 (m, 4H), 1.62-1.45 (m, 3H), 1.42-1.25 (m, 2H), 1.14 (d, J = 6.8 Hz, 3H). LCMS (ES, m/z): 484 $[M + H]^+$. |
| 668 | 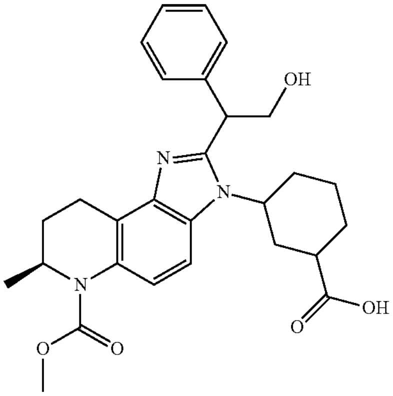 3-((7S)-2-(2-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.88-7.80 (m, 2H), 7.48-7.34 (m, 5H), 5.16-5.00 (m, 2H), 4.87-4.82 (m, 1H), 4.80-4.70 (m, 1H), 4.55-4.47 (m, 1H), 3.83 (s, 3H), 3.22-2.97 (m, 3H), 2.54-2.42 (m, 1H), 2.32-2.13 (m, 4H), 1.99-1.87 (m, 1H), 1.82-1.68 (m, 2H), 1.49-1.39 (m, 1H), 1.34-1.23 (m, 1H), 1.18 (d, J = 6.8H, 3H). LCMS (ES, m/z): 492 $[M + H]^+$. |

TABLE 18-continued

| Example Number | Structure and Compound Name | $^1$H NMR, LCMS |
| --- | --- | --- |
| 669 | 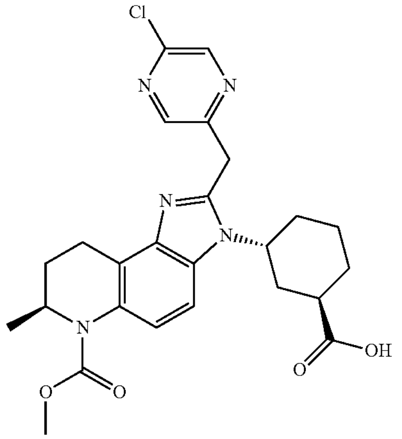 (1R,3R)-3-((S)-2-((5-chloropyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.56 (S, 1H), 8.50 (S, 1H), 7.55 (d, J = 9.0 Hz, 1H), 7.42 (d, J = 8.8 Hz, 1H), 4.89-4.68 (m, 4H), 3.78 (s, 3H), 3.24-3.09 (m, 1H), 2.97-2.80 (m, 2H), 2.45-2.13 (m, 5H), 1.86-1.60 (m, 4H), 1.60-1.41 (m, 1H), 1.14 (d, J = 6.8 Hz, 3H). LCMS (ES, m/z): 498 $[M + H]^+$. |
| 670 | 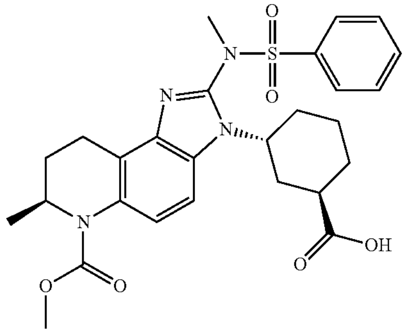 (1R,3R)-3-((S)-6-(methoxycarbonyl)-7-methyl-2-(N-methylphenylsulfonamido)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.95-7.75 (m, 2H), 7.75-7.71 (m, 1H), 7.78-7.72 (m, 2H), 7.65-7.61 (m, 1H), 7.55-7.51 (m, 1H), 4.98-4.86 (m, 1H), 4.81-4.75 (m, 1H), 3.79 (s, 3H), 3.32 (s, 3H), 3.13-2.96 (m, 2H), 2.89-2.79 (m, 1H), 2.51-2.48 (m, 1H), 2.45-2.20 (m, 4H), 2.14-2.07 (m, 1H), 1.92-1.85 (m, 1H), 1.79-1.57 (m, 3H), 1.16 (d, J = 6.4 Hz, 3H). LCMS (ES, m/z): 541 $[M + H]^+$. |
| 671 | 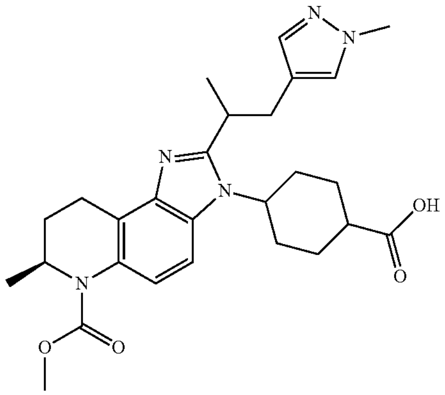 4-((7S)-6-(methoxycarbonyl)-7-methyl-2-(1-(1-methyl-1H-pyrazol-4-yl)propan-2-yl)-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.47-7.23 (m, 2H), 7.17 (s, 1H), 7.07 (s, 1H), 4.79-4.66 (m, 1H), 4.36-4.12 (m, 1H), 3.76 (s, 3H), 3.71 (s, 3H), 3.55-3.39 (m, 1H), 3.26-3.16 (m, 1H), 3.14-2.98 (m, 1H), 2.98-2.83 (m, 2H), 2.43-2.18 (m, 4H), 2.18-2.04 (m, 2H), 1.89-1.77 (m, 1H), 1.77-1.60 (m, 2H), 1.60-1.50 (m, 1H), 1.47 (d, J = 6.8 Hz, 3H), 1.19-1.03 (m, 4H). LCMS (ES, m/z): 494 $[M + H]^+$ |

TABLE 18-continued

| Example Number | Structure and Compound Name | $^1$H NMR, LCMS |
|---|---|---|
| 672 | 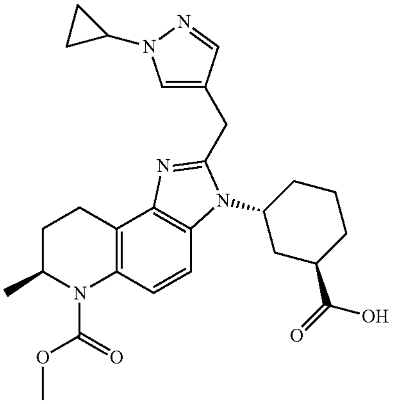 (1R,3R)-3-((S)-2-((1-cyclopropyl-1H-pyrazol-4-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.61 (s, 1H), 7.48 (d, J = 9.2 Hz, 1H), 7.44-7.33 (m, 2H), 4.90-4.92 (m, 1H), 4.80-4.70 (m, 1H), 4.33-4.21 (m, 1H), 4.20-4.11 (m, 1H), 3.78 (s, 3H), 3.64-3.53 (m, 1H), 3.25-3.11 (m, 1H), 2.99-2.79 (m, 2H), 2.39-2.14 (m, 5H), 1.80-1.59 (m, 3H), 1.53-1.41 (m, 2H), 1.14 (d, J = 6.8 Hz, 3H), 1.06-0.94 (m, 4H). LCMS (ES, m/z): 492 [M + H]$^+$. |
| 673 | 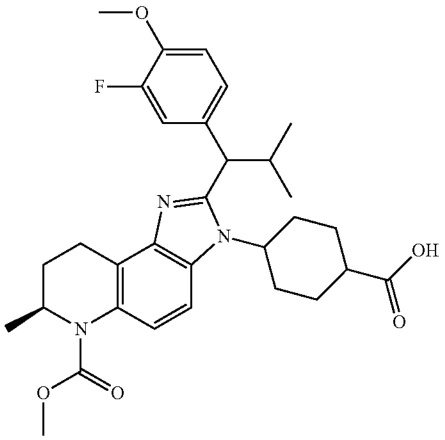 4-((7S)-2-(1-(3-fluoro-4-methoxyphenyl)-2-methylpropyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 300 MHz) δ (ppm): 7.50-7.38 (m, 2H), 7.17-7.03 (m, 3H), 4.85-4.72 (m, 1H), 4.65-4.50 (m, 1H), 4.12-4.00 (m, 1H), 3.85 (s, 3H), 3.80 (s, 3H), 3.15-2.75 (m, 2H), 2.55-1.70 (m, 9H), 1.60-1.25 (m, 2H), 1.17 (d, J = 6.6 Hz, 3H), 1.11-1.08 (m, 4H), 0.92 (d, J = 6.6 Hz, 3H). LCMS (ES, m/z): 552 [M + H]$^+$ |
| 674 | 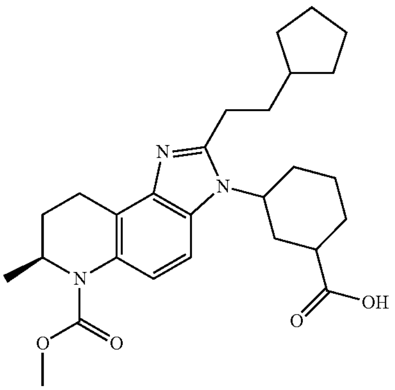 3-((7S)-2-(2-cyclopentyl-1-hydroxyethyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.61 (d, J = 8.8 Hz, 1H), 7.48 (d, J = 9.2 Hz, 1H), 5.13-5.11 (m, 1H), 5.11-5.03 (m, 1H), 4.80-4.76 (m, 1H), 3.79 (s, 3H), 3.24-2.88 (m, 3H), 2.56 2.18 (m, 5H), 2.12-1.94 (m, 4H), 1.90-1.69 (m, 7H), 1.55-1.52 (m, 2H), 1.33-1.26 (m, 3H), 1.15 (d, J = 6.4 Hz, 3H). LCMS (ES, m/z): 484 [M + H]$^+$. |

TABLE 18-continued

| Example Number | Structure and Compound Name | $^1$H NMR, LCMS |
|---|---|---|
| 675 | 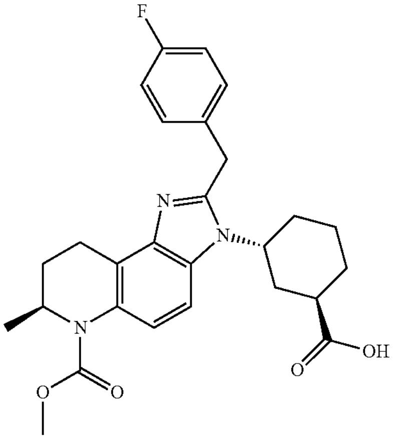 (1R,3R)-3-((S)-2-(4-fluorobenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.50-7.30 (m, 2H), 7.27-7.17 (m, 2H), 7.07-6.92 (m, 2H), 4.77-4.54 (m, 2H), 4.41-4.15 (m, 2H), 3.74 (s, 3H), 3.23-3.07 (m, 1H), 2.98-2.84 (m, 2H), 2.37-2.04 (m, 5H), 1.79-1.55 (m, 3H), 1.30-1.16 (m, 2H), 1.11 (d, J = 6.9 Hz, 3H). LCMS (ES, m/z): 480 $[M + H]^+$ |
| 676 | 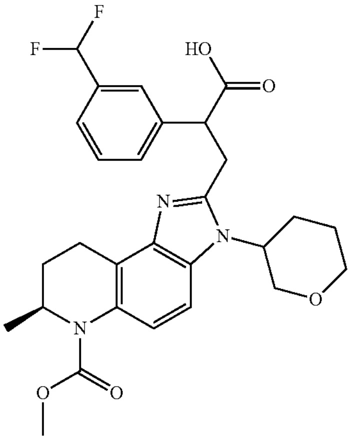 2-(3-(difluoromethyl)phenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1$H-NMR ($CD_3OD$, 300 MHz) δ (ppm): 7.84-7.71 (m, 2H), 7.59-7.50 (m, 4H), 6.95-6.57 (m, 1H), 4.88-4.72 (m, 2H), 4.4-4.36 (m, 1H), 4.13-3.92 (m, 3H), 3.76 (s, 3H), 3.62-3.44 (m, 3H), 3.11-2.85 (m, 2H), 2.61-2.43 (m, 1H), 2.30-2.11 (m, 2H), 2.07-1.78 (m, 3H), 1.14 (d, J = 6.6 Hz, 3H). LCMS (ES, m/z): 528 $[M + H]^+$. |

TABLE 18-continued

| Example Number | Structure and Compound Name | $^1$H NMR, LCMS |
|---|---|---|
| 677 | 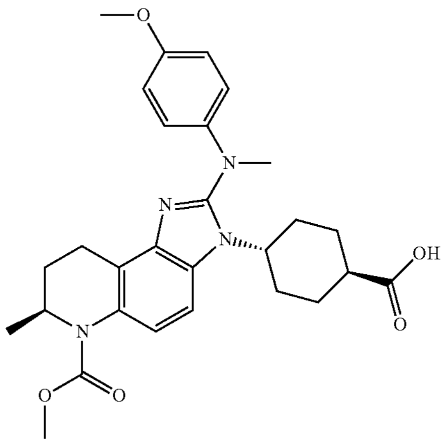 (1S,4R)-4-((S)-6-(methoxycarbonyl)-2-((4-methoxyphenyl)(methyl)amino)-7-methyl-6,7,8,9-tetrahydro-3H-imidazo[4,5-f]quinolin-3-yl)cyclohexane-1-carboxylic acid | LCMS (ES, m/z): 508 [M + H]$^+$ |
| 678 | 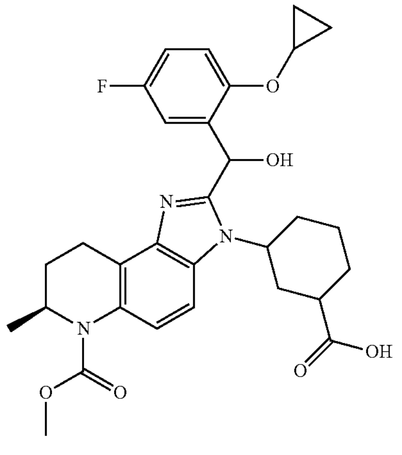 3-((7S)-2-((2-cyclopropoxy-5-fluorophenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.73-7.61 (m, 3H), 7.26-7.09 (m, 2H), 6.31 (s, 1H), 5.00-4.81 (m, 2H), 3.82 (s, 3H), 3.70-3.68 (m, 1H), 3.13-2.94 (m, 3H), 2.47-2.14 (m, 5H), 1.91-1.64 (m, 3H), 1.49-1.25 (m, 2H), 1.17 (d, J = 6.4 Hz, 3H), 0.59-0.55 (m, 2H), 0.12-0.02 (m, 2H). LCMS (ES, m/z): 552 [M + H]$^+$. |

TABLE 18-continued

| Example Number | Structure and Compound Name | $^1$H NMR, LCMS |
|---|---|---|
| 679 | 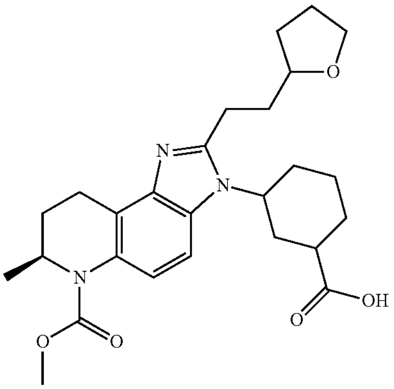 3-((7S)-6-(methoxycarbonyl)-7-methyl-2-(2-(tetrahydrofuran-2-yl)ethyl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.52 (d, J = 9.2 Hz, 1H), 7.38 (d, J = 9.2 Hz, 1H), 4.83-4.69 (m, 2H), 3.98-3.87 (m, 2H), 3.83-3.69 (m, 4H), 3.23-3.12 (m, 1H), 3.11-3.03 (m, 2H), 3.00-2.99 (m, 1H), 2.95-2.85 (m, 1H), 2.48-2.33 (m, 2H), 2.33-2.17 (m, 3H), 2.16-2.04 (m, 2H), 2.03-1.84 (m, 5H), 1.80-1.53 (m, 4H), 1.14 (d, J = 6.8 Hz, 3H). LCMS (ES, m/z): 470 [M + H]$^+$. |
| 680 | 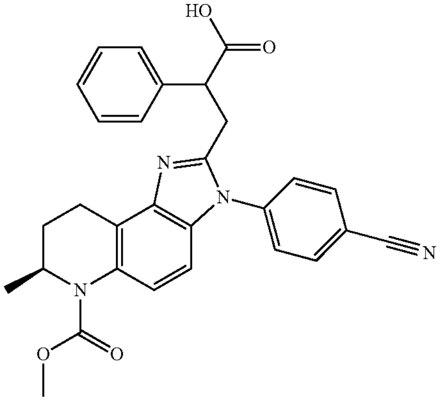 3-((7S)-3-(4-cyanophenyl)-6-(methoxycarbonyl)-7-methyl-6,7,8,9-tetrahydro-3H-imidazo[4,5-f]quinolin-2-yl)-2-phenylpropanoic acid 1$^{st}$ eluting isomer | $^1$H-NMR ($CD_3OD$, 300 MHz) δ (ppm): 7.93 (d, J = 8.7 Hz, 2H), 7.45-7.31 (m, 3H), 7.27-7.14 (m, 3H), 7.13-7.01 (m, 2H), 6.87 (d, J = 90. Hz, 1H), 4.81-4.75 (m, 1H), 4.37-4.18 (m, 1H), 3.75 (s, 3H), 3.62-3.44 (m, 1H), 3.25-3.10 (m, 2H), 3.04-2.86 (m, 1H), 2.37-2.15 (m, 1H), 1.81-1.63 (m, 1H), 1.12 (d, J = 6.6 Hz, 3H). LCMS (ES, m/z): 495 [M + H]$^+$ |
| 681 | 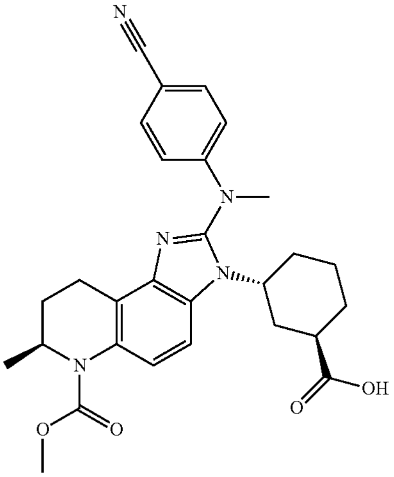 (1R,3R)-3-((S)-2-((4-cyanophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 502 [M + H]$^+$ |

TABLE 18-continued

| Example Number | Structure and Compound Name | $^1$H NMR, LCMS |
|---|---|---|
| 682 | 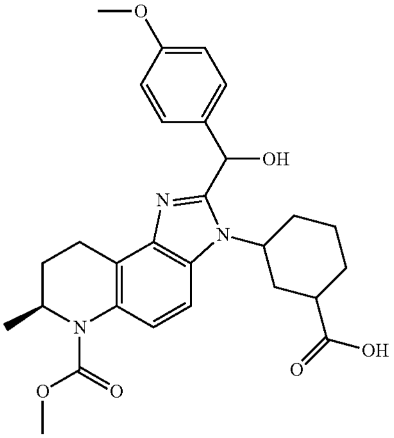 3-((7S)-2-(hydroxy(4-methoxyphenyl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR (DMSO, 400 MHz) δ (ppm): 7.48-7.45 (m, 1H), 7.31-7.24 (m, 3H), 6.89-6.86 (m, 2H), 6.21-6.16 (m, 1H), 5.97-5.96 (m, 1H), 4.83-4.75 (m, 1H), 4.68-4.63 (m, 1H), 3.72 (s, 3H), 3.67 (s, 3H), 3.13-3.06 (m, 1H), 2.89-2.81 (m, 2H), 2.27-2.11 (m, 2H), 2.07-1.87 (m, 3H), 1.68-1.57 (m, 3H), 1.36-1.24 (m, 2H), 1.07 (d, J = 6.4 Hz, 3H). LCMS (ES, m/z): 508 [M + H]$^+$. |
| 683 | 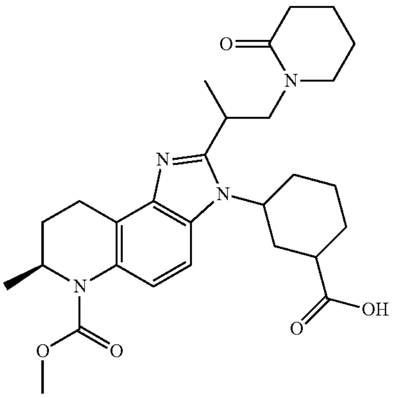 3-((7S)-6-(methoxycarbonyl)-7-methyl-2-(1-(2-oxopiperidin-1-yl)propan-2-yl)-6,7,8,9-tetrahydro-3H-imidazo[4,5-f]quinolin-3-yl)cyclohexane-1-carboxylic acid 4th eluting isomer | $^1$H-NMR ($CD_3OD$, 400 MHz) δ (ppm): 7.91-7.82 (m, 2H), 5.09-5.05 (m, 1H), 4.35-4.29 (m, 1H), 4.90-4.07 (m, 1H), 3.82 (s, 3H), 3.61-3.58 (m, 1H), 3.53-3.47 (m, 1H), 3.41-3.36 (m, 2H), 3.15-3.04 (m, 3H), 2.57-2.54 (m, 1H), 2.46-2.40 (m, 2H), 2.37-2.20 (m, 4H), 2.04-2.01 (m, 2H), 1.92-1.89 (m, 3H), 1.81-1.78 (m, 3H), 1.70-1.59 (m, 4H) 1.17 (d, J = 6.8 Hz, 3H). LCMS (ES, m/z): 511 [M + H]$^+$ |

TABLE 18-continued

| Example Number | Structure and Compound Name | $^1$H NMR, LCMS |
|---|---|---|
| 684 | 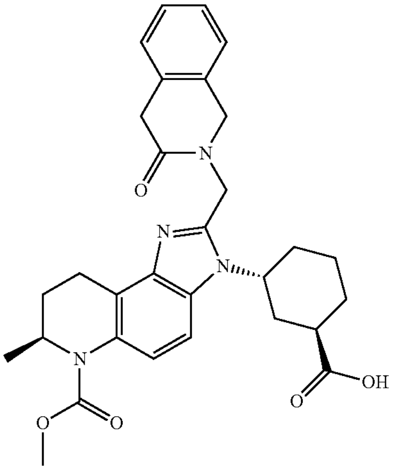 (1R,3R)-3-((S)-6-(methoxycarbonyl)-7-methyl-2-((3-oxo-3,4-dihydroisoquinolin-2(1H)-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.53 (d, J = 9.0 Hz, 1H), 7.44 (d, J = 9.0 Hz, 1H), 7.32-7.18 (m, 3H), 7.17-7.10 (m, 1H), 5.39-5.23 (m, 1H), 4.80-4.67 (m, 2H), 4.66-4.58 (m, 3H), 4.56-4.46 (m, 1H), 3.88-3.64 (m, 4H), 3.26-3.13 (m, 1H), 3.03-2.92 (m, 1H), 2.91-2.84 (m, 1H), 2.48-2.34 (m, 1H), 2.33-2.09 (m, 4H), 1.82-1.60 (m, 4H), 1.58-1.44 (m, 1H), 1.23-1.10 (m, 3H). LCMS (ES, m/z): 531 [M + H]$^+$. |
| 685 | 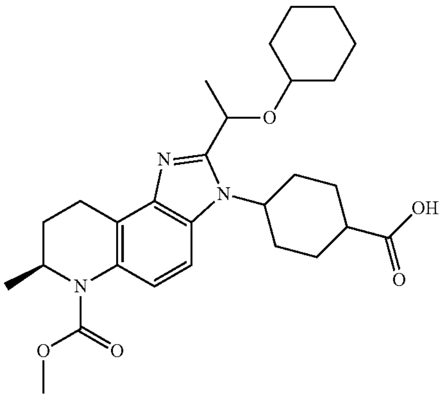 4-((7S)-2-((R)-1-(cyclohexyloxy)ethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.56-7.54 (m, 1H), 7.45-7.41 (m, 1H), 5.18-5.16 (m, 1H), 5.02-4.96 (m, 1H), 4.77-4.74 (m, 1H), 3.79 (s, 3H), 3.42-3.40 (m, 1H), 3.21-3.18 (m, 1H), 2.92-2.88 (m, 1H), 2.62-2.58 (m, 1H), 2.53-2.39 (m, 2H), 2.31-2.25 (m, 3H), 2.07-1.96 (m, 3H), 1.81-1.69 (m, 5H), 1.62 (d, J = 8.0 Hz, 3H), 1.54-1.50 (m, 1H), 1.40-1.32 (m, 2H), 1.33-1.23 (m, 4H), 1.15 (d, J = 6.4 Hz, 3H). LCMS (ES, m/z): 498 [M + H]$^+$. |
| 686 | 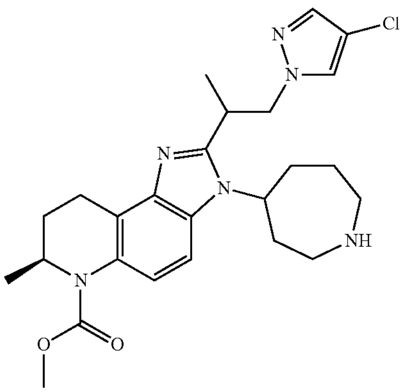 methyl (7S)-3-(azepan-4-yl)-2-(1-(4-chloro-1H-pyrazol-1-yl)propan-2-yl)-7-methyl-3,7,8,9-tetrahydro-6H-imidazo[4,5-f]quinoline-6-carboxylate 1st eluting isomer | $^1$H-NMR ($CD_3OD$, 400 MHz) δ (ppm): 7.46-7.32 (m, 4H), 4.84-4.71 (m, 1H), 4.70-4.55 (m, 2H), 4.55-4.44 (m, 1H), 4.05-3.91 (m, 1H), 3.79 (s, 3H), 3.52-3.36 (m, 3H), 3.30-3.16 (m, 2H), 3.04-2.91 (m, 1H), 2.70-2.60 (m, 1H), 2.51-2.37 (m, 1H), 2.34-2.04 (m, 3H), 2.03-1.86 (m, 1H), 1.82-1.67 (m, 1H), 1.65-1.51 (m, 1H), 1.47 (d, J = 7.2 Hz, 3H), 1.14 (d, J = 6.8 Hz, 3H). LCMS (ES, m/z): 485 [M + H]$^+$. |

TABLE 18-continued

| Example Number | Structure and Compound Name | $^1$H NMR, LCMS |
|---|---|---|
| 687 | 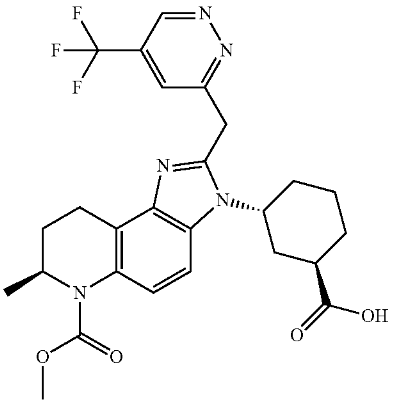 (1R,3R)-3-((S)-6-(methoxycarbonyl)-7-methyl-2-((5-(trifluoromethyl)pyridazin-3-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 9.45 (s, 1H), 8.12 (s, 1H), 7.56 (d, J = 9.2 Hz, 1H), 7.46 (d, J = 8.8 Hz, 1H), 4.84-4.74 (m, 4H), 3.79 (s, 3H), 3.33-3.25 (m, 1H), 3.03-2.96 (m, 2H), 2.46-2.12 (m, 5H), 1.88-1.62 (m, 4H), 1.55-1.41 (m, 1H), 1.16 (d, J = 6.8 Hz, 3H). LCMS (ES, m/z): 532 $[M + H]^+$. |
| 688 | 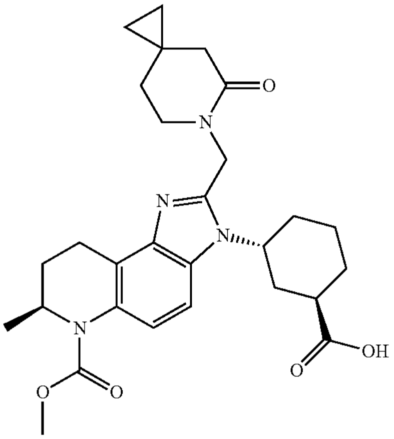 (1R,3R)-3-((S)-6-(methoxycarbonyl)-7-methyl-2-((5-oxo-6-azaspiro[2.5]octan-6-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.56 (d, J = 8.0 Hz, 1H), 7.45 (d, J = 8.8 Hz, 1H), 5.20-5.16 (m, 1H), 4.84-4.79 (m, 1H), 4.76-4.73 (m, 2H), 3.79 (s, 3H), 3.37-3.36 (m, 2H), 3.24-3.16 (m, 1H), 2.96-2.92 (m, 2H), 2.61-2.49 (m, 2H), 2.38-2.23 (m, 5H), 1.91-1.82 (m, 2H), 1.80-1.56 (m, 5H), 1.15 (d, J = 6.4 Hz, 3H), 0.47-0.41 (m, 4H). LCMS (ES, m/z): 509 $[M + H]^+$. |
| 689 | 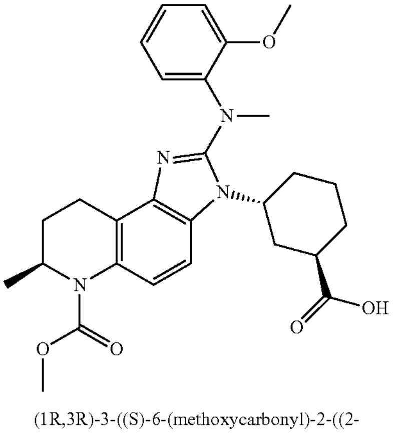 (1R,3R)-3-((S)-6-(methoxycarbonyl)-2-((2-methoxyphenyl)(methyl)amino)-7-methyl-6,7,8,9-tetrahydro-3H-imidazo[4,5-f]quinolin-3-yl)cyclohexane-1-carboxylic acid | LCMS (ES, m/z): 508 $[M + H]^+$ |

TABLE 18-continued

| Example Number | Structure and Compound Name | $^1$H NMR, LCMS |
|---|---|---|
| 690 | 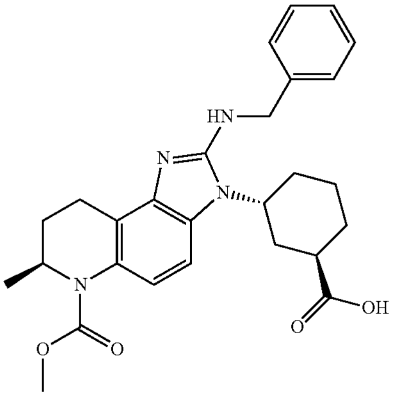 (1R,3R)-3-((S)-2-(benzylamino)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.51-7.39 (m, 2H), 7.39-7.31 (m, 2H), 7.31-7.21 (m, 2H), 7.21-7.07 (m, 1H), 4.87 (s, 2H), 4.64-4.46 (m, 2H), 3.77 (s, 3H), 3.19-3.03 (m, 1H), 2.96-2.82 (m, 1H), 2.81-2.63 (m, 1H), 2.43-2.18 (m, 5H), 2.09-1.94 (m, 1H), 1.91-1.77 (m, 1H), 1.68-1.59 (m, 3H), 1.14 (d, J = 6.8 Hz, 3H). LCMS (ES, m/z): 477 [M + H]$^+$ |
| 691 | 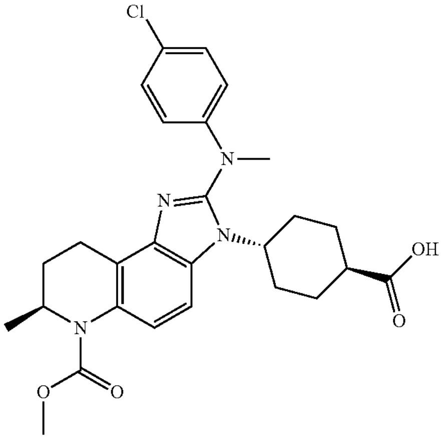 (1S,40-4-((S)-2-((4-chlorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 [M + H]$^+$ |
| 692 | 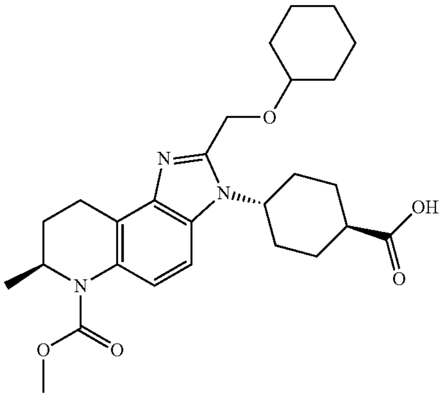 (1S,4r)-4-((S)-2-((cyclohexyloxy)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.60-7.51 (d, J = 8.8 Hz, 1H), 7.50-7.37 (d, J = 8.8 Hz, 1H), 4.87-4.69 (m, 3H), 4.65-4.48 (m, 1H), 3.79 (s, 3H), 3.58-3.48 (m, 1H), 3.23-3.07 (m, 1H), 3.00-2.88 (m, 1H), 2.56-2.48 (m, 1H), 2.47-2.32 (m, 2H), 2.32-2.16 (m, 3H), 2.12-1.88 (m, 4H), 1.81-1.61 (m, 5H), 1.59-1.48 (m, 1H), 1.46-1.23 (m, 5H), 1.21-1.03 (d, J = 6.8 Hz, 3H). LCMS (ES, m/z): 484 [M + H]$^+$. |

TABLE 18-continued

| Example Number | Structure and Compound Name | $^1$H NMR, LCMS |
|---|---|---|
| 693 | 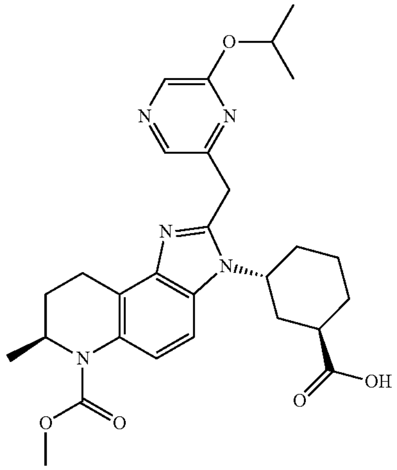 (1R,3R)-3-((S)-2-((6-isopropoxypyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.10 (s, 1H), 7.99 (s, 1H), 7.54 (d, J = 8.8 Hz, 1H), 7.42 (d, J = 8.8 Hz, 1H), 5.21-5.19 (m, 1H), 4.86-4.72 (m, 2H), 4.51-4.39 (m, 2H), 3.79 (s, 3H), 3.25-3.18 (m, 1H), 3.01-2.94 (m, 2H), 2.43-2.19 (m, 5H), 1.85-1.74 (m, 3H), 1.60 (m, 1H), 1.43 (m, 1H), 1.24-1.18 (m, 6H), 1.14 (d, J = 6.8 Hz, 3H). LCMS (ES, m/z): 522 [M + H]$^+$ |
| 694 | 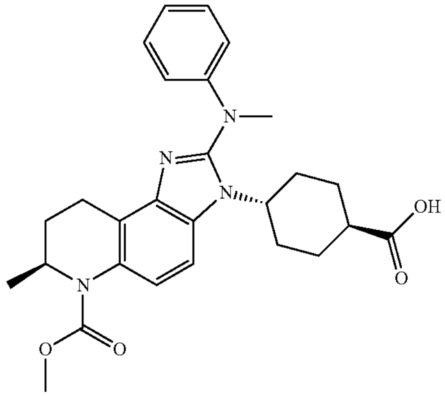 (1S,40-4-((S)-6-(methoxycarbonyl)-7-methyl-2-(methyl(phenyl)amino)-6,7,8,9-tetrahydro-3H-imidazo[4,5-f]quinolin-3-yl)cyclohexane-1-carboxylic acid | LCMS (ES, m/z): 477 [M + H]$^+$ |
| 695 | 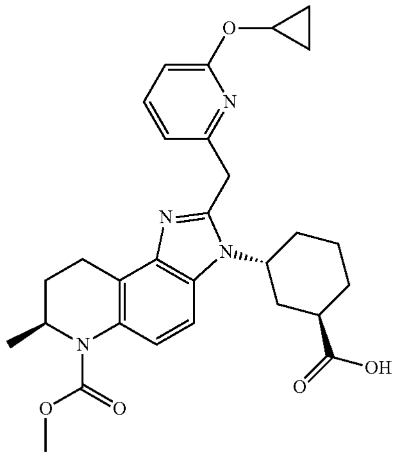 (1R,3R)-3-((S)-2-((6-cyclopropoxypyridin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.93-7.83 (m, 2H), 7.81-7.73 (m, 1H), 7.19 (d, J = 7.6 Hz, 1H), 6.82 (d, J = 8.0 Hz, 1H), 5.01 (s, 2H), 4.83-4.69 (m, 2H), 3.83 (s, 4H), 3.13-2.95 (m, 3H), 2.43-2.17 (m, 5H), 1.97-1.87 (m, 1H), 1.87-1.68 (m, 3H), 1.46-1.35 (m, 1H), 1.17 (d, J = 6.4 Hz, 3H), 0.58-0.38 (m, 4H). LCMS (ES, m/z): 519 [M + H]$^+$. |

TABLE 18-continued

| Example Number | Structure and Compound Name | $^1$H NMR, LCMS |
|---|---|---|
| 696 | 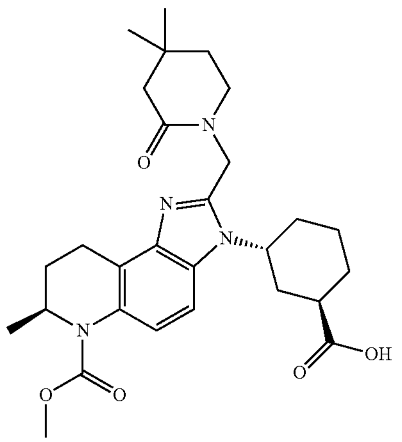<br>(1R,3R)-3-((S)-2-((4,4-dimethyl-2-oxopiperidin-1-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.54-7.43 (m, 2H), 5.15-5.05 (m, 1H), 4.89-4.74 (m, 3H), 3.79 (s, 3H), 3.42-3.32 (m, 2H), 3.19-3.15 (m, 1H), 2.96-2.90 (m, 2H), 2.46-2.18 (m, 7H), 1.95-1.80 (m, 2H), 1.79-1.63 (m, 5H), 1.15 (d J = 6.8 Hz, 3H), 1.07 (s, 3H), 1.03 (s, 3H). LCMS (ES, m/z): 511 $[M + H]^+$ |
| 697 | 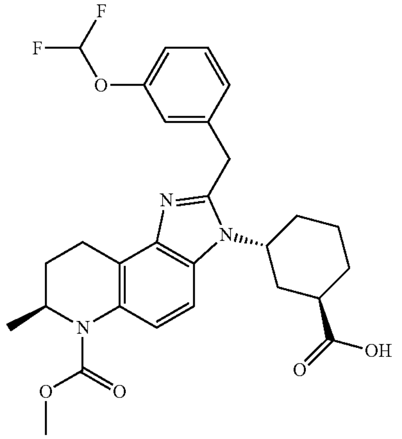<br>(1R,3R)-3-((S)-2-((5-(difluoromethoxy)pyridin-3-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.41-8.35 (m, 2H), 7.60-7.58 (m, 1H), 7.53 (d, J = 8.8 Hz, 1H), 7.43 (d, J = 9.2 Hz, 1H), 7.18-6.73 (m, 1H), 4.86-4.70 (m, 2H), 4.56-4.41 (m, 2H), 3.79 (s, 3H), 3.27-3.13 (m, 1H), 3.04-2.90 (m, 2H), 2.42-2.09 (m, 5H), 1.86-1.62 (m, 3H), 1.56-1.29 (m, 2H), 1.15 (d, J = 6.8 Hz, 3H). LCMS (ES, m/z): 529 $[M + H]^+$. |
| 698 | 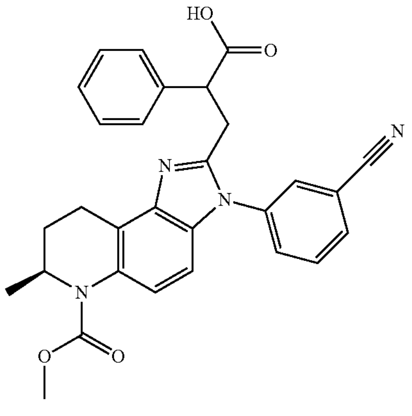<br>3-((7S)-3-(3-cyanophenyl)-6-(methoxycarbonyl)-7-methyl-6,7,8,9-tetrahydro-3H-imidazo[4,5-f]quinolin-2-yl)-2-phenylpropanoic acid<br>1st eluting isomer | $^1$H-NMR (DMSO, 300 MHz) δ (ppm): 12.46 (br, 1H), 8.08-7.93 (m, 1H), 7.87-7.59 (m, 3H), 7.37-7.03 (m, 6H), 6.87 (d, J = 9.0 Hz, 1H), 4.70-4.51 (m, 1H), 4.38-4.17 (m, 1H), 3.62 (s, 3H), 3.49-3.37 (m, 1H), 3.17-2.93 (m, 2H), 2.93-2.75 (m, 1H), 2.22-2.04 (m, 1H), 1.76-1.48 (m, 1H), 1.04 (d, J = 6.6 Hz, 3H). LCMS (ES, m/z): 495 $[M + H]^+$ |

TABLE 18-continued

| Example Number | Structure and Compound Name | $^1$H NMR, LCMS |
|---|---|---|
| 699 | 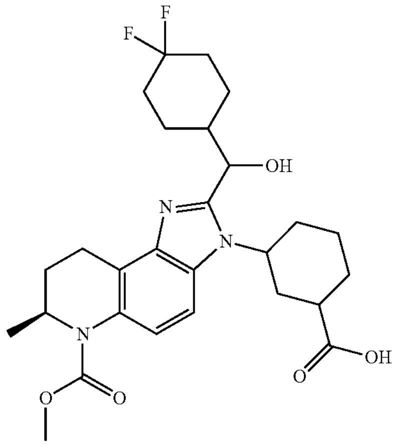<br>3-((7S)-2-((4,4-difluorocyclohexyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid<br>1st eluting isomer | $^1$H-NMR ($CD_3OD$, 400 MHz) δ (ppm): 7.53 (d, J = 9.2 Hz, 1H), 7.42 (d, J = 9.2 Hz, 1H), 5.28-5.12 (m, 1H), 4.80-4.65 (m, 2H), 3.79 (s, 3H), 3.23-3.15 (m, 1H), 3.03-2.96 (m, 1H), 2.93-2.82 (m, 1H), 2.58-2.25 (m, 7H), 2.05-1.81 (m, 5H), 1.79-1.52 (m, 4H), 1.48-1.22 (m, 2H), 1.14 (d, J = 6.4 Hz, 3H), 1.13-1.09 (m 1H). LCMS (ES, m/z): 520 [M + H]$^+$. |
| 700 | 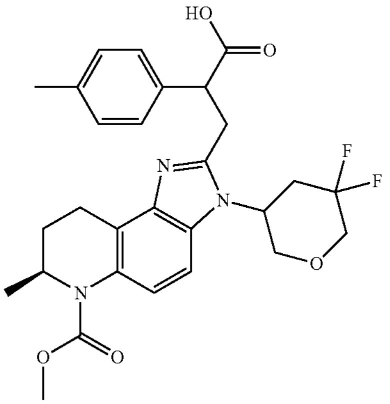<br>3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-(p-tolyl)propanoic acid<br>1st eluting isomer | $^1$H-NMR ($CD_3OD$, 400 MHz) δ (ppm): 7.56-7.37 (m, 2H), 7.27-7.08 (m, 4H), 4.82-4.64 (m, 2H), 4.30-4.23 (m, 1H), 4.12-3.92 (m, 2H), 3.90-3.76 (m, 4H), 3.72-3.60 (m, 1H), 3.23-3.07 (m, 3H), 2.99-2.75 (m, 2H), 2.71-2.59 (m, 1H), 2.37-2.16 (m, 4H), 1.78-1.70 (m, 1H), 1.14 (d, J = 6.0 Hz, 3H). LCMS (ES, m/z): 528 [M + H]$^+$. |

TABLE 18-continued

| Example Number | Structure and Compound Name | $^1$H NMR, LCMS |
|---|---|---|
| 701 | 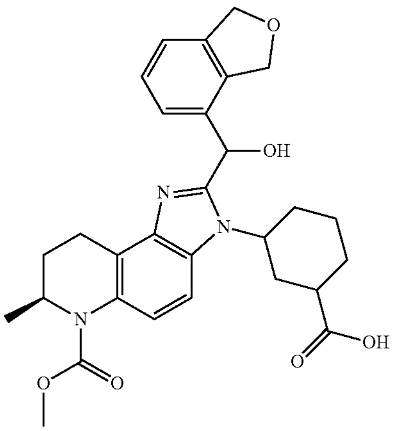 3-((7S)-2-(1,3-dihydroisobenzofuran-4-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.62-7.42 (m, 2H), 7.42-7.33 (m, 1H), 7.32-7.16 (m, 1H), 7.06-6.87 (m, 1H), 6.57 (s, 1H), 5.85-5.60 (m, 1H), 5.36-5.14 (m, 1H), 4.83-4.67 (m, 3H), 4.41-4.19 (m, 1H), 3.79 (s, 3H), 3.31-3.16 (m, 1H), 3.04-2.95 (m, 2H), 2.57-2.41 (m, 1H), 2.41-2.20 (m, 2H), 2.13-1.91 (m, 2H), 1.90-1.72 (m, 1H), 1.63-1.39 (m, 2H), 1.31-1.11 (m, 4H), 1.06-0.79 (m, 1H). LCMS (ES, m/z): 520 $[M + H]^+$ |
| 702 | 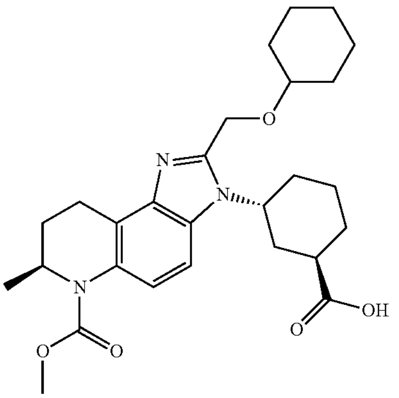 (1R,3R)-3-((S)-2-((cyclohexyloxy)methyl)-6-(methoxycarbonyl)-7-methyl-6,7,8,9-tetrahydro-3H-imidazo[4,5-f]quinolin-3-yl)cyclohexane-1-carboxylic acid | $^1$H NMR ($CD_3OD$, 400 MHz) δ (ppm): 7.91-7.90 (m, 2H), 5.07-5.00 (m, 3H), 4.96-4.87 (m, 1H), 3.83 (s, 3H), 3.68-3.66 (m, 1H), 3.09-3.02 (m, 2H), 2.47-2.41 (m, 3H), 2.28-2.41 (m, 2H), 2.08-1.90 (m, 5H), 1.89-1.78 (m, 3H), 1.74-1.33 (m, 8H), 1.17 (d, J = 6.8, 3H). LCMS (ES, m/z): 484 $[M + H]^+$. |
| 703 | 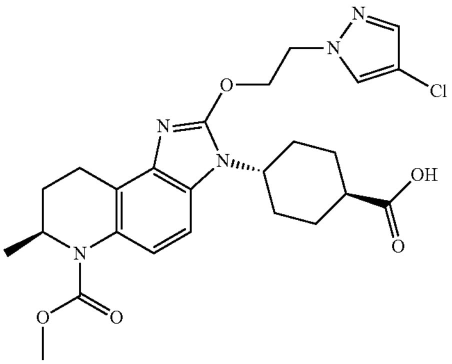 (1S,4R)-4-((S)-2-(2-(4-chloro-1H-pyrazol-1-yl)ethoxy)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.90 (s, 1H), 7.52 (s, 1H), 7.27-7.21 (m, 2H), 4.91-4.87 (m, 2H), 4.74-4.69 (m, 1H), 4.63-4.60 (m, 2H), 4.20-4.14 (m, 1H), 3.77 (s, 3H), 3.15-3.07 (m, 1H), 2.82-2.75 (m, 1H), 2.38-2.28 (m, 1H), 2.26-2.21 (m, 1H), 2.15-1.98 (m, 4H), 1.82-1.75 (m, 2H), 1.68-1.58 (m, 3H), 1.13 (d, J = 6.6 Hz, 3H). LCMS (ES, m/z): 516 $[M + H]^+$ |

TABLE 18-continued

| Example Number | Structure and Compound Name | $^1$H NMR, LCMS |
|---|---|---|
| 704 | 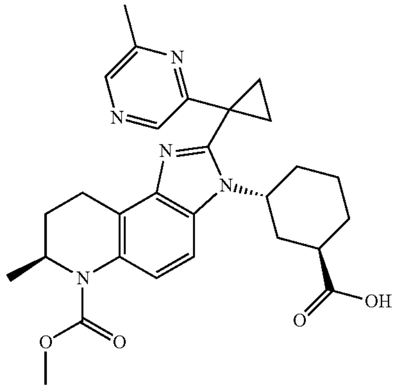 (1R,3R)-3-((S)-6-(methoxycarbonyl)-7-methyl-2-(1-(6-methylpyrazin-2-yl)cyclopropyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.27 (s, 1H), 7.80 (s, 1H), 7.58 (d, J = 8.8 Hz, 1H), 7.48 (d, J = 8.8 Hz, 1H), 4.79-4.76 (m, 2H), 3.80 (s, 3H), 3.33-2.90 (m, 3H), 2.48-2.00 (m, 8H), 1.99-1.37 (m, 9H), 1.17 (d, J = 6.8 Hz, 3H). LCMS (ES, m/z): 504 $[M + H]^+$ |
| 705 | 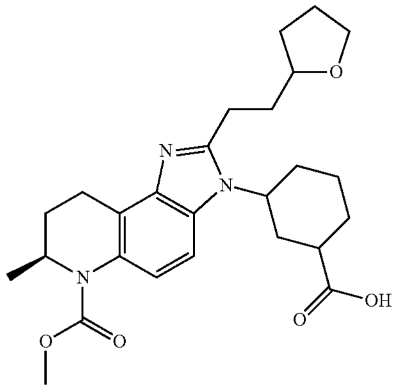 3-((7S)-6-(methoxycarbonyl)-7-methyl-2-(2-(tetrahydrofuran-2-yl)ethyl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.52 (d, J = 9.2 Hz, 1H), 7.39 (d, J = 8.8 Hz, 1H), 4.82-4.69 (m, 2H), 4.07-3.94 (m, 1H), 3.93-3.84 (m, 1H), 3.83-3.70 (m, 4H), 3.23-3.08 (m, 2H), 3.07-2.97 (m, 2H), 2.95-2.85 (m, 1H), 2.51-2.34 (m, 2H), 2.33-2.19 (m, 3H), 2.15-2.02 (m, 2H), 2.01-1.84 (m, 5H), 1.81-1.55 (m, 4H), 1.14 (d, J = 6.4 Hz, 3H). LCMS (ES, m/z): 470 $[M + H]^+$. |
| 706 | 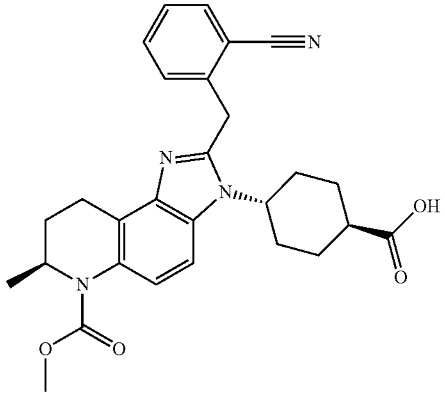 (1S,4R)-4-((S)-2-(2-cyanobenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.82 (d, J = 7.6 Hz, 1H), 7.62-7.40 (m, 4H), 7.26 (d, J = 8.0 Hz, 1H), 4.80-4.70 (m, 1H), 4.65 (s, 2H), 4.30-4.10 (m, 1H), 3.75 (s, 3H), 3.25-3.10 (m, 1H), 2.98-2.85 (m, 1H), 2.45-2.00 (m, 6H), 1.75-1.40 (m, 5H), 1.13 (d, J = 6.4 Hz, 3H). LCMS (ES, m/z): 487 $[M + H]^+$. |

TABLE 18-continued

| Example Number | Structure and Compound Name | $^1$H NMR, LCMS |
|---|---|---|
| 707 | 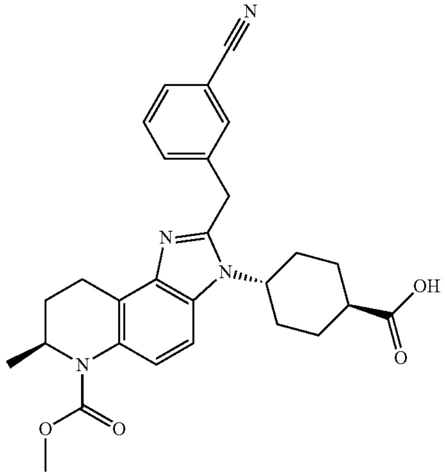 (1S,4R)-4-((S)-2-(3-cyanobenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.75-7.63 (m, 2H), 7.63-7.37 (m, 4H), 4.84-4.69 (m, 1H), 4.49 (s, 2H), 4.32-4.18 (m, 1H), 3.79 (s, 3H), 3.29-3.12 (m, 1H), 3.04-2.91 (m, 1H), 2.51-2.36 (m, 1H), 2.34-2.16 (m, 3H), 2.15-2.00 (m, 2H), 1.85-1.69 (m, 1H), 1.63-1.41 (m, 4H), 1.16 (d, J = 6.8 Hz, 3H). LCMS (ES, m/z): 487 [M + H]$^+$. |
| 708 | 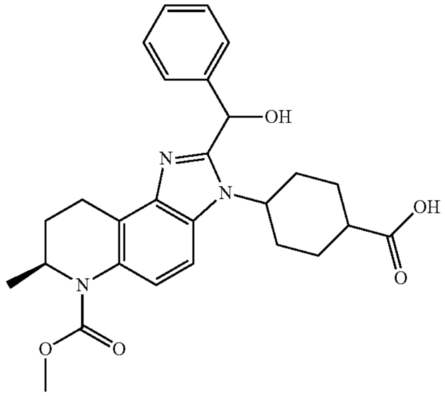 4-((7S)-2-(hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.47-7.28 (m, 7H), 6.25 (s, 1H), 4.84-4.74 (m, 1H), 4.68-4.54 (m, 1H), 3.79 (s, 3H), 3.33-3.18 (m, 1H), 3.03-2.96 (m, 1H), 2.46-2.12 (m, 4H), 2.05-1.72 (m, 4H), 1.59-1.45 (m, 1H), 1.16 (d, J = 6.6 Hz, 3H), 1.14-1.02 (m, 1H), 0.99-0.87 (m, 1H). LCMS (ES, m/z): 478 [M + H]$^+$. |

TABLE 18-continued

| Example Number | Structure and Compound Name | $^1$H NMR, LCMS |
|---|---|---|
| 709 | 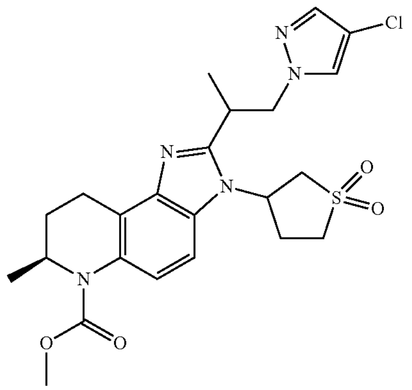<br>methyl (7S)-2-(1-(4-chloro-1H-pyrazol-1-yl)propan-2-yl)-3-((R)-1,1-dioxidotetrahydro thiophen-3-yl)-7-methyl-3,7,8,9-tetrahydro-6H-imidazo[4,5-f]quinoline-6-carboxylate<br>4$^{th}$ eluting isomer | $^1$H-NMR (CD$_3$OD, 300 MHz) δ (ppm): 7.59-7.40 (m, 4H), 5.60-5.40 (m, 1H), 4.92-4.42 (m, 3H), 4.02-3.88 (m, 1H), 3.75-3.35 (m, 6H), 3.32-3.15 (m, 2H), 3.30-2.91 (m, 2H), 2.32-2.24 (m, 2H), 1.73-1.68 (m, 1H), 1.40 (d, J = 6.9 Hz, 3H), 1.12 (d, J = 6.6 Hz, 3H). LCMS (ES, m/z): 506 [M + H]$^+$. |
| 710 | 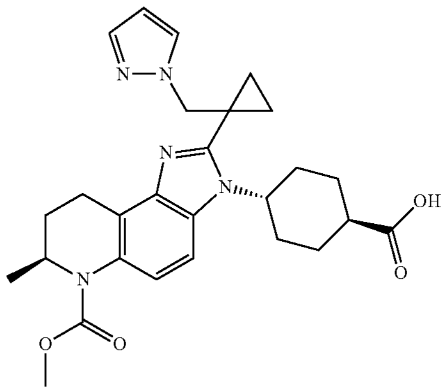<br>(1S,4R)-4-((S)-2-(1-((1H-pyrazol-1-yl)methyl)cyclopropyl)-6-(methoxycarbonyl)-7-methyl-6,7,8,9-tetrahydro-3H-imidazo[4,5-f]quinolin-3-yl)cyclohexane-1-carboxylic acid | $^1$H-NMR (CD$_3$OD, 400 MHz) δ (ppm): 7.57-7.44 (m, 3H), 7.37 (d, J = 8.8 Hz, 1H), 6.27-6.25 (m, 1H), 4.81-4.67 (m, 1H), 4.48-4.38 (m, 3H), 3.77 (s, 3H), 3.22-3.07 (m, 1H), 2.98-2.81 (m, 1H), 2.46-2.17 (m, 4H), 2.12-2.08 (m, 2H), 1.83-1.50 (m, 5H), 1.49-1.37 (m, 2H), 1.26-1.17 (m, 2H), 1.12 (d, J = 6.8 Hz, 3H). LCMS (ES, m/z): 492 [M + H]$^+$. |
| 711 | 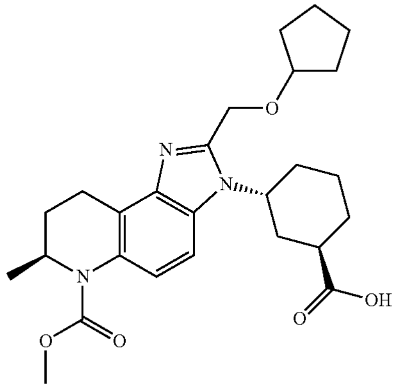<br>(1R,3R)-3-((S)-2-((cyclopentyloxy)methyl)-6-(methoxycarbonyl)-7-methyl-6,7,8,9-tetrahydro-3H-imidazo[4,5-f]quinolin-3-yl)cyclohexane-1-carboxylic acid | $^1$H NMR (CD$_3$OD, 400 MHz) δ (ppm): 7.77-7.56 (m, 1H), 7.47-7.45 (m, 1H), 4.91-4.82 (m, 2H), 4.79-4.65 (m, 1H), 4.18-4.09 (m, 1H), 3.79 (s, 3H), 3.20-3.14 (m, 1H), 2.99-2.92 (m, 2H), 2.47-2.26 (m, 5H), 1.98-1.45 (m, 14H), 1.14 (d, J = 6.8 Hz, 3H). LCMS (ES, m/z): 470 [M + H]$^+$. |

TABLE 18-continued

| Example Number | Structure and Compound Name | $^1$H NMR, LCMS |
| --- | --- | --- |
| 712 | 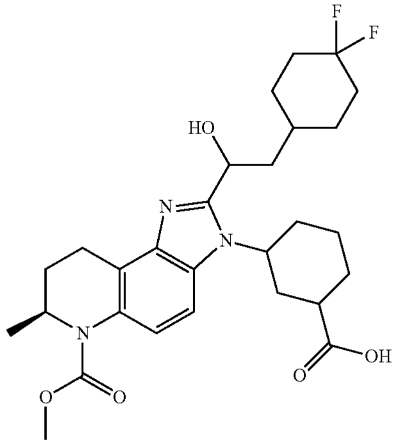 3-((7S)-2-(2-(4,4-difluorocyclohexyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.63-7.49 (m, 1H), 7.46-7.28 (m, 1H), 5.32-5.11 (m, 1H), 5.11-4.97 (m, 1H), 4.82-4.63 (m, 1H), 3.78 (s, 3H), 3.28-3.17 (m, 1H), 3.06-2.88 (m, 2H), 2.63-2.32 (m, 2H), 2.32-2.18 (m, 3H), 2.11-1.89 (m, 8H), 1.84-1.66 (m, 6H), 1.49-1.33 (m, 2H), 1.15 (d, J = 6.8 Hz, 3H). LCMS (ES, m/z): 534 $[M + H]^+$. |
| 713 | 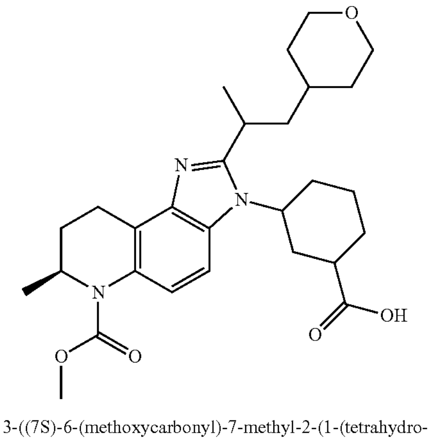 3-((7S)-6-(methoxycarbonyl)-7-methyl-2-(1-(tetrahydro-2H-pyran-4-yl)propan-2-yl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.98-7.78 (m, 2H), 5.14-5.12 (m, 1H), 4.01-3.88 (m, 2H), 3.88-3.69 (m, 4H), 3.50-3.38 (m, 2H), 3.30-3.20 (m, 1H), 3.21-3.06 (m, 2H), 3.06-2.93 (m, 1H), 2.67-2.40 (m, 2H), 2.40-2.18 (m, 3H), 2.12-1.93 (m, 3H), 1.93-1.73 (m, 4H), 1.67-1.61 (m, 3H), 1.56 (d, J = 6.8 Hz, 3H), 1.50-1.29 (m, 2H), 1.18 (d, J = 6.8 Hz, 3H). LCMS (ES, m/z): 498 $[M + H]^+$. |

TABLE 18-continued

| Example Number | Structure and Compound Name | $^1$H NMR, LCMS |
|---|---|---|
| 714 | 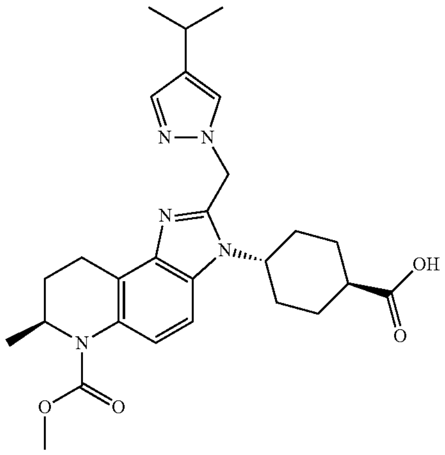 (1S,4R)-4-((S)-2-((4-isopropyl-1H-pyrazol-1-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.61-7.30 (m, 4H), 5.76-5.53 (m, 2H), 4.83-4.69 (m, 1H), 4.53-4.30 (m, 1H), 3.79 (s, 3H), 3.27-3.13 (m, 1H), 3.04-2.93 (m, 1H), 2.93-2.78 (m, 1H), 2.59-2.38 (m, 1H), 2.31-1.99 (m, 5H), 1.87-1.71 (m, 1H), 1.71-1.47 (m, 4H), 1.20 (d, J = 6.8 Hz, 6H), 1.15 (d, J = 6.8 Hz, 6H). .LCMS (ES, m/z): 494 $[M + H]^+$ |
| 715 | 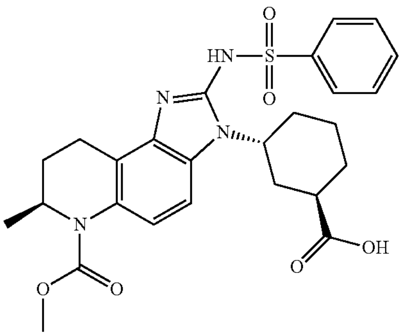 (1R,3R)-3-((S)-6-(methoxycarbonyl)-7-methyl-2-(phenylsulfonamido)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.01-7.95 (m, 2H), 7.59-7.52 (m, 3H), 7.49-7.43 (m, 1H), 7.38-7.31 (m, 1H), 4.92-4.83 (m, 1H), 4.79-4.71 (m, 1H), 3.79 (s, 3H), 3.03-2.96 (m, 1H), 2.90-2.82 (m, 1H), 2.79-2.71 (m, 1H), 2.45-2.39 (m, 1H), 2.38-2.21 (m, 4H), 1.89-1.72 (m, 3H), 1.64-1.52 (m, 2H), 1.16 (d, J = 6.8 Hz, 3H). LCMS (ES, m/z): 527 $[M + H]^+$. |
| 716 | 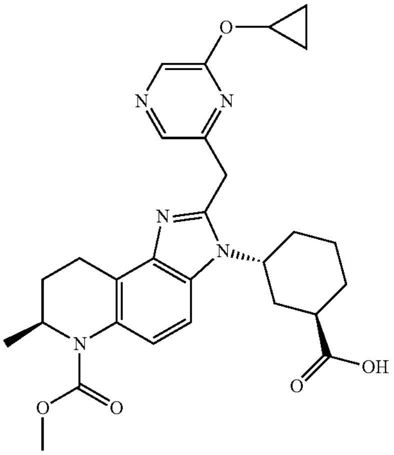 (1R,3R)-3-((S)-2-((6-cyclopropoxypyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.17 (s, 1H), 8.09 (s, 1H), 7.54 (d, J = 9.2 Hz, 1H), 7.42 (d, J = 9.2 Hz, 1) 4.88-4.54 (m, 3H), 4.23-4.21 (m, 1H), 3.78 (s, 3H), 3.19-2.92 (m, 3H), 2.39-2.10 (m, 6H), 1.81-1.69 (m, 4H), 1.45-1.42 (m, 1H), 1.15 (d, J = 6.4 Hz, 3H), 6.70-0.67 (m, 4H). LCMS (ES, m/z): 520 $[M + H]^+$ |

TABLE 18-continued

| Example Number | Structure and Compound Name | $^1H$ NMR, LCMS |
|---|---|---|
| 717 | 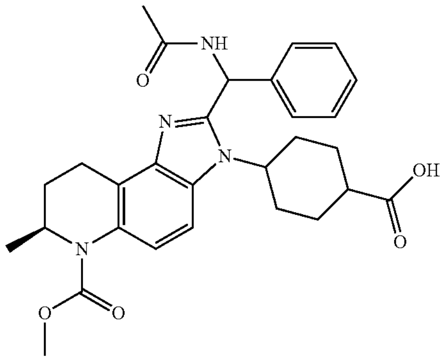 4-((7S)-2-(acetamido(phenyl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 300 MHz) δ (ppm): 7.52-7.28 (m, 7H), 6.57 (s, 1H), 4.81-4.67 (m, 1H), 4.36-4.19 (m, 1H), 3.79 (s, 3H), 3.30-3.21 (m, 1H), 3.04-2.88 (m, 1H), 2.50-1.88 (m, 10H), 1.82-1.57 (m, 2H), 1.38-1.24 (m, 1H), 1.22-1.01 (m, 4H). LCMS (ES, m/z): 519 $[M + H]^+$ |
| 718 | 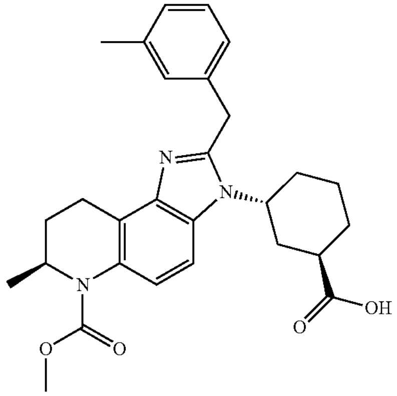 (1R,3R)-3-((S)-6-(methoxycarbonyl)-7-methyl-2-(3-methylbenzyl)-6,7,8,9-tetrahydro-3H-imidazo[4,5-f]quinolin-3-yl)cyclohexane-1-carboxylic acid | $^1H$-NMR ($CD_3OD$, 300 MHz) δ (ppm): 7.51-7.41 (m, 2H), 7.17-7.03 (m, 4H), 4.77-4.69 (m, 2H), 4.43-4.29 (m, 2H), 3.76 (s, 3H), 3.21-3.14 (m, 1H), 2.99-2.92 (m, 2H), 2.43-2.03 (m, 8H), 1.77-1.57 (m, 3H), 1.28-1.12 (m, 5H). LCMS (ES, m/z): 476 $[M + H]^+$. |
| 719 | 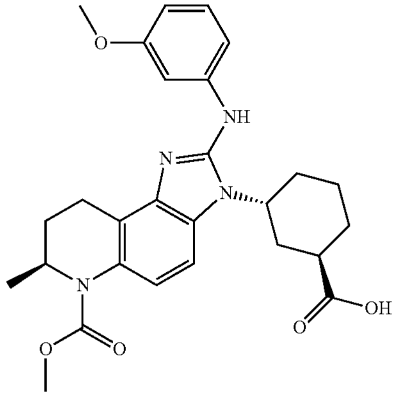 (1R,3R)-3-((S)-6-(methoxycarbonyl)-2-((3-methoxyphenyl)amino)-7-methyl-6,7,8,9-tetrahydro-3H-imidazo[4,5-f]quinolin-3-yl)cyclohexane-1-carboxylic acid | LCMS (ES, m/z): 493 $[M + H]^+$ |

TABLE 18-continued

| Example Number | Structure and Compound Name | $^1$H NMR, LCMS |
|---|---|---|
| 720 | 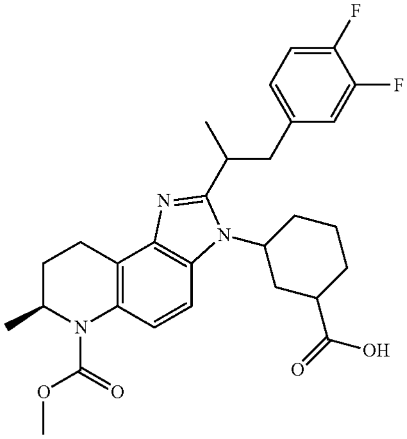 3-((7S)-2-(1-(3,4-difluorophenyl)propan-2-yl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.50-7.42 (d, J = 9.2 Hz, 1H), 7.36-7.26 (d, J = 8.8 Hz, 1H), 7.24-7.13 (m, 1H), 7.16-7.01 (m, 2H), 5.01-4.89 (m, 1H), 4.77-4.66 (m, 1H), 3.76 (s, 3H), 3.71-3.54 (m, 1H), 3.42-3.51 (m, 1H), 3.22-3.10 (m, 1H), 3.04-2.75 (m, 3H), 2.45-2.21 (m, 4H), 2.15-1.96 (m, 1H), 1.95-1.78 (m, 2H), 1.78-1.62 (m, 3H), 1.34 (d, J = 6.8 Hz, 3H), 1.13 (d, J = 6.8 Hz, 3H). LCMS (ES, m/z): 526 $[M + H]^+$. |
| 721 | 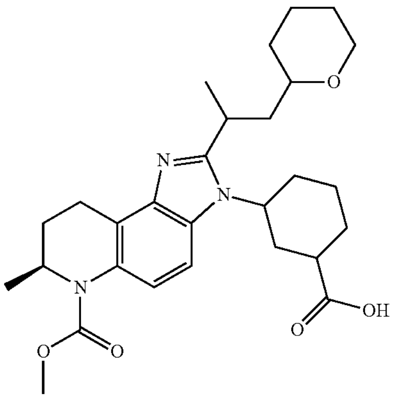 3-((7S)-6-(methoxycarbonyl)-7-methyl-2-(2-(tetrahydro-2H-pyran-2-yl)ethyl)-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.52 (d, J = 9.2 Hz, 1H), 7.39 (d, J = 9.2 Hz, 1H), 4.82-4.69 (m, 2H), 4.02-3.91 (m, 1H), 3.78 (s, 3H), 3.51-3.39 (m, 1H), 3.24-3.14 (m, 1H), 3.13-3.01 (m, 2H), 3.01-2.98 (m, 1H), 2.94-2.84 (m, 1H), 2.52-2.34 (m, 2H), 2.34-2.17 (m, 3H), 2.10-1.82 (m, 5H), 1.79-1.63 (m, 4H), 1.62-1.45 (m, 3H), 1.43-1.25 (m, 2H), 1.14 (d, J = 6.4 Hz, 3H). LCMS (ES, m/z): 484 $[M + H]^+$. |
| 722 | 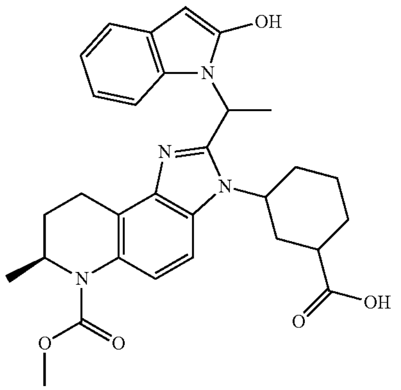 3-((7S)-2-(1-(2-hydroxy-1H-indol-1-yl)ethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 300 MHz) δ (ppm): 7.62-7.39 (m, 2H), 7.23-7.11 (m, 1H), 6.95-6.23 (m, 3H), 4.83-4.71 (m, 1H), 4.45-3.98 (m, 1H), 3.85-3.63 (m, 4H), 3.33-3.15 (m, 1H), 2.93-2.75 (m, 2H), 2.61-2.12 (m, 5H), 2.10-1.55 (m, 6H), 1.41-1.30 (m, 4H), 1.25-1.12 (m, 3H). LCMS (ES, m/z): 531 $[M + H]^+$. |

TABLE 18-continued

| Example Number | Structure and Compound Name | $^1$H NMR, LCMS |
|---|---|---|
| 723 | 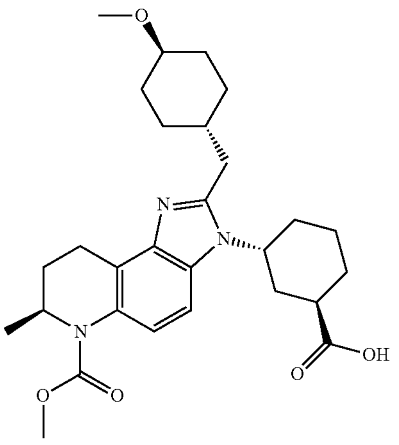 (1R,3R)-3-((S)-6-(methoxycarbonyl)-2-(((1R,4R)-4-methoxycyclohexyl)methyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.49-7.34 (m, 2H), 4.88-4.72 (m, 2H), 3.76 (s, 3H), 3.32-3.00 (m, 5H), 2.93-2.86 (m, 4H), 2.42-2.06 (m, 7H), 1.89-1.66 (m, 8H), 1.32-1.11 (m, 7H). LCMS (ES, m/z): 498 $[M + H]^+$. |
| 724 | 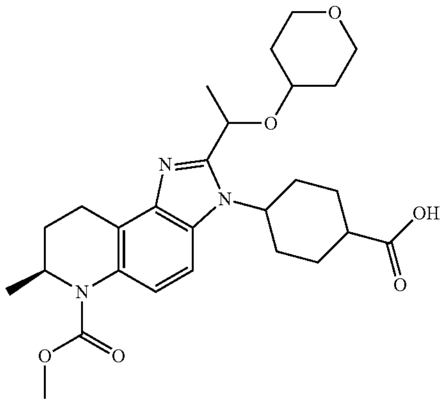 4-((7S)-6-(methoxycarbonyl)-7-methyl-2-(1-((tetrahydro-2H-pyran-4-yl)oxy)ethyl)-6,7,8,9-tetrahydro-3H-imidazo[4,5-f]quinolin-3-yl)cyclohexane-1-carboxylic acid 1st eluting isomer | $^1$H NMR (400 MHz, $CD_3OD$) δ (ppm): 7.60 (d, J = 9.2 Hz, 1H), 7.43 (d, J = 8.8 Hz, 1H), 5.19-5.17 (m, 1H), 4.96-4.93 (m, 1H), 4.88-4.76 (m, 1H), 3.96-3.93 (m, 1H), 3.89-3.87 (m, 1H), 3.79 (s, 3H), 3.64-3.62 (m, 1H), 3.47-3.38 (m, 2H), 3.16-3.14 (m, 1H), 2.94-2.90 (m, 1H), 2.54-2.41 (m, 3H), 2.27-2.24 (m, 3H), 2.06-1.97 (m, 3H), 1.81-1.76 (m, 1H), 1.74-1.55 (m, 8H), 1.14 (d, J = 6.8 Hz, 3H). LCMS (ES, m/z): 500 $[M + H]^+$ |
| 725 | 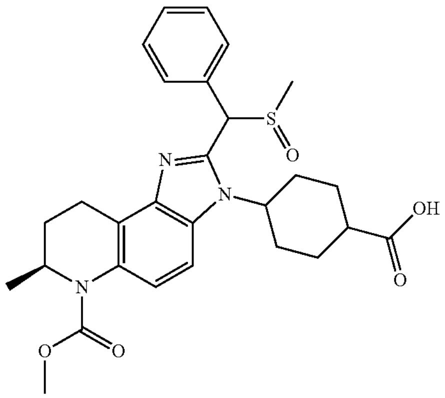 4-((7S)-6-(methoxycarbonyl)-7-methyl-2-((1R)-(methylsulfinyl)(phenyl)methyl)-6,7,8,9-tetrahydro-3H-imidazo[4,5-f]quinolin-3-yl)cyclohexane-1-carboxylic acid 1st eluting isomer | $^1$H-NMR (DMSO, 400 MHz) δ (ppm): 7.66-7.21 (m, 7H), 6.11-5.79 (m, 1H), 4.74-4.57 (m, 1H), 4.55-4.24 (m, 1H), 3.67 (d, J = 5.7 Hz, 3H), 3.21-3.00 (m, 1H), 2.97-2.82 (m, 1H), 2.65 (s, 1H), 2.45 (s, 2H), 2.39-2.09 (m, 3H), 2.09-1.89 (m, 3H), 1.87-1.73 (m, 1H), 1.73-1.40 (m, 2H), 1.31-1.18 (m, 1H), 1.09 (d, J = 6.4 Hz, 3H), 0.89-0.73 (m, 1H). LCMS (ES, m/z): 524 $[M + H]^+$. |

TABLE 18-continued

| Example Number | Structure and Compound Name | $^1$H NMR, LCMS |
|---|---|---|
| 726 | 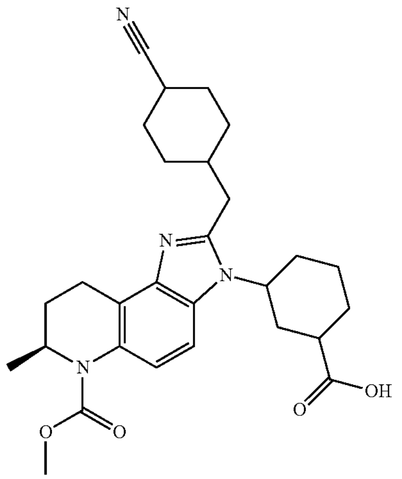 3-((7S)-2-((4-cyanocyclohexyl)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.53 (d, J = 8.8 Hz, 1H), 7.37 (d, J = 8.8 Hz, 1H), 4.81-4.75 (m, 2H), 3.78 (s, 3H), 3.18-3.15 (m, 1H), 3.08-3.06 (m, 1H), 2.97-2.89 (m, 4H), 2.42-2.32 (m, 2H), 2.31-2.24 (m, 3H), 2.03-1.88 (m, 6H), 1.85-1.80 (m, 1H), 1.75-1.70 (m, 5H), 1.51-1.47 (m, 2H), 1.15 (d, J = 6.4 Hz, 3H). LCMS (ES, m/z): 493 $[M + H]^+$. |
| 727 | 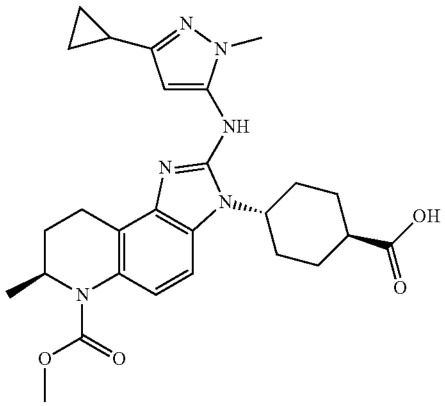 (1S,4r)-4-((S)-2-((3-cyclopropyl-1-methyl-1H-pyrazol-5-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 508 $[M + H]^+$ |

TABLE 18-continued

| Example Number | Structure and Compound Name | $^1$H NMR, LCMS |
|---|---|---|
| 728 | 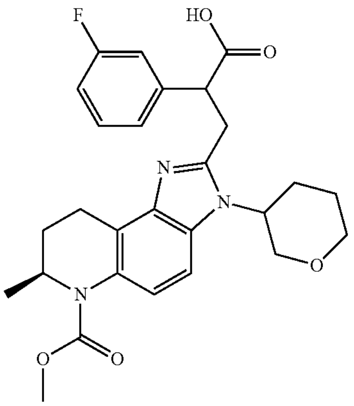 2-(3-fluorophenyl)-3-((7S)-6-(methoxycarbonyl)-7-methyl-3-((S)-tetrahydro-2H-pyran-3-yl)-6,7,8,9-tetrahydro-3H-imidazo[4,5-f]quinolin-2-yl)propanoic acid 2nd eluting isomer | $^1$H-NMR ($CD_3OD$, 300 MHz) δ (ppm): 7.47-7.19 (m, 5H), 7.17-7.14 (m, 1H), 4.74-4.47 (m, 2H), 4.18-3.97 (m, 4H), 3.75-3.45 (m, 5H), 3.42-3.28 (m, 2H), 2.89-2.84 (m, 1H), 2.21-2.20 (m, 2H), 1.76-1.67 (m, 3H), 1.45-1.35 (m, 1H), 1.12 (d, J = 6.6 Hz, 3H). LCMS (ES, m/z): 496 [M + H]$^+$. |
| 729 | 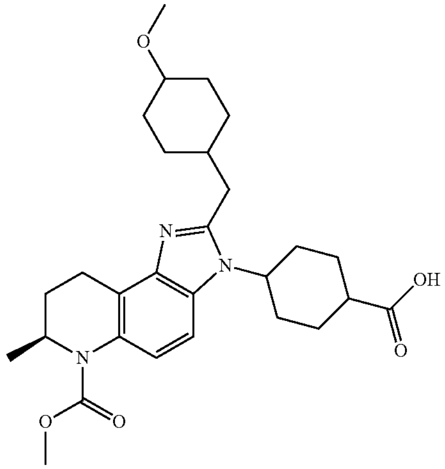 4-((7S)-6-(methoxycarbonyl)-2-((4-methoxycyclohexyl)methyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 300 MHz) δ (ppm): 7.52 (d, J = 9.0 Hz, 1H), 7.38 (d, J = 9.0 Hz, 1H), 4.83-4.67 (m, 1H), 4.44-4.29 (m, 1H), 3.78 (s, 3H), 3.52-3.43 (m, 1H), 3.25-3.11 (m, 1H), 2.98-2.83 (m, 3H), 2.55-2.37 (m, 3H), 2.33-2.15 (m, 4H), 2.05-1.84 (m, 5H), 1.81-1.62 (m, 4H), 1.60-1.36 (m, 7H), 1.14 (d, J = 6.6 Hz, 3H). LCMS (ES, m/z): 498 [M + H]$^+$. |

TABLE 18-continued

| Example Number | Structure and Compound Name | $^1$H NMR, LCMS |
|---|---|---|
| 730 | 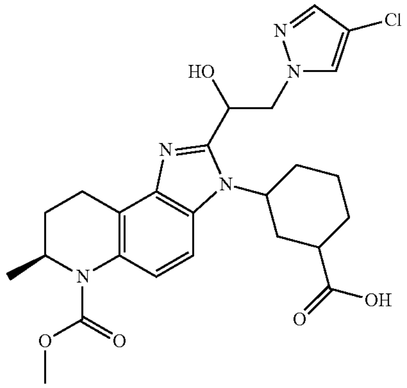 3-((7S)-2-(2-(4-chloro-1H-pyrazol-1-yl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.85 (s, 1H), 7.55 (d, J = 8.8 Hz, 1H), 7.49-7.39 (m, 2H), 5.45-5.35 (m, 1H), 5.06-4.93 (m, 1H), 4.85-4.67 (m, 3H), 3.79 (s, 3H), 3.29-3.17 (m, 1H), 3.00-2.89 (m, 2H), 2.49-2.16 (m, 4H), 2.04-1.95 (m, 1H), 1.93-1.82 (m, 1H), 1.79-1.61 (m, 3H), 1.36-1.28 (m, 1H), 1.15 (d, J = 6.4 Hz, 3H). LCMS (ES, m/z): 516 $[M + H]^+$. |
| 731 | 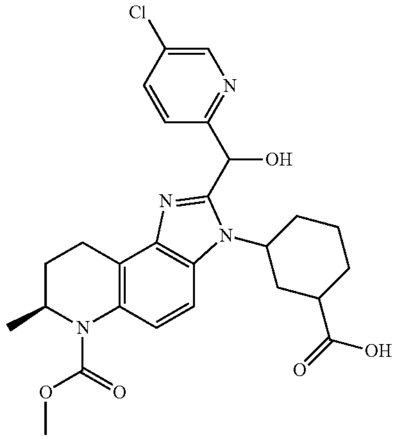 3-((7S)-2-((5-chloropyridin-2-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 8.46 (s, 1H), 8.05-8.01 (m, 1H), 7.95-7.89 (m, 1H), 7.88-7.80 (m, 2H), 6.53 (s, 1H), 5..2-4.88 (m, 1H), 4.85-4.80 (m, 1H), 3.83 (s, 3H), 3.18-2.95 (m, 3H), 2.53-2.10 (m, 5H), 2.02-1.62 (m, 4H), 1.59-1.45 (m, 1H), 1.18 (d, J = 6.8 Hz, 3H). LCMS (ES, m/z): 513 $[M + H]^+$. |
| 732 | 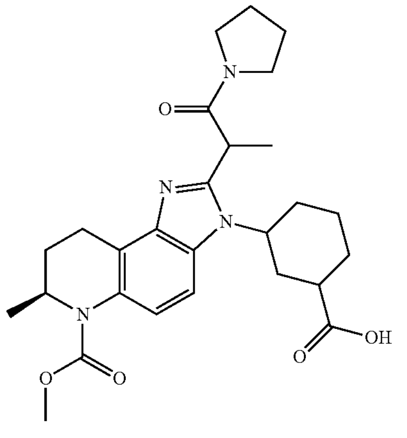 3-((7S)-6-(methoxycarbonyl)-7-methyl-2-(1-oxo-1-(pyrrolidin-1-yl)propan-2-yl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.54-7.48 (m, 1H), 7.42-7.35 (m, 1H), 4.80-4.67 (m, 1H), 4.50-4.45 (m, 1H), 4.41-4.31 (m, 1H), 3.78 (s, 3H), 3.75-3.56 (m, 2H), 3.56-3.40 (m, 2H), 3.30-3.19 (m, 1H), 3.01-2.97-2.86 (m, 2H), 2.56-2.44 (m, 1H), 2.34-2.21 (m, 4H), 2.13-2.00 (m, 2H), 1.97-1.83 (m, 4H), 1.82-1.62 (m, 5H), 1.56-1.42 (m, 1H), 1.14 (d, J = 6.8 Hz, 3H). LCMS (ES, m/z): 497 $[M + H]^+$. |

TABLE 18-continued

| Example Number | Structure and Compound Name | $^1H$ NMR, LCMS |
|---|---|---|
| 733 | 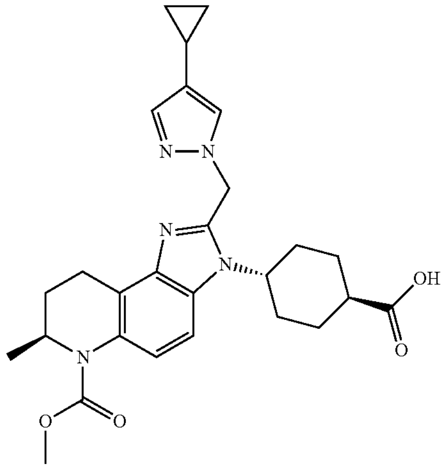 (1S,4R)-4-((S)-2-((4-cyclopropyl-1H-pyrazol-1-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.86-7.81 (m, 2H), 7.68 (s, 1H), 7.38 (s, 1H), 5.96-5.82 (m, 2H), 4.90-4.82 (m, 1H), 4.70-4.57 (m, 1H), 3.82 (s, 3H), 3.19-3.07 (m, 1H), 3.07-2.96 (m, 1H), 2.61-2.51 (m, 1H), 2.40-2.14 (m, 5H), 1.97-1.85 (m, 1H), 1.82-1.72 (m, 2H), 1.71-1.53 (m, 3H), 1.17 (d, J = 6.4 Hz, 3H), 0.94-0.82 (m, 2H), 0.57-0.49 (m, 2H). LCMS (ES, m/z): 492 $[M + H]^+$. |
| 734 | 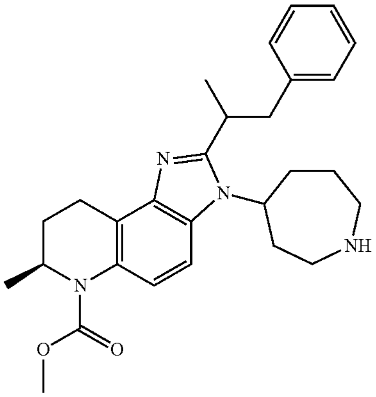 methyl 3-((7S)-azepan-4-yl)-7-methyl-2-(1-phenylpropan-2-yl)-3,7,8,9-tetrahydro-6H-imidazo[4,5-f]quinoline-6-carboxylate 2nd eluting isomer | $^1$H-NMR ($CD_3OD$, 400 MHz) δ (ppm): 7.40-7.20 (m, 2H), 7.18-7.05 (m, 3H), 7.10-6.98 (m, 2H), 4.79-4.66 (m, 1H), 4.37-4.33 (m, 1H), 3.77 (s, 3H), 3.64-3.51 (m, 1H), 3.29-3.02 (m, 4H), 3.02-2.78 (m, 3H), 2.70-2.58 (m, 1H), 2.49-2.32 (m, 1H), 2.32-2.14 (m, 2H), 1.98-1.62 (m, 4H), 1.53 (d, J = 6.8 Hz, 3H), 1.12 (d, J = 6.4 Hz, 3H), 0.79-0.75 (m, 1H). LCMS (ES, m/z): 461 $[M + H]^+$. |
| 735 | 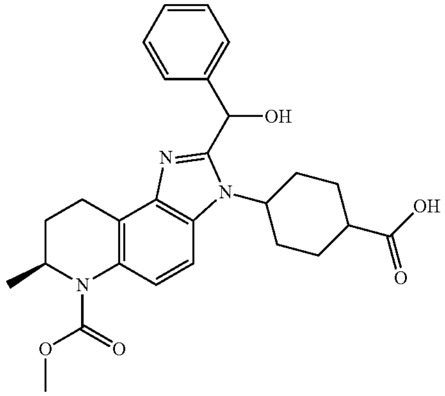 4-((7S)-2-(hydroxy(phenyl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.47-7.28 (m, 7H), 6.25 (s, 1H), 4.84-4.74 (m, 1H), 4.68-4.54 (m, 1H), 3.79 (s, 3H), 3.33-3.18 (m, 1H), 3.08-2.96 (m, 1H), 2.46-1.72 (m, 8H), 1.59-1.45 (m, 1H), 1.16 (d, J = 6.6 Hz, 3H), 1.14-1.05 (m, 1H), 1.01-0.87 (m, 1H). LCMS (ES, m/z): 478 $[M + H]^+$. |

TABLE 18-continued

| Example Number | Structure and Compound Name | $^1$H NMR, LCMS |
|---|---|---|
| 736 | 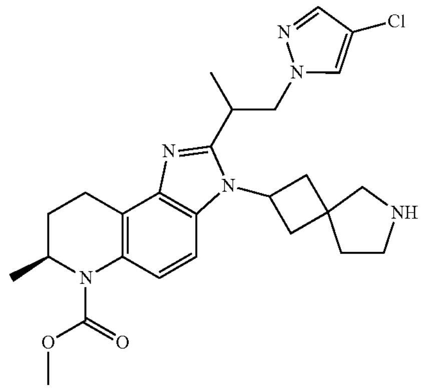 methyl 2-((7S)-1-(4-chloro-1H-pyrazol-1-yl)propan-2-yl)-7-methyl-3-(6-azaspiro[3.4]octan-2-yl)-3,7,8,9-tetrahydro-6H-imidazo[4,5-f]quinoline-6-carboxylate 4$^{th}$ eluting isomer | $^1$H-NMR ($CD_3OD$, 300 MHz) δ (ppm): 7.53 (s, 1H), 7.51-7.40 (m, 3H), 5.08-4.94 (m, 1H), 4.82-4.71 (m, 1H), 4.66-4.52 (m, 1H), 4.52-4.38 (m, 1H), 3.99-3.85 (m, 1H), 3.79 (s, 3H), 3.43-3.36 (m, 4H), 3.29-3.14 (m, 1H), 3.08-2.89 (m, 3H), 2.72-2.54 (m, 1H), 2.54-2.38 (m, 1H), 2.38-2.21 (m, 3H), 1.83-1.67 (m, 1H), 1.43 (d, J = 6.9 Hz, 3H), 1.16 (d, J = 6.6 Hz, 3H). LCMS (ES, m/z): 497 [M + H]$^+$. |
| 737 | 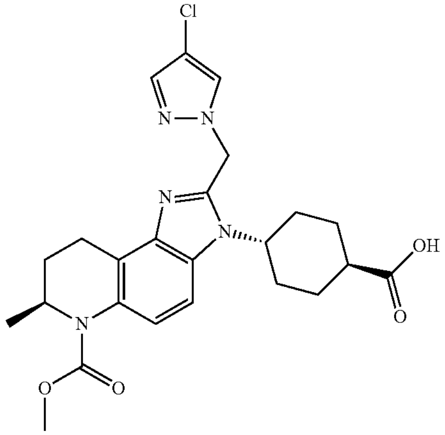 (1S,4R)-4-((S)-2-((4-chloro-1H-pyrazol-1-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.82 (s, 1H), 7.54-7.43 (m, 3H), 5.73-5.63 (m, 2H), 4.78-4.75 (m, 1H), 4.59-4.55 (m, 1H), 3.76 (s, 3H), 3.18-3.13 (m, 1H), 2.99-2.93 (m, 1H), 2.51-2.45 (m, 1H), 2.32-2.20 (m, 3H), 2.13-2.09 (m, 2H), 1.77-1.71 (m, 2H), 1.67-1.58 (m, 3H), 1.12 (d, J = 6.4 Hz, 3H). LCMS (ES, m/z): 486 [M + H]$^+$. |
| 738 | 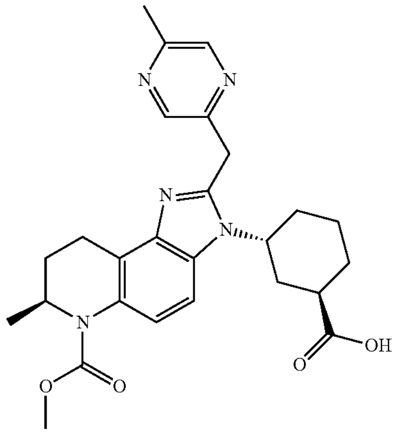 (1R,3R)-3-((S)-6-(methoxycarbonyl)-7-methyl-2-((5-methylpyrazin-2-yl)methyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 8.48 (s, 1H), 8.41 (s, 1H), 7.53-7.38 (m, 2H), 4.77-4.55 (m, 4H), 3.75 (s, 3H), 3.25-2.85 (m, 3H), 2.50 (s, 3H), 2.40-2.15 (m, 5H), 1.80-1.45 (m, 5H), 1.13 (d, J = 6.6 Hz, 3H). LCMS (ES, m/z): 478 [M + H]$^+$. |

TABLE 18-continued

| Example Number | Structure and Compound Name | $^1$H NMR, LCMS |
|---|---|---|
| 739 | 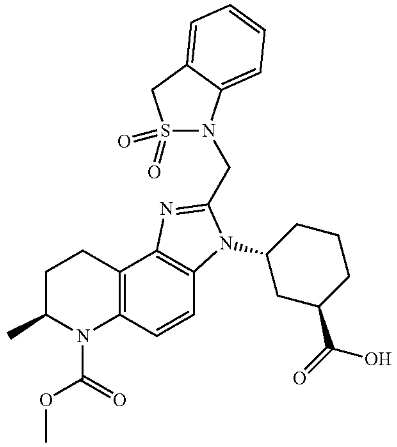 (1R,3R)-3-((S)-2-((2,2-dioxidobenzolclisothiazol-1(3H)-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.57 (d, J = 8.8 Hz, 1H), 7.47 (d, J = 9.2 Hz, 1H), 7.36 (d, J = 7.6 Hz, 1H), 7.32-7.22 (m, 1H), 7.06-7.02 (m, 2H), 5.18-5.05 (m, 1H), 5.02-4.91 (m, 2H), 4.82-4.68 (m, 2H), 4.56-4.43 (m, 1H), 3.79 (s, 3H), 3.28-3.16 (m, 1H), 3.05-2.86 (m, 2H), 2.56-2.41 (m, 1H), 2.38-2.14 (m, 4H), 2.03-1.88 (m, 1H), 1.86-1.72 (m, 2H), 1.68-1.65 (m, 2H), 1.16 (d, J = 6.8 Hz, 3H). LCMS (ES, m/z): 553 [M + H]$^+$. |
| 740 | 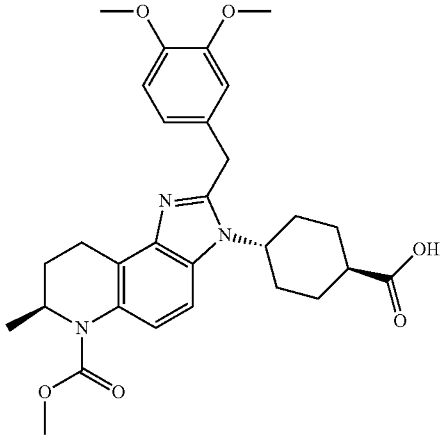 (1S,4R)-4-((S)-2-(3,4-dimethoxybenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.49-7.30 (m, 2H), 6.97-6.84 (m, 2H), 6.82-6.69 (m, 1H), 4.80-4.68 (m, 1H), 4.37-4.24 (m, 3H), 3.82-3.71 (m, 9H), 3.27-3.11 (m, 1H), 3.02-2.86 (m, 1H), 2.50-2.31 (m, 1H), 2.31-2.12 (m, 3H), 2.12-1.97 (m, 2H), 1.81-1.66 (m, 1H), 1.60-1.31 (m, 4H), 1.14 (d, J = 6.6 Hz, 3H). LCMS (ES, m/z): 522 [M + H]$^+$ |
| 741 | 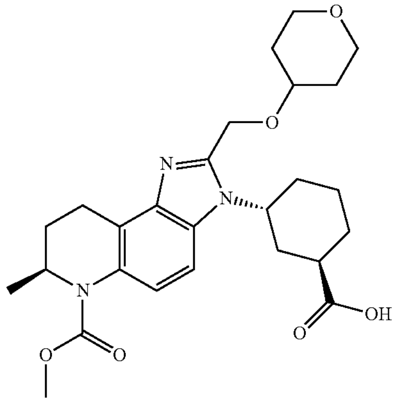 (1R,3R)-3-((S)-6-(methoxycarbonyl)-7-methyl-2-(((tetrahydro-2H-pyran-4-yl)oxy)methyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.57 (d, J = 9.0 Hz, 1H), 7.46 (d, J = 9.0 Hz, 1H), 5.01-4.89 (m, 2H), 4.83-4.67 (m, 2H), 4.03-3.85 (m, 2H), 3.84-3.68 (m, 4H), 3.58-3.43 (m, 2H), 3.27-3.09 (m, 1H), 3.06-2.89 (m, 2H), 2.56-2.15 (m, 5H), 2.09-1.86 (m 4H), 1.82-1.49 (m 5H), 1.14 (d, J = 6.6 Hz, 3H). LCMS (ES, m/z): 486 [M + H]$^+$. |

TABLE 18-continued

| Example Number | Structure and Compound Name | $^1$H NMR, LCMS |
|---|---|---|
| 742 | 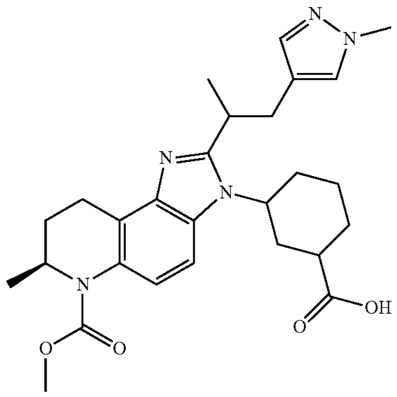 3-((7S)-6-(methoxycarbonyl)-7-methyl-2-(1-(1-methyl-1H-pyrazol-4-yl)propan-2-yl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.42 (d, J = 8.8 Hz, 1H), 7.32 (d, J = 8.8 Hz, 1H), 7.29-7.27 (m, 1H), 7.27-7.22 (s, 1H), 4.73-4.70 (m, 2H), 3.76 (s, 3H), 3.72 (s, 3H), 3.55-3.53 (m, 1H), 3.30-3.21 (m, 1H), 3.05-3.02 (m, 1H), 3.00-2.86 (m, 2H), 2.86-2.77 (m, 1H), 2.29-2.19 (m, 6H), 1.88-1.50 (m, 7H), 1.15-1.12 (d, J = 6.8 Hz, 3H). LCMS (ES, m/z): 494 [M + H]+. |
| 743 | 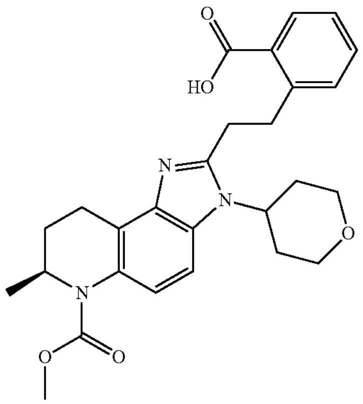 (S)-2-(2-(6-(methoxycarbonyl)-7-methyl-3-(tetrahydro-2H-pyran-4-yl)-6,7,8,9-tetrahydro-3H-imidazo[4,5-f]quinolin-2-yl)ethyl)benzoic acid | $^1$H-NMR ($CD_3OD$, 400 MHz) δ (ppm): 7.86 (d, J = 7.8 Hz, 1H), 7.53-7.47 (m, 1H), 7.47-7.40 (m, 1H), 7.40-7.33 (m, 1H), 7.33-7.22 (m, 2H), 4.85-4.73 (m, 2H), 4.13-4.04 (m, 2H), 3.79 (s, 3H), 3.74-3.66 (m, 2H), 3.43-3.35 (m, 4H), 3.25-3.12 (m, 1H), 3.00-2.88 (m, 1H), 2.66-2.40 (m, 2H), 2.30-2.20 (m, 1H), 1.86-1.51 (m, 3H), 1.14 (d, J = 6.8 Hz, 3H). LCMS (ES, m/z): 478 $[M + H]^+$. |
| 744 | 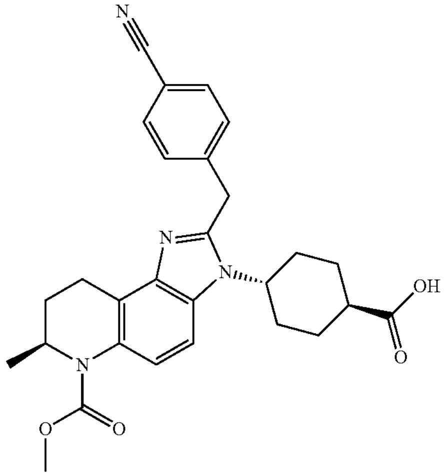 (1S,4R)-4-((S)-2-(4-cyanobenzyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.71 (d, J = 8.4 Hz, 2H), 7.49-7.40 (m, 4H), 4.85-4.70 (m, 1H), 4.50 (s, 2H), 4.30-4.10 (m, 1H), 3.75 (s, 3H), 3.25-3.10 (m, 1H), 3.00-2.90 (m, 1H), 2.45-2.00 (m, 6H), 1.75-1.35 (m, 5H), 1.14 (d, J = 6.4 Hz, 3H). LCMS (ES, m/z): 487 $[M + H]^+$. |

TABLE 18-continued

| Example Number | Structure and Compound Name | $^1$H NMR, LCMS |
|---|---|---|
| 745 | 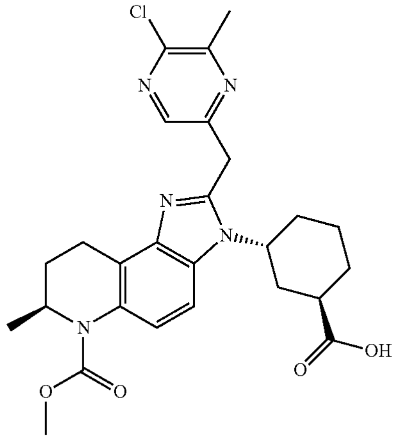 (1R,3R)-3-((S)-2-((5-chloro-6-methylpyrazin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.50 (s, 1H), 7.96-7.84 (m, 2H), 5.05-4.95 (m, 2H), 4.87-4.77 (m, 2H), 3.83 (s, 3H), 3.14-2.94 (m, 3H), 2.53 (s, 3H), 2.50-2.37 (m, 2H), 2.35-2.17 (m, 3H), 2.05-1.79 (m, 4H), 1.60-1.39 (m, 1H), 1.23-1.14 (d, J = 6.8 Hz, 3H). LCMS (ES, m/z): 512 [M + H]$^+$. |
| 746 | 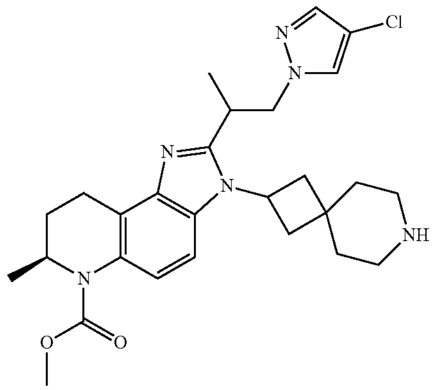 methyl 2-((7S)-1-(4-chloro-1H-pyrazol-1-yl)propan-2-yl)-7-methyl-3-(7-azaspiro[3.5]nonan-2-yl)-3,7,8,9-tetrahydro-6H-imidazo[4,5-f]quinoline-6-carboxylate 2$^{nd}$ eluting isomer | $^1$H-NMR ($CD_3OD$, 400 MHz) δ (ppm): 7.49-7.37 (m, 4H), 4.82-4.70 (m, 2H), 4.60-4.40 (m, 2H), 3.88-3.80 (m, 1H), 3.75 (s, 3H), 3.25-3.15 (m, 1H), 2.98-2.70 (m, 5H), 2.60-2.38 (m, 3H), 2.35-2.15 (m, 2H), 1.80-1.75 (m, 5H), 1.40 (d, J = 6.8 Hz, 3H), 1.13 (d, J = 6.8 Hz, 3H). LCMS (ES, m/z): 511 [M + H]$^+$. |
| 747 | 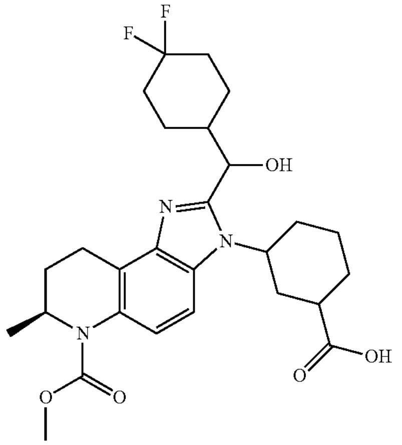 3-((7S)-2-((4,4-difluorocyclohexyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.56 (d, J = 8.8 Hz, 1H), 7.41 (d, J = 8.8 Hz, 1H), 5.03-4.90 (m, 1H), 4.80-4.65 (m, 2H), 3.79 (s, 3H), 3.23-3.15 (m, 1H), 3.03-2.96 (m, 1H), 2.93-2.82 (m, 1H), 2.45-2.32 (m, 2H), 2.30-2.03 (m, 6H), 2.02-1.62 (m, 8H), 1.60-1.45 (m, 3H), 1.14 (d, J = 6.8 Hz, 3H). LCMS (ES, m/z): 520 [M + H]$^+$. |

TABLE 18-continued

| Example Number | Structure and Compound Name | ¹H NMR, LCMS |
|---|---|---|
| 748 | 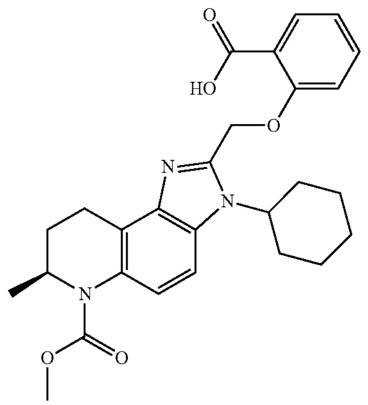 (S)-2-((3-cyclohexyl-6-(methoxycarbonyl)-7-methyl-6,7,8,9-tetrahydro-3H-imidazo[4,5-f]quinolin-2-yl)methoxy)benzoic acid | ¹H-NMR ($CD_3OD$, 400 MHz) δ (ppm): 8.04-7.92 (m, 1H), 7.92-7.82 (m, 2H), 7.73-7.59 (m, 1H), 7.48-7.33 (m, 1H), 7.28-7.12 (m, 1H), 5.85 (s, 2H), 4.87-4.85 (m, 1H), 4.75-4.51 (m, 1H), 3.83 (s, 3H), 3.28-3.01 (m, 2H), 2.43-2.19 (m, 3H), 2.19-2.07 (m, 2H), 2.07-1.97 (m, 2H), 1.97-1.88 (m, 1H), 1.88-1.76 (m, 1H), 1.71-1.42 (m, 3H), 3 1.18 (d, J = 6.8 Hz, 3H). LCMS (ES, m/z): 478 $[M + H]^+$ |
| 749 | 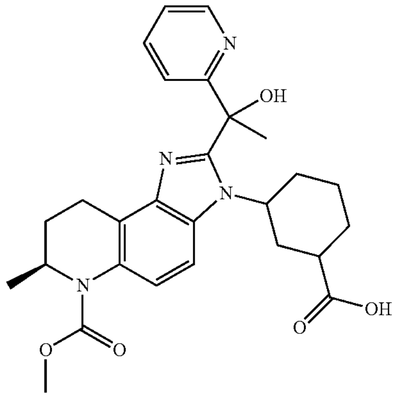 3-((7S)-2-(1-hydroxy-1-(pyridin-2-yl)ethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | ¹H-NMR ($CD_3OD$, 400 MHz) δ (ppm): 8.52-8.50 (m, 1H), 8.00-7.92 (m, 1H), 7.90-7.62 (m, 3H), 7.60-7.31 (m, 1H), 4.852-4.76 (m, 2H), 3.83-3.72 (m, 3H), 3.30-3.21 (m, 1H), 3.07 (m, 1H), 2.87-2.84 (m, 1H), 2.47-2.39 (m, 1H), 2.35-2.28 (m, 4H), 2.18-2.02 (m, 2H), 2.00-1.85 (m, 2H), 1.85-1.67 (m, 2H), 1.59-1.52 (m, 1H), 1.20-1.11 (m, 4H). LCMS (ES, m/z): 493 $[M + H]^+$. |
| 750 | 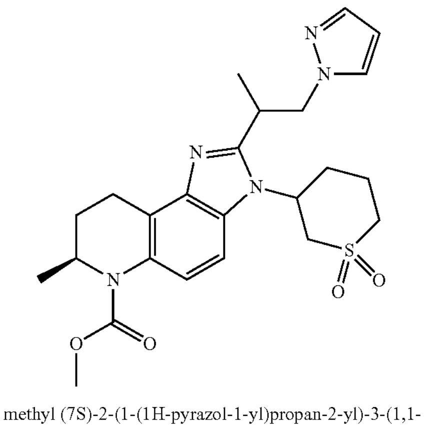 methyl (7S)-2-(1-(1H-pyrazol-1-yl)propan-2-yl)-3-(1,1-dioxidotetrahydro-2H-thiopyran-3-yl)-7-methyl-3,7,8,9-tetrahydro-6H-imidazo[4,5-f]quinoline-6-carboxylate 3rd eluting isomer | ¹H-NMR ($CD_3OD$, 400 MHz) δ (ppm): 7.77-7.56 (m, 3H), 7.44 (s, 1H), 6.22 (t, J = 2.4 Hz, 1H), 4.98-4.92 (m, 1H), 4.84-4.80 (m, 1H), 4.67-4.62 (m, 2H), 4.13-4.01 (m, 1H), 3.99-3.89 (m, 1H), 3.79 (s, 3H), 3.50-3.30 (m, 1H), 3.19-2.99 (m, 3H), 2.80-2.45 (m, 2H), 2.35-2.01 (m, 4H), 1.90-1.75 (m, 1H), 1.57 (d, J = 7.2 Hz, 3) 1.13 (d, J = 6.8 Hz, 3H). LCMS (ES, m/z): 486 $[M + H]^+$. |

TABLE 18-continued

| Example Number | Structure and Compound Name | $^1$H NMR, LCMS |
|---|---|---|
| 751 | 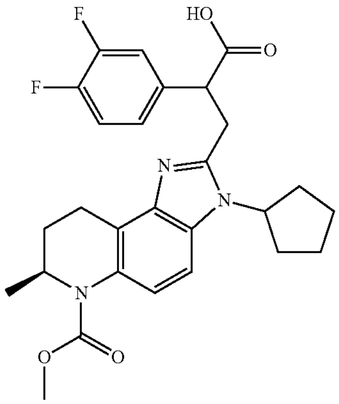 3-((7S)-3-cyclopentyl-6-(methoxycarbonyl)-7-methyl-6,7,8,9-tetrahydro-3H-imidazo[4,5-f]quinolin-2-yl)-2-(3,4-difluorophenyl)propanoic acid 1st eluting isomer | $^1$H-NMR ($CD_3OD$, 400 MHz) δ (ppm): 7.74 (d, J = 8.8 Hz, 1H), 7.56 (d, J = 9.2 Hz, 1H), 7.47-7.38 (m, 1H), 7.35-7.20 (m, 2H), 5.25-5.16 (m, 1H), 4.87-4.79 (m, 1H), 4.34-4.28 (m, 1H), 4.00-3.88 (m, 1H), 3.82 (s, 3H), 3.63-3.47 (m, 1H), 3.13-3.03 (m, 1H), 3.03-2.88 (m, 1H), 2.40-2.16 (m, 3H), 2.16-2.02 (m, 3H), 2.02-1.95 (m, 1H), 1.95-1.82 (m, 3H), 1.17 (d, J = 6.8 Hz, 3H). LCMS (ES, m/z): 498 [M + H]$^+$. |
| 752 | 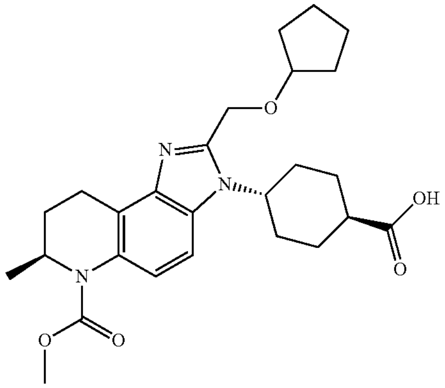 (1S,4R)-4-((S)-2-((cyclopentyloxy)methyl)-6-(methoxycarbonyl)-7-methyl-6,7,8,9-tetrahydro-3H-imidazo[4,5-f]quinolin-3-yl)cyclohexane-1-carboxylic acid | $^1$H NMR ($CD_3OD$, 400 MHz) δ (ppm): 7.57-7.55 (m, 1H), 7.47-7.45 (m, 1H), 4.88-4.75 (m, 3H), 4.56-4.50 (m, 1H), 4.14-4.10 (m, 1H), 3.79 (s, 3H), 3.21-3.12 (m, 1H), 2.97-2.90 (m, 1H), 2.58-2.52 (m, 1H), 2.42-2.36 (m, 2H), 2.28-2.20 (m, 3H), 2.06-2.03 (m, 2H), 1.80-1.61 (m, 11H), 1.14 (d, J = 6.8 Hz, 3H). LCMS (ES, m/z): 470 [M + H]$^+$. |
| 753 | 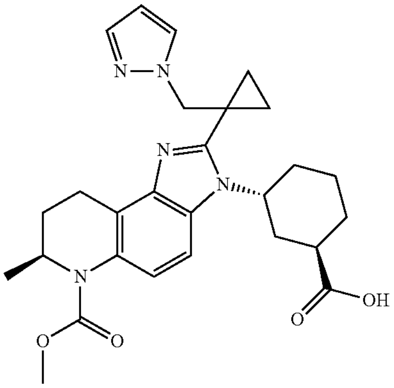 (1R,3R)-3-((S)-2-(1-((1H-pyrazol-1-yl)methyl)cyclopropyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.57-7.48 (m, 2H), 7.44-7.35 (m, 2H), 6.24-6.22 (m, 1H), 5.03-4.98 (m, 1H), 4.88-4.86 (m, 1H), 4.74-4.68 (m, 1H), 4.24-4.17 (m, 1H), 3.78 (s, 3H), 3.12-3.02 (m, 1H), 3.01-2.95 (m, 1H), 2.91-2.75 (m, 1H), 2.65-2.12 (m, 5H), 1.95-1.55 (m, 5H), 1.41-1.30 (m, 2H), 1.30-1.02 (m, 5H). LCMS (ES, m/z): 492 [M + H]$^+$. |

TABLE 18-continued

| Example Number | Structure and Compound Name | $^1$H NMR, LCMS |
|---|---|---|
| 754 | 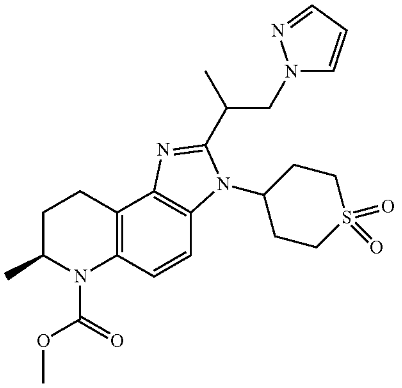<br>methyl (7S)-2-(1(1H-pyrazol-1-yl)propan-2-yl)-3-(1,1-dioxidotetrahydro-2H-thiopyran-4-yl)-7-methyl-3,7,8,9-tetrahydro-6H-imidazo[4,5-f]quinoline-6-carboxylate 2nd eluting isomer | $^1$H-NMR ($CD_3OD$, 400 MHz) δ (ppm): 7.50 (d, J = 1.6 Hz, 1H), 7.38-7.36 (m, 3H), 6.13-6.12 (m, 1H), 4.80-4.60 (m, 3H), 4.55-4.45 (m, 1H), 4.02-3.89 (m, 1H), 3.79 (s, 3H), 3.56-3.38 (m, 2H), 3.28-2.99 (m, 3H), 2.95-2.81 (m, 3H), 2.31-2.11 (m, 2H), 1.65-1.55 (m, 2H), 1.43 (d, J = 7.2 Hz, 3H), 1.13 (d, J = 6.4 Hz, 3H). LCMS (ES, m/z): 486 $[M + H]^+$. |
| 755 | 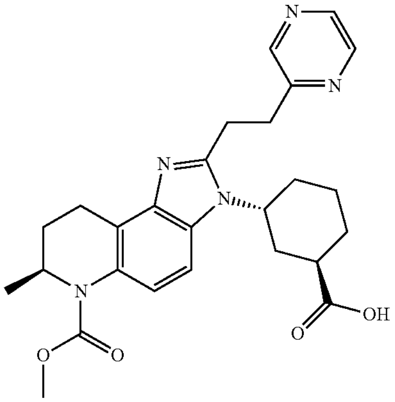<br>(1R,3R)-3-((S)-6-(methoxycarbonyl)-7-methyl-2-(2-(pyrazin-2-yl)ethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.58-8.44 (m, 3H), 7.52 (d, J = 8.8 Hz, 1H), 7.38 (d, J = 9.2 Hz, 1H), 4.82-4.75 (m, 3H), 3.78 (s, 3H), 3.51-3.42 (m, 3H), 3.32-2.12 (m, 1H), 2.29-2.86 (m, 2H), 2.41-2.23 (m, 5H), 1.89-1.65 (m, 5H), 1.15 (d, J = 6.4 Hz, 3H). LCMS (ES, m/z): 478 $[M + H]^+$. |
| 756 | 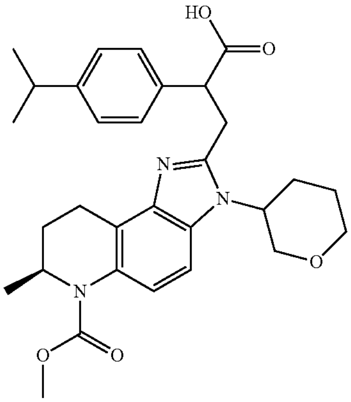<br>2-(4-isopropylphenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 1st eluting isomer | $^1$H-NMR ($CD_3OD$, 300 MHz) δ (ppm): 8.11 (s, 1H), 7.59-7.44 (m, 2H), 7.27-7.15 (m, 4H), 4.86-4.70 (m, 1H), 4.52-4.37 (m, 1H), 4.31-4.20 (m, 1H), 4.00-3.89 (m, 1H), 3.86 (s, 3H), 3.61-3.49 (m, 2H), 3.46-3.36 (m, 1H), 3.22-3.07 (m, 1H), 3.05-2.80 (m, 3H), 2.55-2.35 (m, 1H), 2.32-2.18 (m, 1H), 2.12-2.01 (m, 1H), 1.98-1.82 (m, 2H), 1.81-1.67 (m, 1H), 1.22 (d, J = 6.9 Hz, 6H), 1.14 (d, J = 6.6 Hz, 3H). LCMS (ES, m/z): 520 $[M + H]^+$. |

TABLE 18-continued

| Example Number | Structure and Compound Name | $^1$H NMR, LCMS |
|---|---|---|
| 757 | 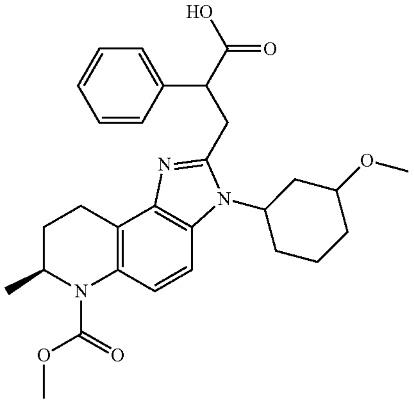 3-((7S)-6-(methoxycarbonyl)-3-(3-methoxycyclohexyl)-7-methyl-6,7,8,9-tetrahydro-3H-imidazo[4,5-f]quinolin-2-yl)-2-phenylpropanoic acid 5$^{th}$ eluting isomer | $^1$H-NMR ($CD_3OD$, 400 MHz) δ (ppm): 7.48-7.41 (m, 2H), 7.32-7.25 (m, 5H), 4.76-4.74 (m, 1H), 4.53-4.50 (m, 1H), 4.26-4.24 (m, 1H), 3.76-3.71 (m, 4H), 3.69-3.65 (m, 1H), 3.42-3.31 (m, 4H), 3.14-3.11 (m, 1H), 2.90-2.86 (m, 1H), 2.33-2.30 (m, 1H), 2.22-2.09 (m, 2H), 2.01-1.96 (m, 1H), 1.78-1.74 (m, 1H), 1.64-1.50 (m, 3H), 1.31-1.28 (m, 1H), 1.14-1.12 (m, 4H). LCMS (ES, m/z): 506 [M + H]+. |
| 758 | 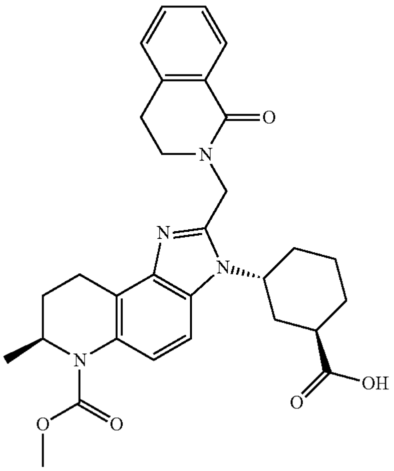 (1R,3R)-3-((S)-6-(methoxycarbonyl)-7-methyl-2-((1-oxo-3,4-dihydroisoquinolin-2(1H)-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.03 (d, J = 8.0 Hz, 1H), 7.56 (d, J = 9.2 Hz, 1H), 7.51-7.43 (m, 2H), 7.38-7.36 (m, 1H), 7.27 (d, J = 6.8 Hz, 1H), 5.54-5.49 (m, 1H), 4.87-4.84 (m, 1H), 4.82-4.74 (m, 2H), 3.79 (s, 3H), 3.72-3.50 (m, 2H), 3.23-3.05 (m, 2H), 3.03-2.96 (m, 3H), 2.48-2.25 (m, 5H), 1.80-1.59 (m, 5H), 1.15 (d, J = 6.4 Hz, 3H). LCMS (ES, m/z): 531 $[M + H]^+$. |
| 759 | 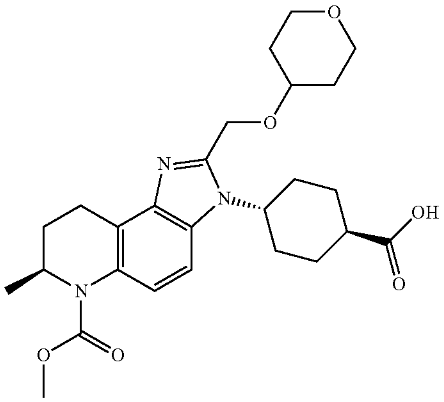 (1S,4R)-4-((S)-6-(methoxycarbonyl)-7-methyl-2-(((tetrahydro-2H-pyran-4-yl)oxy)methyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.57 (d, J = 9.0 Hz, 1H), 7.47 (d, J = 9.3 Hz, 1H), 4.97-4.92 (m, 2H), 4.81-4.78 (m, 1H), 4.61-4.56 (m, 1H), 3.93-3.90 (m, 2H), 3.79 (s, 3H), 3.74-3.70 (m, 1H), 3.51-3.48 (m, 2H), 3.22-3.17 (m, 1H), 2.99-2.94 (m, 1H), 2.64-2.50 (m, 1H), 2.41-2.35 (m, 2H), 2.30-2.16 (m, 3H), 2.13-1.92 (m, 4H), 1.83-1.53 (m, 5H), 1.14 (d, J = 6.6 Hz, 3H). LCMS (ES, m/z): 486 $[M + H]^+$. |

TABLE 18-continued

| Example Number | Structure and Compound Name | $^1$H NMR, LCMS |
|---|---|---|
| 760 | 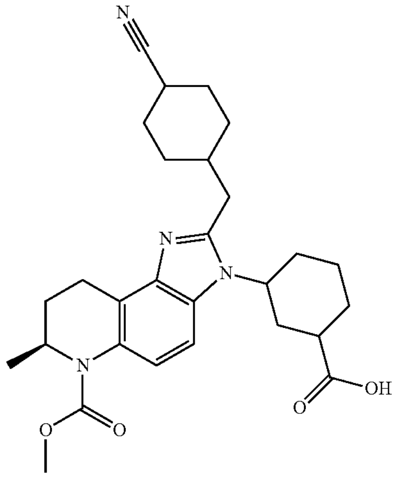<br>3-((7S)-2-((4-cyanocyclohexyl)methyl)-6-(methoxycarbonyl)-7-methyl-6,7,8,9-tetrahydro-3H-imidazo[4,5-f]quinolin-3-yl)cyclohexane-1-carboxylic acid<br>2$^{nd}$ eluting isomer | $^1$H-NMR ($CD_3OD$, 400 MHz) δ (ppm): 7.53 (d, J = 8.8 Hz, 1H), 7.37 (d, J = 8.8 Hz, 1H), 4.83-4.73 (m, 2H), 3.78 (s, 3H), 3.21-3.15 (m, 1H), 3.14-3.12 (m, 1H), 2.92-2.89 (m, 4H), 2.60-2.55 (m, 1H), 2.42-2.39 (m, 2H), 2.32-2.22 (m, 3H), 2.12-2.05 (m, 2H), 2.02-1.96 (m, 2H), 1.90-1.84 (m, 3H), 1.78-1.55 (m, 6H), 1.14 (d, J = 6.8 Hz, 3H). LCMS (ES, m/z): 493 [M + H]$^+$. |
| 761 | 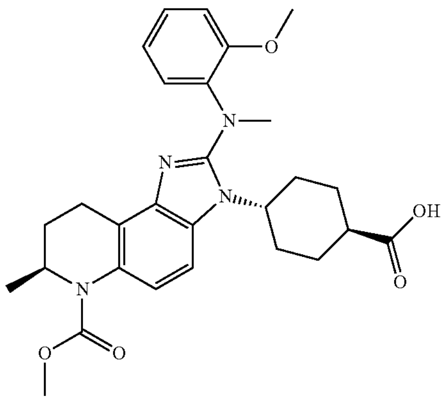<br>(1S,4R)-4-((S)-6-(methoxycarbonyl)-2-((2-methoxyphenyl)(methyl)amino)-7-methyl-6,7,8,9-tetrahydro-3H-imidazo[4,5-f]quinolin-3-yl)cyclohexane-1-carboxylic acid | LCMS (ES, m/z): 507 [M + H]$^+$ |

TABLE 18-continued

| Example Number | Structure and Compound Name | $^1$H NMR, LCMS |
| --- | --- | --- |
| 762 | 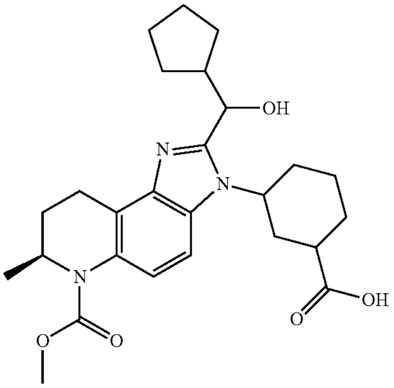 3-((7S)-2-(cyclopentyl(hydroxy)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.56 (d, J = 9.2 Hz, 1H), 7.44 (d, J = 9.2 Hz, 1H), 3.31-5.26 (m, 1H), 4.78-4.76 (m, 2H), 3.79 (s, 3H), 3.17-3.14 (m, 1H), 3.01-2.98 (m, 1H), 2.94-2.84 (m, 2H), 2.53-2.52 (m, 1H), 2.37-2.25 (m, 4H), 2.23-2.08 (m, 1H), 1.77-1.56 (m, 10H), 1.36-1.25 (m, 1H), 1.23-1.20 (m, 1H), 1.15 (d, J = 6.8 Hz, 3H). LCMS (ES, m/z): 470 [M + H]$^+$. |
| 763 | 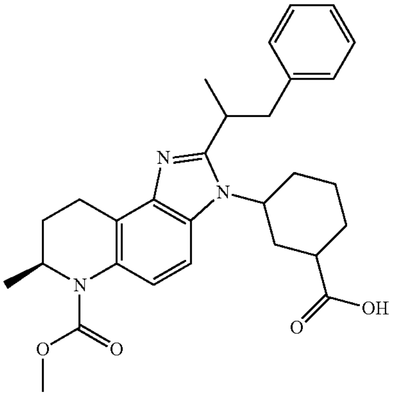 3-((7S)-6-(methoxycarbonyl)-7-methyl-2-(1-phenylpropan-2-yl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.45 (d, J = 8.8 Hz, 1H), 7.32 (d, J = 8.8 Hz, 1H), 7.25-7.05 (m, 5H), 4.95-4.90 (m, 1H), 4.80-4.65 (m, 1H), 3.75 (s, 3H), 3.65-3.55 (m, 1H), 3.40-3.30 (m, 1H), 3.25-3.15 (m, 1H), 3.05-2.80 (m, 3H), 2.41-2.22 (m, 4H), 2.00-1.90 (m, 1H), 1.89-1.60 (m, 5H), 1.36 (d, J = 6.8 Hz, 3H), 1.13 (d, J = 6.4 Hz, 3H). LCMS (ES, m/z): 490 [M + H]$^+$. |
| 764 | 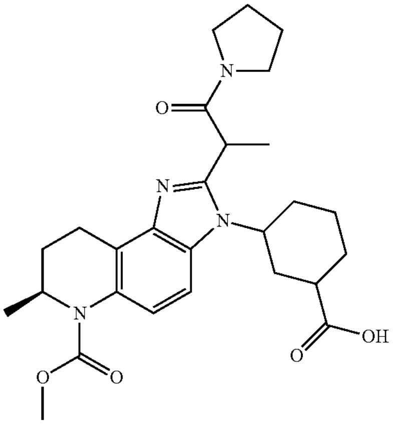 3-((7S)-6-(methoxycarbonyl)-7-methyl-2-(1-oxo-1-(pyrrolidin-1-yl)propan-2-yl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.57-7.50 (m, 1H), 7.43-7.36 (m, 1H), 4.79-4.70 (m, 2H), 4.46-4.36 (m, 1H), 3.78 (s, 3H), 3.70-3.60 (m, 1H), 3.58-3.41 (m, 2H), 3.29-3.13 (m, 2H), 2.99-2.85 (m, 2H), 2.55-2.43 (m, 1H), 2.41-2.19 (m, 4H), 2.02-1.80 (m, 6H), 1.80-1.58 (m, 6H), 1.14 (d, J = 6.8 Hz, 3H). LCMS (ES, m/z): 497 [M + H]$^+$. |

TABLE 18-continued

| Example Number | Structure and Compound Name | $^1$H NMR, LCMS |
|---|---|---|
| 765 | 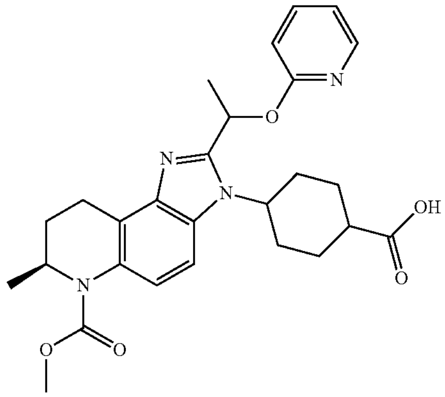 4-((7S)-6-(methoxycarbonyl)-7-methyl-2-(1-(pyridin-2-yloxy)ethyl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 8.16-8.06 (m, 1H), 7.74-7.64 (m, 1H), 7.53 (d, J = 9.2 Hz, 1H), 7.41 (d, J = 9.2 Hz, 1H), 6.97 (t, J = 6.4 Hz, 1H), 6.88 (d, J = 8.4 Hz, 1H), 6.67-6.53 (m, 1H), 4.82-4.63 (m, 2H), 3.78 (s, 3H), 3.29-3.11 (m, 1H), 2.95-2.82 (m, 1H), 2.57-2.31 (m, 3H), 2.30-2.12 (m, 3H), 2.09-1.98 (m, 1H), 1.94-1.81 (m, 4H), 1.77-1.59 (m, 2H), 1.58-1.43 (m, 1H), 1.14 (d, J = 6.8 Hz, 3H). LCMS (ES, m/z): 493 $[M + H]^+$. |
| 766 | 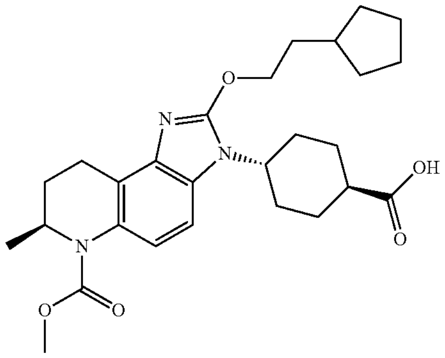 (1S,4R)-4-((S)-2-(2-cyclopentylethoxy)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.30-7.21 (m, 2H), 4.77-4.65 (m, 1H), 4.60-4.53 (m, 2H), 4.33-4.23 (m, 1H), 3.77 (s, 3H), 3.19-3.07 (m, 1H), 2.84-2.72 (m, 1H), 2.48-2.37 (m, 1H), 2.33-2.12 (m, 5H), 2.10-2.00 (m, 1H), 1.98-1.84 (m, 6H), 1.75-1.55 (m, 7H), 1.32-1.24 (m, 2H), 1.13 (d, J = 6.8 Hz, 3H). LCMS (ES, m/z): 484 $[M + H]^+$. |
| 767 | 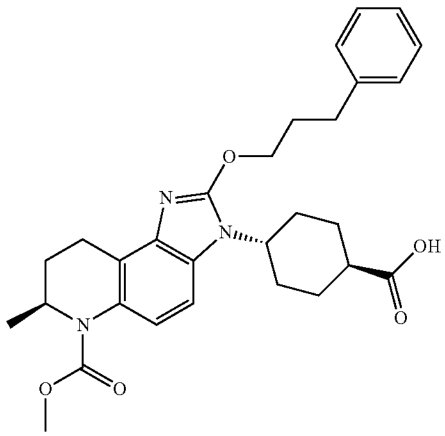 (1S,4R)-4-((S)-6-(methoxycarbonyl)-7-methyl-2-(3-phenylpropoxy)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.53-7.25 (m, 6H), 7.24-7.18 (m, 1H), 4.78-4.67 (m, 1H), 4.63-4.55 (m, 2H), 4.37-4.26 (m, 1H), 3.78 (s, 3H), 3.19-3.04 (m, 2H), 2.92-2.80 (m, 2H), 2.52-2.41 (m, 1H), 2.31-2.18 (m, 6H), 2.06-1.95 (m, 2H), 1.85-1.77 (m, 1H), 1.74-1.61 (m, 3H), 1.14 (d, J = 6.8 Hz, 3H). LCMS (ES, m/z): 506 $[M + H]^+$. |

TABLE 18-continued

| Example Number | Structure and Compound Name | $^1$H NMR, LCMS |
|---|---|---|
| 768 | 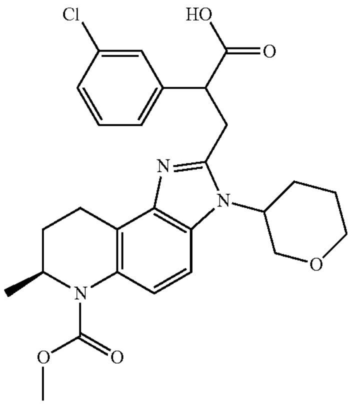<br>2-(3-chlorophenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid<br>2$^{nd}$ eluting isomer | $^1$H-NMR ($CD_3OD$, 300 MHz) δ (ppm): 7.52-7.50 (m, 2H), 7.41-7.38 (m, 1H), 7.33-7.29 (m, 3H), 4.80-4.50 (m, 2H), 4.25-3.89 (m, 7H), 3.75-3.55 (m, 2H), 3.40-2.83 (m, 3H), 2.45-2.15 (m, 2H), 1.85-1.45 (m, 4H), 1.14 (d, J = 6.9 Hz, 3H). LCMS (ES, m/z): 512 [M + H]$^+$. |
| 769 | 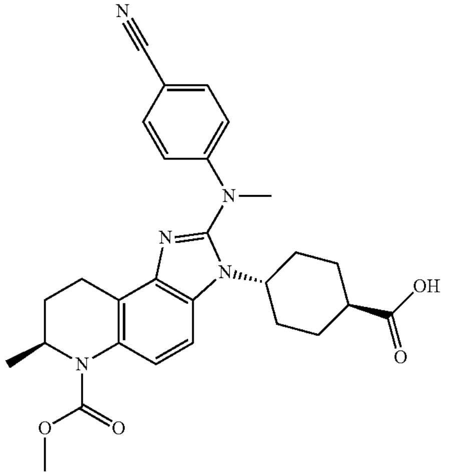<br>(1S,4R)-4-((S)-2-((4-cyanophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 502 [M + H]$^+$ |

TABLE 18-continued

| Example Number | Structure and Compound Name | $^1$H NMR, LCMS |
|---|---|---|
| 770 | 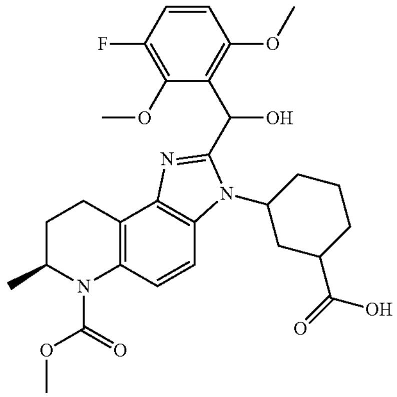 3-((7S)-2-((3-fluoro-2,6-dimethoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.55-7.50 (m, 1H), 7.43-7.41 (m, 1H), 7.17-7.12 (m, 1H), 6.79-6.77 (m, 1H), 6.54 (s, 1H), 4.87-4.70 (m, 2H), 3.83-3.50 (m, 9H), 3.33-3.16 (m, 1H), 2.93-2.82 (m, 2H), 2.51-2.46 (m, 1H), 2.35-2.32 (m, 1H), 2.22-2.20 (m, 3H), 2.05-2.02 (m, 1H), 1.92-1.88 (m, 1H), 1.70-1.68 (m, 3) 1.44 (d, J = 4.0 Hz, 3H). LCMS (ES, m/z): 556 [M + H]$^+$ |
| 771 | 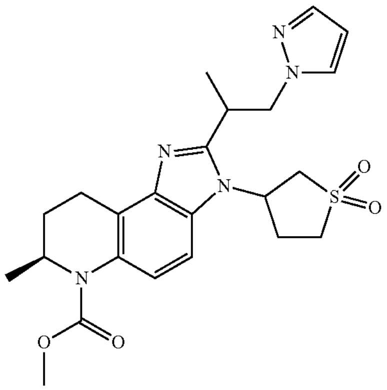 methyl (7S)-2-(1-(1H-pyrazol-1-yl)propan-2-yl)-3-(1,1-dioxidotetrahydrothiophen-3-yl)-7-methyl-3,7,8,9-tetrahydro-6H-imidazo[4,5-f]quinoline-6-carboxylate 4th eluting isomer | $^1$H-NMR ($CD_3OD$, 300 MHz) δ (ppm): 7.53-7.40 (m, 4H), 6.18-6.12 (m, 1H), 5.55-5.38 (m, 1H), 4.80-4.50 (m, 3H), 3.98-3.85 (m, 1H), 3.75 (s, 3H), 3.54-3.15 (m, 5H), 2.98-2.75 (m, 2H), 2.62-2.48 (m, 1H), 2.29-2.15 (m, 1H), 1.75-1.68 (m, 1H), 1.43 (d, J = 6.9 Hz, 3H), 1.12 (d, J = 6.6 Hz, 3H). LCMS (ES, m/z): 472 [M + H]$^+$ |
| 772 | 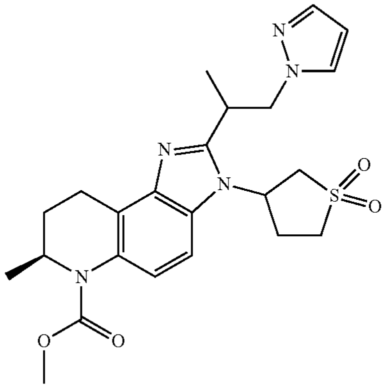 methyl (7S)-2-(1-(1H-pyrazol-1-yl)propan-2-yl)-3-(1,1-dioxidotetrahydrothiophen-3-yl)-7-methyl-3,7,8,9-tetrahydro-6H-imidazo[4,5-f]quinoline-6-carboxylate 3rd eluting isomer | $^1$H-NMR ($CD_3OD$, 300 MHz) δ (ppm): 7.86 (s, 2H), 7.70 (s, 1H), 7.42 (s, 1H), 6.33-6.28 (m, 1H), 5.80-5.55 (m, 1H), 4.92-4.65 (m, 2H), 4.32-4.15 (m, 1H), 3.82-3.75 (m, 4H), 3.55-3.38 (m, 2H), 3.38-2.98 (m, 4H), 2.88-2.65 (m, 1H), 2.35-2.15 (m, 2H), 1.98-1.78 (m, 1H), 1.61 (d, J = 7.2 Hz, 3H), 1.22 (d, J = 6.6 Hz, 3H). LCMS (ES, m/z): 472 [M + H]$^+$. |

TABLE 18-continued

| Example Number | Structure and Compound Name | $^1$H NMR, LCMS |
|---|---|---|
| 773 | 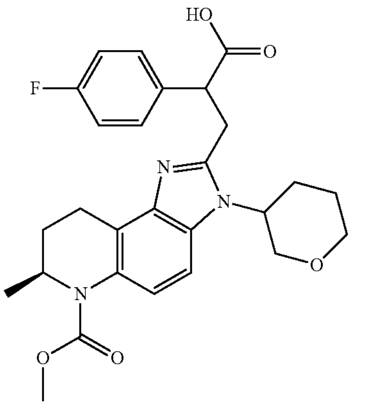 2-(4-fluorophenyl)-3-((7S)-6-(methoxycarbonyl)-7-methyl-3-((S)-tetrahydro-2H-pyran-3-yl)-6,7,8,9-tetrahydro-3H-imidazo[4,5-f]quinolin-2-yl)propanoic acid 2nd eluting isomer | $^1$H-NMR ($CD_3OD$, 400 MHz) δ (ppm): 7.50 (d, J = 8.8 Hz, 1H), 7.45-7.33 (m, 3H), 7.10-6.98 (m, 2H), 4.80-4.67 (m, 1H), 4.54-4.39 (m, 1H), 4.30-4.17 (m, 1H), 4.12-4.02 (m, 1H), 4.02-3.92 (m, 2H), 3.76 (s, 3H), 3.73-3.63 (m, 1H), 3.61-3.50 (m, 1H), 3.30-3.24 (m, 1H), 3.22-3.09 (m, 1H), 2.94-2.83 (m, 1H), 2.45-2.30 (m, 1H), 2.26-2.12 (m, 1H), 1.81-1.66 (m, 3H), 1.46-1.41 (m, 1H), 1.10 (d, J = 6.8 Hz, 3H). LCMS (ES, m/z): 496 $[M + H]^+$. |
| 774 | 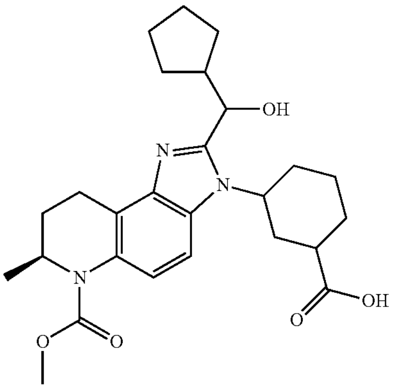 3-((7S)-2-(cyclopentyl(hydroxy)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.56 (d, J = 9.2 Hz, 1H), 7.41 (d, J = 9.2 Hz, 1H), 5.11-5.06 (m, 1H), 4.78-4.73 (m, 2H), 3.79 (s, 3H), 3.21-3.17 (m, 1H), 3.01-2.99 (m, 1H), 2.95-2.90 (m, 1H), 2.70-2.68 (m, 1H), 2.50-2.23 (m, 5H), 1.97-1.76 (m, 3H), 1.75-1.57 (m, 9H), 1.23-1.19 (m, 1H), 1.15 (d, J = 6.8 Hz, 3H). LCMS (ES, m/z): 470 $[M + H]^+$. |
| 775 | 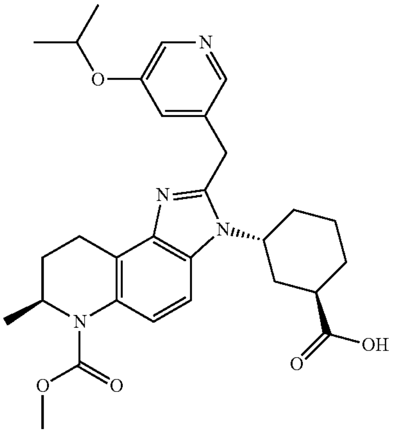 (1R,3R)-3-((S)-2-((5-isopropoxypyridin-3-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.15-8.04 (m, 2H), 7.54-7.50 (m, 1) 7.49-7.45 (m, 1H), 7.31-7.30 (m, 1H), 4.78-4.71 (m, 2H), 4.69-4.60 (m, 1H), 4.49-4.31 (m, 2H), 3.79 (s, 3H), 3.25-3.20 (m, 1H), 3.02-2.95 (m, 2H), 2.41-2.12 (m, 5H), 1.82-1.69 (m, 3H), 1.40-1.31 (m, 8H), 1.16 (d, J = 6.4 Hz, 3H). LCMS (ES, m/z): 521 $[M + H]^+$ |

TABLE 18-continued

| Example Number | Structure and Compound Name | $^1$H NMR, LCMS |
|---|---|---|
| 776 | 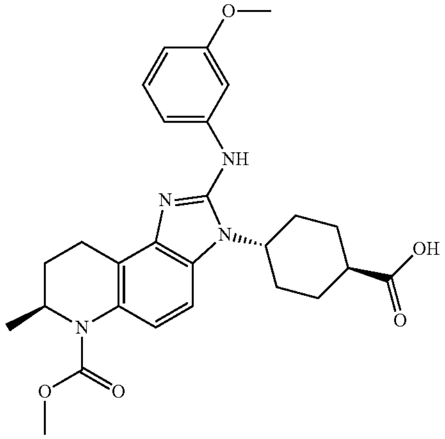 (1S,4R)-4-((S)-6-(methoxycarbonyl)-2-((3-methoxyphenyl)amino)-7-methyl-6,7,8,9-tetrahydro-3H-imidazo[4,5-f]quinolin-3-yl)cyclohexane-1-carboxylic acid | LCMS (ES, m/z): 493 $[M + H]^+$ |
| 777 | 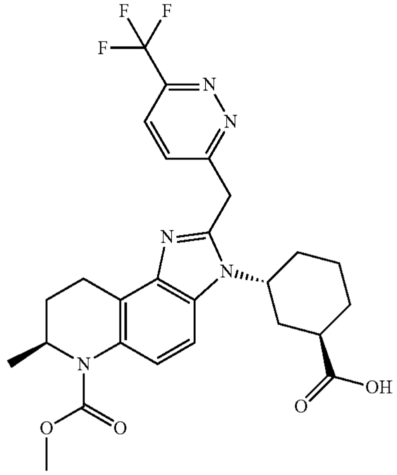 (1R,3R)-3-((S)-6-(methoxycarbonyl)-7-methyl-2-((6-(trifluoromethyl)pyridazin-3-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.25-8.15 (m, 2H), 7.98-7.88 (m, 2H), 4.98-4.82 (m, 4H), 3.84 (s, 3H), 3.16-2.98 (m, 2H), 2.95 (s, 1H), 2.49-2.34 (m, 2H), 2.32-2.14 (m, 3H), 2.09-2.03 (m, 1H), 2.00-1.86 (m, 2H), 1.86-1.75 (m, 1H), 1.54-1.40 (m, 1H), 1.20 (d, J = 6.8 Hz, 3H). LCMS (ES, m/z): 532 $[M + H]^+$. |
| 778 | 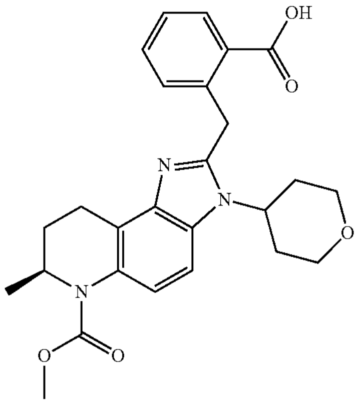 (S)-2-((6-(methoxycarbonyl)-7-methyl-3-(tetrahydro-2H-pyran-4-yl)-6,7,8,9-tetrahydro-3H-imidazo[4,5-f]quinolin-2-yl)methyl)benzoic acid | $^1$H-NMR ($CD_3OD$, 400 MHz) δ (ppm): 8.19 (d, J = 7.6 Hz, 1H), 7.83 (s, 2H), 7.71-7.63 (m, 1H), 7.61-7.53 (m, 1H), 7.46 (d, J = 7.6 Hz, 1H), 5.01 (s, 2H), 4.91-4.95 (m, 1H), 4.84-4.77 (m, 1H), 4.15-4.05 (m, 2H), 3.82 (s, 3H), 3.55-3.44 (m, 2H), 3.12-2.99 (m, 1H), 2.98-2.87 (m, 1H), 2.69-2.50 (m, 2H), 2.30-2.17 (m, 1H), 1.90-1.78 (m, 3H), 1.16 (d, J = 6.8 Hz, 3H). LCMS (ES, m/z): 464 $[M + H]^+$. |

TABLE 18-continued

| Example Number | Structure and Compound Name | $^1$H NMR, LCMS |
|---|---|---|
| 779 | 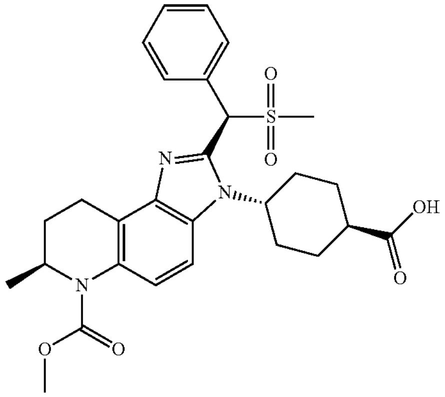 (1R,4r)-4-((S)-6-(methoxycarbonyl)-7-methyl-2-((R)-(methylsulfonyl)(phenyl)methyl)-6,7,8,9-tetrahydro-3H-imidazo[4,5-f]quinolin-3-yl)cyclohexane-1-carboxylic acid | $^1$H-NMR (DMSO, 400 MHz) δ (ppm): 12.48-11.85 (br, 1H), 7.85-7.71 (m, 2H), 7.64 (d, J = 6.0 Hz, 1H), 7.48-7.32 (m, 4H), 6.59-6.41 (m, 1H), 4.72-4.65 (m, 1H), 4.60-4.41 (m, 1H), 3.79 (s, 3H), 3.25 (s, 3H), 3.23-3.12 (m, 1H), 3.02-2.91 (m, 1H), 2.50-2.41 (m, 1H), 2.38-2.25 (m, 1H), 2.25-2.12 (m, 1H), 2.09-1.91 (m, 3H), 1.84-1.79 (m, 1H), 1.79-1.61 (m, 2H), 1.41-1.26 (m, 1H), 1.16 (d, J = 10.0 Hz, 3H). 1.01-0.95 (m, 1H). LCMS (ES, m/z): 540 [M + H]$^+$. |
| 780 | 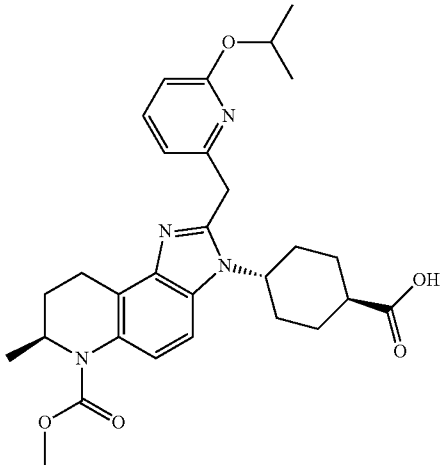 (1S,4R)-4-((S)-2-((6-isopropoxypyridin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.65-7.41 (m, 3H), 6.84-6.82 (m, 1H), 6.61-6.59 (m, 1H), 5.22-5.12 (m, 1H), 4.85-4.79 (m, 1H), 4.49-4.39 (m, 3H), 3.81 (s, 3H), 3.21-3.19 (m, 1H), 2.98-2.94 (m, 1H), 2.47-2.44 (m, 1H), 2.35-2.17 (m, 3H), 2.17-2.08 (m, 2H), 1.17 (m, 1H), 1.62 (m, 2H), 1.51-1.48 (m, 2H), 1.35-1.22 (m, 6H), 1.25-0.99 (m, 3H). LCMS (ES, m/z): 521 [M + H]$^+$ |
| 781 | 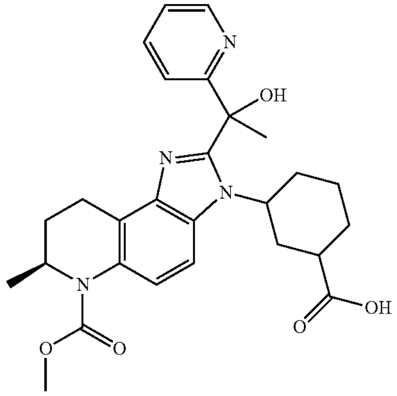 3-((7S)-2-(1-hydroxy-1-(pyridin-2-yl)ethyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 8.45-8.43 (m, 1H), 8.15-7.90 (m, 2H), 7.84 (s, 2H), 7.43-7.41 (m, 1H), 5.15-5.04 (m, 1H), 4.84-4.72 (m, 1H), 3.83 (s, 3H), 3.24-3.20 (m, 1H), 3.17-3.05 (m, 1H), 2.95-2.92 (m, 1H), 2.53-2.50 (m, 1H), 2.43-2.41 (m, 1H), 2.37-2.31 (m, 1H), 2.22 (s, 3H), 2.13-1.99 (m, 2H), 1.88-1.82 (m, 1H), 1.75-1.50 (m, 2H), 1.23-1.10 (m, 4H), 0.99-0.71 (m, 1H). LCMS (ES, m/z): 493 [M + H]$^+$. |

TABLE 18-continued

| Example Number | Structure and Compound Name | $^1$H NMR, LCMS |
| --- | --- | --- |
| 782 | 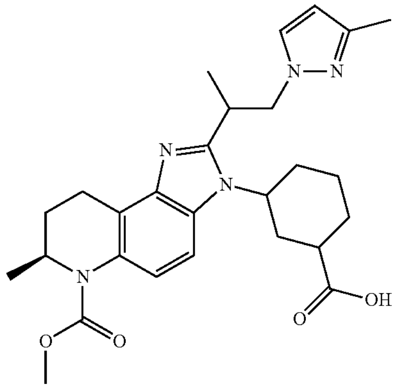 3-((7S)-6-(methoxycarbonyl)-7-methyl-2-(1-(3-methyl-1H-pyrazol-1-yl)propan-2-yl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 300 MHz) δ (ppm): 7.92-7.76 (m, 2H), 7.67-7.56 (m, 1H), 6.05 (s, 1H), 5.12-5.07 (m, 1H), 4.72-4.56 (m, 2H), 4.24-4.05 (m, 1H), 3.81 (s, 3H), 3.21-2.86 (m, 3H), 2.51-2.31 (m, 2H), 2.31-2.09 (m, 3H), 2.09-1.76 (m, 7H), 1.73-1.48 (m, 5H), 1.18 (d, J = 6.9 Hz, 3H). LCMS (ES, m/z): 494 $[M + H]^+$ |
| 783 | 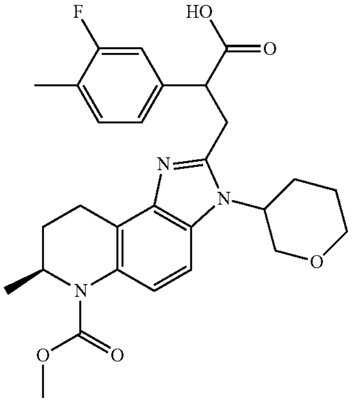 2-(3-fluoro-4-methylphenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 2$^{nd}$ eluting isomer | $^1$H-NMR ($CD_3OD$, 300 MHz) δ (ppm): 7.57-7.54 (m, 1H), 7.46-7.43 (m, 1H), 7.24-7.06 (m, 3H), 4.85-4.75 (m, 1H), 4.62-4.45 (m, 1H), 4.35-4.25 (m, 1H), 4.15-3.95 (m, 3H), 3.80-3.55 (m, 5H), 3.40-3.10 (m, 2H), 2.98-2.85 (m, 1H), 2.45-2.15 (m, 5H), 1.85-1.65 (m, 3H), 1.50-1.40 (m, 1H), 1.15 (d, J = 6.6 Hz, 3H). LCMS (ES, m/z): 510 $[M + H]^+$. |
| 784 | 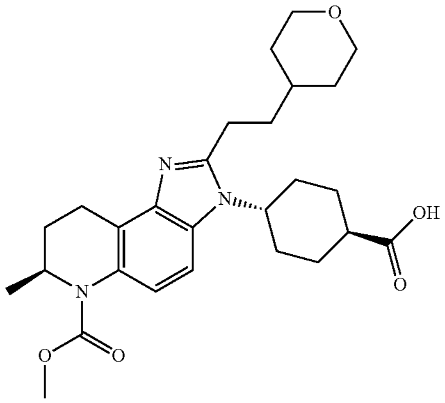 (1S,4R)-4-((S)-6-(methoxycarbonyl)-7-methyl-2-(2-(tetrahydro-2H-pyran-4-yl)ethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.54 (d, J = 9.2 Hz, 1H), 7.41 (d, J = 8.8 Hz, 1H), 4.79-4.75 (m, 1H), 4.38-4.32 (m, 1H), 3.99-3.96 (m, 2H), 3.79 (s, 3H), 3.48-3.42 (m, 2H), 3.20-3.12 (m, 1H), 3.07-3.03 (m, 2H), 2.95-2.88 (m, 1H), 2.62-2.51 (m, 1H), 2.50-2.35 (m, 2H), 2.28-2.24 (m, 3H), 2.01-1.98 (m, 2H), 1.80-1.69 (m, 8H), 1.42-1.33 (m, 2H), 1.14 (d, J = 6.8 Hz, 3H). LCMS (ES, m/z): 484 $[M + H]^+$. |

TABLE 18-continued

| Example Number | Structure and Compound Name | $^1$H NMR, LCMS |
|---|---|---|
| 785 | 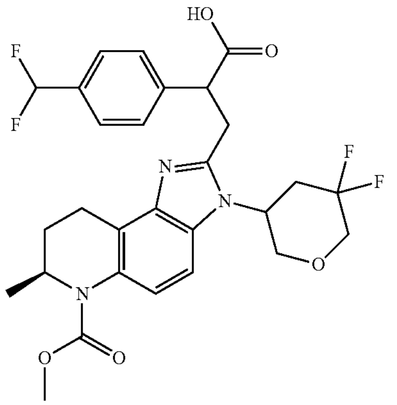 2-(4-(difluoromethyl)phenyl)-3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)propanoic acid 4th eluting isomer | $^1$H-NMR ($CD_3OD$, 400 MHz) δ (ppm): 7.59-7.47 (m, 5H), 7.41 (d, J = 8.8 Hz, 1H), 6.91-6.56 (m, 1H), 4.86-4.67 (m, 2H), 4.42-4.32 (m, 1H), 4.16-4.04 (m, 1H), 4.03-3.93 (m, 1H), 3.92-3.81 (m, 1H), 3.78 (s, 3H), 3.76-3.66 (m, 1H), 3.32-3.26 (m, 2H), 3.23-3.11 (m, 1H), 2.98-2.78 (m, 2H), 2.75-2.63 (m, 1H), 2.31-2.18 (m, 1H), 1.79-1.66 (m, 1H), 1.13 (d, J = 6.8 Hz, 3H). LCMS (ES, m/z): 564 [M + H]$^+$. |
| 786 | 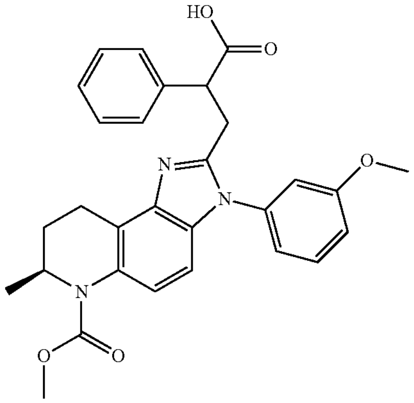 3-((7S)-6-(methoxycarbonyl)-3-(3-methoxyphenyl)-7-methyl-6,7,8,9-tetrahydro-3H-imidazo[4,5-f]quinolin-2-yl)-2-phenylpropanoic acid 2nd eluting isomer | $^1$H-NMR ($CD_3OD$, 400 MHz) δ (ppm): 7.49 (t, J = 8.0 Hz, 1H), 7.36 (d, J = 8.8 Hz, 1H), 7.28-7.18 (m, 3H), 7.18-7.07 (m, 3H), 6.92-6.69 (m, 3H), 4.81-4.68 (m, 1H), 4.33-4.23 (m, 1H), 3.84 (s, 3H), 3.75 (s, 3H), 3.59-3.47 (m, 1H), 3.31-3.16 (m, 2H), 3.00-2.88 (m, 1H), 2.33-2.18 (m, 1H), 1.81-1.67 (m, 1H), 1.14 (d, J = 6.8 Hz, 3H). LCMS (ES, m/z): 500 [M + H]$^+$. |
| 787 | 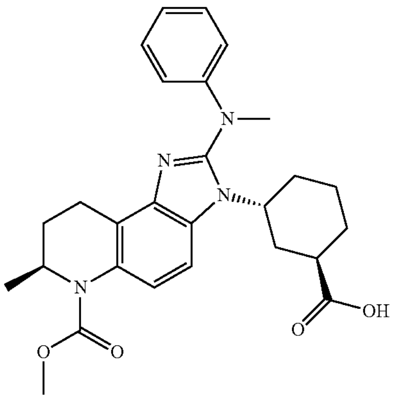 (1R,3R)-3-((S)-6-(methoxycarbonyl)-7-methyl-2-(methyl(phenyl)amino)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.44-7.35 (m, 3H), 7.34-7.28 (m, 3H), 7.04-6.94 (m, 1H), 4.79-4.68 (m, 1H), 4.64-4.58 (m, 1H), 3.78 (s, 3H), 3.68 (s, 3H), 3.18-3.05 (m, 1H), 3.03-2.98 (m, 1H), 2.86-2.78 (m, 1H), 2.48-2.31 (m, 2H), 2.28-2.17 (m, 3H), 2.05-1.92 (m, 1H), 1.95-1.87 (m, 1H), 1.80-1.54 (m, 3H), 1.15 (d, J = 6.8 Hz, 3H). LCMS (ES, m/z): 477 [M + H]$^+$. |

TABLE 18-continued

| Example Number | Structure and Compound Name | $^1$H NMR, LCMS |
|---|---|---|
| 788 | 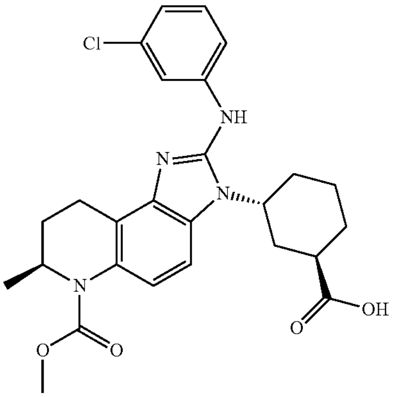 (1R,3R)-3-((S)-2-((3-chlorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 497 $[M + H]^+$ |
| 789 | 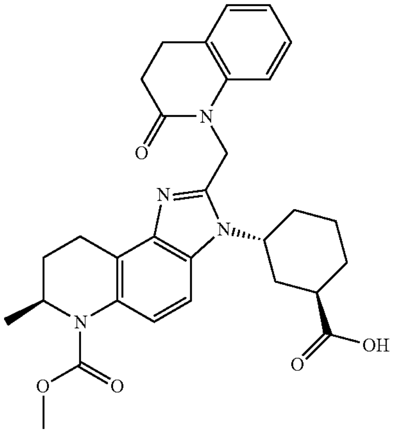 (1R,3R)-3-((S)-6-(methoxycarbonyl)-7-methyl-2-((2-oxo-3,4-dihydroquinolin-1(2H)-yl)methyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.53 (d, J = 9.2 Hz, 1H), 7.39 (d, J = 8.4 Hz, 1H), 7.25-7.00 (m, 4H), 5.62-5.42 (m, 2H), 4.91-4.68 (m, 2H), 3.77 (s, 3H), 3.33-2.79 (m, 7H), 2.46-2.19 (m, 5H), 1.91-1.63 (m, 5H), 1.12 (d, J = 6.4 Hz, 3H). LCMS (ES, m/z): 531 $[M + H]^+$. |
| 790 | 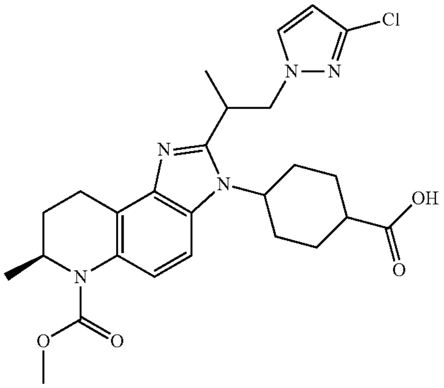 4-((7S)-2-(1-(3-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 300 MHz) δ (ppm): 7.53-7.19 (m, 3H), 6.06 (s, 1H), 4.78-4.63 (m, 1H), 4.63-4.51 (m, 1H), 4.51-4.40 (m, 1H), 4.40-4.22 (m, 1H), 4.05-3.91 (m, 1H), 3.76 (s, 3H), 3.27-3.11 (m, 1H), 3.01-2.78 (m, 1H), 2.54-2.02 (m, 6H), 1.96-1.62 (m, 4H), 1.62-1.47 (m, 1H), 1.42-1.40 (d, J = 6.9 Hz, 3H), 1.14-1.12 (d, J = 6.6 Hz, 3H). LCMS: (ES, m/z): 514 $[M + H]^+$. |

TABLE 18-continued

| Example Number | Structure and Compound Name | $^1$H NMR, LCMS |
|---|---|---|
| 791 | 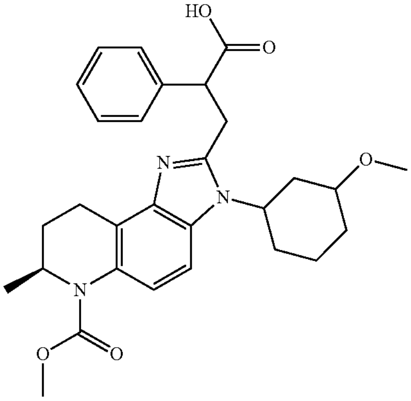 3-((7S)-6-(methoxycarbonyl)-3-(3-methoxycyclohexyl)-7-methyl-6,7,8,9-tetrahydro-3H-imidazo[4,5-f]quinolin-2-yl)-2-phenylpropanoic acid 1st eluting isomer | $^1$H-NMR ($CD_3OD$, 400 MHz) δ (ppm): 7.30-7.19 (m, 7H), 4.29-4.23 (m, 1H), 4.04-4.00 (m, 1H), 3.78 (s, 3H), 3.65-3.60 (m, 1H), 3.42-3.37 (m, 1H), 3.35 (s, 3H), 3.18-3.14 (m, 2H), 2.91-2.88 (m, 1H), 2.13-2.11 (m, 1H), 2.07-2.05 (m, 4H), 1.95-1.89 (m, 2H), 1.86-1.82 (m, 1H), 1.57-1.54 (m, 1H), 1.33-1.30 (m, 1H), 1.21-1.15 (m, 1H), 1.16 (d, J = 6.8 Hz, 3H). LCMS (ES, m/z): 506 [M + H]$^+$. |
| 792 | 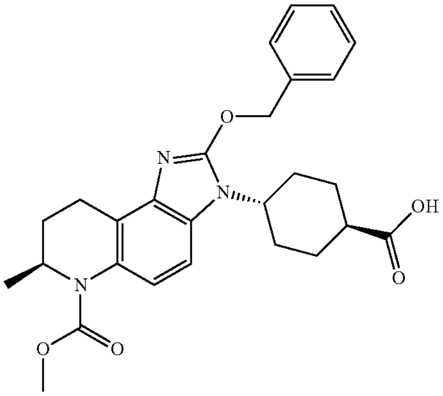 (1S,4R)-4-((S)-2-(benzyloxy)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.55-7.47 (m, 2H), 7.47-7.32 (m, 3H), 7.29-7.19 (m, 2H), 5.56 (s, 2H), 4.75-4.65 (m, 1H), 4.33-4.22 (m, 1H), 3.75 (s, 3H), 3.20-3.06 (m, 1H), 2.83-2.73 (m, 1H), 2.37-2.04 (m, 6H), 1.92-1.80 (m, 2H), 1.71-1.52 (m, 3H), 1.12 (d, J = 6.8 Hz, 3H). LCMS (ES, m/z): 478 [M + H]$^+$. |
| 793 | 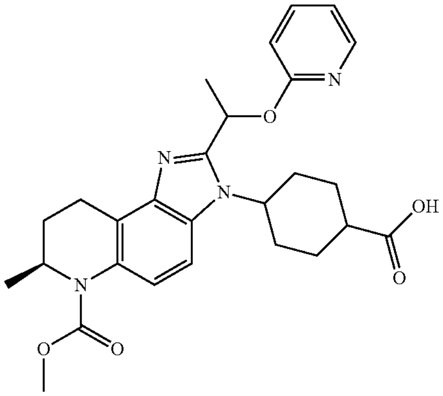 4-((7S)-6-(methoxycarbonyl)-7-methyl-2-(1-(pyridin-2-yloxy)ethyl)-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 8.18-8.06 (m, 1H), 7.77-7.63 (t, J = 7.2 Hz, 1H), 7.52 (d, J = 9.2 Hz, 1H), 7.41 (d, J = 9.2 Hz, 1H), 6.96 (t, J = 6.0 Hz, 1H), 6.87 (d, J = 8.4 Hz, 1H), 6.68-6.54 (m, 1H), 4.80-4.64 (m, 2H), 3.78 (s, 3H), 3.26-3.11 (m, 1H), 2.99-2.85 (m, 1H), 2.56-2.44 (m, 1H), 2.43-2.30 (m, 2H), 2.28-2.11 (m, 3H), 2.08-1.96 (m, 1H), 1.90-1.76 (m, 4H), 1.75-1.57 (m, 2H), 1.56-1.39 (m, 1H), 1.12 (d, J = 6.8 Hz, 3H). LCMS (ES, m/z): 493 [M + H]$^+$. |

TABLE 18-continued

| Example Number | Structure and Compound Name | $^1$H NMR, LCMS |
|---|---|---|
| 794 | 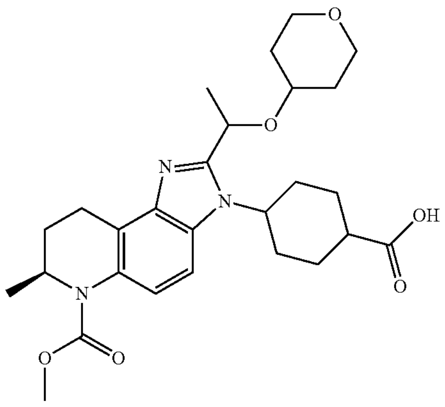 4-((7S)-6-(methoxycarbonyl)-7-methyl-2-(1-((tetrahydro-2H-pyran-4-yl)oxy)ethyl)-6,7,8,9-tetrahydro-3H-imidazo[4,5-f]quinolin-3-yl)cyclohexane-1-carboxylic acid 2nd eluting isomer | $^1$H NMR (400 MHz, $CD_3OD$) δ (ppm): 7.80 (d, J = 9.2 Hz, 1H), 7.74 (d, J = 9.2 Hz, 1H), 5.39-5.37 (m, 1H), 4.95-4.92 (m, 1H), 4.83-4.81 (m, 1H), 3.98-3.88 (m, 2H), 3.82 (s, 3H), 3.73-3.70 (m, 1H), 3.50-3.41 (m, 2H), 3.15-3.11 (m, 1H), 3.00-2.95 (m, 1H), 2.64-2.51 (m, 1H), 2.48-2.45 (m, 2H), 2.31-2.24 (m, 3H), 2.13-2.06 (m, 3H), 1.86-1.83 (m, 2H), 1.76-1.58 (m, 7H), 1.16 (d, J = 6.4 Hz, 3H). LCMS (ES, m/z): 500 [M + H]$^+$ |
| 795 | 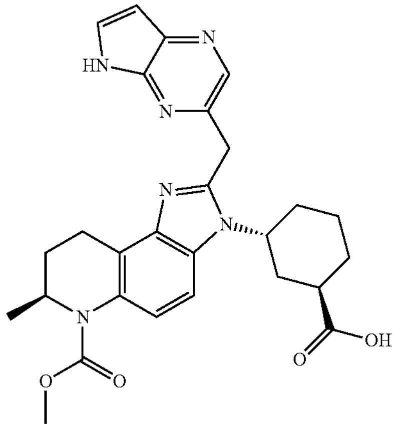 (1R,3R)-3-((S)-2-((5H-pyrrolo[2,3-b]pyrazin-3-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.43 (s, 1H), 7.71 (d, J = 3.6 Hz, 1H), 7.53 (d, J = 8.8 Hz, 1H), 7.42 (d, J = 8.8 Hz, 1H), 6.61 (d, J = 3.6 Hz, 1H), 4.89-4.87 (m, 1H), 4.80-4.69 (m, 3H), 3.79 (s, 3H), 3.24-3.17 (m, 1H), 2.98-2.92 (m, 2H), 2.43-2.17 (m, 5H), 1.79-1.60 (m, 4H), 1.43-1.31 (m, 1H), 1.15 (d, J = 6.4 Hz, 3H). LCMS (ES, m/z): 503 [M + H]$^+$. |
| 796 | 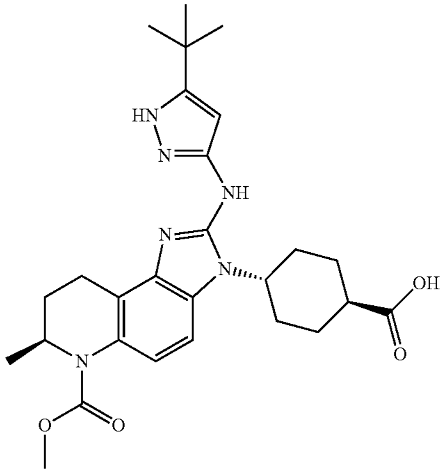 (1S,4R)-4-((S)-2-((5-(tert-butyl)-1H-pyrazol-3-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 510 [M + H]$^+$ |

TABLE 18-continued

| Example Number | Structure and Compound Name | $^1$H NMR, LCMS |
|---|---|---|
| 797 | 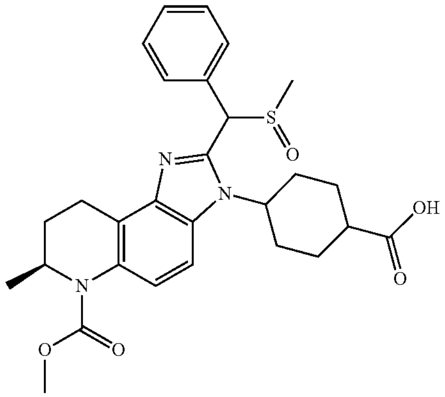<br>4-((7S)-6-(methoxycarbonyl)-7-methyl-2-((methylsulfinyl)(phenyl)methyl)-6,7,8,9-tetrahydro-3H-imidazo[4,5-f]quinolin-3-yl)cyclohexane-1-carboxylic acid 2nd eluting isomer | $^1$H-NMR (DMSO, 400 MHz) δ (ppm): 7.67-7.25 (m, 7H), 6.12-5.79 (m, 1H), 4.75-4.58 (m, 1H), 4.47-4.28 (m, 1H), 3.67 (s, 3H), 3.20-3.04 (m, 1H), 2.98-2.78 (m, 1H), 2.62 (s, 1H), 2.45 (s, 2H), 2.41-2.22 (m, 2H), 2.20-2.08 (m, 1H), 2.08-1.86 (m, 3H), 1.85-1.74 (m, 1H), 1.74-1.54 (m, 2H), 1.29-1.14 (m, 1H), 1.09 (d, J = 6.8 Hz, 3H), 1.02-0.79 (m, 1H). LCMS (ES, m/z): 524 $[M + H]^+$. |
| 798 | 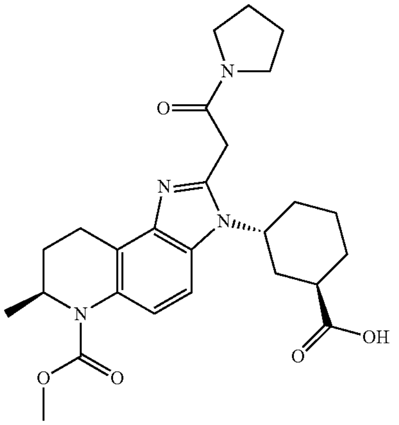<br>(1R,3R)-3-((S)-6-(methoxycarbonyl)-7-methyl-2-(2-oxo-2-(pyrrolidin-1-yl)ethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.53 (d, J = 6.8 Hz, 1H), 7.43-7.40 (d, J = 6.8 Hz, 1H), 4.91-4.89 (m, 2H), 4.85-4.76 (m, 1H), 4.72-4.54 (m, 1H), 3.79-3.69 (m, 5H), 3.51-3.45 (m, 2H), 3.17-3.14 (m, 1H), 2.97-2.90 (m, 2H), 2.35-2.21 (m, 5H), 2.11-1.95 (m, 6H), 1.78-1.72 (m, 2H), 1.64-1.48 (m, 1H).1.14 (d, J = 6.8 Hz, 3H). LCMS (ES, m/z): 483 [M + H]+ |
| 799 | 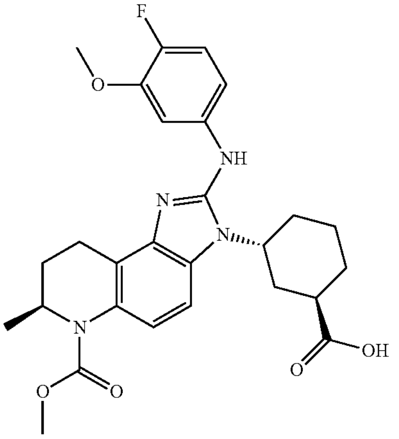<br>(1R,3R)-3-((S)-2-((4-fluoro-3-methoxyphenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 $[M + H]^+$ |

TABLE 18-continued

| Example Number | Structure and Compound Name | $^1$H NMR, LCMS |
|---|---|---|
| 800 | 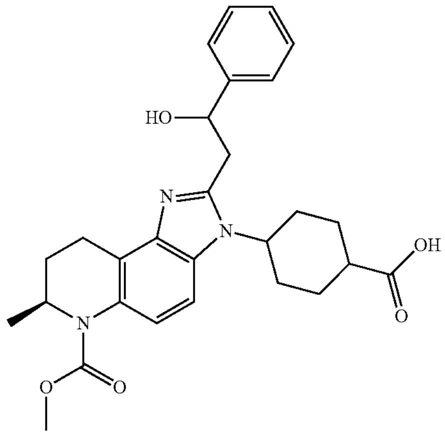 4-((7S)-2-(2-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.52-7.45 (m, 1H), 7.45-7.31 (m, 5H), 7.31-7.23 (m, 1H), 5.17-5.07 (m, 1H), 4.83-4.71 (m, 1H), 4.40-4.28 (m, 1H), 3.79 (s, 3H), 3.51-3.40 (m, 1H), 3.40-3.35 (m, 1H), 3.24-3.11 (m, 1H), 3.00-2.86 (m, 1H), 2.52-2.45 (m, 1H), 2.42-2.13 (m, 4H), 2.13-2.03 (m, 1H), 1.96-1.86 (m, 1H), 1.82-1.71 (m, 1H), 1.72-1.64 (m, 1H), 1.58-1.51 (m, 2H), 1.15 (d, J = 6.4 Hz, 3H). LCMS (ES, m/z): 492 [M + H]$^+$. |
| 801 | 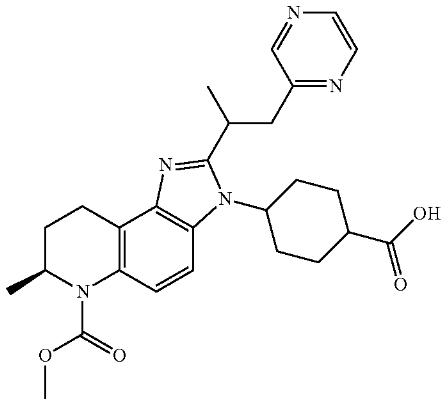 4-((7S)-6-(methoxycarbonyl)-7-methyl-2-(1-(pyrazin-2-yl)propan-2-yl)-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 8.54 (s, 1H), 8.45 (s, 1H), 8.38 (d, J = 2.8 Hz, 1H), 7.45 (d, J = 9.2 Hz, 1H), 7.35 (d, J = 9.2 Hz, 1H), 4.84-4.74 (m, 1H), 4.50-4.35 (m, 1H), 4.01-3.85 (m, 1H), 3.79 (s, 3H), 3.60-3.45 (m, 1H), 3.25-3.11 (m, 2H), 2.96-2.81 (m, 1H), 2.60-2.49 (m, 1H), 2.46-2.11 (m, 5H), 2.01-1.85 (m, 1H), 1.79-1.61 (m, 3H), 1.61-1.51 (m, 1H), 1.50 (d, J = 6.8 Hz, 3H), 1.13 (d, J = 6.8 Hz, 3H). LCMS (ES, m/z): 492 [M + H]$^+$. |
| 802 | 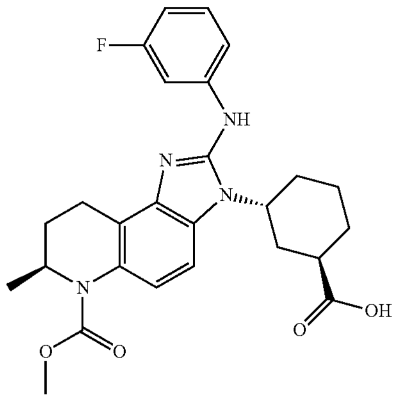 (1R,3R)-3-((S)-2-((3-fluorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 481 [M + H]$^+$ |

TABLE 18-continued

| Example Number | Structure and Compound Name | $^1$H NMR, LCMS |
|---|---|---|
| 803 | 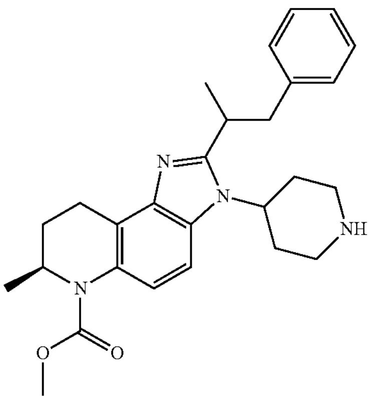<br>methyl (7S)-7-methyl-2-(1-phenylpropan-2-yl)-3-(piperidin-4-yl)-3,7,8,9-tetrahydro-6H-imidazo[4,5-f]quinoline-6-carboxylate<br>1st eluting isomer | $^1$H-NMR ($CD_3OD$, 400 MHz) δ (ppm): 7.45 (d, J = 8.8 Hz, 1H), 7.30 (d, J = 9.2 4.80-4.71 (m, 1H), 4.27-4.13 (m, 1H), 3.79 (s, 3H), 3.68-3.55 (m, 1H), 3.33-3.22 (m, 1H), 3.25-3.06 (m, 3H), 3.05-2.90 (m, 2H), 2.81-2.68 (m, 1H), 2.55-2.44 (m, 1H), 2.39-2.22 (m, 2H), 2.20-2.02 (m, 1H), 1.78-1.66 (m, 2H), 1.56 (d, J = 6.8 Hz, 3H), 1.15 (d, J = 6.8 Hz, 3H), 0.56-0.43 (m, 1H). LCMS (ES, m/z): 447 $[M + H]^+$. |
| 804 | 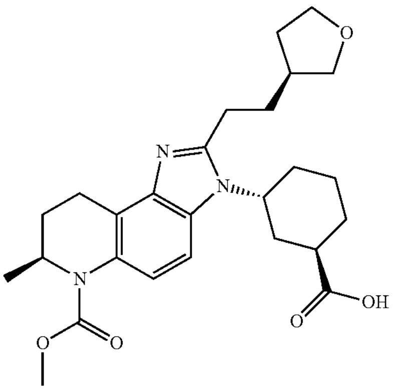<br>(1R,3R)-3-((S)-6-(methoxycarbonyl)-7-methyl-2-(2-((S)-tetrahydrofuran-3-yl)ethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.52 (d, J = 9.2 Hz, 1H), 7.39 (d, J = 9.2 Hz, 1H), 4.83-4.69 (m, 2H), 4.02-3.83 (m, 2H), 3.82-3.69 (m, 4H), 3.52-3.39 (m, 1H), 3.25-3.10 (m, 1H), 3.09-2.85 (m, 4H), 2.50-2.10 (m, 7H), 2.03-1.80 (m, 4H), 1.80-1 55 (m, 4H), 1.14 (d, J = 6.8 Hz, 3H) LCMS (ES, m/z): 470 $[M + H]^+$. |
| 805 | 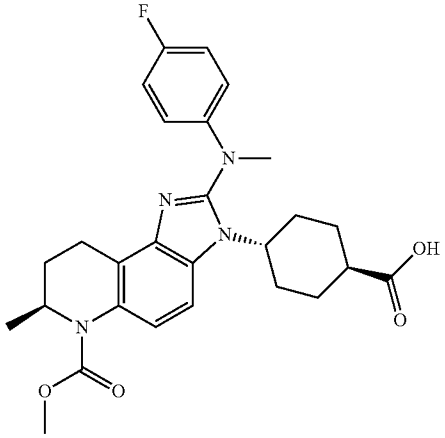<br>(1S,4R)-4-((S)-2-((4-fluorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 495 $[M + H]^+$ |

TABLE 18-continued

| Example Number | Structure and Compound Name | $^1$H NMR, LCMS |
|---|---|---|
| 806 | 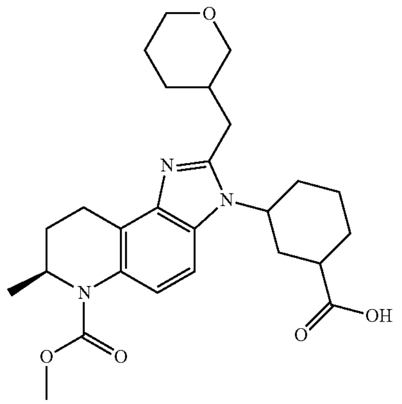 3-((7S)-6-(methoxycarbonyl)-7-methyl-2-((tetrahydro-2H-pyran-3-yl)methyl)-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.61-7.48 (m, 1H), 7.43-7.24 (m, 1H), 4.83-4.64 (m, 2H), 3.97-3.82 (m, 2H), 3.78 (s, 3H), 3.55-3.43 (m, 1H), 3.38-3.35 (m, 1H), 3.24-3.11 (m, 1H), 3.10-2.74 (m, 4H), 2.56-2.33 (m, 2H), 2.33-2.07 (m, 4H), 2.01-1.82 (m, 3H), 1.82-1.57 (m, 5H), 1.47-1.36 (m, 1H), 1.15 (d, J = 6.4 Hz, 3H). LCMS (ES, m/z): 470 $[M + H]^+$. |
| 807 | 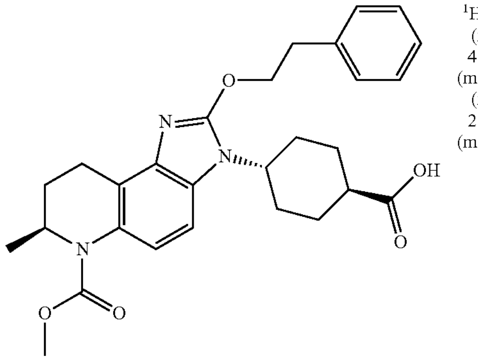 (1S,4R)-4-((S)-6-(methoxycarbonyl)-7-methyl-2-phenethoxy-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.40-7.30 (m, 4H), 7.29-7.22 (m, 2H), 7.21-7.19 (m, 1H), 4.82-4.78 (m, 2H), 4.70-4.59 (m, 1H), 4.21-4.09 (m, 1H), 3.76 (s, 3H), 3.20-3.15 (m, 2H), 3.12-3.05 (m, 1H), 2.81-2.78 (m, 1H), 2.42-2.19 (m, 2H), 2.13-2.04 (m, 4H), 1.81-1.72 (m, 2H), 1.75-1.45 (m, 3H), 1.13 (d, J = 6.8 Hz, 3H). LCMS (ES, m/z): 492 $[M + H]^+$. |
| 808 | 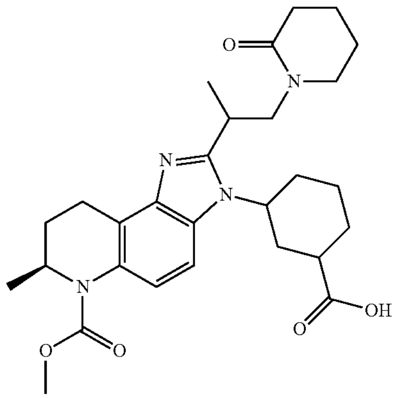 3-((7S)-6-(methoxycarbonyl)-7-methyl-2-(1-(2-oxopiperidin-1-yl)propan-2-yl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.54-7.51 (m, 1H), 7.42-7.39 (m, 1H), 4.78-4.73 (m, 1H), 4.62 (m, 1H), 3.87-3.85 (m, 1H), 3.78-3.61 (m, 4H), 3.28-2.84 (m, 2H), 2.72-2.66 (m, 1H), 2.50-2.18 (m, 5H), 2.15-2.05 (m, 3H), 1.895 (m, 1H), 1.76-1.54 (m, 7H), 1.46 (d, J = 6.4 Hz, 3H), 1.35-1.29 (m, 3H), 1.15 (d, J = 6.4 Hz, 3H). LCMS (ES, m/z): 511 $[M + H]^+$. |

TABLE 18-continued

| Example Number | Structure and Compound Name | $^1$H NMR, LCMS |
|---|---|---|
| 809 | 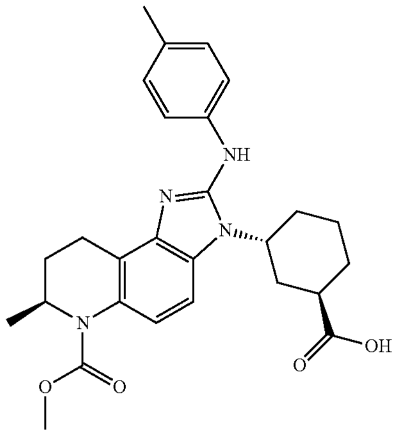 (1R,3R)-3-((S)-6-(methoxycarbonyl)-7-methyl-2-(p-tolylamino)-6,7,8,9-tetrahydro-3H-imidazo[4,5-f]quinolin-3-yl)cyclohexane-1-carboxylic acid | LCMS (ES, m/z): 477 $[M + H]^+$ |
| 810 | 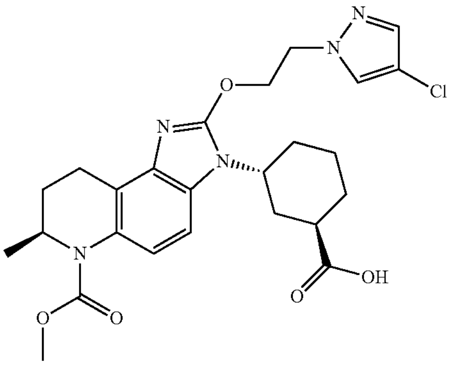 (1R,3R)-3-((S)-2-(2-(4-chloro-1H-pyrazol-1-yl)ethoxy)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.93 (s, 1H), 7.51 (s, 1H), 7.38-7.22 (m, 1H), 7.22-7.06 (m, 1H), 4.94-4.89 (m, 1H), 4.88-4.81 (m, 1H), 4.81-4.65 (m, 1H), 4.65-4.44 (m, 3H), 3.76 (s, 3H), 3.18-3.01 (m, 1H), 2.98-2.83 (m, 1H), 2.83-2.63 (m, 1H), 2.38-2.12 (m, 3H), 2.12-1.93 (m, 2H), 1.87-1.71 (m, 2H), 1.71-1.51 (m, 3H), 1.13 (d, J = 6.8 Hz, 3H). LCMS (ES, m/z): 516 $[M + H]^+$. |
| 811 | 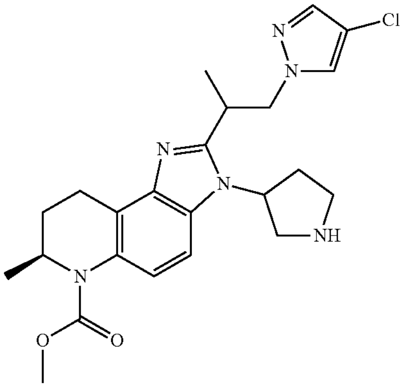 methyl (7S)-2-(1-(4-chloro-1H-pyrazol-1-yl)propan-2-yl)-7-methyl-3-(pyrrolidin-3-yl)-3,7,8,9-tetrahydro-6H-imidazo[4,5-f]quinoline-6-carboxylate 1st eluting isomer | $^1$H-NMR ($CD_3OD$, 300 MHz) δ (ppm): 7.94 (s, 1H), 7.59-7.54 (m, 2H), 7.28 (d, J = 8.7 Hz, 1H), 5.15-4.98 (m, 1H), 4.70-4.40 (m, 3H), 3.98-3.81 (m, 1H), 3.67 (s, 3H), 3.31-2.76 (m, 6H), 2.28-1.95 (m, 3H), 1.68-1.55 (m, 1H), 1.23 (d, J = 6.9 Hz, 3H), 1.06 (d, J = 6.6 Hz, 3H). LCMS (ES, m/z): 457 $[M + H]^+$. |

TABLE 18-continued

| Example Number | Structure and Compound Name | $^1$H NMR, LCMS |
| --- | --- | --- |
| 812 | 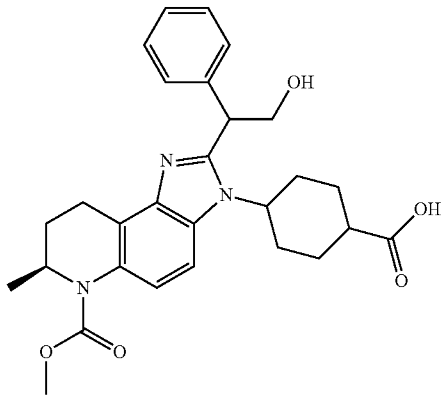 4-((7S)-2-(2-hydroxy-1-phenylethyl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.45-7.42 (m, 1H), 7.41-7.34 (m, 3H), 7.32-7.24 (m, 3H), 4.81-4.73 (m, 1H), 4.60-4.57 (m, 1H), 4.47-4.44 (m, 1H), 4.43-4.17 (m, 2H), 3.76 (s, 3H), 3.30-3.27 (m, 1H), 2.98-2.93 (m, 1H), 2.40-2.28 (m, 3H), 2.27-2.13 (m, 1H), 2.00-1.96 (m, 2H), 1.94-1.83 (m, 1H), 1.80-1.73 (m, 1H), 1.71-1.57 (m, 1H), 1.17-1.13 (m, 4H), 0.98-0.90 (m, 1H). LCMS (ES, m/z): 492 [M + H]$^+$. |
| 813 | 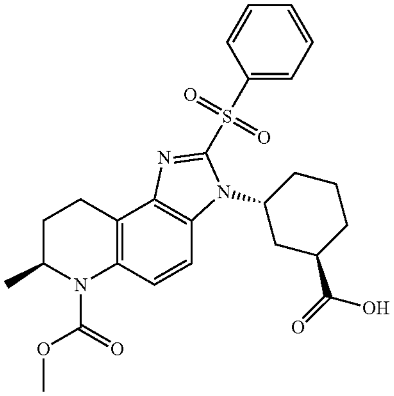 (1R,3R)-3-((S)-6-(methoxycarbonyl)-7-methyl-2-(phenylsulfonyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.18 (d, J = 8.0 Hz, 2H), 7.78-7.75 (m, 1H), 7.69-7.64 (m, 4H), 5.49-5.48 (m, 1H), 4.80-4.76 (m, 1H), 3.79 (s, 3H), 3.23-3.16 (m, 1H), 3.06-2.99 (m, 2H), 2.52-2.48 (m, 1H), 2.25-2.17 (m, 4H), 1.81-1.62 (m, 4H), 1.48-1.45 (m, 1H), 1.13 (d, J = 6.4 Hz, 3H). LCMS (ES, m/z): 512 [M + H]$^+$. |
| 814 | 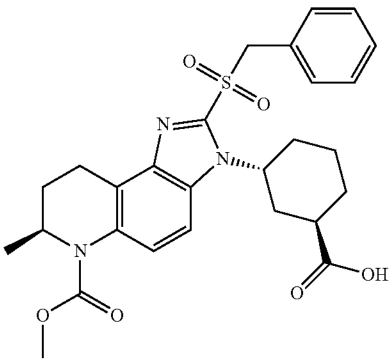 (1R,3R)-3-((S)-2-(benzylsulfonyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.67 (s, 2H), 7.42-7.33 (m, 5H), 5.54-5.51 (m, 1H), 5.04-5.01 (m, 1H), 4.84-4.78 (m, 1H), 3.81 (s, 3H), 3.19-3.5 (m, 1H), 3.07-3.02 (m, 2H), 2.57-2.50 (m, 1H), 2.36-2.33 (m, 1H), 2.26-2.23 (m, 3H), 1.86-1.67 (m, 4H), 1.63-1.55 (m, 1H), 1.38-1.34 (m, 1H), 1.15 (d, J = 6.4 Hz, 3H). LCMS (ES, m/z): 526 [M + H]$^+$. |

TABLE 18-continued

| Example Number | Structure and Compound Name | $^1$H NMR, LCMS |
|---|---|---|
| 815 | 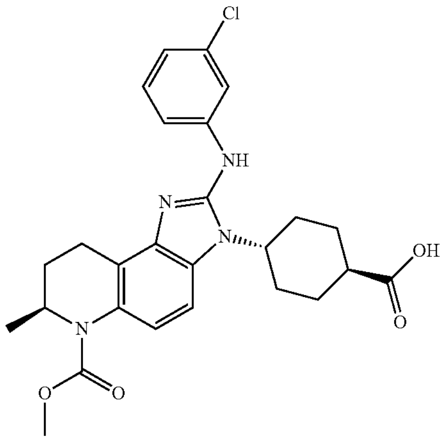<br>(1S,4R)-4-((S)-2-((3-chlorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 497 $[M + H]^+$ |
| 816 | 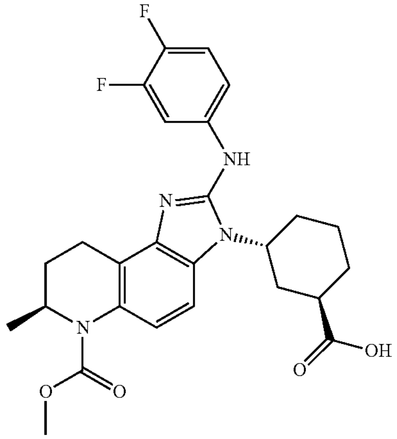<br>(1R,3R)-3-((S)-2-((3,4-difluorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 500 $[M + H]^+$ |
| 817 | 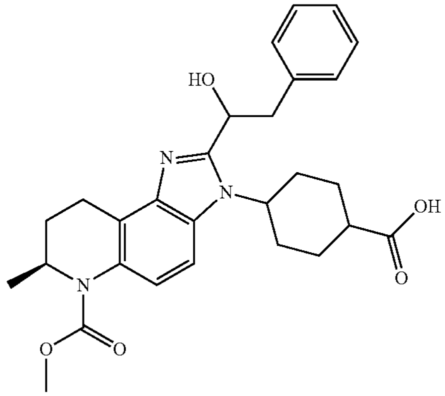<br>4-((7S)-2-(1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid<br>1st eluting isomer | $^1$H NMR ($CD_3OD$, 400 MHz) δ (ppm): 7.48 (d, J = 9.2 Hz, 1H), 7.39 (d, J = 8.8 Hz, 1H), 7.27-7.23 (m, 2H), 7.20-7.17 (m, 3H), 5.29 (t, J = 7.2 Hz, 1H), 4.78-4.75 (m, 1H), 4.68-4.62 (m, 1H), 3.78 (s, 3H), 3.33-3.32 (m, 2H), 3.23-3.21 (m, 1H), 2.93-2.89 (m, 1H), 2.50-2.48 (m, 1H), 2.40-2.30 (m, 1H), 2.27-2.20 (m, 3H), 2.16-2.09 (m, 1H), 1.97-1.92 (m, 1H), 1.75-1.70 (m, 1H), 1.65-1.61 (m, 1H), 1.56-1.51 (m, 2H), 1.15 (d, J = 6.8 Hz, 3H). LCMS (ES, m/z): 492 $[M + H]^+$ |

TABLE 18-continued

| Example Number | Structure and Compound Name | $^1$H NMR, LCMS |
|---|---|---|
| 818 | 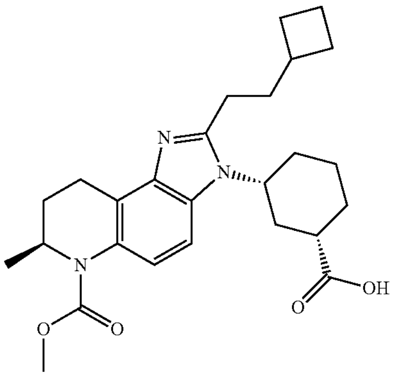 (1S,3R)-3-((S)-2-(2-cyclobutylethyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.51 (d, J = 8.8 Hz, 1H), 7.40 (d, J = 8.4 Hz, 1H), 4.79-4.71 (m, 1H), 4.46-4.35 (m, 1H), 3.78 (s, 3H), 3.22-3.15 (m, 1H), 2.95-2.87 (m, 3H), 2.62-2.58 (m, 1H), 2.50-2.35 (m, 3H), 2.35-2.22 (m, 1H), 2.20-2.03 (m, 5H), 2.01-1.88 (m, 5H), 1.80-1.52 (m, 5H), 1.14 (d, J = 6.4 Hz, 3H). LCMS (ES, m/z): 454 $[M + H]^+$. |
| 819 | 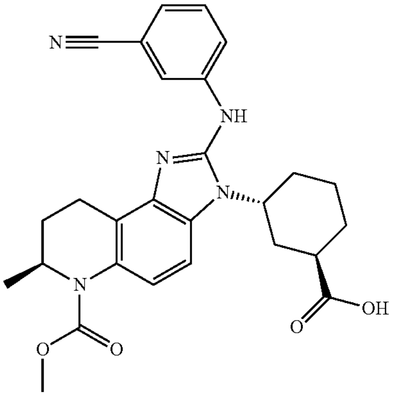 (1R,3R)-3-((S)-2-((3-cyanophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 488 $[M + H]^+$ |
| 820 | 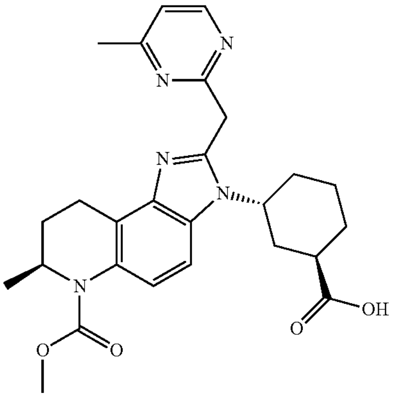 (1R,3R)-3-((S)-6-(methoxycarbonyl)-7-methyl-2-((4-methylpyrimidin-2-yl)methyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 8.52 (d, J = 4.2 Hz, 1H), 7.58 (d, J = 9.0 Hz, 1H), 7.43 (d, J = 9.0 Hz, 1H), 7.23 (d, J = 5.1 Hz, 1H), 4.88-4.49 (m, 4H), 3.79 (s, 3H), 3.28-3.09 (m, 1H), 2.99-2.81 (m, 2H), 2.48 (s, 3H), 2.43-2.12 (m, 5H), 1.93-1.53 (m, 4H), 1.53-1.41 (m, 1H), 1.16-1.14 (d, J = 6.9 Hz, 3H). LCMS (ES, m/z): 478 $[M + H]^+$ |

TABLE 18-continued

| Example Number | Structure and Compound Name | $^1H$ NMR, LCMS |
|---|---|---|
| 821 | 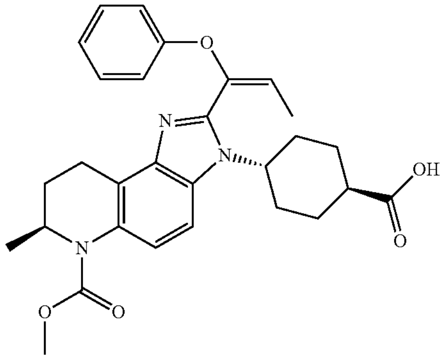 (1S,4R)-4-((S)-6-(methoxycarbonyl)-7-methyl-2-((E)-1-phenoxyprop-1-en-1-yl)-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 7.48 (d, J = 8.8 Hz, 1H), 7.41 (d, J = 8.8 Hz, 1H), 7.27-7.14 (m, 4H), 6.92-6.90 (m, 1H), 5.15-5.04 (m, 1H), 4.73-4.50 (m, 1H), 3.77 (s, 3H), 3.23-3.15 (m, 1H), 2.94-2.85 (m, 1H), 2.60-2.49 (m, 1H), 2.41-2.18 (m, 5H), 1.89-1.70 (m, 2H), 1.86-1.65 (m, 5H), 1.54-1.46 (m, 2H), 1.13 (d, J = 6.8 Hz, 3H) LCMS (ES, m/z): 504 $[M + H]^+$. |
| 822 | 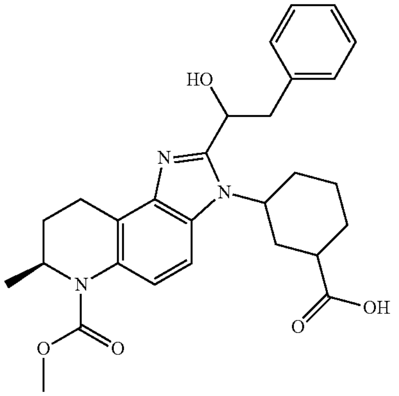 3-((7S)-2-(1-hydroxy-2-phenylethyl)-6-(methoxycarbonyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 7.53 (d, J = 9.2 Hz, 1H), 7.40 (d, J = 8.4 Hz, 1H), 7.36-7.14 (m, 5H), 5.32-5.27 (m, 1H), 5.08-4.98 (m, 1H), 4.82-4.68 (m, 1H), 3.79 (s, 3H), 3.45-3.41 (m, 1H), 3.25-3.21 (m, 2H), 3.01-2.95 (m, 2H), 2.41-2.18 (m, 4H), 2.16-2.02 (m, 1H), 1.98-1.82 (m, 2H), 1.78-1.59 (m, 3H), 1.15 (d, J = 6.4, 3H). LCMS (ES, m/z): 492 $[M + H]^+$ |
| 823 | 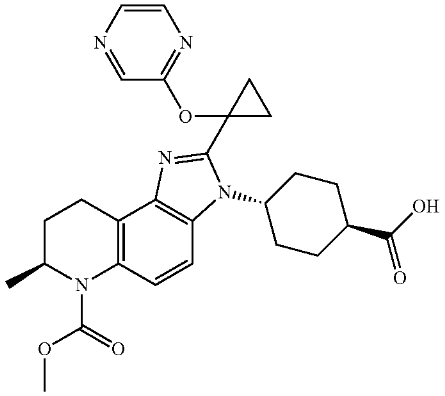 (1S,4R)-4-((S)-6-(methoxycarbonyl)-7-methyl-2-(1-(pyrazin-2-yloxy)cyclopropyl)-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 8.51 (s, 1H), 8.18-8.10 (m, 2H), 7.47-7.35 (m, 2H), 5.12-5.07 (m, 1H), 4.82-4.74 (m, 1H), 3.77 (s, 3H), 3.23-3.15 (m, 1H), 3.00-2.89 (m, 1H), 2.53-2.42 (m, 1H), 2.39-2.30 (m, 2H), 2.32-2.15 (m, 3H), 2.02-1.71 (m, 7H), 1.69-1.57 (m, 2H), 1.13 (d, J = 6.8 Hz, 3H). LCMS (ES, m/z): 506 $[M + H]^+$. |

TABLE 18-continued

| Example Number | Structure and Compound Name | $^1H$ NMR, LCMS |
|---|---|---|
| 824 | 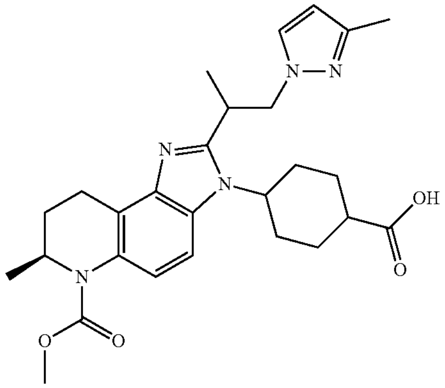<br>4-((7S)-6-(methoxycarbonyl)-7-methyl-2-(1-(3-methyl-1H-pyrazol-1-yl)propan-2-yl)-6,7,8,9-tetrahydro-3H-imidazo[4,5-f]quinolin-3-yl)cyclohexane-1-carboxylic acid<br>2nd eluting isomer | $^1H$-NMR ($CD_3OD$, 300 MHz) δ (ppm): ) 7.47-7.29 (m, 2H), 7.22 (d, J = 2.1 Hz, 1H), 5.90 (s, 1H), 4.79-4.65 (m, 1H), 4.59-4.47 (m, 1H), 4.46-4.34 (m, 1H), 4.34-4.18 (m, 1H), 4.00-3.82 (m, 1H), 3.76 (s, 3H), 3.26-3.16 (m, 1H), 2.98-2.83 (m, 1H), 2.58-2.38 (m, 1H), 2.38-2.03 (m, 8H), 1.93-1.80 (m, 1H), 1.80-1.56 (m, 3H), 1.49-1.35 (m, 4H), 1.14 (d, J = 6.6 Hz, 3H). LCMS (ES, m/z): 494 $[M + H]^+$ |
| 825 | 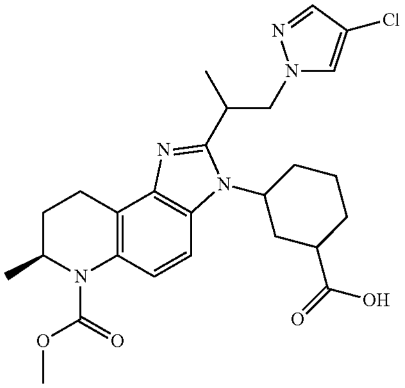<br>3-((7S)-2-(1-(4-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid<br>2nd eluting isomer | $^1H$-NMR ($CD_3OD$, 400 MHz) δ (ppm): 7.90 (s, 1H), 7.87-7.75 (m, 2H), 7.31 (s, 1H), 5.12-5.02 (m, 1H), 4.87-4.72 (m, 1H), 4.71 (d, J = 6.8 Hz, 2H), 4.30-4.15 (m, 1H), 3.79 (s, 3H), 3.18-2.96 (m, 3H), 2.45-2.30 (m, 2H), 2.29-2.18 (m, 2H), 2.14-1.99 (m, 2H), 1.95-1.70 (m, 3H), 1.65-1.60 (m, 1H), 1.57 (d, J = 6.8 Hz, 3H), 1.16 (d, J = 6.8 Hz, 3H). LCMS (ES, m/z): 514 $[M + H]^+$. |
| 826 | 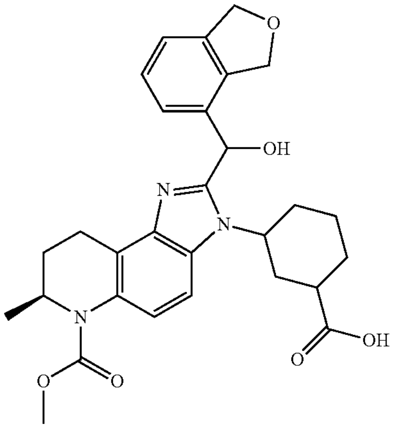<br>3-((7S)-2-((1,3-dihydroisobenzofuran-4-yl)(hydroxy)methyl)-6-(methoxycarbonyl)-7-methyl-6,7,8,9-tetrahydro-3H-imidazo[4,5-f]quinolin-3-yl)cyclohexane-1-carboxylic acid<br>1st eluting isomer | $^1H$-NMR ($CD_3OD$, 400 MHz) δ (ppm): 7.64-7.52 (m, 1H), 7.52-7.41 (m, 1H), 7.41-7.31 (m, 1H), 7.31-7.19 (m, 1H), 7.07-6.91 (m, 1H), 6.60 (s, 1H), 5.63-5.42 (m, 1H), 5.42-5.26 (m, 1H), 4.86-4.58 (m, 4H), 3.79 (s, 3H), 3.32-3.18 (m, 1H), 3.04-2.92 (m, 1H), 2.84-2.61 (m, 1H), 2.44-2.21 (m, 3H), 2.13-1.93 (m, 2H), 1.91-1.72 (m, 3H), 1.72-1.43 (m, 2H), 1.18 (d, J = 6.4 Hz, 3H). LCMS (ES, m/z): 520 $[M + H]^+$ |

TABLE 18-continued

| Example Number | Structure and Compound Name | $^1$H NMR, LCMS |
|---|---|---|
| 827 | 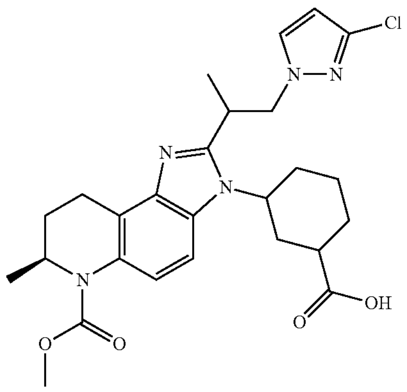 3-((7S)-2-(1-(3-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 300 MHz) δ (ppm): 8.11-7.46 (m, 3H), 6.20 (s, 1H), 5.28-5.01 (m, 1H), 4.79-4.48 (m, 2H), 4.30-4.01 (m, 1H), 3.80 (s, 3H), 3.22-2.87 (m, 3H), 2.64-2.31 (m, 2H), 2.31-2.11 (m, 3H), 2.11-1.79 (m, 4H), 1.73-1.48 (m, 4H), 1.32-1.23 (m, 1H), 1.16 (d, J = 6.6 Hz, 3H). LCMS (ES, m/z): 514 $[M + H]^+$. |
| 828 | 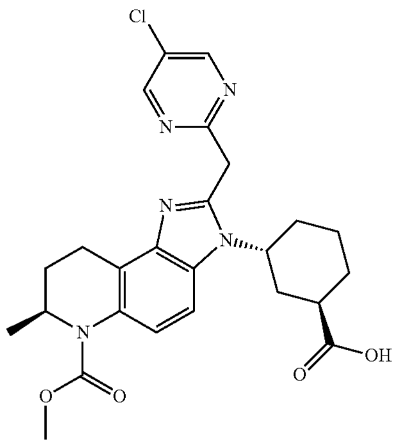 (1R,3R)-3-((S)-2-((5-chloropyrimidin-2-yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.74 (s, 2H), 7.56 (d, J = 9.2 Hz, 1H), 7.42 (d, J = 8.8 Hz, 1H), 4.82-4.65 (m, 2H), 3.79 (s, 3H), 3.17 (m, 1H), 2.97-2.87 (m, 2H), 2.45-2.16 (m, 6H), 1.92-1.54 (m, 6H), 1.15 (d, J = 6.4 Hz, 3H). LCMS (ES, m/z): 498 $[M + H]^+$. |
| 829 | 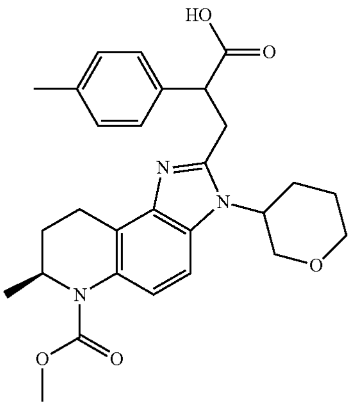 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(p-tolyl)propanoic acid 1st eluting isomer | $^1$H-NMR ($CD_3OD$, 300 MHz) δ (ppm): 7.55 (d, J = 9.0 Hz, 1H), 7.44 (d, J = 9.3 Hz, 1H), 7.25 (d, J = 8.4 Hz, 2H), 7.16 (d, J = 8.1 Hz, 2H), 4.86-4.80 (m, 1H), 4.78-4.54 (m, 1H), 4.29-4.24 (m, 1H), 3.99-3.92 (m, 2H), 3.78-3.54 (m, 5H), 3.38-3.11 (m, 3H), 2.95-2.90 (m, 1H), 2.53-2.34 (m, 1H), 2.33-1.69 (m, 8H), 1.14 (d, J = 6.6 Hz, 3H). LCMS (ES, m/z): 492 $[M + H]^+$. |

TABLE 18-continued
| Example Number | Structure and Compound Name | $^1$H NMR, LCMS |
|---|---|---|
| 830 | 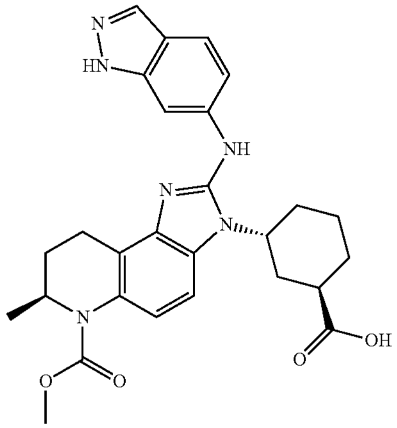 (1R,3R)-3-((S)-2-((1H-indazol-6-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 503 [M + H]$^+$ |
| 831 | 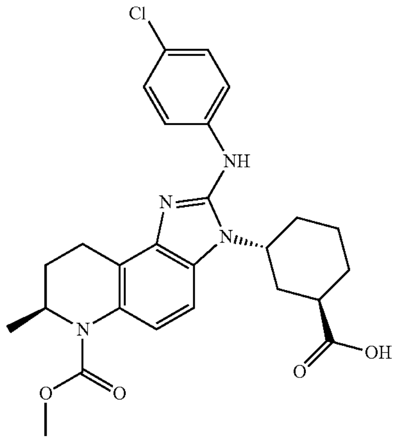 (1R,3R)-3-((S)-2-((4-chlorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 497 [M + H]$^+$ |

TABLE 18-continued

| Example Number | Structure and Compound Name | $^1H$ NMR, LCMS |
| --- | --- | --- |
| 832 | 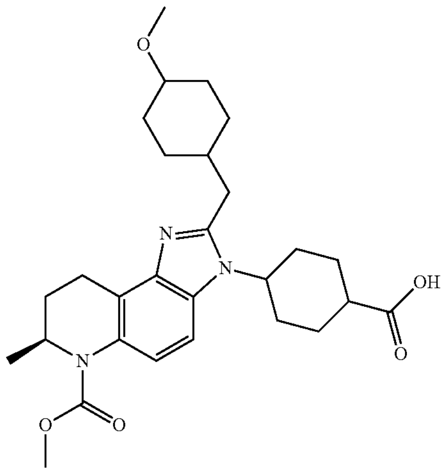 4-((7S)-6-(methoxycarbonyl)-2-((-4-methoxycyclohexyl)methyl)-7-methyl-6,7,8,9-tetrahydro-3H-imidazo[4,5-f]quinolin-3-yl)cyclohexane-1-carboxylic acid 1st eluting isomer | $^1H$-NMR ($CD_3OD$, 300 MHz) δ (ppm): 7.53 (d, J = 9.0 Hz, 1H), 7.39 (d, J = 9.0 Hz, 1H), 4.83-4.66 (m, 1H), 4.47-4.26 (m, 1H), 3.78 (s, 3H), 3.33-3.32 (m, 3H), 3.28-3.06 (m, 2H), 3.01-2.82 (m, 3H), 2.58-2.35 (m, 3H), 2.34-2.17 (m, 3H), 2.16-2.03 (m, 2H), 2.02-1.86 (m, 2H), 1.85-1.55 (m, 6H), 1.31-1.07 (m, 7H). LCMS (ES, m/z): 498 $[M + H]^+$. |
| 833 | 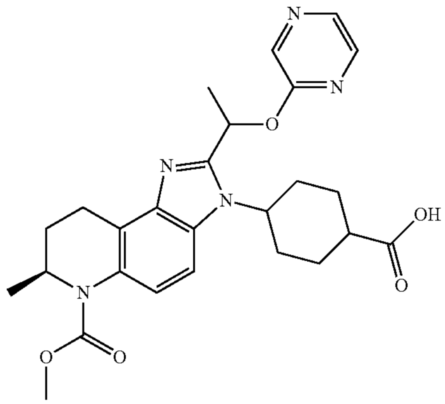 4-((7S)-6-(methoxycarbonyl)-7-methyl-2-(1-(pyrazin-2-yloxy)ethyl)-6,7,8,9-tetrahydro-3H-imidazo[4,5-f]quinolin-3-yl)cyclohexane-1-carboxylic acid 1st eluting isomer | $^1H$-NMR ($CD_3OD$, 400 MHz) δ (ppm): 8.34 (s, 1H), 8.15-8.10 (m, 2H), 7.61-7.40 (m, 2H), 6.59 (t, J = 6.4 Hz, 1H), 4.79-4.62 (m, 2H), 3.77 (s, 3H), 3.23-3.11 (m, 1H), 2.95-2.83 (m, 1H), 2.62-2.31 (m, 3H), 2.30-2.12 (m, 4H), 1.98-1.90 (m, 1H), 1.88 (d, J = 6.8 Hz, 3H), 1.78-1.51 (m, 3H), 1.13 (d, J = 6.4 Hz, 3H). LCMS (ES, m/z): 494 [M + H]+. |

TABLE 18-continued

| Example Number | Structure and Compound Name | $^1$H NMR, LCMS |
|---|---|---|
| 834 | 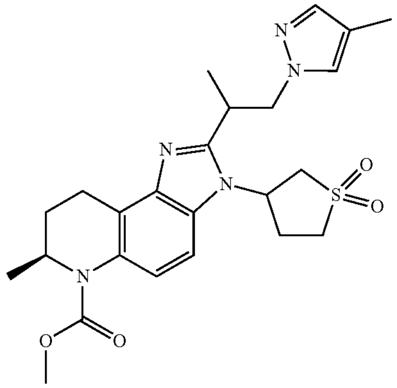 methyl (7S)-3-(1,1-dioxidotetrahydrothiophen-3-yl)-7-methyl-2-(1-(4-methyl-1H-pyrazol-1-yl)propan-2-yl)-3,7,8,9-tetrahydro-6H-imidazo[4,5-f]quinoline-6-carboxylate 3rd eluting isomer | $^1$H-NMR ($CD_3OD$, 300 MHz) δ (ppm): 7.53-7.49 (m, 2H), 7.31 (s, 1H), 7.20 (s, 1H), 5.55-5.35 (m, 1H), 4.97 (s, 1H), 4.78-4.32 (m, 2H), 3.95-3.85 (m, 1H), 3.75-3.58 (m, 3H), 3.52-3.15 (m, 5H), 2.98-2.65 (m, 2H), 2.32-2.12 (m, 2H), 1.95 (s, 3H), 1.76-1.66 (m, 1H), 1.41 (d, J = 6.9 Hz, 3H), 1.12 (d, J = 6.6 Hz, 3H). LCMS (ES, m/z): 486 $[M + H]^+$. |
| 835 | 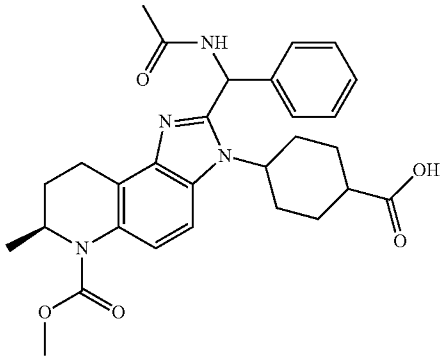 4-((7S)-2-(acetamido(phenyl)methyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 300 MHz) δ (ppm): 7.54-7.29 (m, 7H), 6.57 (s, 1H), 4.82-4.69 (m, 1H), 4.35-4.18 (m, 1H), 3.79 (s, 3H), 3.30-3.19 (m, 1H), 3.04-2.90 (m, 1H), 2.52-1.85 (m, 10H), 1.85-1.54 (m, 2H), 1.40-1.25 (m, 1H), 1.18 (d, J = 6.6 Hz, 3H), 1.13-1.01 (m, 1H). LCMS (ES, m/z): 519 $[M + H]^+$ |
| 836 | 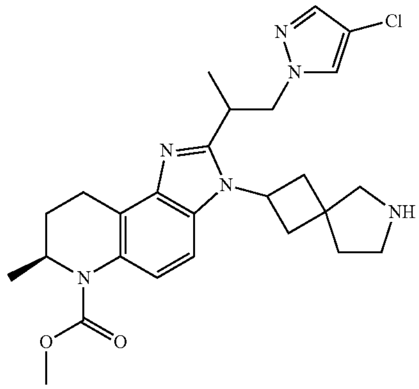 methyl (7S)-2-(1-(4-chloro-1H-pyrazol-1-yl)propan-2-yl)-7-methyl-3-(6-azaspiro[3.4]octan-2-yl)-3,7,8,9-tetrahydro-6H-imidazo[4,5-f]quinoline-6-carboxylate 1st eluting isomer | $^1$H-NMR ($CD_3OD$, 300 MHz) δ (ppm): 7.82-7.59 (m, 3H), 7.37 (s, 1H), 5.22-5.02 (m, 1H), 4.83-4.78 (m, 1H), 4.61 (d, J = 7.2 Hz, 2H), 4.24-3.97 (m, 1H), 3.80 (s, 3H), 3.57-3.44 (m, 2H), 3.42-3.32 (m, 2H), 3.21-2.89 (m, 4H), 2.89-2.70 (m, 1H), 2.70-2.49 (m, 1H), 2.33-2.12 (m, 3H), 1.93-1.76 (m, 1H), 1.55 (d, J = 6.9 Hz, 3H), 1.15 (d, J = 6.6 Hz, 3H). LCMS (ES, m/z): 497 $[M + H]^+$. |

TABLE 18-continued

| Example Number | Structure and Compound Name | $^1$H NMR, LCMS |
|---|---|---|
| 837 | 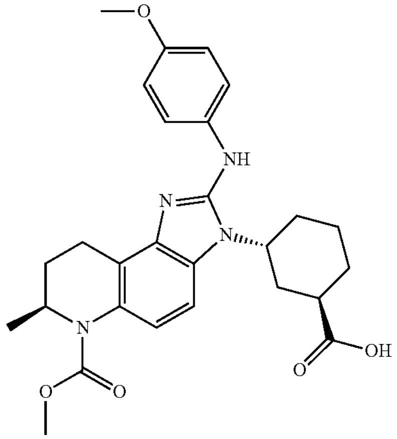 (1R,3R)-3-((S)-6-(methoxycarbonyl)-2-((4-methoxyphenyl)amino)-7-methyl-6,7,8,9-tetrahydro-3H-imidazo[4,5-f]quinolin-3-yl)cyclohexane-1-carboxylic acid | LCMS (ES, m/z): 494 [M + H]$^+$ |
| 838 | 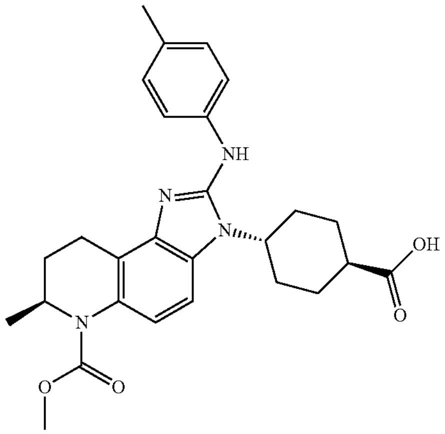 (1S,4R)-4-((S)-6-(methoxycarbonyl)-7-methyl-2-(p-tolylamino)-6,7,8,9-tetrahydro-3H-imidazo[4,5-f]quinolin-3-yl)cyclohexane-1-carboxylic acid | LCMS (ES, m/z): 478 [M + H]$^+$ |
| 839 | 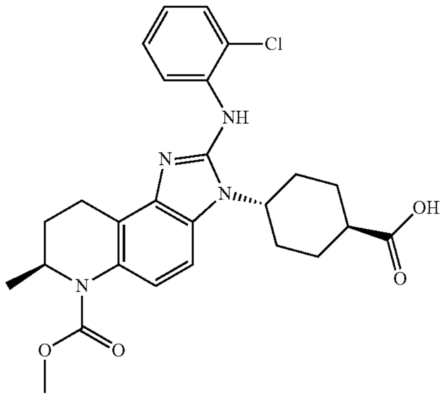 (1S,4R)-4-((S)-2-((2-chlorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 497 [M + H]$^+$ |

TABLE 18-continued

| Example Number | Structure and Compound Name | $^1$H NMR, LCMS |
| --- | --- | --- |
| 840 | 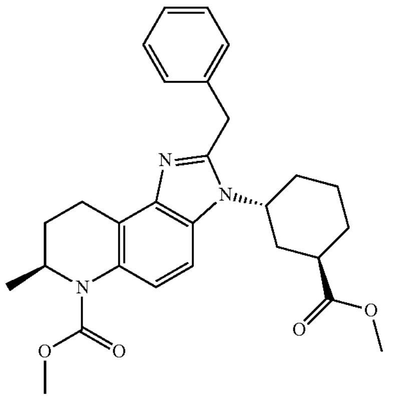 methyl (S)-2-benzyl-3-((1R,3R)-3-(methoxycarbonyl)cyclohexyl)-7-methyl-3,7,8,9-tetrahydro-6H-imidazo[4,5-f]quinoline-6-carboxylate | $^1$H-NMR ($CD_3OD$, 400 MHz) δ (ppm): 7.51-7.38 (m, 2H), 7.34-7.26 (m, 2H), 7.23-7.19 (m, 3H), 4.81-4.63 (m, 2H), 4.62-4.38 (m, 2H), 3.77 (s, 3H), 3.74 (s, 3H), 3.25-3.13 (m, 1H), 3.02-3.86 (m, 2H), 2.55-2.03 (m, 5H), 1.79-1.53 (m, 3H), 1.30-1.15 (m, 2H), 1.13 (d, J = 6.8, 3H). LCMS (ES, m/z): 476 $[M + H]^+$. |
| 841 | 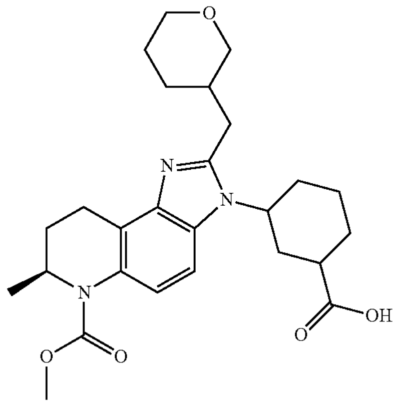 3-((7S)-6-(methoxycarbonyl)-7-methyl-2-((tetrahydro-2H-pyran-3-yl)methyl)-6,7,8,9-tetrahydro-3H-imidazo[4,5-f]quinolin-3-yl)cyclohexane-1-carboxylic acid 1st eluting isomer | $^1$H-NMR ($CD_3OD$, 400 MHz) δ (ppm): 7.63-7.46 (m, 1H), 7.46-7.28 (m, 1H), 4.86-4.68 (m, 2H), 3.92-3.76 (m, 5H), 3.58-3.39 (m, 1H), 3.31-3.11 (m, 2H), 3.09-2.89 (m, 4H), 2.53-2.35 (m, 2H), 2.35-2.12 (m, 4H), 2.01-1.85 (m, 3H), 1.84-1.54 (m, 5H), 1.51-1.37 (m, 1H), 1.15 (d, J = 6.4 Hz, 3H). LCMS (ES, m/z): 470 $[M + H]^+$. |
| 842 | 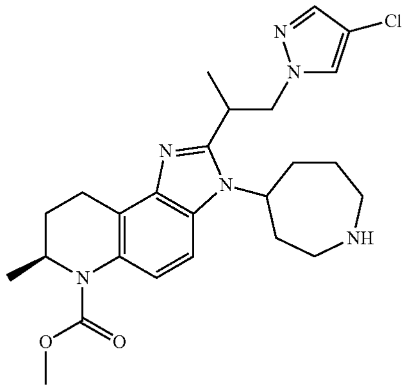 methyl (7S)-3-(azepan-4-yl)-2-(1-(4-chloro-1H-pyrazol-1-yl)propan-2-yl)-7-methyl-3,7,8,9-tetrahydro-6H-imidazo[4,5-f]quinoline-6-carboxylate 4th eluting isomer | $^1$H-NMR ($CD_3OD$, 400 MHz) δ (ppm): 7.55 (s, 1H), 7.52-7.33 (m, 3H), 4.82-4.72 (m, 1H), 4.71-4.57 (m, 2H), 4.56-4.44 (m, 1H), 4.04-3.89 (m, 1H), 3.79 (s, 3H), 3.47-3.34 (m, 3H), 3.28-3.14 (m, 2H), 3.07-2.89 (m, 1H), 2.74-2.60 (m, 1H), 2.59-2.40 (m, 1H), 2.35-2.21 (m, 1H), 2.17-1.85 (m, 3H), 1.84-1.62 (m, 2H), 1.46 (d, J = 7.2 Hz, 3H), 1.15 (d, J = 6.8 Hz, 3H). LCMS (ES, m/z): 485 $[M + H]^+$. |

TABLE 18-continued

| Example Number | Structure and Compound Name | $^1$H NMR, LCMS |
|---|---|---|
| 843 | 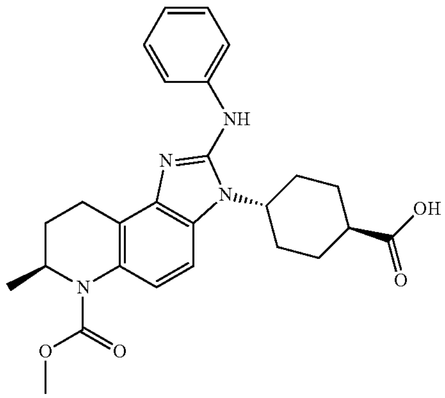<br>(1S,4R)-4-((S)-6-(methoxycarbonyl)-7-methyl-2-(phenylamino)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.43-7.37 (m, 3H), 7.32-7.26 (m, 3H), 6.99 (t, J = 7.6 Hz, 1H), 4.73-4.69 (m, 1H), 4.42-4.40 (m, 1H), 3.76 (s, 3H), 3.09-3.03 (m, 1H), 2.82-2.76 (m, 1H), 2.52-2.36 (m, 3H), 2.35-2.17 (m, 3H), 2.01-1.99 (m, 2H), 1.70-1.62 (m, 3H), 1.12 (d, J = 6.8 Hz, 3H). LCMS (ES, m/z): 463 M + H]$^+$. |
| 844 | 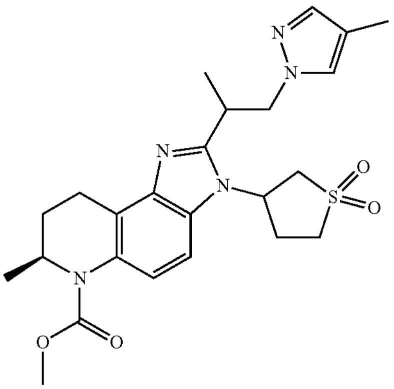<br>methyl (7S)-3-(1,1-dioxidotetrahydrothiophen-3-yl)-7-methyl-2-(1-(4-methyl-1H-pyrazol-1-yl)propan-2-yl)-3,7,8,9-tetrahydro-6H-imidazo[4,5-f]quinoline-6-carboxylate<br>4$^{th}$ eluting isomer | $^1$H-NMR ($CD_3OD$, 300 MHz) δ (ppm): 7.53-7.40 (m, 2H), 7.31 (s, 1H), 7.17 (s, 1H), 5.49-5.38 (m, 1H), 4.89-4.38 (m, 3H), 3.98-3.85 (m, 1H), 3.78 (s, 3H), 3.50-3.15 (m, 3H), 2.98-2.20 (m, 4H), 2.60-2.15 (m, 2H), 1.96 (s, 3H), 1.78-1.65 (m, 1H), 1.42 (d, J = 6.9 Hz, 3) 1.12 (d, J = 6.6 Hz, 3H). LCMS (ES, m/z): 486 [M + H]$^+$. |
| 845 | 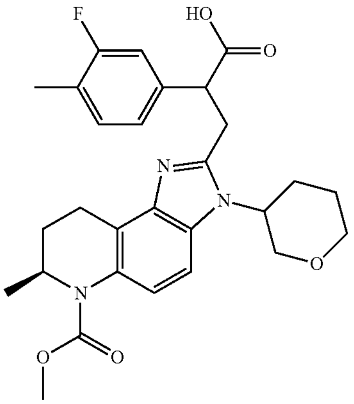<br>2-(3-fluoro-4-methylphenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid<br>1$^{st}$ eluting isomer | $^1$H-NMR ($CD_3OD$, 300 MHz) δ (ppm): 7.61 (d, J = 9.0 Hz, 1H), 7.49 (d, J = 9.0 Hz, 1H), 7.24-7.11 (m, 1H), 7.07-7.04 (m, 2H), 4.81-4.57 (m, 2H), 4.32-4.28 (m, 1H), 4.07-3.96 (m, 2H), 3.79 (s, 3H), 3.77-3.72 (m, 1H), 3.58-3.45 (m, 1H), 3.42-3.33 (m, 2H), 3.14-3.09 (m, 1H), 2.96-2.92 (m, 1H), 2.35-2.30 (m, 1H), 2.26-2.25 (m, 4H), 2.18-2.09 (m, 1H), 1.83-1.74 (m, 2H), 1.44-1.43 (m, 1H), 1.14 (d, J = 6.9 Hz, 3H). LCMS (ES, m/z): 510 [M + H]$^+$. |

TABLE 18-continued

| Example Number | Structure and Compound Name | $^1$H NMR, LCMS |
|---|---|---|
| 846 | 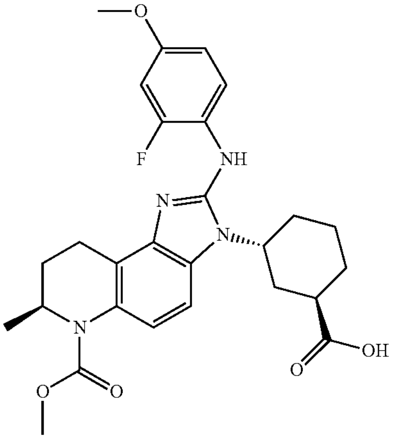 (1R,3R)-3-((S)-2-((2-fluoro-4-methoxyphenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 $[M + H]^+$ |
| 847 | 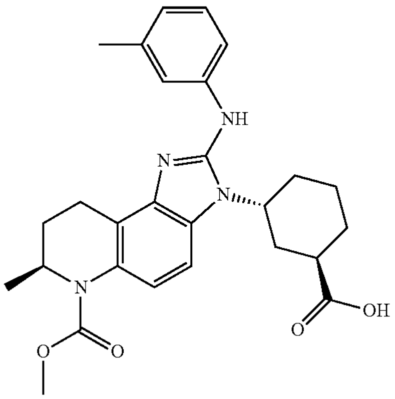 (1R,3R)-3-((S)-6-(methoxycarbonyl)-7-methyl-2-(m-tolylamino)-6,7,8,9-tetrahydro-3H-imidazo[4,5-f]quinolin-3-yl)cyclohexane-1-carboxylic acid | LCMS (ES, m/z): 477 $[M + H]^+$ |
| 848 | 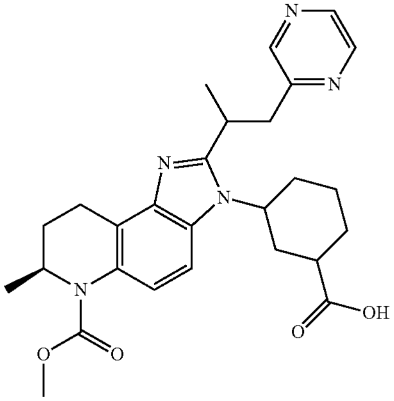 3-((7S)-6-(methoxycarbonyl)-7-methyl-2-(1-(pyrazin-2-yl)propan-2-yl)-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 8.51-8.35 (m, 3H), 7.48 (d, J = 9.2 Hz, 1H), 7.35 (d, J = 8.8 Hz, 1H), 4.87-4.71 (m, 2H), 3.95-3.93 (m, 1H), 3.78 (s, 3H), 3.68-3.63 (m, 1H), 3.34-3.18 (m, 2H), 2.97-2.88 (m, 2H), 2.41-2.08 (m, 5H), 1.92-1.66 (m, 5H), 1.47 (d, J = 6.8 Hz, 3H), 1.13 (d, J = 6.8 Hz, 3H). LCMS (ES, m/z): 492 $[M + H]^+$. |

TABLE 18-continued

| Example Number | Structure and Compound Name | $^1$H NMR, LCMS |
|---|---|---|
| 849 | 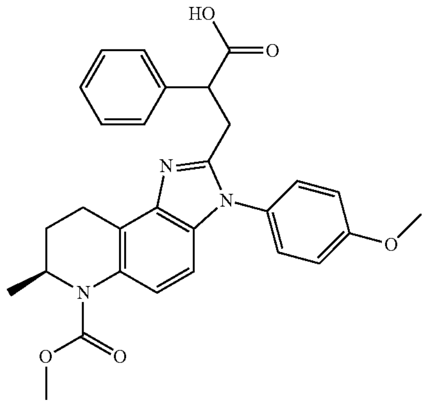 3-((7S)-6-(methoxycarbonyl)-3-(4-methoxyphenyl)-7-methyl-6,7,8,9-tetrahydro-3H-imidazo[4,5-f]quinolin-2-yl)-2-phenylpropanoic acid 1$^{st}$ eluting isomer | $^1$H-NMR ($CD_3OD$, 300 MHz) δ (ppm): 7.32 (d, J = 9.0 Hz, 1H), 7.23-7.08 (m, 9H), 6.79 (d, J = 8.7 Hz, 1H), 4.85-4.70 (m, 1H), 4.45-4.25 (m, 1H), 3.89 (s, 3H), 3.75 (s, 3H), 3.55-3.42 (m, 1H), 3.32-2.85 (m, 3H), 2.32-2.21 (m, 1H), 1.75-1.58 (m, 1H), 1.14 (d, J = 6.9 Hz, 3H). LCMS (ES, m/z): 500 [M + H]$^+$. |
| 850 | 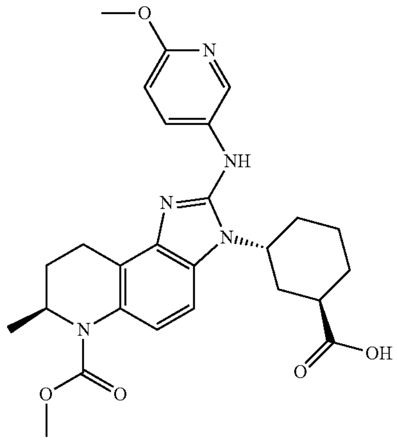 (1R,3R)-3-((S)-6-(methoxycarbonyl)-2-((6-methoxypyridin-3-yl)amino)-7-methyl-6,7,8,9-tetrahydro-3H-imidazo[4,5-f]quinolin-3-yl)cyclohexane-1-carboxylic acid | LCMS (ES, m/z): 494 [M + H]$^+$ |
| 851 | 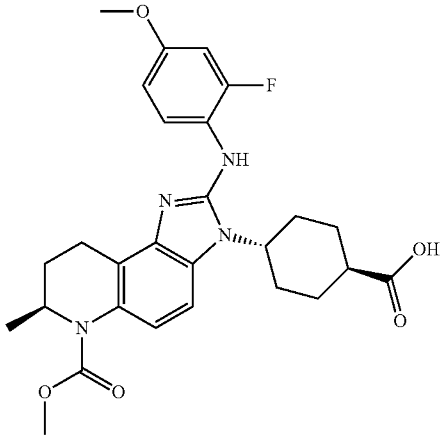 (1S,4R)-4-((S)-2-((2-fluoro-4-methoxyphenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 [M + H]$^+$ |

TABLE 18-continued

| Example Number | Structure and Compound Name | $^1$H NMR, LCMS |
|---|---|---|
| 852 | 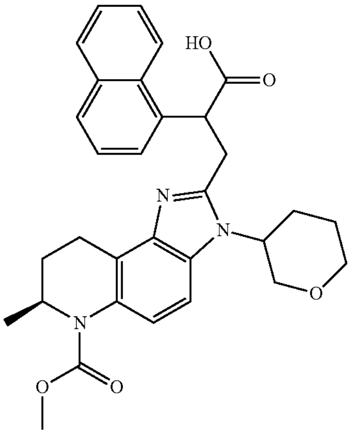 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(naphthalen-1-yl)propanoic acid 2nd eluting isomer | $^1$H-NMR ($CD_3OD$, 300 MHz) δ (ppm): 8.29-8.20 (m, 1H), 7.90-7.70 (m, 2H), 7.55-7.30 (m, 6H), 5.05-5.01 (m, 1H), 4.82-4.71 (m, 1H), 4.2-3.7 (m, 8H), 3.59-3.51 (m, 1H), 3.48-3.33 (m, 1H), 3.33-3.12 (m, 1H), 2.96-2.89 (m, 1H), 2.35-2.18 (m, 1H), 2.18-1.93 (m, 1H), 1.78-1.72 (m, 1H), 1.51-1.42 (m, 1H), 1.18-1.11 (m, 4H), 0.65 (m, 1H). LCMS (ES, m/z): 528 $[M + H]^+$ |
| 853 | 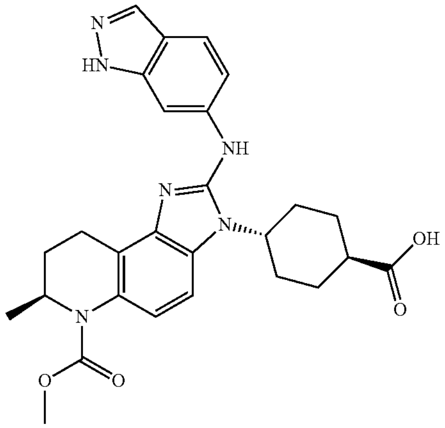 (1S,4R)-4-((S)-2-((1H-indazol-6-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 503 $[M + H]^+$ |
| 854 | 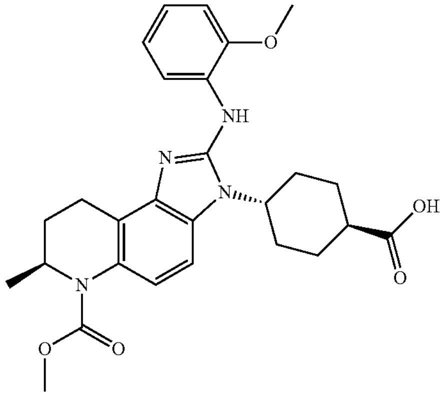 (1S,4R)-4-((S)-6-(methoxycarbonyl)-2-((2-methoxyphenyl)amino)-7-methyl-6,7,8,9-tetrahydro-3H-imidazo[4,5-f]quinolin-3-yl)cyclohexane-1-carboxylic acid | LCMS (ES, m/z): 493 $[M + H]^+$ |

TABLE 18-continued

| Example Number | Structure and Compound Name | $^1H$ NMR, LCMS |
|---|---|---|
| 855 | 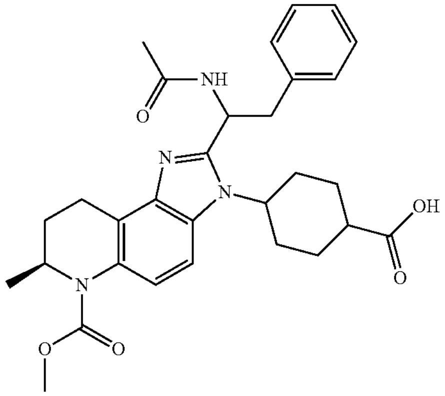 4-((7S)-2-(1-acetamido-2-phenylethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1H$ NMR ($CD_3OD$, 400 MHz) δ (ppm): 7.83-7.74 (m, 2H), 7.29-7.27 (m, 3H), 7.18-7.17 (m, 2H), 5.67-5.63 (m, 1H), 4.86-4.84 (m, 1H), 4.50-4.42 (m, 1H), 3.81 (s, 3H), 3.64-3.60 (m, 1H), 3.28-3.27 (m, 1H), 3.18-3.16 (m, 1H), 3.01-2.95 (m, 1H), 2.53-2.49 (m, 1H), 2.32-2.25 (m, 4H), 2.04-1.88 (m, 6H), 1.70-1.68 (m, 1H), 1.52-1.40 (m, 1H), 1.21 (d, J = 6.4 Hz, 3H), 0.50-0.48 (m, 1H). LCMS (ES, m/z): 533 $[M + H]^+$. |
| 856 | 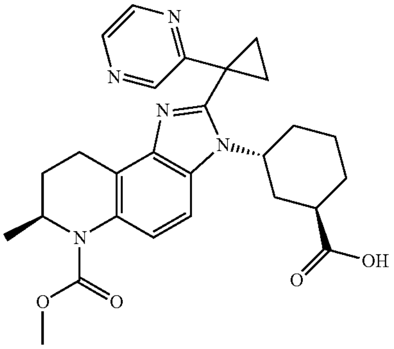 (1R,3R)-3-((S)-6-(methoxycarbonyl)-7-methyl-2-(1-(pyrazin-2-yl)cyclopropyl)-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 8.54 (s, 1H), 8.38 (s, 1H), 8.00 (s, 1H), 7.59 (d, J = 8.4 Hz, 1H), 7.48 (d, J = 8.0 Hz, 1H), 4.84-4.74 (m, 2H), 3.79 (s, 3H), 3.33-3.15 (m, 1H), 3.03-2.96 (m, 1H), 2.86-2.82 (m, 1H), 2.52-2.05 (m, 6H), 1.89-1.55 (m, 7H), 1.45-1.30 (m, 1H), 1.16 (d, J = 6.8 Hz, 3H). LCMS (ES, m/z): 490 $[M + H]^+$. |
| 857 | 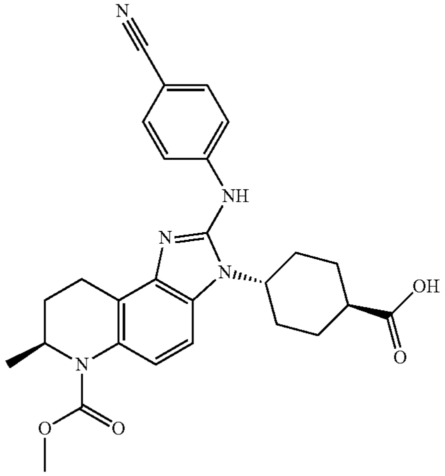 (1S,4R)-4-((S)-2-((4-cyanophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 488 $[M + H]^+$ |

TABLE 18-continued

| Example Number | Structure and Compound Name | $^1$H NMR, LCMS |
|---|---|---|
| 858 | 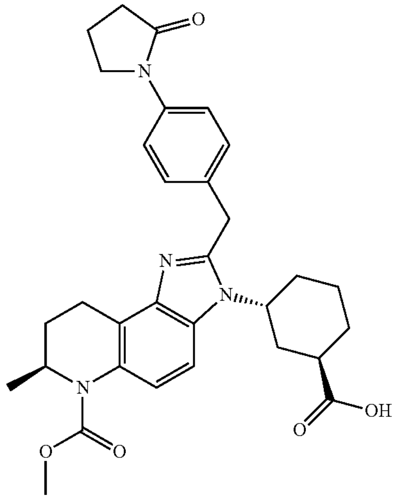 (1R,3R)-3-((S)-6-(methoxycarbonyl)-7-methyl-2-(4-(2-oxopyrrolidin-1-yl)benzyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.60-7.54 (m, 2H), 7.45-7.40 (m, 1H), 7.37-7.30 (m, 3H), 4.78-4.39 (m, 6H), 3.89-3.80 (m, 1H), 3.76 (s, 3H), 3.30-3.20 (m, 1H), 3.12-2.80 (m, 1H), 2.75-2.68 (m, 2H), 2.29-2.09 (m, 7H), 1.77-1.48 (m, 3H), 1.31-1.28 (m, 1H), 1.20-1.12 (m, 4H). LCMS (ES, m/z): 545 [M + H]+. |
| 859 | 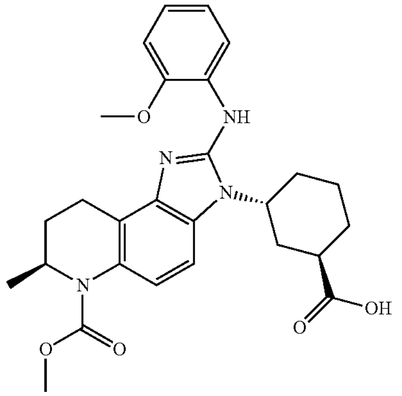 (1R,3R)-3-((S)-6-(methoxycarbonyl)-2-((2-methoxyphenyl)amino)-7-methyl-6,7,8,9-tetrahydro-3H-imidazo[4,5-f]quinolin-3-yl)cyclohexane-1-carboxylic acid | LCMS (ES, m/z): 493 $[M + H]^+$ |
| 860 | 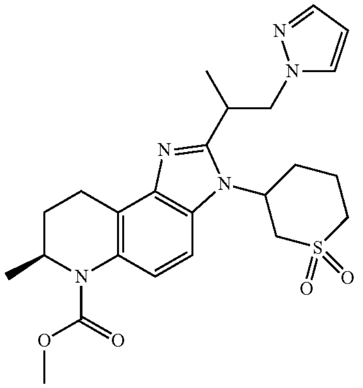 methyl (7S)-2-(1-(1H-pyrazol-1-yl)propan-2-yl)-3-(1,1-dioxidotetrahydro-2H-thiopyran-3-yl)-7-methyl-3,7,8,9-tetrahydro-6H-imidazo[4,5-f]quinoline-6-carboxylate 1$^{st}$ eluting isomer | $^1$H-NMR ($CD_3OD$, 400 MHz) δ (ppm): 7.77-7.66 (m, 2H), 7.58-7.56 (m, 1H), 7.44 (s, 1H), 6.22-6.20 (m, 1H), 4.86-4.79 (m, 2H), 4.67 (d, J = 7.2 Hz, 2H), 4.13-3.95 (m, 2H), 3.79 (s, 3H), 3.50-3.30 (m, 2H), 3.19-2.99 (m, 3H), 2.50-2.31 (m, 1H), 2.28-2.15 (m, 2H), 2.03-1.90 (m, 1H), 1.88-1.76 (m, 1H), 1.57 (d, J = 7.2 Hz, 3H), 1.56-1.47 (m, 1H), 1.13 (d, J = 6.8 Hz, 3H). LCMS (ES, m/z): 486 [M + H]+. |

TABLE 18-continued

| Example Number | Structure and Compound Name | $^1$H NMR, LCMS |
|---|---|---|
| 861 | 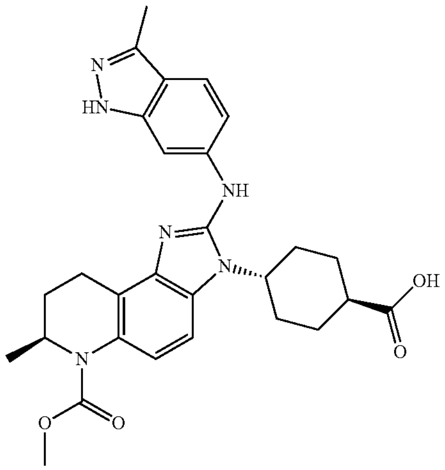 (1S,4R)-4-((S)-6-(methoxycarbonyl)-7-methyl-2-((3-methyl-1H-indazol-6-yl)amino)-6,7,8,9-tetrahydro-3H-imidazo[4,5-f]quinolin-3-yl)cyclohexane-1-carboxylic acid | LCMS (ES, m/z): 518 $[M + H]^+$ |
| 862 | 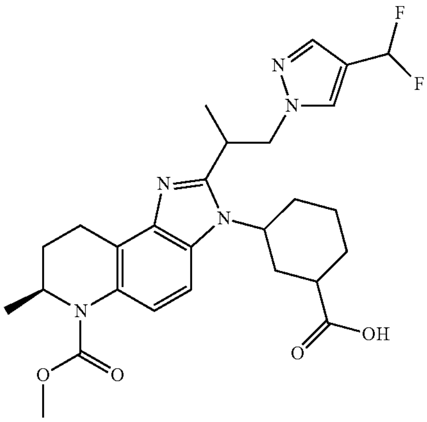 3-((7S)-2-(1-(4-(difluoromethyl)-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 300 MHz) δ (ppm): 7.91 (s, 1H), 7.58 (s, 1H), 7.49-7.34 (m, 2H), 6.89-6.51 (m, 1H), 4.81-4.61 (m, 3H), 4.61-4.32 (m, 1H), 4.03-3.83 (m, 1H), 3.76 (s, 3H), 3.28-3.12 (m, 1H), 3.02-2.79 (m, 2H), 2.49-2.17 (m, 4H), 2.17-2.03 (m, 1H), 1.96-1.81 (m, 2H), 1.80-1.54 (m, 3H), 1.38-1.35 (d, J = 6.9 Hz, 3H), 1.13-1.11 (d, J = 6.6 Hz, 3H). LCMS (ES, m/z): 530 $[M + H]^+$. |
| 863 | 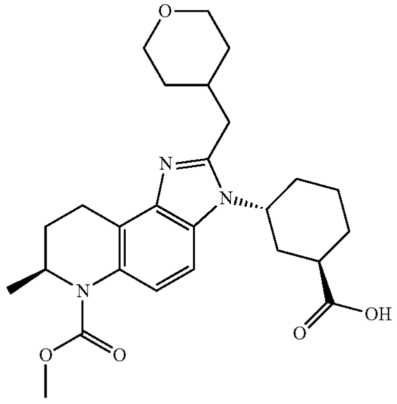 (1R,3R)-3-((S)-6-(methoxycarbonyl)-7-methyl-2-((tetrahydro-2H-pyran-4-yl)methyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.50-7.35 (m, 2H), 4.86-4.77 (m, 2H), 3.94-3.90 (m, 2H), 3.76 (s, 3H), 3.45-3.60 (m, 3H), 2.99-2.86 (m, 4H), 2.45-2.18 (m, 6H), 1.91-1.45 (m, 9H), 1.12 (d, J = 6.6 Hz, 3H). LCMS (ES, m/z): 470 $[M + H]^+$. |

TABLE 18-continued

| Example Number | Structure and Compound Name | $^1$H NMR, LCMS |
|---|---|---|
| 864 | 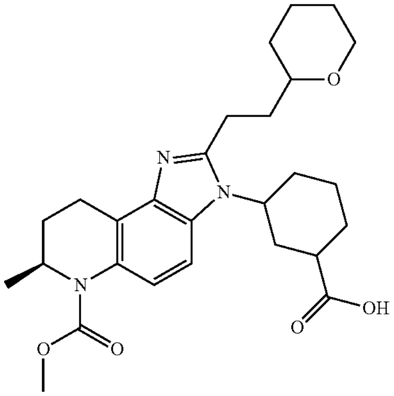 3-((7S)-6-(methoxycarbonyl)-7-methyl-2-(2-(tetrahydro-2H-pyran-2-yl)ethyl)-6,7,8,9-tetrahydro-3H-imidazo[4,5-f]quinolin-3-yl)cyclohexane-1-carboxylic acid 4$^{th}$ eluting isomer | $^1$H-NMR ($CD_3OD$, 400 MHz) δ (ppm): 7.51 (d, J = 8.4 Hz, 1H), 7.41 (d, J = 8.8 Hz, 1H), 4.81-4.68 (m, 1H), 4.54-4.40 (m, 1H), 4.06-3.94 (m, 1H), 3.78 (s, 3H), 3.53-3.43 (m, 1H), 3.38-3.36 (m, 1H), 3.26-2.97 (m, 3H), 2.94-2.83 (m, 1H), 2.69-2.54 (m, 1H), 2.48-2.21 (m, 3H), 2.18-2.01 (m, 3H), 1.99-1.80 (m, 4H), 1.79-1.65 (m, 2H), 1.62-1.49 (m, 4H), 1.41-1.26 (m, 2H), 1.14 (d, J = 6.4 Hz, 3H). LCMS (ES, m/z): 484 [M + H]$^+$. |
| 865 | 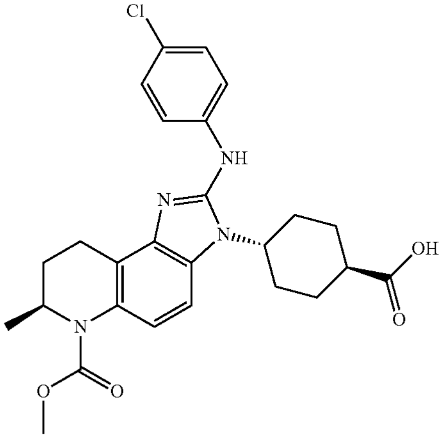 (1S,4R)-4-((S)-2-((4-chlorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 497 [M + H]$^+$ |
| 866 | 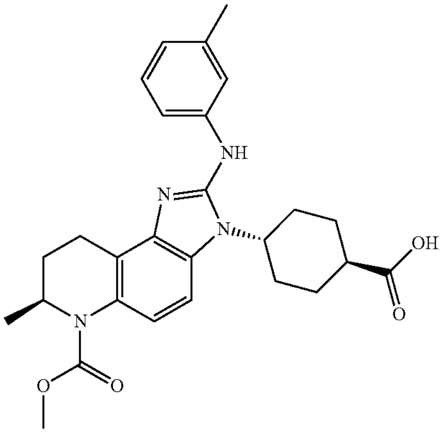 (1S,4R)-4-((S)-6-(methoxycarbonyl)-7-methyl-2-(m-tolylamino)-6,7,8,9-tetrahydro-3H-imidazo[4,5-f]quinolin-3-yl)cyclohexane-1-carboxylic acid | LCMS (ES, m/z): 477 [M + H]$^+$ |

TABLE 18-continued

| Example Number | Structure and Compound Name | $^1$H NMR, LCMS |
|---|---|---|
| 867 | 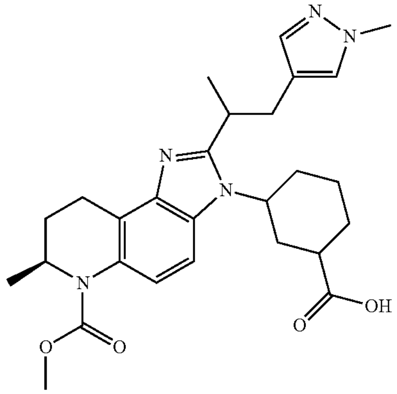 3-((7S)-6-(methoxycarbonyl)-7-methyl-2-(1-(1-methyl-1H-pyrazol-4-yl)propan-2-yl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.49-7.47 (m, 2H), 7.46 (d, J = 9.2 Hz, 1H), 7.29-7.31 (s, 1H), 4.94-4.87 (m, 1H), 4.73-4.68 (m, 1H), 3.76-3.75 (s, 6H), 3.55-3.54 (m, 1H), 3.14-3.30 (m, 2H), 2.92-2.79 (m, 3H), 2.30-2.24 (m, 4H), 2.23-2.08 (m, 1H), 1.93-1.80 (m, 2H), 1.72-1.64 (m, 3H), 1.37-1.39 (d, J = 6.8 Hz, 3H), 1.12-1.34 (d, J = 6.8 Hz, 3H). LCMS (ES, m/z): 494 $[M + H]^+$. |
| 868 | 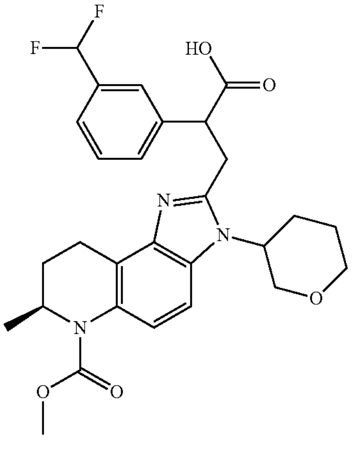 2-(3-(difluoromethyl)phenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 2$^{nd}$ eluting isomer | $^1$H-NMR ($CD_3OD$, 300 MHz) δ (ppm): 7.88-7.79 (m, 2H), 7.59-7.50 (m, 4H), 6.95-6.57 (m, 1H), 4.88-4.72 (m, 2H), 4.4-4.36 (m, 1H), 4.13-3.92 (m, 4H), 3.76 (s, 3H), 3.69-3.60 (m, 2H), 3.11-2.85 (m, 2H), 2.48-2.33 (m, 1H), 2.30-2.11 (m, 1H), 1.97-1.78 (m, 3H), 1.67-1.51 (m, 1H), 1.15 (d, J = 6.6 Hz, 3H). LCMS (ES, m/z): 528 $[M + H]^+$. |

TABLE 18-continued

| Example Number | Structure and Compound Name | $^1$H NMR, LCMS |
|---|---|---|
| 869 | 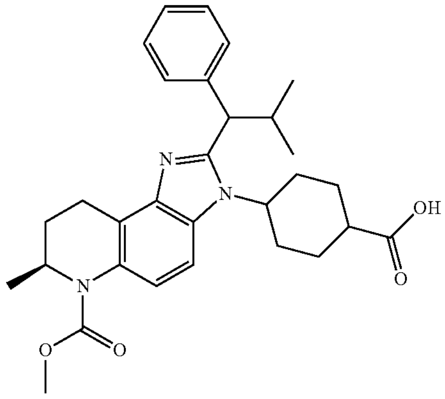 4-((7S)-6-(methoxycarbonyl)-7-methyl-2-(2-methyl-1-phenylpropyl)-6,7,8,9-tetrahydro-3H-imidazo[4,5-f]quinolin-3-yl)cyclohexane-1-carboxylic acid 2nd eluting isomer | $^1$H NMR ($CD_3OD$, 300 MHz) δ (ppm): 7.40-7.29 (m, 6H), 7.24-7.22 (m, 1H), 4.78-4.75 (m, 1H), 4.43-4.69 (m, 1H), 3.98 (d, J = 10.4 Hz, 1H), 3.75 (s, 3H), 3.35-2.28 (m, 1H), 2.96-2.85 (m, 2H), 2.40-2.24 (m, 3H), 2.24-1.65 (m, 6H), 1.39-1.36 (m, 1H), 1.17-1.13 (m, 6H), 0.95-0.88 (m, 4H). LCMS (ES, m/z): 504 [M + H]$^+$. |
| 870 | 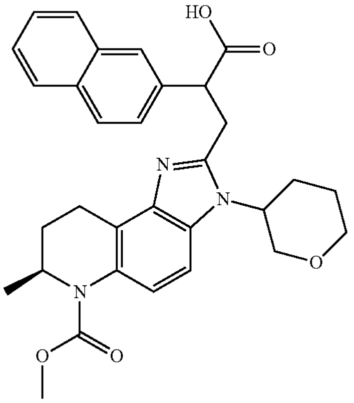 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(naphthalen-2-yl)propanoic acid 2nd eluting isomer | $^1$H-NMR ($CD_3OD$, 400 MHz) δ (ppm): 7.86-7.78 (m, 4H), 7.53-7.52 (m, 1H), 7.47-7.41 (m, 3H), 7.37-7.34 (m, 1H), 4.87-4.72 (m, 1H), 4.44-4.36 (m, 2H), 3.99-3.75 (m, 7H), 3.49-3.43 (m, 2H), 3.32-3.29 (m, 1H), 2.93-2.88 (m, 1H), 2.22-2.17 (m, 2H), 1.77-1.73 (m, 1H), 1.47-1.44 (m, 2H), 1.13 (d, J = 6.4 Hz, 3H), 1.0-0.9 (m, 1H). LCMS (ES, m/z): 528 [M + H]$^+$ |
| 871 | 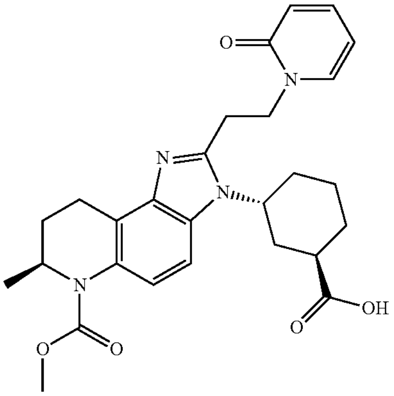 (1R,3R)-3-((S)-6-(methoxycarbonyl)-7-methyl-2-(2-(2-oxopyridin-1(2H)-yl)ethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.62-7.49 (m, 3H), 7.41-7.39 (m, 1H), 6.57-6.55 (m, 1H), 6.35-6.33 (m, 1H), 4.84-4.75 (m, 2H), 4.54-4.49 (m, 2H), 3.78 (s, 3H), 3.56-3.53 (m, 1H), 3.40-3.37 (m, 1H), 3.40-3.37 (m, 1H), 3.33-3.32 (m, 1H), 2.91-2.88 (m, 1H), 2.39-2.20 (m, 5H), 1.89-1.64 (m, 5H), 1.13 (d, J = 6.8 Hz, 3H). LCMS (ES, m/z): 493 [M + H]$^+$. |

TABLE 18-continued

| Example Number | Structure and Compound Name | $^1$H NMR, LCMS |
|---|---|---|
| 872 | 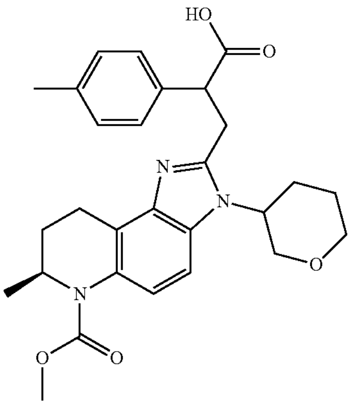 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(p-tolyl)propanoic acid 2nd eluting isomer | $^1$H-NMR ($CD_3OD$, 300 MHz) δ (ppm): 7.45 (d, J = 9 Hz, 1H), 7.34 (d, J = 9 Hz, 1H), 7.24 (d, J = 8.1 Hz, 2H), 7.10 (d, J = 7.8 Hz, 2H), 4.84-4.70 (m, 1H), 4.34-3.85 (m, 5H), 3.75 (s, 3H), 3.65-3.45 (m, 2H), 3.35-3.07 (m, 2H), 2.90-2.80 (m, 1H), 2.35-2.12 (m, 5H), 1.75-1.60 (m, 3H), 1.25-1.18 (m, 1H), 1.12 (d, J = 6.6 Hz, 3H) LCMS (ES, m/z): 492 $[M + H]^+$. |
| 873 | 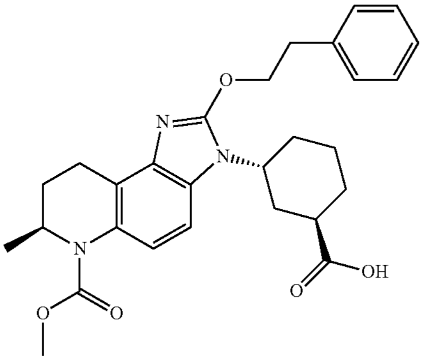 (1R,3R)-3-((S)-6-(methoxycarbonyl)-7-methyl-2-phenethoxy-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.41-7.31 (m, 4H), 7.30-7.15 (m, 3H), 4.81-4.65 (m, 3H), 4.30-4.16 (m, 1H), 3.79 (s, 3H), 3.18-3.01 (m, 3H), 2.84-2.70 (m, 1H), 2.50-2.39 (m, 1H), 2.38-2.11 (m, 2H), 2.08-1.90 (m, 4H), 1.80-1.55 (m, 2H), 1.53-1.35 (m, 2H), 1.16 (d, J = 6.4 Hz, 3H). LCMS (ES, m/z): 492 [M + H]+. |
| 874 | 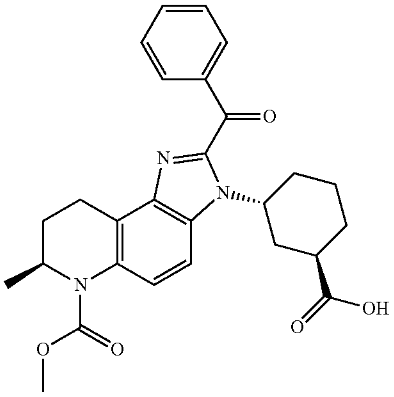 (1R,3R)-3-((S)-2-benzoyl-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.13 (d, J = 7.2 Hz, 2H), 7.81-7.55 (m, 5H), 5.18-5.01 (m, 1H), , 4.84-4.74 (m, 1H), 3.79 (s, 3H), 3.28-3.11 (m, 1H), 3.03-2.92 (m, 2H), 2.62-2.49 (m, 1H), 2.45-2.19 (m, 4H), 2.12-2.01 (m, 1H), 1.90-1.62 (m, 4H), 1.16 (d, J = 6.8 Hz, 3H). LCMS (ES, m/z): 476 $[M + H]^+$. |

TABLE 18-continued

| Example Number | Structure and Compound Name | $^1$H NMR, LCMS |
|---|---|---|
| 875 | 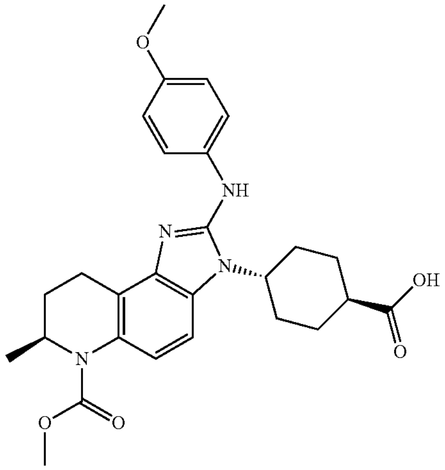 (1S,4R)-4-((S)-6-(methoxycarbonyl)-2-((4-methoxyphenyl)amino)-7-methyl-6,7,8,9-tetrahydro-3H-imidazo[4,5-f]quinolin-3-yl)cyclohexane-1-carboxylic acid | LCMS (ES, m/z): 493 $[M + H]^+$ |
| 876 | 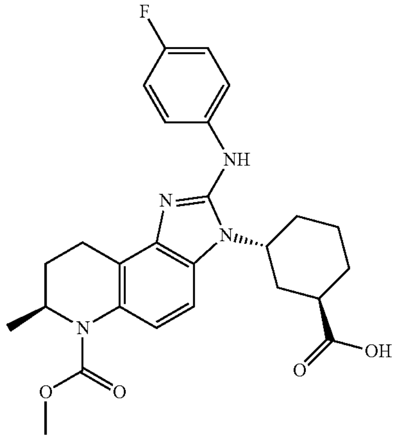 (1R,3R)-3-((S)-2-((4-fluorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 481 $[M + H]^+$ |
| 877 | 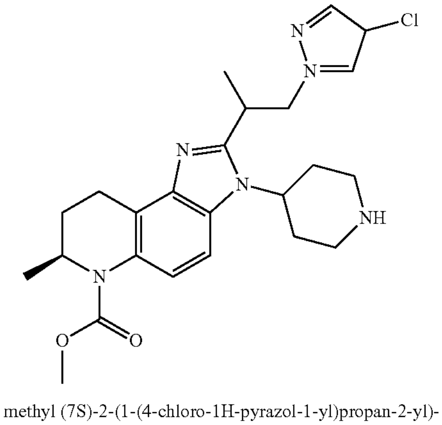 methyl (7S)-2-(1-(4-chloro-1H-pyrazol-1-yl)propan-2-yl)-7-methyl-3-(piperidin-4-yl)-3,7,8,9-tetrahydro-6H-imidazo[4,5-f]quinoline-6-carboxylate 2nd eluting isomer | $^1$H-NMR ($CD_3OD$, 400 MHz) δ (ppm): 7.57-7.47 (m, 2H), 7.40 (s, 1H), 7.36 (d, J = 9.2 Hz, 1H), 4.81-4.69 (m, 1H), 4.66-4.56 (m, 1H), 4.53-4.36 (m, 2H), 4.01-3.88 (m, 1H), 3.77 (s, 3H), 3.26-3.12 (m, 3H), 3.01-2.88 (m, 1H), 2.88-2.70 (m, 2H), 2.48-2.34 (m, 2H), 2.33-2.19 (m, 1H), 1.85-1.78 (m, 1H), 1.76-1.63 (m, 1H), 1.50-1.38 (m, 4H), 1.13 (d, J = 6.4 Hz, 3H). LCMS (ES, m/z): 471 $[M + H]^+$. |

TABLE 18-continued

| Example Number | Structure and Compound Name | $^1$H NMR, LCMS |
|---|---|---|
| 878 | 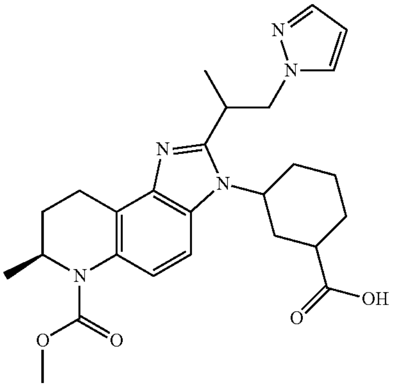 3-((7S)-2-(1-(1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 6 7.89-7.75 (m, 3H), 7.34 (d, J = 1.6 Hz, 1H), 6.27 (t, J = 2.0 Hz, 1H), 5.13-5.02 (m, 1H), 4.85-4.69 (m, 2H), 4.21-4.19 (m, 1H), 3.80 (s, 3H), 3.19-3.06 (m, 1H), 3.04-2.91 (m, 2H), 2.42-2.32 (m, 2H), 2.30-2.17 (m, 2H), 2.13-2.01 (m, 2H), 1.96-1.78 (m, 3H), 1.72-1.57 (m, 4H), 1.34-1.25 (m, 1H), 1.17 (d, J = 6.8 Hz, 3H). LCMS (ES, m/z): 480 [M + H]$^+$. |
| 879 | 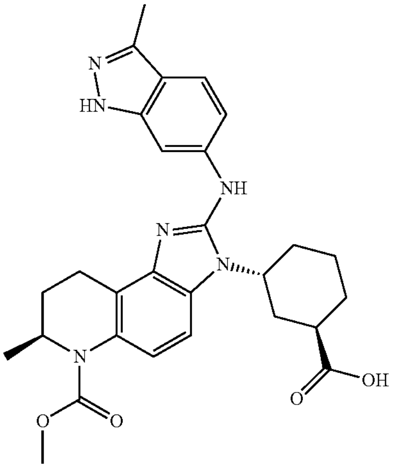 (1R,3R)-3-((S)-6-(methoxycarbonyl)-7-methyl-2-((3-methyl-1H-indazol-6-yl)amino)-6,7,8,9-tetrahydro-3H-imidazo[4,5-f]quinolin-3-yl)cyclohexane-1-carboxylic acid | LCMS (ES, m/z): 518 [M + H]$^+$ |
| 880 | 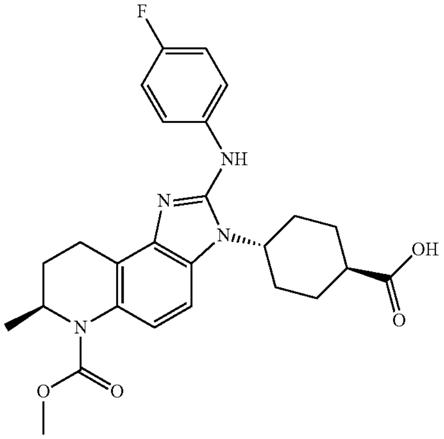 (1S,4R)-4-((S)-2-((4-fluorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 481 [M + H]$^+$ |

TABLE 18-continued

| Example Number | Structure and Compound Name | $^1$H NMR, LCMS |
|---|---|---|
| 881 | 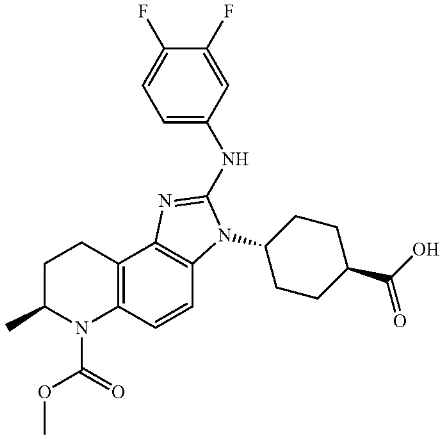 (1S,4R)-4-((S)-2-((3,4-difluorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 499 [M + H]$^+$ |
| 882 | 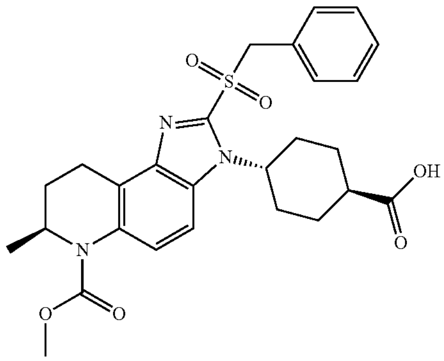 (1S,4R)-4-((S)-2-(benzylsulfonyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.71-7.51 (m, 2H), 7.44-7.13 (m, 5H), 4.94 (s, 2H), 4.85-4.72 (m, 1H), 3.81 (s, 3H), 3.31-3.01 (m, 3H), 2.51-1.76 (m, 7H), 1.71-1.31 (m, 4H), 1.18 (d, J = 6.9 Hz, 3H). LCMS (ES, m/z): 526 [M + H]$^+$. |
| 883 | 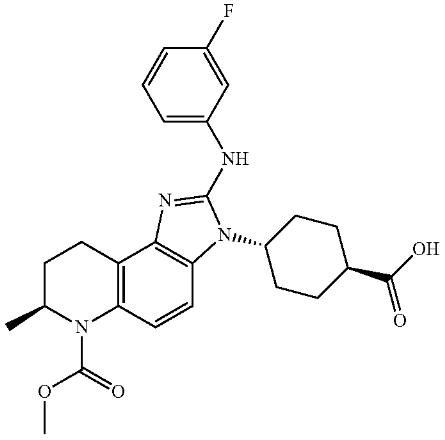 (1S,4R)-4-((S)-2-((3-fluorophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 482 [M + H]$^+$ |

TABLE 18-continued

| Example Number | Structure and Compound Name | $^1$H NMR, LCMS |
|---|---|---|
| 884 | 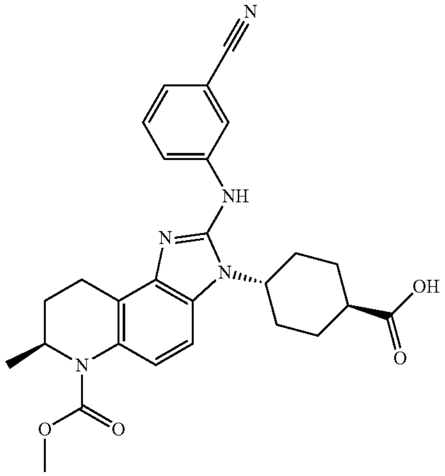 (1S,4r)-4-((S)-2-((3-cyanophenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 488 $[M + H]^+$ |
| 885 | 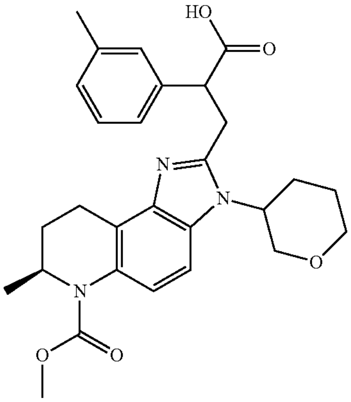 3-((7S)-6-(methoxycarbonyl)-7-methyl-3-(tetrahydro-2H-pyran-3-yl)-6,7,8,9-tetrahydro-3H-imidazo[4,5-f]quinolin-2-yl)-2-(m-tolyl)propanoic acid 2nd eluting isomer | $^1$H-NMR ($CD_3OD$, 400 MHz) δ (ppm): 7.48 (d, J = 9.2 Hz, 1H), 7.37 (d, J = 9.2 Hz, 1H), 7.23-7.15 (m, 2H), 7.14-7.05 (m, 2H), 4.80-4.69 (m, 1H), 4.47-4.32 (m, 1H), 4.26-4.14 (m, 1H), 4.08-4.37 (m, 1H), 3.98-3.90 (m, 2H), 3.76 (s, 3H), 3.71-3.59 (m, 1H), 3.60-3.44 (m, 1H), 3.35-3.33 (m, 1H), 3.23-3.12 (m, 1H), 2.97-2.81 (m, 1H), 2.37-2.14 (m, 5H), 1.80-1.66 (m, 3H), 1.27-1.22 (m, 1H), 1.13 (d, J = 6.4 Hz, 3H). LCMS (ES, m/z): 492 $[M + H]^+$. |
| 886 | 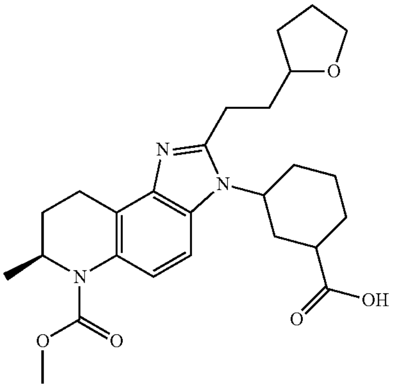 3-((7S)-6-(methoxycarbonyl)-7-methyl-2-(2-(tetrahydrofuran-2-yl)ethyl)-6,7,8,9-tetrahydro-3H-imidazo[4,5-f]quinolin-3-yl)cyclohexane-1-carboxylic acid 4th eluting isomer | $^1$H-NMR ($CD_3OD$, 400 MHz) δ (ppm): 7.52 (d, J = 9.2 Hz, 1H), 7.41 (d, J = 9.2 Hz, 1H), 4.82-4.68 (m, 1H), 4.61-4.43 (m, 1H), 4.02-3.84 (m, 2H), 3.83-3.71 (m, 4H), 3.25-3.00 (m, 3H), 2.99-2.84 (m, 1H), 2.74-2.55 (m, 1H), 2.50-2.24 (m, 3H), 2.23-1.86 (m, 9H), 1.81-1.49 (m, 4H), 1.14 (d, J = 6.4 Hz, 3H). LCMS (ES, m/z): 470 $[M + H]^+$. |

TABLE 18-continued

| Example Number | Structure and Compound Name | $^1$H NMR, LCMS |
|---|---|---|
| 887 | 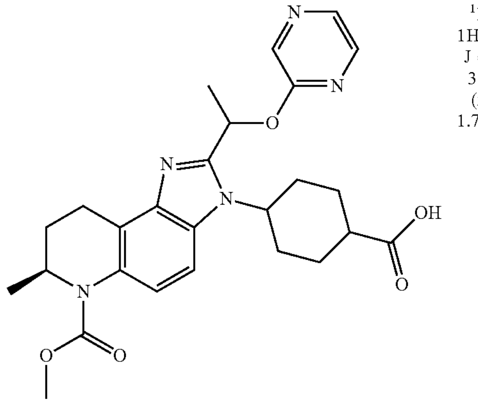 4-((7S)-6-(methoxycarbonyl)-7-methyl-2-(1-(pyrazin-2-yloxy)ethyl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 8.34 (s, 1H), 8.20-8.12 (m, 2H), 7.58-7.39 (m, 2H), 6.59 (t, J = 6.8 Hz, 1H), 4.80-4.63 (m, 2H), 3.78 (s, 3H), 3.21-3.12 (m, 1H), 2.96-2.85 (m, 1H), 2.62-2.37 (m, 3H), 2.29-2.08 (m, 4H), 1.99-1.85 (m, 4H), 1.78-1.49 (m, 3H), 1.11 (d, J = 6.4 Hz, 3H). LCMS (ES, m/z): 494 [M + H]+. |
| 888 | 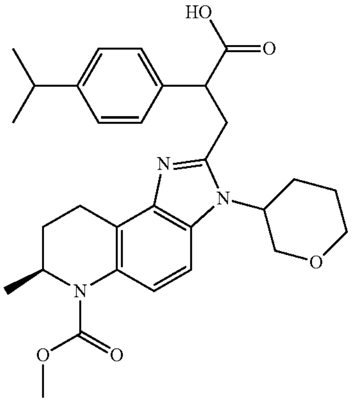 2-(4-isopropylphenyl)-3-((7S)-6-(methoxycarbonyl)-7-methyl-3-((S)-tetrahydro-2H-pyran-3-yl)-6,7,8,9-tetrahydro-3H-imidazo[4,5-f]quinolin-2-yl)propanoic acid 2$^{nd}$ eluting isomer | $^1$H-NMR ($CD_3OD$, 300 MHz) δ (ppm): 7.54-7.35 (m, 2H), 7.31-7.17 (m, 4H), 4.85-4.69 (m, 1H), 4.44-4.28 (m, 1H), 4.28-4.17 (m, 1H), 4.09-3.90 (m, 2H), 3.78 (s, 3H), 3.73-3.60 (m, 1H), 3.60-3.46 (m, 1H), 3.45-3.35 (m, 1H), 3.28-3.11 (m, 1H), 3.01-2.81 (m, 2H), 2.37-2.15 (m, 2H), 1.85-1.66 (m, 3H), 1.23 (d, J = 6.9 Hz, 6H), 1.16 (d, J = 6.6 Hz, 3H), 1.11-0.99 (m, 1H). LCMS (ES, m/z): 520 $[M + H]^+$. |
| 889 | 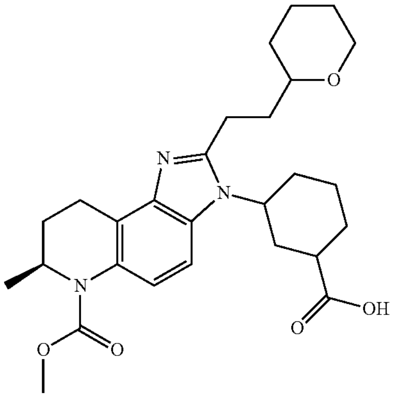 3-((7S)-6-(methoxycarbonyl)-7-methyl-2-(2-(tetrahydro-2H-pyran-2-yl)ethyl)-6,7,8,9-tetrahydro-3H-imidazo[4,5-f]quinolin-3-yl)cyclohexane-1-carboxylic acid 3$^{rd}$ eluting isomer | $^1$H-NMR ($CD_3OD$, 400 MHz) δ (ppm): 7.52 (d, J = 8.8 Hz, 1H), 7.42 (d, J = 8.8 Hz, 1H), 4.80-4.68 (m, 1H), 4.57-4.42 (m, 1H), 4.03-3.93 (m, 1H), 3.79 (s, 3H), 3.56-3.44 (m, 1H), 3.38-3.35 (m, 1H), 3.26-2.98 (m, 3H), 2.97-2.83 (m, 1H), 2.73-2.52 (m, 1H), 2.45-2.03 (m, 6H), 2.00-1.81 (m, 4H), 1.77-1.53 (m, 6H), 1.40-1.26 (m, 2H), 1.14 (d, J = 6.4 Hz, 3H). LCMS (ES, m/z): 484 $[M + H]^+$. |

TABLE 18-continued

| Example Number | Structure and Compound Name | $^1$H NMR, LCMS |
|---|---|---|
| 890 | 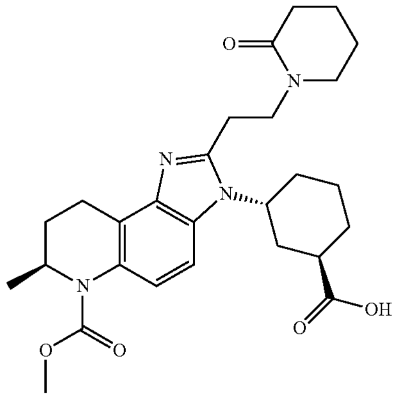 (1R,3R)-3-((S)-6-(methoxycarbonyl)-7-methyl-2-(2-(2-oxopiperidin-1-yl)ethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 8.02-7.72 (m, 2H), 5.16-4.97 (m, 1H), 4.81-4.76 (m, 1H), 4.24-4.03 (m, 1H), 3.82 (s, 3H), 3.79-3.69 (m, 1H), 3.63-3.42 (m, 4H), 3.13-3.04 (m, 1H), 3.04-2.91 (m, 2H), 2.59-2.39 (m, 3H), 2.39-2.19 (m, 4H), 2.19-2.05 (m, 1H), 2.03-1.78 (m, 7H), 1.72-1.56 (m, 1H), 1.17 (d, J = 6.8 Hz, 3H). LCMS (ES, m/z): 497 [M + H]$^+$ |
| 891 | 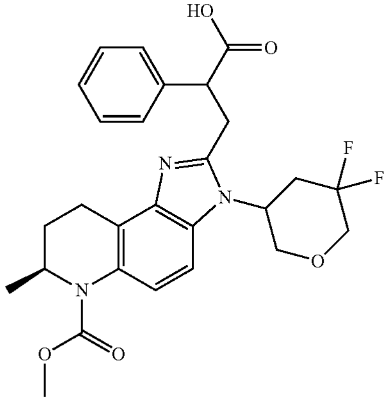 3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-phenylpropanoic acid 3rd eluting isomer | $^1$H-NMR ($CD_3OD$, 400 MHz) δ (ppm): 7.57-7.50 (m, 1H), 7.47-7.34 (m, 6H), 4.84-4.68 (m, 2H), 4.42-4.27 (m, 1H), 4.13-3.93 (m, 2H), 3.9-3.76 (m, 4H), 3.73-3.60 (m, 1H), 3.29-3.21 (m, 2H), 3.20-3.09 (m, 1H), 3.04-2.86 (m, 2H), 2.74-2.59 (m, 1H), 2.31-2.19 (m, 1H), 1.82-1.67 (m, 1H), 1.15 (d, J = 5.6 Hz, 3H). LCMS (ES, m/z): 514 [M + H]$^+$. |
| 892 | 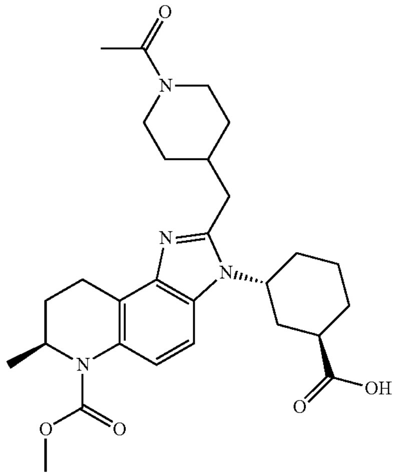 (1R,3R)-3-((S)-2-((1-acetylpiperidin-4yl)methyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 7.54 (d, J = 8.4 Hz, 1H), 7.36 (d, J = 9.0 Hz, 1H), 4.90-4.76 (m, 1H), 4.74-4.54 (m, 1H), 3.95-3.90 (m, 1H), 3.78 (s, 3H), 3.41-3.31 (m, 2H), 3.09-2.87 (m, 3H), 2.80-2.50 (m, 2H), 2.50-2.15 (m, 6H), 2.11 (d, J = 3.9 Hz, 3H), 1.98-1.69 (m, 8H), 1.42-1.38 (m, 2H), 1.14 (d, J = 6.6 Hz, 3H). LCMS (ES, m/z): 511 [M + H]$^+$ |

TABLE 18-continued

| Example Number | Structure and Compound Name | $^1$H NMR, LCMS |
|---|---|---|
| 893 | 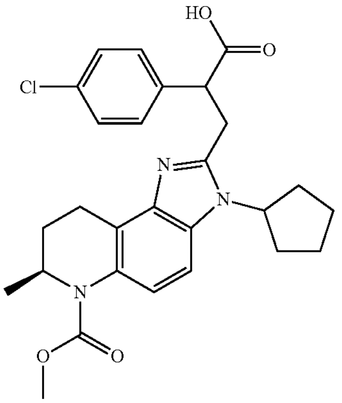 2-(4-chlorophenyl)-3-((7S)-3-cyclopentyl-6-(methoxycarbonyl)-7-methyl-6,7,8,9-tetrahydro-3H-imidazo[4,5-f]quinolin-2-yl)propanoic acid 1$^{st}$ eluting isomer | $^1$H-NMR ($CD_3OD$, 400 MHz) δ (ppm): 7.50-7.42 (m, 1H), 7.40-7.30 (m, 5H), 5.08-4.90 (m, 1H), 4.80-4.70 (m, 1H), 4.35-4.20 (m, 1H), 3.80 (s, 3H), 3.78-3.70 (m, 1H), 3.40-3.32 (m, 1H), 3.18-3.05 (m, 1H), 2.92-2.86 (m, 1H), 2.40-2.16 (m, 3H), 2.12-1.95 (m, 3H), 1.90-1.65 (m, 4H), 1.13 (d, J = 6.8 Hz, 3H). LCMS (ES, m/z): 496 [M + H]$^+$. |
| 894 | 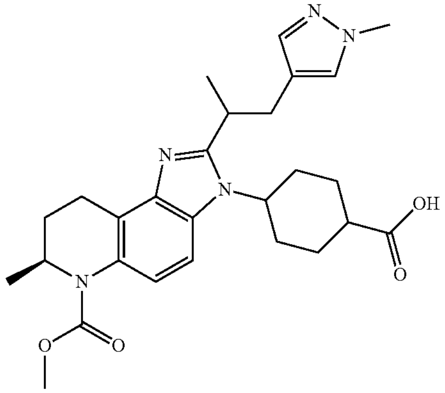 4-((7S)-6-(methoxycarbonyl)-7-methyl-2-(1-(1-methyl-1H-pyrazol-4-yl)propan-2-yl)-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.46-7.29 (m, 2H), 7.26 (s, 1H), 7.08 (s, 1H), 4.75-4.64 (m, 1H), 4.36-4.12 (m, 1H), 3.76 (s, 3H), 3.73 (s, 3H), 3.52-3.39 (m, 1H), 3.26-3.16 (m, 1H), 3.11-2.99 (m, 1H), 2.96-2.84 (m, 2H), 2.40-2.04 (m, 6H), 1.88-1.76 (m, 1H), 1.74-1.50 (m, 3H), 1.46 (d, J = 6.8 Hz, 3H), 1.32-1.17 (m, 1H), 1.14 (d, J = 6.4 Hz, 3H). LCMS (ES, m/z): 494 [M + H]$^+$ |
| 895 | 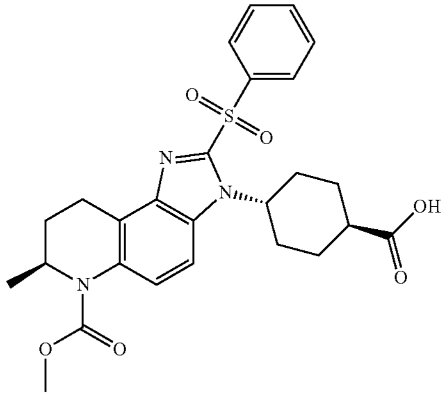 (1S,4R)-4-((S)-6-(methoxycarbonyl)-7-methyl-2-(phenylsulfonyl)-6,7,8,9-tetrahydro-3H-imidazo[4,5-f]quinolin-3-yl)cyclohexane-1-carboxylic acid | $^1$H-NMR ($CD_3OD$, 300 MHz) δ (ppm): 8.19-8.03 (m, 2H), 7.86-7.78 (m, 1H), 7.78-7.67 (m, 2H), 7.67-7.56 (m, 2H), 5.12-4.96 (m, 1H), 4.87-4.68 (m, 1H), 3.79 (s, 3H), 3.29-3.09 (m, 1H), 3.09-2.81 (m, 1H), 2.62-2.43 (m, 1H), 2.38-2.03 (m, 5H), 1.89-1.70 (m, 1H), 1.70-1.47 (m, 4H), 1.15 (d, J = 6.6 Hz, 3H). LCMS (ES, m/z): 512 [M + H]$^+$. |

TABLE 18-continued

| Example Number | Structure and Compound Name | $^1$H NMR, LCMS |
|---|---|---|
| 896 | 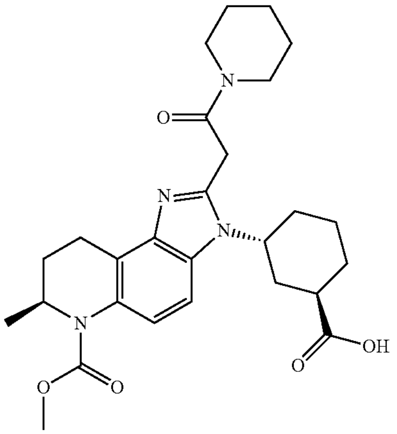<br>(1R,3R)-3-((S)-6-(methoxycarbonyl)-7-methyl-2-(2-oxo-2-(piperidin-1-yl)ethyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.93-7.86 (m, 2H), 4.95-4.92 (m, 2H), 4.62-4.59 (m, 1H), 3.83 (s, 3H), 3.72-3.65 (m, 3H), 3.55-3.53 (m, 1H), 3.08-2.99 (m, 3H), 2.43-2.38 (m, 3H), 2.28-2.24 (m, 2H), 2.126 (m, 1H), 1.97-1.56 (m, 11H), 1.17 (d, J = 6.8 Hz, 3H). LCMS (ES, m/z): 497 $[M + H]^+$ |
| 897 | 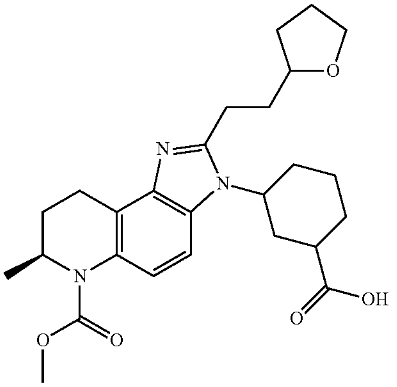<br>3-((7S)-6-(methoxycarbonyl)-7-methyl-2(2-(tetrahydrofuran-2-yl)ethyl)-6,7,8,9-tetrahydro-3H-imidazo[4,5-f]quinolin-3-yl)cyclohexane-1-carboxylic acid 3rd eluting isomer | $^1$H-NMR ($CD_3OD$, 400 MHz) δ (ppm): 7.52 (d, J = 8.4 Hz, 1H), 7.40 (d, J = 8.8 Hz, 1H), 4.81-4.68 (m, 1H), 4.57-4.43 (m, 1H), 3.99-3.84 (m, 2H), 3.83-3.72 (m, 4H), 3.23-3.00 (m, 3H), 2.97-2.83 (m, 1H), 2.66-2.52 (m, 1H), 2.48-2.21 (m, 3H), 2.20-2.02 (m, 4H), 2.01-1.82 (m, 5H), 1.80-1.48 (m, 4H), 1.14 (d, J = 6.4 Hz, 3H). LCMS (ES, m/z): 470 $[M + H]^+$. |
| 898 | 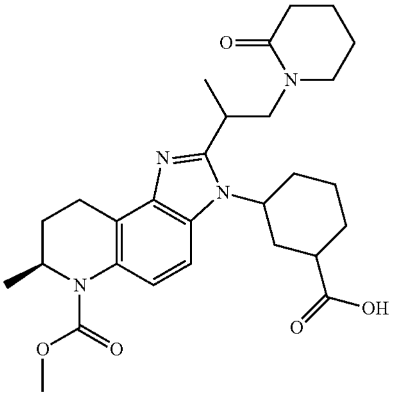<br>3-((7S)-6-(methoxycarbonyl)-7-methyl-2-(1-(2-oxopiperidin-1-yl)propan-2-yl)-6,7,8,9-tetrahydro-3H-imidazo[4,5-f]quinolin-3-yl)cyclohexane-1-carboxylic acid 3rd eluting isomer | $^1$H-NMR ($CD_3OD$, 400 MHz) δ (ppm): 7.92-7.88 (m, 2H), 5.19-5.14 (m, 1H), 4.33-4.26 (m, 1H), 3.99-3.97 (m, 1H), 3.83 (s, 3H), 3.73-3.63 (m, 2H), 3.45-3.42 (m, 1H), 3.25-2.90 (m, 4H), 2.52-2.47 (m, 2H), 2.32-2.22 (m, 5H), 2.11-2.07 (m, 1H), 2.00-1.77 (m, 7H), 1.68-1.59 (m, 4H), 1.18 (d, J = 6.8 Hz, 3H). LCMS (ES, m/z): 511 $[M + H]^+$. |

TABLE 18-continued

| Example Number | Structure and Compound Name | $^1$H NMR, LCMS |
|---|---|---|
| 899 | 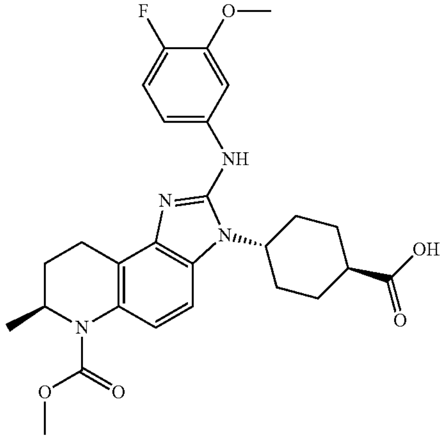 (1S,4R)-4-((S)-2-((4-fluoro-3-methoxyphenyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 [M + H]$^+$ |
| 900 | 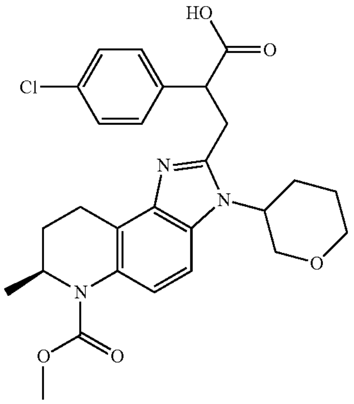 2-(4-chlorophenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 2$^{nd}$ eluting isomer | $^1$H-NMR ($CD_3OD$, 400 MHz) δ (ppm): 7.51 (d, J = 9.2 Hz, 1H), 7.42-7.27 (m, 5H), 4.80-4.69 (m, 1H), 4.51-4.41 (m, 1H), 4.32-4.23 (m, 1H), 4.12-4.02 (m, 1H), 4.01-3.89 (m, 2H), 3.76 (s, 3H), 3.73-3.64 (m, 1H), 3.60-3.47 (m, 1H), 3.36-3.31 (m, 1H), 3.21-3.08 (m, 1H), 2.96-2.82 (m, 1H), 2.43-2.27 (m, 1H), 2.27-2.13 (m, 1H), 1.83-1.65 (m, 3H), 1.49-1.39 (m, 1H), 1.12 (d, J = 6.8 Hz, 3H). LCMS (ES, m/z): 512 [M + H]$^+$. |
| 901 | 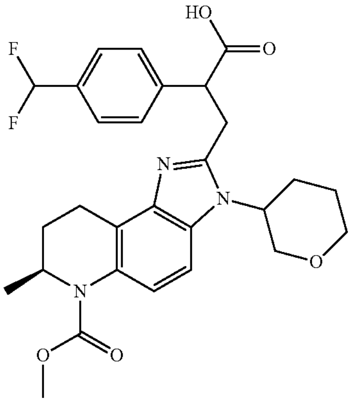 2-(4-(difluoromethyl)phenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 2$^{nd}$ eluting isomer | $^1$H-NMR ($CD_3OD$, 400 MHz) δ (ppm): 7.55-7.52 (m, 5H), 7.41 (d, J = 8.8 Hz, 1H), 6.92-6.59 (m, 1H), 4.82-4.68 (m, 1H), 4.51-4.25 (m, 2H), 4.15-3.91 (m, 3H), 3.78-3.74 (m, 4H), 3.58-3.56 (m, 1H), 3.39-3.37 (m, 1H), 3.25-3.08 (m, 1H), 2.96-2.87 (m, 1H), 2.40-2.13 (m, 2H), 1.75-1.69 (m, 3H), 1.32-1.28 (m, 1H), 1.15 (d, J = 6.8 Hz, 3H). LCMS (ES, m/z): 528 [M + H]$^+$. |

TABLE 18-continued

| Example Number | Structure and Compound Name | $^1H$ NMR, LCMS |
| --- | --- | --- |
| 902 | 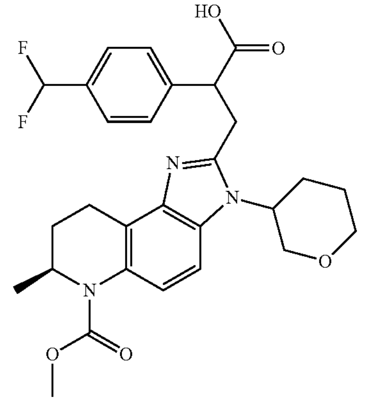 2-(4-(difluoromethyl)phenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 2nd eluting isomer | $^1H$-NMR ($CD_3OD$, 400 MHz) δ (ppm): 7.62-7.49 (m, 5H), 7.42 (d, J = 9.2 Hz, 1H), 6.96-6.59 (m, 1H), 4.83-4.70 (m, 1H), 4.69-4.52 (m, 1H), 4.47-4.35 (m, 1H), 4.07-3.88 (m, 2H), 3.87-3.70 (m, 4H), 3.65-3.54 (m, 1H), 3.50-3.41 (m, 1H), 3.40-3.34 (m, 1H), 3.24-3.10 (m, 1H), 2.99-2.85 (m, 1H), 2.61-2.44 (m, 1H), 2.29-2.19 (m, 1H), 2.17-2.07 (m, 1H), 2.04-1.82 (m, 2H), 1.82-1.66 (m, 1H), 1.14 (d, J = 6.8 Hz, 3H). LCMS (ES, m/z): 528 $[M + H]^+$. |
| 903 | 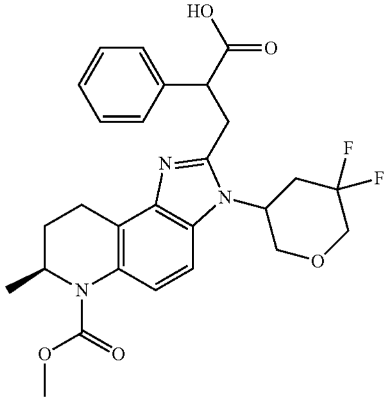 3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-phenylpropanoic acid 4th eluting isomer | $^1H$-NMR ($CD_3OD$, 400 MHz) δ (ppm): 7.54-7.52 (m, 1H), 7.50-7.24 (m, 6H), 4.86-4.69 (m, 2H), 4.38-4.26 (m, 1H), 4.25-4.13 (m, 1H), 4.12-4.02 (m, 1H), 4.01-3.93 (m, 1H), 3.92-3.80 (m, 1H), 3.78 (s, 3H), 3.73-3.58 (m, 1H), 3.31-3.26 (m, 1H), 3.25-3.13 (m, 1H), 3.02-2.88 (m, 1H), 2.87-2.66 (m, 1H), 2.33-2.14 (m, 1H), 1.96-1.82 (m, 1H), 1.80-1.68 (m, 1H), 1.16 (d, J = 6.0 Hz, 3H). LCMS (ES, m/z): 514 $[M + H]^+$. |
| 904 | 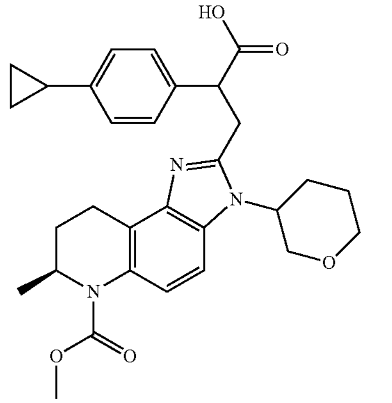 2-(4-cyclopropylphenyl)-3-((7S)-6-(methoxycarbonyl)-7-methyl-3-(tetrahydro-2H-pyran-3-yl)-6,7,8,9-tetrahydro-3H-imidazo[4,5-f]quinolin-2-yl)propanoic acid 2nd eluting isomer | $^1H$-NMR ($CD_3OD$, 400 MHz) δ (ppm): 7.46 (d, J = 8.8 Hz, 1H), 7.38 (d, J = 9.2 Hz, 1H), 7.20 (d, J = 8.0 Hz, 2H), 7.02 (d, J = 6.8 Hz, 2H), 4.76-4.71 (m, 1H), 4.33-4.31 (m, 1H), 4. 20-4.16 (m, 1H), 4.07-3.87 (m, 3H), 3.81 (s, 3H), 3.71-3.69 (m, 1H), 3.69-3.46 (m, 1H), 3.45-3.29 (m, 1H), 3.25-3.11 (m, 1H), 2.91-2.87 (m, 1H), 2.27-2.20 (m, 2H), 1.86-1.84 (m, 1H), 1.73-1.67 (m, 3H), 1.14-1.12 (m, 4H), 0.93-0.91 (m, 2H), 0.63-0.621 (m, 2H). LCMS (ES, m/z): 518 $[M + H]^+$. |

TABLE 18-continued

| Example Number | Structure and Compound Name | $^1$H NMR, LCMS |
|---|---|---|
| 905 | 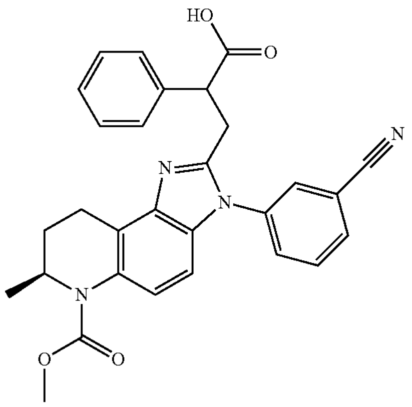 3-((7S)-3-(3-cyanophenyl)-6-(methoxycarbonyl)-7-methyl-6,7,8,9-tetrahydro-3H-imidazo[4,5-f]quinolin-2-yl)-2-phenylpropanoic acid 2$^{nd}$ eluting isomer | $^1$H-NMR (DMSO, 300 MHz) δ (ppm): 12.43 (br, 1H), 8.08-7.91 (m, 2H), 7.89-7.68 (m, 2H), 7.37-7.16 (m, 6H), 6.89 (d, J = 8.7 Hz, 1H), 4.80-4.53 (m, 1H), 4.40-4.20 (m, 1H), 3.62 (s, 3H), 3.47-3.30 (m, 1H), 3.14-2.93 (m, 2H), 2.93-2.74 (m, 1H), 2.26-2.04 (m, 1H), 1.73-1.46 (m, 1H), 1.04 (d, J = 6.6 Hz, 3H). LCMS (ES, m/z): 495 [M + H]$^+$ |
| 906 | 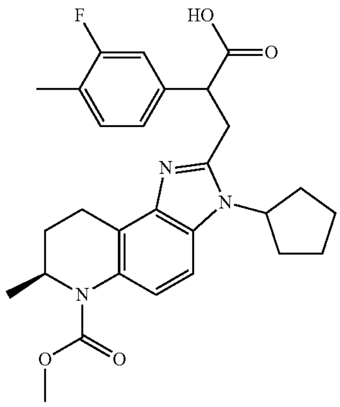 3-((7S)-3-cyclopentyl-6-(methoxycarbonyl)-7-methyl-6,7,8,9-tetrahydro-3H-imidazo[4,5-f]quinolin-2-yl)-2-(3-fluoro-4-methylphenyl)propanoic acid 1$^{st}$ eluting isomer | $^1$H-NMR ($CD_3OD$, 400 MHz) δ (ppm): 7.42 (d, J = 9.2 Hz, 1H), 7.31 (d, J = 8.8 Hz, 1H), 7.18-7.00 (m, 3H), 5.08-4.90 (m, 1H), 4.80-4.70 (m, 1H), 4.25-4.18 (m, 1H), 3.76 (s, 3H), 3.73-3.67 (m, 1H), 3.36-3.33 (m, 1H), 3.14-3.10 (m, 1H), 2.92-2.86 (m, 1H), 2.25-2.16 (m, 6H), 2.08-1.92 (m, 3H), 1.90-1.72 (m, 4H), 1.12 (d, J = 6.8 Hz, 3H). LCMS (ES, m/z): 491 [M + H]$^+$. |
| 907 | 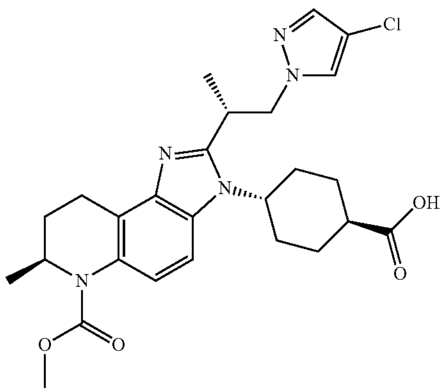 4-((7S)-2-(1-(4-chloro-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.93-7.79 (m, 3H), 7.38 (s, 1H), 4.79-4.46 (m, 2H), 4.46-4.26 (m, 1H), 4.43-4.28 (m, 1H), 3.83 (s, 3H), 3.19-3.07 (m, 1H), 3.07-2.92 (m, 1H), 2.71-2.52 (m, 1H), 2.52-2.31 (m, 2H), 2.31-2.14 (m, 3H), 2.12-1.99 (m, 1H), 1.99-1.84 (m, 1H), 1.84-1.72 (m, 1H), 1.71-1.53 (m, 5H), 1.41-1.26 (m, 1H), 1.21 (d, J = 6.8 Hz, 3H). LCMS (ES, m/z): 514 [M + H]$^+$. |

TABLE 18-continued

| Example Number | Structure and Compound Name | $^1$H NMR, LCMS |
|---|---|---|
| 908 | 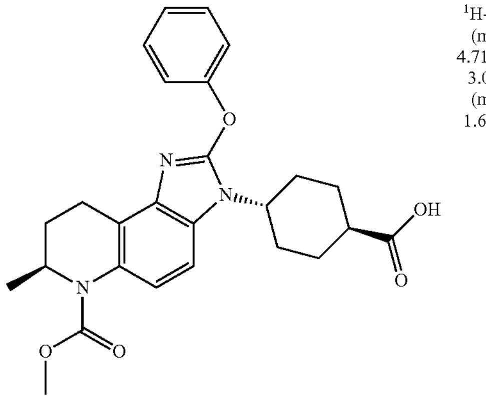 (1S,4R)-4-((S)-6-(methoxycarbonyl)-7-methyl-2-phenoxy-6,7,8,9-tetrahydro-3H-imidazo[4,5-f]quinolin-3-yl)cyclohexane-1-carboxylic acid | $^1$H-NMR ($CD_3OD$, 400 MHz).3 (ppm): 7.47-7.43 (m, 2H), 7.40-7.34 (m, 2H), 7.28-7.25 (m, 3H), 4.71-4.67 (m, 1H), 4.46-4.34 (m, 1H), 3.76 (s, 3H), 3.03-2.97 (m, 1H), 2.75-2.69 (m, 1H), 2.43-2.21 (m, 3H), 2.20-2.16 (m, 3H), 2.07-1.99 (m, 2H), 1.69-1.59 (m, 3H), 1.10 (d, J = 6.4 Hz, 3H). MS: (ES, m/z): 464 [M + H]$^+$. |
| 909 | 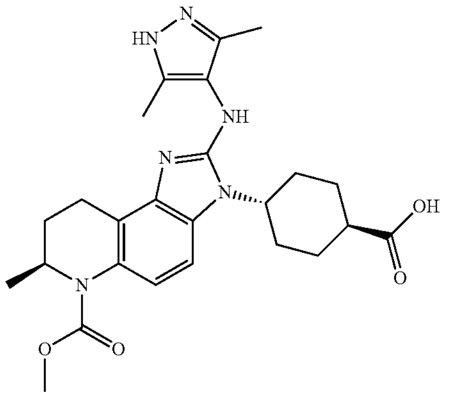 (1S,4R)-4-((S)-2-((3,5-dimethyl-1H-pyrazol-4-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 481 [M + H]$^+$ |
| 910 | 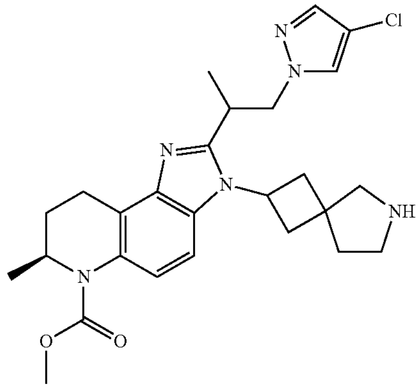 methyl (7S)-2-(1-(4-chloro-1H-pyrazol-1-yl)propan-2-yl)-7-methyl-3-(6-azaspiro[3.4]octan-2-yl)-3,7,8,9-tetrahydro-6H-imidazo[4,5-f]quinoline-6-carboxylate 2$^{nd}$ eluting isomer | $^1$H-NMR ($CD_3OD$, 300 MHz) δ (ppm): 7.56 (s, 1H), 7.49-7.36 (m, 3H), 5.03-4.91 (m, 1H), 4.82-4.69 (m, 1H), 4.66-4.38 (m, 2H), 3.98-3.82 (m, 1H), 3.79 (s, 3H), 3.31-3.19 (m, 1H), 3.19-3.12 (m, 3H), 3.01-2.81 (m, 3H), 2.64-2.53 (m, 1H), 2.53-2.41 (m, 1H), 2.37-2.20 (m, 1H), 2.20-2.03 (m, 2H), 1.83-1.62 (m, 1H), 1.43 (d, J = 6.9 Hz, 3H), 1.40-1.26 (m, 1H), 1.16 (d, J = 6.6 Hz, 3H). LCMS (ES, m/z): 497 [M + H]$^+$. |

TABLE 18-continued

| Example Number | Structure and Compound Name | $^1$H NMR, LCMS |
|---|---|---|
| 911 | 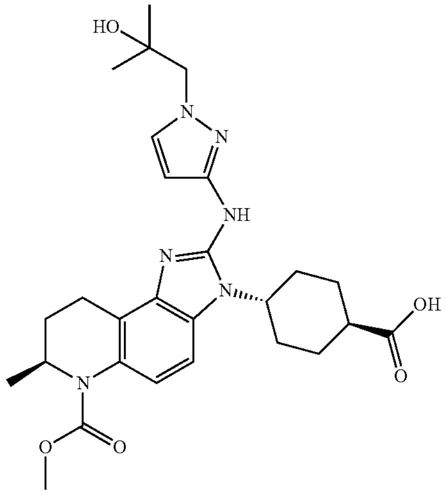 (1S,4R)-4-((S)-2-((1-(2-hydroxy-2-methylpropyl)-1H-pyrazol-3-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 526 [M + H]$^+$ |
| 912 | 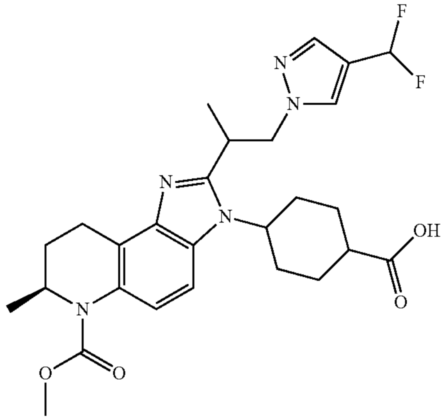 4-((7S)-2-(1-(4-(difluoromethyl)-1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 300 MHz) δ (ppm): 7.75 (s, 1H), 7.64 (s, 1H), 7.54-7.23 (m, 2H), 6.97-6.38 (m, 1H), 4.79-4.61 (m, 2H), 4.61-4.41 (m, 1H), 4.41-4.13 (m, 1H), 4.07-3.89 (m, 1H), 3.76 (s, 3H), 3.28-3.11 (m, 1H), 3.07-2.82 (m, 1H), 2.57-2.41 (m, 1H), 2.32-2.08 (m, 4H), 1.92-1.52 (m, 5H), 1.44-1.22 (m, 4H), 1.13 (d, J = 6.6 Hz, 3H). LCMS (ES, m/z): 530 [M + H]$^+$ |

TABLE 18-continued

| Example Number | Structure and Compound Name | $^1$H NMR, LCMS |
|---|---|---|
| 913 | 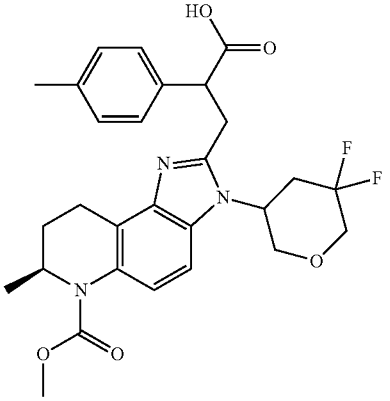 3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-(p-tolyl)propanoic acid 3$^{rd}$ eluting isomer | $^1$H-NMR ($CD_3OD$, 400 MHz) δ (ppm): 7.56-7.31 (m, 2H), 7.27-7.08 (m, 4H), 4.83-4.62 (m, 2H), 4.32-4.19 (m, 1H), 4.10-3.91 (m, 2H), 3.88-3.78 (m, 4H), 3.71-3.57 (m, 1H), 3.27-3.11 (m, 3H), 3.00-2.80 (m, 2H), 2.72-2.55 (m, 1H), 2.32 (s, 3H), 2.27-2.15 (m, 1H), 1.80-1.68 (m, 1H), 1.15 (d, J = 6.0 Hz, 3H). LCMS (ES, m/z): 528 [M + H]$^+$. |
| 914 | 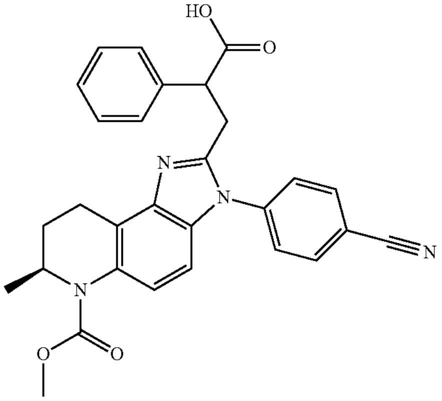 3-((7S)-3-(4-cyanophenyl)-6-(methoxycarbonyl)-7-methyl-6,7,8,9-tetrahydro-3H-imidazo[4,5-f]quinolin-2-yl)-2-phenylpropanoic acid 2$^{nd}$ eluting isomer | $^1$H-NMR ($CD_3OD$, 300 MHz) δ (ppm): 7.93 (d, J = 8.7 Hz, 2H), 7.52-7.33 (m, 3H), 7.28-7.04 (m, 5H), 6.88 (d, J = 8.7 Hz, 1H), 4.82-4.68 (m, 1H), 4.40-4.16 (m, 1H), 3.75 (s, 3H), 3.65-3.44 (m, 1H), 3.25-3.10 (m, 2H), 3.03-2.84 (m, 1H), 2.37-2.16 (m, 1H), 1.83-1.64 (m, 1H), 1.15 (d, J = 6.6 Hz, 3H). LCMS (ES, m/z): 495 [M + H]$^+$ |
| 915 | 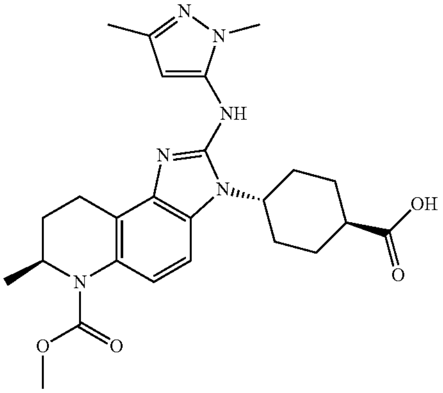 (1S,4R)-4-((S)-2-((1,3-dimethyl-1H-pyrazol-5-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 481 [M + H]$^+$ |

TABLE 18-continued

| Example Number | Structure and Compound Name | $^1H$ NMR, LCMS |
|---|---|---|
| 916 | 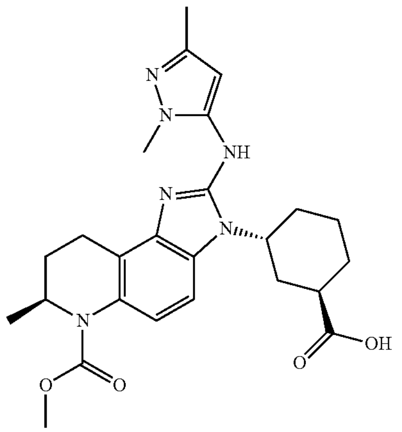 (1R,3R)-3-((S)-2-((1,3-dimethyl-1H-pyrazol-5-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 481 $[M + H]^+$ |
| 917 | 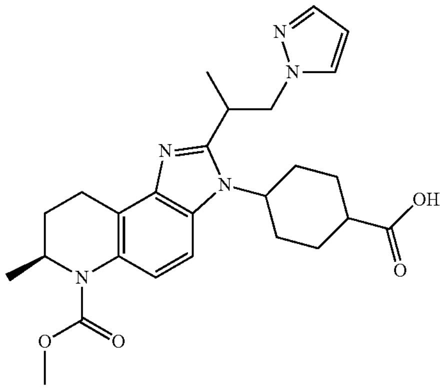 4-((7S)-2-(1-(1H-pyrazol-1-yl)propan-2-yl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1H$-NMR ($CD_3OD$, 400 MHz) δ (ppm): 7.97-7.79 (m, 2H), 7.69 (d, J = 2.4 Hz, 1H), 7.42 (d, J = 2.0 Hz, 1H), 6.29-6.27 (m, 1H), 4.76-4.62 (m, 2H), 4.58-4.39 (m, 1H), 4.39-4.21 (m, 1H), 3.80 (s, 3H), 3.23-3.07 (m, 1H), 3.07-2.85 (m, 1H), 2.64-2.51 (m, 1H), 2.43-2.09 (m, 5H), 2.09-1.97 (m, 1H), 1.97-1.83 (m, 1H), 1.81-1.65 (m, 1H), 1.65-1.42 (m, 5H), 1.32-1.21 (m, 1H), 1.19 (d, J = 6.8 Hz, 3H). LCMS: (ES, m/z): 480 $[M + H]^+$. |
| 918 | 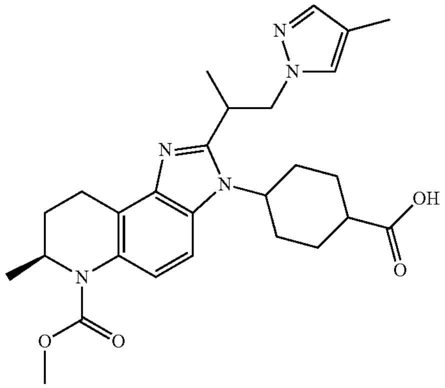 4-((7S)-6-(methoxycarbonyl)-7-methyl-2-(1-(4-methyl-1H-pyrazol-1-yl)propan-2-yl)-6,7,8,9-tetrahydro-3H-imidazo[4,5-f]quinolin-3-yl)cyclohexane-1-carboxylic acid 1st eluting isomer | $^1H$-NMR ($CD_3OD$, 300 MHz) δ (ppm): 7.53-7.39 (m, 1H), 7.39-7.24 (m, 2H), 7.24-7.12 (m, 1H), 4.79-4.66 (m, 1H), 4.66-4.48 (m, 1H), 4.48-4.39 (m, 1H), 4.31-4.19 (m, 1H), 4.01-3.81 (m, 1H), 3.76 (s, 3H), 3.29-3.08 (m, 1H), 3.02-2.82 (m, 1H), 2.64-2.41 (m, 1H), 2.41-2.01 (m, 5H), 1.95 (s, 3H), 1.94-1.79 (m, 1H), 1.79-1.58 (m, 3H), 1.52-1.41 (m, 1H), 1.41 (d, J = 6.9 Hz, 3H), 1.15 (d, J = 6.9 Hz, 3H). LCMS: (ES, m/z): 494 $[M + H]^+$. |

TABLE 18-continued

| Example Number | Structure and Compound Name | $^1$H NMR, LCMS |
|---|---|---|
| 919 | 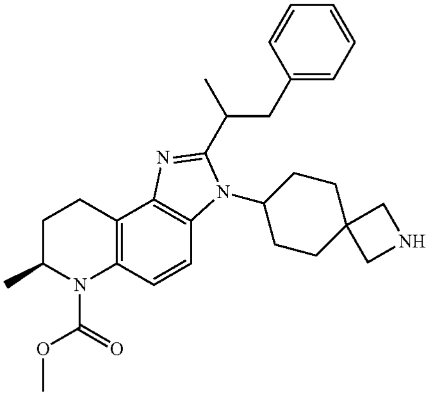 methyl (7S)-7-methyl-2-(1-phenylpropan-2-yl)-3-(2-azaspiro[3.5]nonan-7-yl)-3,7,8,9-tetrahydro-6H-imidazo[4,5-f]quinoline-6-carboxylate 2nd eluting isomer | $^1$H-NMR ($CD_3OD$, 300 MHz) δ (ppm): 7.29 (d, J = 9.0 Hz, 1H), 7.19-7.14 (m, 4H), 7.13-7.05 (m, 2H), 4.85-4.71 (m, 1H), 3.75-3.52 (m, 7H), 3.42 (s, 2H), 3.32-2.80 (m, 4H), 2.26-1.65 (m, 8H), 1.62-1.50 (m, 4H), 1.15 (d, J = 6.6 Hz, 3H), 0.78-0.60 (m, 1H). LCMS (ES, m/z): 487 $[M + H]^+$. |
| 920 | 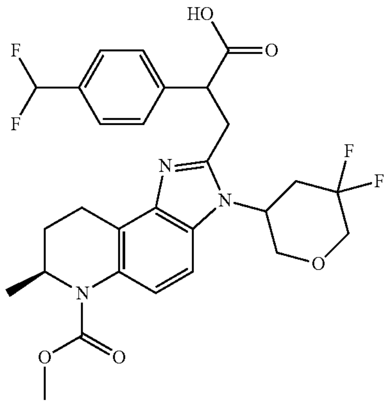 2-(4-(difluoromethyl)phenyl)-3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)propanoic acid 1st eluting isomer | $^1$H-NMR ($CD_3OD$, 400 MHz) δ (ppm): 7.63-7.51 (m, 5H), 7.44 (d, J = 8.8 Hz, 1H), 6.92-6.58 (m, 1H), 4.88-4.84 (m, 1H), 4.83-4.69 (m, 1H), 4.48-4.36 (m, 1H), 4.16-4.06 (m, 1H), 4.04-3.95 (m, 1H), 3.94-3.82 (m, 1H), 3.79 (s, 3H), 3.76-3.67 (m, 1H), 3.54-3.42 (m, 1H), 3.30-3.25 (m, 1H), 3.23-3.12 (m, 1H), 3.00-2.86 (m, 2H), 2.78-2.63 (m, 1H), 2.33-2.16 (m, 1H), 1.80-1.67 (m, 1H), 1.14 (d, J = 6.4 Hz, 3H). LCMS (ES, m/z): 564 $[M + H]^+$. |

TABLE 18-continued

| Example Number | Structure and Compound Name | $^1$H NMR, LCMS |
|---|---|---|
| 921 | 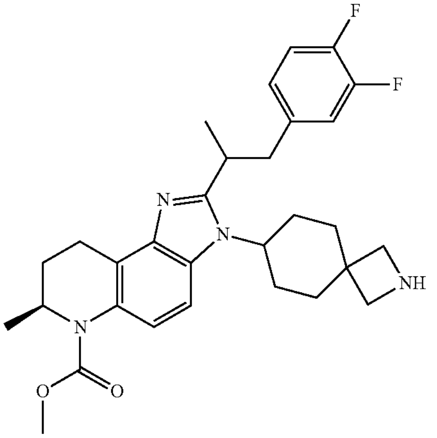<br>methyl (7S)-2-(1-(3,4-difluorophenyl)propan-2-yl)-7-methyl-3-(2-azaspiro[3.5]nonan-7-yl)-3,7,8,9-tetrahydro-6H-imidazo[4,5-f]quinoline-6-carboxylate<br>2nd eluting isomer | $^1$H-NMR ($CD_3OD$, 400 MHz) δ (ppm): 7.32 (d, J = 8.8 Hz, 1H), 7.19 (d, J = 9.2 Hz, 1H), 7.1-6.99 (m, 2H), 6.93-6.82 (m, 1H), 4.82-4.68 (m, 1H), 4.32-4.11 (m, 1H), 3.80-3.72 (m, 3H), 3.72-3.65 (m, 2H), 3.62-3.47 (m, 3H), 3.31-3.13 (m, 2H), 3.12-3.01 (m, 1H), 2.96-2.84 (m, 1H), 2.35-1.97 (m, 5H), 1.82-1.65 (m, 3H), 1.61-1.44 (m, 4H), 1.14 (d, J = 6.8 Hz, 3H), 1.02-0.88 (m, 1H). LCMS (ES, m/z): 523 $[M + H]^+$. |
| 922 | 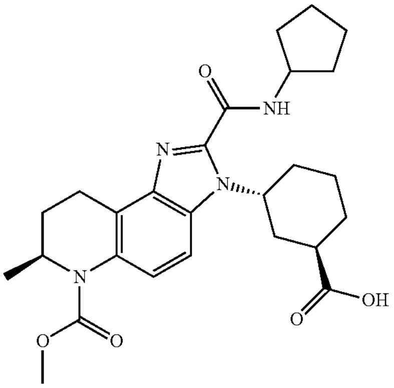<br>(1R,3R)-3-((S)-2-(cyclopentylcarbamoyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.59-7.52 (m, 1H), 7.47-7.39 (m, 1H), 5.06-4.91 (m, 1H), 4.76-4.65 (m, 1H), 4.44-4.33 (m, 1H), 3.80 (s, 3H), 3.39-3.19 (m, 1H), 3.02-2.65 (m, 4H), 2.32-2.05 (m, 5H), 1.92-1.77 (m, 3H), 1.76-1.45 (m, 8H), 1.15 (d, J = 6.8 Hz, 3H). LCMS (ES, m/z): 483 $[M + H]^+$. |
| 923 | 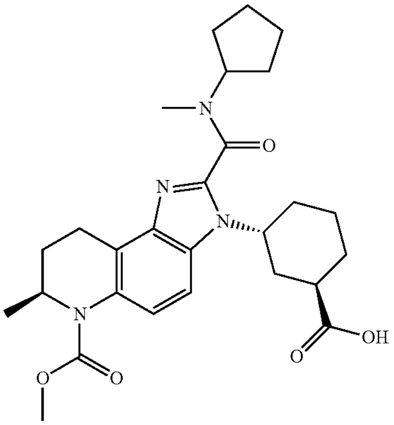<br>(1R,3R)-3-((S)-2-(cyclopentyl(methyl)carbamoyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.46-7.38 (m, 2H), 5.24-5.19 (m, 1H), 4.75-4.69 (m, 1H), 4.68-4.20 (m, 1H), 3.79 (s, 3H), 3.33-3.11 (m, 4H), 2.92-2.56 (m, 4H), 2.23-2.13 (m, 1H), 2.09-1.99 (m, 5H), 1.77-1.46 (m, 10H), 1.15 (d, J = 6.4 Hz, 3H). LCMS (ES, m/z): 497 $[M + H]^+$. |

TABLE 18-continued

| Example Number | Structure and Compound Name | $^1$H NMR, LCMS |
|---|---|---|
| 924 | 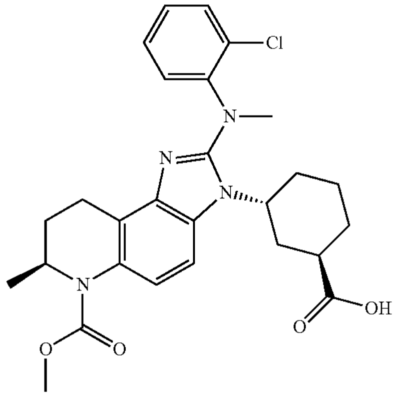 (1R,3R)-3-((S)-2-((2-chlorophenyl)(methyl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 511 [M + H]$^+$ |
| 925 | 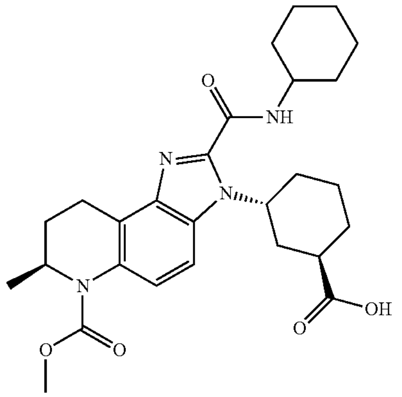 (1R,3R)-3-((S)-2-(cyclohexylcarbamoyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.55 (d, J = 9.6 Hz, 1H), 7.42 (d, J = 9.2 Hz, 1H), 5.02-4.89 (m, 1H), 4.72-4.70 (m, 1H), 4.02-3.98 (m, 1H), 3.79 (s, 3H), 3.26 (m, 1H), 2.98-2.96 (m, 1H), 2.91-2.71 (m, 3H), 2.29-2.12 (m, 3H), 2.14-2.10 (m, 2H), 2.09-1.80 (m, 3H), 1.80-1.62 (m, 4H), 1.60-1.25 (m, 6H), 1.15 (d, J = 6.8 Hz, 3H). LCMS (ES, m/z): 497 [M + H]$^+$. |
| 926 | 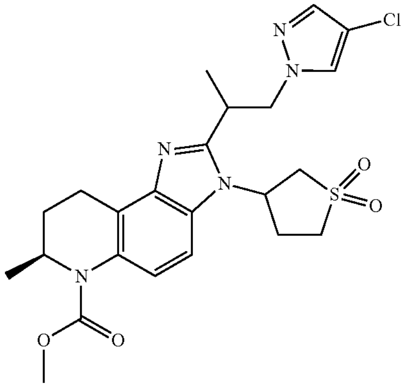 methyl (7S)-2-(1-(4-chloro-1H-pyrazol-1-yl)propan-2-yl)-3-(1,1-dioxidotetrahydrothiophen-3-yl)-7-methyl-3,7,8,9-tetrahydro-6H-imidazo[4,5-f]quinoline-6-carboxylate 2$^{nd}$ eluting isomer | $^1$H-NMR ($CD_3OD$, 300 MHz) δ (ppm): 7.64 (s, 1H), 7.64-7.55 (m, 1H), 7.52-7.44 (m, 2H), 5.58-5.45 (m, 1H), 4.90-4.42 (m, 3H), 4.02-3.89 (m, 1H), 3.77 (s, 3H), 3.72-3.40 (m, 3H), 3.34-3.18 (m, 2H), 2.98-2.72 (m, 2H), 2.39-2.20 (m, 2H), 1.73-1.67 (m, 1H), 1.40 (d, J = 6.9 Hz, 3H), 1.13 (d, J = 6.6 Hz, 3H). LCMS (ES, m/z): 506 [M + H]$^+$. |

TABLE 18-continued

| Example Number | Structure and Compound Name | $^1$H NMR, LCMS |
|---|---|---|
| 927 | 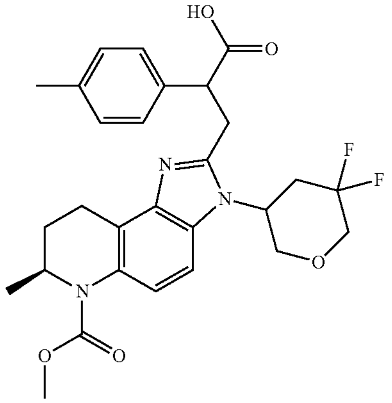 3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)-2-(p-tolyl)propanoic acid 4$^{th}$ eluting isomer | $^1$H-NMR ($CD_3OD$, 400 MHz) δ (ppm): 7.55-7.36 (m, 2H), 7.28-7.05 (m, 4H), 4.83-4.65 (m, 2H), 4.29-4.11 (m, 2H), 4.09-3.90 (m, 2H), 3.91-3.70 (m, 4H), 3.69-3.55 (m, 1H), 3.25-3.11 (m, 2H), 3.01-2.85 (m, 1H), 2.79-2.65 (m, 1H), 2.37-2.15 (m, 4H), 1.82-1.64 (m, 2H), 1.16 (d, J = 6.0 Hz, 3H). LCMS (ES, m/z): 528 [M + H]$^+$. |
| 928 | 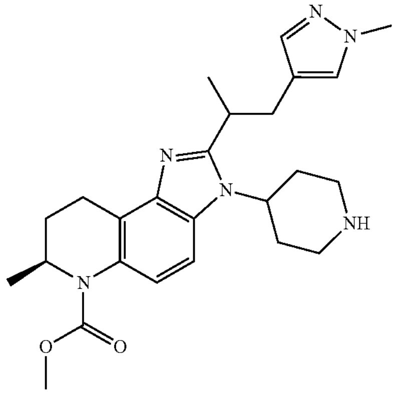 methyl (7S)-7-methyl-2-(1-(1-methyl-1H-pyrazol-4-yl)propan-2-yl)-3-(piperidin-4-yl)-3,7,8,9-tetrahydro-6H-imidazo[4,5-f]quinoline-6-carboxylate 2$^{nd}$ eluting isomer | $^1$H-NMR ($CD_3OD$, 400 MHz) δ (ppm): 7.46 (d, J = 8.8 Hz, 1H), 7.36 (d, J = 8.8 Hz, 1H), 7.15 (d, J = 3.2 Hz, 2H), 4.81-4.67 (m, 1H), 4.63-4.49 (m, 1H), 3.77 (s, 3H), 3.70 (s, 3H), 3.57-3.37 (m, 3H), 3.27-3.17 (m, 1H), 3.17-2.99 (m, 2H), 2.99-2.89 (m, 3H), 2.62-2.44 (m, 2H), 2.33-2.20 (m, 1H), 2.00-1.88 (m, 1H), 1.77-1.64 (m, 1H), 1.49 (d, J = 6.8 Hz, 3H), 1.17-1.04 (m, 4H) . . . LCMS (ES, m/z): 451 [M + H]$^+$ |
| 929 | 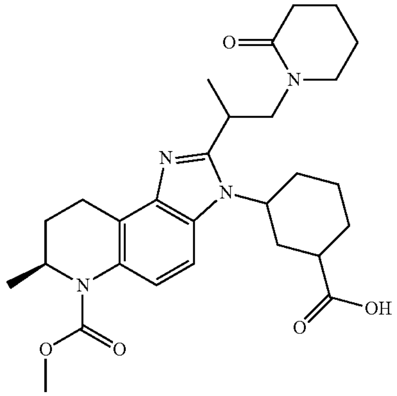 3-((7S)-6-(methoxycarbonyl)-7-methyl-2-(1-(2-oxopiperidin-1-yl)propan-2-yl)-6,7,8,9-tetrahydro-3H-imidazo[4,5-f]quinolin-3-yl)cyclohexane-1-carboxylic acid 2$^{nd}$ eluting isomer | $^1$H-NMR ($CD_3OD$, 400 MHz) δ (ppm): 7.54-7.38 (m, 2H), 4.76-4.74 (m, 1H), 4.61 (m, 1H), 3.88-3.85 (m, 1H), 3.79-3.70 (m, 4H), 3.66-3.62 (m, 1H), 3.37-3.32 (m, 1H), 3.25-3.15 (m, 2H), 2.95-2.90 (m, 1H), 2.65 (m, 1H), 2.39-2.26 (m, 5H), 2.20-2.04 (m, 3H), 1.91-1.88 (m, 1H), 1.74-1.66 (m, 5H). 1.63-1.58 (m, 2H), 1.44 (d, J = 6.8 Hz, 3H), 1.14 (d, J = 6.8 Hz, 3H). LCMS (ES, m/z): 511 [M + H]$^+$. |

TABLE 18-continued

| Example Number | Structure and Compound Name | $^1$H NMR, LCMS |
| --- | --- | --- |
| 930 | 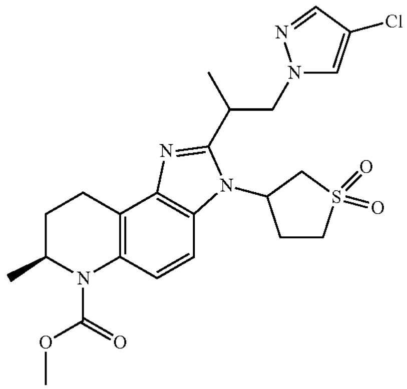 methyl (7S)-2-(1-(4-chloro-1H-pyrazol-1-yl)propan-2-yl)-3-(1,1-dioxidotetrahydrothiophen-3-yl)-7-methyl-3,7,8,9-tetrahydro-6H-imidazo[4,5-f]quinoline-6-carboxylate 1st eluting isomer | $^1$H-NMR ($CD_3OD$, 300 MHz) δ (ppm): 7.63-7.41 (m, 4H), 5.60-5.48 (m, 1H), 4.88 (s, 1H), 4.79-4.45 (m, 2H), 4.01-3.91 (m, 1H), 3.77 (s, 3H), 3.45 (d, J = 9 Hz, 3H), 3.32-3.30 (m, 2H), 2.94-2.92 (m, 2H), 2.65-2.55 (m, 1H), 2.32-2.18 (m, 1H), 1.75-1.65 (m, 1H), 1.40 (d, J = 6.9 Hz, 3H), 1.13 (d, J = 6.6 Hz, 3H). LCMS (ES, m/z): 506 $[M + H]^+$. |
| 931 | 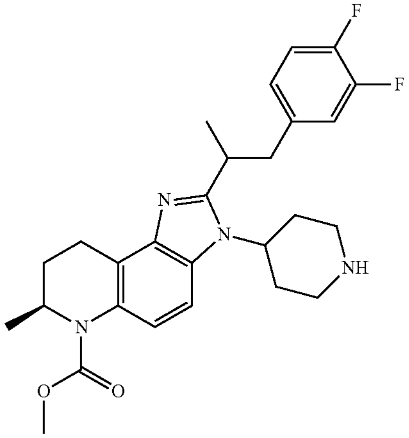 methyl (7S)-2-(1-(3,4-difluorophenyl)propan-2-yl)-7-methyl-3-(piperidin-4-yl)-3,7,8,9-tetrahydro-6H-imidazo[4,5-f]quinoline-6-carboxylate 2nd eluting isomer | $^1$H-NMR ($CD_3OD$, 400 MHz) δ (ppm): 7.51 (d, J = 8.8 Hz, 1H), 7.36 (d, J = 9.2 Hz, 1H), 7.16-7.02 (m, 2H), 6.95-6.88 (m, 1H), 4.81-4.65 (m, 1H), 4.49-4.31 (m, 1H), 3.79 (s, 3H), 3.69-3.57 (m, 1H), 3.33-3.05 (m, 5H), 3.00-2.88 (m, 1H), 2.88-2.75 (m, 1H), 2.76-2.65 (m, 1H), 2.53-2.23 (m, 3H), 1.81-1.65 (m, 2H), 1.51 (d, J = 6.8 Hz, 3H), 1.15 (d, J = 6.8 Hz, 3H), 1.00-0.83 (m, 1H). LCMS (ES, m/z): 483 $[M + H]^+$. |
| 932 | 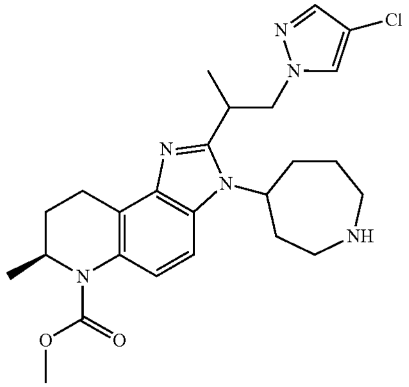 methyl (7S)-3-(azepan-4-yl)-2-((S)-1-(4-chloro-1H-pyrazol-1-yl)propan-2-yl)-7-methyl-3,7,8,9-tetrahydro-6H-imidazo[4,5-f]quinoline-6-carboxylate 3rd eluting isomer | $^1$H-NMR ($CD_3OD$, 400 MHz) δ (ppm): 7.57 (s, 1H), 7.52-7.32 (m, 3H), 4.82-4.68 (m, 1H), 4.70-4.54 (m, 2H), 4.53-4.45 (m, 1H), 4.05-3.88 (m, 1H), 3.78 (s, 3H), 3.30-3.20 (m, 1H), 3.19-3.00 (m, 3H), 2.98-2.87 (m, 2H), 2.57-2.35 (m, 2H), 2.35-2.19 (m, 1H), 2.07-2.01 (m, 1H), 1.98-1.87 (m, 1H), 1.85-1.67 (m, 2H), 1.63-1.48 (m, 1H), 1.45 (d, J = 6.8 Hz, 3H), 1.16 (d, J = 6.4 Hz, 3H). LCMS (ES, m/z): 485 $[M + H]^+$. |

TABLE 18-continued

| Example Number | Structure and Compound Name | $^1$H NMR, LCMS |
|---|---|---|
| 933 | 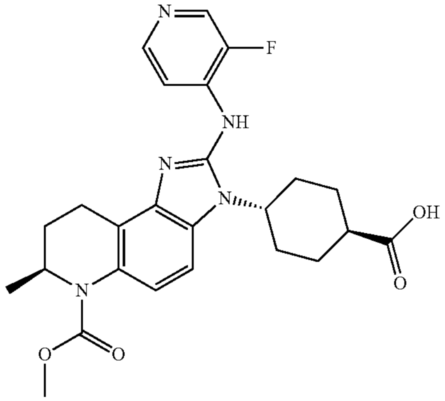 (1S,4R)-4-((S)-2-((3-fluoropyridin-4-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 482 [M + H]$^+$ |
| 934 | 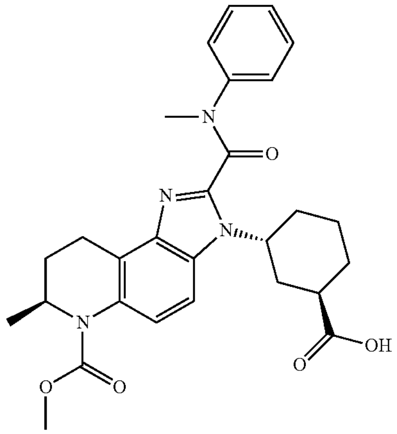 (1R,3R)-3-((S)-6-(methoxycarbonyl)-7-methyl-2-(methyl(phenyl)carbamoyl)-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.63-7.59 (m, 2H), 7.41-7.31 (m, 2H), 7.22-7.11 (m, 3H), 4.94 (m, 2H), 4.88-4.72 (m, 1H), 3.81 (s, 3H), 3.50 (s, 3H), 2.98-2.87 (m, 2H), 2.61-2.51 (m, 2H), 2.28-2.21 (m, 1H), 2.19-2.11 (m, 2H), 1.76-1.73 (m, 2H), 1.66-1.63 (m, 1H). 1.58-1.55 (m, 2H), 1.18 (d, J = 6.4 Hz, 3H). LCMS (ES, m/z): 505 [M + H]$^+$. |
| 935 | 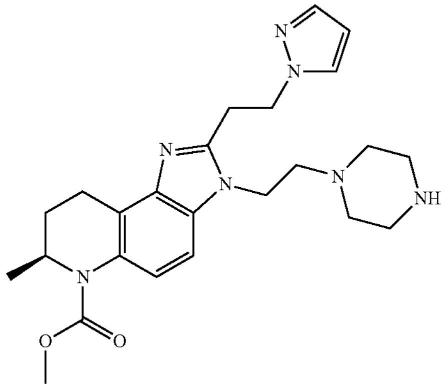 methyl (S)-2-(2-(1H-pyrazol-1-yl)ethyl)-7-methyl-3-(2-(piperazin-1-yl)ethyl)-3,7,8,9-tetrahydro-6H-imidazo[4,5-f]quinoline-6-carboxylate | $^1$H-NMR ($CDCl_3$, 300 MHz) δ (ppm): 7.53 (s, 1H), 7.42 (d, J = 8.7 Hz, 1H), 7.24 (s, 1H), 7.06 (d, J = 8.7 Hz, 1H), 6.13 (t, J = 2.1 Hz, 1H), 4.85-4.76 (m, 1H), 4.72 (t, J = 6.6 Hz, 2H), 3.90 (t, J = 6.6 Hz, 2H), 3.78 (s, 3H), 3.45 (t, J = 6.6 Hz, 2H), 3.31-3.16 (m, 1H), 3.08-2.92 (m, 1H), 2.90-2.82 (m, 4H), 2.51 (t, J = 6.6 Hz, 2H), 2.48-2.41 (m, 4H), 2.31-2.20 (m, 1H), 1.78-1.63 (m, 1H), 1.16 (d, J = 6.6 Hz, 3H). LCMS (ES, m/z): 452 [M + H]$^+$. |

TABLE 18-continued

| Example Number | Structure and Compound Name | $^1$H NMR, LCMS |
|---|---|---|
| 936 | 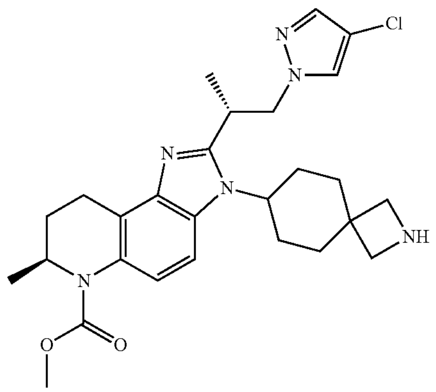 methyl (7S)-2-(1-(4-chloro-1H-pyrazol-1-yl)propan-2-yl)-7-methyl-3-(2-azaspiro[3.5]nonan-7-yl)-3,7,8,9-tetrahydro-6H-imidazo[4,5-f]quinoline-6-carboxylate 1st eluting isomer | $^1$H-NMR (DMSO, 400 MHz) δ (ppm): 8.02 (s, 1H), 7.55 (s, 1H), 7.31-7.15 (m, 2H), 4.62-455 (m, 1H), 4.54-4.35 (m, 2H), 4.30-4.15 (m, 1H), 3.85-3.70 (m, 2H), 3.65 (s, 3H), 3.45-3.35 (m, 2H), 3.35-3.25 (m, 2H), 3.12-3.01 (m, 1H), 2.85-2.75 (m, 1H), 2.20-1.90 (m, 5H), 1.80-1.46 (m, 5H), 1.18 (d, J = 6.8 Hz, 3H), 1.06 (d, J = 6.4 Hz, 3H). LCMS (ES, m/z): 511 [M + H]$^+$. |
| 937 | 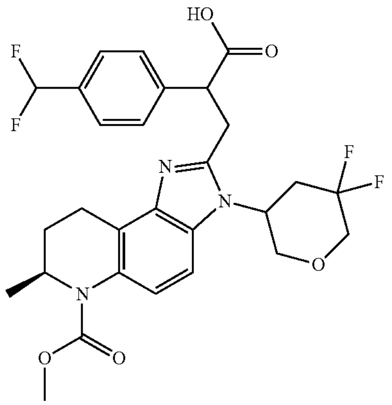 2-(4-(difluoromethyl)phenyl)-3-((7S)-3-(5,5-difluorotetrahydro-2H-pyran-3-yl)-6-(methoxycarbonyl)-7-methyl-6,7,8,9-tetrahydro-3H-imidazo[4,5-f]quinolin-2-yl)propanoic acid 2nd eluting isomer | $^1$H-NMR ($CD_3OD$, 400 MHz) δ (ppm): 7.60-7.47 (m, 5H), 7.43 (d, J = 9.2 Hz, 1H), 6.90-6.56 (m, 1H), 4.88-4.81 (m, 1H), 4.80-4.71 (m, 1H), 4.38-4.28 (m, 1H), 4.25-4.14 (m, 1H), 4.13-4.07 (m, 1H), 4.03-3.93 (m, 1H), 3.94-3.80 (m, 1H), 3.78 (s, 3H), 3.73-3.63 (m, 1H), 3.32-3.26 (m, 1H), 3.24-3.12 (m, 1H), 2.98-2.87 (m, 1H), 2.86-2.70 (m, 1H), 2.34-2.17 (m, 1H), 2.00-1.89 (m, 1H), 1.84-1.69 (m, 1H), 1.15 (d, J = 6.8 Hz, 3H). LCMS (ES, m/z): 564 [M + H]$^+$. |
| 938 | 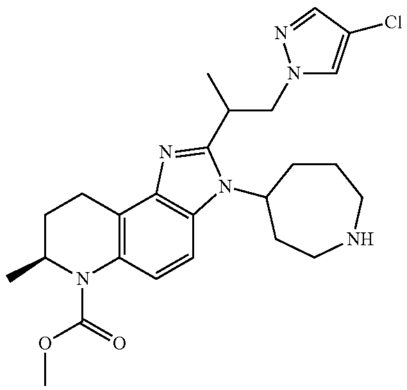 methyl (7S)-3-(azepan-4-yl)-2-(1-(4-chloro-1H-pyrazol-1-yl)propan-2-yl)-7-methyl-3,7,8,9-tetrahydro-6H-imidazo[4,5-f]quinoline-6-carboxylate 2nd eluting isomer | $^1$H-NMR ($CD_3OD$, 400 MHz) δ (ppm): 7.63 (s, 1H), 7.51-7.34 (m, 3H), 4.82-4.73 (m, 1H), 4.72-4.59 (m, 2H), 4.58-4.44 (m, 1H), 4.05-3.88 (m, 1H), 3.79 (s, 3H), 3.55-3.34 (m, 3H), 3.30-3.16 (m, 2H), 3.01-2.87 (m, 1H), 2.75-2.59 (m, 1H), 2.54-2.42 (m, 1H), 2.36-2.23 (m, 1H), 2.21-1.95 (m, 3H), 1.88-1.67 (m, 2H), 1.44 (d, J = 6.8 Hz, 3H), 1.15 (d, J = 6.4 Hz, 3H). LCMS (ES, m/z): 485 [M + H]$^+$. |

TABLE 18-continued

| Example Number | Structure and Compound Name | $^1$H NMR, LCMS |
|---|---|---|
| 939 | 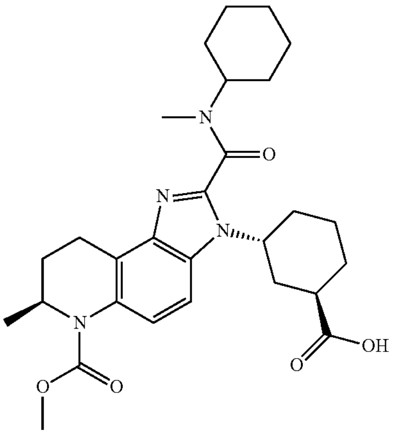<br>(1R,3R)-3-((S)-2-(cyclohexyl(methyl)carbamoyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 7.53-7.46 (m, 2H), 4.98-4.89 (m, 1H), 4.78-4.73 (m, 2H), 3.80 (s, 3H), 3.27-3.21 (m, 1H), 3.15 (s, 3H), 3.05-2.92 (m, 1H), 2.92-2.70 (m, 3H), 2.30-2.15 (m, 3H), 1.98-1.81 (m, 5H), 1.80-1.52 (m, 7H), 1.52-1.40 (m, 2H), 1.31-1.20 (m, 1H), 1.15 (d, J = 6.4 Hz, 3H). LCMS (ES, m/z): 511 $[M + H]^+$. |
| 940 | 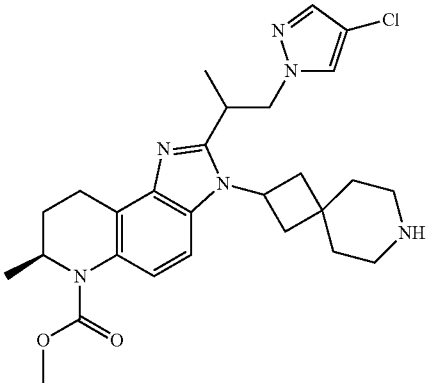<br>methyl (7S)-2-(1-(4-chloro-1H-pyrazol-1-yl)propan-2-yl)-7-methyl-3-(7-azaspiro[3.5]nonan-2-yl)-3,7,8,9-tetrahydro-6H-imidazo[4,5-f]quinoline-6-carboxylate<br>1st eluting isomer | $^1$H-NMR ($CD_3OD$, 400 MHz) δ (ppm): 7.61 (s, 1H), 7.54-7.51 (m, 2H), 7.43 (s, 1H), 5.05-4.95 (m, 2H), 4.85-4.70 (m, 1H), 4.58-4.45 (m, 2H), 4.00-3.85 (m, 1H), 3.75 (s, 3H), 3.25-3.10 (m, 4H), 2.98-2.88 (m, 1H), 2.75-2.55 (m, 3H), 2.30-2.15 (m, 2H), 2.05-1.95 (m, 4H), 1.80-1.70 (m, 1H), 1.43 (d, J = 7.2 Hz, 3H), 1.14 (d, J = 6.8 Hz, 3H). LCMS (ES, m/z): 511 $[M + H]^+$. |
| 941 | 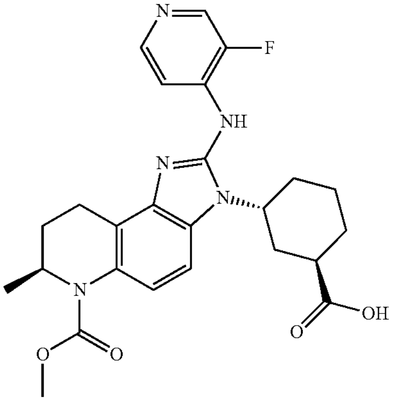<br>(1R,3R)-3-((S)-2-((3-fluoropyridin-4-yl)amino)-6-(methoxycarbonyl)-7-methyl-6,7,8,9-tetrahydro-3H-imidazo[4,5-f]quinolin-3-yl)cyclohexane-1-carboxylic acid | LCMS (ES, m/z): 482 $[M + H]^+$ |

TABLE 18-continued

| Example Number | Structure and Compound Name | $^1$H NMR, LCMS |
| --- | --- | --- |
| 942 | 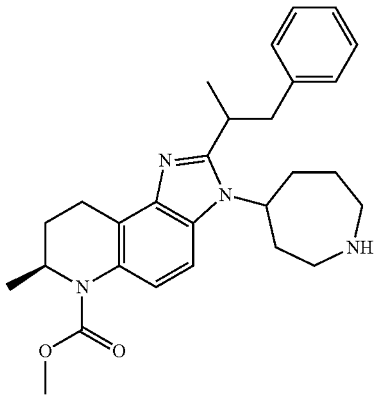 methyl (7S)-3-(azepan-4-yl)-7-methyl-2-(1-phenylpropan-2-yl)-3,7,8,9-tetrahydro-6H-imidazo[4,5-f]quinoline-6-carboxylate 4th eluting isomer | $^1$H-NMR ($CD_3OD$, 400 MHz) δ (ppm): 7.41-7.24 (m, 2H), 7.20-7.03 (m, 5H), 4.79-4.64 (m, 1H), 4.46-4.42 (m, 1H), 3.76 (s, 3H), 3.62-3.49 (m, 1H), 3.31-3.15 (m, 2H), 3.12-3.01 (m, 2H), 2.99-2.78 (m, 3H), 2.71-2.68 (m, 1H), 2.46-2.36 (m, 1H), 2.34-2.12 (m, 2H), 1.95-1.79 (m, 2H), 1.79-1.61 (m, 2H), 1.49 (d, J = 6.8 Hz, 3H), 1.16 (d, J = 6.8 Hz, 3H), 1.02-0.98 (m, 1H). LCMS (ES, m/z): 461 $[M + H]^+$. |
| 943 | 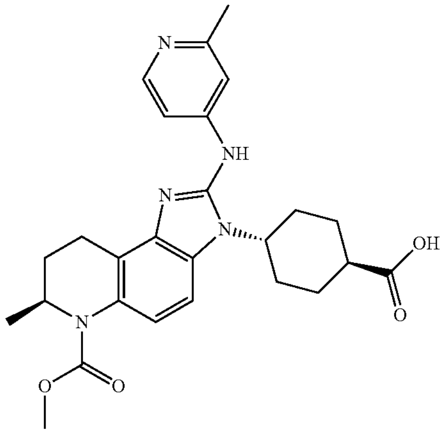 (1S,4R)-4-((S)-6-(methoxycarbonyl)-7-methyl-2-((2-methylpyridin-4-yl)amino)-6,7,8,9-tetrahydro-3H-imidazo[4,5-f]quinolin-3-yl)cyclohexane-1-carboxylic acid | LCMS (ES, m/z): 478 $[M + H]^+$ |
| 944 | 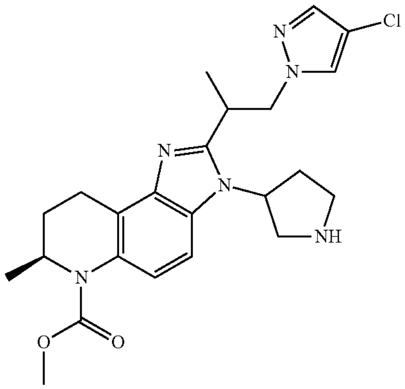 methyl (7S)-2-(1-(4-chloro-1H-pyrazol-1-yl)propan-2-yl)-7-methyl-3-(pyrrolidin-3-yl)-3,7,8,9-tetrahydro-6H-imidazo[4,5-f]quinoline-6-carboxylate 3rd eluting isomer | $^1$H-NMR ($CD_3OD$, 300 MHz) δ (ppm): 7.56 (s, 1H), 7.43 (s, 1H), 7.42-7.36 (m, 2H), 5.16-5.05 (m, 1H), 4.80-4.70 (m, 1H), 4.70-4.59 (m, 1H), 4.55-4.44 (m, 1H), 4.05-3.89 (m, 1H), 3.79 (s, 3H), 3.45-3.35 (m, 1H), 3.29-3.07 (m, 4H), 3.01-2.87 (m, 1H), 2.41-2.20 (m, 3H), 1.80-1.64 (m, 1H), 1.41 (d, J = 6.9 Hz, 3H), 1.13 (d, J = 6.6 Hz, 3H). LCMS (ES, m/z): 457 $[M + H]^+$. |

TABLE 18-continued

| Example Number | Structure and Compound Name | $^1$H NMR, LCMS |
|---|---|---|
| 945 | 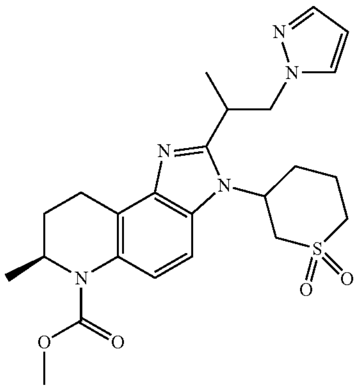<br>methyl (7S)-2-(1-(1H-pyrazol-1-yl)propan-2-yl)-3-(1,1-dioxidotetrahydro-2H-thiopyran-3-yl)-7-methyl-3,7,8,9-tetrahydro-6H-imidazo[4,5-f]quinoline-6-carboxylate<br>4th eluting isomer | $^1$H-NMR ($CD_3OD$, 400 MHz) δ (ppm): 7.77-7.56 (m, 3H), 7.44 (s, 1H), 6.22 (t, J = 2.0 Hz, 1H), 4.99-4.92 (m, 1H), 4.83-4.79 (m, 1H), 4.67 (d, J = 6.0 Hz, 2H), 4.13-4.01 (m, 1H), 3.99-3.89 (m, 1H), 3.79 (s, 3H), 3.50-3.30 (m, 1H), 3.19-2.99 (m, 3H), 2.80-2.45 (m, 2H), 2.35-2.01 (m, 4H), 1.90-1.75 (m, 1H), 1.57 (d, J = 6.8 Hz, 3H), 1.13 (d, J = 6.8 Hz, 3H). LCMS (ES, m/z): 486 $[M + H]^+$. |
| 946 | 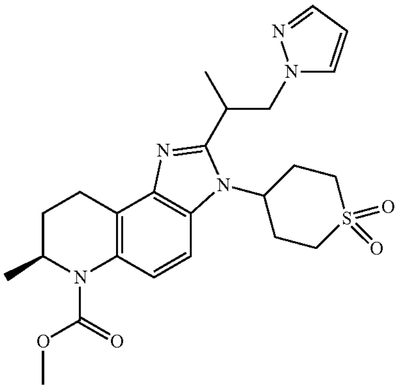<br>methyl (7S)-2-(1-(1H-pyrazol-1-yl)propan-2-yl)-3-(1,1-dioxidotetrahydro-2H-thiopyran-4-yl)-7-methyl-3,7,8,9-tetrahydro-6H-imidazo[4,5-f]quinoline-6-carboxylate<br>1st eluting isomer | $^1$H-NMR ($CD_3OD$, 400 MHz) δ (ppm): 7.61 (d, J = 2.0 Hz, 1H), 7.44 (d, J = 2.0 Hz, 1H), 7.40 (m, 2H), 6.14-6.13 (m, 1H), 4.80-4.60 (m, 3H), 4.55-4.45 (m, 1H), 4.02-3.89 (m, 1H), 3.79 (s, 3H), 3.80-3.35 (m, 2H), 3.28-2.99 (m, 4H), 2.95-2.81 (m, 2H), 2.31-2.11 (m, 2H), 1.65-1.55 (m, 2H), 1.43 (d, J = 7.2 Hz, 3H), 1.13 (d, J = 6.8 Hz, 3H). LCMS (ES, m/z): 486 $[M + H]^+$. |
| 947 | 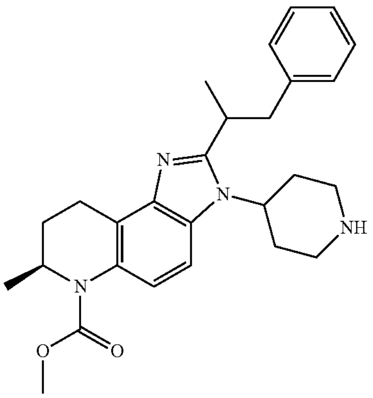<br>methyl (7S)-7-methyl-2-(1-phenylpropan-2-yl)-3-(piperidin-4-yl)-3,7,8,9-tetrahydro-6H-imidazo[4,5-f]quinoline-6-carboxylate<br>2nd eluting isomer | $^1$H-NMR ($CD_3OD$, 400 MHz) δ (ppm): 7.46 (d, J = 8.8 Hz, 1H), 7.33 (d, J = 9.2 Hz, 1H), 7.19-7.06 (m, 5H), 4.81-4.68 (m, 1H), 4.31-4.20 (m, 1H), 3.78 (s, 3H), 3.70-3.56 (m, 1H), 3.28-3.20 (m, 1H), 3.20-3.02 (m, 3H), 3.02-2.88 (m, 2H), 2.80-2.71 (m, 1H), 2.59-2.47 (m, 1H), 2.41-2.30 (m, 1H), 2.30-2.21 (m, 1H), 2.21-1.99 (m, 1H), 1.81-1.68 (m, 2H), 1.53 (d, J = 6.8 Hz, 3H), 1.15 (d, J = 6.8 Hz, 3H), 0.70-0.56 (m, 1H). LCMS (ES, m/z): 447 $[M + H]^+$. |

TABLE 18-continued

| Example Number | Structure and Compound Name | $^1H$ NMR, LCMS |
|---|---|---|
| 948 | 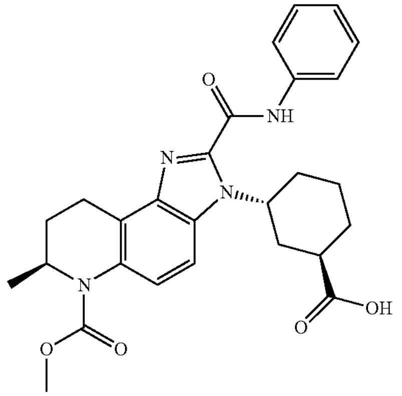 (1R,3R)-3-((S)-6-(methoxycarbonyl)-7-methyl-2-(phenylcarbamoyl)-6,7,8,9-tetrahydro-3H-imidazo[4,5-f]quinolin-3-yl)cyclohexane-1-carboxylic acid | $^1H$-NMR ($CD_3OD$, 400 MHz) δ (ppm): 8.02 (d, J = 8.4 Hz, 2H), 7.65-7.56 (m, 2H), 7.41-7.36 (m, 2H), 7.10-7.06 (m, 1H), 4.88 (m, 1H), 4.80-4.74 (m, 1H), 3.81 (s, 3H), 3.34-3.26 (m, 1H), 3.06-2.76 (m, 4H), 2.27-2.19 (m, 3H), 1.90-1.60 (m, 5H), 1.17 (d, J = 6.8 Hz, 3H). LCMS (ES, m/z): 491 $[M + H]^+$. |
| 949 | 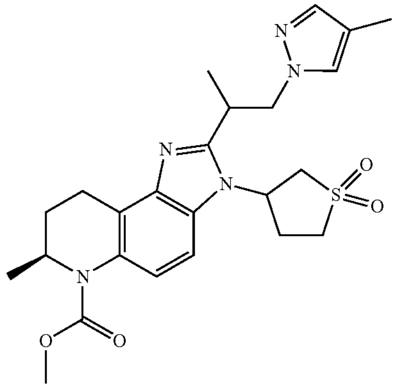 methyl (7S)-3-(1,1-dioxidotetrahydrothiophen-3-yl)-7-methyl-2-(1-(4-methyl-1H-pyrazol-1-yl)propan-2-yl)-3,7,8,9-tetrahydro-6H-imidazo[4,5-f]quinoline-6-carboxylate 1st eluting isomer | $^1H$-NMR ($CD_3OD$, 300 MHz) δ (ppm): 7.53-7.24 (m, 4H), 5.55-5.38 (m, 1H), 4.82-4.65 (m, 1H), 4.55-4.28 (m, 2H), 4.13-3.75 (m, 4H), 3.50-3.20 (m, 5H), 3.18-2.78 (m, 2H), 2.62-2.48 (m, 1H), 2.28-2.16 (m, 1H), 2.08-2.00 (m, 1H), 1.98 (s, 2H), 1.75-1.58 (m, 1H), 1.41 (d, J = 6.9 Hz, 2H), 1.32-1.26 (m, 1H), 1.12 (d, J = 6.6 Hz, 2H). LCMS (ES, m/z): 486 $[M + H]^+$. |
| 950 | 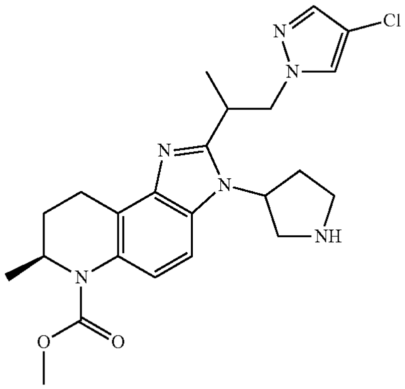 methyl (7S)-2-(1-(4-chloro-1H-pyrazol-1-yl)propan-2-yl)-7-methyl-3-(pyrrolidin-3-yl)-3,7,8,9-tetrahydro-6H-imidazo[4,5-f]quinoline-6-carboxylate 2nd eluting isomer | $^1H$-NMR ($CD_3OD$, 300 MHz) δ (ppm): 8.28-7.93 (m, 1H), 7.62-7.32 (m, 3H), 5.10-4.99 (m, 1H), 4.81-4.62 (m, 2H), 4.53-4.45 (m, 1H), 4.05-3.86 (m, 1H), 3.75 (s, 3H), 3.65-3.52 (m, 3H), 3.26-2.83 (m, 3H), 2.31-1.97 (m, 3H), 1.71-1.56 (m, 1H), 1.43 (d, J = 6.9 Hz, 3H), 1.07 (d, J = 6.9 Hz, 3H). LCMS (ES, m/z): 457 [M + H]+. |

TABLE 18-continued

| Example Number | Structure and Compound Name | $^1$H NMR, LCMS |
|---|---|---|
| 951 | 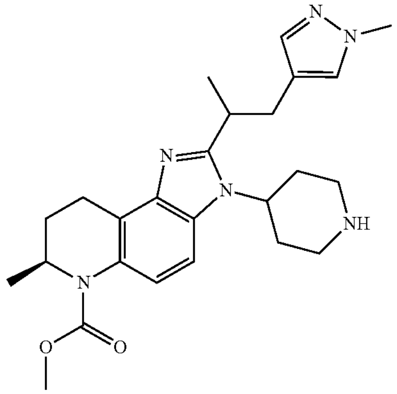 methyl (7S)-7-methyl-2-(1-(1-methyl-1H-pyrazol-4-yl)propan-2-yl)-3-(piperidin-4-yl)-3,7,8,9-tetrahydro-6H-imidazo[4,5-f]quinoline-6-carboxylate 1$^{st}$ eluting isomer | $^1$H-NMR ($CD_3OD$, 400 MHz) δ (ppm): 7.47 (d, J = 9.2 Hz, 1H), 7.36 (d, J = 8.8 Hz, 1H), 7.24 (s, 1H), 7.14 (s, 1H), 4.80-4.67 (m, 1H), 4.62-4.43 (m, 1H), 3.76 (s, 3H), 3.72 (s, 3H), 3.55-3.45 (m, 1H), 3.43-3.33 (m, 2H), 3.28-3.20 (m, 1H), 3.13-2.97 (m, 2H), 2.97-2.84 (m, 3H), 2.67-2.35 (m, 2H), 2.35-2.16 (m, 1H), 1.94-1.84 (m, 1H), 1.76-1.65 (m, 1H), 1.47 (d, J = 6.8 Hz, 3H), 1.26-1.08 (m, 4H). LCMS (ES, m/z): 451 [M + H]$^+$ |
| 952 | 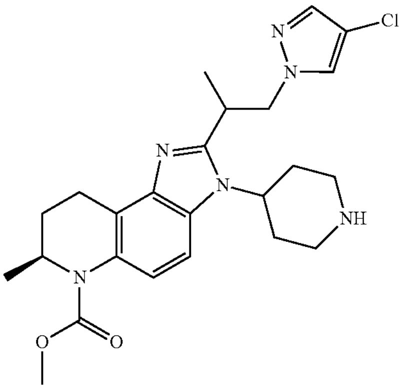 methyl (7S)-2-(1-(4-chloro-1H-pyrazol-1-yl)propan-2-yl)-7-methyl-3-(piperidin-4-yl)-3,7,8,9-tetrahydro-6H-imidazo[4,5-f]quinoline-6-carboxylate 1$^{st}$ eluting isomer | $^1$H-NMR ($CD_3OD$, 400 MHz) δ (ppm): 7.60 (s, 1H), 7.53 (d, J = 9.2 Hz, 1H), 7.43 (s, 1H), 7.36 (d, J = 9.2 Hz, 1H), 4.79-4.69 (m, 1H), 4.67-4.54 (m, 1H), 4.52-4.36 (m, 2H), 4.01-3.88 (m, 1H), 3.76 (s, 3H), 3.29-3.15 (m, 3H), 2.98-2.69 (m, 3H), 2.53-2.19 (m, 3H), 1.85-1.76 (m, 1H), 1.77-1.65 (m, 1H), 1.51-1.41 (m, 1H), 1.40 (d, J = 6.8 Hz, 3H), 1.13 (d, J = 6.4 Hz, 3H). LCMS (ES, m/z): 471 [M + H]$^+$. |
| 953 | 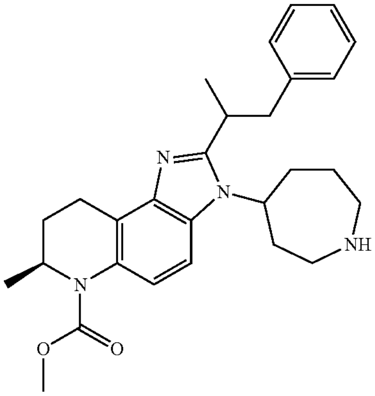 methyl (7S)-3-(azepan-4-yl)-7-methyl-2-(1-phenylpropan-2-yl)-3,7,8,9-tetrahydro-6H-imidazo[4,5-f]quinoline-6-carboxylate 3$^{rd}$ eluting isomer | $^1$H-NMR ($CD_3OD$, 400 MHz) δ (ppm): 7.38-7.25 (m, 2H), 7.21-7.00 (m, 5H), 4.78-4.67 (m, 1H), 4.43-4.39 (m, 1H), 3.75 (s, 3H), 3.65-3.51 (m, 1H), 3.31-3.18 (m, 1H), 3.18-3.12 (m, 1H), 3.11-2.98 (m, 4H), 2.98-2.75 (m, 2H), 2.44-2.32 (m, 1H), 2.32-2.18 (m, 2H), 2.03-1.99 (m, 1H), 1.78-1.59 (m, 2H), 1.54 (d, J = 6.8 Hz, 3H), 1.50-1.35 (m, 1H), 1.16 (d, J = 6.4 Hz, 3H), 0.91-0.86 (m, 1H). LCMS (ES, m/z): 461 [M + H]$^+$. |

TABLE 18-continued

| Example Number | Structure and Compound Name | $^1$H NMR, LCMS |
|---|---|---|
| 954 | 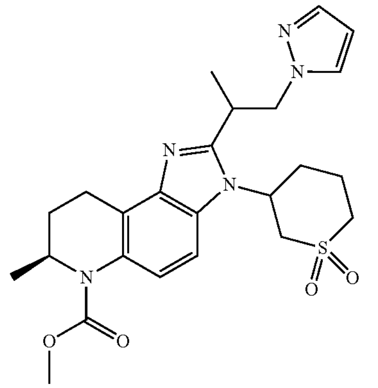 methyl (7S)-2-(1-(1H-pyrazol-1-yl)propan-2-yl)-3-(1,1-dioxidotetrahydro-2H-thiopyran-3-yl)-7-methyl-3,7,8,9-tetrahydro-6H-imidazo[4,5-f]quinoline-6-carboxylate 2$^{nd}$ eluting isomer | $^1$H-NMR ($CD_3OD$, 400 MHz) δ (ppm): 7.82-7.62 (m, 3H), 7.44 (s, 1H), 6.22 (t, J = 2.4 Hz, 1H), 4.86-4.67 (m, 4H), 4.13-3.95 (m, 2H), 3.79 (s, 3H), 3.50-3.30 (m, 2H), 3.19-2.99 (m, 3H), 2.50-2.31 (m, 1H), 2.28-2.15 (m, 2H), 2.03-1.79 (m, 2H), 1.57 (d, J = 6.8 Hz, 3H), 1.56-1.47 (m, 1H), 1.13 (d, J = 6.8 Hz, 3H). LCMS (ES, m/z): 486 [M + H]$^+$. |
| 955 | 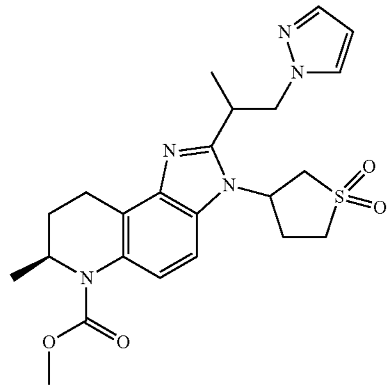 methyl (7S)-2-(1-(1H-pyrazol-1-yl)propan-2-yl)-3-(1,1-dioxidotetrahydrothiophen-3-yl)-7-methyl-3,7,8,9-tetrahydro-6H-imidazo[4,5-f]quinoline-6-carboxylate 2$^{nd}$ eluting isomer | $^1$H-NMR ($CD_3OD$, 300 MHz) δ (ppm): 7.86 (s, 2H), 7.70 (s, 1H), 7.42 (s, 1H), 6.33-6.28 (m, 1H), 5.82-5.60 (m, 1H), 4.92-4.65 (m, 3H), 4.35-4.22 (m, 1H), 3.82-3.75 (m, 4H), 3.72-3.42 (m, 2H), 3.25-2.92 (m, 3H), 2.85-2.65 (m, 1H), 2.35-2.14 (m, 2H), 1.98-1.85 (m, 1H), 1.61 (d, J = 7.2 Hz, 3H), 1.18 (d, J = 6.6 Hz, 3H). LCMS (ES, m/z): 472 [M + H]$^+$. |
| 956 | 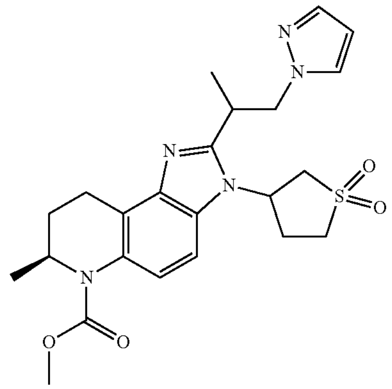 methyl (7S)-2-(1-(1H-pyrazol-1-yl)propan-2-yl)-3-(1,1-dioxidotetrahydrothiophen-3-yl)-7-methyl-3,7,8,9-tetrahydro-6H-imidazo[4,5-f]quinoline-6-carboxylate 1$^{st}$ eluting isomer | $^1$H-NMR ($CD_3OD$, 300 MHz) δ (ppm): 7.53-7.40 (m, 4H), 6.19-6.17 (m, 1H), 5.55-5.38 (m, 1H), 4.80-4.45 (m, 3H), 3.98-3.85 (m, 1H), 3.75 (s, 3H), 3.54-3.10 (m, 5H), 2.95-2.78 (m, 2H), 2.62-2.48 (m, 1H), 2.28-2.15 (m, 1H), 1.75-1.68 (m, 1H), 1.43 (d, J = 6.9 Hz, 3H), 1.13 (d, J = 6.9 Hz, 3H). LCMS (ES, m/z): 472 [M + H]$^+$. |

TABLE 18-continued

| Example Number | Structure and Compound Name | $^1$H NMR, LCMS |
|---|---|---|
| 957 | 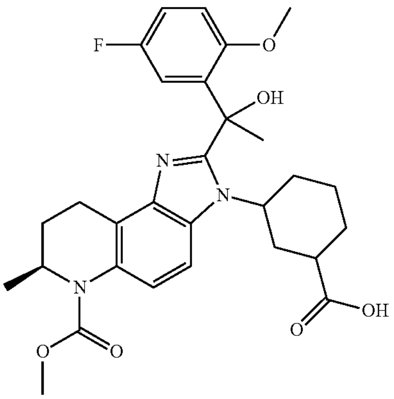 3-((7S)-2-(1-(5-fluoro-2-methoxyphenyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid 2nd eluting isomer | $^1$H-NMR ($CD_3OD$, 400 MHz) δ (ppm): 7.24 (d, J = 8.8 Hz, 1H), 6.99 (d, J = 8.8 Hz, 1H), 6.93-6.84 (m, 2H), 6.66-6.62 (m, 1H), 4.74-4.61 (m, 1H), 4.52-4.39 (m, 1H), 3.86 (s, 3H), 3.79 (s, 3H), 3.05-2.99 (m, 1H), 2.85-2.70 (m, 2H), 2.69-2.58 (m, 1H), 2.55-2.45 (m, 1H), 2.41-2.32 (m, 1H), 2.31-2.20 (m, 1H), 2.18-2.07 (m, 1H), 1.86-1.60 (m, 7H), 1.52-1.35 (m, 1H), 1.06 (d, J = 6.8 Hz, 3H). LCMS (ES, m/z): 540 [M + H]$^+$. |
| 958 | 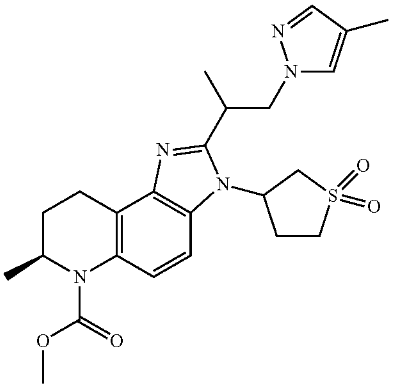 methyl (7S)-3-(1,1-dioxidotetrahydrothiophen-3-yl)-7-methyl-2-(1-(4-methyl-1H-pyrazol-1-yl)propan-2-yl)-3,7,8,9-tetrahydro-6H-imidazo[4,5-f]quinoline-6-carboxylate 2nd eluting isomer | $^1$H-NMR ($CD_3OD$, 300 MHz) δ (ppm): 7.85 (s, 2H), 7.49 (s, 1H), 7.23 (s, 1H), 5.78-5.62 (m, 1H), 4.91-4.53 (m, 3H), 4.28-4.15 (m, 1H), 3.84-3.40 (m, 6H), 3.32-2.94 (m, 3H), 2.86-2.68 (m, 1H), 2.35-2.14 (m, 2H), 2.00 (s, 3H), 1.95-1.84 (m, 1H), 1.58 (d, J = 6.6 Hz, 3) 1.28 (d, J = 6.6 Hz, 3H). LCMS (ES, m/z): 486 [M + H]$^+$. |
| 959 | 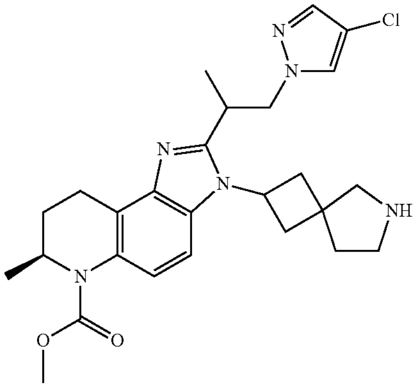 methyl (7S)-2-(1-(4-chloro-1H-pyrazol-1-yl)propan-2-yl)-7-methyl-3-(6-azaspiro[3.4]octan-2-yl)-3,7,8,9-tetrahydro-6H-imidazo[4,5-f]quinoline-6-carboxylate 3rd eluting isomer | $^1$H-NMR ($CD_3OD$, 300 MHz) δ (ppm): 7.56 (s, 1H), 7.52-7.32 (m, 3H), 5.04-4.92 (m, 1H), 4.83-4.69 (m, 1H), 4.68-4.52 (m, 1H), 4.52-4.37 (m, 1H), 4.01-3.82 (m, 1H), 3.79 (s, 3H), 3.31-3.15 (m, 2H), 3.15-3.09 (m, 2H), 3.09-2.82 (m, 4H), 2.72-2.56 (m, 1H), 2.56-2.38 (m, 1H), 2.37-2.21 (m, 1H), 2.18-1.98 (m, 2H), 1.85-1.68 (m, 1H), 1.42 (d, J = 6.9 Hz, 3H), 1.17 (d, J = 6.9 Hz, 3H). LCMS (ES, m/z): 497 [M + H]$^+$. |

TABLE 18-continued

| Example Number | Structure and Compound Name | $^1$H NMR, LCMS |
|---|---|---|
| 960 | 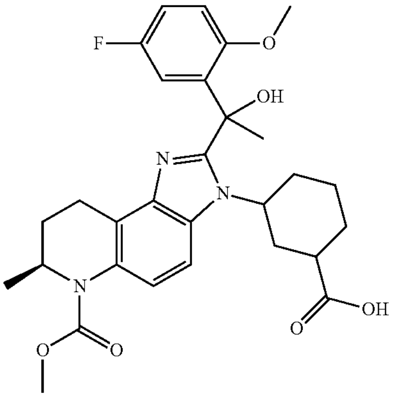 3-((7S)-2-(1-(5-fluoro-2-methoxyphenyl)-1-hydroxyethyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 6.95-6.81 (m, 4H), 6.68-6.65 (m, 1H), 4.74-4.61 (m, 1H), 4.52-4.39 (m, 1H), 3.86 (s, 3H), 3.79 (s, 3H), 2.95-2.60 (m, 4H), 2.49-2.35 (m, 1H), 2.21-2.05 (m, 3H), 1.96-1.85 (m, 2H), 1.80 (s, 3H), 1.72-1.55 (m, 3H), 0.95 (d, J = 6.8 Hz, 3H). LCMS (ES, m/z): 540 [M + H]$^+$. |
| 961 | 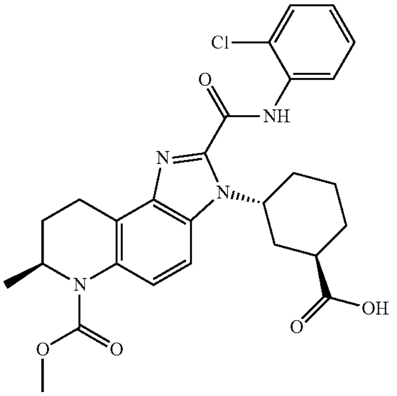 (1R,3R)-3-((S)-2-((2-chlorophenyl)carbamoyl)-6-(methoxycarbonyl)-7-methyl-6,7,8,9-tetrahydro-3H-imidazo[4,5-f]quinolin-3-yl)cyclohexane-1-carboxylic acid | $^1$H-NMR ($CD_3OD$, 400 MHz) δ (ppm): 9.06-9.04 (m, 1H), 7.71-7.63 (m, 2H), 7.51-7.48 (m, 1H), 7.44-7.39 (m, 1H), 7.10-7.05 (m, 1H), 5.07-5.01 (m, 1H), 4.88-4.76 (m, 1H), 3.82 (s, 3H), 3.34-3.26 (m, 1H), 3.09-2.76 (m, 4H), 2.28-2.20 (m, 3H), 1.91-1.60 (m, 5H), 1.17 (d, J = 6.8 Hz, 3H). LCMS (ES, m/z): 525 [M + H]$^+$. |
| 962 | 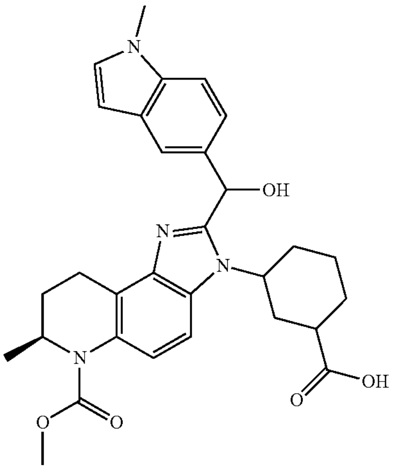 3-((7S)-2-(hydroxy(1-methyl-1H-indol-5-yl)methyl)-6-(methoxycarbonyl)-7-methyl-6,7,8,9-tetrahydro-3H-imidazo[4,5-f]quinolin-3-yl)cyclohexane-1-carboxylic acid 1$^{st}$ eluting isomer | $^1$H-NMR ($CD_3OD$, 400 MHz) δ (ppm): 7.75 (s, 1H), 7.45-7.32 (m, 3H), 7.19-7.15 (m, 2H), 6.43 (s, 1H), 6.42 (s, 1H), 5.04-4.91 (m, 1H), 4.80-4.79 (m, 1H), 3.79 (s, 3H), 3.78 (s, 3H), 3.31-3.22 (m, 1H), 3.11-3.00 (m, 1H), 2.91-2.85 (m, 1H), 2.45-2.31 (m, 2H), 2.28-2.21 (m, 1H), 2.12-2.00 (m, 1H), 1.91-1.70 (m, 2H), 1.55-1.30 (m, 2H), 1.25-1.18 (m, 1H), 1.16 (d, J = 6.8 Hz, 3H), 0.82-0.78 (m, 1H). LCMS (ES, m/z): 531 [M + H]$^+$. |

Example 963: HTRF Biochemical Assay for CBP and BRD4 Activity

The assay was performed in a final volume of 6 μL in assay buffer containing 50 mM Hepes (pH 7.5, (0.5M Hepes, pH 7.5 solution; Teknova H1575)), 0.5 mM GSH, 0.01% BGG (0.22 μM filtered, Sigma, G7516-25G), 0.005% BSA (0.22 μM filtered, EMD Millipore Corporation, 126575) and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 33 μM to 1.7 nM, top to lowest dose, respectively. 3 μL of 2× Protein and 3 μL of 2× Peptide Ligand were added to assay plates (pre-stamped with compound). Plates were incubated for varying times at room temperature prior to measuring the signal. TR-FRET (Time-Resolved Fluorescence Resonance Energy Transfer) was measured on the PHERAstar (BMG, equipped with HTRF optic module [337/520/490]) or on the Envision (PerkinElmer, equipped with the TRF Laser unit, TRF dual mirror D400/D505 and emission filters M520 and M495). Data were reported as percent inhibition compared with control wells based on the following equation: % inh=1−((TR-FRET ratio−AveLow)/(AveHigh−AveLow)) where TR-FRET ratio=(Fluorescence at 520 nm/Fluorescence at 490 nm)*10000), AveLow=average TR-FRET ratio of no enzyme control (n=32), and AveHigh=average TR-FRET ratio of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm. For all assay formats data were reported as percent inhibition compared with control wells based on the following equation: % inh=100*((FLU−AveLow)/(AveHigh−AveLow)) where FLU=measured Fluorescence, AveLow=average Fluorescence of no enzyme control (n=32), and AveHigh=average Fluorescence of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm. $IC_{50}$ values are shown in Table 19, below. As set forth in Table 19 below, an $IC_{50}$ value of greater than or equal to 0.001 μM and less than or equal to 0.01 M is marked "++++"; a value greater than 0.01 μM and less than or equal to 0.1 μM is marked "+++"; a value greater than 0.1 μM and less than or equal to 1 μM is marked "++"; and a value greater than 1 μM and less than 1000 μM is marked "+." Compounds that were not tested in a particular assay are marked "NT."

TABLE 19

| | $IC_{50}$ Values | |
|---|---|---|
| Example No. | CBP $IC_{50}$ (μM gmean) | BRD4 $IC_{50}$ (μM gmean) |
| 1 | + | + |
| 2 | ++ | + |
| 3 | ++ | + |
| 4 | + | + |
| 5 | + | + |
| 6 | ++ | + |
| 7 | ++ | + |
| 8 | ++ | NT |
| 9 | + | + |
| 10 | + | + |
| 11 | + | + |
| 12 | + | + |

TABLE 19-continued

| | $IC_{50}$ Values | |
|---|---|---|
| Example No. | CBP $IC_{50}$ (μM gmean) | BRD4 $IC_{50}$ (μM gmean) |
| 13 | + | + |
| 14 | + | + |
| 15 | + | + |
| 16 | ++++ | + |
| 17 | +++ | + |
| 18 | ++ | + |
| 19 | +++ | + |
| 20 | ++ | + |
| 21 | ++ | + |
| 22 | ++ | + |
| 23 | +++ | + |
| 24 | +++ | + |
| 25 | +++ | + |
| 26 | ++ | + |
| 27 | ++++ | + |
| 28 | ++++ | + |
| 29 | +++ | + |
| 30 | ++ | + |
| 31 | +++ | + |
| 32 | ++ | + |
| 33 | ++ | + |
| 34 | ++ | + |
| 35 | ++ | + |
| 36 | +++ | + |
| 37 | +++ | + |
| 38 | ++ | + |
| 39 | +++ | + |
| 40 | +++ | + |
| 41 | +++ | + |
| 42 | +++ | + |
| 43 | +++ | + |
| 44 | ++ | + |
| 45 | ++ | + |
| 46 | +++ | + |
| 47 | ++ | + |
| 48 | ++ | + |
| 49 | ++ | + |
| 50 | ++ | + |
| 51 | ++ | + |
| 52 | +++ | + |
| 53 | +++ | + |
| 54 | +++ | + |
| 55 | ++ | + |
| 56 | +++ | + |
| 57 | +++ | + |
| 58 | ++ | + |
| 59 | ++ | + |
| 60 | ++++ | + |
| 61 | +++ | + |
| 62 | +++ | + |
| 63 | ++ | + |
| 64 | ++++ | + |
| 65 | +++ | + |
| 66 | +++ | + |
| 67 | ++ | + |
| 68 | ++ | ++ |
| 69 | +++ | + |
| 70 | ++ | + |
| 71 | ++ | + |
| 72 | +++ | + |
| 73 | +++ | + |
| 74 | +++ | + |
| 75 | +++ | ++ |
| 76 | ++++ | ++ |
| 77 | +++ | + |
| 78 | + | + |
| 79 | ++ | + |
| 80 | ++ | + |
| 81 | +++ | + |
| 82 | +++ | + |
| 83 | ++ | + |
| 84 | ++ | + |
| 85 | ++ | + |
| 86 | + | + |
| 87 | + | + |
| 88 | ++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 89 | + | + |
| 90 | ++ | + |
| 91 | ++ | + |
| 92 | +++ | ++ |
| 93 | ++ | + |
| 94 | +++ | + |
| 95 | +++ | + |
| 96 | +++ | + |
| 97 | ++ | + |
| 98 | ++ | + |
| 99 | ++ | + |
| 100 | ++ | + |
| 101 | ++ | + |
| 102 | ++ | + |
| 103 | +++ | + |
| 104 | ++ | + |
| 105 | +++ | + |
| 106 | + | + |
| 107 | ++ | + |
| 108 | +++ | + |
| 109 | +++ | + |
| 110 | +++ | + |
| 111 | + | + |
| 112 | ++ | + |
| 113 | ++ | + |
| 114 | + | + |
| 115 | + | + |
| 116 | ++ | + |
| 117 | + | + |
| 118 | ++ | + |
| 119 | ++ | + |
| 120 | ++ | + |
| 121 | ++ | + |
| 122 | ++ | + |
| 123 | ++ | + |
| 124 | ++ | + |
| 125 | ++ | + |
| 126 | ++ | + |
| 127 | +++ | ++ |
| 128 | ++ | + |
| 129 | +++ | + |
| 130 | ++ | + |
| 131 | +++ | + |
| 132 | + | + |
| 133 | ++ | + |
| 134 | + | + |
| 135 | ++ | + |
| 136 | + | + |
| 137 | + | + |
| 138 | +++ | + |
| 139 | ++ | + |
| 140 | ++++ | ++ |
| 141 | ++++ | + |
| 142 | +++ | + |
| 143 | ++++ | + |
| 144 | +++ | + |
| 145 | +++ | + |
| 146 | ++ | + |
| 147 | ++ | + |
| 148 | ++ | + |
| 149 | +++ | + |
| 150 | + | + |
| 151 | +++ | + |
| 152 | +++ | + |
| 153 | +++ | + |
| 154 | +++ | + |
| 155 | ++++ | + |
| 156 | +++ | + |
| 157 | ++ | + |
| 158 | ++++ | + |
| 159 | +++ | + |
| 160 | ++++ | + |
| 161 | ++++ | + |
| 162 | +++ | + |
| 163 | ++++ | + |
| 164 | ++++ | + |
| 165 | +++ | + |
| 166 | +++ | + |
| 167 | ++++ | + |
| 168 | +++ | + |
| 169 | ++++ | + |
| 170 | +++ | + |
| 171 | ++++ | + |
| 172 | +++ | + |
| 173 | ++++ | + |
| 174 | +++ | + |
| 175 | ++++ | + |
| 176 | ++++ | + |
| 177 | +++ | + |
| 178 | ++++ | + |
| 179 | ++++ | + |
| 180 | +++ | + |
| 181 | ++++ | + |
| 182 | +++ | + |
| 183 | ++++ | + |
| 184 | +++ | + |
| 185 | +++ | + |
| 186 | ++++ | + |
| 187 | ++++ | + |
| 188 | +++ | NT |
| 189 | ++++ | + |
| 190 | +++ | + |
| 191 | ++++ | + |
| 192 | ++ | + |
| 193 | +++ | + |
| 194 | +++ | + |
| 195 | ++ | + |
| 196 | +++ | + |
| 197 | ++ | + |
| 198 | + | + |
| 199 | +++ | + |
| 200 | ++++ | + |
| 201 | +++ | + |
| 202 | ++++ | + |
| 203 | +++ | + |
| 204 | ++++ | + |
| 205 | +++ | + |
| 206 | ++ | + |
| 207 | ++++ | + |
| 208 | +++ | + |
| 209 | +++ | + |
| 210 | +++ | + |
| 211 | ++++ | + |
| 212 | +++ | + |
| 213 | ++++ | + |
| 214 | ++++ | + |
| 215 | +++ | + |
| 216 | ++ | + |
| 217 | ++ | + |
| 218 | ++ | + |
| 219 | ++ | + |
| 220 | ++ | + |
| 221 | ++ | + |
| 222 | ++ | + |
| 223 | +++ | + |
| 224 | ++ | + |
| 225 | ++ | + |
| 226 | ++ | + |
| 227 | ++ | + |
| 228 | ++ | + |
| 229 | + | + |
| 230 | + | + |
| 231 | + | + |
| 232 | + | + |
| 233 | + | + |
| 234 | ++ | + |
| 235 | ++ | + |
| 236 | ++ | + |
| 237 | ++ | + |
| 238 | ++ | + |
| 239 | ++ | + |
| 240 | ++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 241 | +++ | + |
| 242 | ++ | + |
| 243 | ++ | + |
| 244 | +++ | + |
| 245 | +++ | + |
| 246 | ++ | + |
| 247 | + | + |
| 248 | + | + |
| 249 | + | + |
| 250 | + | + |
| 251 | + | + |
| 252 | + | ++ |
| 253 | ++ | + |
| 254 | +++ | + |
| 255 | +++ | + |
| 256 | +++ | + |
| 257 | +++ | + |
| 258 | ++ | + |
| 259 | ++ | + |
| 260 | ++ | + |
| 261 | ++ | + |
| 262 | ++ | + |
| 263 | +++ | + |
| 264 | +++ | + |
| 265 | +++ | + |
| 266 | ++ | + |
| 267 | ++ | + |
| 268 | ++ | + |
| 269 | ++ | + |
| 270 | ++ | + |
| 271 | + | + |
| 272 | ++ | + |
| 273 | ++ | + |
| 274 | ++ | + |
| 275 | ++ | + |
| 276 | +++ | + |
| 277 | +++ | + |
| 278 | +++ | + |
| 279 | ++ | + |
| 280 | ++++ | + |
| 281 | ++ | + |
| 282 | ++ | + |
| 283 | ++++ | + |
| 284 | ++ | + |
| 285 | ++ | + |
| 286 | ++ | + |
| 287 | ++ | + |
| 288 | ++ | + |
| 289 | ++ | + |
| 290 | + | + |
| 291 | ++ | NT |
| 292 | ++ | + |
| 293 | + | + |
| 294 | ++ | + |
| 295 | + | + |
| 296 | + | + |
| 297 | + | + |
| 298 | ++ | + |
| 299 | ++ | + |
| 300 | + | + |
| 301 | ++ | + |
| 302 | ++ | + |
| 303 | ++ | + |
| 304 | ++ | + |
| 305 | ++ | + |
| 306 | + | + |
| 307 | + | + |
| 308 | ++ | + |
| 309 | ++ | + |
| 310 | ++ | + |
| 311 | + | + |
| 312 | ++ | + |
| 313 | ++ | + |
| 314 | ++ | + |
| 315 | + | + |
| 316 | + | + |

TABLE 19-continued

| IC$_{50}$ Values | | |
|---|---|---|
| Example No. | CBP IC$_{50}$ (μM gmean) | BRD4 IC$_{50}$ (μM gmean) |
| 317 | ++ | + |
| 318 | ++ | + |
| 319 | + | + |
| 320 | ++ | + |
| 321 | + | + |
| 322 | ++ | + |
| 323 | ++ | + |
| 324 | ++ | + |
| 325 | ++ | + |
| 326 | ++ | + |
| 327 | ++ | + |
| 328 | + | + |
| 329 | ++ | + |
| 330 | + | + |
| 331 | + | + |
| 332 | ++ | + |
| 333 | ++ | + |
| 334 | + | + |
| 335 | ++ | + |
| 336 | + | + |
| 337 | ++ | + |
| 338 | + | + |
| 339 | ++ | + |
| 340 | ++ | + |
| 341 | ++ | + |
| 342 | ++ | + |
| 343 | + | + |
| 344 | ++ | + |
| 345 | ++ | + |
| 346 | ++ | + |
| 347 | ++ | + |
| 348 | ++ | + |
| 349 | + | + |
| 350 | ++ | + |
| 351 | ++ | + |
| 352 | ++ | + |
| 353 | ++ | + |
| 354 | + | + |
| 355 | + | + |
| 356 | ++ | + |
| 357 | ++ | + |
| 358 | ++ | + |
| 359 | ++ | + |
| 360 | ++ | + |
| 361 | ++ | + |
| 362 | ++ | + |
| 363 | ++ | + |
| 364 | ++ | + |
| 365 | ++ | + |
| 366 | ++ | + |
| 367 | ++ | + |
| 368 | + | + |
| 369 | ++ | + |
| 370 | ++ | + |
| 371 | ++ | + |
| 372 | ++ | + |
| 373 | + | + |
| 374 | ++ | + |
| 375 | + | + |
| 376 | ++ | + |
| 377 | +++ | + |
| 378 | + | + |
| 379 | ++ | + |
| 380 | ++ | + |
| 381 | ++ | + |
| 382 | + | + |
| 383 | +++ | + |
| 384 | ++ | + |
| 385 | ++ | + |
| 386 | +++ | + |
| 387 | ++ | + |
| 388 | ++++ | + |
| 389 | ++++ | + |
| 390 | ++ | + |
| 391 | + | + |
| 392 | ++++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 393 | ++ | + |
| 394 | +++ | + |
| 395 | ++ | + |
| 396 | ++ | + |
| 397 | ++ | + |
| 398 | ++ | + |
| 399 | + | + |
| 400 | ++ | + |
| 401 | ++ | + |
| 402 | ++ | + |
| 403 | + | + |
| 404 | ++++ | + |
| 405 | ++++ | + |
| 406 | ++++ | + |
| 407 | ++++ | + |
| 408 | ++++ | + |
| 409 | ++++ | ++ |
| 410 | ++++ | ++ |
| 411 | ++++ | ++ |
| 412 | ++++ | ++ |
| 413 | ++++ | ++ |
| 414 | ++++ | ++ |
| 415 | ++++ | ++ |
| 416 | ++++ | ++ |
| 417 | ++++ | ++ |
| 418 | ++++ | ++ |
| 419 | ++++ | ++ |
| 420 | ++++ | ++ |
| 421 | ++++ | ++ |
| 422 | ++++ | ++ |
| 423 | ++++ | ++ |
| 424 | ++++ | ++ |
| 425 | ++++ | ++ |
| 426 | ++++ | ++ |
| 427 | ++++ | ++ |
| 428 | ++++ | ++ |
| 429 | ++++ | ++ |
| 430 | ++++ | ++ |
| 431 | ++++ | ++ |
| 432 | ++++ | + |
| 433 | ++++ | ++ |
| 434 | ++++ | ++ |
| 435 | ++++ | ++ |
| 436 | ++++ | ++ |
| 437 | ++++ | ++ |
| 438 | ++++ | ++ |
| 439 | ++++ | ++ |
| 440 | ++++ | ++ |
| 441 | ++++ | ++ |
| 442 | ++++ | ++ |
| 443 | ++++ | + |
| 444 | ++++ | ++ |
| 445 | ++++ | ++ |
| 446 | ++++ | + |
| 447 | ++++ | + |
| 448 | ++++ | ++ |
| 449 | ++++ | + |
| 450 | ++++ | ++ |
| 451 | ++++ | ++ |
| 452 | ++++ | ++ |
| 453 | ++++ | +++ |
| 454 | ++++ | ++ |
| 455 | ++++ | + |
| 456 | ++++ | + |
| 457 | ++++ | ++ |
| 458 | ++++ | ++ |
| 459 | ++++ | + |
| 460 | ++++ | ++ |
| 461 | ++++ | ++ |
| 462 | ++++ | + |
| 463 | ++++ | + |
| 464 | ++++ | ++ |
| 465 | ++++ | ++ |
| 466 | ++++ | + |
| 467 | ++++ | ++ |
| 468 | ++++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 469 | ++++ | +++ |
| 470 | ++++ | ++ |
| 471 | ++++ | + |
| 472 | ++++ | ++ |
| 473 | ++++ | ++ |
| 474 | ++++ | ++ |
| 475 | ++++ | + |
| 476 | ++++ | ++ |
| 477 | ++++ | + |
| 478 | ++++ | ++ |
| 479 | ++++ | + |
| 480 | ++++ | ++ |
| 481 | ++++ | + |
| 482 | ++++ | ++ |
| 483 | ++++ | ++ |
| 484 | ++++ | ++ |
| 485 | ++++ | + |
| 486 | ++++ | ++ |
| 487 | ++++ | ++ |
| 488 | ++++ | ++ |
| 489 | ++++ | + |
| 490 | ++++ | + |
| 491 | ++++ | ++ |
| 492 | ++++ | + |
| 493 | ++++ | ++ |
| 494 | ++++ | ++ |
| 495 | ++++ | + |
| 496 | ++++ | ++ |
| 497 | ++++ | + |
| 498 | ++++ | ++ |
| 499 | ++++ | ++ |
| 500 | ++++ | ++ |
| 501 | ++++ | ++ |
| 502 | ++++ | + |
| 503 | ++++ | ++ |
| 504 | ++++ | + |
| 505 | ++++ | + |
| 506 | ++++ | + |
| 507 | ++++ | ++ |
| 508 | ++++ | + |
| 509 | ++++ | + |
| 510 | ++++ | + |
| 511 | ++++ | + |
| 512 | ++++ | + |
| 513 | ++++ | + |
| 514 | ++++ | + |
| 515 | ++++ | ++ |
| 516 | ++++ | + |
| 517 | ++++ | ++ |
| 518 | ++++ | ++ |
| 519 | ++++ | ++ |
| 520 | ++++ | ++ |
| 521 | ++++ | + |
| 522 | ++++ | + |
| 523 | ++++ | ++ |
| 524 | ++++ | + |
| 525 | ++++ | ++ |
| 526 | ++++ | + |
| 527 | ++++ | ++ |
| 528 | ++++ | ++ |
| 529 | ++++ | + |
| 530 | ++++ | ++ |
| 531 | ++++ | ++ |
| 532 | ++++ | + |
| 533 | ++++ | + |
| 534 | ++++ | + |
| 535 | ++++ | ++ |
| 536 | ++++ | + |
| 537 | ++++ | ++ |
| 538 | ++++ | + |
| 539 | ++++ | + |
| 540 | ++++ | ++ |
| 541 | ++++ | + |
| 542 | ++++ | + |
| 543 | ++++ | ++ |
| 544 | ++++ | + |

TABLE 19-continued

| IC50 Values | | |
|---|---|---|
| Example No. | CBP $IC_{50}$ (μM gmean) | BRD4 $IC_{50}$ (μM gmean) |
| 545 | ++++ | ++ |
| 546 | ++++ | + |
| 547 | ++++ | ++ |
| 548 | ++++ | ++ |
| 549 | ++++ | + |
| 550 | ++++ | + |
| 551 | ++++ | + |
| 552 | ++++ | ++ |
| 553 | ++++ | + |
| 554 | ++++ | ++ |
| 555 | ++++ | + |
| 556 | ++++ | ++ |
| 557 | ++++ | ++ |
| 558 | ++++ | + |
| 559 | ++++ | + |
| 560 | ++++ | + |
| 561 | ++++ | + |
| 562 | ++++ | + |
| 563 | ++++ | + |
| 564 | ++++ | + |
| 565 | ++++ | + |
| 566 | ++++ | ++ |
| 567 | ++++ | ++ |
| 568 | ++++ | + |
| 569 | ++++ | ++ |
| 570 | ++++ | ++ |
| 571 | ++++ | ++ |
| 572 | ++++ | + |
| 573 | ++++ | ++ |
| 574 | ++++ | + |
| 575 | ++++ | + |
| 576 | ++++ | ++ |
| 577 | ++++ | + |
| 578 | ++++ | + |
| 579 | ++++ | ++ |
| 580 | ++++ | + |
| 581 | ++++ | + |
| 582 | ++++ | + |
| 583 | ++++ | + |
| 584 | ++++ | + |
| 585 | ++++ | ++ |
| 586 | ++++ | ++ |
| 587 | ++++ | ++ |
| 588 | ++++ | + |
| 589 | ++++ | + |
| 590 | ++++ | + |
| 591 | ++++ | + |
| 592 | ++++ | ++ |
| 593 | ++++ | + |
| 594 | ++++ | + |
| 595 | ++++ | ++ |
| 596 | ++++ | + |
| 597 | ++++ | + |
| 598 | ++++ | ++ |
| 599 | ++++ | ++ |
| 600 | +++ | ++ |
| 601 | +++ | + |
| 602 | +++ | + |
| 603 | +++ | + |
| 604 | +++ | ++ |
| 605 | +++ | ++ |
| 606 | +++ | +++ |
| 607 | +++ | + |
| 608 | +++ | +++ |
| 609 | +++ | ++ |
| 610 | +++ | + |
| 611 | +++ | + |
| 612 | +++ | ++ |
| 613 | +++ | + |
| 614 | +++ | + |
| 615 | +++ | + |
| 616 | +++ | + |
| 617 | +++ | + |
| 618 | +++ | ++ |
| 619 | +++ | + |
| 620 | +++ | + |

TABLE 19-continued

| IC50 Values | | |
|---|---|---|
| Example No. | CBP $IC_{50}$ (μM gmean) | BRD4 $IC_{50}$ (μM gmean) |
| 621 | +++ | + |
| 622 | +++ | + |
| 623 | +++ | ++ |
| 624 | +++ | ++ |
| 625 | +++ | + |
| 626 | +++ | ++ |
| 627 | +++ | + |
| 628 | +++ | + |
| 629 | +++ | + |
| 630 | +++ | ++ |
| 631 | +++ | + |
| 632 | +++ | + |
| 633 | +++ | + |
| 634 | +++ | + |
| 635 | +++ | ++ |
| 636 | +++ | + |
| 637 | +++ | + |
| 638 | +++ | + |
| 639 | +++ | + |
| 640 | +++ | ++ |
| 641 | +++ | + |
| 642 | +++ | ++ |
| 643 | +++ | + |
| 644 | +++ | + |
| 645 | +++ | + |
| 646 | +++ | + |
| 647 | +++ | ++ |
| 648 | +++ | + |
| 649 | +++ | + |
| 650 | +++ | + |
| 651 | +++ | + |
| 652 | +++ | ++ |
| 653 | +++ | ++ |
| 654 | +++ | + |
| 655 | +++ | + |
| 656 | +++ | + |
| 657 | +++ | + |
| 658 | +++ | ++ |
| 659 | +++ | + |
| 660 | +++ | + |
| 661 | +++ | + |
| 662 | +++ | ++ |
| 663 | +++ | + |
| 664 | +++ | + |
| 665 | +++ | + |
| 666 | +++ | ++ |
| 667 | +++ | ++ |
| 668 | +++ | + |
| 669 | +++ | + |
| 670 | +++ | ++ |
| 671 | +++ | + |
| 672 | +++ | ++ |
| 673 | +++ | + |
| 674 | +++ | + |
| 675 | +++ | + |
| 676 | +++ | + |
| 677 | +++ | ++ |
| 678 | +++ | ++ |
| 679 | +++ | + |
| 680 | +++ | + |
| 681 | +++ | + |
| 682 | +++ | + |
| 683 | +++ | ++ |
| 684 | +++ | ++ |
| 685 | +++ | ++ |
| 686 | +++ | ++ |
| 687 | +++ | + |
| 688 | +++ | + |
| 689 | +++ | ++ |
| 690 | +++ | ++ |
| 691 | +++ | + |
| 692 | +++ | + |
| 693 | +++ | ++ |
| 694 | +++ | ++ |
| 695 | +++ | + |
| 696 | +++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 697 | +++ | + |
| 698 | +++ | + |
| 699 | +++ | + |
| 700 | +++ | + |
| 701 | +++ | + |
| 702 | +++ | + |
| 703 | +++ | ++ |
| 704 | +++ | + |
| 705 | +++ | ++ |
| 706 | +++ | + |
| 707 | +++ | + |
| 708 | +++ | + |
| 709 | +++ | + |
| 710 | +++ | + |
| 711 | +++ | + |
| 712 | +++ | + |
| 713 | +++ | + |
| 714 | +++ | + |
| 715 | +++ | ++ |
| 716 | +++ | ++ |
| 717 | +++ | + |
| 718 | +++ | + |
| 719 | +++ | ++ |
| 720 | +++ | + |
| 721 | +++ | + |
| 722 | +++ | ++ |
| 723 | +++ | + |
| 724 | +++ | + |
| 725 | +++ | + |
| 726 | +++ | + |
| 727 | +++ | ++ |
| 728 | +++ | + |
| 729 | +++ | + |
| 730 | +++ | + |
| 731 | +++ | + |
| 732 | +++ | + |
| 733 | +++ | + |
| 734 | +++ | + |
| 735 | +++ | + |
| 736 | +++ | ++ |
| 737 | +++ | + |
| 738 | +++ | + |
| 739 | +++ | ++ |
| 740 | +++ | + |
| 741 | +++ | + |
| 742 | +++ | + |
| 743 | +++ | + |
| 744 | +++ | + |
| 745 | +++ | + |
| 746 | +++ | ++ |
| 747 | +++ | + |
| 748 | +++ | + |
| 749 | +++ | + |
| 750 | +++ | |
| 751 | +++ | + |
| 752 | +++ | + |
| 753 | +++ | + |
| 754 | +++ | + |
| 755 | +++ | + |
| 756 | +++ | + |
| 757 | +++ | + |
| 758 | +++ | + |
| 759 | +++ | + |
| 760 | +++ | + |
| 761 | +++ | ++ |
| 762 | +++ | + |
| 763 | +++ | + |
| 764 | +++ | + |
| 765 | +++ | ++ |
| 766 | +++ | ++ |
| 767 | +++ | ++ |
| 768 | +++ | + |
| 769 | +++ | + |
| 770 | +++ | + |
| 771 | +++ | + |
| 772 | +++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 773 | +++ | + |
| 774 | +++ | + |
| 775 | +++ | + |
| 776 | +++ | ++ |
| 777 | +++ | + |
| 778 | +++ | + |
| 779 | +++ | + |
| 780 | +++ | + |
| 781 | +++ | + |
| 782 | +++ | + |
| 783 | +++ | + |
| 784 | +++ | + |
| 785 | +++ | + |
| 786 | +++ | + |
| 787 | +++ | + |
| 788 | +++ | ++ |
| 789 | +++ | + |
| 790 | +++ | + |
| 791 | +++ | + |
| 792 | +++ | + |
| 793 | +++ | + |
| 794 | +++ | + |
| 795 | +++ | + |
| 796 | +++ | ++ |
| 797 | +++ | + |
| 798 | +++ | + |
| 799 | +++ | ++ |
| 800 | +++ | ++ |
| 801 | +++ | + |
| 802 | +++ | + |
| 803 | +++ | + |
| 804 | +++ | + |
| 805 | +++ | + |
| 806 | +++ | + |
| 807 | +++ | + |
| 808 | +++ | ++ |
| 809 | +++ | ++ |
| 810 | +++ | + |
| 811 | +++ | + |
| 812 | +++ | + |
| 813 | +++ | + |
| 814 | +++ | + |
| 815 | +++ | ++ |
| 816 | +++ | ++ |
| 817 | +++ | ++ |
| 818 | +++ | ++ |
| 819 | +++ | ++ |
| 820 | +++ | + |
| 821 | +++ | + |
| 822 | +++ | + |
| 823 | +++ | + |
| 824 | +++ | + |
| 825 | +++ | |
| 826 | +++ | ++ |
| 827 | +++ | + |
| 828 | +++ | + |
| 829 | +++ | + |
| 830 | +++ | ++ |
| 831 | +++ | + |
| 832 | +++ | + |
| 833 | +++ | + |
| 834 | +++ | + |
| 835 | +++ | + |
| 836 | +++ | ++ |
| 837 | +++ | + |
| 838 | +++ | ++ |
| 839 | +++ | ++ |
| 840 | +++ | + |
| 841 | +++ | + |
| 842 | +++ | + |
| 843 | +++ | + |
| 844 | +++ | + |
| 845 | +++ | + |
| 846 | +++ | + |
| 847 | +++ | ++ |
| 848 | +++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 849 | +++ | + |
| 850 | +++ | ++ |
| 851 | +++ | + |
| 852 | +++ | + |
| 853 | +++ | ++ |
| 854 | ++ | ++ |
| 855 | ++ | + |
| 856 | ++ | + |
| 857 | ++ | ++ |
| 858 | ++ | + |
| 859 | ++ | ++ |
| 860 | ++ | + |
| 861 | ++ | ++ |
| 862 | ++ | + |
| 863 | ++ | + |
| 864 | ++ | + |
| 865 | ++ | ++ |
| 866 | ++ | ++ |
| 867 | ++ | + |
| 868 | ++ | + |
| 869 | ++ | + |
| 870 | ++ | + |
| 871 | ++ | + |
| 872 | ++ | + |
| 873 | ++ | ++ |
| 874 | ++ | ++ |
| 875 | ++ | ++ |
| 876 | ++ | + |
| 877 | ++ | + |
| 878 | ++ | + |
| 879 | ++ | + |
| 880 | ++ | + |
| 881 | ++ | ++ |
| 882 | ++ | + |
| 883 | ++ | ++ |
| 884 | ++ | ++ |
| 885 | ++ | + |
| 886 | ++ | ++ |
| 887 | ++ | + |
| 888 | ++ | + |
| 889 | ++ | ++ |
| 890 | ++ | ++ |
| 891 | ++ | + |
| 892 | ++ | + |
| 893 | ++ | + |
| 894 | ++ | + |
| 895 | ++ | + |
| 896 | ++ | + |
| 897 | ++ | + |
| 898 | ++ | + |
| 899 | ++ | ++ |
| 900 | ++ | + |
| 901 | ++ | + |
| 902 | ++ | + |
| 903 | ++ | + |
| 904 | ++ | + |
| 905 | ++ | + |
| 906 | ++ | + |
| 907 | ++ | + |
| 908 | ++ | + |
| 909 | ++ | + |
| 910 | ++ | + |
| 911 | ++ | + |
| 912 | ++ | + |
| 913 | ++ | + |
| 914 | ++ | + |
| 915 | ++ | + |
| 916 | ++ | + |
| 917 | ++ | + |
| 918 | ++ | + |
| 919 | ++ | + |
| 920 | ++ | + |
| 921 | ++ | + |
| 922 | ++ | + |
| 923 | ++ | + |
| 924 | ++ | + |

TABLE 19-continued

| IC$_{50}$ Values | | |
|---|---|---|
| Example No. | CBP IC$_{50}$ (μM gmean) | BRD4 IC$_{50}$ (μM gmean) |
| 925 | ++ | + |
| 926 | ++ | + |
| 927 | ++ | + |
| 928 | ++ | + |
| 929 | ++ | + |
| 930 | ++ | + |
| 931 | ++ | + |
| 932 | + | + |
| 933 | + | + |
| 934 | + | + |
| 935 | + | + |
| 936 | + | + |
| 937 | + | + |
| 938 | + | + |
| 939 | + | + |
| 940 | + | + |
| 941 | + | + |
| 942 | + | + |
| 943 | + | + |
| 944 | + | + |
| 945 | + | |
| 946 | + | + |
| 947 | + | + |
| 948 | + | + |
| 949 | + | + |
| 950 | + | + |
| 951 | + | + |
| 952 | + | + |
| 953 | + | + |
| 954 | + | |
| 955 | + | + |
| 956 | + | + |
| 957 | + | + |
| 958 | + | + |
| 959 | + | + |
| 960 | + | + |
| 961 | + | + |
| 962 | + | +++ |

The invention claimed is:

1. A compound of formula (I-h):

(I-h)

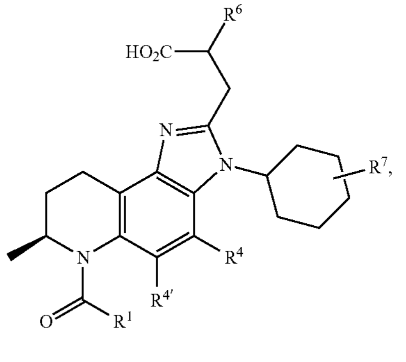

or a pharmaceutically acceptable salt thereof, wherein:

$R^1$ is —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —$OR^5$, —$N(R^5)_2$, or —$NHR^5$;

$R^4$ and $R^{4'}$ are each independently —H, halogen, —OH, —CN, or —$NH_2$;

each $R^5$ is independently —$C_1$-$C_6$alkyl, —$C_3$-$C_8$cycloalkyl, heterocyclyl, aryl, or heteroaryl;

$R^6$ and $R^7$ are each independently, at each occurrence, —$C_1$-$C_6$alkyl, —$C_3$-$C_8$cycloalkyl, —$C_4$-$C_8$cycloalkenyl, heterocyclyl, aryl, spirocycloalkyl, spiroheterocyclyl, heteroaryl, —OH, halogen, oxo, —CN, —$SR^8$, —$OR^8$, —$(CH_2)_n$—$OR^8$, —$NHR^8$, $NR^8R^9$, —$S(O)_2NR^8R^9$, —$S(O)_2R^{8'}$, —$C(O)R^{8'}$, —$C(O)OR^8$, —$C(O)NR^8R^9$, —$NR^8C(O)R^{9'}$, —$NR^8S(O)_2R^{9'}$, —$S(O)R^{8'}$, —$S(O)NR^8R^9$, or —$NR^8S(O)R^{9'}$, wherein each alkyl, cycloalkyl, heterocyclyl, spirocycloalkyl, spiroheterocyclyl, heteroaryl, or aryl is optionally substituted with one or more $R^{10}$;

$R^8$ and $R^9$ are each independently, at each occurrence, —H, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^8$ and $R^9$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{8'}$ and $R^{9'}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, aryl, heteroaryl, wherein each alkyl, alkenyl, alkynyl, cycloalkyl, cycloalkenyl, heterocyclyl, aryl, or heteroaryl is optionally substituted with one or more $R^{10}$ or $R^{11}$; or $R^{8'}$ and $R^{9'}$ may combine with the atom to which they are both attached to form a —$C_3$-$C_8$cycloalkyl, —$C_4$-$C_8$cycloalkenyl, spirocycloalkyl, spiroheterocyclyl, heterocyclyl, heteroaryl, or aryl, wherein the formed —$C_3$-$C_8$cycloalkyl, —$C_4$-$C_8$cycloalkenyl, spirocycloalkyl, spiroheterocyclyl, heterocyclyl, heteroaryl, or aryl is optionally substituted with one or more $R^{10}$ or $R^{11}$;

$R^{10}$ and $R^{11}$ are each independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$OC_3$-$C_6$cycloalkyl, —Oaryl, —Oheteroaryl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6alkyl)_2$, —$C(O)OC_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6alkyl)_2$, or —$N(C_1$-$C_6$alkyl)$S(O)(C_1$-$C_6$alkyl), wherein each alkyl, alkenyl, alkynyl, cycloalkyl, cycloalkenyl, heterocyclyl, heteroaryl, or aryl is optionally substituted with one or more —$R^{12}$;

wherein any two $R^{10}$ or any two $R^{11}$, when on non-adjacent atoms, can combine to form a bridging cycloalkyl or heterocyclyl;

wherein any two $R^{10}$ or any two $R^{11}$, when on adjacent atoms, can combine to form a cycloalkyl, heterocyclyl, aryl or heteroaryl;

$R^{12}$ is independently, at each occurrence, —$C_1$-$C_6$alkyl, —$C_2$-$C_6$alkenyl, —$C_2$-$C_6$alkynyl, —$C_3$-$C_8$cycloalkyl, —$C_4$-$C_8$cycloalkenyl, heterocyclyl, heteroaryl, aryl, —OH, halogen, oxo, —$NO_2$, —CN, —$NH_2$, —$OC_1$-$C_6$alkyl, —$NHC_1$-$C_6$alkyl, —$N(C_1$-$C_6alkyl)_2$, —$S(O)_2NH(C_1$-$C_6$alkyl), —$S(O)_2N(C_1$-$C_6alkyl)_2$, —$S(O)_2C_1$-$C_6$alkyl, —$C(O)C_1$-$C_6$alkyl, —$C(O)NH_2$, —$C(O)NH(C_1$-$C_6$alkyl), —$C(O)N(C_1$-$C_6alkyl)_2$, —$C(O)OC_1$-$C_6$alkyl, —$N(C_1$-$C_6$alkyl)$SO_2C_1$-$C_6$alkyl, —$S(O)(C_1$-$C_6$alkyl), —$S(O)N(C_1$-$C_6alkyl)_2$, or —$N(C_1$-$C_6$alkyl)$S(O)(C_1$-$C_6$alkyl); and n is an integer from 1 to 4.

2. The compound of claim 1, wherein the compound is a compound of formula (I-h'):

(I-h')

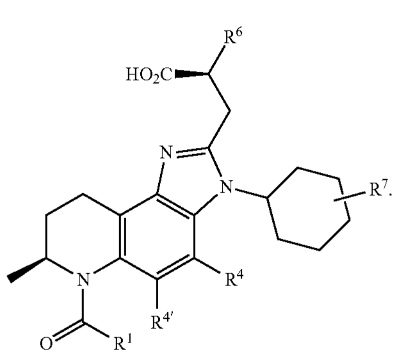

3. The compound of claim 1, wherein the compound is a compound of formula (I-h"):

(I-h")

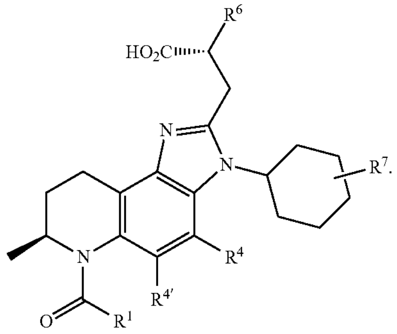

4. The compound of claim 1, wherein $R^1$—$OR^5$.

5. The compound of claim 4, wherein $R^5$ is —$C_1$-$C_6$alkyl.

6. The compound of claim 4, wherein $R^5$ is methyl.

7. The compound of claim 1, wherein $R^4$ is —H.

8. The compound of claim 1, wherein $R^{4'}$ is —H.

9. The compound of claim 1, wherein $R^6$ is aryl and the aryl is optionally substituted with one or more $R^{10}$.

10. The compound of claim 1, wherein $R^6$ is phenyl and the phenyl is optionally substituted with one or more $R^{10}$.

11. The compound of claim 9, wherein each $R^6$ is independently selected from —$C_1$-$C_6$alkyl, halogen, and —$OC_1$-$C_6$alkyl.

12. The compound of claim 1, wherein $R^7$ is selected from —OH, —CN, —$OR^8$, —$(CH_2)_n$—$OR^8$, and —$S(O)_2R^{8'}$.

13. The compound of claim 12, wherein $R^7$ is —$OR^8$, and $R^8$ is —$C_1$-$C_6$alkyl.

14. The compound of claim 12, wherein $R^7$ is —$(CH_2)_n$—$OR^8$, n is 1, and $R^8$ is —H.

15. The compound of claim 12, wherein $R^7$ is —$S(O)_2R^{8'}$ and $R^{8'}$ is —$C_1$-$C_6$alkyl.

16. A compound or a pharmaceutically acceptable salt thereof, wherein the compound is selected from:

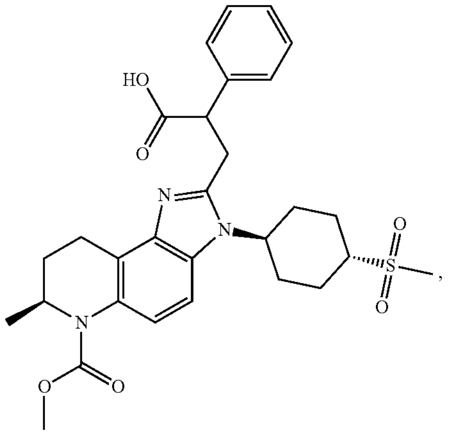
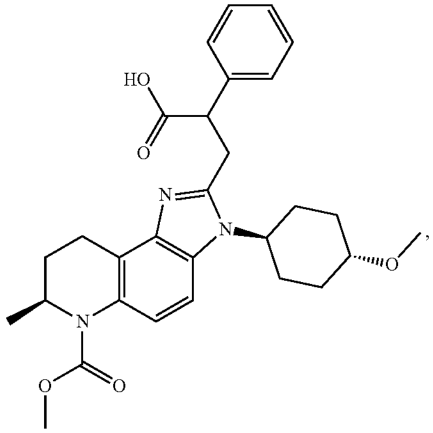
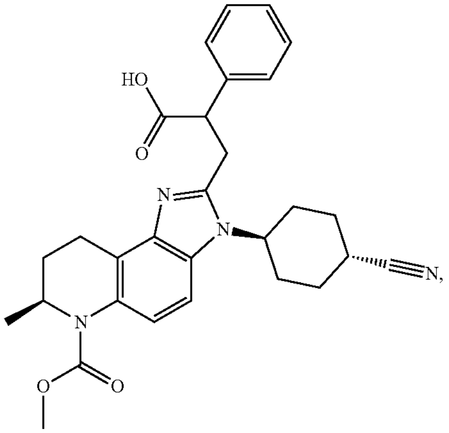
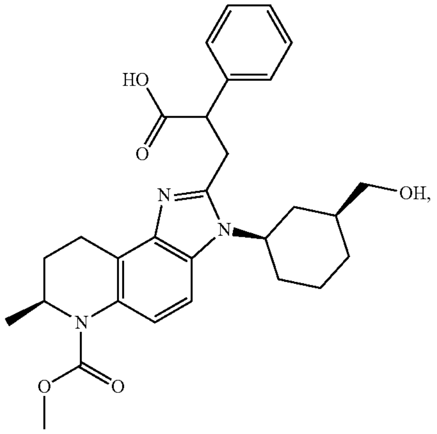
-continued
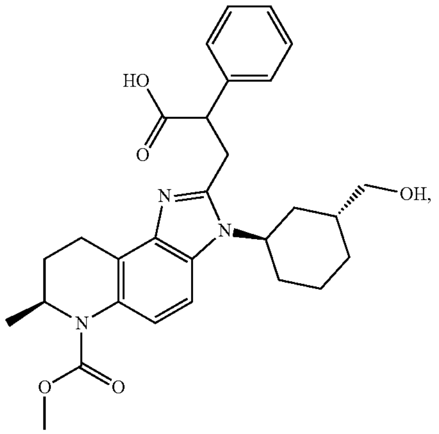
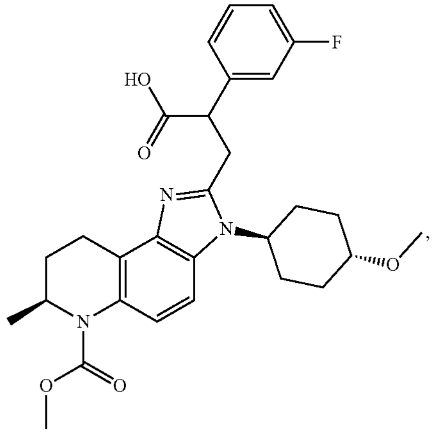
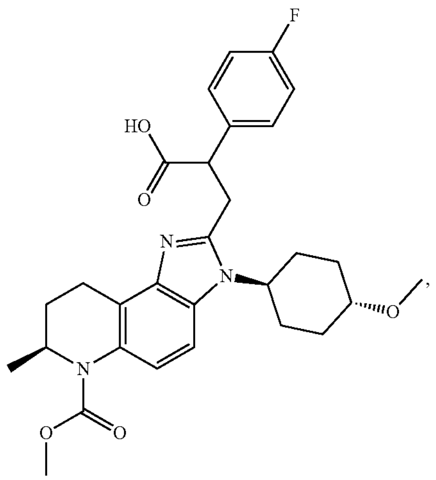

-continued
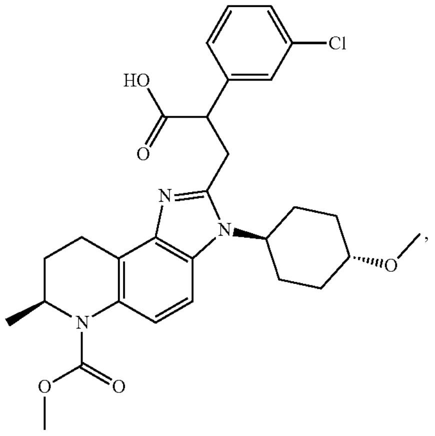
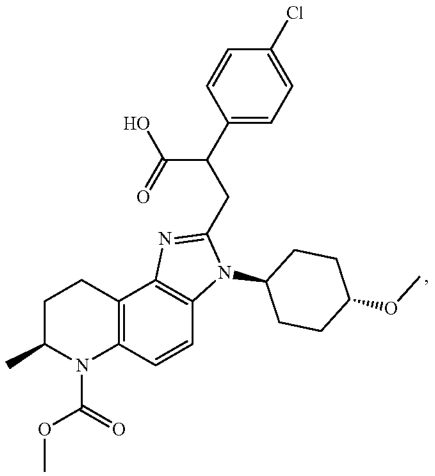
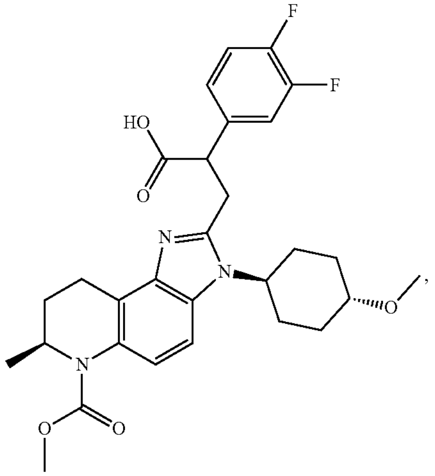
-continued
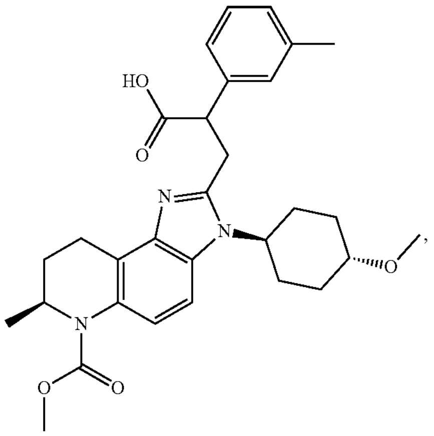
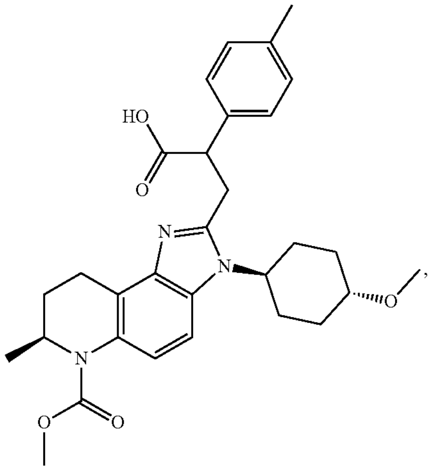
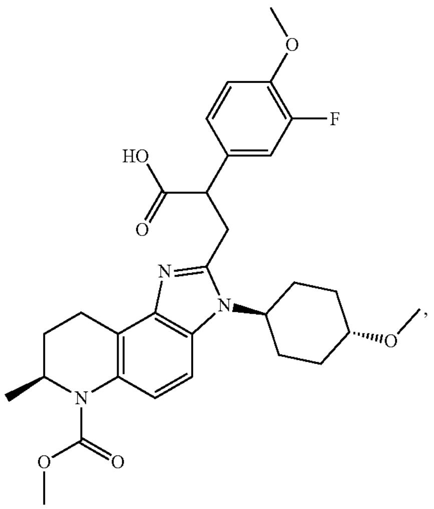

-continued
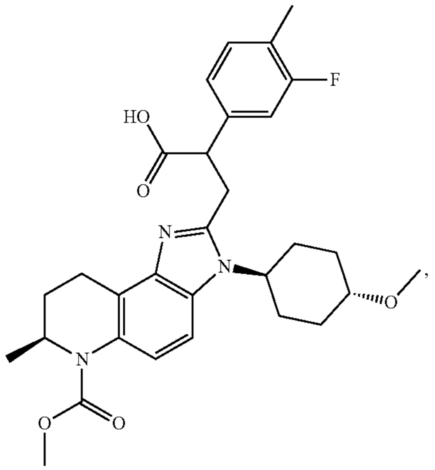
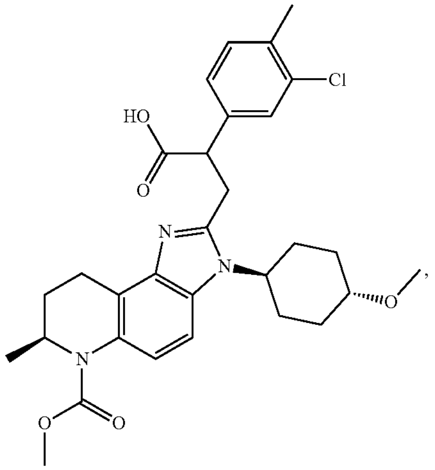
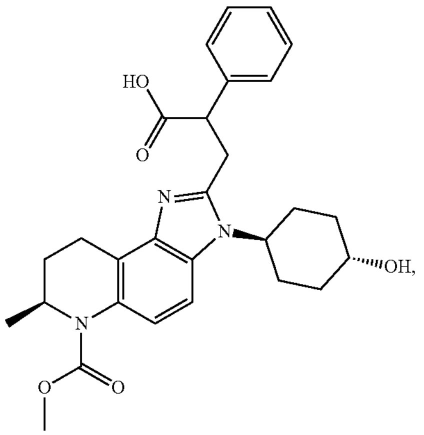
-continued
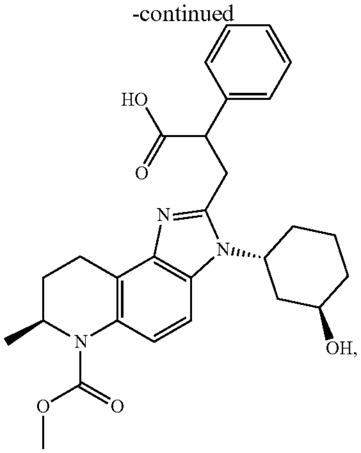
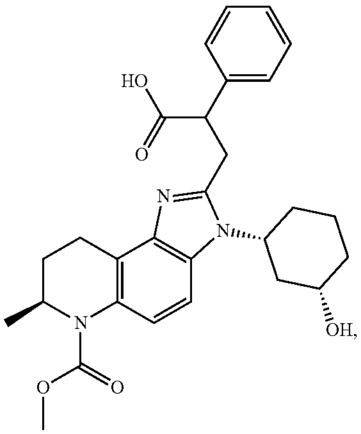
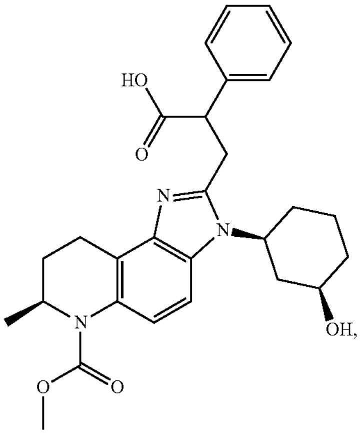
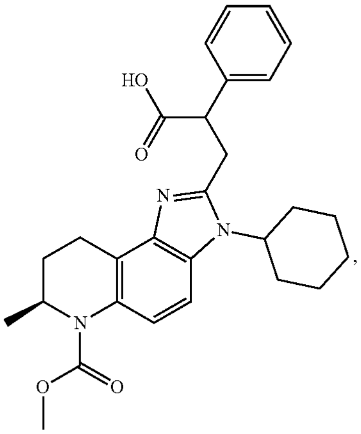

-continued
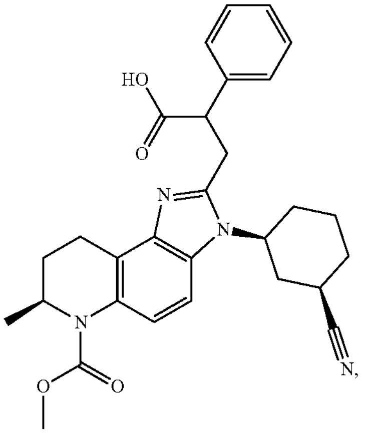
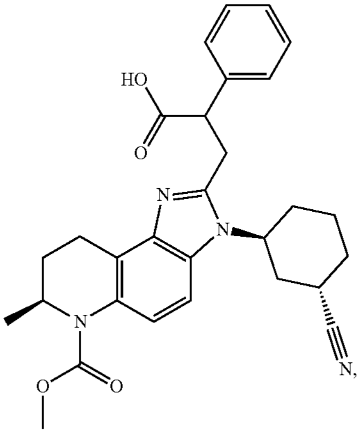
and
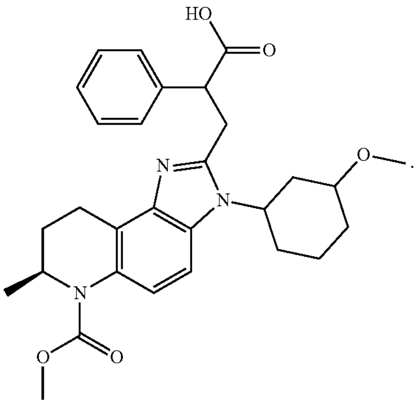
17. The compound of claim 1, or a pharmaceutically acceptable salt thereof, wherein the compound has the structure
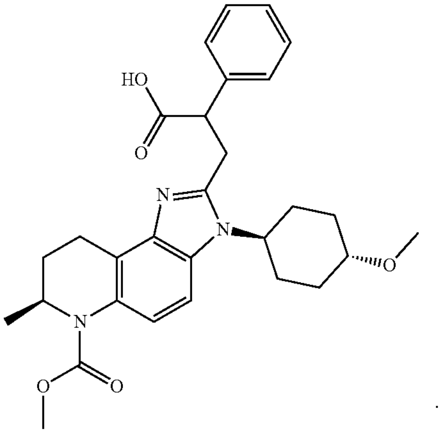
18. The compound of claim 1, or a pharmaceutically acceptable salt thereof, wherein the compound has the structure
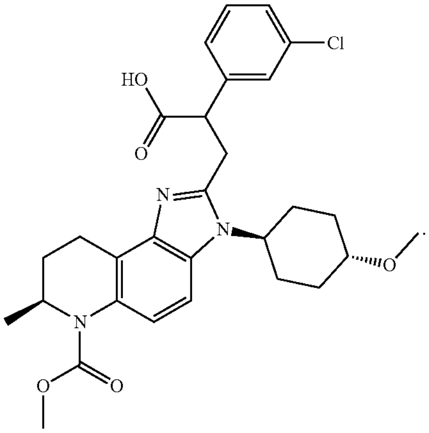
19. The compound of claim 1, or a pharmaceutically acceptable salt thereof, wherein the compound has the structure
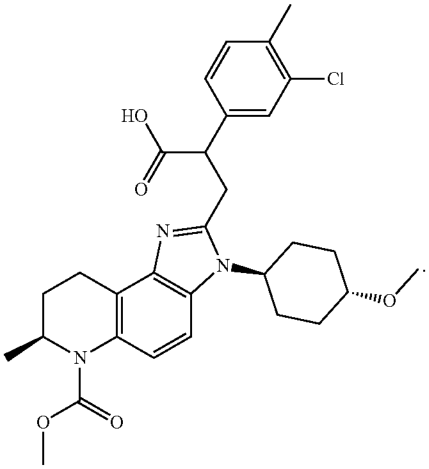

20. A pharmaceutical composition comprising a compound of claim 1, or a pharmaceutically acceptable salt thereof, and a pharmaceutically acceptable carrier.

* * * * *